United States Patent
Watterson et al.

(10) Patent No.: US 11,618,753 B2
(45) Date of Patent: Apr. 4, 2023

(54) AMINOPYRROLOTRIAZINES AS KINASE INHIBITORS

(71) Applicant: BRISTOL-MYERS SQUIBB COMPANY, Princeton, NJ (US)

(72) Inventors: Scott Hunter Watterson, Pennington, NJ (US); Murugaiah Andappan Murugaiah Subbaiah, Hosur (IN); Carolyn Diane Dzierba, Middletown, CT (US); Hua Gong, King of Prussia, PA (US); Jason M. Guernon, Pipersville, PA (US); Junqing Guo, Princeton, NJ (US); Amy C. Hart, Ewing, NJ (US); Guanglin Luo, Madison, CT (US); John E. Macor, Washington Crossing, PA (US); William J. Pitts, Newtown, PA (US); Jianliang Shi, Furlong, PA (US); Brian Lee Venables, Durham, CT (US); Carolyn A. Weigelt, Langhorne, PA (US); Yong-Jin Wu, Madison, CT (US); Zhizhen Barbara Zheng, Cheshire, CT (US); Sing-Yuen Sit, Meriden, CT (US); Jie Chen, Cambridge, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 186 days.

(21) Appl. No.: 16/963,886

(22) PCT Filed: Jan. 24, 2019

(86) PCT No.: PCT/US2019/014918
§ 371 (c)(1),
(2) Date: Jul. 22, 2020

(87) PCT Pub. No.: WO2019/147782
PCT Pub. Date: Aug. 1, 2019

(65) Prior Publication Data
US 2020/0347071 A1 Nov. 5, 2020

Related U.S. Application Data

(60) Provisional application No. 62/622,415, filed on Jan. 26, 2018.

(51) Int. Cl.
*A61K 31/53* (2006.01)
*C07D 253/08* (2006.01)
*C07D 487/04* (2006.01)

(52) U.S. Cl.
CPC ................ *C07D 487/04* (2013.01)

(58) Field of Classification Search
CPC ............... A61K 31/53; C07D 253/08
USPC .......................... 514/243; 544/183
See application file for complete search history.

(56) References Cited

U.S. PATENT DOCUMENTS

| | | |
|---|---|---|
| 2017/0275290 A1 | 9/2017 | Li et al. |
| 2019/0389859 A1 | 12/2019 | Guo et al. |
| 2020/0277296 A1 | 9/2020 | Mertzman et al. |

FOREIGN PATENT DOCUMENTS

| | | |
|---|---|---|
| WO | 2007056170 A2 | 5/2007 |
| WO | 2007064883 A2 | 6/2007 |
| WO | 2007064931 A2 | 6/2007 |
| WO | 2009046448 A1 | 4/2009 |
| WO | 2010126960 A1 | 11/2010 |
| WO | 2011044157 A1 | 4/2011 |
| WO | 2011123493 A1 | 10/2011 |
| WO | 2016064957 A1 | 4/2016 |
| WO | 2016064958 A1 | 4/2016 |
| WO | 2018017435 A1 | 1/2018 |
| WO | 2018148626 A1 | 8/2018 |
| WO | 2019089442 A1 | 5/2019 |
| WO | 2020/056072 A1 | 3/2020 |
| WO | 2020056074 A1 | 3/2020 |

OTHER PUBLICATIONS

U.S. Appl. No. 62/909,920, filed Oct. 3, 2019, Chen, et al.
Bhide et al., "Discovery and SAR of pyrrolo[2,1-.fl[1,2,4]triazin-4-amines as potent and selective PI3Kα inhibitors" Bioorganic & Medicinal Chemistry Letters (2016), 26(17), 4256-4260.

*Primary Examiner* — Douglas M Willis
(74) *Attorney, Agent, or Firm* — Mary K. VanAtten

(57) ABSTRACT

The disclosure relates to compounds of formula I which are useful as kinase modulators including RIPK 1 modulation. The disclosure also provides methods of making and using the compounds for example in treatments related to necrosis or inflammation as well as other indications.

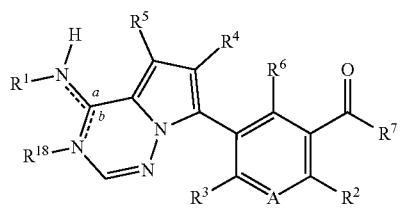

9 Claims, No Drawings

AMINOPYRROLOTRIAZINES AS KINASE INHIBITORS

CROSS REFERENCE TO RELATED APPLICATIONS

This application is a 371 application of PCT/US2019/014918 filed Jan. 24, 2019 which is entitled to priority pursuant to 35 U.S.C. § 119(e) to U.S. provisional patent application No. 62/622,415, filed Jan. 26, 2018, which is incorporated herein in its entirety.

FIELD OF THE INVENTION

The present invention relates to novel compounds that inhibit receptor interacting protein kinases and methods of making and using the same. Specifically, the present invention relates to aminopyrrolotriazines as receptor interacting protein kinase 1 (RIPK1) inhibitors.

BACKGROUND OF THE INVENTION

Apoptosis and necrosis represent two different mechanisms of cell death. Apoptosis is a highly regulated process involving the caspase family of cysteine proteases, and characterized by cellular shrinkage, chromatin condensation, and DNA degradation. In contrast, necrosis is associated with cellular and organelle swelling and plasma membrane rupture with ensuing release of intracellular contents and secondary inflammation (Kroemer et al., (2009) Cell Death Differ 16:3-11). Necrosis has been considered a passive, unregulated form of cell death; however, recent evidence indicates that some necrosis can be induced by regulated signal transduction pathways such as those mediated by receptor interacting protein kinases (RIPKs) especially in conditions where caspases are inhibited or cannot be activated efficiently (Golstein P & Kroemer G (2007) Trends Biochem. Sci. 32:37-43; Festjens et al. (2006) Biochim. Biophys. Acta 1757:1371-1387). Stimulation of the Fas and TNFR family of death domain receptors (DRs) is known to mediate apoptosis in most cell types through the activation of the extrinsic caspase pathway. In addition, in certain cells deficient for caspase-8 or treated with pan-caspase inhibitor Z-VAD, stimulation of death domain receptors (DR) causes a receptor interacting protein kinase 1 (RIPK1) dependent programmed necrotic cell death instead of apoptosis (Holler et al. (2000) Nat. Immunol. 1:489-495; Degterev et al.

(2008) Nat. Chem. Biol. 4:313-321). This novel mechanism of cell death is termed "programmed necrosis" or "necroptosis" (Degterev et al., (2005) Nat Chem Biol 1:112-119).

Necroptosis can be triggered by a number of mechanisms including of TNF receptor activation, Toll-like receptor engagement, genotoxic stress and viral infection. Downstream of the various stimuli, the signaling pathway that results in necroptosis is dependent on RIPK1 and RIPK3 kinase activity. (He et al., (2009) Cell 137:1100-1111; Cho et. al., (2009) Cell 137:1112-1123; Zhang et al., (2009) Science 325:332-336).

Dysregulation of the necroptosis signaling pathway has been linked to inflammatory diseases such as macrophage necrosis in atherosclerosis development, virus-induced inflammation, systemic inflammatory response syndrome and ethanol-induced liver injury, neurodegeneration such as detachment of the retina, ischemia, amyotrophic lateral sclerosis (ALS), non-alcoholic steatohepatitis (NASH) and Gaucher's disease (Trichonas et al., (2010) Proc. Natl. Acad. Sci. 107, 21695-21700; Lin et al., (2013) Cell Rep. 3, 200-210; Cho et al., (2009) Cell, 137, 1112-1123; Duprez et al., (2011) Immunity 35, 908-918; Roychowdhury et al., Hepatology 57, 1773-1783; Vandenabeele et al., (2010) Nature 10, 700-714; Vandenabeele et al., (2010) Sci. Signalling 3, 1-8; Zhang et al., (2010) Cellular & Mol. Immunology 7, 243-249; Moriwaki et al., (2013) Genes Dev. 27, 1640-1649; Ito et al., (2016) Science 353, 603-608; Vitner et al., (2014) Nature Med. 20, 204-208); Afonso, et al., (2015) Clinical Science 129, 721-739.

The PCT publications, WO2016/064957 and WO2016/064958 disclose aminopyrrolotriazines which are active as PI3K inhibitors. Inhibitors of PI3K would not be expected to be inhibitors of RIPK1.

A potent, selective, small molecule inhibitor of RIPK1 activity would block RIPK1-dependent pro-inflammatory signaling and thereby provide a therapeutic benefit in inflammatory diseases characterized by increased and/or dysregulated RIPK1 kinase activity.

DESCRIPTION OF THE INVENTION

The present invention provides novel aminopyrrolotriazines including stereoisomers, tautomers, isotopes, prodrugs, pharmaceutically acceptable salts, salts, or solvates thereof, which are useful as inhibitors of RIPK1.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, isotopes, prodrugs, pharmaceutically acceptable salts, salts, or solvates thereof.

The compounds of the invention may be used in the treatment and/or prophylaxis of conditions associated with aberrant RIPK1 activity.

The compounds of the present invention may be used in therapy.

The compounds of the present invention may be used for the manufacture of a medicament for the treatment and/or prophylaxis of a condition associated with aberrant RIPK1 activity.

The compounds of the present invention may be directed to a method of treating diseases mediated at least partially by RIPK1 including inflammatory diseases, ischemia, neurodegeneration, NASH and Gaucher's disease, which method comprises administering to a patient in need of such treatment a compound of the present invention as described above.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF EMBODIMENTS OF THE INVENTION

In one aspect, the present invention provides, inter alia, compounds of Formula (I) or stereoisomers, tautomers, isotopes, salts, pharmaceutically acceptable salts, solvates, or prodrugs thereof, wherein

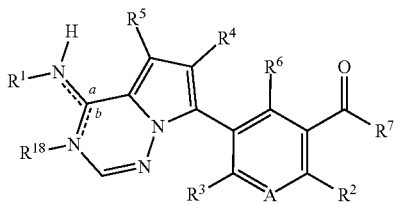

wherein:

A is N or CR;

R is hydrogen, halo, cyano, $C_{1-3}$ alkyl, $C_{1-3}$ deuteroalkyl, $C_{1-3}$ haloalkyl, $C_{1-3}$ alkoxy, $C_{1-3}$ deuteroalkoxy, $C_{1-3}$ haloalkoxy, amino, $C_{1-3}$ alkylamino, or $C_{1-3}$ dialkylamino;

$R^1$ is hydrogen, $C_{1-3}$ alkyl, $C_{1-3}$ haloalkyl, $C_{1-3}$ deuteroalkyl, $C_{1-3}$ alkoxy-$C_{1-3}$ alkyl, or $C_{2-3}$ hydroxyalkyl, C(O)—$C_{1-3}$ alkyl, C(O)—$C_{1-3}$ haloalkyl;

$R^2$ is hydrogen, halo, cyano, $C_{1-3}$ alkyl, $C_{1-3}$ deuteroalkyl, $C_{1-3}$ haloalkyl, $C_{1-3}$ alkoxy, $C_{1-3}$ deuteroalkoxy, $C_{1-3}$ haloalkoxy, amino, $C_{1-3}$ alkylamino, or $C_{1-3}$ dialkylamino;

$R^3$ is hydrogen, halo, cyano, $C_{1-3}$ alkyl, $C_{1-3}$ deuteroalkyl, $C_{1-3}$ haloalkyl, $C_{1-3}$ alkoxy, $C_{1-3}$ deuteroalkoxy, $C_{1-3}$ haloalkoxy, amino, $C_{1-3}$ alkylamino, or $C_{1-3}$ dialkylamino;

$R^4$ is hydrogen, halo, cyano, $C_{1-3}$ alkyl, $C_{1-3}$ deuteroalkyl, $C_{1-3}$ deuteroalkoxy, $C_{1-3}$ haloalkoxy, $C_{1-3}$ alkoxy, amino, $C_{1-3}$ alkylamino, or $C_{1-3}$ dialkylamino, tetrazolyl, $C_{1-3}$ alkyl-tetrazolyl;

$R^5$ is 1) hydrogen, halo, cyano, $C_{1-3}$ alkyl, $C_{1-3}$ deuteroalkyl, $C_{1-3}$ haloalkyl, $C_{1-3}$ haloalkoxy, $C_{1-3}$ hydroxyalkyl, $C_{1-3}$ alkoxyalkyl, aminoalkyl, $C_{1-3}$ alkylaminoalkyl, $C_{1-3}$ dialkylaminoalkyl, amino, $C_{1-3}$ alkylamino, $C_{1-3}$ dialkylamino, ($C_{1-3}$ alkylCONH)—$C_{1-3}$alkyl, ($C_{1-3}$ alkoxyCONH)—$C_{1-3}$alkyl, or ($C_{1-3}$ alkylSO$_2$NH)—$C_{1-3}$alkyl, —(CH$_2$)$_n$—NH—OCH$_3$, $C_{3-6}$ cycloalkyl, methyl-phenyl-SO$_2$—O—; or 2) 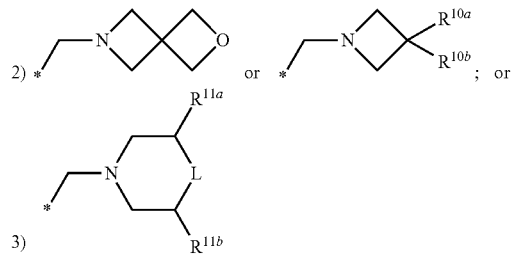

3)

where L is methylene, —C($R^{5a}$)$_2$—, amino, $C_{1-3}$ alkylamino, SO$_2$, or O; or 4) 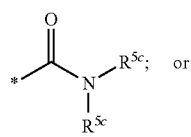

5) 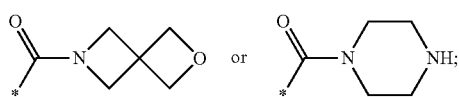

or

6) —(CH$_2$)$_r$— phenyl, —(CH$_2$)$_r$— 4 to 10 membered heterocycle or 4 to 10 membered heteroaryl, wherein the heterocycle and heteroaryl contain 1, 2, 3, or 4 heteroatoms selected from N, O, and S, and wherein any of the phenyl, heterocycle, or heteroaryl may be substituted with 0-3 of halo, $C_{1-3}$ alkyl, or amino; or $R^{5a}$ is independently, hydrogen, halo, $C_{1-3}$ haloalkyl;

$R^{5c}$ is independently selected from hydrogen, $C_{1-3}$ alkyl, $C_{1-3}$ deuteroalkyl, $C_{1-3}$ cyanoalkyl-, $C_{1-3}$ hydroxyalkyl, $C_{1-3}$ (imidazolyl)alkyl, and $C_{1-3}$ ($C_{1-3}$ alkylCO)alkyl;

$R^6$ is hydrogen, halo, cyano, $C_{1-3}$ alkyl, $C_{1-3}$ deuteroalkyl, $C_{1-3}$ haloalkyl, $C_{1-3}$ alkoxy, $C_{1-3}$ deuteroalkoxy, $C_{1-3}$ haloalkoxy, amino, $C_{1-3}$ alkylamino, or $C_{1-3}$ dialkylamino;

$R^7$ is

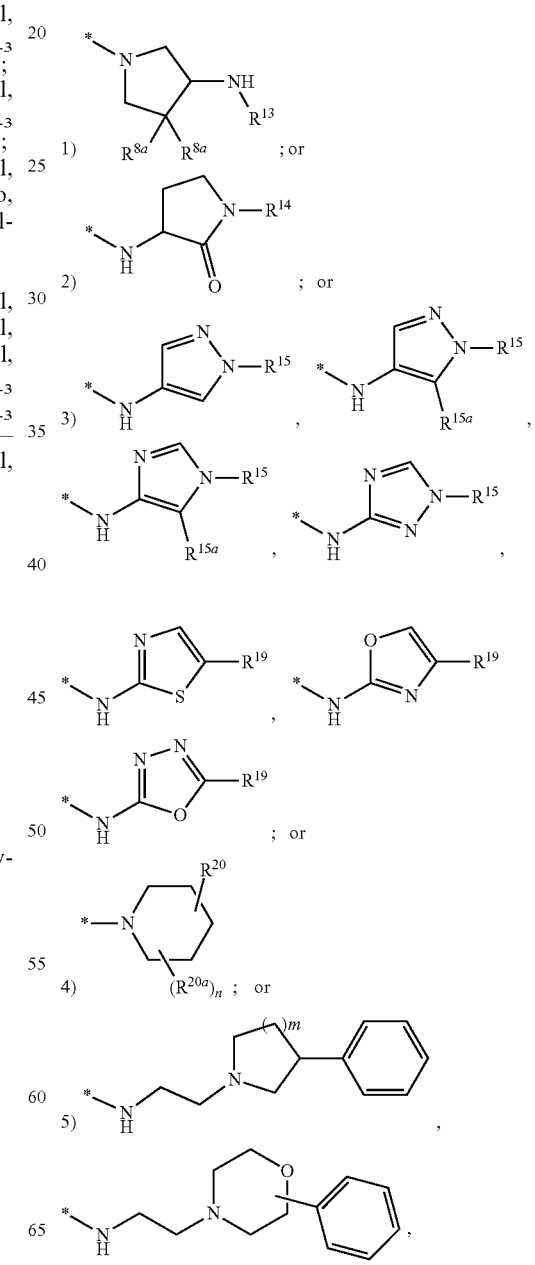

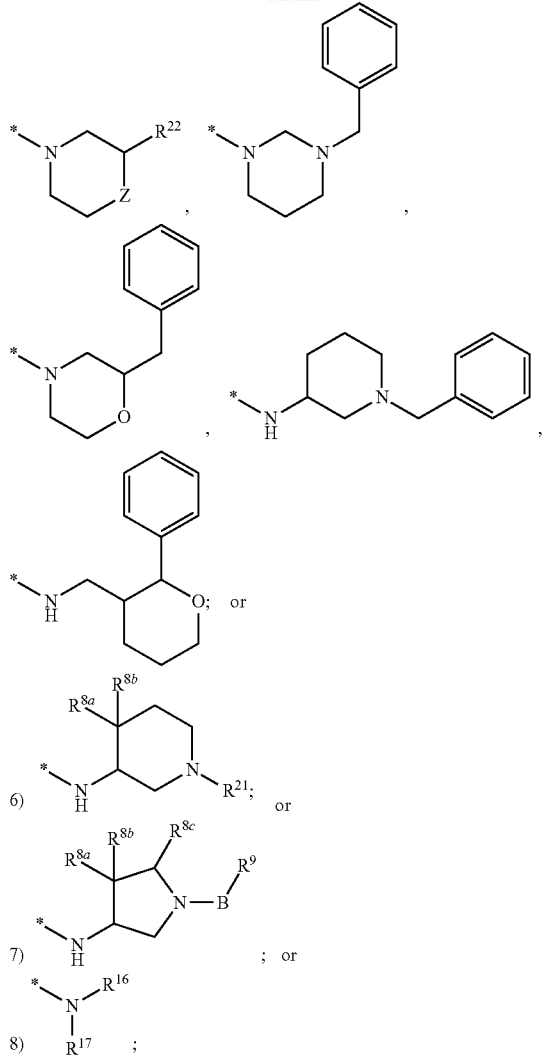

B is absent, CO, C(O)O, C(O)NR$^{12a}$, SO$_2$, or CR$^{12a}$R$^{12b}$;
Z is O, NH, CH$_2$, or CF$_2$;
R$^{8a}$ and R$^{8b}$ are each independently selected from hydrogen, halo, C$_{1-3}$ alkyl, and C$_{1-3}$ haloalkyl;
R$^{8c}$ is hydrogen, or CH$_2$—O—CH$_3$, or CH$_2$—O—CH$_2$-phenyl:
R$^9$ is
1) phenyl, naphthalenyl, pyridyl, pyrimidyl, pyridazinyl, pyrazinyl quinolinyl, benzisoxazolyl, or benzthiazolyl, and each of which are optionally substituted with 1-3 groups selected from halo, cyano, C$_{1-3}$ alkyl, C$_{1-3}$ deuteroalkyl, C$_{1-3}$ haloalkyl, C$_{1-3}$ phenylalkyl, C$_{1-3}$ (phenyl)hydroxyalkyl, C$_{1-3}$ alkoxy, C$_{1-3}$ deuteroalkoxy, C$_{1-3}$ haloalkoxy, and C$_{1-3}$ alkylSO$_2$; or
2) thiazolyl, oxazolyl, isoxazolyl, isothiazolyl, imidazolyl, thiadiazolyl, oxadiazolyl, triazolyl, or tetrazolyl, and each of which are optionally substituted with 1-3 groups selected from halo, cyano, C$_{1-3}$ alkyl, C$_{1-3}$ deuteroalkyl, C$_{1-3}$ haloalkyl, C$_{1-3}$ phenylalkyl, C$_{1-3}$ (phenyl)hydroxyalkyl, C$_{1-3}$ alkoxy, C$_{1-3}$ deuteroalkoxy, C$_{1-3}$ haloalkoxy, and C$_{1-3}$ alkylSO$_2^-$ cyclopropyl; or
3) dihydro-1H-indenyl, tetrandro-5H-benzo[7]annulene, tetrahydronaphthalene, and 6,7-dihydro-5H-cyclopenta[b]pyridine, any of which are substituted with 1-3 groups selected from halo, cyano, C$_{1-3}$ alkyl, C$_{1-3}$ deuteroalkyl, C$_{1-3}$ haloalkyl, C$_{1-3}$ phenylalkyl, C$_{1-3}$ (phenyl)hydroxyalkyl, C$_{1-3}$ alkoxy, C$_{1-3}$ deuteroalkoxy, C$_{1-3}$ haloalkoxy, and C$_{1-3}$ alkylSO$_2$; or
4) C$_{1-6}$alkyl, C$_{1-6}$alkenyl, C$_{1-6}$alkynyl, C$_{1-6}$ deuteroalkyl, C$_{1-6}$haloalkyl, C$_{1-6}$ alkoxyalkyl, C$_{3-6}$ cycloalkyl, or C$_{1-6}$ halocycloalkyl, each of which are optionally substituted with 1-3 groups selected from halo, NH$_2$, —NC(O)O—C$_{1-6}$alkyl, —C(O)—C$_{1-6}$alkyl, hydroxyl, C$_{1-6}$ alkoxy, and C$_{1-6}$haloalkyl, C$_{1-6}$ haloalkoxy, phenyl, thiazolyl, pyrdinyl, wherein the phenyl, pyridinyl, and thiazolyl are optionally substituted with 0-2 of halo, nitro, or C$_{1-6}$haloalkyl; or
5) C$_{0-2}$ (C$_{3-7}$ cycloalkyl)alkyl, cyclohexenyl, oxetanyl, tetrahydrofuranyl, pyrrolidinyl, piperidinyl, dioxanyl, pyridinonyl, or tetrahydrothiophenyl dioxide, each of which are optionally substituted with 1-4 groups selected from halo, hydroxy, C$_{1-3}$ alkyl, and C$_{1-3}$ haloalkyl, C$_{1-3}$ alkoxy, hydroxyl C$_{1-3}$ haloalkyl, C$_{3-6}$ cycloalkyl, C(O)O—C$_{1-6}$ alkyl, and amino;
6) tetrahydropyranyl optionally substituted with 1-4 groups selected from halo, hydroxy, C$_{1-3}$ alkyl, C$_{1-3}$haloalkyl; C$_{1-2}$ (C$_{1-3}$alkoxy)alkyl, C$_{1-4}$ alkoxy, and phenyl;
7) C$_{1-4}$ alkylamino, C$_{1-4}$ dialkylamino, azetidinyl, pyrrolidinyl, or piperidinyl; or B and R$^9$, together with the atom to which they are attached, join to form a C$_{3-6}$ cycloalkyl optionally substituted with 1-2 groups selected from halo, hydroxy, C$_{1-4}$ alkyl, C$_{1-4}$ alkoxy, C$_{2-3}$ hydroxyalkyl, C$_{2-4}$ (hydroxyl)haloalkyl, C$_{3-6}$ hydroxycycloalkyl, and C$_{1-3}$ alkoxycarbonyl;
R$^{10a}$ and R$^{10b}$ are independently selected from hydrogen, halo, cyano, hydroxy, amino, C$_{1-3}$alkylamino, C$_{1-3}$ dialkylamino, acetylamino, (amino)carbonyl, (C$_{1-3}$ alkylamino)carbonyl, and (C$_{1-3}$ dialkylamino)carbonyl;
R$^{11a}$ and R$^{11b}$ are independently selected from hydrogen and C$_{1-6}$ alkyl;
R$^{12a}$ and R$^{12b}$ are independently selected from hydrogen, deuterium, methyl, amino, or OH, or R$^{12a}$ and R$^{12b}$, along with the atom to which they are attached, join together to form C$_{3-6}$ cycloalkyl;
R$^{13}$ is C$_{1-3}$ (phenyl)alkyl- or phenylcarbonyl-, and where the phenyl is optionally substituted with 1-3 groups selected from halo, cyano, C$_{1-3}$ alkyl, C$_{1-3}$ deuteroalkyl, C$_{1-3}$ haloalkyl, C$_{1-3}$ alkoxy, C$_{1-3}$ deuteroalkoxy, and C$_{1-3}$ haloalkoxy;
R$^{14}$ is phenyl, C$_{1-3}$ (phenyl)alkyl-, or phenylcarbonyl, and where the phenyl is optionally substituted with 1-3 groups selected from halo, cyano, C$_{1-3}$ alkyl, C$_{1-3}$ deuteroalkyl, C$_{1-3}$ haloalkyl, C$_{1-3}$ alkoxy, C$_{1-3}$ deuteroalkoxy, and C$_{1-3}$ haloalkoxy;
R$^{15}$ is C$_{1-6}$ alkyl, C$_{1-3}$ haloalkyl, hydroxy-C$_{1-6}$ haloalkyl, C$_{1-3}$ (C$_{3-6}$ cycloalkyl)alkyl, phenyl-C$_{1-3}$ alkyl, phenyl-C$_{1-3}$ haloalkyl-, or phenylcarbonyl, where the phenyl is optionally substituted with 1-3 groups selected from halo, cyano, C$_{1-3}$ alkyl, C$_{1-3}$ deuteroalkyl, C$_{1-3}$ haloalkyl, C$_{1-3}$ alkoxy, C$_{1-3}$ deuteroalkoxy, and C$_{1-3}$ haloalkoxy;
R$^{15a}$ is hydrogen, halo, or C$_{1-3}$ alkyl;
R$^{16}$ is hydrogen, alkyl, or deuteroalkyl;
R$^{17}$ is
1) C$_{1-6}$ (phenyl)alkyl, where the alkyl is optionally substituted with 1-3 groups selected from hydroxy, =O, alkoxy, and haloalkyl, or haloalkoxy, and where the phenyl is optionally substituted with 1-3 groups selected from halo, cyano, hydroxy, NH$_2$, C$_{1-3}$ alkyl, C$_{1-3}$ deuteroalkyl, C$_{1-3}$ haloalkyl, C$_{1-3}$ haloalkoxy, C$_{1-3}$ hydroxyalkyl, $C_{1-3}$ alkoxyalkyl, $C_{3-6}$cycloalkyl, $C_{1-3}$ alkoxy, $C_{1-3}$ ($C_{1-3}$ alkoxy)deuteroalkoxy, $C_{1-3}$ haloalkoxy, and phenoxy;
2) $C_{0-6}$ (cyclopropyl)alkyl, where the alkyl is optionally substituted with 1-3 groups selected from hydroxy, alkoxy, and haloalkyl, and where the phenyl is optionally substituted with 1-3 groups selected from halo, cyano, hydroxy, $C_{1-3}$ alkyl, $C_{1-3}$ deuteroalkyl, $C_{1-3}$ haloalkyl, $C_{1-3}$ hydroxyalkyl, $C_{1-3}$ alkoxyalkyl, $C_{3-6}$ cycloalkyl, $C_{1-3}$ alkoxy, $C_{1-3}$ ($C_{1-3}$ alkoxy)deuteroalkoxy, $C_{1-3}$ haloalkoxy, =N—O—CH$_2$-cyclopropyl, (—OCH$_2$C(CH$_3$)$_2$CH$_2$O—), phenoxy, and phenyl which is substituted with 0-3 of F, C$_1$, or Br;
3) $C_{1-3}$ (phenoxy)alkyl, $C_{1-3}$ (phenylamino)alkyl or $C_{1-3}$ ((phenyl)(alkyl)amino)alkyl where the phenoxy or phenyl is optionally substituted with 1-3 groups selected from halo, cyano, $C_{1-3}$ alkyl, $C_{1-3}$ deuteroalkyl, $C_{1-3}$ haloalkyl, $C_{1-3}$ hydroxyalkyl, $C_{1-3}$ alkoxyalkyl, $C_{1-3}$ alkoxy, $C_{1-3}$ deuteroalkoxy, and $C_{1-3}$ haloalkoxy;
4) $C_{1-2}$ (phenylcyclopropyl)alkyl where the phenyl is optionally substituted with 1-3 groups selected from halo, cyano, $C_{1-3}$ alkyl, $C_{1-3}$ deuteroalkyl, $C_{1-3}$ haloalkyl, $C_{1-3}$ alkoxy, $C_{1-3}$ deuteroalkoxy, and $C_{1-3}$ haloalkoxy;
5) $C_{1-3}$ (pyridyl)alkyl, $C_{1-3}$ (pyrimidyl) alkyl, or $C_{1-3}$ (pyrazinyl)alkyl where the pyridyl, pyrimidyl, and pyridazyl are optionally substituted with 1-2 groups selected from halo, cyano, $C_{1-3}$ alkyl, $C_{1-3}$ deuteroalkyl, $C_{1-3}$ haloalkyl, $C_{1-3}$ hydroxyalkyl, $C_{1-3}$ alkoxy, $C_{3-6}$ cycloalkyl $C_{1-3}$ alkoxy-, $C_{1-3}$ deuteroalkoxy, and $C_{1-3}$ haloalkoxy;
6) $C_{3-7}$ cycloalkyl, wherein the cycloalkly is substituted with 0-3 of halo, OH, =N—O—CH$_2$-cyclopropyl, (—OCH$_2$C(CH$_3$)$_2$CH$_2$O—), phenyl which is substituted with 0-3 of F, C$_1$, Br;
7) $C_{1-3}$ ($C_{1-4}$ alkoxy)alkyl;
$R^{19}$ is —CH$_2$-phenyl, or —C(O)—NR$^{19a}$R$^{19b}$;
$R^{19a}$ is hydrogen or $C_{1-3}$ alkyl;
$R^{19b}$ is hydrogen, $C_{1-6}$ alkyl, $C_{3-6}$ cycloalkyl-$C_{0-3}$ alkyl-, phenyl-$C_{0-3}$ alkyl-, phenyl, wherein each are independently substituted with 0-3 of halo, $C_{1-3}$ alkyl, $C_{1-3}$ haloalkyl, $C_{1-3}$ alkoxy, $C_{1-3}$ haloalkoxy, or phenyl-$C_{1-3}$ haloalkyl-;
$R^{20}$ is H, —CH$_2$-phenyl, —CH(OH)-phenyl, —C(CH$_3$)(OH)-phenyl, phenyl, wherein each of the phenyls are independently substituted with 0-1 F;
$R^{20a}$ is independently methyl, or OH;
$R^{21}$ is phenyl, CO-phenyl, CO—$C_{3-6}$ cycloalkyl, any of which are substituted with 0-4 of F, CO—$C_{1-6}$ alkyl, OH, and with 0-6 F;
$R^{22}$ is $C_{0-1}$ (phenoxy)alkyl, $C_{0-1}$ (phenylthio)alkyl, or $C_{0-1}$ phenylalkyl, and where the phenyl is optionally substituted with 1-3 groups selected from halo, cyano, $C_{1-3}$ alkyl, $C_{1-3}$ deuteroalkyl, $C_{1-3}$ haloalkyl, $C_{1-3}$ alkoxy, $C_{1-3}$ deuteroalkoxy, and $C_{1-3}$ haloalkoxy;
and either $R^1$ or $R^{18}$ are $C_{1-3}$ hydroxyalkyl, $C_{1-3}$ ($C_{1-3}$ alkoxy)alkyl,

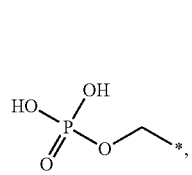
, 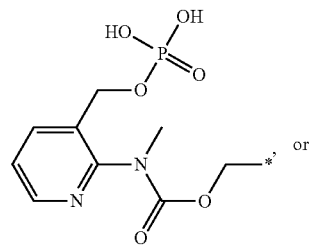 or

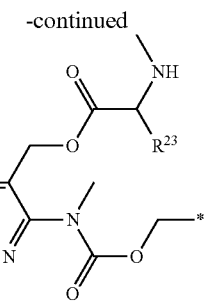

or where $R^{23}$ is $C_{1-3}$ alkyl, $C_{1-3}$ hydroxyalkyl, or ($C_{1-3}$ alkoxy)alkyl;
a is single or double bond; and
b is single or double bond;
provided that when a is a single bond, b is a double bond and $R^{18}$ is absent and when a is a double bond, b is a single bond and $R^1$ is absent;
n is 0, 1, or 2;
m is 1 or 2; and
r is 1 or 2.

In a second aspect of the invention is a compound of formula I, or a pharmaceutically acceptable salt thereof,

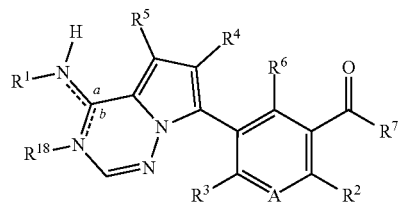

wherein:
A is N, or CR;
R is hydrogen, halo, $C_{1-3}$ alkyl, or $C_{1-3}$ alkoxy;
$R^1$ is hydrogen, $C_{1-3}$ alkyl, $C_{1-3}$ haloalkyl, $C_{1-3}$ deuteroalkyl, $C_{1-3}$ alkoxy-$C_{1-3}$ alkyl, or $C_{2-3}$ hydroxyalkyl;
$R^2$ is hydrogen, halo, cyano, $C_{1-3}$ alkyl, $C_{1-3}$ deuteroalkyl, $C_{1-3}$ haloalkyl, $C_{1-3}$ alkoxy, $C_{1-3}$ deuteroalkoxy, $C_{1-3}$ haloalkoxy, amino, $C_{1-3}$ alkylamino, or $C_{1-3}$ dialkylamino;
$R^3$ is hydrogen, halo, cyano, $C_{1-3}$ alkyl, $C_{1-3}$ deuteroalkyl, $C_{1-3}$ haloalkyl, $C_{1-3}$ alkoxy, $C_{1-3}$ deuteroalkoxy, $C_{1-3}$ haloalkoxy, amino, $C_{1-3}$ alkylamino, or $C_{1-3}$ dialkylamino;
$R^4$ is hydrogen, halo, cyano, $C_{1-3}$ alkyl, $C_{1-3}$ deuteroalkyl, $C_{1-3}$ haloalkoxy, $C_{1-3}$ alkoxy, amino, $C_{1-3}$ alkylamino, or $C_{1-3}$ dialkylamino;
$R^5$ is hydrogen, halo, cyano, $C_{1-3}$ alkyl, $C_{1-3}$ deuteroalkyl, $C_{1-3}$haloalkyl, $C_{1-3}$ hydroxyalkyl, $C_{1-3}$ alkoxyalkyl, aminoalkyl, $C_{1-3}$ alkylaminoalkyl, $C_{1-3}$ dialkylaminoalkyl, amino, $C_1$-3 alkylamino, $C_1$-3 dialkylamino, ($C_{1-3}$ alkylCONH)alkyl, ($C_{1-3}$ alkoxyCONH)alkyl, or ($C_{1-3}$ alkylSO$_2$NH)alkyl;
or $R^5$ is

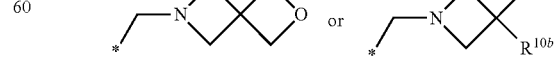

where $R^{10a}$ and $R^{10b}$ are independently selected from hydrogen, halo, cyano, hydroxy, amino, $C_{1-3}$ alkylamino, $C_{1-3}$ dialkylamino, acetylamino, (amino)carbonyl, ($C_{1-3}$ alkylamino)carbonyl, and ($C_{1-3}$ dialkylamino)carbonyl;

or R⁵ is

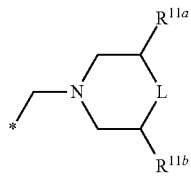

where L is methylene, amino, C₁₋₃ alkylamino, SO₂, or O, and R¹¹ᵃ and R¹¹ᵇ are independently selected from hydrogen and alkyl;

or R⁵ is

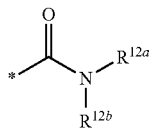

where R¹²ᵃ and R¹²ᵇ are independently selected from hydrogen, C₁₋₃ alkyl, C₁₋₃ deuteroalkyl, C₁₋₃ cyanoalkyl-, C₁₋₃ hydroxyalkyl, C₁₋₃ (imidazolyl)alkyl, and C₁₋₃ (C₁₋₃ alkyl-CO)alkyl;

or R⁵ is

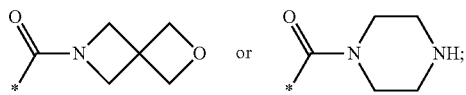 [SMILES: *C(=O)N1CC2(COC2)C1 ; *C(=O)N1CCNCC1]

R⁶ is hydrogen or halo;
R⁷ is

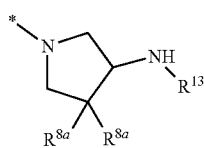

where R¹³ is phenylalkyl or phenylcarbonyl, and where the phenyl is optionally substituted with 1-3 groups selected from halo, cyano, C₁₋₃ alkyl, C₁₋₃ deuteroalkyl, C₁₋₃ haloalkyl, C₁₋₃ alkoxy, C₁₋₃ deuteroalkoxy, and C₁₋₃ haloalkoxy;

or R⁷ is

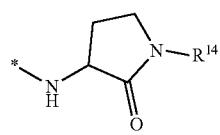

where R¹⁴ is phenyl, phenylalkyl, or phenylcarbonyl, and where the phenyl is optionally substituted with 1-3 groups selected from halo, cyano, C₁₋₃ alkyl, C₁₋₃ deuteroalkyl, C₁₋₃ haloalkyl, C₁₋₃ alkoxy, C₁₋₃ deuteroalkoxy, and C₁₋₃ haloalkoxy;

or R⁷ is

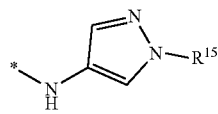

where R¹⁵ is C₁₋₆ alkyl, C₁₋₃ haloalkyl, C₁₋₃ (C₃₋₆ cycloalkyl) alkyl, phenylalkyl, or phenylcarbonyl, where the phenyl is optionally substituted with 1-3 groups selected from halo, cyano, C₁₋₃ alkyl, C₁₋₃ deuteroalkyl, C₁₋₃ haloalkyl, C₁₋₃ alkoxy, C₁₋₃ deuteroalkoxy, and C₁₋₃ haloalkoxy;

or R⁷ is

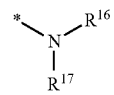

where R¹⁶ is hydrogen, alkyl, or deuteroalkyl;

R¹⁷ is C₁₋₆ phenylalkyl, where the alkyl is optionally substituted with 1-3 groups selected from hydroxy, alkoxy, and haloalkyl, and where the phenyl is optionally substituted with 1-3 groups selected from halo, cyano, hydroxy, C₁₋₃ alkyl, C₁₋₃ deuteroalkyl, C₁₋₃ haloalkyl, C₁₋₃ hydroxyalkyl, C₁₋₃ alkoxyalkyl, C₃₋₆ cycloalkyl, C₁₋₃ alkoxy, C₁₋₃ (C₁₋₃ alkoxy)deuteroalkoxy, C₁₋₃ haloalkoxy, and phenoxy;

or R¹⁷ is C₁₋₃ phenoxyalkyl, C₁₋₃ (phenylamino)alkyl or C₁₋₃ ((phenyl)(alkyl)amino)alkyl where the phenoxy or phenyl is optionally substituted with 1-3 groups selected from halo, cyano, C₁₋₃alkyl, C₁₋₃ deuteroalkyl, C₁₋₃haloalkyl, C₁₋₃ hydroxyalkyl, C₁₋₃alkoxyalkyl, C₁₋₃ alkoxy, C₁₋₃ deuteroalkoxy, and C₁₋₃ haloalkoxy;

or R¹⁷ is C₁₋₂ (phenylcyclopropyl)alkyl where the phenyl is optionally substituted with 1-3 groups selected from halo, cyano, C₁₋₃ alkyl, C₁₋₃ deuteroalkyl, C₁₋₃ haloalkyl, C₁₋₃ alkoxy, C₁₋₃ deuteroalkoxy, and C₁₋₃ haloalkoxy;

or R¹⁷ is C₁₋₃ (pyridyl)alkyl, C₁₋₃ (pyrimidyl) alkyl, or C₁₋₃ (pyrazinyl)alkyl where the pyridyl, pyrimidyl, or pyridazyl is optionally substituted with 1-2 groups selected from halo, cyano, C₁₋₃ alkyl, C₁₋₃ deuteroalkyl, C₁₋₃ haloalkyl, C₁₋₃ hydroxyalkyl, C₁₋₃ alkoxy, C₃₋₆ cycloalkyl C₁₋₃ alkoxy-, C₁₋₃ deuteroalkoxy, or C₁₋₃ haloalkoxy;

or R¹⁷ is C₁₋₃ (C₁₋₄ alkoxy)alkyl;
or R¹⁷ is

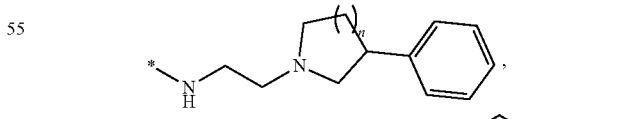

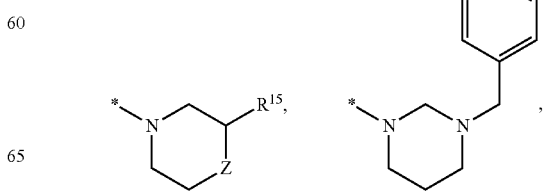

-continued

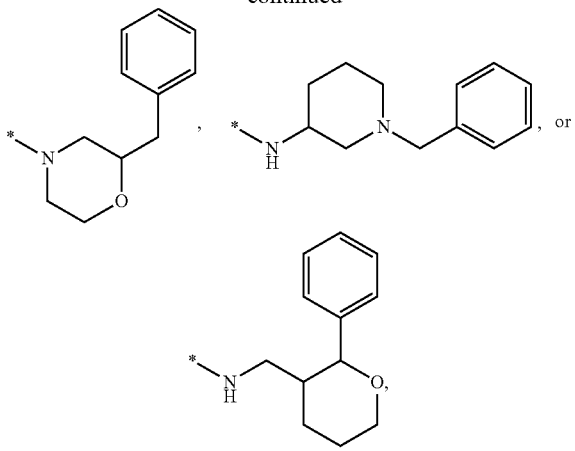

where n is 1-2, Z is O, NH, CH$_2$, or CF$_2$, and R$^{15}$ is C$_{0-1}$ (phenoxy)alkyl, C$_{0-1}$ (phenylthio)alkyl, or C$_{0-1}$ phenylalkyl, and where the phenyl is optionally substituted with 1-3 groups selected from halo, cyano, C$_{1-3}$ alkyl, C$_{1-3}$ deuteroalkyl, C$_{1-3}$ haloalkyl, C$_{1-3}$ alkoxy, C$_{1-3}$ deuteroalkoxy, and C$_{1-3}$ haloalkoxy;
or R$^7$ is

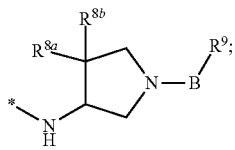

R$^{8a}$ and R$^{8b}$ are each independently selected from hydrogen, halo, C$_{1-3}$ alkyl, and C$_{1-3}$ haloalkyl;
B is CO, C(O)O, C(O)NR$^{12}$a, SO$_2$, or CR$^{12a}$R$^{12b}$;
R$^{12a}$ and R$^{12b}$ are independently selected from hydrogen, deuterium, or methyl, or R$^{12a}$ and R$^{12b}$ taken together is C$_{3-6}$ cycloalkyl;
R$^9$ is phenyl, pyridyl, pyrimidyl, pyridazinyl, quinolinyl, benzisoxazolyl, or benzthiazolyl, and is optionally substituted with 1-3 groups selected from halo, cyano, C$_{1-3}$ alkyl, C$_{1-3}$ deuteroalkyl, C$_{1-3}$ haloalkyl, C$_{1-3}$ phenylalkyl, C$_{1-3}$ (phenyl)hydroxyalkyl, C$_{1-3}$ alkoxy, C$_{1-3}$ deuteroalkoxy, C$_{1-3}$ haloalkoxy, and C$_{1-3}$ alkylSO$_2$;
or R$^9$ is thiazolyl, oxazolyl, isoxazolyl, isothiazolyl, imidazolyl, thiadiazolyl, oxadiazolyl, or tetrazolyl, and is optionally substituted with 1-3 groups selected from halo, cyano, C$_{1-3}$ alkyl, C$_{1-3}$ deuteroalkyl, C$_{1-3}$ haloalkyl, C$_{1-3}$ phenylalkyl, C$_{1-3}$ (phenyl)hydroxyalkyl, C$_{1-3}$ alkoxy, C$_{1-3}$ deuteroalkoxy, C$_{1-3}$ haloalkoxy, and C$_{1-3}$ alkylSO$_2$;
or R$^9$ is C$_{1-6}$alkyl, C$_{1-6}$ deuteroalkyl, C$_{1-6}$haloalkyl, C$_1$balkoxyalkyl, C$_{3-6}$cycloalkyl, or C$_{1-6}$halocycloalkyl and is optionally substituted with 1-3 groups selected from halo, hydroxyl, and haloalkyl;
or R$^9$ is C$_{1-2}$ (C$_{3-6}$ cycloalkyl)alkyl, oxetanyl, tetrahydrofuranyl, and is optionally substituted with 1-4 groups selected from halo, hydroxy, C$_{1-3}$ alkyl, and C$_{1-3}$haloalkyl;
or R$^9$ is tetrahydropyranyl optionally substituted with 1-4 groups selected from halo, hydroxy, C$_{1-3}$ alkyl, C$_{1-3}$ haloalkyl; C$_{1-2}$ (C$_{1-3}$ alkoxy)alkyl, C$_{1-4}$ alkoxy, and phenyl;
or R$^9$ is amino, C$_{1-4}$ alkylamino, C$_{1-4}$ dialkylamino, azetidinyl, pyrrolidinyl, or piperidinyl;
or B and R$^9$ taken together is C$_{3-6}$ cycloalkyl optionally substituted with 1-2 groups selected from halo, hydroxy,
C$_{1-4}$ alkyl, C$_{1-4}$ alkoxy, C$_{2-3}$ hydroxyalkyl, C$_{2-4}$ (hydroxyl) haloalkyl, C$_{3-6}$ hydroxycycloalkyl, and C$_{1-3}$ alkoxycarbonyl;
R$^{18}$ is C$_{1-3}$ hydroxyalkyl, C$_{1-3}$ (C$_{1-3}$ alkoxy)alkyl,

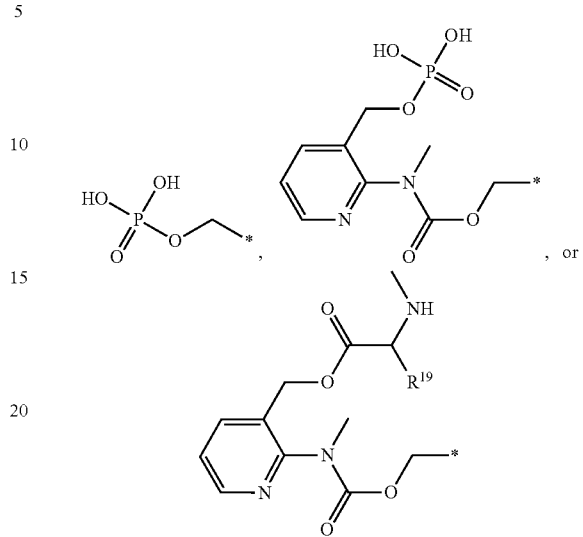

where R$^{19}$ is C$_{1-3}$ alkyl, C$_{1-3}$ hydroxyalkyl, or (C$_{1-3}$ alkoxy) alkyl;
a is single or double bond; and
b is single or double bond;
provided that when a is a single bond, b is a double bond and R$^{18}$ is absent and when a is a double bond, b is a single bond and R$^1$ is absent.

In a third aspect of the invention is a compound of Formula (I), or stereoisomers, tautomers, isotopes, salts, pharmaceutically acceptable salts, solvates, or prodrugs thereof, wherein

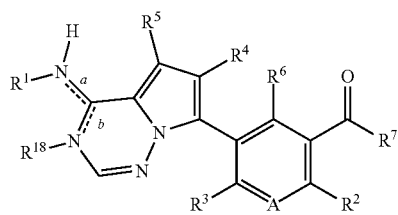

I wherein:
A is N or CR;
R is hydrogen, halo, cyano, C$_{1-3}$ alkyl, C$_{1-3}$ deuteroalkyl, C$_{1-3}$ haloalkyl, C$_{1-3}$ alkoxy, C$_{1-3}$ deuteroalkoxy, C$_{1-3}$ haloalkoxy, amino, C$_{1-3}$ alkylamino, or C$_{1-3}$ dialkylamino;
R$^1$ is hydrogen, C$_{1-3}$ alkyl, C$_{1-3}$ haloalkyl, C$_{1-3}$ deuteroalkyl, C$_{1-3}$ alkoxy-C$_{1-3}$ alkyl, or C$_{2-3}$ hydroxyalkyl, C(O)—C$_{1-3}$ alkyl, C(O)—C$_{1-3}$ haloalkyl;
R$^2$ is hydrogen, halo, cyano, C$_{1-3}$ alkyl, C$_{1-3}$ deuteroalkyl, C$_{1-3}$ haloalkyl, C$_{1-3}$ alkoxy, C$_{1-3}$ deuteroalkoxy, C$_{1-3}$ haloalkoxy, amino, C$_{1-3}$ alkylamino, or C$_{1-3}$ dialkylamino;
R$^3$ is hydrogen, halo, cyano, C$_{1-3}$ alkyl, C$_{1-3}$ deuteroalkyl, C$_{1-3}$ haloalkyl, C$_{1-3}$ alkoxy, C$_{1-3}$ deuteroalkoxy, C$_{1-3}$ haloalkoxy, amino, C$_{1-3}$ alkylamino, or C$_{1-3}$ dialkylamino;
R$^4$ is hydrogen, halo, cyano, C$_{1-3}$ alkyl, C$_{1-3}$ deuteroalkyl, C$_{1-3}$ deuteroalkoxy, C$_{1-3}$ haloalkoxy, C$_{1-3}$ alkoxy, amino, C$_{1-3}$ alkylamino, or C$_{1-3}$ dialkylamino, tetrazolyl, C$_{1-3}$ alkyltetrazolyl;

R$^5$ is 1) hydrogen, halo, cyano, C$_{1-3}$ alkyl, C$_{1-3}$ deuteroalkyl, C$_{1-3}$ haloalkyl, C$_{1-3}$ haloalkoxy, C$_{1-3}$ hydroxyalkyl, C$_{1-3}$alkoxyalkyl, aminoalkyl, C$_{1-3}$ alkylaminoalkyl, C$_{1-3}$ dialkylaminoalkyl, amino, C$_{1-3}$ alkylamino, C$_{1-3}$ dialkylamino, (C$_{1-3}$ alkylCONH)—C$_{1-3}$alkyl, (C$_{1-3}$ alkoxyCONH)—C$_{1-3}$alkyl, or (C$_{1-3}$ alkylSO$_2$NH)—C$_{1-3}$alkyl, —(CH$_2$)$_n$—NH—OCH$_3$, C$_{3-6}$ cycloalkyl, methyl-phenyl-SO$_2$—O—; or

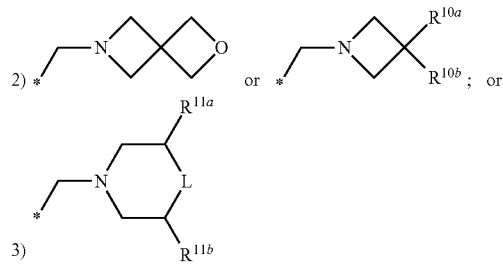

where L is methylene, —C(R$^{5a}$)$_2$—, amino, C$_{1-3}$ alkylamino, SO$_2$, or O; or

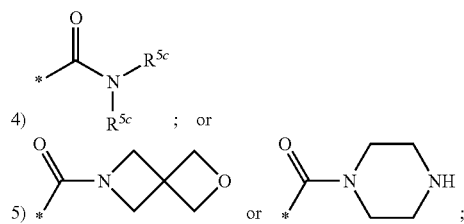

6) —(CH$_2$)$_r$— phenyl, —(CH$_2$)$_r$— 4 to 10 membered heterocycle or 4 to 10 membered heteroaryl, wherein the heterocycle and heteroaryl contain 1, 2, 3, or 4 heteroatoms selected from N, O, and S, and wherein any of the phenyl, heterocycle, or heteroaryl may be substituted with 0-3 of halo, C$_{1-3}$ alkyl, or amino; or R$^{5a}$ is independently, hydrogen, halo, C$_{1-3}$ haloalkyl;

R$^{5c}$ is independently selected from hydrogen, C$_{1-3}$ alkyl, C$_{1-3}$ deuteroalkyl, C$_{1-3}$ cyanoalkyl-, C$_{1-3}$ hydroxyalkyl, C$_{1-3}$ (imidazolyl)alkyl, and C$_{1-3}$ (C$_{1-3}$ alkylCO)alkyl;

R$^6$ is hydrogen, halo, cyano, C$_{1-3}$ alkyl, C$_{1-3}$ deuteroalkyl, C$_{1-3}$ haloalkyl, C$_{1-3}$ alkoxy, C$_{1-3}$ deuteroalkoxy, C$_{1-3}$ haloalkoxy, amino, C$_{1-3}$ alkylamino, or C$_{1-3}$ dialkylamino;

R$^7$ is

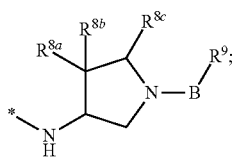

or

B is absent, CO, C(O)O, C(O)NR$^{12a}$, SO$_2$, or CR$^{12a}$R$^{12b}$;
R$^{8a}$ and R$^{8b}$ are each independently selected from hydrogen, halo, C$_1$-3 alkyl, and C$_1$-3 haloalkyl;

R$^{8c}$ is hydrogen, or CH$_2$—O—CH$_3$, or CH$_2$—O—CH$_2$-phenyl:

R$^9$ is 1) phenyl, naphthalenyl, pyridyl, pyrimidyl, pyridazinyl, pyrazinyl quinolinyl, benzisoxazolyl, or benzthiazolyl, and each of which are optionally substituted with 1-3 groups selected from halo, cyano, C$_{1-3}$ alkyl, C$_{1-3}$ deuteroalkyl, C$_{1-3}$ haloalkyl, C$_{1-3}$ phenylalkyl, C$_{1-3}$ (phenyl)hydroxyalkyl, C$_{1-3}$ alkoxy, C$_1$-3 deuteroalkoxy, C$_{1-3}$ haloalkoxy, and C$_{1-3}$ alkylSO$_2$; or 2) thiazolyl, oxazolyl, isoxazolyl, isothiazolyl, imidazolyl, thiadiazolyl, oxadiazolyl, triazolyl, or tetrazolyl, and each of which are optionally substituted with 1-3 groups selected from halo, cyano, C$_{1-3}$ alkyl, C$_{1-3}$ deuteroalkyl, C$_{1-3}$ haloalkyl, C$_{1-3}$ phenylalkyl, C$_{1-3}$ (phenyl)hydroxyalkyl, C$_{1-3}$ alkoxy, C$_{1-3}$ deuteroalkoxy, C$_{1-3}$ haloalkoxy, and C$_{1-3}$ alkylSO$_2^-$ cyclopropyl; or 3) dihydro-1H-indenyl, tetrandro-5H-benzo[7]annulene, tetrahydronaphthalene, and 6,7-dihydro-5H-cyclopenta[b]pyridine, any of which are substituted with 1-3 groups selected from halo, cyano, C$_{1-3}$ alkyl, C$_{1-3}$ deuteroalkyl, C$_{1-3}$ haloalkyl, C$_{1-3}$ phenylalkyl, C$_{1-3}$ (phenyl)hydroxyalkyl, C$_{1-3}$ alkoxy, C$_{1-3}$ deuteroalkoxy, C$_{1-3}$ haloalkoxy, and C$_1$-3 alkylSO$_2$; or 4) C$_{1-6}$ alkyl, C$_{1-6}$alkenyl, C$_{1-6}$alkynyl, C$_{1-6}$ deuteroalkyl, C$_{1-6}$haloalkyl, C$_{1-6}$ alkoxyalkyl, C$_{3-6}$ cycloalkyl, or C$_{1-6}$halocycloalkyl, each of which are optionally substituted with 1-3 groups selected from halo, NH$_2$, —NC(O)O—C$_{1-6}$ alkyl, —C(O)—C$_{1-6}$alkyl, hydroxyl, C$_{1-6}$ alkoxy, and C$_{1-6}$haloalkyl, C$_{1-6}$ haloalkoxy, phenyl, thiazolyl, pyrdinyl, wherein the phenyl, pyridinyl, and thiazolyl are optionally substituted with 0-2 of halo, nitro, or C$_{1-6}$haloalkyl; or 5) C$_{0-2}$ (C$_{3-7}$ cycloalkyl)alkyl, cyclohexenyl, oxetanyl, tetrahydrofuranyl, pyrrolidinyl, piperidinyl, dioxanyl, pyridinonyl, or tetrahydrothiophenyl dioxide, each of which are optionally substituted with 1-4 groups selected from halo, hydroxy, C$_{1-3}$ alkyl, and C$_{1-3}$ haloalkyl, C$_{1-3}$ alkoxy, hydroxyl C$_{1-3}$ haloalkyl, C$_{3-6}$ cycloalkyl, C(O)O—C$_{1-6}$ alkyl, and amino;

6) tetrahydropyranyl optionally substituted with 1-4 groups selected from halo, hydroxy, C$_{1-3}$ alkyl, C$_{1-3}$haloalkyl; C$_{1-2}$ (C$_{1-3}$alkoxy)alkyl, C$_{1-4}$ alkoxy, and phenyl;

7) C$_{1-4}$ alkylamino, C$_{1-4}$ dialkylamino, azetidinyl, pyrrolidinyl, or piperidinyl;

or B and R$^9$, together with the atom to which they are attached, join to form a C$_{3-6}$ cycloalkyl optionally substituted with 1-2 groups selected from halo, hydroxy, C$_{1-4}$ alkyl, C$_{1-4}$ alkoxy, C$_{2-3}$ hydroxyalkyl, C$_{2-4}$ (hydroxyl)haloalkyl, C$_{3-6}$ hydroxycycloalkyl, and C$_{1-3}$ alkoxycarbonyl;

R$^{10a}$ and R$^{10b}$ are independently selected from hydrogen, halo, cyano, hydroxy, amino, C$_{1-3}$alkylamino, C$_{1-3}$ dialkylamino, acetylamino, (amino)carbonyl, (C$_{1-3}$ alkylamino) carbonyl, and (C$_{1-3}$ dialkylamino)carbonyl;

R$^{11a}$ and R$^{11b}$ are independently selected from hydrogen and C$_{1-6}$ alkyl;

R$^{12a}$ and R$^{12b}$ are independently selected from hydrogen, deuterium, methyl, amino, or OH, or R$^{12a}$ and R$^{12b}$, along with the atom to which they are attached, join together to form C$_{3-6}$ cycloalkyl;

alternatively, either $R^1$ or $R^{18}$ are $C_{1-3}$ hydroxyalkyl, $C_{1-3}$ ($C_{1-3}$ alkoxy)alkyl,

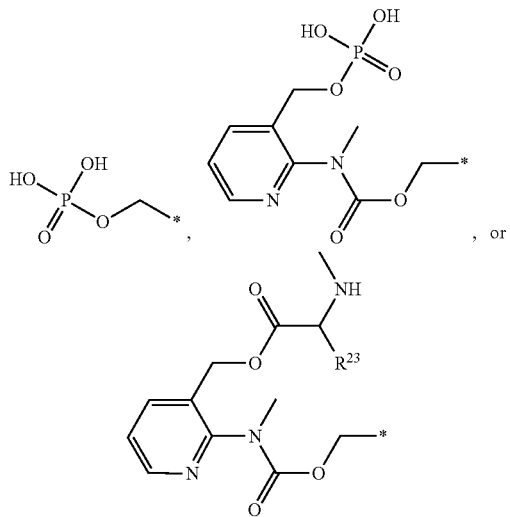

or where $R^{23}$ is $C_{1-3}$ alkyl, $C_{1-3}$ hydroxyalkyl, or ($C_{1-3}$ alkoxy)alkyl;

a is single or double bond; and b is single or double bond;

provided that when a is a single bond, b is a double bond and $R^{18}$ is absent and when a is a double bond, b is a single bond and $R^1$ is absent;

n is 0, 1, or 2;

m is 1 or 2; and r is 1 or 2.

Another aspect of the invention is a compound of formula I where A is N; R1 is hydrogen; $R^2$ is $C_{1-3}$ alkoxy; $R^3$ is hydrogen; $R^4$ is hydrogen; $R^5$ is $C_{1-3}$ haloalkoxy; $R^6$ is hydrogen; a is a single bond, b is a double bond and $R^{18}$ is absent and $R^7$ is

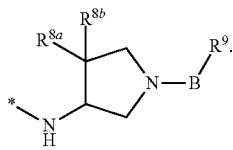

Another aspect of the invention is a compound of formula I where A is N; $R^1$ is hydrogen; $R^2$ is $C_{1-3}$ alkoxy; $R^3$ is hydrogen; $R^4$ is hydrogen; $R^5$ is $C_{1-3}$ haloalkoxy; $R^6$ is hydrogen; a is a single bond, b is a double bond and $R^{18}$ is absent.

Another aspect of the invention is a compound of formula I where $R^7$ is

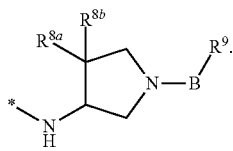

Another aspect of the invention is a compound of formula I where $R^7$ is

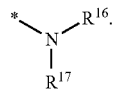

Another embodiment provides a compound of Formula (II), or stereoisomers, tautomers, isotopes, salts, pharmaceutically acceptable salts, solvates, or prodrugs thereof, wherein

II

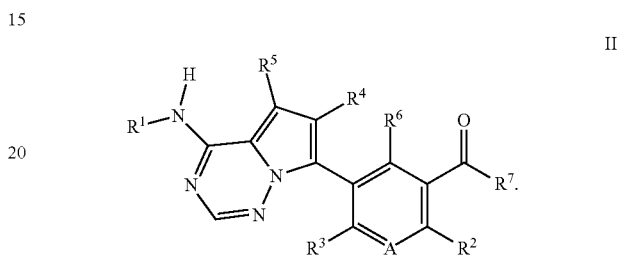

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein $R^5$ is 1) H or $CF_3$; or

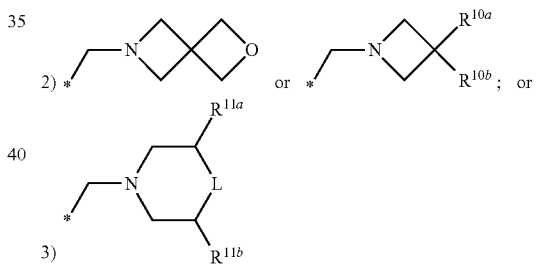

where L is $CH_2$, —O—, $CF_2$, or —CH($CF_3$)—; or

4) 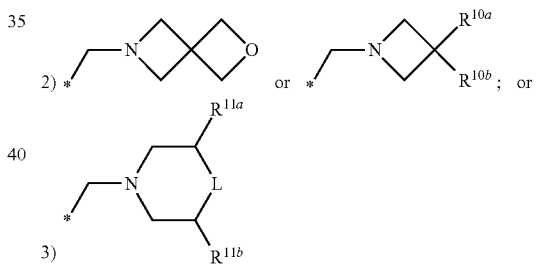

or

5) —$(CH_2)_r$— phenyl, —$(CH_2)_r$-pyrrolidinyl, —$(CH_2)_r$-piperidinyl, —$(CH_2)_r$— azetidinyl, —$(CH_2)_r$— azaspiroheptanyl, —$(CH_2)_r$— benzimidazolyl, —$(CH_2)_r$— azabicyclooctane, —$(CH_2)_r$-azaspirooctane, —$(CH_2)_r$— tetrazolyl, —$(CH_2)_r$— tetrahydroquinolinyl, —$(CH_2)_r$-pyrazolyl, —$(CH_2)_r$-imidazolyl, or —$(CH_2)_r$-triazolyl, any of which may be substituted with 0-3 of halo, $C_{1-3}$ alkyl, or amino.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein R¹ is H;
R² is H, F, CH₃, or OCH₃;
R³ is H or F; and
R⁴ is H.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein

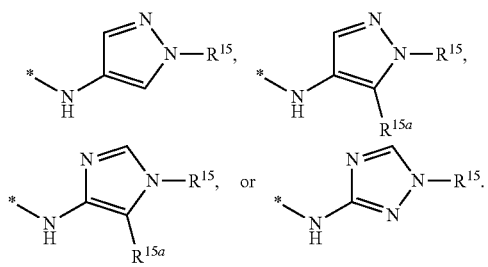

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein
$R^{8a}$ is halo;
$R^{8b}$ is hydrogen;
B is absent, CO, C(O)O, C(O)NR¹²a, SO₂, or $CR^{12a}R^{12b}$.
R⁹ is
1) phenyl, naphthalenyl, pyridyl, pyrimidyl, pyridazinyl, pyrazinyl quinolinyl, benzisoxazolyl, or benzthiazolyl, and each of which are optionally substituted with 1-3 groups selected from halo, cyano, $C_{1-3}$ alkyl, $C_{1-3}$ deuteroalkyl, $C_{1-3}$ haloalkyl, $C_{1-3}$ phenylalkyl, $C_{1-3}$ (phenyl)hydroxyalkyl, $C_{1-3}$ alkoxy, $C_{1-3}$ deuteroalkoxy, $C_{1-3}$ haloalkoxy, and $C_{1-3}$ alkylSO₂; or
2) thiazolyl, oxazolyl, isoxazolyl, isothiazolyl, imidazolyl, thiadiazolyl, oxadiazolyl, triazolyl, or tetrazolyl, and each of which are optionally substituted with 1-3 groups selected from halo, cyano, $C_{1-3}$ alkyl, $C_{1-3}$ deuteroalkyl, $C_{1-3}$ haloalkyl, $C_{1-3}$ phenylalkyl, $C_{1-3}$ (phenyl)hydroxyalkyl, $C_{1-3}$ alkoxy, $C_{1-3}$ deuteroalkoxy, $C_{1-3}$ haloalkoxy, and $C_{1-3}$ alkylSO₂⁻ cyclopropyl; or
3) $C_{1-6}$ alkyl, $C_{1-6}$ alkenyl, $C_{1-6}$ alkynyl, $C_{1-6}$ deuteroalkyl, $C_{1-6}$ haloalkyl, $C_{1-6}$ alkoxyalkyl, $C_{3-6}$ cycloalkyl, or $C_{1-6}$ halocycloalkyl, each of which are optionally substituted with 1-3 groups selected from halo, NH₂, —NC(O)O—$C_{1-6}$ alkyl, —C(O)—$C_{1-6}$ alkyl, hydroxyl, $C_{1-6}$ alkoxy, and $C_{1-6}$ haloalkyl, $C_{1-6}$ haloalkoxy, phenyl, thiazolyl, pyrdinyl, wherein the phenyl, pyridinyl, and thiazolyl are optionally substituted with 0-2 of halo, nitro, or $C_{1-6}$ haloalkyl; or
4) $C_{0-2}$ ($C_{3-7}$ cycloalkyl)alkyl, cyclohexenyl, oxetanyl, tetrahydrofuranyl, pyrrolidinyl, piperidinyl, dioxanyl, pyridinonyl, or tetrahydrothiophenyl dioxide, each of which are optionally substituted with 1-4 groups selected from halo, hydroxy, $C_{1-3}$ alkyl, and $C_{1-3}$ haloalkyl, $C_{1-3}$ alkoxy, hydroxyl $C_{1-3}$ haloalkyl, $C_{3-6}$ cycloalkyl, C(O)O—$C_{1-6}$ alkyl, and amino;
5) tetrahydropyranyl optionally substituted with 1-4 groups selected from halo, hydroxy, $C_{1-3}$ alkyl, $C_{1-3}$ haloalkyl; $C_{1-2}$ ($C_{1-3}$ alkoxy)alkyl, $C_{1-4}$ alkoxy, and phenyl.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein B is CO, C(O)O, or SO₂; and
R⁹ is
1) phenyl, or pyridyl, each of which are optionally substituted with 1-3 from halo; or
2) $C_{2-6}$ alkyl, $C_{2-6}$ deuteroalkyl, $C_{2-6}$ haloalkyl, $C_{2-6}$ alkoxyalkyl, $C_{3-6}$ cycloalkyl, or $C_{1-6}$ halocycloalkyl, each of which are optionally substituted with 1-3 groups selected from halo, hydroxyl, and $C_{1-6}$ haloalkyl; or
3) $C_{1-2}$ ($C_{3-6}$ cycloalkyl)alkyl, of which is optionally substituted with 1-4 groups selected from halo, hydroxy, $C_{1-3}$ alkyl, and $C_{1-3}$ haloalkyl.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein A is N.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein A is CR and R is H or halo.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein
R¹ is H;
R² is H, F, CH₃, or OCH₃;
R³ is H or F; and
R⁴ is H.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein
R⁵ is H, CF₃,

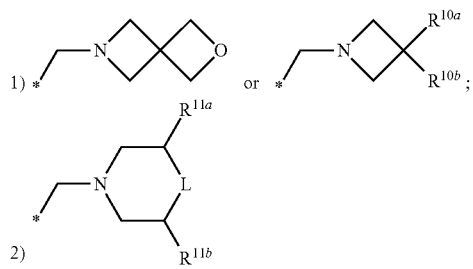

where L is CH₂, —O—, CF₂, or —CH(CF₃)—;

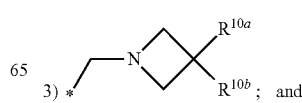

; and

-continued

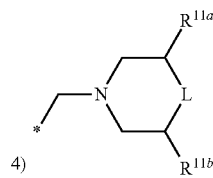

where L is CH₂, —O—, CF₂, or —CH(CF₃)—.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein $R^5$ is 1) hydrogen, halo, cyano, $C_{1-3}$ alkyl, $C_{1-3}$ deuteroalkyl, $C_{1-3}$ haloalkyl, $C_{1-3}$ haloalkoxy, $C_{1-3}$ hydroxyalkyl, $C_{1-3}$ alkoxyalkyl, aminoalkyl, $C_{1-3}$ alkylaminoalkyl, $C_{1-3}$ dialkylaminoalkyl, amino, $C_{1-3}$ alkylamino, $C_{1-3}$ dialkylamino, $(C_{1-3}alkylCONH)$—$C_{1-3}$alkyl, $(C_{1-3}$ alkoxyCONH)—$C_{1-3}$alkyl, or $(C_{1-3}$ alkylSO₂NH)—$C_{1-3}$alkyl, —(CH₂)ₙ—NH—OCH₃, $C_{3-6}$ cycloalkyl, methyl-phenyl-SO₂—O—; or

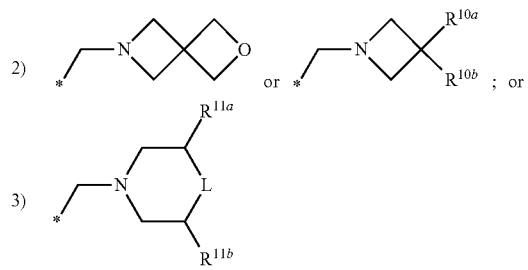

where L is methylene, —C(R⁵ᵃ)₂—, amino, $C_{1-3}$ alkylamino, SO₂, or O; or

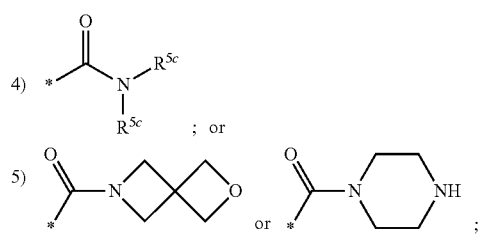

or

6) —(CH₂)ᵣ— phenyl, —(CH₂)ᵣ— 4 to 10 membered heterocycle or 4 to 10 membered heteroaryl, wherein the hterocycle and heteroaryl contain 1, 2, 3, or 4 heteroatoms selected from N, O, and S, and wherein any of the phenyl, heterocycle, or heteroaryl may be substituted with 0-3 of halo, $C_{1-3}$ alkyl, or amino.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein $R^{10a}$ and $R^{10b}$ are independently selected from hydrogen, halo, cyano, hydroxy, amino, $C_{1-3}$ alkylamino, $C_{1-3}$ dialkylamino, acetylamino, (amino)carbonyl, $(C_{1-3}$ alkylamino) carbonyl, and $(C_{1-3}$ dialkylamino)carbonyl; and $R^{11a}$ and $R^{11b}$ are independently selected from hydrogen and alkyl.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein $R^5$ is —(CH₂)ᵣ— phenyl, —(CH₂)ᵣ-pyrrolidinyl, —(CH₂)ᵣ-piperidinyl, —(CH₂)ᵣ-azetidinyl, —(CH₂)ᵣ—azaspiroheptanyl, —(CH₂)ᵣ— benzimidazolyl, —(CH₂)ᵣ—azabicyclooctane, —(CH₂)ᵣ— azaspirooctane, —(CH₂)ᵣ—tetrazolyl, —(CH₂)ᵣ— tetrahydroquinolinyl, —(CH₂)ᵣ-pyrazolyl, —(CH₂)ᵣ-imidazoyl, —(CH₂)ᵣ-triazolyl, any of which may be substituted with 0-3 of halo, $C_{1-3}$ alkyl, or amino.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein $R^7$ is

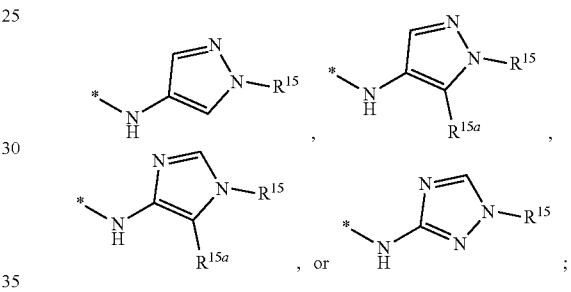

$R^{15}$ is hydroxy-$C_{1-6}$haloalkyl, phenyl-$C_{1-3}$ alkyl, or phenyl-$C_{1-3}$ haloalkyl-, where the phenyl is optionally substituted with 1-3 groups selected from halo, $C_{1-3}$ alkyl, $C_{1-3}$ haloalkyl, $C_{1-3}$ alkoxy, and $C_{1-3}$ haloalkoxy; and $R^{15a}$ is hydrogen, halo, or $C_{1-3}$ alkyl.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein $R^7$ is

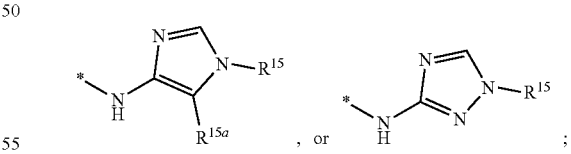

where $R^{15}$ is hydroxy-$C_{1-6}$haloalkyl, phenyl-$C_{1-3}$ alkyl, or phenyl-$C_{1-3}$ haloalkyl-, where the phenyl is optionally substituted with 1-3 groups selected from halo, $C_{1-3}$ alkyl, $C_{1-3}$ haloalkyl, $C_{1-3}$ alkoxy, and $C_{1-3}$ haloalkoxy; and $R^{15a}$ is hydrogen, or $C_{1-3}$ alkyl.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein $R^7$ is

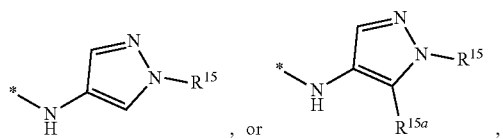

where $R^{15}$ is hydroxy-$C_{1-6}$haloalkyl, phenyl-$C_{1-3}$ alkyl, or phenyl-$C_{1-3}$ haloalkyl-, where the phenyl is optionally substituted with 1-3 groups selected from halo, $C_{1-3}$ alkyl, $C_{1-3}$ haloalkyl, $C_{1-3}$ alkoxy, and $C_{1-3}$ haloalkoxy; and $R^{15a}$ is hydrogen, or $C_{1-3}$ alkyl.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein $R^7$ is

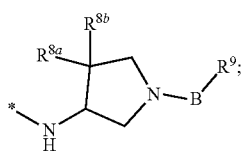

B is absent, CO, C(O)O, C(O)NR$^{12}$a, SO$_2$, or CR$^{12a}$R$^{12}$.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein $R^7$ is

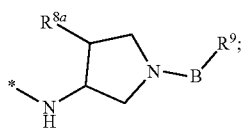

or in another embodiment, $R^7$ is

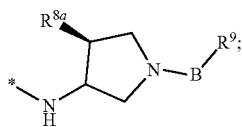

or in another embodiment $R^7$ is

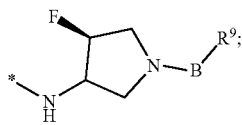

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein $R^{8a}$ is H
$R^{8b}$ is F
B is CO, C(O)O, or SO$_2$, and
$R^9$ is phenyl or pyridyl, and is optionally substituted with 1-3 halo;
or $R^9$ is $C_{2-6}$ alkyl, $C_{2-6}$ deuteroalkyl, $C_{2-6}$ haloalkyl, $C_{2-6}$ alkoxyalkyl, $C_{3-6}$ cycloalkyl, or $C_{1-6}$halocycloalkyl and is optionally substituted with 1-3 groups selected from halo, hydroxyl, and haloalkyl;
or $R^9$ is $C_{1-2}$ ($C_{3-6}$ cycloalkyl)alkyl, and is optionally substituted with 1-4 groups selected from halo, hydroxy, $C_{1-3}$ alkyl, and $C_{1-3}$ haloalkyl.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein either a is a single bond and b is a double bond, or a is a double bond and b is a single bond, and
$R^1$ or $R^{18}$ is $C_{1-3}$ hydroxyalkyl, $C_{1-3}$ ($C_{1-3}$ alkoxy)alkyl,

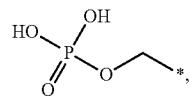

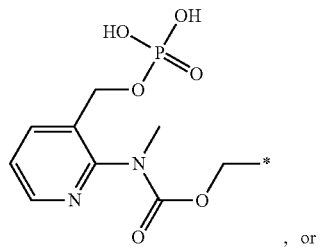

, or

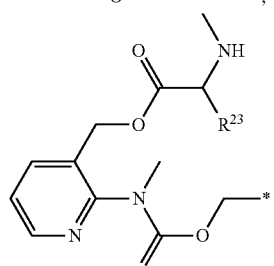

or where $R^{23}$ is $C_{1-3}$ alkyl, $C_{1-3}$ hydroxyalkyl, or ($C_{1-3}$ alkoxy)alkyl.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein the compound is selected from Examples 1 to 541.

Another embodiment provides a compound of Formula (I), (II), or a compound as described in the first, second or third aspect or other embodiments described herein, or stereoisomers, tautomers, isotopes, salts, pharmaceutically acceptable salts, solvates, or prodrugs thereof, wherein the examples are selected from Examples 542 to 1848.

Another embodiment provides a compound of Formula (I), or stereoisomers, tautomers, isotopes, salts, pharmaceutically acceptable salts, solvates, or prodrugs thereof, wherein the compound is selected from the examples.

The present invention is also directed to pharmaceutical compositions useful in treating diseases associated with kinase modulation, including the modulation of receptor interacting protein kinases such as RIPK1, comprising compounds of formula (I), or pharmaceutically-acceptable salts thereof, and pharmaceutically-acceptable carriers or diluents.

The invention further relates to methods of treating diseases associated with kinase modulation, including the modulation of receptor interacting protein kinases such as RIPK1, comprising administering to a patient in need of such treatment a therapeutically-effective amount of a compound according to formula (I).

The present invention also provides processes and intermediates for making the compounds of the present invention or stereoisomers, tautomers, pharmaceutically acceptable salts, solvates, or prodrugs thereof.

The present invention also provides a method for treating proliferative diseases, allergic diseases, autoimmune diseases and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating a disease, comprising administering to a patient in need of such treatment a therapeutically-effective amount of a compound of formula (I), wherein the disease is inflammatory bowel disease, Crohn's disease or ulcerative colitis, psoriasis, systemic lupus erythematosus (SLE), rheumatoid arthritis, multiple sclerosis (MS), ischemia reperfusion, non-alcoholic steatohepatitis (NASH) or transplant rejection.

The present invention also provides a method of treating a condition comprising administering to a patient in need of such treatment a therapeutically-effective amount of a compound of formula (I), wherein the condition is selected from acute myelogenous leukemia, chronic myelogenous leukemia, metastatic melanoma, Kaposi's sarcoma, multiple myeloma, solid tumors, ocular neovasculization, and infantile haemangiomas, B cell lymphoma, pancreatic cancer, pancreatic ductal adenocarcinoma, psoriatic arthritis, multiple vasculitides, idiopathic thrombocytopenic purpura (ITP), myasthenia gravis, allergic rhinitis, Type I diabetes, membranous nephritis, autoimmune hemolytic anemia, autoimmune thyroiditis, cold and warm agglutinin diseases, Evan's syndrome, hemolytic uremic syndrome/thrombotic thrombocytopenic purpura (HUS/TTP), sarcoidosis, Sjogren's syndrome, peripheral neuropathies, pemphigus vulgaris and asthma The present invention also provides a method of treating a condition comprising administering to a patient in need of such treatment a therapeutically-effective amount of a compound of formula (I), wherein the condition is selected from macrophage necrosis in atheroscelerosis development, virus-induced inflammation, systemic inflammatory response syndrome and ethanol-induced liver injury, neurodegeneration such as detachment of the retina, retinal degeneration, wet and dry age-related macular degeneration (AMD), ischemia, amyotrophic lateral sclerosis (ALS), and Gaucher's disease.

The present invention also provides a method of treating a condition comprising administering to a patient in need of such treatment a therapeutically-effective amount of a compound of formula (I), wherein the condition is selected from Inflammatory bowel disease, ulcerative colitis, Crohn's disease, psoriasis, rheumatoid arthritis (RA), non alcoholic steatohepatitis (NASH) and heart failure.

The present invention also provides a method of treating a condition comprising administering to a patient in need of such treatment a therapeutically-effective amount of a compound of formula (I), wherein the condition is selected from inflammatory bowel disease, Crohn's disease, ulcerative colitis, psoriasis, ischemia reperfusion, heart failure and non-alcoholic steatohepatitis (NASH).

The present invention also provides a method for treating rheumatoid arthritis, comprising administering to a patient in need of such treatment a therapeutically-effective amount of a compound of formula (I).

The present invention also provides a method of treating diseases, comprising administering to a patient in need of such treatment a therapeutically-effective amount of a compound of formula (I), or pharmaceutically acceptable salt thereof, in combination with other therapeutic agents.

The present invention also provides the compounds of the present invention or stereoisomers, tautomers, isotopes, salts, pharmaceutically acceptable salts, solvates, or prodrugs thereof, for use in therapy.

In another embodiment, compounds of formula (I) are selected from exemplified examples or combinations of exemplified examples or other embodiments herein.

In another embodiment, the $IC_{50}$ value of compounds of formula (I) in the RIPK1 assays described below is >200 nM.

In another embodiment, the $IC_{50}$ value of compounds of formula (I) in the RIPK1 assays described below is <200 nM.

In another embodiment, the $IC_{50}$ value of compounds of formula (I) in the RIPK1 assays described below is <20 nM.

In another embodiment, compounds of the present invention selectively inhibit RIPK1 over PI3K. In one embodiment, the selectivity is greater than 10×. In another embodiment, the selectivity is greater than 100×.

The present invention also provides the use of the compounds of the present invention or stereoisomers, tautomers, isotopes, salts, pharmaceutically acceptable salts, solvates, or prodrugs thereof, for the manufacture of a medicament for the treatment of cancers, an allergic disease, an autoimmune disease or an inflammatory disease.

The present invention may be embodied in other specific forms without departing from the spirit or essential attributes thereof. This invention encompasses all combinations of preferred aspects and/or embodiments of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

The following are definitions of terms used in this specification and appended claims. The initial definition provided for a group or term herein applies to that group or term throughout the specification and claims, individually or as part of another group, unless otherwise indicated.

When any variable (e.g., $R^3$) occurs more than one time in any constituent or formula for a compound, its definition at each occurrence is independent of its definition at every other occurrence. Thus, for example, if a group is shown to be substituted with 0-2$R^3$, then said group may optionally be substituted with up to two $R^3$ groups and $R^3$ at each occurrence is selected independently from the definition of $R^3$.

Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the present invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

In accordance with a convention used in the art,

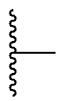

is used in structural formulas herein to depict the bond that is the point of attachment of the moiety or substituent to the core or backbone structure. In certain substructures, an "*" (asterisk) is used to indicate the point of attachment to the rest of the molecule.

A dash "-" that is not between two letters or symbols is used to indicate a point of attachment for a substituent. For example, —CONH$_2$ is attached through the carbon atom.

The term "optionally substituted" in reference to a particular moiety of the compound of Formula (I) (e.g., an optionally substituted heteroaryl group) refers to a moiety having 0, 1, 2, or more substituents. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

As used herein, the term "alkyl" or "alkylene" is intended to include both branched and straight-chain saturated aliphatic hydrocarbon groups having the specified number of carbon atoms. For example, "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl($C_{0-4}$)alkyl includes a substituted lower alkyl having at least one aryl substituent and also includes an aryl directly bonded to another group, i.e., aryl(Co)alkyl. The term "heteroarylalkyl" refers to a substituted alkyl group as defined above where at least one of the substituents is a heteroaryl.

"Alkenyl" or "alkenylene" is intended to include hydrocarbon chains of either straight or branched configuration and having one or more double carbon-carbon bonds that may occur in any stable point along the chain. For example, "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

When reference is made to a substituted alkenyl, alkynyl, alkylene, alkenylene, or alkynylene group, these groups are substituted with one to three substituents as defined above for substituted alkyl groups.

The term "alkoxy" refers to an oxygen atom substituted by alkyl or substituted alkyl, as defined herein. For example, the term "alkoxy" includes the group —O—$C_{1-6}$alkyl such as methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. "Lower alkoxy" refers to alkoxy groups having one to four carbons.

It should be understood that the selections for all groups, including for example, alkoxy, thioalkyl, and aminoalkyl, will be made by one skilled in the field to provide stable compounds.

The term "substituted", as used herein, means that any one or more hydrogens on the designated atom or group is replaced with a selection from the indicated group, provided that the designated atom's normal valence is not exceeded. When a substituent is oxo, or keto, (i.e., =O) then 2 hydrogens on the atom are replaced. Keto substituents are not present on aromatic moieties. Unless otherwise specified, substituents are named into the core structure. For example, it is to be understood that when (cycloalkyl)alkyl is listed as a possible substituent, the point of attachment of this substituent to the core structure is in the alkyl portion. Ring double bonds, as used herein, are double bonds that are formed between two adjacent ring atoms (e.g., Cam, C=N, or N=N).

Combinations of substituents and/or variables are permissible only if such combinations result in stable compounds or useful synthetic intermediates. A stable compound or stable structure is meant to imply a compound that is sufficiently robust to survive isolation from a reaction mixture to a useful degree of purity, and subsequent formulation into an efficacious therapeutic agent. It is preferred that the presently recited compounds do not contain a N-halo, S(O)$_2$H, or S(O)H group.

The term "carbocyclyl" or "carbocyclic" refers to a saturated or unsaturated, or partially unsaturated, monocyclic or bicyclic ring in which all atoms of all rings are carbon. Thus, the term includes cycloalkyl and aryl rings. Monocyclic carbocycles have 3 to 6 ring atoms, still more typically 5 or 6 ring atoms. Bicyclic carbocycles have 7 to 12 ring atoms, e.g., arranged as a bicyclo [4,5], [5,5], [5,6] or [6,6] system, or 9 or 10 ring atoms arranged as a bicyclo [5,6] or [6,6] system. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Carbocycles, can include cyclopropyl, cyclobutyl, cyclopentyl, cyclohexyl, and phenyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a bicyclic ring. When a ring is bridged, the substituents recited for the ring may also be present on the bridge.

The term "aryl" refers to monocyclic or bicyclic aromatic hydrocarbon groups having 6 to 12 carbon atoms in the ring portion, such as phenyl, and naphthyl groups, each of which may be substituted. A preferred aryl group is optionally-substituted phenyl.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like, which optionally may be substituted at any available atoms of the ring(s).

The terms "heterocycloalkyl", "heterocyclo", "heterocyclic", or "heterocyclyl" may be used interchangeably and refer to substituted and unsubstituted non-aromatic 3- to 7-membered monocyclic groups, 7- to 11-membered bicyclic groups, and 10- to 15-membered tricyclic groups, in which at least one of the rings has at least one heteroatom (0, S or N), said heteroatom containing ring preferably having 1, 2, or 3 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain only carbon atoms and may be saturated, partially saturated, or unsaturated. The heterocyclo group may be attached at any available nitrogen or carbon atom. The term "heterocycle" includes "heteroaryl" groups. As valence allows, if said further ring is cycloalkyl or heterocyclo it is additionally optionally substituted with (oxo).

Exemplary monocyclic heterocyclyl groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 1-pyridonyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

The term "heteroaryl" refers to substituted and unsubstituted aromatic 5- or 6-membered monocyclic groups, 9- or 10-membered bicyclic groups, and 11- to 14-membered tricyclic groups which have at least one heteroatom (0, S or N) in at least one of the rings, said heteroatom-containing ring preferably having 1, 2, or 3 heteroatoms selected from O, S, and N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quatemized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. As valence allows, if said further ring is cycloalkyl or heterocyclo it is additionally optionally substituted with (oxo).

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl, and the like.

Exemplary tricyclic heteroaryl groups include carbazolyl, benzindolyl, phenanthrollinyl, acridinyl, phenanthridinyl, xanthenyl and the like.

Unless otherwise indicated, when reference is made to a specifically-named aryl (e.g., phenyl), cycloalkyl (e.g., cyclohexyl), heterocyclo (e.g., pyrrolidinyl, piperidinyl, and morpholinyl) or heteroaryl (e.g., tetrazolyl, imidazolyl, pyrazolyl, triazolyl, thiazolyl, and fiuyl) the reference is intended to include rings having 0 to 3, preferably 0-2, substituents selected from those recited above for the aryl, cycloalkyl, heterocyclo and/or heteroaryl groups, as appropriate.

The term "halo" or "halogen" refers to chloro, bromo, fluoro and iodo.

The term "haloalkyl" means a substituted alkyl having one or more halo substituents. For example, "haloalkyl" includes mono, bi, and trifluoromethyl.

The term "haloalkyl" means a substituted alkyl having one or more halo substituents. For example, "haloalkyl" includes mono, bi, and trifluoromethyl.

The term "haloalkoxy" means an alkoxy group having one or more halo substituents. For example, "haloalkoxy" includes $OCF_3$.

The term "heteroatoms" shall include oxygen, sulfur and nitrogen.

When the term "unsaturated" is used herein to refer to a ring or group, the ring or group may be fully unsaturated or partially unsaturated.

One skilled in the field will understand that, when the designation "$CO_2$" is used herein, this is intended to refer to the group

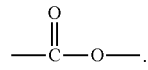

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The compounds of formula (I) may exist in a free form (with no ionization) or can form salts which are also within the scope of this invention. Unless otherwise indicated, reference to an inventive compound is understood to include reference to the free form and to salts thereof. The term "salt(s)" denotes acidic and/or basic salts formed with inorganic and/or organic acids and bases. In addition, the term "salt(s) may include zwitterions (inner salts), e.g., when a compound of formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the formula (I) with an amount of acid or base, such as an equivalent amount, in a medium such as one in which the salt precipitates or in an aqueous medium followed by lyophilization. Specific examples may have been prepared in a specific salt form, however, it is to be understood that compounds may exist in a free form as well as alternative salt forms.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fiunarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quatemized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. In one embodiment, salts include monohydrochloride, hydrogensulfate, methanesulfonate, phosphate or nitrate salts.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fiunaric, toluenesulfonic, methanesulfonic, ethane disulfonic, oxalic, and isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 18th ed., Mack Publishing Company, Easton, Pa., 1990, the disclosure of which is hereby incorporated by reference.

All stereoisomers of the compounds of the instant invention are contemplated, either in admixture or in pure or substantially pure form. Stereoisomers may include compounds which are optical isomers through possession of one or more chiral atoms, as well as compounds which are optical isomers by virtue of limited rotation about one or more bonds (atropisomers). The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Prodrugs and solvates of the inventive compounds are also contemplated. The term "prodrug" denotes a compound which, upon administration to a subject, undergoes chemical conversion by metabolic or chemical processes to yield a compound of the formula (I), and/or a salt and/or solvate thereof. Any compound that will be converted in vivo to provide the bioactive agent (i.e., the compound for formula (I)) is a prodrug within the scope and spirit of the invention. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Various forms of prodrugs are well known in the art. For examples of such prodrug derivatives, see:
a) *Design of Prodrugs*, edited by H. Bundgaard, (Elsevier, 1985) and Methods in Enzymology, Vol. 112, pp. 309-396, edited by K. Widder, et al. (Academic Press, 1985);
b) *A Textbook of Drug Design and Development*, edited by Krosgaard-Larsen and H. Bundgaard, Chapter 5, "Design and Application of Prodrugs," by H. Bundgaard, pp. 113-191 (1991); and
c) H. Bundgaard, *Advanced Drug Delivery Reviews*, Vol. 8, pp. 1-38 (1992), each of which is incorporated herein by reference.

Compounds of the formula (I) and salts thereof may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Cis and trans geometric isomers of the compounds of the present invention are described and may be isolated as a mixture of isomers or as separated isomeric forms. The present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All geometric isomers, tautomers, atropisomers, hydrates, solvates, polymorphs, and isotopically labeled forms of the compounds referred to herein, and mixtures thereof, are considered within the scope of the present invention. Methods of solvation are generally known in the art.

Utility

The compounds of the invention modulate kinase activity, including the modulation of RIPK1. Accordingly, compounds of formula (I) have utility in treating conditions associated with the modulation of kinase activity, and particularly the selective inhibition of RIPK1 activity. In another embodiment, compounds of formula (I) have advantageous selectivity for RIPK1 activity preferably from at least 20 fold to over 1,000 fold more selective.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of RIPK1, compounds of Formula (I) are useful in treating RIPK1-associated conditions including, but not limited to, inflammatory diseases such as Crohn's disease and ulcerative colitis, inflammatory bowel disease, asthma, graft versus host disease, chronic obstructive pulmonary disease and non-alcoholic steatohepatitis (NASH); autoimmune diseases such as Graves' disease, rheumatoid arthritis, systemic lupus erythematosis, psoriasis; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders including ischemia reperfusion, heart failure, solid tumors, ocular neovasculization, and infantile haemangiomas; infectious diseases such as sepsis, septic shock, and Shigellosis; neurodegenerative diseases such as Alzheimer's disease, Parkinson's disease, ALS, cerebral ischemias or neurodegenerative disease caused by traumatic injury; oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, non-alcoholic steatohepatitis (NASH), glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, ALS, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Preferred methods of treatment are those wherein the condition is selected from inflammatory bowel disease, Crohn's disease and ulcerative colitis, allograft rejection, rheumatoid arthritis, psoriasis, ankylosing spondylitis, psoriatic arthritis, non-alcoholic steatohepatitis (NASH), and pemphigus vulgaris. Alternatively preferred methods of treatment are those wherein the condition is selected from ischemia reperfusion injury, including cerebral ischemia reperfusions injury arising from stroke and cardiac ischemia reperfusion injury arising from myocardial infarction.

When the terms "RIPK1-associated condition" or "RIPK1-associated disease or disorder" are used herein, each is intended to encompass all of the conditions identified above as if repeated at length, as well as any other condition that is affected by RIPK1 kinase activity.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit RIPK1.

The methods of treating RIPK1 kinase-associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit RIPK1 and/or treat diseases associated with RIPK1.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; anti-inflammatory anti-bodies such as vedolizumab and ustekinumab, anti-infammatory kinase inhibitors such as TYK2 inhibitors, antiviral agents such as abacavir; antiproliferative agents such as methotrexate, leflunomide, FK506 (tacrolimus, Prograf); anti-coagulent drugs such as clopidogrel, ticagrelor, prasugrel, enoxaparin, eptifibatide, tirofiban; anti-fibrotic drugs such as FGF21 agonist; cytotoxic drugs such as azathiprine and cyclophosphamide; TNF-α inhibitors such as tenidap, anti-TNF antibodies or soluble TNF receptor, and rapamycin (sirolimus or Rapamune) or derivatives thereof, and PD-1 immunotherapy.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating RIPK1 kinase-associated conditions, including IL-1, IL-6, IL-8, IFNγ and TNF-α-mediated conditions, as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th ed., 1985, which is incorporated herein by reference in its entirety.

The compounds of Formula (I) may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrastemal injection or infusion techniques (e.g., as sterile injectable aq. or non-aq. solutions or suspensions); nasally such as by inhalation spray; topically, such as in the form of a cream or ointment; rectally such as in the form of suppositories; or liposomally.

Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as PLASTIBASE® (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 930). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The therapeutically-effective amount of a compound of the present invention may be determined by one of ordinary skill in the art, and includes exemplary dosage amounts for a mammal of from about 0.05 to 1000 mg/kg; 1-1000 mg/kg; 1-50 mg/kg; 5-250 mg/kg; 250-1000 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of RIPK1 enzyme levels.

MLKL Phosphorylation High-Content Assay

HT29-L23 human colorectal adenocarcinoma cells were maintained in RPMI 1640 medium containing 10% heat-inactivated FBS, 1% Penicillin-Streptomycin and 10 mM HEPES. Cells were seeded at 2,000 cells/well in 384w tissue culture-treated microplates (Greiner #781090-3B) and incubated at 37° C. (5% $CO_2$/95% 02) for two days. On the day of assay, the cells were treated with test compounds at final concentrations of 6.25 to 0.106 µM for 30 min at 37° C. (5% $CO_2$/95% 02). Necroptopsis was induced using a mixture of human TNFα (35 ng/mL) (Peprotech #300-01A), SMAC mimetic (from US 2015/0322111 A1) (700 nM) and Z-VAD (140 nM) (BD pharmingen #51-6936). Following six hours incubation at 37° C. (5% $CO_2$/95% 02), the cells were fixed with 4% formaldehyde (ACROS 11969-0010) for 15 min at room temperature and then permeabilized with phosphate buffered saline (PBS) containing 0.2% Triton-X-100 for 10 min. MLKL phosphorylation was detected using anti-MLKL (phospho S358) antibody (Abcam #ab187091) (1:1000 dilution in Blocking Buffer [PBS supplemented with 0.1% BSA]) with overnight incubation at 4° C. After washing three times in PBS, goat anti-rabbit Alexa-488 (1:1000 dilution) (Life Technologies, A11008) and Hoechst 33342 (Life Technologies, H3570) (1:2000 dilution) in Blocking Buffer were added for 1 h at room temperature. Following another three cycles of washes in PBS, the microplates were sealed, and cellular images were acquired in the Cellomics ArrayScan VTI high-content imager equipped with an X1 camera. Fluorescent images were taken using a 10× objective and the 386-23 BGRFRN_BGRFRN and 485-20 BGRFRN_BGRFRN filter sets, for nuclei and MLKL phosphorylation, respectively. The image sets were analyzed using the Compartmental Analysis Bioapplication software (Cellomics). The level of MLKL phosphorylation was quantified as MEAN_CircRingAvgIntenRatio. The maximal inhibitory response was defined by the activity induced by Necls (CAS #: 852391-15-2, 6.25 µM). The IC50 value was defined as the concentration of compound that produces 50% of the maximal inhibition. The data were fitted using the 4-parameter logistic equation to calculate the IC50 and Ymax values.

RIPK1 HTRF Binding Assay

A solution was prepared containing 0.2 nM Anti GST-Tb (Cisbio, 61GSTTLB), 90.6 nM probe and 1 nM His-GST-TVMV-hRIPK1(1-324) in FRET Buffer (20 mM HEPES, 10 mM MgCl2, 0.015% Brij-35, 4 mM DTT, 0.05 mg/mL BSA). Using Formulatrix Tempest, the detection antibody/enzyme/probe solution (2 mL) was dispensed into wells of a 1536 plate (Black Low Binding Polystyrene 1536 Plate (Corning, 3724)) containing 10 nL of compounds of interest at appropriate concentration in DMSO. The plate was incubated at rt for 1 h. FRET was measured using the EnVision plate reader (Excitation: 340 nM, Emission: 520 nM/495 nM). Total signal (0% inhibition) was calculated from wells containing 10 nL DMSO only. Blank signal (100% inhibition) calculated from wells containing 10 nL of 15 nM staurosporine and internal controls.

Cloning and Baculovirus Expression of RIPK1 Construct

The coding region of human RIPK1(1-324) flanked by NdeI site at 5' end and stop codon TGA and XhoI site at 3' end was codon optimized and gene synthesized at GenScript USA Inc. (Piscataway, N.J.) and subcloned into a modified pFastBacl vector (Invitrogen, Carlsbad, Calif.) with N-terminal His-GST-TVMV tag, to generate His-GST-TVMV-hRIPK1(1-324)-pFB. The fidelity of the synthetic fragment was confirmed by sequencing.

Baculovirus was generated for the construct using the Bac-to-Bac baculovirus expression system (Invitrogen) according to the manufacturer's protocol. Briefly, recombinant bacmid was isolated from transformed DH10Bac *E. coli* competent cells (Invitrogen) and used to transfect *Spodoptera frugiperda* (SP)) insect cells (Invitrogen). Baculovirus was harvested 72 hours post transfection and a virus stock was prepared by infecting fresh Sf9 cells at a 1/1000 (v/v) ratio for 66 hours.

For large scale protein production, SP) cells (Expression System, Davis, Calif.) grown in ESF921 insect medium (Expression System) at 2×106 cells/ml were infected with virus stock at a 1/100 (v/v) ratio for 66 hours. The production was carried out either at a 10 L scale in a 22 L cellbag (GE Healthcare Bioscience, Pittsburgh, Pa.) or at a 20 L scale in a 50 L cellbag using WAVE-Bioreactor System 20/50 (GE Healthcare Bioscience). The infected cells were harvested by centrifugation at 2000 rpm for 20 min at 4° C. in a SORVALL® RC12BP centrifuge. The cell pellets was stored at −70° C. before protein was purified.

Purification of His-GST-TVMV-hRIPK1(1-324)

RIPK1 containing cell paste was resuspended in 50 mM Tris pH 7.5, 150 mM NaCl, 10 mM imidazole, 5% glycerol, 5 mM MgSO4, 1 mM TCEP, 25 U/ml Benzonase, and Complete Protease Inhibitor tablets (1/50 ml, Roche Diagnostics, Indianapolis, Ind.). The cells were lysed by nitrogen cavitation using an unstirred pressure vessel @ 525 PSI (Parr Instrument Company, Moline, Ill.). The suspension was clarified by centrifugation at 136,000×g for 40 min, at 4° C. The lysate was decanted from the pellet and passed through a 5 ml NiNTA Superflow cartridge (Qiagen, Valencia, Calif.) using an AKTA Pure (GE Healthcare). Column was eluted with 10 CV linear gradient into 50 mM Tris 7.5, 150 mM NaCl, 500 mM imidazole, 5% glycerol, 1 mM TCEP. Peak fractions were pooled and loaded directly onto 5 ml GSTrap 4B column (GE Healthcare). Column was washed with 50 mM Tris 7.0, 150 mM NaCl, 5% glycerol, 1 mM DTT and eluted in 10 CV linear gradient into 50 mM Tris 8.0, 150 mM NaCl, 20 mM reduced glutathione, 5% glycerol, 1 mM DTT. Fractions identified by SDS-PAGE as containing RIPK1 were pooled and concentrated using 30 kDa MWCO spin concentrators (Amicon Ultra-15, Millipore, Billerica, Mass.) and loaded onto a HiLoad 26/600 Superdex 200 column (GE Healthcare) equilibrated in 25 mM Tris 7.5, 150 mM NaCl, 2 mM TCEP, 5% glycerol. The RIPK1 protein eluted as a dimer off the SEC column.

The yield was ~8 mg/L with a purity >95% as determined by Coomassie stain SDS-PAGE gel analysis. LCMS analysis of the protein showed that the protein had lost the N-terminal methionine, had one phosphorylated site, and was partially acetylated. Protein was aliquoted and stored at −80° C.

Using these assays, the $IC_{50}$ values of the following compounds were determined. See Table A.

TABLE A

| Ex | HTRF Binding Assay (IC50, uM) | pMLKL HCS Cell Assay (IC50, uM) |
|---|---|---|
| 1 | 8.5 | 77 |
| 2 | 5.8 | 31 |
| 3 | 1.7 | 5.0 |
| 4 | 32 | 412 |
| 5 | 147 | 16 |
| 6 | 10 | 30 |
| 7 | 14 | 62 |
| 8 | 2.7 | 11 |
| 9 | 2.1 | 21 |
| 10 | 4.1 | 4.9 |
| 11 | 18 | 153 |
| 12 | 50 | 401 |
| 13 | 14 | 30 |
| 14 | 453 | 2,621 |
| 15 | 32 | 257 |
| 16 | 735 | 1,577 |
| 17 | 8.9 | 9.8 |
| 18 | 12 | 24 |
| 19 | 16 | 47 |
| 20 | 112 | 49 |
| 21 | 25 | 15 |
| 22 | 59 | 167 |
| 23 | 79 | 60 |
| 24 | 56 | 247 |
| 25 | 41 | 71 |
| 26 | 5.8 | 8.2 |
| 27 | 22 | 99 |
| 28 | 2.3 | 3.1 |
| 29 | 46 | 106 |
| 30 | 19 | 13 |
| 31-1 | 7.4 | 13 |
| 31-2 | 2,222 | |
| 32 | 5.3 | 82 |
| 33 | 1.7 | 34 |
| 34 | 5.7 | 28 |
| 35 | 321 | 104 |
| 36 | 8.6 | 98 |
| 37 | 214 | 42 |
| 39 | 1,945 | 327 |
| 38 | 7.0 | 8.4 |
| 40 | 42 | 82 |
| 41-1 | 11 | 10 |
| 41-2 | 121 | 288 |
| 42 | 0.25 | 8.7 |
| 43 | 6.0 | 11 |
| 44-1 | 4.7 | 9.3 |
| 44-2 | 74 | |
| 44-3 | 401 | 296 |
| 44-4 | 517 | 835 |
| 45-1 | 24 | 11 |
| 45-2 | 13 | 22 |
| 46 | 26 | 109 |
| 47 | 51 | 160 |
| 48 | 52 | 8.6 |
| 49 | 1.3 | 0.46 |
| 50 | 2.2 | 3.6 |
| 51 | 4.2 | 3.7 |
| 52 | 7.1 | 42 |
| 53 | | 4.4 |
| 54 | 285 | 263 |
| 55 | 142 | 479 |
| 56 | 42 | 76 |
| 57 | 8.8 | 14 |
| 58 | 2.5 | 4.1 |
| 59 | 50 | 231 |
| 60 | 7.6 | 41 |
| 61 | 7.2 | 30 |
| 62 | 2.3 | 37 |
| 63 | | 123 |
| 64 | | |
| 65 | 2.2 | 3.5 |
| 66 | 42 | 183 |
| 67 | 8.5 | 5.2 |

TABLE A-continued

| Ex | HTRF Binding Assay (IC50, uM) | pMLKL HCS Cell Assay (IC50, uM) |
|---|---|---|
| 68 | 29 | 348 |
| 69 | 8.2 | 74 |
| 70 | 32 | 209 |
| 71 | 4.8 | 65 |
| 72 | 12 | 74 |
| 73 | 1.4 | 33 |
| 74 | 1.5 | 30 |
| 75 | 24 | 81 |
| 76 | 3.4 | 4.1 |
| 77 | 4.5 | 26 |
| 78 | 7.0 | 113 |
| 79 | 17 | 139 |
| 80 | 17 | 261 |
| 81 | 7.7 | 38 |
| 82 | 9.5 | 45 |
| 83 | 57 | 279 |
| 84 |  | 70 |
| 85 |  | 363 |
| 86 | 15 | 33 |
| 87 | 134 | 245 |
| 88 | 31 | 117 |
| 89 | 67 | 87 |
| 90 | 4.2 | 13 |
| 91 | 2.9 | 9.0 |
| 92 | 5.9 | 27 |
| 93 | 16 | 22 |
| 94 | 4.3 | 12 |
| 95 | 39 | 64 |
| 96 | 24 | 82 |
| 97 | 34 | 96 |
| 98 | 98 | 182 |
| 99 | 25 | 218 |
| 100 | 18 | 61 |
| 101 | 15 | 41 |
| 102 | 7.8 | 123 |
| 103 | 12 | 50 |
| 104 | 12 | 45 |
| 105 | 20 | 72 |
| 106 | 7.5 | 12 |
| 107 | 23 | 50 |
| 108 | 19 | 53 |
| 109 | 6.3 | 9.7 |
| 110 | 3.0 | 1.2 |
| 111 | 24 | 112 |
| 112 | 111 | 343 |
| 113 | 19 | 85 |
| 114 | 14 | 50 |
| 115 | 17 | 29 |
| 116 | 20 | 43 |
| 117 | 7.1 | 79 |
| 118 | 15,000 | 402 |
| 119 | 9.7 | 42 |
| 120 | 52 | 303 |
| 121 | 12 | 130 |
| 122 | 12 | 11 |
| 123 | 18 | 5.1 |
| 124 | 89 | 388 |
| 125 | 3.3 | 5.0 |
| 126 | 10 | 16 |
| 127 | 13 | 23 |
| 128 | 68 | 313 |
| 129 | 9.3 | 22 |
| 130 | 38 | 78 |
| 131 | 31 | 73 |
| 132 | 33 | 75 |
| 133 | 7.0 | 16 |
| 134 | 12 | 15 |
| 135 | 13 | 17 |
| 136 | 4,621 | 435 |
| 137 | 19 | 453 |
| 138 | 23 | 82 |
| 139 | 17 | 35 |
| 140 | 5.1 | 11 |
| 141 | 123 | 208 |
| 142 | 24 | 70 |
| 143 | 56 | 311 |
| 144 | 26 | 162 |
| 145 | 53 | 153 |
| 146 | 108 | 419 |
| 147 | 42 | 201 |
| 148 | 174 | 24 |
| 149 | 32 | 26 |
| 150 | 82 | 397 |
| 151 | 18 | 9.0 |
| 152 | 58 | 100 |
| 153 | 3.0 | 14 |
| 154 | 57 | 66 |
| 155 | 217 | 367 |
| 156 | 27 | 100 |
| 157 | 39 | 156 |
| 158 | 42 | 253 |
| 159 | 31 | 65 |
| 160 | 2.0 | 12 |
| 161 | 31 | 43 |
| 162 | 37 | 351 |
| 163 | 57 | 170 |
| 164 | 8,522 | 97 |
| 165 | 5.5 | 1.1 |
| 166 | 3.1 | 0.85 |
| 167 | 7.2 | 9.3 |
| 168 | 4.3 | 2.8 |
| 169 | 2.3 | 1.7 |
| 170 | 17 | 16 |
| 171 | 2.4 | 3.0 |
| 172 | 21 | 30 |
| 173 | 17 | 5.7 |
| 174 | 18 | 6.6 |
| 175 | 95 | 29 |
| 176 | 51 | 66 |
| 177 | 6.2 | 1.0 |
| 178 |  | 330 |
| 179 |  | 48 |
| 180 | 16 | 21 |
| 181 | 6.0 | 5.7 |
| 182 | 151 | 160 |
| 183 | 66 | 85 |
| 184 | 9.0 | 1.8 |
| 185 | 36 | 55 |
| 186 | 120 | 228 |
| 187 | 274 | 307 |
| 188 | 29 | 25 |
| 189 | 14 | 32 |
| 190 | 26 | 37 |
| 191 | 95 | 152 |
| 192 | 125 | 282 |
| 193 | 23 | 66 |
| 194 | 28 | 85 |
| 195 | 59 | 349 |
| 196 | 33 | 5.5 |
| 197 | 26 | 64 |
| 198 | 27 | 14 |
| 199 | 16 | 54 |
| 200 | 71 | 316 |
| 201 | 5.5 | 16 |
| 202 | 51 | 135 |
| 203 | 3.1 | 14 |
| 204 | 281 | 218 |
| 205 | 8.9 | 22 |
| 206 | 1.1 | 21 |
| 207 | 53 | 144 |
| 208 | 4.0 | 4.2 |
| 209 | 132 | 181 |
| 210 | 22 | 90 |
| 211 | 5.6 | 6.2 |
| 212 | 111 | 479 |
| 213 | 4.6 | 2.3 |
| 214 | 3.0 | 26 |
| 215 | 2.6 | 3.4 |
| 216 | 216 | 51 |
| 217 | 5.9 | 4.6 |
| 218 | 3.8 | 3.8 |
| 219 | 174 | 209 |
| 220 | 120 | 89 |
| 221 | 12 | 13 |

TABLE A-continued

| Ex | HTRF Binding Assay (IC50, uM) | pMLKL HCS Cell Assay (IC50, uM) |
| --- | --- | --- |
| 222 | 6.7 | 6.3 |
| 223 | 200 | 412 |
| 224 | 12 | 8.9 |
| 225 | 6.9 | 21 |
| 226 | 51 | 259 |
| 227 | 9.2 | 3.8 |
| 228 | 137 | 174 |
| 229 | 24 | 18 |
| 230 | 3.8 | 15 |
| 231 | 11 | 7.3 |
| 232 | 18 | 6.2 |
| 233 | 10 | 30 |
| 234 | 17 | 15 |
| 235 | 20 | 25 |
| 236 | 384 | 210 |
| 237 | 10 | 39 |
| 238 | 8.5 | 10 |
| 239 | 23 | 68 |
| 240 | 90 | 271 |
| 241 | 38 | 33 |
| 242 | 3.3 | 32 |
| 243 | 7.6 | 45 |
| 244 | 54 | 258 |
| 245 | 17 | 160 |
| 246 | 5.0 | 81 |
| 247 | 3.6 | 24 |
| 248 | 5.8 | 26 |
| 249 | 54 | 201 |
| 250 | 6.5 | 72 |
| 251 | 42 | 223 |
| 252 | 25 | 38 |
| 253 | 14 | 22 |
| 254 | 12 | 38 |
| 255 | 43 | 93 |
| 256 | 20 | 64 |
| 257 | 13 | 32 |
| 258 | 174 | 194 |
| 259 | 14 | 20 |
| 260 | 24 | 191 |
| 261 | 34 | 315 |
| 262 | 45 | 232 |
| 263 | 19 | 102 |
| 264 | 26 | 104 |
| 265 | 47 | 161 |
| 266 | 46 | 220 |
| 267 | 51 | 185 |
| 268 | 136 | 122 |
| 269 | 6.4 | 28 |
| 270 | 4.4 | 1.1 |
| 271 | 8.7 | 26 |
| 272 | 3.7 | 8.3 |
| 273 | 101 | 148 |
| 274 | 13 | 26 |
| 275 | 12 | 27 |
| 276 | 7.2 | 6.9 |
| 277 | 8.0 | 25 |
| 278 | 15,000 | 249 |
| 279 | 22 | 80 |
| 280 | 210 | 351 |
| 281 | 312 | 284 |
| 282 | 267 | 429 |
| 283 | 89 | 142 |
| 284 | 68 | 109 |
| 285 | 3.5 | 22 |
| 286 | 3.3 | 29 |
| 287 | 17 | 20 |
| 288 | 91 | 276 |
| 289 | 45 | 70 |
| 290 | 149 | 162 |
| 291 | 31 | 29 |
| 292 | 81 | 133 |
| 293 | 127 | 53 |
| 294 | 54 | 46 |
| 295 | 20 | 65 |
| 296 | 26 | 63 |
| 297 | 27 | 115 |
| 298 | 30 | 187 |
| 299 | 85 | 195 |
| 300 | 48 | 126 |
| 301 | 12 | 34 |
| 302 | 40 | 12 |
| 303 | 33 | 28 |
| 304 | 9.3 | 30 |
| 305 | 9.5 | 18 |
| 306 | 4.6 | 9.4 |
| 307 | 19 | 21 |
| 308 | 11 | 43 |
| 309 | 75 | 63 |
| 310 | 90 | 294 |
| 311 | 3.3 | 2.3 |
| 312 | 19 | 17 |
| 313 | 74 | 65 |
| 314 | 13 | 29 |
| 315 |  | 19 |
| 316 | 42 | 45 |
| 317 | 26 | 328 |
| 318 | 31 | 124 |
| 319 | 23 | 23 |
| 320 | 96 | 123 |
| 321 | 26 | 120 |
| 322 | 94 | 83 |
| 323 | 97 | 86 |
| 324 | 119 | 178 |
| 325 | 34 | 106 |
| 326 | 85 | 112 |
| 327 | 39 | 120 |
| 328 | 33 | 157 |
| 329 | 57 | 194 |
| 330 | 7.1 | 9.9 |
| 331 | 11 | 27 |
| 332 | 140 | 361 |
| 333 | 46 | 39 |
| 334 | 32 | 23 |
| 335 | 7.1 | 9.0 |
| 336 | 37 | 129 |
| 337 | 1.2 | 12 |
| 338 | 2.4 | 11 |
| 339 | 79 | 90 |
| 340 | 54 | 217 |
| 341 | 3.3 | 11 |
| 342 | 5.6 | 24 |
| 343 | 2.2 | 6.5 |
| 344 | 8.8 | 191 |
| 345 | 18 | 50 |
| 346 | 351 | 239 |
| 347 | 11 | 26 |
| 348 | 11 | 6.4 |
| 349 | 5.1 | 7.2 |
| 350 | 12 | 14 |
| 351 | 23 | 22 |
| 352 | 23 | 13 |
| 353 | 52 | 58 |
| 354 | 221 | 265 |
| 355 | 43 | 7.8 |
| 356 | 16 | 19 |
| 357 | 19 | 16 |
| 358 | 11 | 19 |
| 359 | 19 | 15 |
| 360 | 7.4 | 25 |
| 361 |  | 189 |
| 362 |  | 31 |
| 363 | 76 | 88 |
| 364 | 8.2 | 10 |
| 365 | 31 | 121 |
| 366 | 12 | 18 |
| 367 | 6.9 | 8.7 |
| 368 | 39 | 56 |
| 369 | 11 | 17 |
| 370 | 27 | 130 |
| 371 | 6.0 | 9.2 |
| 372 | 42 | 117 |
| 373 | 44 | 50 |
| 374 | 16 | 13 |
| 375 | 20 | 13 |

TABLE A-continued

| Ex | HTRF Binding Assay (IC50, uM) | pMLKL HCS Cell Assay (IC50, uM) |
|---|---|---|
| 376 | 4.3 | 9.1 |
| 377 | 6.3 | 5.5 |
| 378 | 154 | 251 |
| 379 | 11 | 11 |
| 380 | 11 | 23 |
| 381 | 7.2 | 26 |
| 382 | 29 | 29 |
| 383 | 5.2 | 7.2 |
| 384 | 22 | 51 |
| 385 | 60 | 291 |
| 386 | 2.8 | 1.9 |
| 387 | 8.0 | 15 |
| 388 | 8.0 | 7.2 |
| 389 | 7.2 | 9.9 |
| 390 | 4.5 | 11 |
| 391 | 105 | 215 |
| 392 | 390 | 277 |
| 393 | 255 | 264 |
| 394 | 28 | 76 |
| 395 | 20 | 12 |
| 396 | 93 | 145 |
| 397 |  | 8.7 |
| 398 | 10 | 9.4 |
| 399 | 2.9 | 25 |
| 400 | 46 | 48 |
| 401 | 15 | 27 |
| 402 | 8.5 | 4.8 |
| 403 | 33 | 25 |
| 404 | 25 | 63 |
| 405 | 7.3 | 8.5 |
| 406 | 14 | 10 |
| 407 | 24 | 15 |
| 408 | 17 | 12 |
| 409 | 13 | 9.2 |
| 410 | 7.3 | 6.3 |
| 411 | 5.5 | 3.8 |
| 412 |  | 7.2 |
| 413 | 4.5 | 48 |
| 414 | 2.0 | 11 |
| 415 | 26 | 18 |
| 416 | 20 | 32 |
| 417 | 7.1 | 7.9 |
| 418 | 4.7 | 4.2 |
| 419 | 42 | 19 |
| 420 | 63 | 140 |
| 421 | 15,000 | 37 |
| 422 | 144 | 148 |
| 423 | 39 | 47 |
| 424 | 353 | 24 |
| 425 | 15,000 | 51 |
| 426 | 7.0 | 7.4 |
| 427 | 173 | 405 |
| 428 | 22 | 8.4 |
| 429 | 20 | 4.0 |
| 430 | 26 | 22 |
| 431 | 89 | 74 |
| 432 | 2.3 | 3.0 |
| 433 | 10 | 3.7 |
| 434 | 9.1 | 24 |
| 435 | 14 | 6.0 |
| 436 | 21 | 8.5 |
| 437 | 9.5 | 12 |
| 438 | 2.5 | 2.1 |
| 439 | 5.8 | 11 |
| 440 | 3.0 | 2.7 |
| 441 | 9.1 | 25 |
| 442 | 7.7 | 17 |
| 443 | 2.5 | 21 |
| 444 | 12 | 28 |
| 445 | 2.7 | 0.83 |
| 446 | 100 | 171 |
| 447 | 35 | 126 |
| 448 | 5.6 | 6.7 |
| 449 | 5.3 | 2.8 |
| 450 | 22 | 45 |
| 451 | 3.1 | 4.3 |
| 452 | 37 | 101 |
| 453 | 12 | 23 |
| 454 | 2.9 | 4.0 |
| 455 | 12 | 27 |
| 456 | 20 | 20 |
| 457 | 6.1 | 3.8 |
| 458 | 16 | 5.8 |
| 459 | 13 | 2.6 |
| 460 | 7.4 | 12 |
| 461 | 14 | 15 |
| 462 | 8.7 | 9.1 |
| 463 | 12 | 4.6 |
| 464 | 14 | 33 |
| 465 | 101 | 388 |
| 466 | 48 | 116 |
| 467 | 14 | 31 |
| 468 | 9.5 | 37 |
| 469 | 15 | 79 |
| 470 | 18 | 51 |
| 471 | 9.0 | 143 |
| 472 | 79 | 74 |
| 473 | 58 | 88 |
| 474 | 19 | 98 |
| 475 | 42 | 47 |
| 476 | 206 | 72 |
| 477 | 16 | 72 |
| 478 | 60 | 78 |
| 479 | 9.3 | 8.5 |
| 480 | 22 | 323 |
| 481 | 2.9 | 106 |
| 482 | 40 | 205 |
| 483 | 38 | 44 |
| 484 | 5.1 | 9.7 |
| 485 | 4.8 | 2.9 |
| 486 | 70 | 22 |
| 487 | 4.3 | 1.3 |
| 488 | 3.7 | 12 |
| 489 | 3.0 | 0.76 |
| 490 | 6.0 | 30 |
| 491 | 4.4 | 5.2 |
| 492 | 5.8 | 6.7 |
| 493 | 42 | 106 |
| 494 | 8.3 | 139 |
| 495 | 18 | 313 |
| 496 | 6.7 | 13 |
| 497 | 9.4 | 286 |
| 498 | 11 | 3.8 |
| 499 | 4.3 | 11 |
| 500 | 19 | 36 |
| 501 | 18 | 129 |
| 502 | 5.7 | 58 |
| 503 | 38 | 206 |
| 504 | 8.7 | 46 |
| 505 | 2.8 | 12 |
| 506 | 14 | 94 |
| 507 | 7.9 | 33 |
| 508 | 13 | 110 |
| 509 | 167 | 315 |
| 510 | 34 | 99 |
| 511 | 13 | 41 |
| 512 | 18 | 97 |
| 513 | 40 | 184 |
| 514 | 17 | 170 |
| 515 | 53 | 196 |
| 516 | 36 | 80 |
| 517 | 19 | 11 |
| 518 | 59 | 22 |
| 519 | 49 | 57 |
| 520 | 71 | 77 |
| 521 | 53 | 44 |
| 522 | 103 | 131 |
| 523 | 91 | 20 |
| 524 | 168 | 118 |
| 525 | 240 | 140 |
| 526 | 130 | 108 |
| 527 | 138 | 79 |
| 528 | 108 | 430 |
| 529 | 65 | 47 |

TABLE A-continued

| Ex | HTRF Binding Assay (IC50, uM) | pMLKL HCS Cell Assay (IC50, uM) |
| --- | --- | --- |
| 530 | 29 | 43 |
| 531 | 264 | 313 |
| 532 | 115 | 126 |
| 533 | 258 | 334 |
| 534 | 24 | 23 |
| 535 | 46 | 28 |
| 536 | 27 | 36 |
| 537 | 27 | 21 |
| 538 | 32 | 37 |
| 539 | 44 | 55 |
| 540 | 69 | 96 |
| 541 | 190 | 404 |
| 542 | 4.0 | 58 |
| 543 | 25 | 6,250 |
| 544 | 124 | 5,666 |
| 545 | 30 | 330 |
| 546 | 19 | 107 |
| 547 | 44 | 95 |
| 548 | 30 | 91 |
| 549 | 13 | 18 |
| 550 | 24 | 0.85 |
| 551 | 60 | 532 |
| 552 | 82 | 369 |
| 553 | 145 | 943 |
| 554 | 7.1 | 110 |
| 555 | 144 | 1,535 |
| 556 | 771 | 5,379 |
| 557 | 140 | 1,975 |
| 558 | 1,186 | 6,250 |
| 559 | 263 | 4,453 |
| 560 | 14 | 219 |
| 561 | 21 | 271 |
| 562 | 8.4 | 1.0 |
| 563 |  | 33 |
| 564 | 56 | 39 |
| 565 | 35 | 2.9 |
| 566 | 21 | 31 |
| 567 | 19 | 15 |
| 568 | 6.9 | 5.2 |
| 569 | 3.2 | 3.4 |
| 570 | 6.2 | 1.2 |
| 571 | 12 | 14 |
| 572 |  | 2.8 |
| 573 |  | 17 |
| 574 |  | 22 |
| 575 |  | 13 |
| 576 | 51 | 31 |
| 577 |  | 2.7 |
| 578 |  | 6.7 |
| 579 |  | 24 |
| 580 |  | 41 |
| 581 |  | 20 |
| 582 |  | 5.4 |
| 583 |  | 4.2 |
| 584 |  | 10 |
| 585 |  | 49 |
| 586 | 16 | 3.6 |
| 587 |  | 22 |
| 588 |  | 157 |
| 589 |  | 11 |
| 590 |  | 108 |
| 591 | 309 | 237 |
| 592 | 92 | 86 |
| 593 | 36 | 39 |
| 594 | 65 | 245 |
| 595 | 94 | 202 |
| 596 | 94 | 253 |
| 597 | 7.1 | 9.7 |
| 598 | 10 | 28 |
| 599 | 11 | 29 |
| 600 | 20 | 72 |
| 601 | 11 | 17 |
| 602 | 87 | 178 |
| 603 | 54 | 95 |
| 604 | 11 | 29 |
| 605 | 7.7 | 8.8 |
| 606 | 7.6 | 22 |
| 607 | 3.4 | 8.4 |
| 608 | 13 | 17 |
| 609 | 28 | 79 |
| 610 | 13 | 13 |
| 611 | 9.6 | 35 |
| 612 | 5.4 | 3.1 |
| 613 | 5.8 | 2.7 |
| 614 | 16 | 2.6 |
| 615 | 5.8 | 2.8 |
| 616 | 5.2 | 2.5 |
| 617 | 5.3 | 2.4 |
| 618 | 3.8 | 2.3 |
| 619 | 9.1 | 3.1 |
| 620 | 6.0 | 1.8 |
| 621 | 10 | 1.6 |
| 622 | 12 | 1.2 |
| 623 | 33 | 10 |
| 624 | 26 | 10 |
| 625 | 6.0 | 1.8 |
| 626 | 11 | 2.8 |
| 627 | 7.1 | 3.6 |
| 628 | 5.7 | 3.9 |
| 629 | 13 | 5.5 |
| 630 | 11 | 16 |
| 631 | 15 | 6.6 |
| 632 | 305 | 2.2 |
| 633 | 12 | 3.8 |
| 634 | 7.5 | 2.8 |
| 635 | 9.4 | 7.3 |
| 636 | 8.8 | 13 |
| 637 | 12 | 2.6 |
| 638 | 6.8 | 6.6 |
| 639 | 110 | 68 |
| 640 | 47 | 47 |
| 641 | 5.8 | 7.4 |
| 642 | 4.3 | 3.1 |
| 643 | 15 | 32 |
| 644 | 7.5 | 6.8 |
| 645 | 7.4 | 24 |
| 646 | 6.0 | 4.2 |
| 647 | 32 | 25 |
| 648 | 38 | 21 |
| 649 | 16 | 35 |
| 650 | 7.3 | 4.5 |
| 651 | 12 | 12 |
| 652 | 7.8 | 8.6 |
| 653 | 9.4 | 22 |
| 654 | 14 | 6.7 |
| 655 | 11 | 6.8 |
| 656 | 8.6 | 3.0 |
| 657 | 10 | 13 |
| 658 | 8.2 | 8.2 |
| 659 | 10 | 18 |
| 660 | 13 | 9.4 |
| 661 | 18 | 26 |
| 662 | 3.8 | 1.4 |
| 663 | 6.1 | 2.0 |
| 664 | 14 | 10 |
| 665 | 15 | 25 |
| 666 | 5.1 | 2.9 |
| 667 | 3.9 | 2.6 |
| 668 | 7.9 | 7.9 |
| 669 | 1.8 | 3.0 |
| 670 | 4.2 | 2.9 |
| 671 | 5.9 | 3.9 |
| 672 | 7.4 | 15 |
| 673 | 6.3 | 7.9 |
| 674 | 6.9 | 4.9 |
| 675 | 15 | 3.9 |
| 676 | 10 | 2.5 |
| 677 | 7.5 | 2.1 |
| 678 | 3.8 | 2.9 |
| 679 | 3.2 | 2.7 |
| 680 | 28 | 36 |
| 681 | 6.2 | 19 |
| 682 | 10 | 18 |
| 683 | 28 | 34 |

TABLE A-continued

| Ex | HTRF Binding Assay (IC50, uM) | pMLKL HCS Cell Assay (IC50, uM) |
|---|---|---|
| 684 | 21 | 44 |
| 685 | 5.3 | 29 |
| 686 | 4.9 | 2.7 |
| 687 | 22 | 37 |
| 688 | 7.7 | 29 |
| 689 | 50 | 184 |
| 690 | 282 | 5.0 |
| 691 | 10 | 16 |
| 692 | 4.7 | 15 |
| 693 | 12 | 11 |
| 694 | 12 | 26 |
| 695 | 13 | 86 |
| 696 | 13 | 23 |
| 697 | 9.4 | 32 |
| 698 | 11 | 26 |
| 699 | 51 | 112 |
| 700 | 82 | 105 |
| 701 | 9.5 | 9.0 |
| 702 | 9.3 | 5.1 |
| 703 | 7.9 | 9.0 |
| 704 | 15 | 12 |
| 705 | 30 | 18 |
| 706 | 7.9 | 25 |
| 707 | 119 | 36 |
| 708 | 4.3 | 9.3 |
| 709 | 12 | 4.4 |
| 710 | 10 | 14 |
| 711 | 17 | 12 |
| 712 | 12 | 31 |
| 713 | 13 | 13 |
| 714 | 4.6 | 3.7 |
| 715 | 14 | 124 |
| 716 | 6.9 | 8.7 |
| 717 | 54 | 29 |
| 718 | 11 | 7.3 |
| 719 |  | 122 |
| 720 |  | 10 |
| 721 |  | 129 |
| 722 | 26 | 9.0 |
| 723 |  | 252 |
| 724 |  | 213 |
| 725 |  | 68 |
| 726 |  | 234 |
| 727 |  | 69 |
| 728 |  | 59 |
| 729 |  | 80 |
| 730 |  | 384 |
| 731 |  | 253 |
| 732 |  | 24 |
| 733 |  | 39 |
| 734 | 13 | 26 |
| 735 | 64 | 105 |
| 736 | 27 | 46 |
| 737 | 26 | 27 |
| 738 | 24 | 99 |
| 739 | 39 | 223 |
| 740 | 25 | 20 |
| 741 | 8.8 | 6.1 |
| 742 | 24 | 26 |
| 743 | 22 | 8.8 |
| 744 | 15 | 34 |
| 745 |  | 4.9 |
| 746 |  | 8.1 |
| 747 |  | 26 |
| 748 |  | 3.5 |
| 749 | 9.6 | 2.5 |
| 750 |  | 2.5 |
| 751 |  | 24 |
| 752 |  | 1.2 |
| 753 |  | 25 |
| 754 |  | 16 |
| 755 |  | 9.6 |
| 756 |  | 3.9 |
| 757 |  | 234 |
| 758 |  | 3.4 |
| 759 | 17 | 2.7 |
| 760 |  | 42 |
| 761 | 6.7 | 5.9 |
| 762 |  | 2.0 |
| 763 | 51 | 43 |
| 764 | 29 | 67 |
| 765 | 78 | 195 |
| 766 | 17 | 76 |
| 767 | 9.0 | 25 |
| 768 | 49 | 82 |
| 769 | 157 | 295 |
| 770 | 43 | 335 |
| 771 | 189 | 128 |
| 772 | 46 | 113 |
| 773 | 75 | 230 |
| 774 | 11 | 22 |
| 775 | 88 | 74 |
| 776 | 113 | 143 |
| 777 | 12 | 12 |
| 778 | 10 | 26 |
| 779 | 10 | 48 |
| 780 | 21 | 19 |
| 781 | 5.3 | 26 |
| 782 | 15 | 23 |
| 783 | 6.9 | 8.7 |
| 784 | 3.7 | 2.6 |
| 785 | 17 | 6.2 |
| 786 | 16 | 16 |
| 787 | 7.9 | 12 |
| 788 | 17 | 8.3 |
| 789 | 62 | 29 |
| 790 | 4.9 | 5.1 |
| 791 | 10 | 4.0 |
| 792 | 9.9 | 6.2 |
| 793 | 7.8 | 4.4 |
| 794 | 2.7 | 2.7 |
| 795 | 9.5 | 3.7 |
| 796 | 8.1 | 3.5 |
| 797 | 3.1 | 2.2 |
| 798 | 13 | 4.7 |
| 799 | 6.1 | 4.8 |
| 800 | 7.1 | 3.0 |
| 801 | 6.9 | 1.8 |
| 802 | 8.6 | 14 |
| 803 | 2.9 | 3.4 |
| 804 | 2.0 | 4.9 |
| 805 |  | 2.4 |
| 806 | 4.0 | 2.9 |
| 807 | 11 | 13 |
| 808 | 6.1 | 25 |
| 809 | 5.5 | 15 |
| 810 | 5.2 | 3.9 |
| 811 | 3.8 | 23 |
| 812 | 11 | 27 |
| 813 | 16 | 42 |
| 814 | 3.8 | 4.3 |
| 815 | 7.2 | 11 |
| 816 | 11 | 28 |
| 817 | 8.2 | 22 |
| 818 | 11 | 8.7 |
| 819 | 9.8 | 14 |
| 820 | 4.5 | 16 |
| 821 | 9.5 | 1.8 |
| 822 | 7.9 | 11 |
| 823 | 3.3 | 8.6 |
| 824 | 4.3 | 4.2 |
| 825 | 11 | 8.3 |
| 826 | 4.6 | 2.4 |
| 827 | 2.3 | 9.9 |
| 828 | 8.4 | 13 |
| 829 | 13 | 7.2 |
| 830 | 4.9 | 3.8 |
| 831 | 2.5 | 2.5 |
| 832 | 7.6 | 12 |
| 833 | 6.2 | 8.8 |
| 834 | 7.2 | 10 |
| 835 | 6.1 | 4.1 |
| 836 | 8.3 | 5.2 |
| 837 | 22 | 38 |

TABLE A-continued

| Ex | HTRF Binding Assay (IC50, uM) | pMLKL HCS Cell Assay (IC50, uM) |
|---|---|---|
| 838 | 7.8 | 17 |
| 839 | 29 | 19 |
| 840 | 49 | 77 |
| 841 | 28 | 25 |
| 842 | 9.6 | 23 |
| 843 | 324 | 357 |
| 844 | 15 | 24 |
| 845 | 17 | 36 |
| 846 | 33 | 57 |
| 847 | 28 | 16 |
| 848 | 34 | 272 |
| 849 | 17 | 14 |
| 850 | 60 | 248 |
| 851 | 11 | 15 |
| 852 | 14 | 11 |
| 853 | 26 | 43 |
| 854 | 15 | 22 |
| 855 | 10 | 41 |
| 856 |  | 4.0 |
| 857 |  | 6.3 |
| 858 |  | 7.2 |
| 859 | 17 | 3.5 |
| 860 | 10 | 3.5 |
| 861 | 4.9 | 6.1 |
| 862 | 48 | 103 |
| 863 | 11 | 8.3 |
| 864 | 118 | 131 |
| 865 | 84 | 146 |
| 866 | 104 | 347 |
| 867 | 7.6 | 2.3 |
| 868 | 14 | 9.2 |
| 869 | 6.6 | 5.6 |
| 870 | 8.3 | 8.1 |
| 871 | 13 | 6.2 |
| 872 | 9.1 | 7.6 |
| 873 | 3.4 | 8.6 |
| 874 | 12 | 25 |
| 875 | 12 | 3.2 |
| 876 | 14 | 3.4 |
| 877 | 11 | 3.9 |
| 878 | 13 | 8.9 |
| 879 | 24 | 4.6 |
| 880 |  | 7.4 |
| 881 |  | 5.6 |
| 882 | 7.0 | 5.0 |
| 883 |  | 5.2 |
| 884 |  | 6.6 |
| 885 | 8.7 | 5.0 |
| 886 | 3.7 | 2.6 |
| 887 | 16 | 1.6 |
| 888 | 5.8 | 2.2 |
| 889 | 18 | 12 |
| 890 | 43 | 92 |
| 891 | 32 | 9.3 |
| 892 | 956 | 28 |
| 893 | 15,000 | 17 |
| 894 | 75 | 115 |
| 895 | 12 | 12 |
| 896 | 65 | 64 |
| 897 | 242 | 482 |
| 898 | 42 | 19 |
| 899 | 28 | 48 |
| 900 | 18 | 23 |
| 901 | 7,124 | 141 |
| 902 | 23 | 18 |
| 903 | 29 | 58 |
| 904 | 20 | 15 |
| 905 | 15 | 15 |
| 906 | 7.4 | 20 |
| 907 | 47 | 36 |
| 908 | 25 | 27 |
| 909 | 10 | 5.6 |
| 910 | 6.4 | 3.5 |
| 911 | 12 | 3.5 |
| 912 | 6.7 | 2.3 |
| 913 | 4.1 | 2.8 |
| 914 | 17 | 9.5 |
| 915 | 7.8 | 1.8 |
| 916 | 10 | 15 |
| 917 | 4.0 | 2.6 |
| 918 | 5.5 | 4.6 |
| 919 | 5.0 | 3.2 |
| 920 | 0.73 | 2.3 |
| 921 | 13 | 16 |
| 922 | 9.6 | 4.2 |
| 923 | 3.2 | 5.3 |
| 924 | 5.6 | 5.0 |
| 925 | 5.7 | 5.1 |
| 926 | 13 | 3.0 |
| 927 | 4.6 | 4.3 |
| 928 | 25 | 24 |
| 929 | 69 | 50 |
| 930 | 2.9 | 3.2 |
| 931 | 5.5 | 2.7 |
| 932 | 468 | 7.0 |
| 933 | 9.9 | 11 |
| 934 | 4.7 | 8.1 |
| 935 | 2.7 | 2.0 |
| 936 | 7.0 | 7.5 |
| 937 | 23 | 4.5 |
| 938 | 8.0 | 15 |
| 939 | 2.1 | 3.4 |
| 940 | 9.7 | 3.0 |
| 941 | 3.9 | 2.5 |
| 942 | 20 | 5.0 |
| 943 | 48 | 326 |
| 944 | 2.5 | 22 |
| 945 | 9.4 | 65 |
| 946 | 11 | 65 |
| 947 | 6.6 | 71 |
| 948 | 147 | 22 |
| 949 | 25 | 63 |
| 950 | 10 | 69 |
| 951 | 2.3 | 15 |
| 952 | 3.2 | 24 |
| 953 | 20 | 182 |
| 954 | 2.7 | 20 |
| 955 | 6.8 | 22 |
| 956 | 24 | 185 |
| 957 | 6.1 | 13 |
| 958 | 46 | 78 |
| 959 | 3.6 | 26 |
| 960 | 23 | 194 |
| 961 | 6.5 | 25 |
| 962 | 23 | 130 |
| 963 | 3.2 | 34 |
| 964 | 4.4 | 8.2 |
| 965 |  | 10 |
| 966 |  | 5.6 |
| 967 |  | 16 |
| 968 | 9.8 | 4.1 |
| 969 |  | 8.2 |
| 970 |  | 9.3 |
| 971 |  | 2.9 |
| 972 |  | 6.9 |
| 973 |  | 9.1 |
| 974 |  | 7.4 |
| 975 |  | 8.1 |
| 976 |  | 3.1 |
| 977 |  | 10 |
| 978 |  | 5.8 |
| 979 |  | 19 |
| 980 |  | 33 |
| 981 |  | 24 |
| 982 |  | 8.0 |
| 983 | 3.8 | 2.2 |
| 984 | 8.0 | 4.4 |
| 985 | 15 | 6.7 |
| 986 | 4.0 | 1.6 |
| 987 | 4.9 | 2.9 |
| 988 | 29 | 18 |
| 989 | 2.7 | 1.6 |
| 990 | 6.6 | 2.3 |
| 991 | 3.2 | 1.4 |

TABLE A-continued

| Ex | HTRF Binding Assay (IC50, uM) | pMLKL HCS Cell Assay (IC50, uM) |
|---|---|---|
| 992 | 6.6 | 2.0 |
| 993 | 2.9 | 1.4 |
| 994 | 3.9 | 1.3 |
| 995 | 3.8 | 2.4 |
| 996 | 5.8 | 1.0 |
| 997 | 6.4 | 1.4 |
| 998 | 2.7 | 1.2 |
| 999 | 115 | 3.2 |
| 1000 | 8.4 | 5.4 |
| 1001 | 12 | 65 |
| 1002 | 3.4 | 5.2 |
| 1003 | 4.3 | 3.8 |
| 1004 | 6.2 | 17 |
| 1005 | 7.1 | 2.9 |
| 1006 | 2.4 | 7.2 |
| 1007 | 7.3 | 9.0 |
| 1008 | 2.4 | 5.7 |
| 1009 | 10 | 24 |
| 1010 | 5.6 | 9.6 |
| 1011 | 5.1 | 15 |
| 1012 | 15,000 | 7.1 |
| 1013 | 4.1 | 9.9 |
| 1014 | 3.6 | 3.7 |
| 1015 | 6.5 | 22 |
| 1016 | 2.7 | 5.2 |
| 1017 | 1.5 | 6.9 |
| 1018 | 8.0 | 9.3 |
| 1019 | 7.2 | 8.1 |
| 1020 | 3.7 | 7.6 |
| 1021 | 3.0 | 12 |
| 1022 | 3.4 | 4.6 |
| 1023 |  | 15 |
| 1024 |  | 0.75 |
| 1025 |  | 2.9 |
| 1026 |  | 0.52 |
| 1027 |  | 168 |
| 1028 |  | 254 |
| 1029 |  | 1.3 |
| 1030 |  | 367 |
| 1031 |  | 162 |
| 1032 |  | 85 |
| 1033 |  | 97 |
| 1034 |  | 1.1 |
| 1035 |  | 3.2 |
| 1036 |  | 119 |
| 1037 |  | 3.5 |
| 1038 |  | 6.2 |
| 1039 |  | 0.78 |
| 1040 |  | 58 |
| 1041 |  | 1.5 |
| 1042 |  | 2.9 |
| 1043 |  | 2.3 |
| 1044 | 1.1 | 1.4 |
| 1045 | 3.3 | 4.2 |
| 1046 | 12 | 223 |
| 1047 | 10 | 91 |
| 1048 | 385 | 389 |
| 1049 | 153 | 100 |
| 1050 | 14 | 70 |
| 1051 | 14 | 35 |
| 1052 | 39 | 263 |
| 1053 | 32 | 231 |
| 1054 | 35 | 83 |
| 1055 | 15 | 53 |
| 1056 | 49 | 295 |
| 1057 | 37 | 109 |
| 1058 | 17 | 244 |
| 1059 | 16 | 248 |
| 1060 | 14 | 80 |
| 1061 | 13 | 7.1 |
| 1062 | 14 | 98 |
| 1063 | 49 | 414 |
| 1064 | 35 | 103 |
| 1065 | 23 | 96 |
| 1066 | 12 | 16 |
| 1067 | 83 | 76 |
| 1068 | 39 | 106 |
| 1069 | 90 | 375 |
| 1070 | 23 | 22 |
| 1071 | 42 | 131 |
| 1072 | 41 | 79 |
| 1073 | 47 | 215 |
| 1074 | 43 | 291 |
| 1075 | 37 | 108 |
| 1076 | 37 | 222 |
| 1077 | 42 | 227 |
| 1078 | 40 | 30 |
| 1079 | 3.4 | 40 |
| 1080 | 1.6 | 7.1 |
| 1081 | 5.1 | 7.2 |
| 1082 | 11 | 30 |
| 1083 | 3.7 | 17 |
| 1084 | 3.7 | 21 |
| 1085 | 13 | 50 |
| 1086 | 6.1 | 42 |
| 1087 | 2.8 | 10 |
| 1088 | 7.5 | 9.8 |
| 1089 | 2.9 | 44 |
| 1090 | 9.0 | 41 |
| 1091 | 4.6 | 17 |
| 1092 | 1.7 | 35 |
| 1093 | 3.8 | 36 |
| 1094 | 5.6 | 21 |
| 1095 | 6.3 | 13 |
| 1096 | 3.2 | 25 |
| 1097 | 155 | 310 |
| 1098 | 39 | 26 |
| 1099 | 9.2 | 21 |
| 1100 | 138 | 247 |
| 1101 | 23 | 7.1 |
| 1102 | 12 | 19 |
| 1103 | 35 | 22 |
| 1104 | 12 | 57 |
| 1105 | 32 | 114 |
| 1106 | 25 | 4.3 |
| 1107 | 13 | 4.7 |
| 1108 | 51 | 49 |
| 1109 | 16 | 19 |
| 1110 | 40 | 18 |
| 1111 | 22 | 33 |
| 1112 | 23 | 21 |
| 1113 | 18 | 29 |
| 1114 | 7.6 | 6.4 |
| 1115 | 16 | 25 |
| 1116 | 38 | 49 |
| 1117 | 3.0 | 7.3 |
| 1118 | 3.7 | 3.4 |
| 1119 | 11 | 35 |
| 1120 | 43 | 1.5 |
| 1121 | 62 | 39 |
| 1122 | 4.8 | 8.6 |
| 1123 | 11 | 31 |
| 1124 | 3.6 | 5.5 |
| 1125 | 11 | 11 |
| 1126 | 7.3 | 1.8 |
| 1127 | 5.9 | 14 |
| 1128 | 7.4 | 10 |
| 1129 | 13 | 37 |
| 1130 | 7.9 | 15 |
| 1131 | 84 | 3.3 |
| 1132 | 9.5 | 12 |
| 1133 | 7.7 | 9.5 |
| 1134 | 7.3 | 6.8 |
| 1135 | 46 | 32 |
| 1136 | 19 | 15 |
| 1137 | 75 | 20 |
| 1138 | 7.2 | 0.55 |
| 1139 | 35 | 1.2 |
| 1140 | 5.7 | 1.1 |
| 1141 | 6.0 | 0.75 |
| 1142 | 6.3 | 0.58 |
| 1143 | 5.8 | 0.53 |
| 1144 | 8.8 | 0.34 |
| 1145 | 8.5 | 1.9 |

TABLE A-continued

| Ex | HTRF Binding Assay (IC50, uM) | pMLKL HCS Cell Assay (IC50, uM) |
| --- | --- | --- |
| 1146 | 4.4 | 0.47 |
| 1147 | 6.3 | 1.1 |
| 1148 | 5.2 | 1.0 |
| 1149 | 4.0 | 2.6 |
| 1150 | 4.2 | 1.3 |
| 1151 | 4.0 | 2.8 |
| 1152 | 5.7 | 1.0 |
| 1153 | 7.4 | 2.8 |
| 1154 | 2.6 | 1.0 |
| 1155 | 17 | 11 |
| 1156 | 34 | 3.0 |
| 1157 | 4.8 | 1.7 |
| 1158 | 6.0 | 2.3 |
| 1159 | 4.1 | 0.85 |
| 1160 | 7.3 | 10 |
| 1161 | 5.3 | 2.6 |
| 1162 | 6.6 | 3.2 |
| 1163 | 2.5 | 2.7 |
| 1164 | 2.5 | 6.0 |
| 1165 | 2.5 | 0.65 |
| 1166 | 3.0 | 8.6 |
| 1167 | 2.2 | 1.2 |
| 1168 | 3.3 | 0.37 |
| 1169 | 3.9 | 1.8 |
| 1170 | 3.0 | 0.74 |
| 1171 | 2.4 | 1.3 |
| 1172 | 2.7 | 5.5 |
| 1173 | 2.3 | 0.95 |
| 1174 | 3.6 | 1.3 |
| 1175 | 2.8 | 1.3 |
| 1176 | 3.7 | 1.4 |
| 1177 | 4.7 | 0.79 |
| 1178 | 2.2 | 1.8 |
| 1179 | 3.9 | 2.4 |
| 1180 | 2.3 | 1.1 |
| 1181 | 2.4 | 1.3 |
| 1182 | 214 | 139 |
| 1183 | 341 | 209 |
| 1184 | 50 | 23 |
| 1185 | 121 | 189 |
| 1186 | 32 | 36 |
| 1187 | 127 | 13 |
| 1188 | 76 | 86 |
| 1189 | 92 | 27 |
| 1190 | 77 | 12 |
| 1191 | 123 | 22 |
| 1192 | 183 | 98 |
| 1193 | 209 | 29 |
| 1194 | 267 | 166 |
| 1195 | 77 | 41 |
| 1196 | 360 | 336 |
| 1197 | 150 | 23 |
| 1198 | 81 | 67 |
| 1199 | 97 | 164 |
| 1200 | 54 | 20 |
| 1201 | 62 | 15 |
| 1202 | 15,000 | 40 |
| 1203 | 3.0 | 25 |
| 1204 | 7.8 | 34 |
| 1205 | 11 | 46 |
| 1206 | 7.6 | 40 |
| 1207 | 2.8 | 24 |
| 1208 | 15 | 216 |
| 1209 | 72 | 241 |
| 1210 | 220 | 264 |
| 1211 | 575 | 116 |
| 1212 | 56 | 74 |
| 1213 | 107 | 20 |
| 1214 | 230 | 181 |
| 1215 | 87 | 76 |
| 1216 | 5.5 | 48 |
| 1217 | 6.3 | 67 |
| 1218 | 32 | 98 |
| 1219 | 117 | 270 |
| 1220 | 8.8 | 2.3 |
| 1221 | 5.6 | 3.9 |
| 1222 | 5.3 | 4.7 |
| 1223 | 13 | 41 |
| 1224 | 2.1 | 9.1 |
| 1225 |  | 8.8 |
| 1226 | 2.8 | 8.5 |
| 1227 |  | 2.9 |
| 1228 | 7.5 | 40 |
| 1229 | 3.8 | 1.3 |
| 1230 | 6.6 | 10 |
| 1231 | 35 | 18 |
| 1232 | 11 | 3.3 |
| 1233 | 7.2 | 2.4 |
| 1234 | 23 | 12 |
| 1235 | 34 | 7.7 |
| 1236 | 14 | 3.2 |
| 1237 | 4.8 | 0.90 |
| 1238 | 6.2 | 13 |
| 1239 | 2.2 | 1.1 |
| 1240 | 4.2 | 1.3 |
| 1241 | 5.7 | 0.61 |
| 1242 | 2.2 | 0.44 |
| 1243 | 3.3 | 0.37 |
| 1244 | 6.1 | 2.9 |
| 1245 | 3.5 | 0.75 |
| 1246 | 6.0 | 0.72 |
| 1247 | 8.4 | 0.58 |
| 1248 | 6.1 | 3.1 |
| 1249 | 15 | 2.5 |
| 1250 | 6.6 | 1.5 |
| 1251 | 3.5 | 0.90 |
| 1252 | 2.0 | 0.73 |
| 1253 | 13 | 1.5 |
| 1254 | 5.0 | 1.5 |
| 1255 | 3.4 | 4.7 |
| 1256 | 3.0 | 2.1 |
| 1257 | 19 | 56 |
| 1258 | 4.4 | 0.53 |
| 1259 | 4.3 | 1.6 |
| 1260 | 5.4 | 0.55 |
| 1261 | 11 | 2.8 |
| 1262 | 7.3 | 1.1 |
| 1263 | 5.7 | 2.8 |
| 1264 | 9.4 | 3.9 |
| 1265 | 11 | 0.72 |
| 1266 | 7.6 | 0.87 |
| 1267 | 2.5 | 1.1 |
| 1268 | 4.4 | 1.5 |
| 1269 | 2.1 | 3.0 |
| 1270 | 3.3 | 0.79 |
| 1271 | 1.9 | 1.2 |
| 1272 | 3.6 | 0.38 |
| 1273 | 3.2 | 0.86 |
| 1274 | 2.3 | 0.42 |
| 1275 | 2.4 | 0.98 |
| 1276 | 4.1 | 0.64 |
| 1277 | 2.6 | 1.1 |
| 1278 | 4.8 | 1.9 |
| 1279 | 2.7 | 0.27 |
| 1280 | 2.7 | 0.32 |
| 1281 | 2.6 | 0.43 |
| 1282 | 2.9 | 5.0 |
| 1283 | 2.0 | 2.4 |
| 1284 | 2.0 | 1.7 |
| 1285 | 2.2 | 0.60 |
| 1286 | 4.5 | 2.5 |
| 1287 | 2.7 | 0.75 |
| 1288 | 5.0 | 5.2 |
| 1289 | 5,646 | 0.49 |
| 1290 | 7.5 | 25 |
| 1291 | 2.9 | 2.8 |
| 1292 | 1.9 | 0.58 |
| 1293 | 16 | 3.8 |
| 1294 | 7.0 | 24 |
| 1295 | 2.7 | 0.61 |
| 1296 | 2.3 | 0.69 |
| 1297 | 5.7 | 9.1 |
| 1298 | 1.7 | 1.4 |
| 1299 | 4.0 | 0.58 |

TABLE A-continued

| Ex | HTRF Binding Assay (IC50, uM) | pMLKL HCS Cell Assay (IC50, uM) |
|---|---|---|
| 1300 | 89 | 328 |
| 1301 | 175 | 298 |
| 1302 | 67 | 356 |
| 1303 | 91 | 291 |
| 1304 | 51 | 383 |
| 1305 | 866 | 480 |
| 1306 | 1.9 | 2.8 |
| 1307 | 3.3 | 0.89 |
| 1308 | 9.3 | 1.4 |
| 1309 | 4.4 | 0.62 |
| 1310 | 5.9 | 1.5 |
| 1311 | 2.4 | 0.81 |
| 1312 | 2.0 | 1.9 |
| 1313 | 2.1 | 1.3 |
| 1314 | 4.8 | 11 |
| 1315 | 17 | 52 |
| 1316 | 15 | 6.8 |
| 1317 | 12 | 7.5 |
| 1318 |  | 3.6 |
| 1319 |  | 8.4 |
| 1320 | 44 | 1.8 |
| 1321 |  | 2.3 |
| 1322 | 12 | 23 |
| 1323 | 8.8 | 4.9 |
| 1324 | 5.8 | 8.1 |
| 1325 | 9.2 | 2.9 |
| 1326 | 5.0 | 4.3 |
| 1327 | 3.2 | 1.2 |
| 1328 | 82 | 71 |
| 1329 | 1.6 | 3.7 |
| 1330 | 5.0 | 3.3 |
| 1331 | 19 | 21 |
| 1332 | 5.3 | 0.81 |
| 1333 | 19 | 15 |
| 1334 | 332 | 8.7 |
| 1335 | 18 | 4.4 |
| 1336 | 30 | 15 |
| 1337 | 8.0 | 2.8 |
| 1338 | 5.0 | 4.7 |
| 1339 |  | 39 |
| 1340 |  | 3.3 |
| 1341 |  | 4.1 |
| 1342 |  | 30 |
| 1343 | 106 | 0.87 |
| 1344 | 5.8 | 8.3 |
| 1345 |  | 31 |
| 1346 | 55 | 35 |
| 1347 | 51 | 213 |
| 1348 | 10 | 29 |
| 1349 | 21 | 41 |
| 1350 | 136 | 220 |
| 1351 | 4.4 | 29 |
| 1352 | 14 | 73 |
| 1353 | 19 | 288 |
| 1354 | 20 | 20 |
| 1355 | 19 | 28 |
| 1356 | 16 | 42 |
| 1357 | 42 | 39 |
| 1358 | 331 | 323 |
| 1359 | 167 | 342 |
| 1360 | 7.7 | 105 |
| 1361 | 43 | 30 |
| 1362 |  | 260 |
| 1363 |  | 26 |
| 1364 |  | 45 |
| 1365 |  | 253 |
| 1366 |  | 84 |
| 1367 |  | 64 |
| 1368 |  | 26 |
| 1369 |  | 47 |
| 1370 |  | 122 |
| 1371 |  | 255 |
| 1372 |  | 192 |
| 1373 |  | 20 |
| 1374 |  | 328 |
| 1375 |  | 39 |
| 1376 |  | 37 |
| 1377 |  | 375 |
| 1378 |  | 17 |
| 1379 |  | 134 |
| 1380 | 50 | 242 |
| 1381 | 87 | 71 |
| 1382 | 14 | 26 |
| 1383 | 187 | 364 |
| 1384 | 47 | 45 |
| 1385 | 9.7 | 16 |
| 1386 | 30 | 50 |
| 1387 |  | 4.0 |
| 1388 |  | 4.9 |
| 1389 |  | 85 |
| 1390 |  | 13 |
| 1391 |  | 372 |
| 1392 |  | 3.3 |
| 1393 |  | 18 |
| 1394 |  | 300 |
| 1395 |  | 10 |
| 1396 |  | 33 |
| 1397 |  | 28 |
| 1398 |  | 28 |
| 1399 |  | 3.1 |
| 1400 |  | 4.1 |
| 1401 |  | 78 |
| 1402 |  | 17 |
| 1403 |  | 92 |
| 1404 |  | 93 |
| 1405 |  | 38 |
| 1406 | 136 | 153 |
| 1407 | 38 | 94 |
| 1408 |  | 30 |
| 1409 |  | 224 |
| 1410 |  | 271 |
| 1411 |  | 167 |
| 1412 |  | 433 |
| 1413 |  | 95 |
| 1414 |  | 85 |
| 1415 | 78 | 40 |
| 1416 | 53 | 209 |
| 1417 |  | 4.9 |
| 1418 |  | 132 |
| 1419 | 46 | 99 |
| 1420 | 2.3 | 2.2 |
| 1421 | 109 | 274 |
| 1422 | 17 | 16 |
| 1423 | 3.5 | 25 |
| 1424 | 4.2 | 2.5 |
| 1425 | 2.1 | 1.5 |
| 1426 | 7.8 | 11 |
| 1427 | 30 | 18 |
| 1428 | 3.7 | 2.9 |
| 1429 | 16 | 28 |
| 1430 | 1.2 | 4.2 |
| 1431 | 2.4 | 5.5 |
| 1432 | 32 | 291 |
| 1433 | 4.1 | 11 |
| 1434 | 4.4 | 4.5 |
| 1435 | 5.6 | 7.6 |
| 1436 | 9.2 | 8.4 |
| 1437 |  | 3.0 |
| 1438 |  | 136 |
| 1439 |  | 1.9 |
| 1440 |  | 3.9 |
| 1441 |  | 7.5 |
| 1442 |  | 16 |
| 1443 |  | 2.9 |
| 1444 |  | 4.8 |
| 1445 |  | 7.6 |
| 1446 |  | 1.9 |
| 1447 |  | 7.5 |
| 1448 |  | 1.5 |
| 1449 |  | 131 |
| 1450 | 73 | 164 |
| 1451 |  | 99 |
| 1452 |  | 85 |
| 1453 |  | 318 |

TABLE A-continued

| Ex | HTRF Binding Assay (IC50, uM) | pMLKL HCS Cell Assay (IC50, uM) |
|---|---|---|
| 1454 | 10 | 6.8 |
| 1455 | 61 | 64 |
| 1456 |  | 97 |
| 1457 |  | 7.3 |
| 1458 |  | 8.2 |
| 1459 |  | 2.9 |
| 1460 | 9.5 | 42 |
| 1461 | 4.1 | 32 |
| 1462 | 3.1 | 3.2 |
| 1463 | 2.9 | 2.0 |
| 1464 | 2.8 | 4.7 |
| 1465 | 4.7 | 16 |
| 1466 | 4.5 | 3.3 |
| 1467 | 44 | 16 |
| 1468 | 125 | 278 |
| 1469 | 44 | 212 |
| 1470 | 76 | 287 |
| 1471 | 18 | 94 |
| 1472 | 1.3 | 3.2 |
| 1473 | 3.8 | 12 |
| 1474 | 13 | 14 |
| 1475 | 21 | 191 |
| 1476 | 26 | 77 |
| 1477 | 3.3 | 22 |
| 1478 | 23 | 221 |
| 1479 | 14 | 31 |
| 1480 | 2.0 | 12 |
| 1481 | 36 | 369 |
| 1482 | 2.7 | 17 |
| 1483 | 8.6 | 5.2 |
| 1484 | 0.63 | 1.9 |
| 1485 | 1.5 | 6.6 |
| 1486 | 2.2 | 4.2 |
| 1487 | 3.8 | 31 |
| 1488 | 4.2 | 15 |
| 1489 | 1.3 | 22 |
| 1490 | 1.2 | 12 |
| 1491 | 5.8 | 64 |
| 1492 | 3.2 | 7.6 |
| 1493 | 1.9 | 11 |
| 1494 | 5.9 | 143 |
| 1495 | 15 | 238 |
| 1496 | 12 | 85 |
| 1497 | 2.7 | 9.4 |
| 1498 |  | 223 |
| 1499 | 1.4 | 0.77 |
| 1500 | 3.8 | 1.4 |
| 1501 | 2.7 | 2.6 |
| 1502 | 2.9 | 0.53 |
| 1503 | 4.4 | 2.9 |
| 1504 |  | 10 |
| 1505 | 11 | 2.4 |
| 1506 | 9.3 | 4.3 |
| 1507 | 8.9 | 0.37 |
| 1508 | 15,000 | 8.0 |
| 1509 | 7.0 | 2.1 |
| 1510 | 8.6 | 1.6 |
| 1511 | 66 | 6.0 |
| 1512 | 96 | 5.1 |
| 1513 | 21 | 2.9 |
| 1514 | 6.3 | 4.8 |
| 1515 | 9.7 | 1.5 |
| 1516 | 5.8 | 0.62 |
| 1517 | 5.5 | 1.1 |
| 1518 | 4.6 | 1.6 |
| 1519 | 9.8 | 3.7 |
| 1520 | 7.8 | 3.3 |
| 1521 | 12 | 3.2 |
| 1522 | 14 | 3.8 |
| 1523 | 61 | 59 |
| 1524 | 9.2 | 4.3 |
| 1525 | 10 | 2.6 |
| 1526 | 1,667 | 6.8 |
| 1527 | 87 | 10 |
| 1528 | 96 | 78 |
| 1529 | 66 | 3.8 |
| 1530 | 15,000 | 44 |
| 1531 | 128 | 39 |
| 1532 | 50 | 2.1 |
| 1533 | 27 | 1.9 |
| 1534 | 47 | 1.9 |
| 1535 | 6.0 | 1.5 |
| 1536 | 66 | 7.9 |
| 1537 | 50 | 129 |
| 1538 | 64 | 71 |
| 1539 | 15,000 | 446 |
| 1540 | 19 | 11 |
| 1541 | 3.2 | 0.83 |
| 1542 | 4.1 | 2.5 |
| 1543 |  | 3.2 |
| 1544 |  | 2.3 |
| 1545 | 5.5 | 21 |
| 1546 | 11 | 17 |
| 1547 | 29 | 34 |
| 1548 | 3.0 | 0.60 |
| 1549 | 5.8 | 1.2 |
| 1550 | 4.8 | 2.9 |
| 1551 | 3.2 | 1.2 |
| 1552 | 6.6 | 9.7 |
| 1553 | 6.6 | 1.8 |
| 1554 | 9.2 | 1.4 |
| 1555 | 8.5 | 1.5 |
| 1556 | 28 | 3.5 |
| 1557 | 7.9 | 18 |
| 1558 | 4.3 | 8.8 |
| 1559 | 16 | 64 |
| 1560 | 2.9 | 0.93 |
| 1561 | 7.4 | 0.67 |
| 1562 | 3.8 | 0.55 |
| 1563 | 9.5 | 1.5 |
| 1564 | 3.3 | 1.0 |
| 1565 | 4.2 | 4.1 |
| 1566 | 15 | 8.9 |
| 1567 | 2.3 | 2.1 |
| 1568 | 10 | 46 |
| 1569 | 9.7 | 14 |
| 1570 | 6.7 | 2.0 |
| 1571 |  | 1.4 |
| 1572 |  | 0.41 |
| 1573 |  | 2.7 |
| 1574 | 16 | 0.61 |
| 1575 | 4.7 | 0.55 |
| 1576 | 10 | 0.56 |
| 1577 | 4.6 | 0.45 |
| 1578 | 2.8 | 1.0 |
| 1579 | 38 | 233 |
| 1580 | 25 | 117 |
| 1581 | 3.0 | 0.95 |
| 1582 | 3.7 | 2.3 |
| 1583 | 2.6 | 1.3 |
| 1584 | 15 | 1.9 |
| 1585 | 5.4 | 1.6 |
| 1586 | 2.7 | 0.60 |
| 1587 | 8.3 | 1.4 |
| 1588 | 2.4 | 1.1 |
| 1589 | 1.0 | 0.29 |
| 1590 | 8.2 | 0.82 |
| 1591 |  | 1.1 |
| 1592 | 4.3 | 6.1 |
| 1593 | 5.9 | 10 |
| 1594 | 3.3 | 6.1 |
| 1595 | 5.3 | 13 |
| 1596 | 2.2 | 2.2 |
| 1597 | 6.3 | 8.6 |
| 1598 | 9.5 | 1.2 |
| 1599 | 4.2 | 5.1 |
| 1600 | 11 | 1.6 |
| 1601 | 26 | 4.3 |
| 1602 | 5.1 | 9.5 |
| 1603 | 5.9 | 9.9 |
| 1604 | 11 | 5.7 |
| 1605 | 6.0 | 8.4 |
| 1606 | 2.4 | 2.0 |
| 1607 | 2.9 | 1.2 |

TABLE A-continued

| Ex | HTRF Binding Assay (IC50, uM) | pMLKL HCS Cell Assay (IC50, uM) |
|---|---|---|
| 1608 | 2.8 | 0.59 |
| 1609 | 5.6 | 1.5 |
| 1610 |  | 0.51 |
| 1611 | 4.7 | 5.1 |
| 1612 | 1.5 | 8.4 |
| 1613 | 11 | 4.6 |
| 1614 | 12 | 11 |
| 1615 | 7.4 | 5.5 |
| 1616 | 1.6 | 0.24 |
| 1617 | 4.0 | 1.1 |
| 1618 | 4.2 | 0.68 |
| 1619 | 3.8 | 1.3 |
| 1620 | 13 | 0.96 |
| 1621 | 1.1 | 0.67 |
| 1622 | 3.0 | 1.1 |
| 1623 | 2.7 | 2.3 |
| 1624 | 21 | 1.4 |
| 1625 | 2.4 | 1.1 |
| 1626 | 3.9 | 0.91 |
| 1627 |  | 8.6 |
| 1628 |  | 61 |
| 1629 |  | 9.2 |
| 1630 |  | 24 |
| 1631 |  | 8.3 |
| 1632 |  | 4.1 |
| 1633 | 3.8 | 2.4 |
| 1634 | 5.3 | 3.3 |
| 1635 | 51 | 8.1 |
| 1636 | 2.9 | 2.8 |
| 1637 | 5.1 | 1.2 |
| 1638 | 7.3 | 1.7 |
| 1639 | 7.3 | 1.4 |
| 1640 | 10 | 3.8 |
| 1641 |  | 0.43 |
| 1642 | 19 | 0.81 |
| 1643 |  | 1.4 |
| 1644 |  | 0.92 |
| 1645 |  | 2.5 |
| 1646 |  | 0.34 |
| 1647 | 9.0 | 0.86 |
| 1648 |  | 0.67 |
| 1649 |  | 1.8 |
| 1650 | 23 | 1.7 |
| 1651 |  | 0.68 |
| 1652 |  | 0.77 |
| 1653 |  | 1.1 |
| 1654 |  | 0.44 |
| 1655 | 3.1 | 1.3 |
| 1656 | 8.3 | 1.0 |
| 1657 | 12 | 1.1 |
| 1658 | 7.4 | 1.2 |
| 1659 | 1.6 | 0.48 |
| 1660 | 2.2 | 0.79 |
| 1661 | 36 | 31 |
| 1662 | 43 | 9.5 |
| 1663 | 3.3 | 6.3 |
| 1664 | 28 | 76 |
| 1665 | 92 | 33 |
| 1666 | 11 | 13 |
| 1667 | 20 | 73 |
| 1668 | 2.9 | 9.7 |
| 1669 | 427 | 231 |
| 1670 | 6.6 | 14 |
| 1671 | 4.9 | 8.0 |
| 1672 |  | 55 |
| 1673 |  | 36 |
| 1674 |  | 51 |
| 1675 |  | 134 |
| 1676 |  | 56 |
| 1677 |  | 10 |
| 1678 | 119 | 281 |
| 1679 | 56 | 156 |
| 1680 |  | 159 |
| 1681 | 40 | 121 |
| 1682 | 59 | 200 |
| 1683 |  | 188 |
| 1684 |  | 235 |
| 1685 | 64 | 478 |
| 1686 | 26 | 15 |
| 1687 | 35 | 154 |
| 1688 | 20 | 86 |
| 1689 | 5.1 | 10 |
| 1690 | 28 | 70 |
| 1691 | 8.6 | 13 |
| 1692 | 12 | 59 |
| 1693 | 8.7 | 4.0 |
| 1694 | 46 | 94 |
| 1695 | 13 | 9.0 |
| 1696 | 12 | 9.3 |
| 1697 | 66 | 191 |
| 1698 | 12 | 26 |
| 1699 | 158 | 487 |
| 1700 | 17 | 456 |
| 1701 | 15 | 377 |
| 1702 | 67 | 294 |
| 1703 |  | 309 |
| 1704 | 20 | 272 |
| 1705 | 35 | 150 |
| 1706 | 4.8 | 7.5 |
| 1707 | 10 | 12 |
| 1708 | 34 | 63 |
| 1709 | 27 | 14 |
| 1710 | 6.6 | 49 |
| 1711 |  | 16 |
| 1712 | 28 | 75 |
| 1713 | 121 | 143 |
| 1714 | 15 | 7.8 |
| 1715 | 14 | 38 |
| 1716 | 6.4 | 14 |
| 1717 | 3.4 | 0.65 |
| 1718 | 3.8 | 0.28 |
| 1719 | 4.7 | 1.1 |
| 1720 | 19 | 217 |
| 1721 | 37 | 42 |
| 1722 | 201 | 295 |
| 1723 |  | 3.1 |
| 1724 |  | 0.61 |
| 1725 | 17 | 20 |
| 1726 | 8.4 | 1.4 |
| 1727 | 4.7 | 4.3 |
| 1728 | 93 | 25 |
| 1729 | 75 | 25 |
| 1730 | 13 | 20 |
| 1731 | 60 | 28 |
| 1732 | 52 | 82 |
| 1733 |  | 234 |
| 1734 |  | 284 |
| 1735 |  | 251 |
| 1736 |  | 222 |
| 1737 |  | 36 |
| 1738 |  | 63 |
| 1739 | 62 | 46 |
| 1740 |  | 33 |
| 1741 | 26 | 101 |
| 1742 | 29 | 28 |
| 1743 | 9.8 | 36 |
| 1744 | 8.6 | 11 |
| 1745 | 11 | 4.2 |
| 1746 | 105 | 74 |
| 1747 | 126 | 274 |
| 1748 | 106 | 39 |
| 1749 | 207 | 204 |
| 1750 | 450 | 194 |
| 1751 | 53 | 48 |
| 1752 | 13 | 2.7 |
| 1753 | 9.6 | 4.1 |
| 1754 | 7.9 | 27 |
| 1755 | 177 | 197 |
| 1756 | 7 | 3.2 |
| 1757 | 26 | 25 |
| 1758 | 9.0 | 18 |
| 1759 | 4.4 | 4.0 |
| 1760 | 2.9 | 8.7 |
| 1761 | 8.5 | 3.8 |

TABLE A-continued

| Ex | HTRF Binding Assay (IC50, uM) | pMLKL HCS Cell Assay (IC50, uM) |
|---|---|---|
| 1762 | 3.3 | 3.6 |
| 1763 | 14 | 3.7 |
| 1764 | 8.6 | 7.4 |
| 1765 | 11 | 10 |
| 1766 | 228 | 375 |
| 1767 |  | 47 |
| 1768 | 16 | 34 |
| 1769 | 9.6 | 7.6 |
| 1770 | 376 | 352 |
| 1771 | 139 | 146 |
| 1772 | 20 | 26 |
| 1773 | 9.5 | 0.85 |
| 1774 | 8.7 | 2.7 |
| 1775 | 21 | 9.9 |
| 1776 | 2.2 | 0.74 |
| 1777 | 3.5 | 0.55 |
| 1778 | 4.7 | 12 |
| 1779 | 392 | 485 |
| 1780 | 20 | 39 |
| 1781 | 18 | 22 |
| 1782 | 283 | 239 |
| 1783 | 126 | 169 |
| 1784 | 31 | 49 |
| 1785 | 2.7 | 2.3 |
| 1786 | 7.2 | 9.6 |
| 1787 | 3.7 | 2.9 |
| 1788 | 102 | 131 |
| 1789 | 118 | 67 |
| 1790 | 112 | 95 |
| 1791 | 19 | 31 |
| 1792 | 4.9 | 0.37 |
| 1793 | 1.8 | 2.9 |
| 1794 | 3.2 | 1.0 |
| 1795 | 7.3 | 10 |
| 1796 |  | 243 |
| 1797 |  | 8.4 |
| 1798 | 36 | 15 |
| 1799 | 9.9 | 4.6 |
| 1800 | 17 | 3.0 |
| 1801 | 27 | 7.9 |
| 1802 | 1.9 | 0.45 |
| 1803 | 6.4 | 0.86 |
| 1804 | 15,000 | 420 |
| 1805 | 5.5 | 2.0 |
| 1806 | 27 | 2.2 |
| 1807 | 21 | 16 |
| 1808 | 2.6 | 0.75 |
| 1809 | 5.4 | 1.0 |
| 1810 | 6.5 | 2.8 |
| 1811 | 9.1 | 3.2 |
| 1812 | 5.5 | 0.57 |
| 1813 | 13 | 2.3 |
| 1814 | 11 | 2.1 |
| 1815 | 24 | 2.9 |
| 1816 | 13 | 5.6 |
| 1817 | 20 | 19 |
| 1818 | 15 | 5.1 |
| 1819 | 9.1 | 2.2 |
| 1820 | 27 | 13 |
| 1821 | 6.5 | 14 |
| 1822 | 33 | 9.4 |
| 1823 | 47 | 24 |
| 1824 | 34 | 14 |
| 1825 | 19 | 3.3 |
| 1826 |  | 7.7 |
| 1827 |  | 6.0 |
| 1828 | 23 | 27 |
| 1829 | 3.9 | 9.4 |
| 1830 | 157 | 234 |
| 1831 |  | 242 |
| 1832 | 26 | 172 |
| 1833 | 13 | 46 |
| 1834 | 7.6 | 13 |
| 1835 |  | 110 |
| 1836 | 5.4 | 9.1 |
| 1837 |  | 130 |
| 1838 |  | 105 |
| 1839 |  | 288 |
| 1840 |  | 296 |
| 1841 | 41 | 86 |
| 1842 | 117 | 125 |
| 1843 | 58 | 76 |
| 1844 | 39 | 120 |
| 1845 | 15 | 126 |
| 1846 | 97 | 457 |
| 1847 | 728 | 29 |
| 1848 |  | 0.54 |

TNF-Induced Systemic Inflammatory Response Syndrome (SIRS)

RIPK1 inhibitors were evaluated for efficacy in vivo using a TNF-dependent model of systemic "shock", also known as systemic inflammatory response syndrome (SIRS) (Duprez et al. 2011, Immunity 35(6):908-918). Intravenous injection of murine TNF induces a systemic inflammatory response characterized by a decrease in body temperature and an increase in circulating cytokines (IL-6, KC) in the serum. The addition of zVAD-fmk strongly sensitizes mice to TNF-induced shock through the inhibition of caspases (Cauwels et al., 2003). The combination of pretreatment with zVAD-fmk prior to injection of mTNF forms the basis of the RIPK1-dependent, TNF-induced, inflammatory response in this model.

Female C57/B16 mice (9 to 11 weeks old) were obtained from Jackson Labs (Bar Harbor, Me.). Mice were housed in BMS' animal facility with ad libitum access to food and water. Mice were and allowed to acclimate for at least 2 weeks and typically weighed at least 21 grams before being used in any studies. Group size was 6 mice per treatment. All experiments were conducted with the approval of BMS' Institutional Animal Care and Use Committee (IACUC)

Program compounds were dosed by oral gavage 2 h before IV challenge with 20 µg of murine TNF (#CRT192C, Cell Sciences, Canton Mass.). zVAD-fmk (16.7 mg/kg) was given IV, 15 min before mTNF injection. The RIPK1 kinase inhibitor, necrostatin-1s (Nec-1s) was used as a positive control and was dosed at 6 mg/kg, IV, 30 minutes before mTNF challenge. mTNF was diluted in endotoxin-free PBS and 20 µg/mouse was injected in a volume of 0.1 ml into the retro-orbital sinus. All IV injections were done via the retro-orbital sinus and injection sites were alternated (left and right sides).

Three (3) hours after mTNF injection, mice were assessed for hypothermia and mortality. Rectal body temperature was recorded with an electric thermometer.

Blood samples for PK determination were collected into heparinized microtainer blood tubes (Part #365965, Becton Dickinson, Franklin Lakes N.J.) and mixed well. Dried blood spots (DBS) were prepared by pipetting 10 µl of whole blood, in duplicate, onto bioanalysis cards (#GR2261004, Perkin Elmer, Greenville, S.C.). A serum sample was obtained by collecting blood into a separator tube (#450472, Greiner Bio-One, Austria) and centrifuged (10 min at 10,000 RPM) to separate the serum. All blood samples were obtained from the retro-orbital sinus while under isoflurane anesthesia.

Serum cytokines were evaluated by ELISA assay. IL-6 was measured using OPTeia Kit (Becton Dickinson, Franklin Lakes N.J.) while KC was measured using an R&D Duoset kit (R&D Systems Inc. Minneapolis, Minn.)

Using these assays, the percent protection of body temperature and percent reduction in IL6 and KC serum cytokines of the following compounds were determined. See Table B.

TABLE B

| Ex | Compound dose | % protection from body temperature decrease | % reduction in KC serum cytokines | % reduction in IL6 serum cytokines |
|---|---|---|---|---|
| 10 | 1.0 mg/kg | 70 | 88 | 78 |
| 31-1 | 1.0 mg/kg | 77 | 89 | 77 |
| 311 | 0.1 mg/kg | 81 | 79 | 88 |
| 1224 | 1.0 mg/kg | 72 | 65 | 88 |
| 1605 | 1.0 mg/kg | 46 | 52 | 43 |
| 31-1 | 1.0 mg/kg | 77 | 89 | 77 |

PI3Kδ HTRF Binding Assay

A solution was prepared containing 0.2 nM Anti GST-Tb (Cisbio, 61GSTTLB), 40 nM fluorescein-labeled probe and 1 nM GST-tagged PIK3Cδ in complex with PIK3R1 (Invitrogen #PV5273) in FRET Buffer (20 mM HEPES, 10 mM MgCl2, 0.015% Brij-35, 4 mM DTT, 0.05 mg/mL BSA). Using Formulatrix Tempest, the detection antibody/enzyme/probe solution (2 µL) was dispensed into wells of a 1536 plate (Black Low Binding Polystyrene 1536 Plate (Corning, 3724)) containing 10 nL of compounds of interest at appropriate concentration in DMSO. The plate was incubated at rt for 1 h. FRET was measured using the EnVision plate reader (Excitation: 340 nM, Emission: 520 nM/495 nM). Total signal (0% inhibition) was calculated from wells containing 10 nL DMSO only. Blank signal (100% inhibition) calculated from wells containing 10 nL of 15 nM staurosporine and internal controls. Percent inhibition was determined for test compounds at 11 concentrations. The IC50, defined as the concentration of competing test compound needed to reduce specific binding of the probe by 50%, was calculated using the 4 parameter logistic equation to fit the data. A fold selectivity relative to RIPK1 was calculated by dividing the PI3Kδ IC$_{50}$ by the RIPK1 HTRF IC$_{50}$. See Table C.

TABLE C

| Ex | PIK3Cδ IC50 (nM) | <10 x | Between 10 x and 100 x | >100 x |
|---|---|---|---|---|
| 1 | >1500 | | | x |
| 2 | 1192 | | | x |
| 3 | >1500 | | | x |
| 8 | >1500 | | | x |
| 9 | >1500 | | | x |
| 10 | >1500 | | | x |
| 17 | >1500 | | | x |
| 26 | 232 | | x | |
| 60 | >1500 | | | x |
| 61 | >1500 | | | x |
| 62 | >1500 | | | x |
| 65 | 1419 | | | x |
| 69 | >1500 | | | x |
| 71 | >1500 | | | x |
| 73 | 165 | | | x |
| 74 | 121 | | x | |
| 76 | 1155 | | | x |
| 77 | 260 | | x | |
| 78 | 45 | x | | |
| 81 | 565 | | x | |
| 82 | >1500 | | | x |
| 109 | >1500 | | | x |
| 110 | >1500 | | | x |
| 117 | 528 | | x | |
| 119 | 154 | | x | |
| 125 | 1100 | | | x |
| 129 | 211 | | x | |
| 133 | 162 | | x | |
| 140 | >1500 | | | x |
| 153 | >1500 | | | x |
| 160 | >1500 | | | x |
| 165 | 735 | | | x |
| 166 | 140 | | x | |
| 167 | 137 | | x | |
| 168 | 247 | | x | |
| 169 | 681 | | | x |
| 171 | 280 | | | x |
| 181 | 450 | | x | |
| 184 | 1431 | | | x |
| 243 | >1500 | | | x |
| 246 | 237 | | x | |
| 247 | 236 | | x | |
| 248 | >1500 | | | x |
| 250 | 514 | | x | |
| 269 | 434 | | x | |
| 270 | >1500 | | | x |
| 271 | >1500 | | | x |
| 272 | 285 | | x | |
| 276 | 693 | | x | |
| 277 | 180 | | x | |
| 311 | 608 | | | x |
| 386 | 367 | | | x |
| 426 | 1179 | | | x |
| 481 | 14966 | | | x |
| 487 | >15000 | | | x |
| 489 | 4132 | | | x |
| 491 | 1937 | | | x |
| 502 | 3369 | | | x |
| 505 | >15000 | | | x |
| 554 | >15000 | | | x |
| 569 | 545 | | | x |
| 615 | 78 | | x | |
| 625 | 100 | | x | |
| 645 | 1319 | | | x |
| 646 | 617 | | | x |
| 650 | >15000 | | | x |
| 652 | >15000 | | | x |
| 653 | 1937 | | | x |
| 656 | 1670 | | | x |
| 658 | 103 | | x | |
| 686 | >15000 | | | x |
| 690 | 13214 | | | x |
| 702 | 1739 | | | x |
| 741 | 580 | | x | |
| 781 | 2054 | | | x |
| 783 | 686 | | x | |
| 790 | 1089 | | | x |
| 833 | 974 | | | x |
| 842 | 1180 | | | x |
| 885 | 529 | | x | |
| 886 | 847 | | | x |
| 888 | 487 | | x | |
| 906 | 443 | | x | |
| 910 | 200 | | x | |
| 911 | 35 | x | | |
| 912 | 553 | | x | |
| 918 | 44 | x | | |
| 931 | 558 | | | x |
| 968 | 195 | | x | |
| 986 | 1169 | | | x |
| 990 | 63 | | x | |
| 994 | 553 | | | x |
| 1000 | 306 | | x | |
| 1081 | 141 | | x | |
| 1083 | 170 | | x | |
| 1088 | 558 | | x | |
| 1126 | 2238 | | | x |
| 1128 | 174 | | x | |
| 1138 | >15000 | | | x |
| 1140 | >15000 | | | x |

TABLE C-continued

| | | RIPK1 Selectivity (x fold) | | |
|---|---|---|---|---|
| Ex | PIK3Cδ IC50 (nM) | <10 x | Between 10 x and 100 x | >100 x |
| 1141 | >15000 | | | x |
| 1142 | >15000 | | | x |
| 1143 | >15000 | | | x |
| 1144 | >15000 | | | x |
| 1145 | >15000 | | | x |
| 1146 | >15000 | | | x |
| 1147 | >15000 | | | x |
| 1148 | >15000 | | | x |
| 1149 | >5000 | | | x |
| 1150 | >15000 | | | x |
| 1151 | >15000 | | | x |
| 1152 | >15000 | | | x |
| 1153 | >15000 | | | x |
| 1154 | >15000 | | | x |
| 1157 | >15000 | | | x |
| 1158 | >15000 | | | x |
| 1159 | >15000 | | | x |
| 1160 | >15000 | | | x |
| 1161 | >15000 | | | x |
| 1162 | >15000 | | | x |
| 1163 | >15000 | | | x |
| 1174 | 928 | | | x |
| 1175 | 940 | | | x |
| 1220 | >15000 | | | x |
| 1237 | >15000 | | | x |
| 1238 | >15000 | | | x |
| 1239 | >15000 | | | x |
| 1240 | >15000 | | | x |
| 1241 | >15000 | | | x |
| 1242 | >15000 | | | x |
| 1243 | >15000 | | | x |
| 1244 | >15000 | | | x |
| 1245 | >15000 | | | x |
| 1246 | >15000 | | | x |
| 1247 | >15000 | | | x |
| 1248 | >15000 | | | x |
| 1250 | >15000 | | | x |
| 1251 | >15000 | | | x |
| 1252 | >15000 | | | x |
| 1254 | >15000 | | | x |
| 1255 | >15000 | | | x |
| 1256 | >15000 | | | x |
| 1258 | >15000 | | | x |
| 1259 | >15000 | | | x |
| 1260 | >15000 | | | x |
| 1262 | >15000 | | | x |
| 1263 | >15000 | | | x |
| 1264 | >15000 | | | x |
| 1266 | >15000 | | | x |
| 1267 | >15000 | | | x |
| 1268 | >15000 | | | x |
| 1269 | >15000 | | | x |
| 1270 | >15000 | | | x |
| 1275 | 4974 | | | x |
| 1278 | >15000 | | | x |
| 1285 | 5209 | | | x |
| 1332 | 128 | | x | |
| 1338 | 322 | | x | |
| 1344 | >15000 | | | x |
| 1462 | >15000 | | | x |
| 1500 | >15000 | | | x |
| 1502 | >15000 | | | x |
| 1506 | >15000 | | | x |
| 1509 | >15000 | | | x |
| 1510 | >15000 | | | x |
| 1514 | >15000 | | | x |
| 1515 | >15000 | | | x |
| 1516 | >15000 | | | x |
| 1517 | >15000 | | | x |
| 1518 | >15000 | | | x |
| 1519 | >15000 | | | x |
| 1520 | >15000 | | | x |
| 1524 | >15000 | | | x |
| 1535 | >15000 | | | x |
| 1541 | >15000 | | | x |
| 1542 | >15000 | | | x |
| 1543 | >15000 | | | x |
| 1544 | >15000 | | | x |
| 1548 | >15000 | | | x |
| 1553 | >15000 | | | x |
| 1557 | 13283 | | | x |
| 1558 | >15000 | | | x |
| 1560 | >15000 | | | x |
| 1562 | 5185 | | | x |
| 1563 | >15000 | | | x |
| 1564 | >15000 | | | x |
| 1567 | 3166 | | | x |
| 1577 | >15000 | | | x |
| 1578 | >15000 | | | x |
| 1581 | >15000 | | | x |
| 1595 | >15000 | | | x |
| 1596 | >15000 | | | x |
| 1606 | 437 | | | x |
| 1616 | 14779 | | | x |
| 1617 | 11000 | | | x |
| 1626 | 6268 | | | x |
| 1633 | 5107 | | | x |
| 1638 | 7849 | | | x |
| 1639 | >15000 | | | x |
| 1647 | 7944 | | | x |
| 1655 | 5571 | | | x |
| 1656 | 5261 | | | x |
| 1658 | 9148 | | | x |
| 1659 | >15000 | | | x |
| 1660 | >15000 | | | x |
| 1689 | >5000 | | | x |
| 1693 | >15000 | | | x |
| 1716 | 12742 | | | x |
| 1717 | >15000 | | | x |
| 1718 | >15000 | | | x |
| 1719 | >15000 | | | x |
| 1810 | 53 | x | | |
| 1811 | 148 | | x | |
| 1812 | 261 | | x | |
| 1819 | 1412 | | | x |
| 1836 | >15000 | | | x |
| 31-1 | 335 | | x | |

Methods of Preparation

Compounds of Formula (I), and intermediates used in the preparation of compounds of Formula (I), can be prepared using procedures shown in the following examples and related procedures. The methods and conditions used in these examples, and the actual compounds prepared in these examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

Abbreviations as used herein, are defined as follows: "1×" for once, "2×" for twice, "3×" for thrice, "aq" or "aq." for aqueous, "° C." for degrees Celsius, "eq" for equivalent or equivalents, "g" for gram or grams, "mg" for milligram or milligrams, "L" for liter or liters, "mL" for milliliter or milliliters, "μL" for microliter or microliters, "N" for normal, "M" for molar, "mmol" for millimole or millimoles, "min" for minute or minutes, "h" for hour or hours, "rt" for room temperature, "ON" for overnight, "RT" for retention time, "atm" for atmosphere, "psi" for pounds per square inch, "conc." for concentrate, "sat" or "saturated" for saturated, "CVs" for column volumes, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" or "LC/MS" for liquid chromatography mass spectrometry, "HPLC" for high pressure liquid chromatography, "RP HPLC" for reverse phase HPLC, "TLC" or "tlc" for thin layer chromatography, "SFC" for supercritical fluid chromatography, "NMR" for nuclear magnetic resonance spectroscopy, "nOe" for nuclear Overhauser effect spectroscopy, "$^1$H" for proton, "S" for delta, "s" for singlet, "d" for doublet, "t" for triplet, "q" for quartet, "m" for multiplet, "br" for broad, "MHz" for megahertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc tert-butyloxycarbonyl
AcOH or HOAc acetic acid
Ac$_2$O acetic anhydride
Boc (tert-butoxy)carbonyl
BOP benzotriazol-1-yloxytris(dimethylamino)phosphonium hexafluorophosphate
CBz carbobenzyloxy
CH$_2$Cl$_2$ dichloromethane
CH$_3$CN or ACN acetonitrile
CDCl$_3$ deutero-chloroform
CHCl$_3$ chloroform
Cs$_2$CO$_3$ cesium carbonate
DAST diethylaminosulfur trifluoride
DCE 1,2 dichloroethane
DCM dichloromethane
DIEA/DIPEA/Hünig's Base diisopropylethylamine
DMAP 4-dimethylaminopyridine
DME 1,2-dimethoxyethane
DMF dimethyl formamide
DMSO dimethyl sulfoxide
EDC N-(3-dimthylaminopropyl) N'-ethylcarbodiimide
EDCI N-(3-dimthylaminopropyl) N'-ethylcarbodiimide hydrochloride
Et$_3$N or TEA triethylamine
EtOAc ethyl acetate
Et$_2$O diethyl ether
EtOH ethanol
HCl hydrochloric acid
HATU O-(7-azabenzotriazol-1-yl)-N,N,N',N'-tetramethyluronium hexafluorophosphate
Hex hexane
HMDS hexamethyldisilazane
HOBt or HOBT 1-hydroxybenzotriazole
H$_2$SO$_4$ sulfuric acid
K$_2$CO$_3$ potassium carbonate
KOAc potassium acetate
K$_3$PO$_4$ potassium phosphate
LAH lithium aluminum hydride
LG leaving group
LiOH lithium hydroxide
MeOH methanol
MeI iodomethane
MgSO$_4$ magnesium sulfate
NaCl sodium chloride
NaH sodium hydride
NaHCO$_3$ sodium bicarbonate
Na$_2$CO$_3$ sodium carbonate
NaOH sodium hydroxide
Na$_2$SO$_3$ sodium sulfite
Na$_2$SO$_4$ sodium sulfate
NBS N-bromosuccinimide
NCS N-chlorosuccinimide
NH$_3$ ammonia
NH$_4$Cl ammonium chloride
NH$_4$OH ammonium hydroxide
NIS N-iodosuccinimide
NMP N-methylpyrrolidine
OAc acetate
OTf triflate or trifluoromethanesulfonate
Pd$_2$(dba)$_3$ tris(dibenzylideneacetone)dipalladium(O)
Pd(OAc)$_2$ palladium(II) acetate
Pd/C palladium on carbon
PdCl$_2$(dppf) [1,1'-bis(diphenylphosphino)-ferrocene]dichloropalladium(II)
PG protecting group
pin pinachol
PMB para-methoxybenzyl
POCl$_3$ phosphorus oxychloride
i-PrOH or IPA isopropanol
SiO$_2$ silica oxide
TBAI tetra-n-butylammonium iodide
TFA trifluoroacetic acid
THF tetrahydrofuran
AIBN azobisisobutyronitrile
ACN Acetonitrile
DAST diethylaminosulfur trifluoride
DBU 1,8-diazabicyclo[5.4.0]undec-7-ene
DCE 1,2 dichloroethane
IPA isopropyl alcohol
TBAF tetra-n-butylammonium fluoride The compounds of the present invention may be synthesized by many methods available to those skilled in the art of organic chemistry (Maffrand, J. P. et al., Heterocycles, 16(1):35-7 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Proton magnetic resonance ($^1$H NMR) spectra were recorded on either a Bruker Avance 400, a Bruker 500 or a JEOL Eclipse 500 spectrometer and are reported in ppm relative to the reference solvent of the sample in which they were run. HPLC and LC-MS analyses were conducted using a Shimadzu SCL-10A liquid chromatograph and a SPD UV-vis detector at 220 nm with the MS detection performed with either a Micromass Platform LC spectrometer or a Waters Micromass ZQ spectrometer. All flash cohum chromatography was performed on EM Science silica gel 60 (particle size of 40-60 μm). All reagents were purchased from commercial sources and used without further purification unless otherwise noted. All reactions were performed under an inert atmosphere. HPLC analyses were performed using the following conditions. All final compounds had an HPLC purity of ≥95% unless specifically mentioned.

The substituents as labeled in the schemes and Examples, for example as "R", $R^1$, or $R^2$, etc., do not necessarily correspond with the substituent labels as found in the claims.

Scheme 1 illustrates an approach to the synthesis of compounds exemplified by 3. Functionalization of starting material 1 can be achieved through amidation (Tetrahedron, 61:10827-10852, 2005) to yield bromide 2. Amidation of 1 can also be accomplished via the anhydride or acid chloride in conjunction with base. A Suzuki coupling reaction (Miyaura, N. and Suzuki, A. Chemical Reviews, 95:2457-2483, 1995) of 2 and 4 can provide compounds of the type exemplified by 3. The Suzuki reaction can be accomplished via in situ conversion of 2 to its respective boronate ester or boronic acid, followed by coupling with 4. Initial in situ formation of the boronate ester or boronic acid derived from 4, followed by coupling with bromide 2 can also be effective to generate compounds depicted by 3. Additionally discrete isolation of the boronate derived from either 2 or 4 could also be used in the transformation.

A trifluoromethyl group can be incorporated on the heterocyclic portion of the molecule as described in Scheme 2. Protection of the amino group in 4 preceded iodination to yield compound 6. Although para-methoxybenzyl groups are delineated in Scheme 2, those familiar in the art could envisage a variety of protecting groups to be suitable for these transformations. Trifluoromethylation yielded 7 in a chemoselective manner. Deprotection under acidic conditions at elevated temperatures provided the substituted heterocyclic core 8. Bromide 8 can undergo a Suzuki coupling reaction with a phenyl boronic acid or boronate ester exemplified by 9 to yield the coupled product 10. As delineated in Scheme 1, reversing the couplings may be feasible and known to those in the art. Furthermore, although the phenyl and substituted analogs implied in the scheme will all work in the transformation, utilization of a six-membered heteroarene could also be used. Should 9 be an ester instead of a carboxylic acid, a hydrolysis step following the Suzuki reaction could be performed. Suitable bases may include lithium hydroxide monohydrate, sodium hydroxide or others known to those in the art. Compounds exemplified by 11 can be formed by an amide coupling mediated by BOP reagent as shown in the scheme or an alternative amide coupling reagent. Use of an anhydride or carboxylic acid chloride may also effect this transformation.

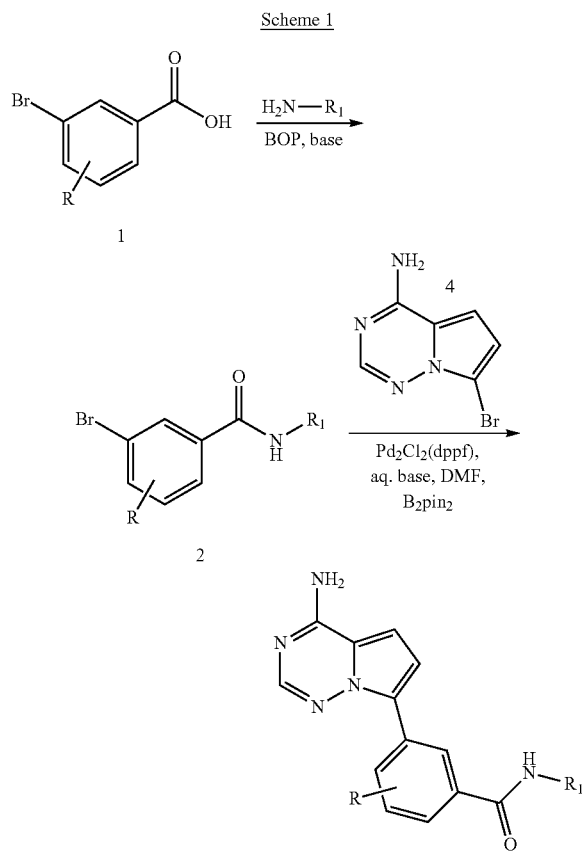

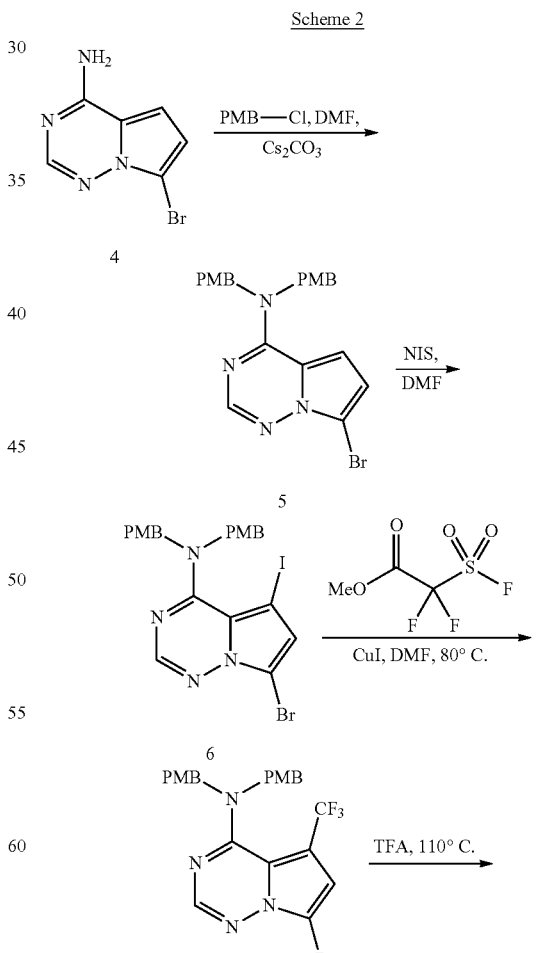

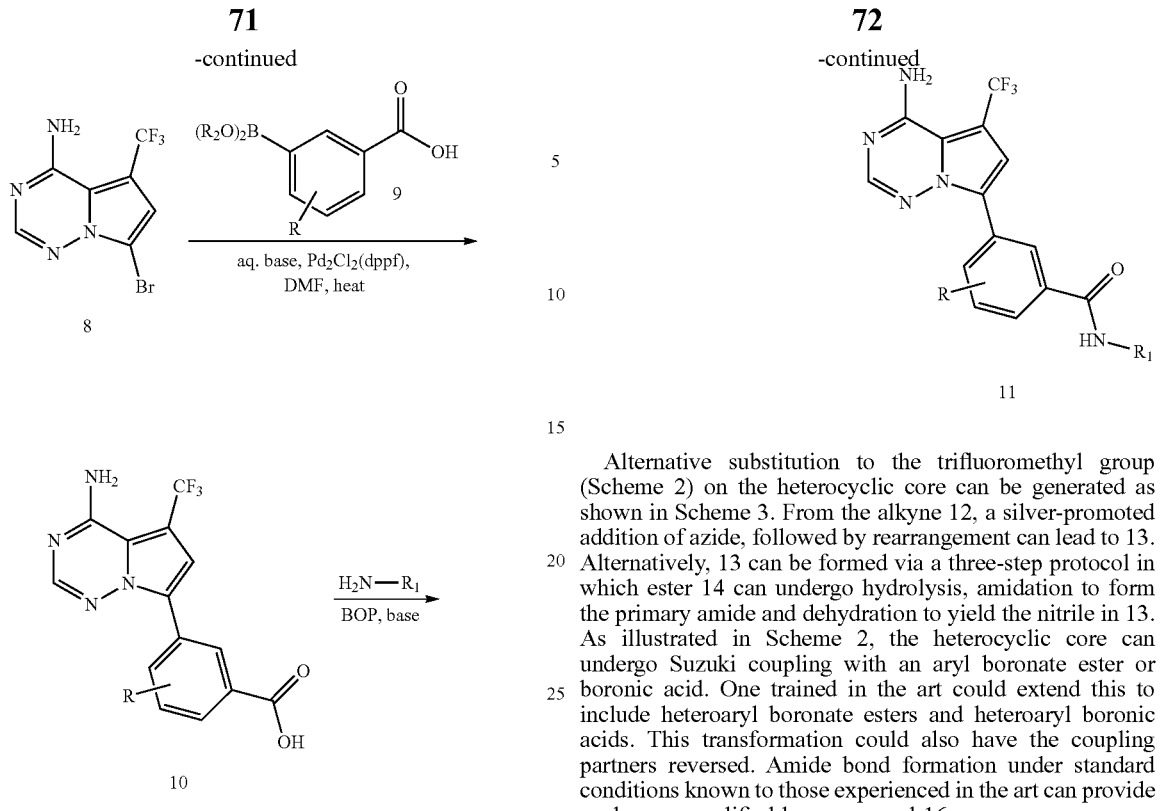

Alternative substitution to the trifluoromethyl group (Scheme 2) on the heterocyclic core can be generated as shown in Scheme 3. From the alkyne 12, a silver-promoted addition of azide, followed by rearrangement can lead to 13. Alternatively, 13 can be formed via a three-step protocol in which ester 14 can undergo hydrolysis, amidation to form the primary amide and dehydration to yield the nitrile in 13. As illustrated in Scheme 2, the heterocyclic core can undergo Suzuki coupling with an aryl boronate ester or boronic acid. One trained in the art could extend this to include heteroaryl boronate esters and heteroaryl boronic acids. This transformation could also have the coupling partners reversed. Amide bond formation under standard conditions known to those experienced in the art can provide analogs exemplified by compound 16.

Scheme 3

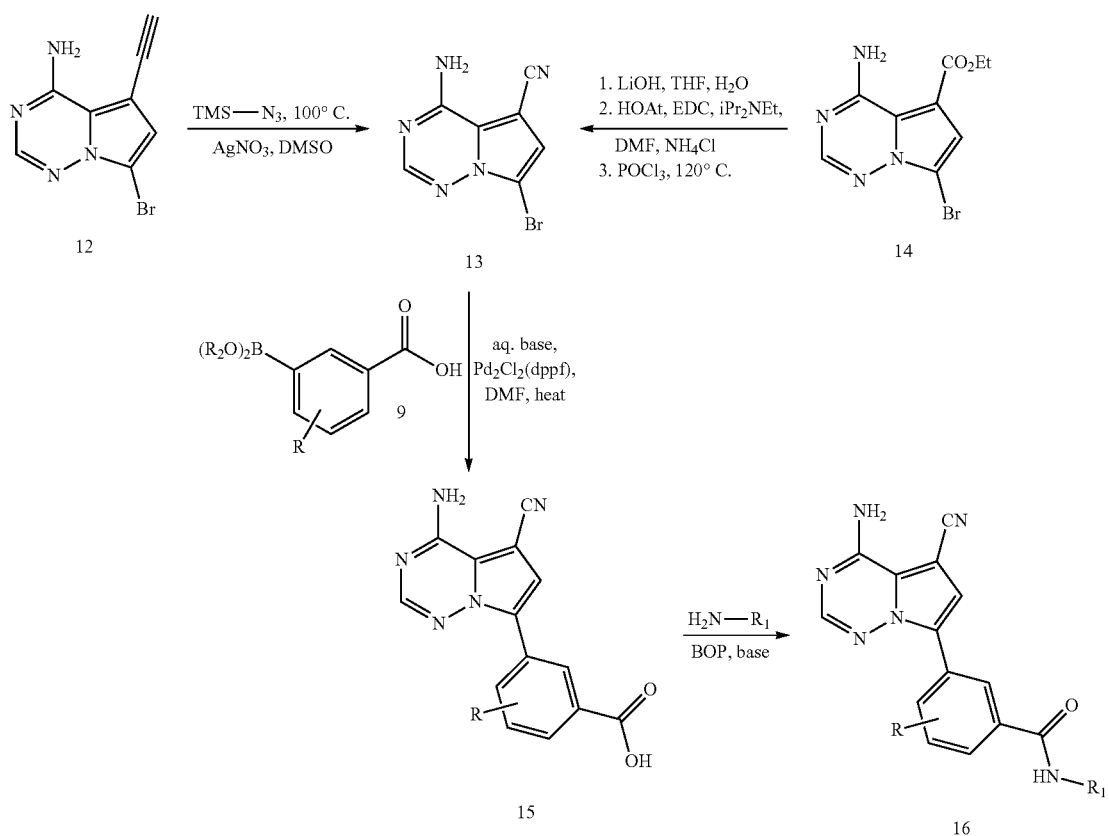

Scheme 4 details access to a heterocyclic system which can be substituted at the 6- and 7-positions, rather than the 5- and 7-positions described in earlier schemes. Ketone 17 can be converted to the corresponding difluoroalkane 18 at low temperatures with DAST. Following pyrrolidine deprotection, MnO2 mediated oxidation can yield pyrrole 20. N-Amination can precede cyclization to the pyrrolotriazine core 22. The amino group can be installed via conversion to the chloride and subsequent displacement with ammonia. Bromination under standard conditions can provide the heterocyclic core, 24. As illustrated in Scheme 2, the heterocyclic core can undergo Suzuki coupling with an aryl boronate ester or boronic acid. One trained in the art could extend this to include heteroaryl boronate esters and heteroaryl boronic acids. This transformation could also have the coupling partners reversed. Amide bond formation under standard conditions known to those experienced in the art can provide analogs exemplified by compound 26.

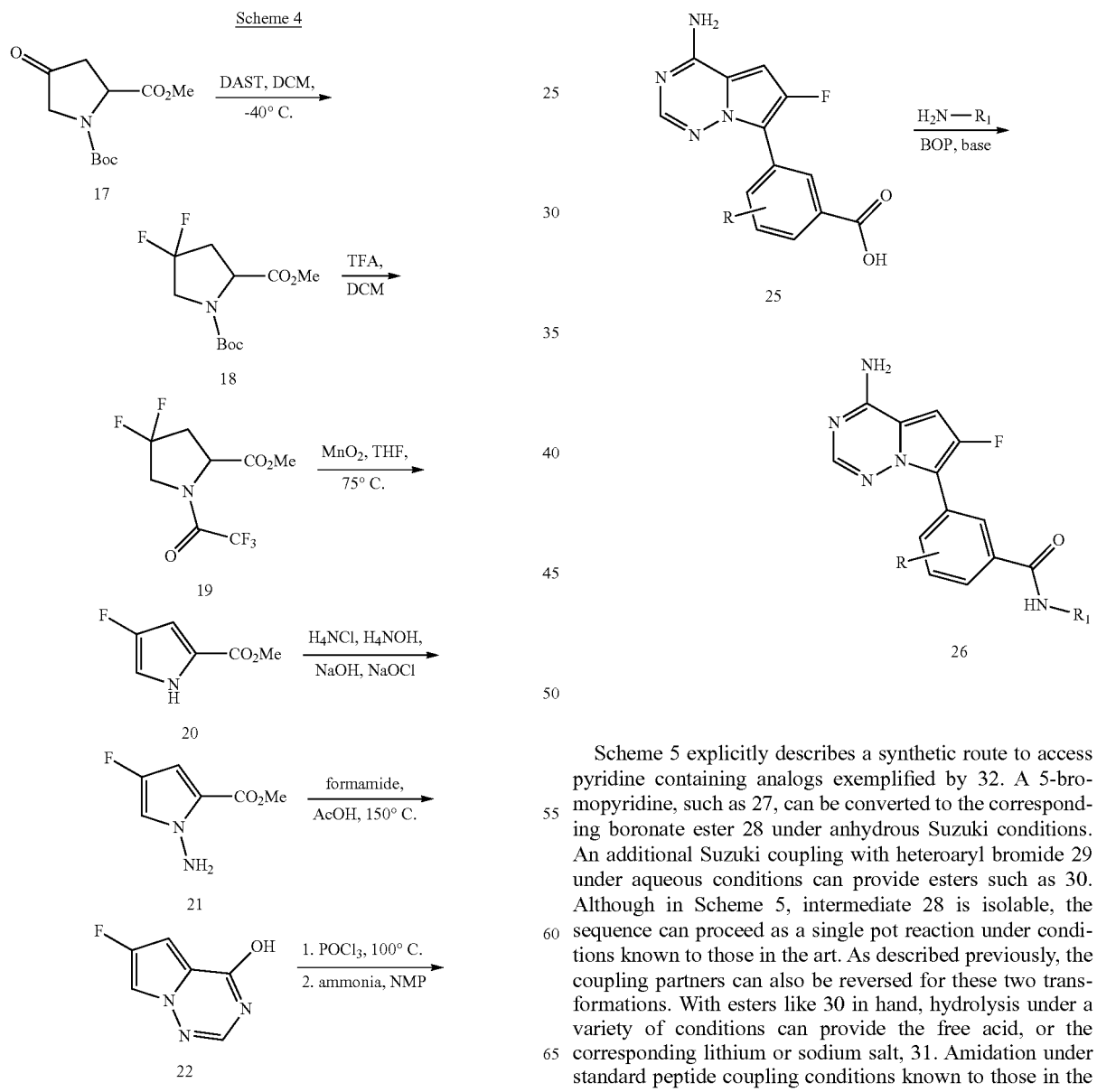

Scheme 5 explicitly describes a synthetic route to access pyridine containing analogs exemplified by 32. A 5-bromopyridine, such as 27, can be converted to the corresponding boronate ester 28 under anhydrous Suzuki conditions. An additional Suzuki coupling with heteroaryl bromide 29 under aqueous conditions can provide esters such as 30. Although in Scheme 5, intermediate 28 is isolable, the sequence can proceed as a single pot reaction under conditions known to those in the art. As described previously, the coupling partners can also be reversed for these two transformations. With esters like 30 in hand, hydrolysis under a variety of conditions can provide the free acid, or the corresponding lithium or sodium salt, 31. Amidation under standard peptide coupling conditions known to those in the art can yield analogs similar to 32.

Scheme 5

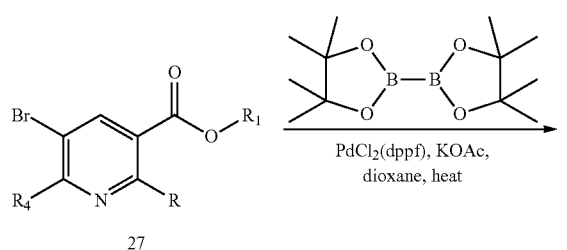

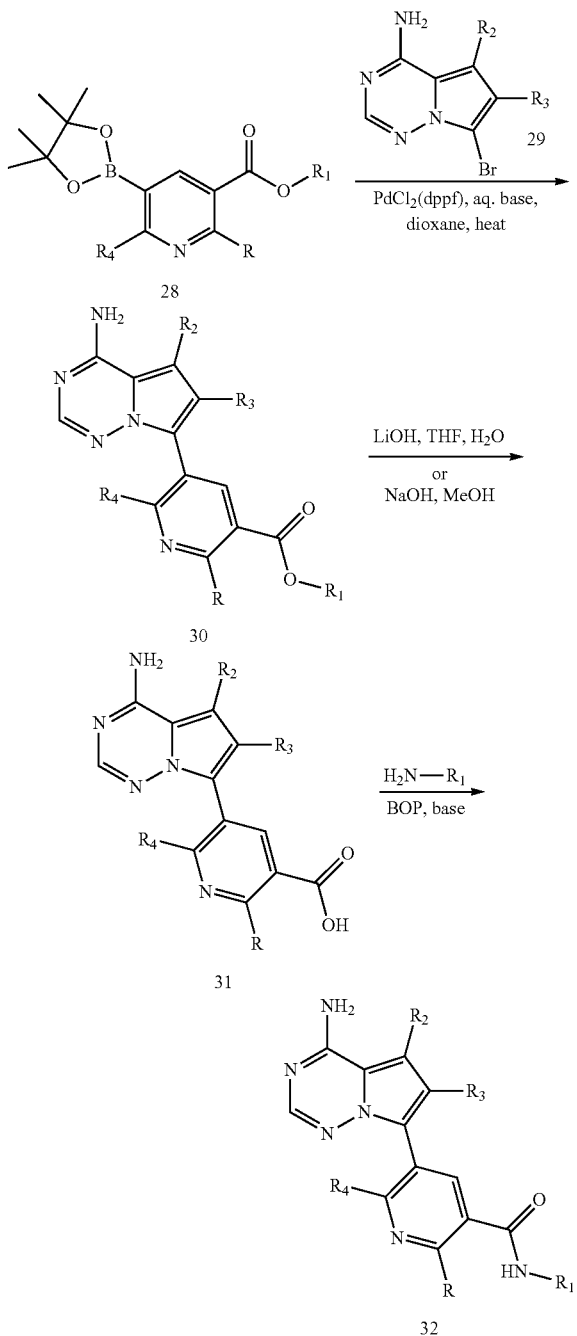

Scheme 6 highlights another route available to access compounds exemplified by 32. Nicotinic acid derivatives such as 33 can undergo amidation to yield 34. In addition to amide coupling under a variety of conditions, 34 can also be accessed via coupling of the anhydride or acid chloride. Conversion of 34 to the corresponding boronate ester 35 can proceed under anhydrous Suzuki conditions. 35 can be isolated discreetly or used in situ in the subsequent Suzuki reaction with pyrrolotriazine 29. As in previously examples, the coupling partners can be switched in the Suzuki reactions wherein 29 can be converted to the boronate ester (discreetly or in situ) and subsequently coupled with bromide 34.

Scheme 6

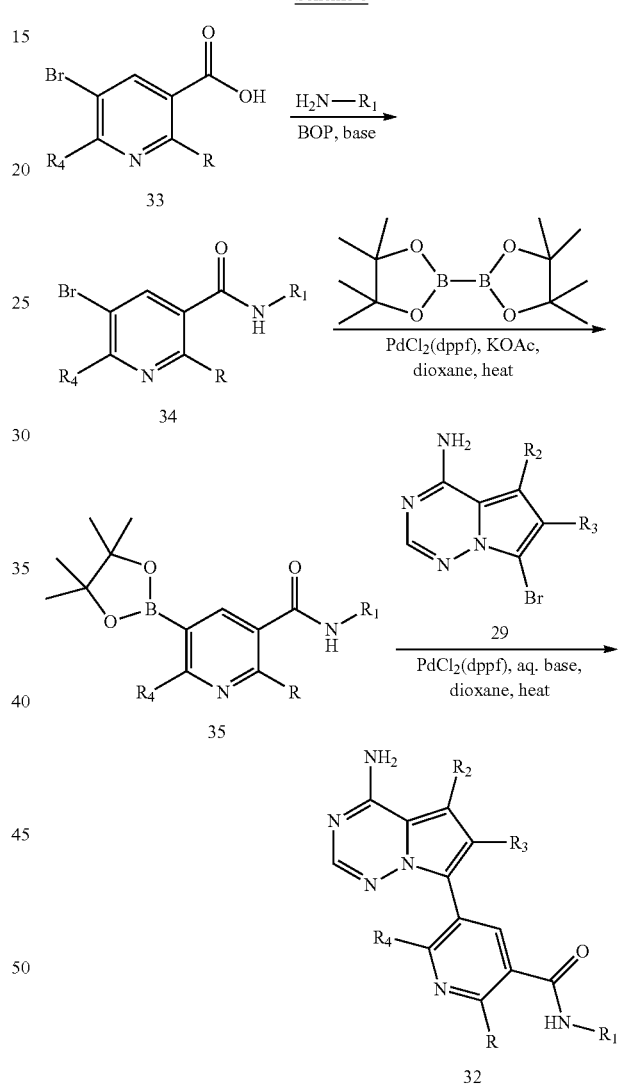

In addition to the aryl and pyridyl coupling partners described vide infra, five-membered rings can also be utilized to generate compounds similar to 42. Conversion of ketone 36 to vinyl triflate 37 can proceed at low temperature using Comins' reagent as the source of the triflate. Conversion to the boronate ester under anhydrous Suzuki conditions can yield 38. Subsequent Suzuki coupling with a pyrrolotriazine such as 29 can yield a coupled product similar to 39. Lithium hydroxide mediated hydrolysis can provide the carboxylic acid or its lithium salt. Alternative bases known to those in the art can be used in this hydrolysis. Amide coupling can proceed with BOP reagent as depicted in the scheme or with alternative peptide coupling reagents known to those in the art. Boc deprotection can provide the final analogs similar to 42.

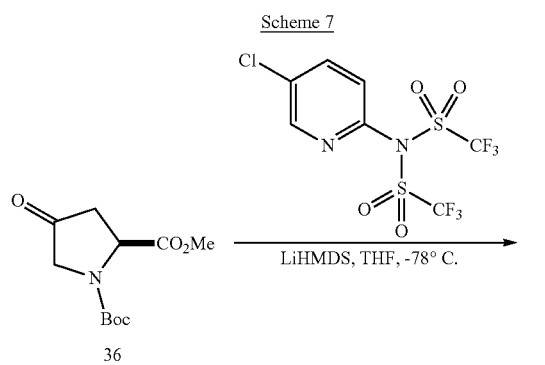

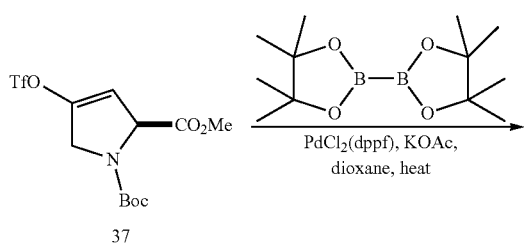

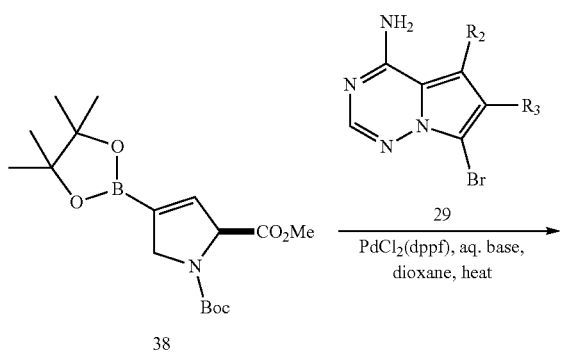

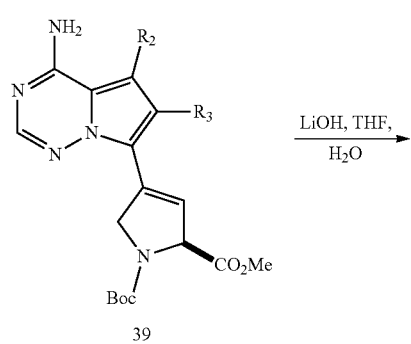

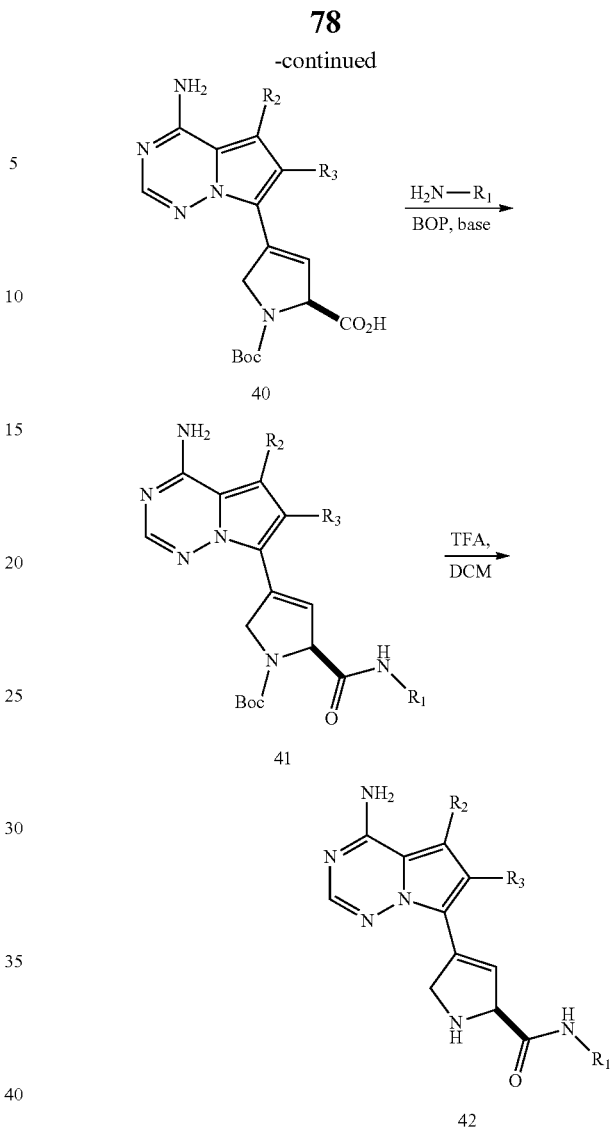

In addition to the pyrrolotriazines exemplified above, a variety of other substituted pyrrolotriazines can also be accessed. These are described in the subsequent schemes. Treatment of pyrrolotriazine 4 with NCS can yield the chlorinated pyrrolotriazine 43 (Scheme 8). This intermediate can be used in the same fashion as 4, 8, 13, 24 or 29 as described in the earlier schemes.

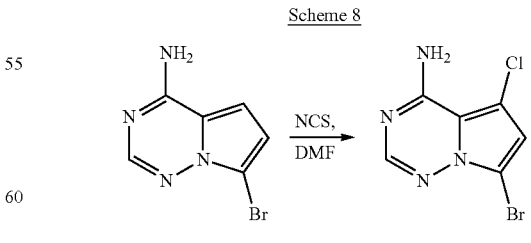

Scheme 9 illustrates access to the 5-methylpyrrolotriazine core, 46. Bromination at the 7-position of 44 under standard conditions can yield 45. The chloride can be displaced using ammonium hydroxide to yield 46. This intermediate can be used in the same fashion as 4, 8, 13, 24 or 29 as described in the earlier schemes.

Scheme 9

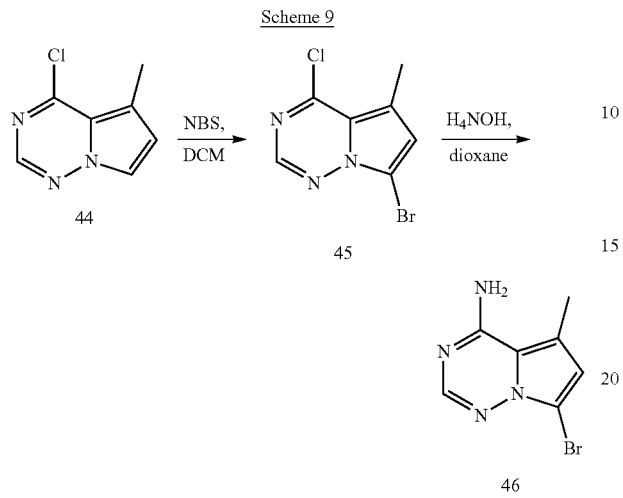

Larger groups can also be generated at the 5-position of the pyrrolotriazine as shown in Scheme 10. Ammonium hydroxide can be used to displace chloride from the core in 47 and yield the amine shown in 48. Treatment of 48 with an alcohol in the presence of base can induce displacement of triethylammonium bromide yielding adducts exemplified by 49. In similar fashion, primary or secondary amines can also displace triethylammonium bromide at elevated temperatures to provide analogs similar to 50. These intermediates can be used in the same fashion as 4, 8, 13, 24 or 29 as described in the earlier schemes.

Scheme 10

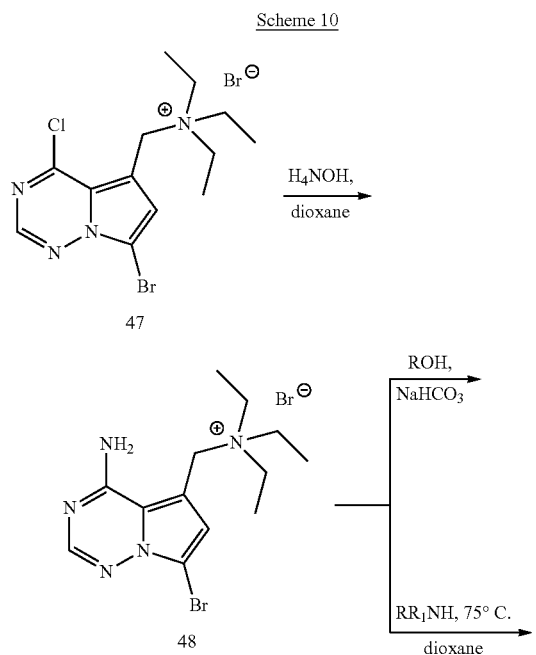

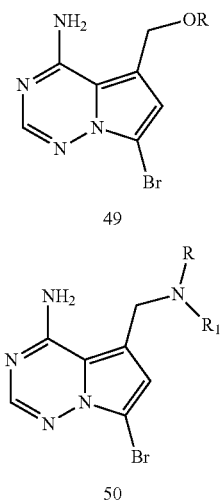

As an alternative to substitution on the pyrrole portion of the heteroarene, the triazine can also be substituted (Scheme 11). Compound 51 can undergo coupling and cyclization to form pyrrolotriazine 52 in the presence of formadine acetate at elevated temperatures. Bromination under standard conditions can yield 53. Treatment with POCl₃ can provide chloride 54. The chloride can be displaced with primary or secondary amines in the presence of base and at elevated temperatures to yield compounds exemplified 55. These intermediates can be used in the same fashion as 4, 8, 13, 24 or 29 as described in the earlier schemes.

Scheme 11

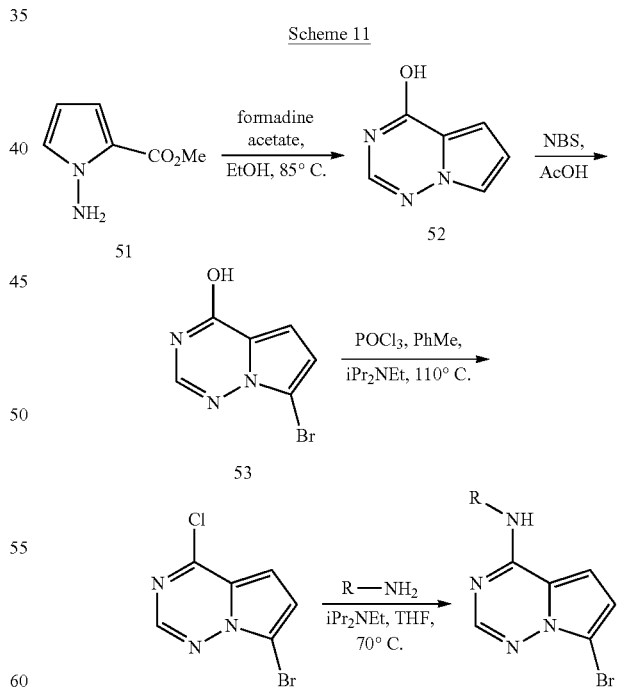

Modifications to the pyrrolotriazine can also be done at a later stage in the synthetic sequence as shown in Scheme 12. Pyridines similar to 56 can undergo Suzuki coupling reaction with 14 to yield analogs such as 57. Ester hydrolysis cab be accomplished with sodium hydroxide, however other bases known to those in the art can also be effective for the hydrolysis. Amide coupling under standard peptide coupling conditions can be employed to yield compounds exemplified by 59. Alternative coupling can occur utilizing methods known to those in the art, such as use of the acid chloride or anhydride.

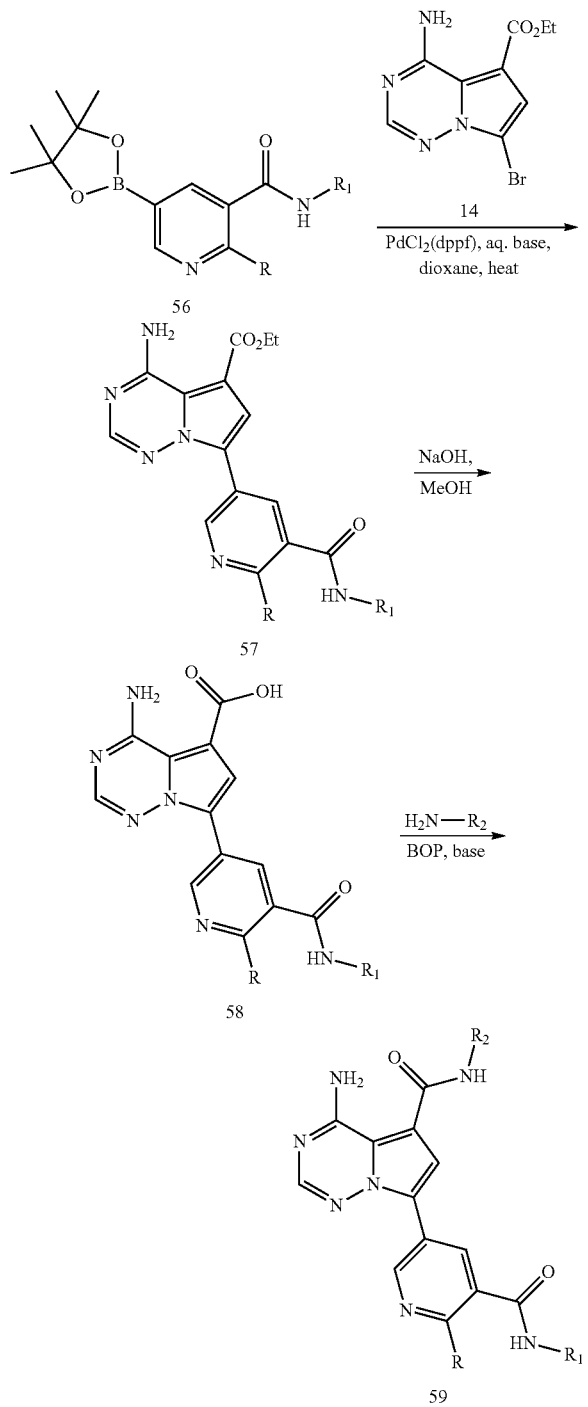

In the case of nicotinic acid derivatives which may not be commercially available, 2-chloropyridine 60 can be dis-placed to yield 61 (Scheme 13). Intermediate 61 can be converted to the boronate ester or boronic acid and be used in Suzuki coupling reactions with any of the pyrrolotriazine analogs described herein. It can also be used in similar fashion with a pyrrolotriazine boronate ester or boronic acid. As depicted in Scheme 13, hydrolysis of the ester under standard conditions can yield acid 62. This can undergo coupling with any primary or secondary amines as described previously. The amide compound could then be taken into the Suzuki reaction utilizing the protocols described in the preceding schemes.

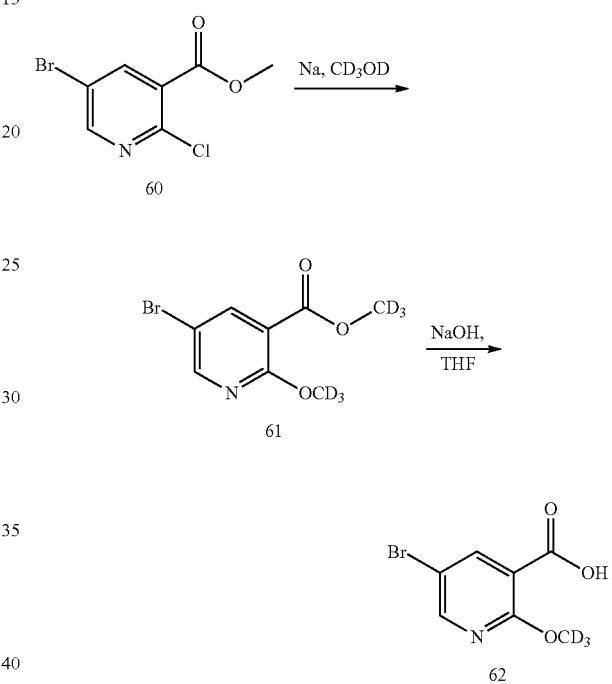

The next set of schemes describe various ways in which a substituted pyrrolidine can be incorporated in both achiral and chiral fashion. Scheme 14 delineates incorporation of cis-racemic or diastereomerically mixed 63. Carboxylic acid 31 can undergo amide coupling with 63 in the presence of base and BOP reagent. Alternative amide bond coupling reagents known to those in the art may also be used. Deprotection of the Boc group under acidic conditions can provide secondary amine 65 as the penultimate compound. This intermediate can be coupled with sulfonyl chlorides to yield a sulfonamide (66). Alternatively, 65 can undergo alkylation with an alkyl halide in the presence of base at an elevated temperature to provide compounds similar to 68. One familiar with the art could also use an epoxide in place of the alkyl halide to provide a hydroxyl containing analog of 68. Amide coupling of 65 with a carboxylic acid in the presence of a coupling reagent such as BOP reagent or others known to those in the art can yield analogs characterized by 70. One familiar with the art can also utilize 65 in additional transformations to yield carbamate and urea analogs. Use of chiral SFC purification on the sulfonamide, tertiary amine, or amide can yield the preferred isomers shown (67, 69 and 71). Chiral prep HPLC could also separate the racemic or diastereomeric mixture.

Scheme 14

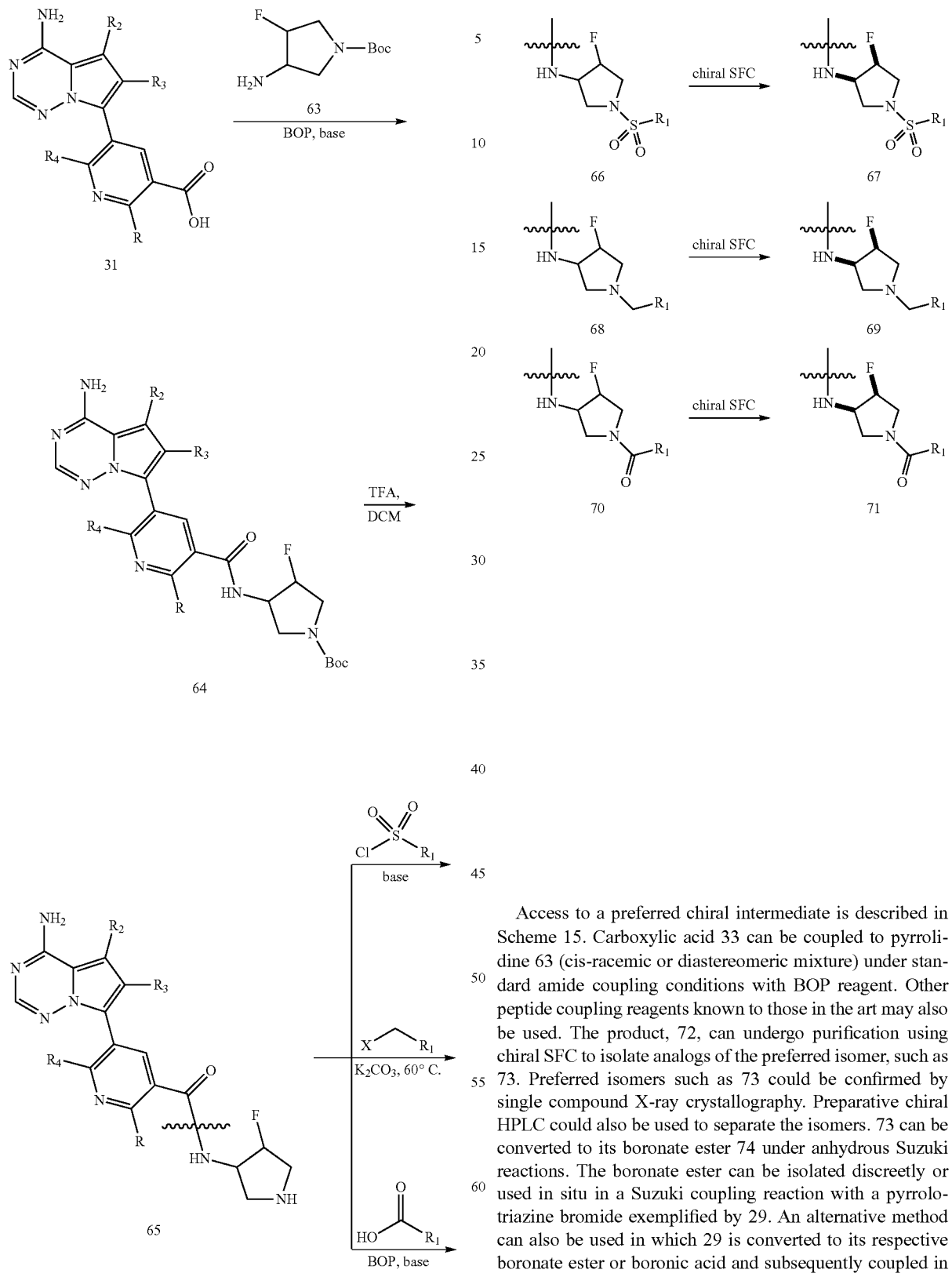

Access to a preferred chiral intermediate is described in Scheme 15. Carboxylic acid 33 can be coupled to pyrrolidine 63 (cis-racemic or diastereomeric mixture) under standard amide coupling conditions with BOP reagent. Other peptide coupling reagents known to those in the art may also be used. The product, 72, can undergo purification using chiral SFC to isolate analogs of the preferred isomer, such as 73. Preferred isomers such as 73 could be confirmed by single compound X-ray crystallography. Preparative chiral HPLC could also be used to separate the isomers. 73 can be converted to its boronate ester 74 under anhydrous Suzuki reactions. The boronate ester can be isolated discreetly or used in situ in a Suzuki coupling reaction with a pyrrolotriazine bromide exemplified by 29. An alternative method can also be used in which 29 is converted to its respective boronate ester or boronic acid and subsequently coupled in situ or in a separate step with bromide 73. Analogs exemplified by 75 can undergo Boc deprotection and be functionalized in subsequent steps as described for Scheme 14.

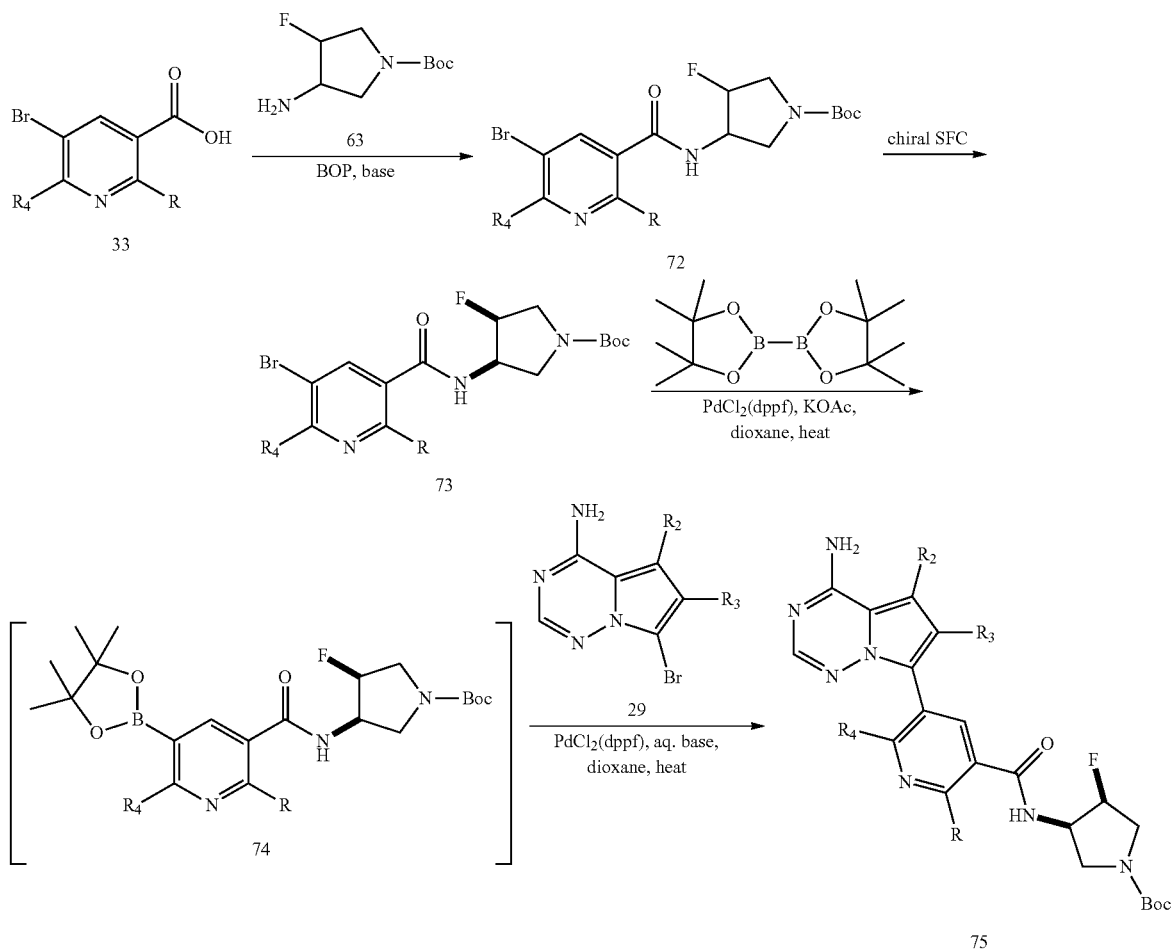

Chiral separation of pyrrolidine 63 can also be accomplished before it is coupled with the carboxylic acid described in the previous schemes. Protection of the amino group of 63 with Cbz-Cl can yield 76 (Scheme 16). One familiar with the art could envisage the use of a variety of amine protecting groups in place of carbobenzyloxy which would have orthogonal deprotection conditions to the Boc carbamate. Pyrrolidine 76, whether it is cis-racemic or a diastereomeric mixture, can undergo separation to the preferred enantiomerically pure isomer 77 using chiral SFC. Chiral preparative HPLC could be a suitable alternative to isolate the desired isomer. Chemoselective deprotection of the Cbz group can yield 78. Amine 78 was determined to be the preferred isomer based on synthesis and comparison to the analogs derived from 73 for which a crystal structure was determined.

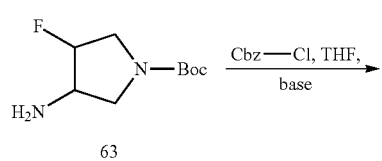

Scheme 16

-continued

As shown in Scheme 17, 78 can also be isolated in enantiomerically pure form using chiral SFC on 63. One familiar with the art could also use chiral prepHPLC in the same fashion. Use of an amide bond coupling reagent can generate the amide derived from 78 and 31 to yield analogs exemplified by 79. In this delineation, conversion to amides characterized by 71 can be accomplished by Boc deprotection and subsequent amide bond formation. Alternative peptide coupling reagents known to those in the art could be used to generate intermediates like 79 or final compounds similar to 71. Additionally, intermediates similar to 80 can undergo alternative functionalization as described in Scheme 14.

Scheme 17

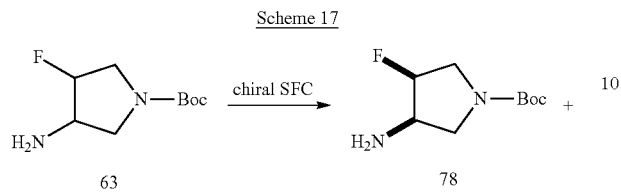

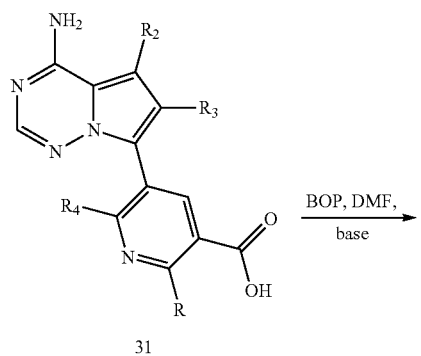

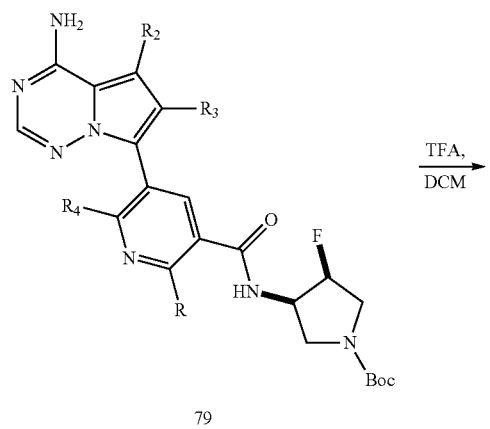

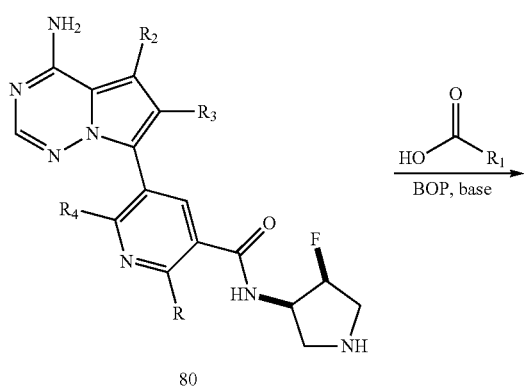

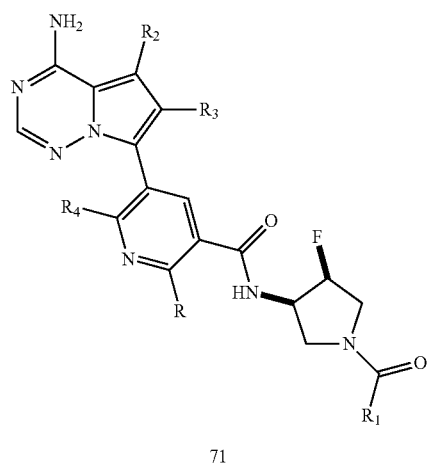

Chiral pyrrolidine 78 can also be coupled with phenyl or substituted phenyl analogs exemplified by 81 (Scheme 18). Amide 82 can be formed using BOP reagent or other peptide coupling reagents known to those in the art. Subsequent Boc deprotection under acidic conditions can yield 83. The secondary amine can undergo a second amide coupling mediated by BOP reagent or an alternative peptide coupling reagent to yield compounds similar to 84. Intermediates characterized by 83 can also be converted to the tertiary amine, sulfonamide, urea or carbamate analogs, by similar methods to those depicted in Scheme 14 or alternatives known to those in the art.

Scheme 18

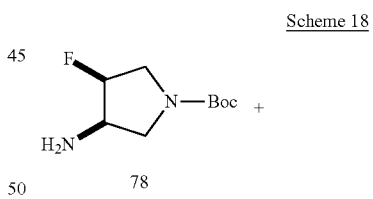

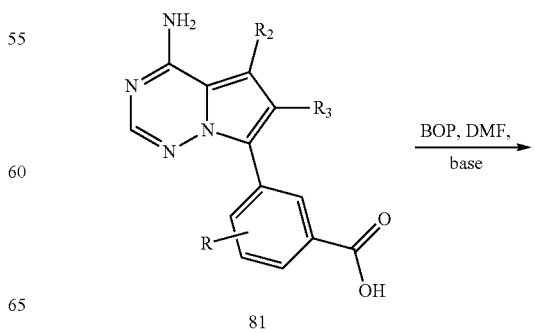

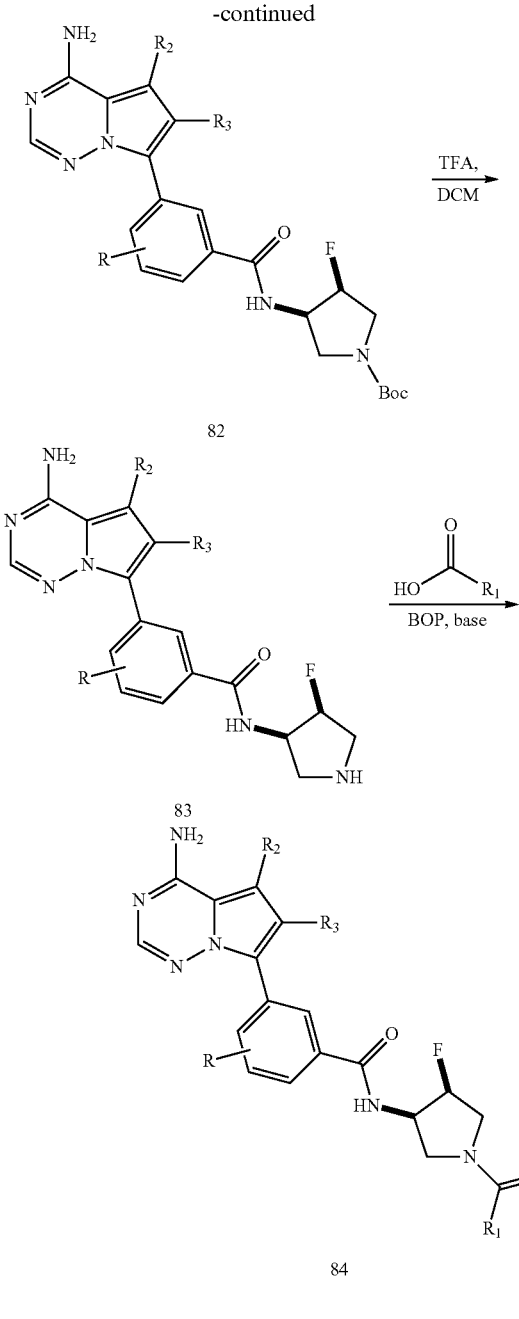

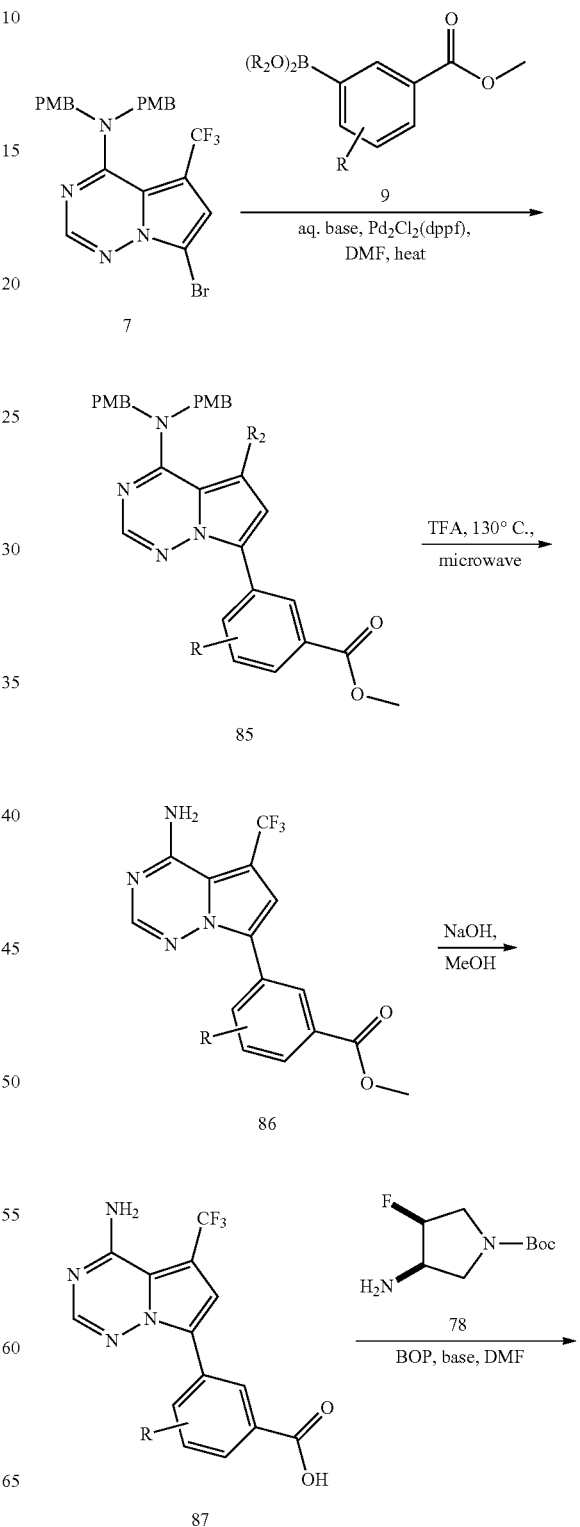

Scheme 19

In some instances, the Suzuki reaction with substituted phenyl boronate esters or boronic acids may proceed in higher yield with less side product formation when coupled with 7 (Scheme 19). Alternative protecting groups in 7, such as Boc, would be available and known to those experienced in the art. One familiar with the art could also generate the boronate ester or boronic acid of 7 and couple with the bromide, chloride or iodide of 9. The Suzuki coupling of partners related to 7 and 9 can be done with isolable boronate esters or boronic acids or ones generated in situ. Removal of the para-methoxybenzyl groups can occur in the presence of trifluoroacetic acid at high temperature under microwave conditions. Other deprotection conditions for the PMB groups are available to those familiar with the art. Hydrolysis of esters similar to 86 can proceed under basic conditions to provide the carboxylic acid or the carboxylate salt. Sodium hydroxide or lithium hydroxide could be used for this transformation. Carboxylic acids or carboxylates exemplified by 87 can undergo coupling with 78 under standard amide coupling conditions known to those in the art. Amides similar to 88 can be converted to the secondary amine and coupled with a variety of functional groups utilizing similar methods to those disclosed in Scheme 14.

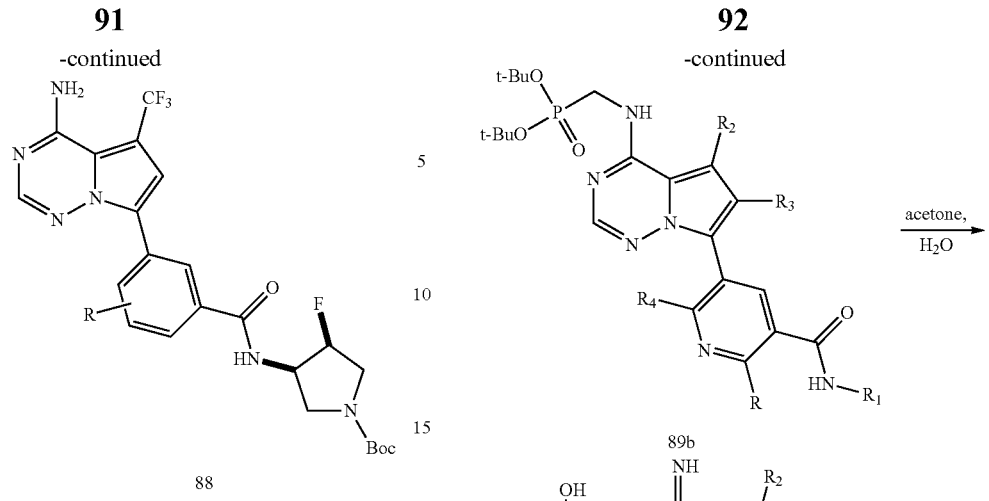

88

Further functionalization of the final products described herein to contain solubilizing prodrugs is described in Scheme 20. Compounds exemplified by 32 can be alkylated at the pyrrolotriazine using suitable electrophiles, such as di-tert-butyl(chloromethyl)phosphate, to generate intermediates characterized by 89. Alternative electrophiles which may provide additional solubility in a deprotected state may be used in place of the di-tert-butyl(chloromethyl)phosphate and would be known to those in the art. When necessitated by the electrophile, alternative coupling conditions, known to those in the art, may be used in place of the specific conditions listed for the transformation of 32 into 89. Deprotection of the tert-butyl groups can yield the final prodrug 90. These conditions could be modified by methods known to those in the art to suit the solubilizing group added in the first step.

Scheme 20

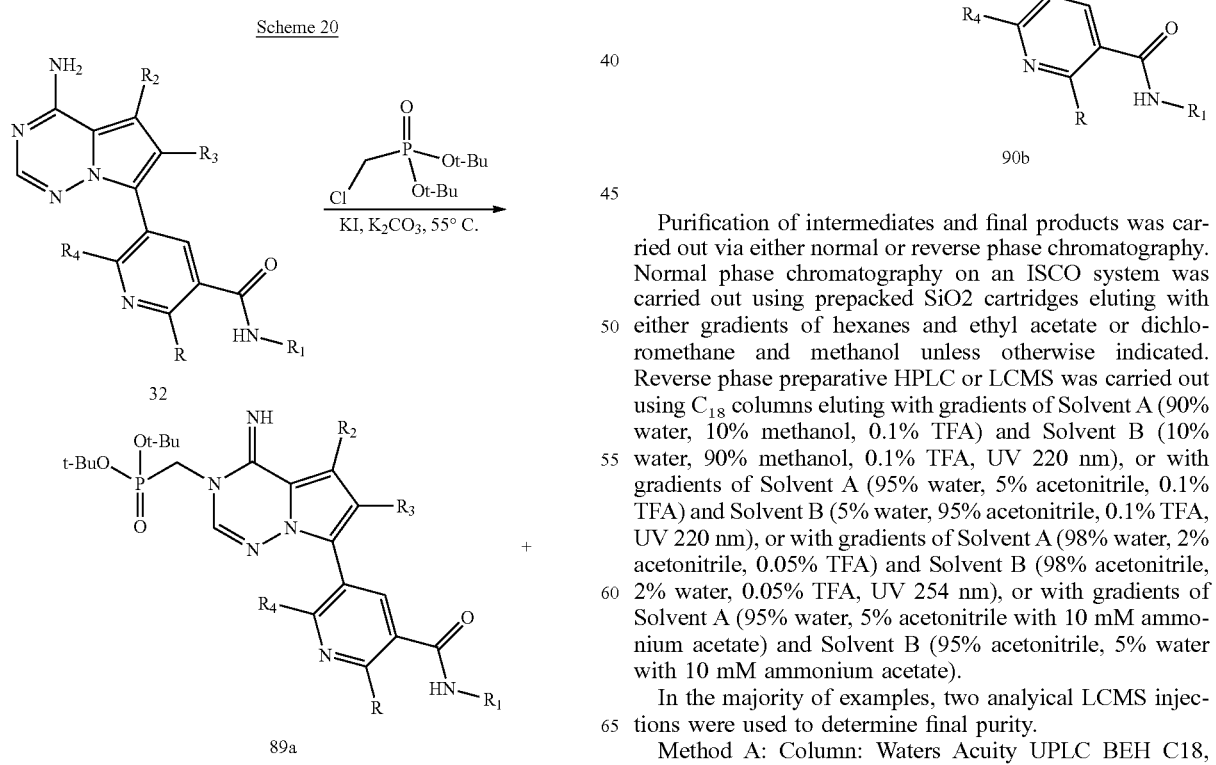

Purification of intermediates and final products was carried out via either normal or reverse phase chromatography. Normal phase chromatography on an ISCO system was carried out using prepacked SiO2 cartridges eluting with either gradients of hexanes and ethyl acetate or dichloromethane and methanol unless otherwise indicated. Reverse phase preparative HPLC or LCMS was carried out using $C_{18}$ columns eluting with gradients of Solvent A (90% water, 10% methanol, 0.1% TFA) and Solvent B (10% water, 90% methanol, 0.1% TFA, UV 220 nm), or with gradients of Solvent A (95% water, 5% acetonitrile, 0.1% TFA) and Solvent B (5% water, 95% acetonitrile, 0.1% TFA, UV 220 nm), or with gradients of Solvent A (98% water, 2% acetonitrile, 0.05% TFA) and Solvent B (98% acetonitrile, 2% water, 0.05% TFA, UV 254 nm), or with gradients of Solvent A (95% water, 5% acetonitrile with 10 mM ammonium acetate) and Solvent B (95% acetonitrile, 5% water with 10 mM ammonium acetate).

In the majority of examples, two analyical LCMS injections were used to determine final purity.

Method A: Column: Waters Acuity UPLC BEH C18, 2.1×50 mm, 1.7 μM particles; Mobile phase A: 5:95 acetonitrile:water with 10 mM ammonium acetate; Mobile phase B: 95:5 acetonitrile:water with 10 mM ammonium acetate; Temperature: 50° C.; Gradient: 0-100% B over 3 minutes, then a 0.75 minute hold at 100% B; Flow: 1.11 mL/min; Detection: UV at 220 nm.

Method B: Column: Waters Acquity UPLC BEH C18, 2.1×50 mm, 1.7 μm particles; Mobile phase A: 5:95 acetonitrile:water with 0.1% TFA; Mobile phase B: 95:5 acetonitrile:water with 0.1% TFA; Temperature: 50° C.; Gradient: 0-100% B over 3 min, then a 0.75 min hold at 100% B; Flow: 1.11 mL/min; Detection: UV at 220 nm. In a minority of examples analytical HPLC injections were used to determine final purity.

Method C: Column: XBridge C18, 3.0×150 mm, 3.5 μM particles; Mobile phase A: 5:95 methanol:water with 10 mM ammonium bicarbonate; Mobile phase B: 95:5 methanol:water with 10 mM ammonium bicarbonate; Gradient: 0-100% B over 15 minutes; Flow: 1 mL/min; Detection: UV at 220 and 254 nm.

Method D: Column: XBridge Phenyl, 3.0×150 mm, 3.5 μM particles; Mobile phase A: 5:95 methanol:water with 10 mM ammonium bicarbonate; Mobile phase B: 95:5 methanol:water with 10 mM ammonium bicarbonate; Gradient: 0-100% B over 15 minutes; Flow: 1 mL/min; Detection: UV at 220 and 254 nm.

A majority of mass spectra runs were: LCMS (ESI) m/z: [M+H]$^+$ BEH C18, 2.11×50 mm, 1.7 μm; Mobile phase A: 2:98 water:acetonitrile with 0.1% TFA; Mobile phase B: 98:2 acetonitrile:water with 0.1% TFA; Gradient: 0-100% B over 2 minutes; Flow: 0.8 mL/min; Detection: UV at 220 nm.

LC/MS methods for determining retention times:

Method 1: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Method 2: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm).

Method 3: Column: Waters XBridge C18, 2.1 mm×50 mm, 1.7 Åμm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm)

Method 4: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm)

Method 5: Column=Waters Acquity UPLC BEH C18, 2.1×50 mm, 1.7-μm particles; Mobile Phase A=5:95 acetonitrile:water with 0.1% trifluoroacetic acid; Mobile Phase B=95:5 acetonitrile:water with 0.1% trifluoroacetic acid; Temperature=50° C.; Gradient=0-100% B over 3 minutes, then a 0.75-minute hold at 100% B; Flow=1.0 mL/min; Detection=UV at 220 nm.

Method 6: Column=Waters Acquity UPLC BEH C18, 2.1×50 mm, 1.7-μm particles; Mobile Phase A=5:95 acetonitrile:water with 10 mM ammonium acetate; Mobile Phase B=95:5 acetonitrile:water with 10 mM ammonium acetate; Temperature=50° C.; Gradient=0-100% B over 3 minutes, then a 0.75-minute hold at 100% B; Flow: =1.0 mL/min; Detection=UV at 220 nm.

HPLC Methods:

Analytical HPLC analyses were carried out following methods A and B, and preparatory reverse-phase scale purifications were performed using methods C and D.

HPLC Method A. A linear gradient using 5% acetonitrile, 95% water, and 0.05% TFA (solvent A) and 95% acetonitrile, 5% water, and 0.05% TFA (solvent B; t=0 min, 10% B; t=15 min, 100% B) was employed on a SunFire C18 3.5 μm 3.5 mm×150 mm column. Flow rate was 0.5 mL/min, and UV detection was set to 220 nm. The LC column was maintained at ambient temperature.

HPLC Method B. A linear gradient using 5% acetonitrile, 95% water, and 0.05% TFA (solvent A) and 95% acetonitrile, 5% water, and 0.05% TFA (solvent B; t=0 min, 10% B; t=15 min, 100% B (20 min)) was employed on an XBridge Ph 3.5 μm 3.0 mm×150 mm column. Flow rate was 0.5 mL/min, and UV detection was set to 220 nm. The LC column was maintained at ambient temperature.

HPLC Method C. Column Waters XBridge C18, 19 mm×200 mm, 5 μm particles; guard column Waters XBridge C18, 19 mm×10 mm, 5 μm particles; mobile phase A, water with 20 mM ammonium acetate; mobile phase B, 95:5 methanol/water with 20 mM ammonium acetate; gradient, 25-65% B over 40 min, then a 5 min hold at 100% B; flow, 20 mL/min.

HPLC Method D. Column Waters Sunfire C18 OBD, 50 mm×300 mm, 10 μm particles; guard column Waters Sunfire C18 OBD, 50 mm×50 mm, 10 μm particles; mobile phase A, 10:90 methanol/water with 0.1% trifluoroacetic acid; mobile phase B, 90:10 methanol/water with 0.1% trifluoroacetic acid; gradient, 0-100% B over 30 min, then a 5 min hold at 100% B; flow, 150 mL/min.

NMR spectra were run with water suppression, unless otherwise noted. When water suppression affected characterization of the compounds by NMR, it is noted in the text.

Example 1: 3-{4-aminopyrrolo[2,1-f][1,2,4]triazin-7-yl}-N-(3-phenylbutyl)benzamide

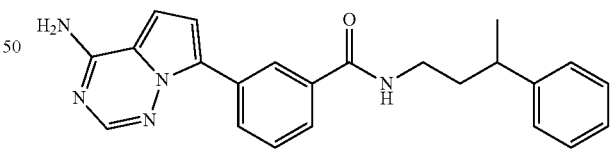

1A: N-(3-phenylbutyl)-3-(4,4,5,5-tetramethyl-1,3,2-dioxaborolan-2-yl)benzamide: To a solution of 3-carboxyphenylboronic acid pinacol ester (1.0 g, 4.03 mmol), 3-phenylbutan-1-amine (0.602 g, 4.03 mmol) and Hünig's base (1.478 mL, 8.46 mmol) in DMF (12 mL) was added BOP (1.783 g, 4.03 mmol). The reaction mixture was stirred at rt for 90 min. The reaction mixture was diluted with EtOAc (150 mL) then washed with 10% LiCl solution (50 mL×2), water (50 mL) and brine (50 mL). The organics were dried over anhydrous sodium sulfate and concentrated in vacuo.

The crude product was purified by column chromatography on the Isco system (80 g, 0-20% EtOAc/CH$_2$Cl$_2$) to yield N-(3-phenylbutyl)-3-(4,4,5,5-tetramethyl-1,3,2-dioxaborolan-2-yl)benzamide (0.818 g, 2.157 mmol, 53.5% yield) as a clear, viscous oil. MS ESI (m/z) 380.0 (M+H)

1: In a Bohdan Miniblock N-(3-phenylbutyl)-3-(4,4,5,5-tetramethyl-1,3,2-dioxaborolan-2-yl)benzamide (15 mg, 0.040 mmol) and 7-bromopyrrolo[2,1-f][1,2,4]triazin-4-amine (16.9 mg, 0.079 mmol) were dissolved in DMF (400 µl). To the vial was added $PdCl_2(dppf)-CH_2Cl_2$ adduct (3.23 mg, 3.95 µmol), followed by tripotassium phosphate (59.3 µl, 0.119 mmol). The reaction mixture was capped, degassed and purged with $N_2$. After stirring 1 h at 100° C., the mixture was cooled to rt. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-minute hold at 100% B; Flow: 20 mL/min. Fractions containing the desired product were combined and dried via centrifugal evaporation to yield the final product (6.8 mg, 17.6 µmol, 44%).

MS ESI m/z 386.2 (M+H)

$^1$H NMR (500 MHz, DMSO-$d_6$) δ 8.56-8.47 (m, 1H), 8.41 (s, 1H), 8.24 (br d, J=7.7 Hz, 1H), 7.95 (s, 1H), 7.92-7.76 (m, 2H), 7.73 (br d, J=7.7 Hz, 1H), 7.53 (t, J=7.8 Hz, 1H), 7.36-7.24 (m, 4H), 7.22-7.16 (m, 1H), 7.10 (d, J=4.5 Hz, 1H), 7.04 (d, J=4.5 Hz, 1H), 3.23 (dq, J=13.2, 6.5 Hz, 1H), 3.18-3.09 (m, 1H), 2.85-2.75 (m, 1H), 1.84 (q, J=7.3 Hz, 2H), 1.24 (br d, J=6.8 Hz, 3H).

Example 2: 3-[4-amino-5-(trifluoromethyl)pyrrolo[2,1-f][1,2,4]triazin-7-yl]-N-(3-phenylbutyl)benzamide

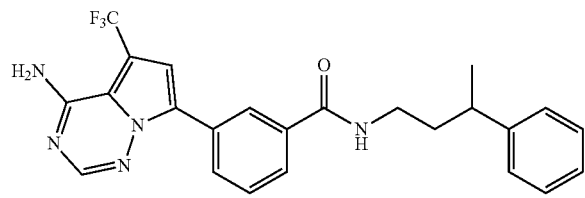 [SMILES: CC(CCNC(=O)c1cccc(-c2cc(C(F)(F)F)c3c(N)ncnn23)c1)c1ccccc1]

2A: 7-Bromo-N,N-bis(4-methoxybenzyl)pyrrolo[1,2-f][1,2,4]triazin-4-amine: A solution of 7-bromopyrrolo[2,1-f][1,2,4]triazin-4-amine (120 mg, 0.563 mmol) in N,N-dimethylformamide (2.5 mL) was treated with 4-methoxybenzyl chloride (0.168 mL, 1.239 mmol), then with cesium carbonate (459 mg, 1.408 mmol), added in one portion. The mixture was stirred at rt for 22 h. The mixture was diluted with water and extracted twice with ethyl acetate. The combined organic layers were washed with brine, dried over sodium sulfate and concentrated to provide a yellow semisolid. The material was chromatographed on an ISCO Companion 4 g silica gel column and eluted with EtOAc/hexane gradient (5-30%). The product containing fractions were collected and concentrated to give 7-bromo-N,N-bis(4-methoxybenzyl)pyrrolo[2,1-f][1,2,4]triazin-4-amine (147.8 mg, 0.316 mmol, 56% yield).

MS ESI (m/z) 453, 455 (M+H)

$^1$H NMR (400 MHz, CDCl$_3$) δ 8.14 (s, 1H), 7.23 (d, J=8.6 Hz, 4H), 6.93-6.88 (m, 4H), 6.61 (d, J=1.3 Hz, 2H), 4.94 (s, 4H), 3.83 (s, 6H).

(Alternatively sodium hydride can be used instead of cesium carbonate.)

2B: 7-Bromo-5-iodo-N,N-bis(4-methoxybenzyl)pyrrolo[1,2-f][1,2,4]triazin-4-amine: To a solution of 7-bromo-N,N-bis(4-methoxybenzyl)pyrrolo[2,1-f][1,2,4]triazin-4-amine (4.3 g, 9.49 mmol) and NIS (2.134 g, 9.49 mmol) in DMF (20 mL) was added 10 drops of TFA. The reaction mixture was stirred at rt for 16 h. Additional NIS (130 mg, 0.05 eq) was added and the mixture was stirred at rt for 1 h. The reaction mixture was poured into an ice-water and 1.5M $K_2HHPO_4$ (~1:1) mixture to afford a yellow precipitate. The precipitate was filtered. The filter cake was washed with water twice. The filter cake was triturated with ethyl acetate to give 2.98 g white solid as clean product. The mother liquor was concentrated and triturated with MeOH to give another 1.43 g crystalline white solid as clean product. The two batches were combined to provide 7-bromo-5-iodo-N,N-bis(4-methoxybenzyl)pyrrolo[2,1-f][1,2,4]triazin-4-amine (4.41 g, 7.60 mmol, 80% yield).

MS ESI (m/z) 579, 581 (M+H)

$^1$H NMR (400 MHz, CDCl$_3$) δ 8.13 (s, 1H), 7.29 (s, 1H), 7.07-7.03 (m, 4H), 6.89-6.85 (m, 4H), 4.64 (s, 4H), 3.83 (s, 6H).

2C: 7-Bromo-N,N-bis(4-methoxybenzyl)-5-(trifluoromethyl)pyrrolo[1,2 f][1,2,4]triazin-4-amine: A mixture of 7-bromo-5-iodo-N,N-bis(4-methoxybenzyl)pyrrolo[2,1-f][1,2,4]triazin-4-amine (0.2 g, 0.345 mmol) and copper(I) iodide (0.072 g, 0.380 mmol) in a capped pressure reaction vial was placed under vacuum, then filled with nitrogen. The degassing process was repeated twice. To the above solid mixture was added DMF (3 mL). The resulting suspension was degassed three times. To the above suspension was added methyl 2,2-difluoro-2-(fluorosulfonyl)acetate (0.265 g, 1.381 mmol). The reaction vial was placed in a 80° C. heating block and heated for 3 h. The reaction mixture was cooled to room temperature then filtered through Celite. The filter cake was washed with ethyl acetate three times. The combined filtrate was washed with 5% ammonia (2×), 10% LiCl, water and brine, then concentrated to give 7-bromo-N,N-bis(4-methoxybenzyl)-5-(trifluoromethyl)pyrrolo[2,1-f][1,2,4]triazin-4-amine (211 mg, 0.291 mmol, 84% yield).

MS ESI (m/z) 521, 523 (M+H)

$^1$H NMR (400 MHz, CDCl$_3$) δ 8.21 (s, 1H), 7.10 (s, 1H), 6.96-6.93 (m, 4H), 6.84-6.82 (m, 4H), 4.58 (s, 4H), 3.81-3.79 (m, 6H).

2D: 7-Bromo-5-(trifluoromethyl)pyrrolo[2,1-f][1,2,4]triazin-4-amine: 7-Bromo-N,N-bis(4-methoxybenzyl)-5-(trifluoromethyl)pyrrolo[2,1-f][1,2,4]triazin-4-amine (1.2 g, 2.302 mmol) in TFA (10 mL) in a pressure reaction vial was placed in a 110° C. heating block and heated for 4 h. The reaction mixture was concentrated. The residue was dissolved in dichloromethane and chromatographed on an ISCO Companion 24 g silica gel column, eluting with EtOAc/Hexane gradient (0-100%). The product containing fractions were collected and concentrated. The yellow oily residue was triturated with methanol to give 7-bromo-5-(trifluoromethyl)pyrrolo[2,1-f][1,2,4]triazin-4-amine (502 mg, 1.79 mmol, 78% yield).

MS ESI (m/z) 281, 283 (M+H)

$^1$H NMR (400 MHz, DMSO-$d_6$) δ 8.18 (s, 1H), 7.38 (s, 1H).

2E: 3-(4-amino-5-(trifluoromethyl)pyrrolo[2,1-f][1,2,4]triazin-7-yl)benzoic acid: To a solution of 7-bromo-5-(trifluoromethyl)pyrrolo[2,1-f][1,2,4]triazin-4-amine (150 mg, 0.534 mmol) and 3-boronobenzoic acid (106 mg, 0.640 mmol) in DMF (3 mL) was added potassium phosphate tribasic (0.801 mL, 1.601 mmol) (2M in $H_2O$). Nitrogen was sparged through the reaction mixture for 5 min and then $PdCl_2(dppf)-CH_2Cl_2$ adduct (43.6 mg, 0.053 mmol) was added. Sparging was continued for 5 min. The reaction vessel was sealed and heated to 100° C. for 3 h. After cooling to rt, methanol was added to induce precipitation. Isolation of the precipitate afforded 3-(4-amino-5-(trifluoromethyl)pyrrolo[2,1-f][1,2,4]triazin-7-yl)benzoic acid (100 mg, 0.310 mmol, 58.1% yield) as a white solid.

MS ESI (m/z) 323.1 (M+H).

2: To a solution of 3-(4-amino-5-(trifluoromethyl)pyrrolo[2,1-f][1,2,4]triazin-7-yl)benzoic acid (20 mg, 0.062 mmol) and 3-phenylbutan-1-amine (13.89 mg, 0.093 mmol) in DMF (1 mL) was added Hunig's base (0.033 mL, 0.186 mmol) and BOP (30.2 mg, 0.068 mmol). The resultant mixture was stirred at rt for 1 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 min, then a 5-minute hold at 100% B; Flow: 20 mL/min. Fractions containing the desired product were combined and dried via centrifugal evaporation to yield the final product (3.3 mg, 7.3 μmol, 12%).

MS ESI m/z 454.3 (M+H)

1H NMR (500 MHz, DMSO-d6) δ 8.52 (br. s., 1H), 8.35 (s, 1H), 8.25-8.10 (m, 2H), 7.81 (d, J=7.7 Hz, 1H), 7.65-7.48 (m, 2H), 7.38-7.21 (m, 4H), 7.20-7.12 (m, 1H), 3.30-3.10 (m, 2H), 2.84-2.71 (m, 1H), 1.83 (q, J=7.2 Hz, 2H), 1.29-1.16 (m, 4H).

Example 3: 5-[4-amino-5-(trifluoromethyl)pyrrolo[2,1-f][1,2,4]triazin-7-yl]-N-(1-benzyl-1H-pyrazol-4-yl)-2-fluorobenzamide

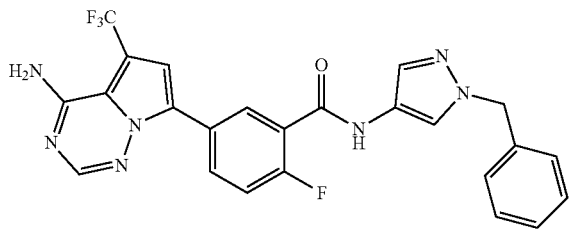 [SMILES: Nc1ncnn2c(-c3ccc(F)c(C(=O)Nc4cnn(Cc5ccccc5)c4)c3)cc(C(F)(F)F)c12]

3A: 5-(4-amino-5-(trifluoromethyl)pyrrolo[2,1-f][1,2,4]triazin-7-yl)-2-fluorobenzoic acid: To a solution of 7-bromo-5-(trifluoromethyl)pyrrolo[2,1-f][1,2,4]triazin-4-amine (500 mg, 1.779 mmol) and 5-borono-2-fluorobenzoic acid (360 mg, 1.957 mmol) in 1,4-dioxane (13 mL) was added potassium phosphate tribasic (2.67 mL, 5.34 mmol) (2M in H₂O). After bubbling nitrogen through for 5 min, PdCl₂(dppf) (130 mg, 0.178 mmol) was added. The reaction mixture was sparged with nitrogen for an additional 5 min. The reaction vessel was sealed and heated to 100° C. for 3 h. The crude mixture was filtered to remove the catalyst and concentrated. The crude residue was purified by recrystallization with MeOH to yield 5-(4-amino-5-(trifluoromethyl)pyrrolo[2,1-f][1,2,4]triazin-7-yl)-2-fluorobenzoic acid (500 mg, 1.3% mmol, 78% yield) as a white solid.

MS ESI m/z 587.0 (M+H).

3: To a solution of 5-(4-amino-5-(trifluoromethyl)pyrrolo[2,1-f][1,2,4]triazin-7-yl)-2-fluorobenzoic acid (20 mg, 0.059 mmol) and 1-benzyl-1H-pyrazol-4-amine (15.27 mg, 0.088 mmol) in DMF (1 mL) was added Hunig's base (0.031 mL, 0.176 mmol) and BOP (28.6 mg, 0.065 mmol). The resultant mixture was stirred at RT for 15 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 min, then a 5-minute hold at 100% B; Flow: 20 mL/min. Fractions containing the desired product were combined and dried via centrifugal evaporation to yield the final product (6.4 mg, 13 μmol, 22%).

MS ESI m/z 495.8 (M+H)

1H NMR (500 MHz, DMSO-d6) δ 10.62 (s, 1H), 8.35 (d, J=5.1 Hz, 1H), 8.24 (br. s., 1H), 8.15 (s, 1H), 8.18 (s, 1H), 7.59 (s, 1H), 7.62 (s, 1H), 7.48 (t, J=9.2 Hz, 1H), 7.39-7.20 (m, 5H), 5.32 (s, 2H).

Example 4: 3-{4-amino-6-fluoropyrrolo[2,1-f][1,2,4]triazin-7-yl}-N-[(2-phenoxyphenyl)methyl]benzamide

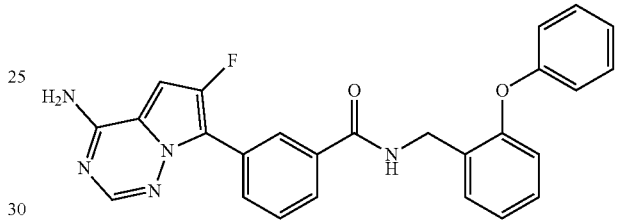

4A: 1-(tert-Butyl) 2-methyl 4,4-difluoropyrrolidine-1,2-dicarboxylate: To a solution of 1-tert-butyl 2-methyl 4-oxopyrrolidine-1,2-dicarboxylate (2 g, 8.22 mmol) in DCM (10 mL) cooled in a dry ice-acetonitrile bath was added DAST (1.63 mL, 12.3 mmol) dropwise at first, but then portionwise. The reaction mixture was stirred at −40° to rt over the weekend. The reaction mixture was poured slowly into a saturated aqueous solution of sodium bicarbonate cooled in an ice bath. The mixture was extracted with dichloromethane (3×), and the combined organic phases was washed with water and concentrated. The residue was purified by ISCO flash chromatography (0-100% ethyl acetate/hexane, 40 g silica gel column) to give 1.40 g of 1-(tert-butyl) 2-methyl 4,4-difluoropyrrolidine-1,2-dicarboxylate light brown oil.

4B: Methyl 4,4-difluoro-1-(2,2,2-trifluoroacetyl)pyrrolidine-2-carboxylate: A light brown solution of 1-tert-butyl 2-methyl 4,4-difluoropyrrolidine-1,2-dicarboxylate (1.4 g, 5.28 mmol) in TFA (10 mL) and DCM (10 mL) was stirred at rt ON. The reaction mixture was concentrated and rotavaped a few times with dichloromethane to give 2.01 g of methyl 4,4-difluoro-1-(2,2,2-trifluoroacetyl)pyrrolidine-2-carboxylate brown oil. Used without further purification.

4C: Methyl 4-fluoro-1H-pyrrole-2-carboxylate: To a solution of methyl 4,4-difluoro-1-(2,2,2-trifluoroacetyl)pyrrolidine-2-carboxylate (1.4 g, 5.36 mmol) in THF (15 mL) was added manganese dioxide (2.33 g, 26.8 mmol). The black reaction mixture was heated in a 75° C. heating block for 3.5 h. The reaction mixture was filtered through celite, and the filtrate was concentrated and purified by ISCO flash chromatography (0-70% ethyl acetate/hexane, 24 g silica gel column) to give 605 mg off methyl 4-fluoro-1H-pyrrole-2-carboxylate as a white solid.

¹H NMR (400 MHz, CDCl₃) δ 6.74 (td, J=3.4, 1.8 Hz, 1H), 6.63 (t, J=2.0 Hz, 1H), 3.88 (s, 3H).

4D: Methyl 1-amino-4-fluoro-1H-pyrrole-2-carboxylate: To a solution of methyl 4-fluoro-1H-pyrrole-2-carboxylate (600 mg, 4.19 mmol) in diethyl ether (20 mL) was added ammonium chloride (1.57 g, 29.3 mmol), ammonium hydroxide (3.5 mL, 27.0 mmol) and 1 N sodium hydroxide (14 mL, 4.19 mmol). Sodium hypochlorite (36 mL, 35.0 mmol) (commercial bleach) was added to the above reaction mixture over 20 min. Bubbling was noted during the addition of the bleach. The reaction mixture was stirred for 1.5 h at rt, then 0.5 mL BuaNOAc (1M aq solution) was added. After 1 h, methyltrioctylammonium chloride (50.8 mg, 0.126 mmol) was added, and the reaction mixture was stirred for 1 h. The layers of the reaction mixture were separated, and the aqueous phase of the reaction mixture was extracted with ether (2×). The combined organic phases were washed with a saturated aqueous sodium bisulfite solution and then dried over anhydrous sodium sulfate. Concentration under reduced pressure followed by purification by ISCO flash chromatography (0-80% ethyl acetate/hexane, 24 g silica gel column) provided 320 mg of methyl 1-amino-4-fluoro-1H-pyrrole-2-carboxylate as a white solid.

$^1$H NMR (400 MHz, CDCl$_3$) δ 6.81-6.76 (m, 1H), 6.51 (d, J=2.4 Hz, 1H), 3.85 (s, 3H).

4E: 6-Fluoropyrrolo[2,1-f][1,2,4]triazin-4(3H)-one: A solution of methyl 1-amino-4-fluoro-1H-pyrrole-2-carboxylate (597 mg, 3.78 mmol), formamide (6462 mg, 143 mmol) and acetic acid (432 μl, 7.55 mmol) was heated at 150° C. for 1.5 h. Pressure built up in the vial. The reaction mixture was split in half and heated at 150° C. for 30 min. The reaction mixture was diluted with water, filtered, and dried to give 6-fluoropyrrolo[2,1-f][1,2,4]triazin-4(3H)-one as a brown solid.

4F: 6-Fluoropyrrolo[2,1-f][1,2,4]triazin-4-amine: A suspension of 6-fluoropyrrolo[2,1-f][1,2,4]triazin-4(3H)-one (410 mg, 2.68 mmol) in phosphorus oxychloride (1.25 mL, 13.4 mmol) was heated at 100° C. for 6 h. The reaction mixture was concentrated, and the residue was dissolved in dichloromethane, cooled in an ice-water bath and water was added. The organic phase was separated and washed with water. Concentration under reduced pressure afforded a residue which was dissolved in NMP (5 mL) and treated with ammonia (5 mL). After 2 h, the reaction mixture was extracted with ethyl acetate (3×). The combined organic phases were washed with water and concentrated. The residue was purified by ISCO flash chromatography (0-100% ethyl acetate/hexane, 40 g silica gel column) to give 180 mg of 6-fluoropyrrolo[2,1-f][1,2,4]triazin-4-amine as a white solid.

4G: 7-Bromo-6-fluoropyrrolo[2,1-f][1,2,4]triazin-4-amine: To a solution of 6-fluoropyrrolo[2,1-f][1,2,4]triazin-4-amine (800 mg, 5.26 mmol) in THF (10 mL) was added NBS (234 mg, 1.32 mmol). More 6-fluoropyrrolo[2,1-f][1,2,4]triazin-4-amine (400 mg, 2.63 mmol) was added. The reaction mixture was stirred ON. The reaction was not complete, so additional NBS (70 mg, 0.39 mmol, 0.15 eq) was added. After 0.5 h, the reaction mixture was diluted with ethyl acetate, washed with 1.5 M aqueous sodium phosphate dibasic, washed with water, and concentrated to give 810 mg of 7-bromo-6-fluoropyrrolo[2,1-f][1,2,4]triazin-4-amine white solid.

$^1$H NMR (400 MHz, DMSO-d6) δ 8.02 (s, 1H), 7.90 (br. s., 2H), 6.91 (s, 1H).

4H: 3-(4-amino-6-fluoropyrrolo[2,1-f][1,2,4]triazin-7-yl) benzoic acid: A mixture of 7-bromo-6-fluoropyrrolo[2,1-f][1,2,4]triazin-4-amine (0.200 g, 0.866 mmol), 3-(4,4,5,5-tetramethyl-1,3,2-dioxaborolan-2-yl)benzoic acid (0.258 g, 1.039 mmol), tripotassium phosphate (2 M in water) (1.299 mL, 2.60 mmol), and N,N-dimethylformamide (4.0 mL) was degassed with vacuum and nitrogen (3×). 1,1'-Bis(diphenylphosphino)ferrocene palladium dichloride —CH$_2$Cl$_2$ adduct (0.071 g, 0.087 mmol) was added, and the reaction mixture was degassed (2×). The reaction mixture was immersed in an oil bath at 95° C. and stirred ON. The reaction mixture was cooled to rt and diluted with water (2 mL), followed by 1N aqueous hydrochloric acid (2 mL), resulting in a precipitate. The solid was collected by vacuum filtration and dried under reduced pressure to give 3-(4-amino-6-fluoropyrrolo[2,1-f][1,2,4]triazin-7-yl)benzoic acid (0.236 g, 0.867 mmol, 100%) as a tan solid.

MS ESI (m/z) 273.1 (M+H).

4: To a solution of 3-(4-amino-6-fluoropyrrolo[2,1-f][1,2,4]triazin-7-yl)benzoic acid (15 mg, 0.055 mmol) and (2-phenoxyphenyl)methanamine (16.47 mg, 0.083 mmol) in DMF (1 mL) was added Hunig's base (0.029 mL, 0.165 mmol) and BOP (26.8 mg, 0.061 mmol). The resultant mixture was stirred at rt for 15 min. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 25 min, then a 5-minute hold at 100% B; Flow: 20 mL/min. Fractions containing the desired product were combined and dried via centrifugal evaporation to yield the final product (18.3 mg, 32.2 μmol, 59%).

MS ESI m/z 453.9 (M+H)

1H NMR (500 MHz, DMSO-d6) δ 9.03 (br. s., 1H), 8.32 (s, 1H), 8.03 (d, J=7.5 Hz, 1H), 7.81 (d, J=7.7 Hz, 2H), 7.59 (t, J=7.7 Hz, 1H), 7.43-7.32 (m, 3H), 7.28 (t, J=7.4 Hz, 1H), 7.15 (t, J=7.4 Hz, 1H), 7.08 (t, J=7.2 Hz, 1H), 6.96 (d, J=7.8 Hz, 2H), 6.92-6.82 (m, 2H), 4.49 (d, J=5.2 Hz, 2H).

Example 5: 3-{4-amino-5-cyanopyrrolo[2,1-f][1,2,4]triazin-7-yl}-N-(3-hydroxy-3-phenylpropyl)benzamide

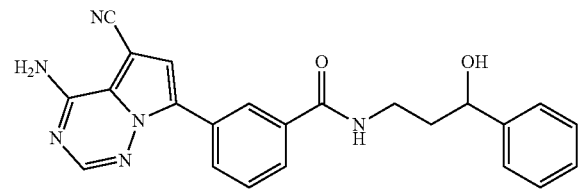 [SMILES: N#Cc1cc(-c2cccc(C(=O)NCCC(O)c3ccccc3)c2)n2ncnc(N)c12]

5A: 4-Amino-7-bromopyrrolo[1,2-f][1,2,4]triazine-5-carbonitrile: 4-Amino-7-bromopyrrolo[2,1-f][1,2,4]triazine-5-carbonitrile was prepared by nitrogenation of 7-bromo-5-ethynylpyrrolo[2,1-f][1,2,4]triazin-4-amine using the method described in *Angew. Chem. Int. Ed.*, 52:6677-6680 (2013). A mixture of 7-bromo-5-ethynylpyrrolo[2,1-f][1,2,4]triazin-4-amine (470 mg, 1.98 mmol), azidotrimethylsilane (457 mg, 3.97 mmol), silver carbonate (54.7 mg, 0.198 mmol) and DMSO (10 mL) was placed in a pressure reaction vial, the vial flushed with nitrogen and the mixture stirred at 100° C. for 15 h. The mixture was cooled to rt and diluted with water (100 mL) under vigorous stirring. The mixture was filtered to collect the product which was washed with water and ether and dried with suction to give crude 4-amino-7-bromopyrrolo[2,1-f][1,2,4]triazine-5-carbonitrile (400 mg).

¹H NMR (400 MHz, DMSO-d₆) δ 8.19 (s, 1H), 7.50 (s, 1H).

An alternate preparation to 5A:

5A-1: 4-Amino-7-bromopyrrolo[2,1-f][1,2,4]triazine-5-carboxamide: A suspension of ethyl 4-amino-7-bromopyrrolo[2,1-f][1,2,4]triazine-5-carboxylate (5.3 g, 18.59 mmol), THF (40 mL), MeOH (20 mL) and lithium hydroxide monohydrate (4.68 g, 112 mmol) dissolved in water (20 mL) was stirred at rt for 15 h and 50° C. for 1 h. The mixture was cooled to rt and made acidic (pH=2) by dropwise addition of concentrated HCl, diluted with water (200 mL) and the white precipitate collected by filtration. The product was washed with water and sucked dry and then dried further by concentrating a suspension of the solid in 20% MeOH/toluene (2×100 mL) under reduced pressure. 5A-2: The product from above was treated with DMF (40 mL) and DIPEA (19.48 mL, 112 mmol) and stirred for 5 min until most of the solid had dissolved. 1-hydroxy-7-azabenzotriazole (3.80 g, 27.9 mmol) and 1-(3-dimethylaminopropyl)-3-ethylcarbodiimide hydrochloride (5.35 g, 27.9 mmol) were added to the mixture, the resulting yellow mixture was stirred for 5 min and then treated with ammonium chloride (3.98 g, 74.4 mmol) and stirred at rt for 16 h. The mixture was diluted with water (20 mL), stirred for 5 min and filtered to collect the precipitate. The collected solid was washed with saturated NaHCO₃ (100 mL) and water (200 mL), dried under suction, and then dried in vacuo to give 4-amino-7-bromopyrrolo[2,1-f][1,2,4]triazine-5-carboxamide as a white solid (4.5 g, 95%).

MS ESI (m/z) 255.8 (M+H)

¹H NMR (400 MHz, DMSO-d₆) δ 10.41 (br. s., 1H), 8.24 (br. s., 1H), 8.11 (br. s., 1H), 8.01 (s, 1H), 7.67 (br. s., 1H), 7.48 (s, 1H). LC-MS: m/z=255.8, (M+H)⁺.

5A: 4-Amino-7-bromopyrrolo[2,1-f][1,2,4]triazine-5-carboxamide (1.0 g, 3.91 mmol) was placed in a 20 mL Biotage® pressure reaction vial and treated with phosphorus oxychloride (7.28 ml, 78 mmol). The vial was capped and heated for 20 h in a 120° C. heating block. The resulting brown mixture was cooled to rt and poured slowly into 2 M NaOH (75 mL) cooled to 0° C., keeping the temperature below 35° C. The resulting mixture was stirred for 10 min and then made basic to pH 7.5 with 5 M NaOH. The mixture was filtered to collect the yellow solid which was washed with water, dried under suction and dried in vacuo. The filtrate was kept at rt ON after which time more of the product crystallized. The second crop was collected, washed with water, dried and combined with the first crop to give 4-amino-7-bromopyrrolo[2,1-f][1,2,4]triazine-5-carbonitrile (0.68 g, 73% yield).

MS ESI m/z 237.8 (M+H)

1H NMR (400 MHz, DMSO-d6) δ 8.19 (s, 1H), 7.50 (s, 2H).

5B: 3-(4-amino-5-cyanopyrrolo[2,1-f][1,2,4]triazin-7-yl)benzoic acid: A mixture of 4-amino-7-bromopyrrolo[2,1-f][1,2,4]triazine-5-carbonitrile (0.200 g, 0.840 mmol), 3-(4,4,5,5-tetramethyl-1,3,2-dioxaborolan-2-yl)benzoic acid (0.250 g, 1.008 mmol), tripotassium phosphate (2 M in water) (1.260 mL, 2.52 mmol), and N,N-dimethylformamide (4.0 mL) was degassed with vacuum and nitrogen (3×). PdCl₂(dppf)₂-CH₂Cl₂ adduct (0.069 g, 0.084 mmol) was added, and the reaction mixture was degassed (2×). The reaction mixture was stirred at rt for 5 h. Water (4 mL) was added with stirring. Concentrated hydrochloric acid was added dropwise until a precipitate formed. The solid was collected by vacuum filtration and dried under reduced pressure to give 3-(4-amino-5-cyanopyrrolo[2,1-f][1,2,4]triazin-7-yl)benzoic acid (0.212 g, 0.759 mmol, 90% yield) as a light brown solid.

MS ESI (m/z) 280.1 (M+H).

5: A mixture of 3-(4-amino-5-cyanopyrrolo[2,1-f][1,2,4]triazin-7-yl)benzoic acid (0.025 g, 0.090 mmol), 3-amino-1-phenylpropan-1-ol (0.020 g, 0.134 mmol), Hunig's base (0.047 mL, 0.269 mmol), and BOP (0.044 g, 0.098 mmol) in N,N-dimethylformamide (1.0 mL) was stirred at RT for 60 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 5-minute hold at 100% B; Flow: 20 mL/min. Fractions containing the desired product were combined and dried via centrifugal evaporation to yield the final product (14.0 mg, 33.9 µmol, 38%).

MS ESI m/z 413.2 (M+H)

¹H NMR (500 MHz, DMSO-d6) δ 8.56 (br s, 1H), 8.39 (s, 1H), 8.22-8.13 (m, 2H), 7.84 (br d, J=7.6 Hz, 1H), 7.69 (s, 1H), 7.59 (br t, J=7.7 Hz, 1H), 7.40-7.29 (m, 4H), 7.29-7.20 (m, 1H), 5.38 (br d, J=4.3 Hz, 1H), 4.64 (br d, J=5.0 Hz, 1H), 3.49 (br s, 1H), 3.36 (br d, J=5.8 Hz, 1H), 1.91-1.84 (m, 2H).

Example 6: 3-{4-amino-5-cyanopyrrolo[2,1-f][1,2,4]triazin-7-yl}-N-(1-benzyl-1H-pyrazol-4-yl)benzamide

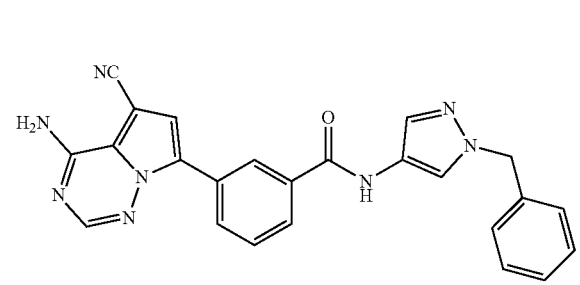 [SMILES: N#Cc1cc(-c2cccc(C(=O)Nc3cnn(Cc4ccccc4)c3)c2)n2ncnc(N)c12]

A mixture of 3-(4-amino-5-cyanopyrrolo[2,1-f][1,2,4]triazin-7-yl)benzoic acid (0.025 g, 0.090 mmol), 1-benzyl-1H-pyrazol-4-amine (0.023 g, 0.134 mmol), Hunig's base (0.047 mL, 0.269 mmol), and BOP (0.044 g, 0.098 mmol) in N,N-dimethylformamide (1.0 mL) was stirred at RT for 60 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-minute hold at 100% B; Flow: 20 mL/min. Fractions containing the desired product were combined and dried via centrifugal evaporation to yield the final product (37.0 mg, 85.2 µmol, 95%).

MS ESI m/z 434.9 (M+H)

¹H NMR (500 MHz, DMSO-d₆) δ 10.57 (s, 1H), 8.52 (br s, 1H), 8.26-8.14 (m, 3H), 7.95 (br d, J=7.3 Hz, 1H), 7.74 (s, 1H), 7.70-7.59 (m, 2H), 7.41-7.23 (m, 6H), 5.33 (s, 2H).

Example 7: 3-{4-amino-5-cyanopyrrolo[2,1-f][1,2,4]triazin-7-yl}-N-(3-phenylbutyl)benzamide

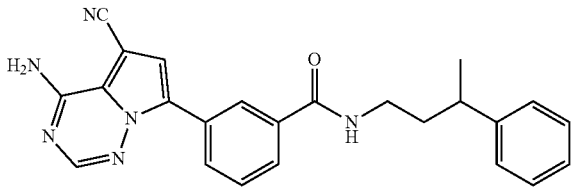 [SMILES: CC(CCNC(=O)c1cccc(-c2cc(C#N)c3c(N)ncnn23)c1)c1ccccc1]

A mixture of 3-(4-amino-5-cyanopyrrolo[2,1-f][1,2,4]triazin-7-yl)benzoic acid (0.025 g, 0.090 mmol), 3-phenylbutan-1-amine (0.020 g, 0.134 mmol), Hunig's base (0.047 mL, 0.269 mmol), and BOP (0.044 g, 0.098 mmol) in N,N-dimethylformamide (1.0 mL) was stirred at rt for 60 min. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 40-65% B over 25 min, then a 2-minute hold at 65% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 35-60% B over 25 min, then a 2-minute hold at 60% B; Flow: 20 mL/min. Fractions containing the desired product were combined and dried via centrifugal evaporation to yield the final product (8.0 mg, 12.5 μmol, 14%).

MS ESI m/z 411.1 (M+H)

$^1$H NMR (500 MHz, DMSO-$d_6$) δ 8.53 (br s, 1H), 8.35 (s, 1H), 8.18 (s, 1H), 8.14 (br d, J=7.7 Hz, 1H), 7.81 (br d, J=7.7 Hz, 1H), 7.66 (s, 1H), 7.58 (t, J=7.8 Hz, 1H), 7.32-7.23 (m, 5H), 7.20-7.15 (m, 1H), 3.63-3.55 (m, 1H), 3.26-3.18 (m, 1H), 3.17-3.08 (m, 1H), 2.84-2.73 (m, 1H), 1.82 (q, J=7.2 Hz, 2H), 1.23 (br d, J=6.9 Hz, 3H).

Example 8 5-{4-amino-5-fluoropyrrolo[2,1-f][1,2,4]triazin-7-yl}-N-(1-benzyl-1H-pyrazol-4-yl)-2-methoxypyridine-3-carboxamide

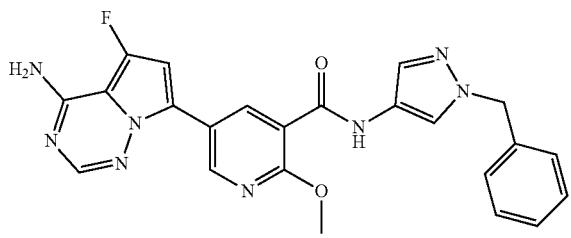 [SMILES: COc1ncc(-c2cc(F)c3c(N)ncnn23)cc1C(=O)Nc1cnn(Cc2ccccc2)c1]

8A: N-(1-benzyl-1H-pyrazol-4-yl)-5-bromo-2-methoxynicotinamide: A mixture of 5-bromo-2-methoxynicotinic acid (0.500 g, 2.155 mmol), 1-benzyl-1H-pyrazol-4-amine (0.560 g, 3.23 mmol), Hunig's base (1.129 mL, 6.46 mmol) and BOP (1.048 g, 2.370 mmol) in tetrahydrofuran (12 mL) was stirred at rt for 3 h. The reaction mixture was diluted with ethyl acetate, washed with water, washed with brine and dried over anhydrous sodium sulfate. Concentration under reduced pressure followed by purification by ISCO flash chromatography (24 g column; 0%-100% ethyl acetate in hexane) afforded N-(1-benzyl-1H-pyrazol-4-yl)-5-bromo-2-methoxynicotinamide (0.689 g, 1.779 mmol, 83% yield) as a white solid.

8B: N-(1-benzyl-1H-pyrazol-4-yl)-2-methoxy-5-(4,4,5,5-tetramethyl-1,3,2-dioxaborolan-2-yl)nicotinamide: A mixture of N-(1-benzyl-1H-pyrazol-4-yl)-5-bromo-2-methoxynicotinamide (0.689 g, 1.779 mmol), 4,4,4',4',5,5,5',5'-octamethyl-2,2'-bi(1,3,2-dioxaborolane) (0.542 g, 2.135 mmol), and potassium acetate (0.262 g, 2.67 mmol) in dioxane (15 mL) was degassed (3×) with vacuum/nitrogen. 1,1'-Bis(diphenylphosphino)ferrocene palladium dichloride—$CH_2Cl_2$ adduct (0.145 g, 0.178 mmol) was added, and the mixture was degassed (2×). The reaction mixture was immersed in an oil bath at 80° C. and stirred ON. The mixture was diluted with ethyl acetate, washed with water and brine. The organic layer was collected, and the aqueous layers were sequentially extracted with ethyl acetate (2×). The combined organic layers were dried over anhydrous sodium sulfate and concentrated. Purification by ISCO flash chromatography (40 g column; 0%-100% ethyl acetate in hexane) afforded N-(1-benzyl-1H-pyrazol-4-yl)-2-methoxy-5-(4,4,5,5-tetramethyl-1,3,2-dioxaborolan-2-yl)nicotinamide (0.501 g, 1.154 mmol, 64.8% yield) as a white solid.

MS ESI (m/z) 435.2 (M+H).

8: A mixture of 7-bromo-5-fluoropyrrolo[2,1-f][1,2,4]triazin-4-amine (0.035 g, 0.151 mmol), N-(1-benzyl-1H-pyrazol-4-yl)-2-methoxy-5-(4,4,5,5-tetramethyl-1,3,2-dioxaborolan-2-yl)nicotinamide (0.079 g, 0.182 mmol), tripotassium phosphate (2 M in water) (0.227 mL, 0.454 mmol), and dioxane (2 mL) was degassed with vacuum and nitrogen (3×). 1,1'-Bis(diphenylphosphino)palladium dichloride-$CH_2Cl_2$ adduct (0.012 g, 0.015 mmol) was added and the reaction mixture was degassed (2×). The reaction mixture was immersed in an oil bath at 95° C. and stirred ON. The reaction mixture was diluted with ethyl acetate, washed with water, and washed with brine. The organic layer was collected, and the aqueous layers were sequentially extracted with ethyl acetate. The combined organic layers were dried over anhydrous sodium sulfate and concentrated under reduced pressure. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 25 min, then a 5-minute hold at 100% B; Flow: 20 mL/min. Fractions containing the desired product were combined and dried via centrifugal evaporation to yield the final product (67.0 mg, 146.1 μmol, 97%).

MS ESI m/z 459.2 (M+H)

$^1$H NMR (500 MHz, DMSO-$d_6$) δ 10.35 (s, 1H), 8.90 (d, J=2.0 Hz, 1H), 8.73 (d, J=2.0 Hz, 1H), 8.15 (s, 1H), 7.86 (s, 1H), 7.63 (s, 1H), 7.39-7.23 (m, 6H), 7.08 (s, 1H), 5.31 (s, 2H), 4.01 (s, 3H).

Example 9: 5-{4-amino-5-cyanopyrrolo[2,1-f][1,2,4]triazin-7-yl}-N-(1-benzyl-1H-pyrazol-4-yl)-2-methoxypyridine-3-carboxamide

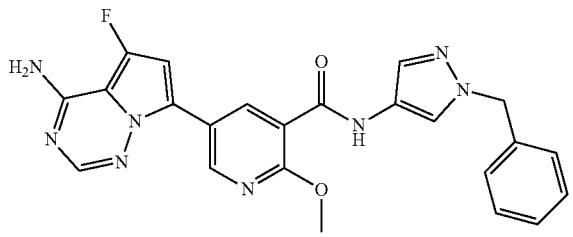 [SMILES: COc1ncc(-c2cc(F)c3c(N)ncnn23)cc1C(=O)Nc1cnn(Cc2ccccc2)c1]

A mixture of 4-amino-7-bromopyrrolo[2,1-f][1,2,4]triazine-5-carbonitrile (0.050 g, 0.210 mmol), N-(1-benzyl-1H-pyrazol-4-yl)-2-methoxy-5-(4,4,5,5-tetramethyl-1,3,2-dioxaborolan-2-yl)nicotinamide (0.091 g, 0.210 mmol), tripotassium phosphate (2 M in water) (0.315 mL, 0.630 mmol), and dioxane (2 mL) was degassed with vacuum and nitrogen (3×). 1,1'-Bis(diphenylphosphino)ferrocene palladium dichloride-CH$_2$Cl$_2$ adduct (0.017 g, 0.021 mmol) was added, and the reaction mixture was degassed (2×). The reaction mixture was immersed in an oil bath at 95° C. and stirred ON. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 5-minute hold at 100% B; Flow: 20 mL/min. Fractions containing the desired product were combined and dried via centrifugal evaporation to yield the final product (4.0 mg, 8.6 μmol, 4%).

MS ESI m/z 466.2 (M+H)

$^1$H NMR (500 MHz, DMSO-d$_6$) δ 10.35 (s, 1H), 8.89 (s, 1H), 8.70 (s, 1H), 8.23-8.13 (m, 2H), 7.74 (s, 1H), 7.63 (s, 1H), 7.39-7.23 (m, 5H), 5.32 (s, 2H), 4.03 (s, 3H).

Example 10: 5-[4-amino-5-(trifluoromethyl)pyrrolo[2,1-f][1,2,4]triazin-7-yl]-N-[(3S)-3-(4-chlorophenyl)-3-hydroxypropyl]-2-methoxypyridine-3-carboxamide

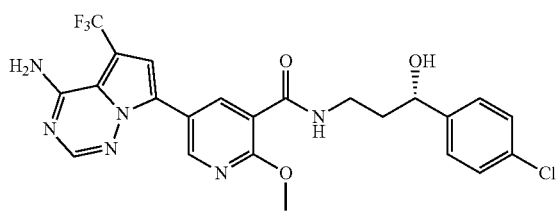 [SMILES: COc1ncc(-c2cc(C(F)(F)F)c3c(N)ncnn23)cc1C(=O)NCC[C@H](O)c1ccc(Cl)cc1]

10A: methyl 5-(4-amino-5-(trifluoromethyl)pyrrolo[2,1-f][1,2,4]triazin-7-yl)-2-methoxynicotinate: A mixture of 7-bromo-5-(trifluoromethyl)pyrrolo[2,1-f][1,2,4]triazin-4-amine (1.774 g, 6.31 mmol), methyl 2-methoxy-5-(4,4,5,5-tetramethyl-1,3,2-dioxaborolan-2-yl)nicotinate (2.22 g, 7.57 mmol), tripotassium phosphate (2 M in water) (9.47 mL, 18.93 mmol), and dioxane (35 mL) was degassed with vacuum and nitrogen (3×). 1,1'-Bis(diphenylphosphino)ferrocene palladium dichloride —CH$_2$Cl$_2$ adduct (0.515 g, 0.631 mmol) was added, and the reaction mixture was degassed (2×). The reaction mixture was immersed in an oil bath at 70° C. and stirred ON. The reaction mixture was diluted with ethyl acetate (40 mL) and water (40 mL) and stirred for 2 h. The resulting precipitate was collected by vacuum filtration and washed well with ethyl acetate, water, and ethyl acetate. The compound was dried to give methyl 5-(4-amino-5-(trifluoromethyl)pyrrolo[2,1-f][1,2,4]triazin-7-yl)-2-methoxynicotinate (1.34 g, 3.65 mmol, 57.8% yield) as an off-white solid. Additional product was in the filtrate.

MS ESI (m/z) 300.1 (M+H).

10B: 5-(4-amino-5-(trifluoromethyl)pyrrolo[2,1-f][1,2,4]triazin-7-yl)-2-methoxynicotinic acid, lithium salt: A mixture of methyl 5-(4-amino-5-(trifluoromethyl)pyrrolo[2,1-f][1,2,4]triazin-7-yl)-2-methoxynicotinate (1.34 g, 3.65 mmol) and lithium hydroxide, H$_2$O (0.153 g, 3.65 mmol) in a mixture of methanol (10 mL), tetrahydrofuran (10.00 mL), and water (5.00 mL) was stirred at rt ON. The heterogeneous reaction mixture was filtered under reduced pressure, and the resulting solid was dried overnight to give 5-(4-amino-5-(trifluoromethyl)pyrrolo[2,1-f][1,2,4]triazin-7-yl)-2-methoxynicotinic acid (1.05 g, 2.97 mmol, 81% yield) as a white solid.

MS ESI (m/z) 354.1 (M+H).

10: A mixture of 5-(4-amino-5-(trifluoromethyl)pyrrolo[2,1-f][1,2,4]triazin-7-yl)-2-methoxynicotinic acid, lithium salt (0.023 g, 0.064 mmol), (S)-3-amino-1-(4-chlorophenyl)propan-1-ol, HCl (0.021 g, 0.096 mmol), Hunig's base (0.033 mL, 0.192 mmol), and BOP (0.031 g, 0.070 mmol) in N,N-dimethylformamide (1.0 mL) was stirred at RT for 60 min. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 22 min, then a 2-minute hold at 70% B; Flow: 20 mL/min. Fractions containing the desired product were combined and dried via centrifugal evaporation to yield the final product (27.1 mg, 36.2 μmol, 57%).

MS ESI m/z 521.2 (M+H)

$^1$H NMR (500 MHz, DMSO-d6) δ 8.89 (d, J=2.4 Hz, 1H), 8.78 (d, J=2.3 Hz, 1H), 8.51 (br t, J=5.2 Hz, 1H), 8.17 (s, 1H), 7.60 (s, 1H), 7.39 (s, 4H), 5.52 (d, J=4.3 Hz, 1H), 4.74-4.68 (m, 1H), 4.04 (s, 3H), 3.43-3.35 (m, 2H), 1.93-1.79 (m, 2H).

Example 11: tert-butyl (3S)-3-{5-[4-amino-5-(trifluoromethyl)pyrrolo[2,1-f][1,2,4]triazin-7-yl]-2-methoxypyridine-3-amido}pyrrolidine-1-carboxylate

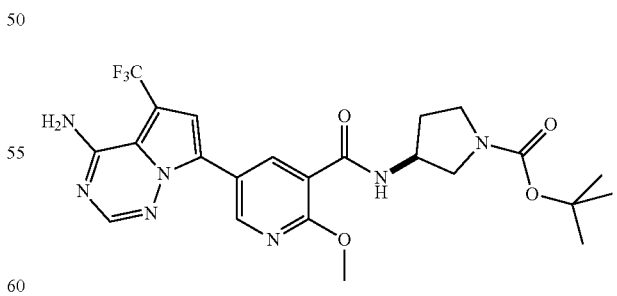

To a solution of 5-(4-amino-5-(trifluoromethyl)pyrrolo[2,1-f][1,2,4]triazin-7-yl)-2-methoxynicotinic acid (500 mg, 1.415 mmol) and (S)-tert-butyl 3-aminopyrrolidine-1-carboxylate (264 mg, 1.415 mmol) in 1,4-dioxane (10 mL) was added Hunig's base (0.742 mL, 4.25 mmol) and BOP (689 mg, 1.557 mmol). The resultant mixture was stirred at rt for 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 min, then a 5-minute hold at 100% B; Flow: 20 mL/min. Fractions containing the desired product were combined and dried via centrifugal evaporation to yield the final product (18.3 mg, 32.2 μmol, 59%).

MS ESI m/z 522.3 (M+H)

$^1$H NMR (500 MHz, DMSO-d$_6$) δ 8.95-8.81 (m, 1H), 8.65-8.57 (m, 1H), 8.47-8.37 (m, 1H), 8.19-8.06 (m, 1H), 7.66-7.51 (m, 1H), 4.51-4.35 (m, 1H), 4.04-3.93 (m, 3H), 3.64-3.52 (m, 1H), 3.49-3.42 (m, 2H), 3.43-3.15 (m, 3H), 2.18-2.04 (m, 1H), 1.98-1.82 (m, 1H), 1.45-1.30 (m, 9H)

Example 12: 5-[4-amino-5-(trifluoromethyl)pyrrolo[2,1-f][1,2,4]triazin-7-yl]-2-methoxy-N-[(3S)-1-(4-methylbenzoyl)pyrrolidin-3-yl]pyridine-3-carboxamide

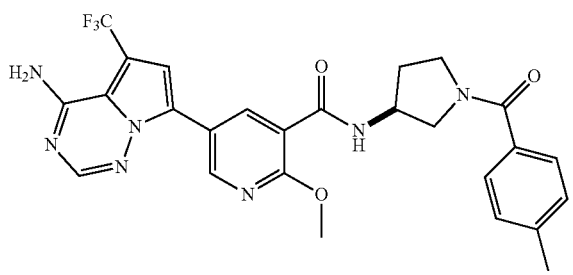

12A: (S)-5-(4-amino-5-(trifluoromethyl)pyrrolo[2,1-f][1,2,4]triazin-7-yl)-2-methoxy-N-(pyrrolidin-3-yl)nicotinamide: A solution of (S)-tert-butyl 3-(5-(4-amino-5-(trifluoromethyl)pyrrolo[2,1-f][1,2,4]triazin-7-yl)-2-methoxynicotinamido)pyrrolidine-1-carboxylate (500 mg, 0.959 mmol) in neat TFA (3 mL, 38.9 mmol) was stirred at rt for 30 min. The reaction mixture was evaporated to remove the TFA and further dried on the vacuum pump to yield (S)-5-(4-amino-5-(trifluoromethyl)pyrrolo[2,1-f][1,2,4]triazin-7-yl)-2-methoxy-N-(pyrrolidin-3-yl)nicotinamide (13.0 mg, 0.023 mmol, 65%).

MS ESI m/z 422.1 (M+H)

12: To a solution of (S)-5-(4-amino-5-(trifluoromethyl)pyrrolo[2,1-f][1,2,4]triazin-7-yl)-2-methoxy-N-(pyrrolidin-3-yl)nicotinamide (15 mg, 0.036 mmol) in THF (1.5 mL) was added Hunig's base (0.031 mL, 0.178 mmol) and 4-methylbenzoic acid (5.33 mg, 0.039 mmol), and then BOP (18.89 mg, 0.043 mmol) was added. The resultant mixture was stirred at rt for 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 3-minute hold at 100% B; Flow: 20 mL/min. Fractions containing the desired product were combined and dried via centrifugal evaporation to yield the final product (13.0 mg, 24.1 μmol, 67%).

MS ESI m/z 540.2 (M+H)

1H NMR (500 MHz, DMSO-d6) δ 8.86 (d, J=16.0 Hz, 1H), 8.68-8.56 (m, 1H), 8.54-8.47 (m, 1H), 8.14 (d, J=13.5 Hz, 1H), 7.57 (d, J=15.4 Hz, 1H), 7.40 (d, J=7.8 Hz, 1H), 7.42 (d, J=7.9 Hz, 1H), 7.29-7.19 (m, 2H), 4.36 (d, J=5.2 Hz, 1H), 4.00 (s, 1H), 3.96 (s, 2H), 3.57-3.47 (m, 1H), 3.38 (d, J=7.0 Hz, 1H), 2.32 (br. s., 3H), 2.25-2.09 (m, 1H), 2.05-1.98 (m, 1H).

Example 13: 5-[4-amino-5-(trifluoromethyl)pyrrolo[2,1-f][1,2,4]triazin-7-yl]-2-methyl-N-(4,4,4-trifluoro-3-hydroxy-3-phenylbutyl)pyridine-3-carboxamide

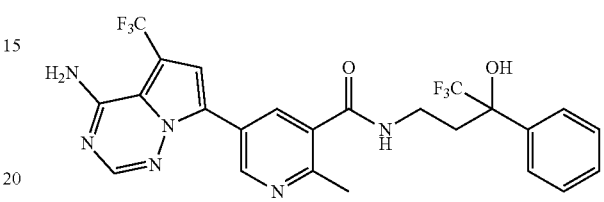

13A: ethyl 2-methyl-5-(4,4,5,5-tetramethyl-1,3,2-dioxaborolan-2-yl)nicotinate: To an oven-dried 10 mL vial were added ethyl 5-bromo-2-methylnicotinate (1 g, 4.10 mmol), bis(pinacolato)diboron (217 mg, 0.854 mmol) and potassium acetate (1.206 g, 12.29 mmol). 1,4-Dioxane (15 mL) was introduced into the vial and nitrogen gas was blown through the mixture for 10 min. PdCl$_2$(dppf) (0.150 g, 0.205 mmol) was added to the reaction mixture and nitrogen gas was blown through the mixture for 10 min. The resultant mixture was heated to reflux at 80° C. ON. The reaction mixture was filtered through a pad of Celite and concentrated. The crude material was purified by ISCO flash chromatography (20%-80% EtOAc/hexanes) to yield ethyl 2-methyl-5-(4,4,5,5-tetramethyl-1,3,2-dioxaborolan-2-yl)nicotinate (0.9 g, 3.09 mmol, 75% yield) as a white solid.

MS ESI m/z 209.9 (mass of corresponding boronic acid)

13B: 5-(4-amino-5-(trifluoromethyl)pyrrolo[2,1-f][1,2,4]triazin-7-yl)$_2$-methylnicotinic acid: To a solution of 7-bromo-5-(trifluoromethyl)pyrrolo[2,1-f][1,2,4]triazin-4-amine (300 mg, 1.067 mmol) and ethyl 2-methyl-5-(4,4,5,5-tetramethyl-1,3,2-dioxaborolan-2-yl)nicotinate (373 mg, 1.281 mmol) in 1,4-dioxane (8 mL) was added potassium phosphate tribasic (1.601 mL, 3.20 mmol)(2M in H$_2$O). Nitrogen was bubbled through the mixture for 5 min and then PdCl$_2$(dppf) (78 mg, 0.107 mmol) was added. Nitrogen was bubbled through the mixture for another 5 min. The reaction vessel was sealed and heated to 100° C. for 3 h. The reaction mixture was cooled to rt. 1N NaOH (10 mL) was added and the mixture stirred at rt for 2 h. The reaction mixture was filtered and concentrated. The crude material was purified by recrystallization with MeOH to yield 5-(4-amino-5-(trifluoromethyl)pyrrolo[2,1-f][1,2,4]triazin-7-yl) 2-methylnicotinic acid, sodium salt (300 mg, 0.890 mmol, 83% yield) as a white solid. MS ESI m/z 366.1 (M+H)

$^1$H NMR (400 MHz, CD$_3$OD) δ 9.27 (d, J=2.2 Hz, 1H), 9.06 (d, J=2.2 Hz, 1H), 8.10 (s, 1H), 7.44 (s, 1H), 2.93 (s, 3H)

13: To a solution of 5-(4-amino-5-(trifluoromethyl)pyrrolo[2,1-f][1,2,4]triazin-7-yl)-2-methylnicotinic acid, sodium salt (25 mg, 0.074 mmol) and 4-amino-1,1,1-trifluoro-2-phenylbutan-2-ol (17.06 mg, 0.078 mmol) in 1,4-dioxane (2 mL) was added Hunig's base (0.039 mL, 0.222 mmol) and BOP (39.3 mg, 0.089 mmol). The resultant mixture was stirred at RT for 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 4-minute hold at 100% B; Flow: 20 mL/min. Fractions containing the desired product were combined and dried via centrifugal evaporation to yield the final product (7.6 mg, 14.1 μmol, 19%).

MS ESI m/z 539.4 (M+H)

1H NMR (500 MHz, DMSO-d6) δ 9.24-9.10 (m, 1H), 8.45 (t, J=5.2 Hz, 1H), 8.31-8.23 (m, 1H), 8.19 (s, 1H), 7.70-7.56 (m, 3H), 7.51-7.40 (m, 2H), 7.39-7.31 (m, 1H), 3.35-3.24 (m, 1H), 3.01-2.87 (m, 1H), 2.54 (s, 3H), 2.36-2.20 (m, 1H).

Example 14: 5-[4-amino-5-(trifluoromethyl)pyrrolo[2,1-f][1,2,4]triazin-7-yl]-N-(1-benzoyl-4-methylpyrrolidin-3-yl)-2-methoxypyridine-3-carboxamide

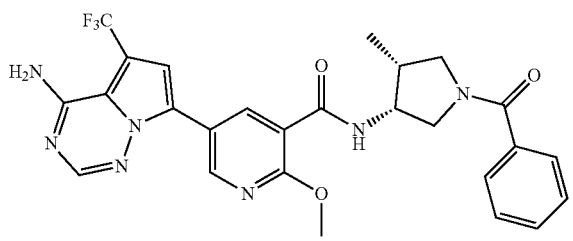 [SMILES: COc1ncc(-c2cc(C(F)(F)F)c3c(N)ncnn23)cc1C(=O)N[C@H]1CN(C(=O)c2ccccc2)C[C@H]1C]

14A: (3R,4R)-benzyl 3-(5-(4-amino-5-(trifluoromethyl)pyrrolo[2,1-f][1,2,4]triazin-7-yl)-2-methoxynicotinamido)-4-methylpyrrolidine-1-carboxylate: To a solution of 5-(4-amino-5-(trifluoromethyl)pyrrolo[2,1-f][1,2,4]triazin-7-yl)-2-methoxynicotinic acid (100 mg, 0.283 mmol) and (3R,4R)-benzyl 3-amino-4-methylpyrrolidine-1-carboxylate (73.0 mg, 0.311 mmol) in 1,4-dioxane (3 mL) and DMF (1 mL) was added DIEA (0.148 mL, 0.849 mmol) and BOP (150 mg, 0.340 mmol). The reaction mixture was stirred at rt for 30 min. The crude residue was purified by prep-HPLC to yield (3R,4R)-benzyl 3-(5-(4-amino-5-(trifluoromethyl)pyrrolo[2,1-f][1,2,4]triazin-7-yl)-2-methoxynicotinamido)-4-methylpyrrolidine-1-carboxylate (120 mg, 0.211 mmol, 74.4% yield) as a white solid.

MS ESI m/z 570.3 (M+H)

14B: 5-(4-amino-5-(trifluoromethyl)pyrrolo[2,1-f][1,2,4]triazin-7-yl)-2-methoxy-N-((3R,4R)-4-methylpyrrolidin-3-yl)nicotinamide, TFA: A solution of (3R,4R)-benzyl 3-(5-(4-amino-5-(trifluoromethyl)pyrrolo[2,1-f][1,2,4]triazin-7-yl)-2-methoxynicotinamido)-4-methylpyrrolidine-1-carboxylate (100 mg, 0.176 mmol) in TFA (1 mL, 12.98 mmol) was stirred at rt for 2 d. The reaction mixture was concentrated and further dried on vacuum pump. The crude material was used in the next step without purification.

14: To a solution of 5-(4-amino-5-(trifluoromethyl)pyrrolo[2,1-f][1,2,4]triazin-7-yl)-2-methoxy-N-(4-methylpyrrolidin-3-yl)nicotinamide, TFA (20 mg, 0.046 mmol) in THF (1 mL) was added benzoic acid (6.73 mg, 0.055 mmol), Hunig's base (0.024 mL, 0.138 mmol) and BOP (24.38 mg, 0.055 mmol). The resultant mixture was stirred at rt for 1 h. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 19 min, then a 5-minute hold at 100% B; Flow: 20 mL/min. Fractions containing the desired product were combined and dried via centrifugal evaporation to yield the final product (10.2 mg, 18 μcool, 40%).

MS ESI m/z 540.2 (M+H)

1H NMR (500 MHz, DMSO-d$_6$) δ 8.90 (d, J=15.9 Hz, 1H), 8.62 (br. s., 1H), 8.46 (d, J=7.9 Hz, 1H), 8.16 (d, J=17.1 Hz, 1H), 7.60 (d, J=18.3 Hz, 1H), 7.56-7.47 (m, 2H), 7.45 (br. s., 3H), 4.61 (br. s., 1H), 4.02 (s, 1H), 3.98 (s, 1H), 3.84-3.74 (m, 1H), 3.61-3.49 (m, 1H), 3.44-3.32 (m, 2H), 1.09 (d, J=6.4 Hz, 1H), 1.02-0.88 (m, 2H)

Example 15: 5-[4-amino-5-(trifluoromethyl)pyrrolo[2,1-f][1,2,4]triazin-7-yl]-N-[1-(3,3-dimethylbutanoyl)-4-methylpyrrolidin-3-yl]-2-methoxypyridine-3-carboxamide

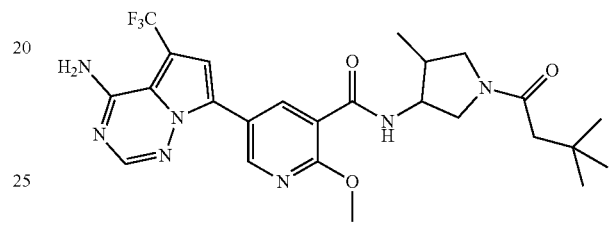

To a solution of 5-(4-amino-5-(trifluoromethyl)pyrrolo[2,1-f][1,2,4]triazin-7-yl)-2-methoxy-N-(4-methylpyrrolidin-3-yl)nicotinamide (15 mg, 0.034 mmol) in THF (1 mL) was added 3,3-dimethylbutanoic acid (4.00 mg, 0.034 mmol), Hunig's base (0.018 mL, 0.103 mmol) and BOP (18.28 mg, 0.041 mmol). The resultant mixture was stirred at rt for 1 h. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 25-65% B over 20 min, then a 5-minute hold at 100% B; Flow: 20 mL/min. Fractions containing the desired product were combined and dried via centrifugal evaporation to yield the final product (8.5 mg, 11.2 μmol, 33%).

MS ESI m/z 534 (M+H)

1H NMR (500 MHz, DMSO-d$_6$) δ 8.89 (s, 1H), 8.63 (br. s., 1H), 8.42-8.25 (m, 1H), 8.20-8.11 (m, 1H), 7.60 (d, J=3.7 Hz, 1H), 4.51 (d, J=17.4 Hz, 1H), 4.05-3.94 (m, 3H), 3.80-3.63 (m, 1H), 3.24-3.14 (m, 1H), 2.17-2.08 (m, 2H), 1.06-0.91 (m, 13H).

Example 16: 5-[4-amino-5-(trifluoromethyl)pyrrolo[2,1-f][1,2,4]triazin-7-yl]-N-(1-cyclohexanecarbonyl-4-methylpyrrolidin-3-yl)-2-methoxypyridine-3-carboxamide

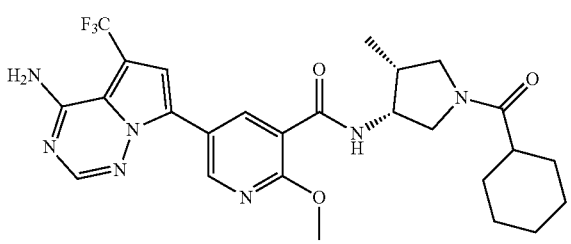 [SMILES: COc1ncc(-c2cc(C(F)(F)F)c3c(N)ncnn23)cc1C(=O)N[C@H]1CN(C(=O)C2CCCCC2)C[C@H]1C]

5-[4-amino-5-(trifluoromethyl)pyrrolo[2,1-f][1,2,4]triazin-7-yl]-N-(1-cyclohexanecarbonyl-4-methylpyrrolidin-3-yl)-2-methoxypyridine-3-carboxamide: To a solution of 5-(4-amino-5-(trifluoromethyl)pyrrolo[2,1-f][1,2,4]triazin-7-yl)-2-methoxy-N-(4-methylpyrrolidin-3-yl)nicotinamide (20 mg, 0.046 mmol) in THF (1 mL) was added cyclohexanecarboxylic acid (11.78 mg, 0.092 mmol), Hunig's base (0.024 mL, 0.138 mmol) and BOP (24.38 mg, 0.055 mmol). The resultant mixture was stirred at rt for 1 h. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-100% B over 19 min, then a 5-minute hold at 100% B; Flow: 20 mL/min. Fractions containing the desired product were combined and dried via centrifugal evaporation to yield the final product (6.9 mg, 13 μmol, 28%).

MS ESI m/z 546.3 (M+H)

1H NMR (500 MHz, DMSO-d6) δ 8.88 (s, 1H), 8.58 (d, J=11.9 Hz, 1H), 8.44-8.30 (m, 1H), 8.14 (s, 1H), 7.57 (s, 1H), 4.48 (br. s., 1H), 3.98 (s, 3H), 3.50 (d, J=5.2 Hz, 1H), 3.23 (d, J=9.2 Hz, 1H), 3.04 (br. s., 1H), 2.37 (br. s., 1H), 1.73 (br. s., 1H), 1.70-1.54 (m, 5H), 1.26 (br. s., 3H), 1.21 (br. s., 1H), 1.13 (br. s., 1H), 1.05-0.91 (m, 3H).

Example 17: 5-[4-amino-5-(trifluoromethyl)pyrrolo[2,1-f][1,2,4]triazin-7-yl]-N-[(3S)-3-(4-chlorophenyl)-3-hydroxypropyl]-2-fluoropyridine-3-carboxamide

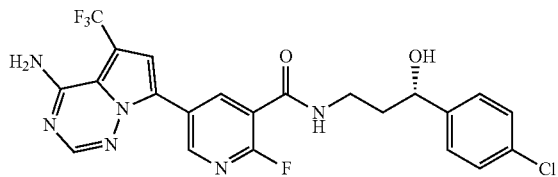 [SMILES: Nc1ncnn2c(-c3cnc(F)c(C(=O)NCC[C@H](O)c4ccc(Cl)cc4)c3)cc(C(F)(F)F)c12]

17A: methyl 2-fluoro-5-(4,4,5,5-tetramethyl-1,3,2-dioxaborolan-2-yl)nicotinate: To an oven-dried 10 mL vial were added methyl 5-bromo-2-fluoronicotinate (1 g, 4.27 mmol), bis(pinacolato)diboron (217 mg, 0.854 mmol) and potassium acetate (1.258 g, 12.82 mmol). 1,4-Dioxane (20 mL) was introduced into the vial and nitrogen gas was blown through for 10 min. PdCl$_2$(dppf) (0.156 g, 0.214 mmol) was added to the reaction mixture and degassing continued for 10 min. The mixture was heated to reflux at 80° C. ON. The reaction mixture was filtered through a pad of Celite to remove the catalyst, and the filter cake was washed with EtOAc twice. The obtained organic solutions were concentrated. The crude residue was purified by flash column chromatography (ISCO, 80 g silica gel column, 20-50% EtOAc/hexanes) to yield methyl 2-fluoro-5-(4,4,5,5-tetramethyl-1,3,2-dioxaborolan-2-yl)nicotinate (1 g, 3.56 mmol, 83%) as a white solid. MS ESI m/z 200.0 (M+H for the boronic acid)

17B: 5-(4-amino-5-(trifluoromethyl)pyrrolo[2,1-f][1,2,4]triazin-7-yl)-2-fluoronicotinic acid: To a solution of 7-bromo-5-(trifluoromethyl)pyrrolo[2,1-f][1,2,4]triazin-4-amine (300 mg, 1.067 mmol) and methyl 2-fluoro-5-(4,4,5,5-tetramethyl-1,3,2-dioxaborolan-2-yl)nicotinate (330 mg, 1.174 mmol) in 1,4-dioxane (15 mL) was added potassium phosphate tribasic (1.601 mL, 3.20 mmol) (2M in H$_2$O). The mixture was degassed by bubbling nitrogen through for 5 min. PdCl$_2$(dppf) (78 mg, 0.107 mmol) was added and degassing continued for another 5 min. The reaction vessel was sealed and heated to 100° C. for 3 h. 1N NaOH (5 mL) was added and the reaction mixture was stirred for another 2 h. The reaction mixture was filtered through a pad of Celite to remove the catalyst and concentrated. Purification by prepHPLC yielded 5-(4-amino-5-(trifluoromethyl)pyrrolo[2,1-f][1,2,4]triazin-7-yl)-2-fluoronicotinic acid (260 mg, 0.762 mmol, 71.4% yield) as a white solid.

MS ESI m/z 342.0 (M+H)

$^1$H NMR (400 MHz, CD$_3$OD) δ 9.03 (dd, J=8.8, 2.6 Hz, 1H), 8.97-8.92 (m, 1H), 8.06 (s, 1H), 7.34 (s, 1H).

17: To a solution of 5-(4-amino-5-(trifluoromethyl)pyrrolo[2,1-f][1,2,4]triazin-7-yl)-2-fluoronicotinic acid (15 mg, 0.044 mmol) and (S)-3-amino-1-(4-chlorophenyl)propan-1-ol (8.57 mg, 0.046 mmol) in 1,4-dioxane (2 mL) was added Hunig's base (0.023 mL, 0.132 mmol) and BOP (23.33 mg, 0.053 mmol). The resultant mixture was stirred at rt for 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-minute hold at 100% B; Flow: 20 mL/min. Fractions containing the desired product were combined and dried via centrifugal evaporation to yield the final product (4.8 mg, 9.4 μmol, 21%).

MS ESI m/z 508.9 (M+H)

1H NMR (500 MHz, DMSO-d6) δ 8.95 (s, 1H), 8.77 (d, J=8.8 Hz, 1H), 8.62 (br. s., 1H), 8.18 (s, 1H), 7.70 (s, 1H), 7.37 (s, 4H), 4.67 (d, J=5.2 Hz, 1H), 3.35 (d, J=5.8 Hz, 2H), 1.95-1.79 (m, 2H).

Example 18: 5-[4-amino-5-(trifluoromethyl)pyrrolo[2,1-f][1,2,4]triazin-7-yl]-N-[3-(4-fluorophenyl)-3-hydroxypropyl]pyridine-3-carboxamide

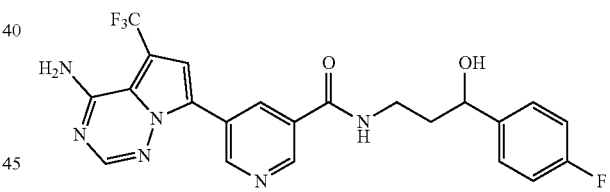

18A: 5-(4-amino-5-(trifluoromethyl)pyrrolo[2,1-f][1,2,4]triazin-7-yl)nicotinic acid, sodium salt: To a solution of 7-bromo-5-(trifluoromethyl)pyrrolo[2,1-f][1,2,4]triazin-4-amine (300 mg, 1.067 mmol) and methyl 5-(4,4,5,5-tetramethyl-1,3,2-dioxaborolan-2-yl)nicotinate (337 mg, 1.281 mmol) in 1,4-dioxane (8 mL) was added potassium phosphate tribasic (1.601 mL, 3.20 mmol)(2M in H$_2$O). Nitrogen was bubbled through for 5 min and PdCl$_2$(dppf) (78 mg, 0.107 mmol) was added. Nitrogen sparged was continued for 5 min. The reaction vessel was sealed and heated to 100° C. for 3 h. After cooling to rt, 1 N NaOH (10 mL) was added, and the mixture was stirred at rt for 2 h. The mixture was filtered and concentrated. The crude material was purified by recrystallization with MeOH to yield 5-(4-amino-5-(trifluoromethyl)pyrrolo[2,1-f][1,2,4]triazin-7-yl)nicotinic acid (260 mg, 0.804 mmol, 75% yield) as a white solid.

MS ESI m/z 587.0 (M+H)

$^1$H NMR (400 MHz, CD$_3$OD) δ 9.35 (d, J=2.2 Hz, 1H), 9.14 (d, J=2.0 Hz, 1H), 9.02 (t, J=2.0 Hz, 1H), 8.10 (s, 1H), 7.40 (s, 1H).

18: To a solution of 5-(4-amino-5-(trifluoromethyl)pyrrolo[2,1-f][1,2,4]triazin-7-yl)nicotinic acid, sodium salt (20 mg, 0.062 mmol) and 3-amino-1-(4-fluorophenyl)propan-1-ol (11.52 mg, 0.068 mmol) in THF (1.5 mL) was added BOP (32.8 mg, 0.074 mmol) and Hunig's base (0.032 mL, 0.186 mmol). The resultant mixture was stirred at rt for 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 5-minute hold at 100% B; Flow: 20 mL/min. Fractions containing the desired product were combined and dried via centrifugal evaporation to yield the final product (4.7 mg, 9.9 μmol, 16%).

MS ESI m/z 475.2 (M+H)

1H NMR (500 MHz, DMSO-d6) δ 9.34 (br. s., 1H), 8.94 (br. s., 1H), 8.78 (br. s., 1H), 8.73 (br. s., 1H), 8.21 (s, 1H), 7.72 (s, 1H), 7.46-7.35 (m, 2H), 7.14 (t, J=8.6 Hz, 2H), 5.43 (br. s., 1H), 4.67 (d, J=5.0 Hz, 1H), 3.37 (d, J=6.6 Hz, 1H), 1.88 (q, J=6.8 Hz, 2H).

Example 19: 5-[4-amino-5-(trifluoromethyl)pyrrolo[2,1-f][1,2,4]triazin-7-yl]-N-[(3S,4S)-1-cyclopentanecarbonyl-4-methylpyrrolidin-3-yl]-2-methoxypyridine-3-carboxamide

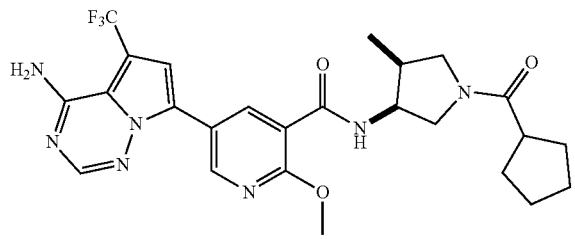

To a solution of 5-(4-amino-5-(trifluoromethyl)pyrrolo[2,1-f][1,2,4]triazin-7-yl)-2-methoxy-N-((3S,4S)-4-methylpyrrolidin-3-yl)nicotinamide (20 mg, 0.046 mmol) in THF (1 mL) was added Hunig's base (0.024 mL, 0.138 mmol) and cyclopentanecarbonyl chloride (6.09 mg, 0.046 mmol). The resultant mixture was stirred at rt for 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-60% B over 20 min, then a 4-minute hold at 100% B; Flow: 20 mL/min. Fractions containing the desired product were combined and dried via centrifugal evaporation to yield the final product (19.2 mg, 36.1 μmol, 79%).

MS ESI m/z 532.2 (M+H)

1H NMR (500 MHz, DMSO-d6) δ 8.87 (br. s., 1H), 8.59 (d, J=4.4 Hz, 1H), 8.40 (dd, J=18.8, 7.7 Hz, 1H), 8.15 (br. s., 1H), 7.58 (br. s., 1H), 4.53 (br. s., 1H), 4.48 (br. s., 1H), 3.98 (s, 3H), 3.51 (d, J=6.7 Hz, 1H), 3.28-3.13 (m, 1H), 2.86-2.72 (m, 1H), 1.75 (br. s., 2H), 1.60 (br. s., 4H), 1.50 (br. s., 2H), 1.00 (t, J=6.4 Hz, 3H).

Example 20: 5-[4-amino-5-(trifluoromethyl)pyrrolo[2,1-f][1,2,4]triazin-7-yl]-N-[(3S)-3-(4-chlorophenyl)-3-hydroxypropyl]-2-methoxy-6-methylpyridine-3-carboxamide

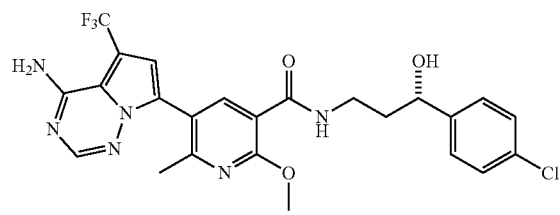 [SMILES: COc1nc(C)c(-c2cc(C(F)(F)F)c3c(N)ncnn23)cc1C(=O)NCC[C@H](O)c1ccc(Cl)cc1]

20A: methyl 2-methoxy-6-methyl-5-(4,4,5,5-tetramethyl-1,3,2-dioxaborolan-2-yl)nicotinate: To an oven-dried 10 mL vial were added methyl 5-bromo-2-methoxy-6-methylnicotinate (200 mg, 0.769 mmol), 4,4,4',4',5,5,5',5'-octamethyl-2,2'-bi(1,3,2-dioxaborolane) (234 mg, 0.923 mmol)(bis(pinacolato)diboron) and potassium acetate (226 mg, 2.307 mmol). 1,4-Dioxane (5 mL) was introduced into the vial and nitrogen gas was blown through the mixture for 10 min. PdCl₂(dppf) (28.1 mg, 0.038 mmol) was added to the reaction mixture and sparging continued for 10 min. The reaction mixture was heated to reflux at 65° C. ON. After cooling to rt, the reaction mixture was filtered through a pad of Celite and concentrated. The crude material was purified by ISCO flash chromatography (20%-50% EtOAc/hexanes) to yield methyl 2-methoxy-6-methyl-5-(4,4,5,5-tetramethyl-1,3,2-dioxaborolan-2-yl)nicotinate (230 mg, 0.599 mmol, 78% yield) as a white solid.

MS ESI m/z 308.2 (mass of corresponding boronic acid)

20B: 5-(4-amino-5-(trifluoromethyl)pyrrolo[2,1-f][1,2,4]triazin-7-yl)-2-methoxy-6-methylnicotinic acid: To a solution of 7-bromo-5-(trifluoromethyl)pyrrolo[2,1-f][1,2,4]triazin-4-amine (200 mg, 0.712 mmol) and methyl 2-methoxy-6-methyl-5-(4,4,5,5-tetramethyl-1,3,2-dioxaborolan-2-yl)nicotinate (230 mg, 0.747 mmol) in 1,4-dioxane (30 mL) was added potassium phosphate tribasic (1.067 mL, 2.135 mmol)(2M in H₂O). The reaction mixture was sparged with nitrogen for 5 min and then PdCl₂(dppf) (41.7 mg, 0.057 mmol) was added. The nitrogen sparged was continued for another 5 min. The reaction vessel was sealed and heated to 100° C. for 12 h. The cooled reaction mixture was filtrated through a pad of Celite to remove catalyst. To the filtrate was added sodium hydroxide (0.356 mL, 3.56 mmol)(10 M in water), and the resultant mixture was stirred at rt 2 h. The crude material was purified by recrystallization with MeOH to yield 5-(4-amino-5-(trifluoromethyl)pyrrolo[2,1-f][1,2,4]triazin-7-yl)-2-methoxy-6-methylnicotinic acid, sodium salt (120 mg, 0.327 mmol, 45.9% yield) as a white solid. MS ESI m/z 368.1 (M+H)

20: To a solution of 5-(4-amino-5-(trifluoromethyl)pyrrolo[2,1-f][1,2,4]triazin-7-yl)-2-methoxy-6-methylnicotinic acid, sodium salt (20 mg, 0.054 mmol) and (S)-3-amino-1-(4-chlorophenyl)propan-1-ol (10.61 mg, 0.057 mmol) in 1,4-dioxane (2 mL) was added Hunig's base (0.029 mL, 0.163 mmol) and BOP (28.9 mg, 0.065 mmol). The resultant mixture was stirred at RT for 30 min. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 30-70% B over 20 min, then a 5-minute hold at 100% B; Flow: 20 mL/min. Fractions containing the desired product were combined and dried via centrifugal evaporation to yield the final product (7.5 mg, 9.8 μmol, 18%).

MS ESI m/z 534.9 (M+H)

1H NMR (500 MHz, DMSO-d6) δ 8.53-8.41 (m, 1H), 8.10 (s, 1H), 8.03 (s, 1H), 7.36 (s, 4H), 4.68 (dd, J=7.5, 4.4 Hz, 1H), 4.02 (s, 3H), 3.35 (d, J=6.1 Hz, 2H), 2.30 (s, 3H), 1.97-1.73 (m, 2H).

Example 21: 5-[4-amino-5-(trifluoromethyl)pyrrolo[2,1-f][1,2,4]triazin-7-yl]-N-[(3S,4S)-1-cyclohexanecarbonyl-4-methylpyrrolidin-3-yl]-2-methylpyridine-3-carboxamide

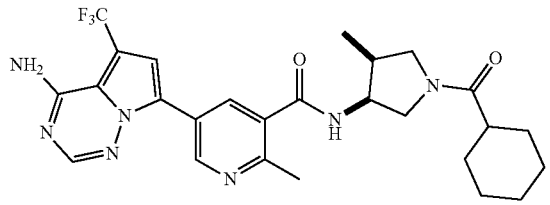

21A: (3S,4S)-3-(5-(4-amino-5-(trifluoromethyl)pyrrolo[2,1-f][1,2,4]triazin-7-yl)-2-methylnicotinamido)-4-methylpyrrolidine-1-carboxylate: To a solution of 5-(4-amino-5-(trifluoromethyl)pyrrolo[2,1-f][1,2,4]triazin-7-yl)-2-methylnicotinic acid (80 mg, 0.237 mmol) and benzyl (3S,4S)-3-amino-4-methylpyrrolidine-1-carboxylate (61.1 mg, 0.261 mmol) in 1,4-dioxane (3 mL) and DMF (1 mL) was added DIEA (0.124 mL, 0.712 mmol) and BOP (126 mg, 0.285 mmol). The resultant mixture was stirred at rt for 30 min. The crude material was purified by prep-HPLC to yield benzyl (3S,4S)-3-(5-(4-amino-5-(trifluoromethyl)pyrrolo[2,1-f][1,2,4]triazin-7-yl)-2-methylnicotinamido)-4-methylpyrrolidine-1-carboxylate (80 mg, 0.137 mmol, 57.9% yield) as a white solid.

MS ESI m/z 554.3 (M+H)

21B: 5-(4-amino-5-(trifluoromethyl)pyrrolo[2,1-f][1,2,4]triazin-7-yl)-2-methyl-N-((3S,4S)-4-methylpyrrolidin-3-yl)nicotinamide: A solution of (3S,4S)-benzyl 3-(5-(4-amino-5-(trifluoromethyl)pyrrolo[2,1-f][1,2,4]triazin-7-yl)-2-methylnicotinamido)-4-methylpyrrolidine-1-carboxylate (50 mg, 0.090 mmol) in TFA (1 mL, 12.98 mmol) was stirred at rt for 2 d. The reaction mixture was concentrated and further dried on vacuum pump to provide 5-(4-amino-5-(trifluoromethyl)pyrrolo[2,1-f][1,2,4]triazin-7-yl)-2-methyl-N-((3S,4S)-4-methylpyrrolidin-3-yl)nicotinamide (30 mg, 0.072 mmol, 79%).

MS ESI m/z 420.2 (M+H)

21: To a solution of 5-(4-amino-5-(trifluoromethyl)pyrrolo[2,1-f][1,2,4]triazin-7-yl)-2-methyl-N-((3S,4S)-4-methylpyrrolidin-3-yl)nicotinamide (15 mg, 0.036 mmol) in THF (1 mL) was added BOP (18.98 mg, 0.043 mmol), Hunig's base (0.019 mL, 0.107 mmol) and cyclohexanecarboxylic acid (5.04 mg, 0.039 mmol). The resultant mixture was stirred at rt for 30 min. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 25 min, then a 5-minute hold at 100% B; Flow: 20 mL/min. Fractions containing the desired product were combined and dried via centrifugal evaporation to yield the final product (3.8 mg, 5.0 μmol, 14%).

MS ESI m/z 530.4 (M+H)

1H NMR (500 MHz, DMSO-d6) δ 9.11 (br. s., 1H), 8.69 (d, J=8.2 Hz, 1H), 8.34 (br. s., 1H), 8.14 (d, J=6.1 Hz, 1H), 7.65 (d, J=5.9 Hz, 1H), 7.31 (s, 2H), 7.21 (s, 2H), 7.11 (s, 2H), 4.51 (br. s., 1H), 3.58-3.43 (m, 2H), 2.32 (br. s., 1H), 1.76-1.60 (m, 4H), 1.58 (br. s., 1H), 1.38-1.19 (m, 4H), 1.13 (d, J=14.7 Hz, 1H), 0.99 (t, J=7.9 Hz, 3H).

Example 22: 5-[4-amino-5-(trifluoromethyl)pyrrolo[2,1-f][1,2,4]triazin-7-yl]-N-[(3S,4S)-1-(3,3-difluorocyclopentanecarbonyl)-4-(fluoromethyl)pyrrolidin-3-yl]-2-methylpyridine-3-carboxamide

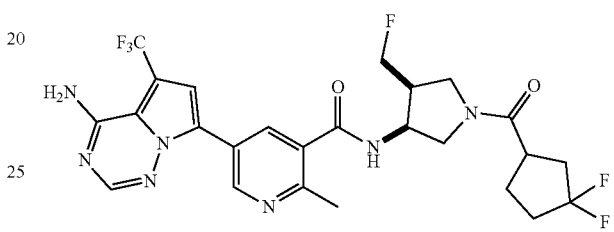

22A: (3S,4S)-benzyl 3-amino-4-(fluoromethyl)pyrrolidine-1-carboxylate, TFA: To a solution of (3S,4S)-benzyl 3-((tert-butoxycarbonyl)amino)-4-(fluoromethyl)pyrrolidine-1-carboxylate (100 mg, 0.284 mmol) in THF (3 mL) was added TFA (0.219 mL, 2.84 mmol). The mixture was stirred at rt for 30 min. The mixture was concentrated and the obtained crude material was used in the next step without purification.

MS ESI m/z 253.3 (M+H).

22B: (3S,4S)-benzyl 3-(5-(4-amino-5-(trifluoromethyl)pyrrolo[2,1-f][1,2,4]triazin-7-yl)-2-methylnicotinamido)-4-(fluoromethyl)pyrrolidine-1-carboxylate: To a solution of 5-(4-amino-5-(trifluoromethyl)pyrrolo[2,1-f][1,2,4]triazin-7-yl)-2-methylnicotinic acid (80 mg, 0.237 mmol) and (3S,4S)-benzyl 3-amino-4-(fluoromethyl)pyrrolidine-1-carboxylate, TFA (65.8 mg, 0.261 mmol) in 1,4-dioxane (3 mL) and DMF (1 mL) was added DIEA (0.124 mL, 0.712 mmol) and BOP (126 mg, 0.285 mmol). The mixture was stirred at rt for 30 min. Purification by prep-HPLC provided (3S,4S)-benzyl 3-(5-(4-amino-5-(trifluoromethyl)pyrrolo[2,1-f][1,2,4]triazin-7-yl)-2-methylnicotinamido)-4-(fluoromethyl)pyrrolidine-1-carboxylate (100 mg, 0.175 mmol, 73.8% yield) as a white solid.

MS ESI m/z 571.8 (M+H).

22C: 5-(4-amino-5-(trifluoromethyl)pyrrolo[2,1-f][1,2,4]triazin-7-yl)-N-((3S,4S)-4-(fluoromethyl)pyrrolidin-3-yl)-2-methylnicotinamide, TFA: A solution of (3S,4S)-benzyl 3-(5-(4-amino-5-(trifluoromethyl)pyrrolo[2,1-f][1,2,4]triazin-7-yl)-2-methylnicotinamido)-4-(fluoromethyl)pyrrolidine-1-carboxylate (80 mg, 0.140 mmol) in TFA (0.5 mL, 6.49 mmol) (neat) was stirred at rt for 20 h. The reaction mixture was evaporated and further concentrated on a vacuum pump to yield 5-(4-amino-5-(trifluoromethyl)pyrrolo[2,1-f][1,2,4]triazin-7-yl)-N-((3S,4S)-4-(fluoromethyl)pyrrolidin-3-yl)-2-methylnicotinamide, TFA (60 mg, 0.137 mmol, 98%). The obtained crude material was used in the next step without purification.

MS ESI m/z 437.8 (M+H).

22: To a solution of 5-(4-amino-5-(trifluoromethyl)pyrrolo[2,1-f][1,2,4]triazin-7-yl)-N-((3S,4S)-4-(fluoromethyl)pyrrolidin-3-yl)-2-methylnicotinamide, TFA (15 mg, 0.034 mmol) and 3,3-difluorocyclopentanecarboxylic acid (6.18 mg, 0.041 mmol) in 1,4-dioxane (2 mL) was added Hunig's base (0.018 mL, 0.103 mmol) and BOP (18.20 mg, 0.041 mmol). The resultant mixture was stirred at RT for 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 4-minute hold at 100% B; Flow: 20 mL/min. Fractions containing the desired product were combined and dried via centrifugal evaporation to yield the final product (5.1 mg, 9.0 μmol, 26%).

MS ESI m/z 570.2 (M+H)

1H NMR (500 MHz, DMSO-d6) δ 9.15 (dd, J=6.0, 1.7 Hz, 1H), 8.87-8.69 (m, 1H), 8.34 (s, 1H), 8.16 (d, J=5.2 Hz, 1H), 7.65 (d, J=8.5 Hz, 1H), 4.74 (br. s., 1H), 4.69 (br. s., 1H), 4.65-4.54 (m, 1H), 4.54-4.46 (m, 1H), 3.89-3.68 (m, 1H), 3.20-3.06 (m, 1H), 2.91 (br. s., 1H), 2.82 (br. s., 1H), 2.55 (d, J=3.4 Hz, 3H), 2.38-2.21 (m, 2H), 2.19-1.95 (m, 3H), 1.86-1.73 (m, 1H).

Example 23: 5-[4-amino-5-(trifluoromethyl)pyrrolo[2,1-f][1,2,4]triazin-7-yl]-N-[(3S,4S)-1-(3,3-difluorocyclopentanecarbonyl)-4-methylpyrrolidin-3-yl]-2-(trifluoromethyl)pyridine-3-carboxamide

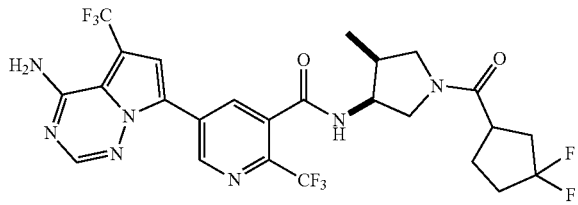

23A: ethyl 5-(4,4,5,5-tetramethyl-1,3,2-dioxaborolan-2-yl)-2-(trifluoromethyl)nicotinate: A mixture of ethyl 5-bromo-2-(trifluoromethyl)nicotinate (0.500 g, 1.678 mmol), 4,4,4',4',5,5,5',5'-octamethyl-2,2'-bi(1,3,2-dioxaborolane) (0.511 g, 2.013 mmol), and potassium acetate (0.247 g, 2.52 mmol) in 1,4-dioxane (100 mL) was degassed (3×) with vacuum/nitrogen. 1,1'-Bis(diphenylphosphino)ferrocene palladium dichloride —CH₂Cl₂ adduct (0.137 g, 0.168 mmol) was added, and the mixture was degassed (2×). The reaction mixture was immersed in an oil bath at 80° C. and stirred ON. The mixture was diluted with ethyl acetate and filtered under reduced pressure. The organic layer was washed with water and brine. The organic layer was collected, and the aqueous layers were extracted with ethyl acetate (2×). The combined organic layers were dried over anhydrous sodium sulfate and concentrated. Purification by ISCO flash chromatography (40 g column; 0%-100% ethyl acetate in hexane) afforded ethyl 5-(4,4,5,5-tetramethyl-1,3,2-dioxaborolan-2-yl)-2-(trifluoromethyl)nicotinate (0.342 g, 0.991 mmol, 59.1% yield) as a white solid.

MS ESI m/z 264.1 (M+H of the boronic acid).

23B: ethyl 5-(4-amino-5-(trifluoromethyl)pyrrolo[2,1-f][1,2,4]triazin-7-yl)-2-(trifluoromethyl)nicotinate: A mixture of 7-bromo-5-(trifluoromethyl)pyrrolo[2,1-f][1,2,4]triazin-4-amine (0.232 g, 0.826 mmol), ethyl 5-(4,4,5,5-tetramethyl-1,3,2-dioxaborolan-2-yl)-2-(trifluoromethyl)nicotinate (0.342 g, 0.991 mmol), tripotassium phosphate (2 M in water) (1.239 ml, 2.477 mmol), and 1,4-dioxane (6 mL) was degassed with vacuum and nitrogen (3×). 1,1'-Bis(diphenylphosphino)ferrocene palladium dichloride —CH₂Cl₂ adduct (0.067 g, 0.083 mmol) was added, and the reaction mixture was degassed (2×). The reaction mixture was immersed in an oil bath at 70° C. and stirred ON. The reaction mixture was diluted with ethyl acetate, washed with water and washed with brine. The organic layer was collected and the aqueous layers were extracted with ethyl acetate (2×). The combined organic layers were dried over anhydrous sodium sulfate and concentrated. The residue was triturated with dichloromethane and dried to give ethyl 5-(4-amino-5-(trifluoromethyl)pyrrolo[2,1-f][1,2,4]triazin-7-yl)-2-(trifluoromethyl)nicotinate (0.218 g, 0.520 mmol, 63.0% yield) as a white solid.

MS ESI m/z 420.2 (M+H).

23C: 5-(4-amino-5-(trifluoromethyl)pyrrolo[2,1-f][1,2,4]triazin-7-yl)-2-(trifluoromethyl)nicotinic acid, lithium salt: A mixture of ethyl 5-(4-amino-5-(trifluoromethyl)pyrrolo[2,1-f][1,2,4]triazin-7-yl)-2-(trifluoromethyl)nicotinate (0.218 g, 0.520 mmol) and lithium hydroxide, H₂O (0.022 g, 0.520 mmol) in a mixture of methanol (1 mL), tetrahydrofuran (1 mL), and water (0.500 mL) was stirred at rt ON. The heterogeneous reaction mixture was filtered under reduced pressure, and the resulting solid was dried overnight to give 5-(4-amino-5-(trifluoromethyl)pyrrolo[2,1-f][1,2,4]triazin-7-yl)-2-(trifluoromethyl)nicotinic acid, lithium salt (0.203 g, 0.519 mmol, 100% yield) as a white solid.

MS ESI m/z 392.1 (M+H).

23D: (3S,4S)-benzyl 3-(5-(4-amino-5-(trifluoromethyl)pyrrolo[2,1-f][1,2,4]triazin-7-yl)-2-(trifluoromethyl)nicotinamido)-4-methylpyrrolidine-1-carboxylate: To a suspension of 5-(4-amino-5-(trifluoromethyl)pyrrolo[2,1-f][1,2,4]triazin-7-yl)-2-(trifluoromethyl)nicotinic acid, lithium salt (50 mg, 0.128 mmol) and (3S,4S)-benzyl 3-amino-4-methylpyrrolidine-1-carboxylate (32.9 mg, 0.141 mmol) in 1,4-dioxane (3 mL) and DMF (1 mL) was added DIEA (0.067 mL, 0.383 mmol) and BOP (67.8 mg, 0.153 mmol). The mixture was stirred at rt for 1 h. Purification by prep-HPLC provided (3S,4S)-benzyl 3-(5-(4-amino-5-(trifluoromethyl)pyrrolo[2,1-f][1,2,4]triazin-7-yl)-2-(trifluoromethyl)nicotinamido)-4-methylpyrrolidine-1-carboxylate (45 mg, 0.074 mmol, 58.0% yield) as a white solid.

MS ESI m/z 607.8 (M+H).

23E: 5-(4-amino-5-(trifluoromethyl)pyrrolo[2,1-f][1,2,4]triazin-7-yl)-N-((3S,4S)-4-methylpyrrolidin-3-yl)-2-(trifluoromethyl)nicotinamide, TFA: A solution of (3S,4S)-benzyl 3-(5-(4-amino-5-(trifluoromethyl)pyrrolo[2,1-f][1,2,4]triazin-7-yl)-2-(trifluoromethyl)nicotinamido)-4-methylpyrrolidine-1-carboxylate (50 mg, 0.082 mmol) in TFA (1 mL, 12.98 mmol) was stirred at room temperature for 2 d. The reaction mixture was concentrated and further dried on vacuum pump to provide 5-(4-amino-5-(trifluoromethyl)pyrrolo[2,1-f][1,2,4]triazin-7-yl)-N-((3S,4S)-4-methylpyrrolidin-3-yl)-2-(trifluoromethyl)nicotinamide, TFA (30 mg, 0.063 mmol, 77%). The crude product was used directly in the next step without purification.

MS ESI m/z 473.8 (M+H).

23: To a solution of 5-(4-amino-5-(trifluoromethyl)pyrrolo[2,1-f][1,2,4]triazin-7-yl)-N-((3S,4S)-4-methylpyrrolidin-3-yl)-2-(trifluoromethyl)nicotinamide, TFA (15 mg, 0.032 mmol) and 3,3-difluorocyclopentanecarboxylic acid (5.71 mg, 0.038 mmol) in 1,4-dioxane (2 mL) was added Hunig's base (0.017 mL, 0.095 mmol) and BOP (16.82 mg, 0.038 mmol). The resultant mixture was stirred at RT for 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 4-minute hold at 100% B; Flow: 20 mL/min. Fractions containing the desired product were combined and dried via centrifugal evaporation to yield the final product (4.5 mg, 7.4 μmol, 23%).

MS ESI m/z 606 (M+H)

1H NMR (500 MHz, DMSO-d6) δ 9.44 (br. s., 1H), 8.95 (t, J=9.8 Hz, 1H), 8.70 (br. s., 1H), 8.21 (d, J=4.5 Hz, 1H), 7.88 (d, J=8.8 Hz, 1H), 4.53 (d, J=19.9 Hz, 1H), 3.59-3.46 (m, 2H), 3.12-3.04 (m, 1H), 3.00 (br. s., 1H), 2.34-2.18 (m, 2H), 2.14-1.92 (m, 3H), 1.76 (br. s., 1H), 0.99 (t, J=5.9 Hz, 3H).

Example 24: 5-[4-amino-5-(trifluoromethyl)pyrrolo [2,1-f][1,2,4]triazin-7-yl]-N-[(3S,4S)-1-(4,4-difluorocyclohexanecarbonyl)-4-methylpyrrolidin-3-yl]-2-(trifluoromethyl)pyridine-3-carboxamide

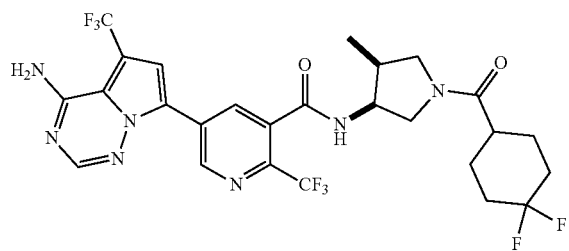

To a solution of 5-(4-amino-5-(trifluoromethyl)pyrrolo[2,1-f][1,2,4]triazin-7-yl)-N-((3S,4S)-4-methylpyrrolidin-3-yl)-2-(trifluoromethyl)nicotinamide (15 mg, 0.032 mmol) and 4,4-difluorocyclohexanecarboxylic acid (6.24 mg, 0.038 mmol) in 1,4-dioxane (2 mL) was added Hunig's base (0.017 mL, 0.095 mmol) and BOP (16.82 mg, 0.038 mmol). The resultant mixture was stirred at rt for 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-70% B over 20 min, then a 4-minute hold at 100% B; Flow: 20 mL/min. Fractions containing the desired product were combined and dried via centrifugal evaporation to yield the final product (4.9 mg, 7.9 μmol, 25%).

MS ESI m/z 620.1 (M+H)

1H NMR (500 MHz, DMSO-d6) δ 9.47 (br. s., 1H), 8.95 (d, J=8.5 Hz, 1H), 8.85 (d, J=8.2 Hz, 1H), 8.72 (br. s., 1H), 8.23 (d, J=5.3 Hz, 1H), 7.91 (d, J=8.4 Hz, 1H), 4.56 (br. s., 1H), 4.52 (br. s., 1H), 2.06 (br. s., 1H), 2.01 (br. s., 2H), 1.94-1.70 (m, 5H), 1.61-1.43 (m, 2H), 1.00 (t, J=7.4 Hz, 4H).

Example 25: 5-[4-amino-5-(trifluoromethyl)pyrrolo [2,1-f][1,2,4]triazin-7-yl]-N-[(3R,4S)-1-(4,4-difluorocyclohexanecarbonyl)-4-fluoropyrrolidin-3-yl]-2-methylpyridine-3-carboxamide

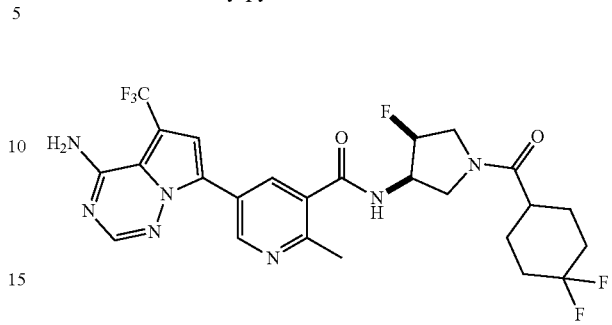

25A: tert-butyl 3-(5-(4-amino-5-(trifluoromethyl)pyrrolo [2,1-f][1,2,4]triazin-7-yl)-2-methylnicotinamido)-4-fluoropyrrolidine-1-carboxylate: To a solution of 5-(4-amino-5-(trifluoromethyl)pyrrolo[2,1-f][1,2,4]triazin-7-yl)-2-methylnicotinic acid (500 mg, 1.483 mmol) and tert-butyl 3-amino-4-fluoropyrrolidine-1-carboxylate (333 mg, 1.631 mmol) in 1,4-dioxane (10 mL) and DMF (2 mL) was added DIEA (0.777 mL, 4.45 mmol) and BOP (787 mg, 1.779 mmol) The resultant mixture was stirred at rt for 30 min.

The crude material was purified by ISCO flash chromatography (silica gel, 40 g, 5% MeOH/DCM) to yield tert-butyl 3-(5-(4-amino-5-(trifluoromethyl)pyrrolo[2,1-f][1,2,4]triazin-7-yl)-2-methylnicotinamido)-4-fluoropyrrolidine-1-carboxylate (1.0 g, 1.433 mmol, 97% yield) as a white solid.

MS ESI m/z 524.3 (M+H)

$^1$H NMR (400 MHz, CD$_3$OD) δ 9.21-9.02 (m, 1H), 8.74-8.55 (m, 1H), 8.52-8.31 (m, 1H), 8.24-7.99 (m, 1H), 7.56-7.45 (m, 1H), 7.40-7.23 (m, 1H), 5.40-5.12 (m, 1H), 4.86-4.56 (m, 1H), 3.98-3.83 (m, 1H), 3.85-3.54 (m, 2H), 2.83-2.58 (m, 3H), 1.63-1.41 (m, 9H).

The racemic material was separated into the corresponding homochiral enantiomers using the following preparative SFC conditions: Preparative column Lux Cellulose-4 (5×25 cm, 5 μm); BPR pressure 100 bars; Temperature 40° C.; Flow rate 300 mL/min; Mobile phase CO$_2$/MeOH with 0.1% NH$_4$OH (80/20); Detector Wavelength 263 nM; Separation program sequence injection; injection 0.60 mL with cycle time 5.2 min; Sample preparation 1.1 g/18 mL DCM+ 18 mL MeOH, 30.6 mg/mL. The purity of the isolated fractions (Peak 1; retention time 10.91 min and Peak 2; retention time 12.27 min) was determined by the following analytical SFC conditions: Analytical column Lux Cellose-4 (0.46×25 cm, 5 μm); BPR pressure 100 bars; Temperature 40° C.; Flow rate 3.0 mL/min; Mobile phase COiJMeOH with 0.1% NH$_4$OH (80/20); Detector Wavelength UV 200-400 nm MS positive ion mode, scan from my 200-900. The absolute stereochemistry was determined by comparison of final analogs with analogs derived from material for which X-ray crystallographic information was available.

25B: 5-(4-amino-5-(trifluoromethyl)pyrrolo[2,1-f][1,2,4] triazin-7-yl)-N-((3R,4S)-4-fluoropyrrolidin-3-yl)-2-methylnicotinamide, TFA: A solution of tert-butyl 3-(5-(4-amino-5-(trifluoromethyl)pyrrolo[2,1-f][1,2,4]triazin-7-yl)-2-methylnicotinamido)-(3R,4S)-4-fluoropyrrolidine-1-carboxylate (200 mg, 0.382 mmol) in TFA (1 mL, 12.98 mmol) (1 mL, neat) was stirred at rt for 30 min, evaporation of TFA and further dried in vacuum pump to yield 5-(4-amino-5-(trifluoromethyl)pyrrolo[2,1-f][1,2,4]triazin-7-yl)-

N-(4-fluoropyrrolidin-3-yl)-2-methylnicotinamide, TFA (162 mg, 0.383 mmol, 100% yield) as colorless oil, which was used directly in next step without purification.

MS ESI m/z 424.3 (M+H).

25: To a solution of 5-(4-amino-5-(trifluoromethyl)pyrrolo[2,1-f][1,2,4]triazin-7-yl)-N-((3R,4S)-4-fluoropyrrolidin-3-yl)-2-methylnicotinamide, TFA (15 mg, 0.035 mmol) and 4,4-difluorocyclohexanecarboxylic acid (6.98 mg, 0.043 mmol) in 1,4-dioxane (2 mL) was added Hünig's base (0.019 mL, 0.106 mmol) and BOP (18.80 mg, 0.043 mmol). The resultant mixture was stirred at rt for 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 4-minute hold at 100% B; Flow: 20 mL/min. Fractions containing the desired product were combined and dried via centrifugal evaporation to yield the final product (7.1 mg, 12.5 μmol, 36%).

MS ESI m/z 569.9 (M+H)

1H NMR (500 MHz, DMSO-d6) δ 9.16 (s, 1H), 9.00-8.81 (m, 1H), 8.37 (s, 1H), 8.18 (s, 1H), 7.67 (d, J=2.7 Hz, 1H), 5.31 (br d, J=12.8 Hz, 1H), 4.07 (br 1, J=9.2 Hz, 1H), 3.95 (br s, 1H), 3.56 (br s, 1H), 3.25 (br d, J=10.7 Hz, 1H), 2.58 (d, J=4.9 Hz, 3H), 2.05 (br d, J=7.6 Hz, 2H), 1.95-1.80 (m, 2H), 1.76 (br d, J=15.3 Hz, 1H), 1.66-1.47 (m, 2H).

Example 26: 2-amino-5-[4-amino-5-(trifluoromethyl)pyrrolo[2,1-f][1,2,4]triazin-7-yl]-N-[(3R)-3-(4-chlorophenyl)-3-hydroxypropyl]pyridine-3-carboxamide

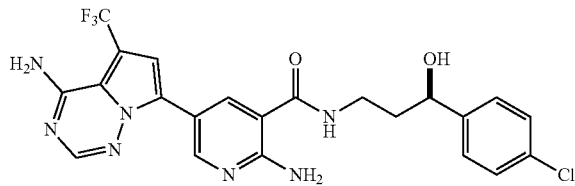 [SMILES: Nc1ncc(-c2cc(C(F)(F)F)c3c(N)ncnn23)cc1C(=O)NCC[C@@H](O)c1ccc(Cl)cc1]

26A: Methyl 2-amino-5-(4,4,5,5-tetramethyl-1,3,2-dioxaborolan-2-yl)nicotinate: A mixture of methyl 2-amino-5-bromonicotinate (1 g, 4.33 mmol), 4,4,4',4',5,5,5',5'-octamethyl-2,2'-bi(1,3,2-dioxaborolane) (1.319 g, 5.19 mmol), potassium acetate (1.274 g, 12.98 mmol) in dioxane (20 mL) was degassed (3×) with vacuum/nitrogen. 1,1'-Bis(diphenylphosphino)ferrocene-palladium(II)dichloride dichloromethane complex (0.353 g, 0.433 mmol) was added, and the mixture was degassed (2×) and filled with N₂. The reaction mixture was immersed in an oil bath at 80° C. and stirred ON. The mixture was diluted with ethyl acetate, and washed with water and brine. The organic layer was collected, and the aqueous layers were sequentially extracted with ethyl acetate (2×). The combined organic layers were dried over anhydrous sodium sulfate and concentrated. After purification by Biotage flash chromatography (40 g column; 0%-100% ethyl acetate in hexane), the obtained product was triturated with ether to afford methyl 2-amino-5-(4,4,5,5-tetramethyl-1,3,2-dioxaborolan-2-yl)nicotinate (0.6 g, 2.157 mmol, 49.8% yield) as a light tan solid.

MS ESI m/z 279.18 (M+H)

26B: 2-amino-5-(4-amino-5-(trifluoromethyl)pyrrolo[2,1-f][1,2,4]triazin-7-yl)nicotinic acid: To a solution of 7-bromo-5-(trifluoromethyl)pyrrolo[2,1-f][1,2,4]triazin-4-amine (50 mg, 0.178 mmol), and methyl 2-amino-5-(4,4,5,5-tetramethyl-1,3,2-dioxaborolan-2-yl)nicotinate (54.4 mg, 0.196 mmol) in 1,4-dioxane (2 mL) was added potassium phosphate tribasic (0.267 mL, 0.534 mmol) (2M in H₂O). The mixture was sparged with nitrogen for 5 min and 1,1'-bis(diphenylphosphino)ferrocene-palladium(II)dichloride dichloromethane complex (14.53 mg, 0.018 mmol) was added. Sparging was continued for another 5 min. The reaction vessel was sealed and heated to 100° C. for 16 h. The reaction mixture was filtrated through a pad of Celite to remove catalyst. Sodium hydroxide (0.089 mL, 0.890 mmol)(10 M in water) was added to the filtrate and the resultant mixture was stirred at rt for another 2 h. MeOH was added to crash out the product which was isolated by filtration to yield 2-amino-5-(4-amino-5-(trifluoromethyl)pyrrolo[2,1-f][1,2,4]triazin-7-yl)nicotinic acid (56 mg, 0.166 mmol, 93% yield) as a tan solid.

MS ESI m/z 338.97 (M+H)

1H NMR (400 MHz, DMSO-d₆) δ 8.91-8.69 (m, 2H), 8.31-8.10 (m, 1H), 7.61-7.48 (m, 1H).

26: A mixture of 2-amino-5-(4-amino-5-(trifluoromethyl)pyrrolo[2,1-f][1,2,4]triazin-7-yl)nicotinic acid (15 mg, 0.044 mmol), (S)-3-amino-1-(4-chlorophenyl)propan-1-ol (9.06 mg, 0.049 mmol), BOP (23.54 mg, 0.053 mmol), Hünig's base (0.023 mL, 0.133 mmol) in DMF (1 mL) was stirred at rt for 20 min. It was then concentrated and submitted to preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 22-62% B over 22 min, then a 4-minute hold at 100% B; Flow: 20 mL/min. Fractions containing the desired product were combined and dried via centrifugal evaporation to obtain (R)-2-amino-5-(4-amino-5-(trifluoromethyl)pyrrolo[2,1-f][1,2,4]triazin-7-yl)-N-(3-(4-chlorophenyl)-3-hydroxypropyl)nicotinamide (8.8 mg, 0.017 mmol, 39.2% yield) as a white solid.

MS ESI m/z 506 (M+H)

1H NMR (500 MHz, DMSO-d6) δ 8.84-8.71 (m, 1H), 8.55-8.46 (m, 1H), 8.30-8.23 (m, 1H), 8.16-8.04 (m, 1H), 7.45-7.39 (m, 1H), 7.39-7.29 (m, 4H), 4.69-4.58 (m, 1H), 3.38-3.24 (m, 2H), 1.94-1.80 (m, 2H).

Example 27: 5-[4-amino-5-(trifluoromethyl)pyrrolo[2,1-f][1,2,4]triazin-7-yl]-N-[4-fluoro-1-(4-fluorobenzoyl)pyrrolidin-3-yl]-2-methoxypyridine-3-carboxamide

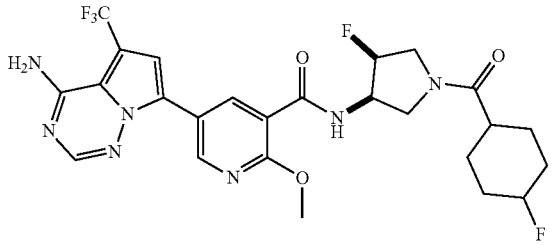

27A: (3R,4S)-tert-butyl 3-(5-(4-amino-5-(trifluoromethyl)pyrrolo[2,1-f][1,2,4]triazin-7-yl)-2-methoxynicotinamido)-4-fluoropyrrolidine-1-carboxylate: To a solution of 5-(4-amino-5-(trifluoromethyl)pyrrolo[2,1-f][1,2,4]triazin-7-yl)-2-methoxynicotinic acid (100 mg, 0.283 mmol) and (3R,4S)-tert-butyl 3-amino-4-fluoropyrrolidine-1-carboxylate (63.6 mg, 0.311 mmol) in 1,4-dioxane (3 mL) and DMF (1 mL) was added DIEA (0.148 mL, 0.849 mmol) and BOP (150 mg, 0.340 mmol) The resultant mixture was stirred at rt for 30 min. The crude material was purified by prep-HPLC to yield (3R,4S)-tert-butyl 3-(5-(4-amino-5-(trifluoromethyl)pyrrolo[2,1-f][1,2,4]triazin-7-yl)-2-methoxynicotinamido)-4-fluoropyrrolidine-1-carboxylate (80 mg, 0.148 mmol, 52.4% yield) as a white solid.

MS ESI m/z 540.3 (M+H)

27B: 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide, TFA: A solution of (3R,4S)-tert-butyl 3-(5-(4-amino-5-(trifluoromethyl)pyrrolo[2,1-f][1,2,4]triazin-7-yl)-2-methoxynicotinamido)-4-fluoropyrrolidine-1-carboxylate (80 mg, 0.148 mmol) in TFA (0.5 mL, 6.49 mmol)(neat) was stirred at rt for 1 h. The reaction mixture was concentrated and further dried on vacuum pump. The resultant crude material was proceeded to next step without purification.

MS ESI m/z 440.3 (M+H)

27: To a solution of 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide, TFA (15 mg, 0.034 mmol) and 4-fluorobenzoic acid (5.74 mg, 0.041 mmol) in 1,4-dioxane (2 mL) was added Hunig's base (0.018 mL, 0.102 mmol) and BOP (18.12 mg, 0.041 mmol). The resultant mixture was stirred at rt for 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 min, then a 5-minute hold at 100% B; Flow: 20 mL/min. Fractions containing the desired product were combined and dried via centrifugal evaporation to yield the final product (1.1 mg, 2.0 μmol, 6%).

MS ESI m/z 562.4 (M+H)

1H NMR (500 MHz, DMSO-d6) δ 9.03-8.84 (m, 1H), 8.76 (br s, 1H), 8.58 (br d, J=7.0 Hz, 1H), 8.51 (br d, J=7.3 Hz, 1H), 8.16 (br d, J=12.8 Hz, 1H), 7.73-7.57 (m, 3H), 7.44-7.24 (m, 2H), 4.60-4.83 (m, 1H), 4.04 (br d, J=4.9 Hz, 3H), 3.98 (br s, 1H), 3.94-3.76 (m, 1H), 2.56-2.53 (m, 2H), 1.00 (d, J=6.1 Hz, 1H).

Example 28: 5-[4-amino-5-(trifluoromethyl)pyrrolo[2,1-f][1,2,4]triazin-7-yl]-N-[(3R)-3-(4-chlorophenyl)-3-methoxypropyl]-2-methoxypyridine-3-carboxamide

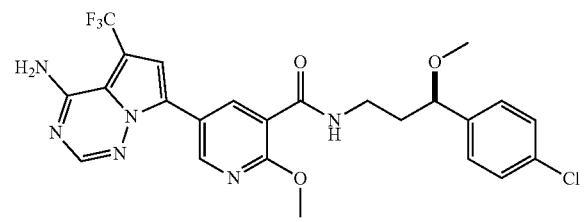 [SMILES: COc1ncc(-c2cc(C(F)(F)F)c3c(N)ncnn23)cc1C(=O)NCC[C@@H](OC)c1ccc(Cl)cc1]

28A: (R)-3-(4-chlorophenyl)-3-methoxypropan-1-amine, TFA: To a solution of (R)-tert-butyl (3-(4-chlorophenyl)-3-hydroxypropyl)carbamate (50 mg, 0.175 mmol) in THF (2 mL) was added sodium hydride (14.00 mg, 0.350 mmol). After stirring for 30 min, iodomethane (0.012 mL, 0.192 mmol) was added. The resultant mixture was stirred for 1 h. 1N HCl (1 mL) was added to quench the reaction and the mixture was purified by prep-HPLC to yield (R)-tert-butyl (3-(4-chlorophenyl)-3-methoxypropyl)carbamate (45 mg, 0.150 mmol, 86% yield). The crude residue was treated with TFA (0.5 mL, 6.49 mmol) (neat). The reaction mixture was concentrated and dried under vacuum to yield (R)-3-(4-chlorophenyl)-3-methoxypropan-1-amine (30 mg, 0.150 mmol, 86% yield). MS ESI (m/z) 200.1 (M+H).

28: To a solution of 5-(4-amino-5-(trifluoromethyl)pyrrolo[2,1-f][1,2,4]triazin-7-yl)-2-methoxynicotinic acid (10 mg, 0.028 mmol) and (R)-3-(4-chlorophenyl)-3-methoxypropan-1-amine (6.22 mg, 0.031 mmol) in 1,4-dioxane (2 mL) was added Hünig's base (0.015 mL, 0.085 mmol) and BOP (15.02 mg, 0.034 mmol). The resultant mixture was stirred at RT for 30 min. Purification by preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-90% B over 19 min, then a 5-minute hold at 100% B; Flow: 20 mL/min. yielded (R)-5-(4-amino-5-(trifluoromethyl)pyrrolo[2,1-f][1,2,4]triazin-7-yl)-N-(3-(4-chlorophenyl)-3-methoxypropyl)-2-methoxynicotinamide (8.4 mg, 0.015 mmol, 53.8% yield) as a white solid.

MS ESI m/z 535.2 (M+H)

1H NMR (500 MHz, DMSO-d6) δ 8.85 (d, J=2.4 Hz, 1H), 8.71 (d, J=2.4 Hz, 1H), 8.42 (br t, J=5.5 Hz, 1H), 8.14 (s, 1H), 7.56 (s, 1H), 7.42 (d, J=8.5 Hz, 2H), 7.34 (d, J=8.2 Hz, 2H), 4.30 (dd, J=7.6, 5.2 Hz, 1H), 4.03 (s, 3H), 3.62 (br s, 1H), 3.34 (dt, J=14.6, 7.2 Hz, 2H), 3.17-3.12 (m, 3H), 1.97-1.80 (m, 2H).

Example 29: 5-[4-amino-5-(trifluoromethyl)pyrrolo[2,1-f][1,2,4]triazin-7-yl]-N-[(3S)-3-(4-chlorophenyl)-3-methoxypropyl]-2-methoxypyridine-3-carboxamide

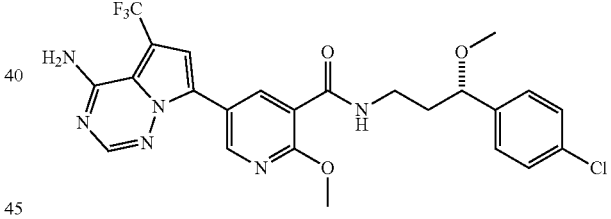

29A: (S)-3-(4-chlorophenyl)-3-methoxypropan-1-amine, TFA: To a solution of (S)-tert-butyl (3-(4-chlorophenyl)-3-hydroxypropyl)carbamate (100 mg, 0.350 mmol) in THF (3 mL) was added sodium hydride (28.0 mg, 0.700 mmol). After stirring 30 min, iodomethane (0.024 mL, 0.385 mmol) was added. The resultant mixture was stirred for 1 h. 1N HCl (2 mL) was added to quench the reaction and the reaction mixture was purified by prep-HPLC to yield (S)-tert-butyl (3-(4-chlorophenyl)-3-methoxypropyl)carbamate (90 mg, 0.300 mmol, 86% yield). The crude residue was treated with TFA (0.5 mL, 6.49 mmol) (neat). The reaction mixture was concentrated and dried under vacuum to yield (S)-3-(4-chlorophenyl)-3-methoxypropan-1-amine, TFA (60 mg, 0.300 mmol, 86% yield).

29: To a solution of 5-(4-amino-5-(trifluoromethyl)pyrrolo[2,1-f][1,2,4]triazin-7-yl)-2-methoxynicotinic acid (10 mg, 0.028 mmol) and (S)-3-(4-chlorophenyl)-3-methoxypropan-1-amine (6.22 mg, 0.031 mmol) in 1,4-dioxane (2 mL) was added Hünig's base (0.015 mL, 0.085 mmol) and BOP (15.02 mg, 0.034 mmol). The resultant mixture was stirred at rt for 30 min. Purification by preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 40-90% B over 19 min, then a 5-minute hold at 100% B; Flow: 20 mL/min. yielded (S)-5-(4-amino-5-(trifluoromethyl)pyrrolo[2,1-f][1,2,4]triazin-7-yl)-N-(3-(4-chlorophenyl)-3-methoxypropyl)-2-methoxynicotinamide (8.4 mg, 0.016 mmol, 55.5% yield) as a white solid.

MS ESI m/z 535 (M+H)

1H NMR (500 MHz, DMSO-d6) δ 8.87 (d, J=2.4 Hz, 1H), 8.74 (d, J=2.1 Hz, 1H), 8.40 (br t, J=5.5 Hz, 1H), 8.16 (s, 1H), 7.58 (s, 1H), 7.43 (d, J=8.2 Hz, 2H), 7.35 (d, J=8.5 Hz, 2H), 4.31 (dd, J=7.8, 5.0 Hz, 1H), 4.03 (s, 3H), 3.46 (br s, 1H), 3.40-3.28 (m, 1H), 3.18-3.14 (m, 3H), 2.56-2.53 (m, 2H), 1.98-1.80 (m, 2H).

Example 30: 5-[4-amino-5-(trifluoromethyl)pyrrolo[2,1-f][1,2,4]triazin-7-yl]-N-[(3S)-3-(4-chlorophenyl)-3-hydroxypropyl]-2-(methylamino)pyridine-3-carboxamide

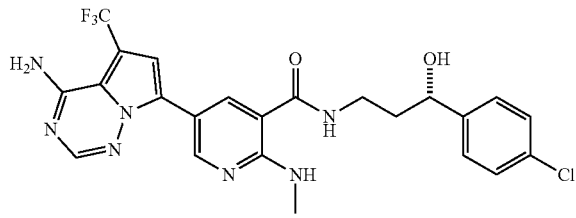 [SMILES: CNc1ncc(-c2cc(C(F)(F)F)c3c(N)ncnn23)cc1C(=O)NCC[C@H](O)c1ccc(Cl)cc1]

30A: methyl 2-(methylamino)-5-(4,4,5,5-tetramethyl-1,3,2-dioxaborolan-2-yl)nicotinate: To an oven-dried 10 mL vial were added methyl 5-bromo-2-(methylamino)nicotinate (0.6 g, 2.448 mmol), bis(pinacolato)diboron (217 mg, 0.854 mmol) and potassium acetate (0.721 g, 7.34 mmol). 1,4-Dioxane (20 mL) was introduced into the vial and nitrogen gas was blown through for 10 min. PdCl₂(dppf) (0.090 g, 0.122 mmol) was added to the reaction mixture and nitrogen gas was blown through the mixture for 10 min. The resultant mixture was heated to reflux at 80° C. ON. The reaction mixture was filtered to remove the catalyst, and the filtrate was concentrated in vacuo. The crude residue was purified by ISCO flash chromatography (40 g silical gel 10%-60% EtOAc/hexanes) to yield methyl 2-(methylamino)-5-(4,4,5,5-tetramethyl-1,3,2-dioxaborolan-2-yl)nicotinate (500 mg, 1.712 mmol, 69.9% yield) as a white solid.

MS ESI (m/z) 211.1 (M+H for the boronic acid).

30B: 5-(4-amino-5-(trifluoromethyl)pyrrolo[2,1-f][1,2,4]triazin-7-yl)-2-(methylamino)nicotinic acid: To a solution of 7-bromo-5-(trifluoromethyl)pyrrolo[2,1-f][1,2,4]triazin-4-amine (100 mg, 0.356 mmol) and methyl 2-(methylamino)-5-(4,4,5,5-tetramethyl-1,3,2-dioxaborolan-2-yl)nicotinate (114 mg, 0.391 mmol) in 1,4-dioxane (30 mL) was added potassium phosphate tribasic (0.534 mL, 1.067 mmol) (2M in H₂O). The reaction mixture was sparged with nitrogen for 5 min, then PdCl₂(dppf) (20.83 mg, 0.028 mmol) was added. The nitrogen sparge continued for 5 min. The reaction vessel was sealed and heated to 100° C. for 12 h. Water (2 mL) was added, and the crushed solid (methyl ester) was obtained by filtration. The obtained solid was then redissolved in MeOH (2 mL) and THF (2 mL), then sodium hydroxide (0.178 mL, 1.779 mmol) (1 M in water) was added. The resultant mixture was stirred at 60° C. for 12 h. The crude material was purified by prep-HPLC to yield 5-(4-amino-5-(trifluoromethyl)pyrrolo[2,1-f][1,2,4]triazin-7-yl)-2-(methylamino)nicotinic acid (50 mg, 0.142 mmol, 39.9% yield) as a white solid. The Methoxy byproduct (formed during hydrolysis) was also obtained 5-(4-amino-5-(trifluoromethyl)pyrrolo[2,1-f][1,2,4]triazin-7-yl)-2-methoxynicotinic acid (30 mg, 0.085 mmol, 23.87% yield) as a white solid.

MS ESI (m/z) 353.1 (M+H).

30: To a solution of 5-(4-amino-5-(trifluoromethyl)pyrrolo[2,1-f][1,2,4]triazin-7-yl)-2-(methylamino)nicotinic acid (15 mg, 0.043 mmol) and (S)-3-amino-1-(4-chlorophenyl)propan-1-ol (8.70 mg, 0.047 mmol) in 1,4-dioxane (2 mL) was added Hunig's base (0.022 mL, 0.128 mmol) and BOP (22.60 mg, 0.051 mmol). The resultant mixture was stirred at rt for 30 min. Purification was accomplished with preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 min, then a 5-minute hold at 100% B; Flow: 20 mL/min. Fractions containing the desired product were combined and dried via centrifugal evaporation to yield (S)-5-(4-amino-5-(trifluoromethyl)pyrrolo[2,1-f][1,2,4]triazin-7-yl)-N-(3-(4-chlorophenyl)-3-hydroxypropyl)-2-(methylamino)nicotinamide (3.8 mg, 7.24 μmol, 16.99% yield) as a white solid.

MS ESI m/z 520.4 (M+H)

1H NMR (500 MHz, DMSO-d6) δ 8.89 (d, J=2.1 Hz, 1H), 8.51 (br t, J=5.2 Hz, 1H), 8.36-8.23 (m, 2H), 8.13 (s, 1H), 7.42 (s, 1H), 7.37 (s, 4H), 5.42 (d, J=4.6 Hz, 1H), 4.65 (br d, J=5.2 Hz, 1H), 3.31 (br d, J=6.4 Hz, 1H), 2.95 (d, J=4.9 Hz, 3H), 2.73-2.54 (m, 1H), 1.93-1.79 (m, 2H), 1.00 (d, J=6 Hz, 1H).

Example 31-1 and 31-2: 5-[4-amino-5-(trifluoromethyl)pyrrolo[2,1-f][1,2,4]triazin-7-yl]-N-[1-(3,3-difluorocyclobutanecarbonyl)-(3R,4S)-4-fluoropyrrolidin-3-yl]-2-methoxypyridine-3-carboxamide and 5-[4-amino-5-(trifluoromethyl)pyrrolo[2,1-f][1,2,4]triazin-7-yl]-N-[1-(3,3-difluorocyclobutanecarbonyl)-(3S,4R)-4-fluoropyrrolidin-3-yl]-2-methoxypyridine-3-carboxamide

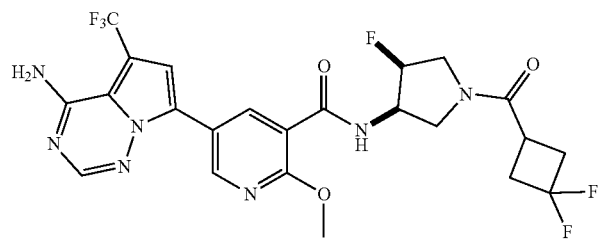

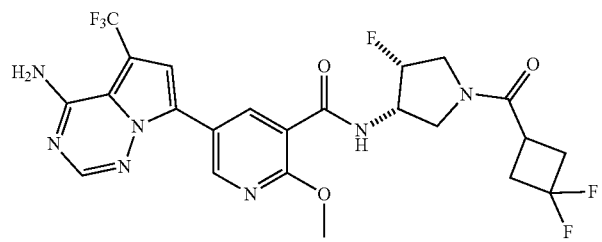

31A: tert-Butyl 3-(5-(4-amino-5-(trifluoromethyl)pyrrolo[2,1-f][1,2,4]triazin-7-yl)-2-methoxy-nicotinamido)-4-fluoropyrrolidine-1-carboxylate: A heterogeneous mixture of 5-(4-amino-5-(trifluoromethyl)pyrrolo[2,1-f][1,2,4]triazin-7-yl)-2-methoxynicotinic acid, lithium salt (2.04 g, 5.66 mmol), tert-butyl 3-amino-4-fluoropyrrolidine-1-carboxylate (mixture of cis enantiomer) (1.39 g, 6.80 mmol), Hünig's base (2.97 mL, 17.0 mmol) and BOP (2.76 g, 6.23 mmol) in N,N-dimethylformamide (20 mL) was stirred at rt for 60 min (homogeneous). The mixture was diluted with ethyl acetate, washed with 10% aqueous lithium hydroxide (2×) and washed with brine. The organic layer was collected, and the aqueous layers were sequentially extracted with ethyl acetate (2×). The combined organic layers were dried over anhydrous sodium sulfate and concentrated under reduced pressure. The resulting residue was triturated with methanol with sonication and filtered to give tert-butyl 3-(5-(4-amino-5-(trifluoromethyl)pyrrolo[2,1-f][1,2,4]triazin-7-yl)-2-methoxynicotinamido)-4-fluoropyrrolidine-1-carboxylate (1.31 g, 2.43 mmol, 43% yield) as a light tan solid. A second crop of tert-butyl 3-(5-(4-amino-5-(trifluoromethyl)pyrrolo[2,1-f][1,2,4]triazin-7-yl)-2-methoxynicotinamido)-4-fluoropyrrolidine-1-carboxylate (0.273 g, 0.506 mmol, 9% yield) was isolated. The filtrate was concentrated and purified by ISCO flash chromatography (40 g column; 0%-10% methanol in dichloromethane) to give (3R,4S)-tert-butyl 3-(5-(4-amino-5-(trifluoromethyl)pyrrolo[2,1-f][1,2,4]triazin-7-yl)-2-methoxynicotinamido)-4-fluoropyrrolidine-1-carboxylate (0.273 g, 0.506 mmol, 9% yield).

MS ESI (m/z) 540.3 (M+H).

31B: tert-Butyl 3-(5-(4-amino-5-(trifluoromethyl)pyrrolo[2,1-f][1,2,4]triazin-7-yl)-2-methoxynicotinamido)-4-fluoropyrrolidine-1-carboxylate: Intermediate 31A was separated by chiral SFC using the following preparative conditions: Column: Cellulose-4 (3×25 cm, 5 µm), BPR pressure 100 bars, Temperature: 35° C., Flow rate: 200 mL/min, Mobil phase: CO$_2$/MeOH (60/40), Detector wavelength: 220 nm, Separation program: stack injection, Injection: 3.5 mL with cycle time of 3.65 min, Sample preparation: 1.21 g/100 mL MeOH:DCM (1:1), 13.1 mg/mL, and Throughput: 753 mg/hr. Peak 1 eluted at 4.15 min and Peak 2 eluted at 6.56 min. Peak 2 was concentrated under reduced pressure to give tert-butyl 3-(5-(4-amino-5-(trifluoromethyl)pyrrolo[2,1-f][1,2,4]triazin-7-yl)-2-methoxynicotinamido)-4-(3R,4S)-fluoropyrrolidine-1-carboxylate (0.480 g, 0.890 mmol, 73.3% yield) as white solid. Peak 1 was determined to be in the (3S,4R) configuration and Peak 2 was determined to be in the (3R,4S) configuration. Determination of chirality was based on comparison to the final compounds derived from an orthogonal synthesis in which a crystal structure was obtained.

31C: 5-(4-Amino-5-(trifluoromethyl)pyrrolo[2,1-f][1,2,4]triazin-7-yl)-N-((3R,4S)-4-fluoropyrrolidin-3-yl)-2-methoxynicotinamide: A mixture of tert-butyl 3-(5-(4-amino-5-(trifluoromethyl)pyrrolo[2,1-f][1,2,4]triazin-7-yl)-2-methoxynicotinamido)-4-fluoropyrrolidine-1-carboxylate (homochiral—Peak 2; cis stereochemistry) (0.480 g, 0.890 mmol) and trifluoroacetic acid (16.79 ml, 218 mmol) was stirred at rt for 45 min.

The solvent was removed under reduced pressure, and the residue was diluted with dichloromethane and washed with a 1.5M aqueous solution of potassium phosphate dibasic. The organic layer was collected, and the aqueous layer was extracted with dichloromethane (2×), adjusted to a pH of ~10 with 2.0 M aqueous potassium phosphate tribasic, and then extracted with ethyl acetate (2×). The combined organic layers were dried over anhydrous sodium sulfate and concentrated under reduced pressure to give 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide (0.355 g, 0.808 mmol, 91% yield) as a white solid.

MS ESI (m/z) 440.2 (M+H).

31-1: A mixture of 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide (0.020 g, 0.046 mmol), 3,3-difluorocyclobutanecarboxylic acid (6.20 mg, 0.046 mmol), Hunig's base (0.024 mL, 0.137 mmol), and BOP (0.022 g, 0.050 mmol) in N,N-dimethylformamide (1.0 mL) was stirred at RT for 60 min. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 20-60% B over 20 min, then a 4-minute hold at 100% B; Flow: 20 mL/min. Fractions containing the desired product were combined and dried via centrifugal evaporation to yield 5-[4-amino-5-(trifluoromethyl)pyrrolo[2,1-f][1,2,4]triazin-7-yl]-N-[1-(3,3-difluorocyclobutanecarbonyl)-(3R,4S)-4-fluoropyrrolidin-3-yl]-2-methoxypyridine-3-carboxamide (20.0 mg, 25.5 µmol, 55%). This was later characterized as the (3R,4S) isomer.

MS ESI m/z 558.3 (M+H)

$^1$H NMR (400 MHz, DMSO-d6) δ 8.92 (br s, 1H), 8.84-8.75 (m, 1H), 8.58-8.49 (m, 1H), 8.22-8.17 (m, 1H), 7.67-7.61 (m, 1H), 5.45-5.19 (m, 1H), 4.88-4.58 (m, 1H), 4.05 (d, J=4.9 Hz, 3H), 4.00-3.84 (m, 1H), 3.83-3.69 (m, 1H), 3.45-3.36 (m, 1H), 3.31-3.24 (m, 1H), 3.24-3.11 (m, 1H), 2.90-2.70 (m, 4H).

31-2: Following a similar protocol to 31C and 31-1, Peak 1 from 31B was carried forward to yield 5-[4-amino-5-(trifluoromethyl)pyrrolo[2,1-f][1,2,4]triazin-7-yl]-N-[1-(3,3-difluorocyclobutanecarbonyl)-(3R,4R)-4-fluoropyrrolidin-3-yl]-2-methoxypyridine-3-carboxamide: A mixture of 5-(4-amino-5-(trifluoromethyl)pyrrolo[2,1-f][1,2,4]triazin-7-yl)-N-(4-fluoropyrrolidin-3-yl)-2-methoxynicotinamide (0.019 g, 0.043 mmol), 3,3-difluorocyclobutanecarboxylic acid (5.89 mg, 0.043 mmol), Hunig's base (0.023 mL, 0.130 mmol), and BOP (0.021 g, 0.048 mmol) in N,N-dimethylformamide (1.0 mL) was stirred at rt for 60 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 25-65% B over 20 minutes, then a 5-minute hold at 100% B; Flow: 20 mL/min. Fractions containing the desired product were combined and dried via centrifugal evaporation to afford 5-(4-amino-5-(trifluoromethyl)pyrrolo[2,1-f][1,2,4]triazin-7-yl)-N-(1-(3,3-difluorocyclobutanecarbonyl)-4-fluoropyrrolidin-3-yl)-2-methoxynicotinamide (16.4 mg, 0.029 mmol, 67%).

MS ESI m/z 558.2 (M+H)

$^1$H NMR (500 MHz, DMSO-d6) δ 8.92 (d, J=2.1 Hz, 1H), 8.78 (dd, J=17.7, 2.1 Hz, 1H), 8.52 (br dd, J=10.2, 7.8 Hz, 1H), 8.17 (s, 1H), 7.61 (s, 1H), 5.45-5.16 (m, 1H), 4.87-4.55 (m, 1H), 4.04 (d, J=6.1 Hz, 3H), 4.00-3.57 (m, 3H), 3.46-3.22 (m, 1H), 3.22-3.07 (m, 1H), 2.89-2.68 (m, 4H).

Example 32: 5-{4-amino-5-chloropyrrolo[2,1-f][1,2,4]triazin-7-yl}-N-[(3S)-3-(4-chlorophenyl)-3-hydroxypropyl]-2-methoxypyridine-3-carboxamide

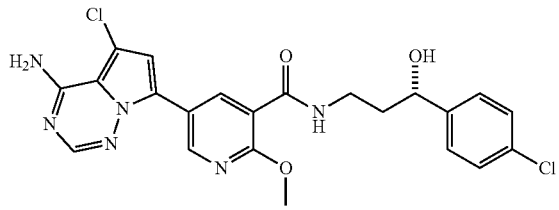 [SMILES: COc1ncc(-c2cc(Cl)c3c(N)ncnn23)cc1C(=O)NCC[C@H](O)c1ccc(Cl)cc1]

32A: 7-Bromo-5-chloropyrrolo[2,1-f][1,2,4]triazin-4-amine: A mixture of 7-bromopyrrolo[2,1-f][1,2,4]triazin-4-amine (100 mg, 0.469 mmol) and NCS (62.7 mg, 0.469 mmol) in DMF (2 mL) was stirred at rt for 3 h. It was then diluted with water, filtered, washed with water, dried to obtain 7-bromo-5-chloropyrrolo[2,1-f][1,2,4]triazin-4-amine (100 mg, 0.404 mmol, 86% yield) as a white solid.

MS ESI m/z 248.88 (M+H).

$^1$H NMR (400 MHz, CDCl$_3$) δ 7.96 (s, 1H), 6.82 (s, 1H).

32B: 5-(4-amino-5-chloropyrrolo[2,1-f][1,2,4]triazin-7-yl)-2-methoxynicotinic acid, sodium salt: To a solution of 7-bromo-5-chloropyrrolo[2,1-f][1,2,4]triazin-4-amine (100 mg, 0.404 mmol) and methyl 2-methoxy-5-(4,4,5,5-tetramethyl-1,3,2-dioxaborolan-2-yl)nicotinate (130 mg, 0.444 mmol) in 1,4-dioxane (2 mL) was added potassium phosphate tribasic (0.606 mL, 1.212 mmol) (2M in H$_2$O). After bubbling nitrogen through the mixture for 5 min, 1,1'-bis(diphenylphosphino)ferrocene-palladium(II)dichloride dichloromethane complex (33.0 mg, 0.040 mmol) was added. Nitrogen was bubbled through the mixture for another 5 min. The reaction vessel was sealed and heated to 100° C. for 2 h. The reaction mixture was filtered through a pad of Celite to remove the catalyst. To the solution was added sodium hydroxide (2.020 mL, 2.020 mmol) (10 M in water) and the resultant mixture was stirred at rt for another 2 h. The product was isolated by crystallization in MeOH and filtration to yield 5-(4-amino-5-chloropyrrolo[2,1-f][1,2,4]triazin-7-yl)-2-methoxynicotinic acid, sodium salt as a tan solid.

MS ESI m/z 319.95 (M+H).

32: A mixture of 5-(4-amino-5-chloropyrrolo[2,1-f][1,2,4]triazin-7-yl)-2-methoxynicotinic acid, sodium salt (20 mg, 0.063 mmol), (S)-3-amino-1-(4-chlorophenyl)propan-1-ol, HCl (15.28 mg, 0.069 mmol), BOP (33.2 mg, 0.075 mmol), Hunig's base (0.033 mL, 0.188 mmol) in DMF (1 mL) was stirred at rt for 20 min. It was then concentrated and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 32-72% B over 20 min, then a 4-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 14-54% B over 20 min, then a 4-minute hold at 100% B; Flow: 20 mL/min. Fractions containing the desired product were combined and dried via centrifugal evaporation to obtain (S)-5-(4-amino-5-chloropyrrolo[2,1-f][1,2,4]triazin-7-yl)-N-(3-(4-chlorophenyl)-3-hydroxypropyl)-2-methoxynicotinamide (7.1 mg, 0.015 mmol, 23.29% yield) as a white solid.

MS ESI m/z 487.1 (M+H)

1H NMR (500 MHz, DMSO-d6) δ 9.00-8.79 (m, 1H), 8.85-8.54 (m, 1H), 8.50-8.26 (m, 1H), 8.07-7.83 (m, 1H), 7.48-7.31 (m, 4H), 7.28-6.97 (m, 1H), 4.89-4.66 (m, 1H), 4.05-3.98 (m, 1H), 3.54-3.30 (m, 1H), 2.09-1.68 (m, 2H).

Example 33: 5-{4-amino-5-chloropyrrolo[2,1-f][1,2,4]triazin-7-yl}-N-(1-benzyl-1H-pyrazol-4-yl)-2-methoxypyridine-3-carboxamide

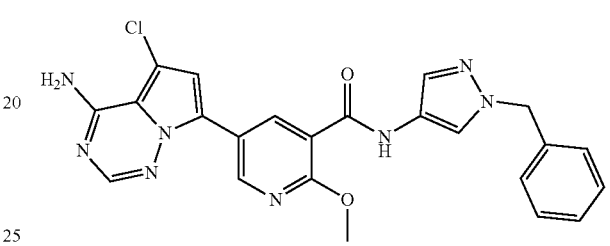

A mixture of 5-(4-amino-5-chloropyrrolo[2,1-f][1,2,4]triazin-7-yl)-2-methoxynicotinic acid (20 mg, 0.063 mmol), 1-benzyl-1H-pyrazol-4-amine (10.84 mg, 0.063 mmol), BOP (33.2 mg, 0.075 mmol), Hunig's base (0.033 mL, 0.188 mmol) in DMF (1 mL) was stirred at rt for 20 min. It was then concentrated and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 32-72% B over 20 min, then a 4-minute hold at 100% B; Flow: 20 mL/min. Fractions containing the desired product were combined and dried via centrifugal evaporation to obtain 5-(4-amino-5-chloropyrrolo[2,1-f][1,2,4]triazin-7-yl)-N-(1-benzyl-1H-pyrazol-4-yl)-2-methoxynicotinamide (6.2 mg, 0.013 mmol, 20.87% yield) as a white solid.

MS ESI m/z 475.1 (M+H)

1H NMR (500 MHz, DMSO-d6) δ 10.29-10.05 (m, 1H), 8.95-8.79 (m, 1H), 8.79-8.56 (m, 1H), 8.21-8.02 (m, 1H), 8.02-7.84 (m, 1H), 7.73-7.55 (m, 1H), 7.41-7.21 (m, 6H), 5.42-5.17 (m, 2H), 3.28-3.24 (m, 3H).

Example 34: 5-[4-amino-5-(trifluoromethyl)pyrrolo[2,1-f][1,2,4]triazin-7-yl]-N-[1-(3,3-difluorocyclopentanecarbonyl)-(3R,4S)$_4$-fluoropyrrolidin-3-yl]-2-methoxypyridine-3-carboxamide

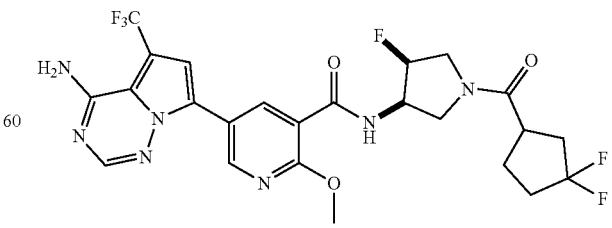

34A: tert-Butyl 3-(5-(4-amino-5-(trifluoromethyl)pyrrolo[2,1-f][1,2,4]triazin-7-yl)-2-methoxy-nicotinamido)-4-fluororopyrrolidine-1-carboxylate: A heterogeneous mixture of 5-(4-amino-5-(trifluoromethyl)pyrrolo[2,1-f][1,2,4]triazin-7-yl)-2-methoxynicotinic acid, lithium salt (2.04 g, 5.66 mmol), tert-butyl 3-amino-4-fluoropyrrolidine-1-carboxylate (mixture of cis enantiomer) (1.39 g, 6.80 mmol), Hunig's base (2.97 mL, 17.0 mmol) and BOP (2.76 g, 6.23 mmol) in N,N-dimethylformamide (20 mL) was stirred at rt for 60 min (homogeneous). The mixture was diluted with ethyl acetate, washed with 10% aqueous lithium hydroxide (2×) and washed with brine. The organic layer was collected, and the aqueous layers were sequentially extracted with ethyl acetate (2×). The combined organic layers were dried over anhydrous sodium sulfate and concentrated under reduced pressure. The resulting residue was triturated with methanol with sonication and filtered to give tert-butyl 3-(5-(4-amino-5-(trifluoromethyl)pyrrolo[2,1-f][1,2,4]triazin-7-yl)-2-methoxynicotinamido)-4-fluoropyrrolidine-1-carboxylate (1.31 g, 2.43 mmol, 43% yield) as a light tan solid. A second crop of (3R,4S)-tert-butyl 3-(5-(4-amino-5-(trifluoromethyl)pyrrolo[2,1-f][1,2,4]triazin-7-yl)-2-methoxynicotinamido)-4-fluoropyrrolidine-1-carboxylate (0.273 g, 0.506 mmol, 9% yield) was isolated. The filtrate was concentrated and purified by ISCO flash chromatography (40 g column; 0%-10% methanol in dichloromethane) to give (3R,4S)-tert-butyl 3-(5-(4-amino-5-(trifluoromethyl)pyrrolo[2,1-f][1,2,4]triazin-7-yl)-2-methoxynicotinamido)-4-fluoropyrrolidine-1-carboxylate (0.273 g, 0.506 mmol, 9% yield).

MS ESI (m/z) 540.3 (M+H).

34B: tert-Butyl 3-(5-(4-amino-5-(trifluoromethyl)pyrrolo[2,1-f][1,2,4]triazin-7-yl)-2-methoxynicotinamido)-4-fluoropyrrolidine-1-carboxylate: Intermediate 34A was separated by chiral SFC using the following preparative conditions: Column: Cellulose-4 (3×25 cm, 5 um), BPR pressure 100 bars, Temperature: 35° C., Flow rate: 200 mL/min, Mobil phase: $CO_2$/MeOH (60/40), Detector wavelength: 220 nm, Separation program: stack injection, Injection: 3.5 mL with cycle time of 3.65 min, Sample preparation: 1.21 g/100 mL MeOH:DCM (1:1), 13.1 mg/mL, and Throughput: 753 mg/hr. Peak 2 was concentrated under reduced pressure to give tert-butyl 3-(5-(4-amino-5-(trifluoromethyl)pyrrolo[2,1-f][1,2,4]triazin-7-yl)-2-methoxynicotinamido)-(3R,4S)-4-fluoropyrrolidine-1-carboxylate (0.480 g, 0.890 mmol, 73.3% yield) as white solid. The product was >99% pure by UPLC with a ret. time=1.22 min.—Column: Phenomenex Kinetex C18 2.1×50 mm (1.5 min. gradient); Solvent A=10% MeCN, 90% $H_2O$, 0.1% TFA; Solvent B=90% MeCN, 10% $H_2O$, 0.1% TFA. LC/MS M+1=540.3. Chiral Purity: 99.5% ee.

34C: 5-(4-Amino-5-(trifluoromethyl)pyrrolo[2,1-f][1,2,4]triazin-7-yl)-N-((3R,4S)-4-fluoropyrrolidin-3-yl)-2-methoxynicotinamide: A mixture of tert-butyl 3-(5-(4-amino-5-(trifluoromethyl)pyrrolo[2,1-f][1,2,4]triazin-7-yl)-2-methoxynicotinamido)-(3R,4S)-4-fluoropyrrolidine-1-carboxylate (homochiral—Peak 2; cis stereochemistry) (0.480 g, 0.890 mmol) and trifluoroacetic acid (16.79 ml, 218 mmol) was stirred at rt for 45 min. The solvent was removed under reduced pressure, and the residue was diluted with dichloromethane and washed with a 1.5M aqueous solution of potassium phosphate dibasic. The organic layer was collected, and the aqueous layer was extracted with dichloromethane (2×), adjusted to a pH of ~10 with 2.0M aqueous potassium phosphate tribasic, and then extracted with ethyl acetate (2×). The combined organic layers were dried over anhydrous sodium sulfate and concentrated under reduced pressure to give 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide (0.355 g, 0.808 mmol, 91% yield) as a white solid.

MS ESI (m/z) 440.2 (M+H).

34: A mixture of 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide (0.020 g, 0.046 mmol), 3,3-difluorocyclopentanecarboxylic acid (8.88 mg, 0.059 mmol), Hunig's base (0.024 mL, 0.137 mmol), and BOP (0.022 g, 0.050 mmol) in N,N-dimethylformamide (1.0 mL) was stirred at RT for 60 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 10-80% B over 20 min, then a 4-minute hold at 100% B; Flow: 20 mL/min. Fractions containing the desired product were combined and dried via centrifugal evaporation to yield the final product (15.0 mg, 26.2 µmol, 57%).

MS ESI m/z 572.3 (M+H)

$^1$H NMR (500 MHz, DMSO-d6) δ 8.88 (s, 1H), 8.74 (br d, J=18.3 Hz, 1H), 8.56 (br t, J=8.5 Hz, 1H), 8.14 (s, 1H), 7.56 (s, 1H), 5.41-5.20 (m, 1H), 4.84-4.58 (m, 1H), 4.03 (d, J=6.7 Hz, 3H), 3.81-3.71 (m, 3H), 3.54-3.37 (m, 1H), 3.29-3.11 (m, 2H), 2.31 (br dd, J=16.3, 9.0 Hz, 2H), 2.23-2.11 (m, 1H), 2.11-1.99 (m, 2H), 1.86-1.71 (m, 1H).

Example 35: 2-amino-5-[4-amino-5-(trifluoromethyl)pyrrolo[2,1-f][1,2,4]triazin-7-yl]-N-(1-tert-butyl-1H-pyrazol-4-yl)pyridine-3-carboxamide

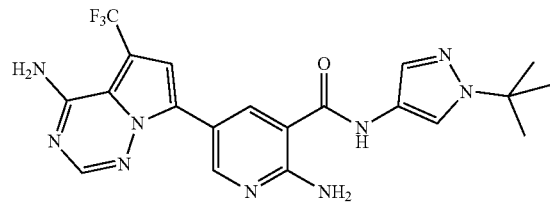 [SMILES: CC(C)(C)n1cc(NC(=O)c2cc(-c3cc(C(F)(F)F)c4c(N)ncnn34)cnc2N)cn1]

A mixture of 2-amino-5-(4-amino-5-(trifluoromethyl)pyrrolo[2,1-f][1,2,4]triazin-7-yl)nicotinic acid (20 mg, 0.059 mmol), 1-(tert-butyl)-1H-pyrazol-4-amine (9.88 mg, 0.071 mmol), BOP (31.4 mg, 0.071 mmol), Hunig's base (0.031 mL, 0.177 mmol) in DMF (1 mL) was stirred at rt for 20 min. It was then filtered and purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 4-minute hold at 100% B; Flow: 20 mL/min. Fractions containing the desired product were combined and dried via centrifugal evaporation to yield 2-amino-5-(4-amino-5-(trifluoromethyl)pyrrolo[2,1-f][1,2,4]triazin-7-yl)-N-(1-(tert-butyl)-1H-pyrazol-4-yl)nicotinamide (11.9 mg, 0.026 mmol, 43.8% yield) as a white solid.

MS ESI m/z 460.1 (M+H)

1H NMR (500 MHz, DMSO-d6) δ 10.43-10.12 (m, 1H), 8.96-8.71 (m, 1H), 8.63-8.37 (m, 1H), 8.19-7.94 (m, 2H), 7.72-7.54 (m, 1H), 7.55-7.40 (m, 1H), 3.89 (s, 3H), 1.54 (s, 9H).

Example 36: 5-{4-amino-5-chloropyrrolo[2,1-f][1,2,4]triazin-7-yl}-N-[(3R)-3-(4-chlorophenyl)-3-hydroxypropyl]-2-methoxypyridine-3-carboxamide

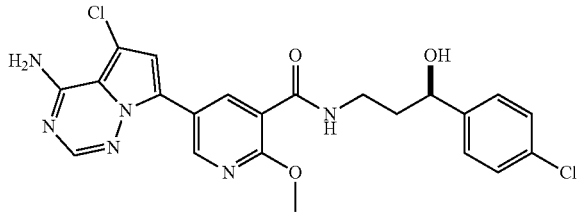 [SMILES: COc1ncc(-c2cc(Cl)c3c(N)ncnn23)cc1C(=O)NCC[C@@H](O)c1ccc(Cl)cc1]

A mixture of 5-(4-amino-5-chloropyrrolo[2,1-f][1,2,4]triazin-7-yl)-2-methoxynicotinic acid (20 mg, 0.063 mmol), (R)-3-amino-1-(4-chlorophenyl)propan-1-ol, HCl (15.28 mg, 0.069 mmol), BOP (33.2 mg, 0.075 mmol), Hunig's base (0.033 mL, 0.188 mmol) in DMF (1 mL) was stirred at rt for 20 min. It was then concentrated and purified via preparative LC/MS with the following conditions: Column: waters xbridge c-18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 32-72% B over 20 min, then a 4-minute hold at 100% B; Flow: 20 mL/min. Fractions containing the desired product were combined and dried via centrifugal evaporation to yield (R)-5-(4-amino-5-chloropyrrolo[2,1-f][1,2,4]triazin-7-yl)-N-(3-(4-chlorophenyl)-3-hydroxypropyl)-2-methoxynicotinamide (4.8 mg, 9.85 μmol, 15.74% yield) as a white solid.

MS ESI m/z 487 (M+H)

1H NMR (500 MHz, DMSO-d6) δ 9.03-8.66 (m, 2H), 8.49-8.21 (m, 1H), 8.13-7.82 (m, 1H), 7.53-7.28 (m, 4H), 7.27-7.12 (m, 1H), 5.50-5.23 (m, 1H), 4.84-4.53 (m, 1H), 3.55-3.31 (m, 1H), 2.14-1.75 (m, 2H).

Example 37: 5-[4-amino-5-(trifluoromethyl)pyrrolo[2,1-f][1,2,4]triazin-7-yl]-N-[1-(3,3-difluorocyclobutanecarbonyl)-4-fluoropyrrolidin-3-yl]-2-methoxypyridine-3-carboxamide (homochiral, trans

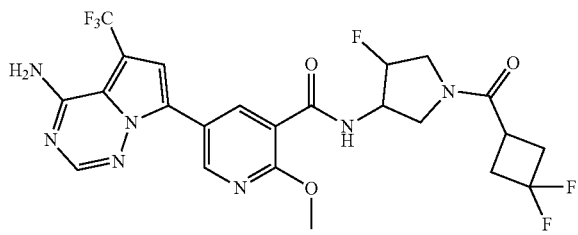 [SMILES: COc1ncc(-c2cc(C(F)(F)F)c3c(N)ncnn23)cc1C(=O)NC1CN(C(=O)C2CC(F)(F)C2)CC1F]

37A: tert-Butyl 3-(5-(4-amino-5-(trifluoromethyl)pyrrolo[2,1-f][1,2,4]triazin-7-yl)-2-methoxynicotinamido)-4-fluoropyrrolidine-1-carboxylate: A mixture of 5-(4-amino-5-(trifluoromethyl)pyrrolo[2,1-f][1,2,4]triazin-7-yl)-2-methoxynicotinic acid, lithium salt (0.254 g, 0.705 mmol), tert-butyl 3-amino-4-fluoropyrrolidine-1-carboxylate (mixture of trans enantiomers) (0.173 g, 0.846 mmol), Hunig's base (0.369 mL, 2.12 mmol) and BOP (0.343 g, 0.776 mmol) in N,N-dimethylformamide (3.0 mL) was stirred at rt for 60 min. The reaction mixture was diluted with ethyl acetate and washed with water and brine. The organic layer was collected, and the aqueous layers were sequentially extracted with ethyl acetate (2×). The combined organic layers were dried over anhydrous sodium sulfate and concentrated to give the crude product. The product was triturated with methanol with sonication and collected by vacuum filtration. The filtrate was concentrated, and the residue was suspended in methanol with sonication. The solid was collected, and the combined lots were dried under reduced pressure to yield tert-butyl 3-(5-(4-amino-5-(trifluoromethyl)pyrrolo[2,1-f][1,2,4]triazin-7-yl)-2-methoxynicotinamido)-4-fluoropyrrolidine-1-carboxylate (0.289 g, 0.536 mmol, 76% yield) as a white solid.

MS ESI (m/z) 540.3 (M+H)

37B: Intermediate 37A was separated by chiral SFC using the following preparative conditions: Column: Cellulose-4 (3×25 cm, 5 um), BPR pressure 100 bars, Temperature: 35° C., Flow rate: 200 mL/min, Mobil phase: $CO_2$/MeOH (60/40), Detector wavelength: 220 nm, Separation program: stack injection, Injection: 1.0 mL with cycle time of 2.9 min, Sample preparation: 0.289 g/18 mL MeOH:DCM (1:1), 16.1 mg/mL, and throughput: 332 mg/hr. Peak 1 eluted at 4.35 min and Peak 2 eluted at 4.96 min. Peak 1 was concentrated under reduced pressure to give tert-butyl 3-(5-(4-amino-5-(trifluoromethyl)pyrrolo[2,1-f][1,2,4]triazin-7-yl)-2-methoxynicotinamido)-4-fluoropyrrolidine-1-carboxylate (homochiral, trans, absolute stereochemistry undefined) (0.135 g, 0.248 mmol, 92% yield) as a white solid.

1H-NMR (400 MHz, DMSO-d6) δ 8.95-8.90 (m, 1H), 8.63-8.58 (m, 2H), 8.18 (s, 1H), 7.61 (s, 1H), 4.58-4.44 (m, 1H), 4.02-3.97 (m, 3H), 3.72-3.62 (m, 1H), 3.60-3.51 (m, 1H), 3.50-3.38 (m, 1H), 3.30 (s, 2H), and 1.43 (s, 9H).

37C: 5-(4-Amino-5-(trifluoromethyl)pyrrolo[2,1-f][1,2,4]triazin-7-yl)-N-(4-fluoropyrrolidin-3-yl)-2-methoxynicotinamide (homochiral, trans, absolute stereochemistry undefined): A mixture of tert-butyl 3-(5-(4-amino-5-(trifluoromethyl)pyrrolo[2,1-f][1,2,4]triazin-7-yl)-2-methoxynicotinamido)-4-fluoropyrrolidine-1-carboxylate (0.132 g, 0.245 mmol) and trifluoroacetic acid (3.00 mL, 38.9 mmol) was stirred at rt for 30 min. The solvent was removed under reduced pressure, and the residue was diluted with ethyl acetate, washed with a saturated aqueous solution of sodium bicarbonate, and washed with brine. The organic layer was collected, and the aqueous layers were sequentially extracted with ethyl acetate (2×). The combined organic layers were dried over anhydrous sodium sulfate and concentrated under reduced pressure to give 5-(4-amino-5-(trifluoromethyl)pyrrolo[2,1-f][1,2,4]triazin-7-yl)-N-(4-fluoropyrrolidin-3-yl)-2-methoxynicotinamide (homochiral, trans, absolute stereochemistry undefined) (0.101 g, 0.230 mmol, 94% yield) as a white solid.

MS ESI (m/z) 440.3 (M+H).

37: A mixture of 5-(4-amino-5-(trifluoromethyl)pyrrolo[2,1-f][1,2,4]triazin-7-yl)-N-(4-fluoropyrrolidin-3-yl)-2-methoxynicotinamide (homochiral, trans, absolute stereochemistry undefined) (0.020 g, 0.046 mmol), 3,3-difluorocyclobutanecarboxylic acid (8.05 mg, 0.059 mmol), Hünig's base (0.024 mL, 0.137 mmol), and BOP (0.022 g, 0.050 mmol) in N,N-dimethylformamide (1.0 mL) was stirred at rt for 60 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-80% B over 19 min, then a 5-minute hold at 100% B; Flow: 20 mL/min. Fractions containing the desired product were combined and dried via centrifugal evaporation to yield the final product (15.0 mg, 26.9 μmol, 59%).

MS ESI m/z 558 (M+H)

¹H NMR (500 MHz, DMSO-d₆) δ 8.92 (d, J=2.1 Hz, 1H), 8.64-8.55 (m, 2H), 8.17 (d, J=1.5 Hz, 1H), 7.59 (s, 1H), 5.32-5.12 (m, 1H), 4.64-4.50 (m, 1H), 3.98 (s, 3H), 3.93-3.77 (m, 1H), 3.77-3.55 (m, 2H), 3.47-3.33 (m, 1H), 3.22-3.09 (m, 1H), 2.86-2.74 (m, 4H).

Example 38: 5-{4-amino-5-methylpyrrolo[2,1-f][1,2,4]triazin-7-yl}-N-[(3S)-3-(4-chlorophenyl)-3-hydroxypropyl]-2-methoxypyridine-3-carboxamide

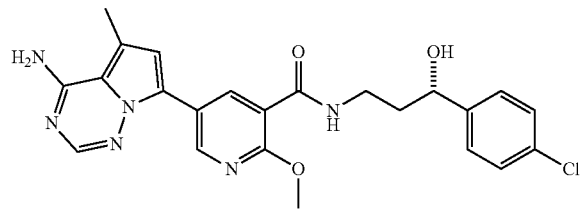 [SMILES: COc1ncc(-c2cc(C)c3c(N)ncnn23)cc1C(=O)NCC[C@H](O)c1ccc(Cl)cc1]

38A: 7-bromo-4-chloro-5-methylpyrrolo[2,1-f][1,2,4]triazine: A mixture of 4 chloro-5-methylpyrrolo[2,1-f][1,2,4]triazine (110 mg, 0.656 mmol) and NBS (117 mg, 0.656 mmol) in DCM (2 mL) and TFA (0.2 mL) was stirred at rt for 3 h. It was diluted with water and the precipitate was filtered, rinsing with water to obtain 7-bromo-4-chloro-5-methylpyrrolo[2,1-f][1,2,4]triazine (150 mg, 0.609 mmol, 93% yield) as a white solid.

MS ESI (m/z) 247.9 (M+H)

¹H NMR (400 MHz, CDCl₃) δ 8.24 (s, 1H), 6.86 (s, 1H), 2.69 (s, 3H).

38B: 7-bromo-5-methylpyrrolo[2,1-f][1,2,4]triazin-4-amine: To a mixture of 7-bromo-4-chloro-5-methylpyrrolo[2,1-f][1,2,4]triazine (120 mg, 0.487 mmol) in dioxane (2 mL) was added ammonium hydroxide (0.677 mL, 4.87 mmol). The reaction mixture was stirred at rt for 16 h. It was then concentrated to obtain 7-bromo-5-methylpyrrolo[2,1-f][1,2,4]triazin-4-amine (110 mg, 0.484 mmol, 100% yield) as a white solid.

MS ESI (m/z) 228.9 (M+H)

¹H NMR (400 MHz, CD₃OD) δ 7.97-7.64 (m, 1H), 6.57 (s, 1H), 2.57 (s, 3H).

38C: 5-(4-amino-5-methylpyrrolo[2,1-f][1,2,4]triazin-7-yl)-2-methoxynicotinic acid: To a solution of 7-bromo-5-methylpyrrolo[2,1-f][1,2,4]triazin-4-amine (80 mg, 0.352 mmol) and methyl 2-methoxy-5-(4,4,5,5-tetramethyl-1,3,2-dioxaborolan-2-yl)nicotinate (114 mg, 0.388 mmol) in 1,4-dioxane (2 mL) was added potassium phosphate tribasic (0.528 mL, 1.057 mmol) (2M in H₂O). The mixture was degassed by bubbling nitrogen through the mixture for 5 min and then 1,1'-bis(diphenylphosphino)ferrocene-palladium(II)dichloride dichloromethane complex (28.8 mg, 0.035 mmol) was added. Nitrogen was bubbled through the mixture for another 5 min. The reaction vessel was sealed and heated to 100° C. for 3 h. The reaction mixture was filtrated through a pad of Celite to remove catalyst. Sodium hydroxide (0.176 mL, 1.762 mmol) (10 M in water) was added and the resultant mixture was stirred at rt for another 2 h. Methanol was added and the solid isolated by filtration to afford 5-(4-amino-5-methylpyrrolo[2,1-f][1,2,4]triazin-7-yl)-2-methoxynicotinic acid, sodium salt (60 mg, 0.200 mmol, 56.9% yield) as a brown solid.

38: A mixture of 5-(4-amino-5-methylpyrrolo[2,1-f][1,2,4]triazin-7-yl)-2-methoxynicotinic acid (20 mg, 0.067 mmol), (S)-3-amino-1-(4-chlorophenyl)propan-1-ol, HCl (16.33 mg, 0.074 mmol), BOP (35.5 mg, 0.080 mmol), Hunig's base (0.035 mL, 0.200 mmol) in DMF (1 mL) was stirred at rt for 20 min. It was then concentrated and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 5-minute hold at 100% B; Flow: 20 mL/min. Fractions containing the desired product were combined and dried via centrifugal evaporation to yield (S)-5-(4-amino-5-methylpyrrolo[2,1-f][1,2,4]triazin-7-yl)-N-(3-(4-chlorophenyl)-3-hydroxypropyl)-2-methoxynicotinamide (10.1 mg, 0.022 mmol, 32.4% yield) as a white solid.

MS ESI m/z 467.1 (M+H)

¹H NMR (500 MHz, DMSO-d6) δ 8.86 (d, J=2.6 Hz, 1H), 8.76 (d, J=2.6 Hz, 1H), 8.38 (br t, J=5.3 Hz, 1H), 7.81 (s, 1H), 7.44-7.33 (m, 4H), 7.08 (br s, 2H), 6.88 (s, 1H), 5.40 (d, J=4.4 Hz, 1H), 4.75-4.67 (m, 1H), 4.03 (s, 3H), 3.44-3.35 (m, 1H), 2.53 (s, 3H), 1.95-1.81 (m, 2H).

Example 39: (2S)-4-{4-aminopyrrolo[2,1-f][1,2,4]triazin-7-yl}-N-{[2-fluoro-5-(trifluoromethoxy)phenyl]methyl}-2,5-dihydro-1H-pyrrole-2-carboxamide

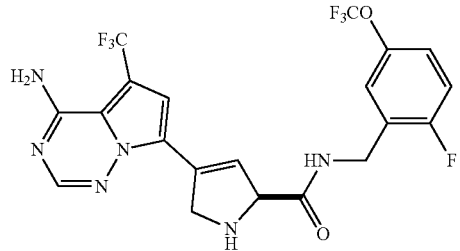 [SMILES: Nc1ncnn2c(C3=C[C@@H](C(=O)NCc4cc(OC(F)(F)F)ccc4F)NC3)cc(C(F)(F)F)c12]

39A: 1-(tert-butyl) 2-methyl (S)-4-(((trifluoromethyl)sulfonyl)oxy)-2,5-dihydro-1H-pyrrole-1,2-dicarboxylate: To a mixture of (S)-1-tert-butyl 2-methyl 4-oxopyrrolidine-1,2-dicarboxylate (4.45 g, 18.29 mmol) in THF (48.8 ml) at −78° C. was added LiHMDS (21.95 ml, 21.95 mmol). The mixture was allowed to stir at −78° C. for 1 h. A solution of 2-[N,N-bis(trifluoromethanesulfonyl)amino]-5-chloropyridine (7.18 g, 18.29 mmol) in THF (12.20 ml) was then added to the reaction mixture which was stirred at −78° C. for an additional 1 h. The mixture was allowed to come to −20° C. and continued to stir at that temperature ON. The reaction mixture was quenched by the addition of water. The resulting mixture was extracted with diethyl ether (3×). The combined extracts were washed with 1 N aqueous sodium hydroxide, brine, dried over MgSO4, filtered and concentrated in vacuo. Purification by flash chromatography (Silica, 120 g, 0-100% EtOAc/Hexanes) gave (S)-1-tert-butyl 2-methyl 4-(((trifluoromethyl)sulfonyl)oxy)-1H-pyrrole-1,2(2H,5H)-dicarboxylate (1.18 g, 2.99 mmol, 16% yield).

Parent ion not observed by LCMS.

¹H NMR (500 MHz, CDCl₃) δ 5.85-5.65 (m, 1H), 5.14-4.97 (m, 1H), 4.45-4.36 (m, 1H), 4.34 (s, 1H), 3.79 (s, 3H), 1.52-1.44 (m, 9H).

39B: 1-(tert-butyl) 2-methyl (S)-4-(4,4,5,5-tetramethyl-1,3,2-dioxaborolan-2-yl)-2,5-dihydro-1H-pyrrole-1,2-dicarboxylate: A mixture of bis(pinacolato)diboron (3.18 g, 12.51 mmol), (S)-1-tert-butyl 2-methyl 4-(((trifluoromethyl)sulfonyl)oxy)-1H-pyrrole-1,2(2H,5H)-dicarboxylate (4.27 g, 11.38 mmol), [1,1'-bis(diphenylphosphino)ferrocene]dichloropalladium(II) (0.416 g, 0.569 mmol) and potassium acetate (3.35 g, 34.1 mmol) in dioxane (65.0 ml) was sparged with nitrogen for 5 min. The mixture was brought to 100° C. and stirred ON. The mixture was filtered and diluted with EtOAc. The mixture was washed with water, brine, dried over MgSO4, filtered and concentrated in vacuo. Purification by flash chromatography (Silica, 120 g, EtOAc/Hexanes) gave (S)-1-tert-butyl 2-methyl 4-(4,4,5,5-tetramethyl-1,3,2-dioxaborolan-2-yl)-1H-pyrrole-1,2(2H,5H)-dicarboxylate (3.85 g, 10.90 mmol, 96% yield).

Parent ion not observed by LCMS.

¹H NMR (500 MHz, CDCl₃) δ 6.39-6.28 (m, 1H), 5.17-4.98 (m, 1H), 4.41-4.25 (m, 2H), 3.76-3.76 (m, 1H), 3.74 (d, J=6.4 Hz, 2H), 1.51-1.43 (m, 9H), 1.30-1.28 (m, 13H).

39C: 1-(tert-butyl) 2-methyl (S)-4-(4-aminopyrrolo[2,1-f][1,2,4]triazin-7-yl)-2,5-dihydro-1H-pyrrole-1,2-dicarboxylate: A mixture of 7-bromopyrrolo[2,1-f][1,2,4]triazin-4-amine (250 mg, 1.174 mmol), (S)-1-tert-butyl 2-methyl 4-(4,4,5,5-tetramethyl-1,3,2-dioxaborolan-2-yl)-1H-pyrrole-1,2(2H,5H)-dicarboxylate (912 mg, 2.58 mmol) and potassium phosphate tribasic (2 M in water) (1760 µl, 3.52 mmol) in DMF (6593 µl) was sparged with nitrogen for 5 min. PdCl₂(dppf)-CH₂Cl₂ adduct (96 mg, 0.117 mmol) was added to the reaction mixture which was sparged with nitrogen for an additional 5 min. The mixture was brought to 100° C. and stirred for 30 min. The reaction mixture was then diluted with EtOAc, washed with water, brine, dried over MgSO4, filtered and concentrated in vacuo. Purification by flash chromatography (Silica, 40 g, 40-70% EtOAc/Hexanes) gave (S)-1-tert-butyl 2-methyl 4-(4-aminopyrrolo[2,1-f][1,2,4]triazin-7-yl)-1H-pyrrole-1,2(2H,5H)-dicarboxylate (165 mg, 0.459 mmol, 39.1% yield). MS ESI (m/z) 360.1 (M+H)

39D: (S)-4-(4-aminopyrrolo[2,1-f][1,2,4]triazin-7-yl)-1-(tert-butoxycarbonyl)-2,5-dihydro-1H-pyrrole-2-carboxylic acid, lithium salt: To a mixture of (S)-1-tert-butyl 2-methyl 4-(4-aminopyrrolo[2,1-f][1,2,4]triazin-7-yl)-1H-pyrrole-1,2(2H,5H)-dicarboxylate (165 mg, 0.459 mmol) in THF (2952 µl), MeOH (1312 µl), and water (328 µl) was added LiOH (12.09 mg, 0.505 mmol). The resulting mixture was stirred at rt for 3 d. The mixture was concentrated in vacuo and dried under high vac. The remaining residue was used in the next step without purification. MS ESI (m/z) 346.1 (M+H)

39E: tert-butyl (S)-4-(4-aminopyrrolo[2,1-f][1,2,4]triazin-7-yl)-2-((2-fluoro-5-(trifluoromethoxy)benzyl)carbamoyl)-2,5-dihydro-1H-pyrrole-1-carboxylate: To a mixture of (S)-4-(4-aminopyrrolo[2,1-f][1,2,4]triazin-7-yl)-1-(tert-butoxycarbonyl)-2,5-dihydro-1H-pyrrole-2-carboxylic acid, lithium salt (15 mg, 0.043 mmol), 2-fluoro-5-(trifluoromethoxy)benzylamine (9.08 mg, 0.043 mmol) and BOP (23.05 mg, 0.052 mmol) in dioxane (2172 µl) was added Hunig's base (22.76 µl, 0.130 mmol). The resulting mixture was stirred at rt ON. The mixture was diluted with EtOAc, washed with water, brine, dried over MgSO4, filtered and concentrated in vacuo. The crude material was used in the next step without further purification.

MS ESI (m/z) 537.3 (M+H)

39: To a mixture of (5)-tert-butyl 4-(4-aminopyrrolo[2,1-f][1,2,4]triazin-7-yl)-2-((2-fluoro-5-(trifluoromethoxy)benzyl)carbamoyl)-2,5-dihydro-1H-pyrrole-1-carboxylate (23.07 mg, 0.043 mmol) in DCM (2 mL) was added TFA (400 µl, 5.19 mmol). The resulting mixture was stirred at rt for 2 h. The mixture was then concentrated to dryness. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 18-58% B over 19 min, then a 4-minute hold at 100% B; Flow: 20 mL/min. Fractions containing the desired product were combined and dried via centrifugal evaporation to yield the final product (3.3 mg, 7.6 µmol, 18%).

MS ESI m/z 437.1 (M+H)

¹H NMR (500 MHz, DMSO-d6) δ 8.54 (1, J=6.6 Hz, 1H), 7.93 (s, 1H), 7.61 (br s, 1H), 7.34-7.24 (m, 2H), 7.24-7.15 (m, 1H), 6.92 (d, J=4.8 Hz, 1H), 6.83 (d, J=2.2 Hz, 1H), 6.64 (d, J=4.8 Hz, 1H), 4.72-4.60 (m, 1H), 4.45-4.30 (m, 2H), 4.28-4.09 (m, 2H), two exchangeable protons not seen.

Example 40: cis-racemic-5-[4-amino-5-(trifluoromethyl)pyrrolo[2,1-f][1,2,4]triazin-7-yl]-N-[1-(cyclohexylmethyl)-4-fluoropyrrolidin-3-yl]-2-methoxypyridine-3-carboxamide

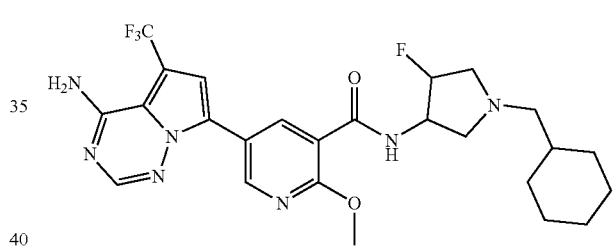

A mixture of (bromomethyl)cyclohexane (5.91 µL, 0.043 mmol), 5-(4-amino-5-(trifluoromethyl)pyrrolo[2,1-f][1,2,4]triazin-7-yl)-N-cis-(4-fluoropyrrolidin-3-yl)-2-methoxynicotinamide, TFA (15 mg, 0.034 mmol), and K₂CO₃ (28.3 mg, 0.205 mmol) in DMF (60 µL) was brought to 60° C. and stirred ON. The reaction mixture was diluted with 0.5 mL of DMF and filtered. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-90% B over 20 min, then a 4-minute hold at 100% B; Flow: 20 mL/min. Fractions containing the desired product were combined and dried via centrifugal evaporation to yield the final product (1.9 mg, 3.5 µmol, 10%).

MS ESI m/z 536.2 (M+H)

Example 41-1 and 41-2: 5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]-2-methylpyridine-3-carboxamide and 5-[4-amino-5-(trifluoromethyl)pyrrolo[2,1-f][1,2,4]triazin-7-yl]-N-[(3S,4R)-4-fluoro-1-(4-fluorobenzoyl)pyrrolidin-3-yl]-2-methylpyridine-3-carboxamide

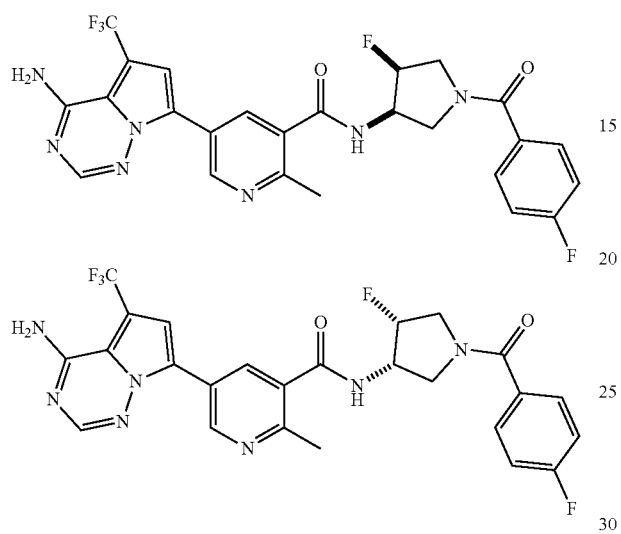

41-1: To a solution of 5-(4-amino-5-(trifluoromethyl)pyrrolo[2,1-f][1,2,4]triazin-7-yl)-N-(4-(3R,4S)-fluoropyrrolidin-3-yl)-2-methylnicotinamide (example 25) (17 mg, 0.040 mmol) and 4-fluorobenzoic acid (6.75 mg, 0.048 mmol) in 1,4-dioxane (2 mL) was added Hunig's base (0.021 mL, 0.120 mmol) and BOP (21.31 mg, 0.048 mmol). The resultant mixture was stirred at RT for 30 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-55% B over 20 min, then a 4-minute hold at 100% B; Flow: 20 mL/min. Fractions containing the desired product were combined and dried via centrifugal evaporation to yield the final product (6.3 mg, 11.5 μmol, 29%).

MS ESI m/z 546.2 (M+H)

1H NMR (500 MHz, DMSO-d6) δ 9.23-9.11 (m, 1H), 8.99-8.81 (m, 1H), 8.48-8.31 (m, 1H), 8.24-8.15 (m, 1H), 7.76-7.58 (m, 3H), 7.37-7.28 (m, 2H), 5.52-5.16 (m, 1H), 4.87-4.53 (m, 1H), 4.09-3.75 (m, 3H), 3.66-3.49 (m, 1H), 3.47-3.35 (m, 1H), 3.22-3.10 (m, 1H), 2.62-2.53 (m, 4H), 1.07-0.91 (m, 1H).

41-2: Utilizing the opposite enantiomer of 5-(4-amino-5-(trifluoromethyl)pyrrolo[2,1-f][1,2,4]triazin-7-yl)-N-((3R,4R)-4-fluoropyrrolidin-3-yl)-2-methylnicotinamide, a similar sequence could be carried out to yield 41-2: To a solution of 5-(4-amino-5-(trifluoromethyl)pyrrolo[2,1-f][1,2,4]triazin-7-yl)-N-(4-fluoropyrrolidin-3-yl)-2-methylnicotinamide (15 mg, 0.035 mmol) and 4-fluorobenzoic acid (5.96 mg, 0.043 mmol) in 1,4-dioxane (2 mL) was added Hunig's base (0.019 mL, 0.106 mmol) and BOP (18.80 mg, 0.043 mmol). The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 10-50% B over 19 min, then a 5-minute hold at 100% B; Flow: 20 mL/min. Fractions containing the desired product were combined and dried via centrifugal evaporation to yield the final product (7.5 mg, 9.7 μmol, 28%).

MS ESI m/z 546.1 (M+H)

1H NMR (500 MHz, DMSO-d6) δ 9.27-9.10 (m, 1H), 9.06-8.79 (m, 1H), 8.45-8.30 (m, 1H), 8.23-8.09 (m, 1H), 7.79-7.58 (m, 3H), 7.35-7.22 (m, 2H), 5.52-5.15 (m, 1H), 4.90-4.55 (m, 1H), 4.15-3.75 (m, 2H), 3.68-3.45 (m, 1H), 2.63-2.57 (m, 1H), 1.32-1.10 (m, 4H).

Example 42: 5-{4-amino-5-methylpyrrolo[2,1-f][1,2,4]triazin-7-yl}-N-(1-benzyl-1H-pyrazol-4-yl)-2-methoxypyridine-3-carboxamide

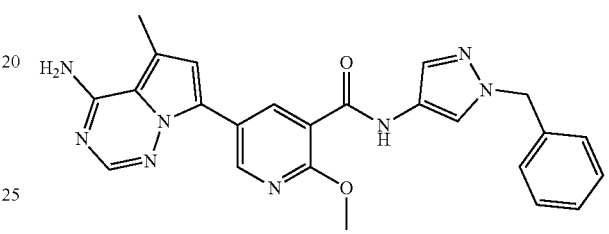

A mixture of 5-(4-amino-5-methylpyrrolo[2,1-f][1,2,4]triazin-7-yl)-2-methoxynicotinic acid (20 mg, 0.067 mmol), 1-benzyl-1H-pyrazol-4-amine (12.73 mg, 0.074 mmol), BOP (35.5 mg, 0.080 mmol), Hunig's base (0.035 mL, 0.200 mmol) in DMF (1 mL) was stirred at rt for 20 min. It was then concentrated and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 30-70% B over 20 min, then a 4-minute hold at 100% B; Flow: 20 mL/min. Fractions containing the desired product were combined and dried via centrifugal evaporation to yield 5-(4-amino-5-methylpyrrolo[2,1-f][1,2,4]triazin-7-yl)-N-(1-benzyl-1H-pyrazol-4-yl)-2-methoxynicotinamide (6.1 mg, 0.013 mmol, 20.08% yield) as a white solid.

MS ESI m/z 455.1 (M+H)

$^1$H NMR (500 MHz, DMSO-d$_6$) δ 10.27-10.00 (m, 1H), 8.98-8.84 (m, 1H), 8.84-8.60 (m, 1H), 8.33-8.07 (m, 1H), 7.92-7.75 (m, 1H), 7.75-7.55 (m, 1H), 7.47-7.24 (m, 5H), 7.17-7.00 (m, 2H), 6.97-6.73 (m, 1H), 5.41-5.23 (m, 2H), 4.09-3.98 (m, 3H), 2.56-2.52 (m, 3H).

Example 43: 5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]-2-methoxypyridine-3-carboxamide

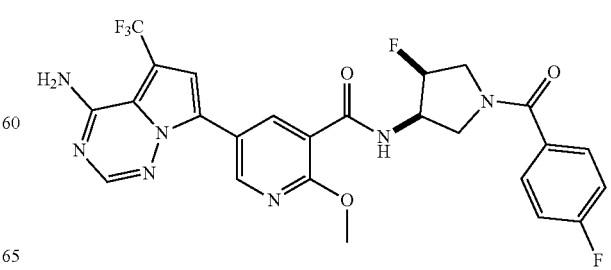

43A: tert-butyl (racemic)-3-(((benzyloxy)carbonyl)amino)-4-fluoropyrrolidine-1-carboxylate (mixture of cis isomers): To a solution of tert-butyl-3-amino-4-fluoropyrrolidine-1-carboxylate (100 mg, 0.490 mmol, mixture of cis isomers) and N-methylmorpholine (0.108 mL, 0.979 mmol) in THF (3 mL) at 0° C. was added Cbz-Cl (0.084 mL, 0.588 mmol) dropwise. The reaction mixture was warmed to 23° C. and stirred for 16 h. The reaction mixture was diluted with water (30 mL) which was extracted with $CH_2Cl_2$ (30 mL×2). The combined organic phases were washed with brine (30 mL) and dried over $Na_2SO_4$. Filtration and concentration yielded a crude product. The crude product was purified on silica gel column with Hexanes/EtOAc (100/0 to 60/40) to yield tert-butyl (racemic)-3-(((benzyloxy)carbonyl)amino)-4-fluoropyrrolidine-1-carboxylate (165.6 mg, 0.489 mmol, 100% yield).

MS ESI m/z 339.1 (M+H)

$^1$H NMR (400 MHz, $CD_3OD$) δ 7.42-7.29 (m, 5H), 5.19-5.08 (m, 3H), 5.08-4.95 (m, 1H), 4.41-4.24 (m, 1H), 3.82-3.71 (m, 1H), 3.71-3.49 (m, 2H), 3.17 (td, J=10.3, 2.8 Hz, 1H), 1.48 (s, 9H).

43B: tert-butyl (3R,4S)-3-(((benzyloxy)carbonyl)amino)-4-fluoropyrrolidine-1-carboxylate: tert-butyl (racemic)-3-(((benzyloxy)carbonyl)amino)-4-fluoropyrrolidine-1-carboxylate (165.6 mg, 0.489 mml) was separated via preparative SFC with the following conditions: Preparative Column: AD-H (3×25 cm, 5 µm, #repack); BPR pressure: 100 bars; Temperature: 35° C.; Flow rate: 180 mL/min; Mobile Phase: $CO_2$/MeOH (80/20); Detector Wavelength: 220 nm. Fractions from peak 1 were collected to yield tert-butyl (3R,4R)-3-(((benzyloxy)carbonyl)amino)-4-fluoropyrrolidine-1-carboxylate (61 mg, 0.180 mmol, 37% yield, chiral purity: >99.75%). Fractions from peak 2 were collected to yield tert-butyl (3R,4S)-3-(((benzyloxy)carbonyl)amino)-4-fluoropyrrolidine-1-carboxylate (61.5 mg, 0.182 mmol, 37.0% yield, chiral purity: >99.75%) as the desired product.

Chiral Analytical Conditions: Analytical Column: AD-H (0.46×25 cm, 5 µm); BPR pressure: 140 bars; Temperature: 35° C.; Flow rate: 3.0 mL/min; Mobile Phase: $CO_2$/MeOH (85/15); Detector Wavelength: UV 200-400 nm. Absolute stereochemistry was determined by taking both isomers forward and comparing with the final compounds generated from material for which crystallographic information was available.

MS ESI m/z 339.1 (M+H).

43C: tert-butyl (3R,4S)-3-amino-4-fluoropyrrolidine-1-carboxylate: A suspension solution of tert-butyl (3R,4S)-3-(((benzyloxy)carbonyl)amino)-4-fluoropyrrolidine-1-carboxylate (61 mg, 0.180 mmol) and $Pd(OH)_2$ (12.66 mg, 0.018 mmol) in MeOH (3 mL) was stirred at 23° C. under $H_2$ balloon (0.363 mg, 0.180 mmol) for 16 h. The reaction mixture was concentrated to give tert-butyl (3R,4S)-3-amino-4-fluoropyrrolidine-1-carboxylate (32 mg, 0.157 mmol, 87% yield).

$^1$H NMR (400 MHz, $CDCl_3$) δ 4.97 (t, J=3.4 Hz, 1H), 4.90-4.78 (m, 1H), 5.10-4.76 (m, 1H), 3.87-3.42 (m, 4H), 3.15-3.00 (m, 1H), 1.49 (s, 9H).

43D: tert-butyl (3R,4S)-3-(5-(4-amino-5-(trifluoromethyl)pyrrolo[2,1-f][1,2,4]triazin-7-yl)-2-methoxynicotinamido)-4-fluoropyrrolidine-1-carboxylate: To a solution of 5-(4-amino-5-(trifluoromethyl)pyrrolo[2,1-f][1,2,4]triazin-7-yl)-2-methoxynicotinic acid (50 mg, 0.142 mmol), tert-butyl (3R,4S)-3-amino-4-fluoropyrrolidine-1-carboxylate (28.9 mg, 0.142 mmol) and DIPEA (0.074 mL, 0.425 mmol) in DMF (2 mL) was added BOP (75 mg, 0.170 mmol). The reaction mixture was stirred for 1 h. The crude material was purified on silica gel column with Hexanes/EtOAc (100/0 to 0/100) to yield tert-butyl (3R,4S)-3-(5-(4-amino-5-(trifluoromethyl)pyrrolo[2,1-f][1,2,4]triazin-7-yl)-2-methoxynicotinamido)-4-fluoropyrrolidine-1-carboxylate (73 mg, 0.135 mmol, 96% yield).

MS ESI m/z 540.1 (M+H)

$^1$H NMR (400 MHz, $CD_3OD$) δ 8.99 (d, J=2.4 Hz, 1H), 8.96 (s, 1H), 8.09 (s, 1H), 7.43 (s, 1H), 5.38-5.17 (m, 1H), 4.83 (br s, 1H), 4.18 (s, 3H), 4.03-3.92 (m, 1H), 3.84-3.63 (m, 2H), 3.29-3.18 (m, 1H), 1.51 (s, 9H).

43E: 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide: To a solution of tert-butyl (3R,4S)-3-(5-(4-amino-5-(trifluoromethyl)pyrrolo[2,1-f][1,2,4]triazin-7-yl)-2-methoxynicotinamido)-4-fluoropyrrolidine-1-carboxylate (73 mg, 0.135 mmol) in $CH_2Cl_2$ (1 mL) was added TFA (0.261 mL, 3.38 mmol) and stirred at 23° C. for 1 h. The reaction mixture was concentrated and triturated with ether (3 mL). The solid was collected as 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide, TFA (74 mg, 0.133 mmol, 98% yield).

MS ESI m/z 440.1 (M+H)

$^1$H NMR (500 MHz, $CD_3OD$) δ 9.05-8.94 (m, 2H), 8.09 (s, 1H), 7.44 (s, 1H), 5.57-5.38 (m, 1H), 5.05-4.91 (m, 1H), 4.18 (s, 3H), 3.90-3.66 (m, 3H), 3.54-3.35 (m, 1H)

43: To a solution of 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide, 1.0 TFA (15 mg, 0.027 mmol), 4-fluorobenzoic acid (3.80 mg, 0.027 mmol) and Hunig's base (0.017 mL, 0.095 mmol) in DMF (1 mL) was added BOP (14.39 mg, 0.033 mmol) and the mixture was stirred at 23° C. for 16 h. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 24-64% B over 20 min, then a 4-minute hold at 100% B; Flow: 20 mL/min. Fractions containing the desired product were combined and dried via centrifugal evaporation to yield the final product (10.4 mg, 15.4 µmol, 57%).

MS ESI m/z 562.3 (M+H)

$^1$H NMR (500 MHz, DMSO-d6) δ 8.93 (br d, J=8.5 Hz, 1H), 8.78 (br s, 1H), 8.63-8.46 (m, 1H), 8.19 (br d, J=13.1 Hz, 1H), 7.72-7.56 (m, 3H), 7.36-7.26 (m, 2H), 5.49-5.16 (m, 1H), 4.90-4.62 (m, 1H), 4.05 (br d, J=4.9 Hz, 6H), 3.70-3.38 (m, 1H).

Example 44: 5-[4-amino-5-(trifluoromethyl)pyrrolo[2,1-f][1,2,4]triazin-7-yl]-N-[4-fluoro-1-(3,3,3-trifluoro-2-hydroxypropyl)pyrrolidin-3-yl]-2-methoxypyridine-3-carboxamide

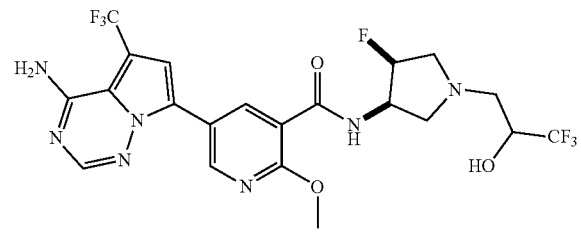

A mixture of 3-bromo-1,1,1-trifluoropropan-2-ol (14.46 mg, 0.075 mmol), 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide, TFA (15 mg, 0.027 mmol), and $K_2CO_3$ (22.48 mg, 0.163 mmol) in DMF (60 µL) was brought to 60° C. and stirred ON. The reaction mixture was diluted with EtOAc, washed with water, brine, dried over $MgSO_4$, filtered and concentrated in vacuo. Purification by prep HPLC (C18, Acetonitrile/Water/Ammonium acetate) gave 5-(4-amino-5-(trifluoromethyl)pyrrolo[2,1-f][1,2,4]triazin-7-yl)-N-(4-fluoro-1-(3,3,3-trifluoro-2-hydroxypropyl)pyrrolidin-3-yl)-2-methoxynicotinamide (isolate 01, first eluting peak, racemic).

MS ESI m/z 552.3 (M+H)

$^1$H NMR (500 MHz, $CD_3OD$) δ 8.97 (q, J=2.4 Hz, 2H), 8.08 (s, 1H), 7.41 (s, 1H), 5.40-5.12 (m, 1H), 4.77-4.64 (m, 1H), 4.19-4.17 (m, 3H), 4.17-4.10 (m, 1H), 3.29-2.98 (m, 3H), 2.94-2.86 (m, 1H), 2.85-2.74 (m, 2H).

Racemic material (at alcohol center) was separated by Chiral SFC (Chiralpak AS 5 µm, 30×250 mm, 10% MeOH (0.1% DEA) in $CO_2$, 150 bar, 35° C.) to give the homochiral title compound: 5-(4-amino-5-(trifluoromethyl)pyrrolo[2,1-f][1,2,4]triazin-7-yl)-N-((3R,4S)-4-fluoro-1-(3,3,3-trifluoro-2-hydroxypropyl)pyrrolidin-3-yl)-2-methoxynicotinamide (first eluting peak (24.10 min), absolute stereochemistry at alcohol center undefined).

44-1: MS ESI m/z 552.2 (M+H)

$^1$H NMR (500 MHz, $CDCl_3$) δ 9.02 (d, J=2.4 Hz, 1H), 8.99 (d, J=2.6 Hz, 1H), 8.55-8.44 (m, 1H), 8.13 (s, 1H), 7.28 (s, 2H), 5.87 (br s, 2H), 5.35-5.08 (m, 1H), 4.88-4.74 (m, 1H), 4.20 (s, 3H), 4.04 (ddd, J=9.8, 6.5, 3.6 Hz, 1H), 3.41-3.21 (m, 2H), 3.10-2.72 (m, 4H).

44-2: And its enantiomer (second eluting peak (25.51 min), absolute stereochemistry at alcohol center undefined):

MS ESI m/z 552.3 (M+H)

$^1$H NMR (500 MHz, $CDCl_3$) δ 9.02 (d, J=2.4 Hz, 1H), 9.00-8.97 (m, 1H), 8.55-8.44 (m, 1H), 8.12 (s, 1H), 7.28 (s, 1H), 5.97 (br s, 2H), 5.33-5.07 (m, 1H), 4.91-4.67 (m, 1H), 4.25-4.16 (m, 3H), 4.12-4.00 (m, 1H), 3.45-3.28 (m, 2H), 3.19-3.06 (m, 1H), 3.01-2.86 (m, 2H), 2.82-2.73 (m, 1H).

The other two enantiomers derived from the opposite enantiomer of the pyrrolidine could be obtained from similar chemistry to produce two additional enantiomers:

44-3: 5-(4-amino-5-(trifluoromethyl)pyrrolo[2,1-f][1,2,4]triazin-7-yl)-N-((3S,4S)-4-fluoro-1-(3,3,3-trifluoro-2-hydroxypropyl)pyrrolidin-3-yl)-2-methoxynicotinamide (first eluting peak, absolute stereochemistry at alcohol center undefined).

MS ESI m/z 552.2 (M+H)

1H NMR (500 MHz, $CD_3OD$) δ 8.94 (q, J=2.5 Hz, 2H), 8.06 (s, 1H), 7.38 (s, 1H), 5.31-5.12 (m, 1H), 4.74-4.61 (m, 1H), 4.18-4.08 (m, 4H), 3.27-3.14 (m, 2H), 3.13-2.99 (m, 1H), 2.89 (dd, J=13.0, 2.7 Hz, 1H), 2.84-2.71 (m, 2H).

44-4: 5-(4-amino-5-(trifluoromethyl)pyrrolo[2,1-f][1,2,4]triazin-7-yl)-N-((3S,4S)-4-fluoro-1-(3,3,3-trifluoro-2-hydroxypropyl)pyrrolidin-3-yl)-2-methoxynicotinamide (second eluting peak, absolute stereochemistry at alcohol center undefined).

MS ESI m/z 552.2 (M+H)

$^1$H NMR (500 MHz, $CD_3OD$) δ 8.96 (q, J=2.4 Hz, 2H), 8.06 (s, 1H), 7.39 (s, 1H), 5.31-5.12 (m, 1H), 4.75-4.63 (m, 1H), 4.19-4.07 (m, 4H), 3.27-3.13 (m, 2H), 3.12-3.00 (m, 1H), 2.90-2.73 (m, 3H).

Example 45: 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(deutero)methoxypyridine-3-carboxamide

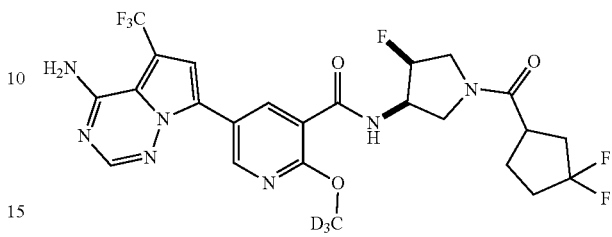

45A: Methyl d3 5-bromo-2-methoxy d3-nicotinate: Sodium (0.514 g, 22.36 mmol) was added to $CD_3OD$ (10 mL) and stirred until the reaction was complete. Methyl 5-bromo-2-chloronicotinate (2.0 g, 7.98 mmol) was added and the reaction mixture stirred for 16 h. The reaction mixture was acidified with concentrated HCl solution to pH 7, diluted with $CH_2Cl_2$ (100 mL) and washed with water (20 mL) and brine (20 mL). The combined organics were dried over $Na_2SO_4$, filtered and concentrated in vacuo to yield methyl d3 5-bromo-2-methoxy d3-nicotinate (1.67 g, 6.62 mmol, 83% yield).

MS ESI m/z 251.1 (M+H)

$^1$H NMR (400 MHz, $CD_3OD$) δ 8.42 (d, J=2.6 Hz, 1H), 8.30 (d, J=2.6 Hz, 1H).

45B: 5-Bromo-2-methoxy d3-nicotinic acid: A solution of methyl d3 5-bromo-2-methoxy d3-nicotinate (800 mg, 3.17 mmol) and NaOH (4.76 mL, 4.76 mmol) in MeOH (15 mL) was heated to 100° C. for 30 min under microwave. The reaction mixture was concentrated to yield 5-bromo-2-methoxy d3-nicotinic acid for the next reaction.

MS ESI m/z 235.1 (M+H)

45C: (Racemic)-tert-butyl 3-(5-bromo-2-methox d3-ynicotinamido)-4-fluoropyrrolidine-1-carboxylate (mixture of cis-isomers): To a solution of 5-bromo-2-methoxy d3-nicotinic acid (750 mg, 3.19 mmol), (racemic)-cis-1-boc-3-amino-4-fluoropyrrolidine (652 mg, 3.19 mmol) and DIPEA (0.669 mL, 3.83 mmol) in DMF (15 mL) was added BOP (1693 mg, 3.83 mmol). The reaction mixture was stirred at 23° C. for 1 h. The reaction mixture was concentrated. EtOAc (150 mL) was added and it was washed with water (50 mL), brine (50 mL) and dried over $Na_2SO_4$. Filtration and concentration yielded a crude product which was triturated with water (50 mL). The solid was collected as (racemic)-tert-butyl 3-(5-bromo-2-methox d3-ynicotinamido)-4-fluoropyrrolidine-1-carboxylate (1.23 g, 2.92 mmol, 92% yield) as a mixture of cis isomers.

MS ESI m/z 421.1 (M+H)

$^1$H NMR (400 MHz, $CD_3OD$) δ 8.44-8.36 (m, 2H), 5.35-5.12 (m, 1H), 4.82-4.66 (m, 1H), 4.01-3.89 (m, 1H), 3.81-3.57 (m, 2H), 3.24 (td, J=10.3, 4.8 Hz, 1H), 1.50 (s, 9H)

45D (3R,4S)-tert-butyl 3-(5-bromo-2-methoxy d3-nicotinamido)-4-fluoropyrrolidine-1-carboxylate (Peak2 from chiral separation): (racemic)-tert-butyl 3-(5-bromo-2-methox d3-ynicotinamido)-4-fluoropyrrolidine-1-carboxylate (1.23 g, 2.92 mml) was separated via preparative SFC with the following conditions: Preparative Column: OJH (5×25 cm, 805211), BPR pressure: 100 bars; Temperature: 35° C.; Flow rate: 280 mL/min; Mobile Phase: $CO_2$/MeOH (90/10); Detector Wavelength: 220 nm. Fractions from peak 1 were collected to yield tert-butyl (3R,4R)-3-(((benzyloxy)carbonyl)amino)-4-fluoropyrrolidine-1-carboxylate (414.6 mg, 0.984 mmol, 34% yield, chiral purity: >99%). Fractions from peak 2 were collected to yield tert-butyl (3R,4S)-3-(((benzyloxy)carbonyl)amino)-4-fluoropyrrolidine-1-carboxylate (426 mg, 1.0117 mmol, 34.6% yield, chiral purity: >99%) as the desired product. Chiral Analytical Conditions: Analytical Column: OJH (0.46×25 cm, 5 μm); BPR pressure: 140 bars; Temperature: 35° C.; Flow rate: 3.0 mL/min; Mobile Phase: $CO_2$/MeOH (90/10); Detector Wavelength: UV 220 nm. Absolute stereochemistry was determined based on crystallographic information from a closely related substrate.

MS ESI m/z 421.1 (M+H).

$^1$H NMR (400 MHz, $CD_3OD$) δ 8.44-8.37 (m, 2H), 5.33-5.13 (m, 1H), 4.82-4.66 (m, 1H), 4.00-3.89 (m, 1H), 3.79-3.57 (m, 2H), 3.24 (td, J=10.4, 5.0 Hz, 1H), 1.50 (s, 9H).

45E: (5-(((3R,4S)-1-(tert-Butoxycarbonyl)-4-fluoropyrrolidin-3-yl)carbamoyl)-6-(methoxy-d3)pyridin-3-yl)boronic acid: A degassed solution of tert-butyl (3R,4S)-3-(5-bromo-2-(methoxy-d3)nicotinamido)-4-fluoropyrrolidine-1-carboxylate (200 mg, 0.475 mmol), 4,4,4',4',5,5,5',5'-octamethyl-2,2'-bi(1,3,2-dioxaborolane) (157 mg, 0.617 mmol), potassium acetate (74.5 mg, 0.760 mmol) and $PdCl_2$(dppf)-$CH_2Cl_2$ adduct (31.0 mg, 0.038 mmol) in dioxane (4 mL) was heated to 65° C. for 16 h. The reaction mixture was filtered through Celite. The solution was concentrated to afford the product which was used as-is.

MS ESI m/z 387.1 (M+H).

45F: tert-Butyl (3R,4S)-3-(5-(4-amino-5-(trifluoromethyl)pyrrolo[2,1-f][1,2,4]triazin-7-yl)-2-(methoxy-d3)nicotinamido)-4-fluoropyrrolidine-1-carboxylate: A degassed solution of 7-bromo-5-(trifluoromethyl)pyrrolo[2,1-f][1,2,4]triazin-4-amine (130 mg, 0.463 mmol), (5-(((3R,4S)-1-(tert-butoxycarbonyl)-4-fluoropyrrolidin-3-yl)carbamoyl)-6-(methoxy-d3)pyridin-3-yl)boronic acid (184 mg, 0.476 mmol), tripotassium phosphate (2 M in water) (0.694 mL, 1.388 mmol) and 1,1'-Bis(diphenyllphosphino)ferrocene palladium dichloride —$CH_2Cl_2$ adduct (37.8 mg, 0.046 mmol) was stirred at 70° C. for 5 h. The reaction mixture was diluted with EtOAc (80 mL) and washed with 10% LiCl solution (20×2 mL) and brine (20 mL). The organics were dried over anhydrous sodium sulfate, filtered and concentrated to yield a crude product which was triturated in MeOH (2 mL). The solid was collected as the desired product. The filtrate was concentrated and purified on silica gel column with Hexanes/EtOAc (100/0 to 0/100) to yield the second batch product which was combined with above product to yield tert-butyl (3R,4S)-3-(5-(4-amino-5-(trifluoromethyl)pyrrolo[2,1-f][1,2,4]triazin-7-yl)-2-(methoxy-d3)nicotinamido)-4-fluoropyrrolidine-1-carboxylate (208 mg, 0.382 mmol, 83% yield).

MS ESI m/z 543.1 (M+H).

45G: 5-(4-Amino-5-(trifluoromethyl)pyrrolo[2,1-f][1,2,4]triazin-7-yl)-N-((3R,4S)-4-fluoropyrrolidin-3-yl)-2-(methoxy-d3)nicotinamide: To a solution of tert-butyl (3R,4S)-3-(5-(4-amino-5-(trifluoromethyl)pyrrolo[2,1-f][1,2,4]triazin-7-yl)-2-(methoxy-d3)nicotinamido)-4-fluoropyrrolidine-1-carboxylate (208 mg, 0.383 mmol) in $CH_2Cl_2$ (2 mL) was added TFA (0.886 mL, 11.50 mmol) and the reaction mixture was stirred 1 h. The reaction mixture was concentrated and triturated ether (3 mL). The solid was collected as 5-(4-amino-5-(trifluoromethyl)pyrrolo[2,1-f][1,2,4]triazin-7-yl)-N-((3R,4S)-4-fluoropyrrolidin-3-yl)-2-(methoxy-d3)nicotinamide, TFA (203 mg, 0.365 mmol, 95% yield).

MS ESI m/z 443.1 (M+H).

$^1$H NMR (400 MHz, $CD_3OD$) δ 8.99 (q, J=2.4 Hz, 2H), 8.09 (s, 1H), 7.44 (s, 1H), 5.58-5.38 (m, 1H), 5.07-4.92 (m, 1H), 3.93-3.74 (m, 3H), 3.55-3.47 (m, 1H).

45: To a solution of 5-(4-amino-5-(trifluoromethyl)pyrrolo[2,1-f][1,2,4]triazin-7-yl)-N-((3R,4S)-4-fluoropyrrolidin-3-yl)-2-(methoxy-d3)nicotinamide, TFA (120 mg, 0.216 mmol), 3,3-difluorocyclopentanecarboxylic acid (32.4 mg, 0.216 mmol) and Hunig's base (0.132 mL, 0.755 mmol) in DMF (1 mL) was added BOP (114 mg, 0.259 mmol). The reaction mixture was stirred at 23° C. for 2 h. The crude material was purified via preparative SFC with the following conditions: Preparative Column: Chiralpak AD (30×250 mm, 5 micron); BPR pressure: 120 bars; Column Oven Temp: 40° C.; Flow rate: 100 mL/min; Mobile Phase: $CO_2$/IPA (0.1% DEA) (65/35); Detector Wavelength: 220 nm. Fractions were collected to yield 45-1: Peak 1, first eluting isomer 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(deutero)methoxypyridine-3-carboxamide (9.3 mg, 0.016 mmol, 13.9%). The absolute stereochemistry at the cyclopentane is unknown.

MS ESI m/z 575.4 (M+H)

$^1$H NMR (500 MHz, DMSO-d6) δ 8.90 (s, 1H), 8.76 (dd, J=18.3, 2.1 Hz, 1H), 8.55 (br dd, J=10.7, 7.6 Hz, 1H), 8.16 (s, 1H), 7.58 (s, 1H), 5.43-5.19 (m, 1H), 4.85-4.57 (m, 1H), 4.14-3.42 (m, 3H), 3.30-3.13 (m, 2H), 2.42-2.24 (m, 2H), 2.22-1.99 (m, 3H), 1.87-1.68 (m, 1H).

45-2: Peak 2, second eluting isomer, 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(deutero)methoxypyridine-3-carboxamide (9.7 mg, 0.016 mmol, 14.5% yield, chiral purity: >99%). The absolute stereochemistry at the cyclopentane is unknown.

MS ESI m/z 575.2 (M+H) $^1$H NMR (500 MHz, DMSO-d6) δ 8.92 (s, 1H), 8.79 (dd, J=19.5, 2.1 Hz, 1H), 8.54 (br dd, J=11.4, 7.8 Hz, 1H), 8.17 (s, 1H), 7.61 (s, 1H), 5.44-5.18 (m, 1H), 4.86-4.58 (m, 1H), 4.10-3.45 (m, 3H), 3.36-3.05 (m, 2H), 2.40-2.25 (m, 2H), 2.23-1.99 (m, 3H), 1.88-1.72 (m, 1H).

Example 46: 5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]-2-(deutero)methoxy-6-methylpyridine-3-carboxamide 46A: Methyl-d3 5-bromo-2-(methoxy-d3)-6-methylnicotinate: To a rapidly stirring mixture of 5-bromo-2-hydroxy-6-methylnicotinic acid (1.20 g, 5.17 mmol) and iodomethane-d3 (1.931 mL, 31.0 mmol) in chloroform (100 mL) was added silver carbonate (7.13 g, 25.9 mmol). The reaction mixture was stirred in the dark [aluminum foil wrap] for 4 d. The reaction mixture was filtered through Celite, then concentrated to an oil. This material was loaded onto a 40 g ISCO column and purified by flash 10 chromatography, eluting with 0-75% EtOAc in hexanes. Afforded methyl-d3 5-bromo-2-(methoxy-d3)-6-methylnicotinate (732 mg, 2.64 mmol, 51.1% yield) as a white solid.

MS (ESI) m/z 268.0 (M+H)

46B: (6-(methoxy-d3)-5-((methoxy-d3)carbonyl)-2-methylpyridin-3-yl)boronic acid: A degassed solution of methyl-d3 5-bromo-2-(methoxy-d3)-6-methylnicotinate (100 mg, 0.376 mmol), 4,4,4',4',5,5,5',5'-octamethyl-2,2'-bi (1,3,2-dioxaborolane) (124 mg, 0.488 mmol), potassium acetate (59.0 mg, 0.601 mmol) and $PdCl_2(dppf)$-$CH_2Cl_2$ adduct (24.55 mg, 0.030 mmol) in dioxane (2 mL) was heated to 65° C. for 16 h. The reaction mixture was filtered through Celite. The solution was concentrated to afford the product which was used as-is.

MS ESI m/z 232.1 (M+H).

46C: methyl-d3 5-(4-amino-5-(trifluoromethyl)pyrrolo[2,1-f][1,2,4]triazin-7-yl)-2-(methoxy-d3)-6-methylnicotinate: A degassed solution of 7-bromo-5-(trifluoromethyl)pyrrolo[2,1-f][1,2,4]triazin-4-amine (100 mg, 0.356 mmol), (6-(methoxy-d3)-5-((methoxy-d3)carbonyl)-2-methylpyridin-3-yl)boronic acid (86 mg, 0.374 mmol), tripotassium phosphate (2 M in water) (0.534 mL, 1.067 mmol) and 1,1'-bis(diphenylphosphino)ferrocene palladium dichloride —$CH_2Cl_2$ adduct (29.1 mg, 0.036 mmol) was stirred at 70° C. for 1 h. The reaction mixture was purified by flash column chromatography, eluting with Hexanes/EtOAc (100/0 to 0/100) to yield methyl-d3 5-(4-amino-5-(trifluoromethyl)pyrrolo[2,1-f][1,2,4]triazin-7-yl)-2-(methoxy-d3)-6-methylnicotinate (38.4 mg, 0.099 mmol, 27.9% yield)

MS ESI m/z 388.1 (M+H).

$^1$H NMR (400 MHz, DMSO-d6) δ 8.15 (s, 1H), 8.07 (s, 1H), 7.32 (s, 1H), 2.34 (s, 3H).

46D: 5-(4-amino-5-(trifluoromethyl)pyrrolo[2,1-f][1,2,4]triazin-7-yl)-2-(methoxy-d3)-6-methylnicotinic acid, sodium salt: A solution of methyl-d3 5-(4-amino-5-(trifluoromethyl)pyrrolo[2,1-f][1,2,4]triazin-7-yl)-2-(methoxy-d3)-6-methylnicotinate (38 mg, 0.098 mmol) and NaOH 1 N solution (0.123 mL, 0.123 mmol) in MeOH (1 mL) was heated to 100° C. for 10 min under microwave. The reaction mixture was concentrated to yield 5-(4-amino-5-(trifluoromethyl)pyrrolo[2,1-f][1,2,4]triazin-7-yl)-2-(methoxy-d3)-6-methylnicotinic acid, sodium salt (40 mg, 0.108 mmol, 110% yield).

MS ESI m/z 371.1 (M+H).

46E: 5-(4-amino-5-(trifluoromethyl)pyrrolo[2,1-f][1,2,4]triazin-7-yl)-N-((3R,4S)-4-fluoropyrrolidin-3-yl)-2-(methoxy-d3)-6-methylnicotinamide: A solution of 5-(4-amino-5-(trifluoromethyl)pyrrolo[2,1-f][1,2,4]triazin-7-yl)-2-(methoxy-d3)-6-methylnicotinic acid, sodium salt (40 mg, 0.108 mmol), tert-butyl (3R,4S)-3-amino-4-fluoropyrrolidine-1-carboxylate (22.06 mg, 0.108 mmol) and DIPEA (0.057 mL, 0.324 mmol) in DMF (1 mL) was added BOP (57.3 mg, 0.130 mmol). The reaction mixture was stirred at rt for 2 h. The reaction mixture was diluted with EtOAc (80 mL) and washed with 10% LiCl solution (2×20 mL) and brine (20 mL). The organics were dried over sodium sulfate, filtered and concentrated in vacuo. The crude product was purified by flash column chromatography, eluting with Hexanes/EtOAc (100/0 to 0/100) to yield 5-(4-amino-5-(trifluoromethyl)pyrrolo[2,1-f][1,2,4]triazin-7-yl)-N-((3R,4S)-4-fluoropyrrolidin-3-yl)-2-(methoxy-d3)-6-methylnicotinamide (58.8 mg, 0.106 mmol, 98%).

MS ESI m/z 557.1 (M+H).

$^1$H NMR (400 MHz, CD$_3$OD) δ 8.32 (s, 1H), 7.99 (s, 1H), 7.16 (s, 1H), 5.37-5.15 (m, 1H), 4.84-4.66 (m, 1H), 4.02-3.90 (m, 1H), 3.84-3.57 (m, 2H), 3.28-3.20 (m, 1H), 2.39 (s, 3H), 1.51 (s, 9H).

46F: 5-(4-amino-5-(trifluoromethyl)pyrrolo[2,1-f][1,2,4]triazin-7-yl)-N-((3R,4S)-4-fluoropyrrolidin-3-yl)-2-(methoxy-d3)-6-methylnicotinamide, TFA: A solution of tert-butyl (3R,4S)-3-(5-(4-amino-5-(trifluoromethyl)pyrrolo[2,1-f][1,2,4]triazin-7-yl)-2-(methoxy-d3)-6-methylnicotinamido)-4-fluoropyrrolidine-1-carboxylate (58 mg, 0.104 mmol) in $CH_2Cl_2$ (1 mL) was added TFA (0.201 mL, 2.61 mmol) and stirred at 23° C. for 1 h. The reaction mixture was concentrated and triturated in ether (2 mL). The solid was collected as 5-(4-amino-5-(trifluoromethyl)pyrrolo[2,1-f][1,2,4]triazin-7-yl)-N-((3R,4S)-4-fluoropyrrolidin-3-yl)-2-(methoxy-d3)-6-methylnicotinamide, TFA (65.5 mg, 0.115 mmol, 110% yield)

MS ESI m/z 457.1 (M+H).

46: A solution of 5-(4-amino-5-(trifluoromethyl)pyrrolo[2,1-f][1,2,4]triazin-7-yl)-N-((3R,4S)-4-fluoropyrrolidin-3-yl)-2-(methoxy-d3)-6-methylnicotinamide, 1.0 TFA (15 mg, 0.026 mmol), 4-fluorobenzoic acid (3.68 mg, 0.026 mmol) and Hunig's base (0.016 mL, 0.092 mmol) in DMF (1 mL) was added BOP (13.96 mg, 0.032 mmol) and stirred at 23° C. for 5 h. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 28-68% B over 20 min, then a 4-minute hold at 100% B; Flow: 20 mL/min. Fractions containing the desired product were combined and dried via centrifugal evaporation to yield the final product (6.2 mg 9.0 μmol, 34%).

MS ESI m/z 579.2 (M+H)

$^1$H NMR (500 MHz, DMSO-d6) δ 8.51-8.36 (m, 1H), 8.15 (br d, J=8.5 Hz, 1H), 8.10-8.03 (m, 1H), 7.70-7.59 (m, 2H), 7.34-7.26 (m, 3H), 5.45-5.15 (m, 1H), 4.87-4.60 (m, 1H), 4.07-3.74 (m, 3H), 3.69-3.50 (m, 1H), 2.34 (br d, J=5.2 Hz, 3H)

Example 47: 5-(4-amino-5-chloropyrrolo[2,1-f][1,2,4]triazin-7-yl)-2-methoxy-N-(1-neopentyl-1H-pyrazol-4-yl)nicotinamide

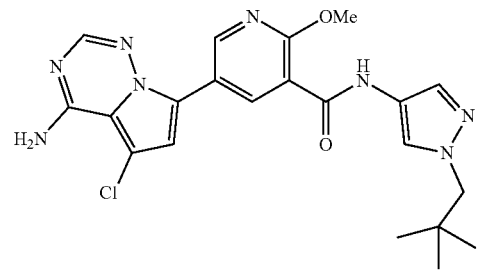 [SMILES: COc1ncc(-c2cc(Cl)c3c(N)ncnn23)cc1C(=O)Nc1cnn(CC(C)(C)C)c1]

47A: 1-neopentyl-4-nitro-1H-pyrazole: A mixture of 1-iodo-2,2-dimethylpropane (0.705 mL, 5.31 mmol), 4-nitro-1H-pyrazole (500 mg, 4.42 mmol) and K$_2$CO$_3$ (1222 mg, 8.84 mmol) in DMF (10 mL) was heated at 70° C. for 48 h. It was then diluted with EtOAc. The organic layer was washed with 1 N NaOH, water and dried over MgSO4, filtered and concentrated to obtain 1-neopentyl-4-nitro-1H-pyrazole (800 mg, 4.37 mmol, 99% yield) as an oil.

¹H NMR (400 MHz, CDCl₃) δ 8.16-8.07 (m, 2H), 3.95 (s, 2H), 1.02 (s, 9H).

47B: 1-neopentyl-1H-pyrazol-4-amine: A mixture of 1-neopentyl-4-nitro-1H-pyrazole (500 mg, 2.73 mmol) and Pd/C (100 mg, 0.094 mmol) in MeOH (5 mL) was stirred under a hydrogen balloon for 5 h. It was then filtered over celite and the filtrate concentrated to obtain 1-neopentyl-1H-pyrazol-4-amine (400 mg, 2.61 mmol, 96% yield) as an oil.

¹H NMR (400 MHz, CDCl₃) δ 7.21-7.16 (m, 1H), 7.04-6.99 (m, 1H), 3.81-3.68 (m, 2H), 0.96 (s, 9H).

47: A mixture of 5-(4-amino-5-chloropyrrolo[2,1-f][1,2,4]triazin-7-yl)-2-methoxynicotinic acid (20 mg, 0.063 mmol), 1-neopentyl-1H-pyrazol-4-amine (11.50 mg, 0.075 mmol), BOP (33.2 mg, 0.075 mmol) and Hunig's base (0.033 mL, 0.188 mmol) in DMF (1 mL) was stirred at rt for 20 min. It was then concentrated and submitted to preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 22-62% B over 22 min, then a 4-minute hold at 100% B; Flow: 20 mL/min. Fractions containing the desired product were combined and dried via centrifugal evaporation to obtain 5-(4-amino-5-chloropyrrolo[2,1-f][1,2,4]triazin-7-yl)-2-methoxy-N-(1-neopentyl-1H-pyrazol-4-yl)nicotinamide (5.9 mg, 0.013 mmol, 20.73% yield) as a white solid.

MS ESI m/z 455.1 (M+H)

¹H NMR (500 MHz, DMSO-d6) δ 10.19-10.12 (m, 1H), 8.91-8.83 (m, 1H), 8.79-8.66 (m, 1H), 8.04-7.96 (m, 1H), 7.96-7.91 (m, 1H), 7.66-7.57 (m, 1H), 7.26-7.16 (m, 1H), 4.06 (s, 3H), 3.89 (s, 2H), 0.92 (s, 9H).

Example 48: 5-(4-amino-5-(trifluoromethyl)pyrrolo[2,1-f][1,2,4]triazin-7-yl)-2-methoxy-N-(1-neopentyl-1H-pyrazol-4-yl)nicotinamide

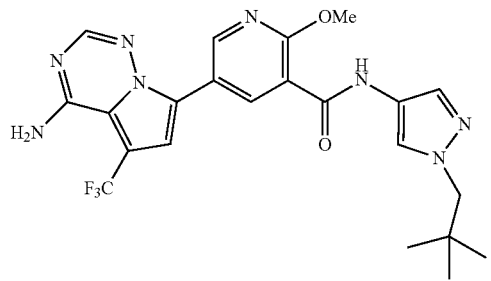 [SMILES: COc1ncc(-c2cc(C(F)(F)F)c3c(N)ncnn23)cc1C(=O)Nc1cnn(CC(C)(C)C)c1]

48A: 1-neopentyl-4-nitro-1H-pyrazole: A mixture of 1-iodo-2,2-dimethylpropane (0.705 mL, 5.31 mmol), 4-nitro-1H-pyrazole (500 mg, 4.42 mmol) and K.CO₃ (1222 mg, 8.84 mmol) in DMF (10 mL) was heated at 70° C. for 48 h. It was then diluted with EtOAc. The organic layer was washed with 1 N NaOH, water and dried over MgSO4, filtered and concentrated to obtain 1-neopentyl-4-nitro-1H-pyrazole (800 mg, 4.37 mmol, 99% yield) as an oil.

¹H NMR (400 MHz, CDCl₃) δ 8.16-8.07 (m, 2H), 3.95 (s, 2H), 1.02 (s, 9H).

48B: 1-neopentyl-1H-pyrazol-4-amine: A mixture of 1-neopentyl-4-nitro-1H-pyrazole (500 mg, 2.73 mmol) and Pd/C (100 mg, 0.094 mmol) in MeOH (5 mL) was stirred under a hydrogen balloon for 5 h. It was then filtered and concentrated to obtain 1-neopentyl-1H-pyrazol-4-amine (400 mg, 2.61 mmol, 96% yield) as an oil.

¹H NMR (400 MHz, CDCl₃) δ 7.21-7.16 (m, 1H), 7.04-6.99 (m, 1H), 3.81-3.68 (m, 2H), 0.96 (s, 9H). 48: 5-(4-amino-5-(trifluoromethyl)pyrrolo[2,1-f][1,2,4]triazin-7-yl)-2-methoxy-N-(1-neopentyl-1H-pyrazol-4-yl)nicotinamide: A mixture of 5-(4-amino-5-(trifluoromethyl)pyrrolo[2,1-f][1,2,4]triazin-7-yl)-2-methoxynicotinic acid (20 mg, 0.057 mmol), 1-neopentyl-1H-pyrazol-4-amine (10.41 mg, 0.068 mmol), BOP (30.0 mg, 0.068 mmol) and Hunig's base (0.030 mL, 0.170 mmol) in DMF (1 mL) was stirred at rt for 20 min. It was then concentrated and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 32-72% B over 25 min, then a 5-minute hold at 100% B; Flow: 20 mL/min. Fractions containing the desired product were combined and dried via centrifugal evaporation to obtain 5-(4-amino-5-(trifluoromethyl)pyrrolo[2,1-f][1,2,4]triazin-7-yl)-2-methoxy-N-(1-neopentyl-1H-pyrazol-4-yl)nicotinamide (12.6 mg, 0.026 mmol, 45.6% yield) as a white solid.

MS ESI m/z 489.2 (M+H)

¹H NMR (500 MHz, DMSO-d₆) δ 10.21-10.06 (m, 1H), 9.01-8.85 (m, 1H), 8.84-8.58 (m, 1H), 8.22-8.05 (m, 1H), 8.09-7.97 (m, 1H), 7.73-7.53 (m, 2H), 4.07 (s, 3H), 3.85 (s, 2H), 0.93 (s, 9H).

Example 49: 5-(4-amino-5-(methoxymethyl)pyrrolo[2,1-f][1,2,4]triazin-7-yl)-N-(1-benzyl-1H-pyrazol-4-yl)-2-methoxynicotinamide

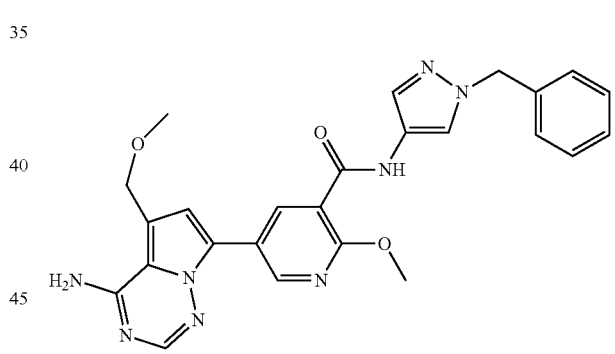

49A: N-((4-amino-7-bromopyrrolo[2,1-f][1,2,4]triazin-5-yl)methyl)-N,N-diethylethanaminium, bromide salt: A mixture of N-((7-bromo-4-chloropyrrolo[2,1-f][1,2,4]triazin-5-yl)methyl)-N,N-diethylethanaminium, bromide salt (3.5 g, 8.20 mmol) (see WO 2015054358) and concentrated ammonium hydroxide (11.41 mL, 82 mmol) in dioxane (10 mL) was stirred at rt for 4 h. It was then concentrated to obtain N-((4-amino-7-bromopyrrolo[2,1-f][1,2,4]triazin-5-yl)methyl)-N,N-diethylethanaminium, bromide salt (3.3 g, 7.74 mmol, 94% yield) as an off-white solid.

MS ESI m/z 326.1 (M+H).

1H NMR (400 MHz, DMSO-d₆) δ 8.21-8.00 (m, 1H), 7.13-7.03 (m, 1H), 4.95-4.75 (m, 2H), 3.29-3.12 (m, 6H), 1.35-1.18 (m, 9H).

49B: 7-Bromo-5-(methoxymethyl)pyrrolo[2,1-f][1,2,4]triazin-4-amine: A mixture of N-((4-amino-7-bromopyrrolo[2,1-f][1,2,4]triazin-5-yl)methyl)-N,N-diethylethanaminium bromide salt (40 mg, 0.122 mmol) and sodium bicarbonate (51.3 mg, 0.611 mmol) in MeOH (3 mL) was heated at 75° C. for 3 h. The reaction mixture was diluted with water and extracted with EtOAc. The organic layer was washed with water, dried over MgSO$_4$, filtered and concentrated to obtain 7-bromo-5-(methoxymethyl)pyrrolo[2,1-f][1,2,4]triazin-4-amine (30 mg, 0.117 mmol, 95% yield) as a white solid.

MS ESI m/z 258.9. (M+H).

$^1$H NMR (400 MHz, DMSO-d6) δ 7.96-7.90 (m, 1H), 6.86-6.76 (m, 1H), 4.76-4.60 (m, 2H), 3.32 (s, 3H).

49C: N-(1-benzyl-1H-pyrazol-4-yl)-5-bromo-2-methoxynicotinamide: A mixture of 5-bromo-2-methoxynicotinic acid (500 mg, 2.155 mmol), 1-benzyl-1H-pyrazol-4-amine, HCl (452 mg, 2.155 mmol), Hunig's base (1.129 mL, 6.46 mmol) and BOP (1144 mg, 2.59 mmol) in DMF (5 mL) was stirred at rt for 2 h. The reaction mixture was diluted with water, extracted with EtOAc, dried over MgSO4, filtered and concentrated to obtain N-(1-benzyl-1H-pyrazol-4-yl)-5-bromo-2-methoxynicotinamide (750 mg, 1.937 mmol, 90% yield) as an oil.

MS ESI m/z 388.76 (M+H).

$^1$H NMR (400 MHz, CDCl$_3$) δ 9.76-9.34 (m, 1H), 8.70-8.57 (m, 1H), 8.44-8.31 (m, 1H), 7.65-7.60 (m, 1H), 7.42-7.29 (m, 5H), 5.36-5.31 (m, 2H), 4.21-4.17 (m, 3H).

49: 5-(4-amino-5-(methoxymethyl)pyrrolo[2,1-f][1,2,4]triazin-7-yl)-N-(1-benzyl-1H-pyrazol-4-yl)-2-methoxynicotinamide: A mixture of N-(1-benzyl-1H-pyrazol-4-yl)-5-bromo-2-methoxynicotinamide (25 mg, 0.065 mmol), 4,4,4',4',5,5,5',5'-octamethyl-2,2'-bi(1,3,2-dioxaborolane) (19.67 mg, 0.077 mmol) and potassium acetate (19.01 mg, 0.194 mmol) in dioxane (2 mL) was degassed and back-filled with N$_2$. 1,1'-bis(diphenylphosphino)ferrocene-palladium(II)dichloride dichloromethane complex (5.27 mg, 6.46 µmol) was added and the mixture degassed and back-filled with N$_2$ three times, then heated at 100° C. for 3 h. After cooling to rt, 7-bromo-5-(methoxymethyl)pyrrolo[2,1-f][1,2,4]triazin-4-amine (16.60 mg, 0.065 mmol), 2 M potassium phosphate tribasic (0.097 mL, 0.194 mmol) and 1,1'-bis(diphenylphosphino)ferrocene-palladium(II)dichloride dichloromethane complex (5.27 mg, 6.46 µmol) were added and the reaction mixture was heated at 100° C. for another 5 h. The reaction mixture was filtered and then purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 26-66% B over 20 min, then a 6-minute hold at 100% B; Flow: 20 mL/min. Fractions containing the desired product were combined and dried via centrifugal evaporation to obtain 5-(4-amino-5-(methoxymethyl)pyrrolo[2,1-f][1,2,4]triazin-7-yl)-N-(1-benzyl-1H-pyrazol-4-yl)-2-methoxynicotinamide (3.4 mg, 7.02 µmol, 10.87% yield) as a white solid.

MS ESI m/z 485.0 (M+H)

$^1$H NMR (500 MHz, DMSO-d$_6$) δ 10.27-9.99 (m, 1H), 9.07-8.84 (m, 1H), 8.85-8.59 (m, 1H), 8.27-8.02 (m, 1H), 8.09-7.82 (m, 1H), 7.77-7.56 (m, 1H), 7.44-7.26 (m, 5H), 7.18-6.76 (m, 1H), 5.33 (s, 2H), 4.75 (s, 2H), 4.06 (s, 3H), 3.38 (s, 3H).

Example 50: (S)-5-(4-amino-5-(methoxymethyl)pyrrolo[2,1-f][1,2,4]triazin-7-yl)-N-(3-(4-chlorophenyl)-3-hydroxypropyl)-2-methoxynicotinamide

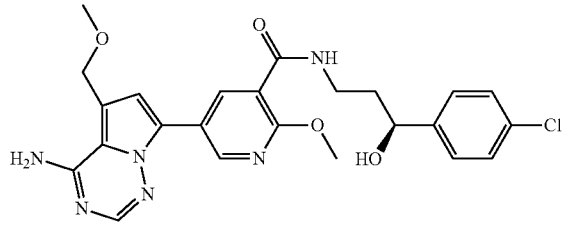

50A: 7-Bromo-5-(methoxymethyl)pyrrolo[2,1-f][1,2,4]triazin-4-amine: A mixture of N-((4-amino-7-bromopyrrolo[2,1-f][1,2,4]triazin-5-yl)methyl)-N,N-diethylethanaminium (40 mg, 0.122 mmol) and sodium bicarbonate (51.3 mg, 0.611 mmol) in MeOH (3 mL) was heated at 75° C. for 3 h. It was then diluted with water and extracted with EtOAc. The organics were washed with water, dried over MgSO4, filtered and concentrated to obtain 7-bromo-5-(methoxymethyl)pyrrolo[2,1-f][1,2,4]triazin-4-amine (30 mg, 0.117 mmol, 95% yield) as a white solid.

MS ESI m/z 258.9 (M+H)

$^1$H NMR (400 MHz, DMSO-d$_6$) δ 7.96-7.90 (m, 1H), 6.86-6.76 (m, 1H), 4.76-4.60 (m, 2H), 3.32 (s, 3H).

50B: (S)-5-bromo-N-(3-(4-chlorophenyl)-3-hydroxypropyl)-2-methoxynicotinamide: A mixture of 5-bromo-2-methoxynicotinic acid (200 mg, 0.862 mmol), (S)-3-amino-1-(4-chlorophenyl)propan-1-ol, HCl (191 mg, 0.862 mmol), Hunig's base (0.452 mL, 2.59 mmol) and BOP (457 mg, 1.034 mmol) in DMF (1 mL) was stirred at rt for 2 h. It was diluted with water, extracted with EtOAc, dried over MgSO4, filtered and concentrated to obtain (S)-5-bromo-N-(3-(4-chlorophenyl)-3-hydroxypropyl)-2-methoxynicotinamide (300 mg, 0.751 mmol, 87% yield) as a white solid.

MS ESI m/z 400.75 (M+H).

$^1$H NMR (400 MHz, CDCl$_3$) δ 8.71-8.58 (m, 1H), 8.38-8.31 (m, 1H), 7.38-7.30 (m, 4H), 4.83-4.68 (m, 1H), 4.12 (s, 3H), 4.01-3.89 (m, 1H), 3.49-3.40 (m, 1H), 2.03-1.90 (m, 2H).

50: (S)-5-(4-amino-5-(methoxymethyl)pyrrolo[2,1-f][1,2,4]triazin-7-yl)-N-(3-(4-chlorophenyl)-3-hydroxypropyl)-2-methoxynicotinamide: A mixture of (S)-5-bromo-N-(3-(4-chlorophenyl)-3-hydroxypropyl)-2-methoxynicotinamide (30 mg, 0.075 mmol), 4,4,4',4',5,5,5',5'-octamethyl-2,2'-bi(1,3,2-dioxaborolane) (22.87 mg, 0.090 mmol), potassium acetate (22.10 mg, 0.225 mmol) in dioxane (2 mL) was degassed and back-filled with N$_2$. 1,1'-bis(diphenylphosphino)ferrocene-palladium(II)dichloride dichloromethane complex (6.13 mg, 7.51 µmol) was added and the mixture degassed and back-filled with N$_2$ three times, then heated at 100° C. for 3 h. After cooling to rt, 7-bromo-5-(methoxymethyl)pyrrolo[2,1-f][1,2,4]triazin-4-amine (19.30 mg, 0.075 mmol), 2 M potassium phosphate tribasic (0.113 mL, 0.225 mmol) and 1,1'-bis(diphenylphosphino)ferrocene-palladium(II)dichloride dichloromethane complex (6.13 mg, 7.51 µmol) were added and the reaction was heated at 100° C. for another 5 h. The reaction mixture was filtered and then purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 24-64% B over 22 min, then a 6-minute hold at 100% B; Flow: 20 mL/min. Fractions containing the desired product were combined and dried via centrifugal evaporation to obtain (S)-5-(4-amino-5-(methoxymethyl)pyrrolo[2,1-f][1,2,4]triazin-7-yl)-N-(3-(4-chlorophenyl)-3-hydroxypropyl)-2-methoxynicotinamide (5.7 mg, 0.011 mmol, 15.28% yield) as a white solid.

MS ESI m/z 497.0 (M+H)

$^1$H NMR (500 MHz, DMSO-d$_6$) δ 9.01-8.70 (m, 2H), 8.58-8.24 (m, 1H), 8.11-7.68 (m, 1H), 7.48-7.31 (m, 6H), 7.14-6.93 (m, 1H), 5.56-5.18 (m, 1H), 4.86-4.53 (m, 3H), 4.12-3.89 (m, 3H), 3.47-3.29 (m, 5H), 2.04-1.76 (m, 2H).

Example 51: 5-(4-amino-5-(hydroxymethyl)pyrrolo[2,1-f][1,2,4]triazin-7-yl)-N-(1-benzyl-1H-pyrazol-4-yl)-2-methoxynicotinamide

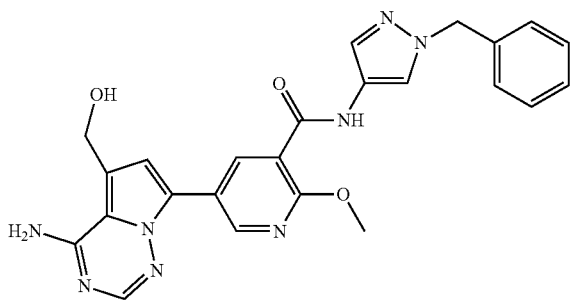 [SMILES: COc1ncc(-c2cc(CO)c3c(N)ncnn23)cc1C(=O)Nc1cnn(Cc2ccccc2)c1]

51A: (7-bromo-4-chloropyrrolo[2,1-f][1,2,4]triazin-5-yl)methanol: A mixture of 7-bromo-5-(bromomethyl)-4-chloropyrrolo[2,1-f][1,2,4]triazine (50 mg, 0.154 mmol) (see WO 2015054358), sodium bicarbonate (32.3 mg, 0.384 mmol) in acetonitrile (3 mL)/water (0.3 mL) was stirred at rt for 3 d. It was then extracted with EtOAc. The organic layer was washed with water, dried over MgSO$_4$, filtered and concentrated to obtain a yellow solid, which was then purified by Biotage flash chromatography, eluting with 40% EtOAc/hexanes to isolate (7-bromo-4-chloropyrrolo[2,1-f][1,2,4]triazin-5-yl)methanol (34 mg, 0.130 mmol, 84% yield) as a light yellow solid.

MS ESI m/z 263.8 (M+H).

$^1$H NMR (400 MHz, DMSO-d6) δ 8.59-8.46 (m, 1H), 7.35-7.23 (m, 1H), 5.48-5.35 (m, 1H), 4.97-4.84 (m, 2H).

51B: (4-amino-7-bromopyrrolo[2,1-f][1,2,4]triazin-5-yl)methanol: A mixture of (7-bromo-4-chloropyrrolo[2,1-f][1,2,4]triazin-5-yl)methanol (130 mg, 0.495 mmol) and ammonium hydroxide (0.19 mL, 4.95 mmol) in dioxane (2 mL) was stirred at rt for 3 h. It was then concentrated to obtain (4-amino-7-bromopyrrolo[2,1-f][1,2,4]triazin-5-yl)methanol (120 mg, 0.494 mmol, 100% yield) as a white solid.

MS ESI m/z 245.0 (M+H)

$^1$H NMR (400 MHz, DMSO-d6) δ 8.01-7.84 (m, 3H), 6.85-6.73 (m, 1H), 6.28-6.07 (m, 1H), 4.86-4.60 (m, 2H).

51: A mixture of N-(1-benzyl-1H-pyrazol-4-yl)-5-bromo-2-methoxynicotinamide (30 mg, 0.077 mmol), 4,4,4',4',5,5,5',5'-octamethyl-2,2'-bi(1,3,2-dioxaborolane) (23.61 mg, 0.093 mmol) and potassium acetate (22.81 mg, 0.232 mmol) in dioxane (2 mL) was degassed and back-filled with N$_2$. 1,1'-bis(diphenylphosphino)ferrocene-palladium(II)dichloride dichloromethane complex (6.33 mg, 7.75 µmol) was added and the mixture was degassed and back-filled with N$_2$ three times, then heated at 100° C. for 3 h. After cooling to rt, (4-amino-7-bromopyrrolo[2,1-f][1,2,4]triazin-5-yl)methanol (22.60 mg, 0.093 mmol), 2 M potassium phosphate tribasic (0.116 mL, 0.232 mmol) and 1,1'-bis(diphenylphosphino)ferrocene-palladium(II)dichloride dichloromethane complex (6.33 mg, 7.75 µmol) were added and the reaction was heated at 100° C. for 5 h. The reaction mixture was filtered and purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 18-58% B over 20 min, then a 5-minute hold at 100% B; Flow: 20 mL/min. Fractions containing the desired product were combined and dried via centrifugal evaporation. The material was further purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 4-43% B over 26 min, then a 6-minute hold at 100% B; Flow: 20 mL/min. Fractions containing the desired product were combined and dried via centrifugal evaporation to obtain 5-(4-amino-5-(hydroxymethyl)pyrrolo[2,1-f][1,2,4]triazin-7-yl)-N-(1-benzyl-1H-pyrazol-4-yl)-2-methoxynicotinamide (3.0 mg, 8.24%) as a white solid.

MS ESI m/z 471.1 (M+H)

$^1$H NMR (500 MHz, DMSO-d$_6$) δ 10.28-10.09 (m, 1H), 9.04-8.87 (m, 1H), 8.82-8.66 (m, 1H), 8.13-8.07 (m, 1H), 7.83 (br s, 1H), 7.43-7.23 (m, 5H), 7.10-6.96 (m, 1H), 5.43-5.22 (m, 2H), 4.91-4.57 (m, 2H), 4.05 (s, 3H).

Example 52: (S)-5-(4-amino-5-(hydroxymethyl)pyrrolo[2,1-f][1,2,4]triazin-7-yl)-N-(3-(4-chlorophenyl)-3-hydroxypropyl)-2-methoxynicotinamide

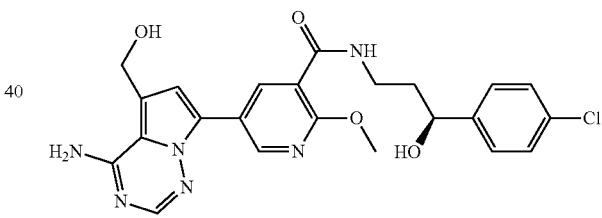

52A: (7-bromo-4-chloropyrrolo[2,1-f][1,2,4]triazin-5-yl)methanol: A mixture of 7-bromo-5-(bromomethyl)-4-chloropyrrolo[2,1-f][1,2,4]triazine (50 mg, 0.154 mmol) and sodium bicarbonate (32.3 mg, 0.384 mmol) in acetonitrile (3 mL)/water (0.3 mL) was stirred at rt for 3 d. It was then extracted with EtOAc. The organic layer was washed with water, dried over MgSO$_4$, filtered and concentrated to obtain a yellow solid. The crude material was purified by Biotage flash chromatography, eluting with 40% EtOAc/hexanes to isolate (7-bromo-4-chloropyrrolo[2,1-f][1,2,4]triazin-5-yl)methanol (34 mg, 0.130 mmol, 84% yield) as a light yellow solid.

MS ESI m/z 263.8 (M+H)

$^1$H NMR (400 MHz, DMSO-d$_6$) δ 8.59-8.46 (m, 1H), 7.35-7.23 (m, 1H), 5.48-5.35 (m, 1H), 4.97-4.84 (m, 2H).

52B: (4-amino-7-bromopyrrolo[2,1-f][1,2,4]triazin-5-yl)methanol: A mixture of (7-bromo-4-chloropyrrolo[2,1-f][1,2,4]triazin-5-yl)methanol (130 mg, 0.495 mmol) and ammonium hydroxide (0.19 mL, 4.95 mmol) in dioxane (2 mL) was stirred at rt for 3 h. It was then concentrated to obtain -(4-amino-7-bromopyrrolo[2,1-f][1,2,4]triazin-5-yl)methanol (120 mg, 0.494 mmol, 100% yield) as a white solid.

MS ESI m/z 245.0 (M+H)

$^1$H NMR (400 MHz, DMSO-d$_6$) δ 8.01-7.84 (m, 3H), 6.85-6.73 (m, 1H), 6.28-6.07 (m, 1H), 4.86-4.60 (m, 2H).

52: A mixture of (S)-5-bromo-N-(3-(4-chlorophenyl)-3-hydroxypropyl)-2-methoxynicotinamide (30 mg, 0.075 mmol), 4,4,4',4',5,5,5',5'-octamethyl-2,2'-bi(1,3,2-dioxaborolane) (22.87 mg, 0.090 mmol), potassium acetate (22.10 mg, 0.225 mmol) in dioxane (2 mL) was degassed and back-filled with N$_2$. 1,1'-Bis(diphenylphosphino)ferrocene-palladium(II)dichloride dichloromethane complex (6.13 mg, 7.51 μmol) was added and the mixture degassed and back-filled with N$_2$ three times. The reaction mixture was heated at 100° C. for 3 h. After cooling to rt, (4-amino-7-bromopyrrolo[2,1-f][1,2,4]triazin-5-yl)methanol (21.89 mg, 0.090 mmol), 2 M potassium phosphate tribasic (0.113 mL, 0.225 mmol) and 1,1'-bis(diphenylphosphino)ferrocene-palladium(II)dichloride dichloromethane complex (6.13 mg, 7.51 μmol) were added and the reaction was heated at 100° C. for another 5 h. The reaction mixture was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 min, then a 4-minute hold at 100% B; Flow: 20 mL/min. Fractions containing the desired product were combined and dried via centrifugal evaporation to obtain (S)-5-(4-amino-5-(hydroxymethyl)pyrrolo[2,1-f][1,2,4]triazin-7-yl)-N-(3-(4-chlorophenyl)-3-hydroxypropyl)-2-methoxynicotinamide (3.4 mg, 7.04 μmol, 9.38% yield) as a white solid.

MS ESI m/z 493.1 (M+H)

$^1$H NMR (500 MHz, DMSO-d$_6$) δ 8.93-8.83 (m, 1H), 8.83-8.73 (m, 1H), 8.43-8.30 (m, 1H), 7.94-7.86 (m, 1H), 7.78-7.69 (m, 2H), 7.42-7.28 (m, 4H), 7.03-6.92 (m, 1H), 6.10-5.96 (m, 1H), 5.45-5.34 (m, 1H), 4.84-4.76 (m, 2H), 4.75-4.66 (m, 1H), 4.05 (s, 3H), 3.47-3.36 (m, 2H), 1.97-1.76 (m, 2H).

Example 53: 5-(4-amino-5-(aminomethyl)pyrrolo[2,1-f][1,2,4]triazin-7-yl)-N-(1-benzyl-1H-pyrazol-4-yl)-2-methoxynicotinamide

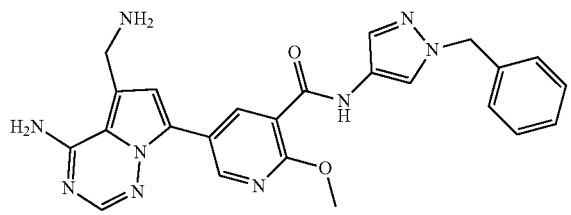 [SMILES: COc1ncc(-c2cc(CN)c3c(N)ncnn23)cc1C(=O)Nc1cnn(Cc2ccccc2)c1]

53A: 5-(aminomethyl)-7-bromopyrrolo[2,1-f][1,2,4]triazin-4-amine: A mixture of N-((4-amino-7-bromopyrrolo[2,1-f][1,2,4]triazin-5-yl)methyl)-N,N-diethylethanaminium, bromide salt (70 mg, 0.172 mmol) and concentrated ammonium hydroxide (0.5 mL, 12.84 mmol) in dioxane (2 mL) was heated at 75° C. for 16 h. It was then concentrated to obtain 5-(aminomethyl)-7-bromopyrrolo[2,1-f][1,2,4]triazin-4-amine (40 mg, 96%) as a white solid.

MS ESI m/z 243.9 (M+H)

$^1$H NMR (400 MHz, DMSO-d$_6$) δ 7.98 (s, 1H), 6.96 s, 1H), 4.33 (s, 2H).

53: A mixture of N-(1-benzyl-1H-pyrazol-4-yl)-5-bromo-2-methoxynicotinamide (25 mg, 0.065 mmol), 4,4,4',4',5,5,5',5'-octamethyl-2,2'-bi(1,3,2-dioxaborolane) (19.67 mg, 0.077 mmol), potassium acetate (19.01 mg, 0.194 mmol) in dioxane (2 mL) was degassed and back-filled with N$_2$. 1,1'-Bis(diphenylphosphino)ferrocene-palladium(II)dichloride dichloromethane complex (5.27 mg, 6.46 μmol) was added and the mixture degassed and back-filled with N$_2$ three times. The reaction mixture was heated at 100° C. for 3 h. After cooling to rt, 5-(aminomethyl)-7-bromopyrrolo[2,1-f][1,2,4]triazin-4-amine (15.63 mg, 0.065 mmol), 2 M potassium phosphate tribasic (0.097 mL, 0.194 mmol), 1,1'-bis(diphenylphosphino)ferrocene-palladium(II)dichloride dichloromethane complex (5.27 mg, 6.46 μmol) were added and the reaction was heated at 100° C. for 5 h. The reaction mixture was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 6-46% B over 20 min, then a 4-minute hold at 100% B; Flow: 20 mL/min. Fractions containing the desired product were combined and dried via centrifugal evaporation to obtain 5-(4-amino-5-(aminomethyl)pyrrolo[2,1-f][1,2,4]triazin-7-yl)-N-(1-benzyl-1H-pyrazol-4-yl)-2-methoxynicotinamide (8.7 mg, 0.019 mmol, 28.7% yield) as a white solid.

MS ESI m/z 470.2 (M+H)

$^1$H NMR (500 MHz, DMSO-d$_6$) δ 10.25-10.07 (m, 1H), 8.97-8.85 (m, 1H), 8.80-8.60 (m, 1H), 8.20-8.09 (m, 1H), 8.05-7.89 (m, 1H), 7.70-7.63 (m, 1H), 7.37-7.25 (m, 4H), 7.24-7.19 (m, 1H), 5.42-5.23 (m, 2H), 4.52-4.32 (m, 2H), 4.08 (s, 3H).

Example 54: S)—N-(3-(4-chlorophenyl)-3-hydroxypropyl)-5-(4-((2-hydroxyethyl)amino)pyrrolo[2,1-f][1,2,4]triazin-7-yl)-2-methoxynicotinamide

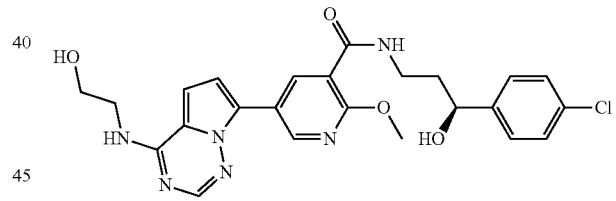

54A: Pyrrolo[2,1-f][1,2,4]triazin-4-ol: To a stirred solution of methyl 1-amino-1H-pyrrole-2-carboxylate (3 g, 21.41 mmol) in ethanol (60 mL) was added formamidine acetate (22.29 g, 214 mmol) at rt. The reaction mixture was stirred at 85° C. for 16 h. The reaction was evaporated to dryness. It was diluted with EtOAc, washed with water. The organic layer was dried over MgSO$_4$, filtered and concentrated to obtain a brown solid, which was washed with ether to obtain pyrrolo[2,1-f][1,2,4]triazin-4-ol (2.6 g, 19.24 mmol, 90% yield) as a pale brown solid.

MS ESI m/z 136.0 (M+H)

$^1$H NMR (400 MHz, DMSO-d$_6$) δ 7.95-7.73 (m, 1H), 7.70-7.41 (m, 1H), 6.98-6.73 (m, 1H), 6.63-6.40 (m, 1H).

54B: 7-Bromopyrrolo[2,1-f][1,2,4]triazin-4-ol: To a mixture of pyrrolo[2,1-f][1,2,4]triazin-4-ol (2.8 g, 20.72 mmol) in CH$_2$Cl$_2$ (40 mL) at 0° C. was added acetic acid (20 mL) followed by slow addition of NBS (3.32 g, 18.65 mmol). The reaction mixture was stirred at 0° C. for 1 h. Saturated aqueous NaHCO$_3$ was added to the reaction mixture. The mixture was extracted with EtOAc and washed saturated aqueous NaHCO$_3$ (5×). The organics were dried over MgSO$_4$, filtered and concentrated to obtain 7-bromopyrrolo[2,1-f][1,2,4]triazin-4-ol (3.9 g, 18.22 mmol, 88% yield) as a tan solid.

MS ESI m/z 214.0 (M+H)

$^1$H NMR (400 MHz, DMSO-d$_6$) δ 12.19-11.66 (m, 1H), 8.50-7.64 (m, 1H), 7.43-6.86 (m, 1H), 6.86-6.35 (m, 1H).

54C: 7-Bromo-4-chloropyrrolo[2,1-f][1,2,4]triazine: A mixture of 7 bromopyrrolo[2,1-f][1,2,4]triazin-4-ol (3.9 g, 18.22 mmol), POCl$_3$ (5.10 mL, 54.7 mmol) and Hunig's base (3.18 mL, 18.22 mmol) in PhCH3 (50 mL) was heated at reflux for 16 h.

The reaction mixture was concentrated and cooled to 0° C. Saturated aqueous NaHCO$_3$ was added and a light brown precipitate was formed. The precipitate was isolated by filtration, washing with water and drying under vacuum to obtain 7-bromo-4-chloropyrrolo[2,1-f][1,2,4]triazine (3.7 g, 15.92 mmol, 87% yield) as a tan solid.

MS ESI m/z 233.8 (M+H)

$^1$H NMR (400 MHz, CDCl$_3$) δ 8.51-8.33 (m, 1H), 7.12-7.08 (m, 1H), 7.08-7.03 (m, 1H).

54D: 2-((7-Bromopyrrolo[2,1-f][1,2,4]triazin-4-yl)amino)ethanol: A mixture of 2-aminoethanol (0.286 mL, 4.73 mmol), 7-bromo-4-chloropyrrolo[2,1-f][1,2,4]triazine (1 g, 4.30 mmol) and Hunig's Base (0.902 mL, 5.16 mmol) in THF (10 mL) was heated at 70° C. for 16 h. It was diluted with EtOAc and washed with diluted HCl and water. The organics were dried over MgSO$_4$, filtered and concentrated to obtain 2-((7-bromopyrrolo[2,1-f][1,2,4]triazin-4-yl)amino)ethanol (1 g, 3.89 mmol, 90% yield) as a tan solid.

MS ESI m/z 258.9 (M+H)

$^1$H NMR (400 MHz, CDCl$_3$) δ 8.21-8.06 (m, 1H), 8.06-8.03 (m, 1H), 6.85-6.60 (m, 2H), 6.17-5.80 (m, 1H), 3.99-3.89 (m, 2H), 3.88-3.80 (m, 2H). 54E: 2-methoxy-5-(4,4,5,5-tetramethyl-1,3,2-dioxaborolan-2-yl)nicotinic acid: A mixture of methyl 2-methoxy-5-(4,4,5,5-tetramethyl-1,3,2-dioxaborolan-2-yl)nicotinate (100 mg, 0.341 mmol), 1 N NaOH (1.706 mL, 1.706 mmol) in MeOH (1 mL) was stirred at rt for 1 h. It was concentrated and the pH adjusted to 5 using 1 N HCl. The resulting white solid was filtered and washed with water to obtain 2-methoxy-5-(4,4,5,5-tetramethyl-1,3,2-dioxaborolan-2-yl)nicotinic acid as the desired product.

$^1$H NMR (400 MHz, CDCl$_3$) δ 9.08-8.77 (m, 1H), 8.82-8.66 (m, 1H), 4.23 (s, 3H), 1.35 (s, 12H).

54F: (S)—N-(3-(4-chlorophenyl)-3-hydroxypropyl)-2-methoxy-5-(4,4,5,5-tetramethyl-1,3,2-dioxaborolan-2-yl)nicotinamide: A mixture of 2-methoxy-5-(4,4,5,5-tetramethyl-1,3,2-dioxaborolan-2-yl)nicotinic acid (30 mg, 0.107 mmol), (S)-3-amino-1-(4-chlorophenyl)propan-1-ol, HCl (23.87 mg, 0.107 mmol), Hunig's base (0.056 mL, 0.322 mmol) and BOP (57.0 mg, 0.129 mmol) in DMF (1 mL) was stirred at rt for 2 h. It was diluted with water, extracted with EtOAc, dried over MgSO4, filtered and concentrated to obtain (S)—N-(3-(4-chlorophenyl)-3-hydroxypropyl)-2-methoxy-5-(4,4,5,5-tetramethyl-1,3,2-dioxaborolan-2-yl) nicotinamide (40 mg, 0.090 mmol, 83% yield) as a white solid.

MS ESI (m/z) 367.0 (M+H).

54: A mixture of (S)—N-(3-(4-chlorophenyl)-3-hydroxypropyl)-2-methoxy-5-(4,4,5,5-tetramethyl-1,3,2-dioxaborolan-2-yl)nicotinamide (40 mg, 0.090 mmol), 2-((7-bromopyrrolo[2,1-f][1,2,4]triazin-4-yl)amino)ethanol (23.02 mg, 0.090 mmol), 2 M potassium phosphate tribasic (0.134 mL, 0.269 mmol) in dioxane (2 mL) was degassed and back-filled with N$_2$. To the reaction mixture was added 1,1'-bis(diphenylphosphino)ferrocene-palladium(II)dichloride dichloromethane complex (7.31 mg, 8.95 μmol) and the reaction mixture was heated at 100° C. for 2 h. The reaction mixture was filtered and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 18-58% B over 20 min, then a 5-minute hold at 100% B; Flow: 20 mL/min. Fractions containing the desired product were combined and dried via centrifugal evaporation to obtain (S)—N-(3-(4-chlorophenyl)-3-hydroxypropyl)-5-(4-((2-hydroxyethyl)amino)pyrrolo[2,1-f][1,2,4]triazin-7-yl)-2-methoxynicotinamide (16.9 mg, 0.034 mom, 38.0% yield) as a white solid.

MS ESI m/z 497.3 (M+H)

$^1$H NMR (500 MHz, DMSO-d$_6$) δ 8.94-8.82 (m, 1H), 8.81-8.69 (m, 1H), 8.51-8.33 (m, 1H), 8.29-8.09 (m, 1H), 8.06-7.88 (m, 1H), 7.44-7.31 (m, 4H), 7.12-6.97 (m, 2H), 5.56-5.39 (m, 1H), 4.77-4.62 (m, 1H), 4.05 (s, 3H), 3.71-3.55 (m, 4H), 3.46-3.24 (m, 2H), 2.06-1.81 (m, 2H).

Example 55: N-(1-benzyl-1H-pyrazol-4-yl)-5-(4-((2-hydroxyethyl)amino)pyrrolo[2,1-f][1,2,4]triazin-7-yl)-2-methoxynicotinamide

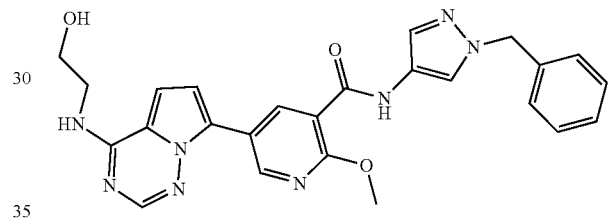

55A: N-(1-benzyl-1H-pyrazol-4-yl)-5-bromo-2-methoxynicotinamide: A mixture of 5-bromo-2-methoxynicotinic acid (500 mg, 2.155 mom), 1-benzyl-1H-pyrazol-4-amine, HCl (452 mg, 2.155 mom), Hunig's base (1.129 mL, 6.46 mom) and BOP (1144 mg, 2.59 mom) in DMF (5 mL) was stirred at rt for 2 h. The reaction mixture was diluted with water, extracted with EtOAc, dried over MgSO$_4$, filtered and concentrated to obtain N-(1-benzyl-1H-pyrazol-4-yl)-5-bromo-2-methoxynicotinamide (750 mg, 1.937 mmol, 90% yield) as an oil.

MS ESI m/z 388.8 (M+H)

$^1$H NMR (400 MHz, CDCl$_3$) δ 9.76-9.34 (m, 1H), 8.70-8.57 (m, 1H), 8.44-8.31 (m, 1H), 7.65-7.60 (m, 1H), 7.42-7.29 (m, 5H), 5.36-5.31 (m, 2H), 4.21-4.17 (m, 3H).

55: A mixture of N-(1-benzyl-1H-pyrazol-4-yl)-5-bromo-2-methoxynicotinamide (30 mg, 0.077 mmol), 4,4,4',4',5,5,5',5'-octamethyl-2,2'-bi(1,3,2-dioxaborolane) (23.61 mg, 0.093 mmol) and potassium acetate (22.81 mg, 0.232 mmol) in dioxane (2 mL) was degassed and back-filled with N$_2$. To the mixture was added 1,1'-bis(diphenylphosphino)ferrocene-palladium(II)dichloride dichloromethane complex (6.33 mg, 7.75 μmol) and it was heated at 100° C. for 3 h. After cooling to rt, 2-((7-bromopyrrolo[2,1-f][1,2,4]triazin-4-yl)amino)ethan-1-ol (23.90 mg, 0.093 mmol) and potassium phosphate tribasic (0.116 mL, 0.232 mmol) were added and the reaction mixture was degassed and back-filled with N$_2$. To the mixture was added 1,1'-bis(diphenylphosphino) ferrocene-palladium(II)dichloride dichloromethane complex (6.33 mg, 7.75 μmol) and the reaction was heated at 100° C. for another 12 h. It was then filtered and purified with prep HPLC to obtain N-(1-benzyl-1H-pyrazol-4-yl)-5-

(4-((2-hydroxyethyl)amino)pyrrolo[2,1-f][1,2,4]triazin-7-yl)-2-methoxynicotinamide (2 mg, 4.13 µmol, 5.33% yield) as a white solid.

MS ESI m/z 485.2 (M+H)

$^1$H NMR (500 MHz, DMSO-d$_6$) δ 10.20-10.02 (m, 1H), 8.97-8.87 (m, 1H), 8.81-8.69 (m, 1H), 8.24-8.15 (m, 1H), 8.14-8.06 (m, 1H), 8.04-7.91 (m, 1H), 7.72-7.52 (m, 1H), 7.40-7.24 (m, 5H), 7.12-7.02 (m, 2H), 5.40-5.20 (m, 2H), 4.06 (s, 3H), 3.73-3.50 (m, 4H).

Example 56: N-(1-benzyl-1H-pyrazol-4-yl)-2-methoxy-5-(4-((2-methoxyethyl)amino)pyrrolo[2,1-f][1,2,4]triazin-7-yl)nicotinamide

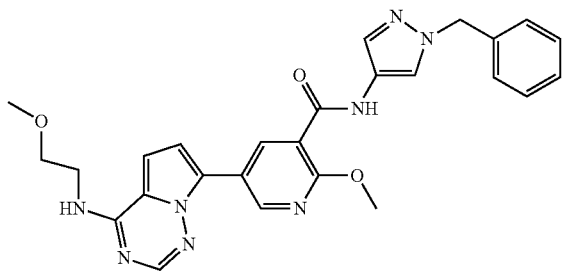 [SMILES: COCCNc1ncnn2c(-c3cnc(OC)c(C(=O)Nc4cnn(Cc5ccccc5)c4)c3)ccc12]

56A: 7-bromo-N-(2-methoxyethyl)pyrrolo[2,1-f][1,2,4]triazin-4-amine: A mixture of 2-methoxyethanamine (71.1 mg, 0.946 mmol), 7-bromo-4-chloropyrrolo[2,1-f][1,2,4]triazine (200 mg, 0.860 mmol), Hunig's base (0.180 mL, 1.032 mmol) in THF (5 mL) was heated at 70° C. for 16 h. The mixture was diluted with water. The tan solid was filtered, washed with water and dried to obtain 7-bromo-N-(2-methoxyethyl)pyrrolo[2,1-f][1,2,4]triazin-4-amine (199 mg, 0.734 mmol, 85% yield) as a tan solid MS ESI m/z 272.92 (M+H).

$^1$H NMR (400 MHz, CD$_3$OD) δ 7.98-7.88 (m, 1H), 7.00-6.92 (m, 1H), 6.74-6.68 (m, 1H), 3.83-3.73 (m, 2H), 3.68-3.61 (m, 2H), 3.40 (s, 3H).

56B: 2-methoxy-5-(4-((2-methoxyethyl)amino)pyrrolo[2,1-f][1,2,4]triazin-7-yl)nicotinic acid: To a solution of 7-bromo-N-(2-methoxyethyl)pyrrolo[2,1-f][1,2,4]triazin-4-amine (130 mg, 0.480 mmol) and methyl 2-methoxy-5-(4,4,5,5-tetramethyl-1,3,2-dioxaborolan-2-yl)nicotinate (141 mg, 0.480 mmol) in 1,4-dioxane (2 mL) was added potassium phosphate tribasic (0.719 mL, 1.439 mmol) (2M in H$_2$O). After bubbling nitrogen through for 5 min, 1,1'-bis(diphenylphosphino)ferrocene-palladium(II)dichloride dichloromethane complex (39.2 mg, 0.048 mmol) was added. Nitrogen bubbling was maintained an additional 5 min. The reaction vessel was sealed and heated to 100° C. for 16 h. The reaction mixture was filtrated through a pad of Celite to remove the catalyst. NaOH (0.240 mL, 2.398 mmol) (10 M in water) was added and the mixture was stirred at rt for 2 h. Methanol was added and the solid isolated by filtration to yield 2-methoxy-5-(4-((2-methoxyethyl)amino)pyrrolo[2,1-f][1,2,4]triazin-7-yl)nicotinic acid (100 mg, 61%) as a tan solid.

MS ESI m/z 344.03 (M+H).

56: A mixture of 2-methoxy-5-(4-((2-methoxyethyl)amino)pyrrolo[2,1-f][1,2,4]triazin-7-yl)nicotinic acid (20 mg, 0.058 mmol), 1-benzyl-1H-pyrazol-4-amine (12.11 mg, 0.070 mmol), BOP (30.9 mg, 0.070 mmol) and Hunig's base (0.031 mL, 0.175 mmol) in DMF (1 mL) was stirred at rt for 20 min. It was concentrated and purified via preparative LC-MS: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 8-48% B over 20 min, then a 6-minute hold at 100% B; Flow: 20 mL/min. Fractions containing the desired product were combined and dried via centrifugal evaporation to obtain N-(1-benzyl-1H-pyrazol-4-yl)-2-methoxy-5-(4-((2-methoxyethyl)amino)pyrrolo[2,1-f][1,2,4]triazin-7-yl)nicotinamide (9.4 mg, 0.019 mmol, 32.4% yield) as a white solid.

MS ESI m/z 499.2 (M+H)

$^1$H NMR (500 MHz, DMSO-d$_6$) δ 8.98-8.89 (m, 1H), 8.79-8.70 (m, 1H), 8.33-8.24 (m, 1H), 8.17-8.06 (m, 1H), 8.03-7.92 (m, 1H), 7.67-7.61 (m, 1H), 7.41-7.25 (m, 5H), 7.14-7.01 (m, 2H), 5.35-5.26 (m, 2H), 4.09-4.01 (m, 3H), 3.77-3.64 (m, 2H), 3.63-3.53 (m, 2H), 3.35-3.30 (m, 1H).

Example 57: (S)-5-(4-amino-5-(((2-hydroxyethyl)amino)methyl)pyrrolo[2,1-f][1,2,4]triazin-7-yl)-N-(3-(4-chlorophenyl)-3-hydroxypropyl)-2-methoxynicotinamide

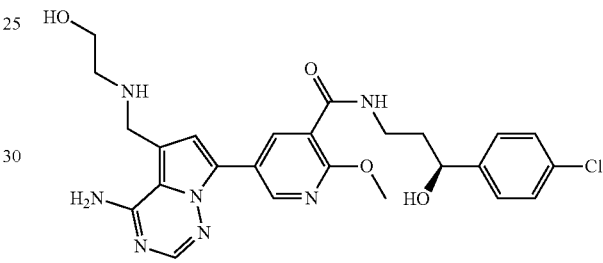

57A: N-((4-amino-7-bromopyrrolo[2,1-f][1,2,4]triazin-5-yl)methyl)-N,N-diethylethanaminium, bromide salt: A mixture of N-((7-bromo-4-chloropyrrolo[2,1-f][1,2,4]triazin-5-yl)methyl)-N,N-diethylethanaminium, bromide salt (3.5 g, 8.20 mmol) and concentrated ammonium hydroxide (11.41 mL, 82 mmol) in dioxane (10 mL) was stirred at rt for 4 h. It was then concentrated to obtain N-((4-amino-7-bromopyrrolo[2,1-f][1,2,4]triazin-5-yl)methyl)-N,N-diethylethanaminium, bromide salt (3.3 g, 7.74 mmol, 94% yield) as an off-white solid.

MS ESI m/z 326.1 (M+H)

$^1$H NMR (400 MHz, DMSO-d6) δ 8.21-8.00 (m, 1H), 7.13-7.03 (m, 1H), 4.95-4.75 (m, 2H), 3.29-3.12 (m, 6H), 1.35-1.18 (m, 9H).

57B: 2-(((4-amino-7-bromopyrrolo[2,1-f][1,2,4]triazin-5-yl)methyl)amino)ethan-1-ol: A mixture of N-((4-amino-7-bromopyrrolo[2,1-f][1,2,4]triazin-5-yl)methyl)-N,N-diethylethanaminium (40 mg, 0.122 mmol) and 2-aminoethan-1-ol (0.1 mL, 1.222 mmol) in dioxane (1 mL) was heated at 75° C. for 72 h. It was then diluted with EtOAc and washed with water. The organics were dried over MgSO$_4$, filtered and concentrated to obtain 2-(((4-amino-7-bromopyrrolo[2,1-f][1,2,4]triazin-5-yl)methyl)amino)ethan-1-ol (26 mg, 0.091 mmol, 74.3% yield) as a light orange solid.

MS ESI m/z 287.8 (M+H)

$^1$H NMR (400 MHz, CDCl$_3$) δ 8.02-7.73 (m, 1H), 6.67-6.35 (m, 1H), 4.10-3.99 (m, 2H), 3.86-3.78 (m, 2H), 2.99-2.74 (m, 2H).

57: A mixture of (S)-5-bromo-N-(3-(4-chlorophenyl)-3-hydroxypropyl)-2-methoxynicotinamide (25 mg, 0.063 mmol), 4,4,4',4',5,5,5',5'-octamethyl-2,2'-bi(1,3,2-dioxaborolane) (19.06 mg, 0.075 mmol) and potassium acetate (18.42 mg, 0.188 mmol) in dioxane (2 mL) was degassed and back-filled with N₂. To the mixture was added 1,1'-bis(diphenylphosphino)ferrocene-palladium(II) dichloride dichloromethane complex (5.11 mg, 6.26 μmol) and the reaction was degassed and back-filled with N₂. The reaction mixture was heated at 100° C. for 6 h. It was cooled to rt and potassium phosphate tribasic (0.094 mL, 0.188 mmol), 2-(((4-amino-7-bromopyrrolo[2,1-f][1,2,4]triazin-5-yl)methyl)amino)ethan-1-ol (17.90 mg, 0.063 mmol) and 1,1'-bis(diphenylphosphino)ferrocene-palladium(II) dichloride dichloromethane complex (5.11 mg, 6.26 μmol) were added. The reaction mixture was degassed and back-filled with N₂ and heated for 6 h. The reaction mixture was cooled to rt, filtered and purified by prep HPLC to obtain (S)-5-(4-amino-5-(((2-hydroxyethyl)amino)methyl)pyrrolo[2,1-f][1,2,4]triazin-7-yl)-N-(3-(4-chlorophenyl)-3-hydroxypropyl)-2-methoxynicotinamide (9.7 mg, 0.018 mmol, 29.5% yield) as a white solid.

MS ESI m/z 526.0 (M+H)

¹H NMR (500 MHz, DMSO-d₆) δ 8.97-8.90 (m, 1H), 8.79-8.72 (m, 1H), 8.47-8.28 (m, 1H), 8.05-7.92 (m, 1H), 7.43-7.37 (m, 4H), 7.33-7.24 (m, 1H), 4.79-4.68 (m, 1H), 4.62-4.44 (m, 2H), 4.07 (s, 3H), 3.77-3.68 (m, 2H), 3.50-3.34 (m, 2H), 3.18-3.01 (m, 2H).

Example 58: 5-(4-amino-5-(((2-hydroxyethyl)amino)methyl)pyrrolo[2,1-f][1,2,4]triazin-7-yl)-N-(1-benzyl-1H-pyrazol-4-yl)-2-methoxynicotinamide

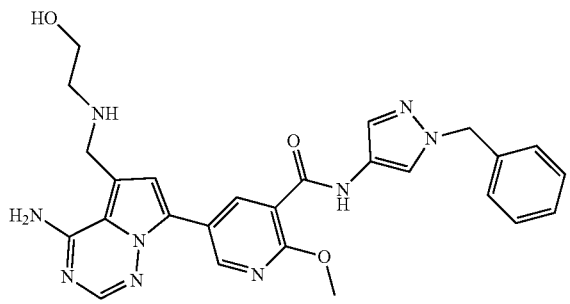 [SMILES: COc1ncc(-c2cc(CNCCO)c3c(N)ncnn23)cc1C(=O)Nc1cnn(Cc2ccccc2)c1]

A mixture of N-(1-benzyl-1H-pyrazol-4-yl)-5-bromo-2-methoxynicotinamide (25 mg, 0.065 mmol), 4,4,4',4',5,5,5',5'-octamethyl-2,2'-bi(1,3,2-dioxaborolane) (19.67 mg, 0.077 mmol), potassium acetate (19.01 mg, 0.194 mmol) in dioxane (2 mL) was degassed and back-filled with N₂. 1,1'-Bis(diphenylphosphino)ferrocene-palladium(II)dichloride dichloromethane complex (5.27 mg, 6.46 μmol) was added and the reaction mixture degassed and back-filled with N₂ three times. The reaction mixture was heated at 100° C. for 3 h. After cooling to rt, 2-(((4-amino-7-bromopyrrolo[2,1-f][1,2,4]triazin-5-yl)methyl)amino)ethan-1-ol (18.47 mg, 0.065 mmol), 2 M potassium phosphate tribasic (0.097 mL, 0.194 mmol) and 1,1'-bis(diphenylphosphino)ferrocene-palladium(II)dichloride dichloromethane complex (5.27 mg, 6.46 μmol) were added and the reaction was heated at 100° C. for 5 h. The reaction mixture was cooled to rt and purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 1-41% B over 25 min, then a 6-minute hold at 100% B; Flow: 20 mL/min. Fractions containing the desired product were combined and dried via centrifugal evaporation to obtain 5-(4-amino-5-(((2-hydroxyethyl)amino)methyl)pyrrolo[2,1-f][1,2,4]triazin-7-yl)-N-(1-benzyl-1H-pyrazol-4-yl)-2-methoxynicotinamide (11.1 mg, 0.022 mmol, 33.5% yield) as a white solid.

MS ESI m/z 514.1 (M+H)

¹H NMR (500 MHz, DMSO-d₆) δ 10.24-10.06 (m, 1H), 8.96-8.87 (m, 1H), 8.77-8.57 (m, 1H), 8.16-8.05 (m, 1H), 8.08-7.96 (m, 1H), 7.78-7.51 (m, 1H), 7.42-7.25 (m, 6H), 5.39-5.23 (m, 2H), 4.64-4.49 (m, 2H), 4.16-4.01 (m, 3H), 3.78-3.61 (m, 2H), 3.17-2.98 (m, 2H).

Example 59: 3-(4-aminopyrrolo[2,1-f][1,2,4]triazin-7-yl)-N-(3-hydroxy-3-phenylpropyl)benzamide

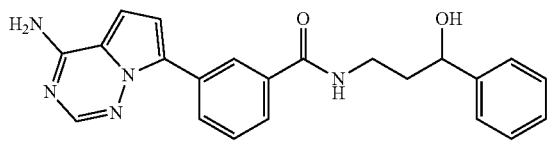 [SMILES: Nc1ncnn2c(-c3cccc(C(=O)NCCC(O)c4ccccc4)c3)ccc12]

59A: A mixture of 7-bromopyrrolo[2,1-f][1,2,4]triazin-4-amine (0.200 g, 0.939 mmol), 3-(4,4,5,5-tetramethyl-1,3,2-dioxaborolan-2-yl)benzoic acid (0.279 g, 1.127 mmol), tripotassium phosphate (2 M in water) (1.408 mL, 2.82 mmol), and N,N-dimethylformamide (4.0 mL) was degassed with vacuum and nitrogen (3×). 1,1'-Bis(di-tert-butylphosphino)ferrocene palladium dichloride (0.069 g, 0.094 mmol) was added, and the reaction mixture was degassed (2×). The reaction mixture was immediately immersed in an oil bath at 95° C. and stirred overnight. The reaction mixture was cooled to rt and then diluted with water (2 mL) followed by 1N aqueous hydrochloric acid (2 mL), resulting in a precipitate. The solid was collected by vacuum filtration and dried under reduced pressure to give 3-(4-aminopyrrolo[2,1-f][1,2,4]triazin-7-yl)benzoic acid (0.117 g, 0.460 mmol, 49.0% yield) as a gray solid.

MS ESI m/z 255.1 (M+H)

59: A mixture of 3-(4-aminopyrrolo[2,1-f][1,2,4]triazin-7-yl)benzoic acid (0.025 g, 0.098 mmol), 3-amino-1-phenylpropan-1-ol (0.022 g, 0.147 mmol), Hunig's Base (0.052 mL, 0.295 mmol), and BOP (0.048 g, 0.108 mmol) in N,N-dimethylformamide (1.0 mL) was stirred at rt for 60 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 10-55% B over 20 minutes, then a 3-minute hold at 100% B; Flow: 20 mL/min. Fractions containing the desired product were combined and dried via centrifugal evaporation to yield the final product (34.0 mg, 87 μmol, 88%).

MS ESI m/z 388.2 (M+H)

1H NMR (500 MHz, DMSO-d6) δ 8.53 (br s, 1H), 8.42 (s, 1H), 8.23 (br d, J=7.7 Hz, 1H), 7.94 (s, 1H), 7.89-7.65 (m, 3H), 7.54 (br t, J=7.8 Hz, 1H), 7.41-7.28 (m, 4H), 7.27-7.17 (m, 1H), 7.13-6.99 (m, 2H), 4.65 (br s, 1H), 3.59-3.43 (m, 2H), 3.40-3.29 (m, 1H), 1.97-1.78 (m, 2H).

Example 60: 3-(4-aminopyrrolo[2,1-f][1,2,4]triazin-7-yl)-N-(1-benzyl-1H-pyrazol-4-yl)benzamide

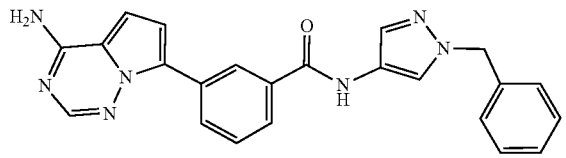 [SMILES: Nc1ncnn2c(-c3cccc(C(=O)Nc4cnn(Cc5ccccc5)c4)c3)ccc12]

A mixture of 3-(4-aminopyrrolo[2,1-f][1,2,4]triazin-7-yl)benzoic acid (0.025 g, 0.098 mmol), 1-benzyl-1H-pyrazol-4-amine (0.026 g, 0.147 mmol), Hunig's Base (0.052 mL, 0.295 mmol), and BOP (0.048 g, 0.108 mmol) in N,N-dimethylformamide (1.0 mL) was stirred at rt for 60 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 15-100% B over 20 minutes, then a 2-minute hold at 100% B; Flow: 20 mL/min. Fractions containing the desired product were combined and dried via centrifugal evaporation to yield the final product (30.0 mg, 72 µmol, 73%).

MS ESI m/z 410.3 (M+H)

$^1$H NMR (500 MHz, DMSO-$d_6$) δ 10.69-10.42 (m, 1H), 8.54 (s, 1H), 8.26 (br d, J=7.6 Hz, 1H), 8.15 (s, 1H), 7.95 (s, 1H), 7.90-7.69 (m, 3H), 7.68-7.55 (m, 2H), 7.43-7.21 (m, 5H), 7.16-6.97 (m, 2H), 5.32 (s, 2H).

Example 61: 5-(4-amino-6-fluoropyrrolo[2,1-f][1,2,4]triazin-7-yl)-2-methoxy-N-(3-phenylbutyl)nicotinamide

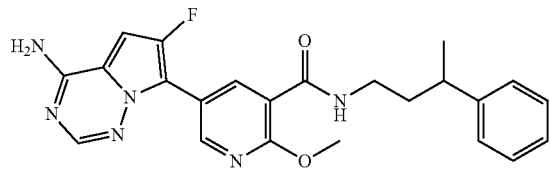 [SMILES: COc1ncc(-c2c(F)cc3c(N)ncnn23)cc1C(=O)NCCC(C)c1ccccc1]

61A: A mixture of 7-bromo-6-fluoropyrrolo[2,1-f][1,2,4]triazin-4-amine (0.131 g, 0.569 mmol), methyl 2-methoxy-5-(4,4,5,5-tetramethyl-1,3,2-dioxaborolan-2-yl)nicotinate (0.200 g, 0.682 mmol), tripotassium phosphate (2 M in water) (0.853 mL, 1.706 mmol) and dioxane (4.0 mL) was degassed with vacuum and nitrogen (3×). 1,1'-Bis(diphenylphosphino)ferrocene palladium dichloride —CH$_2$Cl$_2$ adduct (0.046 g, 0.057 mmol) was added, and the reaction mixture was degassed (2×). The reaction mixture was immersed in an oil bath at 95° C. and stirred ON. The reaction mixture was diluted with ethyl acetate, then washed with water and brine. The organic layer was collected, and the aqueous layers were sequentially extracted with ethyl acetate. The combined organic layers were dried over anhydrous sodium sulfate and concentrated under reduced pressure. The product was triturated with dichloromethane, sonicated and isolated to give methyl 5-(4-amino-6-fluoropyrrolo[2,1-f][1,2,4]triazin-7-yl)-2-methoxynicotinate (0.052 g, 0.164 mmol, 28.8% yield) as a tan solid.

MS ESI m/z 318.1 (M+H)

61B: A heterogeneous mixture of methyl 5-(4-amino-6-fluoropyrrolo[2,1-f][1,2,4]triazin-7-yl)-2-methoxynicotinate (0.052 g, 0.164 mmol) and lithium hydroxide, H$_2$O (6.88 mg, 0.164 mmol) in a mixture of methanol (1 mL), tetrahydrofuran (1 mL) and water (0.500 mL) was stirred at rt ON. The solvent was removed under reduced pressure, and the residue was dried well to give 5-(4-amino-6-fluoropyrrolo[2,1-f][1,2,4]triazin-7-yl)-2-methoxynicotinic acid, lithium salt (0.051 g, 0.164 mmol, 100% yield) as a light brown solid. The compound was used without further purification.

MS ESI m/z 304.1 (M+H)

61: A mixture of 5-(4-amino-6-fluoropyrrolo[2,1-f][1,2,4]triazin-7-yl)-2-methoxynicotinic acid, lithium salt (0.025 g, 0.081 mmol), 3-phenylbutan-1-amine (0.018 g, 0.121 mmol), Hünig's base (0.042 mL, 0.242 mmol) and BOP (0.039 g, 0.089 mmol) in N,N-dimethylformamide (1.0 mL) was stirred at rt for 60 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 40-80% B over 20 minutes, then a 8-minute hold at 100% B; Flow: 20 mL/min. Fractions containing the desired product were combined and dried via centrifugal evaporation to yield the final product (10.4 mg, 24 µmol, 29%).

MS ESI m/z 435.2 (M+H)

$^1$H NMR (500 MHz, DMSO-$d_6$) δ 8.76 (s, 1H), 8.57 (d, J=1.4 Hz, 1H), 8.29 (br t, J=5.1 Hz, 1H), 7.99 (s, 1H), 7.87 (br s, 2H), 7.36-7.12 (m, 5H), 6.90 (s, 1H), 4.02 (s, 3H), 3.32-3.11 (m, 2H), 2.88-2.73 (m, 1H), 1.82 (q, J=7.2 Hz, 2H), 1.23 (br d, J=6.9 Hz, 3H).

Example 62: 5-(4-amino-6-fluoropyrrolo[2,1-f][1,2,4]triazin-7-yl)-N-(1-benzyl-1H-pyrazol-4-yl)-2-methoxynicotinamide

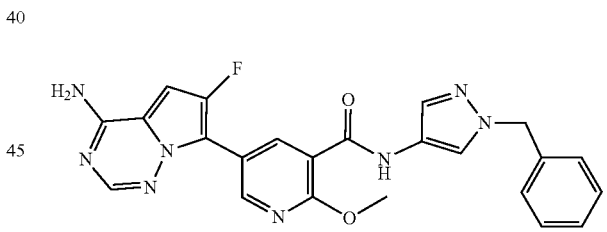

A mixture of 5-(4-amino-6-fluoropyrrolo[2,1-f][1,2,4]triazin-7-yl)-2-methoxynicotinic acid, lithium salt (0.025 g, 0.081 mmol), 1-benzyl-1H-pyrazol-4-amine (0.021 g, 0.121 mmol), Hunig's Base (0.042 mL, 0.242 mmol), and BOP (0.039 g, 0.089 mmol) in N,N-dimethylformamide (1.0 mL) was stirred at room temperature for 60 min. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 20-60% B over 20 minutes, then a 5-minute hold at 100% B; Flow: 20 mL/min. Fractions containing the desired product were combined and dried via centrifugal evaporation. Fractions containing the desired product were combined and dried via centrifugal evaporation to yield the final product (11.2 mg, 23 µmol, 29%).

MS ESI m/z 459.1 (M+H)

¹H NMR (500 MHz, DMSO-d₆) δ 10.31 (s, 1H), 8.79 (s, 1H), 8.59 (d, J=2.0 Hz, 1H), 8.15 (s, 1H), 8.01 (s, 1H), 7.89 (br s, 2H), 7.64 (s, 1H), 7.45-7.20 (m, 5H), 6.91 (s, 1H), 5.31 (s, 2H), 4.04 (s, 3H).

Example 63: (S)-5-(4-amino-5-(aminomethyl)pyrrolo[2,1-f][1,2,4]triazin-7-yl)-N-(3-(4-chlorophenyl)-3-hydroxypropyl)-2-methoxynicotinamide

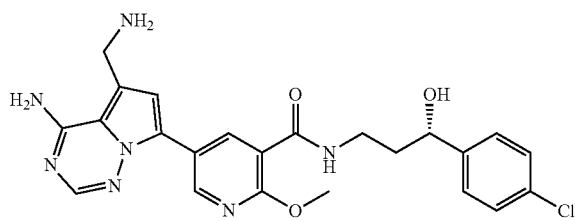 [SMILES: COc1ncc(-c2cc(CN)c3c(N)ncnn23)cc1C(=O)NCC[C@H](O)c1ccc(Cl)cc1]

A mixture of (S)-5-bromo-N-(3-(4-chlorophenyl)-3-hydroxypropyl)-2-methoxynicotinamide (25 mg, 0.063 mmol), 4,4,4',4',5,5,5',5'-octamethyl-2,2'-bi(1,3,2-dioxaborolane) (19.67 mg, 0.077 mmol), potassium acetate (19.01 mg, 0.194 mmol) in 1,4-dioxane (2 mL) was degassed and back-filled with N2. 1,1'-Bis(diphenylphosphino)ferrocene-palladium(II)dichloride dichloromethane complex (5.27 mg, 6.46 µmol) was added and the solution was degassed and back-filled with N₂ three times. The reaction mixture was then heated at 100° C. for 6 h. The mixture was cooled to room temperature and 5-(aminomethyl)-7-bromopyrrolo[2,1-f][1,2,4]triazin-4-amine (15.14 mg, 0.063 mmol), potassium phosphate tribasic (0.097 mL, 0.194 mmol) (2M in water), 1,1'-bis(diphenylphosphino)ferrocene-palladium(II) dichloride dichloromethane complex (5.27 mg, 6.46 µmol) was added. The reaction mixture was heated at 100° C. for 5 h. The mixture was cooled to room temperature and filtered through celite. The crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 7-47% B over 20 minutes, then a 6-minute hold at 100% B; Flow: 20 mL/min. Fractions containing the desired product were combined and dried via centrifugal evaporation to obtain (S)-5-(4-amino-5-(aminomethyl)pyrrolo[2,1-f][1,2,4]triazin-7-yl)-N-(3-(4-chlorophenyl)-3-hydroxypropyl)-2-methoxynicotinamide (4.7 mg, 9.75 µmol, 16% yield).

MS ESI m/z 482.0 (M+H)

1H NMR (500 MHz, DMSO-d6) δ 9.10-8.84 (m, 1H), 8.82-8.54 (m, 1H), 8.50-8.31 (m, 1H), 8.05-7.69 (m, 1H), 7.43-7.35 (m, 4H), 7.16-7.11 (m, 1H), 4.79-4.67 (m, 1H), 4.32-4.26 (m, 2H), 4.06 (s, 3H), 3.48-3.32 (m, 2H), 1.98-1.80 (m, 2H).

Example 64: (7-(5-(((3R,4S)-1-(3,3-difluorocyclobutane-1-carbonyl)-4-fluoropyrrolidin-3-yl)carbamoyl)-6-methoxypyridin-3-yl)-4-imino-5-(trifluoromethyl)pyrrolo[2,1-f][1,2,4]triazin-3(4H)-yl) methyl dihydrogen phosphate

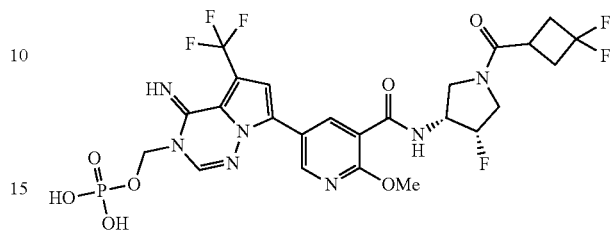

To a mixture of 5-(4-amino-5-(trifluoromethyl)pyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide (300 mg, 0.538 mmol), potassium iodide (313 mg, 1.884 mmol), and potassium carbonate (223 mg, 1.614 mmol) in acetonitrile (6 mL) was added di-tert-butyl (chloromethyl) phosphate (487 mg, 1.884 mmol) and the mixture was heated at 55° C. for 15 h. It was then cooled to rt and filtered through a pad of celite and washed with about 100 ml of acetonitrile. The filtrate was then concentrated in vacuum to obtain a yellow oil. The above yellow oil was dissolved in 3 mL of acetone and 3 mL of water. The resulting mixture was heated at 50° C. for 2 h. The solution turned from yellow to light yellow. It was then filtered and purified by a preparative HPLC. Column: waters sunfire prep C18 OBD, 5 mM 30×150 mm, solvent: A; 10% MeCN/90% water, 0.1% TFA; solvent B; 90% MeCN/10% water, 0.1% TFA; flow rate: 50 mL/min; Gradient: 10% B-60% B over 15 min, 60% B-100% B over 0.5 min, then hold at 100% B for 3.5 min. The fractions containing the desired product were collected and dried by a lyophilizer to obtain (7-(5-(((3R,4S)-1-(3,3-difluorocyclobutane-1-carbonyl)-4-fluoropyrrolidin-3-yl)carbamoyl)-6-methoxypyridin-3-yl)-4-imino-5-(trifluoromethyl)pyrrolo[2,1-f][1,2,4]triazin-3(4H)-yl)methyl dihydrogen phosphate (145 mg, 0.217 mmol, 56.5% yield) as a white solid.

MS ESI m/z 668.0 (M+H)

1H NMR (500 MHz, CD₃OD) δ 8.96-8.86 (m, 2H), 8.59-8.50 (m, 1H), 7.76-7.66 (m, 1H), 5.97-5.89 (m, 2H), 5.43-5.22 (m, 1H), 4.98-4.74 (m, 1H), 4.22-4.17 (m, 3H), 4.17-4.09 (m, 1H), 3.98-3.69 (m, 2H), 3.53-3.35 (m, 1H), 3.27-3.17 (m, 1H), 2.91-2.79 (m, 4H).

Example 65: 5-[4-amino-5-(trifluoromethyl)pyrrolo[2,1-f][1,2,4]triazin-7-yl]-N-(1-benzyl-1H-pyrazol-4-yl)-2-methoxybenzamide

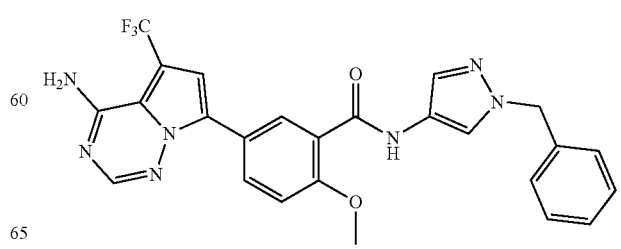

65A: 5-(4-amino-5-(trifluoromethyl)pyrrolo[2,1-f][1,2,4]triazin-7-yl)-2-methoxybenzoic acid:

To a solution of 7-bromo-5-(trifluoromethyl)pyrrolo[2,1-f][1,2,4]triazin-4-amine (200 mg, 0.712 mmol) and 5-borono-2-methoxybenzoic acid (167 mg, 0.854 mmol) in DMF (3 mL) was added potassium phosphate tribasic (1.067 mL, 2.135 mmol) (2M in $H_2O$). The reaction mixture was degassed by nitrogen sparge (5 min). $PdCl_2$(dppf)-$CH_2Cl_2$ adduct (58.1 mg, 0.071 mmol) was added and the nitrogen sparge maintained for another 5 min. The reaction vessel was sealed and heated to 90° C. for 12 h. Methanol was added and the solid product isolated to yield 5-(4-amino-5-(trifluoromethyl)pyrrolo[2,1-f][1,2,4]triazin-7-yl)-2-methoxybenzoic acid (160 mg, 0.431 mmol, 60.6% yield) as a white solid.

MS ESI m/z 353.1 (M+H)

1H NMR (400 MHz, $CD_3OD$) d 8.46 (d, J=2.3 Hz, 1H), 8.21-8.15 (m, 1H), 8.03 (s, 1H), 7.21 (d, J=2.6 Hz, 2H), 4.01 (s, 3H).

65: To a solution of 5-(4-amino-5-(trifluoromethyl)pyrrolo[2,1-f][1,2,4]triazin-7-yl)-2-methoxybenzoic acid (20 mg, 0.057 mmol) and 1-benzyl-1H-pyrazol-4-amine (14.75 mg, 0.085 mmol) in DMF (1 mL) was added DIEA (0.030 mL, 0.170 mmol) and BOP (27.6 mg, 0.062 mmol). The mixture was stirred at rt for 15 min. The crude material was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-75% B over 20 minutes, then a 5-minute hold at 100% B; Flow: 20 mL/min. Fractions containing the desired product were combined and dried via centrifugal evaporation to afford 5-[4-amino-5-(trifluoromethyl)pyrrolo[2,1-f][1,2,4]triazin-7-yl]-N-(1-benzyl-1H-pyrazol-4-yl)-2-methoxybenzamide (1.5 mg, 0.020 mmol, 35%).

MS ESI m/z 508.0 (M+H)

1H NMR (500 MHz, DMSO-d6) δ 10.23 (s, 1H), 8.32 (s, 1H), 8.16-8.05 (m, 3H), 7.62 (s, 1H), 7.46 (s, 1H), 7.40-7.21 (m, 6H), 5.29 (s, 2H), 3.92 (s, 2H).

Example 66: 5-{4-amino-5-fluoropyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide

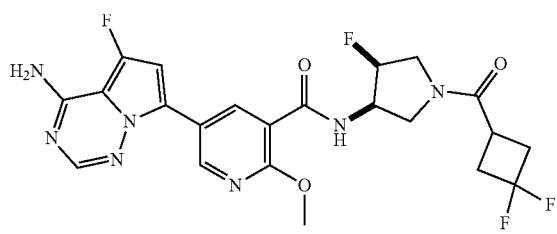

To a solution of 5-(4-amino-5-fluoropyrrolo[2,1-f][1,2,4]triazin-7-yl)-N-((3R,4S)-4-fluoropyrrolidin-3-yl)-2-methoxynicotinamide, 1.0 TFA (14 mg, 0.028 mmol), 3,3-difluorocyclobutane-1-carboxylic acid (3.79 mg, 0.028 mmol) and DIPEA (0.017 mL, 0.097 mmol) in DMF (1 mL) was added BOP (14.76 mg, 0.033 mmol). The reaction mixture was stirred at rt 2 h. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 9-49% B over 20 minutes, then a 4-minute hold at 100% B; Flow: 20 mL/min. Fractions containing the desired product were combined and dried via centrifugal evaporation to provide 5-{4-amino-5-fluoropyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide, TFA (8.7 mg, 0.013 mmol, 46%)

MS ESI m/z 508.1 (M+H)

1H NMR (500 MHz, DMSO-d6) δ 8.89 (d, J=1.8 Hz, 1H), 8.82-8.71 (m, 1H), 8.54 (br dd, J=7.0, 4.9 Hz, 1H), 7.90 (s, 1H), 7.09 (s, 1H), 5.44-5.16 (m, 1H), 4.87-4.57 (m, 1H), 4.03 (d, J=6.4 Hz, 3H), 3.99-3.23 (m, 4H), 3.17 (s, 1H), 2.93-2.63 (m, 4H).

Example 67: 5-(4-amino-5-(trifluoromethyl)pyrrolo[2,1-f][1,2,4]triazin-7-yl)-N-((3R,4S)-1-(3,3-difluorocyclobutane-1-carbonyl)-4-fluoropyrrolidin-3-yl)-4-fluoro-2-methylbenzamide

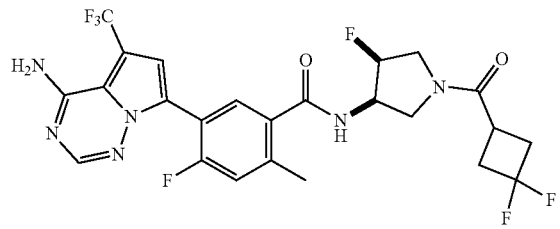

67A: methyl 5-(4-(bis(4-methoxybenzyl)amino)-5-(trifluoromethyl)pyrrolo[2,1-f][1,2,4]triazin-7-yl)-4-fluoro-2-methylbenzoate: A degassed solution of methyl 4-fluoro-2-methyl-5-(4,4,5,5-tetramethyl-1,3,2-dioxaborolan-2-yl)benzoate (174 mg, 0.591 mmol), tripotassium phosphate (2 M in water) (0.806 mL, 1.611 mmol), 1,1'-bis(diphenylphosphino)ferrocene palladium dichloride —$CH_2Cl_2$ adduct (43.9 mg, 0.054 mmol) and 7-bromo-N,N-bis(4-methoxybenzyl)-5-(trifluoromethyl)pyrrolo[2,1-f][1,2,4]triazin-4-amine (280 mg, 0.537 mmol) in DMF (10 mL) was divided into 4 equal portions which were stirred at 135° C. for 60 min under microwave. The reaction mixture was diluted with EtOAc (150 mL) which was washed with 10% lithium chloride solution (50×2 mL) and brine (50 mL) and dried over $Na_2SO_4$. Filtration and concentration yielded crude product which was purified on silica gel column with Hexanes/EtOAc (100/0 to 80/20) to yield methyl 5-(4-(bis(4-methoxybenzyl)amino)-5-(trifluoromethyl)pyrrolo[2,1-f][1,2,4]triazin-7-yl)-4-fluoro-2-methylbenzoate (232.5 mg, 0.359 mmol, 66.9% yield).

MS ESI m/z 609.2 (M+H)

1H NMR (400 MHz, $CDCl_3$) δ 8.53 (d, J=7.6 Hz, 1H), 8.16 (s, 1H), 7.05-6.97 (m, 5H), 6.87 (d, J=8.6 Hz, 5H), 4.64 (s, 4H), 3.94 (s, 3H), 3.83 (s, 6H), 2.71 (s, 3H). 67B: methyl 5-(4-amino-5-(trifluoromethyl)pyrrolo[2,1-f][1,2,4]triazin-7-yl)-4-fluoro-2-methylbenzoate: A solution of methyl 5-(4-(bis(4-methoxybenzyl)amino)-5-(trifluoromethyl)pyrrolo[2,1-f][1,2,4]triazin-7-yl)-4-fluoro-2-methylbenzoate (232 mg, 0.381 mmol) in TFA (2 mL) was heated to 130° C. for 25 min under microwave. The reaction mixture was concentrated and diluted with water (50 mL). The organics were washed with 1.5M Na$_2$HPO$_4$ solution (20 mL×2), water (20 mL) and brine (20 mL).

The organics were dried over anhydrous sodium sulfate, filtered and concentrated in vacuo to yield a crude product which was purified on silica gel column with Hexanes/EtOAc (100/0 to 20/80) to yield methyl 5-(4-amino-5-(trifluoromethyl)pyrrolo[2,1-f][1,2,4]triazin-7-yl)-4-fluoro-2-methylbenzoate (151 mg, 0.398 mmol, 104% yield).

MS ESI m/z 375.1 (M+H)

1H NMR (400 MHz, DMSO-d6) δ 8.32 (d, J=7.6 Hz, 1H), 8.12 (s, 1H), 7.42 (d, J=11.3 Hz, 1H), 7.37 (s, 1H), 3.84 (s, 3H), 2.61 (s, 3H).

67C: sodium 5-(4-amino-5-(trifluoromethyl)pyrrolo[2,1-f][1,2,4]triazin-7-yl)-4-fluoro-2-methylbenzoate, sodium salt: A solution of methyl 5-(4-amino-5-(trifluoromethyl)pyrrolo[2,1-f][1,2,4]triazin-7-yl)-4-fluoro-2-methylbenzoate (151 mg, 0.410 mmol) and NaOH 1 M solution (0.615 mL, 0.615 mmol) in MeOH (2 mL) was heated to 100° C. under microwave for 30 min. The reaction mixture was concentrated to yield sodium 5-(4-amino-5-(trifluoromethyl)pyrrolo[2,1-f][1,2,4]triazin-7-yl)-4-fluoro-2-methylbenzoate, sodium salt (151 mg, 0.401 mmol, 98% yield).

67D: tert-butyl (3R,4S)-3-(5-(4-amino-5-(trifluoromethyl)pyrrolo[2,1-f][1,2,4]triazin-7-yl)-4-fluoro-2-methylbenzamido)-4-fluoropyrrolidine-1-carboxylate: To a solution of 5-(4-amino-5-(trifluoromethyl)pyrrolo[2,1-f][1,2,4]triazin-7-yl)-4-fluoro-2-methylbenzoic acid, sodium salt (151 mg, 0.426 mmol), tert-butyl (3R,4S)-3-amino-4-fluoropyrrolidine-1-carboxylate (96 mg, 0.469 mmol) and DIPEA (0.223 mL, 1.279 mmol) in DMF (3 mL) was added BOP (226 mg, 0.511 mmol). The reaction mixture was stirred at rt 2 h. The reaction mixture was diluted with EtOAc (80 mL) which was washed with 10% lithium chloride solution (30×2 mL) and brine (30 mL). The organics were dried over Na$_2$SO$_4$. Filtration and concentration yielded a crude product which was purified on a silica gel column with Hexanes/EtOAc (100/0 to 20/80) to yield tert-butyl (3R,4S)-3-(5-(4-amino-5-(trifluoromethyl)pyrrolo[2,1-f][1,2,4]triazin-7-yl)-4-fluoro-2-methylbenzamido)-4-fluoropyrrolidine-1-carboxylate (163.7 mg, 0.303 mmol, 71.1% yield).

MS ESI m/z 542.1 (M+H).

67E: 5-(4-amino-5-(trifluoromethyl)pyrrolo[2,1-f][1,2,4]triazin-7-yl)-4-fluoro-N-((3R,4S)-4-fluoropyrrolidin-3-yl)-2-methylbenzamide, TFA: A solution of tert-butyl (3R,4S)-3-(5-(4-amino-5-(trifluoromethyl)pyrrolo[2,1-f][1,2,4]triazin-7-yl)-4-fluoro-2-methylbenzamido)-4-fluoropyrrolidine-1-carboxylate (163.7 mg, 0.303 mmol) in TFA (2 mL) was stirred at 23° C. for 1 h. The reaction mixture was concentrated and triturated with ether (10 mL). The solid was collected as 5-(4-amino-5-(trifluoromethyl)pyrrolo[2,1-f][1,2,4]triazin-7-yl)-4-fluoro-N-((3R,4S)-4-fluoropyrrolidin-3-yl)-2-methylbenzamide, TFA (150 mg, 0.271 mmol, 89% yield).

MS ESI m/z 441.0.

67: To a solution of 5-(4-amino-5-(trifluoromethyl)pyrrolo[2,1-f][1,2,4]triazin-7-yl)-4-fluoro-N-((3R,4S)-4-fluoropyrrolidin-3-yl)-2-methylbenzamide, TFA (15 mg, 0.027 mmol), 3,3-difluorocyclobutane-1-carboxylic acid (4.05 mg, 0.030 mmol) and DIPEA (0.024 mL, 0.135 mmol) in DMF (1 mL) was added BOP (14.36 mg, 0.032 mmol). The reaction mixture was stirred at rt 2 h. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 26% B, 26-66% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to provide 5-(4-amino-5-(trifluoromethyl)pyrrolo[2,1-f][1,2,4]triazin-7-yl)-N-((3R,4S)-1-(3,3-difluorocyclobutane-1-carbonyl)-4-fluoropyrrolidin-3-yl)-4-fluoro-2-methylbenzamide (6.4 mg, 0.011 mmol, 42%).

MS ESI m/z 559.3 (M+H)

1H NMR (500 MHz, DMSO-d6) δ 8.56 (br dd, J=14.6, 7.1 Hz, 1H), 8.08 (s, 1H), 7.82-7.75 (m, 1H), 7.34-7.24 (m, 2H), 5.39-5.13 (m, 1H), 4.76-4.45 (m, 1H), 3.95-3.78 (m, 2H), 3.77-3.56 (m, 2H), 3.21-3.03 (m, 1H), 2.89-2.67 (m, 4H), 2.44 (d, J=2.7 Hz, 3H).

Example 68: 5-{4-amino-5-[(2-acetamidoethyl)carbamoyl]pyrrolo[2,1-f][1,2,4]triazin-7-yl}-N-[(3S)-3-(4-chlorophenyl)-3-hydroxypropyl]-2-methoxypyridine-3-carboxamide

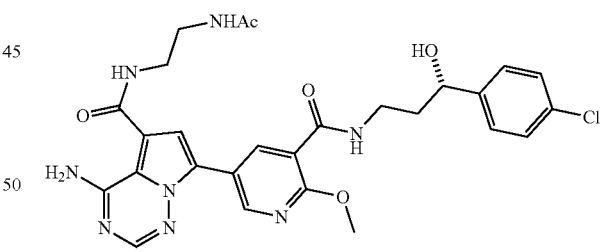

68A: (S)-5-bromo-N-(3-(4-chlorophenyl)-3-hydroxypropyl)-2-methoxynicotinamide: A solution of 5-bromo-2-methoxynicotinic acid (0.50 g, 2.155 mmol), BOP (1.144 g, 2.59 mmol), (S)-3-amino-1-(4-chlorophenyl)propan-1-ol (0.527 g, 2.370 mmol), and triethylamine (1.051 ml, 7.54 mmol) in DMF (10.77 ml) was stirred at rt 75 min. DMF was removed under vacuum. EtOAc and 10% aq LiCl solution were added. The layers were separated, and the EtOAc layer was washed with 10% aq LiCl solution, sat. aq NaHCO₃ solution, brine, dried over Na₂SO₄ and evaporated under vacuum to yield a tan-brown oil (1.56 g). The crude product was dissolved in CH₂Cl₂ and purified by flash column chromatography (Teledyne-Isco RediSep Rf 24 g column; eluting with 0-100% EtOAc in hexanes) to yield (S)-5-bromo-N-(3-(4-chlorophenyl)-3-hydroxypropyl)-2-methoxynicotinamide (0.785 g, 91%) as a white solid.

MS ESI m/z 402.9 (M+H)

68B: (S)—N-(3-(4-chlorophenyl)-3-hydroxypropyl)-2-methoxy-5-(4,4,5,5-tetramethyl-1,3,2-dioxaborolan-2-yl)nicotinamide: A mixture of (S)-5-bromo-N-(3-(4-chlorophenyl)-3-hydroxypropyl)-2-methoxynicotinamide (0.7847 g, 1.963 mmol), 4,4,4',4',5,5,5',5'-octamethyl-2,2'-bi(1,3,2-dioxaborolane) (0.598 g, 2.356 mmol), and potassium acetate (0.289 g, 2.95 mmol) in dioxane (9.67 ml) was degassed (4×) with vacuum/nitrogen. 1,1'-Bis(diphenylphosphino)ferrocene palladium dichloride —CH₂Cl₂ adduct (0.160 g, 0.1% mmol) was added, and the mixture was vacuum/nitrogen degassed again (2×). The reaction mixture was immersed in an oil bath at 80° C. and stirred ON. After cooling to rt, the reaction mixture was filtered through Celite, rinsing with dioxane. The filtrate was evaporated to dryness under vacuum. Ether was added, followed by a 2-minute sonication. The mixture was filtered through Celite and the filtrate was evaporated under vacuum to yield a brown oil (1.57 g). The crude product was dissolved in CH₂Cl₂ and filtered through a 25 mm syringe filter with a 0.45 micron Nylon membrane. Flash chromatography on silica gel (Teledyne-Isco RediSep Rf 40 g column; eluting with 0-100% EtOAc in hexanes) yielded (S)—N-(3-(4-chlorophenyl)-3-hydroxypropyl)-2-methoxy-5-(4,4,5,5-tetramethyl-1,3,2-dioxaborolan-2-yl)nicotinamide (0.492 g, 1.102 mmol, 56%) as an off-white solid.

MS ESI m/z 447.1/449.1 (M+H).

68C: ethyl (S)-4-amino-7-(5-((3-(4-chlorophenyl)-3-hydroxypropyl)carbamoyl)-6-methoxypyridin-3-yl)pyrrolo[2,1-f][1,2,4]triazine-5-carboxylate: A combination of ethyl 4-amino-7-bromopyrrolo[2,1-f][1,2,4]triazine-5-carboxylate (0.262 g, 0.92 mmol) and (S)—N-(3-(4-chlorophenyl)-3-hydroxypropyl)-2-methoxy-5-(4,4,5,5-tetramethyl-1,3,2-dioxaborolan-2-yl)nicotinamide (0.4921 g, 1.102 mmol) in tripotassium phosphate (2.0 M aq solution) (1.380 ml, 2.76 mmol) was degassed with N₂. 1,1'-Bis(diphenylphosphino)ferrocene-palladium(ii)dichloride dichloromethane complex (0.075 g, 0.092 mmol) was added, followed by more degassing. The reaction mixture was heated at 105° C. for 2.5 h. The reaction mixture was diluted with EtOAc (25 mL).

The layers were separated, and the organics were washed with saturated aqueous sodium bicarbonate (2×) and brine, dried over Na₂SO₄, filtered and evaporated under vacuum to yield an oil (0.48 g). The crude product was suspended in ether and sonicated for 2 min. The solid was collected by filtration, rinsed with ether, and dried under vacuum to yield a pale green solid. The product was triturated with methanol (including the ether filtrate stripped of ether) to yield ethyl (S)-4-amino-7-(5-((3-(4-chlorophenyl)-3-hydroxypropyl)carbamoyl)-6-methoxypyridin-3-yl)pyrrolo[2,1-f][1,2,4]triazine-5-carboxylate (0.327 g, 0.623 mmol, 68%) as a pale gray powder.

MS ESI m/z 525.0/527.0 (M+H)

1H NMR (400 MHz, DMSO-d6) δ 9.25-9.11 (m, 1H), 8.88 (br s, 1H), 8.72 (s, 1H), 8.57-8.37 (m, 2H), 8.12 (s, 1H), 7.56 (s, 1H), 7.40 (s, 4H), 5.52 (br d, J=3.9 Hz, 1H), 4.72 (br d, J=3.2 Hz, 1H), 4.37 (q, J=7.1 Hz, 2H), 4.04 (s, 3H), 3.39 (br d, J=5.6 Hz, 2H), 2.01-1.73 (m, 2H), 1.37 (br t, J=7.0 Hz, 3H).

68D: (S)-4-amino-7-(5-((3-(4-chlorophenyl)-3-hydroxypropyl)carbamoyl)-6-methoxypyridin-3-yl)pyrrolo[2,1-f][1,2,4]triazine-5-carboxylic acid: A thick suspension of ethyl (S)-4-amino-7-(5-((3-(4-chlorophenyl)-3-hydroxypropyl)carbamoyl)-6-methoxypyridin-3-yl)pyrrolo[2,1-f][1,2,4]triazine-5-carboxylate (0.327 g, 0.623 mmol) in THF (1.87 mL), ethanol (1.87 mL) and sodium hydroxide (1.0 N) (1.869 mL, 1.869 mmol) was stirred at rt for 16 h. The reaction solution was immersed in a 0° C. ice bath and 1N HCl was slowly added until a pH of 7 was reached. The precipitate was collected by filtration, rinsed with water and dried under vacuum. The filtrate was concentrated under vacuum to remove ethanol and THF, and a second crop was collected and combined with the first crop. The solid was suspended in ether, sonicated for 2 minutes, collected by filtration, rinsed with ether and dried under vacuum to yield (S)-4-amino-7-(5-((3-(4-chlorophenyl)-3-hydroxypropyl)carbamoyl)-6-methoxypyridin-3-yl)pyrrolo[2,1-f][1,2,4]triazine-5-carboxylic acid (0.241 g, 0.485 mmol, 78%) as a pale tan solid.

MS ESI m/z 497.0/499.0 (M+H)

1H NMR (400 MHz, DMSO-d6) δ 9.92-9.58 (m, 1H), 8.85 (d, J=2.3 Hz, 1H), 8.75 (d, J=2.2 Hz, 1H), 8.51 (br t, J=5.2 Hz, 1H), 8.33 (br s, 1H), 8.08 (s, 1H), 7.50 (s, 1H), 7.40 (s, 4H), 5.52 (br d, J=3.1 Hz, 1H), 4.71 (br s, 1H), 4.04 (s, 3H), 3.44-3.39 (m, 2H), 1.86 (dt, J=14.6, 7.2 Hz, 2H).

68: A solution of (S)-4-amino-7-(5-((3-(4-chlorophenyl)-3-hydroxypropyl)carbamoyl)-6-methoxypyridin-3-yl)pyrrolo[2,1-f][1,2,4]triazine-5-carboxylic acid (10.0 mg, 0.020 mmol), BOP (10.68 mg, 0.024 mmol), N-(2-aminoethyl)acetamide (2.261 mg, 0.022 mmol) and triethylamine (9.82 µl, 0.070 mmol) in DMF (201 µl) was stirred at rt for 16 h. The reaction mixture was diluted with methanol and filtered through a syringe filter with a 0.45 micron Nylon membrane. The crude material was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 18-58% B over 20 minutes, then a 4-minute hold at 100% B; Flow: 20 mL/min. Fractions containing the desired product were combined and dried via centrifugal evaporation to yield (S)—N-(2-acetamidoethyl)-4-amino-7-(5-((3-(4-chlorophenyl)-3-hydroxypropyl)carbamoyl)-6-methoxypyridin-3-yl)pyrrolo[2,1-f][1,2,4]triazine-5-carboxamide (3.3 mg, 28%).

MS ESI m/z 581.1 (M+H)

1H NMR (500 MHz, DMSO-d6) δ 10.46-10.18 (m, 1H), 8.94 (d, J=2.1 Hz, 1H), 8.75 (br t, J=5.3 Hz, 1H), 8.67 (d, J=2.4 Hz, 1H), 8.55 (br t, J=5.3 Hz, 1H), 8.19 (br s, 1H), 8.04 (br t, J=5.6 Hz, 1H), 8.02 (s, 1H), 7.72 (s, 1H), 7.39 (s, 4H), 4.71 (br s, 1H), 4.05 (s, 3H), 3.49-3.42 (m, 1H), 3.42-3.31 (m, 2H), 3.25 (q, J=6.3 Hz, 2H), 1.94-1.85 (m, 2H), 1.83 (s, 3H).

TABLE 1

Compounds in Table 1 were prepared by the methods detailed in Examples 4 and 61. Compounds are racemic.

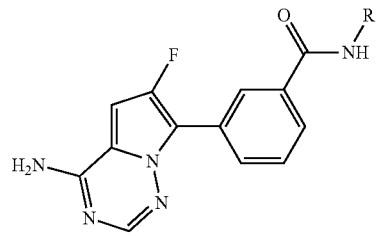

| Ex | Name | R | Obs. MS Ion | NMR Assignments (500 MHz, DMSO-d6) δ |
|---|---|---|---|---|
| 69 | 3-{4-amino-6-fluoropyrrolo[2,1-f][1,2,4]triazin-7-yl}-N-(3-phenylbutyl)benzamide | | 404.2 | 8.50 (br t, J = 5.2 Hz, 1H), 8.34-8.28 (m, 1H), 8.06-7.96 (m, 2H), 7.86 (br s, 2H), 7.78 (br d, J = 7.7 Hz, 1H), 7.62-7.54 (m, 1H), 7.34-7.22 (m, 4H), 7.21-7.12 (m, 1H), 6.96-6.86 (m, 1H), 3.53-3.47 (m, 1H), 3.26-3.08 (m, 2H), 2.85-2.74 (m, 1H), 2.55 (m, 3H), 1.87-1.77 (m, 2H) |
| 70 | 3-{4-amino-6-fluoropyrrolo[2,1-f][1,2,4]triazin-7-yl}-N-(3-hydroxy-3-phenylpropyl)benzamide | | 405.9 | 8.58-8.51 (m, 1H), 8.33-8.28 (m, 1H), 8.05-7.95 (m, 2H), 7.88-7.80 (m, 2H), 7.79-7.73 (m, 1H), 7.64-7.55 (m, 1H), 7.40-7.27 (m, 4H), 7.25-7.17 (m, 1H), 6.93-6.86 (m, 1H), 5.46-5.40 (m, 1H), 4.68-4.58 (m, 1H), 3.39-3.29 (m, 2H), 1.93-1.82 (m, 2H) |
| 71 | 3-{4-amino-6-fluoropyrrolo[2,1-f][1,2,4]triazin-7-yl}-N-(1-benzyl-1H-pyrazol-4-yl)benzamide | | 428.2 | 10.64-10.58 (m, 1H), 8.41 (s, 1H), 8.17-8.12 (m, 1H), 8.06 (br d, J = 7.7 Hz, 1H), 7.99 (s, 1H), 7.92-7.79 (m, 3H), 7.68-7.60 (m, 2H), 7.39-7.22 (m, 5H), 6.94-6.88 (m, 1H), 5.33-5.25 (m, 2H) |

TABLE 2

Compounds in Table 2 were prepared by the methods detailed in Example 2. In cases were a tertiary amide was generated, the entire amine will be delineated. When diastereomers were separated, they are included as separate entries.

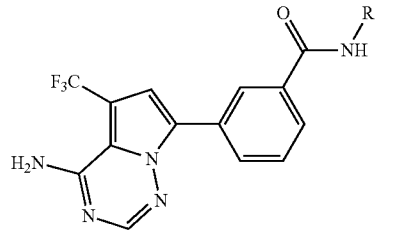

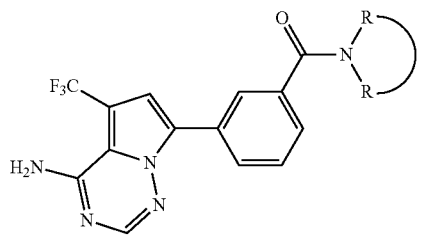

| Ex | Name | R | Obs. MS Ion | NMR Assignments (500 MHz, DMSO-d6) δ |
|---|---|---|---|---|
| 72 | 3-[4-amino-5-(trifluoromethyl)pyrrolo[2,1-f][1,2,4]triazin-7-yl]-N-(3-hydroxy-3-phenylpropyl)benzamide | | 455.9 | 8.55 (br t, J = 5.1 Hz, 1H), 8.39 (s, 1H), 8.22 (br d, J = 7.7 Hz, 1H), 8.16 (s, 1H), 7.83 (br d, J = 7.6 Hz, 1H), 7.62-7.52 (m, 2H), 7.40-7.28 (m, 4H), 7.27-7.17 (m, 1H), 4.70-4.61 (m, 1H), 3.53-3.49 (m, 2H), 3.40-3.31 (m, 1H), 1.95-1.83 (m, 2H) |
| 73 | 3-[4-amino-5-(trifluoromethyl)pyrrolo[2,1-f][1,2,4]triazin-7-yl]-N-[(3R)-3-(4-chlorophenyl)-3-hydroxypropyl]benzamide | | 489.9 | 8.55 (br s, 1H), 8.40 (br s, 1H), 8.27-8.13 (m, 2H), 7.83 (br d, J = 5.3 Hz, 1H), 7.57 (br s, 2H), 7.38 (br s, 4H), 4.66 (br s, 1H), 2.59-2.53 (m, 1H), 1.96-1.81 (m, 2H) (peaks lost with solvent suppression) |
| 74 | 3-[4-amino-5-(trifluoromethyl)pyrrolo[2,1-f][1,2,4]triazin-7-yl]-N-[3-(4-fluorophenyl)-3-hydroxypropyl]benzamide | | 474.2 | 8.60-8.51 (m, 1H), 8.45-8.36 (m, 1H), 8.27-8.20 (m, 1H), 8.17 (s, 1H), 7.90-7.80 (m, 1H), 7.65-7.54 (m, 2H), 7.45-7.36 (m, 2H), 7.14 (br t, J = 8.8 Hz, 2H), 5.46-5.37 (m, 1H), 4.70-4.61 (m, 1H), 3.49-3.29 (m, 1H), 1.93-1.82 (m, 2H) |
| 75 | 3-[4-amino-5-(trifluoromethyl)pyrrolo[2,1-f][1,2,4]triazin-7-yl]-N-[1-(cyclopropylmethyl)-1H-pyrazol-4-yl]benzamide | | 441.9 | 10.56-10.52 (m, 1H), 8.57-8.51 (m, 1H), 8.26 (br d, J = 7.7 Hz, 1H), 8.19 (s, 1H), 8.13 (s, 1H), 7.95 (br d, J = 7.7 Hz, 1H), 7.70-7.58 (m, 3H), 3.96 (br d, J = 7.1 Hz, 2H), 1.28-1.19 (m, 1H), 0.58-0.50 (m, 2H), 0.40-0.32 (m, 2H) |

TABLE 2-continued

Compounds in Table 2 were prepared by the methods detailed in Example 2. In cases were a tertiary amide was generated, the entire amine will be delineated. When diastereomers were separated, they are included as separate entries.

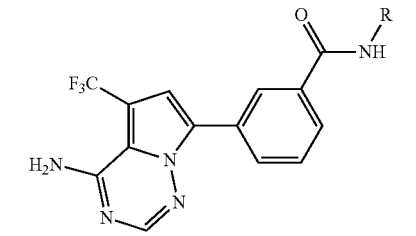

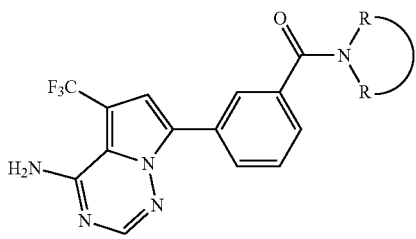

| Ex | Name | R | Obs. MS Ion | NMR Assignments (500 MHz, DMSO-d6) δ |
|---|---|---|---|---|
| 76 | 3-[4-amino-5-(trifluoromethyl)pyrrolo[2,1-f][1,2,4]triazin-7-yl]-N-(1-benzyl-1H-pyrazol-4-yl)benzamide, 2 TFA | | 478.3 | 10.62-10.53 (m, 1H), 8.51 (s, 1H), 8.24 (br d, J = 7.7 Hz, 1H), 8.11 (s, 2H), 7.98-7.90 (m, 1H), 7.70-7.61 (m, 2H), 7.59 (s, 1H), 7.40-7.22 (m, 5H), 5.32 (s, 2H) |
| 77 | 3-[4-amino-5-(trifluoromethyl)pyrrolo[2,1-f][1,2,4]triazin-7-yl]-N-[(3S)-3-(4-chlorophenyl)-3-hydroxypropyl]benzamide | | 490.1 | 8.60-8.53 (m, 1H), 8.43-8.33 (m, 1H), 8.26-8.13 (m, 2H), 7.87-7.78 (m, 1H), 7.64-7.51 (m, 2H), 7.37 (br s, 4H), 5.55-5.45 (m, 1H), 4.71-4.60 (m, 1H), 3.41-3.31 (m, 1H), 1.93-1.80 (m, 2H) |
| 78 | 3-[4-amino-5-(trifluoromethyl)pyrrolo[2,1-f][1,2,4]triazin-7-yl]-N-[(3S)-1-benzylpyrrolidin-3-yl]benzamide | | 481.2 | 8.57 (br d, J = 6.9 Hz, 1H), 8.39 (s, 1H), 8.26-8.19 (m, 1H), 8.19-8.13 (m, 1H), 7.88-7.83 (m, 1H), 7.64-7.52 (m, 2H), 7.38-7.27 (m, 4H), 7.28-7.18 (m, 1H), 4.48-4.35 (m, 1H), 3.41-3.32 (m, 1H), 2.85 (s, 1H), 2.69-2.59 (m, 1H), 2.48-2.41 (m, 3H), 2.25-2.12 (m, 1H), 1.82 (br dd, J = 13.1, 7.1 Hz, 1H) |
| 79 | 3-[4-amino-5-(trifluoromethyl)pyrrolo[2,1-f][1,2,4]triazin-7-yl]-N-[(3S)-1-benzoylpyrrolidin-3-yl]benzamide | | 494.9 | 8.79-8.65 (m, 1H), 8.46-8.33 (m, 1H), 8.26-8.12(01, 2H), 7.93-7.76 (m, 1H), 7.65-7.39 (m, 7H), 4.61-4.35 (m, 1H), 3.86-3.67(01, 1H), 3.62-3.58 (m, 1H), 3.42-3.31 (m, 1H), 3.20-3.13 (m, 1H), 2.30-2.11 (m, 1H), 1.90 (s, 1H) |

TABLE 2-continued

Compounds in Table 2 were prepared by the methods detailed in Example 2. In cases were a tertiary amide was generated, the entire amine will be delineated. When diastereomers were separated, they are included as separate entries.

| Ex | Name | R | Obs. MS Ion | NMR Assignments (500 MHz, DMSO-d6) δ |
|---|---|---|---|---|
| 80 | 3-[4-amino-5-(trifluoromethyl)pyrrolo[2,1-f][1,2,4]triazin-7-yl]-N-[(3S)-1-benzylpiperidin-3-yl]benzamide | | 495.1 | 8.35 (s, 1H), 8.27 (br d, J = 7.9 Hz, 1H), 8.23-8.18 (m, 1H), 8.18-8.13 (m, 1H), 7.87-7.79 (m, 1H), 7.62-7.53 (m, 2H), 7.36-7.28 (m, 4H), 7.27-7.20 (m, 1H), 4.03-3.93 (m, 1H), 3.55-3.46 (m, 1H), 3.42-3.33 (m, 1H), 2.93-2.84 (m, 1H), 2.77-2.68 (m, 1H), 1.98-1.88 (m, 2H), 1.87-1.79 (m, 1H), 1.75-1.66 (m, 1H), 1.60-1.48 (m, 1H), 1.42-1.29 (m, 1H) |
| 81 | 7-{3-[(3R)-3-[(4-fluorophenyl)methyl]piperidine-1-carbonyl]phenyl}-5-(trifluoromethyl)pyrrolo[2,1-f][1,2,4]triazin-4-amine | | 498.2 | 8.22-8.12 (m, 1H), 8.11-8.01 (m, 2H), 8.00-7.90 (m, 1H), 7.61-7.48 (m, 2H), 7.47-7.33 (m, 1H), 7.31-7.18 (m, 2H), 7.16-7.05 (m, 1H), 7.02-6.88 (m, 1H), 6.65 (br s, 1H), 4.42-4.14 (m, 1H), 3.11-2.97 (m, 1H), 2.89-2.76 (m, 1H), 2.73-2.54 (m, 2H), 2.30-2.15 (m, 1H), 1.78 (m, 2H), 1.65-1.57 (m, 1H), 1.54-1.34 (m, 1H), 1.32-1.16 (m, 1H) |
| 82 | 7-{3-[(3S)-3-[(4-fluorophenyl)methyl]piperidine-1-carbonyl]phenyl}-5-(trifluoromethyl)pyrrolo[2,1-f][1,2,4]triazin-4-amine | | 497.9 | 8.16 (s, 1H), 8.12-8.02 (m, 2H), 8.00-7.93 (m, 1H), 7.54 (br s, 2H), 7.47-7.34 (m, 1H), 7.33-7.20 (m, 2H), 7.18-7.07 (m, 1H), 6.97 (br s, 1H), 6.73-6.61 (m, 1H), 4.45-4.29 (m, 1H), 3.62-3.50 (m, 1H), 3.11-2.98 (m, 1H), 2.89-2.77 (m, 1H), 2.74-2.56 (m, 2H), 2.30-2.18 (m, 1H), 1.79 (m, 2H), 1.61 (br s, 1H), 1.54-1.35 (m, 1H), 1.32-1.18 (m, 1H) |

TABLE 2-continued

Compounds in Table 2 were prepared by the methods detailed in Example 2. In cases were a tertiary amide was generated, the entire amine will be delineated. When diastereomers were separated, they are included as separate entries.

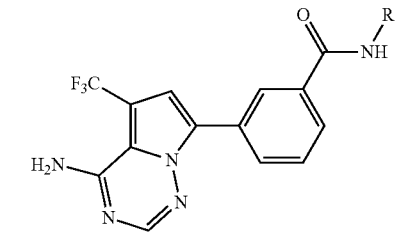

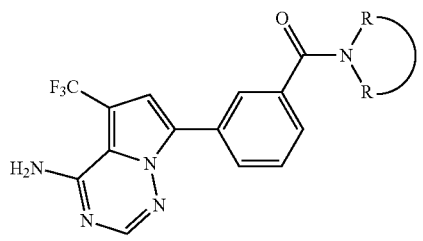

| Ex | Name | R | Obs. MS Ion | NMR Assignments (500 MHz, DMSO-d6) δ |
|----|------|---|-------------|--------------------------------------|
| 83 | 3-[4-amino-5-(trifluoromethyl)pyrrolo[2,1-f][1,2,4]triazin-7-yl]-N-[(3R,4S)-4-fluoro-1-(4-hydroxyoxane-4-carbonyl)pyrrolidin-3-yl]benzamide | | 537.4 | 8.77-8.65 (m, 1H), 8.44 (s, 1H), 8.24 (br d, J = 7.9 Hz, 1H), 8.16 (s, 1H), 7.90 (br d, J = 7.6 Hz, 1H), 7.61 (t, J = 7.9 Hz, 1H), 7.56 (s, 1H), 5.53 (s, 1H), 5.35-5.10 (m, 1H), 4.68-4.48 (m, 1H), 4.45-4.28 (m, 1H), 4.04-3.10 (m, 5H), 2.10-1.95 (m, 1H), 1.90-1.79 (m, 1H), 1.66-1.44 (m, 2H); 1 pyrrolidine CH not observed in full due to water suppression |
| 84 | 3-[4-amino-5-(trifluoromethyl)pyrrolo[2,1-f][1,2,4]triazin-7-yl]-N-[(3R,4S)-4-fluoro-1-(1-hydroxycyclopentanecarbonyl)pyrrolidin-3-yl]benzamide | | 521.2 | 8.75 (br dd, J = 18.9, 6.7 Hz, 1H), 8.43 (s, 1H), 8.23 (br d, J = 7.6 Hz, 1H), 8.15 (s, 1H), 7.91 (br d, J = 7.9 Hz, 1H), 7.62 (t, J = 7.8 Hz, 1H), 7.55 (s, 1H), 5.36 (s, 1H), 5.33-5.14 (m, 1H), 4.73-4.49 (m, 1H), 4.37-3.67 (m, 3H), 3.52 (br t, J = 11.0 Hz, 1H), 2.12 (br d, J = 6.7 Hz, 1H), 2.00-1.83 (m, 1H), 1.80-1.50 (m, 6H) |
| 85 | 3-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxypropanoyl]pyrrolidin-3-yl]benzamide | | 535.3 | 8.79 (br dd, J = 16.2, 7.0 Hz, 1H), 8.42 (br s, 1H), 8.22 (br d, J = 7.6 Hz, 1H), 8.14 (s, 1H), 7.89 (br d, J = 7.6 Hz, 1H), 7.61 (t, J = 7.8 Hz, 1H), 7.54 (s, 1H), 7.08-6.80 (m, 1H), 5.39-5.17 (m, 1H), 4.99-4.81 (m, 1H), 4.78-4.58 (m, 1H), 4.21 (br t, J = 9.3 Hz, 1H), 4.18-4.08 (m, 1H), 3.95-3.80 (m, 1H), 3.71-3.48 (m, 1H) |

TABLE 2-continued

Compounds in Table 2 were prepared by the methods detailed in Example 2. In cases were a tertiary amide was generated, the entire amine will be delineated. When diastereomers were separated, they are included as separate entries.

| Ex | Name | R | Obs. MS Ion | NMR Assignments (500 MHz, DMSO-d6) δ |
|---|---|---|---|---|
| 86 | 3-[4-amino-5-(trifluoromethyl)pyrrolo[2,1-f][1,2,4]triazin-7-yl]-N-[(3R,4S)-1-(3,4-difluorobenzoyl)-4-fluoropyrrolidin-3-yl]benzamide | | 549.2 | 8.75-8.52 (m, 1H), 8.48-8.33 (m, 1H), 8.21 (br s, 1H), 8.13 (br s, 1H), 7.88 (br d, J = 15.4 Hz, 1H), 7.60 (br s, 2H), 7.54-7.45 (m, 2H), 7.42 (br s, 1H), 5.48-5.08 (m, 1H), 4.90-4.53 (m, 1H), 4.08-3.59 (m, 4H) |
| 87 | 3-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl)benzamide, TFA | | 495.1 | 8.64-8.51 (m, 1H), 8.45 (br s, 1H), 8.24 (br d, J = 7.7 Hz, 1H), 8.16 (s, 1H), 7.92 (br d, J = 7.4 Hz, 1H), 7.60 (t, J = 7.8 Hz, 1H), 7.54 (s, 1H), 5.41-5.12 (m, 1H), 4.72-4.50 (m, 1H), 4.47-4.25 (m, 1H), 4.10-3.42 (m, 3H), 1.38-1.29 (m, 6H); water suppression is obscuring one pyrrolidine CH |
| 88 | 3-[4-amino-5-(trifluoromethyl)pyrrolo[2,1-f][1,2,4]triazin-7-yl]-N-[(3R,4S)-4-fluoro-1-(3-fluoro-2,2-dimethylpropanoyl)pyrrolidin-3-yl]benzamide | | 511.1 | 8.59 (br d, J = 6.2 Hz, 1H), 8.45 (br s, 1H), 8.24 (br d, J = 7.5 Hz, 1H), 8.16 (br s, 1H), 7.92 (br d, J = 7.3 Hz, 1H), 7.61 (t, J = 7.9 Hz, 1H), 7.53 (br s, 1H), 5.36-5.14 (m, 1H), 4.76-4.57 (m, 1H), 4.56-4.31 (m, 2H), 4.09-3.57 (m, 3H), 1.25 (br s, 3H), 1.23 (br s, 3H); water suppression is obscuring one pyrrolidine CH |
| 89 | 3-[4-amino-5-(trifluoromethyl)pyrrolo[2,1-f][1,2,4]triazin-7-yl]-N-[(3R,4S)-4-fluoro-1-(2-methylpropanoyl)pyrrolidin-3-yl]benzamide | | 479.1 | 8.69-8.56 (m, 1H), 8.42 (br s, 1H), 8.22 (br d, J = 8.1 Hz, 1H), 8.15-8.09 (m, 1H), 7.89 (br s, 1H), 7.64-7.57 (m, 1H), 7.51 (br s, 1H), 5.42-5.13 (m, 1H), 4.83-4.50 (m, 1H), 4.00 (br t, J = 9.2 Hz, 1H), 3.93-3.77 (m, 2H), 3.76-3.71 (m, 1H), |

TABLE 2-continued

Compounds in Table 2 were prepared by the methods detailed in Example 2. In cases were a tertiary amide was generated, the entire amine will be delineated. When diastereomers were separated, they are included as separate entries.

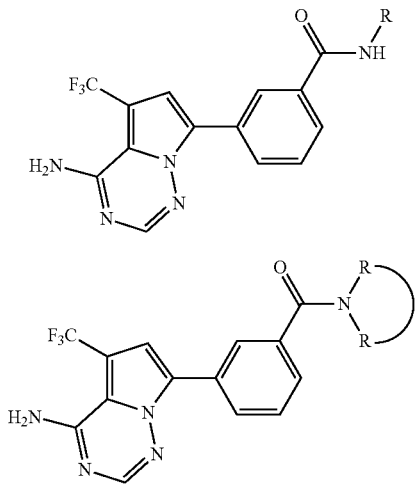

| Ex | Name | R | Obs. MS Ion | NMR Assignments (500 MHz, DMSO-d6) δ |
|---|---|---|---|---|
| | | | | 2.76-2.59 (m, 1H), 1.02 (br s, 6H) |
| 90 | 3-[4-amino-5-(trifluoromethyl)pyrrolo[2,1-f][1,2,4]triazin-7-yl]-N-[(3R,4S)-1-(3,3-dimethylbutanoyl)-4-fluoropyrrolidin-3-yl]benzamide, TFA | | 506.9 | 8.68-8.53 (m, 1H), 8.43 (br s, 1H), 8.23 (br d, J = 7.6 Hz, 1H), 8.15 (s, 1H), 7.91 (br d, J = 7.7 Hz, 1H), 7.61 (br t, J = 7.7 Hz, 1H), 7.52 (s, 1H), 5.41-5.13 (m, 1H), 4.80-4.49 (m, 1H), 4.07-3.48 (m, 4H), 2.28-2.07 (m, 2H), 1.01 (s, 9H) |
| 91 | 3-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]benzamide | | 531.1 | 8.73-8.51 (m, 1H), 8.48-8.34 (m, 1H), 8.22 (br dd, J = 18.1, 7.7 Hz, 1H), 8.13 (br d, J = 11.9 Hz, 1H), 7.95-7.82 (m, 1H), 7.65-7.41 (m, 4H), 7.34-7.26 (m, 2H), 5.46-5.12 (m, 1H), 4.88-4.56 (m, 1H), 4.06-3.50 (m, 4H) |
| 92 | 3-[4-amino-5-(trifluoromethyl)pyrrolo[2,1-f][1,2,4]triazin-7-yl]-N-[(3R,4S)-4-fluoro-1-(3-fluorobenzoyl)pyrrolidin-3-yl]benzamide | | 531.1 | 8.75-8.51 (m, 1H), 8.47-8.33 (m, 1H), 8.20 (br s, 1H), 8.11 (br s, 1H), 7.95-7.82 (m, 1H), 7.59 (br d, J = 6.2 Hz, 1H), 7.55-7.44 (m, 2H), 7.41-7.26 (m, 3H), 5.46-5.14 (m, 1H), 4.85-4.55 (m, 1H), 4.08-3.60 (m, 4H) |
| 93 | 3-[4-amino-5-(trifluoromethyl)pyrrolo[2,1-f][1,2,4]triazin-7-yl]-N-[(3R,4S)-4-fluoro-1-(1-fluorocyclobutanecarbonyl)pyrrolidin-3-yl]benzamide | | 509.1 | 8.63 (br d, J = 5.3 Hz, 1H), 8.42 (br s, 1H), 8.22 (br d, J = 7.0 Hz, 1H), 8.14 (s, 1H), 7.90 (br d, J = 7.6 Hz, 1H), 7.60 (t, J = 7.8 Hz, 1H), 7.51 (s, 1H), 5.40-5.12 (m, 1H), 4.82-4.55 (m, 1H), 3.99-3.55 (m, 4H), 2.78-2.65 (m, 1H), 2.65-2.56 (m, 1H), 2.48-2.23 (m, 2H), 1.88 (br dd, J = 10.1, 3.9 Hz, 1H), 1.67-1.47 (m, 1H) |

TABLE 2-continued

Compounds in Table 2 were prepared by the methods detailed in Example 2. In cases were a tertiary amide was generated, the entire amine will be delineated. When diastereomers were separated, they are included as separate entries.

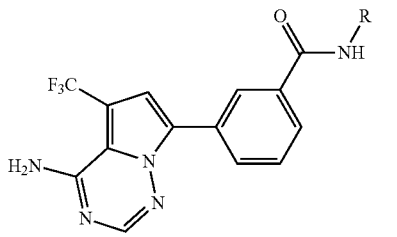

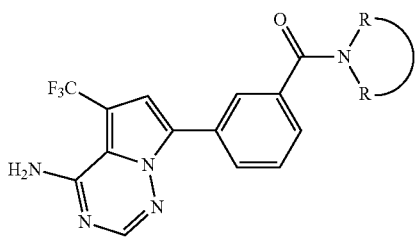

| Ex | Name | R | Obs. MS Ion | NMR Assignments (500 MHz, DMSO-d6) δ |
|---|---|---|---|---|
| 94 | 3-[4-amino-5-(trifluoromethyl)pyrrolo[2,1-f][1,2,4]triazin-7-yl]-N-[(3R,4S)-1-(3,5-difluoropyridine-4-carbonyl)-4-fluoropyrrolidin-3-yl]benzamide | | 550.0 | 8.78-8.57 (m, 3H), 8.45-8.33 (m, 1H), 8.19 (br dd, J = 17.5, 7.7 Hz, 1H), 8.10 (br d, J = 11.8 Hz, 1H), 7.92-7.80 (m, 1H), 7.64-7.53 (m, 1H), 7.48 (br d, J = 19.7 Hz, 1H), 5.46-5.15 (m, 1H), 4.88-4.66 (m, 1H), 4.10-3.80 (m, 4H) |
| 95 | 3-[4-amino-5-(trifluoromethyl)pyrrolo[2,1-f][1,2,4]triazin-7-yl]-N-[(3R,4S)-4-fluoro-1-[1-(trifluoromethyl)cyclobutanecarbonyl]pyrrolidin-3-yl)benzamide | | 559.2 | 8.62 (br s, 1H), 8.44 (br s, 1H), 8.29-8.21 (m, 1H), 8.16 (s, 1H), 7.92 (br d, J = 7.1 Hz, 1H), 7.62 (t, J = 7.8 Hz, 1H), 7.53 (s, 1H), 5.40-5.17 (m, 1H), 4.84-4.54 (m, 1H), 3.87-3.52 (m, 4H), 2.84-2.63 (m, 2H), 2.48-2.35 (m, 2H), 2.08-1.95 (m, 1H), 1.81 (br d, J = 9.5 Hz, 1H) |
| 96 | 3-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]benzamide | | 497.1 | 8.72 (br dd, J = 16.2, 7.0 Hz, 1H), 8.46 (s, 1H), 8.27 (br d, J = 6.1 Hz, 1H), 8.19 (br s, 1H), 7.93 (br d, J = 7.6 Hz, 1H), 7.63 (t, J = 7.8 Hz, 1H), 7.58 (s, 1H), 5.40-5.16 (m, 1H), 4.83-4.58 (m, 1H), 4.24-3.36 (m, 4H), 1.62-1.49 (m, 6H). |
| 97 | 3-[4-amino-5-(trifluoromethyl)pyrrolo[2,1-f][1,2,4]triazin-7-yl]-N-[(3R,4S)-4-fluoro-1-(1-fluorocyclopropane-carbonyl)pyrrolidin-3-yl]benzamide | | 495.2 | 8.75 (br dd, J = 18.8, 6.9 Hz, 1H), 8.47 (s, 1H), 8.27 (br d, J = 7.6 Hz, 1H), 8.18 (s, 1H), 7.93 (br d, J = 7.0 Hz, 1H), 7.63 (br t, J = 7.8 Hz, 1H), 7.58 (s, 1H), 5.44-5.19 (m, 1H), 4.87-4.60 (m, 1H), 4.29-3.29 (m, 4H), 1.46-1.08 (m, 4H). |

TABLE 2-continued

Compounds in Table 2 were prepared by the methods detailed in Example 2. In cases were a tertiary amide was generated, the entire amine will be delineated. When diastereomers were separated, they are included as separate entries.

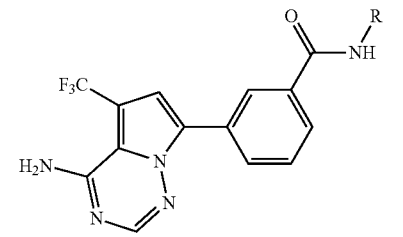

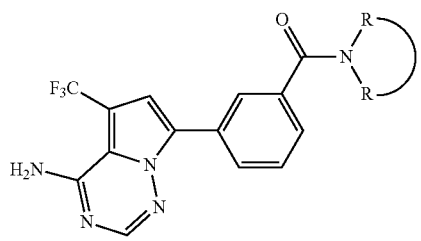

| Ex | Name | R | Obs. MS Ion | NMR Assignments (500 MHz, DMSO-d6) δ |
|---|---|---|---|---|
| 98 | 3-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]benzamide, TFA | | 519.2 | 8.67 (br dd, J = 18.7, 6.9 Hz, 1H), 8.43 (s, 1H), 8.23 (br d, J = 7.7 Hz, 1H), 8.14 (s, 1H), 7.90 (br d, J = 7.8 Hz, 1H), 7.62 (t, J = 7.7 Hz, 1H), 7.52 (s, 1H), 5.41-5.18 (m, 1H), 4.80-4.55 (m, 1H). |
| 99 | 3-[4-amino-5-(trifluoromethyl)pyrrolo[2,1-f][1,2,4]triazin-7-yl]-N-[(3R,4S)-4-fluoro-1-[1-(trifluoromethyl)cyclopentane-carbonyl]pyrrolidin-3-yl]benzamide | | 573.2 | 8.74 (br d, J = 5.2 Hz, 1H), 8.45 (s, 1H), 8.25 (br d, J = 5.2 Hz, 1H), 8.17 (s, 1H), 7.91 (br d, J = 7.3 Hz, 1H), 7.62 (br t, J = 7.8 Hz, 1H), 7.56 (s, 1H), 5.35-5.14 (m, 1H), 4.78-4.54 (m, 1H), 4.29-3.29 (m, 4H), 2.46-1.48 (m, 8H). |
| 100 | 3-[4-amino-5-(trifluoromethyl)pyrrolo[2,1-f][1,2,4]triazin-7-yl]-N-[(3R,4S)-4-fluoro-1-(3-fluorocyclobutane-carbonyl)pyrrolidin-3-yl]benzamide | | 509.0 | 8.78-8.65 (m, 1H), 8.45 (s, 1H), 8.26 (br d, J = 7.6 Hz, 1H), 8.18 (s, 1H), 7.91 (br d, J = 7.9 Hz, 1H), 7.61 (br t, J = 7.6 Hz, 1H), 7.58 (s, 1H), 5.41-4.99 (m, 2H), 4.83-4.54 (m, 1H), 3.90-3.79 (m, 1H), 3.79-3.54 (m, 2H), 3.54-3.40 (m, 1H), 2.54 (s, 2H), 2.49-2.31 (m, 3H) |
| 101 | 3-[4-amino-5-(trifluoromethyl)pyrrolo[2,1-f][1,2,4]triazin-7-yl]-N-[(3R,4S)-4-fluoro-1-(3-fluoroaclobutane-carbonyl)pyrrolidin-3-yl]benzamide | | 509.0 | 8.68-8.54 (m, 1H), 8.45 (s, 1H), 8.25 (br d, J = 7.7 Hz, 1H), 8.16 (s, 1H), 7.92 (br d, J = 7.7 Hz, 1H), 7.66-7.58 (m, 1H), 7.54 (s, 1H), 5.41-5.15 (m, 1H), 5.12-4.87 (m, 1H), 4.84-4.55 (m, 1H), 3.95-3.56 (m, 3H), 3.55-3.40 (m, 1H), 2.86-2.67 (m, 1H), 2.64-2.54 (m, 2H), 2.38-2.15 (m, 2H) |

TABLE 2-continued

Compounds in Table 2 were prepared by the methods detailed in Example 2. In cases were a tertiary amide was generated, the entire amine will be delineated. When diastereomers were separated, they are included as separate entries.

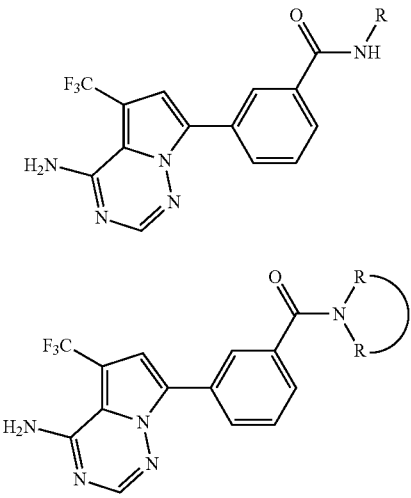

| Ex | Name | R | Obs. MS Ion | NMR Assignments (500 MHz, DMSO-d6) δ |
|---|---|---|---|---|
| 102 | 3-[4-amino-5-(trifluoromethyl)pyrrolo[2,1-f][1,2,4]triazin-7-yl]-N-[(3R,4S)-4-fluoro-1-(4-fluorocyclohexanecarbonyl)pyrrolidin-3-yl]benzamide | | 537.2 | 8.75-8.65 (m, 1H), 8.45 (s, 1H), 8.26 (br d, J = 7.9 Hz, 1H), 8.17 (s, 1H), 7.91 (br d, J = 7.9 Hz, 1H), 7.62 (td, J = 7.6, 3.1 Hz, 1H), 7.57 (s, 1H), 5.42-5.14 (m, 1H), 4.95-4.54 (m, 2H), 4.05 (br t, J = 9.3 Hz, 1H), 3.98-3.48 (m, 3H), 3.17 (d, J = 5.2 Hz, 1H), 2.00-1.86 (m, 2H), 1.72-1.43 (m, 5H); 1 pyrrolidine CH not observed due to water suppression |
| 103 | 3-[4-amino-5-(trifluoromethyl)pyrrolo[2,1-f][1,2,4]triazin-7-yl]-N-[(3R,4S)-4-fluoro-1-(4-fluorocyclohexanecarbonyl)pyrrolidin-3-yl]benzamide | | 537.3 | 8.76-8.64 (m, 1H), 8.45 (s, 1H), 8.26 (br d, J = 7.9 Hz, 1H), 8.17 (s, 1H), 7.94-7.88 (m, 1H), 7.66-7.58 (m, 1H), 7.57 (s, 1H), 5.42-5.14 (m, 1H), 4.87-4.40 (m, 2H), 4.04 (br t, J = 9.2 Hz, 1H), 3.97-3.83 (m, 1H), 3.82-3.73 (m, 1H), 3.73-3.58 (m, 1H), 2.47-2.33 (m, 1H), 2.06 (br d, J = 5.5 Hz, 2H), 1.91-1.68 (m, 2H), 1.58-1.32 (m, 4H) |
| 104 | 3-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]benzamide | | 531.4 | 8.74-8.50 (m, 1H), 8.49-8.35 (m, 1H), 8.23 (br s, 1H), 8.14 (s, 1H), 7.97-7.82 (m, 1H), 7.67-7.55 (m, 3H), 7.52 (br s, 1H), 7.28 (br t, J = 8.8 Hz, 2H), 5.45-5.15 (m, 1H), 4.86-4.56 (m, 1H), 3.93 (br s, 1H), 3.83 (br d, J = 17.5 Hz, 1H), 3.76-3.61 (m, 1H), 3.46-3.38 (m, 1H) |

TABLE 2-continued

Compounds in Table 2 were prepared by the methods detailed in Example 2. In cases were a tertiary amide was generated, the entire amine will be delineated. When diastereomers were separated, they are included as separate entries.

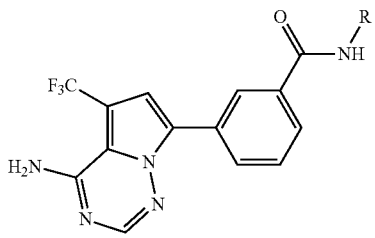

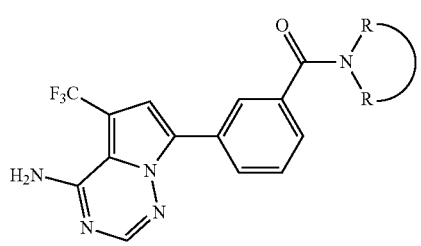

| Ex | Name | R | Obs. MS Ion | NMR Assignments (500 MHz, DMSO-d6) δ |
|---|---|---|---|---|
| 105 | 3-[4-amino-5-(trifluoromethyl)pyrrolo[2,1-f][1,2,4]triazin-7-yl]-N-[(3R,4S)-1-(4,4-difluorocyclohexane-carbonyl)-4-fluoropyrrolidin-3-yl]benzamide | | 555.4 | 8.80-8.68 (m, 1H), 8.43 (s, 1H), 8.24 (br d, J = 7.3 Hz, 1H), 8.15 (s, 1H), 7.90 (br d, J = 7.6 Hz, 1H), 7.61 (td, J = 7.6, 4.6 Hz, 1H), 7.55 (s, 1H), 5.45-5.13 (m, 1H), 4.85-4.55 (m, 1H), 4.06 (br t, J = 9.2 Hz, 1H), 4.00-3.89 (m, 1H), 3.88-3.68 (m, 1H), 3.68-3.36 (m, 1H), 2.72-2.57 (m, 1H), 2.05 (br s, 2H), 1.95-1.70 (m, 4H), 1.58 (br d, J = 6.4 Hz, 2H) |
| 106 | 3-[4-amino-5-(trifluoromethyl)pyrrolo[2,1-f][1,2,4]triazin-7-yl]-N-[(3R,4S)-1-(3,3-difluorocyclo-pentanecarbonyl)-4- | | 541.2 | 8.62 (br dd, J = 17.6, 6.9 Hz, 1H), 8.45 (s, 1H), 8.26 (br d, J = 7.8 Hz, 1H), 8.17 (s, 1H), 7.92 (br d, J = 7.8 Hz, 1H), 7.62 (td, J = 7.7, 3.5 Hz, 1H), 7.55 (s, 1H), 5.44-5.13 (m, 1H), 4.83-4.60 (m, 1H), |

TABLE 2-continued

Compounds in Table 2 were prepared by the methods detailed in Example 2. In cases were a tertiary amide was generated, the entire amine will be delineated. When diastereomers were separated, they are included as separate entries.

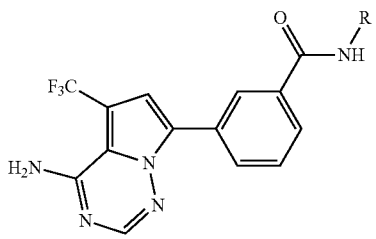

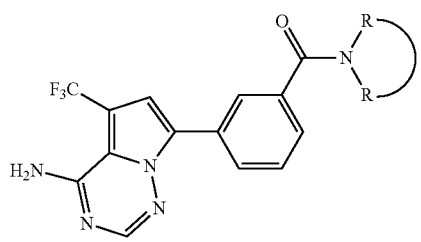

| Ex | Name | R | Obs. MS Ion | NMR Assignments (500 MHz, DMSO-d6) δ |
|---|---|---|---|---|
|  | fluoropyrrolidin-3-yl]benzamide |  |  | 4.12-3.98 (m, 1H), 3.98-3.83 (m, 2H), 3.82-3.58 (m, 2H), 2.41-2.26 (m, 2H), 2.24-2.14 (m, 1H), 2.13-2.06 (m, 2H), 1.93-1.75 (m, 1H) |
| 107 | 3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]benzamide |  | 513.3 | 8.87-8.72 (m, 1H), 8.46 (br s, 1H), 8.26 (br d, J = 7.6 Hz, 1H), 8.17 (s, 1H), 7.97-7.88 (m, 1H), 7.63 (td, J = 1.1, 2.6 Hz, 1H), 7.59-7.55 (m, 1H), 5.46-5.17 (m, 1H), 4.91-4.63 (m, 1H), 4.28-4.08 (m, 1H), 4.07-3.91 (m, 1H), 3.90-3.80 (m, 1H), 3.78-3.62 (m, 1H), 3.12-2.84 (m, 1H), 2.03-1.81 (m, 2H) |
| 108 | 3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]benzamide |  | 527.0 | 8.76 (br dd, J = 19.2, 7.0 Hz, 1H), 8.42 (s, 1H), 8.22 (br d, J = 7.6 Hz, 1H), 8.14 (s, 1H), 7.89 (br d, J = 7.6 Hz, 1H), 7.61 (td, J = 7.8, 2.1 Hz, 1H), 7.54 (s, 1H), 5.39-5.13 (m, 1H), 4.83-4.53 (m, 1H), 3.90 (br t, J = 9.2 Hz, 1H), 3.86-3.79 (m, 1H), 3.78-3.67 (m, 1H), 3.56-3.38 (m, 1H), 3.22-3.05 (m, 1H), 2.89-2.68 (m, 4H) |

TABLE 3

Compounds in Table 3 were prepared by the methods detailed in Example 31. In cases were a tertiary amide was generated, the entire amine will be delineated. When diastereomers were separated, they are included as separate entries.

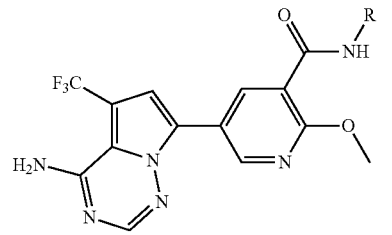

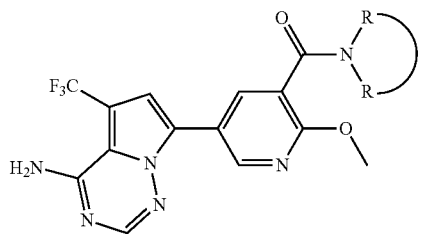

| Ex | Name | R | Obs. MS Ion | NMR Assignments (500 MHz, DMSO-d6) δ |
|----|------|---|-------------|--------------------------------------|
| 109 | 5-[4-amino-5-(trifluoromethyl)pyrrolo[2,1-f][1,2,4]triazin-7-yl]-2-methoxy-N-(3-phenylbutyl)pyridine-3-carboxamide | | 484.9 | 8.92-8.85 (m, 1H), 8.75-8.68 (m, 1H), 8.32-8.24 (m, 1H), 8.20-8.13 (m, 1H), 7.62-7.55 (m, 1H), 7.34-7.24 (m, 4H), 7.22-7.14 (m, 1H), 4.02 (s, 3H), 3.24-3.14 (m, 1H), 2.86-2.75 (m, 1H), 2.55 (s, 2H), 1.87-1.77 (m, 2H), 1.27-1.20 (m, 3H) |
| 110 | 5-[4-amino-5-(trifluoromethyl)pyrrolo[2,1-f][1,2,4]triazin-7-yl]-N-(1-benzyl-1H-pyrazol-4-yl)-2-methoxypyridine-3-carboxamide | | 509.1 | 10.30 (s, 1H), 8.97-8.86 (m, 1H), 8.78-8.66 (m, 1H), 8.24-8.07 (m, 2H), 7.67-7.56 (m, 2H), 7.41-7.19 (m, 5H), 5.38-5.26 (m, 2H), 4.06-3.97 (m, 3H) |
| 111 | 5-[4-amino-5-(trifluoromethyl)pyrrolo[2,1-f][1,2,4]triazin-7-yl]-2-methoxy-N-[3-(2-methylpropoxy)propyl]pyridine-3-carboxamide | | 466.9 | 8.86 (d, J = 2.1 Hz, 1H), 8.72 (d, J = 2.1 Hz, 1H), 8.38 (br. s., 1H), 8.15 (s, 1H), 7.57 (s, 1H), 4.01 (s, 3H), 3.43 (t, J = 6.1 Hz, 1H), 3.36 (d, J = 6.1 Hz, 2H), 3.14 (d, J = 6.6 Hz, 2H), 1.85-1.69 (m, 3H), 0.84 (d, J = 6.6 Hz, 6H). |
| 112 | 5-[4-amino-5-(trifluoromethyl)pyrrolo[2,1-f][1,2,4]triazin-7-yl]-N-[3-(tert-butoxy)propyl]-2-methoxypyridine-3-carboxamide | | 466.9 | 8.88 (d, J = 2.0 Hz, 1H), 8.75 (d, J = 2.0 Hz, 1H), 8.30 (t, J = 5.2 Hz, 1H), 8.17 (s, 1H), 7.60 (s, 1H), 4.02 (s, 3H), 1.71 (t, J = 6.4 Hz, 2H), 1.14 (s, 9H). |

TABLE 3-continued

Compounds in Table 3 were prepared by the methods detailed in Example 31. In cases were a tertiary amide was generated, the entire amine will be delineated. When diastereomers were separated, they are included as separate entries.

| Ex | Name | R | Obs. MS Ion | NMR Assignments (500 MHz, DMSO-d6) δ |
|---|---|---|---|---|
| 113 | 5-[4-amino-5-(trifluoromethyl)pyrrolo[2,1-f][1,2,4]triazin-7-yl]-N-[3-(4-fluorophenoxy)propyl]-2-methoxypyridine-3-carboxamide | | 505.2 | 8.88 (d, J = 2.2 Hz, 1H), 8.73 (d, J = 2.2 Hz, 1H), 8.45 (t, J = 5.4 Hz, 1H), 8.16 (s, 1H), 7.60 (s, 1H), 7.12 (t, J = 8.8 Hz, 2H), 6.96 (dd, J = 8.9, 4.3 Hz, 2H), 4.10-3.96 (m, 5H), 3.53-3.42 (m, 1H), 2.05-1.93 (m, 2H). |
| 114 | 5-[4-amino-5-(trifluoromethyl)pyrrolo[2,1-f][1,2,4]triazin-7-yl]-N-[1-(cyclopropylmethyl)-1H-pyrazol-4-yl]-2-methoxypyridine-3-carboxamide | | 472.9 | 10.33-10.27 (m, 1H), 8.98-8.90 (m, 1H), 8.81-8.74 (m, 1H), 8.23-8.16 (m, 1H), 8.15-8.08 (m, 1H), 7.68-7.56 (m, 2H), 4.10-4.01 (m, 3H), 3.96 (d, J = 7.1 Hz, 2H), 1.30-1.17 (m, 1H), 0.60-0.48 (m, 2H), 0.37 (br d, J = 4.5 Hz, 2H) |
| 115 | 5-[4-amino-5-(trifluoromethyl)pyrrolo[2,1-f][1,2,4]triazin-7-yl]-2-methoxy-N-[1-(2,2,2-trifluoroethyl)-1H-pyrazol-4-yl]pyridine-3-carboxamide | | 501.1 | 10.49-10.39 (m, 1H), 9.00-8.91 (m, 1H), 8.80-8.71 (m, 1H), 8.30-8.22 (m, 1H), 8.21-8.14 (m, 1H), 7.78-7.70 (m, 1H), 7.68-7.58 (m, 1H), 5.21-5.08 (m, 2H), 4.09-3.98 (m, 3H) |
| 116 | 5-[4-amino-5-(trifluoromethyl)pyrrolo[2,1-f][1,2,4]triazin-7-yl]-N-(3-hydroxy-3-phenylpropyl)-2-methoxypyridine-3-carboxamide | | 487.1 | 8.94-8.85 (m, 1H), 8.82-8.71 (m, 1H), 8.63-8.48 (m, 1H), 8.26-8.08 (m, 1H), 7.64-7.53 (m, 1H), 7.42-7.32 (m, 4H), 7.29-7.18 (m, 1H), 5.54-5.40 (m, 2H), 4.79-4.60 (m, 1H), 4.09-3.95 (m, 6H), 3.55-3.33 (m, 1H), 1.95-1.76 (m, 2H) |

TABLE 3-continued

Compounds in Table 3 were prepared by the methods detailed in Example 31. In cases were a tertiary amide was generated, the entire amine will be delineated. When diastereomers were separated, they are included as separate entries.

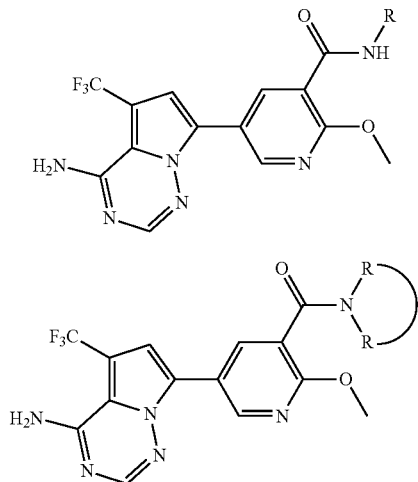

| Ex | Name | R | Obs. MS Ion | NMR Assignments (500 MHz, DMSO-d6) δ |
|---|---|---|---|---|
| 117 | 5-[4-amino-5-(trifluoromethyl)pyrrolo[2,1-f][1,2,4]triazin-7-yl]-N-(3-hydroxy-3-phenylpropyl)-2-methoxypyridine-3-carboxamide | | 487.2 | 8.94-8.85 (m, 1H), 8.82-8.71 (m, 1H), 8.63-8.48 (m, 1H), 8.26-8.08 (m, 1H), 7.64-7.53 (m, 1H), 7.42-7.32 (m, 4H), 7.29-7.18 (m, 1H), 5.54-5.40 (m, 2H), 4.79-4.60 (m, 1H), 4.09-3.95 (m, 6H), 3.55-3.33 (m, 1H), 1.95-1.76 (m, 2H) |
| 118 | 5-[4-amino-5-(trifluoromethyl)pyrrolo[2,1-f][1,2,4]triazin-7-yl]-N-{[(1S,2S)-2-[3,5-bis(trifluoromethyl)phenyl]cyclopropyl]methyl}-2-methoxypyridine-3-carboxamide | | 619.3 | 8.89 (s, 1H), 8.75 (s, 1H), 8.55 (br. s., 1H), 8.15 (s, 1H), 7.84 (s, 1H), 7.78 (s, 2H), 7.60 (s, 1H), 3.99 (s, 3H), 2.22 (d, J = 4.0 Hz, 1H), 1.56 (br. s., 1H), 1.23 (br. s., 2H), 114 (d, J = 5.2 Hz, 1H). |
| 119 | 5-[4-amino-5-(trifluoromethyl)pyrrolo[2,1-f][1,2,4]triazin-7-yl]-N-[(3S)-1-benzylpyrrolidin-3-yl]-2-methoxypyridine-3-carboxamide | | 512 | 8.91-8.86 (m, 1H), 8.75-8.63 (m, 1H), 8.39 (br d, J = 7.2 Hz, 1H), 8.16 (s, 1H), 7.63-7.57 (m, 1H), 7.33 (br d, J = 3.6 Hz, 4H), 7.30-7.22 (m, 1H), 4.42-4.34 (m, 1H), 4.03 (s, 3H), 3.68-3.52 (m, 1H), 2.76-2.66 (m, 2H), 2.49-2.41 (m, 3H), 2.30-2.17 (m, 1H), 1.72 (br d, J = 6.1 Hz, 1H) |
| 120 | 5-[4-amino-5-(trifluoromethyl)pyrrolo[2,1-f][1,2,4]triazin-7-yl]-N-[(3R)-1-benzylpyrrolidin-3-yl]-2-methoxypyridine-3-carboxamide | | 512.2 | 8.91-8.85 (m, 1H), 8.72-8.66 (m, 1H), 8.43-8.36 (m, 1H), 8.19-8.13 (m, 1H), 7.63-7.56 (m, 1H), 7.37-7.30 (m, 4H), 7.29-7.21 (m, 1H), 4.44-4.34 (m, 1H). 3.69-3.54 (m, 1H), |

TABLE 3-continued

Compounds in Table 3 were prepared by the methods detailed in Example 31. In cases were a tertiary amide was generated, the entire amine will be delineated. When diastereomers were separated, they are included as separate entries.

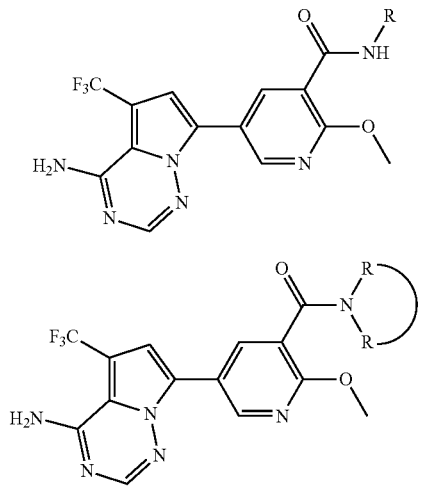

| Ex | Name | R | Obs. MS Ion | NMR Assignments (500 MHz, DMSO-d6) δ |
|---|---|---|---|---|
| | | | | 2.75-2.67 (m, 2H), 2.49-2.41 (m, 3H), 2.30-2.17 (m, 1H), 1.76-1.68 (m, 1H) |
| 121 | 5-[4-amino-5-(trifluoromethyl)pyrrolo[2,1-f][1,2,4]triazin-7-yl]-N-[(3S)-1-benzoylpyrrolidin-3-yl]-2-methoxypyridine-3-carboxamide | | 526.2 | 8.92-8.86 (m, 1H), 8.67-8.48 (m, 2H), 8.21-8.13 (m, 1H), 7.60 (br d, J = 15.9 Hz, 1H), 7.55-7.48 (m, 2H), 7.47-7.39 (m, 3H), 4.59-4.52 (m, 1H), 4.44-4.34 (m, 1H), 4.04-3.94 (m, 3H), 3.81-3.66 (m, 1H), 3.61-3.33 (m, 1H), 2.25-2.12 (m, 1H), 2.06-1.91 (m, 1H) (peaks lost with solvent suppression) |
| 122 | 7-{5-[(3S)-3-[(4-fluorophenyl)methyl]piperidine-1-carbonyl]-6-methoxypyridin-3-yl}-5-(trifluoromethyl)pyrrolo[2,1-f][1,2,4]triazin-4-amine | | 528.9 | 8.92-8.78 (m, 1H), 8.35-8.24 (m, 1H), 8.21-8.09 (m, 1H), 7.65-7.52 (m, 1H), 7.33-7.21 (m, 1H), 7.12 (br t, J = 8.7 Hz, 1H), 7.04 (br s, 1H), 6.98-6.84 (m, 1H), 6.57 (br s, 1H), 4.47-4.11 (m, 1H), 4.01-3.79 (m, 3H), 3.50-3.40 (m, 1H), 3.32-3.06 (m, 1H), 3.06-2.84 (m, 1H), 2.79-2.56 (m, 2H), 2.40-2.14 (m, 1H), 1.85-1.65 (m, 3H), 1.63-1.52 (m, 1H), 1.49-1.33 (m, 1H), 1.29-1.15 (m, 1H) |
| 123 | 7-{5-[(3R)-3-[(4-fluorophenyl)methyl]piperidine-1-carbonyl]-6-methoxypyridin-3-yl]-5- | | 528.9 | 8.92-8.79 (m, 1H), 8.37-8.24 (m, 1H), 8.22-8.11 (m, 1H), 7.63-7.54 (m, 1H), 7.27 (br s, 1H), 7.18-7.08 (m, 1H), 7.08- |

TABLE 3-continued

Compounds in Table 3 were prepared by the methods detailed in Example 31. In cases were a tertiary amide was generated, the entire amine will be delineated. When diastereomers were separated, they are included as separate entries.

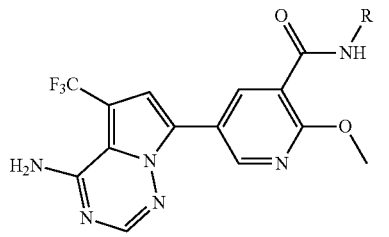

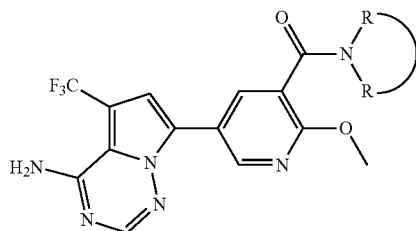

| Ex | Name | R | Obs. MS Ion | NMR Assignments (500 MHz, DMSO-d6) δ |
|---|---|---|---|---|
| | (trifluoromethyl)pyrrolo[2,1-f][1,2,4]triazin-4-amine | | | 6.99 (m, 1H), 6.99-6.83 (m, 1H), 6.63-6.50 (m, 1H), 4.55-4.11 (m, 1H), 3.99-3.81 (m, 3H), 3.31-2.84 (m, 2H), 2.79-2.58 (m, 2H), 1.86-1.66 (m, 3H), 1.65-1.53 (m, 1H), 1.50-1.36 (m, 1H), 1.25 (br d, J = 10.4 Hz, 1H) |
| 124 | 7-[5-(3-benzylpyrrolidine-1-carbonyl)-6-methoxypyridin-3-yl]-5-(trifluoromethyl)pyrrolo[2,1-f][1,2,4]triazin-4-amine | | 497.2 | 8.90-8.83 (m, 1H), 8.35 (dd, J = 9.3, 2.0 Hz, 1H), 8.19-8.12 (m, 1H), 7.63-7.55 (m, 1H), 7.36-7.09 (m, 5H), 4.00-3.91 (m, 3H), 3.65-3.39 (m, 1H), 3.32-3.09 (m, 2H), 2.97-2.89 (m, 1H), 2.75-2.67 (m, 1H), 2.65-2.57 (m, 1H), 2.48-2.41 (m, 1H), 1.89 (br s, 1H), 1.70-1.53 (m, 1H) |
| 125 | 5-[4-amino-5-(trifluoromethyl)pyrrolo[2,1-f][1,2,4]triazin-7-yl]-N-[3-(4-fluorophenyl)-3-hydroxypropyl]-2-methoxypyridine-3-carboxamide | | 505.2 | 1H NMR (400 MHz, CD3OD) δ 8.93 (q, J = 2.5 Hz, 2H), 8.04 (s, 1H), 7.59 (s, 1H), 7.38 (dd, J = 8.5, 5.4 Hz, 2H), 7.29 (s, 1H), 7.02 (t, J = 8.8 Hz, 2H), 4.88-4.77 (m, 1H), 4.21-4.13 (m, 3H), 2.04 (d, J = 6.5 Hz, 2H) |
| 126 | 5-[4-amino-5-(trifluoromethyl)pyrrolo[2,1-f][1,2,4]triazin-7-yl]-2-methoxy-N-[(2-phenyloxan-3-yl)methyl]pyridine-3-carboxamide | | | 1H NMR (400 MHz, CD3OD) δ 8.93 (q, J = 2.5 Hz, 2H), 8.04 (s, 1H), 7.59 (s, 1H), 7.38 (dd, J = 8.5, 5.4 Hz, 2H), 7.29 (s, 1H), 7.02 (t, J = 8.8 Hz, 2H), 4.88-4.77 (m, 1H), 4.21-4.13 (m, 3H), 2.04 (d, J = 6.5 Hz, 2H) |

TABLE 3-continued

Compounds in Table 3 were prepared by the methods detailed in Example 31. In cases were a tertiary amide was generated, the entire amine will be delineated. When diastereomers were separated, they are included as separate entries.

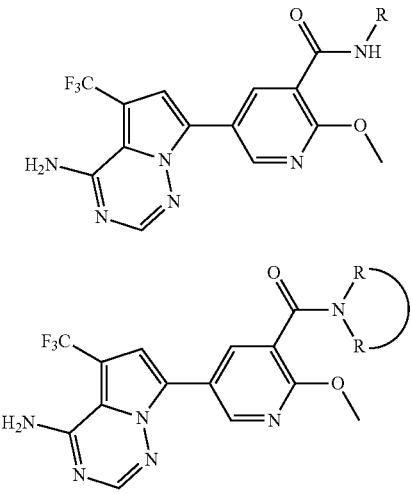

| Ex | Name | R | Obs. MS Ion | NMR Assignments (500 MHz, DMSO-d6) δ |
|---|---|---|---|---|
| 127 | 5-[4-amino-5-(trifluoromethyl)pyrrolo[2,1-f][1,2,4]triazin-7-yl]-2-methoxy-N-[(2-phenyloxan-3-yl)melhyl]pyridine-3-carboxamide | | 527.2 | 8.83 (d, J = 2.1 Hz, 1H), 8.63 (d, J = 2.1 Hz, 1H), 8.13 (s, 1H), 8.03 (d, J = 5.5 Hz, 1H), 7.55 (s, 1H), 7.40-7.28 (m, 4H), 7.21 (d, J = 6.1 Hz, 1H), 4.67 (s, 1H), 4.12 (d, J = 7.3 Hz, 1H), 3.97 (s, 3H), 2.90-2.78 (m, 1H), 2.23 (br. s., 1H), |
| | | | | 2.00-1.86 (m, 2H), 1.82 (d, J = 12.5 Hz, 1H), 1.37 (d, J = 13.1 Hz, 1H). |
| 128 | 5-[4-amino-5-(trifluoromethyl)pyrrolo[2,1-f][1,2,4]triazin-7-yl]-2-methoxy-N-[(2-phenyloxan-3-yl)methyl]pyridine-3-carboxamide | | 527.1 | 8.83 (d, J = 2.1 Hz, 1H), 8.63 (d, J = 2.1 Hz, 1H), 8.13 (s, 1H), 8.03 (d, J = 5.5 Hz, 1H), 7.55 (s, 1H), 7.40-7.28 (m, 4H), 7.21 (d, J = 6.1 Hz, 1H), 4.67 (s, 1H), 4.12 (d, J = 7.3 Hz, 1H), 3.97 (s, 3H), 2.90-2.78 (m, 1H), 2.23 (br. s., 1H), |
| | | | | 2.00-1.86 (m, 2H), 1.82 (d, J = 12.5 Hz, 1H), 1.37 (d, J = 13.1 Hz, 1H). |
| 129 | 7-(5-{3-[(3-fluorophenyl)methyl]piperidine-1-carbonyl}-6-methoxypyridin-3-yl)-5-(trifluoromethyl)pyrrolo[2,1-f][1,2,4]triazin-4-amine | | 529.3 | 8.91-8.83 (m, 1H), 8.39-8.31 (m, 1H), 8.19-8.12 (m, 1H), 7.62-7.56 (m, 1H), 7.35-7.09 (m, 5H), 3.99-3.91 (m, 3H), 3.66-3.37 (m, 3H), 3.32-3.10 (m, 2H), 2.98-2.88 (m, 1H), 2.76-2.67 (m, 1H), 2.64-2.57 (m, 1H), 2.48-2.41 (m, 1H), 2.01-1.82 (m, 1H), 1.69-1.53 (m, 1H) |

TABLE 3-continued

Compounds in Table 3 were prepared by the methods detailed in Example 31. In cases were a tertiary amide was generated, the entire amine will be delineated. When diastereomers were separated, they are included as separate entries.

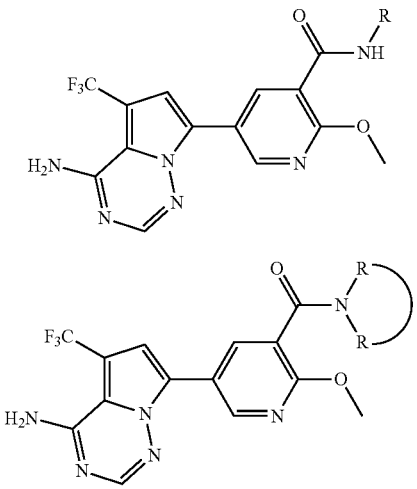

| Ex | Name | R | Obs. MS Ion | NMR Assignments (500 MHz, DMSO-d6) δ |
|---|---|---|---|---|
| 130 | 7-(6-methoxy-5-{3-[(4-methylphenyl)methyl]piperidine-1-carbonyl}pyridin-3-yl)-5-(trifluoromethyl)pyrrolo[2,1-f][1,2,4]triazin-4-amine | | 525.2 | 8.94-8.77 (m, 1H), 8.34-8.09 (m, 2H), 7.67-7.49 (m, 1H), 7.16-7.04 (m, 2H), 6.96-6.81 (m, 1H), 6.76-6.67 (m, 1H), 6.59-6.47 (m, 1H), 4.48-4.09 (m, 1H), 3.98-3.80 (m, 3H), 3.31-3.07 (m, 1H), 3.05-2.85 (m, 1H), 2.77-2.59 (m, 1H), 2.45-2.36 (m, 1H), 2.31-2.21 (m, 2H), 2.19-2.08 (m, 1H), 1.99-1.90 (m, 1H), 1.86-1.65 (m, 3H), 1.62-1.51 (m, 1H), 1.47-1.31 (m, 1H), 1.27-1.13 (m, 1H) |
| 131 | 7-(6-methoxy-5-{3-[(4-melhoxyphenyl)methyl]piperidine-1-carbonyl}pyridin-3-yl)-5-(trifluoromethyl)pyrrolo[2,1-f][1,2,4]triazin-4-amine | | 541.2 | 8.96-8.79 (m, 1H), 8.36-8.23 (m, 1H), 8.21-8.10 (m, 1H), 7.68-7.53 (m, 1H), 7.19-7.07 (m, 1H), 6.96-6.83 (m, 1H), 6.79 (br d, J = 7.7 Hz, 1H), 6.68 (br d, J = 7.5 Hz, 1H), 6.42-6.32 (m, 1H), 4.49-4.14 (m, 1H), 4.02-3.80 (m, 3H), 3.73 (s, 3H), 3.32-3.21 (m, 1H), 3.20-3.07 (m, 1H), 3.06-2.81 (m, 1H), 2.79-2.61 (m, 1H), 2.47-2.33 (m, 1H), 2.32-2.10 (m, 1H), 1.85-1.62 (m, 2H), 1.59 (br s, 2H), 1.33-1.11 (m, 1H) |
| 132 | 7-(5-{3-[(4-chlorophenyl)methyl]piperidine-1-carbonyl}-6-methoxypyridin-3-yl)-5-(trifluoromethyl) | | 544.9 | 8.96-8.77 (m, 1H), 8.36-8.10 (m, 2H), 7.66-7.52 (m, 1H), 7.37 (br d, J = 7.9 Hz, 1H), 7.30-7.23 (m, 1H), 7.20-7.12 (m, 1H), 7.04 (br d, J = |

TABLE 3-continued

Compounds in Table 3 were prepared by the methods detailed in Example 31. In cases were a tertiary amide was generated, the entire amine will be delineated. When diastereomers were separated, they are included as separate entries.

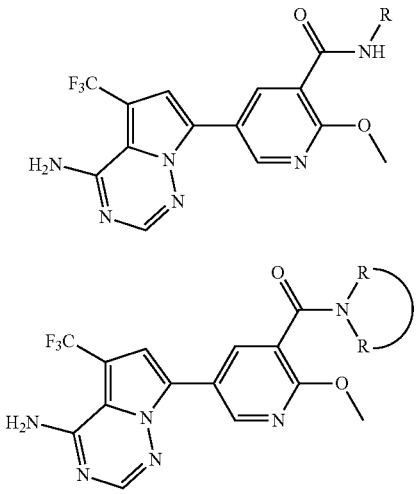

| Ex | Name | R | Obs. MS Ion | NMR Assignments (500 MHz, DMSO-d6) δ |
|---|---|---|---|---|
| | pyrrolo[2,1-f][1,2,4]triazin-4-amine | | | 7.3 Hz, 1H), 6.96-6.87 (m, 1H), 6.84-6.74 (m, 1H), 4.47-4.11 (m, 1H), 3.99-3.82 (m, 3H), 3.33-3.22 (m, 1H), 3.19-2.86 (m, 1H), 2.83-2.58 (m, 2H), 2.40-2.15 (m, 1H), 1.88-1.66 (m, 3H), 1.66-1.34 (m, 1H), 1.33-1.17 (m, 1H) |
| 133 | 7-{5-[(3S)-3-[(3-fluorophenyl)methyl]piperidine-1-carbonyl]-6-methoxypyridin-3-yl}-5-(trifluoromethyl)pyrrolo[2,1-f][1,2,4]triazin-4-amine | | 529 | 8.88 (br s, 1H), 8.37-8.24 (m, 1H), 8.22-8.07 (m, 1H), 7.64-7.52 (m, 1H), 7.33-7.21 (m, 1H), 7.13 (br t, J = 8.6 Hz, 2H), 7.08-7.00 (m, 1H), 7.00-6.88 (m, 3H), 6.56 (br s, 3H), 4.47-4.12 (m, 1H), 4.00-3.79 (m, 3H), 3.31-3.21 (m, 1H), 3.19-2.84 (m, 1H), 2.80-2.63 (m, 1H), 2.36-2.25 (m, 1H), 2.25-2.13 (m, 1H), 1.85-1.65 (m, 2H), 1.63-1.54 (m, 1H), 1.51-1.34 (m, 1H), 1.34-1.15 (m, 2H) |
| 134 | 5-[4-amino-5-(trifluoromethyl)pyrrolo[2,1-f][1,2,4]triazin-7-yl]-N-[3-(3,4-difluorophenyl)-3-hydroxypropyl]-2-methoxypyridine-3-carboxamide | | 522.8 | 1H NMR (400 MHz, CD$_3$OD) δ 8.97-8.87 (m, 2H), 8.02 (s, 1H), 7.38 (s, 2H), 7.29-7.21 (m, 1H), 7.14-7.03 (m, 2H), 4.74 (dd, J = 8.7, 4.0 Hz, 1H), 4.22-4.11 (m, 3H), 3.77-3.61 (m, 1H), 3.56-3.45 (m, 1H), 2.12-1.84 (m, 2H) |

TABLE 3-continued

Compounds in Table 3 were prepared by the methods detailed in Example 31. In cases were a tertiary amide was generated, the entire amine will be delineated. When diastereomers were separated, they are included as separate entries.

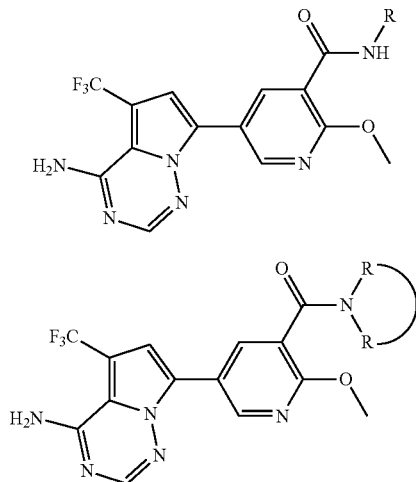

| Ex | Name | R | Obs. MS Ion | NMR Assignments (500 MHz, DMSO-d6) δ |
|---|---|---|---|---|
| 135 | 5-[4-amino-5-(trifluoromethyl)pyrrolo[2,1-f][1,2,4]triazin-7-yl]-N-[3-(3,4-difluorophenyl)-3-hydroxypropyl]-2-methoxypyridine-3-carboxamide | | 522.7 | 1H NMR (400 MHz, CD₃OD) δ 8.97-8.87 (m, 2H), 8.02 (s, 1H), 7.38 (s,2H), 7.29-7.21 (m, 1H), 7.14-7.03 (m, 2H), 4.74 (dd, J = 8.7, 4.0 Hz, 1H), 4.22-4.11 (m, 3H), 3.77-3.61 (m, 1H), 3.56-3.45 (m, 1H), 2.12-1.84 (m, 2H) |
| 136 | 5-[4-amino-5-(trifluoromethyl)pyrrolo[2,1-f][1,2,4]triazin-7-yl]-N-(1-benzyl-2-oxopyrrolidin-3-yl)-2-methoxypyridine-3-carboxamide•2 TFA | | 526.1 | 8.92 (d, J = 2.6 Hz, 1H), 8.83 (d, J = 2.2 Hz, 1H), 8.58 (d, J = 7.0 Hz, 1H), 8.18 (s, 1H), 7.58 (s, 1H), 7.40-7.34 (m, 2H), 7.33-7.24 (m, 3H), 4.65-4.59 (m, 1H), 4.45 (s, 2H), 4.09 (s, 3H), 3.32-3.24 (m, 2H, partially suppressed), 2.48-2.41 (m, 1H), 2.09-2.01 (m, 1H) |
| 137 | 5-[4-amino-5-(trifluoromethyl)pyrrolo[2,1-f][1,2,4]triazin-7-yl]-N-(1-benzyl-5-oxopyrrolidin-3-yl)-2-methoxypyridine-3-carboxamide | | 526.1 | 8.90 (d, J = 2.6 Hz, 1H), 8.63 (d, J = 2.6 Hz, 1H), 8.51 (br d, J = 6.6 Hz, 1H), 8.16 (s, 1H), 7.55 (s, 1H), 7.38-7.31 (m, 2H), 7.31-7.25 (m, 3H), 4.61-4.55 (m, 1H), 4.49-4.44 (m, 1H), 4.39 (d, J = 15.0 Hz, 1H), 4.01 (s, 3H), 3.64 (dd, J = 10.1, 7.5 Hz, 1H), 3.27-3.16 (m, 1H, mostly suppressed), 2.77 (dd, J = 17.1, 8.6 Hz, 1H), 2.47 (d, J = 5.5 Hz, 1H) |
| 138 | 7-[5-(3-benzyl-4,4-difluoropiperidine-1-carbonyl)-6-methoxypyridin-3-yl]-5-(trifluoromethyl) | | 547.3 | 8.93 (br s, 1H), 8.43-8.32 (m, 1H), 8.24-8.12 (m, 2H), 7.76-7.51 (m, 2H), 7.40-7.23 (m, 4H), 7.11 (br s, 1H), 7.05-6.96 (m, |

TABLE 3-continued

Compounds in Table 3 were prepared by the methods detailed in Example 31. In cases were a tertiary amide was generated, the entire amine will be delineated. When diastereomers were separated, they are included as separate entries.

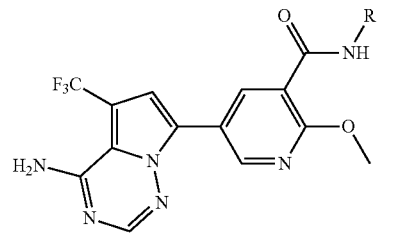

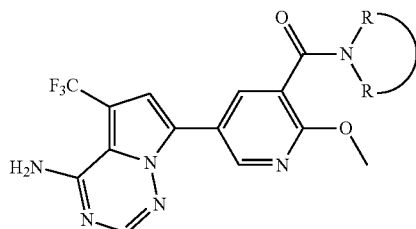

| Ex | Name | R | Obs. MS Ion | NMR Assignments (500 MHz, DMSO-d6) δ |
|---|---|---|---|---|
|  | pyrrolo[2,1-f][1,2,4]triazin-4-amine, 2 TFA |  |  | 1H), 6.91-6.81 (m, 1H), 6.76-6.67 (m, 1H), 4.61-4.37 (m, 1H), 4.33-4.22 (m, 1H), 4.19-4.00 (m, 1H), 3.99-3.93 (m, 2H), 3.88-3.79 (m, 1H), 3.67 (br s, 1H), 3.30-3.12 (m, 1H), 3.09-2.91 (m, 2H), 2.42-2.20 (m, 3H), 2.13-1.94 (m, 2H) |
| 139 | 7-[5-(2-benzylmorpholine-4-carbonyl)-6-methoxypyridin-3-yl]-5-(trifluoromethyl)pyrrolo[2,1-f][1,2,4]triazin-4-amine, TFA |  | 513 | 8.91 (s, 1H), 8.36 (br s, 1H), 8.16 (s, 1H), 7.60 (s, 2H), 7.37-6.92 (m, 5H), 4.33 (br s, 1H), 4.02-3.87 (m, 2H), 3.87-3.72 (m, 1H), 3.72-3.57 (m, 1H), 3.49-3.39 (m, 1H), 3.18 (br d, J = 4.9 Hz, 2H), 2.95 (br s, 1H), 2.84 (br d, J = 5.8 Hz, 1H), 2.58-2.54 (m, 3H) |
| 140 | 5-[4-amino-5-(trifluoromethyl)pyrrolo[2,1-f][1,2,4]triazin-7-yl]-N-[(3R)-3-(4-chlorophenyl)-3-hydroxypropyl]-2-methoxypyridine-3-carboxamide |  | 521.2 | 8.89 (d, J = 2.3 Hz, 1H), 8.78 (d, J = 2.4 Hz, 1H), 8.51 (br t, J = 5.3 Hz, 1H), 8.17 (s, 1H), 7.60 (s, 1H), 7.39 (s, 4H), 5.52 (d, J = 4.3 Hz, 1H), 4.74-4.68 (m, 1H), 4.04 (s, 3H), 3.42-3.35 (m, 2H), 1.92-1.79 (m, 2H). |
| 141 | 5-[4-amino-5-(trifluoromethyl)pyrrolo[2,1-f][1,2,4]triazin-7-yl]-2-methoxy-N-(4,4,4-trifluoro-3-hydroxy-3-phenylbutyl)pyridine-3-carboxamide |  | 555.2 | 1H NMR, racemic material (400 MHz, CDCl₃) δ 8.88 (d, J = 2.4 Hz, 1H), 8.91 (d, J = 2.3 Hz, 1H), 8.28 (t, J = 5.8 Hz, 1H), 8.12 (s, 1H), 7.63 (d, J = 7.7 Hz, 2H), 7.44-7.34 (m, 3H), 7.34-7.29 (m, 1H), 4.19 (s, 3H), 3.58 (dt, J = 14.0, 7.0 Hz, 1H), 3.52-3.36 (m, 1H), |

TABLE 3-continued

Compounds in Table 3 were prepared by the methods detailed in Example 31. In cases were a tertiary amide was generated, the entire amine will be delineated. When diastereomers were separated, they are included as separate entries.

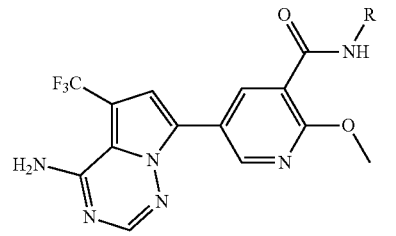

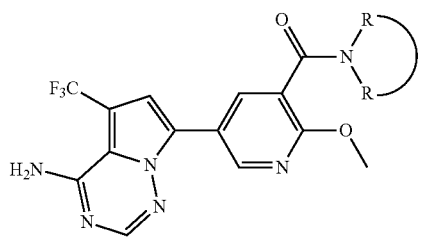

| Ex | Name | R | Obs. MS Ion | NMR Assignments (500 MHz, DMSO-d6) δ |
|---|---|---|---|---|
|  |  |  |  | 2.72 (dt, J = 14.3, 7.3 Hz, 1H), 2.41 (dt, J = 14.6, 5.7 Hz, 1H) |
| 142 | 5-[4-amino-5-(trifluoromethyl)pyrrolo[2,1-f][1,2,4]triazin-7-yl]-2-methoxy-N-(4,4,4-trifluoro-3-hydroxy-3-phenylbutyl)pyridine-3-carboxamide |  | 555.2 | 1H NMR, racemic material (400 MHz, CDCl3) δ 8.88 (d, J = 2.4 Hz, 1H), 8.91 (d, J = 2.3 Hz, 1H), 8.28 (t, J = 5.8 Hz, 1H), 8.12 (s, 1H), 7.63 (d, J = 7.7 Hz, 2H), 7.44-7.34 (m, 3H), 7.34-7.29 (m, 1H), 4.19 (s, 3H), 3.58 (dt, J = 14.0, 7.0 Hz, 1H), 3.52-3.36 (m, 1H), 2.72 (dt, J = 14.3, 7.3 Hz, 1H), 2.41 (dt, J = 14.6, 5.7 Hz, 1H) |
| 143 | 5-[4-amino-5-(trifluoromethyl)pyrrolo[2,1-f][1,2,4]triazin-7-yl]-2-methoxy-N-{2-[methyl(phenyl)amino]ethyl}pyridine-3-carboxamide |  | 486.1 | 8.98-8.82 (m, 1H), 8.82-8.61 (m, 1H), 8.47-8.25 (m, 1H), 8.24-8.00 (m, 1H), 7.62-7.43 (m, 1H), 7.23-7.06 (m, 2H), 6.92-6.78 (m, 2H), 6.65-6.52 (m, 1H), 4.08-3.98 (m, 3H), 3.60-3.44 (m, 2H), 3.22-3.14 (m, 2H), 3.97 (s, 3H). |
| 144 | 5-[4-amino-5-(trifluoromethyl)pyrrolo[2,1-f][1,2,4]triazin-7-yl]-N-(1-tert-butyl-1H-pyrazol-4-yl)-2-methoxypyridine-3-carboxamide |  | 475.1 | 10.30-9.91 (m, 1H), 9.16-8.86 (m, 1H), 8.86-8.69 (m, 1H), 8.28-8.13 (m, 1H), 8.13-7.91 (m, 1H), 7.76-7.46 (m, 2H), 3.32-3.06 (m, 3H), 1.59 (s, 9H). |

TABLE 3-continued

Compounds in Table 3 were prepared by the methods detailed in Example 31. In cases were a tertiary amide was generated, the entire amine will be delineated. When diastereomers were separated, they are included as separate entries.

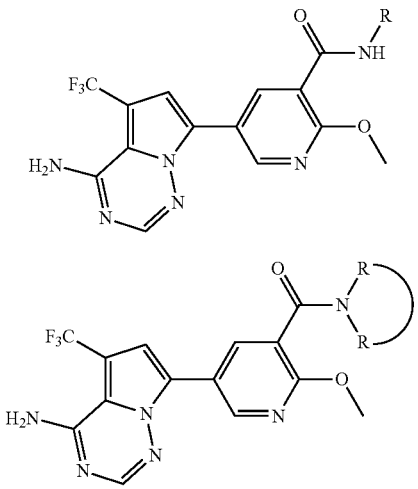

| Ex | Name | R | Obs. MS Ion | NMR Assignments (500 MHz, DMSO-d6) δ |
|---|---|---|---|---|
| 145 | 5-[4-amino-5-(trifluoromethyl)pyrrolo[2,1-f][1,2,4]triazin-7-yl]-N-[3-(4-chlorophenyl)-3-hydroxybutyl]-2-methoxypyridine-3-carboxamide | | 535.0 | 8.91-8.80 (m, 1H), 8.78-8.66 (m, 1H), 8.54-8.43 (m, 1H), 8.22-8.06 (m, 1H), 7.64-7.53 (m, 1H), 7.52-7.46 (m, 2H), 7.39-7.32 (m, 2H), 7.29-7.23 (m, 1H), 7.18-7.13 (m, 1H), 7.08-7.03 (m, 1H), 4.11-3.97 (m, 3H), 3.68-3.47 (m, 1H), 3.33-3.12 (m, 2H), 2.11-1.88 (m, 2H), 1.31-1.16 (m, 1H) |
| 146 | 5-[4-amino-5-(trifluoromethyl)pyrrolo[2,1-f][1,2,4]triazin-7-yl]-N-[3-(4-chlorophenyl)-3-hydroxy-4-methylpentyl]-2-methoxypyridine-3-carboxamide | | 563.1 | 8.93-8.82 (m, 1H), 8.81-8.66 (m, 1H), 8.41-8.24 (m, 1H), 8.26-8.09 (m, 1H), 7.67-7.54 (m, 1H), 7.50-7.42 (m, 2H), 7.39-7.32 (m, 2H), 4.96-4.85 (m, 1H), 4.11-3.99 (m, 3H), 3.93-3.84 (m, 1H), 3.48-3.35 (m, 1H), 3.24-3.01 (m, 2H), 2.23-2.11 (m, 1H), 2.09-1.91 (m, 2H), 0.95-0.84 (m, 3H), 0.70-0.54 (m, 3H) |
| 147 | 5-[4-amino-5-(trifluoromethyl)pyrrolo[2,1-f][1,2,4]triazin-7-yl]-N-[3-(4-chlorophenyl)-3-hydroxypentyl]-2-methoxypyridine-3-carboxamide | | 549.4 | 8.95-8.82 (m, 1H), 8.76-8.65 (m, 1H), 8.37-8.24 (m, 1H), 8.17-8.08 (m, 1H), 7.58-7.47 (m, 1H), 7.48-7.41 (m, 2H), 7.38-7.30 (m, 2H), 4.11-4.01 (m, 3H), 3.24-3.13 (m, 1H), 2.58-2.54 (m, 1H), 2.16-2.03 (m, 1H), 2.03-1.92 (m, 1H), 1.84-1.68 (m, 2H), 0.73-0.62 (m, 3H) |

TABLE 3-continued

Compounds in Table 3 were prepared by the methods detailed in Example 31. In cases were a tertiary amide was generated, the entire amine will be delineated. When diastereomers were separated, they are included as separate entries.

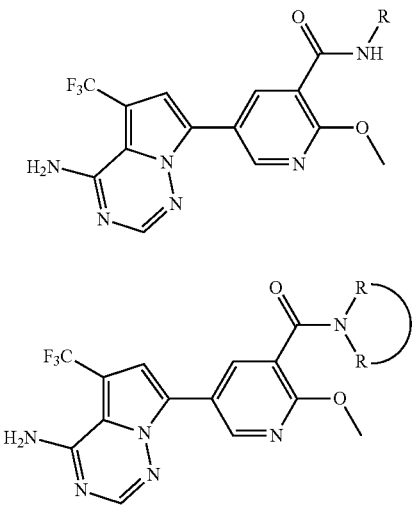

| Ex | Name | R | Obs. MS Ion | NMR Assignments (500 MHz, DMSO-d6) δ |
|---|---|---|---|---|
| 148 | 5-[4-amino-5-(trifluoromethyl)pyrrolo[2,1-f][1,2,4]triazin-7-yl]-N-[3-(4-chlorophenyl)-3-oxopropyl]-2-methoxypyridine-3-carboxamide | (4-chlorophenyl propanoyl) | 519.2 | 8.89 (d, J = 2.1 Hz, 1H), 8.81 (d, J = 2.4 Hz, 1H), 8.52 (br t, J = 5.5 Hz, 1H), 8.17 (s, 1H), 8.02 (d, J = 8.5 Hz, 3H), 7.66-7.58 (m, 3H), 4.03 (s, 3H), 3.68 (q, J = 6.3 Hz, 2H), 2.66-2.55 (m, 1H) |
| 149 | 5-[4-amino-5-(trifluoromethyl)pyrrolo[2,1-f][1,2,4]triazin-7-yl]-N-[3-(4-fluorophenyl)-3-oxopropyl]-2-methoxypyridine-3-carboxamide | (4-fluorophenyl propanoyl) | 503.1 | 8.94-8.86 (m, 1H), 8.84-8.79 (m, 1H), 8.60-8.50 (m, 1H), 8.21-8.15 (m, 1H), 8.13-8.06 (m, 2H), 7.66-7.55 (m, 1H), 7.42-7.32 (m, 2H), 4.11-3.98 (m, 3H), 3.72-3.64 (m, 2H), 3.39-3.29 (m, 1H), 2.59-2.54 (m, 1H) |
| 150 | 7-[5-(3-benzyl-1,3-diazinane-1-carbonyl)-6-methoxypyridin-3-yl]-5-(trifluoromethyl)pyrrolo[2,1-f][1,2,4]triazin-4-amine | (3-benzyl-1,3-diazinane) | 512.2 | 8.95-8.76 (m, 1H), 8.42-8.30 (m, 1H), 8.17 (d, J = 17.6 Hz, 1H), 7.68-7.58 (m, 1H), 7.39-7.26 (m, 2H), 7.05 (br d, J = 7.0 Hz, 1H), 6.98-6.86 (m, 2H), 4.35 (s, 1H), 4.01 (s, 1H), 3.88 (s, 1H), 3.93-3.36 (m, 6H), 3.18 (d, J = 5.2 Hz, 1H), 2.94-2.61 (m, 3H). |

TABLE 4

Compounds in Table 4 were prepared by similar methods to those detailed in Examples 1 and 51. When diastereomers were separated, they are included as separate entries.

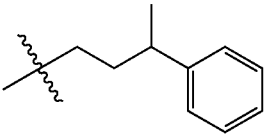 [SMILES: *CCC(C)c1ccccc1]

| Ex | Name | R | Obs. MS Ion | NMR Assignments (500 MHz, DMSO-d6) δ |
|----|------|---|-------------|---------------------------------------|
| 151 | 5-{4-aminopyrrolo[2,1-f][1,2,4]triazin-7-yl}-2-methoxy-N-(3-phenylbutyl)pyridine-3-carboxamide | 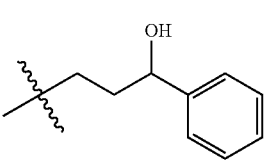 [SMILES: *CCC(O)c1ccccc1] | 417.2 | 8.91-8.84 (m, 1H), 8.74-8.68 (m, 1H), 8.34-8.25 (m, 1H), 7.97-7.66 (m, 3H), 7.33-7.21 (m, 4H), 7.20-7.12 (m, 1H), 7.11-7.05 (m, 1H), 7.02 (d, J = 4.5 Hz, 1H), 4.00 (s, 3H), 3.25-3.14 (m, 2H), 2.84-2.74 (m, 1H), 1.87-1.75 (m, 2H) |
| 152 | 5-{4-aminopyrrolo[2,1-f][1,2,4]triazin-7-yl}-N-(3-hydroxy-3-phenylpropyl)-2-methoxypyridine-3-carboxamide | 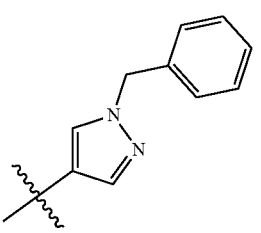 [SMILES: *c1cnn(Cc2ccccc2)c1] | 419.1 | 8.94-8.88 (m, 1H), 8.83-8.76 (m, 1H), 8.59-8.53 (m, 1H), 7.97-7.67 (m, 3H), 7.40-7.29 (m, 4H), 7.26-7.18 (m, 1H), 7.10-7.06 (m, 1H), 7.06-6.98 (m, 1H), 4.73-4.66 (m, 1H), 4.05-3.98 (m, 3H), 3.53-3.44 (m, 1H), 3.42-3.32 (m, 1H), 1.93-1.80 (m, 2H) |
| 153 | 5-{4-aminopyrrolo[2,1-f][1,2,4]triazin-7-yl}-N-(1-benzyl-1H-pyrazol-4-yl)-2-methoxypyridine-3-carboxamide | 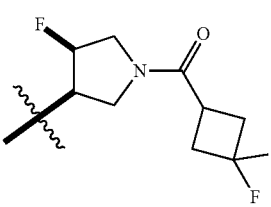 | 440.9 | 10.39-10.27 (m, 1H), 9.01-8.89 (m, 1H), 8.82-8.69 (m, 1H), 8.20-8.09 (m, 1H), 8.02-7.72 (m, 3H), 7.68-7.57 (m, 1H) 7.43-7.21 (m, 5H), 7.13 (br d, J = 4.0 Hz, 1H), 7.04 (br d, J = 4.0 Hz, 1H), 5.42-5.25 (m, 2H), 4.11-3.94 (m, 3H) |
| 154 | 5-{4-aminopyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide, TFA | 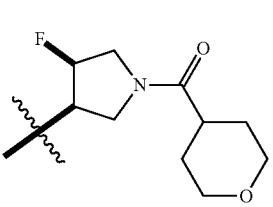 [SMILES: *[C@@H]1CN(C(=O)C2CCOCC2)C[C@@H]1F] | 490.2 | 8.94 (s, 1H), 8.80 (dd, J = 18.8, 2.3 Hz, 1H), 8.57-8.50 (m, 1H), 8.05 (d, J = 2.4 Hz, 1H), 7.18 (br s, 1H), 5.42-5.21 (m, 1H), 4.86-4.61 (m, 1H), 4.09-3.11 (m, 8H), 2.88-2.69 (m, 4H) |
| 155 | 5-{4-aminopyrrolo[2,1-f][1,2,4]triazin-7-yl}-N-[(3R,4S)-4-fluoro-1-(oxane-4-carbonyl)pyrrolidin-3-yl]-2-methoxypyridine-3-carboxamide |  | 484.2 | 8.94 (s, 1H), 8.88-8.78 (m, 1H), 8.45 (br dd, J = 17.2, 7.4 Hz, 1H), 7.94 (s, 1H), 7.09 (d, J = 4.5 Hz, 1H), 7.04 (d, J = 4.3 Hz, 1H), 5.43-5.20 (m, 1H), 4.86-4.60 (m, 1H), 4.19-3.16 (m, 11H), 2.80-2.65 (m, 1H), 1.67-1.49 (m, 4H) |

TABLE 4-continued

*Compounds in Table 4 were prepared by similar methods to those detailed in Examples 1 and 51. When diastereomers were separated, they are included as separate entries.*

| Ex | Name | R | Obs. MS Ion | NMR Assignments (500 MHz, DMSO-d6) δ |
|---|---|---|---|---|
| 156 | 5-{4-aminopyrrolo[2,1-f][1,2,4]triazin-7-yl}-N-[(3R,4S)-1-(2,2-difluorocycloprop-anecarbonyl)-4-fluoropyrrolidin-3-yl]-2-methoxypyridine-3-carboxamide | | 476.1 | 8.98-8.93 (m, 1H), 8.89-8.79 (m, 1H), 8.55-8.42 (m, 1H), 7.94 (s, 1H), 7.09 (br d, J = 4.3 Hz, 1H), 7.04 (d, J = 4.4 Hz, 1H), 5.48-5.22 (m, 1H), 4.92-4.65 (m, 1H), 4.35-3.27 (m, 7H), 3.11-2.83 (m, 1H), 2.02-1.79 (m, 2H) |
| 157 | 5-{4-aminopyrrolo[2,1-f][1,2,4]triazin-7-yl}-N-[(3R,4S)-4-fluoro-1-(3-fluorocyclobutane-carbonyl)pyrrolidin-3-yl]-2-methoxypyridine-3-carboxamide | | 472.1 | 8.96 (d, J = 2.1 Hz, 1H), 8.82 (dd, J = 15.3, 2.1 Hz, 1H), 8.51 (br dd, J = 15.6, 7.6 Hz, 1H), 7.96 (s, 1H), 7.93-7.71 (m, 2H), 7.12 (d, J = 4.3 Hz, 1H), 7.05 (d, J = 4.3 Hz, 1H), 5.45-5.21 (m, 1H), 5.11-4.89 (m, 1H), 4.85-4.57 (m, 1H), 4.04 (d, J = 4.3 Hz, 3H), 4.00-3.15 (m, 4H), 2.85-2.69 (m, 1H), 2.61-2.48 (m, 2H merge with DMSO), 2.36-2.16 (m, 2H) |
| 158 | 5-{4-aminopyrrolo[2,1-f][1,2,4]triazin-7-yl}-N-[(3R,4S)-1-(4,4-difluorocyclohex-anecarbonyl)-4-fluoropyrrolidin-3-yl]-2-methoxypyridine-3-carboxamide | | 518.0 | 8.93 (s, 1H), 8.86-8.78 (m, 1H), 8.55 (dd, J = 13.6, 7.5 Hz, 1H), 7.94 (s, 1H), 7.10 (d, J = 4.6 Hz, 1H), 7.05-7.01 (m, 1H), 5.43-5.18 (m, 1H), 4.87-4.58 (m, 1H), 4.16-3.14 (m, 7H), 2.13-1.71 (m, 7H), 1.65-1.51 (m, 2H) |
| 159 | 5-{4-aminopyrrolo[2,1-f][1,2,4]triazin-7-yl}-N-[(3R,4S)-4-fluoro-1-(4-fluorobenzoyl)pyrrolidin-3-yl]-2-methoxypyridine-3-carboxamide | | 494.1 | 8.95-8.90 (m, 1H), 8.79 (br s, 1H), 8.64-8.50 (m, 1H), 7.93 (br d, J = 12.2 Hz, 1H), 7.68-7.58 (m, 2H), 7.33-7.24 (m, 2H), 7.13-7.06 (m, 1H), 7.05-6.99 (m, 1H), 5.48-5.16 (m, 1H), 4.89-4.59 (m, 1H), 4.06-3.46 (m, 7H) |

TABLE 5

Compounds in Table 5 were prepared by similar methods as those detailed in Example 31. Compounds listed are racemic.

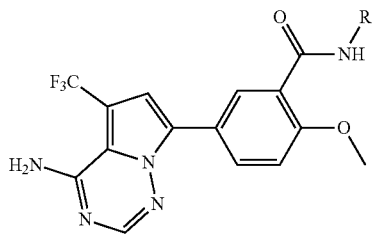

| Ex | Name | "R" Structure | Obs. MS Ion | NMR Assignments (500 MHz, DMSO-d6) δ |
|---|---|---|---|---|
| 160 | 5-[4-amino-5-(trifluoromethyl)pyrrolo[2,1-f][1,2,4]triazin-7-yl]-2-methoxy-N-(3-phenylbutyl)benzamide | | 484.3 | 8.32-8.26 (m, 1H), 8.25-8.18 (m, 1H), 8.09 (s, 1H), 8.06 (d, J = 8.8 Hz, 1H), 7.40 (s, 1H), 7.33-7.26 (m, 2H), 7.23 (d, J = 6.9 Hz, 3H), 7.19-7.13 (m, 1H), 3.90 (s, 1H), 3.25-3.09 (m, 2H), 2.85-2.69 (m, 1H), 1.79 (q, J = 7.1 Hz, 2H), 1.21 (d, J = 6.9 Hz, 3H). |
| 161 | 5-[4-amino-5-(trifluoromethyl)pyrrolo[2,1-f][1,2,4]triazin-7-yl]-N-(3-hydroxy-3-phenylpropyl)-2-methoxybenzamide | | 486.3 | 8.46 (br. s., 1H), 8.41-8.31 (m, 1H), 8.17-8.04 (m, 2H), 7.44 (s, 1H), 7.39-7.29 (m, 4H), 7.29-7.18 (m, 2H), 5.46 (d, J = 4.1 Hz, 1H), 4.76-4.63 (m, 1H), 3.94 (s, 2H), 3.50 (br. s., 2H), 3.37 (br. s., 1H), 1.95-1.75 (m, 2H). |
| 162 | 5-[4-amino-5-(trifluoromethyl)pyrrolo[2,1-f][1,2,4]triazin-7-yl]-2-methoxy-N-[(2-phenoxyphenyl)methyl]benzamide | | 534 | 8.71 (t, J = 5.8 Hz, 1H), 8.39 (d, J = 1.9 Hz, 1H), 8.19-8.04 (m, 2H), 7.50-7.41 (m, 2H), 7.38 (t, J = 7.8 Hz, 2H), 7.32-7.24 (m, 2H), 7.21-7.15 (m, 1H), 7.11 (t, J = 7.3 Hz, 1H), 6.99 (d, J = 8.1 Hz, 2H), 6.89 (d, J = 8.0 Hz, 1H), 4.52 (d, J = 5.8 Hz, 2H), 3.90 (s, 2H). |
| 163 | 5-[4-amino-5-(trifluoromethyl)pyrrolo[2,1-f][1,2,4]triazin-7-yl]-N-{[2-(cyclopropylmethoxy)phenyl]methyl}-2-methoxybenzamide | | 512.1 | 8.60 (t, J = 5.7 Hz, 1H), 8.47-8.38 (m, 1H), 8.19-8.05 (m, 2H), 7.44 (s, 1H), 7.35-7.16 (m, 3H), 7.02-6.85 (m, 2H), 4.51 (d, J = 5.8 Hz, 2H), 3.96 (s, 3H), 3.90 (d, J = 6.7 Hz, 2H), 1.26 (br. s., 1H), 0.57 (d, J = 7.4 Hz, 2H), 0.36 (d, J = 4.5 Hz, 2H). |
| 164 | 5-[4-amino-5-(trifluoromethyl)pyrrolo[2,1-f][1,2,4]triazin-7-yl]-N-[(3-chloropyrazin-2-yl)methyl]-2-methoxybenzamide | | 477.9 | 9.11 (br. s., 1H), 8.68 (s, 1H), 8.58 (br. s., 1H), 8.47 (br. s., 1H), 8.15 (br. s., 2H), 7.47 (s, 1H), 7.34 (d, J = 8.7 Hz, 1H), 4.79 (d, J = 4.6 Hz, 2H), 4.03 (s, 3H). |

TABLE 6

Compounds in Table 6 were prepared by the methods detailed in Examples 13, 21 and 22. In cases were a tertiary amide was generated, the entire amine will be delineated. Compounds without defined stereochemistry were isolated as racemic or diastereomeric mixtures.

| Ex | Name | R | Obs. MS Ion | NMR Assignments (500 MHz, DMSO-d6) δ |
|---|---|---|---|---|
| 165 | 5-[4-amino-5-(trifluoromethyl)pyrrolo[2,1-f][1,2,4]triazin-7-yl]-N-[(3R)-3-(4-chlorophenyl)-3-hydroxypropyl]-2-methylpyridine-3-carboxamide | (R)-3-hydroxy-3-(4-chlorophenyl)propyl | 505.2 | 9.22-9.09 (m, 1H), 8.55-8.43 (m, 1H), 8.40-8.31 (m, 1H), 8.19 (s, 1H), 7.68 (s, 1H), 7.44-7.34 (m, 5H), 5.41 (d, J = 4.6 Hz, 1H), 4.73-4.63 (m, 1H), 3.35 (br. s., 2H), 1.85 (q, J = 6.8 Hz, 2H). |
| 166 | 5-[4-amino-5-(trifluoromethyl)pyrrolo[2,1-f][1,2,4]triazin-7-yl]-N-(1-benzyl-1H-pyrazol-4-yl)-2-methylpyridine-3-carboxamide | 1-benzyl-1H-pyrazol-4-yl | 493.1 | 10.62 (s, 1H), 9.23 (s, 1H), 8.52 (s, 1H), 8.20 (s, 1H), 8.16 (s, 1H), 7.74 (s, 1H), 7.56 (s, 1H), 7.43-7.19 (m, 5H), 5.33 (s, 2H), 2.60 (s, 3H). |
| 167 | 5-[4-amino-5-(trifluoromethyl)pyrrolo[2,1-f][1,2,4]triazin-7-yl]-N-(3-hydroxy-3-phenylpropyl)-2-methylpyridine-3-carboxamide | 3-hydroxy-3-phenylpropyl | 471.3 | 9.16 (s, 1H), 8.49 (br. s., 1H), 8.36 (s, 1H), 8.19 (s, 1H), 7.69 (s, 1H), 7.43-7.28 (m, 4H), 7.28-7.19 (m, 1H), 4.66 (d, J = 4.9 Hz, 1H), 3.45-3.24 (m, 1H), 2.56 (s, 3H), 1.92-1.81 (m, 2H). |
| 168 | 5-[4-amino-5-(trifluoromethyl)pyrrolo[2,1-f][1,2,4]triazin-7-yl]-N-[3-(4-fluorophenyl)-3-hydroxypropyl]-2-methylpyridine-3-carboxamide | 3-(4-fluorophenyl)-3-hydroxypropyl | 489.1 | 9.15 (s, 1H), 8.54-8.44 (m, 1H), 8.35 (s, 1H), 8.18 (s, 1H), 7.68 (s, 1H), 7.47-7.34 (m, 2H), 7.15 (t, J = 8.7 Hz, 2H), 5.37 (d, J = 4.3 Hz, 1H), 4.67 (d, J = 4.9 Hz, 1H), 2.56 (s, 3H), 1.85 (q, J = 7.0 Hz, 2H). |
| 169 | 5-[4-amino-5-(trifluoromethyl)pyrrolo[2,1-f][1,2,4]triazin-7-yl]-N-[(3S)-3-(4-chlorophenyl)-3-hydroxypropyl]-2-methylpyridine-3-carboxamide | (S)-3-hydroxy-3-(4-chlorophenyl)propyl | 505.1 | 9.22-9.09 (m, 1H), 8.52-8.43 (m, 1H), 8.39-8.31 (m. 1H), 8.19 (s, 1H), 7.68 (s, 1H), 7.39 (s, 5H), 5.50-5.35 (m, 1H), 4.67 (d, J = 4.9 Hz, 1H), 3.32 (br. s., 1H), 1.85 (q, J = 6.7 Hz, 2H). |

TABLE 6-continued

Compounds in Table 6 were prepared by the methods detailed in Examples 13, 21 and 22. In cases were a tertiary amide was generated, the entire amine will be delineated. Compounds without defined stereochemistry were isolated as racemic or diastereomeric mixtures.

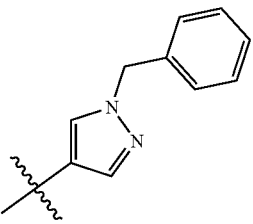 [SMILES: *c1cnn(Cc2ccccc2)c1]

| Ex | Name | R | Obs. MS Ion | NMR Assignments (500 MHz, DMSO-d6) δ |
|---|---|---|---|---|
| 170 | 5-[4-amino-5-(trifluoromethyl)pyrrolo[2,1-f][1,2,4]triazin-7-yl]-N-[1-(cyclopropylmethyl)-1H-pyrazol-4-yl]-2-methylpyridine-3-carboxamide | 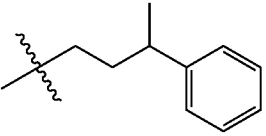 [SMILES: *CCC(C)c1ccccc1] | 457.2 | 10.58 (s, 1H), 9.31-9.18 (m, 1H), 8.53 (s, 1H), 8.21 (s, 1H), 8.11 (s, 1H), 7.74 (s, 1H), 7.53 (s, 1H), 3.97 (d, J=7.0 Hz, 2H), 2.61 (s, 3H), 1.24 (br. s., 1H), 0.53 (d, J = 7.0 Hz, 2H), 0.37 (d, J = 4.3 Hz, 2H). |
| 171 | 5-[4-amino-5-(trifluoromethyl)pyrrolo[2,1-f][1,2,4]triazin-7-yl]-2-methyl-N-(3-phenylbutyl)pyridine-3-carboxamide, 2 TFA |  | 469.1 | 9.12 (s, 1H), 8.57-8.45 (m, 1H), 8.31 (s, 1H), 8.16 (s, 1H), 7.65 (s, 1H), 7.34-7.21 (m, 4H), 7.21-7.13 (m, 1H), 2.88-2.76 (m, 1H), 2.54 (d, J = 3.4 Hz, 4H), 1.81 (q, J = 7.3 Hz, 2H), 1.23 (d, J = 6.7 Hz, 3H). |
| 172 | 7-{5-[(3S)-3-[(4-fluorophenyl)methyl]piperidine-1-carbonyl]-6-methylpyridin-3-yl}-5-(trifluoromethyl)pyrrolo[2,1-f][1,2,4]triazin-4-amine, 2 TFA |  | 513.3 | 9.32-9.03 (m, 1H), 8.35-8.11 (m, 2H), 7.76-7.57 (m, 1H), 7.38-7.21 (m, 2H), 7.19-7.09 (m, 2H), 7.08-6.95 (m, 1H), 6.93-6.79 (m, 1H), 6.49 - 6.37 (m, 1H), 4.54-4.22 (m, 1H), 3.34-3.06 (m, 1H), 2.83-2.61 (m, 2H), 2.55 (s, 3H), 2.46-2.31 (m, 3H), 2.23-2.07 (m, 1H), 1.90-1.67 (m, 2H), 1.65-1.37 (m, 1H), 1.33-1.19 (m, 1H) |
| 173 | 7-{5-[(3S)-3-[(3-fluorophenyl)methyl]piperidine-1-carbonyl]-6-methylpyridin-3-yl}-5-(trifluoromethyl)pyrrolo[2,1-f][1,2,4]triazin-4-amine | | 513 | 9.12 (br s, 1H), 8.30-8.08 (m, 2H), 7.72-7.59 (m, 1H), 7.32-7.22 (m, 1H), 7.18-7.09 (m, 1H), 7.04-6.77 (m, 2H), 6.47-6.34 (m, 1H), 4.56-4.18 (m, 1H), 3.32-3.12 (m, 1H), 3.11-2.94 (m, 1H), 2.82-2.62 (m, 1H), 2.60-2.55 (m, 3H), 2.46-2.29 (m, 3H), 2.18-2.07 (m, 1H), 1.89-1.67 (m, 2H), 1.63-1.43 (m, 1H), 1.34-1.13 (m, 1H) |

TABLE 6-continued

Compounds in Table 6 were prepared by the methods detailed in Examples 13, 21 and 22. In cases were a tertiary amide was generated, the entire amine will be delineated. Compounds without defined stereochemistry were isolated as racemic or diastereomeric mixtures.

| Ex | Name | R | Obs. MS Ion | NMR Assignments (500 MHz, DMSO-d6) δ |
|---|---|---|---|---|
| 174 | 7-{5-[(3R)-3-[(4-fluorophenyl)methyl]piperidine-1-carbonyl]-6-methylpyridin-3-yl}-5-(trifluoromethyl)pyrrolo[2,1-f][1,2,4]triazin-4-amine | 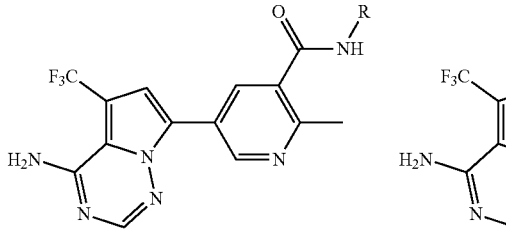 | 513.3 | 9.19-9.02 (m, 1H), 8.32-8.10 (m, 2H), 7.74-7.59 (m, 1H), 7.35-7.22 (m, 1H), 7.13 (br t, J = 8.6 Hz, 1H), 7.04-6.82 (m, 2H), 6.48-6.37 (m, 1H), 4.54-4.26 (m, 1H), 3.33-3.23 (m, 1H), 3.20-2.93 (m, 2H), 2.83-2.59 (m, 2H), 2.46-2.33 (m, 3H), 1.94 (br d, J = 6.7 Hz, 2H), 1.64-1.36 (m, 1H) |
| 175 | 5-[4-amino-5-(trifluoromethyl)pyrrolo[2,1-f][1,2,4]triazin-7-yl]-N-[(3S,4S)-1-cyclopentanecarbonyl-4-methylpyrrolidin-3-yl]-2-methylpyridine-3-carboxamide, 2 TFA | 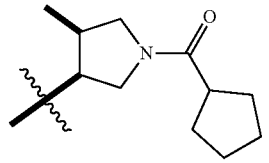 [SMILES: *[C@@H]1CN(C(=O)C2CCCC2)C[C@@H]1C] | 515.9 | 9.17 (br. s., 1H), 8.79-8.60 (m, 1H), 8.37 (s, 1H), 8.18 (d, J = 6.1 Hz, 1H), 7.69 (d, J = 9.2 Hz, 1H), 4.70-4.46 (m, 1H), 3.79 (dd, J = 10.7, 5.9 Hz, 1H), 3.71-3.60 (m, 1H), 3.27-3.13 (m, 1H), 3.08-2.97 (m, 1H), 2.93 (q, J = 7.3 Hz, 1H), 2.78 (br. s., 1H), 1.84-1.70 (m, 2H), 1.70-1.55 (m, 4H), 1.50 (br. s., 2H), 1.16 (t, J = 7.2 Hz, 2H), 1.01 (t, J = 6.7 Hz, 3H). |
| 176 | 5-[4-amino-5-(trifluoromethyl)pyrrolo[2,1-f][1,2,4]triazin-7-yl]-2-methyl-N-[1-(2,2,2-trifluoroethyl)-1H-pyrazol-4-yl]pyridine-3-carboxamide | 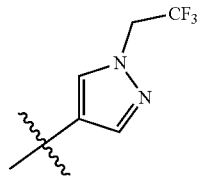 [SMILES: *c1cnn(CC(F)(F)F)c1] | 485.2 | 10.77 (br. s., 1H), 9.25 (d, J = 1.9 Hz, 1H), 8.55 (d, J = 1.9 Hz, 1H), 8.26 (s, 1H), 8.21 (s, 1H), 7.75 (s, 1H), 7.67 (s, 1H), 5.14 (q, J = 9.0 Hz, 2H), 2.61 (s, 3H). |
| 177 | 5-[4-amino-5-(trifluoromethyl)pyrrolo[2,1-f][1,2,4]triazin-7-yl]-N-[(3S)-3-(4-chlorophenyl)-3-methoxypropyl]-2-methylpyridine-3-carboxamide | 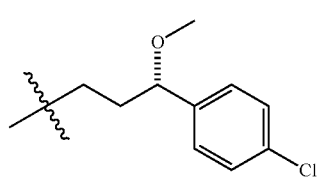 [SMILES: *CC[C@H](OC)c1ccc(Cl)cc1] | 519.2 | 9.15 (d, J = 1.8 Hz, 1H), 8.52 (brt, J = 5.3 Hz, 1H), 8.35 (d, J = 2.1 Hz, 1H), 8.18 (s, 1H), 7.73 (s, 1H), 7.68 (s, 1H), 7.48-7.39 (m, J = 8.5 Hz, 2H), 7.39-7.31 (m, J = 8.5 Hz, 2H), 4.29 (dd, J = 7.8, 5.0 Hz, 1H), 3.90 (s, 1H), 3.42 (s, 1H), 3.35-3.22 (m, 1H), 3.14 (s, 2H), 2.80-2.65 (m, 1H), 2.58-2.54 (m, 3H), 1.94 (dt, J = 13.7, 6.9 Hz, 1H), 1.86-1.72 (m, 1H). |

TABLE 6-continued

Compounds in Table 6 were prepared by the methods detailed in Examples 13, 21 and 22. In cases were a tertiary amide was generated, the entire amine will be delineated. Compounds without defined stereochemistry were isolated as racemic or diastereomeric mixtures.

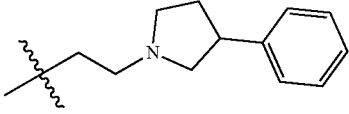 [SMILES: *CCN1CCC(c2ccccc2)C1]

| Ex | Name | R | Obs. MS Ion | NMR Assignments (500 MHz, DMSO-d6) δ |
|---|---|---|---|---|
| 178 | 5-[4-amino-5-(trifluoromethyl)pyrrolo[2,1-f][1,2,4]triazin-7-yl]-2-methyl-N-[2-(3-phenylpyrrolidin-1-yl)ethyl]pyridine-3-carboxamide, TFA | | 510.2 | 9.17 (d, J = 1.8 Hz, 1H), 8.81 (br t, J = 5.6 Hz, 1H), 8.42 (d, J = 1.8 Hz, 1H), 8.15 (s, 1H), 7.63 (s, 1H), 7.35 (br d, J = 4.3 Hz, 5H), 7.30-7.20 (m, 2H), 3.82-3.60 (m, 5H), 3.46 (brs, 2H), 2.91 (br d, J = 5.5 Hz, 1H), 2.66-2.54 (m, 4H), 2.48-1.84 (m, 2H) |
| 179 | 5-[4-amino-5-(trifluoromethyl)pyrrolo[2,1-f][1,2,4]triazin-7-yl]-2-methyl-N-[2-(3-phenylpiperidin-1-yl)ethyl]pyridine-3-carboxamide, TFA | | 524.4 | 9.15 (d, J = 2.2 Hz, 1H), 8.79 (t, J = 6.0 Hz, 1H), 8.37 (d, J = 2.3 Hz, 1H), 8.15 (s, 1H), 7.62 (s, 1H), 7.29 (ddt, J = 21.4, 14.2, 7.4 Hz, 6H), 3.31 (s, 1H), 3.16 (d, J = 12.8 Hz, 1H), 3.01 (s, 2H), 2.56 (s, 3H), 1.99 (s, 1H), 1.88 (t, J = 16.9 Hz, 2H), 1.69 (d, J = 12.6 Hz, 1H) |

TABLE 7

Compounds in Table 7 were prepared by the methods detailed in Example 23. In cases were a tertiary amide was generated, the entire amine will be delineated.

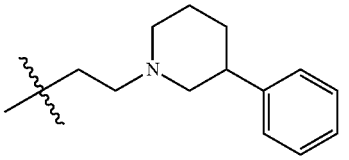 [SMILES: *CCN1CCCC(c2ccccc2)C1]

| Ex | Name | R | Obs. MS Ion | NMR Assignments (500 MHz, DMSO-d6) δ |
|---|---|---|---|---|
| 180 | 5-[4-amino-5-(trifluoromethyl)pyrrolo[2,1-f][1,2,4] triazin-7-yl]-N-[(3S)-3-(4-chlorophenyl)-3-hydroxypropyl]-2-(trifluoromethyl)pyridine-3-carboxamide | 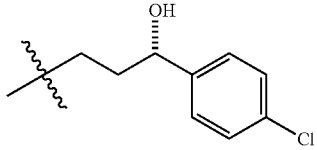 [SMILES: *CC[C@H](O)c1ccc(Cl)cc1] | 559.3 | 9.47-9.42 (m, 1H), 8.79 (br s, 1H), 8.67 (br s, 1H), 8.22 (s, 1H), 7.89 (s, 1H), 7.42-7.32 (m, 6H), 5.54 (br s, 1H), 4.69-4.61 (m, 2H), 3.31 (q, J = 6.5 Hz, 2H), 1.81 (q, J = 6.8 Hz, 2H) |

TABLE 7-continued

Compounds in Table 7 were prepared by the methods detailed in Example 23. In cases were a tertiary amide was generated, the entire amine will be delineated.

| Ex | Name | R | Obs. MS Ion | NMR Assignments (500 MHz, DMSO-d6) δ |
|---|---|---|---|---|
| 181 | 5-[4-amino-5-(trifluoromethyl)pyrrolo[2,1-f][1,2,4] triazin-7-yl]-N-[(3R)-3-(4-chlorophenyl)-3-hydroxypropyl]-2-(trifluoromethyl)pyridine-3-carboxamide, 2 TFA | *(structure: -CH2CH2CH(OH)-C6H4-Cl)* | 559.1 | 9.47 (brs, 1H), 8.83-8.74 (m, 1H), 8.74-8.67 (m, 1H), 8.26 (br s, 1H), 7.93 (br s, 1H), 7.33 (s, 4H), 5.47 (brs, 1H), 4.66 (br d, J = 4.9 Hz, 2H), 3.32 (q, J = 6.1 Hz, 1H), 1.88-1.76 (m, 2H) |
| 182 | 7-{5-[(3S)-3-[(4-fluorophenyl)methyl]piperidine-1-carbonyl]-6-(trifluoromethyl)pyridin-3-yl}-5-(trifluoromethyl)pyrrolo[2,1-f][1,2,4]triazin-4-amine | *(structure: (3S)-3-(4-fluorobenzyl)piperidine)* | 567.2 | 9.52-9.33 (m, 1H), 8.68-8.49 (m, 1H), 8.32-8.14 (m, 1H), 7.96-7.78 (m, 1H), 7.56-7.41 (m, 1H), 7.32-7.21 (m, 1H), 7.15-7.06 (m, 1H), 6.98-6.77 (m, 1H), 6.42-6.29 (m, 1H), 4.51-4.18 (m, 1H), 3.29-3.04 (m, 1H), 3.00-2.84 (m, 1H), 2.82-2.58 (m, 1H), 2.47-2.23 (m, 1H), 2.17-2.00 (m, 1H), 1.93-1.64 (m, 2H), 1.62-1.47 (m, 1H), 1.43-1.15 (m, 2H) |
| 183 | 7-{5-[(3R)-3-[(4-fluorophenyl)methyl]piperidine-1-carbonyl]-6-(trifluoromethyl)pyridin-3-yl}-5-(trifluoromethyl)pyrrolo[2,1-f][1,2,4]triazin-4-amine | *(structure: (3R)-3-(4-fluorobenzyl)piperidine)* | 567.4 | 9.55-9.42 (m, 1H), 8.72-8.54 (m, 1H), 8.33-8.19 (m, 1H), 7.98-7.87 (m, 1H), 7.28 (br dd, J = 8.1, 5.8 Hz, 1H), 7.18-7.09 (m, 1H), 7.03-6.78 (m, 1H), 6.50-6.35 (m, 1H), 4.54-4.21 (m, 1H), 3.72-3.47 (m, 2H), 3.32-3.10 (m, 1H), 3.06-2.90 (m, 1H), 2.86-2.55 (m, 2H), 1.91-1.69 (m, 2H), 1.63-1.42 (m, 1H), 1.37-1.14 (m, 1H) |
| 184 | 5-[4-amino-5-(trifluoromethyl)pyrrolo[2,1-f][1,2,4]triazin-7-yl]-N-(1-benzyl-1H-pyrazol-4-yl)-2-(trifluoromethyl)pyridine-3-carboxamide | *(structure: 1-benzyl-1H-pyrazol-4-yl)* | 547.4 | 10.94-10.84 (m, 1H), 9.56 (s, 1H), 8.88 (s, 1H), 8.27 (s, 1H), 8.21-8.10 (m, 1H), 7.97 (s, 1H), 7.55 (s, 1H), 7.41-7.24 (m, 5H), 5.33 (s, 2H) |

TABLE 8

Compounds in Table 8 were prepared by the methods detailed in Example 44. All of the compounds are cis, racemic at the fluoropyrrolidine. In some instances a mixture of diastereomers were isolated.

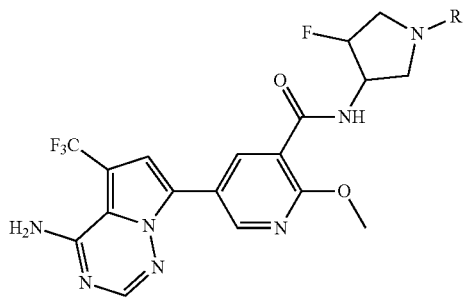

| Ex | Name | R | Obs. MS Ion | NMR Assignments (500 MHz, DMSO-d6) δ |
|---|---|---|---|---|
| 185 | 5-[4-amino-5-(trifluoromethyl)pyrrolo[2,1-f][1,2,4]triazin-7-yl]-N-{1-[(3,3-difluorocyclobutyl)methyl-4-fluoropyrrolidin-3-yl}-2-methoxypyridine-3-carboxamide, 2 TFA | (cyclobutyl with 2 F, -CH2- linker) | 544.2 | N/A |
| 186 | 5-[4-amino-5-(trifluoromethyl)pyrrolo[2,1-f][1,2,4]triazin-7-yl]-N-{4-fluoro-1-[(oxolan-3-yl)methyl]pyrrolidin-3-yl}-2-methoxypyridine-3-carboxamide | (oxolan-3-yl with -CH2- linker) | 524.1 | 8.92 (d, J = 2.4 Hz, 1H), 8.88-8.84 (m, 1H), 8.44 (br s, 1H), 8.18 (s, 1H), 7.63 (s, 1H), 5.35-5.03 (m, 1H), 4.53 (br dd, J = 10.9, 4.2 Hz, 1H), 4.05 (s, 3H), 3.80-3.67 (m, 2H), 3.62 (q, J = 7.7 Hz. 1H), 3.40-3.36 (m, 1H), 3.16-2.54 (m, 4H), 2.47-2.27 (m, 3H), 2.01-1.92 (m, 1H), 1.59-1.51 (m, 1H) |
| 187 | 5-[4-amino-5-(trifluoromethyl)pyrrolo[2,1-f][1,2,4]triazin-7-yl]-N-[4-fluoro-1-(3-methoxypropyl)pyrrolidin-3-yl]-2-methoxypyridine-3-carboxamide | -(CH2)3-OMe | 512.2 | 8.92 (d, J = 2.4 Hz, 1H), 8.88-8.84 (m, 1H), 8.45 (br s, 1H), 8.18 (s, 1H), 7.63 (s, 1H), 5.41-5.06 (m, 1H), 4.67-4.42 (m, 1H), 4.05 (s, 3H), 4.05-4.03 (m, 1H), 3.39-3.35 (m, 2H), 3.31-3.24 (m, 1H), 3.23 (s, 3H), 3.14-2.70 (m, 2H), 2.70-2.53 (m, 2H), 1.73-1.67 (m, 2H) |
| 188 | 5-[4-amino-5-(trifluoromethyl)pyrrolo[2,1-f][1,2,4]triazin-7-yl]-N-{1-[2-(2,2-difluorocyclopropyl)ethyl]-4-fluoropyrrolidin-3-yl}-2-methoxypyridine-3-carboxamide, 2 TFA | (2,2-difluorocyclopropyl with -CH2CH2- linker) | 544.2 | 8.94 (d, J = 2.1 Hz, 1H), 8.86-8.76 (m, 1H), 8.63 (br d, J = 1.8 Hz, 1H), 8.18 (s, 1H), 7.63 (s, 1H), 5.65-5.25 (m, 1H), 5.18-4.62 (m, 1H), 4.14-3.96 (m, 4H), 3.80-3.20 (m, 5H), 1.99-1.83 (m, 1H), 1.82-1.66 (m, 2H), 1.65-1.51 (m, 1H), 1.35-1.17 (m, 1H) |

TABLE 8-continued

Compounds in Table 8 were prepared by the methods detailed in Example 44.
All of the compounds are cis, racemic at the fluoropyrrolidine. In some instances a mixture of diastereomers were isolated.

| Ex | Name | R | Obs. MS Ion | NMR Assignments (500 MHz, DMSO-d6) δ |
|---|---|---|---|---|
| 189 | 5-[4-amino-5-(trifluoromethyl)pyrrolo[2,1-f][1,2,4]triazin-7-yl]-N-[1-(cyclobutylmethyl)-4-fluoropyrrolidin-3-yl]-2-methoxypyridine-3-carboxamide, 2 TFA |  | 508.1 | N/A |
| 190 | 5-[4-amino-5-(trifluoromethyl)pyrrolo[2,1-f][1,2,4]triazin-7-yl]-N-[1-(2-cyclopropylethyl)-4-fluoropyrrolidin-3-yl]-2-methoxypyridine-3-carboxamide, 2 TFA | 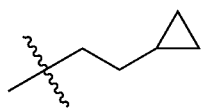 [SMILES: *CCC1CC1] | 508.2 | 8.94 (d, J = 2.3 Hz, 1H), 8.80 (br d, J = 10.7 Hz, 1H), 8.63 (br s, 1H), 8.18 (s, 1H), 7.63 (s, 1H), 5.58-5.29 (m, 1H), 5.17-4.62 (m, 1H), 4.05 (s, 3H), 4.01-3.87 (m, 1H), 3.78-3.18 (m, 5H), 1.55 (br d, J = 3.1 Hz, 2H), 0.71 (br s, 1H), 0.50-0.42 (m, 2H), 0.13 (br s, 2H) |
| 191 | 5-[4-amino-5-(trifluoromethyl)pyrrolo[2,1-f][1,2,4]triazin-7-yl]-N-{4-fluoro-1-[(oxan-2-yl)methyl]pyrrolidin-3-yl}-2-methoxypyridine-3-carboxamide | 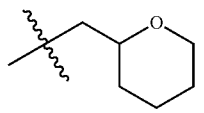 [SMILES: *CC1CCCCO1] | 538.2 | 8.92 (d, J = 2.4 Hz, 1H), 8.86 (s, 1H), 8.45 (br s, 1H), 8.18 (s, 1H), 7.63 (s, 1H), 5.41-4.97 (m, 1H), 4.69-4.36 (m, 1H), 4.05 (s, 3H), 3.87 (br d, J = 10.4 Hz, 1H), 3.63-3.39 (m, 2H), 3.21-2.54 (m, 6H), 1.77 (br d, J = 8.1 Hz, 1H), 1.65-1.54 (m, 1H), 1.52-1.35 (m, 3H), 1.31-1.08 (m, 1H) |
| 192 | 5-[4-amino-5-(trifluoromethyl)pyrrolo[2,1-f][1,2,4]triazin-7-yl]-N-[1-(2-ethoxyethyl)-4-fluoropyrrolidin-3-yl]-2-methoxypyridine-3-carboxamide | 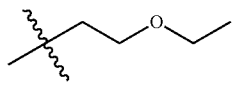 [SMILES: *CCOCC] | 512.2 | 8.92 (d, J = 2.4 Hz, 1H), 8.85 (d, J = 2.4 Hz, 1H), 8.46 (br s, 1H), 8.18 (s, 1H), 7.63 (s, 1H), 5.36-4.99 (m, 1H), 4.68-4.39 (m, 1H), 4.05 (s, 3H), 3.53-3.47 (m, 2H), 3.44 (q, J = 7.0 Hz, 2H), 3.24-2.59 (m, 6H), 1.12 (t, J = 7.0 Hz, 3H) |
| 193 | 5-[4-amino-5-(trifluoromethyl)pyrrolo[2,1-f][1,2,4]triazin-7-yl]-N-{4-fluoro-1-[4,4,4-trifluoro-3-(trifluoromethyl)butyl]pyrrolidin-3-yl}-2-methoxypyridine-3-carboxamide | 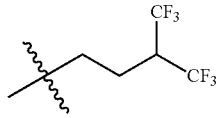 [SMILES: *CCC(C(F)(F)F)C(F)(F)F] | 618.1 | N/A |

TABLE 8-continued

Compounds in Table 8 were prepared by the methods detailed in Example 44.
All of the compounds are cis, racemic at the fluoropyrrolidine. In some instances a mixture of diastereomers were isolated.

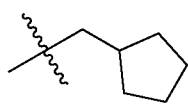 [SMILES: *CC1CCCC1]

| Ex | Name | R | Obs. MS Ion | NMR Assignments (500 MHz, DMSO-d6) δ |
|---|---|---|---|---|
| 194 | 5-[4-amino-5-(trifluoromethyl)pyrrolo[2,1-f][1,2,4]triazin-7-yl]-N-[1-(cyclopentylmethyl)-4-fluoropyrrolidin-3-yl]-2-methoxypyridine-3-carboxamide | 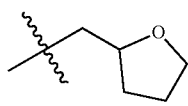 [SMILES: *CC1CCCO1] | 522.1 | N/A |
| 195 | 5-[4-amino-5-(trifluoromethyl)pyrrolo[2,1-f][1,2,4]triazin-7-yl]-N-{4-fluoro-1-[(oxolan-2-yl)methyl]pyrrolidin-3-yl}-2-methoxypyridine-3-carboxamide | 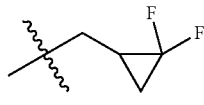 [SMILES: *CC1CC1(F)F] | 524.2 | N/A |
| 196 | 5-[4-amino-5-(trifluoromethyl)pyrrolo[2,1-f][1,2,4]triazin-7-yl]-N-{1-[(2,2-difluorocyclopropyl)methyl]-4-fluoropyrrolidin-3-yl}-2-methoxypyridine-3-carboxamide |  | 530.2 | 8.93 (d, J = 2.3 Hz, 1H), 8.89-8.82 (m, 1H), 8.49 (br s, 1H), 8.18 (s, 1H), 7.63 (s, 1H), 5.38-5.11 (m, 1H), 4.68-4.42 (m, 1H), 4.05 (s, 3H), 3.25-2.57 (m, 6H), 2.04-1.76 (m, 1H), 1.72-1.48 (m, 1H), 1.38-1.13 (m, 1H) |
| 197 | 5-[4-amino-5-(trifluoromethyl)pyrrolo[2,1-f][1,2,4]triazin-7-yl]-N-[1-(cyclopropylmethyl)-4-fluoropyrrolidin-3-yl]-2-methoxypyridine-3-carboxamide | 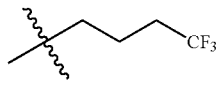 [SMILES: *CCCC(F)(F)F] | 494 | 8.92 (d, J = 2.6 Hz, 1H), 8.87 (d, J = 2.6 Hz, 1H), 8.37 (br d, J = 7.3 Hz, 1H), 8.17 (s, 1H), 7.57 (s, 1H), 5.35-5.04 (m, 1H), 4.70-4.40 (m, 1H), 4.08 (s, 3H), 3.18-3.06 (m, 1H, partially suppressed), 3.04-2.97 (m, 1H), 2.91-2.75 (m, 1H), 2.64 (t, J = 8.4 Hz, 1H), 2.37 (d, J = 6.6 Hz, 2H), 0.96-0.77 (m, 1H), 0.49-0.44 (m, 2H), 0.14-0.10 (m, 2H) |
| 198 | 5-[4-amino-5-(trifluoromethyl)pyrrolo[2,1-f][1,2,4]triazin-7-yl]-N-[4-fluoro-1-(4,4,4-trifluorobutyl)pyrrolidin-3-yl]-2-methoxypyridine-3-carboxamide, 2 TFA |  | 550.2 | 8.94 (d, J = 2.4 Hz, 1H), 8.81 (br s, 1H), 8.63 (br s, 1H), 8.18 (s, 1H), 7.63 (s, 1H), 5.65-5.23 (m, 1H), 5.17-4.63 (m, 1H), 4.05 (s, 3H), 3.83-3.10 (m, 6H), 2.45-2.27 (m, 2H), 1.95-1.79 (m, 2H) |

TABLE 8-continued

Compounds in Table 8 were prepared by the methods detailed in Example 44.
All of the compounds are cis, racemic at the fluoropyrrolidine. In some instances a mixture of diastereomers were isolated.

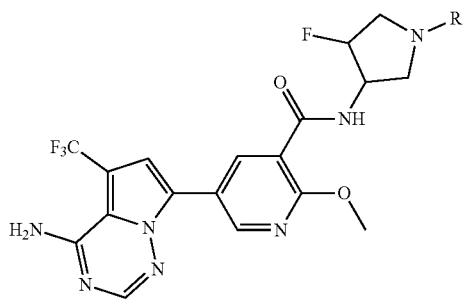

| Ex | Name | R | Obs. MS Ion | NMR Assignments (500 MHz, DMSO-d6) δ |
|---|---|---|---|---|
| 199 | 5-[4-amino-5-(trifluoromethyl)pyrrolo[2,1-f][1,2,4]triazin-7-yl]-N-(1-cyclopentyl-4-fluoropyrrolidin-3-yl)-2-methoxypyridine-3-carboxamide | cyclopentyl-CH< | 508.1 | N/A |
| 200 | 5-[4-amino-5-(trifluoromethyl)pyrrolo[2,1-f][1,2,4]triazin-7-yl]-N-{4-fluoro-1-[(3-methyloxetan-3-yl)methyl]pyrrolidin-3-yl}-2-methoxypyridine-3-carboxamide, 2 TFA | (3-methyloxetan-3-yl)methyl | 524.2 | N/A |
| 201 | 5-[4-amino-5-(trifluoromethyl)pyrrolo[2,1-f][1,2,4]triazin-7-yl]-N-{1-[(1,3-benzoxazol-2-yl)methyl]-4-fluoropyrrolidin-3-yl}-2-methoxypyridine-3-carboxamide | (1,3-benzoxazol-2-yl)methyl | 571.1 | 8.92 (d, J = 2.6 Hz, 1H), 8.84 (d, J = 2.6 Hz, 1H), 8.16 (s, 1H), 7.80-7.69 (m, 2H), 7.57 (s, 1H), 7.43-7.35 (m, 2H), 5.35-5.16 (m, 1H), 4.66-4.56 (m, 1H), 4.14-4.08 (m, 2H), 4.07 (s, 3H), 3.41-3.03 (m, 3H), 2.86 (t, J = 8.6 Hz, 1H). |
| 202 | 5-[4-amino-5-(trifluoromethyl)pyrrolo[2,1-f][1,2,4]triazin-7-yl]-N-{4-fluoro-1-[(quinolin-4-yl)methyl]pyrrolidin-3-yl}-2-methoxypyridine-3-carboxamide | (quinolin-4-yl)methyl | 581.1 | 8.91 (d, J = 2.6 Hz, 1H), 8.87 (d, J = 4.4 Hz, 1H), 8.83 (d, J = 2.6 Hz, 1H), 8.37 (br d, J = 7.0 Hz, 1H), 8.29 (d, J = 8.4 Hz, 1H), 8.05 (d, J = 8.4 Hz, 1H), 7.79-7.74 (m, 1H), 7.64 (t, J = 7.2 Hz, 1H), 7.57-7.54 (m, 2H), 5.34-5.16 (m, 1H), 4.66-4.56 (m, 1H), 4.26-4.17 (m, 2H), 4.05 (s, 3H), 3.14-2.87 (m, 3H), 2.75 (t, J = 8.3 Hz, 1H), |

TABLE 8-continued

Compounds in Table 8 were prepared by the methods detailed in Example 44.
All of the compounds are cis, racemic at the fluoropyrrolidine. In some instances a
mixture of diastereomers were isolated.

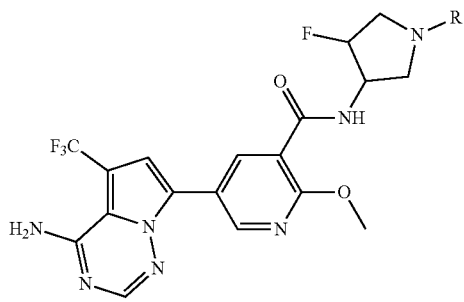

| Ex | Name | R | Obs. MS Ion | NMR Assignments (500 MHz, DMSO-d6) δ |
|---|---|---|---|---|
| 203 | 5-[4-amino-5-(trifluoromethyl)pyrrolo[2,1-f][1,2,4]triazin-7-yl]-N-{4-fluoro-1-[(pyridin-3-yl)methyl]pyrrolidin-3-yl}-2-methoxypyridine-3-carboxamide | -CH2-(pyridin-3-yl) | 531.1 | 8.92 (d, J = 2.2 Hz, 1H), 8.84 (d, J = 2.6 Hz, 1H), 8.54 (s, 1H), 8.48 (dd, J = 4.8, 1.5 Hz, 1H), 8.16 (s, 1H), 7.74 (br d, J = 7.7 Hz, 1H), 7.57 (s, 1H), 7.37 (dd, J = 7.7, 4.8 Hz, 1H), 5.33-5.13 (m, 1H), 4.62-4.52 (m, 1H), 4.08 (s, 3H), 3.80-3.66 (m, 2H), 3.20-2.76 (m, 3H), 2.64 (t, J = 8.4 Hz, 1H). |
| 204 | 5-[4-amino-5-(trifluoromethyl)pyrrolo[2,1-f][1,2,4]triazin-7-yl]-N-(4-fluoro-1-{[6-(trifluoromethyl)pyridin-2-yl]methyl}pyrrolidin-3-yl)-2-methoxypyridine-3-carboxamide, 2 TFA | -CH2-(6-CF3-pyridin-2-yl) | 599.1 | 8.93 (d, J = 2.6 Hz, 1H), 8.82 (d, J = 2.2 Hz, 1H), 8.47 (br d, J = 7.0 Hz, 1H), 8.19-8.13 (m, 2H), 7.89-7.80 (m, 2H), 7.57 (s, 1H), 5.49-5.23 (m, 1H), 4.91-4.68 (m, 1H), 4.35 (br s, 2H), 4.07 (s, 3H), 3.69-3.02 (m, 4H). |
| 205 | 5-[4-amino-5-(trifluoromethyl)pyrrolo[2,1-f][1,2,4]triazin-7-yl]-N-{4-fluoro-1-[(6-methylpyridin-2-yl)methyl]pyrrolidin-3-yl}-2-methoxypyridine-3-carboxamide | -CH2-(6-methylpyridin-2-yl) | 545.2 | 8.92 (d, J = 2.6 Hz, 1H), 8.85 (d, J = 2.6 Hz, 1H), 8.37 (br d, J = 7.3 Hz, 1H), 8.16 (s, 1H), 7.65 (t, J = 7.7 Hz, 1H), 7.57 (s, 1H), 7.23 (d, J = 7.7 Hz, 1H), 7.12 (d, J = 1.1 Hz, 1H), 5.36-5.09 (m, 1H), 4.65-4.50 (m, 1H), 4.08 (s, 3H), 3.81-3.74 (m, 2H), 3.13 (dd, J = 11.7, 4.8 Hz, 1H), 2.96-2.86 (m, 1H), 2.70 (t, J = 8.4 Hz, 1H), 2.46 (s, 3H). |
| 206 | 5-[4-amino-5-(trifluoromethyl)pyrrolo[2,1-f][1,2,4]triazin-7-yl]-N-{4-fluoro-1-[(1,3-thiazol-4-yl)methyl]pyrrolidin-3-yl}-2-methoxypyridine-3-carboxamide | -CH2-(1,3-thiazol-4-yl) | 537 | 9.04 (d, J = 1.8 Hz, 1H), 8.92 (d, J = 2.6 Hz, 1H), 8.84 (d, J = 2.2 Hz, 1H), 8.35 (br d, J = 1.1 Hz, 1H), 8.16 (s, 1H), 7.58-7.52 (m, 2H), 5.32-5.11 (m, 1H), 4.64-4.45 (m, 1H), 4.07 (s, 3H), 3.92-3.85 (m, 2H), 3.25-3.11 (m, 1H), 3.08-3.04 (m, 1H), 2.98-2.88 (m, 1H), 2.70 (t, J = 8.8 Hz, 1H). |

TABLE 8-continued

Compounds in Table 8 were prepared by the methods detailed in Example 44.
All of the compounds are cis, racemic at the fluoropyrrolidine. In some instances a
mixture of diastereomers were isolated.

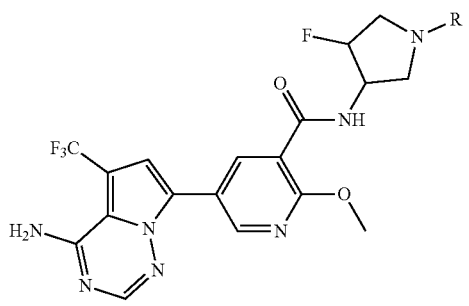

| Ex | Name | R | Obs. MS Ion | NMR Assignments (500 MHz, DMSO-d6) δ |
|---|---|---|---|---|
| 207 | 5-[4-amino-5-(trifluoromethyl)pyrrolo[2,1-f][1,2,4]triazin-7-yl]-N-{1-[(5-cyclopropyl-1,3,4-thiadiazol-2-yl)methyl]-4-fluoropyrrolidin-3-yl}-2-methoxypyridine-3-carboxamide | | 578.2 | 8.92 (d, J = 2.6 Hz, 1H), 8.84 (d, J = 2.6 Hz, 1H), 8.36 (br d, J = 7.0 Hz, 1H), 8.17 (s, 1H), 7.57 (s, 1H), 5.34-5.12 (m, 1H), 4.65-4.51 (m, 1H), 4.12 (d, J = 2.9 Hz, 2H), 4.08 (s, 3H), 3.31-3.14 (m, 1H), 3.13-3.04 (m, 1H), 3.04-2.91 (m, 1H), 2.77 (t, J = 8.8 Hz, 1H), 2.49-2.44 (m, 1H), 1.25-1.17 (m, 2H), 1.05-0.97 (m, 2H). |
| 208 | 5-[4-amino-5-(trifluoromethyl)pyrrolo[2,1-f][1,2,4]triazin-7-yl]-N-{4-fluoro-1-[(2-methyl-1,3-thiazol-4-yl)methyl]pyrrolidin-3-yl}-2-methoxypyridine-3-carboxamide | | 551 | 8.92 (d, J = 2.6 Hz, 1H), 8.85 (d, J = 2.2 Hz, 1H), 8.36 (br d, J = 7.3 Hz, 1H), 8.17 (s, 1H), 7.57 (s, 1H), 7.27 (s, 1H), 5.31-5.09 (m, 1H), 4.61-4.43 (m, 1H), 4.07 (s, 3H), 3.80-3.73 (m, 2H), 3.26-3.09 (m, 1H), 3.07-3.02 (m, 1H), 2.96-2.86 (m, 1H), 2.69 (t, J = 8.6 Hz, 1H), 2.64 (s, 3H). |
| 209 | 5-[4-amino-5-(trifluoromethyl)pyrrolo[2,1-f][1,2,4]triazin-7-yl]-N-{1-[(3,5-dimethyl-1,2-oxazol-4-yl)methyl]-4-fluoropyrrolidin-3-yl}-2-methoxypyridine-3-carboxamide, 2 TFA | | 549.2 | 8.93 (d, J = 2.6 Hz, 1H), 8.83 (d, J = 2.2 Hz, 1H), 8.47 (br d, J = 7.0 Hz, 1H), 8.17 (s, 1H), 7.58 (s, 1H), 5.52-5.22 (m, 1H), 4.93-4.64 (m, 1H), 4.07 (s, 3H), 4.00-3.12 (m, 6H), 2.45 (s, 3H), 2.28 (s, 3H). |
| 210 | 5-[4-amino-5-(trifluoromethyl)pyrrolo[2,1-f][1,2,4]triazin-7-yl]-N-{4-fluoro-1-[(pyridin-2-yl)methyl]pyrrolidin-3-yl}-2-methoxypyridine-3-carboxamide | | 531.2 | 8.92 (d, J = 2.2 Hz, 1H), 8.85 (d, J = 2.2 Hz, 1H), 8.51 (br s, 1H), 8.37 (brd, J = 7.3 Hz, 1H), 8.16 (s, 1H), 7.78 (t, J = 7.7 Hz, 1H), 7.57 (s, 1H), 7.45 (br d, J = 7.3 Hz, 1H), 7.33-7.17 (m, 1H), 5.35-5.11 (m, 1H), 4.63-4.53 (m, 1H), 4.08 (s, 3H), 3.88-3.79 (m, 2H), 3.15-2.84 (m, 3H), 2.71 (br t, J = 8.3 Hz, 1H). |

TABLE 8-continued

Compounds in Table 8 were prepared by the methods detailed in Example 44.
All of the compounds are cis, racemic at the fluoropyrrolidine. In some instances a
mixture of diastereomers were isolated.

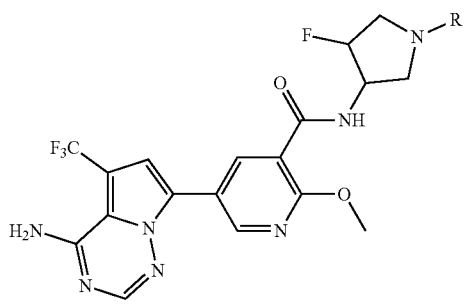

| Ex | Name | R | Obs. MS Ion | NMR Assignments (500 MHz, DMSO-d6) δ |
|---|---|---|---|---|
| 211 | 5-[4-amino-5-(trifluoromethyl)pyrrolo[2,1-f][1,2,4]triazin-7-yl]-N-{1-[(3,4-difluorophenyl)methyl]-4-fluoropyrrolidin-3-yl}-2-methoxypyridine-3-carboxamide | | 566.1 | 8.92 (d, J = 2.6 Hz, 1H), 8.84 (d, J = 2.6 Hz, 1H), 8.36 (br d, J = 7.0 Hz, 1H), 8.16 (s, 1H), 7.57 (s, 1H), 7.43-7.31 (m, 2H), 7.20 (br s, 1H), 5.35-5.12 (m, 1H), 4.65-4.47 (m, 1H), 4.08 (s, 3H), 3.71 (br d, J = 8.4 Hz, 2H), 3.26-2.76 (m, 3H), 2.70-2.56 (m, 1H). |
| 212 | 5-[4-amino-5-(trifluoromethyl)pyrrolo[2,1-f][1,2,4]triazin-7-yl]-N-{1-[(1-cyclopropyl-1H-1,2,3,4-tetrazol-5-yl)methyl]-4-fluoropyrrolidin-3-yl}-2-methoxypyridine-3-carboxamide | | 562.2 | 8.92 (d, J = 2.6 Hz, 1H), 8.84 (d, J = 2.2 Hz, 1H), 8.37 (br d, J = 7.7 Hz, 1H), 8.16 (s, 1H), 7.57 (s, 1H), 5.34-5.14 (m, 1H), 4.66-4.56 (m, 1H), 4.20-4.12 (m, 2H), 4.07 (s, 3H), 3.87 (tt, J = 7.3, 3.7 Hz, 1H), 3.29-3.07 (m, 2H), 3.06-2.95 (m, 1H), 2.79 (t, J = 8.4 Hz, 1H), 1.28-1.19 (m, 4H). |
| 213 | 5-[4-amino-5-(trifluoromethyl)pyrrolo[2,1-f][1,2,4]triazin-7-yl]-N-{4-fluoro-1-[(4-fluorophenyl)methyl]pyrrolidin-3-yl}-2-methoxypyridine-3-carboxamide | | 548.1 | 8.91 (d, J = 2.6 Hz, 1H), 8.83 (d, J = 2.6 Hz, 1H), 8.36 (br d, J = 7.0 Hz, 1H), 8.16 (s, 1H), 7.56 (s, 1H), 7.41-7.27 (m, 2H), 7.15 (t, J = 8.8 Hz, 2H), 5.33-5.11 (m, 1H), 4.67-4.45 (m, 1H), 4.07 (s, 3H), 3.75-3.65 (m, 2H), 3.34-2.74 (m, 3H), 2.68-2.57 (m, 1H). |
| 214 | 5-[4-amino-5-(trifluoromethyl)pyrrolo[2,1-f][1,2,4]triazin-7-yl]-N-{1-[(2-cyanophenyl)methyl]-4-fluoropyrrolidin-3-yl}-2-methoxypyridine-3-carboxamide | | 555.1 | 8.92 (d, J = 2.6 Hz, 1H), 8.84 (d, J = 2.6 Hz, 1H), 8.37 (br d, J = 7.3 Hz, 1H), 8.16 (s, 1H), 7.81 (d, J = 7.0 Hz, 1H), 7.74-7.66 (m, 1H), 7.65-7.61 (m, 1H), 7.57 (s, 1H), 7.49 (t, J = 7.5 Hz, 1H), 5.39-5.13 (m, 1H), 4.66-4.51 (m, 1H), 4.08 (s, 3H), 3.95-3.84 (m, 2H), 3.19-3.09 (m, 1H), 3.06-2.98 (m, 1H), 2.96-2.80 (m, 1H), 2.69 (t, J = 8.3 Hz, 1H). |

TABLE 8-continued

Compounds in Table 8 were prepared by the methods detailed in Example 44.
All of the compounds are cis, racemic at the fluoropyrrolidine. In some instances a mixture of diastereomers were isolated.

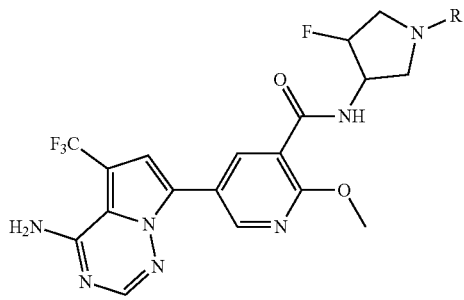

| Ex | Name | R | Obs. MS Ion | NMR Assignments (500 MHz, DMSO-d6) δ |
|---|---|---|---|---|
| 215 | 5-[4-amino-5-(trifluoromethyl)pyrrolo[2,1-f][1,2,4]triazin-7-yl]-N-(1-benzyl-4-fluoropyrrolidin-3-yl)-2-methoxypyridine-3-carboxamide | benzyl | 530.1 | 8.91 (d, J = 2.6 Hz, 1H), 8.84 (d, J = 2.6 Hz, 1H), 8.36 (br d, J = 8.1 Hz, 1H), 8.16 (s, 1H), 7.57 (s, 1H), 7.34 (d, J = 4.4 Hz, 4H), 7.31-7.18 (m, 1H), 5.34-5.11 (m, 1H), 4.64-4.45 (m, 1H), 4.08 (s, 3H), 3.76-3.62 (m, 2H), 3.17-3.02 (m, 1H), 2.95 (dd, J = 8.8, 7.7 Hz, 1H), 2.89-2.74 (m, 1H), 2.61 (t, J = 8.3 Hz, 1H). |
| 216 | 5-[4-amino-5-(trifluoromethyl)pyrrolo[2,1-f][1,2,4]triazin-7-yl]-N-(4-fluoro-1-{[4-(trifluoromethyl)phenyl]methyl}pyrrolidin-3-yl)-2-methoxypyridine-3-carboxamide | 4-CF3-benzyl | 598.1 | 8.91 (d, J = 2.6 Hz, 1H), 8.84 (d, J = 2.2 Hz, 1H), 8.37 (br d, J = 7.3 Hz, 1H), 8.16 (s, 1H), 7.69 (d, J = 8.1 Hz, 2H), 7.59-7.55 (m, 3H), 5.34-5.13 (m, 1H), 4.68-4.48 (m, 1H), 4.08 (s, 3H), 3.84-3.77 (m, 2H), 3.19-3.04 (m, 1H), 3.03-2.94 (m, 1H), 2.92-2.77 (m, 1H), 2.65 (t, J = 8.4 Hz, 1H). |
| 217 | 5-[4-amino-5-(trifluoromethyl)pyrrolo[2,1-f][1,2,4]triazin-7-yl]-N-{4-fluoro-1-[(2-fluorophenyl)methyl]pyrrolidin-3-yl}-2-methoxypyridine-3-carboxamide | 2-F-benzyl | 548.2 | 8.91 (d, J = 2.4 Hz, 1H), 8.84 (d, J = 2.4 Hz, 1H), 8.43 (br d, J = 7.5 Hz, 1H), 8.17 (s, 1H), 7.61 (s, 1H), 7.45 (br t, J = 7.0 Hz, 1H), 7.39-7.30 (m, 1H), 7.24-7.14 (m, 2H), 5.37-5.11 (m, 1H), 4.61-4.46 (m, 1H), 4.05 (s, 3H), 3.75 (s, 2H), 3.18-3.03 (m, 1H), 2.95 (t, J = 8.2 Hz, 1H), 2.89-2.75 (m, 1H), 2.62-2.58 (m, 1H). |
| 218 | 5-[4-amino-5-(trifluoromethyl)pyrrolo[2,1-f][1,2,4]triazin-7-yl]-N-{1-[(2-bromo-1,3-thiazol-5-yl)methyl]-4-fluoropyrrolidin-3-yl}-2-methoxypyridine-3-carboxamide | 2-bromo-thiazol-5-ylmethyl | 615 | 8.92 (d, J = 2.6 Hz, 1H), 8.84 (d, J = 2.6 Hz, 1H), 8.35 (br d, J = 7.3 Hz, 1H), 8.17 (s, 1H), 7.58 (d, J = 6.2 Hz, 2H), 5.32-5.11 (m, 1H), 4.66-4.45 (m, 1H), 4.08 (s, 3H), 3.99-3.91 (m, 2H), 3.14-3.07 (m, 1H), 3.03 (dd, J = 9.2, 7.7 Hz, 1H), 2.96-2.84 (m, 1H), 2.69 (t, J = 8.3 Hz, 1H). |

TABLE 8-continued

Compounds in Table 8 were prepared by the methods detailed in Example 44.
All of the compounds are cis, racemic at the fluoropyrrolidine. In some instances a
mixture of diastereomers were isolated.

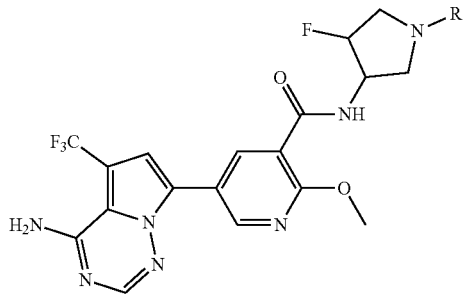

| Ex | Name | R | Obs. MS Ion | NMR Assignments (500 MHz, DMSO-d6) δ |
|---|---|---|---|---|
| 219 | 5-[4-amino-5-(trifluoromethyl)pyrrolo[2,1-f][1,2,4]triazin-7-yl]-N-{1-[(1-benzyl-1H-imidazol-5-yl)methyl]-4-fluoropyrrolidin-3-yl}-2-methoxypyridine-3-carboxamide | | 610.2 | 8.92 (d, J = 2.2 Hz, 1H), 8.84 (d, J = 2.6 Hz, 1H), 8.32 (br d, J = 7.0 Hz, 1H), 8.17 (s, 1H), 7.72 (s, 1H), 7.57 (s, 1H), 7.42-7.23 (m, 3H), 7.23-7.17 (m, 2H), 6.87 (s, 1H), 5.27 (s, 2H), 5.25-5.09 (m, 1H), 4.55-4.45 (m, 1H), 4.06 (s, 3H), 3.58-3.51 (m, 2H), 3.08-2.94 (m, 1H), 2.92-2.86 (m, 1H), 2.83-2.69 (m, 1H), 2.55 (br t, J = 8.6 Hz, 1H). |
| 220 | 5-[4-amino-5-(trifluoromethyl)pyrrolo[2,1-f][1,2,4]triazin-7-yl]-N-{1-[(1-ethyl-1H-imidazol-5-yl)methyl]-4-fluoropyrrolidin-3-yl}-2-methoxypyridine-3-carboxamide | | 548.2 | 8.92 (d, J = 2.6 Hz, 1H), 8.85 (d, J = 2.6 Hz, 1H), 8.34 (br d, J = 6.2 Hz, 1H), 8.16 (s, 1H), 7.57 (s, 2H), 5.40-5.08 (m, 1H), 4.66-4.42 (m, 1H), 4.07 (s, 3H), 4.02 (d, J = 7.0 Hz, 2H), 3.68 (br s, 2H), 3.11-2.98 (m, 1H), 2.96-2.88 (m, 1H), 2.87-2.75 (m, 1H), 2.67-2.56 (m, 1H), 1.35 (t, J = 7.2 Hz, 3H). |
| 221 | 5-[4-amino-5-(trifluoromethyl)pyrrolo[2,1-f][1,2,4]triazin-7-yl]-N-{1-[(3-bromo-1,2-oxazol-5-yl)methyl]-4-fluoropyrrolidin-3-yl}-2-methoxypyridine-3-carboxamide | | 599 | 8.92 (d, J = 2.6 Hz, 1H), 8.83 (d, J = 2.2 Hz, 1H), 8.36 (br d, J = 1.1 Hz, 1H), 8.17 (s, 1H), 7.57 (s, 1H), 6.75 (s, 1H), 5.32-5.12 (m, 1H), 4.64-4.49 (m, 1H), 4.07 (s, 3H), 3.99-3.89 (m, 2H), 3.18-3.10 (m, 1H), 3.07 (t, J = 8.4 Hz, 1H), 3.01-2.87 (m, 1H), 2.74 (t, J = 8.4 Hz, 1H). |
| 222 | 5-[4-amino-5-(trifluoromethyl)pyrrolo[2,1-f][1,2,4]triazin-7-yl]-N-{1-[(1,3-benzothiazol-2-yl)methyl]-4-fluoropyrrolidin-3-yl}-2-methoxypyridine-3-carboxamide | | 587.1 | 8.93 (d, J = 2.6 Hz, 1H), 8.85 (d, J = 2.6 Hz, 1H), 8.41 (br d, J = 7.0 Hz, 1H), 8.16 (s, 1H), 8.07 (d, J = 1.1 Hz, 1H), 7.95 (d, J = 8.4 Hz, 1H), 7.58 (s, 1H), 7.54-7.46 (m, 1H), 7.45-7.40 (m, 1H), 5.37-5.17 (m, 1H), 4.72-4.58 (m, 1H), 4.26-4.19 (m, 2H), 4.10 (s, 3H), 3.39-3.02 (m, 3H), 2.89 (t, J = 8.8 Hz, 1H). |

TABLE 8-continued

Compounds in Table 8 were prepared by the methods detailed in Example 44.
All of the compounds are cis, racemic at the fluoropyrrolidine. In some instances a mixture of diastereomers were isolated.

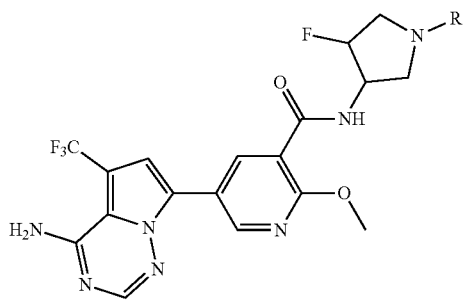

| Ex | Name | R | Obs. MS Ion | NMR Assignments (500 MHz, DMSO-d6) δ |
|---|---|---|---|---|
| 223 | 5-[4-amino-5-(trifluoromethyl)pyrrolo[2,1-f][1,2,4]triazin-7-yl]-N-(4-fluoro-1-{[1-(2-methoxyethyl)-1H-imidazol-5-yl]methyl}pyrrolidin-3-yl)-2-methoxypyridine-3-carboxamide | | 578.2 | 8.92 (d, J = 2.6 Hz, 1H), 8.85 (d, J = 2.6 Hz, 1H), 8.35 (br d, J = 7.3 Hz, 1H), 8.16 (s, 1H), 7.57 (s, 1H), 7.54 (s, 1H), 6.79 (s, 1H), 5.32-5.11 (m, 1H), 4.62-4.47 (m, 1H), 4.16 (t, J = 5.5 Hz, 2H), 4.07 (s, 3H), 3.72-3.64 (m, 2H), 3.63 (t, J = 5.5 Hz, 2H), 3.25 (S, 3H), 3.09-2.95 (m, 1H), 2.93-2.87 (m, 1H), 2.87-2.76 (m, 1H), 2.59 (t, J = 8.4 Hz, 1H). |
| 224 | 5-[4-amino-5-(trifluoromethyl)pyrrolo[2,1-f][1,2,4]triazin-7-yl]-N-{1-[(4-chlorophenyl)methyl]-4-fluoropyrrolidin-3-yl}-2-methoxypyridine-3-carboxamide | | 564 | 8.91 (d, J = 2.2 Hz, 1H), 8.84 (d, J = 2.6 Hz, 1H), 8.36 (br d, J = 8.1 Hz, 1H), 8.16 (s, 1H), 7.56 (s, 1H), 7.44-7.31 (m, 4H), 5.33-5.09 (m, 1H), 4.63-4.48 (m, 1H), 4.08 (s, 3H), 3.73-3.65 (m, 2H), 3.15-3.02 (m, 1H), 2.98-2.92 (m, 1H), 2.87-2.77 (m, 1H), 2.62 (t, J = 8.3 Hz, 1H). |
| 225 | 5-[4-amino-5-(trifluoromethyl)pyrrolo[2,1-f][1,2,4]triazin-7-yl]-N-{4-fluoro-1-[(quinolin-2-yl)methyl]pyrrolidin-3-yl}-2-methoxypyridine-3-carboxamide | | 581.1 | 8.92 (d, J = 2.2 Hz, 1H), 8.84 (d, J = 2.6 Hz, 1H), 8.38 (br d, J = 8.1 Hz, 1H), 8.34 (d, J = 8.4 Hz, 1H), 8.16 (s, 1H), 8.01-7.97 (m, 1H), 7.96 (br d, J = 8.4 Hz, 1H), 7.78-7.72 (m, 1H), 7.64 (d, J = 8.4 Hz, 1H), 7.61-7.56 (m, 2H), 5.33-5.17 (m, 1H), 4.68-4.55 (m, 1H), 4.08 (s, 3H), 4.06-3.98 (m, 2H), 3.28-3.19 (m, 1H), 3.13-3.06 (m, 1H), 3.04-2.90 (m, 1H), 2.76 (t, J = 8.6 Hz, 1H). |

TABLE 8-continued

Compounds in Table 8 were prepared by the methods detailed in Example 44.
All of the compounds are cis, racemic at the fluoropyrrolidine. In some instances a
mixture of diastereomers were isolated.

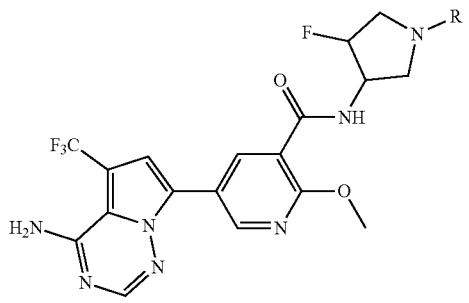

| Ex | Name | R | Obs. MS Ion | NMR Assignments (500 MHz, DMSO-d6) δ |
|---|---|---|---|---|
| 226 | 5-[4-amino-5-(trifluoromethyl)pyrrolo[2,1-f][1,2,4]triazin-7-yl]-N-{4-fluoro-1-[(quinolin-8-yl)methyl]pyrrolidin-3-yl}-2-methoxypyridine-3-carboxamide | (quinolin-8-ylmethyl) | 581.1 | 8.94 (dd, J = 4.2, 1.7 Hz, 1H), 8.91 (d, J = 2.6 Hz, 1H), 8.84 (d, J = 2.6 Hz, 1H), 8.40-8.35 (m, 2H), 8.16 (s, 1H), 7.89 (d, J = 8.1 Hz, 1H), 7.85 (d, J = 6.2 Hz, 1H), 7.62 (t, J = 7.5 Hz, 1H), 7.57 (s, 1H), 7.55 (dd, J = 8.3, 4.2 Hz, 1H), 5.34-5.14 (m, 1H), 4.64-4.54 (m, 1H), 4.42 (s, 2H), 4.07 (s, 3H), 3.26-3.17 (m, 1H), 3.12-3.05 (m, 1H), 3.02-2.91 (m, 1H), 2.76 (t, J = 8.4 Hz, 1H). |
| 227 | 5-[4-amino-5-(trifluoromethyl)pyrrolo[2,1-f][1,2,4]triazin-7-yl]-N-{1-[(3-cyanophenyl)methyl]-4-fluoropyrrolidin-3-yl}-2-methoxypyridine-3-carboxamide | (3-cyanobenzyl) | 555 | 8.92 (d, J = 2.6 Hz, 1H), 8.84 (d, J = 2.2 Hz, 1H), 8.37 (br d, J = 7.3 Hz, 1H), 8.16 (s, 1H), 7.77 (s, 1H), 7.72 (br d, J = 1.1 Hz, 1H), 7.71-7.68 (m, 1H), 7.59-7.55 (m, 2H), 5.33-5.09 (m, 1H), 4.65-4.52 (m, 1H), 4.08 (s, 3H), 3.82-3.73 (m, 2H), 3.18-3.04 (m, 1H), 3.00-2.95 (m, 1H), 2.91-2.78 (m, 1H), 2.65 (t, J = 8.3 Hz, 1H). |
| 228 | 5-[4-amino-5-(trifluoromethyl)pyrrolo[2,1-f][1,2,4]triazin-7-yl]-N-(4-fluoro-1-{[3-(trifluoromethyl)phenyl]methyl}pyrrolidin-3-yl)-2-methoxypyridine-3-carboxamide | (3-trifluoromethylbenzyl) | 598.1 | 8.92 (d, J = 2.6 Hz, 1H), 8.84 (d, J = 2.6 Hz, 1H), 8.37 (br d, J = 7.3 Hz, 1H), 8.16 (s, 1H), 7.69-7.58 (m, 4H), 7.57 (s, 1H), 5.33-5.15 (m, 1H), 4.66-4.51 (m, 1H), 4.07 (s, 3H), 3.85-3.78 (m, 2H), 3.15-3.04 (m, 1H), 3.00-2.96 (m, 1H), 2.90-2.81 (m, 1H), 2.66 (t, J = 8.6 Hz, 1H). |
| 229 | 5-[4-amino-5-(trifluoromethyl)pyrrolo[2,1-f][1,2,4]triazin-7-yl]-N-{1-[(2,6-dichlorophenyl)methyl]-4-fluoropyrrolidin-3-yl}-2-methoxypyridine-3-carboxamide | (2,6-dichlorobenzyl) | 598 | 8.91 (d, J = 2.2 Hz, 1H), 8.84 (d, J = 2.6 Hz, 1H), 8.34 (br d, J = 8.1 Hz, 1H), 8.16 (s, 1H), 7.56 (s, 1H), 7.48 (d, J = 8.1 Hz, 2H), 7.38-7.31 (m, 1H), 5.33-5.11 (m, 1H), 4.57-4.47 (m, 1H), 4.06 (s, 3H), 3.97 (s, 2H), 3.30-3.16 (m, 1H), 3.08-3.03 (m, 1H), 2.99-2.89 (m, 1H), 2.73 (t, J = 8.3 Hz, 1H). |

TABLE 8-continued

Compounds in Table 8 were prepared by the methods detailed in Example 44.
All of the compounds are cis, racemic at the fluoropyrrolidine. In some instances a
mixture of diastereomers were isolated.

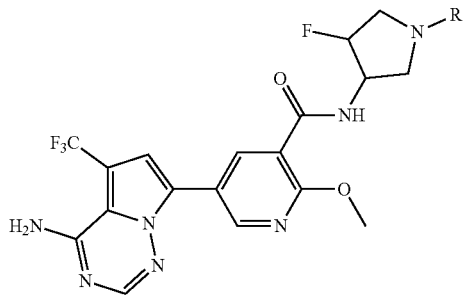

| Ex | Name | R | Obs. MS Ion | NMR Assignments (500 MHz, DMSO-d6) δ |
|---|---|---|---|---|
| 230 | 5-[4-amino-5-(trifluoromethyl)pyrrolo[2,1-f][1,2,4]triazin-7-yl]-N-{4-fluoro-1-[(5-fluoropyridin-3-yl)methyl]pyrrolidin-3-yl}-2-methoxypyridine-3-carboxamide, 2 TFA | | 549.1 | 8.93 (d, J = 2.4 Hz, 1H), 8.81 (d, J = 2.4 Hz, 1H), 8.70-8.49 (m, 2H), 8.17 (s, 1H), 8.01-7.77 (m, 1H), 7.61 (s, 1H), 7.27-6.95 (m, 1H), 5.56-5.16 (m, 1H), 4.88-4.45 (m, 1H), 4.05 (s, 3H), 4.01-3.94 (m, 2H), 3.67-3.57 (m, 1H), 3.54-3.46 (m, 1H), 3.39-3.28 (m, 1H), 3.13-3.05 (m, 1H). |
| 231 | 5-[4-amino-5-(trifluoromethyl)pyrrolo[2,1-f][1,2,4]triazin-7-yl]-N-{4-fluoro-1-[(pyridin-4-yl)methyl]pyrrolidin-3-yl}-2-methoxypyridine-3-carboxamide | | 531.2 | 8.92 (d, J = 2.6 Hz, 1H), 8.84 (d, J = 2.6 Hz, 1H), 8.53 (d, J = 5.9 Hz, 2H), 8.37 (br d, J = 8.1 Hz, 1H), 8.16 (s, 1H), 7.57 (s, 1H), 7.35 (d, J = 5.9 Hz, 2H), 5.34-5.10 (m, 1H), 4.67-4.50 (m, 1H), 4.08 (s, 3H), 3.79-3.71 (m, 2H), 3.12-3.05 (m, 1H), 3.01-2.96 (m, 1H), 2.93-2.76 (m, 1H), 2.67 (t, J = 8.4 Hz, 1H). |
| 232 | 5-[4-amino-5-(trifluoromethyl)pyrrolo[2,1-f][1,2,4]triazin-7-yl]-N-(4-fluoro-1-{[2-(trifluoromethyl)phenyl]methyl}pyrrolidin-3-yl)-2-methoxypyridine-3-carboxamide | | 598.2 | 8.92 (d, J = 2.6 Hz, 1H), 8.85 (d, J = 2.6 Hz, 1H), 8.37 (br d, J = 7.7 Hz, 1H), 8.16 (s, 1H), 7.79 (d, J = 7.7 Hz, 1H), 7.73-7.66 (m, 2H), 7.57 (s, 1H), 7.48-7.47 (m, 1H), 5.35-5.11 (m, 1H), 4.66-4.56 (m, 1H), 4.08 (s, 3H), 3.93-3.85 (m, 2H), 3.18-3.07 (m, 1H), 2.99 (t, J = 8.3 Hz, 1H), 2.93-2.83 (m, 1H), 2.70 (t, J = 8.3 Hz, 1H). |
| 233 | 5-[4-amino-5-(trifluoromethyl)pyrrolo[2,1-f][1,2,4]triazin-7-yl]-N-{4-fluoro-1-[(4-methylphenyl)methyl]pyrrolidin-3-yl}-2-methoxypyridine-3-carboxamide | | 544.2 | 8.92 (d, J = 2.2 Hz, 1H), 8.85 (d, J = 2.2 Hz, 1H), 8.35 (br d, J = 7.7 Hz, 1H), 8.16 (s, 1H), 7.57 (s, 1H), 7.25-7.18 (m, J = 7.7 Hz, 2H), 7.18-7.12 (m, 2H), 5.31-5.08 (m, 1H), 4.54 (td, J = 13.8, 7.0 Hz, 1H), 4.08 (s, 3H), 3.69-3.61 (m, 2H), 3.15-2.98 (m, 1H), 2.96-2.90 (m, 1H), 2.85-2.74 (m, 1H), 2.59 (br t, J = 8.6 Hz, 1H), 2.30 (s, 3H). |

TABLE 8-continued

Compounds in Table 8 were prepared by the methods detailed in Example 44.
All of the compounds are cis, racemic at the fluoropyrrolidine. In some instances a mixture of diastereomers were isolated.

| Ex | Name | R | Obs. MS Ion | NMR Assignments (500 MHz, DMSO-d6) δ |
|---|---|---|---|---|
| 234 | 5-[4-amino-5-(trifluoromethyl)pyrrolo[2,1-f][1,2,4]triazin-7-yl]-N-{1-[(2,5-difluorophenyl)methyl]-4-fluoropyrrolidin-3-yl}-2-methoxypyridine-3-carboxamide | 2,5-difluorobenzyl | 566.2 | 8.92 (d, J = 2.6 Hz, 1H), 8.84 (d, J = 2.6 Hz, 1H), 8.36 (br d, J = 7.3 Hz, 1H), 8.16 (s, 1H), 7.57 (s, 1H), 7.31-7.26 (m, 1H), 7.23 (td, J = 9.2, 4.4 Hz, 1H), 7.19-7.12 (m, 1H), 5.32-5.14 (m, 1H), 4.63-4.53 (m, 1H), 4.07 (s, 3H), 3.81-3.71 (m, 2H), 3.15-3.05 (m, 1H), 3.02-2.98 (m, 1H), 2.93-2.80 (m, 1H), 2.67 (t, J = 8.6 Hz, 1H). |
| 235 | 5-[4-amino-5-(trifluoromethyl)pyrrolo[2,1-f][1,2,4]triazin-7-yl]-N-{4-fluoro-1-[(4-fluoro-3-methylphenyl)methyl]pyrrolidin-3-yl}-2-methoxypyridine-3-carboxamide | 4-fluoro-3-methylbenzyl | 562.2 | 8.91 (d, J = 2.6 Hz, 1H), 8.84 (d, J = 2.4 Hz, 1H), 8.42 (br d, J = 7.3 Hz, 1H), 8.17 (s, 1H), 7.61 (s, 1H), 7.24 (br d, J = 7.0 Hz, 1H), 7.20-7.14 (m, 1H), 7.14-7.06 (m, 1H), 5.34-5.10 (m, 1H), 4.62-4.40 (m, 1H), 4.05 (s, 3H), 3.71-3.55 (m, 2H), 3.14-2.99 (m, 1H), 2.92 (br s, 1H), 2.84-2.72 (m, 1H), 2.62-2.54 (m, 1H), 2.29-2.18 (m, 3H). |
| 236 | 5-[4-amino-5-(trifluoromethyl)pyrrolo[2,1-f][1,2,4]triazin-7-yl]-N-(4-fluoro-1-{[3-fluoro-4-(trifluoromethoxy)phenyl]methyl}pyrrolidin-3-yl)-2-methoxypyridine-3-carboxamide | 3-fluoro-4-(trifluoromethoxy)benzyl | 632.2 | 8.92 (d, J = 2.4 Hz, 1H), 8.83 (d, J = 2.4 Hz, 1H), 8.44 (d, J = 7.6 Hz, 1H), 8.17 (s, 1H), 7.61 (s, 1H), 7.57-7.45 (m, 2H), 7.30 (d, J = 8.2 Hz, 1H), 5.33-5.13 (m, 1H), 4.71-4.49 (m, 1H), 4.05 (s, 3H), 3.81-3.68 (m, 2H), 3.19-3.02 (m, 1H), 2.95 (t, J = 8.2 Hz, 1H), 2.90-2.76 (m, 1H), 2.64 (t, J = 8.4 Hz, 1H). |
| 237 | 5-[4-amino-5-(trifluoromethyl)pyrrolo[2,1-f][1,2,4]triazin-7-yl]-N-{4-fluoro-1-[(3-methylphenyl)methyl]pyrrolidin-3-yl}-2-methoxypyridine-3-carboxamide | 3-methylbenzyl | 544.2 | 8.92 (d, J = 2.6 Hz, 1H), 8.85 (d, J = 2.6 Hz, 1H), 8.36 (br d, J = 1.1 Hz, 1H), 8.16 (s, 1H), 7.57 (s, 1H), 7.28-7.18 (m, 1H), 7.16-7.10 (m, 2H), 7.08 (br d, J = 1.1 Hz, 1H), 5.31-5.10 (m, 1H), 4.64-4.45 (m, 1H), 4.08 (s, 3H), 3.73-3.57 (m, 2H), 3.14-3.02 (m, 1H), 3.00-2.91 (m, 1H), 2.88-2.73 (m, 1H), 2.60 (s, 1H), 2.31 (s, 3H). |

TABLE 8-continued

Compounds in Table 8 were prepared by the methods detailed in Example 44.
All of the compounds are cis, racemic at the fluoropyrrolidine. In some instances a
mixture of diastereomers were isolated.

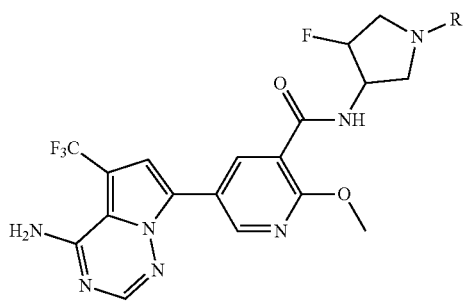

| Ex | Name | R | Obs. MS Ion | NMR Assignments (500 MHz, DMSO-d6) δ |
|---|---|---|---|---|
| 238 | 5-[4-amino-5-(trifluoromethyl)pyrrolo[2,1-f][1,2,4]triazin-7-yl]-N-{1-[(3,5-difluorophenyl)methyl]-4-fluoropyrrolidin-3-yl}-2-methoxypyridine-3-carboxamide | 3,5-difluorobenzyl | 566.2 | 8.92 (d, J = 2.2 Hz, 1H), 8.84 (d, J = 2.6 Hz, 1H), 8.37 (br d, J = 7.7 Hz, 1H), 8.16 (s, 1H), 7.57 (s, 1H), 7.06 (br d, J = 6.6 Hz, 3H), 5.34-5.13 (m, 1H), 4.70-4.49 (m, 1H), 4.08 (s, 3H), 3.80-3.67 (m, 2H), 3.18-3.04 (m, 1H), 3.02-2.94 (m, 1H), 2.92-2.79 (m, 1H), 2.68-2.64 (m, 1H). |
| 239 | 5-[4-amino-5-(trifluoromethyl)pyrrolo[2,1-f][1,2,4]triazin-7-yl]-N-{1-[(5-bromopyridin-3-yl)methyl]-4-fluoropyrrolidin-3-yl}-2-methoxypyridine-3-carboxamide, 2 TFA | 5-bromopyridin-3-ylmethyl | 609 | 8.97-8.90 (m, 1H), 8.86-8.79 (m, 1H), 8.75-8.39 (m, 3H), 8.17 (s, 1H), 8.10-8.00 (m, 1H), 7.62 (s, 1H), 5.52-5.09 (m, 1H), 4.73-4.44 (m, 1H), 4.05 (s, 3H), 3.94-3.66 (m, 1H), 3.55-3.12 (m, 5H). |
| 240 | 5-[4-amino-5-(trifluoromethyl)pyrrolo[2,1-f][1,2,4]triazin-7-yl]-N-{4-fluoro-1-[(naphthalen-1-yl)methyl]pyrrolidin-3-yl}-2-methoxypyridine-3-carboxamide | naphthalen-1-ylmethyl | 580.1 | 8.91 (d, J = 2.2 Hz, 1H), 8.83 (d, J = 2.6 Hz, 1H), 8.34 (br d, J = 7.3 Hz, 1H), 8.28 (d, J = 8.1 Hz, 1H), 8.15 (s, 1H), 7.93 (d, J = 1.1 Hz, 1H), 7.85 (d, J = 8.1 Hz, 1H), 7.59-7.49 (m, 4H), 7.49-7.45 (m, 1H), 5.35-5.13 (m, 1H), 4.63-4.48 (m, 1H), 4.17-4.10 (m, 2H), 4.04 (s, 3H), 3.17-3.08 (m, 1H), 3.03-2.99 (m, 1H), 2.95-2.85 (m, 1H), 2.67 (t, J = 8.4 Hz, 1H). |
| 241 | 5-[4-amino-5-(trifluoromethyl)pyrrolo[2,1-f][1,2,4]triazin-7-yl]-N-{1-[(4-cyanophenyl)methyl]-4-fluoropyrrolidin-3-yl}-2-methoxypyridine-3-carboxamide | 4-cyanobenzyl | 555.1 | 8.92 (d, J = 2.6 Hz, 1H), 8.84 (d, J = 2.6 Hz, 1H), 8.37 (br d, J = 7.0 Hz, 1H), 8.16 (s, 1H), 7.79 (d, J = 8.1 Hz, 2H), 7.57 (d, J = 3.3 Hz, 2H), 7.55 (s, 1H), 5.33-5.14 (m, 1H), 4.66-4.52 (m, 1H), 4.08 (s, 3H), 3.86-3.74 (m, 2H), 3.13-3.05 (m, 1H), 3.00-2.95 (m, 1H), 2.92-2.78 (m, 1H), 2.68-2.63 (m, 1H). |

TABLE 8-continued

Compounds in Table 8 were prepared by the methods detailed in Example 44.
All of the compounds are cis, racemic at the fluoropyrrolidine. In some instances a
mixture of diastereomers were isolated.

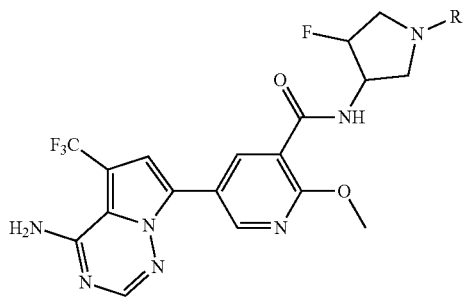

| Ex | Name | R | Obs. MS Ion | NMR Assignments (500 MHz, DMSO-d6) δ |
|---|---|---|---|---|
| 242 | 5-[4-amino-5-(trifluoromethyl)pyrrolo[2,1-f][1,2,4]triazin-7-yl]-N-{4-fluoro-1-[(5-methyl-1,2-oxazol-3-yl)methyl]pyrrolidin-3-yl}-2-methoxypyridine-3-carboxamide | | 535.1 | 8.92 (d, J = 2.2 Hz, 1H), 8.84 (d, J = 2.6 Hz, 1H), 8.36 (br d, J = 8.1 Hz, 1H), 8.17 (s, 1H), 7.57 (s, 1H), 6.20 (s, 1H), 5.30-5.12 (m, 1H), 4.61-4.49 (m, 1H), 4.07 (s, 3H), 3.79-3.66 (m, 2H), 3.21-3.08 (m, 1H, partially suppressed), 3.05-2.98 (m, 1H), 2.95-2.82 (m, 1H), 2.68 (t, J = 8.4 Hz, 1H), 3.41 (s, 3H) |

TABLE 9

Compounds in Table 9 were prepared by the methods detailed in Example 3. For
tertiary amides, the full amine is depicted as the R group. In cases of undefined
stereochemistry, compounds were isolated as racemic or diastereomeric mixtures.

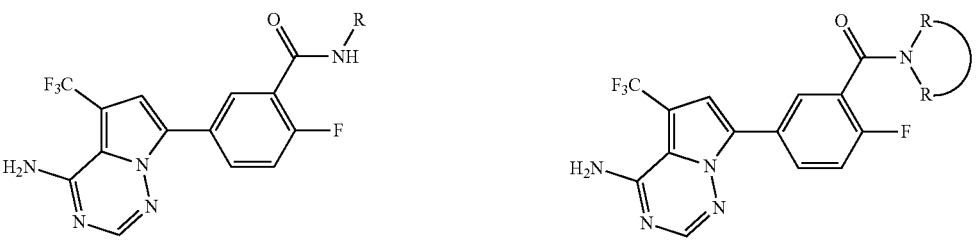

| Ex | Name | R | Obs. MS Ion | NMR Assignments (500 MHz, DMSO-d6) δ |
|---|---|---|---|---|
| 243 | 5-[4-amino-5-(trifluoromethyl)pyrrolo[2,1-f][1,2,4]triazin-7-yl]-2-fluoro-N-(3-phenylbutyl)benzamide | | 472.1 | 8.43 (br. s., 1H), 8.21 (d, J = 5.4 Hz, 1H), 8.15 (br. s., 2H), 7.56 (s, 1H), 7.41 (t, J = 9.1 Hz, 1H), 7.29 (d, J = 7.2 Hz, 2H), 7.27-7.22 (m, 2H), 7.19 (d, J = 7.0 Hz, 1H), 3.26-3.07 (m, 2H), 2.80 (d, J = 6.8 Hz, 1H), 1.80 (d, J = 7.1 Hz, 2H), 1.23 (d, J = 6.6 Hz, 3H) |

TABLE 9-continued

Compounds in Table 9 were prepared by the methods detailed in Example 3. For tertiary amides, the full amine is depicted as the R group. In cases of undefined stereochemistry, compounds were isolated as racemic or diastereomeric mixtures.

| Ex | Name | R | Obs. MS Ion | NMR Assignments (500 MHz, DMSO-d6) δ |
|---|---|---|---|---|
| 244 | 5-[4-amino-5-(trifluoromethyl)pyrrolo[2,1-f][1,2,4]triazin-7-yl]-2-fluoro-N-[(2-phenoxyphenyl)methyl]benzamide | | 521.8 | 8.89 (br. s., 1H), 8.26 (d, J = 4.9 Hz, 1H), 8.19 (dd, J = 6.0, 2.5 Hz, 1H), 7.56 (s, 1H), 7.49-7.41 (m, 2H), 7.37 (t, J = 7.8 Hz, 2H), 7.30 (t, J = 7.6 Hz, 1H), 7.19 (t, J = 7.4 Hz, 1H), 7.10 (t, J = 7.3 Hz, 1H), 7.00 (d, J = 8.0 Hz, 2H), 6.89 (d, J = 8.0 Hz, 1H), 4.51 (d, J = 5.6 Hz, 2H) |
| 245 | 5-[4-amino-5-(trifluoromethyl)pyrrolo[2,1-f][1,2,4]triazin-7-yl]-2-fluoro-N-(3-hydroxy-3-phenylpropyl)benzamide | | 474.1 | 8.44 (br. s., 1H), 8.26 (d, J = 4.8 Hz, 1H), 8.17 (s, 2H), 7.57 (s, 1H), 7.48-7.42 (m, 1H), 7.39-7.29 (m, 4H), 7.27-7.18 (m, 1H), 4.66 (d, J = 4.5 Hz, 1H), 1.86 (q, J = 6.6 Hz, 2H) |
| 246 | 5-[4-amino-5-(trifluoromethyl)pyrrolo[2,1-f][1,2,4]triazin-7-yl]-N-[(3R)-3-(4-chlorophenyl)-3-hydroxypropyl]-2-fluorobenzamide | | 508.2 | 8.43 (br. s., 1H), 8.29-8.22 (m, 1H), 8.21-8.13 (m, 2H), 7.57 (s, 1H), 7.47-7.35 (m, 4H) 5.45 (d, J = 4.6 Hz, 1H), 4.72-4.63 (m, 1H), 3.36-3.27 (m, 1H), 1.91-1.79 (m, 2H). |
| 247 | 5-[4-amino-5-(trifluoromethyl)pyrrolo[2,1-f][1,2,4]triazin-7-yl]-2-fluoro-N-[3-(4-fluorophenyl)-3-hydroxypropyl]benzamide | | 492.3 | 8.44 (br. s., 1H), 8.26 (d, J = 6.7 Hz, 1H), 8.21-8.14 (m, 2H), 7.56 (s, 1H), 7.46-7.35 (m, 3H), 7.15 (t, J = 8.7 Hz, 2H), 5.41 (d, J = 4.3 Hz, 1H), 4.73-4.64 (m, 1H), 3.34 (d, J = 6.4 Hz, 1H), 1.85 (q, J = 6.8 Hz, 2H). |
| 248 | 5-[4-amino-5-(trifluoromethyl)pyrrolo[2,1-f][1,2,4]triazin-7-yl]-N-[(3S)-3-(4-chlorophenyl)-3-hydroxypropyl]-2-fluorobenzamide | | 508.1 | 8.43 (br. s., 1H), 8.25 (d, J = 6.7 Hz, 1H), 8.17 (s, 2H), 7.56 (s, 1H), 7.47-7.33 (m, 4H), 5.46 (d, J = 4.3 Hz, 1H), 4.73-4.61 (m, 1H), 3.34 (d, J = 4.9 Hz, 1H), 1.91-1.77 (m, 2H). |
| 249 | 5-[4-amino-5-(trifluoromethyl)pyrrolo[2,1-f][1,2,4]triazin-7-yl]-2-fluoro-N-(4,4,4-trifluoro-3-hydroxy-3-phenylbutyl)benzamide | | 542.2 | 8.44-8.29 (m, 1H), 8.23-8.11 (m, 3H), 7.66-7.59 (m, 2H), 7.58-7.53 (m, 1H), 7.47-7.34 (m, 4H), 3.45-3.37 (m, 2H), 3.36-3.27 (m, 1H), 3.20-3.12 (m, 1H), 3.02-2.91 (m, 1H), 2.35-2.21 (m, 1H) |

TABLE 9-continued

Compounds in Table 9 were prepared by the methods detailed in Example 3. For tertiary amides, the full amine is depicted as the R group. In cases of undefined stereochemistry, compounds were isolated as racemic or diastereomeric mixtures.

| Ex | Name | R | Obs. MS Ion | NMR Assignments (500 MHz, DMSO-d6) δ |
|---|---|---|---|---|
| 250 | 5-[4-amino-5-(trifluoromethyl) pyrrolo[2,1-f][1,2,4]triazin-7-yl]-2-fluoro-N-[(2-phenyloxan-3-yl)methyl]benzamide | 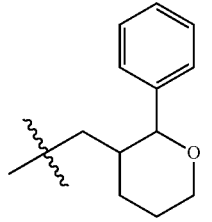 [SMILES: *CC1CCCOC1c1ccccc1] | 514.1 | 8.19 (br. s., 1H), 8.15 (br. s., 3H), 7.53 (s, 1H), 7.45-7.29 (m, 5H), 7.23 (d, J = 6.7 Hz, 1H), 4.68 (br. s., 1H), 4.13 (d, J = 6.7 Hz, 1H), 2.72 (d, J = 13.4 Hz, 1H), 2.24 (br. s., 1H), 1.97 (d, J = 13.1 Hz, 1H), 1.91 (br. s., 1H), 1.79 (br. s., 1H), 1.37 (d, J = 13.1 Hz, 1H). |
| 251 | tert-butyl (3S)-3-{5-[4-amino-5-(trifluoromethyl) pyrrolo[2,1-f][1,2,4]triazin-7-yl]-2-fluorobenzamido} pyrrolidine-1-carboxylate | 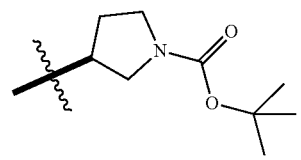 [SMILES: *[C@H]1CCN(C(=O)OC(C)(C)C)C1] | 531.1 | 8.81-8.66 (m, 1H), 8.25-8.08 (m, 3H), 7.56-7.48 (m, 1H), 7.48-7.32 (m, 1H), 4.48-4.34 (m, 2H), 3.21-3.13 (m, 3H), 2.57-2.53 (m, 2H), 2.17-2.05 (m, 1H), 1.98-1.80 (m, 1H), 1.45-1.28 (m, 9H) |
| 252 | 5-[4-amino-5-(trifluoromethyl) pyrrolo[2,1-f][1,2,4]triazin-7-yl]-2-fluoro-N-[(3R,4S)-4-fluoro-1-(3-fluorocyclobutanecarbonyl) pyrrolidin-3-yl]benzamide | 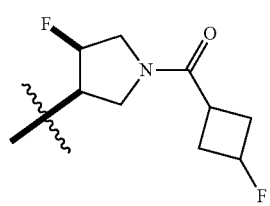 [SMILES: *[C@@H]1CN(C(=O)C2CC(F)C2)C[C@@H]1F] | 527.2 | 8.75 (br dd, J = 13.6, 7.2 Hz, 1H), 8.28-8.20 (m, 2H), 8.18 (s, 1H), 7.58 (d, J = 2.4 Hz, 1H), 7.45 (t, J = 9.3 Hz, 1H), 5.38-5.02 (m, 2H), 4.79-4.56 (m, 1H), 3.94-3.16 (m, 4H), 3.24-3.16 (m, 1H), 2.59-2.32 (m, 5H merge with DMSO) |
| 253 | 5-[4-amino-5-(trifluoromethyl) pyrrolo[2,1-f][1,2,4]triazin-7-yl]-2-fluoro-N-[(3R,4S)-4-fluoro-1-(3-fluorocyclobutanecarbonyl) pyrrolidin-3-yl]benzamide | 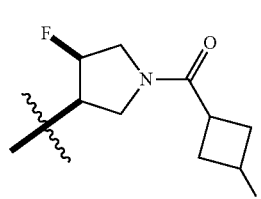 | 527.2 | 8.62 (br d, J = 7.0 Hz, 1H), 8.25 (br d, J = 4.5 Hz, 1H), 8.18 (dt, J = 5.8, 2.7 Hz, 1H), 8.14 (s, 1H), 7.51 (s, 1H), 7.45-7.38 (m, 1H), 5.38-5.18 (m, 1H), 5.07-4.88 (m, 1H), 4.79-4.52 (m, 1H), 3.93-3.14 (m, 4H merge with water), 2.65-2.37 (m, 2H merge with DMSO), 2.85-2.68 (m, 1H), 2.33-2.13 (m, 2H) |
| 254 | 5-[4-amino-5-(trifluoromethyl) pyrrolo[2,1-f][1,2,4]triazin-7-yl]-N-[(3R,4S)-1-(3,3-difluorocyclobutanecarbonyl)-4-fluoropyrrolidin-3-yl]-2-fluorobenzamide | 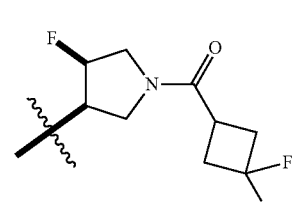 | 545.0 | 8.62 (br d, J = 7.0 Hz, 1H), 8.25 (br t, J = 5.3 Hz, 1H), 8.21-8.16 (m, 1H), 8.14 (s, 1H), 7.51 (s, 1H), 7.45-7.37 (m, 1H), 5.39-5.18 (m, 1H), 4.81-4.53 (m, 1H), 3.93 3.27 (m, 4H merge with water), 3.21-3.09 (m, 1H), 2.87-2.68 (m, 4H) |

TABLE 9-continued

Compounds in Table 9 were prepared by the methods detailed in Example 3. For tertiary amides, the full amine is depicted as the R group. In cases of undefined stereochemistry, compounds were isolated as racemic or diastereomeric mixtures.

| Ex | Name | R | Obs. MS Ion | NMR Assignments (500 MHz, DMSO-d6) δ |
|---|---|---|---|---|
| 255 | 5-[4-amino-5-(trifluoromethyl) pyrrolo[2,1-f][1,2,4]triazin-7-yl]-N-[(3R,4S)-1-(4,4-difluorocyclohexanecarbonyl)-4-fluoropyrrolidin-3-yl]-2-fluorobenzamide, TFA | | 573.1 | 8.76 (br dd, J = 18.6, 7.3 Hz, 1H), 8.29-8.20 (m, 2H), 8.18 (s, 1H), 7.58 (br s, 1H), 7.49-7.41 (m, 1H), 5.42-5.17 (m, 1H), 4.85-4.57 (m, 1H), 4.15-3.23 (m, 4H), 2.06 (br d, J = 11.6 Hz, 2H), 1.99-1.68 (m, 5H), 1.59 (br d, J = 11.6 Hz, 2H) |
| 256 | 5-[4-amino-5-(trifluoromethyl) pyrrolo[2,1-f][1,2,4]triazin-7-yl]-2-fluoro-N-[(3R,4S)-4-fluoro-1-(4-fluorobenzoyl) pyrrolidin-3-yl]benzamide | | 549.3 | 8.73-8.54 (m, 1H), 8.30-8.11 (m, 3H), 7.62 (br d, J = 5.9 Hz, 2H), 7.50 (br s, 1H), 7.41 (br s, 1H), 7.33-7.22 (m, 2H), 5.45-5.17 (m, 1H), 4.83-4.56 (m, 1H), 4.03-3.33 (m, 4H merge with water) |
| 257 | 5-[4-amino-5-(trifluoromethyl) pyrrolo[2,1-f][1,2,4]triazin-7-yl]-N-[(3R,4S)-1-(3,3-difluorocyclopentanecarbonyl)-4-fluoropyrrolidin-3-yl]-2-fluorobenzamide | | 559.2 | 8.62 (br d, J = 5.8 Hz, 1H), 8.25 (br t, J = 6.1 Hz, 1H), 8.21-8.16 (m, 1H), 8.14 (s, 1H), 7.51 (s, 1H), 7.42 (td, J = 9.4, 3.7 Hz, 1H), 5.42-5.18 (m, 1H), 4.82-4.54 (m, 1H), 4.09-3.83 (m, 2H), 3.75-3.41 (m, 3H merge with water), 3.26-3.07 (m, 1H), 2.70-2.45(m, 2H merge with DMSO), 2.41-2.00 (m, 4H), 1.91-1.69 (m, 1H) |
| 258 | 5-[4-amino-5-(trifluoromethyl) pyrrolo[2,1-f][1,2,4]triazin-7-yl]-2-fluoro-N-[(3R,4S)-4-fluoro-1-(oxane-4-carbonyl)pyrrolidin-3-yl]benzamide | | 539.2 | 8.74 (br dd, J = 11.1, 7.8 Hz, 1H), 8.30-8.20 (m, 2H), 8.19 (s, 1H), 7.59 (d, J = 3.4 Hz, 1H), 7.45 (td, J = 9.3, 3.1 Hz, 1H), 5.41-5.17 (m, 1H), 4.83-4.56 (m, 1H), 4.15-2.98 (m, 8H merge with water), 2.78-2.63 (m, 1H), 1.67-1.52 (m, 4H) |
| 259 | 5-[4-amino-5-(trifluoromethyl) pyrrolo[2,1-f][1,2,4]triazin-7-yl]-N-[(3R,4S)-1-(2,2-difluorocyclopropanecarbonyl)-4-fluoropyrrolidin-3-yl]-2-fluorobenzamide | | 531.3 | 8.77-8.60 (m, 1H), 8.28-8.22 (m, 1H), 8.21-8.15 (m, 1H), 8.14 (s, 1H), 7.50 (s, 1H), 7.45-7.37 (m, 1H), 5.45-5.18 (m, 1H), 4.84-4.58 (m, 1H), 4.26-3.48 (m, 4H merge with water), 3.06-2.77 (m, 1H), 1.99-1.77 (m, 2H) |

TABLE 9-continued

Compounds in Table 9 were prepared by the methods detailed in Example 3. For tertiary amides, the full amine is depicted as the R group. In cases of undefined stereochemistry, compounds were isolated as racemic or diastereomeric mixtures.

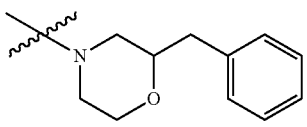 [SMILES: *N1CCOC(Cc2ccccc2)C1]

| Ex | Name | R | Obs. MS Ion | NMR Assignments (500 MHz, DMSO-d6) δ |
|---|---|---|---|---|
| 260 | 7-[3-(2-benzylmorpholine-4-carbonyl)-4-fluorophenyl]-5-(trifluoromethyl)pyrrolo[2,1-f][1,2,4]triazin-4-amine | (2-benzylmorpholin-4-yl) | 500.3 | 8.13 (s, 2H), 8.10-7.98 (m, 1H), 7.51 (br d, J = 8.7 Hz, 1H), 7.44-6.98 (m, 6H), 4.0-2.65 (m, 9H merge with water) |

TABLE 10

Compounds in Table 10 were prepared by the methods detailed in Examples 11 and 12. In cases were stereochemistry is undefined, a mixture of diastereomers was isolated.

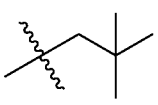

| Ex | Name | R | Obs. MS Ion | NMR Assignments (500 MHz, DMSO-d6) δ |
|---|---|---|---|---|
| 261 | 5-[4-amino-5-(trifluoromethyl)pyrrolo[2,1-f][1,2,4]triazin-7-yl]-N-[(3S)-1-(3,3-dimethylbutanoyl)pyrrolidin-3-yl]-2-methoxypyridine-3-carboxamide | *tert*-butylmethyl | 520.0 | 8.85 (s, 1H), 8.59 (s, 1H), 8.13 (s, 1H), 7.55 (s, 1H), 4.52-4.34 (m, 1H), 3.97 (s, 3H), 3.61-3.51 (m, 1H), 3.48-3.40 (m, 1H), 3.40-3.29 (m, 1H), 2.21-2.07 (m, 3H), 2.02-1.95 (m, 1H), 0.97 (d, J = 6.4 Hz, 10H) |
| 262 | 5-[4-amino-5-(trifluoromethyl)pyrrolo[2,1-f][1,2,4]triazin-7-yl]-2-methoxy-N-[(3S)-1-[3,3,3-trifluoro-2-methyl-2-(trifluoromethyl)propanoyl]pyrrolidin-3-yl]pyridine-3-carboxamide | -C(CH3)(CF3)2 | 613.9 | 8.89 (s, 1H), 8.62 (s, 1H), 8.50 (d, J = 5.9 Hz, 1H), 8.15 (s, 1H), 7.59 (s, 1H), 4.48 (br. s., 1H), 3.98 (s, 4H), 1.85 (br. s., 4H), 1.31-1.11 (m, 2H) |
| 263 | 5-[4-amino-5-(trifluoromethyl)pyrrolo[2,1-f][1,2,4]triazin-7-yl]-N-[(3S)-1-[3,3,3-cyclohexanecarbonylpyrrolidin-3-yl]-2-methoxypyridine-3-carboxamide | cyclohexyl | 532.1 | 8.88 (d, J = 1.8 Hz, 1H), 8.62 (br. s., 1H), 8.53-8.39 (m, 1H), 8.15 (s, 1H), 7.58 (s, 1H), 4.49 (d, J = 5.5 Hz, 1H), 3.98 (s, 3H), 3.60-3.52 (m, 1H), 3.37-3.26 (m, 1H), 2.42-2.31 (m, 1H), 2.08 (dd, J = 13.7, 7.3 Hz, 1H), 1.96-1.85 (m, 1H), 1.68 (br. s., 4H), 1.61 (br. s., 1H), 1.38- |

TABLE 10-continued

Compounds in Table 10 were prepared by the methods detailed in Examples 11 and 12. In cases were stereochemistry is undefined, a mixture of diastereomers was isolated.

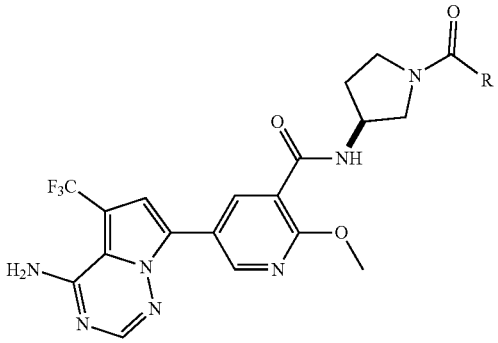

| Ex | Name | R | Obs. MS Ion | NMR Assignments (500 MHz, DMSO-d6) δ |
|---|---|---|---|---|
| | | | | 1.19 (m, 6H), 1.15 (d, J = 9.2 Hz, 1H) |
| 264 | 5-[4-amino-5-(trifluoromethyl) pyrrolo[2,1-f][1,2,4]triazin-7-yl]-N-[(3S)-1-cyclopentanecarbon ylpyrrolidin-3-yl]-2-methoxypyridine-3-carboxamide | cyclopentyl | 518.3 | 8.89 (s, 1H), 8.63 (s, 1H), 8.55-8.40 (m, 1H), 8.16 (d, J = 2.4 Hz, 1H), 7.59 (s, 1H), 4.50 (d, J = 5.2 Hz, 1H), 4.47-4.39 (m, 1H), 3.99 (d, J = 2.1 Hz, 3H), 3.70-3.54 (m, 1H), 3.40-3.26 (m, 1H), 2.91-2.75 (m, 1H), 2.16-2.07 (m, 1H), 1.96-1.88 (m, 1H), 1.77 (d, J = 7.9 Hz, 2H), 1.63 (br. s., 4H), 1.52 (br. s., 2H) |
| 265 | 5-[4-amino-5-(trifluoromethyl) pyrrolo[2,1-f][1,2,4]triazin-7-yl]-N-[(3S)-1-cyclobutanecarbonylpyrrolidin-3-yl]-2-methoxypyridine-3-carboxamide | cyclobutyl | 504.3 | 8.89 (s, 1H), 8.62 (s, 1H), 8.44 (dd, J = 12.7, 6.9 Hz, 1H), 8.16 (d, J = 3.1 Hz, 1H), 7.59 (s, 1H), 4.51-4.37 (m, 1H), 3.99 (s, 3H), 3.66-3.53 (m, 1H), 3.35-3.18 (m, 2H), 2.25-2.03 (m, 5H), 2.02-1.94 (m, 1H), 1.94-1.83 (m, 2H), 1.74 (br. s., 1H) |
| 266 | 5-[4-amino-5-(trifluoromethyl) pyrrolo[2,1-f][1,2,4]triazin-7-yl]-N-[(3S)-1-(3,3-difluorocyclobutanecarbonyl) pyrrolidin-3-yl]-2-methoxypyridine-3-carboxamide | 3,3-difluorocyclobutyl | 540.4 | 8.89 (t, J = 2.1 Hz, 1H), 8.62 (dd, J = 4.9, 2.3 Hz, 1H), 8.50 (t, J = 8.1 Hz, 1H), 8.17 (d, J = 2.8 Hz, 1H), 7.66-7.55 (m, 1H), 4.58-4.38 (m, 1H), 3.99 (s, 3H), 3.70 (dd, J = 10.6, 6.3 Hz, 1H), 3.49-3.41 (m, 2H), 3.20-3.06 (m, 1H), 2.86-2.69 (m, 4H), 2.25-2.07 (m, 1H), 2.06-1.86 (m, 1H) |
| 267 | 5-[4-amino-5-(trifluoromethyl) pyrrolo[2,1-f][1,2,4]triazin-7-yl]-N-[(3S)-1-(3,3-difluorocyclopentanecarbonyl) pyrrolidin-3-yl]-2-methoxypyridine-3-carboxamide | 3,3-difluorocyclopentyl | 554.0 | 8.89 (s, 1H), 8.62 (br. s., 1H), 8.48 (dd, J = 16.6, 6.9 Hz, 1H), 8.16 (d, J = 2.4 Hz, 1H), 7.59 (s, 1H), 4.51 (d, J = 5.8 Hz, 1H), 4.44 (br. s., 1H), 3.99 (s, 3H), 3.86-3.74 (m, 1H), 3.62 (br. s., 1H), 3.24-3.07 (m, 1H), 2.34-2.24 (m, 2H), 2.17-1.99 (m, 4H), 1.99-1.88 (m, 1H), 1.87-1.72 (m, 1H). |

TABLE 11

Compounds in Table 11 were prepared by the methods detailed in Example 17.
In the case of undefined stereochemistry, a racemic mixture was isolated.

| Ex | Name | R | Obs. MS Ion | NMR Assignments (500 MHz, DMSO-d6) δ |
|---|---|---|---|---|
| 268 | 5-[4-amino-5-(trifluoromethyl)pyrrolo[2,1-f][1,2,4]triazin-7-yl]-N-[1-(cyclopropylmethyl)-1H-pyrazol-4-yl]-2-fluoropyridine-3-carboxamide | | 461.3 | 0.75 (br. s., 1H), 9.06 (d, J = 1.9 Hz, 1H), 8.93 (dd, J = 8.8, 2.3 Hz, 1H), 8.23 (s, 1H), 8.13 (s, 1H), 7.80 (s, 1H), 7.57 (s, 1H), 3.97 (d, J = 7.2 Hz, 2H), 1.23 (t, J = 7.4 Hz, 1H), 0.62-0.48 (m, 2H), 0.37 (q, J = 4.7 Hz, 2H) |
| 269 | 5-[4-amino-5-(trifluoromethyl)pyrrolo[2,1-f][1,2,4]triazin-7-yl]-N-[(3R)-3-(4-chlorophenyl)-3-hydroxypropyl]-2-fluoropyridine-3-carboxamide | | 509.0 | 8.99 (s, 1H), 8.81 (d, J = 8.1 Hz, 1H), 8.62 (br. s., 1H), 8.21 (s, 1H), 7.75 (s, 1H), 7.39 (s, 4H), 4.68 (d, J = 4.9 Hz, 1H), 3.48 (br. s., 1H), 1.95-1.73 (m, 2H) |
| 270 | 5-[4-amino-5-(trifluoromethyl)pyrrolo[2,1-f][1,2,4]triazin-7-yl]-N-(1-benzyl-1H-pyrazol-4-yl)-2-fluoropyridine-3-carboxamide | | 497.2 | 10.80 (br. s., 1H), 9.03 (br. s., 1H), 8.90 (d, J = 8.6 Hz, 1H), 8.17 (s, 1H), 8.21 (s, 1H), 7.77 (br. s., 1H), 7.61 (s, 1H), 7.43-7.19 (m, 5H), 5.33 (s, 2H) |
| 271 | 5-[4-amino-5-(trifluoromethyl)pyrrolo[2,1-f][1,2,4]triazin-7-yl]-2-fluoro-N-(3-phenylbutyl)pyridine-3-carboxamide | | 473.1 | 8.96 (br. s., 1H), 8.75 (d, J = 8.2 Hz, 1H), 8.59 (br. s., 1H), 7.72 (s, 1H), 7.40-7.22 (m, 3H), 7.22-7.12 (m, 2H), 3.18 (br. s., 1H), 2.82 (d, J = 13.7 Hz, 2H), 1.82 (d, J = 7.0 Hz, 1H), 1.62 (d, J = 7.0 Hz, 1H), 1.24 (d, J = 6.4 Hz, 2H), 1.17 (d, J = 6.4 Hz, 2H) |
| 272 | 5-[4-amino-5-(trifluoromethyl)pyrrolo[2,1-f][1,2,4]triazin-7-yl]-2-fluoro-N-[3-(4-fluorophenyl)-3-hydroxypropyl]pyridine-3-carboxamide | | 493.0 | 8.98 (s, 1H), 8.81 (d, J = 8.9 Hz, 1H), 8.61 (br. s., 1H), 8.21 (s, 1H), 7.74 (s, 1H), 7.40 (t, J = 6.9 Hz, 2H), 7.15 (t, J = 8.5 Hz, 2H), 5.42 (d, J = 4.3 Hz, 1H), 4.68 (d, J = 5.2 Hz, 1H), 1.86 (q, J = 6.7 Hz, 2H). |
| 273 | 5-[4-amino-5-(trifluoromethyl)pyrrolo[2,1-f][1,2,4]triazin-7-yl]-2-fluoro-N-(4,4,4-trifluoro-3-hydroxy-3-phenylbutyl)pyridine-3-carboxamide | | 543.3 | 9.00 (s, 1H), 8.77 (d, J = 8.8 Hz, 1H), 8.22 (s, 1H), 7.74 (s, 1H), 7.63 (d, J = 7.6 Hz, 2H), 7.50-7.42 (m, 2H), 7.42-7.31 (m, 1H), 2.99 (br. s., 1H), 2.36-2.23 (m, 1H), 1.62 (s, 1H). |

TABLE 12

*Compounds in Table 12 were prepared by the methods detailed in Example 18. For tertiary amides, the entire amine is shown as the R group. When diastereomers were separated, they are included as separate entries. Undefined stereochemistry denotes isolation as a racemic or diastereomeric mixture.*

| Ex | Name | R | Obs. MS Ion | NMR Assignments (500 MHz, DMSO-d6) δ |
|---|---|---|---|---|
| 274 | 5-[4-amino-5-(trifluoromethyl)pyrrolo[2,1-f][1,2,4]triazin-7-yl]-N-[(3R)-3-(4-chlorophenyl)-3-hydroxypropyl]pyridine-3-carboxamide | | 491.1 | 9.35 (s, 1H), 8.95 (s, 1H), 8.79 (s, 1H), 8.72 (br. s., 1H), 8.22 (s, 1H), 7.73 (s, 1H), 7.53-7.34 (m, 4H), 5.45 (br. s., 1H), 4.76-4.58 (m, 1H), 1.97-1.78 (m, 2H). |
| 275 | 5-[4-amino-5-(trifluoromethyl)pyrrolo[2,1-f][1,2,4]triazin-7-yl]-N-(3-phenylbutyl)pyridine-3-carboxamide | | 455.3 | 9.34 (s, 1H), 8.93 (s, 1H), 8.76 (br. s., 1H), 8.67 (br. s., 1H), 8.21 (s, 1H), 7.71 (s, 1H), 7.36-7.23 (m, 4H), 7.22-7.13 (m, 1H), 3.31-3.09 (m, 2H), 2.88-2.75 (m, 1H), 1.95-1.78 (m, 2H), 1.24 (d, J = 6.7 Hz, 3H). |
| 276 | 5-[4-amino-5-(trifluoromethyl)pyrrolo[2,1-f][1,2,4]triazin-7-yl]-N-(1-benzyl-1H-pyrazol-4-yl)pyridine-3-carboxamide | | 479.1 | 9.38 (s, 1H), 9.06 (s, 1H), 8.92 (br. s., 1H), 8.22 (s, 1H), 8.18 (s, 1H), 7.76 (s, 1H), 7.66 (s, 1H), 7.42-7.18 (m, 5H), 5.34 (s, 2H). |
| 277 | 5-[4-amino-5-(trifluoromethyl)pyrrolo[2,1-f][1,2,4]triazin-7-yl]-N-[(3S)-3-(4-chlorophenyl)-3-hydroxypropyl]pyridine-3-carboxamide | | 491.0 | 9.35 (s, 1H), 8.94 (s, 1H), 8.78 (br. s., 1H), 8.69 (br. s., 1H), 8.21 (s, 1H), 7.72 (s, 1H), 7.38 (br. s., 4H), 5.43 (d, J = 4.3 Hz, 1H), 4.67 (d, J = 4.9 Hz, 1H), 1.88 (d, J = 6.7 Hz, 2H). |
| 278 | 5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]pyridine-3-carboxamide | | 498.0 | 9.39 (s, 1H), 9.03 (s, 1H), 8.84 (s, 2H), 8.21 (s, 1H), 7.70 (s, 1H), 5.45-5.19 (m, 1H), 4.84-4.62 (m, 1H), 4.24-3.20 (m, 4H merge with water), 1.58 (s, 3H), 1.54 (s, 3H) |
| 279 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]pyridine-3-carboxamide | | 550.2 | 9.42 (br s, 1H), 9.05 (br s, 1H), 9.02-8.92 (m, 1H), 8.88 (br s, 1H), 8.25 (br s, 1H), 7.77 (br s, 1H), 5.41-5.22 (m, 1H), 4.80-4.59 (m, 1H), 4.54-3.39 (m, 4H merge with water), 1.58 (br s, 3H) |

TABLE 12-continued

*Compounds in Table 12 were prepared by the methods detailed in Example 18. For tertiary amides, the entire amine is shown as the R group. When diastereomers were separated, they are included as separate entries. Undefined stereochemistry denotes isolation as a racemic or diastereomeric mixture.*

| Ex | Name | R | Obs. MS Ion | NMR Assignments (500 MHz, DMSO-d6) δ |
|---|---|---|---|---|
| 280 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]pyridine-3-carboxamide | | 556.2 | 9.39 (s, 1H), 9.03 (s, 1H), 9.00-8.89 (m, 1H), 8.85 (s, 1H), 8.23 (s, 1H), 7.74 (s, 1H), 5.43-5.19 (m, 1H), 4.89-4.60 (m, 1H), 4.18-3.27 (m, 4H merge with water), 2.07 (br d, J = 7.9 Hz, 2H), 1.98-1.71 (m, 5H), 1.68-1.52 (m, 2H) |
| 281 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]pyridine-3-carboxamide | | 513.9 | 9.37 (br s, 1H), 9.12-8.96 (m, 2H), 8.84 (br s, 1H), 8.20 (s, 1H), 7.72 (s, 1H), 5.46-5.20 (m, 1H), 4.91-4.62 (m, 1H), 4.29-3.39 (m, 4H merge with water), 3.10-2.84 (m, 1H), 2.03-1.81 (m, 2H) |
| 282 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]pyridine-3-carboxamide | | 527.9 | 9.38 (s, 1H), 9.02 (s, 1H), 8.91-8.78 (m, 2H), 8.21 (s, 1H), 7.70 (s, 1H), 5.43-5.19 (m, 1H), 4.88-4.56 (m, 1H), 3.97-3.26 (m, 4H merge with water), 2.91-2.70 (m, 3H), 2.60-2.46 (m, 2H merge with DMSO) |
| 283 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]pyridine-3-carboxamide, TFA | | 542.0 | 9.38 (s, 1H), 9.05-8.93 (m, 2H), 8.84 (s, 1H), 8.21 (s, 1H), 7.72 (s, 1H), 5.43-5.19 (m, 1H), 4.87-4.58 (m, 1H), 4.14-3.38 (m, 4H merge with water), 3.29-3.08 (m, 1H), 2.40-2.25 (m, 2H), 2.23-1.98 (m, 3H), 1.89-1.73 (m, 1H) |
| 284 | 5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]pyridine-3-carboxamide, TFA | | 532.1 | 9.36 (br d, J = 12.5 Hz, 1H), 9.07-9.00 (m, 1H), 8.99-8.92 (m, 1H), 8.88-8.76 (m, 1H), 8.20 (br d, J = 8.9 Hz, 1H), 7.71 (br d, J = 13.1 Hz, 1H), 7.63 (br d, J = 7.6 Hz, 2H), 7.30 (br t, J = 8.2 Hz, 2H), 5.47-5.16 (m, 1H), 4.88-4.60 (m, 1H), 4.12-3.54 (m, 4H merge with water) |

TABLE 12-continued

Compounds in Table 12 were prepared by the methods detailed in Example 18.
For tertiary amides, the entire amine is shown as the R group. When diastereomers were
separated, they are included as separate entries. Undefined stereochemistry denotes
isolation as a racemic or diastereomeric mixture.

| Ex | Name | R | Obs. MS Ion | NMR Assignments (500 MHz, DMSO-d6) δ |
|---|---|---|---|---|
| 285 | 7-{5-[(3R)-3-[(4-fluorophenyl)methyl]piperidine-1-carbonyl]pyridin-3-yl]-5-(trifluoromethyl)pyrrolo[2,1-f][1,2,4]triazin-4-amine | | 499.2 | 9.26 (br s, 1H), 8.63-8.33 (m, 2H), 8.21 (s, 1H), 7.75 (br d, J = 19.8 Hz, 1H), 7.28 (br s, 1H), 7.15 (br d, J = 8.2 Hz, 1H), 6.99 (br s, 1H), 6.65 (br s, 1H), 3.57-2.20 (m, 6H merge with DMSO), 1.89-1.59 (m, 3H), 1.57-1.38 (m, 1H), 1.27 (br d, J = 7.0 Hz, 1H) |
| 286 | 7-{5-[(3S)-3-[(4-fluorophenyl)methyl]piperidine-1-carbonyl]pyridin-3-yl}-5-(trifluoromethyl)pyrrolo[2,1-f][1,2,4]triazin-4-amine, TFA | | 499.1 | 9.22 (br s, 1H), 8.63-8.23 (m, 2H), 8.16 (s, 1H), 7.66 (br s, 1H), 7.37-6.87 (m, 3H), 6.74-6.51 (m, 1H), 3.86-3.46 (m, 3H merge with water), 2.98-2.24 (m, 2H merge with DMSO), 1.95-1.12 (m, 6H) |
| 287 | 7-[5-(2-benzylmorpholine-4-carbonyl)pyridin-3-yl]-5-(trifluoromethyl)pyrrolo[2,1-f][1,2,4]triazin-4-amine | | 483.0 | 9.28 (s, 1H), 8.64-8.41 (m, 2H), 8.20 (s, 1H), 7.74 (br s, 1H), 7.40-7.18 (m, 3H), 7.15-6.89 (m, 2H), 4.05-2.41 (m, 9H merge with DMSO) |

TABLE 13

Compounds in Table 13 were prepared by the methods detailed in Example 20.
Undefined stereochemistry implies isolation as a racemic mixture.

| Ex | Name | R | Obs. MS Ion | NMR Assignments (500 MHz, DMSO-d6) δ |
|---|---|---|---|---|
| 288 | 5-[4-amino-5-(trifluoromethyl)pyrrolo[2,1-f][1,2,4]triazin-7-yl]-2-methoxy-6-methyl-N-(4,4,4-trifluoro-3-hydroxy-3-phenylbutyl)pyridine-3-carboxamide | | 569.3 | 8.28 (t, J = 5.3 Hz, 1H), 8.02 (s, 1H), 8.06 (s, 1H), 7.59 (d, J = 7.6 Hz, 2H), 7.39 (t, J = 7.5 Hz, 2H), 7.35-7.29 (m, 1H), 7.25 (s, 1H), 4.00 (s, 3H), 3.63 (br. s., 1H), 3.24 (d, J = 4.9 Hz, 1H), 3.11 (d, J = 5.8 Hz, 1H), 2.29 (s, 3H), 2.25-2.13 (m, 1H) |

TABLE 13-continued

| | | | Obs. MS Ion | NMR Assignments |
|---|---|---|---|---|
| 289 | 5-[4-amino-5-(trifluoromethyl)pyrrolo[2,1-f][1,2,4]triazin-7-yl]-N-[(3R)-3-(4-chlorophenyl)-3-hydroxypropyl]-2-methoxy-6-methylpyridine-3-carboxamide | 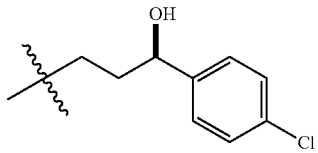 [SMILES: *CC[C@@H](O)c1ccc(Cl)cc1] | 535.3 | 8.47 (t, J = 5.2 Hz, 1H), 8.10 (s, 1H), 8.03 (s, 1H), 7.36 (s, 4H), 7.26 (s, 1H), 4.68 (dd, J = 7.6, 4.6 Hz, 1H), 4.02 (s, 3H), 3.35 (d, J = 5.8 Hz, 2H), 2.30 (s, 3H), 1.92-1.72 (m, 2H). |
| 290 | 5-[4-amino-5-(trifluoromethyl)pyrrolo[2,1-f][1,2,4]triazin-7-yl]-N-[1-(cyclopropylmethyl)-1H-pyrazol-4-yl]-2-methoxy-6-methylpyridine-3-carboxamide | 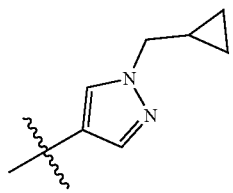 [SMILES: *c1cnn(CC2CC2)c1] | 487.1 | 10.17 (s, 1H), 8.04 (s, 1H), 7.60 (s, 1H), 7.29 (s, 1H), 4.05 (s, 3H), 3.93 (d, J = 7.3 Hz, 2H), 2.33 (s, 3H), 1.22 (br. s., 2H), 0.51 (d, J = 7.3 Hz, 2H), 0.34 (d, J = 4.3 Hz, 2H). |

TABLE 14

Compounds in Table 14 were prepared by the methods detailed in Example 21. When diastereomers were separated, they are included as separate entries. Undefined stereochemistry indicates isolation of product was a mixture of diastereomers.

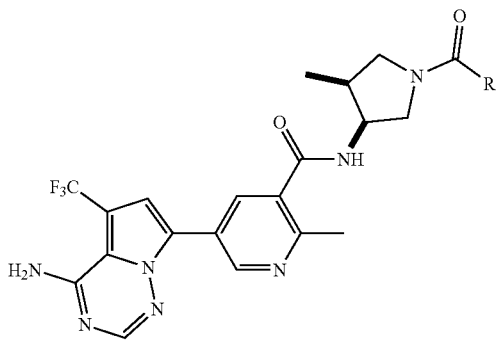

| Ex | Name | R | Obs. MS Ion | NMR Assignments (500 MHz, DMSO-d6) δ |
|---|---|---|---|---|
| 291 | 5-[4-amino-5-(trifluoromethyl)pyrrolo[2,1-f][1,2,4]triazin-7-yl]-N-[(3S,4S)-1-benzoyl-4-methylpyrrolidin-3-yl]-2-methylpyridine-3-carboxamide | phenyl | 524.1 | 9.19 (s, 1H), 8.70 (t, J = 8.4 Hz, 1H), 8.43 (s, 1H), 8.20 (s, 1H), 7.72 (s, 1H), 7.57-7.36 (m, 7H), 2.59 (s, 3H), 1.73 (br. s., 2H), 1.08 (d, J = 6.7 Hz, 2H), 0.97 (d, J = 6.7 Hz, 2H). |
| 292 | 5-[4-amino-5-(trifluoromethyl)pyrrolo[2,1-f][1,2,4]triazin-7-yl]-N-[(3S,4S)-1-(3,3-difluorocyclobutanecarbonyl)-4-methylpyrrolidin-3-yl]-2-methylpyridine-3-carboxamide | 3,3-difluorocyclobutyl | 538.1 | 9.16 (d, J = 5.2 Hz, 1H), 8.73-8.56 (m, 1H), 8.38 (s, 1H), 8.17 (d, J = 5.5 Hz, 1H), 7.68 (d, J = 9.8 Hz, 1H), 4.57 (d, J = 13.4 Hz, 1H), 3.62-3.36 (m, 1H), 3.15-2.98 (m, 2H), 2.86-2.67 (m, 4H), 2.56 (s, 4H), 1.01 (d, J = 6.7 Hz, 3H). |
| 293 | 5-[4-amino-5-(trifluoromethyl)pyrrolo[2,1-f][1,2,4]triazin-7-yl]-N-[(3S,4S)-1-(4,4-difluorocyclohexanecarbonyl)-4-methylpyrrolidin-3-yl]-2-methylpyridine-3-carboxamide | 4,4-difluorocyclohexyl | 566.5 | 8.71 (d, J = 8.5 Hz, 1H), 8.63 (d, J = 8.2 Hz, 1H), 8.36 (s, 1H), 7.67 (d, J = 7.6 Hz, 1H), 4.59 (br. s., 1H), 4.53 (br. s., 1H), 377-3.65 (m, 1H), 3.02 (t, J = 10.5 Hz, 1H), 2.55 (s, 3H), 2.06 (s, 1H), 2.02 (br. s., 2H), 1.87 (d, J = 14.0 Hz, 1H), 1.84-1.70 (m, 3H), 1.56 (d, J = 12.2 Hz, 2H), 1.30-1.22 (m, 3H), 1.02 (t, J = 7.3 Hz, 3H). |

TABLE 14-continued

| | | | Obs. MS Ion | NMR Assignments (500 MHz, DMSO-d6) δ |
|---|---|---|---|---|
| 294 | 5-[4-amino-5-(trifluoromethyl)pyrrolo[2,1-f][1,2,4]triazin-7-yl]-N-[(3S,4S)-1-(3,3-difluoro-cyclopentanecarbonyl)-4-methylpyrrolidin-3-yl]-2-methylpyridine-3-carboxamide | 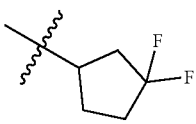 [SMILES: *C1CCC(F)(F)C1] | 552.5 | 9.14 (d, J = 4.3 Hz, 1H), 8.76-8.59 (m, 1H), 8.36 (s, 1H), 8.16 (d, J = 4.6 Hz, 1H), 7.66 (d, J = 8.5 Hz, 1H), 4.63-4.48 (m, 1H), 3.80 (br. s., 1H), 3.43 (br. s., 1H), 3.22-3.06 (m, 2H), 2.55 (d, J = 4.6 Hz, 3H), 2.39-2.19 (m, 2H), 2.04 (d, J = 17.1 Hz, 3H), 1.79 (d, J = 8.5 Hz, 1H), 1.01 (t, J = 6.1 Hz, 3H) |

TABLE 15

Compounds in Table 15 were prepared by the methods detailed in Examples 14 and 19. When diastereomers were separated, they are included as separate entries. If the stereochemistry is undefined, the product was isolated as a mixture of diastereomers.

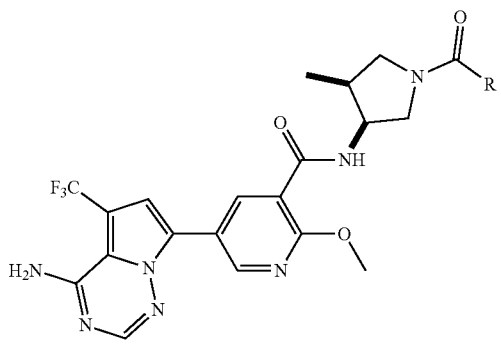

| Ex | Name | R | Obs. MS Ion | NMR Assignments (500 MHz, DMSO-d6) δ |
|---|---|---|---|---|
| 295 | 5-[4-amino-5-(trifluoromethyl)pyrrolo[2,1-f][1,2,4]triazin-7-yl]-N-[(3S,4S)-1-benzoyl-4-methylpyrrolidin-3-yl]-2-methoxypyridine-3-carboxamide | phenyl | 540.3 | 8.87 (dd, J = 15.9, 2.1 Hz, 1H), 8.59 (d, J = 1.9 Hz, 1H), 8.56-8.47 (m, 1H), 8.42 (d, J = 7.9 Hz, 1H), 8.14 (d, J = 17.4 Hz, 1H), 7.64-7.41 (m, 6H), 4.61 (br. s., 1H), 4.46 (br. s., 1H), 4.00 (s, 2H), 3.96 (s, 1H), 3.86-3.72 (m, 2H), 3.40-3.19 (m, 1H), 1.07 (d, J = 6.8 Hz, 1H), 0.95 (d, J = 6.7 Hz, 2H). |
| 296 | 5-[4-amino-5-(trifluoromethyl)pyrrolo[2,1-f][1,2,4]triazin-7-yl]-N-[(3S,4S)-1-cyclohexane-carbonyl-4-methylpyrrolidin-3-yl]-2-methoxypyridine-3-carboxamide | cyclohexyl | 546.4 | 8.88 (br. s., 1H), 8.60 (d, J = 11.4 Hz, 1H), 8.47-8.30 (m, 1H), 8.16 (br. s., 1H), 7.60 (br. s., 1H), 7.26 (br. s., 1H), 7.16 (br. s., 1H), 7.06 (br. s., 1H), 4.55 (br. s., 1H), 4.49 (br. s., 1H), 3.98 (s, 3H), 2.42 (d, J = 13.0 Hz, 1H), 2.38-2.26 (m, 1H), 1.75-1.53 (m, 5H), 1.42-1.20 (m, 4H), 1.14 (br. s., 1H), 1.00 (t, J = 7.4 Hz, 3H). |
| 297 | 5-[4-amino-5-(trifluoromethyl)pyrrolo[2,1-f][1,2,4]triazin-7-yl]-N-[(3S,4S)-1-(3,3-difluoro-cyclopentanecarbonyl)-4-methylpyrrolidin-3-yl]-2-methoxypyridine-3-carboxamide | 3,3-difluorocyclopentyl | 567.9 | 8.87 (br. s., 1H), 8.64-8.54 (m, 1H), 8.48-8.35 (m, 1H), 8.15 (s, 1H), 7.59 (br. s., 1H), 4.63-4.44 (m, 1H), 3.98 (s, 3H), 3.26-3.03 (m, 2H), 2.55 (s, 2H), 2.39-2.21 (m, 2H), 2.11 (d, J = 17.5 Hz, 1H), 2.04 (d, J = 14.0 Hz, 2H), 1.77 (br. s., 2H), 1.06-0.95 (m, 3H) |

TABLE 15-continued

| | | | Obs. MS Ion | NMR Assignments |
|---|---|---|---|---|
| 298 | 5-[4-amino-5-(trifluoromethyl) pyrrolo[2,1-f][1,2,4]triazin-7-yl]-N-[(3S,4S)-1-(3,3-difluorocyclo-butanecarbonyl)-4-methyl-pyrrolidin-3-yl]-2-methoxy-pyridine-3-carboxamide | | 554.4 | 8.88 (br. s., 1H), 8.64-8.55 (m, 1H), 8.48-8.35 (m, 1H), 8.16 (d, J = 2.6 Hz, 1H), 7.60 (d, J = 3.3 Hz, 1H), 4.56 (br. s., 1H), 4.52 (br. s., 1H), 4.04-3.94 (m, 3H), 3.14-3.02 (m, 2H), 2.77 (dd, J = 15.7, 8.1 Hz, 5H), 1.07-0.97 (m, 4H). |
| 299 | 5-[4-amino-5-(trifluoromethyl) pyrrolo[2,1-f][1,2,4]triazin-7-yl]-N-[(3S,4S)-1-(4,4-difluorocyclo-hexanecarbonyl)-4-methyl-pyrrolidin-3-yl]-2-methoxy-pyridine-3-carboxamide | | 582.2 | 8.88 (d, J = 1.8 Hz, 1H), 8.60 (dd, J = 14.2, 2.0 Hz, 1H), 8.46-8.31 (m, 1H), 8.15 (s, 1H), 7.58 (s, 1H), 4.65-4.45 (m, 1H), 4.03-3.95 (m, 3H), 3.74 (br. s., 1H), 3.55 (br. s., 1H), 3.40 (br. s., 1H), 3.25 (t, J = 9.6 Hz, 1H), 3.11-2.98 (m, 1H), 2.04 (d, J = 15.6 Hz, 2H), 1.93-1.71 (m, 4H), 1.56 (d, J = 10.7 Hz, 2H), 1.01 (t, J = 6.9 Hz, 3H). |

TABLE 16

Compounds in Table 16 were prepared by the methods detailed in Examples 27, 31, 34 and 43. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 300 | 5-[4-amino-5-(trifluoromethyl) pyrrolo[2,1-f][1,2,4]triazin-7-yl]-N-[(3R,4S)-1-(4,4-difluorocyclo-hexanecarbonyl)-4-fluoro-pyrrolidin-3-yl]-2-methoxy-pyridine-3-carboxamide | | 586.0 | 8.92 (s, 1H), 8.81 (s, 1H), 8.76 (s, 1H), 8.62-8.49 (m, 1H), 8.17 (s, 1H), 7.62 (s, 1H), 4.91-4.61 (m, 1H), 4.11 (s, 1H), 4.04 (d, J = 8.2 Hz, 3H), 3.93-3.82 (m, 1H), 3.32-3.12 (m, 1H), 3.00 (s, 1H), 2.05 (br. s., 2H), 1.96-1.72 (m, 4H), 1.58 (d, J = 12.5 Hz, 2H). |
| 301 | 5-[4-amino-5-(trifluoromethyl) pyrrolo[2,1-f][1,2,4]triazin-7-yl]-N-[4-fluoro-1-(4-fluorocyclo-hexanecarbonyl)pyrrolidin-3-yl]-2-methoxypyridine-3-carboxamide | | 568.4 | $^1$H NMR (400 MHz, CD$_3$OD) δ 9.01-8.90 (m, 2H), 8.72-8.37 (m, 1H), 8.10-7.99 (m, 1H), 7.34-7.18 (m, 1H), 5.46-5.13 (m, 1H), 4.95-4.70 (m, 2H), 4.21-4.08 (m, 4H), 4.03-3.74 (m, 2H), 3.51-3.38 (m, 1H), 2.55-2.33 (m, 1H), 2.21-2.01 (m, 2H), 1.95-1.80 (m, 2H), 1.72-1.38 (m, 4H) |
| 302 | 5-[4-amino-5-(trifluoromethyl) pyrrolo[2,1-f][1,2,4]triazin-7-yl]-N-[4-fluoro-1-(4-fluorocyclo-hexanecarbonyl)pyrrolidin-3-yl]-2-methoxypyridine-3-carboxamide | | 568.3 | $^1$H NMR (400 MHz, CD$_3$OD) δ 9.06-8.91 (m, 2H), 8.72-8.43 (m, 1H), 8.14-7.98 (m, 1H), 7.32-7.22 (m, 1H), 5.53-5.28 (m, 1H), 5.28-5.15 (m, 1H), 5.04-4.70 (m, 1H), 4.27-4.09 (m, 4H), 4.04-3.81 (m, 2H), 3.80-3.60 (m, 1H), 3.54-3.39 (m, 1H), 2.51-2.30 (m, 1H), 2.26-2.09 (m, 2H), 1.98-1.80 (m, 2H), 1.70-1.40 (m, 4H) |
| 303 | 5-[4-amino-5-(trifluoromethyl) pyrrolo[2,1-f][1,2,4]triazin-7-yl]-N-[(3R,4S)-1-(2,2-difluorocyclo-propanecarbonyl)-4-fluoro-pyrrolidin-3-yl]-2-methoxy-pyridine-3-carboxamide | | 544.5 | 8.98-8.86 (m, 1H), 8.71-8.54 (m, 2H), 8.24-8.07 (m, 1H), 7.67-7.52 (m, 1H), 5.44-5.11 (m, 1H), 4.72-4.50 (m, 1H), 4.20-4.03 (m, 1H), 4.03-3.94 (m, 3H), 3.92-3.54 (m, 2H), 3.55-3.36 (m, 1H), 3.12-2.84 (m, 1H), 2.04-1.76 (m, 2H), 1.34-1.17 (m, 1H). |

TABLE 16-continued

Compounds in Table 16 were prepared by the methods detailed in Examples 27, 31, 34 and 43. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 304 | 5-[4-amino-5-(trifluoromethyl)pyrrolo[2,1-f][1,2,4]triazin-7-yl]-N-[(3R,4S)-1-(2,2-difluoro-1-methylcyclopropanecarbonyl)-4-fluoropyrrolidin-3-yl]-2-methoxypyridine-3-carboxamide | | 558.2 | 8.92-8.88 (m, 1H), 8.75 (d, J = 2.0 Hz, 1H), 8.56-8.42 (m, 1H), 8.14 (s, 1H), 7.55 (s, 1H), 5.48-5.22 (m, 1H), 4.90-4.58 (m, 1H), 4.19-3.99 (m, 4H), 3.98-3.57 (m, 3H), 1.94-1.70 (m, 1H), 1.53 (br s, 1H), 1.41 (br d, J = 8.3 Hz, 3H) |
| 305 | 5-[4-amino-5-(trifluoromethyl)pyrrolo[2,1-f][1,2,4]triazin-7-yl]-N-[(3R,4S)-1-(3,4-difluorobenzoyl)-4-fluoropyrrolidin-3-yl]-2-methoxypyridine-3-carboxamide | | 580.2 | 8.95-8.87 (m, 1H), 8.76 (d, J = 2.1 Hz, 1H), 8.60-8.47 (m, 1H), 8.16 (d, J = 12.5 Hz, 1H), 7.71-7.62 (m, 1H), 7.59 (br d, J = 13.1 Hz, 1H), 7.56-7.48 (m, 1H), 7.45 (br d, J = 8.9 Hz, 1H), 5.48-5.15 (m, 1H), 4.87-4.60 (m, 1H), 4.03 (d, J = 3.1 Hz, 3H), 4.01-3.92 (m, 1H), 3.88-3.75 (m, 1H), 3.71-3.48 (m, 1H); 1 CH suppressed |
| 306 | 5-[4-amino-5-(trifluoromethyl)pyrrolo[2,1-f][1,2,4]triazin-7-yl]-N-[(3R,4S)-1-(2,6-difluorobenzoyl)-4-fluoropyrrolidin-3-yl]-2-methoxypyridine-3-carboxamide | | 580.0 | 8.91 (dd, J = 15.9, 2.4 Hz, 1H), 8.80-8.68 (m, 1H), 8.61-8.49 (m, 1H), 8.16 (d, J = 15.6 Hz, 1H), 7.64-7.54 (m, 2H), 7.25 (br t, J = 8.5 Hz, 2H), 5.49-5.17 (m, 1H), 4.94-4.68 (m, 1H), 4.14-3.93 (m, 4H), 3.92-3.83 (m, 1H), 3.82-3.61 (m, 1H), 3.59-3.44 (m, 1H) |
| 307 | 5-[4-amino-5-(trifluoromethyl)pyrrolo[2,1-f][1,2,4]triazin-7-yl]-N-[(3R,4S)-4-fluoro-1-[(2S)-3,3,3-trifluoro-2-hydroxy-2-methyl-propanoyl]pyrrolidin-3-yl]-2-methoxypyridine-3-carboxamide | | 580.2 | 8.92 (d, J = 1.8 Hz, 1H), 8.76 (dd, J = 5.3, 2.3 Hz, 1H), 8.59-8.47 (m, 1H), 8.17 (s, 1H), 7.61 (s, 1H), 7.05 (d, J = 8.5 Hz, 1H), 5.39-5.14 (m, 1H), 4.80-4.54 (m, 1H), 4.42-4.34 (m, 1H), 4.33-4.20 (m, 1H), 4.03 (s, 3H), 3.80-3.67 (m, 1H), 3.60 (br t, J = 11.0 Hz, 1H), 1.52 (d, J = 10.7 Hz, 3H) |
| 308 | 5-[4-amino-5-(trifluoromethyl)pyrrolo[2,1-f][1,2,4]triazin-7-yl]-N-[(3R,4S)-4-fluoro-1-(4-methylpentanoyl)pyrrolidin-3-yl]-2-methoxypyridine-3-carboxamide | | 538.1 | 8.88 (s, 1H), 8.74 (dd, J = 16.3, 2.3 Hz, 1H), 8.54 (dd, J = 11.7, 7.5 Hz, 1H), 8.13 (s, 1H), 7.56 (s, 1H), 5.41-5.15 (m, 1H), 4.84-4.53 (m, 1H), 4.02 (d, J = 5.2 Hz, 3H), 3.99-3.83 (m, 1H), 3.81-3.62 (m, 1H), 3.43 (t, J = 10.2 Hz, 1H), 3.24-3.11 (m, 1H), 2.30-2.12 (m, 2H), 1.52 (dquin, J = 13.1, 6.7 Hz, 1H), 1.44-1.31 (m, 2H), 0.85 (d, J = 6.4 Hz, 6H) |
| 309 | 5-[4-amino-5-(trifluoromethyl)pyrrolo[2,1-f][1,2,4]triazin-7-yl]-N-[(3R,4S)-4-fluoro-1-(5-fluoro-pyridine-2-carbonyl)pyrrolidin-3-yl]-2-methoxypyridine-3-carboxamide | | 563.0 | 8.92 (dd, J = 7.1, 2.1 Hz, 1H), 8.77 (dd, J = 11.3, 2.1 Hz, 1H), 8.65-8.58 (m, 1H), 8.51-8.43 (m, 1H), 8.16 (d, J = 8.2 Hz, 1H), 7.94 (dd, J = 8.7, 4.7 Hz, 1H), 7.89-7.82 (m, 1H), 7.57 (d, J = 8.6 Hz, 1H), 5.43-5.22 (m, 1H), 4.87-4.65 (m, 1H), 4.35-4.20 (m, 1H), 4.19-4.09 (m, 1H), 4.09-4.02 (m, 3H), 3.99-3.86 (m, 1H), 3.82-3.50 (m, 1H) |
| 310 | 5-[4-amino-5-(trifluoromethyl)pyrrolo[2,1-f][1,2,4]triazin-7-yl]-N-[(3R,4S)-4-fluoro-1-propanoylpyrrolidin-3-yl]-2-methoxypyridine-3-carboxamide | | 496.4 | 8.90 (d, J = 2.1 Hz, 1H), 8.76 (dd, J = 15.9, 2.1 Hz, 1H), 8.52 (br dd, J = 12.5, 7.6 Hz, 1H), 8.16 (s, 1H), 7.59 (s, 1H), 5.44-5.17 (m, 1H), 4.86-4.54 (m, 1H), 4.03 (d, J = 4.6 Hz, 3H), 3.96 (t, J = 9.2 Hz, 1H), 3.92-3.83 (m, 1H), 3.78-3.59 (m, 1H), 3.45-3.15 (m, 1H), 2.39-2.14 (m, 2H), 0.99 (td, J = 7.4, 3.5 Hz, 3H) |

TABLE 16-continued

Compounds in Table 16 were prepared by the methods detailed in Examples 27, 31, 34 and 43. When diastereomers were separated, they are included as separate entries. If the stereochemistry is undefined, the product was isolated as a mixture of diastereomers.

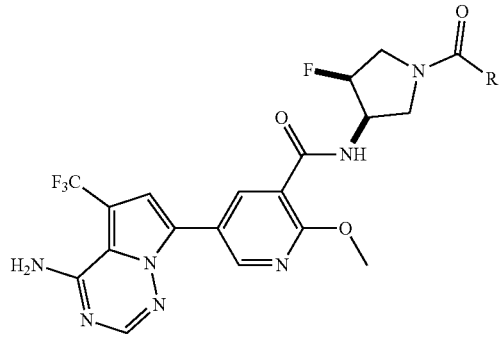

| Ex | Name | R | Obs. MS Ion | NMR Assignments (500 MHz, DMSO-d6) δ |
|---|---|---|---|---|
| 311 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methyl-propanoyl]pyrrolidin-3-yl]-2-methoxypyridine-3-carboxamide | | 580.2 | 8.96-8.88 (m, 1H), 8.76 (dd, J = 11.0, 2.1 Hz, 1H), 8.60-8.47 (m, 1H), 8.16 (s, 1H), 7.60 (d, J = 3.1 Hz, 1H), 7.13 (d, J = 4.3 Hz, 1H), 4.76-4.57 (m, 1H), 4.52-4.45 (m, 1H), 4.39-4.26 (m, 1H), 4.03 (d, J = 2.1 Hz, 3H), 3.99-3.33 (m, 2H), 1.53 (s, 3H) partial suppression |
| 312 | 5-[4-amino-5-(trifluoromethyl)pyrrolo[2,1-f][1,2,4]triazin-7-yl]-N-[(3R,4S)-4-fluoro-1-[1-(trifluoromethyl)cyclohexanecarbonyl]pyrrolidin-3-yl]-2-methoxypyridine-3-carboxamide, TFA | | 618.1 | 8.89 (d, J = 2.1 Hz, 1H), 8.74 (br s, 1H), 8.62-8.48 (m, 1H), 8.14 (s, 1H), 7.57 (s, 1H), 5.44-5.14 (m, 1H), 4.83-4.60 (m, 1H), 4.02 (s, 3H), 3.97-3.36 (m, 3H, partial suppression), 2.45-2.37 (m, 1H), 1.76-1.47 (m, 4H), 1.41 (br s, 1H), 1.33-0.99 (m, 4H) |
| 313 | 5-[4-amino-5-(trifluoromethyl)pyrrolo[2,1-f][1,2,4]triazin-7-yl]-N-[(3R,4S)-4-fluoro-1-(2-methylpyridine-4-carbonyl)pyrrolidin-3-yl]-2-methoxy-pyridine-3-carboxamide | | 559.2 | 8.88 (dd, J = 11.6, 2.1 Hz, 1H), 8.73 (dd, J = 8.7, 2.3 Hz, 1H), 8.62-8.48 (m, 2H), 8.13 (d, J = 13.7 Hz, 1H), 7.56 (d, J = 15.3 Hz, 1H), 7.36 (d, J = 11.9 Hz, 1H), 7.29 (dd, J = 12.2, 4.9 Hz, 1H), 5.45-5.15 (m, 1H), 4.84-4.60 (m, 1H), 4.06-3.98 (m, 3H), 3.97-3.41 (m, 3H, partial suppression), 2.54 (s, 3H) |
| 314 | 5-[4-amino-5-(trifluoromethyl)pyrrolo[2,1-f][1,2,4]triazin-7-yl]-N-[(3R,4S)-4-fluoro-1-(3-fluoro-2,2-dimethylpropanoyl)pyrrolidin-3-yl]-2-methoxypyridine-3-carboxamide | | 542.2 | 8.93 (d, J = 2.4 Hz, 1H), 8.80 (br s, 1H), 8.52 (br d, J = 6.1 Hz, 1H), 8.18 (s, 1H), 7.62 (s, 1H), 5.39-5.17 (m, 1H), 4.88-4.62 (m, 1H), 4.58-4.30 (m, 2H), 4.06 (s, 3H), 1.27-1.22 (m, 6H); 4 pyrrolidine CHs not observed due to water suppression |
| 315 | 5-[4-amino-5-(trifluoromethyl)pyrrolo[2,1-f][1,2,4]triazin-7-yl]-N-[(3R,4S)-4-fluoro-1-(1-hydroxycyclopentanecarbonyl)pyrrolidin-3-yl]-2-methoxy-pyridine-3-carboxamide, TFA | | 552.0 | 8.90 (d, J = 2.4 Hz, 1H), 8.76 (br d, J = 2.4 Hz, 1H), 8.57-8.46 (m, 1H), 8.15 (s, 1H), 7.58 (s, 1H), 5.38-5.16 (m, 1H), 4.74-4.53 (m, 1H), 4.45-4.34 (m, 1H), 4.32-4.20 (m, 1H), 4.03 (s, 3H), 3.99-3.79 (m, 1H), 3.77-3.60 (m, 1H), 2.16-2.05 (m, 1H), 1.99-1.83 (m, 1H), 1.79-1.61 (m, 4H), 1.56 (br d, J = 2.7 Hz, 2H) |
| 316 | 5-[4-amino-5-(trifluoromethyl)pyrrolo[2,1-f][1,2,4]triazin-7-yl]-N-[(3R,4S)-4-fluoro-1-(1-hydroxycyclobutanecarbonyl)pyrrolidin-3-yl]-2-methoxy-pyridine-3-carboxamide, TFA | | 538.3 | 8.90 (d, J = 2.1 Hz, 1H), 8.75 (d, J = 2.1 Hz, 1H), 8.52 (br dd, J = 13.7, 7.6 Hz, 1H), 8.16 (s, 1H), 7.58 (s, 1H), 5.35-5.18 (m, 1H), 4.74-4.56 (m, 1H), 4.16-4.07 (m, 1H), 4.03 (s, 3H), 3.99-3.81 (m, 1H), 3.80-3.62 (m, 1H), 3.47-3.27 (m, 1H), 2.62-2.55 (m, 1H), 2.47-2.38 (m, 1H), 2.12-2.03 (m, 1H), 2.03-1.93 (m, 1H), 1.77-1.65 (m, 1H), 1.53-1.40 (m, 1H) |
| 317 | 5-[4-amino-5-(trifluoromethyl)pyrrolo[2,1-f][1,2,4]triazin-7-yl]-N-[(3R,4S)-4-fluoro-1-(3-hydroxy-3-methylbutanoyl)pyrrolidin-3-yl]-2-methoxypyridine-3-carboxamide | | 540.1 | 8.88 (br s, 1H), 8.74 (br d, J = 13.1 Hz, 1H), 8.57 (br d, J = 6.4 Hz, 1H), 8.14 (s, 1H), 7.56 (s, 1H), 5.43-5.17 (m, 1H), 4.83-4.55 (m, 1H), 4.14-3.11 (m. 7 H merge with water), 2.47-2.31 (m, 2H), 1.19 (br s, 6H) |
| 318 | 5-[4-amino-5-(trifluoromethyl)pyrrolo[2,1-f][1,2,4]triazin-7-yl]-N-[(3R,4S)-4-fluoro-1-[(2S)-3,3,3-trifluoro-2-hydroxypropanoyl]pyrrolidin-3-yl]-2-methoxy-pyridine-3-carboxamide | | 566.2 | 8.91 (d, J = 1.8 Hz, 1H), 8.76 (br s, 1H), 8.61-8.50 (m, 1H), 8.16 (s, 1H), 7.60 (s, 1H), 5.44-5.20 (m, 1H), 4.94 (br d, J = 5.8 Hz, 1H), 4.83-4.60 (m, 1H), 4.20-3.97 (m, 4H), 3.95-3.85 (m, 2H), 3.82-3.66 (m, 1H), 3.55 (br t, J = 10.7 Hz, 1H) |

TABLE 16-continued

Compounds in Table 16 were prepared by the methods detailed in Examples 27, 31, 34 and 43. When diastereomers were separated, they are included as separate entries. If the stereochemistry is undefined, the product was isolated as a mixture of diastereomers.

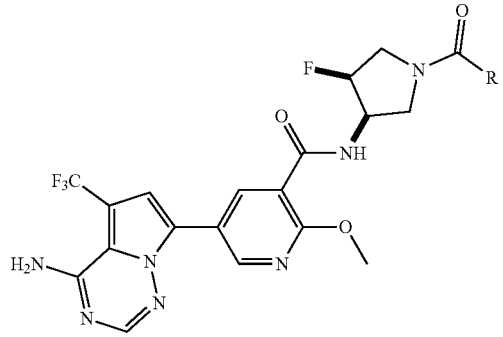

| Ex | Name | R | Obs. MS Ion | NMR Assignments (500 MHz, DMSO-d6) δ |
|---|---|---|---|---|
| 319 | 5-[4-amino-5-(trifluoromethyl)pyrrolo[2,1-f][1,2,4]triazin-7-yl]-N-[(3R,4S)-4-fluoro-1-(2-hydroxy-2-methylbutanoyl)pyrrolidin-3-yl]-2-methoxypyridine-3-carboxamide | | 540.3 | 8.91 (s, 1H), 8.77 (br s, 1H), 8.44 (br s, 1H), 8.15 (s, 1H), 7.56 (s, 1H), 5.37-5.15 (m, 1H), 5.08-4.99 (m, 1H), 4.73-4.24 (m, 2H), 4.05 (s, 3H), 3.93-3.85 (m, 1H), 3.81-3.62 (m, 1H), 3.56-3.45 (m, 1H), 1.79-1.66 (m, 1H), 1.57 (dq, J = 13.9, 7.2 Hz, 1H), 1.33-1.26 (m, 3H), 0.88-0.77 (m, 3H) |
| 320 | 5-[4-amino-5-(trifluoromethyl)pyrrolo[2,1-f][1,2,4]triazin-7-yl]-N-[(3R,4S)-4-fluoro-1-(1-hydroxycyclopropanecarbonyl)pyrrolidin-3-yl]-2-methoxypyridine-3-carboxamide | | 524.2 | 8.92 (d, J = 2.2 Hz, 1H), 8.78 (d, J = 1.8 Hz, 1H), 8.47 (br d, J = 4.3 Hz, 1H), 8.16 (s, 1H), 7.56 (s, 1H), 5.44-5.19 (m, 1H), 4.80-4.58 (m, 1H), 4.51-3.34 (m, 7H merge with water), 1.19-1.08 (m, 1H), 0.98-0.84 (m, 2H), 0.82-0.71 (m, 1H) |
| 321 | 5-[4-amino-5-(trifluoromethyl)pyrrolo[2,1-f][1,2,4]triazin-7-yl]-N-[(3R,4S)-4-fluoro-1-[(2R)-2-hydroxy-4-methylpentanoyl]pyrrolidin-3-yl]-2-methoxypyridine-3-carboxamide | | 554.3 | 8.92 (s, 1H), 8.79 (br d, J = 10.3 Hz, 1H), 8.46 (br dd, J = 19.2, 7.3 Hz, 1H), 8.16 (s, 1H), 7.57 (s, 1H), 5.44-5.19 (m, 1H), 4.84-4.57 (m, 1H), 4.26-3.34 (m, 8H merge with water), 1.86-1.72 (m, 1H), 1.52-1.30 (m, 2H), 0.92 (br d, J = 6.2 Hz, 6H) |
| 322 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxypropanoyl]pyrrolidin-3-yl]-2-methoxypyridine-3-carboxamide | | 566.0 | 8.93 (d, J = 2.4 Hz, 1H), 8.79 (dd, J = 6.9, 2.2 Hz, 1H), 8.48 (br dd, J = 18.2, 7.4 Hz, 1H), 8.17 (s, 1H), 7.58 (s, 1H), 5.45-5.23 (m, 1H), 5.00-4.85 (m, 1H), 4.84-4.64 (m, 1H), 4.36-3.26 (m, 7H) |
| 323 | 5-[4-amino-5-(trifluoromethyl)pyrrolo[2,1-f][1,2,4]triazin-7-yl]-N-[(3R,4S)-4-fluoro-1-[(2S)-2-hydroxy-3,3-dimethylbutanoyl]pyrrolidin-3-yl]-2-methoxypyridine-3-carboxamide | | 554.3 | 8.93 (s, 1H), 8.82-8.75 (m, 1H), 8.45 (br dd, J = 12.8, 7.4 Hz, 1H), 8.17 (s, 1H), 7.58 (s, 1H), 5.41-5.21 (m, 1H), 4.77-4.61 (m, 1H), 4.28-3.24 (m, 8H), 0.94 (s, 9H) |
| 324 | 5-[4-amino-5-(trifluoromethyl)pyrrolo[2,1-f][1,2,4]triazin-7-yl]-N-[(3R,4S)-4-fluoro-1-[(2S)-2-hydroxy-4-methylpentanoyl]pyrrolidin-3-yl]-2-methoxypyridine-3-carboxamide | | 554.3 | 8.93 (d, J = 2.2 Hz, 1H), 8.82-8.76 (m, 1H), 8.46 (br dd, J = 18.4, 7.4 Hz, 1H), 8.17 (s, 1H), 7.58 (s, 1H), 5.42-5.20 (m, 1H), 4.84-4.61 (m, 1H), 4.28-3.16 (m, 8H merge with water), 1.85-1.71 (m, 1H), 1.52-1.34 (m, 2H), 0.97-0.87 (m, 6H) |
| 325 | 5-[4-amino-5-(trifluoromethyl)pyrrolo[2,1-f][1,2,4]triazin-7-yl]-N-[(3R,4S)-4-fluoro-1-(oxolane-2-carbonyl)pyrrolidin-3-yl]-2-methoxypyridine-3-carboxamide | | 538.3 | 8.90 (s, 1H), 8.80-8.72 (m, 1H), 8.54-8.39 (m, 1H), 8.14 (s, 1H), 7.54 (s, 1H), 5.43-5.20 (m, 1H), 4.82-4.59 (m, 1H), 4.57-4.44 (m, 1H), 4.24-3.40 (m, 9H merge with water), 2.12-1.94 (m, 2H), 1.92-1.76 (m, 2H) |
| 326 | 5-[4-amino-5-(trifluoromethyl)pyrrolo[2,1-f][1,2,4]triazin-7-yl]-N-[(3R,4S)-4-fluoro-1-(oxane-2-carbonyl)pyrrolidin-3-yl]-2-methoxypyridine-3-carboxamide | | 552.2 | 8.90 (br s, 1H), 8.81-8.72 (m, 1H), 8.53-8.41 (m, 1H), 8.14 (s, 1H), 7.54 (s, 1H), 5.42-5.20 (m, 1H), 4.82-4.52 (m, 1H), 4.27-3.40 (m, 10H merge with water), 1.89-1.40 (m, 6H) |

TABLE 16-continued

Compounds in Table 16 were prepared by the methods detailed in Examples 27, 31, 34 and 43. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 327 | 5-[4-amino-5-(trifluoromethyl)pyrrolo[2,1-f][1,2,4]triazin-7-yl]-N-[(3R,4S)-4-fluoro-1-(oxane-3-carbonyl)pyrrolidin-3-yl]-2-methoxypyridine-3-carboxamide | | 552.2 | 8.93 (br s, 1H), 8.84-8.74 (m, 1H), 8.52 (br dd, J = 15.9, 7.3 Hz, 1H), 8.18 (s, 1H), 7.62 (s, 1H), 5.43-5.18 (m, 1H), 4.86-4.55 (m, 1H), 4.22-3.14 (m, 11H), 2.70 (br d, J = 10.4 Hz, 1H), 1.97- 1.78 (m, 1H), 1.59 (br d, 3H) |
| 328 | 5-[4-amino-5-(trifluoromethyl)pyrrolo[2,1-f][1,2,4]triazin-7-yl]-N-[(3R,4S)-4-fluoro-1-(2,6,6-trimethyloxane-2-carbonyl)pyrrolidin-3-yl]-2-methoxy-pyridine-3-carboxamide | | 594.4 | 8.93 (dd, J = 9.5, 2.1 Hz, 1H), 8.85-8.71 (m, 1H), 8.59-8.47 (m, 1H), 8.18 (d, J = 1.2 Hz, 1H), 7.61 (d, J = 4.6 Hz, 1H), 5.43-5.19 (m 1H), 4.98-4.49 (m, 2H), 4.05 (d, J = 11.6 Hz, 3H), 3.96-3.14 (m, 3H), 2.27 (br d, J = 9.5 Hz, 1H), 1.84-1.66 (m, 1H), 1.55-1.40 (m, 2H), 1.37-0.97 (m, 11H) |
| 329 | 5-[4-amino-5-(trifluoromethyl)pyrrolo[2,1-f][1,2,4]triazin-7-yl]-N-[(3R,4S)-4-fluoro-1-(3-methyloxetane-3-carbonyl)pyrrolidin-3-yl]-2-methoxypyridine-3-carboxamide | | 538.4 | 8.92 (d, J = 2.3 Hz, 1H), 8.79 (br d, J = 16.6 Hz, 1H), 8.43 (br s, 1H), 8.16 (s, 1H), 7.57 (s, 1H), 5.40-5.19 (m, 1H), 4.89 (br d, J = 5.8 Hz, 1H), 4.86-4.62 (m, 2H), 4.32-4.19 (m, 2H), 4.06 (s, 3H), 3.94-3.63 (m, 2H), 3.59-3.29 (m, 2H), 1.58 (br d, J = 7.2 Hz, 3H) |
| 330 | 5-[4-amino-5-(trifluoromethyl)pyrrolo[2,1-f][1,2,4]triazin-7-yl]-N-[(3R,4S)-4-fluoro-1-(1-fluorocyclobutanecarbonyl)pyrrolidin-3-yl]-2-methoxypyridine-3-carboxamide | | 540.4 | 8.91 (s, 1H), 8.76 (d, J = 2.1 Hz, 1H), 8.53 (br dd, J = 14.0, 7.6 Hz, 1H), 8.16 (d, J = 1.8 Hz, 1H), 7.60 (s, 1H), 5.39-5.19 (m, 1H), 4.85-4.62 (m, 1H), 4.03 (s, 3H), 3.99-3.93 (m, 1H), 3.93-3.85 (m, 1H), 3.85-3.78 (m, 1H), 3.77-3.65 (m, 1H), 2.78-2.56 (m, 2H), 2.47-2.23 (m, 2H), 1.87 (dt, J = 10.4, 3.8 Hz, 1H), 1.63-1.49 (m, 1H) |
| 331 | 5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-methoxypyridine-3-carboxamide | | 526.1 | 8.91 (d, J = 2.4 Hz, 1H), 8.76 (br s, 1H), 8.60-8.49 (m, 1H), 8.17 (s, 1H), 7.60 (s, 1H), 5.45-5.19 (m, 1H), 4.91-4.63 (m, 1H), 4.30-4.18 (m, 1H), 4.03 (s, 3H), 3.98-3.86 (m, 1H), 3.80 (br s, 1H), 3.76-3.63 (m, 1H), 1.46-1.20 (m, 3H), 1.20-1.05 (m, 1H) |
| 332 | 5-[4-amino-5-(trifluoromethyl)pyrrolo[2,1-f][1,2,4]triazin-7-yl]-N-[(3R,4S)-1-(dimethylcarbamoyl)-4-fluoropyrrolidin-3-yl]-2-methoxypyridine-3-carboxamide | | 511.2 | 8.90 (d, J = 2.1 Hz, 1H), 8.78 (d, J = 2.1 Hz, 1H), 8.48 (br d, J = 7.3 Hz, 1H), 8.16 (s, 1H), 7.59 (s, 1H), 5.33-5.14 (m, 1H), 4.68-4.49 (m, 1H), 4.04 (s, 3H), 3.88-3.73 (m, 1H), 3.63 (t, J = 9.2 Hz, 1H), 2.76 (s, 6H); 2 pyrrolidine CHs lost in water suppression |
| 333 | 5-[4-amino-5-(trifluoromethyl)pyrrolo[2,1-f][1,2,4]triazin-7-yl]-N-[(3R,4S)-4-fluoro-1-(pyrrolidine-1-carbonyl)pyrrolidin-3-yl]-2-methoxypyridine-3-carboxamide, TFA | | 537.2 | 8.90 (d, J = 2.1 Hz, 1H), 8.77 (d, J = 2.1 Hz, 1H), 8.49 (br d, J = 7.6 Hz, 1H), 8.16 (s, 1H), 7.59 (s, 1H), 5.33-5.13 (m, 1H), 4.70-4.53 (m, 1H), 4.04 (s, 3H), 3.85-3.77 (m, 1H), 3.71 (br t, J = 9.2 Hz, 1H), 3.40-3.27 (m, 2H), 3.26-3.17 (m, 2H), 1.88-1.77 (m, 2H), 1.76-1.64 (m, 2H); 2 pyrrolidine CHs lost in water suppression |
| 334 | 5-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-2-methoxypyridine-3-carboxamide | | 550.1 | 8.92 (d, J = 2.1 Hz, 1H), 8.78 (dd, J = 14.0, 2.1 Hz, 1H), 8.56 (br dd, J = 13.6, 7.5 Hz, 1H), 8.18 (s, 1H), 7.61 (s, 1H), 5.45-5.19 (m, 1H), 4.86-4.56 (m, 1H), 4.13-3.13 (m, 9H) |

TABLE 16-continued

Compounds in Table 16 were prepared by the methods detailed in Examples 27, 31, 34 and 43. When diastereomers were separated, they are included as separate entries. If the stereochemistry is undefined, the product was isolated as a mixture of diastereomers.

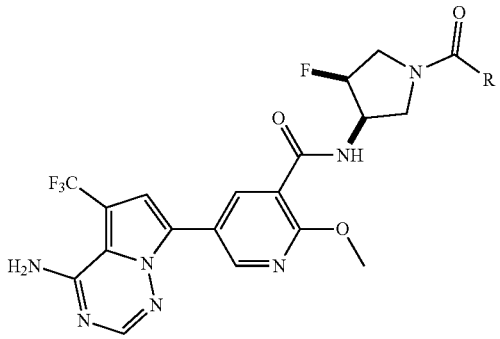

| Ex | Name | R | Obs. MS Ion | NMR Assignments (500 MHz, DMSO-d6) δ |
|---|---|---|---|---|
| 335 | 5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-methoxypyridine-3-carboxamide | isobutyl group | 524.2 | 8.94 (d, J = 2.1 Hz, 1H), 8.80 (dd, J = 14.6, 2.4 Hz, 1H), 8.52 (br dd, J = 14.3, 7.6 Hz, 1H), 8.19 (s, 1H), 7.63 (s, 1H), 5.43-5.19 (m, 1H), 4.88-4.57 (m, 1H), 4.06 (d, J = 4.9 Hz, 3H), 4.03-3.16 (m, 4H), 2.25-1.97 (m, 3H), 0.99-0.84 (m, 6H) |
| 336 | 5-[4-amino-5-(trifluoromethyl)pyrrolo[2,1-f][1,2,4]triazin-7-yl]-N-[(3R,4S)-4-fluoro-1-(pyridine-3-carbonyl)pyrrolidin-3-yl]-2-methoxypyridine-3-carboxamide | 3-pyridyl | 545.2 | 8.89 (br s, 1H), 8.74 (br s, 2H), 8.67 (br d, J = 3.5 Hz, 1H), 8.57-8.43 (m, 1H), 8.13 (br d, J = 9.1 Hz, 1H), 7.97 (br s, 1H), 7.57-7.46 (m, 2H), 5.49-5.20 (m, 1H), 4.89-4.64 (m, 1H), 4.05 (br s, 3H), 3.99-3.45 (m, 4H) |
| 337 | 5-[4-amino-5-(trifluoromethyl)pyrrolo[2,1-f][1,2,4]triazin-7-yl]-N-[(3R,4S)-4-fluoro-1-(3,3,3-trifluoro-2,2-dimethylpropanoyl)pyrrolidin-3-yl]-2-methoxy-pyrrolidine-3-carboxamide, TFA | C(CH3)2CF3 | 578.2 | 8.93 (d, J = 2.4 Hz, 1H), 8.80 (br s, 1H), 8.53 (br d, J = 5.5 Hz, 1H), 8.18 (s, 1H), 7.61 (s, 1H), 5.43-5.19 (m, 1H), 4.87-4.60 (m, 1H), 4.05 (s, 3H), 4.01-3.14 (m, 4H merge with water), 1.49 (s, 3H), 1.45 (s, 3H) |
| 338 | 5-[4-amino-5-(trifluoromethyl)pyrrolo[2,1-f][1,2,4]triazin-7-yl]-N-[(3R,4S)-1-(3,3-dimethylbutanoyl)-4-fluoro-pyrrolidin-3-yl]-2-methoxypyridine-3-carboxamide | neopentyl | 538.3 | 8.91 (s, 1H), 8.78 (br d, J = 12.8 Hz, 1H), 8.45 (br dd, J = 14.6, 7.5 Hz, 1H), 8.15 (s, 1H), 7.56 (s, 1H), 5.41-5.18 (m, 1H), 4.84-4.54 (m, 1H), 4.11-3.17 (m, 9H merge with water), 1.02 (s, 9H) |
| 339 | 5-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-2-methoxy-pyridine-3-carboxamide, TFA | C(CH3)2OH | 526.0 | 8.94 (d, J = 1.8 Hz, 1H), 8.79 (br s, 1H), 8.59-8.45 (m, 1H), 8.19 (s, 1H), 7.63 (s, 1H), 5.39-5.17 (m, 2H), 4.77-4.54 (m, 1H), 4.51-4.27 (m, 1H), 4.05 (s, 3H), 3.97-3.55 (m, 2H), 2.94 (br d, J = 7.6 Hz, 1H), 1.35-1.27 (m, 6H) |
| 340 | 5-[4-amino-5-(trifluoromethyl)pyrrolo[2,1-f][1,2,4]triazin-7-yl]-N-[(3R,4S)-4-fluoro-1-(3-methoxypropanoyl)pyrrolidin-3-yl]-2-methoxypyridine-3-carboxamide | CH2CH2OCH3 | 526.1 | 8.94 (d, J = 1.8 Hz, 1H), 8.80 (dd, J = 14.6, 2.1 Hz, 1H), 8.53 (br dd, J = 14.5, 7.5 Hz, 1H), 8.19 (s, 1H), 7.63 (s, 1H), 5.42-5.20 (m, 1H), 4.86-4.55 (m, 1H), 4.12-3.28 (m, 12H merge with water), 2.60-2.43 (m, 2 H merge with DMSO) |
| 341 | 5-[4-amino-5-(trifluoromethyl)pyrrolo[2,1-f][1,2,4]triazin-7-yl]-N-[(3R,4S)-(2,5-difluorobenzoyl)-4-fluoropyrrolidin-3-yl]-2-methoxypyridine-3-carboxamide, TFA | 2,5-difluorophenyl | 580.1 | 8.93 (dd, J = 14.1, 2.1 Hz, 1H), 8.82-8.70 (m, 1H), 8.56-8.39 (m, 1H), 8.16 (d, J = 13.8 Hz, 1H), 7.57 (d, J = 16.7 Hz, 1H), 7.38 (br d, J = 5.0 Hz, 3H), 5.52-5.18 (m, 1H), 4.92-4.65 (m, 1H), 4.06 (d, J = 17.8 Hz, 3H), 3.99-3.22 (m, 4H) |
| 342 | 5-[4-amino-5-(trifluoromethyl)pyrrolo[2,1-f][1,2,4]triazin-7-yl]-N-[(3R,4S)-4-fluoro-1-(3-fluorobenzoyl)pyrrolidin-3-yl]-2-methoxypyridine-3-carboxamide | 3-fluorophenyl | 562.1 | 8.91-8.84 (m, 1H), 8.76-8.68 (m, 1H), 8.65-8.53 (m, 1H), 8.12 (d, J = 13.7 Hz, 1H), 7.58-7.48 (m, 2H), 7.43-7.28 (m, 3H), 5.47-5.16 (m, 1H), 4.87-4.60 (m, 1H), 4.07-3.26 (m, 7H merge with water) |

TABLE 16-continued

Compounds in Table 16 were prepared by the methods detailed in Examples 27, 31, 34 and 43. When diastereomers were separated, they are included as separate entries. If the stereochemistry is undefined, the product was isolated as a mixture of diastereomers.

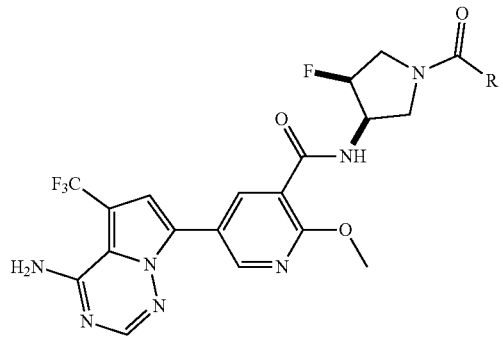

| Ex | Name | R | Obs. MS Ion | NMR Assignments (500 MHz, DMSO-d6) δ |
|---|---|---|---|---|
| 343 | 5-[4-amino-5-(trifluoromethyl)pyrrolo[2,1-f][1,2,4]triazin-7-yl]-N-[(3R,4S)-7-yl]-N-[(3R,4S)-4-fluoro-1-(2-fluorobenzoyl)pyrrolidin-3-yl]-2-methoxypyridine-3-carboxamide | 2-fluorophenyl | 562.2 | 8.90 (br d, J = 14.7 Hz, 1H), 8.80-8.69 (m, 1H), 8.56-8.41 (m, 1H), 8.14 (br d, J = 15.3 Hz, 1H), 7.58-7.43 (m, 3H), 7.36-7.25 (m, 2H), 5.50-5.17 (m, 1H), 4.91-4.63 (m, 1H), 4.13-3.33 (m, 7H merge with water) |
| 344 | 5-[4-amino-5-(trifluoromethyl)pyrrolo[2,1-f][1,2,4]triazin-7-yl]-N-[(3R,4S)-4-fluoro-1-(2-methyl-2-phenylpropanoyl)pyrrolidin-3-yl]-2-methoxypyridine-3-carboxamide | 2-methyl-2-phenylpropyl | 586.4 | 8.89 (br d, J = 7.6 Hz, 1H), 8.75-8.65 (m, 1H), 8.48-8.25 (m, 1H), 8.16 (br s, 1H), 7.58 (br d, J = 5.8 Hz, 1H), 7.43-7.33 (m, 2H), 7.30-7.20 (m, 3H), 5.25-4.91 (m, 1H), 4.62-4.28 (m, 1H), 4.00 (br d, J = 19.5 Hz, 3H), 3.93-3.02 (m, 4H), 1.49 (br s, 3H), 1.43 (br d, J = 12.8 Hz, 3H) |
| 345 | 5-[4-amino-5-(trifluoromethyl)pyrrolo[2,1-f][1,2,4]triazin-7-yl]-N-[(3R,4S)-4-fluoro-1-(2-methylpropanoyl)pyrrolidin-3-yl]-2-methoxypyridine-3-carboxamide | isopropyl | 509.9 | 8.94 (d, J = 2.3 Hz, 1H), 8.84-8.76 (m, 1H), 8.51-8.34 (m, 1H), 8.17 (s, 1H), 7.59 (s, 1H), 5.44-5.15 (m, 1H), 4.89-4.56 (m, 1H), 4.08 (br d, J = 3.6 Hz, 3H), 3.98-3.15 (m, 4H), 2.78-2.60 (m, 1H), 1.09-0.98 (m, 6H) |
| 346 | 5-[4-amino-5-(trifluoromethyl)pyrrolo[2,1-f][1,2,4]triazin-7-yl]-N-[(3R,4S)-4-fluoro-1-(oxetane-3-carbonyl)pyrrolidin-3-yl]-2-methoxypyridine-3-carboxamide | oxetan-3-yl | 524.0 | 8.93 (d, J = 2.2 Hz, 1H), 8.80 (dd, J = 12.5, 2.3 Hz, 1H), 8.49-8.39 (m, 1H), 8.17 (s, 1H), 7.58 (s, 1H), 5.44-5.21 (m, 1H), 4.83-4.58 (m, 5H), 4.17-3.18 (m, 8H) |
| 347 | 5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-methoxypyridine-3-carboxamide, TFA | 2-fluoro-2-methylpropyl | 528.4 | 8.93 (s, 1H), 8.77 (d, J = 2.4 Hz, 1H), 8.59-8.49 (m, 1H), 8.18 (s, 1H), 7.61 (s, 1H), 5.40-5.17 (m, 1H), 4.87-4.62 (m, 1H), 4.28-4.17 (m, 1H), 4.13-3.99 (m, 4H), 3.98-3.86 (m, 1H), 3.81-3.52 (m, 1H), 1.63-1.48 (m, 6H) |
| 348 | 5-(4-amino-5-(trifluoromethyl)pyrrolo[2,1-f][1,2,4]triazin-7-yl)-N-(4-fluoro-1-(3-fluorocyclobutane-1-carbonyl)pyrrolidin-3-yl)-2-methoxynicotinamide | 3-fluorocyclobutyl | 540.3 (isomers) | (400 MHz, CD3OD) δ 9.01-8.88 (m, 2H), 8.69-8.46 (m, 1H), 8.11-8.02 (m, 1H), 7.37-7.24 (m, 1H), 5.41-5.29 (m, 1H), 5.24-5.16 (m, 1H), 5.08-4.96 (m, 1H), 4.94-4.73 (m, 2H), 4.23-4.04 (m, 4H), 4.02-3.91 (m, 1H), 3.90-3.63 (m, 2H), 2.79-2.37 (m, 5H) |
| 349 | 5-(4-amino-5-(trifluoromethyl)pyrrolo[2,1-f][1,2,4]triazin-7-yl)-N-(4-fluoro-1-(3-fluorocyclobutane-1-carbonyl)pyrrolidin-3-yl)-2-methoxynicotinamide | 3-fluorocyclobutyl | 540.3 (isomers) | (400 MHz, CD3OD) δ 9.01-8.87 (m, 2H), 8.65-8.40 (m, 1H), 8.10-7.98 (m, 1H), 7.31-7.15 (m, 1H), 5.42-5.05 (m, 2H), 4.94-4.68 (m, 1H), 4.22-4.11 (m, 4H), 4.09-3.98 (m, 1H), 3.97-3.88 (m, 1H), 3.85-3.61 (m, 2H), 2.75-2.37 (m, 4H) |

TABLE 17

Compounds in Table 17 were prepared by the methods detailed in Examples 25 and 41. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 350 | 5-[4-amino-5-(trifluoromethyl) pyrrolo[2,1-f][1,2,4]triazin-7-yl]-N-[(3R,4S)-1-(3,3-difluoro-cyclobutanecarbonyl)-4-fluoro-pyrrolidin-3-yl]-2-methyl-pyridine-3-carboxamide | | 541.9 | 9.21-9.11 (m, 1H), 9.04-8.87 (m, 1H), 8.43-8.32 (m, 1H), 8.22-8.10 (m, 1H), 7.73-7.55 (m, 1H), 4.87-4.55 (m, 1H), 3.98-3.79 (m, 1H), 3.72-3.65 (m, 1H), 3.46-3.36 (m, 1H), 3.34-3.25 (m, 1H), 3.21-3.07 (m, 1H), 2.89-2.68 (m, 3H), 2.61-2.53 (m, 4H), 2.53-2.46 (m, 3H). |
| 351 | 5-[4-amino-5-(trifluoromethyl) pyrrolo[2,1-f][1,2,4]triazin-7-yl]-N-[(3R,4S)-1-(3,3-difluoro-cyclopentanecarbonyl)-4-fluoropyrrolidin-3-yl]-2-methylpyridine-3-carboxamide | | 556.0 (isomers) | cyclopentane isomers 9.24-9.10 (m, 1H), 9.03-8.82 (m, 1H), 8.44-8.32 (m, 1H), 8.25-8.13 (m, 1H), 7.74-7.61 (m, 1H), 5.51-5.16 (m, 1H), 4.88-4.53 (m, 1H), 4.15-3.98 (m, 1H), 3.98-3.80 (m, 1H), 3.78-3.65 (m, 1H), 3.56-3.42 (m, 1H), 3.36-3.10 (m, 2H), 2.61-2.57 (m, 3H), 2.39-2.23 (m, 2H), 2.22-1.98 (m, 3H), 1.91-1.71 (m, 1H), 1.07-0.94 (m, 1H) |
| 352 | 5-[4-amino-5-(trifluoromethyl) pyrrolo[2,1-f][1,2,4]triazin-7-yl]-N-[(3R,4S)-1-(3,3-difluoro-cyclopentanecarbonyl)-4-fluoropyrrolidin-3-yl]-2-methyl-pyridine-3-carboxamide | | 556.0 (isomers) | cyclopentane isomers 9.24-9.10 (m, 1H), 9.03-8.82 (m, 1H), 8.44-8.32 (m, 1H), 8.25-8.13 (m, 1H), 7.74-7.61 (m, 1H), 5.51-5.16 (m, 1H), 4.88-4.53 (m, 1H), 4.15-3.98 (m, 1H), 3.98-3.80 (m, 1H), 3.78-3.65 (m, 1H), 3.56-3.42 (m, 1H), 3.36-3.10 (m, 2H), 2.61-2.57 (m, 3H), 2.39-2.23 (m, 2H), 2.22-1.98 (m, 3H), 1.91-1.71 (m, 1H), 1.07-0.94 (m, 1H) |
| 353 | 5-[4-amino-5-(trifluoromethyl) pyrrolo[2,1-f][1,2,4]triazin-7-yl]-N-[(3R,4S)-4-fluoro-1-(2-methylpropanoyl)pyrrolidin-3-yl]-2-methylpyridine-3-carboxamide | | 494.4 | 9.27-9.11 (m, 1H), 9.01-8.84 (m, 1H), 8.52-8.36 (m, 1H), 8.25-8.11 (m, 1H), 7.80-7.63 (m, 1H), 5.44-5.17 (m, 1H), 4.84-4.52 (m, 1H), 4.08-3.97 (m, 1H), 3.96-3.41 (m, 2H), 2.74-2.56 (m, 4H), 1.09-0.93 (m, 6H). |
| 354 | 5-[4-amino-5-(trifluoromethyl) pyrrolo[2,1-f][1,2,4]triazin-7-yl]-N-[1-(2,2-difluorocyclopropane-carbonyl)-4-fluoropyrrolidin-3-yl]-2-methylpyridine-3-carboxamide | | 528.2, (isomers) | cyclopropyl isomers 9.28-9.12 (m, 1H), 9.05-8.84 (m, 1H), 8.46-8.33 (m, 1H), 8.26-8.12 (m, 1H), 7.79-7.60 (m, 1H), 5.50-5.18 (m, 1H), 4.87-4.56 (m, 1H), 4.35-4.00 (m, 1H), 3.96-3.57 (m, 2H), 3.58-3.45 (m, 1H), 3.39-2.81 (m, 2H), 2.63-2.56 (m, 3H), 2.02-1.80 (m, 2H), 1.05-0.96 (m, 1H) |
| 355 | 5-[4-amino-5-(trifluoromethyl) pyrrolo[2,1-f][1,2,4]triazin-7-yl]-N-[1-(2,2-difluorocyclopropanecarbonyl)-4-fluoropyrrolidin-3-yl]-2-methyl-pyridine-3-carboxamide | | 528.2, (isomers) | cyclopropyl isomers 9.28-9.12 (m, 1H), 9.05-8.84 (m, 1H), 8.46-8.33 (m, 1H), 8.26-8.12 (m, 1H), 7.79-7.60 (m, 1H), 5.50-5.18 (m, 1H), 4.87-4.56 (m, 1H), 4.35-4.00 (m, 1H), 3.96-3.57 (m, 2H), 3.58-3.45 (m, 1H), 3.39-2.81 (m, 2H), 2.63-2.56 (m, 3H), 2.02-1.80 (m, 2H), 1.05-0.96 (m, 1H) |
| 356 | 5-[4-amino-5-(trifluoromethyl)pyrrolo[2,1-f][1,2,4]triazin-7-yl]-N-[4-fluoro-1-(3-fluorocyclobutanecarbonyl) pyrrolidin-3-yl]-2-methylpyridine-3-carboxamide | | 524.1 | $^1$H NMR (400 MHz, CD$_3$OD) δ 9.20-9.09 (m, 1H), 8.57-8.37 (m, 1H), 8.12-7.98 (m, 1H), 7.39-7.31 (m, 1H), 5.45-5.15 (m, 1H), 4.93-4.59 (m, 2H), 4.13-3.85 (m, 2H), 3.85-3.56 (m, 2H), 3.47-3.38 (m, 1H), 2.75-2.70 (m, 3H), 2.69-2.32 (m, 6H), 1.22-1.05 (m, 1H) |

TABLE 17-continued

Compounds in Table 17 were prepared by the methods detailed in Examples 25 and 41. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 357 | 5-[4-amino-5-(trifluoromethyl)pyrrolo[2,1-f][1,2,4]triazin-7-yl]-N-[4-fluoro-1-(3-fluorocyclobutanecarbonyl)pyrrolidin-3-yl]-2-methylpyridine-3-carboxamide | 3-fluorocyclobutyl | 524.1 | ¹H NMR (400 MHz, CD₃OD) δ 9.13 (dd, J = 11.2, 2.0 Hz, 1H), 8.45 (dd, J = 7.2, 2.1 Hz, 1H), 8.05 (d, J = 1.2 Hz, 1H), 7.36 (s, 2H), 7.34 (d, J = 5.5 Hz, 1H), 5.34-5.05 (m, 2H), 4.86-4.56 (m, 1H), 4.07-3.57 (m, 3H), 3.45-3.37 (m, 1H), 3.29-3.14 (m, 1H), 2.71 (s, 3H), 2.67-2.37 (m, 4H) |
| 358 | 5-[4-amino-5-(trifluoromethyl)pyrrolo[2,1-f][1,2,4]triazin-7-yl]-N-[1-(4,4-difluorocyclohexanecarbonyl)-4-fluoropyrrolidin-3-yl]-2-methyl-pyridine-3-carboxamide | 4,4-difluorocyclohexyl | 570.2 | 9.24-9.09 (m, 1H), 9.04-8.84 (m, 1H), 8.48-8.30 (m, 1H), 8.22-8.12 (m, 1H), 7.73-7.57 (m, 1H), 5.48-5.16 (m, 1H), 4.87-4.46 (m, 1H), 4.20-3.77 (m, 2H), 3.71-3.52 (m, 2H), 3.31-3.11 (m, 1H), 2.60-2.56 (m, 3H), 2.16-1.96 (m, 2H), 1.96-1.70 (m, 4H), 1.63-1.47 (m, 2H), 1.29-1.17 (m, 1H), 1.03-0.91 (m, 1H) |
| 359 | 5-[4-amino-5-(trifluoromethyl)pyrrolo[2,1-f][1,2,4]triazin-7-yl]-N-[4-fluoro-1-(4-fluorocyclohexanecarbonyl)pyrrolidin-3-yl]-2-methylpyridine-3-carboxamide | 4-fluorocyclohexyl | 552.4 | 9.25-9.13 (m, 1H), 8.98-8.80 (m, 1H), 8.49-8.33 (m, 1H), 8.26-8.13 (m, 1H), 7.78-7.59 (m, 1H), 5.47-5.15 (m, 1H), 4.81-4.40 (m, 2H), 4.13-3.80 (m, 2H), 3.72-3.41 (m, 1H), 3.32-3.06 (m, 1H), 2.59 (d, J = 6.4 Hz, 3H), 2.48-2.30 (m, 1H), 2.18-1.94 (m, 2H), 1.90-1.72 (m, 2H), 1.55-1.35 (m, 4H), 1.09-0.91 (m, 1H) |
| 360 | 5-[4-amino-5-(trifluoromethyl)pyrrolo[2,1-f][1,2,4]triazin-7-yl]-N-[4-fluoro-1-(4-fluorocyclohexanecarbonyl)pyrrolidin-3-yl]-2-methylpyridine-3-carboxamide | 4-fluorocyclohexyl | 552.4 | 9.25-9.13 (m, 1H), 8.98-8.80 (m, 1H), 8.49-8.33 (m, 1H), 8.26-8.13 (m, 1H), 7.78-7.59 (m, 1H), 5.47-5.15 (m, 1H), 4.81-4.40 (m, 2H), 4.13-3.80 (m, 2H), 3.72-3.41 (m, 1H), 3.32-3.06 (m, 1H), 2.59 (d, J = 6.4 Hz, 3H), 2.48-2.30 (m, 1H), 2.18-1.94 (m, 2H), 1.90-1.72 (m, 2H), 1.55-1.35 (m, 4H), 1.09-0.91 (m, 1H) |
| 361 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxypropanoyl]pyrrolidin-3-yl]-2-methylpyridine-3-carboxamide, TFA | (R)-CH(OH)CF₃ | 550.1 | 9.19 (dd, J = 4.6, 1.8 Hz, 1H), 8.97-8.86 (m, 1H), 8.41 (dd, J = 6.1, 1.8 Hz, 1H), 8.21 (s, 1H), 7.70 (d, J = 2.4 Hz, 1H), 6.95-6.73 (m, 1H), 5.47-5.20 (m, 1H), 5.06-4.86 (m, 1H), 4.82-4.60 (m, 1H), 4.26 (br t, J = 9.2 Hz, 1H), 4.22-4.10 (m, 1H), 3.98-3.82 (m, 1H), 3.82-3.69 (m, 1H), 2.59 (s, 3H) |
| 362 | 5-[4-amino-5-(trifluoromethyl)pyrrolo[2,1-f][1,2,4]triazin-7-yl]-N-[(3R,4S)-4-fluoro-1-(1-hydroxycyclopentane-carbonyl)pyrrolidin-3-yl]-2-methyl-pyridine-3-carboxamide, TFA | 1-hydroxycyclopentyl | 536.3 | 9.15 (s, 1H), 8.93 (br dd, J = 17.5, 6.9 Hz, 1H), 8.39 (s, 1H), 8.16 (s, 1H), 7.66 (s, 1H), 5.38-5.13 (m, 1H), 4.72-4.47 (m, 1H), 4.37-4.29 (m, 1H), 4.28-4.17 (m, 1H), 3.34 (br t, J = 11.1 Hz, 1H), 2.57 (s, 3H), 2.16-2.04 (m, 1H), 1.96-1.81 (m, 1H), 1.78-1.60 (m, 4H), 1.55 (br s, 2H); 1 pyrrolidine CH obscured by water suppression |
| 363 | 5-[4-amino-5-(trifluoromethyl)pyrrolo[2,1-f][1,2,4]triazin-7-yl]-N-[(3R,4S)-4-fluoro-1-(1-hydroxycyclobutane-carbonyl)pyrrolidin-3-yl]-2-methyl-pyridine-3-carboxamide, TFA | 1-hydroxycyclobutyl | 522.3 | 9.18 (s, 1H), 8.93 (br t, J = 7.2 Hz, 1H), 8.42 (br d, J = 3.7 Hz, 1H), 8.19 (s, 1H), 7.68 (s, 1H), 5.38-5.18 (m, 1H), 4.70-4.53 (m, 1H), 4.10-3.94 (m, 1H), 3.90-3.72 (m, 1H), 3.55-3.28 (m, 1H), 2.58 (s, 4H), 2.48-2.33 (m, 1H), 2.14-2.04 (m, 1H), 1.99 (br d, J = 8.2 Hz, 1H), 1.74 (br d, J = 4.9 Hz, 1H), 1.53-1.39 (m, 1H); 1 pyrrolidine CH obscured by water suppression |
| 364 | 5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-methylpyridine-3-carboxamide, TFA | isobutyl | 508.2 | 9.14 (s, 1H), 8.80 (br dd, J = 12.1, 7.1 Hz, 1H), 8.35 (s, 1H), 8.16 (s, 1H), 7.16 (s, 1H), 5.43-5.19 (m, 1H), 4.78-4.51 (m, 1H), 3.97 (br t, J = 9.2 Hz, 1H), 3.92-3.82 (m, 1H), 3.82-3.65 (m, 1H), 2.58 (d, J = 1.9 Hz, 3H), 2.25-2.09 (m, 2H), 2.05-1.94 (m, 1H), 0.94-0.87 (m, 6H); 1 pyrrolidine CH obscured by water suppression |

TABLE 17-continued

Compounds in Table 17 were prepared by the methods detailed in Examples 25 and 41. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 365 | 5-[4-amino-5-(trifluoromethyl)pyrrolo[2,1-f][1,2,4]triazin-7-yl]-N-[(3R,4S)-4-fluoro-1-[(2S)-2-hydroxy-4-methyl-pentanoyl]pyrrolidin-3-yl]-2-methyl-pyridine-3-carboxamide | isobutyl-CH(OH)- | 538.3 | 9.16 (br s, 1H), 8.88 (br t, J = 8.1 Hz, 1H), 8.38 (s, 1H), 8.18 (d, J = 1.5 Hz, 1H), 7.68 (s, 1H), 5.43-5.16 (m, 1H), 4.92 (br t, J = 7.0 Hz, 1H), 4.77-4.53 (m, 1H), 4.27-4.06 (m, 2H), 4.06-3.93 (m, 1H), 3.89 (s, 1H), 3.83-3.72 (m, 1H), 2.57 (s, 3H), 1.74 (br d, J = 5.5 Hz, 1H), 1.47-1.25 (m, 2H), 0.89 (br t, J = 6.4 Hz, 6H) |
| 366 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methylpyridine-3-carboxamide | C(CH3)(OH)(CF3)- | 564.2 | 9.17 (s, 1H), 8.94-8.83 (m, 1H), 8.38 (s, 1H), 8.18 (s, 1H), 7.68 (s, 1H), 5.39-5.16 (m, 1H), 4.70-4.54 (m, 1H), 4.45-4.37 (m, 1H), 4.36-4.24 (m, 1H), 4.06-3.91 (m, 1H), 3.87-3.80 (m, 1H), 2.57 (s, 3H), 1.52 (s, 3H) |
| 367 | 5-[4-amino-5-(trifluoromethyl)pyrrolo[2,1-f][1,2,4]triazin-7-yl]-N-[(3R,4S)-1-(2,5-difluorobenzoyl)-4-fluoro-pyrrolidin-3-yl]-2-methylpyridine-3-carboxamide | 2,5-difluorophenyl | 564.2 | 9.18 (dd, J = 16.8, 1.5 Hz, 1H), 8.96-8.79 (m, 1H), 8.45-8.30 (m, 1H), 8.19 (d, J = 15.0 Hz, 1H), 7.72-7.63 (m, 1H), 7.39 (br d, J = 4.6 Hz, 3H), 5.45-5.18 (m, 1H), 4.85-4.59 (m, 1H), 4.05-3.96 (m, 1H), 3.86-3.72 (m, 1H), 3.65 (br t, J = 9.2 Hz, 1H), 3.57-3.44 (m, 1H), 2.54 (s, 3H) |
| 368 | 5-[4-amino-5-(trifluoromethyl)pyrrolo[2,1-f][1,2,4]triazin-7-yl]-N-[(3R,4S)-4-fluoro-1-[(2R)-2-hydroxy-4-methylpentanoyl]pyrrolidin-3-yl]-2-methylpyridine-3-carboxamide | isobutyl-CH(OH)- | 538.2 | 9.19 (br s, 1H), 8.96-8.84 (m, 1H), 8.41 (br s, 1H), 8.21 (s, 1H), 7.70 (s, 1H), 5.51-5.18 (m, 1H), 5.07-4.92 (m, 1H), 4.80-4.53 (m, 1H), 4.22-4.07 (m, 1H), 4.07-3.98 (m, 1H), 3.95-3.85 (m, 2H), 3.81-3.49 (m, 1H), 2.60 (s, 3H), 1.84-1.71 (m, 1H), 1.46-1.29 (m, 2H), 0.97-0.87 (m, 6H) |
| 369 | 5-[4-amino-5-(trifluoromethyl)pyrrolo[2,1-f][1,2,4]triazin-7-yl]-N-[(3R,4S)-4-fluoro-1-(1-fluorocyclopropane-carbonyl)pyrrolidin-3-yl]-2-methyl-pyridine-3-carboxamide | 1-fluorocyclopropyl | 510.2 | 9.20 (s, 1H), 8.92 (br dd, J = 17.2, 7.5 Hz, 1H), 8.41 (br s, 1H), 8.21 (s, 1H), 7.70 (s, 1H), 5.49-5.22 (m, 1H), 4.86-4.58 (m, 1H), 4.22 (br d, J = 7.0 Hz, 1H), 4.14-3.99 (m, 1H), 3.94-3.70 (m, 2H), 2.60 (s, 3H), 1.46-1.28 (m, 3H), 1.15 (br d, J = 10.1 Hz, 1H) |
| 370 | 5-[4-amino-5-(trifluoromethyl)pyrrolo[2,1-f][1,2,4]triazin-7-yl]-N-[(3R,4S)-4-fluoro-1-[(2S)-3,3,3-trifluoro-2-hydroxy-propanoyl]pyrrolidin-3-yl]-2-methyl-pyridine-3-carboxamide | CH(OH)(CF3)- | 550.2 | 9.15 (br s, 1H), 8.88-8.77 (m, 1H), 8.36 (br s, 1H), 8.16 (s, 1H), 7.62 (s, 1H), 5.46-5.19 (m, 1H), 4.88 (br s, 1H), 4.80-4.55 (m, 1H), 4.21-3.51 (m, 5H), 2.58 (s, 3H) |
| 371 | 5-[4-amino-5-(trifluoromethyl)pyrrolo[2,1-f][1,2,4]triazin-7-yl]-N-[(3R,4S)-4-fluoro-1-(1-fluorocyclobutanecarbonyl)pyrrolidin-3-yl]-2-methylpyridine-3-carboxamide | 1-fluorocyclobutyl | 524.2 | 9.16 (br s, 1H), 8.94-8.85 (m, 1H), 8.38 (br d, J = 6.1 Hz, 1H), 8.18 (br d, J = 1.8 Hz, 1H), 7.67 (br d, J = 4.6 Hz, 1H), 5.43-5.18 (m, 1H), 4.79-4.58 (m, 1H), 3.98-3.64 (m, 4H), 2.78-2.54 (m, 4H), 2.45-2.23 (m, 2H), 1.86 (br dd, J = 10.1, 3.7 Hz, 1H), 1.59-1.45 (m, 1H); 1 cyclobutyl CH under solvent |
| 372 | 5-[4-amino-5-(trifluoromethyl)pyrrolo[2,1-f][1,2,4]triazin-7-yl]-N-[(3R,4S)-4-fluoro-1-[(2S)-3,3,3-trifluoro-2-hydroxy-2-methylpropanoyl]pyrrolidin-3-yl]-2-methylpyridine-3-carboxamide, TFA | C(CH3)(OH)(CF3)- | 564.2 | 9.18 (br s, 1H), 8.97-8.83 (m, 1H), 8.41 (br s, 1H), 8.19 (s, 1H), 7.69 (s, 1H), 5.42-5.14 (m, 1H), 4.78-4.47 (m, 1H), 4.38-4.17 (m, 1H), 4.10-3.80 (m, 2H), 3.78-3.59 (m, 1H), 2.58 (s, 3H), 1.53 (s, 3H) |

TABLE 17-continued

Compounds in Table 17 were prepared by the methods detailed in Examples 25 and 41. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 373 | 5-[4-amino-5-(trifluoromethyl)pyrrolo[2,1-f][1,2,4]triazin-7-yl]-N-[(3R,4S)-4-fluoro-1-[(2S)-2-hydroxy-3,3-dimethyl-butanoyl]pyrrolidin-3-yl]-2-methyl-pyridine-3-carboxamide | | 538.3 | 9.17 (br s, 1H), 8.93-8.83 (m, 1H), 8.42-8.36 (m, 1H), 8.19 (s, 1H), 7.68 (d, J = 3.7 Hz, 1H), 5.41-5.17 (m, 1H), 4.98-4.83 (m, 1H), 4.75-4.51 (m, 1H), 4.20-4.00 (m, 1H), 3.87-3.71 (m, 2H), 3.70-3.55 (m, 1H), 2.58 (s, 3H), 0.91 (br d, J = 4.0 Hz, 9H) |
| 374 | 5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-methylpyridine-3-carboxamide | | 512.2 | 9.17 (br d, J = 2.1 Hz, 1H), 8.87 (br dd, J = 13.9, 7.2 Hz, 1H), 8.39 (br s, 1H), 8.19 (s, 1H), 7.68 (d, J = 3.1 Hz, 1H), 5.40-5.18 (m, 1H), 4.81-4.54 (m, 1H), 4.22-3.52 (m, 4H), 2.58 (s, 3H), 1.58-1.48 (m, 6H) |

TABLE 18

Compounds in Table 18 were prepared by the methods detailed in Example 45. When diastereomers were separated, they are included as separate entries.

| Ex | Name | R | Obs. MS Ion | NMR Assignments (500 MHz, DMSO-d6) δ |
|---|---|---|---|---|
| 375 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-(deutero)methoxypyridine-3-carboxamide | | 589.2 | 8.94 (d, J = 1.8 Hz, 1H), 8.86-8.76 (m, 1H), 8.61-8.46 (m, 1H), 8.19 (s, 1H), 7.63 (s, 1H), 5.46-5.19 (m, 1H), 4.92-4.57 (m, 1H), 4.21-3.16 (m, 4H), 2.71-2.58 (m, 1H), 2.07 (br d, J = 12.5 Hz, 2H), 1.99-1.72 (m, 4H), 1.68-1.52 (m, 2H) |
| 376 | 5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]-2-(deutero)methoxypyridine-3-carboxamide | | 565.4 | 8.93 (br d, J = 8.5 Hz, 1H), 8.78 (br s, 1H), 8.62-8.48 (m, 1H), 8.18 (br d, J = 13.1 Hz, 1H), 7.70-7.58 (m, 3H), 7.36-7.26 (m, 2H), 5.48-5.19 (m, 1H), 4.89-4.64 (m, 1H), 4.09-3.77 (m, 3H), 3.70-3.50 (m, 1H) |

TABLE 18-continued

Compounds in Table 18 were prepared by the methods detailed in Example 45.
When diastereomers were separated, they are included as separate entries.

| Ex | Name | R | Obs. MS Ion | NMR Assignments (500 MHz, DMSO-d6) δ |
|---|---|---|---|---|
| 377 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(Deutro)methoxypyridine-3-carboxamide | difluorocyclopropyl | 547.2 | 8.93 (dd, J = 5.2, 2.4 Hz, 1H), 8.86-8.73 (m, 1H), 8.63-8.48 (m, 1H), 8.18 (d, J = 0.9 Hz, 1H), 7.62 (d, J = 2.7 Hz, 1H), 5.46-5.23 (m, 1H), 4.91-4.62 (m, 1H), 4.18-3.60 (m, 4H), 3.04-2.86 (m, 1H), 2.03-1.81 (m, 2H). |
| 378 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(Deutro)methoxypyridine-3-carboxamide | difluorocyclopropyl | 527.2 | 8.92 (s, 1H), 8.77 (s, 1H), 8.63-8.50 (m, 1H), 8.18 (s, 1H), 7.61 (s, 1H), 5.48-5.19 (m, 1H), 4.94-4.63 (m, 1H), 4.35-3.26 (m, 4H), 3.15-2.97 (m, 1H), 2.02-1.75 (m, 2H). |
| 379 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(deutero)methoxypyridine-3-carboxamide | fluorocyclobutyl | 543.2 | 8.93 (d, J = 2.3 Hz, 1H), 8.78 (dd, J = 11.9, 2.4 Hz, 1H), 8.54 (br dd, J = 13.6, 7.6 Hz, 1H), 8.18 (s, 1H), 7.63 (s, 1H), 5.40-5.01 (m, 2H), 4.86-4.58 (m, 1H), 3.96-3.15 (m, 5H), 2.60-2.33 (m, 4H merge with DMSO) |
| 380 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(deutero)methoxypyridine-3-carboxamide | fluorocyclobutyl | 543.1 | 8.92 (d, J = 2.4 Hz, 1H), 8.78 (dd, J = 10.8, 2.4 Hz, 1H), 8.51 (dd, J = 13.0, 7.6 Hz, 1H), 8.18 (s, 1H), 7.62 (s, 1H), 5.42-5.16 (m, 1H), 5.13-4.85 (m, 1H), 4.85-4.55 (m, 1H), 3.98-3.63 (m, 3H), 3.43-3.19 (m, 5H), 2.86-2.68 (m, 1H), 2.61-2.53 (m, 1H), 2.35-2.03 (m, 4H) |
| 381 | 5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-(deutero)methoxypyridine-3-carboxamide | 2-fluoro-2-methylpropyl | 531.2 | 8.92 (s, 1H), 8.77 (s, 1H), 8.60-8.46 (m, 1H), 8.17 (s, 1H), 7.61 (s, 1H), 5.43-5.16 (m, 1H), 4.86-4.55 (m, 1H), 4.28-3.16 (m, 4H), 1.61-1.47 (m, 6H) |
| 382 | 5-[4-amino-5-(trifluoromethyl)pyrrolo[2,1-f][1,2,4]triazin-7-yl]-N-[(3R,4S)-4-fluoro-1-(2-methylpropanoyl)pyrrolidin-3-yl]-2-(deutero)methoxypyridine-3-carboxamide | isopropyl | 513.0 | 8.92 (d, J = 2.1 Hz, 1H), 8.79 (dd, J = 14.0, 2.1 Hz, 1H), 8.53 (br dd, J = 18.3, 7.6 Hz, 1H), 8.17 (s, 1H), 7.61 (s, 1H), 5.44-5.19 (m, 1H), 4.85-4.58 (m, 1H), 4.12-3.15 (m, 4H merge with water), 2.76-2.61 (m, 1H), 1.08-0.97 (m, 6H) |
| 383 | 5-[4-amino-5-(trifluoromethyl)pyrrolo[2,1-f][1,2,4]triazin-7-yl]-N-[(3R,4S)-1-(2,5-difluorobenzoyl)-4-fluoropyrrolidin-3-yl]-2-(deutero)methoxypyridine-3-carboxamide, TFA | 2,5-difluorophenyl | 583.0 | 8.91 (br d, J = 13.8 Hz, 1H), 8.82-8.67 (m, 1H), 8.56-8.40 (m, 1H), 8.15 (br d, J = 13.6 Hz, 1H), 7.55 (br d, J = 16.2 Hz, 1H), 7.36 (br d, J = 3.7 Hz, 3H), 5.50-5.18 (m, 1H), 4.94-4.62 (m, 1H), 4.11-3.15 (m, 4H merge with water) |
| 384 | 5-[4-amino-5-(trifluoromethyl)pyrrolo[2,1-f][1,2,4]triazin-7-yl]-N-[(3R,4S)-4-fluoro-1-[(2S)-3,3,3-trifluoro-2-hydroxy-2-methylpropanoyl]pyrrolidin-3-yl]-2-(deutero)methoxypyridine-3-carboxamide | C(CF₃)(OH)(CH₃) | 583.0 | 8.93 (s, 1H), 8.78 (br d, J = 3.4 Hz, 1H), 8.61-8.47 (m, 1H), 8.19 (s, 1H), 7.63 (s, 1H), 7.06 (br d, J = 7.3 Hz, 1H), 5.44-5.16 (m, 1H), 4.84-4.56 (m, 1H), 4.43-3.15 (m, 4H merge with water), 1.54 (br d, J = 10.7 Hz, 3H) |

TABLE 18-continued

Compounds in Table 18 were prepared by the methods detailed in Example 45.
When diastereomers were separated, they are included as separate entries.

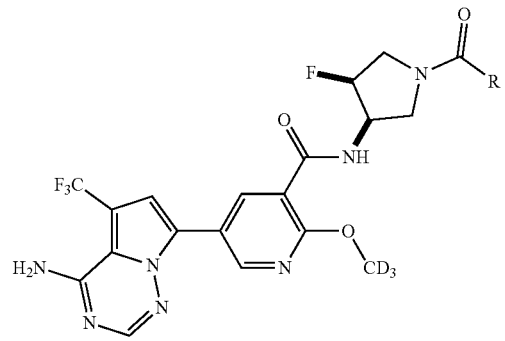

| Ex | Name | R | Obs. MS Ion | NMR Assignments (500 MHz, DMSO-d6) δ |
|---|---|---|---|---|
| 385 | 5-[4-amino-5-(trifluoromethyl)pyrrolo[2,1-f][1,2,4]triazin-7-yl]-N-[(3R,4S)-4-fluoro-1-(3-hydroxy-3-methyl-butanoyl)pyrrolidin-3-yl]-2-(deutero)methoxypyridine-3-carboxamide, TFA | ⋎OH | 543.1 | 8.92 (d, J = 2.1 Hz, 1H), 8.79 (dd, J = 12.1, 2.3 Hz, 1H), 8.53 (br dd, J = 11.6, 7.6 Hz, 1H), 8.18 (s, 1H), 7.61 (s, 1H), 5.42-5.20 (m, 1H), 4.85-4.57 (m, 1H), 4.15-3.15 (m, 4H merge with water), 2.48-2.31 (m, 2H), 1.20 (s, 6H) |
| 386 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-(deutero)methoxy-pyridine-3-carboxamide | ⋎CF$_3$/OH | 583.1 | 8.91 (br s, 1H), 8.78 (br d, J = 6.7 Hz, 1H), 8.52-8.38 (m, 1H), 8.16 (s, 1H), 7.56 (br s, 1H), 5.39-5.18 (m, 1H), 4.76-4.60 (m, 1H), 4.56-4.27 (m, 1H), 4.10-3.70 (m, 3H) 1.55 (s, 3H) |
| 387 | 5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-(deutero)methoxypyridine-3-carboxamide, TFA | ⋎ | 527.3 | 8.93 (s, 1H), 8.79 (br d, J = 14.6 Hz, 1H), 8.52 (br dd, J = 14.0, 7.6 Hz, 1H), 8.18 (s, 1H), 7.62 (s, 1H), 5.42-5.17 (m, 1H), 4.87-4.57 (m, 1H), 4.09-3.15 (m, 4H merge with water), 2.21-1.97 (m, 3H), 0.97-0.87 (m, 6H) |
| 388 | 5-[4-amino-5-(trifluoromethyl)pyrrolo[2,1-f][1,2,4]triazin-7-yl]-N-[(3R,4S)-1-(3,3-dimethylbutanoyl)-4-fluoropyrrolidin-3-yl]-2-(deutero)methoxy-pyridine-3-carboxamide | ⋎ | 541.1 | 8.93 (d, J = 1.8 Hz, 1H), 8.79 (dd, J = 13.7, 2.1 Hz, 1H), 8.52 (br dd, J = 14.6, 7.6 Hz, 1H), 8.18 (s, 1H), 7.62 (s, 1H), 5.42-5.15 (m, 1H), 4.85-4.51 (m, 1H), 4.08-3.15 (m, 6H merge with water), 1.02 (s, 9H) |
| 389 | 5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-(deutero)methoxypyridine-3-carboxamide, TFA | (2-fluorophenyl) | 565.2 | 8.91 (br d, J = 15.6 Hz, 1H), 8.80-8.70 (m, 1H), 8.64-8.49 (m, 1H), 8.16 (br d, J = 15.9 Hz, 1H), 7.63-7.44 (m, 3H), 7.37-7.29 (m, 2H), 5.49-5.18 (m, 1H), 4.90-4.64 (m, 1H), 4.08-3.32 (m, 4H merge with water) |
| 390 | 5-(4-amino-5-(trifluoromethyl)pyrrolo[2,1-f][1,2,4]triazin-7-yl)-N-((3R,4S)-1-(3,3-difluorocyclobutane-1-carbonyl)-4-fluoropyrrolidin-3-yl)-2-(methoxy-d3)nicotinamide | (3,3-difluorocyclobutyl) | 561.2 | 8.94 (d, J = 2.4 Hz, 1H), 8.89-8.68 (m, 1H), 8.61-8.51 (m, 1H), 8.19 (s, 1H), 7.63 (s, 1H), 7.29-6.93 (m, 1H), 5.46-5.11 (m, 1H), 4.93-4.49 (m, 1H), 4.16-3.54 (m, 3H), 3.32-3.23 (m, 1H), 3.23-3.13 (m, 2H), 2.91-2.69 (m, 4H). |

TABLE 19

Compounds in Table 19 were prepared by the methods detailed in Examples 67 and 31. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 391 | 5-[4-amino-5-(trifluoromethyl)pyrrolo[2,1-f][1,2,4]triazin-7-yl]-2-fluoro-N-[(3R,4S)-4-fluoro-1-(2-fluorobenzoyl)pyrrolidin-3-yl]-4-methylbenzamide | 2-fluorophenyl | 563.1 | 8.72-8.50 (m, 1H), 8.03 (br d, J = 13.4 Hz, 1H), 7.62-7.40 (m, 3H), 7.37-7.26 (m, 3H), 7.25-7.16 (m, 1H), 5.41-5.10 (m, 1H), 4.81-4.52 (m, 1H), 4.01-3.35 (m, 4H), 2.14 (d, J = 13.7 Hz, 3H) |
| 392 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-fluoro-4-methylbenzamide | 3,3-difluorocyclopentyl | 573.3 | 8.62 (br d, J = 4.6 Hz, 1H), 8.01 (s, 1H), 7.58 (dd, J = 7.2, 4.4 Hz, 1H), 7.32 (dd, J = 11.3, 3.7 Hz, 1H), 7.21 (s, 1H), 5.37-5.10 (m, 1H), 4.75-4.46 (m, 1H), 4.06-3.04 (m, 6H), 2.38-2.21 (m, 2H), 2.14 (br d, J = 1.5 Hz, 3H), 2.07-1.96 (m, 2H), 1.84-1.67 (m, 1H) |
| 393 | 5-[4-amino-5-(trifluoromethyl)pyrrolo[2,1-f][1,2,4]triazin-7-yl]-2-fluoro-N-[(3R,4S)-4-fluoro-1-(3-methylbutanoyl)pyrrolidin-3-yl]-4-methylbenzamide | isobutyl | 525.4 | 8.62 (br d, J = 4.3 Hz, 1H), 8.06 (br s, 1H), 7.59 (dd, J = 7.2, 4.1 Hz, 1H), 7.33 (br dd, J = 11.4, 2.3 Hz, 1H), 7.22 (s, 1H), 5.36-5.10 (m, 1H), 4.75-4.45 (m, 1H) 3.98-3.74 (m, 1H), 3.66 (br s, 2H), 3.49-3.19 (m, 1H), 2.21-2.05 (m, 5H), 2.04-1.92 (m, 1H), 0.95-0.82 (m, 6H) |
| 394 | 5-[4-amino-5-(trifluoromethyl)pyrrolo[2,1-f][1,2,4]triazin-7-yl]-2-fluoro-N-[(3R,4S)-4-fluoro-1-[(2R)-3,3,3-trifluoro-2-hydroxy-2-methylpropanoyl]pyrrolidin-3-yl]-4-methylbenzamide | (2R)-3,3,3-trifluoro-2-hydroxy-2-methylpropanoyl | 581.3 | 8.59 (br dd, J = 14.6, 7.0 Hz, 1H), 8.03 (s, 1H), 7.60 (t, J = 6.7 Hz, 1H), 7.33 (br dd, J = 11.3 Hz, 1H), 7.22 (s, 1H), 5.34-5.10 (m, 1H), 4.67-4.48 (m, 1H), 4.43-4.21 (m, 1H), 4.07-3.30 (m, 2H), 2.15 (s, 3H), 1.51 (s, 3H); 2 pyrrolidine CHs not observed in full due to water suppression |

TABLE 20

Compounds in Table 20 were prepared by the methods detailed in Examples 67 and 31. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 395 | 5-[4-amino-5-(trifluoromethyl)pyrrolo[2,1-f][1,2,4]triazin-7-yl]-2-chloro-4-fluoro-N-[(3R,4S)-4-fluoro-1-(1-hydroxycyclobutanecarbonyl)pyrrolidin-3-yl]benzamide | 1-hydroxycyclobutyl | 559.0 | 8.93 (br t, J = 7.2 Hz, 1H), 8.09 (s, 1H), 7.90 (br dd, J = 7.5, 3.8 Hz, 1H), 7.68 (br dd, J = 9.8, 2.4 Hz, 1H), 7.36 (s, 1H), 6.00 (d, J = 3.4 Hz, 1H), 5.30-5.12 (m, 1H), 4.65-4.45 (m, 1H), 4.04-3.93 (m, 1H), 3.83-3.60 (m, 2H), 3.50-3.25 (m, 1H), 2.49-2.31 (m, 2H), 2.12-2.01 (m, 1H), 1.96 (br d, J = 8.9 Hz, 1H), 1.78-1.66 (m, 1H), 1.51-1.38 (m, 1H) |
| 396 | 5-[4-amino-5-(trifluoromethyl)pyrrolo[2,1-f][1,2,4]triazin-7-yl]-2-chloro-4-fluoro-N-[(3R,4S)-4-fluoro-1-(3-hydroxy-3-methylbutanoyl)pyrrolidin-3-yl]benzamide | 2-hydroxy-2-methylpropyl | 561.0 | 8.94 (br dd, J = 18.3, 7.3 Hz, 1H), 8.11 (s, 1H), 7.91 (dd, J = 7.3, 4.0 Hz, 1H), 7.71 (d, J = 9.8 Hz, 1H), 7.37 (s, 1H), 5.38-5.12 (m, 1H), 4.82 (d, J = 3.7 Hz, 1H), 4.74-4.45 (m, 1H), 4.02 (br t, J = 9.2 Hz, 1H), 3.95-3.77 (m, 1H), 3.74-3.52 (m, 1H), 3.27-3.12 (m, 1H), 2.46-2.25 (m, 2H), 1.18 (s, 6H) |
| 397 | 5-[4-amino-5-(trifluoromethyl)pyrrolo[2,1-f][1,2,4]triazin-7-yl]-2-chloro-4-fluoro-N-[(3R,4S)-4-fluoro-1-(1-hydroxycyclopentanecarbonyl)pyrrolidin-3-yl]benzamide, TFA | 1-hydroxycyclopentyl | 573.0 | 8.80 (br s, 1H), 8.09 (s, 1H), 7.92 (br d, J = 7.3 Hz, 1H), 7.64 (br d, J = 9.9 Hz, 1H), 7.34 (s, 1H), 5.37-5.11 (m, 1H), 4.65-4.43 (m, 1H), 4.07-3.56 (m, 4H), 2.19-2.04 (m, 1H), 2.00-1.85 (m, 1H), 1.79-1.49 (m, 6H) |
| 398 | 5-[4-amino-5-(trifluoromethyl)pyrrolo[2,1-f][1,2,4]triazin-7-yl]-2-chloro-4-fluoro-N-[(3R,4S)-4-fluoro-1-(3-methylbutanoyl)pyrrolidin-3-yl]benzamide | isobutyl | 545.0 | 8.81 (br dd, J = 11.5, 7.4 Hz, 1H), 8.09 (s, 1H), 7.92 (br d, J = 7.5 Hz, 1H), 7.64 (br d, J = 9.8 Hz, 1H), 7.34 (s, 1H), 5.35-5.11 (m, 1H), 4.73-4.47 (m, 1H), 3.92 (br t, J = 9.1 Hz, 1H), 3.87-3.79 (m, 1H), 3.78-3.72 (m, 1H), 3.22 (br t, J = 11.0 Hz, 1H), 2.15-2.07 (m, 2H), 2.03-1.95 (m, 1H), 0.90 (br d, J = 5.4 Hz, 6H) |
| 399 | 5-[4-amino-5-(trifluoromethyl)pyrrolo[2,1-f][1,2,4]triazin-7-yl]-2-chloro-4-fluoro-N-[(3R,4S)-4-fluoro-1-(2-fluorobenzoyl)pyrrolidin-3-yl]benzamide | 2-fluorophenyl | 583.0 | 8.92-8.73 (m, 1H), 8.09 (d, J = 16.3 Hz, 1H), 7.99-7.84 (m, 1H), 7.70-7.59 (m, 1H), 7.52 (br s, 1H), 7.44 (q, J = 7.3 Hz, 1H), 7.36 (s, 1H), 7.33-7.27 (m, 2H), 5.41-5.11 (m, 1H), 4.82-4.55 (m, 1H), 3.99 (br dd, J = 11.3, 9.3 Hz, 1H), 3.91-3.80 (m, 1H), 3.58 (br t, J = 9.2 Hz, 1H), 3.53-3.42 (m, 1H) |
| 400 | 5-[4-amino-5-(trifluoromethyl)pyrrolo[2,1-f][1,2,4]triazin-7-yl]-2-chloro-4-fluoro-N-[(3R,4S)-4-fluoro-1-[(2R)-3,3,3-trifluoro-2-hydroxypropanoyl]pyrrolidin-3-yl]benzamide | (2R)-1,1,1-trifluoro-2-hydroxyethyl | 587.2 | 8.12 (s, 1H), 7.96 (br dd, J = 7.2, 4.1 Hz, 1H), 7.68 (d, J = 10.0 Hz, 1H), 7.37 (s, 1H), 5.41-5.18 (m, 1H), 4.98-4.82 (m, 1H), 4.76-4.54 (m, 1H), 4.23 (br t, J = 9.3 Hz, 1H), 4.18-4.04 (m, 1H), 3.81-3.68 (m, 1H), 3.49 (br t, J = 10.6 Hz, 1H) |
| 401 | 5-[4-amino-5-(trifluoromethyl)pyrrolo[2,1-f][1,2,4]triazin-7-yl]-2-chloro-4-fluoro-N-[(3R,4S)-4-fluoro-1-(2-fluoro-2-methylpropanoyl)pyrrolidin-3-yl] | 2-fluoro-2-methylpropyl | 549.0 | 8.88-8.76 (m, 1H), 8.10 (s, 1H), 7.93 (br d, J = 7.6 Hz, 1H), 7.65 (d, J = 10.0 Hz, 1H), 7.35 (s, 1H), 5.39-5.12 (m, 1H), 4.76-4.47 (m, 1H), 4.23-4.09 (m, 1H), 4.08-3.95 (m, 1H), 3.94-3.82 (m, 1H), 3.80-3.65 (m, 1H), |

TABLE 20-continued

Compounds in Table 20 were prepared by the methods detailed in Examples 67 and 31. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
|  | benzamide |  |  | 1.59-1.46 (m, 6H) |
| 402 | 5-[4-amino-5-(trifluoromethyl)pyrrolo[2,1-f][1,2,4]triazin-7-yl]-2-chloro-4-fluoro-N-[(3R,4S)-4-fluoro-1-[(2R)-3,3,3-trifluoro-2-hydroxy-2-methylpropanoyl]pyrrolidin-3-yl]benzamide | C(CH₃)(OH)(CF₃) | 601.2 | 8.87-8.76 (m, 1H), 8.10 (br s, 1H), 7.93 (br d, J = 6.6 Hz, 1H), 7.65 (br d, J = 9.8 Hz, 1H), 7.35 (s, 1H), 5.34-5.12 (m, 1H), 4.66-4.48 (m, 1H), 4.40 (br t, J = 9.3 Hz, 1H), 4.36-4.23 (m, 1H), 4.06-3.89 (m, 1H), 3.87-3.80 (m, 1H), 3.79-3.66 (m, 1H), 1.52 (br s, 3H) |
| 403 | 5-[4-amino-5-(trifluoromethyl)pyrrolo[2,1-f][1,2,4]triazin-7-yl]-2-chloro-4-fluoro-N-[(3R,4S)-4-fluoro-1-(3,3,3-trifluoropropanoyl)pyrrolidin-3-yl]benzamide | CH₂CF₃ | 571.1 | 8.85 (br dd, J = 19.9, 7.2 Hz, 1H), 8.09 (br d, J = 2.0 Hz, 1H), 7.95-7.89 (m, 1H), 7.65 (br d, J = 9.7 Hz, 1H), 7.34 (s, 1H), 5.39-5.13 (m, 1H), 4.74-4.48 (m, 1H), 3.99 (br t, J = 8.9 Hz, 1H), 3.93-3.77 (m, 2H), 3.75-3.63 (m, 1H), 3.31-3.18 (m, 1H); 1 pyrrolidine CH obscured by water suppression |
| 404 | 5-[4-amino-5-(trifluoromethyl)pyrrolo[2,1-f][1,2,4]triazin-7-yl]-2-chloro-4-fluoro-N-[(3R,4S)-4-fluoro-1-(3-fluoropyridine-2-carbonyl)pyrrolidin-3-yl]benzamide | 3-fluoropyridin-2-yl | 584.0 | 8.92-8.74 (m, 1H), 8.48 (br s, 1H), 8.11 (d, J = 15.6 Hz, 1H), 8.01-7.88 (m, 1H), 7.86 (t, J = 9.2 Hz, 1H), 7.71-7.56 (m, 2H), 7.35 (br d, J = 19.7 Hz, 1H), 5.45-5.15 (m, 1H), 4.87-4.56 (m, 1H), 4.04 (br dd, J = 11.7, 9.0 Hz, 1H), 3.88-3.80 (m, 1H), 3.80-3.41 (m, 2H) |
| 405 | 5-[4-amino-5-(trifluoromethyl)pyrrolo[2,1-f][1,2,4]triazin-7-yl]-2-chloro-4-fluoro-N-[(3R,4S)-4-fluoro-1-(4-fluorobenzoyl)pyrrolidin-3-yl]benzamide | 4-fluorophenyl | 583.0 | 8.93-8.71 (m, 1H), 8.08 (br s, 1H), 8.00-7.81 (m, 1H), 7.64 (br d, J = 2.6 Hz, 1H), 7.59 (br dd, J = 8.4, 5.6 Hz, 2H), 7.33 (br s, 1H), 7.26 (br t, J = 8.8 Hz, 2H), 5.42-5.12 (m, 1H), 4.80-4.51 (m, 1H), 4.11-3.62 (m, 3H); 1 pyrrolidine CH obscured by water suppression |
| 406 | 5-[4-amino-5-(trifluoromethyl)pyrrolo[2,1-f][1,2,4]triazin-7-yl]-2-chloro-N-[(3R,4S)-1-(3,3-difluorocyclobutanecarbonyl)-4-fluoropyrrolidin-3-yl]-4-fluorobenzamide | 3,3-difluorocyclobutyl | 579.1 | 8.83 (br t, J = 8.5 Hz, 1H), 8.10 (s, 1H), 7.93 (dd, J = 7.4, 2.6 Hz, 1H), 7.65 (br d, J = 9.6 Hz, 1H), 7.35 (s, 1H), 5.39-5.14 (m, 1H), 4.79-4.50 (m, 1H), 3.95-3.81 (m, 1H), 3.78-3.61 (m, 3H), 3.21-3.04 (m, 1H), 2.87-2.66 (m, 4H) |
| 407 | 5-[4-amino-5-(trifluoromethyl)pyrrolo[2,1-f][1,2,4]triazin-7-yl]-2-chloro-N-[(3R,4S)-1-(4,4-difluorocyclohexanecarbonyl)-4-fluoropyrrolidin-3-yl]-4-fluorobenzamide | 4,4-difluorocyclohexyl | 607.1 | 8.82 (br dd, J = 16.3, 7.5 Hz, 1H), 8.09 (s, 1H), 7.92 (br d, J = 7.5 Hz, 1H), 7.68-7.60 (m, 1H), 7.35 (s, 1H), 5.39-5.10 (m, 1H), 4.78-4.45 (m, 1H), 4.03 (br t, J = 9.3 Hz, 1H), 3.95-3.78 (m, 2H), 3.75-3.67 (m, 1H), 2.68-2.57 (m, 1H), 2.03 (s, 2H), 1.93-1.69 (m, 4H), 1.65-1.50 (m, 2H) |
| 408 | 5-[4-amino-5-(trifluoromethyl)pyrrolo[2,1-f][1,2,4]triazin-7-yl]-2-chloro-N-[(3R,4S)-1-(2,2-difluorocyclopropanecarbonyl)-4-fluoropyrrolidin-3-yl]-4-fluorobenzamide | 2,2-difluorocyclopropyl | 565.1 | 8.93-8.78 (m, 1H), 8.13 (s, 1H) 7.97 (br d, J = 7.6 Hz, 1H), 7.69 (br d, J = 9.9 Hz, 1H), 7.37 (s, 1H), 5.44-5.15 (m, 1H), 4.86-4.53 (m, 1H), 4.29-3.43 (m, 4H), 3.09-2.82 (m, 1H), 2.02-1.79 (m, 2H) |

TABLE 20-continued

Compounds in Table 20 were prepared by the methods detailed in Examples 67 and 31. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|----|------|---|-------------|--------------------------------------|
| 409 | 5-[4-amino-5-(trifluoromethyl)pyrrolo[2,1-f][1,2,4]triazin-7-yl]-2-chloro-4-fluoro-N-[(3R,4S)-4-fluoro-1-(3-fluorocyclobutanecarbonyl)pyrrolidin-3-yl]benzamide | (3-fluorocyclobutyl) | 561.1 | 8.93 (dd, J = 16.8, 7.3 Hz, 1H), 8.11 (s, 1H), 7.91 (dd, J = 7.5, 4.7 Hz, 1H), 7.71 (d, J = 9.8 Hz, 1H), 7.37 (s, 1H), 5.36-4.98 (m, 2H), 4.78-4.47 (m, 1H), 3.94-3.13 (m, 5H), 2.49-2.29 (m, 4H) |
| 410 | 5-[4-amino-5-(trifluoromethyl)pyrrolo[2,1-f][1,2,4]triazin-7-yl]-2-chloro-N-[(3R,4S)-1-(3,3-difluorocyclopentanecarbonyl)-4-fluoropyrrolidin-3-yl]-4-fluorobenzamide | (3,3-difluorocyclopentyl) | 593.0 | NA |

TABLE 21

Compounds in Table 21 were prepared by the methods detailed in Examples 67 and 31. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|----|------|---|-------------|--------------------------------------|
| 411 | 5-[4-amino-5-(trifluoromethyl)pyrrolo[2,1-f][1,2,4]triazin-7-yl]-4-fluoro-N-[(3R,4S)-4-fluoro-1-(3-fluorocyclobutanecarbonyl)pyrrolidin-3-yl]-2-methylbenzamide | (3-fluorocyclobutyl) | 541.4 | 8.55 (br dd, J = 11.5, 7.1 Hz, 1H), 8.07 (s, 1H), 7.77 (br d, J = 7.2 Hz, 1H), 7.31-7.24 (m, 2H), 5.38-5.13 (m, 1H), 5.08-4.84 (m, 1H), 4.73-4.47 (m, 1H), 3.92-3.77 (m, 2H), 3.77-3.61 (m, 2H), 2.72 (td, J = 16.7, 8.3 Hz, 1H), 2.43 (s, 3H), 2.32-2.13 (m, 2H); 2 CH from cyclobutyl obscured by water suppression |
| 412 | 5-[4-amino-5-(trifluoromethyl)pyrrolo[2,1-f][1,2,4]triazin-7-yl]-4-fluoro-N-[(3R,4S)-4-fluoro-1-(2-fluorobenzoyl)pyrrolidin-3-yl]-2-methylbenzamide | (2-fluorophenyl) | 563.3 | 8.78-8.59 (m, 1H), 8.09 (br d, J = 16.5 Hz, 1H), 7.84-7.69 (m, 1H), 7.58-7.49 (m, 1H), 7.48-7.41 (m, 1H), 7.37-7.25 (m, 4H), 5.44-5.09 (m, 1H), 4.84-4.53 (m, 1H), 4.06-3.30 (m, 3H), 2.47-2.35 (m 3H); 1 pyrrolidine CH not observed due to water suppression |

TABLE 21-continued

Compounds in Table 21 were prepared by the methods detailed in Examples 67 and 31. When diastereomers were separated, they are included as separate entries. If the stereochemistry is undefined, the product was isolated as a mixture of diastereomers.

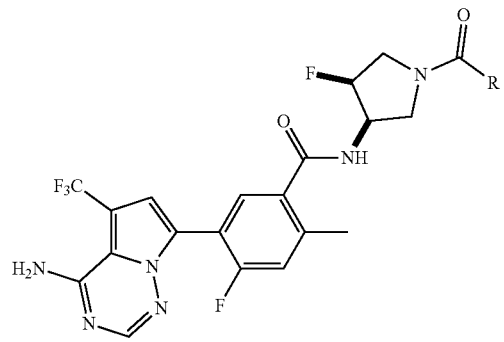

| Ex | Name | R | Obs. MS Ion | NMR Assignments (500 MHz, DMSO-d6) δ |
|---|---|---|---|---|
| 413 | 5-[4-amino-5-(trifluoromethyl)pyrrolo[2,1-f][1,2,4]triazin-7-yl]-4-fluoro-N-[(3R,4S)-4-fluoro-1-(3-hydroxy-3-methylbutanoyl)pyrrolidin-3-yl]-2-methylbenzamide | | 541.4 | 8.70 (br dd, J = 13.9, 7.2 Hz, 1H), 8.08 (s, 1H), 7.74 (dd, J = 7.2, 2.0 Hz, 1H), 7.33-7.27 (m, 2H), 5.40-5.08 (m, 1H), 4.85 (d, J = 5.5 Hz, 1H), 4.73-4.44 (m, 1H), 4.00 (br t, J = 9.2 Hz, 1H), 3.96-3.75 (m, 1H), 3.43 (br t, J = 10.2 Hz, 1H), 3.24 (br t, J = 11.0 Hz, 1H), 2.46-2.24 (m, 5H), 1.17 (s, 6H) |
| 414 | 5-[4-amino-5-(trifluoromethyl)pyrrolo[2,1-f][1,2,4]triazin-7-yl]-4-fluoro-N-[(3R,4S)-4-fluoro-1-[(2R)-3,3,3-trifluoro-2-hydroxy-2-methylpropanoyl]pyrrolidin-3-yl]-2-methylbenzamide | | 581.3 | 8.72-8.59 (m, 1H), 8.10 (s, 1H), 7.78 (br d, J = 5.8 Hz, 1H), 7.36-7.27 (m, 2H), 5.35-5.13 (m, 1H), 4.67-4.48 (m, 1H), 4.42-4.23 (m, 1H), 4.03-3.85 (m, 1H), 3.84-3.71 (m, 1H), 3.70-3.56 (m, 1H), 2.43 (s, 3H), 1.51 (br d, J = 2.1 Hz, 3H) |
| 415 | 5-[4-amino-5-(trifluoromethyl)pyrrolo[2,1-f][1,2,4]triazin-7-yl]-4-fluoro-N-[(3R,4S)-4-fluoro-1-[(2R)-3,3,3-trifluoro-2-hydroxy-propanoyl]pyrrolidin-3-yl]-2-methylbenzamide | | 567.3 | 8.72 (br dd, J = 18.9, 7.3 Hz, 1H), 8.08 (s, 1H), 7.75 (dd, J = 7.3, 3.1 Hz, 1H), 7.34-7.26 (m, 2H), 6.99-6.76 (m, 1H), 5.42-5.14 (m, 1H), 5.00-4.79 (m, 1H), 4.74-4.52 (m, 1H), 4.23-3.23 (m, 4H), 2.42 (s, 3H) |
| 416 | 5-[4-amino-5-(trifluoromethyl)pyrrolo[2,1-f][1,2,4]triazin-7-yl]-4-fluoro-N-[(3R,4S)-4-fluoro-1-(2-hydroxy-2-methylpropanoyl)pyrrolidin-3-yl]-2-methylbenzamide | | 527.3 | 8.71-8.58 (m, 1H), 8.10 (s, 1H), 7.77 (br d, J = 7.3 Hz, 1H), 7.36-7.26 (m, 2H), 5.39-5.10 (m, 2H), 4.64-4.42 (m, 1H), 4.39-4.21 (m, 1H), 4.02-3.81 (m, 1H), 3.79-3.71 (m, 1H), 3.69-3.57 (m, 1H), 2.43 (s, 3H), 1.35-1.25 (m, 6H) |
| 417 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-4-fluoro-2-methylbenzamide, TFA | | 573.4 | 8.68 (br dd, J = 18.3, 7.0 Hz, 1H), 8.09 (s, 1H), 7.76 (br d, J = 7.0 Hz, 1H), 7.35-7.27 (m, 2H), 5.42-5.11 (m, 1H), 4.79-4.45 (m, 1H), 4.05-3.49 (m, 3H), 3.34-3.06 (m, 1H), 2.43 (br d, J = 4.0 Hz, 3H), 2.37-2.23 (m, 2H), 2.21-1.94 (m, 3H), 1.86-1.69 (m, 1H); 1 pyrrolidine CH obscured in water suppression |
| 418 | 5-[4-amino-5-(trifluoromethyl)pyrrolo[2,1-f][1,2,4]triazin-7-yl]-4-fluoro-N-[(3R,4S)-4-fluoro-1-(3-fluorocyclobutanecarbonyl)pyrrolidin-3-yl]-2-methylbenzamide | | 541.1 | 8.67 (br dd, J = 14.2, 7.2 Hz, 1H), 8.09 (s, 1H), 7.75 (br dd, J = 7.2, 2.3 Hz, 1H), 7.34-7.26 (m, 2H), 5.37-4.97 (m, 2H), 4.75-4.45 (m, 1H), 3.87-3.12 (m, 5H), 2.49-2.29 (m, 7H) |

TABLE 22

Compounds in Table 22 were prepared by the methods detailed in Examples 67 and 31. When diastereomers were separated, they are included as separate entries. If the stereochemistry is undefined, the product was isolated as a mixture of diastereomers.

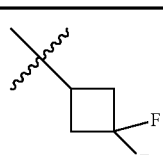

| Ex | Name | R | Obs. MS Ion | NMR Assignments (500 MHz, DMSO-d6) δ |
|---|---|---|---|---|
| 419 | 3-[4-amino-5-(trifluoromethyl) pyrrolo[2,1-f][1,2,4]triazin-7-yl]-N-[(3R,4S)-1-(3,3-difluorocyclobutane-carbonyl)-4-fluoropyrrolidin-3-yl]-4-fluorobenzamide | 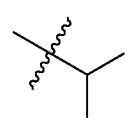 [SMILES: *C(C)C] | 545.2 | 8.79 (br dd, J = 17.1, 7.0 Hz, 1H), 8.32 (br d, J = 6.1 Hz, 1H), 8.13 (s, 1H), 8.08 (br s, 1H), 7.53 (br t, J = 8.2 Hz, 1H), 7.42 (s, 1H), 5.41-5.15 (m, 1H), 4.83-4.52 (m, 1H), 3.98-3.68 (m, 2H), 3.54-3.39 (m, 1H), 3.19 (br dd, J = 11.4, 5.0 Hz, 1H), 2.92-2.67 (m, 4H); 1 pyrrolidine CH obscured in water suppression |
| 420 | 3-[4-amino-5-(trifluoromethyl) pyrrolo[2,1-f][1,2,4]triazin-7-yl]-4-fluoro-N-[(3R,4S)-4-fluoro-1-(2-methylpropanoyl)pyrrolidin-3-yl] benzamide, TFA | 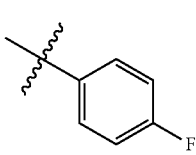 [SMILES: *c1ccc(F)cc1] | 497.1 | 8.71 (br dd, J = 18.9, 7.0 Hz, 1H), 8.30 (br d, J = 4.9 Hz, 1H), 8.10 (s, 1H), 8.06 (br s, 1H), 7.49 (dt, J = 9.1, 4.5 Hz, 1H), 7.39 (s, 1H), 5.39-5.12 (m, 1H), 4.81-4.50 (m, 1H), 3.99 (br t, J = 9.0 Hz, 1H), 3.90 (br d, J = 7.0 Hz, 1H), 3.86-3.75 (m, 1H), 3.74-3.54 (m, 1H), 2.76-2.58 (m, 1H), 1.07-0.92 (m, 6H) |
| 421 | 3-[4-amino-5-(trifluoromethyl) pyrrolo[2,1-f][1,2,4]triazin-7-yl]-4-fluoro-N-[(3R,4S)-4-fluoro-1-(4-fluorobenzoyl)pyrrolidin-3-yl] benzamide, TFA | 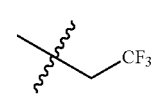 | 549.2 | 8.83-8.62 (m, 1H), 8.36-8.21 (m, 1H), 8.13-7.97 (m, 2H), 7.61 (br s, 2H), 7.54-7.42 (m, 1H), 7.37 (br d, J = 12.8 Hz, 1H), 7.28 (br t, J = 8.7 Hz, 2H), 5.42-5.11 (m, 1H), 4.85-4.50 (m, 1H), 4.08-3.57 (m, 2H); 2 pyrrolidine CHs obscured due to the water suppression |
| 422 | 3-[4-amino-5-(trifluoromethyl)pyrrolo [2,1-f][1,2,4]triazin-7-yl]-4-fluoro-N-[(3R,4S)-4-fluoro-1-(3,3,3-trifluoropropanoyl)pyrrolidin-3-yl]benzamide | 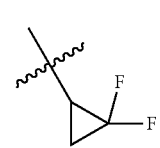 [SMILES: *C1CC1(F)F] | 537.2 | 8.84-8.70 (m, 1H), 8.29 (br d, J = 4.9 Hz, 1H), 8.09 (s, 1H), 8.05 (br s, 1H), 7.49 (br t, J = 8.7 Hz, 1H), 7.38 (br s, 1H), 5.43-5.15 (m, 1H), 4.82-4.49 (m, 1H), 3.98 (br t, J = 8.9 Hz, 1H), 3.95-3.74 (m, 2H), 3.73-3.61 (m, 1H), 3.40 (br t, J = 10.5 Hz, 1H); 1 pyrrolidine CH lost in water suppression |
| 423 | 3-[4-amino-5-(trifluoromethyl)pyrrolo [2,1-f][1,2,4]triazin-7-yl]-N-[(3R,4S)-1-(2,2-difluorocyclopropanecarbonyl)-4-fluoropyrrolidin-3-yl]-4-fluoro-benzamide | 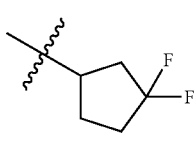 | 531.0 | 8.83-8.68 (m, 1H), 8.31 (br s, 1H), 8.14-8.03 (m, 2H), 7.56-7.45 (m, 1H), 7.39 (s, 1H), 5.44-5.14 (m, 1H), 4.89-4.53 (m, 1H), 4.27-3.55 (m, 4H), 3.12-2.81 (m, 1H), 2.03-1.80 (m, 2H) |
| 424 | 3-[4-amino-5-(trifluoromethyl) pyrrolo[2,1-f][1,2,4]triazin-7-yl]-N-[(3R,4S)-1-(3,3-difluorocyclopentane-carbonyl)-4-fluoropyrrolidin-3-yl]-4-fluorobenzamide | 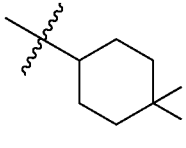 | 559.0 | 8.72 (br dd, J = 18.9, 6.7 Hz, 1H), 8.30 (br d, J = 5.2 Hz, 1H), 8.10 (s, 1H), 8.06 (br s, 1H), 7.50 (td, J = 9.0, 4.6 Hz, 1H), 7.39 (s, 1H), 5.37-5.11 (m, 1H), 4.81-4.51 (m, 1H), 4.09-3.36 (m, 4H), 3.28-3.05 (m, 1H), 2.40-2.24 (m, 2H), 2.23-1.97 (m, 3H), 1.87-1.72 (m, 1H) |
| 425 | 3-[4-amino-5-(trifluoromethyl) pyrrolo[2,1-f][1,2,4]triazin-7-yl]-N-[(3R,4S)-1-(4,4-difluorocyclohexane-carbonyl)-4-fluoropyrrolidin-3-yl]-4-fluorobenzamide | | 573.1 | 8.72 (br dd, J = 20.0, 6.9 Hz, 1H), 8.30 (br d, J = 5.5 Hz, 1H), 8.10 (s, 1H), 8.05 (br s, 1H), 7.49 (td, J = 9.0, 4.9 Hz, 1H), 7.38 (s, 1H), 5.41-5.11 (m, 1H), 4.82-4.52 (m, 1H), 4.11-3.52 (m, 3H), 2.67-2.55 (m, 1H), 2.04 (br d, J = 9.5 Hz, 2H), 1.95-1.70 (m, 4H), 1.58 (br s, 2H); 1 pyrrolidine CH obscured due to water suppression |

TABLE 22-continued

Compounds in Table 22 were prepared by the methods detailed in Examples 67 and 31. When diastereomers were separated, they are included as separate entries. If the stereochemistry is undefined, the product was isolated as a mixture of diastereomers.

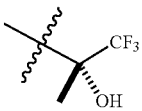 [SMILES: *[C@@](C)(O)C(F)(F)F]

| Ex | Name | R | Obs. MS Ion | NMR Assignments (500 MHz, DMSO-d6) δ |
|---|---|---|---|---|
| 426 | 3-[4-amino-5-(trifluoromethyl)pyrrolo[2,1-f][1,2,4]triazin-7-yl]-4-fluoro-N-[(3R,4S)-4-fluoro-1-[(2R)-3,3,3-trifluoro-2-hydroxy-2-methylpropanoyl]pyrrolidin-3-yl]benzamide, TFA | | 567.2 | 8.71 (br dd, J = 17.4, 7.0 Hz, 1H), 8.30 (br d, J = 6.4 Hz, 1H), 8.10 (s, 1H), 8.06 (br s, 1H), 7.49 (br t, J = 9.2 Hz, 1H), 7.38 (br d, J = 3.7 Hz, 1H), 5.34-5.13 (m, 1H), 4.71-4.48 (m, 1H), 4.43-4.23 (m, 1H), 4.03-3.89 (m, 1H), 3.84-3.58 (m, 2H), 1.52 (s, 3H) |
| 427 | 3-[4-amino-5-(trifluoromethyl)pyrrolo[2,1-f][1,2,4]triazin-7-yl]-4-fluoro-N-[(3R,4S)-4-fluoro-1-(2-hydroxy-2-methylpropanoyl)pyrrolidin-3-yl]benzamide, TFA | | 513.0 | 8.73 (br dd, J = 18.0, 6.7 Hz, 1H), 8.31 (br d, J = 6.4 Hz, 1H), 8.12-8.02 (m, 2H), 7.50 (br t, J = 9.2 Hz, 1H), 7.40 (s, 1H), 5.37-5.11 (m, 1H), 4.69-4.50 (m, 1H), 4.42-4.26 (m, 1H), 4.03-3.50 (m, 3H), 1.35-1.27 (m, 6H) |

TABLE 23

Compounds in Table 23 were prepared by similar methods as detailed in Example 44. When diastereomers were separated, they are included as separate entries. If the stereochemistry is undefined, the product was isolated as a mixture of diastereomers.

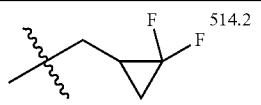

| Ex | Name | R | Obs. MS Ion | NMR Assignments (500 MHz, DMSO-d6) δ |
|---|---|---|---|---|
| 428 | 5-[4-amino-5-(trifluoromethyl)pyrrolo[2,1-f][1,2,4]triazin-7-yl]-N-[(3R 4S)-1-[(2,2-difluorocyclopropyl)methyl]-4-fluoropyrrolidin-3-yl]1-2-methylpyridine-3-carboxamide | | 514.2 | 9.16 (d, J = 2.1 Hz, 1H), 8.76 (d, J = 7.6 Hz, 1H), 8.37 (d, J = 2.1 Hz, 1H), 8.20 (s, 1H), 7.70 (s, 1H), 5.31-5.08 (m, 1H), 4.62-4.35 (m, 1H), 3.21-2.64 (m, 4H), 2.56 (s, 3H), 2.02-1.75 (m, 1H), 1.59 (tdd, J = 12.1, 7.8, 4.3 Hz, 1H), 1.34-1.07 (m, 3H) |

TABLE 23-continued

*Compounds in Table 23 were prepared by similar methods as detailed in Example 44. When diastereomers were separated, they are included as separate entries. If the stereochemistry is undefined, the product was isolated as a mixture of diastereomers.*

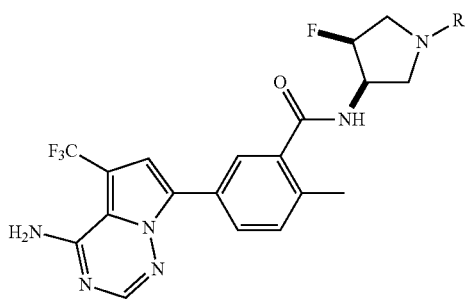

| Ex | Name | R | Obs. MS Ion | NMR Assignments (500 MHz, DMSO-d6) δ |
|---|---|---|---|---|
| 429 | 5-[4-amino-5-(trifluoromethyl)pyrrolo[2,1-f][1,2,4]triazin-7-yl]-N-[(3R,4S)-1-|(2,2-difluorocyclopropyl)methyl]-4-fluoropyrrolidin-3-yl]-2-methylpyridine-3-carboxamide | ⸺CH₂⸺(2,2-difluorocyclopropyl) | 514.2 | 9.47-8.98 (m, 1H), 8.89-8.63 (m, 1H), 8.48-8.28 (m, 1H), 8.26-8.05 (m, 1H), 7.84-7.60 (m, 1H), 5.34-4.95 (m, 1H), 4.70-4.32 (m, 1H), 3.14-2.54 (m, 7H), 2.00-1.70 (m, 1H), 1.68-1.39 (m, 1H), 1.34-1.01 (m, 3H) |
| 430 | 5-[4-amino-5-(trifluoromethyl)pyrrolo[2,1-f][1,2,4]triazin-7-yl]-N-[(3R,4S)-4-fluoro-1-(3,3,3-trifluoro-2-hydroxypropyl)pyrrolidin-3-yl]-2-methylpyridine-3-carboxamide | ⸺CH₂⸺CH(OH)⸺CF₃ | 536.2 | 9.16 (d, J = 2.0 Hz, 1H), 8.72 (d, J = 7.5 Hz, 1H), 8.37 (d, J = 2.0 Hz, 1H), 8.20 (s, 1H), 7.70 (s, 1H), 6.22 (d, J = 6.4 Hz, 1H), 5.32-5.06 (m, 1H), 4.62-4.40 (m, 1H), 4.17-3.96 (m, 1H), 3.27-3.12 (m, 1H), 3.06 (br t, J = 8.5 Hz, 2H), 2.91-2.61 (m, 5H), 2.56 (s, 3H) |
| 431 | 5-[4-amino-5-(trifluoromethyl)pyrrolo[2,1-f][1,2,4]triazin-7-yl]-N-[(3R,4S)-4-fluoro-1-(3,3,3-trifluoro-2-hydroxypropyl)pyrrolidin-3-yl]-2-methylpyridine-3-carboxamide | ⸺CH₂⸺CH(OH)⸺CF₃ | 536.2 | 9.23-9.03 (m, 1H), 8.89-8.63 (m, 1H), 8.49-8.27 (m, 1H), 8.26-8.03 (m, 1H), 7.83-7.53 (m, 1H), 6.03 (s, 1H), 5.39-4.90 (m, 1H), 4.66-4.35 (m, 1H), 4.19-3.93 (m, 1H), 3.22-2.62 (m, 11H) |

TABLE 24

Compounds in Table 24 were prepared by the methods detailed in Example 44 or by the methods detailed in or by the Example 1361, below. All of the compounds are enantiopure fluoropyrrolidine as drawn. When diastereomers were separated, they are included as separate entries. If the stereochemistry is undefined, the product was isolated as a mixture of diastereomers.

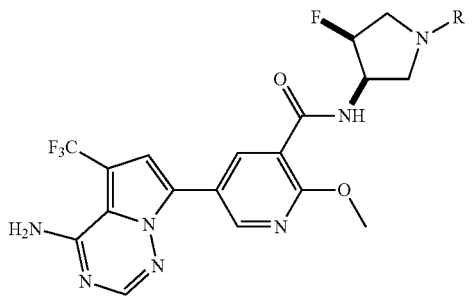

| Ex | Name | R | Obs. MS Ion | NMR Assignments (500 MHz, DMSO-d6) δ |
|---|---|---|---|---|
| 432 | 5-[4-amino-5-(trifluoromethyl)pyrrolo[2,1-f][1,2,4]triazin-7-yl]-N-[(3R,4S)-4-fluoro-1-(1-phenylethyl)pyrrolidin-3-yl]-2-methoxypyridine-3-carboxamide | 1-phenylethyl | 544.2 | 8.90 (d, J = 2.4 Hz, 1H), 8.83 (d, J = 2.3 Hz, 1H), 8.35 (br d, J = 7.3 Hz, 1H), 8.15 (s, 1H), 7.55 (s, 1H), 7.39-7.28 (m, 4H), 7.28-7.10 (m, 1H), 5.34-5.03 (m, 1H), 4.62-4.42 (m, 1H), 4.11-4.04 (m, 3H), 3.65-3.28 (m, 2H), 3.05-2.75 (m, 2H), 2.58-2.55 (m, 1H), 1.33 (d, J = 6.6 Hz, 3H) |
| 433 | 5-[4-amino-5-(trifluoromethyl)pyrrolo[2,1-f][1,2,4]triazin-7-yl]-N-[(3R,4S)-4-fluoro-1-(1-phenylethyl)pyrrolidin-3-yl]-2-methoxypyridine-3-carboxamide | 1-phenylethyl | 544.2 | 8.90 (d, J = 2.1 Hz, 1H), 8.82 (d, J = 2.1 Hz, 1H), 8.36 (br d, J = 7.4 Hz, 1H), 8.14 (s, 1H), 7.54 (s, 1H), 7.34 (d, J = 4.3 Hz, 4H), 7.30-7.15 (m, 1H), 5.31-5.03 (m, 1H), 4.60-4.38 (m, 1H), 4.06 (s, 3H), 3.56-3.33 (m, 1H), 3.22-3.06 (m, 1H), 2.87-2.77 (m, 1H), 2.77-2.63 (m, 1H), 2.58-2.53 (m, 1H), 1.32 (d, J = 6.5 Hz, 3H) |
| 434 | 5-[4-amino-5-(trifluoromethyl)pyrrolo[2,1-f][1,2,4]triazin-7-yl]-N-[(3R,4S)-1-[1-(3-cyanophenyl)ethyl]-4-fluoropyrrolidin-3-yl]-2-methoxypyridine-3-carboxamide | 1-(3-cyanophenyl)ethyl | 569.2 | 8.90 (d, J =2.4 Hz, 1H), 8.86-8.77 (m, 1H), 8.43 (br d, J = 7.6 Hz, 1H), 8.16 (s, 1H), 7.80 (s, 1H), 7.72 (br t, J = 6.7 Hz, 2H), 7.59 (s, 1H), 7.58-7.52 (m, 1H), 5.31-5.08 (m, 1H), 4.63-4.45 (m, 1H), 4.06 (s, 3H), 3.58 (q, J = 6.4 Hz, 1H), 3.03-2.96 (m, 1H), 2.96-2.88 (m, 1H), 2.87-2.69 (m, 1H), 2.51-2.47 (m, 1H), 1.32 (d, J = 6.7 Hz, 3H) |
| 435 | 5-[4-amino-5-(trifluoromethyl)pyrrolo[2,1-f][1,2,4]triazin-7-yl]-N-[(3R,4S)-1-[1-(3-cyanophenyl)ethyl]-4-fluoropyrrolidin-3-yl]-2-methoxypyridine-3-carboxamide | 1-(3-cyanophenyl)ethyl | 569.1 | 8.90 (d, J = 2.4 Hz, 1H), 8.86-8.76 (m, 1H), 8.44 (br d, J = 7.6 Hz, 1H), 8.16 (s, 1H), 7.79 (s, 1H), 7.76-7.68 (m, 2H), 7.63-7.54 (m, 2H), 5.32-5.06 (m, 1H), 4.60-4.41 (m, 1H), 4.05 (s, 3H), 3.67-3.43 (m, 1H), 3.26-3.04 (m, 1H), 2.79 (t, J = 8.1 Hz, 1H), 2.75-2.62 (m, 1H), 2.60-2.56 (m, 1H), 1.32 (d, J = 6.4 Hz, 3H) |

TABLE 24-continued

Compounds in Table 24 were prepared by the methods detailed in Example 44 or by the methods detailed in or by the Example 1361, below. All of the compounds are enantiopure fluoropyrrolidine as drawn. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 436 | 5-[4-amino-5-(trifluoromethyl)pyrrolo[2,1-f][1,2,4]triazin-7-yl]-N-[(3R,4S)-1-[1-(2,4-difluorophenyl)ethyl]-4-fluoropyrrolidin-3-yl]-2-methoxypyridine-3-carboxamide | 2,4-difluorophenyl ethyl | 580.2 | 8.91 (s, 1H), 8.82 (br s, 1H), 8.40 (br d, J = 7.3 Hz, 1H), 8.16 (s, 1H), 7.67-7.48 (m, 2H), 7.25-7.16 (m, 1H), 7.13 (br t, J = 8.3 Hz, 1H), 5.43-5.08 (m, 1H), 4.74-4.47 (m, 1H), 4.07 (s, 4H), 3.37-2.65 (br d, J = 5.8 Hz, 4H), 1.42 (brd, J = 6.3 Hz, 3H) |
| 437 | 5-[4-amino-5-(trifluoromethyl)pyrrolo[2,1-f][1,2,4]triazin-7-yl]-N-[(3R,4S)-1-[1-(2,4-difluorophenyl)ethyl]-1-4-fluoropyrrolidin-3-yl]-2-methoxypyridine-3-carboxamide | 2,4-difluorophenyl ethyl | 580.4 | 8.91 (s, 1H), 8.83 (s, 1H), 8.39 (br d, J =7.5 Hz, 1H), 8.15 (s, 1H), 7.64-7.51 (m, 2H), 7.18 (br t, J = 9.7 Hz, 1H), 7.11 (br t, J = 7.7 Hz, 1H), 5.44-5.05 (m, 1H), 4.73-4.41 (m, 1H), 4.15-3.98 (m, 4H), 3.72-2.88 (m, 3H), 2.70 (br d, J = 11.0 Hz, 1H), 1.41 (br d, J = 6.4 Hz, 3H) |
| 438 | 5[4-amino-5-(trifluoromethyl)pyrrolo[2,1-f][1,2,4]triazin-7-yl]-N-[(3R,4S)-4-fluoro-1-[1-(pyridin-4-yl)ethyl]pyrrolidin-3-yl]-2-methoxypyridine-3-carboxamide, 2 TFA | pyridin-4-yl ethyl | 545.2 | 8.90 (d, J = 2.4 Hz, 1H), 8.82 (d, J = 2.1 Hz, 1H), 8.53 (br d, J = 4.6 Hz, 2H), 8.49-8.38 (m, 1H), 8.16 (s, 1H), 7.58 (s, 1H), 7.37 (br d, J = 5.2 Hz, 2H), 5.40-5.04 (m, 1H), 4.65-4.37 (m, 1H), 4.05 (s, 3H), 3.51-3.47 (m, 1H, partially suppressed), 3.19-3.05 (m, 1H), 2.83 (br t, J = 8.4 Hz, 1H), 2.77-2.66 (m, 1H), 2.60-2.55 (m, 1H), 1.31 (d, J = 6.4 Hz, 3H) |
| 439 | 5-[4-amino-5-(trifluoromethyl)pyrrolo[2,1-f][1,2,4]triazin-7-yl]-N-[(3R,4S)-4-fluoro-1-[1-(pyridin-4-yl)ethyl]pyrrolidin-3-yl]-2-methoxypyridine-3-carboxamide, 2 TFA | pyridin-4-yl ethyl | 545.2 | 8.90 (d, J = 2.1 Hz, 1H), 8.82 (d, J = 2.1 Hz, 1H), 8.53 (br s, 2H), 8.49-8.38 (m, 1H), 8.16 (s, 1H), 7.59 (s, 1H), 7.39 (br d, J = 4.9 Hz, 2H), 5.33-5.09 (m, 1H), 4.70-4.39 (m, 1H), 4.06 (s, 3H), 3.57-3.47 (m, 1H, partially suppressed), 3.11-2.74 (m, 3H), 2.55 (br t, J = 8.7 Hz, 1H), 1.32 (d, J = 6.4 Hz, 3H) |

TABLE 24-continued

Compounds in Table 24 were prepared by the methods detailed in Example 44 or by the methods detailed in or by the Example 1361, below. All of the compounds are enantiopure fluoropyrrolidine as drawn. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 440 | 5-[4-amino-5-(trifluoromethyl)pyrrolo[2,1-f][1,2,4]triazin-7-yl]-N-[(3R,4S)-4-fluoro-1-[1-(5-fluoropyridin-3-yl)ethyl]pyrrolidin-3-yl]-2-methoxypyridine-3-carboxamide | | 562.8 | 8.91 (d, J = 2.4 Hz, 1H), 8.82 (d, J = 2.4 Hz, 1H), 8.52-8.44 (m, 2H), 8.42 (br d, J = 7.6 Hz, 1H), 8.17 (s, 1H), 7.70 (br d, J = 10.1 Hz, 1H), 7.60 (s, 1H), 5.30-5.09 (m, 1H), 4.62-4.46 (m, 1H), 4.06 (s, 3H), 3.69-3.62 (m, 1H), 3.06-2.97 (m, 1H), 2.94 (dd, J =12.1, 4.7 Hz, 1H), 2.91-2.77 (m, 1H), 2.57-2.53 (m, 1H), 1.36 (d, J = 6.4 Hz, 3H) |
| 441 | 5-[4-amino-5-(trifluoromethyl)pyrrolo[2,1-f][1,2,4]triazin-7-yl]-N-[(3R,4S)-4-fluoro-1-[1-(5-fluoropyridin-3-yl)ethyl]pyrrolidin-3-yl]-2-methoxypyridine-3-carboxamide | | 563.4 | 8.91 (d, J = 2.1 Hz, 1H), 8.83 (d, J = 2.1 Hz, 1H), 8.49 (d, J =2.4 Hz, 1H), 8.47-8.40 (m, 2H), 8.16 (s, 1H), 7.694 (br d, J = 9.8 Hz, 1H), 7.60 (s, 1H), 5.31-5.12 (m, 1H), 4.61-4.43 (m, 1H), 4.05 (s, 3H), 3.65 (br d, J = 6.4 Hz, 1H), 3.22-3.04 (m, 1H), 2.83 (br t, J = 8.2 Hz, 1H), 2.77-2.64 (m, 1H), 2.60 (br t, J = 8.4 Hz, 1H), 1.36 (d, J = 6.4 Hz, 3H) |
| 442 | 5-[4-amino-5-(trifluoromethyl)pyrrolo[2,1-f][1,2,4]triazin-7-yl]-N-[(3R,4S)-4-fluoro-1-[1-(2-methyl-1,3-thiazol-4-yl)ethyl]pyrrolidin-3-yl]-2-methoxypyridine-3-carboxamide | | 565.2 | 8.90 (d, J = 2.1 Hz, 1H), 8.83 (d, J = 2.4 Hz, 1H), 8.41 (br d, J = 7.3 Hz, 1H), 8.16 (s, 1H), 7.59 (s, 1H), 7.27 (s, 1H), 5.32-5.02 (m, 1H), 4.53-4.30 (m, 1H), 4.04 (s, 3H), 3.79 (q, J = 6.6 Hz, 1H), 3.26-3.08 (m, 1H), 2.93 (t, J = 8.1 Hz, 1H), 2.87-2.71 (m, 1H), 2.64 (s, 3H), 2.59 (br t, J = 8.5 Hz, 1H), 1.37 (d, J = 6.7 Hz, 3H) |
| 443 | 5-[4-amino-5-(trifluoromethyl)pyrrolo[2,1-f][1,2,4]triazin-7-yl]-N-[(3R,4S)-4-fluoro-1-[1-(2-methyl-1,3-thiazol-4-yl)ethyl]pyrrolidin-3-yl]-2-methoxypyridine-3-carboxamide | | 565.2 | 8.90 (d, J = 2.1 Hz, 1H), 8.83 (d, J = 2.1 Hz, 1H), 8.41 (br d, J = 7.0 Hz, 1H), 8.17 (s, 1H), 7.60 (s, 1H), 7.28 (s, 1H), 5.28-5.03 (m, 1H), 4.53-4.33 (m, 1H), 4.05 (s, 3H), 3.83 (br d, J = 5.5 Hz, 1H), 3.45 (br d, J = 15.6 Hz, 1H), 3.23-2.81 (m, 2H), 2.64 (s, 3H), 2.61-2.57 (m, 1H), 1.37 (br d, J = 6.7 Hz, 3H) |

TABLE 24-continued

Compounds in Table 24 were prepared by the methods detailed in Example 44 or by the methods detailed in or by the Example 1361, below. All of the compounds are enantiopure fluoropyrrolidine as drawn. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 444 | 5-[4-amino-5-(trifluoromethyl)pyrrolo[2,1-f][1,2,4]triazin-7-yl]-N-[(3R,4S)-4-fluoro-1-[1-(1,3-thiazol-5-yl)ethyl]pyrrolidin-3-yl]-2-methoxypyridine-3-carboxamide | (1-thiazol-5-yl-ethyl) | 551.2 | 9.04 (s, 1H), 8.92 (d, J = 2.4 Hz, 1H), 8.84 (d, J = 2.1 Hz, 1H), 8.42 (br d, J = 7.6 Hz, 1H), 8.17 (s, 1H), 7.81 (s, 1H), 7.61 (s, 1H), 5.39-5.03 (m, 1H), 4.61-4.38 (m, 1H), 4.10 - 4.03 (m, 4H), 3.26-3.05 (m, 1H), 2.91 (t, J = 8.4 Hz, 1H), 2.84-2.69 (m, 1H), 2.62 (br t, J = 8.7 Hz, 1H), 1.41 (d, J = 6.4 Hz, 3H) |
| 445 | 5-[4-amino-5-(trifluoromethyl)pyrrolo[2,1-f][1,2,4]triazin-7-yl]-N-[(3R,4S)-4-fluoro-1-[1-(1,3-thiazol-5-yl)ethyl]pyrrolidin-3-yl]-2-methoxypyridine-3-carboxamide | (1-thiazol-5-yl-ethyl) | 551.2 | 9.03 (s, 1H), 8.92 (d, J = 2.1 Hz, 1H), 8.84 (d, J = 2.4 Hz, 1H), 8.41 (br d, J = 7.3 Hz, 1H), 8.18 (s, 1H), 7.82 (s, 1H), 7.61 (s, 1H), 5.35-5.07 (m, 1H), 4.66-4.38 (m, 1H), 4.15-4.00 (m, 4H), 3.10-2.97 (m, 2H), 2.93-2.81 (m, 1H), 2.59-2.55 (m, 1H), 1.42 (d, J = 6.4 Hz, 3H) |
| 446 | 5[4-amino-5-(trifluoromethyl)pyrrolo[2,1-f][1,2,4]triazin-7-yl]-N-[(3R,4S)-4-fluoro-1-(3,3,3-trifluoro-1-phenylpropyl)pyrrolidin-3-yl]-2-methoxypyridine-3-carboxamide | (3,3,3-trifluoro-1-phenylpropyl) | 612.1 | 8.92 (d, J = 2.4 Hz, 1H), 8.85 (s, 1H), 8.44 (br d, J = 7.6 Hz, 1H), 8.17 (s, 1H), 7.91 (br d, J = 6.7 Hz, 1H), 7.71 (br d, J = 8.2 Hz, 2H), 7.6 (s, 1H), 7.48 (br s, 1H), 5.30-5.07 (m, 1H), 4.58 (br d, J = 18.6 Hz, 1H), 4.07 (s, 3H), 3.92-3.69 (m, 1H), 3.19-2.67 (m, 6H, partially suppressed), 1.33 (br d, J = 6.1 Hz, 3H) |
| 447 | 5-[4-amino-5-(trifluoromethyl)pyrrolo[2,1-f][1,2,4]triazin-7-yl]-N-[(3R,4S)-4-fluoro-1-(3,3,3-trifluoro-1-phenylpropyl)pyrrolidin-3-yl]-2-methoxypyridine-3-carboxamide | (3,3,3-trifluoro-1-phenylpropyl) | 612.1 | 8.66 (d, J = 2.4 Hz, 1H), 8.57 (d, J = 2.1 Hz, 1H), 8.21 (br d, J = 7.3 Hz, 1H), 7.92 (s, 1H), 7.64 (br d, J = 7.9 Hz, 1H), 7.49 (br t, J = 7.6 Hz, 1H), 7.45 (br d, J = 7.9 Hz, 1H), 7.36 (s, 1H), 7.28-7.21 (m, 1H), 5.08-4.88 (m, 1H), 4.37-4.20 (m, 1H), 3.80 (s, 3H), 3.51 (br s, 1H), 3.04-2.84 (m, 3H, partially suppressed), 2.58-2.37 (m, 2H), 2.35-2.30 (m, 1H), 1.07 (br d, J = 6.1 Hz, 3H) |

TABLE 24-continued

Compounds in Table 24 were prepared by the methods detailed in Example 44 or by the methods detailed in or by the Example 1361, below. All of the compounds are enantiopure fluoropyrrolidine as drawn. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 448 | 5-[4-amino-5-(trifluoromethyl)pyrrolo[2,1-f][1,2,4]triazin-7-yl]-N-[(3R,4S)-4-fluoro-1-[1-(2-fluorophenyl)ethyl]pyrrolidin-3-yl]-2-methoxypyridine-3-carboxamide | 2-fluorophenyl-CH(CH₃)- | 562.3 | 8.91 (d, J = 2.1 Hz, 1H), 8.84 (d, J = 2.1 Hz, 1H), 8.43 (br d, J = 7.6 Hz, 1H), 8.17 (s, 1H), 7.61 (s, 1H), 7.52 (br t, J = 6.9 Hz, 1H), 7.42-7.27 (m, 1H), 7.27-7.12 (m, 2H), 5.38-5.07 (m, 1H), 4.71-4.43 (m, 1H), 4.07 (s, 3H), 3.87 (q, J = 6.7 Hz, 1H), 3.18 (d, J = 5.5 Hz, 1H), 3.06-2.92 (m, 2H), 2.87-2.73 (m, 1H), 1.35 (d, J = 6.7 Hz, 3H) |
| 449 | 5-[4-amino-5-(trifluoromethyl)pyrrolo[2,1-f][1,2,4]triazin-7-yl]-N-[(3R,4S)-4-fluoro-1-[1-(2-fluorophenyl)ethyl]pyrrolidin-3-yl]-2-methoxypyridine-3-carboxamide | 2-fluorophenyl-CH(CH₃)- | 562.1 | 8.91 (d, J = 2.4 Hz, 1H), 8.83 (d, J = 2.1 Hz, 1H), 8.43 (br d, J = 7.3 Hz, 1H), 8.16 (s, 1H), 7.60 (s, 1H), 7.56-7.46 (m, 1H), 7.42-7.27 (m, 1H), 7.27-7.20 (m, 1H), 7.20-7.14 (m, 1H), 5.36-4.98 (m, 1H), 4.65-4.37 (m, 1H), 4.05 (s, 3H), 3.84 (q, J = 6.6 Hz, 1H), 3.18 (d, J = 5.2 Hz, 1H), 3.17-3.07 (m, 1H), 2.85 (t, J = 8.1 Hz, 1H), 2.80-2.64 (m, 1H), 1.35 (d, J = 6.4 Hz, 3H) |
| 450 | 5-[4-amino-5-(trifluoromethyl)pyrrolo[2,1-f][1,2,4]triazin-7-yl]-N-[(3R,4S)-4-fluoro-1-[1-(3-fluoropyridin-2-yl)ethyl]pyrrolidin-3-yl]-2-methoxypyridine-3-carboxamide | 3-fluoropyridin-2-yl-CH(CH₃)- | 563.2 | 8.92 (d, J = 2.1 Hz, 1H), 8.84 (d, J = 2.1 Hz, 1H), 8.47 (br s, 1H), 8.44-8.37 (m, 1H), 8.19 (s, 1H), 7.73 (br s, 1H), 7.63 (s, 1H), 7.44 (br s, 1H), 5.33-5.04 (m, 1H), 4.60-4.34 (m, 1H), 4.29-4.11 (m, 1H), 4.05 (s, 3H), 3.57-2.60 (m, 4H, partially suppressed), 1.45 (br d, J = 6.7 Hz, 3H) |
| 451 | 5-[4-amino-5-(trifluoromethyl)pyrrolo[2,1-f][1,2,4]triazin-7-yl]-N-[(3R,4S)-4-fluoro-1-[phenyl(deutero)methyl]pyrrolidin-3-yl]-2-methoxypyridine-3-carboxamide | phenyl-CD₂- | 532.2 | 8.91 (d, J = 2.4 Hz, 1H), 8.84 (d, J = 2.1 Hz, 1H), 8.44 (br d, J = 7.6 Hz, 1H), 8.16 (s, 1H), 7.60 (s, 1H), 7.37-7.32(m, 4H), 7.32-7.18 (m, 1H), 5.33-5.05 (m, 1H), 4.64-4.44 (m, 1H), 4.05 (s, 3H), 3.22-2.99 (m, 1H), 2.91 (t, J = 8.2 Hz, 1H), 2.87-2.72 (m, 1H), 2.59 (t, J = 8.4 Hz, 1H) |

TABLE 24-continued

Compounds in Table 24 were prepared by the methods detailed in Example 44 or by the methods detailed in or by the Example 1361, below. All of the compounds are enantiopure fluoropyrrolidine as drawn. When diastereomers were separated, they are included as separate entries. If the stereochemistry is undefined, the product was isolated as a mixture of diastereomers.

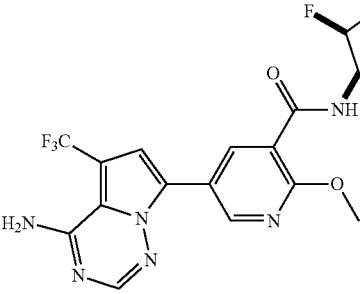

| Ex | Name | R | Obs. MS Ion | NMR Assignments (500 MHz, DMSO-d6) δ |
|---|---|---|---|---|
| 452 | 5-[4-amino-5-(trifluoromethyl)pyrrolo[2,1-f][1,2,4]triazin-7-yl]-N-[(3R,4S)-4-fluoro-1-[1-(pyrimidin-4-yl)ethyl]pyrrolidin-3-yl]-2-methoxypyridine-3-carboxamide | 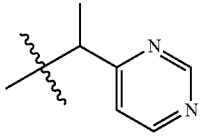 [SMILES: *C(C)c1ccncn1] | 546.3 | 9.12 (s, 1H), 8.90 (d, J = 2.4 Hz, 1H), 8.82 (d, J = 2.4 Hz, 1H), 8.78 (d, J = 5.2 Hz, 1H), 8.44 (br d, J = 7.6 Hz, 1H), 8.16 (s, 1H), 7.59 (s, 1H), 7.57 (d, J = 5.2 Hz, 1H), 5.29-5.09 (m, 1H), 4.61-4.47 (m, 1H), 4.05 (s, 3H), 3.68 (q, J = 6.6 Hz, 1H), 3.22-3.00 (m, 2H), 2.94-2.81 (m, 1H), 2.61 (br t, J = 8.5 Hz, 1H), 1.35 (d, J = 6.7 Hz, 3H) |
| 453 | 5-[4-amino-5-(trifluoromethyl)pyrrolo[2,1-f][1,2,4]triazin-7-yl]-N-[(3R,4S)-4-fluoro-1-[1-(pyrimidin-4-yl)ethyl]pyrrolidin-3-yl]-2-methoxypyridine-3-carboxamide | 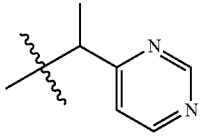 [SMILES: *C(C)c1ccncn1] | 546.0 | 9.12 (s, 1H), 8.90 (d, J = 2.4 Hz, 1H), 8.82 (d, J = 2.4 Hz, 1H), 8.79 (d, J = 5.2 Hz, 1H), 8.45 (br d, J = 7.6 Hz, 1H), 8.16 (s, 1H), 7.59 (s, 1H), 7.57 (d, J = 5.5 Hz, 1H), 5.34-5.12 (m, 1H), 4.59-4.43 (m, 1H), 4.05 (s, 3H), 3.67 (q, J = 6.7 Hz, 1H), 3.24-3.05 (m, 1H), 2.92 (t, J = 8.4 Hz, 1H), 2.90-2.74 (m, 1H), 2.66 (br t, J = 8.4 Hz, 1H), 1.35 (d, J = 6.7 Hz, 3H) |
| 454 | 5-[4-amino-5-(trifluoromethyl)pyrrolo[2,1-f][1,2,4]triazin-7-yl]-N-[(3R,4S)-4-fluoro-1-[1-(3-fluoropyridin-4-yl)ethyl]pyrrolidin-3-yl]-2-methoxypyridine-3-carboxamide | 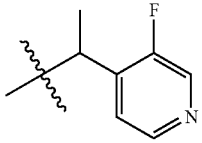 [SMILES: *C(C)c1ccncc1F] | 563.2 | 8.91 (d, J = 2.4 Hz, 1H), 8.87-8.78 (m, 1H), 8.54 (s, 1H), 8.50-8.40 (m, 2H), 8.16 (s, 1H), 7.60 (s, 1H), 7.55 (t, J = 5.5 Hz, 1H) 5.37-4.99 (m, 1H), 4.64-4.40 (m, 1H), 4.05 (s, 3H), 3.89 (q, J = 6.5 Hz, 1H), 3.24-3.04 (m, 1H), 2.89 (t, J = 8.1 Hz, 1H), 2.84-2.70 (m, 1H), 2.60 (br t, J = 8.2 Hz, 1H), 1.36 (d, J = 6.7 Hz, 3H) |
| 455 | 5-[4-amino-5-(trifluoromethyl)pyrrolo[2,1-f][1,2,4]triazin-7-yl]-N-[(3R,4S)-4-fluoro-1-[1-(3-fluoropyridin-4-yl)ethyl]pyrrolidin-3-yl]-2-methoxypyridine-3-carboxamide | 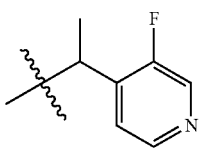 [SMILES: *C(C)c1ccncc1F] | 563.2 | 8.91 (d, J = 2.4 Hz, 1H), 8.83 (d, J = 2.4 Hz, 1H), 8.53 (s, 1H), 8.49-8.39 (m, 2H), 8.17 (s, 1H), 7.60 (s, 1H), 7.56 (t, J = 5.5 Hz, 1H), 5.36-5.02 (m, 1H), 4.66-4.41 (m, 1H), 4.06 (s, 3H), 3.99-3.87 (m, 1H), 3.11-2.95 (m, 2H), 2.91-2.76 (m, 1H), 2.58 (br t, J = 8.5 Hz, 1H), 1.36 (d, J = 6.7 Hz, 3H) |

TABLE 24-continued

Compounds in Table 24 were prepared by the methods detailed in Example 44 or by the methods detailed in or by the Example 1361, below. All of the compounds are enantiopure fluoropyrrolidine as drawn. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| 456 | 5-[4-amino-5-(trifluoromethyl)pyrrolo[2,1-f][1,2,4]triazin-7-yl]-N-[(3R,4S)-4-fluoro-1-[1-(pyridin-3-yl)ethyl]pyrrolidin-3-yl]-2-methoxypyridine-3-carboxamide | | 545.0 | 8.91 (d, J = 2.1 Hz, 1H), 8.83 (d, J = 2.1 Hz, 1H), 8.55 (s, 1H), 8.49 (br d, J = 3.7 Hz, 1H), 8.46-8.32 (m, 1H), 8.21-8.13 (m, 1H), 7.77 (br d, J = 7.6 Hz, 1H), 7.70-7.51 (m, 1H), 7.39 (dd, J = 7.5, 4.7 Hz, 1H), 5.32-5.06 (m, 1H), 4.56-4.43 (m, 1H), 4.08-4.03 (m, 3H), 3.55 (br q, J = 6.7 Hz, 1H), 3.24-3.07 (m, 1H), 2.80 (t, J = 8.2 Hz, 1H), 2.75-2.62 (m, 1H), 2.59-2.56 (m, 1H), 1.35 (d, J = 6.7 Hz, 3H) |
| 457 | 5-[4-amino-5-(trifluoromethyl)pyrrolo[2,1-f][1,2,4]triazin-7-yl]-N-[(3R,4S)-4-fluoro-1-[1-(pyridin-3- | | 545.0 | 8.91 (d, J = 2.1 Hz, 1H), 8.88-8.78 (m, 1H), 8.56 (s, 1H), 8.47 (br d, J = 4.3 Hz, 1H), 8.45-8.33 (m, 1H), 8.17 (s, 1H), 7.77 (br d, J = 7.6 Hz, 1H), 7.61 (s, 1H), 7.38 (dd, J = 7.6, 4.9 Hz, 1H), 5.31-5.07 (m, 1H), 4.61-4.45 (m, 1H), 4.06 (s, 3H), 3.57 (q, J = 6.3 Hz, 1H), 3.03-2.95 (m, 1H), 2.95-2.78 (m, 2H), 2.50-2.46 (m, 1H), 1.35 (d, J = 6.7 Hz, 3H) |
| 458 | 5-[4-amino-5-(trifluoromethyl)pyrrolo[2,1-f][1,2,4]triazin-7-yl]-N-[(3R,4S)-1-[1-(3,5-difluorophenyl)ethyl]1-4-fluoropyrrolidin-3-yl]-2-methoxypyridine-3-carboxamide | | 580.2 | 8.90 (d, J = 2.4 Hz, 1H), 8.82 (d, J = 2.4 Hz, 1H), 8.44 (br d, J = 7.3 Hz, 1H), 8.16 (s, 1H), 7.58 (s, 1H), 7.15-7.03 (m, 3H), 5.36-5.11 (m, 1H), 4.58-4.44 (m, 1H), 4.05 (s, 3H), 3.51 (m, 1H, partially suppressed), 3.23-2.99 (m, 1H), 2.82 (br t, J = 8.2 Hz, 1H), 2.77-2.64 (m, 1H), 2.62-2.56 (m, 1H), 1.30 (d, J = 6.7 Hz, 3H) |
| 459 | 5-[4-amino-5-(trifluoromethyl)pyrrolo[2,1-f][1,2,4]triazin-7-yl]-N-[(3R,4S)-4-(3,5-difluorophenyl)ethyl]-4-fluoropyrrolidin-3-yl]-2-methoxypyridine-3-carboxamide | | 580.2 | 8.90 (d, J = 2.1 Hz, 1H), 8.82 (d, J = 2.1 Hz, 1H), 8.43 (br d, J = 7.6 Hz, 1H), 8.16 (s, 1H), 7.59 (s, 1H), 7.08 (br d, J = 7.3 Hz, 3H), 5.31-4.96 (m, 1H), 4.61-4.47 (m, 1H), 4.06 (s, 3H), 3.60-3.40 (m, 2H, partially suppressed), 3.05-2.90 (m, 2H), 2.88-2.68 (m, 1H), 1.31 (br d, J = 6.4 Hz, 3H) |

TABLE 24-continued

Compounds in Table 24 were prepared by the methods detailed in Example 44 or by the methods detailed in or by the Example 1361, below. All of the compounds are enantiopure fluoropyrrolidine as drawn. When diastereomers were separated, they are included as separate entries. If the stereochemistry is undefined, the product was isolated as a mixture of diastereomers.

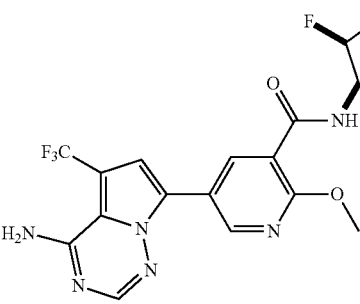

| Ex | Name | R | Obs. MS Ion | NMR Assignments (500 MHz, DMSO-d6) δ |
|---|---|---|---|---|
| 460 | 5-[4-amino-5-(trifluoromethyl)pyrrolo[2,1-f][1,2,4]triazin-7-yl]-N-[(3R,4S)-4-(3,4-difluorophenyl)ethyl]-4-fluoropyrrolidin-3-yl]-2-methoxypyridine-3-carboxamide | 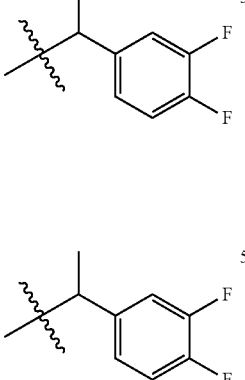 | 580.2 | 8.93-8.88 (m, 1H), 8.84-8.81 (m, 1H), 8.42 (br d, J = 7.7 Hz, 1H), 8.16 (s, 1H), 7.60 (s, 1H), 7.45-7.32 (m, 2H), 7.20 (br s, 1H), 5.30-5.03 (m, 1H), 4.60-4.40 (m, 1H), 4.05 (s, 3H), 3.52-3.35 (m, 2H, partially suppressed), 3.02-2.89 (m, 2H), 2.84-2.73 (m, 1H), 1.29 (d, J = 6.6 Hz, 3H) |
| 461 | 5-[4-amino-5-(trifluoromethyl)pyrrolo[2,1-f][1,2,4]triazin-7-yl]-N-[(3R,4S)-4-(3,4-difluorophenyl)ethyl]-4-fluoropyrrolidin-3-yl]-2-methoxypyridine-3-carboxamide | 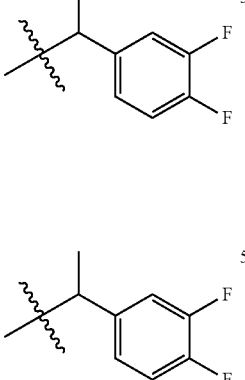 | 580.1 | 8.90 (d, J = 2.2 Hz, 1H), 8.83 (d, J = 2.2 Hz, 1H), 8.43 (br d, J = 7.3 Hz, 1H), 8.16 (s, 1H), 7.60 (s, 1H), 7.42-7.36 (m, 2H), 7.20 (br s, 1H), 5.42-5.05 (m, 1H), 4.59-4.41 (m, 1H), 4.04 (s, 3H), 3.46-3.35 (m, 2H, partially suppressed), 3.18-3.06 (m, 1H, partially suppressed), 2.79 (br t, J = 8.3 Hz, 1H), 2.73-2.62 (m, 1H), 2.56-2.52 (m, 2H), 1.29 (d, J = 6.6 Hz, 3H |
| 462 | 5-[4-amino-5-(trifluoromethyl)pyrrolo[2,1-f][1,2,4]triazin-7-yl]-N-[(3R,4S)-4-fluoro-1-[1-(4-fluorophenyl)ethyl]pyrrolidin-3-yl]-2-methoxypyridine-3-carboxamide | 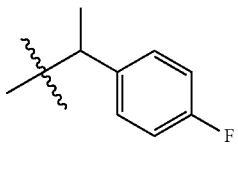 [SMILES: *C(C)c1ccc(F)cc1] | 562.2 | 8.91 (d, J = 2.2 Hz, 1H), 8.84 (d, J = 1.8 Hz, 1H), 8.41 (br d, J = 7.3 Hz, 1H), 8.17 (s, 1H), 7.61 (s, 1H), 7.38 (dd, J = 8.1, 5.9 Hz, 2H), 7.15 (t, J = 8.6 Hz, 2H), 5.31-5.08 (m, 1H), 4.58-4.39 (m, 1H), 4.06 (s, 3H), 3.53-3.31 (m, 1H), 3.04-2.85 (m, 2H), 2.83-2.69 (m, 1H), 2.47 (br t, J = 8.6 Hz, 1H), 1.30 (d, J = 6.2 Hz, 3H) |
| 463 | 5-[4-amino-5-(trifluoromethyl)pyrrolo[2,1-f][1,2,4]triazin-7-yl]-N-[(3R,4S)-4-fluoro-1-[1-(4-fluorophenyl)ethyl]pyrrolidin-3-yl]-2-methoxypyridine-3-carboxamide | 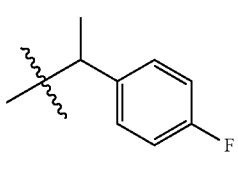 [SMILES: *C(C)c1ccc(F)cc1] | 562.2 | 8.90 (d, J = 2.2 Hz, 1H), 8.83 (d, J = 2.2 Hz, 1H), 8.42 (br d, J = 7.7 Hz, 1H), 8.16 (s, 1H), 7.59 (s, 1H), 7.37 (dd, J = 8.3, 5.7 Hz, 2H), 7.16 (t, J = 8.8 Hz, 2H), 5.29-5.09 (m, 1H), 4.55-4.35 (m, 1H), 4.04 (s, 3H), 3.49-3.35 (m, 1H, partially suppressed), 3.23-3.04 (m, 1H), 2.77 (t, J = 8.3 Hz, 1H), 2.71-2.62 (m, 1H), 2.55-2.52 (m, 1H), 1.30 (d, J = 6.6 Hz, 3H) |

TABLE 24-continued

Compounds in Table 24 were prepared by the methods detailed in Example 44 or by the methods detailed in or by the Example 1361, below. All of the compounds are enantiopure fluoropyrrolidine as drawn. When diastereomers were separated, they are included as separate entries. If the stereochemistry is undefined, the product was isolated as a mixture of diastereomers.

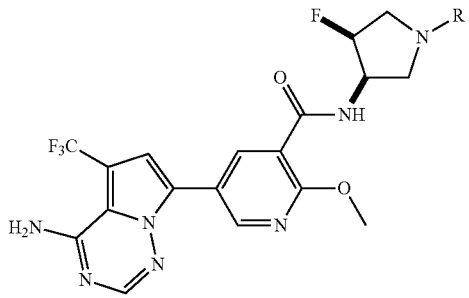

| Ex | Name | R | Obs. MS Ion | NMR Assignments (500 MHz, DMSO-d6) δ |
|---|---|---|---|---|
| 464 | 5-[4-amino-5-(trifluoromethyl)pyrrolo[2,1-f][1,2,4]triazin-7-yl]-N-[(3R,4S)-4-fluoro-1-[(5-fluoropyridin-2-yl)methyl]pyrrolidin-3-yl]-2-methoxypyridine-3-carboxamide | | 549.2 | 8.90 (d, J = 2.2 Hz, 1H), 8.83 (d, J = 2.2 Hz, 1H), 8.52-8.47 (m, 1H), 8.45 (br d, J = 7.7 Hz, 1H), 8.16 (s, 1H), 7.71 (td, J = 8.6, 2.9 Hz, 1H), 7.60 (s, 1H), 7.52 (dd, J = 8.8, 4.8 Hz, 1H), 5.33-5.09 (m, 1H), 4.62-4.41 (m, 1H), 4.05 (s, 3H), 3.85-3.77 (m, 2H), 3.22-3.04 (m, 1H), 2.99 (t, J = 8.3 Hz, 1H), 2.94-2.78 (m, 1H), 2.67 (t, J = 8.4 Hz, 1H) |
| 465 | 5-[4-amino-5-(trifluoromethyl)pyrrolo[2,1-f][1,2,4]triazin-7-yl]-N-[(3R,4S)-4-fluoro-1-(2-hydroxy-2-phenylethyl)pyrrolidin-3-yl]-2-methoxypyridine-3-carboxamide | | 560.1 | 8.93 (br d, J = 2.6 Hz, 1H), 8.86-8.78 (m, 1H), 8.53 (br s, 1H), 8.18 (s, 1H), 7.62 (br s, 1H), 7.44-7.38 (m, 2H), 7.36 (br s, 2H), 7.34-7.26 (m, 1H), 5.48-5.16 (m 1H), 4.99-4.39 (m, 2H), 4.05 (s, 3H), 3.66-2.88 (m, 6H, partially suppressed) |

TABLE 25

Compounds in Table 25 were prepared by similar methods as those detailed in Example 68.

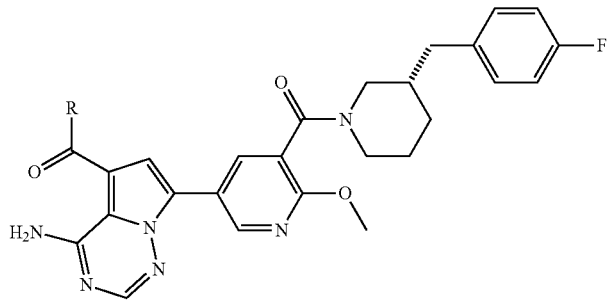

| Ex | Name | R | Obs. MS Ion | NMR Assignments (500 MHz, DMSO-d6) δ |
|---|---|---|---|---|
| 466 | 7-{5-[(3S)-3-[(4-fluorophenyl)methyl]piperidine-1-carbonyl]-6-methoxypyridin-3-yl}-5-{2-oxa-6-azaspiro[3.3]heptane-6-carbonyl}pyrrolo[2,1-f][1,2,4]triazin-4-amine | azaspiro group | 586.4 | Unassigned due to rotomers |
| 467 | 4-amino-N-ethyl-7-{5-[(3S)-3-[(4-fluorophenyl)methyl]piperidine-1-carbonyl]-6-methoxypyridin-3-yl}pyrrolo[2,1-f][1,2,4]triazine-5-carboxamide | NHEt | 532.3 | Unassigned due to rotomers |
| 468 | 4-amino-N-(cyanomethyl)-7-{5-[(3S)-3-[(4-fluorophenyl)methyl]piperidine-1-carbonyl]-6-methoxypyridin-3-yl}pyrrolo[2,1-f][1,2,4]triazine-5-carboxamide | NHCH2CN | 543.2 | Unassigned due to rotomers |
| 469 | 4-amino-7-{5-[(3S)-3-[(4-fluorophenyl)methyl]piperidine-1-carbonyl]-6-methoxypyridin-3-yl}-N-(2-hydroxyethyl)pyrrolo[2,1-f][1,2,4]triazine-5-carboxamide | NHCH2CH2OH | 548.3 | Unassigned due to rotomers |
| 470 | 4-amino-7-{5-[(3S)-3-[(4-fluorophenyl)methyl]piperidine-1-carbonyl]-6-methoxypyridin-3-yl}-N,N-dimethylpyrrolo[2,1-f][1,2,4]triazine-5-carboxamide | N(CH3)2 | 532.2 | Unassigned due to rotomers |

TABLE 25-continued

Compounds in Table 25 were prepared by similar methods as those detailed in Example 68.

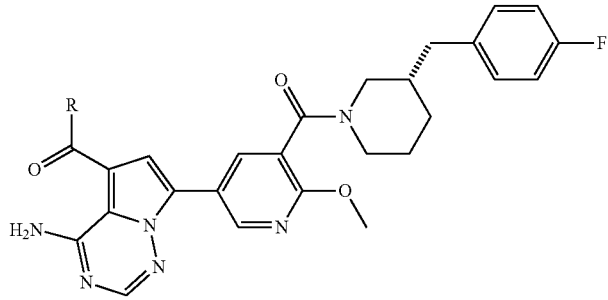

| Ex | Name | R | Obs. MS Ion | NMR Assignments (500 MHz, DMSO-d6) δ |
|---|---|---|---|---|
| 471 | N-{2-[(4-amino-7-{5-[(3S)-3-[(4-fluorophenyl)methyl]piperidine-1-carbonyl]-6-methoxypyridin-3-yl}pyrrolo[2,1-f][1,2,4]triazin-5-yl)formamido]ethyl}acetamide | | 589.2 | Unassigned due to rotomers |

TABLE 26

Compounds in Table 26 were prepared by the methods detailed in Example 68.

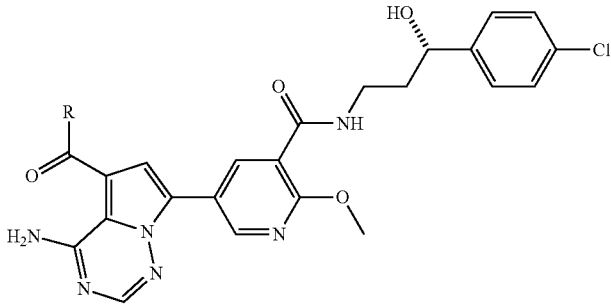

| Ex | Name | R | Obs. MS Ion | NMR Assignments (500 MHz, DMSO-d6) δ |
|---|---|---|---|---|
| 472 | 5-[4-amino-5-(ethylcarbamoyl)pyrrolo[2,1-f][1,2,4]triazin-7-yl]-N-[(3S)-3-(4-chlorophenyl)-3-hydroxypropyl]-2-methoxypyridine-3-carboxamide | | 524.4 | 10.44 (br s, 1H), 8.95 (d, J = 2.4 Hz, 1H), 8.68 (d, J = 2.4 Hz, 1H), 8.67-8.63 (m, 1H), 8.54 (br t, J = 5.3 Hz, 1H), 8.20 (br s, 1H), 8.05 (br s, 1H), 7.75 (s, 1H), 7.40 (s, 4H), 5.55 (d, J = 4.3 Hz, 1H), 4.72 (dt, J = 7.9, 4.2 Hz, 1H), 4.05 (s, 3H), 3.18 (d, J = 5.2 Hz, 1H), 1.97-1.70 (m, 2H), 1.18 (t, J = 7.2 Hz, 3H) |
| 473 | 5-{4-amino-5-[(cyanomethyl)carbamoyl]pyrrolo[2,1-f][1,2,4]triazin-7-yl}-N-[(3S)-3-(4-chlorophenyl)-3-hydroxypropyl]-2-methoxypyridine-3-carboxamide | | 535.1 | 10.00 (br s, 1H), 9.49-9.29 (m, 1H), 8.92 (d, J = 2.1 Hz, 1H), 8.67 (d, J = 2.4 Hz, 1H), 8.59-8.49 (m, 1H), 8.33 (br s, 1H), 8.07 (s, 1H), 7.72 (s, 1H), 7.48-7.05 (m, 4H), 4.72 (br dd, J = 7.6, 4.6 Hz, 1H), 4.39 (br d, J = 5.2 Hz, 2H), 4.15-3.86 (m, 3H), 1.67 (br d, J = 8.2 Hz, 2H) |

TABLE 26-continued

Compounds in Table 26 were prepared by the methods detailed in Example 68.

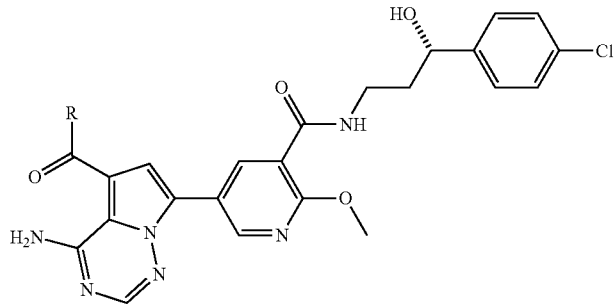

| Ex | Name | R | Obs. MS Ion | NMR Assignments (500 MHz, DMSO-d6) δ |
|---|---|---|---|---|
| 474 | 5-{4-amino-5-[(2-hydroxyethyl)carbamoyl}pyrrolo[2,1-f][1,2,4]triazin-7-yl}-N-[(3S)-3-(4-chlorophenyl)-3-hydroxypropyl]-2-methoxypyridine-3-carboxamide | H N OH | 540.1 | 10.39-10.13 (m, 1H), 8.84 (d, J =2.1 Hz, 1H), 8.64 (d, J = 2.1 Hz, 1H), 8.61 (br t, J =5.3 Hz, 1H), 8.56 (br t, J = 5.3 Hz, 1H), 8.00 (br s, 1H), 7.95 (s, 1H), 7.64 (s, 1H), 7.40-7.29 (m, 4H), 4.82-4.38 (m, 1H), 3.98-3.92 (m, 2H), 3.56 (br s, 2H), 3.47-3.18 (m, 4H), 2.01-1.71 (m, 2H) |
| 475 | 5-[4-amino-5-(propylcarbamoyl)pyrrolo[2,1 f][1,2,4]triazin-7-yl]-N-[(3S)-3-(4-chlorophenyl)-3-hydroxypropyl]-2-methoxypyrine-3-carboxamide, TFA | H N | | 10.64 (br s, 1H), 8.94 (d, J = 1.8 Hz, 1H), 8.71 (br t, J = 5.3 Hz, 1H), 8.68 (d, J = 2.4 Hz, 1H), 8.55 (br t, J = 5.3 Hz, 1H), 8.37 (br s, 1H), 8.05 (s, 1H), 7.78 (s, 1H), 7.39 (s, 4H), 4.72 (dd, J = 7.6, 4.6 Hz, 1H), 4.05 (s, 3H), 3.40 (br d, J = 7.0 Hz, 1H), 3.28 (q, J = 6.6 Hz, 2H), 1.97-1.72 (m, 2H), 1.65-1.46 (m, 2H), 0.93 (t, J = 7.3 Hz, 3H) |
| 476 | 5-[4-amino-5-(dimethylcarbamoyl)pyrrolo[2,1-f][1,2,4]triazin-7-yl]-N-[(3S)-3-(4-chlorophenyl)-3-hydroxypropyl]-2-methoxypyridine-3-carboxamide | N | 524.2 | 8.90 (d, J = 2.1 Hz, 1H), 8.77 (d, J = 2.4 Hz, 1H), 8.52 (br t, J = 5.2 Hz, 2H), 8.08 (br s, 1H), 8.06 (s, 1H), 7.43 (s, 1H), 7.40 (s, 4H), 5.54 (d, J = 4.3 Hz, 1H), 4.72 (dt, J = 7.9, 4.3 Hz, 1H), 4.04 (s, 3H), 2.51 (br s, 6H), 1.95-1.79 (m, 4H) |
| 477 | 5-[4-amino-5-(methylcarbamoyl)pyrrolo[2,1-f][1,2,4]triazin-7-yl]-N-[(3S)-3-(4-chlorophenyl)-3-hydroxypropyl]-2-methoxypyridine-3-carboxamide, TFA | H N | 510.0 | 10.46 (br s, 1H), 8.90 (d, J = 2.1 Hz, 1H), 8.69 (br t, J = 4.6 Hz, 1H), 8.67 (d, J = 2.4 Hz, 1H), 8.55 (br t, J = 5.3 Hz, 1H), 8.20 (br s, 1H), 8.01 (s, 1H), 7.66 (s, 1H), 7.38 (s, 4H), 4.71 (br d, J = 3.1 Hz, 1H), 4.04 (s, 3H), 3.55 (br s, 1H), 3.45-3.32 (m, 1H), 2.84 (d, J = 4.3 Hz, 3H), 1.94-1.79 (m, 2H) |

TABLE 27

Compounds in Table 27 were prepared by the methods detailed in Examples 57 and 63. The compounds are a mixture of diastereomers at the secondary alcohol.

| Ex | Name | R | Obs. MS Ion | NMR Assignments (500 MHz, DMSO-d6) δ |
|---|---|---|---|---|
| 478 | 5-(4-amino-5-{[(2-hydroxyethyl)amino]methyl}pyrrolo[2,1-f][1,2,4]triazin-7-yl)-N-[(3R,4S)-4-fluoro-1-(3,3,3-trifluoro-2-hydroxypropyl)pyrrolidin-3-yl]-2-methoxypyridine-3-carboxamide, TFA | -NH-CH₂CH₂-OH | 557.1 | 8.68 (br s, 1H), 8.60-8.47 (m, 1H), 8.36 (br d, J = 7.6 Hz, 1H), 7.76 (s, 1H), 7.03 (s, 1H), 5.27-4.98 (m, 1H), 4.70-4.50 (m, 1H), 4.34-4.26 (m, 2H), 4.25-4.09 (m, 1H), 3.80 (s, 3H), 3.53-3.34 (m, 1H, partially suppressed), 3.28-2.96 (m, 1H), 2.86 (br d, J = 1.2 Hz, 2H) |
| 479 | 5-{4-amino-5-[(dimethylamino)methyl]pyrrolo[2,1-f][1,2,4]triazin-7-yl}-N-[(3R,4S)-4-fluoro-1-(3,3,3-trifluoro-2-hydroxypropyl)pyrrolidin-3-yl]-2-methoxypyridine-3-carboxamide | -N(CH₃)₂ | 541.2 | 8.93 (s, 1H), 8.86 (br s, 1H), 8.44 (br d, J = 7.6 Hz, 1H), 7.90 (s, 1H), 7.05 (br s, 1H), 5.34-5.02 (m, 1H), 4.68-4.43 (m, 1H), 4.11 (br d, J = 5.5 Hz, 1H), 4.04 (s, 3H), 3.78-3.34 (m, 1H), 3.26-2.57 (m, 7H, partially suppressed), 2.27 (br s, 6H, partially suppressed) |
| 480 | 5-[-amino-5-({2-oxa-6-azaspiro[3.3]heptan-6-yl}methyl)pyrrolo[2,1-f][1,2,4]triazin-7-yl]-N-[(3R,4S)-4-fluoro-1-(3,3,3-trifluoro-2-hydroxypropyl)pyrrolidin-3-yl]-2-methoxypyridine-3-carboxamide | 2-oxa-6-azaspiro[3.3]heptan-6-yl | 595.2 | 9.06-8.92 (m, 1H), 8.85-8.69 (m, 1H), 8.65-8.56 (m, 1H), 8.10-7.89 (m, 1H), 7.39-7.32 (m, 1H), 5.58-5.25 (m, 1H), 4.97-4.74 (m, 1H), 4.74-4.56 (m, 2H), 4.56-4.34 (m, 1H), 4.11-4.00 (m, 3H), 4.00-3.80 (m, 3H), 3.75-3.21 (m, 3H), 3.21-3.10 (m, 1H) |
| 481 | 5-{4-amino-5-[(morpholin-4-yl)methyl]pyrrolo[2,1-f][1,2,4]triazin-7-yl}-N-[(3R,4S)-4-fluoro-1-(3,3,3-trifluoro-2-hydroxypropyl)pyrrolidin-3-yl]-2-methoxypyridine-3-carboxamide | morpholin-4-yl | 583.1 | 8.66 (s, 1H), 8.55 (br d, J = 6.4 Hz, 1H), 8.33 (br d, J = 7.3 Hz, 1H), 7.73 (br s, 1H), 6.91 (br s 1H), 5.34-4.95 (m, 1H), 4.75-4.34 (m, 1H), 4.17 (br d, J = 5.2 Hz, 1H), 3.79 (s, 3H), 3.49-2.87 (m, 16 H, partially carboxamide suppressed) |
| 482 | 5-{4-amino-5-[(3-aminoazetidin-1-yl)methyl]pyrrolo[2,1-f][1,2,4]triazin-7-yl}-N[(3R,4S)-4-fluoro-1-(3,3,3-trifluoro-2- | 3-aminoazetidin-1-yl | 568.2 | 8.93 (s, 1H), 8.84-8.77 (m, 1H), 8.60 (br d, J = 7.3 Hz, 1H), 8.03 (s, 1H), 5.59-5.26 (m, 1H), 5.05-4.72 (m, 1H), 4.65-4.40 (m, 1H), 4.05 (s, 3H), 3.95-3.13 (m, 11H, partially suppressed), 2.25- |

TABLE 27-continued

Compounds in Table 27 were prepared by the methods detailed in Examples 57 and 63. The compounds are a mixture of diastereomers at the secondary alcohol.

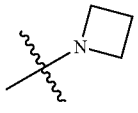

| Ex | Name | R | Obs. MS Ion | NMR Assignments (500 MHz, DMSO-d6) δ |
|---|---|---|---|---|
| | hydroxypropyl) pyrrolidin-3-yl]-2-methoxypyridine-3-carboxamide, TFA | | | 2.50 (m, 2H) |
| 483 | 5-{4-amino-5-[(azetidin-1-yl)methyl]pyrrolo[2,1-f][1,2,4]triazin-7-yl}-N-[(3R,4S)-4-fluoro-1-(3,3,3-trifluoro-2-hydroxypropyl)pyrrolidin-3-yl]-2-methoxypyridine-3-carboxamide, TFA | 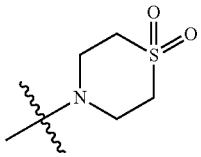 [SMILES: *N1CCS(=O)(=O)CC1] | 553.2 | 8.99-8.90 (m, 1H), 8.84-8.72 (m, 1H), 8.67-8.44 (m, 1H), 8.14-7.96 (m, 1H), 7.36-7.27 (m, 1H), 5.56-5.22 (m, 1H), 4.79-4.64 (m, 2H), 4.64-4.40 (m, 1H), 4.24-4.10 (m, 2H), 4.08-3.97 (m, 5H), 2.44-2.27 (m, 2H) |
| 484 | 5-{4-amino-5-[(1,1-dioxo-thiomorpholin-4-yl)methyl]pyrrolo[2,1-f][1,2,4]triazin-7-yl}-N[(3R,4S)-4-fluoro-1-(3,3,3-trifluoro-2-hydroxypropyl)pyrrolidin-3-yl]-2-methoxypyridine-3-carboxamide, TFA | | 631.2 | 9.05-8.87 (m, 1H), 8.86-8.69 (m, 1H), 8.69-8.50 (m, 1H), 8.05-7.86 (m, 1H), 7.16-7.14 (m, 1H), 7.14-7.12 (m, 1H), 7.05-7.01 (m, 1H), 5.61-5.17 (m, 1H), 4.99-4.67 (m, 1H), 4.67-4.37 (m, 1H), 4.09-4.00 (m, 3H), 4.02-3.89 (m, 2H), 3.31-3.14 (m, 4H), 3.11-2.94 (m, 4H) |

TABLE 28

Compounds in Table 28 were prepared by the methods detailed in Examples 57 and 63.

| Ex | Name | R | Obs. MS Ion | NMR Assignments (500 MHz, DMSO-d6) δ |
|---|---|---|---|---|
| 485 | 5-{4-amino-5-[(dimethylamino)methyl]pyrrolo[2,1-f][1,2,4]triazin-7-yl}-N-[(3R,4S)-1-(3,3-difluorocyclobutane carbonyl)-4-fluoropyrrolidin-3-yl]-2-methoxypyridine-3-carboxamide | -N(CH3)2 | 547.1 | 9.68-9.39 (m, 1H), 9.06-8.83 (m, 1H), 8.86-8.66 (m, 1H), 8.60-8.43 (m, 1H), 7.96-7.84 (m, 1H), 7.81-7.65 (m, 1H), 7.11-6.94 (m, 1H), 5.46-5.19 (m, 1H), 4.87-4.57 (m, 1H), 4.09-4.01 (m, 3H), 3.99-3.68 (m, 3H), 3.69-3.59 (m, 2H), 3.30-3.23 (m, 1H), 3.22-3.10 (m, 1H), 2.89-2.66 (m, 4H), 2.35-2.18 (m, 6H) |
| 486 | 5-{4-amino-5-[(methylamino)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide | -NHCH3 | 533.1 | (600 MHz, DMSO-d6) δ 8.98-8.90 (m, 1H), 8.84-8.71 (m, 1H), 8.55-8.37 (m, 1H), 7.88-7.81 (m, 1H), 7.08-7.01 (m, 1H), 5.43-5.18 (m, 1H), 4.90-4.56 (m, 1H), 4.08-4.00 (m, 3H), 4.00-3.22 (m, 6H), 3.22-3.09 (m, 1H), 2.89-2.70 (m, 4H), 2.35-2.28 (m, 3H) |
| 487 | 5-{4-amino-5-[(morpholin-4-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide, TFA | morpholine | 589.3 | 8.99-8.83 (m, 1H), 8.79-8.63 (m, 1H), 8.61-8.40 (m, 1H), 8.12-7.90 (m, 1H), 7.12-7.01 (m, 1H), 5.46-5.15 (m, 1H), 4.88-4.58 (m, 1H), 4.09-3.99 (m, 3H), 3.30-3.23 (m, 1H), 3.97-3.08 (m, 5H), 2.90-2.66 (m, 4H) |
| 488 | 5-{4-amino-5-[(3-hydroxyazetidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide, TFA | 3-hydroxyazetidine | 575.2 | 8.67 (m, 1H), 8.66-8.39 9.08-8.86 (m, 1H), 8.85-(m, 1H), 8.15-7.99 (m, 1H), 7.39-7.27 (m, 1H), 5.48-5.17 (m, 1H), 5.05-4.15 (m, 6H), 4.16-4.02 (m, 3H), 3.98-3.10 (m, 7H), 2.96-2.67 (m, 4H) |
| 489 | 5-{4-amino-5-[(3,3-difluoroazetidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide, TFA | 3,3-difluoroazetidine | 595.2 | 9.03-8.83 (m, 1H), 8.81-8.65 (m, 1H), 8.65-8.43 (m, 1H), 8.14-8.02 (m, 1H), 7.27-7.19 (m, 1H), 5.43-5.16 (m, 1H), 4.92-4.59 (m, 1H), 4.29-4.12 (m, 4H), 4.09-4.01 (m, 3H), 4.01-3.00 (m, 7H), 2.90-2.67 (m, 4H) |

TABLE 28-continued

Compounds in Table 28 were prepared by the methods detailed in Examples 57 and 63.

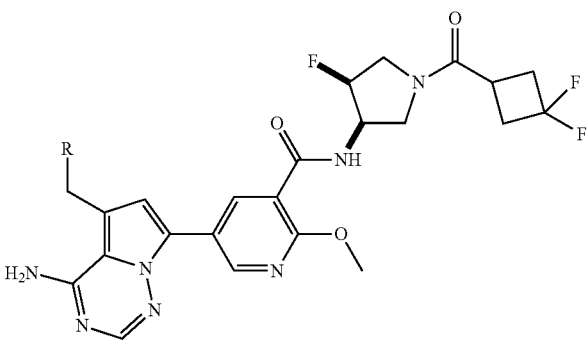

| Ex | Name | R | Obs. MS Ion | NMR Assignments (500 MHz, DMSO-d6) δ |
|---|---|---|---|---|
| 490 | 5-{4-amino-5-[(2,6-dimethylmorpholin-4-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide, TFA | 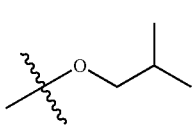 [SMILES: *OCC(C)C] | 617.2 | 9.09-8.87 (m, 1H), 8.83-8.65 (m, 1H), 8.63-8.44 (m, 1H), 8.17-7.95 (m, 1H), 7.17-7.09 (m, 1H), 5.45-5.13 (m, 1H), 5.01-4.45 (m, 1H), 4.14-4.01 (m, 3H), 4.01-3.07 (m, 7H), 2.92-2.68 (m, 4H), 1.20-1.07 (m, 6H) |
| 491 | 5-{4-amino-5-[(propan-2-yloxy)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide, TFA | 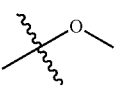 | 562.1 | 9.06-8.85 (m, 1H), 8.81-8.72 (m, 1H), 8.59-8.46 (m, 1H), 8.00-7.89 (m, 1H), 7.17-7.11 (m, 1H), 5.44-5.16 (m, 1H), 4.92-4.52 (m, 3H), 4.08-4.00 (m, 3H), 4.00-3.06 (m, 6H), 2.89-2.67 (m, 4H), 1.21-1.13 (m, 6H) |
| 492 | 5-[4-amino-5-(methoxymethyl)pyrrolo[2,1-f][1,2,4]triazin-7-yl]-N-[(3R,4S)-1-(3,3-difluorocyclobutanecarbonyl)-4-fluoropyrrolidin-3-yl]-2-methoxypyridine-3-carboxamide | 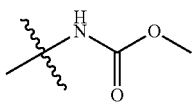 | 534.1 | 9.00-8.87 (m, 1H), 8.87-8.72 (m, 1H), 8.58-8.40 (m, 1H), 8.02-7.86 (m, 1H), 7.18-6.96 (m, 1H), 5.49-5.13 (m, 1H), 5.00-4.49 (m, 3H), 4.12-4.00 (m, 3H), 3.99-3.23 (m, 5H), 3.36 (s, 3H), 3.23-3.07 (m, 2H), 2.88-2.68 (m, 4H) |
| 493 | methyl N-{[4-amino-7-(5-{[(3R,4S)-1-(3,3-difluorocyclobutanecarbonyl)-4-fluoropyrrolidin-3-yl]carbamoyl}-6-methoxypyridin-3-yl)pyrrolo[2,1-f][1,2,4]triazin-5-yl]methyl}carbamate, TFA | 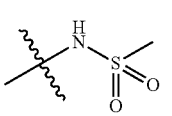 [SMILES: *NS(C)(=O)=O] | 577.2 | 8.91 (s, 1H), 8.74 (dd, J = 18.0, 2.1 Hz, 1H), 8.53 (br dd, J = 10.4, 7.9 Hz, 1H), 7.92 (s, 1H), 7.87 (br s, 1H), 7.69-7.38 (m, 2H), 7.01 (s, 1H), 5.51-5.15 (m, 1H), 4.93-4.57 (m, 1H), 4.47 (br d, J = 5.8 Hz, 2H), 4.04 (s, 3H), 3.99-3.60 (m, 3H), 3.57 (s, 3H, partially suppressed), 3.44-3.09 (m, 2H, partially suppressed), 2.99-2.66 (m, 4H) |
| 494 | 5-[4-amino-5-(methanesulfonamidomethyl)pyrrolo[2,1-f][1,2,4]triazin-7-yl]-N-[(3R,4S)-1-(3,3-difluorocyclobutanecarbonyl)-4-fluoropyrrolidin-3-yl]-2-methoxypyridine-3-carboxamide, TFA | | 597.2 | 9.00-8.86 (m, 1H), 8.84-8.70 (m, 1H), 8.63-8.41 (m, 1H), 8.10-7.92 (m, 1H), 7.82-7.63 (m, 1H), 7.17-7.14 (m, 1H), 5.52-5.08 (m, 1H), 4.93-4.60 (m, 1H), 4.56-4.42 (m, 2H), 4.10-4.00 (m, 3H), 4.00-3.10 (m, 5H), 3.09- |

TABLE 28-continued

Compounds in Table 28 were prepared by the methods detailed in Examples 57 and 63.

| Ex | Name | R | Obs. MS Ion | NMR Assignments (500 MHz, DMSO-d6) δ |
|---|---|---|---|---|
| | | | | 2.93 (m, 3H), 2.90-2.65 (m, 4H) |
| 495 | 5-[4-amino-5-(acetamidomethyl)pyrrolo[2,1-f][1,2,4]triazin-7-yl]-N-[(3R,4S)-1-(3,3-difluorocyclobutanecarbonyl)-4-fluoropyrrolidin-3-yl]-2-methoxypyridine-3-carboxamide, TFA | | 561.2 | 8.98-8.86 (m, 1H), 8.86-8.76 (m, 1H), 8.76-8.63 (m, 1H), 8.58-8.42 (m, 2H), 8.15-7.90 (m, 1H), 7.13-7.08 (m, 1H), 5.48-5.18 (m, 1H), 5.01-4.57 (m, 1H), 4.57-4.36 (m, 2H), 4.14-4.00 (m, 3H), 4.00-3.02 (m, 5H), 2.91-2.66 (m, 4H), 1.97-1.83 (m, 3H) |
| 496 | 5-[4-amino-5-({2-oxa-6-azaspiro[3.3]heptan-6-yl}methyl)pyrrolo[2,1-f][1,2,4]triazin-7-yl]-N-[(3R,4S)-1-(3,3-difluorocyclobutanecarbonyl)-4-fluoropyrrolidin-3-yl]-2-methoxypyridine-3-carboxamide | | 601.2 | 9.59 (br d, J = 6.4 Hz, 1H), 8.90 (s, 1H), 8.84-8.69 (m, 1H), 8.53 (br t, J = 7.6 Hz, 1H), 7.86 (s, 1H), 7.63 (br d, J = 9.2 Hz, 1H), 7.01 (s, 1H), 5.48-5.16 (m, 1H), 4.92-4.64 (m, 3H), 4.63 (s, 3H), 4.15-3.06 (m, 13H), 2.95-2.66 (m, 4H) |
| 497 | 5-{4-amino-5-[(3-aminoazetidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide | | 574.2 | 8.99-8.90 (m, 1H), 8.85-8.71 (m, 1H), 8.57-8.48 (m, 1H), 7.98-7.86 (m, 1H), 7.10-7.02 (m, 1H), 5.44-5.10 (m, 1H), 4.88-4.49 (m, 1H), 4.10-4.01 (m, 3H), 4.01-3.07 (m, 12H), 2.92-2.69 (m, 4H) |
| 498 | 5-{4-amino-5-[(azetidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide | | 559.3 | 10.12-9.66 (m, 1H), 9.02-8.86 (m, 1H), 8.85-8.70 (m, 1H), 8.59-8.47 (m, 1H), 8.01-7.85 (m, 1H), 7.85-7.54 (m, 1H), 7.19-6.74 (m, 1H), 5.46-5.15 (m, 1H), 4.95-4.44 (m, 1H), 4.12-4.01 (m, 3H), 4.01-3.57 (m, 5H), 3.41-3.27 (m, 2H), 3.27-3.11 (m, 4H), 2.89-2.65 (m, 4H), 2.16-1.99 (m, 2H) |
| 499 | 5-{4-amino-5-[(1,1-dioxo-thiomorpholin-4-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine- | | 637.2 | 9.00-8.85 (m, 1H), 8.84-8.65 (m, 1H), 8.58-8.41 (m, 1H), 7.97-7.89 (m, 1H), 7.12-7.04 (m, 1H), 5.47-5.17 (m, 1H), 4.94-4.59 (m, 1H), 4.13-4.00 (m, 3H), 3.99-3.56 (m, 5H), 3.24-3.11 (m, 4H), |

TABLE 28-continued

Compounds in Table 28 were prepared by the methods detailed in Examples 57 and 63.

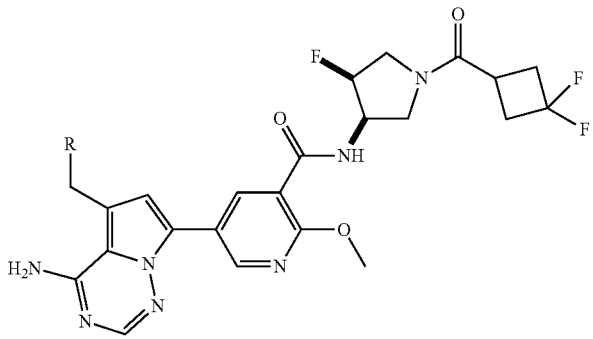

| Ex | Name | R | Obs. MS Ion | NMR Assignments (500 MHz, DMSO-d6) δ |
|---|---|---|---|---|
| | 3-carboxamide | | | 3.08-2.93 (m, 4H), 2.89-2.66 (m, 4H) |
| 500 | 5-(4-amino-5-{[(2-hydroxyethyl)amino]methyl}pyrrolo[2,1-f][1,2,4]triazin-7-yl)-N-[(3R,4S)-1-(3,3-difluorocyclobutanecarbonyl)-4-fluoropyrrolidin-3-yl]-2-methoxypyridine-3-carboxamide | H-N-CH2CH2-OH | 563.2 | (600 MHz, DMSO-d6) δ 8.98-8.88 (m, 1H), 8.84-8.71 (m, 1H), 8.60-8.45 (m, 1H), 7.89-7.76 (m, 1H), 7.11-7.03 (m, 1H), 5.43-5.17 (m, 1H) 4.88-4.54 (m, 1H), 4.09-4.01 (m, 3H), 3.99-3.45 (m, 6H), 3.33-3.24 (m, 2H), 3.23-3.10 (m, 1H), 2.88-2.71 (m, 4H), 2.69-2.58 (m, 2H) |
| 501 | 5-{4-amino-5-[(4-methylpiperazin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide | 4-methylpiperazinyl | 602.2 | (600 MHz, DMSO-d6) δ 9.65-9.38 (m, 1H), 9.00-8.85 (m, 1H), 8.85-8.69 (m, 1H), 8.61-8.42 (m, 1H), 7.93-7.85 (m, 1H), 7.83-7.67 (m, 1H), 7.11-6.98 (m, 1H), 5.47-5.17 (m, 1H), 4.90-4.57 (m, 1H), 4.09-4.00 (m, 3H), 4.00-3.51 (m, 5H), 3.30-3.24 (m, 1H), 3.24-3.10 (m, 1H), 2.89-2.71 (m, 4H), 2.18 (s, 3H) |

TABLE 29

Compounds in Table 29 were prepared by similar methods as to those detailed in Example 1468, below.

| Ex | Name | R | Obs. MS Ion | NMR Assignments (500 MHz, DMSO-d6) δ |
|---|---|---|---|---|
| 502 | 5-[4-amino-5-(trifluoromethyl)pyrrolo[2,1-f][1,2,4]triazin-7-yl]-N-[(3R,4S)-1-(2-cyanobenzenesulfonyl)-4-fluoropyrrolidin-3-yl]-2-methoxypyridine-3-carboxamide | 2-CN-phenyl | 605.2 | 8.91 (d, J = 2.1 Hz, 1H), 8.73 (d, J = 2.1 Hz, 1H), 8.51 (br d, J = 7.3 Hz, 1H), 8.23-8.15 (m, 2H), 8.15-8.08 (m, 1H), 7.98 (t, J = 7.6 Hz, 1H), 7.95-7.89 (m, 1H), 7.60 (s, 1H), 5.38-5.18 (m, 1H), 4.82-4.60 (m, 1H), 4.01 (s, 3H), 3.86-3.74 (m, 2H), 3.33-3.22 (m, 1H, partially suppressed), 3.18 (d, J = 5.2 Hz, 1H, partially suppressed) |
| 503 | 5-[4-amino-5-(trifluoromethyl)pyrrolo[2,1-f][1,2,4]triazin-7-yl]-N-[(3R,4S)-4-fluoro-1-[(2-methyl-1,3-thiazol-5-yl)sulfonyl]pyrrolidin-3-yl]-2-methoxypyridine-3-carboxamide | 2-methylthiazol-5-yl | 601.2 | 8.91 (d, J = 2.4 Hz, 1H), 8.72 (d, J = 2.1 Hz, 1H), 8.51 (br d, J = 7.3 Hz, 1H), 8.24 (s, 1H), 8.17 (s, 1H), 7.60 (s, 1H), 5.35-5.11 (m, 1H), 4.72-4.48 (m, 1H), 4.01 (s, 3H), 3.84-3.54 (m, 3H, partially suppressed), 3.25 (t, J = 10.1 Hz, 1H), 2.76 (s, 3H) |
| 504 | 5-[4-amino-5-(trifluoromethyl)pyrrolo[2,1-f][1,2,4]triazin-7-yl]-N-[(3R,4S)-4-fluoro-1-(3-fluorobenzenesulfonyl)pyrrolidin-3-yl]-2-methoxypyridine-3-carboxamide | 3-F-phenyl | 598.2 | 8.90 (d, J = 2.1 Hz, 1H), 8.70 (d, J = 2.4 Hz, 1H), 8.46 (d, J = 7.6 Hz, 1H), 8.15 (s, 1H), 7.76-7.68 (m, 4H), 7.63-7.59 (m, 1H), 7.58 (s, 1H), 5.29-5.10 (m, 1H), 4.63-4.43 (m, 1H), 3.99 (s, 3H), 3.83-3.46 (m, 3H, partially suppressed), 3.23-3.14 (m, 1H) |
| 505 | 5-[4-amino-5-(trifluoromethyl)pyrrolo[2,1-f][1,2,4]triazin-7-yl]-N-[(3R,4S)-4-fluoro-1-(4-fluorobenzenesulfonyl)pyrrolidin-3-yl]-2-methoxypyridine-3-carboxamide, TFA | 4-F-phenyl | 597.9 | 8.91 (d, J = 2.4 Hz, 1H), 8.72 (d, J = 2.4 Hz, 1H), 8.45 (br d, J = 7.3 Hz, 1H), 8.17 (s, 1H), 7.96 (dd, J = 8.5, 5.2 Hz, 2H), 7.60 (s, 1H), 7.51 (t, J = 8.9 Hz, 2H), 5.32-5.03 (m, 1H), 4.66-4.38 (m, 1H), 4.01 (s, 3H), 3.78-3.52 (m, 3H, partially suppressed), 3.20-3.12 (m, 1H) |

TABLE 29-continued

Compounds in Table 29 were prepared by similar methods as to those detailed in Example 1468, below.

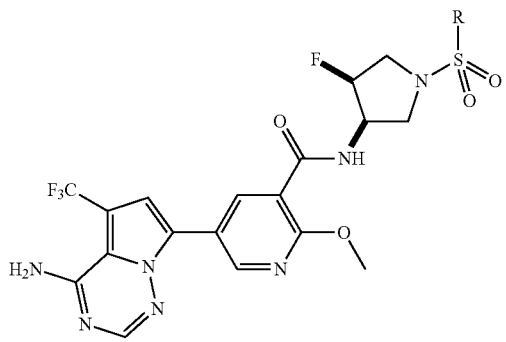

| Ex | Name | R | Obs. MS Ion | NMR Assignments (500 MHz, DMSO-d6) δ |
|---|---|---|---|---|
| 506 | 5-[4-amino-5-(trifluoromethyl)pyrrolo[2,1-f][1,2,4]triazin-7-yl]-N-[(3R,4S)-4-fluoro-1-(pyridine-3-sulfonyl)pyrrolidin-3-yl]-2-methoxypyridine-3-carboxamide | 3-pyridyl | 581.0 | 9.04 (s, 1H), 8.91 (d, J = 2.4 Hz, 2H), 8.71 (d, J = 2.4 Hz, 1H), 8.45 (br d, J = 7.3 Hz, 1H), 8.30 (br d, J = 8.2 Hz, 1H), 8.17 (s, 1H), 7.71 (dd, J = 7.9, 4.9 Hz, 1H), 7.60 (s, 1H), 5.33-5.06 (m, 1H), 4.69-4.50 (m, 1H), 4.00 (s, 3H), 3.81-3.65 (m, 3H), 3.21 (t, J = 9.9 Hz, 1H, partially suppressed) |
| 507 | 5-[4-amino-5-(trifluoromethyl)pyrrolo[2,1-f][1,2,4]triazin-7-yl]-N-[(3R,4S)-4-fluoro-1-(pyridine-3-sulfonyl)pyrrolidin-3-yl]-2-methoxypyridine-3-carboxamide | phenyl | 580.1 | (600 MHz, DMSO-d6) δ 8.98-8.87 (m, 1H), 8.72 (d, J = 2.2 Hz, 1H), 8.44 (d, J = 7.3 Hz, 1H), 8.17 (s, 1H), 7.87 (d, J = 7.3 Hz, 2H), 7.75 (t, J = 7.3 Hz, 1H), 7.70-7.64 (m, 2H), 7.60 (s, 1H), 5.30-5.12 (m, 1H), 4.57-4.36 (m, 1H), 3.99 (s, 3H), 3.76-3.53 (m, 3H), 3.15 (t, J = 9.9 Hz, 1H) |

TABLE 30

Compounds in Table 30 were prepared by the methods detailed in Examples 4 and 61. When diastereomers were separated, they are included as separate entries. If the stereochemistry is undefined, the product was isolated as a mixture of diastereomers.

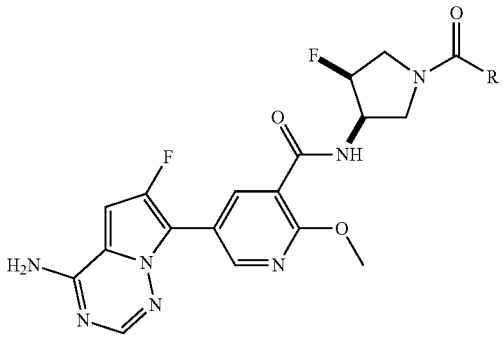

| Ex | Name | R | Obs. MS Ion | NMR Assignments (500 MHz, DMSO-d6) δ |
|---|---|---|---|---|
| 508 | 5-{4-amino-6-fluoropyrrolo[2,1-f][1,2,4]triazin-7-yl}-N-[(3R,4S)-1-(3,3-difluorocyclobutane-carbonyl)-4-fluoropyrrolidin-3-yl]-2-methoxypyridine-3-carboxamide | 3,3-difluorocyclobutyl | 508.4 | 8.83 (dd, J = 6.6, 2.0 Hz, 1H), 8.65 (dd, J = 16.6, 2.3 Hz, 1H), 8.53 (br t, J = 8.4 Hz, 1H), 8.02 (s, 1H), 7.89 (br s, 2H), 6.91 (s, 1H), 5.43-5.19 (m, 1H), 4.87-4.55 (m, 1H), 4.05 (d, J = 6.1 Hz, 3H), 4.00-3.23 (m, 4H), 3.23-3.11 (m, 1H), 2.90-2.66 (m, 4H) |
| 509 | 5-{4-amino-6-fluoropyrrolo[2,1-f][1,2,4]triazin-7-yl}-N-[(3R,4S)-4-fluoro-1-(oxane-4-carbonyl)pyrrolidin-3-yl]-2-methoxypyridine-3-carboxamide, TFA | oxan-4-yl | 502.2 | 8.84 (br d, J = 5.0 Hz, 1H), 8.74-8.63 (m, 1H), 8.45 (br dd, J = 18.0, 7.4 Hz, 1H), 8.04 (s, 1H), 6.96 (s, 1H), 5.48-5.21 (m, 1H), 4.88-4.56 (m, 1H), 4.23-3.31 (m, 11H), 2.80-2.62 (m, 1H), 1.69-1.51 (m, 4H) |
| 510 | 5-{4-amino-6-fluoropyrrolo[2,1-f][1,2,4]triazin-7-yl}-N-[(3R,4S)-1-(4,4-difluorocyclohexane-carbonyl)-4-fluoropyrrolidin-3-yl]-2-methoxypyridine-3-carboxamide | 4,4-difluorocyclohexyl | 536.3 | 8.83 (dd, J = 8.1, 2.0 Hz, 1H), 8.70-8.61 (m, 1H), 8.54 (dd, J = 17.7, 7.6 Hz, 1H), 8.01 (s, 1H), 7.89 (br s, 2H), 6.91 (s, 1H), 5.45-5.19 (m, 1H), 4.87-4.59 (m, 1H), 4.20-3.15 (m, 7H), 2.15-1.72 (m, 7H), 1.65-1.50 (m, 2H) |
| 511 | 5-{4-amino-6-fluoropyrrolo[2,1-f][1,2,4]triazin-7-yl}-N-[(3R,4S)-1-(3,3-difluorocyclopentane-carbonyl)-4-fluoropyrrolidin-3-yl]-2-methoxypyridine-3-carboxamide, TFA | 3,3-difluorocyclopentyl | 522.2 | 8.86-8.80 (m, 1H), 8.70-8.62 (m, 1H), 8.53 (br dd, J = 13.3, 8.1 Hz, 1H), 8.09-7.98 (m, 1H), 6.96 (s, 1H), 5.45-5.20 (m, 1H), 4.88-4.59 (m, 1H), 4.19-3.41 (m, 6H), 3.33-2.88 (m, 2H), 2.41-2.25 (m, 2H), 2.23-1.99 (m, 3H), 1.88-1.73 (m, 1H) |
| 512 | 5-{4-amino-6-fluoropyrrolo[2,1-f][1,2,4]triazin-7-yl}-N-[(3R,4S)-4-fluoro-1-(4-fluorobenzoyl)pyrrolidin-3-yl]-2-methoxypyridine-3-carboxamide | 4-fluorophenyl | 512.0 | 8.82 (br s, 1H), 8.64 (br s, 1H), 8.60-8.47 (m, 1H), 8.01 (br d, J = 11.3 Hz, 1H), 7.88 (br s, 2H), 7.71-7.59 (m, 2H), 7.34-7.24 (m, 2H), 6.91 (br d, J = 7.3 Hz, 1H), 5.47-5.17 (m, 1H), 4.90-4.59 (m, 1H), 4.11-3.41 (m, 7H) |
| 513 | 5-{4-amino-6-fluoropyrrolo[2,1-f][1,2,4]triazin-7-yl}-N-[(3R,4S)-4-fluoro-1-(4-fluorocyclohexanecar-bonyl)pyrrolidin-3-yl]- | 4-fluorocyclohexyl | 518.2 | 8.83 (br d, J = 7.3 Hz, 1H), 8.70-8.63 (m, 1H), 8.52 (br dd, J = 17.9, 7.5 Hz, 1H), 8.02 (s, 1H), 7.89 (br s, 2H), 6.92 (s, 1H), 5.44-5.19 (m, 1H), 4.97-4.42 (m, 2H), 4.16-3.11 (m, 7H), 2.06 (br d, |

TABLE 30-continued

Compounds in Table 30 were prepared by the methods detailed in Examples 4 and 61. When diastereomers were separated, they are included as separate entries. If the stereochemistry is undefined, the product was isolated as a mixture of diastereomers.

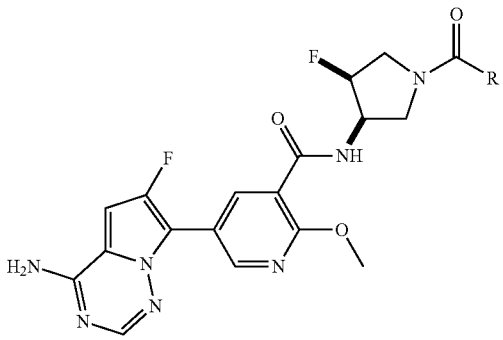

| Ex | Name | R | Obs. MS Ion | NMR Assignments (500 MHz, DMSO-d6) δ |
|---|---|---|---|---|
| | 2-methoxypyridine-3-carboxamide | | | J = 10.1 Hz, 1H), 1.94 (br d, J = 10.1 Hz, 1H), 1.78 (br s, 1H), 1.70-1.35 (m, 6H) |
| 514 | 5-{4-amino-6-fluoropyrrolo[2,1-f][1,2,4]triazin-7-yl}-N-[(3R,4S)-1-(2,2-difluorocyclopropane-carbonyl)-4-fluoropyrrolidin-3-yl]-2-methoxypyridine-3-carboxamide, TFA | | 494.0 | 8.87-8.79 (m, 1H), 8.72-8.50 (m, 2H), 8.04 (s, 1H), 6.95 (s, 1H) 5.48-5.22 (m, 1H), 4.93-4.63 (m, 1H), 4.37-3.23 (m, 7H), 3.12-2.85 (m, 1H), 2.03-1.81 (m, 2H) |

TABLE 31

Compounds in Table 31 were prepared by the methods detailed in Example 46. When diastereomers were separated, they are included as separate entries.

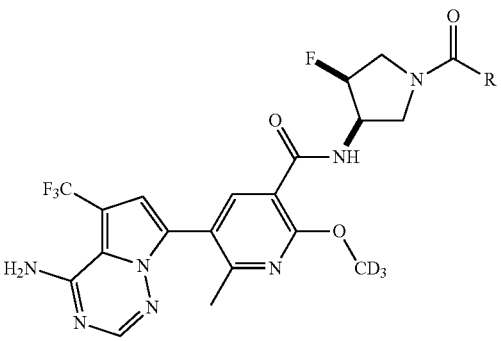

| Ex | Name | R | Obs. MS Ion | NMR Assignments (500 MHz, DMSO-d6) δ |
|---|---|---|---|---|
| 515 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(deutero)methoxy-6-methylpyridine-3-carboxamide | | 589.3 | 8.47 (br dd, J = 11.6, 7.6 Hz, 1H), 8.16 (d, J = 14.6 Hz, 1H), 8.07 (s, 1H), 7.31 (s, 1H), 5.45-5.20 (m, 1H), 4.87-4.56 (m, 1H), 4.09-3.10 (m, 5H merge with water), 2.39-2.01 (m, 8H), 1.89-1.73 (m, 1H) |

TABLE 31-continued

Compounds in Table 31 were prepared by the methods detailed in Example 46.
When diastereomers were separated, they are included as separate entries.

| Ex | Name | R | Obs. MS Ion | NMR Assignments (500 MHz, DMSO-d6) δ |
|---|---|---|---|---|
| 516 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(deutero)methoxy-6-methylpyridine-3-carboxamide | | 589.4 | 8.43 (br dd, J = 14.2, 7.8 Hz, 1H), 8.15 (d, J = 13.7 Hz, 1H), 8.06 (s, 1H), 7.31 (s, 1H), 5.43-5.19 (m, 1H), 4.83-4.61 (m, 1H), 4.12-3.16 (m, 5H merge with water), 2.43-1.99 (m, 8H), 1.87-1.71 (m, 1H) |
| 517 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-(deutero)methoxy-6-methylpyridine-3-carboxamide | | 597.2 | 8.41-8.29 (m, 1H), 8.16 (br d, J = 5.1 Hz, 1H), 8.05 (s, 1H), 7.26 (s, 1H), 5.39-5.17 (m, 1H), 4.77-4.56 (m, 1H), 4.62-3.30 (m, 4H merge with water), 2.34 (s, 3H), 1.54 (s, 3H) |
| 518 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(Deutero)methoxy-6-methylpyridine-3-carboxamide | | 557.0 | 8.41 (br dd, J = 15.4, 7.5 Hz, 1H), 8.15 (d, J = 10.7 Hz, 1H), 8.07 (s, 1H), 7.31 (s, 1H), 5.40-5.18 (m, 1H), 5.09-4.88 (m, 1H), 4.85-4.53 (m, 1H), 3.97-3.52 (m, 3H), 3.44-3.16 (m, 1H), 2.86-2.67 (m, 1H), 2.60-2.48 (m, 2H merge with DMSO), 2.35 (d, J = 2.7 Hz, 3H), 2.31-2.15 (m, 2H). |
| 519 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(Deutero)methoxy-6-methylpyridine-3-carboxamide | | 556.9 | 8.51-8.36 (m, 1H), 8.15 (br d, J = 8.5 Hz, 1H), 8.10-8.03 (m, 1H), 7.70-7.59 (m, 2H), 7.34-7.26 (m, 3H), 5.45-5.15 (m, 1H), 4.87-4.60 (m, 1H), 4.07-3.74 (m, 3H), 3.69-3.50 (m, 1H), 2.34 (br d, J = 5.2 Hz, 3H) |
| 520 | (5-(4-amino-5-(trifluoromethyl)pyrrolo[2,1-f][1,2,4]triazin-7-yl)-N-((3R,4S)-1-(3,3-difluorocyclobutane-1-carbonyl)-4-fluoropyrrolidin-3-yl)-2-(methoxy-d3)-6-methylnicotinamide | | 575.1 | 8.41 (br dd, J = 12.1, 7.8 Hz, 1H), 8.16 (d, J = 14.0 Hz, 1H), 8.07 (s, 1H), 7.32 (s, 1H), 7.24-6.98 (m, 1H), 5.46-5.08 (m, 1H), 4.93-4.53 (m, 1H), 4.07-3.59 (m, 2H), 3.22-3.04 (m, 1H), 3.04-2.87 (m, |

TABLE 31-continued

Compounds in Table 31 were prepared by the methods detailed in Example 46.
When diastereomers were separated, they are included as separate entries.

| Ex | Name | R | Obs. MS Ion | NMR Assignments (500 MHz, DMSO-d6) δ |
|----|------|---|-------------|--------------------------------------|
|    |      |   |             | 1H), 2.79 (br dd, J = 12.5, 8.2 Hz, 4H), 2.56 (s, 3H) |

TABLE 32

Compounds in Table 32 were prepared by similar methods as to those detailed in Examples 67 and 31. When diastereomers were separated, they are included as separate entries. If the stereochemistry is undefined, the product was isolated as a mixture of diastereomers.

| Ex | Name | R | Obs. MS Ion | NMR Assignments (500 MHz, DMSO-d6) δ |
|----|------|---|-------------|--------------------------------------|
| 521 | 5-[4-amino-5-(trifluoromethyl)pyrrolo[2,1-f][1,2,4]triazin-7-yl]-4-chloro-2-fluoro-N-[(3R,4S)-4-fluoro-1-(1-fluorocyclobutane-carbonyl)pyrrolidin-3-yl]benzamide | | 561.2 | 8.88 (br d, J = 6.7 Hz, 1H), 8.05 (s, 1H), 7.81-7.68 (m, 2H), 7.31 (d, J = 2.1 Hz, 1H), 5.36-5.12 (m, 1H), 4.79-4.53 (m, 1H), 4.00-3.50 (m, 3H merge with water), 3.53-3.33 (m, 1H), 2.73-2.22 (m, 4H merge with MeOH), 1.93-1.77 (m, 1H), 1.59-1.47 (m, 1H) |
| 522 | 5-[4-amino-5-(trifluoromethyl)pyrrolo[2,1-f][1,2,4]triazin-7-yl]-4-chloro-2-fluoro-N-[(3R,4S)-4-fluoro-1-(2-fluoro-2-methylpropanoyl)pyrrolidin-3-yl]benzamide | | 549.2 | 8.93-8.82 (m, 1H), 8.05 (s, 1H), 7.82-7.71 (m, 2H), 7.31 (s, 1H), 5.36-5.12 (m, 1H), 4.75-4.48 (m, 1H), 4.16-3.16 (m, 4H merge with water), 1.59-1.46 (m, 6H) |

TABLE 32-continued

Compounds in Table 32 were prepared by similar methods as to those detailed in Examples 67 and 31. When diastereomers were separated, they are included as separate entries. If the stereochemistry is undefined, the product was isolated as a mixture of diastereomers.

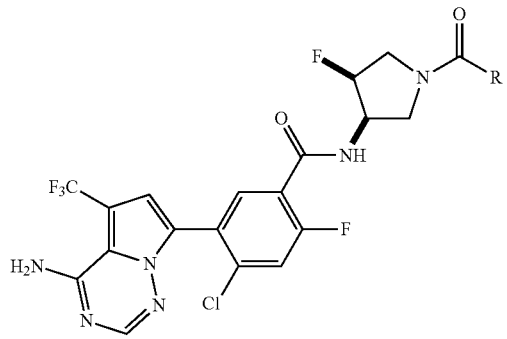

| Ex | Name | R | Obs. MS Ion | NMR Assignments (500 MHz, DMSO-d6) δ |
|---|---|---|---|---|
| 523 | 5-[4-amino-5-(trifluoromethyl)pyrrolo[2,1-f][1,2,4]triazin-7-yl]-4-chloro-N-[(3R,4S)-1-(3,3-difluorocyclopentane-carbonyl)-4-fluoropyrrolidin-3-yl]-2-fluorobenzamide | | 593.2 | 8.87 (br t, J = 8.7 Hz, 1H), 8.06 (s, 1H), 7.83-7.71 (m, 2H), 7.31 (s, 1H), 5.38-5.14 (m, 1H), 4.83-4.49 (m, 1H), 4.06-3.21 (m, 4H merge with water), 3.22-3.08 (m, 1H), 2.38-2.21 (m, 2H), 2.21-1.98 (m, 3H), 1.85-1.68 (m, 1H) |
| 524 | 5-[4-amino-5-(trifluoromethyl)pyrolo[2,1-f][1,2,4]triazin-7-yl]-4-chloro-N-[(3R,4S)-1-(3,3-difluorocyclobutane-carbonyl)-4-fluoropyrrolidin-3-yl]-2-fluorobenzamide, TFA | | 579.2 | 8.85 (br dd, J = 15.4, 7.3 Hz, 1H), 8.08 (s, 1H), 7.84-7.72 (m, 2H), 7.33 (s, 1H), 5.38-5.12 (m, 1H), 4.80-4.50 (m, 1H), 3.95-3.23 (m, 4H), 3.20-3.07 (m, 1H), 2.88-2.66 (m, 4H) |

TABLE 33

Compounds in Table 33 were prepared by similar methods as to those detailed in Examples 67 and 31. For tertiary amides, the full amine is depicted as the R group. When diastereomers were separated, they are included as separate. If the stereochemistry is undefined, the product was isolated as a mixture of diastereomers.

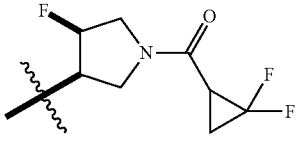 [SMILES: *[C@@H]1CN(C(=O)C2CC2(F)F)C[C@@H]1F]

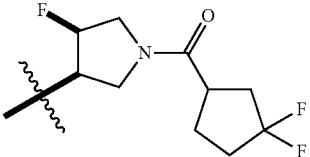 [SMILES: *[C@@H]1CN(C(=O)C2CCC(F)(F)C2)C[C@@H]1F]

| Ex | Name | R | Obs. MS Ion | NMR Assignments (500 MHz, DMSO-d6) δ |
|---|---|---|---|---|
| 525 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2,6-dimethylpyridine-3-carboxamide | 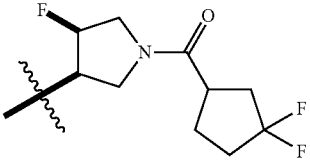 [SMILES: *[C@@H]1CN(C(=O)C2CCC(F)(F)C2)C[C@@H]1F] | 542.2 | 8.90-8.75 (m, 1H), 8.07 (s, 1H), 7.78 (br d, J = 7.8 Hz, 1H), 7.30 (s, 1H), 5.45-5.13 (m, 1H), 4.88-4.52 (m, 1H), 4.23-3.22 (m, 4H), 3.11-2.95 (m, 1H), 2.59 (br d, J = 6.3 Hz, 3H), 2.33 (s, 3H), 2.00-1.76 (m, 2H) |
| 526 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2,6-dimethylpyridine-3-carboxamide | | 570.3 | 8.85-8.74 (m, 1H), 8.07 (s, 1H), 7.77 (d, J = 2.1 Hz, 1H), 7.29 (s, 1H), 5.44-5.15 (m, 1H), 4.79-4.50 (m, 1H, 4.02-3.06 (m, 5H), 2.59 (d, J = 3.7 Hz, 3H), 2.38-1.98 (m, 8H), 1.86-1.69 (m, 1H) |
| 527 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2,6-dimethylpyridine-3-carboxamide | | 570.1 | 8.79 (br dd, J = 18.8, 7.2 Hz, 1H), 8.07 (s, 1H), 7.76 (s, 1H), 7.29 (s, 1H), 5.43-5.14 (m, 1H), 4.80-4.49 (m, 1H), 4.12-3.12 (m, 5H merge with water), 2.59 (d, J = 4.6 Hz, 3H), 2.40-1.98 (m, 8H), 1.83-1.71 (m, 1H) |
| 528 | 7-[5-(2-benzylmorpholine-4-carbonyl)-2,6-dimethylpyridin-3-yl]-5-(trifluoromethyl)pyrrolo[2,1-f][1,2,4]triazin-4- | 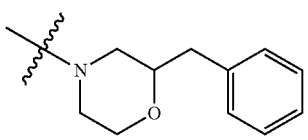 [SMILES: *N1CCOC(Cc2ccccc2)C1] | 511.2 | 8.09-8.02 (m, 1H), 7.90-7.76 (m, 1H), 7.38-7.20 (m, 5H), 7.19-7.04 (m, 4H), 4.32 (br t, J = 12.1 |

TABLE 33-continued

Compounds in Table 33 were prepared by similar methods as to those detailed in Examples 67 and 31. For tertiary amides, the full amine is depicted as the R group. When diastereomers were separated, they are included as separate. If the stereochemistry is undefined, the product was isolated as a mixture of diastereomers.

| Ex | Name | R | Obs. MS Ion | NMR Assignments (500 MHz, DMSO-d6) δ |
|---|---|---|---|---|
| | amine, TFA | | | Hz, 1H), 3.97-3.57 (m, 1H), 3.33-2.59 (m, 4H), 2.48 (br s, 3H), 2.42-2.36 (m, 3H) |
| 529 | 7-{5-[(3S)-3-[(4-fluorophenyl)methyl]piperidine-1-carbonyl]-2,6-dimethylpyridin-3-yl}-5-(trifluoromethyl)pyrrolo[2,1-f][1,2,4]triazin-4-amine, TFA | | 527.2 | 8.04 (d, J = 6.1 Hz, 1H), 7.74-7.51 (m, 1H), 7.38-6.97 (m, 5H), 4.27 (br d, J = 12.2 Hz, 1H), 3.50-2.62 (m, 3H), 2.57-2.48 (m, 2H merge with DMSO), 2.46-2.27 (m, 6H), 1.79-1.50 (m, 3H), 1.48-1.13 (m, 2H) |
| 530 | 7-{5-[(3R)-3-[(4-fluorophenyl)methyl]piperidine-1-carbonyl]-2,6-dimethylpyridin-3-yl}-5-(trifluoromethyl)pyrrolo[2,1-f][1,2,4]triazin-4-amine, TFA | | 527.4 | 8.04 (br d, J = 7.3 Hz, 1H), 7.36-6.97 (m, 6H), 4.44-4.17 (m, 1H), 3.68-2.95 (m, 3H), 2.91-2.62 (m, 2H), 2.47 (s, 2H), 2.40 (s, 3H), 2.36 (s, 1H), 1.81-1.52 (m, 3H), 1.48-1.13 (m, 2H) |
| 531 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2,6-dimethylpyridine-3-carboxamide | | 538.0 | 8.77 (br dd, J = 17.7, 7.3 Hz, 1H), 8.08 (s, 1H), 7.77 (d, J = 2.1 Hz, 1H), 7.30 (s, 1H), 5.38-5.01 (m, 2H), 4.77-4.49 (m, 1H), 3.94-3.52 (m, 3H), 3.45-3.12 (m, 2H), 2.59 (d, J = 2.1 Hz, 3H), 2.58-2.35 (m, 4H merge with DMSO), 2.33 (s, |

TABLE 33-continued

Compounds in Table 33 were prepared by similar methods as to those detailed in Examples 67 and 31. For tertiary amides, the full amine is depicted as the R group. When diastereomers were separated, they are included as separate. If the stereochemistry is undefined, the product was isolated as a mixture of diastereomers.

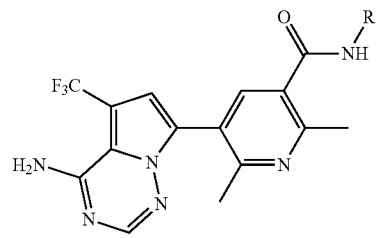

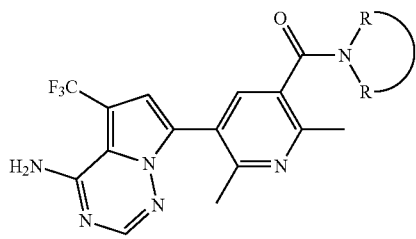

| Ex | Name | R | Obs. MS Ion | NMR Assignments (500 MHz, DMSO-d6) δ |
|---|---|---|---|---|
| | | | | 3H) |
| 532 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2,6-dimethylpyridine-3-carboxamide | | 538.3 | 8.83-8.71 (m, 1H), 8.08 (s, 1H), 7.77 (d, J = 3.4 Hz, 1H), 7.30 (s, 1H), 5.40-5.15 (m, 1H), 5.10-4.87 (m, 1H), 4.79-4.49 (m, 1H), 3.96-3.54 (m, 3H), 3.45-3.16 (m, 1H), 2.73 (td, J = 15.3, 7.6 Hz, 1H), 2.60 (d, J = 2.1 Hz, 3H), 2.58-2.47 (m, 2H merge with DMSO), 2.33 (s, 3H), 2.30-2.14 (m, 2H) |

TABLE 34

Compounds in Table 34 were prepared by similar methods as to those detailed in Examples 67 and 31. For tertiary amides, the full amine is depicted as the R group. When diastereomers were separated, they are included as separate entries. If the stereochemistry is undefined, the product was isolated as a mixture of diastereomers.

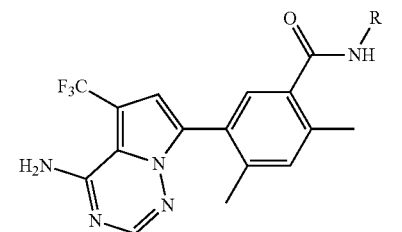

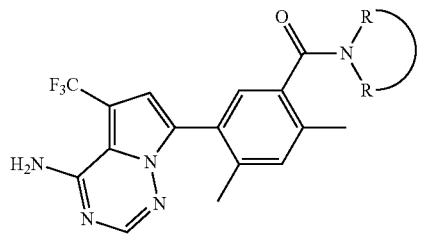

| Ex | Name | R | Obs. MS Ion | NMR Assignments (500 MHz, DMSO-d6) δ |
|---|---|---|---|---|
| 533 | 5-[4-amino-5-(trifluoromethyl)pyrrolo[2,1-f][1,2,4]triazin-7-yl]-N-[(3R,4S)-4-fluoro-1-(oxolane-3-carbonyl)pyrrolidin-3-yl]-2,4-dimethylbenzamide | | 535.2 | 8.51-8.41 (m, 1H), 8.02 (s, 1H), 7.36 (br d, J = 2.7 Hz, 1H), 7.25 (br s, 1H), 7.14 (s, 1H), 5.38-5.13 (m, 1H), 4.73-4.47 (m, 1H), 4.05-3.38 (m, 9H), 2.41 (br d, J = 4.3 Hz, 3H), 2.15-1.87 (m, 5H) |
| 534 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2,4-dimethylbenzamide | | 537.4 | 8.57 (br dd, J = 10.4, 7.6 Hz, 1H), 8.03 (s, 1H), 7.36 (s, 1H), 7.26 (s, 1H), 7.17 (s, 1H), 5.36-5.01 (m, 2H), 4.72-4.46 (m, 1H), 3.87-3.15 (m, 4H), 2.69-2.29 (m, 8H merge with DMSO), 2.11 (s, 3H) |
| 535 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2,4-dimethylbenzamide | | 537.3 | 8.60 (br t, J = 7.9 Hz, 1H), 8.02 (s, 1H), 7.34 (s, 1H), 7.26 (s, 1H), 7.16 (s, 1H), 5.34-5.13 (m, 1H), 5.07-4.87 (m, 1H), 4.72-4.46 (m, 1H), 3.90-3.15 (m, 4H merge with water), 2.78-2.68 (m, 1H), 2.59-2.47 (m, 2 H merge with DMSO), 2.39 (br d, J = 2.1 Hz, 3H), 2.29-2.15 (m, 2H), 2.10 (s, 3H) |
| 536 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2,4-dimethylbenzamide | | 569.2 | 8.46 (br t, J = 6.8 Hz, 1H), 8.01 (s, 1H), 7.35 (s, 1H), 7.25 (br s, 1H), 7.13 (s, 1H), 5.38-5.13 (m, 1H), 4.74-4.47 (m, 1H), 4.00-3.24 (m, 4H merge with water), 3.22-3.09 (m, 1H), 2.40 (d, J = 4.4 Hz, 3H), 2.35-1.71 (m, 9H) |

TABLE 34-continued

Compounds in Table 34 were prepared by similar methods as to those detailed in Examples 67 and 31. For tertiary amides, the full amine is depicted as the R group. When diastereomers were separated, they are included as separate entries. If the stereochemistry is undefined, the product was isolated as a mixture of diastereomers.

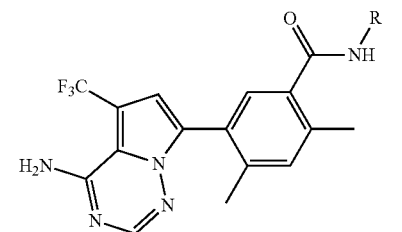

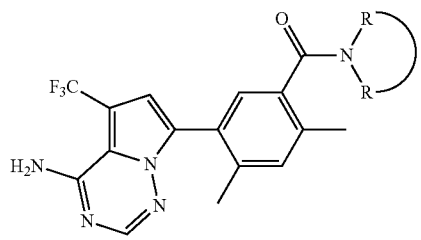

| Ex | Name | R | Obs. MS Ion | NMR Assignments (500 MHz, DMSO-d6) δ |
|----|------|---|-------------|-----------------------------------------|
| 537 | 5-[4-amino-5-(trifluoromethyl)pyrrolo[2,1-f][1,2,4]triazin-7-yl]-N-[(3R,4S)-1-(3,3-difluorocyclobutane-carbonyl)-4-fluoropyrrolidin-3-yl]-2,4-dimethylbenzamide | | 555.2 | 8.46 (br t, J = 6.8 Hz, 1H), 8.01 (s, 1H), 7.35 (s, 1H), 7.25 (s, 1H), 7.13 (s, 1H), 5.36-5.12 (m, 1H), 4.74-4.46 (m, 1H), 3.90-3.26 (m, 4H merge with water), 3.16-3.06 (m, 1H), 2.86-2.66 (m, 4H), 2.40 (d, J = 3.2 Hz, 3H), 2.11 (s, 3H) |
| 538 | 5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]-2,4-dimethylbenzamide | | 559.2 | 8.59-8.37 (m, 1H), 8.01 (br s, 1H), 7.59 (dd, J = 8.2, 5.6 Hz, 2H), 7.43-7.20 (m, 4H), 7.12 (br s, 1H), 5.42-5.13 (m, 1H), 4.75-4.50 (m, 1H), 3.99-3.33 (m, 4H merge with water), 2.40 (br d, J = 13.0 Hz, 3H), 2.10 (br s, 3H) |
| 539 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2,4-dimethylbenzamide | | 583.2 | 8.46 (br t, J = 8.0 Hz, 1H), 8.01 (s, 1H), 7.35 (d, J = 2.7 Hz, 1H), 7.25 (br d, J = 3.2 Hz, 1H), 7.13 (s, 1H), 5.38-5.13 (m, 1H), 4.74-4.47 (m, 1H), 4.03-3.46 (m, 4H merged with water), 2.40 (d, J = 5.6 Hz, 3H), 2.11 (s, 3H), 2.04 (br s, 2H), 1.95-1.70 (m, 5H), 1.65-1.51 (m, 2H) |
| 540 | 5-[4-amino-5-(trifluoromethyl)pyrrolo[2,1 f][1,2,4]triazin-7-yl]-N-[(3R,4S)-1-(2,2-difluorocyclopropane-carbonyl)-4-fluoropyrrolidin-3-yl]-2 4-dimethylbenzamide | | 541.1 | 8.56-8.43 (m, 1H), 8.02 (s, 1H), 7.37 (br d, J = 6.8 Hz, 1H), 7.25 (s, 1H), 7.14 (s, 1H), 5.42-5.15 (m, 1H), 4.80-4.51 (m, 1H), 4.24-3.38 (m, 5H merge with water), 2.42 (br d, J = 5.0 Hz, 3H), 2.11 (s, 3H), 2.00-1.78 (m, 2H) |

TABLE 34-continued

Compounds in Table 34 were prepared by similar methods as to those detailed in Examples 67 and 31. For tertiary amides, the full amine is depicted as the R group. When diastereomers were separated, they are included as separate entries. If the stereochemistry is undefined, the product was isolated as a mixture of diastereomers.

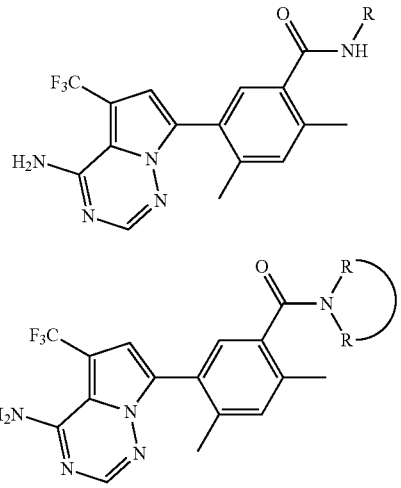

| Ex | Name | R | Obs. MS Ion | NMR Assignments (500 MHz, DMSO-d6) δ |
|---|---|---|---|---|
| 541 | 7-{5-[(3R)-3-[(4-fluorophenyl)methyl]piperidine-1-carbonyl]-2,4-dimethylphenyl}-5-(trifluoromethyl)pyrrolo[2,1-f][1,2,4]triazin-4-amine | 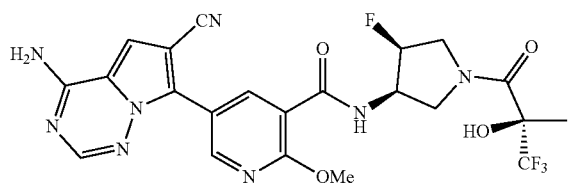 | 526.3 | 8.01 (br d, J = 5.8 Hz, 1H), 7.25 (br s, 2H), 7.20-6.78 (m, 5H), 4.27 (br d, J = 11.0 Hz, 1H), 3.52-3.28 (m, 2H merge with water), 3.18 (d, J = 5.2 Hz, 1H), 3.04-2.89 (m, 1H), 2.27-2.01 (m, 6H), 1.72 (br s, 2H), 1.62-1.47 (m, 1H), 1.44-1.29 (m, 1H), 1.28-1.08 (m, 2H) |

Example 542: 5-(4-amino-6-cyanopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide Method 1—To a resealable pressure tube was added 4-amino-7-bromopyrrolo[2,1-f][1,2,4]triazine-6-carbonitrile (13.66 mg, 0.057 mmol, made according to WO2007/056170, page 391 in Step 3), N-((3R,4S)-4-fluoro-1-((R)-3,3,3-trifluoro-2-hydroxy-2-methylpropanoyl)pyrrolidin-3-yl)-2-methoxy-5-(4,4,5,5-tetramethyl-1,3,2-dioxaborolan-2-yl)nicotinamide (29 mg, 0.057 mmol, as prepared in Example 1559A) and dioxane (1 mL). The mixture was chilled in a dry ice acetone bath until frozen. Usual freeze-purge cycles were repeated five times. To this frozen solid was added PdCl$_2$(dppf)-CH$_2$Cl$_2$ adduct (3.52 mg, 4.30 μmol) and a 2.0 M aqueous stock solution of tripotassium phosphate (0.086 mL, 0.172 mmol). The mixture was vacuum purged and filled with nitrogen. The pressure vessel was then sealed and warmed to room temperature forming a pale yellow biphasic mixture. Once thawed, it was immersed into an oil bath at 101° C. for 4 h, and then at 95° C. for another 6 h. The crude reaction mixture was diluted with 4 mL ethyl acetate and 2 mL water. The organic residues were extracted into the ethyl acetate layer and the extraction was repeated two more times. The clear organic extracts were combined, concentrated and submitted to chromatographic purification. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 9% B, 9-49% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to yield the product (9.3 mg, 28% yield).

MS ESI m/z 537.2 (M+H)$^+$ $^1$H NMR (500 MHz, DMSO-d$_6$) δ 8.75 (br s, 1H), 8.62-8.46 (m, 2H), 8.31 (br d, J=16.8 Hz, 2H), 8.04 (s, 1H), 7.48 (s, 1H), 7.06 (br d, J=5.8 Hz, 1H), 5.37-5.17 (m, 1H), 4.75-4.58 (m, 1H), 4.53-4.25 (m, 1H), 4.07 (s, 3H), 4.00-3.52 (m, 2H), 1.54 (s, 3H).

Method 2, Step A: To a resealable pressure tube was added 4-amino-7-bromopyrrolo[2,1-f][1,2,4]triazine-6-carbonitrile (13.66 mg, 0.057 mmol, made in according to WO2007/056170, page 391 in Step 3), methyl 2-methoxy-5-(4,4,5,5-tetramethyl-1,3,2-dioxaborolan-2-yl)nicotinate (217 mg, 0.739 mmol, prepared as described in example 10A) and PdCl$_2$(dppf)-CH$_2$Cl$_2$ adduct (41.2 mg, 0.050 mmol), the dry mixture was chilled in a dry ice bath until cold. To this mixture was added dioxane (2 mL) and a 2.0 M aqueous stock solution of potassium phosphate (1.008 mL, 2.016 mmol). The solid mixture was vacuum purged and filled with nitrogen. The pressure vessel was then sealed and warmed to rt forming a pale yellow biphasic mixture. Once thawed, it was immersed into an oil bath at 95° C. for 6 h. LCMS analyses showed complete transformation into the desired product. It was diluted with 4 mL ethyl acetate, extracted with 2×2 mL water to get rid of the inorganic substances. The remaining residue (contained both organic phase and solids) was triturated with methanol, filtered and concentrated to give the crude desired product (226 mg, xx mmol, 100%). This material was used in the next step immediately.

Step B: Sodium 5-(4-amino-6-cyanopyrrolo[2,1-f][1,2,4]triazin-7-yl)-2-methoxynicotinate: The crude material from Step A methyl 5-(4-amino-6-cyanopyrrolo[2,1-f][1,2,4]triazin-7-yl)-2-methoxynicotinate (226 mg, 0.697 mmol) was suspended in methanol (2.5 mL) at room temperature. To this turbid mixture was added water (0.7 mL) and a 1.0 N stock solution of sodium hydroxide (0.697 mL, 0.697 mmol). The mixture was stirred at 50° C. ON forming a somewhat thinner suspension. All the volatile solvents were evaporated and the crude sodium carboxylate was dried to constant weight (240 mg, xx mmol, 100%).

MS ESI m/z 333.0 (M+Na)$^+$ $^1$H NMR (400 MHz, DMSO-d6) δ 8.83-8.79 (m, 1H), 8.62-8.58 (m, 1H), 8.47-8.43 (m, 0.5H), 8.34-8.24 (br. s, 2H), 8.18-8.16 (m, 0.5H), 8.03 (s, 1H), 7.47 (s, 1H), 4.04-4.01 (m, 3H).

Step C: tert-Butyl (3R,4S)-3-(5-(4-amino-6-cyanopyrrolo[2,1-f][1,2,4]triazin-7-yl)-2-methoxynicotinamido)-4-fluoropyrrolidine-1-carboxylate: To the crude, dried sodium salt from Step B (0.045 g, 0.136 mmol) and PyBOP (0.106 g, 0.204 mmol) in a resealable pressure vessel was added tert-butyl (3R,4S)-3-amino-4-fluoropyrrolidine-1-carboxylate (0.028 g, 0.136 mmol), followed by DMF (4 mL) and N,N-diisopropylethylamine (0.071 mL, 0.408 mmol). The suspension was stirred at rt and became clear after an hour. It was allowed to stir at 56° C. ON. All the volatile solvents were evaporated under high vacuum. The residue was taken up in ethyl acetate (6 mL), washed with water (3×1 mL) to remove most of the water soluble inorganic materials, and the aqueous layers were combined and back-extracted with ethyl acetate (3×1 mL) to recover as much of the desired product as possible. The organic layers were combined, concentrated to a crude solid and used in the next step without further purification.

MS ESI m/z 519.1 (M+Na)$^+$ $^1$H NMR (500 MHz, DMSO-d$_6$) δ 8.56 (s, 1H), 8.42 (br s, 2H), 8.20 (br s, 1H), 8.03 (s, 1H), 5.38-4.93 (m, 1H), 4.81-4.24 (m, 1H), 4.08 (s, 3H), 3.84-3.70 (m, 1H), 3.67-3.43 (m, 3H), 2.98-2.81 (m, 1H), 1.41 (s, 9H).

Step D: 5-(4-Amino-6-cyanopyrrolo[2,1-f][1,2,4]triazin-7-yl)-N-((3R,4S)-4-fluoropyrrolidin-3-yl)-2-methoxynicotinamide: To the suspension of tert-butyl (3R,4S)-3-(5-(4-amino-6-cyanopyrrolo[2,1-f][1,2,4]triazin-7-yl)-2-methoxynicotinamido)-4-fluoropyrrolidine-1-carboxylate (110 mg, 0.222 mmol) in DCM (2 mL) at rt was added TFA (0.4 mL, 5.19 mmol) forming a clear solution. The mixture was stirred at rt 1 h. and the reaction mixture was evaporated to dryness under high vacuum.

Step E: 5-(4-Amino-6-cyanopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide:5-(4-Amino-6-cyanopyrrolo[2,1-f][1,2,4]triazin-7-yl)-N-((3R,4S)-4-fluoropyrrolidin-3-yl)-2-methoxynicotinamide (88 mg, 0.222 mmol) was mixed with (R)-3,3,3-trifluoro-2-hydroxy-2-methylpropanoic acid (35.1 mg, 0.222 mmol) and PyBOP (116 mg, 0.222 mmol). The addition of DMF (2 mL) and N,N-diisopropylethylamine (0.116 mL, 0.666 mmol) followed. The suspension was stirred at rt and became solubilized soon after. The clear solution was stirred for a total of 4 h. It was evaporated to dryness, and the residue taken into ethyl acetate and filtered over a short bed of silica gel. The crude mixture was purified using reverse phase preparative HPLC to give 100 mg of the desired product. Characterization matched that of the material obtained by method 1.

Example 543: 5-(4-amino-6-(1H-tetrazol-5-yl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide

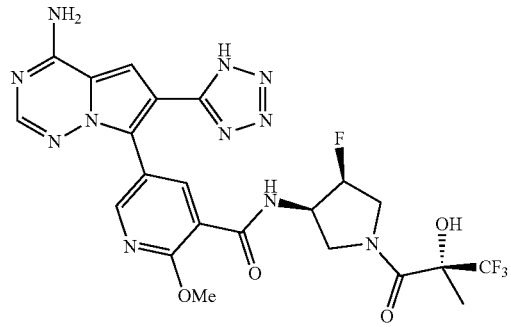 [SMILES: COc1ncc(-c2c(-c3nnn[nH]3)cc3c(N)ncnn23)cc1C(=O)N[C@@H]1CN(C(=O)[C@@](C)(O)C(F)(F)F)C[C@@H]1F]

To a mixture of benzene (0.7 mL) and 1,4-dioxane (0.4 mL) in a small resealable pressure vessel was added 5-(4-amino-6-cyanopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (11.6 mg, 0.022 mmol) Tri-n-butyltin azide (100 µL, 0.364 mmol) was added via a pipet. The contents in the tube were briefly flushed with a stream of nitrogen, sealed and warmed to 120° C. ON. The reaction mixture was purified by reverse phase HPLC to give the desired product (12.5 mg, 0.022 mmol, 88% yield).

MS ESI m/z 580.2 (M+H)$^+$ $^1$H NMR (500 MHz, DMSO-d$_6$) δ 8.57-8.44 (m, 2H), 8.37 (br d, J=9.2 Hz, 1H), 8.26-7.93 (1H), 7.90 (s, 1H), 7.49-7.43 (m, 1H), 7.10 (br d, J=7.0 Hz, 1H), 5.38-5.16 (m, 1H), 4.75-4.58 (m, 1H), 4.53-4.25 (m, 1H), 4.06 (s, 3H), 4.03-3.52 (m, 2H), 1.54 (s, 3H).

Examples 544 and 545: 5-(4-amino-6-(1-methyl-1H-tetrazol-5-yl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (544) and 5-(4-amino-6-(2-methyl-2H-tetrazol-5-yl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (545)

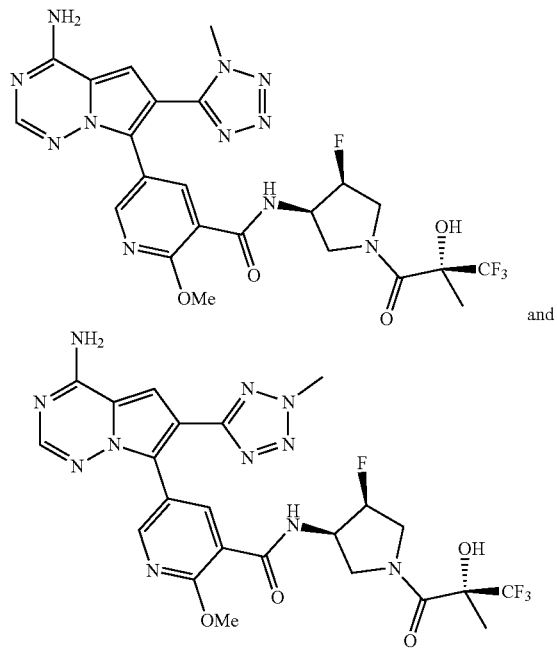
and

544: To a suspension of the crude material from Example 543, 5-(4-amino-6-(1H-tetrazol-5-yl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (50 mg, 0.086 mmol) in acetonitrile (2 mL) at rt was added pulverized potassium carbonate (50 mg, 0.362 mmol) and iodomethane (50 µl, 0.800 mmol). Stirring was continued at rt 1 h. The crude reaction suspension was filtered over a short bed of silica gel, washed with ethyl acetate and concentrated into a gum. Obtained 5-(4-amino-6-(1-methyl-1H-tetrazol-5-yl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (1.8 mg, 3.03 µmol, 3.51% yield)

MS ESI m/z 594.2 (M+H)$^+$ $^1$H NMR (500 MHz, DMSO-d$_6$) δ 8.55-8.43 (m, 1H), 8.36 (br s, 1H), 8.34-8.28 (m, 1H), 8.28-8.06 (m, 1H), 7.98 (s, 1H), 7.52-7.48 (m, 1H), 5.26 (s, 1H), 4.73-4.57 (m, 1H), 4.52-4.25 (m, 1H), 4.04 (s, 3H), 4.03-3.99 (m, 3H), 3.98-3.75 (m, 1H), 3.75-3.68 (m, 1H), 3.58 (br 1, J=11.0 Hz, 1H), 1.54 (s, 3H).

545: Obtained 5-(4-amino-6-(2-methyl-2H-tetrazol-5-yl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (1.58 mg, 2.66 µmol, 3.09% yield).

MS ESI m/z 594.2 (M+H)$^+$ $^1$H NMR (500 MHz, DMSO-d$_6$) δ 8.58-8.45 (m, 2H), 8.41-8.22 (m, 2H), 8.21-7.97 (m, 1H), 7.92-7.88 (m, 1H), 7.61 (s, 1H), 5.37-5.17 (m, 1H), 4.57 (s, 1H), 4.52-4.27 (m, 1H), 4.34 (s, 3H), 4.07 (s, 3H), 4.00-3.75 (m, 2H), 3.74-3.42 (m, 1H), 1.54 (s, 3H).

Example 546: (S)-5-(4-amino-6-cyanopyrrolo[2,1-f][1,2,4]triazin-7-yl)-N-(3-(4-chlorophenyl)-3-hydroxypropyl)-2-methoxynicotinamide

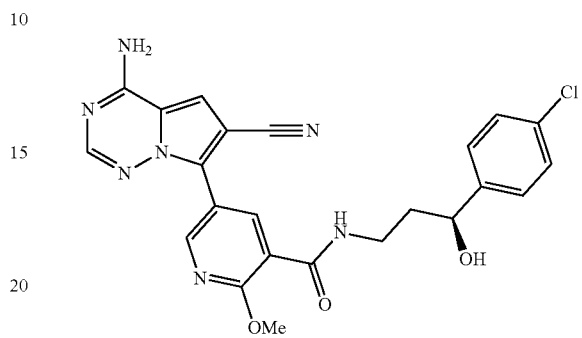

Example 546 was prepared using (S)-3-(4-chlorophenyl)-3-hydroxypropan-1-aminium chloride instead, in accordance with the procedure as described for Example 542, Method 2 Step 3. (S)-5-(4-amino-6-cyanopyrrolo[2,1-f][1,2,4]triazin-7-yl)-N-(3-(4-chlorophenyl)-3-hydroxypropyl)-2-methoxynicotinamide (6.01 mg, 0.013 mmol, 17% yield).

MS ESI m/z 478.1 (M+H)$^+$

1H NMR (500 MHz, DMSO-d6) δ 8.72 (s, 1H), 8.57 (s, 1H), 8.56-8.49 (m, 1H), 8.36-8.23 (m, 2H), 8.02 (s, 1H), 7.50-7.46 (m, 1H), 7.39 (s, 4H), 5.52 (br s, 1H), 4.71 (br d, J=8.5 Hz, 1H), 4.07 (s, 3H), 3.40-3.30 (m, 1H), 1.96-1.74 (m, 2H).

Example 547: (R)-5-(4-amino-6-cyanopyrrolo[2,1-f][1,2,4]triazin-7-yl)-N-(3-(4-chlorophenyl)-3-hydroxypropyl)-2-methoxynicotinamide

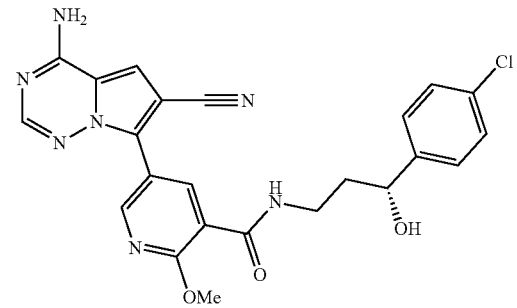 [SMILES: COc1ncc(-c2c(C#N)cc3c(N)ncnn23)cc1C(=O)NCC[C@@H](O)c1ccc(Cl)cc1]

Example 547 was prepared using (R)-3-(4-chlorophenyl)-3-hydroxypropan-1-aminium chloride instead, in accordance with the procedure as described for Example 542, Method 2 Step 3. Obtained (R)-5-(4-amino-6-cyanopyrrolo[2,1-f][1,2,4]triazin-7-yl)-N-(3-(4-chlorophenyl)-3-hydroxypropyl)-2-methoxynicotinamide (6.21 mg, 0.013 mmol, 25% yield)

MS ESI m/z 478.1 (M+H)$^+$ $^1$H NMR (500 MHz, DMSO-d$_6$) δ 8.72 (d, J=1.8 Hz, 1H), 8.57 (d, J=2.1 Hz, 1H), 8.56-8.50 (m, 1H), 8.37-8.23 (m, 2H), 8.02 (s, 1H), 7.50-7.44 (m, 1H), 7.39 (s, 4H), 5.52 (br d, J=3.7 Hz, 1H), 4.75-4.65 (m, 1H), 4.07 (s, 3H), 3.37 (br d, J=9.5 Hz, 1H), 1.95-1.77 (m, 2H).

Example 548: (R)-5-(4-amino-6-cyanopyrrolo[2,1-f][1,2,4]triazin-7-yl)-N-(1-(2-fluoro-5-(trifluoromethoxy)phenyl)ethyl)-2-methoxynicotinamide

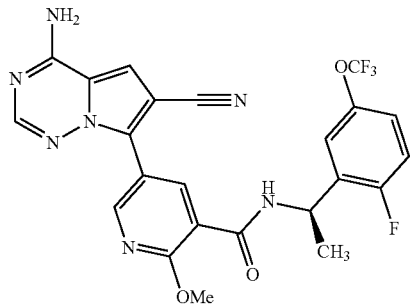 [SMILES: COc1ncc(-c2c(C#N)cc3c(N)ncnn23)cc1C(=O)N[C@H](C)c1cc(OC(F)(F)F)ccc1F]

Example 548 was prepared using (R)-1-(2-fluoro-5-(trifluoromethoxy)phenyl)ethan-1-amine hydrochloride instead, in accordance with the procedure as described for Example 542, Method 2 Step 3. Obtained (R)-5-(4-amino-6-cyanopyrrolo[2,1-f][1,2,4]triazin-7-yl)-N-(1-(2-fluoro-5-(trifluoromethoxy)phenyl)ethyl)-2-methoxynicotinamide (2.33 mg, 4.52 µmol, 6.8% yield).

MS ESI m/z 516.1 (M+H)$^+$ $^1$H NMR (500 MHz, DMSO-d$_6$) δ 8.90 (br d, J=7.6 Hz, 1H), 8.71 (s, 1H), 8.38 (s, 1H), 8.36-8.21 (m, 2H), 8.03-7.97 (m, 1H), 7.53 (br s, 1H), 7.47 (s, 1H), 7.42-7.29 (m, 1H), 7.27-6.97 (m, 1H), 5.42-5.28 (m, 1H), 4.06 (s, 3H), 1.47 (br d, J=7.0 Hz, 3H).

Example 549: (R)-5-(4-amino-6-cyanopyrrolo[2,1-f][1,2,4]triazin-7-yl)-N-(1-(2-fluoro-5-(trifluoromethyl)phenyl)ethyl)-2-methoxynicotinamide

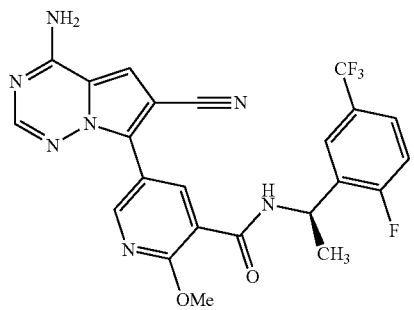 [SMILES: COc1ncc(-c2c(C#N)cc3c(N)ncnn23)cc1C(=O)N[C@H](C)c1cc(C(F)(F)F)ccc1F]

Prepared using (R)-1-(2-fluoro-5-(trifluoromethyl)phenyl)ethan-1-amine hydrochloride instead, in accordance with the procedure as described for Example 542, Method 2 Step 3. Obtained (R)-5-(4-amino-6-cyanopyrrolo[2,1-f][1,2,4]triazin-7-yl)-N-(1-(2-fluoro-5-(trifluoromethyl)phenyl)ethyl)-2-methoxynicotinamide (2.21 mg, 4.43 µmol, 7.7% yield).

MS ESI m/z 500.1 (M+H)$^+$ $^1$H NMR (500 MHz, DMSO-d$_6$) δ 9.00-8.93 (m, 1H), 8.74-8.68 (m, 1H), 8.37 (s, 1H), 8.36-8.21 (m, 2H), 8.01 (s, 1H), 7.88 (s, 1H), 7.78-7.69 (m, 1H), 7.52-7.40 (m, 2H), 5.46-5.33 (m, 1H), 4.06 (s, 3H), 1.48 (br d, J=6.7 Hz, 3H).

Example 550 5-(4-amino-6-cyanopyrrolo[2,1-f][1,2,4]triazin-7-yl)-N-(1-benzyl-1H-pyrazol-4-yl)-2-methoxynicotinamide

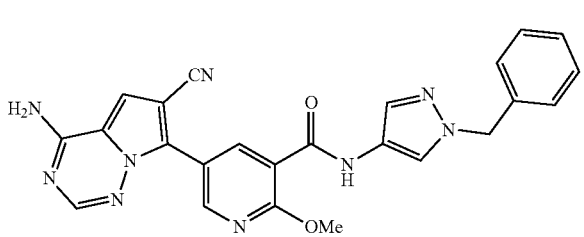 [SMILES: COc1ncc(-c2c(C#N)cc3c(N)ncnn23)cc1C(=O)Nc1cnn(Cc2ccccc2)c1]

A suspension of crude sodium 5-(4-amino-6-cyanopyrrolo[2,1-f][1,2,4]triazin-7-yl)-2-methoxynicotinate (prepared in accordance with the procedure as described for Example 542, Method 2, Step 2) (30 mg, 0.090 mmol), 1-benzyl-1H-pyrazol-4-amine (15.64 mg, 0.090 mmol), BOP (39.9 mg, 0.090 mmol) and DIPEA (0.079 mL, 0.451 mmol) in DMF (1 mL) was stirred at rt ON. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate. The material was further purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid. Fractions containing the desired product were combined and dried via centrifugal evaporation to give the final product (8.5 mg, 20% yield).

MS ESI m/z 466.1 (M+H)$^+$ $^1$H NMR (500 MHz, DMSO-d$_6$) δ 10.31 (s, 1H), 8.73 (s, 1H), 8.51 (d, J=2.1 Hz, 1H), 8.36-8.24 (m, 2H), 8.15 (s, 1H), 8.02 (s, 1H), 7.62 (s, 1H), 7.48 (s, 1H), 7.38-7.32 (m, 2H), 7.32-7.28 (m, 1H), 7.26 (d, J=7.0 Hz, 2H), 5.32 (s, 2H), 4.07 (s, 3H).

TABLE 35

Compounds in Table 35 were prepared by the following the methods described in Example 550. When diastereomers were separated, they are included as separate entries. If the stereochemistry is undefined, the product was isolated as a mixture of diastereomers.

| Ex | Name | R | Obs. MS Ion | $^1$H NMR Assignments (500 MHz, DMSO-$d_6$) δ |
|---|---|---|---|---|
| 551 | 5-(4-amino-6-cyanopyrrolo[2,1-f][1,2,4]triazin-7-yl)-N-((3R,4S)-1-(2,2-difluorocyclopropane-1-carbonyl)-4-fluoropyrrolidin-3-yl)-2-methoxynicotinamide | 2,2-difluorocyclopropyl | 501.1 | 8.74 (br s, 1H), 8.65-8.52 (m, 2H), 8.33 (br d, J = 17.7 Hz, 2H), 8.04 (s, 1H), 7.48 (s, 1H), 5.45-5.20 (m, 1H), 4.91-4.63 (m, 1H), 4.35-4.11 (m, 1H), 4.09-4.04 (m, 3H), 4.03-3.58 (m, 3H), 3.21-2.84 (m, 1H), 2.01-1.80 (m, 2H). |
| 552 | 5-(4-amino-6-cyanopyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide | 3,3-difluorocyclobutyl | 515.2 | 8.75 (dd, J = 7.9, 2.1 Hz, 1H), 8.57 (br d, J = 1.5 Hz, 1H), 8.56-8.52 (m, 1H), 8.33 (br d, J = 15.3 Hz, 2H), 8.03 (s, 1H), 7.48 (s, 1H), 5.42-5.18 (m, 1H), 4.86-4.58 (m, 1H), 4.07 (br d, J = 6.1 Hz, 3H), 4.01-3.57 (m, 3H), 3.24-3.09 (m, 1H), 2.89-2.66 (m, 5H). |
| 553 | 5-(4-amino-6-cyanopyrrolo[2,1-f][1,2,4]triazin-7-yl)-N-((3R,4S)-1-(3,3-difluorocyclopentane-1-carbonyl)-4-fluoropyrrolidin-3-yl)-2-methoxynicotinamide | 3,3-difluorocyclopentyl | 529.2 | 8.74 (br d, J = 8.2 Hz, 1H), 8.57 (br s, 1H), 8.54 (br s, 1H), 8.33 (br d, J = 16.8 Hz, 2H), 8.03 (s, 1H), 7.48 (s, 1H), 5.42-5.19 (m, 1H), 4.84-4.59 (m, 1H), 4.07 (br d, J = 6.7 Hz, 3H), 4.13-4.02 (m, 1H), 4.02-3.81 (m, 2H), 3.79-3.42 (m, 1H), 3.35-3.10 (m, 1H), 2.33 (br dd, J = 17.5, 9.3 Hz, 2H), 2.21-1.98 (m, 3H), 1.88-1.69 (m, 1H). |
| 554 | 5-(4-amino-6-cyanopyrrolo[2,1-f][1,2,4]triazin-7-yl)-N-((3R,4S)-4-fluoro-1-(1-(trifluoromethyl)cyclopropane-1-carbonyl)pyrrolidin-3-yl)-2-methoxynicotinamide | 1-(trifluoromethyl)cyclopropyl | 533.1 | 8.74 (br s, 1H), 8.59 (br s, 1H), 8.55 (br s, 1H), 8.33 (br d, J = 15.3 Hz, 2H), 8.03 (s, 1H), 7.48 (s, 1H), 5.31 (d, J = 53.7 Hz, 1H), 4.81-4.63 (m, 1H), 4.24-4.14 (m, 1H), 4.06 (s, 3H), 4.03-3.48 (m, 3H), 1.41-1.20 (m, 4H). |
| 555 | 5-(4-amino-6-cyanopyrrolo[2,1-f][1,2,4]triazin-7-yl)-N-((3R,4S)-1-(4,4-difluorocyclohexane-1-carbonyl)-4-fluoropyrrolidin-3-yl)-2-methoxynicotinamide | 4,4-difluorocyclohexyl | 543.2 | 8.75 (br d, J = 10.7 Hz, 1H), 8.61-8.50 (m, 2H), 8.42-8.30 (m, 2H), 8.05 (s, 1H), 7.49 (s, 1H), 5.45-5.18 (m, 1H), 4.90-4.58 (m, 1H), 4.15-4.09 (m, 1H), 4.07 (br d, J = 8.2 Hz, 3H), 4.02-3.44 (m, 3H), 2.12-1.71 (m, 7H), 1.65-1.50 (m, 2H). |
| 556 | 5-(4-amino-6-cyanopyrrolo[2,1-f][1,2,4]triazin-7-yl)-N-((3R,4S)-4-fluoro-1-(4-(trifluoromethyl)cyclohexane-1-carbonyl)pyrrolidin-3-yl)-2-methoxynicotinamide Isomer 1 | 4-(trifluoromethyl)cyclohexyl | 575.2 | 8.74 (br d, J = 9.5 Hz, 1H), 8.59-8.50 (m, 2H), 8.41-8.30 (m, 2H), 8.04 (s, 1H), 7.48 (s, 1H), 5.40-5.17 (m, 1H), 4.85-4.59 (m, 1H), 4.12-4.02 (m, 4H), 3.99-3.53 (m, 3H), 2.37-2.21 (m, 1H), 1.93-1.71 (m, 5H), 1.49-1.30 (m, 4H). |
| 557 | 5-(4-amino-6-cyanopyrrolo[2,1-f][1,2,4]triazin-7-yl)-N-((3R,4S)-4-fluoro-1-(4-(trifluoromethyl)cyclohexane-1-carbonyl)pyrrolidin-3-yl)-2-methoxynicotinamide Isomer 2 | 4-(trifluoromethyl)cyclohexyl | 575.2 | 8.75 (dd, J = 8.1, 2.3 Hz, 1H), 8.61-8.48 (m, 2H), 8.33 (br d, J = 16.5 Hz, 2H), 8.03 (s, 1H), 7.48 (s, 1H), 5.39-5.18 (m, 1H), 4.84-4.59 (m, 1H), 4.10-4.00 (m, 4H), 3.94-3.43 (m, 3H), 2.39-2.21 (m, 1H), 1.93-1.68 (m, 5H), 1.69-1.47 (m, 4H). |

TABLE 35-continued

Compounds in Table 35 were prepared by the following the methods described in Example 550. When diastereomers were separated, they are included as separate entries. If the stereochemistry is undefined, the product was isolated as a mixture of diastereomers.

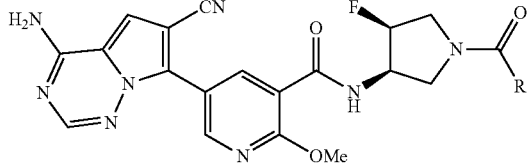

| Ex | Name | R | Obs. MS Ion | $^1$H NMR Assignments (500 MHz, DMSO-$d_6$) δ |
|---|---|---|---|---|
| 558 | 5-(4-amino-6-cyanopyrrolo[2,1-f][1,2,4]triazin-7-yl)-N-((3R,4S)-4-fluoro-1-(4-hydroxy-4-(trifluoromethyl)cyclohexane-1-carbonyl)pyrrolidin-3-yl)-2-methoxynicotinamide | cyclohexyl-OH, CF$_3$ | 591.1 | 8.75 (dd, J = 8.9, 2.1 Hz, 1H), 8.60-8.50 (m, 2H), 8.36 (br s, 1H), 8.32 (br s, 1H), 8.04 (s, 1H), 7.49 (d, J = 1.2 Hz, 1H), 5.40-5.18 (m, 1H), 4.85-4.59 (m, 1H), 4.07 (d, J = 7.0 Hz, 3H), 4.06-3.43 (m, 5H), 2.10-1.47 (m, 9H). |
| 559 | 5-(4-amino-6-cyanopyrrolo[2,1-f][1,2,4]triazin-7-yl)-N-((3R,4S)-4-fluoro-1-(3-hydroxy-3-(trifluoromethyl)cyclobutane-1-carbonyl)pyrrolidin-3-yl)-2-methoxynicotinamide | cyclobutyl-OH, CF$_3$ | 563.1 | 8.74 (dd, J = 6.1, 2.1 Hz, 1H), 8.59-8.50 (m, 2H), 8.35 (br s, 1H), 8.31 (br s, 1H), 8.03 (s, 1H), 7.47 (s, 1H), 5.39-5.18 (m, 1H), 4.82-4.57 (m, 1H), 4.06 (d, J = 5.2 Hz, 3H), 3.95-3.54 (m, 3H), 3.30-3.14 (m, 1H), 3.01-2.89 (m, 1H), 2.65-2.53 (m, 2H), 2.43-2.31 (m, 2H). |
| 560 | 5-(4-amino-6-cyanopyrrolo[2,1-f][1,2,4]triazin-7-yl)-N-((3R,4S)-4-fluoro-1-(3,3,3-trifluoro-2,2-dimethylpropanoyl)pyrrolidin-3-yl)-2-methoxynicotinamide | C(Me)(Me)CF$_3$ | 535.1 | 8.73 (s, 1H), 8.55 (br s, 2H), 8.33 (br s, 1H), 8.23 (br s, 1H), 8.00 (s, 1H), 7.46 (s, 1H), 5.37-5.17 (m, 1H), 4.80-4.57 (m, 1H), 4.05 (s, 3H), 3.97-3.40 (m, 4H), 1.46 (s, 3H), 1.43 (s, 3H). |
| 561 | 5-(4-amino-6-cyanopyrrolo[2,1-f][1,2,4]triazin-7-yl)-N-((3R,4S)-4-fluoro-1-(2-fluoro-2-methylpropanoyl)pyrrolidin-3-yl)-2-methoxynicotinamide | C(Me)(Me)F | 485.1 | 8.74 (d, J = 2.4 Hz, 1H), 8.60-8.49 (m, 2H), 8.34 (br s, 1H), 8.31 (br s, 1H), 8.03 (s, 1H), 7.48 (s, 1H), 5.39-5.16 (m, 1H), 4.84-4.60 (m, 1H), 4.26-4.07 (m, 1H), 4.06 (s, 3H), 4.05-3.52 (m, 3H), 1.58-1.54 (m, 3H), 1.53-1.50 (m, 3H). |

Example 562: 5-(4-amino-5-(trifluoromethyl)pyrrolo[2,1-f][1,2,4]triazin-7-yl)-3-fluoro-N-((3R,4S)-4-fluoro-1-(4,4,4-trifluoro-3-hydroxy-3-(trifluoromethyl)butanoyl) pyrrolidin-3-yl)-2-methylbenzamide

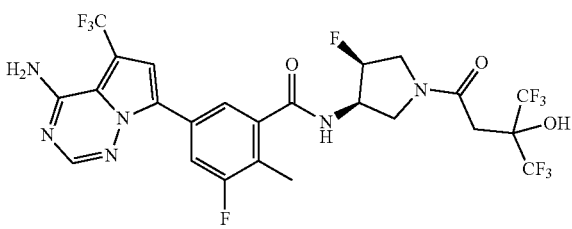 [SMILES: Cc1c(F)cc(-c2cc(C(F)(F)F)c3c(N)ncnn23)cc1C(=O)N[C@@H]1CN(C(=O)CC(O)(C(F)(F)F)C(F)(F)F)C[C@@H]1F]

562A: (3-fluoro-5-(methoxycarbonyl)-4-methylphenyl)boronic acid: A degassed solution of methyl 5-bromo-3-fluoro-2-methylbenzoate (430 mg, 1.740 mmol), 4,4,4',4',5,5,5',5'-octamethyl-2,2'-bi(1,3,2-dioxaborolane) (575 mg, 2.263 mmol), potassium acetate (273 mg, 2.78 mmol) and PdCl$_2$(dppf)-CH$_2$Cl$_2$ adduct (114 mg, 0.139 mmol) in dioxane (10 mL) was heated to 65° C. for 16 h. The reaction mixture was used as-is.

562B: methyl 5-(4-amino-5-(trifluoromethyl)pyrrolo[2,1-f][1,2,4]triazin-7-yl)-3-fluoro-2-methylbenzoate: A degassed solution of 7-bromo-5-(trifluoromethyl)pyrrolo[2,1-f][1,2,4]triazin-4-amine (450 mg, 1.601 mmol), (3-fluoro-5-(methoxycarbonyl)-4-methylphenyl)boronic acid (367 mg, 1.729 mmol), tripotassium phosphate (2 M in water) (2.402 mL, 4.80 mmol) and 1,1'-bis(diphenylphosphino)ferrocene palladium dichloride —CH$_2$Cl$_2$ adduct (78 mg, 0.096 mmol) was stirred at 75° C. for 2 h. The reaction mixture was purified on a silica gel column with Hexanes/EtOAc (100/0 to 0/100) to yield methyl 5-(4-amino-5-(trifluoromethyl)pyrrolo[2,1-f][1,2,4]triazin-7-yl)-3-fluoro-2-methylbenzoate (547 mg, 1.334 mmol, 83% yield).

MS ESI m/z 369.1 (M+H)$^+$ $^1$H NMR (400 MHz, CD$_3$OD) δ 8.34 (s, 1H), 8.14-8.07 (m, 2H), 7.44 (s, 1H), 3.96 (s, 3H), 2.52 (d, J=2.3 Hz, 3H).

562C: 5-(4-amino-5-(trifluoromethyl)pyrrolo[2,1-f][1,2,4]triazin-7-yl)-3-fluoro-2-methylbenzoic acid, sodium salt: A solution of methyl 5-(4-amino-5-(trifluoromethyl)pyrrolo[2,1-f][1,2,4]triazin-7-yl)-3-fluoro-2-methylbenzoate (547 mg, 1.485 mmol) and NaOH, 1 M solution (2.2 mL, 2.23 mmol) in MeOH (10 mL) was heated to 100° C. for 15 min. The reaction mixture was concentrated to yield 5-(4-amino-5-(trifluoromethyl) pyrrolo[2,1-f][1,2,4]triazin-7-yl)-3-fluoro-2-methylbenzoic acid, sodium salt (619 mg, 1.747 mmol, —100% yield).

562D: tert-butyl (3R,4S)-3-(5-(4-amino-5-(trifluoromethyl)pyrrolo[2,1-f][1,2,4]triazin-7-yl)-3-fluoro-2-methylbenzamido)-4-fluoropyrrolidine-1-carboxylate: To a solution of 5-(4-amino-5-(trifluoromethyl)pyrrolo[2,1-f][1,2,4]triazin-7-yl)-3-fluoro-2-methylbenzoic acid, sodium salt (526 mg, 1.485 mmol), tert-butyl (3R,4S)-3-amino-4-fluoropyrrolidine-1-carboxylate (334 mg, 1.633 mmol) and DIPEA (0.778 mL, 4.45 mmol) in DMF (8 mL) was added BOP (788 mg, 1.782 mmol). The reaction mixture was stirred at 23° C. for 2 h. The reaction mixture was diluted with EtOAc (80 mL) which was washed with 10% LiCl solution (2×30 mL), brine (30 mL) and dried over $Na_2SO_4$. Filtration and concentration yielded tert-butyl (3R,4S)-3-(5-(4-amino-5-(trifluoromethyl)pyrrolo[2,1-f][1,2,4]triazin-7-yl)-3-fluoro-2-methylbenzamido)-4-fluoropyrrolidine-1-carboxylate (515 mg, 0.953 mmol, 64% yield).

MS ESI m/z 541.1 (M+H)$^+$ $^1$H NMR (400 MHz, $CD_3OD$) δ 8.11 (s, 1H), 8.03 (dd, J=11.3, 1.5 Hz, 1H), 7.91 (s, 1H), 7.47 (s, 1H), 5.39-5.20 (m, 1H), 4.82-4.65 (m, 1H), 3.96-3.41 (m, 4H), 2.38 (d, J=2.0 Hz, 3H), 1.51 (s, 9H).

562E: 5-(4-amino-5-(trifluoromethyl)pyrrolo[2,1-f][1,2,4]triazin-7-yl)-3-fluoro-N-((3R,4S)-4-fluoropyrrolidin-3-yl)-2-methylbenzamide, 1.25 TFA: A solution of tert-butyl (3R,4S)-3-(5-(4-amino-5-(trifluoromethyl)pyrrolo[2,1-f][1,2,4]triazin-7-yl)-3-fluoro-2-methylbenzamido)-4-fluoropyrrolidine-1-carboxylate (515 mg, 0.953 mmol) and TFA (1.835 mL, 23.82 mmol) in $CH_2Cl_2$ (5 mL) was stirred at 23° C. for 1 h. The reaction mixture was concentrated and triturated in ether (20 mL). The solid was collected as 5-(4-amino-5-(trifluoromethyl)pyrrolo[2,1-f][1,2,4]triazin-7-yl)-3-fluoro-N-((3R,4S)-4-fluoropyrrolidin-3-yl)-2-methylbenzamide, 1.25 TFA (578.5 mg, 0.949 mmol, 100% yield).

MS ESI m/z 441.1 (M+H)$^+$ $^1$H NMR (400 MHz, $CD_3OD$) δ 8.10 (s, 1H), 8.07-8.02 (m, 1H), 7.94 (s, 1H), 7.47 (s, 1H), 5.56-5.38 (m, 1H), 4.98-4.90 (m, 1H), 3.90-3.60 (m, 4H), 2.38 (d, J=2.0 Hz, 3H).

562: To a solution of 5-(4-amino-5-(trifluoromethyl)pyrrolo[2,1-f][1,2,4]triazin-7-yl)-3-fluoro-N-((3R,4S)-4-fluoropyrrolidin-3-yl)-2-methylbenzamide, 1.25 TFA (15 mg, 0.026 mmol), 4,4,4-trifluoro-3-hydroxy-3-(trifluoromethyl)butanoic acid (5.8 mg, 0.026 mmol) and DIPEA (0.013 mL, 0.077 mmol) in DMF (1 mL) was added BOP (13.7 mg, 0.031 mmol) and stirred at 23° C. for 16 h. The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 min, then a 3-min hold at 100% B; Flow: 20 mL/min. Fractions containing the desired product were combined and dried via centrifugal evaporation to yield the final product (5.2 mg, 7.63 μmol, 30%).

MS ESI m/z 649.2 (M+H)$^+$

1H NMR (500 MHz, DMSO-d6) δ 8.92-8.81 (m, 1H), 8.20 (s, 1H), 8.12-8.03 (m, 1H), 7.90 (br d, J=5.2 Hz, 1H), 7.65 (d, J=4.9 Hz, 1H), 5.46-5.20 (m, 1H), 4.86-4.56 (m, 1H), 4.22-3.32 (m, 4H merge with water), 3.20-2.90 (m, 2H), 2.29 (s, 3H).

Example 563: 5-(4-amino-5-(trifluoromethyl)pyrrolo[2,1-f][1,2,4]triazin-7-yl)-N-(4,4-difluoro-1-((R)-3,3,3-trifluoro-2-hydroxy-2-methylpropanoyl)pyrrolidin-3-yl)-2-methoxynicotinamide

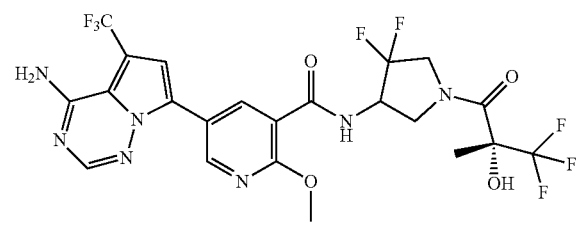 [SMILES: COc1ncc(-c2cc(C(F)(F)F)c3c(N)ncnn23)cc1C(=O)NC1CN(C(=O)[C@@](C)(O)C(F)(F)F)CC1(F)F]

563A: tert-butyl 4-(5-(4-amino-5-(trifluoromethyl)pyrrolo[2,1-f][1,2,4]triazin-7-yl)-2-methoxynicotinamido)-3,3-difluoropyrrolidine-1-carboxylate: To a solution of 5-(4-amino-5-(trifluoromethyl)pyrrolo[2,1-f][1,2,4]triazin-7-yl)-2-methoxynicotinic acid (130 mg, 0.368 mmol), tert-butyl 4-amino-3,3-difluoropyrrolidine-1-carboxylate (82 mg, 0.368 mmol) and DIPEA (0.193 mL, 1.104 mmol) in DMF (2 mL) was added BOP (195 mg, 0.442 mmol). The reaction mixture was stirred at 23° C. for 2 h. The reaction mixture was diluted with EtOAc (80 mL) which was washed with 10% LiCl solution (2×30 mL), brine (30 mL) and dried over anhydrous sodium sulfate. Filtration and concentration yielded tert-butyl 4-(5-(4-amino-5-(trifluoromethyl)pyrrolo[2,1-f][1,2,4]triazin-7-yl)-2-methoxynicotinamido)-3,3-difluoropyrrolidine-1-carboxylate (248 mg, 0.439 mmol, ~100% yield).

MS ESI m/z 558.1 (M+H)$^+$ $^1$H NMR (400 MHz, DMSO-d$_6$) δ 8.94 (d, J=2.4 Hz, 1H), 8.69 (d, J=2.4 Hz, 1H), 8.65 (d, J=8.7 Hz, 1H), 8.18 (s, 1H), 7.63 (s, 1H), 5.14-4.94 (m, 1H), 4.03 (s, 3H), 3.90-3.47 (m, 4H), 1.43 (s, 9H).

563B: 5-(4-amino-5-(trifluoromethyl)pyrrolo[2,1-f][1,2,4]triazin-7-yl)-N-(4,4-difluoropyrrolidin-3-yl)-2-methoxynicotinamide, TFA: This compound was prepared using the procedure reported to prepare 562E. 5-(4-amino-5-(trifluoromethyl)pyrrolo[2,1-f][1,2,4]triazin-7-yl)-N-(4,4-difluoropyrrolidin-3-yl)-2-methoxynicotinamide, TFA was isolated (259.5 mg, 0.373 mmol, —100% yield).

MS ESI m/z 458.1 (M+H)$^+$ $^1$H NMR (400 MHz, $CD_3OD$) δ 9.01 (s, 2H), 8.08 (s, 1H), 7.44 (s, 1H), 5.08-4.95 (m, 1H), 4.20 (s, 3H), 4.05-3.47 (m, 4H).

563: This compound was prepared using the procedure reported to prepare Example 562. 5-(4-amino-5-(trifluoromethyl)pyrrolo[2,1-f][1,2,4]triazin-7-yl)-N-(4,4-difluoro-1-((R)-3,3,3-trifluoro-2-hydroxy-2-methylpropanoyl)pyrrolidin-3-yl)-2-methoxynicotinamide (13.3 mg, 21 μmol, 29%) was isolated.

MS ESI m/z 598.0 (M+H)$^+$

1H NMR (500 MHz, DMSO-d6) δ 8.86 (d, J=1.5 Hz, 1H), 8.72 (br t, J=8.2 Hz, 1H), 8.63 (br d, J=4.9 Hz, 1H), 8.11 (s, 1H), 7.53 (s, 1H), 5.14-4.87 (m, 1H), 4.46-4.24 (m, 1H), 4.04-3.77 (m, 7H merge with water), 1.53 (br d, J=14.0 Hz, 3H).

Example 564: 2-chloro-3-fluoro-N-((3R,4S)-4-fluoro-1-((R)-3,3,3-trifluoro-2-hydroxy-2-methylpropanoyl)pyrrolidin-3-yl)-5-(4-((R)-3,3,3-trifluoro-2-hydroxy-2-methylpropanamido)-5-(trifluoromethyl)pyrrolo[2,1-f][1,2,4]triazin-7-yl)benzamide

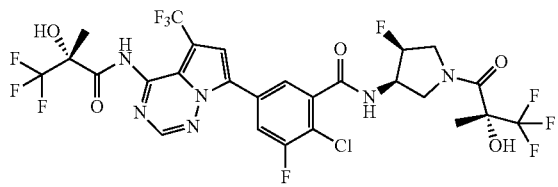 [SMILES: C[C@@](O)(C(=O)Nc1ncnn2c(-c3cc(F)c(Cl)c(C(=O)N[C@@H]4CN(C(=O)[C@@](C)(O)C(F)(F)F)C[C@@H]4F)c3)cc(C(F)(F)F)c12)C(F)(F)F]

To a solution of 5-(4-amino-5-(trifluoromethyl)pyrrolo[2,1-f][1,2,4]triazin-7-yl)-2-chloro-3-fluoro-N-((3R,4S)-4-fluoropyrrolidin-3-yl)benzamide, 1.0 TFA (15 mg, 0.026 mmol), (R)-3,3,3-trifluoro-2-hydroxy-2-methylpropionic acid (4.13 mg, 0.026 mmol) and DIPEA (0.014 mL, 0.078 mmol) in DMF (1 mL) was added BOP (11.54 mg, 0.026 mmol). The reaction mixture was stirred at 23° C. for 2 h The crude material was purified via preparative LC/MS with the following conditions: Column: XBridge C18, 19×200 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 min, then a 3-min hold at 100% B; Flow: 20 mL/min. Fractions containing the desired product were combined and dried via centrifugal evaporation to yield the final product (4 mg, 5.40 μmol, 21%).

MS ESI m/z 741.2 (M+H)+

1H NMR (500 MHz, DMSO-d6) δ 9.10-8.91 (m, 1H), 8.35 (br d, J=8.5 Hz, 1H), 8.16-8.05 (m, 1H), 7.95 (s, 1H), 7.87-7.63 (m, 1H), 7.29-6.98 (m, 1H), 5.40-5.13 (m, 1H), 4.73-4.52 (m, 1H), 4.46-4.25 (m, 1H), 4.08-3.53 (m, 3H), 1.59-1.42 (m, 6H).

Example 565: 5-(4-amino-5-(trifluoromethyl)pyrrolo[2,1-f][1,2,4]triazin-7-yl)-4-fluoro-N-((3R,4S)-4-fluoro-1-(4,4,4-trifluoro-3-hydroxy-3-(trifluoromethyl)butanoyl) pyrrolidin-3-yl)-2-methoxybenzamide

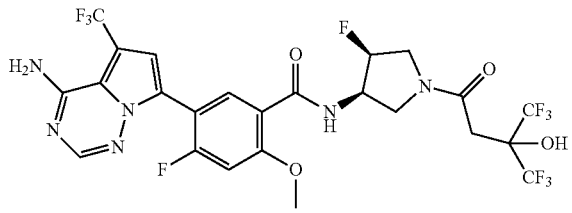 [SMILES: COc1cc(F)c(-c2cc(C(F)(F)F)c3c(N)ncnn23)cc1C(=O)N[C@@H]1CN(C(=O)CC(O)(C(F)(F)F)C(F)(F)F)C[C@@H]1F]

This compound was prepared using the procedure reported to prepare Example 563. 5-(4-amino-5-(trifluoromethyl)pyrrolo[2,1-f][1,2,4]triazin-7-yl)-4-fluoro-N-((3R,4S)-4-fluoro-1-(4,4,4-trifluoro-3-hydroxy-3-(trifluoromethyl)butanoyl) pyrrolidin-3-yl)-2-methoxybenzamide (9.7 mg, 14 μmol, 54%) was isolated.

MS ESI m/z 665.1 (M+H)+

1H NMR (500 MHz, DMSO-d6) δ 8.46-8.35 (m, 1H), 8.17 (br dd, J=16.2, 8.5 Hz, 1H), 8.08 (s, 1H), 7.32-7.19 (m, 2H), 5.43-5.19 (m, 1H), 4.87-4.59 (m, 1H), 4.21-3.24 (m, 7H merge with water), 3.12-2.87 (m, 2H).

Example 566: 5-(4-amino-5-(trifluoromethyl)pyrrolo[2,1-f][1,2,4]triazin-7-yl)-N-((3R,4S)-1-(3,3-difluorocyclobutane-1-carbonyl)-4-fluoropyrrolidin-3-yl)-2-(methylamino)benzamide

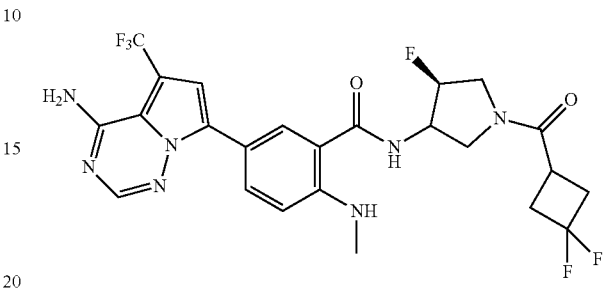

566A: methyl 2-(((benzyloxy)carbonylxmethyl)amino)-5-bromobenzoate: To a solution of methyl 5-bromo-2-(methylamino)benzoate (200 mg, 0.819 mmol) and N-methylmorpholine (0.135 mL, 1.229 mmol) in THF (5 mL) at 0° C. was added benzyl chloroformate (0.13 mL, 0.901 mmol). The reaction mixture was warmed up to 23° C. and stirred for 16 h. The reaction mixture was diluted with EtOAc (100 mL) which was washed with 10% LiCl solution (2×20 mL), brine (20 mL) and dried over anhydrous sodium sulfate. Filtration and concentration yielded methyl 2-(((benzyloxy)carbonylxmethyl)amino)-5-bromobenzoate (267.6 mg, 0.688 mmol, 84% yield).

MS ESI m/z 378.1 (M+H)+

1H NMR (400 MHz, CDCl3) δ 8.02 (d, J=2.5 Hz, 1H), 7.51-7.30 (m, 6H), 6.58 (d, J=9.0 Hz, 1H), 5.42 (s, 2H), 3.88 (s, 3H), 2.83 (s, 3H)

566B: sodium 5-bromo-2-(methylamino)benzoate: A solution of methyl 2-(((benzyloxy)carbonylXmethyl)amino)-5-bromobenzoate (267.6 mg, 0.708 mmol) and NaOH, 1 N solution (1.4 mL, 1.415 mmol) in MeOH (3 mL) was heated to 100° C. for 15 min and 110° C. for 2 h under microwave. The reaction mixture was concentrated to yield sodium 5-bromo-2-(methylamino)benzoate (246 mg, 0.976 mmol, —100% yield).

566C: tert-butyl (3R,4S)-3-(5-bromo-2-(methylamino)benzamido)-4-fluoropyrrolidine-1-carboxylate: To a solution of sodium 5-bromo-2-(methylamino)benzoate (246 mg, 0.976 mmol), tert-butyl (3R,4S)-3-amino-4-fluoropyrrolidine-1-carboxylate (130 mg, 0.634 mmol) and DIPEA (0.223 mL, 1.279 mmol) in DMF (4 mL) was added BOP (282 mg, 0.637 mmol). The reaction mixture was stirred at 23° C. for 3 d. The reaction mixture was diluted with EtOAc (100 mL) which was washed with 10% LiCl solution (2×20 mL), brine (20 mL) and dried over anhydrous sodium sulfate. Filtration and concentration yielded a crude product which was purified on a silica gel column with Hexanes/EtOAc (100/0 to 0/100) to yield tert-butyl (3R,4S)-3-(5-bromo-2-(methylamino)benzamido)-4-fluoropyrrolidine-1-carboxylate (189 mg, 0.420 mmol, 43% yield).

MS ESI m/z 416.1 (M+H)+

1H NMR (400 MHz, DMSO-d6) δ 8.53 (br dd, J=11.8, 6.8 Hz, 1H), 7.79 (br d, J=6.1 Hz, 1H), 7.44 (dd, J=8.9, 2.3 Hz, 1H), 6.96-6.95 (m, 1H), 5.31-5.07 (m, 1H), 4.67-4.42 (m, 1H), 3.78-3.45 (m, 4H), 2.84-2.74 (m, 3H), 1.42 (s, 9H).

566D: tert-butyl (3R,4R)-3-fluoro-4-(2-(methylamino)-5-(4,4,5,5-tetramethyl-1,3,2-dioxaborolan-2-yl)benzamido)

pyrrolidine-1-carboxylate: A degassed solution of tert-butyl (3R,4S)-3-(5-bromo-2-(methylamino)benzamido)-4-fluoropyrrolidine-1-carboxylate (189 mg, 0.454 mmol), 4,4,4',4',5,5,5',5'-octamethyl-2,2'-bi(1,3,2-dioxaborolane) (121 mg, 0.477 mmol), potassium acetate (71.3 mg, 0.726 mmol) and PdCl$_2$(dppf)-CH$_2$Cl$_2$ adduct (18.54 mg, 0.023 mmol) in dioxane (5 mL) was heated to 100° C. for 16 h. The reaction mixture was used as-is.

MS ESI m/z 464.1 (M+H)$^+$

566E: tert-butyl (3R,4S)-3-(5-(4-amino-5-(trifluoromethyl)pyrrolo[2,1-f][1,2,4]triazin-7-yl)-2-(methylamino)benzamido)-4-fluoropyrrolidine-1-carboxylate: A degassed solution of 7-bromo-5-(trifluoromethyl)pyrrolo[2,1-f][1,2,4]triazin-4-amine (130 mg, 0.463 mmol), tert-butyl (3R,4R)-3-fluoro-4-(2-(methylamino)-5-(4,4,5,5-tetramethyl-1,3,2-dioxaborolan-2-yl)benzamido)pyrrolidine-1-carboxylate (210 mg, 0.453 mmol), tripotassium phosphate (2 M in water) (0.694 mL, 1.388 mmol) and 1,1'-bis(diphenylphosphino)ferrocene palladium dichloride —CH$_2$Cl$_2$ adduct (18.89 mg, 0.023 mmol) was stirred at 100° C. for 4 h. The reaction mixture was purified on a silica gel column with Hexanes/EtOAc (100/0 to 0/100) to yield tert-butyl (3R,4S)-3-(5-(4-amino-5-(trifluoromethyl)pyrrolo[2,1-f][1,2,4]triazin-7-yl)-2-(methylamino)benzamido)-4-fluoropyrrolidine-1-carboxylate (54.6 mg, 0.091 mmol, 20% yield).

MS ESI m/z 538.1 (M+H)$^+$.

566F: 5-(4-amino-5-(trifluoromethyl)pyrrolo[2,1-f][1,2,4]triazin-7-yl)-N-((3R,4S)-4-fluoropyrrolidin-3-yl)-2-(methylamino)benzamide, TFA (54.8 mg, 0.099 mmol, 98% yield) was prepared using the procedure reported to prepare Example 562E.

MS ESI m/z 438.1 (M+H)$^+$

566: 5-(4-amino-5-(trifluoromethyl)pyrrolo[2,1-f][1,2,4]triazin-7-yl)-N-((3R,4S)-1-(3,3-difluorocyclobutane-1-carbonyl)-4-fluoropyrrolidin-3-yl)-2-(methylamino)benzamide was prepared using the procedure reported to prepare Example 562.

MS ESI m/z 556.2 (M+H)$^+$

1H NMR (500 MHz, DMSO-d6) δ 8.64-8.49 (m, 1H), 8.12-8.08 (m, 2H), 8.05 (br d, J=5.2 Hz, 1H), 7.80-7.68 (m, 1H), 7.39 (s, 1H), 6.79 (dd, J=9.2, 1.8 Hz, 1H), 5.43-5.15 (m, 1H), 4.82-4.46 (m, 1H), 4.22-3.37 (m, 4H merge with water), 3.19-3.16 (m, 1H), 2.91-2.68 (m, 7H).

Example 567: 5-(4-amino-5-(trifluoromethyl)pyrrolo[2,1-f][1,2,4]triazin-7-yl)-2-ethyl-3-fluoro-N-((3R,4S)-4-fluoro-1-(4,4,4-trifluoro-3-hydroxy-3-(trifluoromethyl) butanoyl)pyrrolidin-3-yl)benzamide

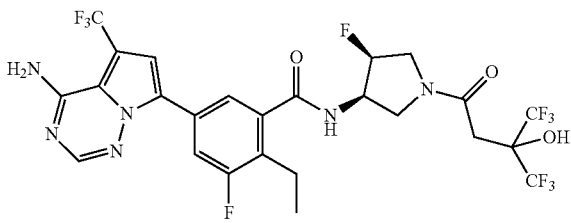 [SMILES: CCc1c(F)cc(-c2cc(C(F)(F)F)c3c(N)ncnn23)cc1C(=O)N[C@@H]1CN(C(=O)CC(O)(C(F)(F)F)C(F)(F)F)C[C@@H]1F]

567A: methyl 5-bromo-2-(bromomethyl)-3-fluorobenzoate: To a solution of methyl 5-bromo-3-fluoro-2-methylbenzoate (500 mg, 2.024 mmol) at 75° C. was added NBS (720 mg, 4.05 mmol), followed by AIBN (83 mg, 0.506 mmol). The reaction mixture was stirred at 75° C. for 2.5 h and cooled to rt. The reaction mixture was purified on a silica gel column with Hexanes/EtOAc (100/0 to 50/50) to yield methyl 5-bromo-2-(bromomethyl)-3-fluorobenzoate (649.6 mg, 1.949 mmol, 96% yield).

$^1$H NMR (400 MHz, CD$_3$OD) δ 7.95 (t, J=1.5 Hz, 1H), 7.66 (dd, J=9.3, 2.0 Hz, 1H), 4.97 (d, J=1.8 Hz, 2H), 3.97 (s, 3H).

567B: methyl 5-bromo-2-ethyl-3-fluorobenzoate: To a solution of copper(I) iodide (466 mg, 2.448 mmol) in Et$_2$O (5 mL) under N$_2$ at 0° C. as added methyllithium, 1.6M in Et$_2$O (3.1 mL, 4.90 mmol) which was stirred for 30 min. The reaction mixture was cooled to −78° C. and methyl 5-bromo-2-(bromomethyl)-3-fluorobenzoate (532 mg, 1.632 mmol) in Et$_2$O (5 mL) was added dropwise. The reaction mixture was stirred at −78° C. for 1 h. The reaction mixture temperature was raised to 0° C., it was stirred for 30 min and quenched with saturated NH$_4$Cl solution. The aqueous phase was extracted with Et$_2$O (100 mL). The organic layer was washed with water (50 mL), brine (50 mL) and dried over Na$_2$SO$_4$. Filtration and concentration yielded a crude product which was purified on a silica gel column with Hexanes/CH$_2$Cl$_2$ (100/0 to 80/20) to yield methyl 5-bromo-2-ethyl-3-fluorobenzoate (260 mg, 0.996 mmol, 61% yield).

$^1$H NMR (400 MHz, CD$_3$OD) δ 7.81-7.77 (m, 1H), 7.52 (dd, J=9.4, 2.0 Hz, 1H), 3.92 (s, 3H), 2.94 (qd, J=7.4, 2.1 Hz, 2H), 1.20 (t, J=7.5 Hz, 3H).

567C: sodium 5-bromo-2-ethyl-3-fluorobenzoate was prepared using the procedure reported to prepare Example 562C (263 mg, 0.978 mmol, 98% yield).

567D: tert-butyl (3R,4S)-3-(5-bromo-2-ethyl-3-fluorobenzamido)-4-fluoropyrrolidine-1-carboxylate was prepared using the procedure reported to prepare Example 566C (351 mg, 0.810 mmol, 83% yield).

MS ESI m/z 433.1 (M+H)$^+$ $^1$H NMR (400 MHz, CD$_3$OD) δ 7.41 (dd, J=9.5, 1.9 Hz, 1H), 7.37 (s, 1H), 5.35-5.17 (m, 1H), 4.77-4.59 (m, 1H), 3.86 (q, J=9.1 Hz, 1H), 3.78-3.57 (m, 2H), 3.33-3.31 (m, 1H merge with MeOH), 2.74 (q, J=7.5 Hz, 2H), 1.50 (s, 9H), 1.20 (t, J=7.5 Hz, 3H).

569E: tert-butyl (3R,4S)-3-(2-ethyl-3-fluoro-5-(4,4,5,5-tetramethyl-1,3,2-dioxaborolan-2-yl)benzamido)-4-fluoropyrrolidine-1-carboxylate was prepared using the procedure reported to prepare Example 566D.

MS ESI m/z 481.1 (M+H)$^+$

567F: tert-butyl (3R,4S)-3-(5-(4-amino-5-(trifluoromethyl)pyrrolo[2,1-f][1,2,4]triazin-7-yl)-2-ethyl-3-fluorobenzamido)-4-fluoropyrrolidine-1-carboxylate was prepared using the procedure reported to prepare Example 566E (403 mg, 0.727 mmol, 90% yield).

MS ESI m/z 555.1 (M+H)$^+$

567G: 5-(4-amino-5-(trifluoromethyl)pyrrolo[2,1-f][1,2,4]triazin-7-yl)-2-ethyl-3-fluoro-N-((3R,4S)-4-fluoropyrrolidin-3-yl)benzamide, TFA was prepared using the procedure reported to prepare Example 562E (395 mg, 0.695 mmol, 96% yield).

MS ESI m/z 455.1 (M+H)$^+$

567: 5-(4-amino-5-(trifluoromethyl)pyrrolo[2,1-f][1,2,4]triazin-7-yl)-2-ethyl-3-fluoro-N-((3R,4S)-4-fluoro-1-(4,4,4-trifluoro-3-hydroxy-3-(trifluoromethyl) butanoyl)pyrrolidin-3-yl)benzamide was prepared using the procedure reported to prepare Example 562.

MS ESI m/z 663.0 (M+H)$^+$

1H NMR (500 MHz, DMSO-d6) δ 8.98-8.94 (m, 1H), 8.92-8.87 (m, 1H), 8.21 (s, 1H), 8.07 (br dd, J=11.8, 4.8 Hz, 1H), 7.86 (br d, J=7.8 Hz, 1H), 7.65 (d, J=6.6 Hz, 1H), 5.46-5.22 (m, 1H), 4.82-4.55 (m, 1H), 4.20-3.35 (m, 4H merge with water), 3.13-2.92 (m, 2H), 2.75 (br d, J=5.1 Hz, 2H), 1.18 (br t, J=7.3 Hz, 3H).

Example 568: 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-4-fluoro-2-methoxybenzamide

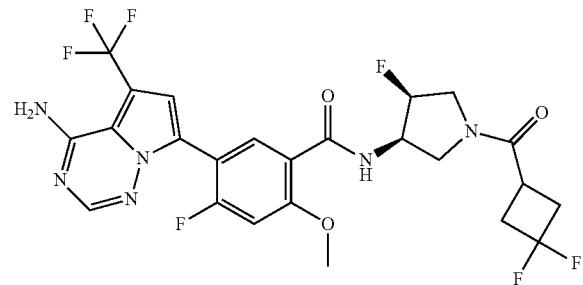 [SMILES: COc1cc(F)c(-c2cc(C(F)(F)F)c3c(N)ncnn23)cc1C(=O)N[C@@H]1CN(C(=O)C2CC(F)(F)C2)C[C@@H]1F]

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-4-fluoro-2-methoxybenzamide was prepared using the procedure reported to prepare Example 562.

MS ESI m/z 575.3 (M+H)$^+$

LC/MS retention time using Method 1=1.74 min

Example 569: 5-[4-amino-5-(trifluoromethyl)pyrrolo[2,1-f][1,2,4]triazin-7-yl]-3-fluoro-N-[(3R,4S)-4-fluoro-1-[(2R)-3,3,3-trifluoro-2-hydroxy-2-methylpropanoyl]pyrrolidin-3-yl]-2-methylbenzamide

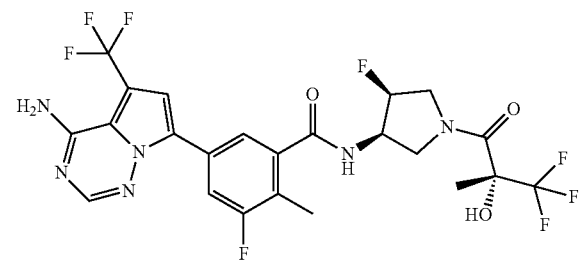 [SMILES: Cc1c(F)cc(-c2cc(C(F)(F)F)c3c(N)ncnn23)cc1C(=O)N[C@@H]1CN(C(=O)[C@@](C)(O)C(F)(F)F)C[C@@H]1F]

5-[4-amino-5-(trifluoromethyl)pyrrolo[2,1-f][1,2,4]triazin-7-yl]-3-fluoro-N-[(3R,4S)-4-fluoro-1-[(2R)-3,3,3-trifluoro-2-hydroxy-2-methylpropanoyl]pyrrolidin-3-yl]-2-methylbenzamide was prepared using the procedure reported to prepare Example 562.

MS ESI m/z 581.3 (M+H)$^+$

LC/MS retention time using Method 2=1.71 min

Example 570: 5-[4-amino-5-(trifluoromethyl)pyrrolo[2,1-f][1,2,4]triazin-7-yl]-3-fluoro-N-[(3R,4S)-4-fluoro-1-[4,4,4-trifluoro-3-hydroxy-3-(trifluoromethyl)butanoyl]pyrrolidin-3-yl]-2-(fluoromethyl)benzamide

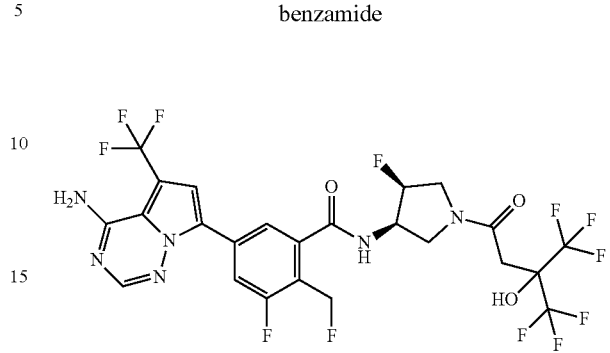

570A: methyl 5-bromo-2-(bromomethyl)-3-fluorobenzoate was prepared using the procedure reported to prepare Example 567A (648 mg, 1.962 mmol, 97% yield).

$^1$H NMR (400 MHz, CDCl$_3$) δ 7.97-7.94 (m, 1H), 7.47 (dd, J=8.9, 2.0 Hz, 1H), 4.96 (d, J=1.9 Hz, 2H), 4.01-3.98 (m, 3H).

570B: methyl 5-bromo-3-fluoro-2-(fluoromethyl)benzoate: To a solution of methyl 5-bromo-2-(bromomethyl)-3-fluorobenzoate (648 mg, 1.988 mmol) in THF (10 mL) was added tetrabutylammonium fluoride (6.0 mL, 5.96 mmol) at 0° C. The reaction mixture was warmed to room temperature and stirred for 1 h. The reaction mixture was concentrated to yield a crude product which was diluted with EtOAc (100 mL). The organics were washed with water (20 mL×2), brine (20 mL) and dried over Na$_2$SO$_4$. Filtration and concentration yielded a crude product which was purified on a silica gel column with Hexanes/EtOAc (100/0 to 50/50) to yield methyl 5-bromo-3-fluoro-2-(fluoromethyl)benzoate (269 mg, 1.015 mmol, 51% yield).

$^1$H NMR (400 MHz, CDCl$_3$) δ 7.93 (d, J=0.9 Hz, 1H), 7.50 (dt, J=8.9, 1.6 Hz, 1H), 5.84 (d, J=1.9 Hz, 1H), 5.72 (d, J=2.0 Hz, 1H), 3.97 (s, 3H).

570C: sodium 5-bromo-3-fluoro-2-(fluoromethyl)benzoate: A solution of methyl 5-bromo-3-fluoro-2-(fluoromethyl)benzoate (269 mg, 1.015 mmol) and NaOH, 1N solution (1.5 mL, 1.522 mmol) in MeOH (9 mL) was heated to 100° C. for 15 min under microwave. The reaction mixture was concentrated to yield sodium 5-bromo-3-fluoro-2-(fluoromethyl)benzoate (304 mg, 1.114 mmol, ~100% yield).

570D: tert-butyl (3R,4S)-3-(5-bromo-3-fluoro-2-(fluoromethyl)benzamido)-4-fluoropyrrolidine-1-carboxylate was prepared using the procedure reported to prepare Example 566C. (285 mg, 0.579 mmol, 57% yield)

MS ESI m/z 437.1 (M+H)$^+$ $^1$H NMR (400 MHz, CDCl$_3$) δ 7.59 (s, 1H), 7.45 (br d, J=8.8 Hz, 1H), 6.47 (br d, J=4.3 Hz, 1H), 5.67-5.46 (m, 2H), 5.30-5.09 (m, 1H), 4.87-4.67 (m, 1H), 4.08-3.97 (m, 1H), 3.91-3.55 (m, 2H), 3.30-3.17 (m, 1H), 1.50 (s, 9H).

570E: tert-butyl (3S,4R)-3-fluoro-4-(3-fluoro-2-(fluoromethyl)-5-(4,4,5,5-tetramethyl-1,3,2-dioxaborolan-2-yl)benzamido)pyrrolidine-1-carboxylate was prepared using the procedure reported to prepare Example 566D.

570F: tert-butyl (3R,4S)-3-(5-(4-amino-5-(trifluoromethyl)pyrrolo[2,1-f][1,2,4]triazin-7-yl)-3-fluoro-2-(fluoromethyl)benzamido)-4-fluoropyrrolidine-1-carboxylate was prepared using the procedure reported to prepare Example 566E (368 mg, 0.584 mmol, 90% yield).

MS ESI m/z 559.1 (M+H)$^+$

¹H NMR (400 MHz, CD₃OD) δ 8.21 (d, J=11.7 Hz, 1H), 8.14 (s, 1H), 8.06 (s, 1H), 7.58 (s, 1H), 5.70 (s, 1H), 5.58 (s, 1H), 5.38-5.18 (m, 1H), 4.81-4.68 (m, 1H), 3.96-3.85 (m, 1H), 3.80-3.57 (m, 3H), 3.37-3.30 (m, 1H), 1.22 (s, 9H).

570G: 5-(4-amino-5-(trifluoromethyl)pyrrolo[2,1-f][1,2,4]triazin-7-yl)-3-fluoro-2-(fluoromethyl)-N-((3R,4S)-4-fluoropyrrolidin-3-yl)benzamide, TFA was prepared using the procedure reported to prepare Example 562E (309 mg, 0.540 mmol, 82% yield).

MS ESI m/z 459.1 (M+H)⁺

570: 5-[4-amino-5-(trifluoromethyl)pyrrolo[2,1-f][1,2,4]triazin-7-yl]-3-fluoro-N-[(3R,4S)-4-fluoro-1-[4,4,4-trifluoro-3-hydroxy-3-(trifluoromethyl)butanoyl]pyrrolidin-3-yl]-2-(fluoromethyl)benzamide was prepared using the procedure reported to prepare Example 562 (5.9 mg, 8.9 μmol, 34% yield).

MS ESI m/z 667.1 (M+H)⁺

¹H NMR (500 MHz, DMSO-d6) δ 9.09-8.97 (m, 1H), 8.93-8.85 (m, 1H), 8.29-8.19 (m, 2H), 8.03 (br d, J=5.8 Hz, 1H), 7.74 (d, J=4.9 Hz, 1H), 5.70-5.53 (m, 2H), 5.45-5.22 (m, 1H), 4.86-4.55 (m, 1H), 4.22-3.63 (m, 3H), 3.55-2.89 (m, 3H merge with water).

Example 571: 3-[4-amino-5-(trifluoromethyl)pyrrolo[2,1-f][1,2,4]triazin-7-yl]-6-ethyl-2-fluoro-N-[(3R,4S)-4-fluoro-1-[4,4,4-trifluoro-3-hydroxy-3-(trifluoromethyl)butanoyl]pyrrolidin-3-yl]benzamide

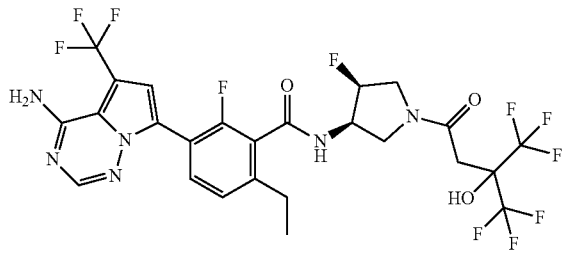 [SMILES: CCc1ccc(-c2cc(C(F)(F)F)c3c(N)ncnn23)c(F)c1C(=O)N[C@@H]1CN(C(=O)CC(O)(C(F)(F)F)C(F)(F)F)C[C@@H]1F]

Method 1: 571A ethyl 3-bromo-6-(bromomethyl)-2-fluorobenzoate was prepared using the procedure reported to prepare Example 567A (298 mg, 0.877 mmol, 92% yield).

¹H NMR (400 MHz, CDCl₃) δ 7.62 (dd, J=8.2, 6.8 Hz, 1H), 7.18-7.07 (m, 1H), 4.62 (s, 2H), 4.54-4.43 (m, 2H), 1.45 (t, J=7.2 Hz, 3H).

Method 1: 571B ethyl 3-bromo-6-ethyl-2-fluorobenzoate was prepared using the procedure reported to prepare Example 567B (105 mg, 0.382 mmol, 44% yield).

¹H NMR (400 MHz, CDCl₃) δ 7.53 (dd, J=8.1, 7.2 Hz, 1H), 6.95 (d, J=8.3 Hz, 1H), 4.45 (q, J=7.1 Hz, 2H), 2.69 (q, J=7.6 Hz, 2H), 1.42 (t, J=7.1 Hz, 3H), 1.24 (t, J=7.5 Hz, 3H)

Method 1: 571C sodium 3-bromo-6-ethyl-2-fluorobenzoate was prepared using the procedure reported to prepare Example 562C (88 mg, 0.327 mmol, 95% yield).

Method 2: 571D 1-bromo-4-ethyl-2-fluorobenzene: To a solution of 3-fluoro-4-bromo-acetophenone (2.0 g, 9.22 mmol) in TFA (18 mL) at 0° C. was added triethylsilane (2.94 mL, 18.43 mmol). The reaction mixture was warmed to 23° C. and stirred for 16 h. The reaction mixture was diluted with ether (150 mL) and washed with water (50 mL), 1.5 M Na₂HPO₄ solution (50 mL), water (50 mL) and brine (50 mL). The combined organics were dried over anhydrous sodium sulfate. Filtration and concentration yielded a crude product which was purified on a silica gel column with hexanes. The product was collected as 1-bromo-4-ethyl-2-fluorobenzene (1.35 g, 6.65 mmol, 72% yield).

¹H NMR (400 MHz, CD₃OD) δ 7.45 (dd, J=6.6, 2.0 Hz, 1H), 7.23-7.17 (m, 1H), 7.14-7.06 (m, 1H), 2.64 (q, J=7.6 Hz, 2H), 1.23 (t, J=7.6 Hz, 3H).

Method 2: 571E 3-bromo-6-ethyl-2-fluorobenzoic acid: To a solution of diisopropylamine (1.137 mL, 7.98 mmol) in THF (14 mL) was added 2.5 M n-butyllithium in Hexanes (2.9 mL, 7.31 mmol) dropwise at −20° C. under N₂. After stirring for 20 min, the mixture was cooled to −78° C., then 1-bromo-4-ethyl-2-fluorobenzene (1.35 g, 6.65 mmol) in THF (1 mL) was added dropwise. After stirring at −78° C. for 45 min, a piece of dry ice, carbon dioxide (2.9 g, 66.5 mmol) was added. The reaction mixture was allowed to warm to rt ON. The reaction mixture was quenched with dropwise addition of saturated aqueous ammonium chloride (1 mL) and concentrated to yield a crude product which was dissolved in EtOAc (20 mL). The organic phase was extracted with 1 N NaOH (3×20 mL). The combined aqueous layers were acidified with conc. HCl in an ice-water bath until pH ~2. The aqueous layer was extracted with EtOAc (80 mL). The organic layer was washed with brine (20 mL) and dried over Na₂SO₄. Filtration and concentration yielded 3-bromo-6-ethyl-2-fluorobenzoic acid (1.10 g, 4.45 mmol, 67% yield).

MS ESI m/z 247.1 (M+H)⁺

¹H NMR (400 MHz, CD₃OD) δ 7.74 (dd, J=6.2, 2.2 Hz, 1H), 7.69 (dd, J=6.0, 2.3 Hz, 1H), 2.69 (q, J=7.6 Hz, 2H), 1.26 (t, J=7.6 Hz, 3H).

571F: tert-butyl (3R,4S)-3-(3-bromo-6-ethyl-2-fluorobenzamido)-4-fluoropyrrolidine-1-carboxylate was prepared using the procedure reported to prepare Example 566C (121.4 mg, 0.280 mmol, 86% yield).

MS ESI m/z 433.1 (M+H)⁺

¹H NMR (400 MHz, CDCl₃) δ 7.54 (t, J=7.8 Hz, 1H), 6.99 (br d, J=8.1 Hz, 1H), 6.21-6.07 (m, 1H), 5.31-5.10 (m, 1H), 4.94-4.73 (m, 1H), 4.10-4.00 (m, 1H), 3.91-3.54 (m, 2H), 3.28-3.15 (m, 1H), 2.71 (br d, J=7.2 Hz, 2H), 1.51 (s, 9H), 1.30-1.20 (m, 3H)

571G: tert-butyl (3R,4S)-3-(6-ethyl-2-fluoro-3-(4,4,5,5-tetramethyl-1,3,2-dioxaborolan-2-yl)benzamido)-4-fluoropyrrolidine-1-carboxylate was prepared using the procedure reported to prepare Example 566D.

571F: tert-butyl (3R,4S)-3-(3-(4-amino-5-(trifluoromethyl)pyrrolo[2,1-f][1,2,4]triazin-7-yl)-6-ethyl-2-fluorobenzamido)-4-fluoropyrrolidine-1-carboxylate was prepared using the procedure reported to prepare Example 566E (168.3 mg, 0.276 mmol, 97% yield).

MS ESI m/z 555.1 (M+H)⁺

¹H NMR (400 MHz, CDCl₃) δ 8.09 (s, 1H), 7.93 (1, J=7.8 Hz, 1H), 7.22 (s, 2H), 6.32-6.16 (m, 1H), 5.83 (br s, 2H), 5.33-5.11 (m, 1H), 4.98-4.75 (m, 1H), 4.10-4.00 (m, 1H), 3.91-3.53 (m, 2H), 3.31-3.14 (m, 1H), 2.89-2.74 (m, 2H), 1.50 (s, 9H), 1.36-1.29 (m, 3H).

571 G: 3-(4-amino-5-(trifluoromethyl)pyrrolo[2,1-f][1,2,4]triazin-7-yl)-6-ethyl-2-fluoro-N-((3R,4S)-4-fluoropyrrolidin-3-yl)benzamide, TFA was prepared using the procedure reported to prepare Example 562E (146.4 mg, 0.258 mmol, 93% yield).

MS ESI m/z 455.1 (M+H)⁺

571: 3-[4-amino-5-(trifluoromethyl)pyrrolo[2,1-f][1,2,4]triazin-7-yl]-6-ethyl-2-fluoro-N-[(3R,4S)-4-fluoro-1-[4,4,4-trifluoro-3-hydroxy-3-(trifluoromethyl)butanoyl]pyrrolidin-3-yl]benzamide was prepared using the procedure reported to prepare Example 562 (6.4 mg, 9.7 μmol, 46% yield).

MS ESI m/z 663.3 (M+H)⁺

¹H NMR (500 MHz, DMSO-d₆) δ 9.19-9.05 (m, 1H), 8.09 (s, 1H), 7.84-7.73 (m, 1H), 7.33-7.23 (m, 2H), 5.45-5.17 (m, 1H), 4.85-4.53 (m, 1H), 4.19-3.22 (m, 4H merge with water), 3.12-2.87 (m, 2H), 2.66 (q, J=7.7 Hz, 2H), 1.20 (br t, J=6.7 Hz, 3H).

TABLE 36

Compounds in Table 36 were prepared by the methods detailed in Example 562. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 572 | 3-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-5-methoxybenzamide | H | 2-fluorophenyl | 561.2 | 1.67 (2) |
| 573 | 3-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-5-methoxybenzamide | H | CH(Me)CF₃ | 563.0 | 1.7 (1) |
| 574 | 3-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-5-methoxybenzamide | H | 3-fluorocyclobutyl | 539.2 | 1.53 (2) |
| 575 | 3-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-5-methoxybenzamide | H | 3-fluorocyclobutyl | 539.2 | 1.6 (1) |
| 576 | 3-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-5-methoxybenzamide | H | 1-fluorocyclopropyl | 525.1 | 1.6 (2) |
| 577 | 3-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-5-methoxybenzamide | H | CH₂C(OH)(CF₃)₂ | 647.3 | 1.93 (2) |

TABLE 36-continued

Compounds in Table 36 were prepared by the methods detailed in Example 562. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R[1] | R[2] | Obs. MS Ion | RT (Method) |
|---|---|---|---|---|---|
| 578 | 3-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-5-methoxybenzamide | H |  | 579.1 | 1.65 (2) |
| 579 | 3-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-5-methoxybenzamide | H |  | 593.3 | 1.63 (2) |
| 580 | 3-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-5-methoxybenzamide | H |  | 585.3 | 1.75 (1) |
| 581 | 3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-5-methoxybenzamide | H |  | 543.2 | 1.59 (2) |
| 582 | 3-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-5-methoxybenzamide | H |  | 593.3 | 1.74 (1) |
| 583 | 3-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-5-methoxybenzamide | H |  | 577.3 | 1.83 (1) |
| 584 | 3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-5-methoxybenzamide | H |  | 557.2 | 1.65 (2) |

TABLE 36-continued

Compounds in Table 36 were prepared by the methods detailed in Example 562. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 585 | 3-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-5-methoxybenzamide | H | —C(Me)(Me)F | 527.3 | 1.64 (2) |
| 586 | 3-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-5-methoxybenzamide | H | —CH₂CH(CF₃)CF₃ | 631.4 | 1.92 (1) |
| 587 | 3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-5-methoxybenzamide | H | 3,3-difluorocyclopentyl | 571.3 | 1.74 (1) |
| 588 | 3-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-5-methoxybenzamide | H | —C(Me)(Me)OH | 525.2 | 1.4 (2) |
| 589 | 3-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-5-methoxybenzamide | H | —CH₂CH(Me)Me | 523.1 | 1.68 (1) |
| 590 | 3-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-5-methoxybenzamide | H | —CH₂CF₃ | 549.2 | 1.6 (2) |
| 591 | 5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2,3-dimethoxybenzamide | OMe | —CH₂CH(Me)CF₃ | 607.2 | 1.86 (2) |
| 592 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2- | OMe | —C(CF₃)(OH)— (2R) | 609.1 | 1.67 (2) |

TABLE 36-continued

*Compounds in Table 36 were prepared by the methods detailed in Example 562. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.*

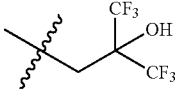

| Ex | Name | R¹ | R² | Obs. MS Ion | RT (Method) |
|---|---|---|---|---|---|
| | methylpropanoyl]pyrrolidin-3-yl]-2,3-dimethoxybenzamide | | | | |
| 593 | 5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2,3-dimethoxybenzamide | OMe | 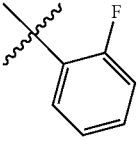 [SMILES: *c1ccccc1F] | 677.2 | 2.11 (1) |
| 594 | 5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2,3-dimethoxybenzamide | OMe | 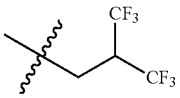 [SMILES: *CC(C(F)(F)F)C(F)(F)F] | 591.3 | 1.75 (2) |
| 595 | 5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2,3-dimethoxybenzamide | OMe | | 661.1 | 2.05 (1) |

TABLE 37

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

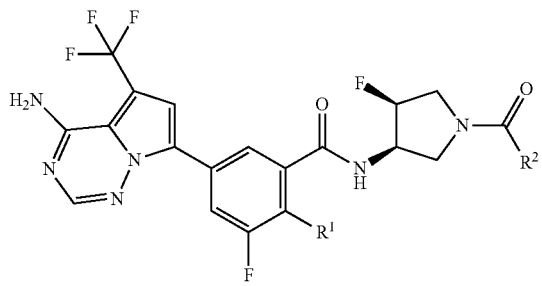

| Ex | Name | R¹ | R² | Obs. MS Ion | RT (Method) |
|---|---|---|---|---|---|
| 596 | 3-[4-amino-5-(trifluoromethyl)pyrrolo[2,1-f][1,2,4]triazin-7-yl]-5-fluoro-N-[(3R,4S)-4-fluoro-1-[(2R)-3,3,3-trifluoro-2-hydroxypropanoyl]pyrrolidin-3-yl]benzamide | H | -C(H)(OH)-CF₃ | 553.0 | 1.73 (2) |
| 597 | 3-[4-amino-5-(trifluoromethyl)pyrrolo[2,1-f][1,2,4]triazin-7-yl]-5-fluoro-N-[(3R,4S)-4-fluoro-1-(3-fluorocyclobutanecarbonyl)pyrrolidin-3-yl]benzamide | H | 3-fluorocyclobutyl | 527.3 | 1.64 (2) |
| 598 | 3-[4-amino-5-(trifluoromethyl)pyrrolo[2,1-f][1,2,4]triazin-7-yl]-5-fluoro-N-[(3R,4S)-4-fluoro-1-(3,3,3-trifluoro-2,2-dimethylpropanoyl)pyrrolidin-3-yl]benzamide | H | -C(Me)₂-CF₃ | 565.3 | 1.9 (2) |
| 599 | 3-[4-amino-5-(trifluoromethyl)pyrrolo[2,1-f][1,2,4]triazin-7-yl]-5-fluoro-N-[(3R,4S)-4-fluoro-1-(2-fluoro-2-methylpropanoyl)pyrrolidin-3-yl]benzamide | H | -C(Me)₂-F | 515.4 | 1.75 (2) |
| 600 | 3-[4-amino-5-(trifluoromethyl)pyrrolo[2,1-f][1,2,4]triazin-7-yl]-5-fluoro-N-[(3R,4S)-4-fluoro-1-(2-methylpropanoyl)pyrrolidin-3-yl]benzamide | H | -CH(Me)₂ | 497.1 | 1.7 (2) |
| 601 | 3-[4-amino-5-(trifluoromethyl)pyrrolo[2,1-f][1,2,4]triazin-7-yl]-5-fluoro-N-[(3R,4S)-4-fluoro-1-(3-methylbutanoyl)pyrrolidin-3-yl]benzamide | H | -CH₂-CH(Me)₂ | 511.3 | 1.76 (2) |
| 602 | 3-[4-amino-5-(trifluoromethyl)pyrrolo[2,1-f][1,2,4]triazin-7-yl]-5-fluoro-N-[(3R,4S)-4-fluoro-1-(2-hydroxy-2-methylpropanoyl)pyrrolidin-3-yl]benzamide | H | -C(Me)₂-OH | 513.1 | 1.41 (1) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

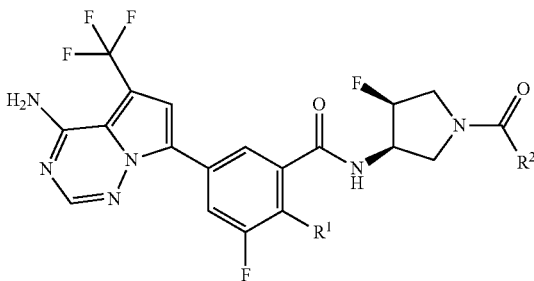

| Ex | Name | R¹ | R² | Obs. MS Ion | RT (Method) |
|---|---|---|---|---|---|
| 603 | 3-[4-amino-5-(trifluoromethyl)pyrrolo[2,1-f][1,2,4]triazin-7-yl]-5-fluoro-N-[(3R,4S)-4-fluoro-1-(3,3,3-trifluoropropanoyl)pyrrolidin-3-yl]benzamide | H | CH₂CF₃ | 537.3 | 1.69 (2) |
| 604 | 3-[4-amino-5-(trifluoromethyl)pyrrolo[2,1-f][1,2,4]triazin-7-yl]-N-[(3R,4S)-1-(2,2-dimethylpropanoyl)-4-fluoropyrrolidin-3-yl]-5-fluorobenzamide | H | C(Me)₃ | 511.4 | 1.78 (2) |
| 605 | 3-[4-amino-5-(trifluoromethyl)pyrrolo[2,1-f][1,2,4]triazin-7-yl]-N-[(3R,4S)-1-cyclobutanecarbonyl-4-fluoropyrrolidin-3-yl]-5-fluorobenzamide | H | cyclobutyl | 509.3 | 1.65 (1) |
| 606 | 3-[4-amino-5-(trifluoromethyl)pyrrolo[2,1-f][1,2,4]triazin-7-yl]-5-fluoro-N-[(3R,4S)-4-fluoro-1-(4-fluorobenzoyl)pyrrolidin-3-yl]benzamide | H | 4-fluorophenyl | 549.0 | 1.87 (2) |
| 607 | 3-[4-amino-5-(trifluoromethyl)pyrrolo[2,1-f][1,2,4]triazin-7-yl]-5-fluoro-N-[(3R,4S)-4-fluoro-1-(2-fluorobenzoyl)pyrrolidin-3-yl]benzamide | H | 2-fluorophenyl | 549.3 | 1.72 (1) |
| 608 | 3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-5-fluorobenzamide | H | 2,2-difluorocyclopropyl | 531.3 | 1.69 (2) |
| 609 | 3-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-5-fluorobenzamide | H | 4,4-difluorocyclohexyl | 573.3 | 1.8 (2) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R$^1$ | R$^2$ | Obs. MS Ion | RT (Method) |
|---|---|---|---|---|---|
| 610 | 3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-5-fluorobenzamide | H | 3,3-difluorocyclopentyl | 559.1 | 1.86 (2) |
| 611 | 3-[4-amino-5-(trifluoromethyl)pyrrolo[2,1-f][1,2,4]triazin-7-yl]-5-fluoro-N-[(3R,4S)-4-fluoro-1-(3-fluorocyclobutanecarbonyl)pyrrolidin-3-yl]benzamide | H | 3-fluorocyclobutyl | 527.3 | 1.67 (2) |
| 612 | 5-[4-amino-5-(trifluoromethyl)pyrrolo[2,1-f][1,2,4]triazin-7-yl]-3-fluoro-N-[(3R,4S)-4-fluoro-1-(1-fluorocyclopropanecarbonyl)pyrrolidin-3-yl]-2-(fluoromethyl)benzamide | CH$_2$F | 1-fluorocyclopropyl | 545.2 | 1.67 (3) |
| 613 | 5-[4-amino-5-(trifluoromethyl)pyrrolo[2,1-f][1,2,4]triazin-7-yl]-3-fluoro-N-[(3R,4S)-4-fluoro-1-(2-fluoro-2-methylpropanoyl)pyrrolidin-3-yl]-2-(fluoromethyl)benzamide | CH$_2$F | C(Me)$_2$F | 547.2 | 1.7 (4) |
| 614 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-3-fluoro-2-(fluoromethyl)benzamide | CH$_2$F | 2,2-difluorocyclopropyl | 563.3 | 1.63 (3) |
| 615 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-3-fluoro-2-(fluoromethyl)benzamide | CH$_2$F | 3,3-difluorocyclobutyl | 577.3 | 1.73 (4) |
| 616 | 5-(4-amino-5-(trifluoromethyl)pyrrolo[2,1-f][1,2,4]triazin-7-yl)-3-fluoro-N-((3R,4S)-4-fluoro-1-(3-fluorocyclobutane-1-carbonyl)pyrrolidin-3-yl)-2-(fluoromethyl)benzamide | CH$_2$F | 3-fluorocyclobutyl | 559.1 | 1.61 (4) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

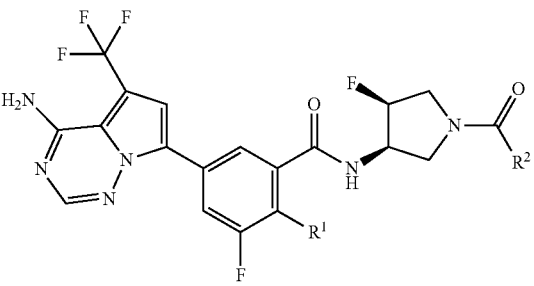

| Ex | Name | $R^1$ | $R^2$ | Obs. MS Ion | RT (Method) |
|---|---|---|---|---|---|
| 617 | 5-[4-amino-5-(trifluoromethyl)pyrrolo[2,1-f][1,2,4]triazin-7-yl]-3-fluoro-N-[(3R,4S)-4-fluoro-1-[(2R)-3,3,3-trifluoro-2-hydroxy-2-methylpropanoyl]pyrrolidin-3-yl]-2-(fluoromethyl)benzamide | $CH_2F$ |  | 599.3 | 1.66 (4) |
| 618 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-3-fluoro-2-(fluoromethyl)benzamide | $CH_2F$ |  | 591.1 | 1.74 (4) |
| 619 | 5-[4-amino-5-(trifluoromethyl)pyrrolo[2,1-f][1,2,4]triazin-7-yl]-N-[(3R,S5)-1-(4,4-difluorocyclohexanecarbonyl)-4-fluoropyrrolidin-3-yl]-3-fluoro-2-(fluoromethyl)benzamide | $CH_2F$ |  | 605.0 | 1.73 (4) |
| 620 | 5-[4-amino-5-(trifluoromethyl)pyrrolo[2,1-f][1,2,4]triazin-7-yl]-3-fluoro-N-[(3R,4S)-4-fluoro-1-(4,4,4-trifluoro-3-methylbutanoyl)pyrrolidin-3-yl]-2-(fluoromethyl)benzamide | $CH_2F$ |  | 597.1 | 1.82 (4) |
| 621 | 5-[4-amino-5-(trifluoromethyl)pyrrolo[2,1-f][1,2,4]triazin-7-yl]-3-fluoro-N-[(3R,4S)-4-fluoro-1-(4,4,4-trifluoro-3-hydroxy-3-methylbutanoyl)pyrrolidin-3-yl]-2-(fluoromethyl)benzamide | $CH_2F$ |  | 613.3 | 1.69 (3) |
| 622 | 5-[4-amino-5-(trifluoromethyl)pyrrolo[2,1-f][1,2,4]triazin-7-yl]-3-fluoro-N-[(3R,4S)-4-fluoro-1-[4,4,4-trifluoro-3-(trifluoromethyl)butanoyl]pyrrolidin-3-yl]-2-(fluoromethyl)benzamide | $CH_2F$ |  | 651.0 | 1.94 (4) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

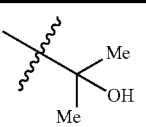

| Ex | Name | R¹ | R² | Obs. MS Ion | RT (Method) |
|---|---|---|---|---|---|
| 623 | 5-[4-amino-5-(trifluoromethyl)pyrrolo[2,1-f][1,2,4]triazin-7-yl]-3-fluoro-N-[(3R,4S)-4-fluoro-1-(2-hydroxy-2-methylpropanoyl)pyrrolidin-3-yl]-2-(fluoromethyl)benzamide | CH₂F | 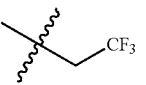 | 545.1 | 1.46 (4) |
| 624 | 5-[4-amino-5-(trifluoromethyl)pyrrolo[2,1-f][1,2,4]triazin-7-yl]-3-fluoro-N-[(3R,4S)-4-fluoro-1-(3,3,3-trifluoropropanoyl)pyrrolidin-3-yl]-2-(fluoromethyl)benzamide | CH₂F | 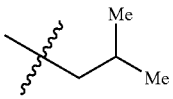 [SMILES: *CC(C)C] | 569.2 | 1.64 (3) |
| 625 | 5-[4-amino-5-(trifluoromethyl)pyrrolo[2,1-f][1,2,4]triazin-7-yl]-3-fluoro-N-[(3R,4S)-4-fluoro-1-(3-methylbutanoyl)pyrrolidin-3-yl]-2-(fluoromethyl)benzamide | CH₂F | 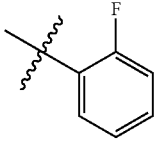 [SMILES: *c1ccccc1F] | 543.2 | 1.71 (4) |
| 626 | 5-[4-amino-5-(trifluoromethyl)pyrrolo[2,1-f][1,2,4]triazin-7-yl]-3-fluoro-N-[(3R,4S)-4-fluoro-1-(2-fluorobenzoyl)pyrrolidin-3-yl]-2-(fluoromethyl)benzamide | CH₂F | 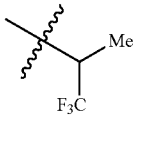 | 581.2 | 1.82 (4) |
| 627 | 5-[4-amino-5-(trifluoromethyl)pyrrolo[2,1-f][1,2,4]triazin-7-yl]-3-fluoro-N-[(3R,4S)-4-fluoro-1-(3,3,3-trifluoro-2-methylpropanoyl)pyrrolidin-3-yl]-2-(fluoromethyl)benzamide | CH₂F | 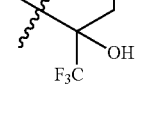 | 583.1 | 1.83 (4) |
| 628 | 5-[4-amino-5-(trifluoromethyl)pyrrolo[2,1-f][1,2,4]triazin-7-yl]-3-fluoro-N-[(3R,4S)-4-fluoro-1-[2-hydroxy-2-(trifluoromethyl)butanoyl]pyrrolidin-3-yl]-2-(fluoromethyl)benzamide | CH₂F | 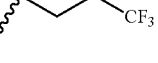 | 613.1 | 1.77 (4) |
| 629 | 5-[4-amino-5-(trifluoromethyl)pyrrolo[2,1-f][1,2,4]triazin-7-yl]-2-chloro-3-fluoro-N-[(3R,4S)-4-fluoro-1-(4,4,4-trifluoro-3-hydroxy-3-methylbutanoyl)pyrrolidin-3-yl]benzamide | Cl | | 615.3 | 1.86 (4) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 630 | 5-[4-amino-5-(trifluoromethyl)pyrrolo[2,1-f][1,2,4]triazin-7-yl]-2-chloro-3-fluoro-N-[(3R,4S)-4-fluoro-1-(2-fluoro-2-methylpropanoyl)pyrrolidin-3-yl]benzamide | Cl | C(Me)(Me)F | 549.3 | 1.85 (4) |
| 631 | 5-[4-amino-5-(trifluoromethyl)pyrrolo[2,1-f][1,2,4]triazin-7-yl]-2-chloro-N-[(3R,4S)-1-(2,2-difluorocyclopropanecarbonyl)-4-fluoropyrrolidin-3-yl]-3-fluorobenzamide | Cl | 2,2-difluorocyclopropyl | 565.1 | 1.78 (4) |
| 632 | 5-[4-amino-5-(trifluoromethyl)pyrrolo[2,1-f][1,2,4]triazin-7-yl]-2-chloro-3-fluoro-N-[(3R,4S)-4-fluoro-1-[4,4,4-trifluoro-3-(trifluoromethyl)butanoyl]pyrrolidin-3-yl]benzamide | Cl | CH(CF₃)CH₂ with CF₃ | 653.3 | 2.08 (4) |
| 633 | 5-[4-amino-5-(trifluoromethyl)pyrrolo[2,1-f][1,2,4]triazin-7-yl]-2-chloro-3-fluoro-N-[(3R,4S)-4-fluoro-1-(3,3,3-trifluoro-2-methylpropanoyl)pyrrolidin-3-yl]benzamide | Cl | CH(Me)(CF₃) | 585.3 | 1.88 (4) |
| 634 | 5-[4-amino-5-(trifluoromethyl)pyrrolo[2,1-f][1,2,4]triazin-7-yl]-2-chloro-3-fluoro-N-[(3R,4S)-4-fluoro-1-(4,4,4-trifluoro-3-methylbutanoyl)pyrrolidin-3-yl]benzamide | Cl | CH₂CH(Me)(CF₃) | 599.3 | 1.54 (3) |
| 635 | 5-[4-amino-5-(trifluoromethyl)pyrrolo[2,1-f][1,2,4]triazin-7-yl]-2-chloro-N-[(3R,4S)-1-(3,3-difluorocyclobutanecarbonyl)-4-fluoropyrrolidin-3-yl]-3-fluorobenzamide | Cl | 3,3-difluorocyclobutyl | 579.0 | 1.85 (4) |
| 636 | 5-[4-amino-5-(trifluoromethyl)pyrrolo[2,1-f][1,2,4]triazin-7-yl]-2-chloro-3-fluoro-N-[(3R,4S)-4-fluoro-1-(1-fluorocyclopropanecarbonyl)pyrrolidin-3-yl]benzamide | Cl | 1-fluorocyclopropyl | 547.3 | 1.32 (3) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

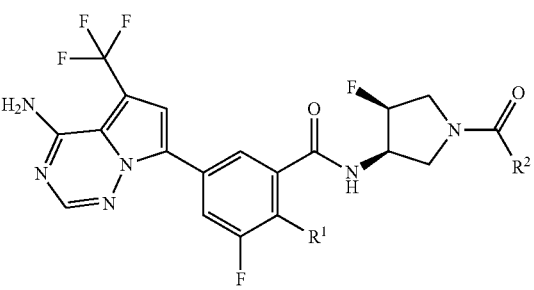

| Ex | Name | R¹ | R² | Obs. MS Ion | RT (Method) |
|---|---|---|---|---|---|
| 637 | 5-[4-amino-5-(trifluoromethyl)pyrrolo[2,1-f][1,2,4]triazin-7-yl]-2-chloro-3-fluoro-N-[(3R,4S)-4-fluoro-1-[4,4,4-trifluoro-3-hydroxy-3-(trifluoromethyl)butanoyl]pyrrolidin-3-yl]benzamide | Cl | C(CF₃)(OH)(CF₃) | 669.2 | 2.12 (4) |
| 638 | 5-[4-amino-5-(trifluoromethyl)pyrrolo[2,1-f][1,2,4]triazin-7-yl]-2-chloro-3-fluoro-N-[(3R,4S)-4-fluoro-1-(3-fluorocyclobutanecarbonyl)pyrrolidin-3-yl]benzamide | Cl | 3-fluorocyclobutyl | 561.0 | 1.72 (4) |
| 639 | 5-[4-amino-5-(trifluoromethyl)pyrrolo[2,1-f][1,2,4]triazin-7-yl]-2-chloro-3-fluoro-N-[(3R,4S)-4-fluoro-1-(2 hydroxy-2-yl]benzamide | Cl | C(Me)(Me)(OH) | 547.1 | 1.6 (4) |
| 640 | 5-[4-amino-5-(trifluoromethyl)pyrrolo[2,1-f][1,2,4]triazin-7-yl]-2-chloro-3-fluoro-N-[(3R,4S)-4-fluoro-1-(3,3,3-trifluoropropanoyl)pyrrolidin-3-yl]benzamide | Cl | CH₂CF₃ | 570.9 | 1.79 (4) |
| 641 | 5-[4-amino-5-(trifluoromethyl)pyrrolo[2,1-f][1,2,4]triazin-7-yl]-2-chloro-3-fluoro-N-[(3R,4S)-4-fluoro-1-(3-methylbutanoyl)pyrrolidin-3-yl]benzamide | Cl | CH₂CH(Me)Me | 545.1 | 1.81 (3) |
| 642 | 5-[4-amino-5-(trifluoromethyl)pyrrolo[2,1-f][1,2,4]triazin-7-yl]-2-chloro-3-fluoro-N-[(3R,4S)-4-fluoro-1-(2-fluorobenzoyl)pyrrolidin-3-yl]benzamide | Cl | 2-fluorophenyl | 583.3 | 1.81 (3) |
| 643 | 5-[4-amino-5-(trifluoromethyl)pyrrolo[2,1-f][1,2,4]triazin-7-yl]-2-chloro-N-[(3R,4S)-1-(4,4-difluorocyclohexanecarbonyl)-4-fluoropyrrolidin-3-yl]-3-fluorobenzamide | Cl | 4,4-difluorocyclohexyl | 607.2 | 1.88 (4) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 644 | 5-[4-amino-5-(trifluoromethyl)pyrrolo[2,1-f][1,2,4]triazin-7-yl]-2-chloro-N-[(3R,4S)-1-(3,3-difluorocyclopentanecarbonyl)-4-fluoropyrrolidin-3-yl]-3-fluorobenzamide | Cl | 3,3-difluorocyclopentyl | 593.3 | 1.87 (4) |
| 645 | 5-[4-amino-5-(trifluoromethyl)pyrrolo[2,1-f][1,2,4]triazin-7-yl]-2-ethyl-3-fluoro-N-[(3R,4S)-4-fluoro-1-(2-fluorobenzoyl)pyrrolidin-3-yl]benzamide | Et | 2-fluorophenyl | 577.2 | 1.92 (4) |
| 646 | 5-[4-amino-5-(trifluoromethyl)pyrrolo[2,1-f][1,2,4]triazin-7-yl]-2-ethyl-3-fluoro-N-[(3R,4S)-4-fluoro-1-(3-methylbutanoyl)pyrrolidin-3-yl]benzamide | Et | isobutyl (CH₂CH(Me)₂) | 539.2 | 1.86 (3) |
| 647 | 5-[4-amino-5-(trifluoromethyl)pyrrolo[2,1-f][1,2,4]triazin-7-yl]-2-ethyl-3-fluoro-N-[(3R,4S)-4-fluoro-1-(2-hydroxy-2-methylpropanoyl)pyrrolidin-3-yl]benzamide | Et | C(Me)₂OH | 541.1 | 1.65 (4) |
| 648 | 5-[4-amino-5-(trifluoromethyl)pyrrolo[2,1-f][1,2,4]triazin-7-yl]-2-ethyl-3-fluoro-N-[(3R,4S)-4-fluoro-1-(3,3,3-trifluoropropanoyl)pyrrolidin-3-yl]benzamide | Et | CH₂CF₃ | 565.3 | 1.87 (4) |
| 649 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-ethyl-3-fluorobenzamide | Et | 2,2-difluorocyclopropyl | 559.3 | 1.79 (3) |
| 650 | 5-[4-amino-5-(trifluoromethyl)pyrrolo[2,1-f][1,2,4]triazin-7-yl]-2-ethyl-3-fluoro-N-[(3R,4S)-4-fluoro-1-[(2R)-3,3,3-trifluoro-2-hydroxy-2-methylpropanoyl]pyrrolidin-3-yl]benzamide | Et | (2R)-C(Me)(OH)CF₃ | 595.3 | 1.86 (3) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

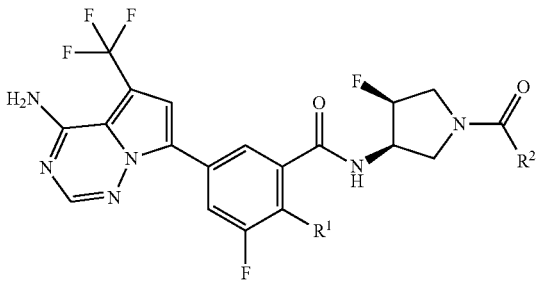

| Ex | Name | R¹ | R² | Obs. MS Ion | RT (Method) |
|---|---|---|---|---|---|
| 651 | 5-[4-amino-5-(trifluoromethyl)pyrrolo[2,1-f][1,2,4]triazin-7-yl]-2-ethyl-3-fluoro-N-[(3R,4S)-4-fluoro-1-[2-hydroxy-2-(trifluoromethyl)butanoyl]pyrrolidin-3-yl]benzamide | Et | | 609.1 | 1.88 (3) |
| 652 | 5-[4-amino-5-(trifluoromethyl)pyrrolo[2,1-f][1,2,4]triazin-7-yl]-2-ethyl-3-fluoro-N-[(3R,4S)-4-fluoro-1-(4,4,4-trifluoro-3-methylbutanoyl)pyrrolidin-3-yl]benzamide | Et | | 593.2 | 2.02 (4) |
| 653 | 5-[4-amino-5-(trifluoromethyl)pyrrolo[2,1-f][1,2,4]triazin-7-yl]-2-ethyl-3-fluoro-N-[(3R,4S)-4-fluoro-1-(4,4,4-trifluoro-3-hydroxy-3-methylbutanoyl)pyrrolidin-3-yl]benzamide | Et | | 609.2 | 1.91 (4) |
| 654 | 54-[4-amino-5-(trifluoromethyl)pyrrolo[2,1-f][1,2,4]triazin-7-yl]-2-ethyl-3-fluoro-N-[(3R,4S)-4-fluoro-1-[4,4,4-trifluoro-3-(trifluoromethyl)butanoyl]pyrrolidin-3-yl]benzamide | Et | | 647.0 | 2.18 (4) |
| 655 | 5-[4-amino-5-(trifluoromethyl)pyrrolo[2,1-f][1,2,4]triazin-7-yl]-2-ethyl-3-fluoro-N-[(3R,4S)-4-fluoro-1-(3-fluorocyclobutanecarbonyl)pyrrolidin-3-yl]benzamide | Et | | 555.3 | 1.85 (4) |
| 656 | 5-[4-amino-5-(trifluoromethyl)pyrrolo[2,1-f][1,2,4]triazin-7-yl]-2-ethyl-3-fluoro-N-[(3R,4S)-4-fluoro-1-(3-fluorocyclobutanecarbonyl)pyrrolidin-3-yl]benzamide | Et | | 555.1 | 1.84 (3) |
| 657 | 5-[4-amino-5-(trifluoromethyl)pyrrolo[2,1-f][1,2,4]triazin-7-yl]-2-ethyl-3-fluoro-N-[(3R,4S)-4-fluoro-1-(1-fluorocyclopropanecarbonyl)pyrrolidin-3-yl]benzamide | Et | | 541.3 | 1.94 (4) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 658 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-ethyl-3-fluorobenzamide | Et | 3,3-difluorocyclopentyl | 587.1 | 1.93 (4) |
| 659 | 5-[4-amino-5-(trifluoromethyl)pyrrolo[2,1-f][1,2,4]triazin-7-yl]-2-ethyl-3-fluoro-N-[(3R,4S)-4-fluoro-1-(2-fluoro-2-methylpropanoyl)pyrrolidin-3-yl]benzamide | Et | C(Me)(Me)F | 543.1 | 1.86 (3) |
| 660 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-ethyl-3-fluorobenzamide | Et | 4,4-difluorocyclohexyl | 601.1 | 1.96 (3) |
| 661 | 5-[4-amino-5-(trifluoromethyl)pyrrolo[2,1-f][1,2,4]triazin-7-yl]-2-ethyl-3-fluoro-N-[(3R,4S)-4-fluoro-1-(3,3,3-trifluoro-2-methylpropanoyl)pyrrolidin-3-yl]benzamide | Et | CH(Me)(CF₃) | 579.3 | 1.94 (3) |
| 662 | 5-[4-amino-5-(trifluoromethyl)pyrrolo[2,1-f][1,2,4]triazin-7-yl]-3-fluoro-N-[(3R,4S)-4-fluoro-1-(4,4,4-trifluoro-3-methylbutanoyl)pyrrolidin-3-yl]-2-methylbenzamide | Me | CH₂CH(Me)CF₃ | 579 | 1.96 (2) |
| 663 | 5-[4-amino-5-(trifluoromethyl)pyrrolo[2,1-f][1,2,4]triazin-7-yl]-N-[(3R,4S)-1-cyclobutanecarbonyl-4-fluoropyrrolidin-3-yl]-3-fluoro-2-methylbenzamide | Me | cyclobutyl | 523.4 | 1.67 (1) |
| 664 | 5-[4-amino-5-(trifluoromethyl)pyrrolo[2,1-f][1,2,4]triazin-7-yl]-3-fluoro-N-[(3R,4S)-4-fluoro-1-(3,3,3-trifluoropropanoyl)pyrrolidin-3-yl]-2-methylbenzamide | Me | CH₂CF₃ | 551.3 | 1.78 (2) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

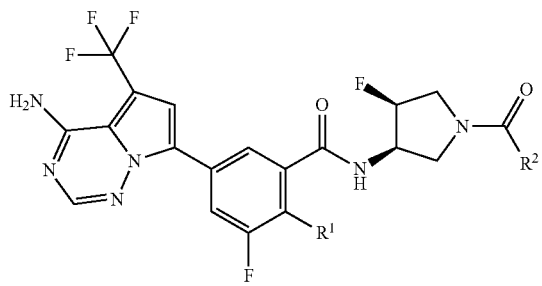

| Ex | Name | $R^1$ | $R^2$ | Obs. MS Ion | RT (Method) |
|---|---|---|---|---|---|
| 665 | 5-[4-amino-5-(trifluoromethyl)pyrrolo[2,1-f][1,2,4]triazin-7-yl]-3-fluoro-N-[(3R,4S)-4-fluoro-1-(2-hydroxy-2-methylpropanoyl)pyrrolidin-3-yl]-2-methylbenzamide | Me | C(Me)(Me)OH | 527.3 | 1.5 (2) |
| 666 | 5-[4-amino-5-(trifluoromethyl)pyrrolo[2,1-f][1,2,4]triazin-7-yl]-N-[(3R,4S)-1-(2,2-dimethylpropanoyl)-4-fluoropyrrolidin-3-yl]-3-fluoro-2-methylbenzamide | Me | C(Me)(Me)Me | 525.4 | 1.74 (1) |
| 667 | 5-[4-amino-5-(trifluoromethyl)pyrrolo[2,1-f][1,2,4]triazin-7-yl]-3-fluoro-N-[(3R,4S)-4-fluoro-1-(3-methylbutanoyl)pyrrolidin-3-yl]-2-methylbenzamide | Me | CH2CH(Me)Me | 525.3 | 1.72 (1) |
| 668 | 5-[4-amino-5-(trifluoromethyl)pyrrolo[2,1-f][1,2,4]triazin-7-yl]-3-fluoro-N-[(3R,4S)-4-fluoro-1-(2-methylpropanoyl)pyrrolidin-3-yl]-2-methylbenzamide | Me | CH(Me)Me | 511.1 | 1.64 (2) |
| 669 | 5-[4-amino-5-(trifluoromethyl)pyrrolo[2,1-f][1,2,4]triazin-7-yl]-3-fluoro-N-[(3R,4S)-4-fluoro-1-(2-fluorobenzoyl)pyrrolidin-3-yl]-2-methylbenzamide | Me | 2-F-C6H4 | 563.3 | 1.74 (1) |
| 670 | 5-[4-amino-5-(trifluoromethyl)pyrrolo[2,1-f][1,2,4]triazin-7-yl]-3-fluoro-N-[(3R,4S)-4-fluoro-1-(4-fluorobenzoyl)pyrrolidin-3-yl]-2-methylbenzamide | Me | 4-F-C6H4 | 563.3 | 1.76 (1) |
| 671 | 5-[4-amino-5-(trifluoromethyl)pyrrolo[2,1-f][1,2,4]triazin-7-yl]-3-fluoro-N-[(3R,4S)-4-fluoro-1-(1-hydroxycyclobutanecarbonyl)pyrrolidin-3-yl]-2-methylbenzamide | Me | 1-HO-cyclobutyl | 539.1 | 1.54 (2) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 672 | 5-[4-amino-5-(trifluoromethyl)pyrrolo[2,1-f][1,2,4]triazin-7-yl]-3-fluoro-N-[(3R,4S)-4-fluoro-1-[(2R)-3,3,3-trifluoro-2-hydroxypropanoyl]pyrrolidin-3-yl]-2-methylbenzamide | Me | —CH(OH)CF₃ | 567.2 | 1.61 (1) |
| 673 | 5-[4-amino-5-(trifluoromethyl)pyrrolo[2,1-f][1,2,4]triazin-7-yl]-3-fluoro-N-[(3R,4S)-4-fluoro-1-(2-fluoro-2-methylpropanoyl)pyrrolidin-3-yl]-2-methylbenzamide | Me | —C(Me)(Me)F | 529.3 | 1.71 (1) |
| 674 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-3-fluoro-2-methylbenzamide | Me | 4,4-difluorocyclohexyl | 587.4 | 1.77 (1) |
| 675 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-3-fluoro-2-methylbenzamide | Me | 2,2-difluorocyclopropyl | 545.3 | 1.65 (1) |
| 676 | 5-[4-amino-5-(trifluoromethyl)pyrrolo[2,1-f][1,2,4]triazin-7-yl]-3-fluoro-N-[(3R,4S)-4-fluoro-1-(3,3,3-trifluoro-2,2-dimethylpropanoyl)pyrrolidin-3-yl]-2-methylbenzamide | Me | —C(Me)(Me)CF₃ | 579.3 | 1.78 (1) |
| 677 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-3-fluoro-2-methylbenzamide | Me | 3,3-difluorocyclobutyl | 559.4 | 1.71 (1) |
| 678 | 5-[4-amino-5-(trifluoromethyl)pyrrolo[2,1-f][1,2,4]triazin-7-yl]-3-fluoro-N-[(3R,4S)-4-fluoro-1-(3-fluorocyclobutanecarbonyl)pyrrolidin-3-yl]-2-methylbenzamide | Me | 3-fluorocyclobutyl | 541.3, 541.3 | 1.66 (2) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

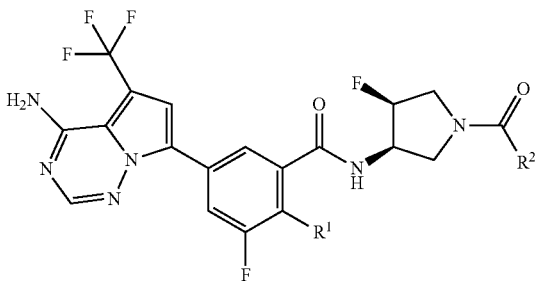

| Ex | Name | R$^1$ | R$^2$ | Obs. MS Ion | RT (Method) |
|---|---|---|---|---|---|
| 679 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-3-fluoro-2-methylbenzamide | Me | 3,3-difluorocyclopentyl | 573.4 | 1.75 (1) |
| 680 | 5-[4-amino-5-(trifluoromethyl)pyrrolo[2,1-f][1,2,4]triazin-7-yl]-3-fluoro-N-[(3R,4S5)-4-fluoro-1-(3-methylbutanoyl)pyrrolidin-3-yl]-2-methoxybenzamide | OMe | isobutyl | 541.1 | 1.75 (2) |
| 681 | 5-[4-amino-5-(trifluoromethyl)pyrrolo[2,1-f][1,2,4]triazin-7-yl]-3-fluoro-N-[(3R,4S)-4-fluoro-1-(2-fluorobenzoyl)pyrrolidin-3-yl]-2-methoxybenzamide | OMe | 2-fluorophenyl | 579.3 | 1.84 (1) |
| 682 | 5-[4-amino-5-(trifluoromethyl)pyrrolo[2,1-f][1,2,4]triazin-7-yl]-N-[(3R,4S)-1-cyclobutanecarbonyl-4-fluoropyrrolidin-3-yl]-3-fluoro-2-methoxybenzamide | OMe | cyclobutyl | 539.1 | 1.73 (1) |
| 683 | 5-[4-amino-5-(trifluoromethyl)pyrrolo[2,1-f][1,2,4]triazin-7-yl]-3-fluoro-N-[(3R,4S)-4-fluoro-1-(4-fluorobenzoyl)pyrrolidin-3-yl]-2-methoxybenzamide | OMe | 4-fluorophenyl | 579.3 | 1.54 (1) |
| 684 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-3-fluoro-2-methoxybenzamide | OMe | 3,3-difluorocyclobutyl | 575.2 | 1.52 (1) |
| 685 | 5[-4-amino-5-(trifluoromethyl)pyrrolo[2,1-f][1,2,4]triazin-7-yl]-3-fluoro-N-[(3R,4S)-4-fluoro-1-(2-fluoro-2-methylpropanoyl)pyrrolidin-3-yl]-2-methoxybenzamide | OMe | 2-fluoro-2-methylpropyl | 545.1 | 1.65 (2) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

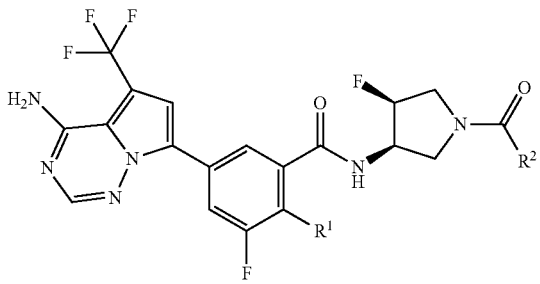

| Ex | Name | R[1] | R[2] | Obs. MS Ion | RT (Method) |
|---|---|---|---|---|---|
| 686 | 5-[4-amino-5-(trifluoromethyl)pyrrolo[2,1-f][1,2,4]triazin-7-yl]-3-fluoro-N-[(3R,4S)-4-fluoro-1-[(2S)-3,3,3-trifluoro-2-hydroxy-2-methylpropanoyl]pyrrolidin-3-yl]-2-methoxybenzamide | OMe | CF$_3$, OH | 597.2 | 1.65 (2) |
| 687 | 5[-4-amino-5-(trifluoromethyl)pyrrolo[2,1-f][1,2,4]triazin-7-yl]-3-fluoro-N-[(3R,4S)-4-fluoro-1-(3-fluorocyclobutanecarbonyl)pyrrolidin-3-yl]-2-methoxybenzamide | OMe | F-cyclobutyl | 557.3 | 1.82 (4) |
| 688 | 5-[4-amino-5-(trifluoromethyl)pyrrolo[2,1-f][1,2,4]triazin-7-yl]-3-fluoro-N-[(3R,4S)-4-fluoro-1-(1-fluorocyclopropanecarbonyl)pyrrolidin-3-yl]-2-methoxybenzamide | OMe | F-cyclopropyl | 543.3 | 1.96 (3) |
| 689 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-3-fluoro-2-methoxybenzamide | OMe | 4,4-F$_2$-cyclohexyl | 603.1 | 2.05 (4) |
| 690 | 5-[4-amino-5-(trifluoromethyl)pyrrolo[2,1-f][1,2,4]triazin-7-yl]-3-fluoro-N-[(3R,4S)-4-fluoro-1-[4,4,4-trifluoro-3-hydroxy-3-(trifluoromethyl)butanoyl]pyrrolidin-3-yl]-2-methoxybenzamide | OMe | CF$_3$, OH, CF$_3$ | 665.3 | 2.11 (3) |
| 691 | 5-[4-amino-5-(trifluoromethyl)pyrrolo[2,1-f][1,2,4]triazin-7-yl]-3-fluoro-N-[(3R,4S)-4-fluoro-1-[4,4,4-trifluoro-3-(trifluoromethyl)butanoyl]pyrrolidin-3-yl]-2-methoxybenzamide | OMe | CF$_3$, CF$_3$ | 649.0 | 2.23 (4) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 692 | 5-[4-amino-5-(trifluoromethyl)pyrrolo[2,1-f][1,2,4]triazin-7-yl]-3-fluoro-N-[(3R,4S)-4-fluoro-1-[2-hydroxy-2-(trifluoromethyl)butanoyl]pyrrolidin-3-yl]-2-methoxybenzamide | OMe | C(CF$_3$)(OH)(CH$_2$Me) | 611.3 | 1.87 (3) |
| 693 | 5-[4-amino-5-(trifluoromethyl)pyrrolo[2,1-f][1,2,4]triazin-7-yl]-3-fluoro-N-[(3R,4S)-4-fluoro-1-(4,4,4-trifluoro-3-methylbutanoyl)pyrrolidin-3-yl]-2-methoxybenzamide | OMe | CH$_2$CH(Me)(CF$_3$) | 595.4 | 1.99 (3) |
| 694 | 5-[4-amino-5-(trifluoromethyl)pyrrolo[2,1-f][1,2,4]triazin-7-yl]-3-fluoro-N-[(3R,4S)-4-fluoro-1-(3,3,3-trifluoro-2-methylpropanoyl)pyrrolidin-3-yl]-2-methoxybenzamide | OMe | CH(Me)(CF$_3$) | 581.0 | 1.9 (3) |
| 695 | 5-[4-amino-5-(trifluoromethyl)pyrrolo[2,1-f][1,2,4]triazin-7-yl]-3-fluoro-N-[(3R,4S)-4-fluoro-1-(4-fluorocyclohexanecarbonyl)pyrrolidin-3-yl]-2-methoxybenzamide | OMe | 4-fluorocyclohexyl | 585.3 | 1.85 (3) |
| 696 | 5-[4-amino-5-(trifluoromethyl)pyrrolo[2,1-f][1,2,4]triazin-7-yl]-3-fluoro-N-[(3R,4S)-4-fluoro-1-(4,4,4-trifluoro-3-hydroxy-3-methylbutanoyl)pyrrolidin-3-yl]-2-methoxybenzamide | OMe | CH$_2$C(Me)(OH)(CF$_3$) | 611.1 | 2.01 (4) |
| 697 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-3-fluoro-2-methoxybenzamide | OMe | 2,2-difluorocyclopropyl | 561.3 | 1.94 (4) |
| 698 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-3- | OMe | 3,3-difluorocyclopentyl | 589.3 | 1.92 (4) |

TABLE 37-continued

Compounds in Table 37 were prepared by the methods detailed in Examples 569 and 570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

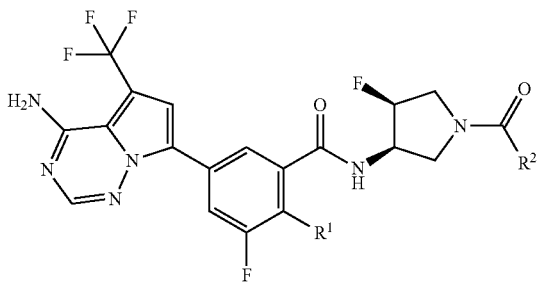

| Ex | Name | R¹ | R² | Obs. MS Ion | RT (Method) |
|---|---|---|---|---|---|
| | fluoro-2-methoxybenzamide | | | | |
| 699 | 5-[4-amino-5-(trifluoromethyl)pyrrolo[2,1-f][1,2,4]triazin-7-yl]-3-fluoro-N-[(3R,4S)-4-fluoro-1-(3,3,3-trifluoropropanoyl)pyrrolidin-3-yl]-2-methoxybenzamide | OMe | ⸻CH₂CF₃ | 567.3 | 1.81 (4) |
| 700 | 5-[4-amino-5-(trifluoromethyl)pyrrolo[2,1-f][1,2,4]triazin-7-yl]-3-fluoro-N-[(3R,4S)-4-fluoro-1-(2-hydroxy-2-methylpropanoyl)pyrrolidin-3-yl]-2-methoxybenzamide | OMe | ⸻C(Me)(Me)OH | 543.4 | 1.53 (3) |

TABLE 38

Compounds in Table 38 were prepared by the methods detailed in Example 562. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

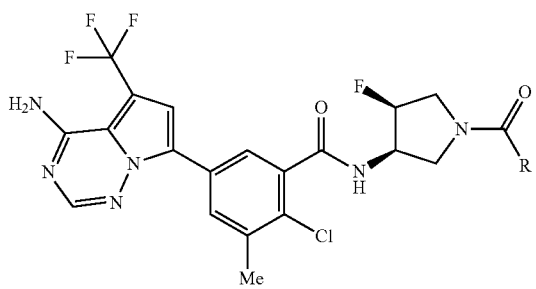

| Ex | Name | R | Obs. MS Ion | RT (Method) |
|---|---|---|---|---|
| 701 | 5-[4-amino-5-(trifluoromethyl)pyrrolo[2,1-f][1,2,4]triazin-7-yl]-2-chloro-N-[(3R,4S)-4-fluoro-1-(4,4,4-trifluoro-3-methylbutanoyl)pyrrolidin-3-yl]-3-methylbenzamide | ⸻CH₂CH(Me)CF₃ | 595.0 | 1.96 (4) |

TABLE 38-continued

Compounds in Table 38 were prepared by the methods detailed in Example 562. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R | Obs. MS Ion | RT (Method) |
|---|---|---|---|---|
| 702 | 5-[4-amino-5-(trifluoromethyl)pyrrolo[2,1-f][1,2,4]triazin-7-yl]-2-chloro-N-[(3R,4S)-4-fluoro-1-[4,4,4-trifluoro-3-hydroxy-3-(trifluoromethyl)butanoyl]pyrrolidin-3-yl]-3-methylbenzamide | | 665.2 | 2.11 (4) |
| 703 | 5-[4-amino-5-(trifluoromethyl)pyrrolo[2,1-f][1,2,4]triazin-7-yl]-2-chloro-N-[(3R,4S)-4-fluoro-1-[2-hydroxy-2-(trifluoromethyl)butanoyl]pyrrolidin-3-yl]-3-methylbenzamide | | 611.3 | 1.87 (4) |
| 704 | 5-[4-amino-5-(trifluoromethyl)pyrrolo[2,1-f][1,2,4]triazin-7-yl]-2-chloro-N-[(3R,4S)-1-(2,2-difluorocyclopropanecarbonyl)-4-fluoropyrrolidin-3-yl]-3-methylbenzamide | | 561.0 | 1.81 (4) |
| 705 | 5-[4-amino-5-(trifluoromethyl)pyrrolo[2,1-f][1,2,4]triazin-7-yl]-2-chloro-N-[(3R,4S)-4-fluoro-1-(2-fluoro-2-methylpropanoyl)pyrrolidin-3-yl]-3-methylbenzamide | | 545.2 | 1.85 (4) |
| 706 | 5-[4-amino-5-(trifluoromethyl)pyrrolo[2,1-f][1,2,4]triazin-7-yl]-2-chloro-N-[(3R,4S)-1-(3,3-difluorocyclobutanecarbonyl)-4-fluoropyrrolidin-3-yl]-3-methylbenzamide | | 575.3 | 1.84 (4) |
| 707 | 5-[4-amino-5-(trifluoromethyl)pyrrolo[2,1-f][1,2,4]triazin-7-yl]-2-chloro-N-[(3R,4S)-4-fluoro-1-(2-hydroxy-2-methylpropanoyl)pyrrolidin-3-yl]-3-methylbenzamide | | 543.0 | 1.62 (4) |
| 708 | 5-[4-amino-5-(trifluoromethyl)pyrrolo[2,1-f][1,2,4]triazin-7-yl]-2-chloro-N-[(3R,4S)-4-fluoro-1-(2-fluorobenzoyl)pyrrolidin-3-yl]-3-methylbenzamide | | 579.0 | 1.86 (4) |
| 709 | 5-[4-amino-5-(trifluoromethyl)pyrrolo[2,1-f][1,2,4]triazin-7-yl]-2-chloro-N-[(3R,4S)-4-fluoro-1-[4,4,4-trifluoro-3- | | 649.2 | 2.08 (4) |

TABLE 38-continued

Compounds in Table 38 were prepared by the methods detailed in Example 562. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

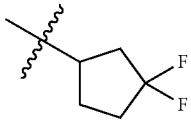 [SMILES: *C1CCC(F)(F)C1]

| Ex | Name | R | Obs. MS Ion | RT (Method) |
|---|---|---|---|---|
|  | (trifluoromethyl)butanoyl]pyrrolidin-3-yl]-3-methylbenzamide |  |  |  |
| 710 | 5-[4-amino-5-(trifluoromethyl)pyrrolo[2,1-f][1,2,4]triazin-7-yl]-2-chloro-N-[(3R,4S)-1-(3,3-difluorocyclopentanecarbonyl)-4-fluoropyrrolidin-3-yl]-3-methylbenzamide | 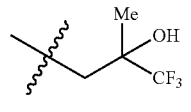 | 589.0 | 1.89 (4) |
| 711 | 5-[4-amino-5-(trifluoromethyl)pyrrolo[2,1-f][1,2,4]triazin-7-yl]-2-chloro-N-[(3R,4S)-4-fluoro-1-(4,4,4-trifluoro-3-hydroxy-3-methylbutanoyl)pyrrolidin-3-yl]-3-methylbenzamide | 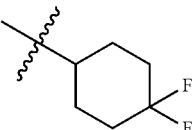 | 611.2 | 1.75 (3) |
| 712 | 5-[4-amino-5-(trifluoromethyl)pyrrolo[2,1-f][1,2,4]triazin-7-yl]-2-chloro-N-[(3R,4S)-1-(4,4-difluorocyclohexanecarbonyl)-4-fluoropyrrolidin-3-yl]-3-methylbenzamide | 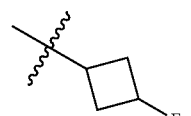 | 603.2 | 1.79 (3) |
| 713 | 5-[4-amino-5-(trifluoromethyl)pyrrolo[2,1-4-fluoro-1-(3-fluorocyclobutanecarbonyl)pyrrolidin-3-yl]-3-methylbenzamide | 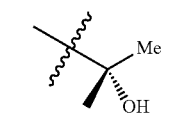 | 557.1 | 1.63 (3) |
| 714 | 5-[4-amino-5-(trifluoromethyl)pyrrolo[2,1-f][1,2,4]triazin-7-yl]-2-chloro-N-[(3R,4S)-4-fluoro-1-[(2S)-3,3,3-trifluoro-2-hydroxy-2-methylpropanoyl]pyrrolidin-3-yl]-3-methylbenzamide | 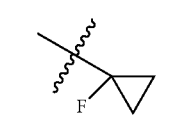 | 597.2 | 1.69 (3) |
| 715 | 5-[4-amino-5-(trifluoromethyl)pyrrolo[2,1-f][1,2,4]triazin-7-yl]-2-chloro-N-[(3R,4S)-4-fluoro-1-(1-fluorocyclopropanecarbonyl)pyrrolidin-3-yl]-3-methylbenzamide | 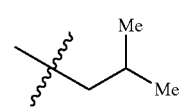 [SMILES: *CC(C)C] | 543.2 | 1.72 (3) |
| 716 | 5-[4-amino-5-(trifluoromethyl)pyrrolo[2,1-f][1,2,4]triazin-7-yl]-2-chloro-N-[(3R,4S)-4-fluoro-1-(3-methylbutanoyl)pyrrolidin-3-yl]-3-methylbenzamide | 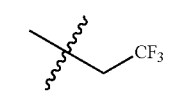 [SMILES: *CC(F)(F)F] | 541.1 | 1.74 (3) |
| 717 | 5-[4-amino-5-(trifluoromethyl)pyrrolo[2,1-f][1,2,4]triazin-7-yl]-2-chloro-N-[(3R,4S)-4-fluoro-1-(3,3,3- |  | 567.3 | 1.67 (3) |

TABLE 38-continued

Compounds in Table 38 were prepared by the methods detailed in Example 562. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

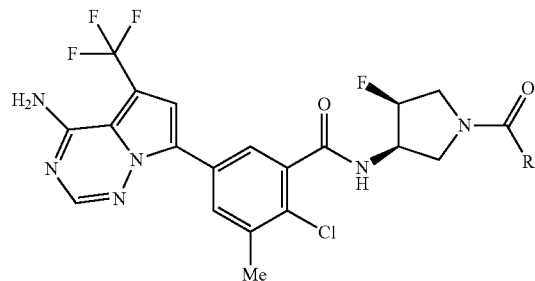

| Ex | Name | R | Obs. MS Ion | RT (Method) |
|---|---|---|---|---|
|  | trifluoropropanoyl)pyrrolidin-3-yl]-3-methylbenzamide |  |  |  |
| 718 | 5-[4-amino-5-(trifluoromethyl)pyrrolo[2,1-f][1,2,4]triazin-7-yl]-2-chloro-N-[(3R,4S)-4-fluoro-1-(3,3,3-trifluoro-2-methylpropanoyl)pyrrolidin-3-yl]-3-methylbenzamide | (Me, F₃C) | 581.2 | 1.77 (3) |

TABLE 39

Compounds in Table 39 were prepared by the methods detailed in Examples 562 and 571. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

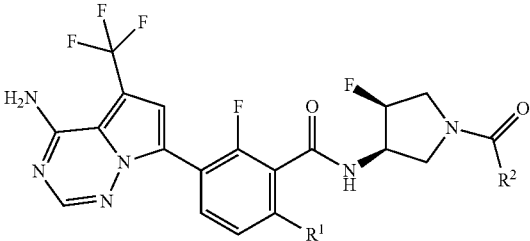

| Ex | Name | R¹ | R² | Obs. MS ion | RT (Method) |
|---|---|---|---|---|---|
| 719 | 3-[4-amino-5-(trifluoromethyl)pyrrolo[2,1-f][1,2,4]triazin-7-yl]-2,6-difluoro-N-[(3R,4S)-4-fluoro-1-(3-methylbutanoyl)pyrrolidin-3-yl]benzamide | F | (Me, Me) | 529.3 | 1.65 (4) |
| 720 | 3-[4-amino-5-(trifluoromethyl)pyrrolo[2,1-f][1,2,4]triazin-7-yl]-2,6-difluoro-N-[(3R,4S)-4-fluoro-1-[4,4,4-trifluoro-3-hydroxy-3-(trifluoromethyl)butanoyl]pyrrolidin-3-yl]benzamide | F | (CF₃, OH, CF₃) | 653 | 1.95 (4) |
| 721 | 3-[4-amino-5-(trifluoromethyl)pyrrolo[2,1-f][1,2,4]triazin-7-yl]-2,6-difluoro-N-[(3R,4S)-4-fluoro-1-(4,4,4-trifluoro-3-hydroxy-3-methylbutanoyl)pyrrolidin-3-yl]benzamide | F | (Me, OH, CF₃) | 599.1 | 1.67 (4) |

TABLE 39-continued

Compounds in Table 39 were prepared by the methods detailed in Examples 562 and 571. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

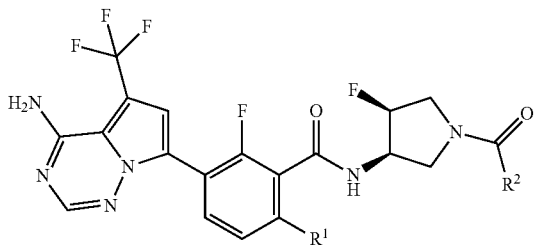

| Ex | Name | R¹ | R² | Obs. MS ion | RT (Method) |
|----|------|----|----|-------------|-------------|
| 722 | 3-[4-amino-5-(trifluoromethyl)pyrrolo[2,1-f][1,2,4]triazin-7-yl]-2,6-difluoro-N-[(3R,4S)-4-fluoro-1-[(2R)-3,3,3-trifluoro-2-hydroxy-2-methylpropanoyl]pyrrolidin-3-yl]benzamide | F | | 585.0 | 1.52 (4) |
| 723 | 3-[4-amino-5-(trifluoromethyl)pyrrolo[2,1-f][1,2,4]triazin-7-yl]-2,6-difluoro-N-[(3R,4S)-4-fluoro-1-(3-fluorocyclobutanecarbonyl)pyrrolidin-3-yl]benzamide | F | | 545.1 | 1.58 (4) |
| 724 | 3-[4-amino-5-(trifluoromethyl)pyrrolo[2,1-f][1,2,4]triazin-7-yl]-2,6-difluoro-N-[(3R,4S)-4-fluoro-1-(3-fluorocyclobutanecarbonyl)pyrrolidin-3-yl]benzamide | F | | 545.2 | 1.56 (4) |
| 725 | 3-[4-amino-5-(trifluoromethyl)pyrrolo[2,1-f][1,2,4]triazin-7-yl]-2,6-difluoro-N-[(3R,4S)-4-fluoro-1-(2-fluorobenzoyl)pyrrolidin-3-yl]benzamide | F | | 567.1 | 1.67 (4) |
| 726 | 3-[4-amino-5-(trifluoromethyl)pyrrolo[2,1-f][1,2,4]triazin-7-yl]-2,6-difluoro-N-[(3R,4S)-4-fluoro-1-(3,3,3-trifluoro-2-methylpropanoyl)pyrrolidin-3-yl]benzamide | F | | 569.2 | 1.61 (3) |
| 727 | 3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2,6-difluorobenzamide | F | | 563.2 | 1.57 (3) |
| 728 | 3-[4-amino-5-(trifluoromethyl)pyrrolo[2,1-f][1,2,4]triazin-7-yl]-2,6-difluoro-N-[(3R,4S)-4-fluoro-1-(4,4,4-trifluoro-3-methylbutanoyl)pyrrolidin-3-yl]benzamide | F | | 583.2 | 1.78 (4) |
| 729 | 3-[4-amino-5-(trifluoromethyl)pyrrolo[2,1-f][1,2,4]triazin-7-yl]-2,6-difluoro-N-[(3R,4S)-4-fluoro-1-[2-hydroxy-2-(trifluoromethyl)butanoyl]pyrrolidin-3-yl]benzamide | F | | 599.1 | 1.69 (4) |

TABLE 39-continued

Compounds in Table 39 were prepared by the methods detailed in Examples 562 and 571. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

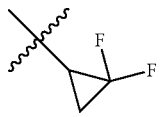

| Ex | Name | R¹ | R² | Obs. MS ion | RT (Method) |
|---|---|---|---|---|---|
| 730 | 3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2,6-difluorobenzamide | F | 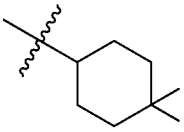 | 549.2 | 1.5 (3) |
| 731 | 3-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2,6-difluorobenzamide | F | 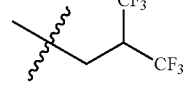 | 591.1 | 1.64 (3) |
| 732 | 3-[4-amino-5-(trifluoromethyl)pyrrolo[2,1-f][1,2,4]triazin-7-yl]-2,6-difluoro-N-[(3R,4S)-4-fluoro-1[4,4,4-trifluoro-3-(trifluoromethyl)butanoyl]pyrrolidin-3-yl]benzamide | F | 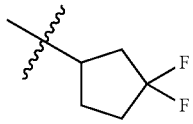 [SMILES: *C1CCC(F)(F)C1] | 637.2 | 1.85 (3) |
| 733 | 3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2,6-difluorobenzamide | F | 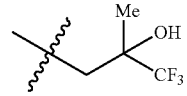 [SMILES: *CC(C)(O)C(F)(F)F] | 577.2 | 1.67 (4) |
| 734 | 3-[4-amino-5-(trifluoromethyl)pyrrolo[2,1-f][1,2,4]triazin-7-yl]-6-ethyl-2-fluoro-N-[(3R,4S)-4-fluoro-1-(4,4,4-trifluoro-3-hydroxy-3-methylbutanoyl)pyrrolidin-3-yl]benzamide | Et | 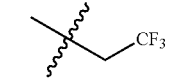 [SMILES: *CC(F)(F)F] | 609.3 | 1.81 (4) |
| 735 | 3-[4-amino-5-(trifluoromethyl)pyrrolo[2,1-f][1,2,4]triazin-7-yl]-6-ethyl-2-fluoro-N-[(3R,4S)-4-fluoro-1-(3,3,3-trifluoropropanoyl)pyrrolidin-3-yl]benzamide | Et | 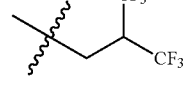 | 565.3 | 1.77 (4) |
| 736 | 3-[4-amino-5-(trifluoromethyl)pyrrolo[2,1-f][1,2,4]triazin-7-yl]-6-ethyl-2-fluoro-N-[(3R,4S)-4-fluoro-1-[4,4,4-trifluoro-3-(trifluoromethyl)butanoyl]pyrrolidin-3-yl]benzamide | Et | 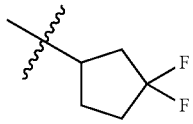 [SMILES: *C1CCC(F)(F)C1] | 647.3 | 2.07 (4) |
| 737 | 3-[4-amino-5-(trifluoromethyl)pyrrolo[2,1-f][1,2,4]triazin-7-yl]-6-ethyl-2-fluoro-N-[(3R,4S)-4-fluoro-1-[(2R)-3,3,3-trifluoro-2-hydroxy-2-methylpropanoyl]pyrrolidin-3-yl]benzamide | Et |  | 595.3 | 1.78 (4) |
| 738 | 3-[4-amino-5-(trifluoromethyl)pyrrolo[2,1-f][1,2,4]triazin-7-yl]-6-ethyl-2-fluoro-N-[(3R,4S)-4-fluoro-1-(3-methylbutanoyl)pyrrolidin-3-yl]benzamide | Et | 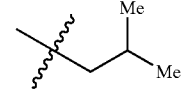 [SMILES: *CC(C)C] | 539.3 | 1.84 (4) |

TABLE 39-continued

Compounds in Table 39 were prepared by the methods detailed in Examples 562 and 571. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS ion | RT (Method) |
|---|---|---|---|---|---|
| 739 | 3-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-6-ethyl-2-fluorobenzamide | Et | 4,4-difluorocyclohexyl | 601.1 | 1.84 (3) |
| 740 | 3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-6-ethyl-2-fluorobenzamide | Et | 2,2-difluorocyclopropyl | 559.3 | 1.76 (4) |
| 741 | 3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-6-ethyl-2-fluorobenzamide | Et | 3,3-difluorocyclobutyl | 573.3 | 1.82 (4) |
| 742 | 3-[4-amino-5-(trifluoromethyl)pyrrolo[2,1-f][1,2,4]triazin-7-yl]-6-ethyl-2-fluoro-N-[(3R,4S)-4-fluoro-1-(3-fluorocyclobutanecarbonyl)pyrrolidin-3-yl]benzamide | Et | 3-fluorocyclobutyl | 555.3 | 1.69 (3) |
| 743 | 3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-6-ethyl-2-fluorobenzamide | Et | 3,3-difluorocyclopentyl | 587.0 | 1.86 (4) |
| 744 | 3-[4-amino-5-(trifluoromethyl)pyrrolo[2,1-f][1,2,4]triazin-7-yl]-6-ethyl-2-fluoro-N-[(3R,4S)-4-fluoro-1-(2-fluorobenzoyl)pyrrolidin-3-yl]benzamide | Et | 2-fluorophenyl | 577.1 | 1.8 (3) |
| 745 | 3-[4-amino-5-(trifluoromethyl)pyrrolo[2,1-f][1,2,4]triazin-7-yl]-2-fluoro-N-[(3R,4S)-4-fluoro-1-[2-hydroxy-2-(trifluoromethyl)butanoyl]pyrrolidin-3-yl]-6-methylbenzamide | Me | C(CF₃)(OH)(Me)Et | 595.3 | 1.63 (3) |
| 746 | 3-[4-amino-5-(trifluoromethyl)pyrrolo[2,1-f][1,2,4]triazin-7-yl]-2-fluoro-N-[(3R,4S)-4-fluoro-1-(4,4,4-trifluoro-3-hydroxy-3-methylbutanoyl)pyrrolidin-3-yl]-6-methylbenzamide | Me | CH₂C(Me)(OH)(CF₃) | 595.0 | 1.6 (3) |

TABLE 39-continued

Compounds in Table 39 were prepared by the methods detailed in Examples 562 and 571. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

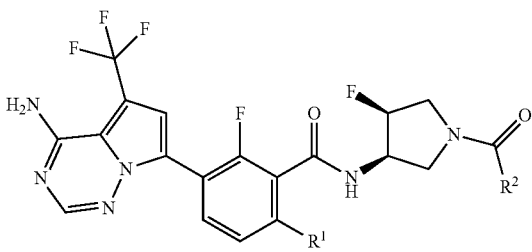

| Ex | Name | R¹ | R² | Obs. MS ion | RT (Method) |
|---|---|---|---|---|---|
| 747 | 3-[4-amino-5-(trifluoromethyl)pyrrolo[2,1-f][1,2,4]triazin-7-yl]-2-fluoro-N-[(3R,4S)-4-fluoro-1-(1-fluorocyclopropanecarbonyl)pyrrolidin-3-yl]-6-methylbenzamide | Me | 1-fluorocyclopropyl | 527.3 | 1.57 (3) |
| 748 | 3-[4-amino-5-(trifluoromethyl)pyrrolo[2,1-f][1,2,4]triazin-7-yl]-2-fluoro-N-[(3R,4S)-4-fluoro-1-(3-methylbutanoyl)pyrrolidin-3-yl]-6-methylbenzamide | Me | isobutyl | 525.3 | 1.6 (3) |
| 749 | 3-[4-amino-5-(trifluoromethyl)pyrrolo[2,1-f][1,2,4]triazin-7-yl]-2-fluoro-N-[(3R,4S)-4-fluoro-1-(3-fluorocyclobutanecarbonyl)pyrrolidin-3-yl]-6-methylbenzamide | Me | 3-fluorocyclobutyl | 541.3, 541.3 | 1.53, 1.56 (4) |
| 750 | 3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-fluoro-6-methylbenzamide | Me | 3,3-difluorocyclobutyl | 559.3 | 1.59 (3) |
| 751 | 3-[4-amino-5-(trifluoromethyl)pyrrolo[2,1-f][1,2,4]triazin-7-yl]-2-fluoro-N-[(3R,4S)-4-fluoro-1-(3,3,3-trifluoro-2-methylpropanoyl)pyrrolidin-3-yl]-6-methylbenzamide | Me | CH(Me)CF₃ | 565.1 | 1.65 (4) |
| 752 | 3-[4-amino-5-(trifluoromethyl)pyrrolo[2,1-f][1,2,4]triazin-7-yl]-2-fluoro-N-[(3R,4S)-4-fluoro-1-(4,4,4-trifluoro-3-methylbutanoyl)pyrrolidin-3-yl]-6-methylbenzamide | Me | CH₂CH(Me)CF₃ | 579.3 | 1.72 (3) |
| 753 | 3-[4-amino-5-(trifluoromethyl)pyrrolo[2,1-f][1,2,4]triazin-7-yl]-2-fluoro-N-[(3R,4S)-4-fluoro-1-(2-fluoro-2-methylpropanoyl)pyrrolidin-3-yl]-6-methylbenzamide | Me | CMe₂F | 529.1 | 1.56 (3) |
| 754 | 3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-fluoro-6-methylbenzamide | Me | 2,2-difluorocyclopropyl | 545.2 | 1.57 (4) |

TABLE 39-continued

Compounds in Table 39 were prepared by the methods detailed in Examples 562 and 571. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

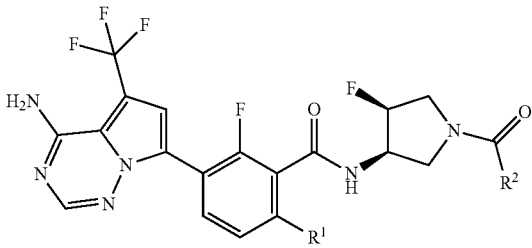

| Ex | Name | R¹ | R² | Obs. MS ion | RT (Method) |
|---|---|---|---|---|---|
| 755 | 3-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-fluoro-6-methylbenzamide | Me | 4,4-difluorocyclohexyl | 587.4 | 1.74 (3) |
| 756 | 3-[4-amino-5-(trifluoromethyl)pyrrolo[2,1-f][1,2,4]triazin-7-yl]-2-fluoro-N-[(3R,4S)-4-fluoro-1-(2-fluorobenzoyl)pyrrolidin-3-yl]-6-methylbenzamide | Me | 2-fluorophenyl | 562.9 | 1.66 (3) |
| 757 | 3-[4-amino-5-(trifluoromethyl)pyrrolo[2,1-f][1,2,4]triazin-7-yl]-2-fluoro-N-[(3R,4S)-4-fluoro-1-(2-hydroxy-2-methylpropanoyl)pyrrolidin-3-yl]-6-methylbenzamide | Me | C(Me)₂OH | 527.3 | 1.37 (4) |
| 758 | 3-[4-amino-5-(trifluoromethyl)pyrrolo[2,1-f][1,2,4]triazin-7-yl]-2-fluoro-N-[(3R,4S)-4-fluoro-1-[(2R)-3,3,3-trifluoro-2-hydroxy-2-methylpropanoyl]pyrrolidin-3-yl]-6-methylbenzamide | Me | C(Me)(CF₃)OH | 581.3 | 1.63 (3) |
| 759 | 3-[4-amino-5-(trifluoromethyl)pyrrolo[2,1-f][1,2,4]triazin-7-yl]-2-fluoro-N-[(3R,4S)-4-fluoro-1-[4,4,4-trifluoro-3-hydroxy-3-(trifluoromethyl)butanoyl]pyrrolidin-3-yl]-6-methylbenzamide | Me | CH₂C(CF₃)₂OH | 649.2 | 1.96 (4) |
| 760 | 3-[4-amino-5-(trifluoromethyl)pyrrolo[2,1-f][1,2,4]triazin-7-yl]-2-fluoro-N-[(3R,4S)-4-fluoro-1-(3,3,3-trifluoropropanoyl)pyrrolidin-3-yl]-6-methylbenzamide | Me | CH₂CF₃ | 551.0 | 1.66 (4) |
| 761 | 3-[4-amino-5-(trifluoromethyl)pyrrolo[2,1-f][1,2,4]triazin-7-yl]-2-fluoro-N-[(3R,4S)-4-fluoro-1-[4,4,4-trifluoro-3-(trifluoromethyl)butanoyl]pyrrolidin-3-yl]-6-methylbenzamide | Me | CH₂CH(CF₃)₂ | 633.3 | 1.86 (3) |
| 762 | 3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-fluoro-6-methylbenzamide | Me | 3,3-difluorocyclopentyl | 573.3 | 1.67 (4) |
| 763 | 3-[4-amino-5-(trifluoromethyl)pyrrolo[2,1-f][1,2,4]triazin-7-yl]-N-[(3R,4S)-1-cyclobutanecarbonyl-4-fluoropyrrolidin-3-yl]-2-fluorobenzamide | H | cyclobutyl | 509.0 | 1.54 (1) |

TABLE 39-continued

Compounds in Table 39 were prepared by the methods detailed in Examples 562 and 571. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

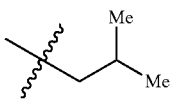

| Ex | Name | R¹ | R² | Obs. MS ion | RT (Method) |
|---|---|---|---|---|---|
| 764 | 3-[4-amino-5-(trifluoromethyl)pyrrolo[2,1-f][1,2,4]triazin-7-yl]-2-fluoro-N-[(3R,4S)-4-fluoro-1-(3-methylbutanoyl)pyrrolidin-3-yl]benzamide | H | 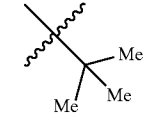 | 511.2 | 1.67 (2) |
| 765 | 3-[4-amino-5-(trifluoromethyl)pyrrolo[2,1-f][1,2,4]triazin-7-yl]-N-[(3R,4S)-1-(2,2-dimethylpropanoyl)-4-fluoropyrrolidin-3-yl]-2-fluorobenzamide | H | 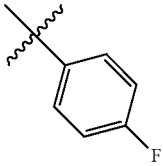 [SMILES: *c1ccc(F)cc1] | 511.1 | 1.61 (1) |
| 766 | 3-[4-amino-5-(trifluoromethyl)pyrrolo[2,1-f][1,2,4]triazin-7-yl]-2-fluoro-N-[(3R,4S)-4-fluoro-1-(4-fluorobenzoyl)pyrrolidin-3-yl]benzamide | H | 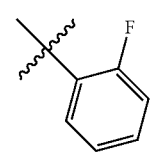 | 549.3 | 1.7 (2) |
| 767 | 3-[4-amino-5-(trifluoromethyl)pyrrolo[2,1-f][1,2,4]triazin-7-yl]-2-fluoro-N-[(3R,4S)-4-fluoro-1-(2-fluorobenzoyl)pyrrolidin-3-yl]benzamide | H | 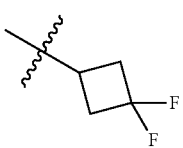 [SMILES: *C1CC(F)(F)C1] | 549.1 | 1.68 (2) |
| 768 | 3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-fluorobenzamide | H | 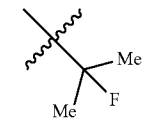 [SMILES: *C(C)(C)F] | 545.1 | 1.65 (2) |
| 769 | 3-[4-amino-5-(trifluoromethyl)pyrrolo[2,1-f][1,2,4]triazin-7-yl]-2-fluoro-N-[(3R,4S)-4-fluoro-1-(2-fluoro-2-methylpropanoyl)pyrrolidin-3-yl]benzamide | H | 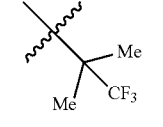 [SMILES: *C(C)(C)C(F)(F)F] | 515.3 | 1.62 (2) |
| 770 | 3-[4-amino-5-(trifluoromethyl)pyrrolo[2,1-f][1,2,4]triazin-7-yl]-2-fluoro-N-[(3R,4S)-4-fluoro-1-(3,3,3-trifluoro-2,2-dimethylpropanoyl)pyrrolidin-3-yl]benzamide | H | 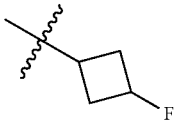 [SMILES: *C1CC(F)C1] | 565.3 | 1.82 (2) |
| 771 | 3-[4-amino-5-(trifluoromethyl)pyrrolo[2,1-f][1,2,4]triazin-7-yl]-2-fluoro-N-[(3R,4S)-4-fluoro-1-(3-fluorocyclobutanecarbonyl)pyrrolidin-3-yl]benzamide | H |  | 527.3, 527.3 | 1.48 (1) |

TABLE 39-continued

Compounds in Table 39 were prepared by the methods detailed in Examples 562 and 571. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

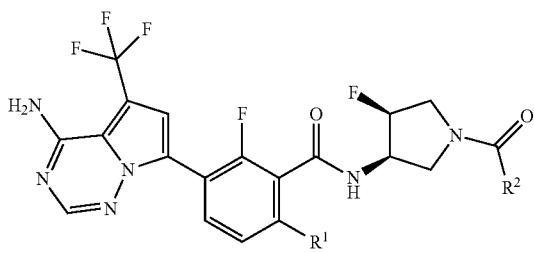

| Ex | Name | R¹ | R² | Obs. MS ion | RT (Method) |
|---|---|---|---|---|---|
| 772 | 3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-fluorobenzamide | H | 3,3-difluorocyclopentyl | 559.3 | 1.62 (1) |
| 773 | 3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-fluorobenzamide | H | 2,2-difluorocyclopropyl | 531.0 | 1.59 (1) |
| 774 | 3-[4-amino-5-(trifluoromethyl)pyrrolo[2,1-f][1,2,4]triazin-7-yl]-2-fluoro-N-[(3R,4S)-4-fluoro-1-[(2R)-3,3,3-trifluoro-2-hydroxy-2-methylpropanoyl]pyrrolidin-3-yl]benzamide | H | (2R)-CF₃/OH/Me | 567.3 | 1.57 (2) |

TABLE 40

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

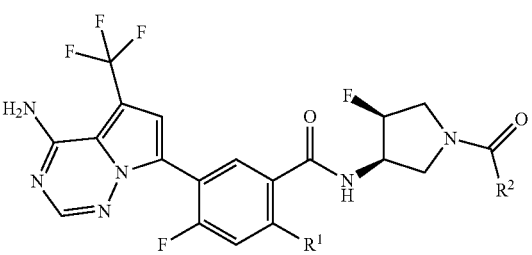

| Ex | Name | R¹ | R² | Obs. MS Ion | RT (Method) |
|---|---|---|---|---|---|
| 775 | 5-[4-amino-5-(trifluoromethyl)pyrrolo[2,1-f][1,2,4]triazin-7-yl]-2,4-difluoro-N-[(3R,4S)-4-fluoro-1-(3,3,3-trifluoropropanoyl)pyrrolidin-3-yl]benzamide | F | CH₂CF₃ | 555.3 | 1.8 (3) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

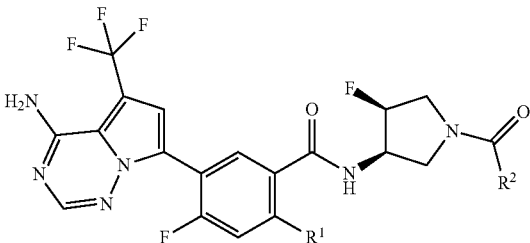

| Ex | Name | R$^1$ | R$^2$ | Obs. MS Ion | RT (Method) |
|---|---|---|---|---|---|
| 776 | 5-[4-amino-5-(trifluoromethyl)pyrrolo[2,1-f][1,2,4]triazin-7-yl]-2,4-difluoro-N-[(3R,4S)-4-fluoro-1-(2-hydroxy-2-methylpropanoyl)pyrrolidin-3-yl]benzamide | F | (C(Me)(Me)OH) | 531.1 | 1.57 (4) |
| 777 | 5-[4-amino-5-(trifluoromethyl)pyrrolo[2,1-f][1,2,4]triazin-7-yl]-2,4-difluoro-N-[(3R,4S)-4-fluoro-1-(3-methylbutanoyl)pyrrolidin-3-yl]benzamide | F | (CH2CH(Me)Me) | 529.3 | 1.79 (4) |
| 778 | 5-[4-amino-5-(trifluoromethyl)pyrrolo[2,1-f][1,2,4]triazin-7-yl]-2,4-difluoro-N-[(3R,4S)-4-fluoro-1-(3-fluorocyclobutanecarbonyl)pyrrolidin-3-yl]benzamide | F | (3-fluorocyclobutyl) | 545.3 | 1.70 (4) |
| 779 | 5-[4-amino-5-(trifluoromethyl)pyrrolo[2,1-f][1,2,4]triazin-7-yl]-2,4-difluoro-N-[(3R,4S)-4-fluoro-1-(1-fluorocyclopropanecarbonyl)pyrrolidin-3-yl]benzamide | F | (1-fluorocyclopropyl) | 531.2 | 1.92 (3) |
| 780 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2,4-difluorobenzamide | F | (3,3-difluorocyclobutyl) | 563.1 | 1.79 (4) |
| 781 | 5-[4-amino-5-(trifluoromethyl)pyrrolo[2,1-f][1,2,4]triazin-7-yl]-2,4-difluoro-N-[(3R,4S)-4-fluoro-1-[2-hydroxy-2-(trifluoromethyl)butanoyl]pyrrolidin-3-yl]benzamide | F | (C(CF3)(OH)CH2Me) | 599.1 | 1.93 (4) |
| 782 | 5-[4-amino-5-(trifluoromethyl)pyrrolo[2,1-f][1,2,4]triazin-7-yl]-2,4-difluoro-N-[(3R,4S)-4-fluoro-1-(2-fluoro-2-methylpropanoyl)pyrrolidin-3-yl]benzamide | F | (C(Me)(Me)F) | 533.1 | 1.81 (4) |
| 783 | 5-[4-amino-5-(trifluoromethyl)pyrrolo[2,1-f][1,2,4]triazin-7-yl]-2,4-difluoro-N-[(3R,4S)-4-fluoro-1-[4,4,4-trifluoro-3-(trifluoromethyl)butanoyl]pyrrolidin-3-yl]benzamide | F | (CH2CH(CF3)CF3) | 637.2 | 2.22 (4) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 784 | 5-[4-amino-5-(trifluoromethyl)pyrrolo[2,1-f][1,2,4]triazin-7-yl]-2,4-difluoro-N-[(3R,4S)-4-fluoro-1-[4,4,4-trifluoro-3-hydroxy-3-(trifluoromethyl)butanoyl]pyrrolidin-3-yl]benzamide | F | [CH₂-C(CF₃)(OH)(CF₃)] | 653.0 | 2.14 (3) |
| 785 | 5-[4-amino-5-(trifluoromethyl)pyrrolo[2,1-f][1,2,4]triazin-7-yl]-2,4-difluoro-N-[(3R,4S)-4-fluoro-1-(4,4,4-trifluoro-3-methylbutanoyl)pyrrolidin-3-yl]benzamide | F | [CH₂-CH(Me)(CF₃)] | 583.0 | 1.89 (4) |
| 786 | 5-[4-amino-5-(trifluoromethyl)pyrrolo[2,1-f][1,2,4]triazin-7-yl]-2,4-difluoro-N-[(3R,4S)-4-fluoro-1-(4,4,4-trifluoro-3-hydroxy-3-methylbutanoyl)pyrrolidin-3-yl]benzamide | F | [CH₂-C(Me)(OH)(CF₃)] | 599.0 | 1.78 (4) |
| 787 | 5-[4-amino-5-(trifluoromethyl)pyrrolo[2,1-f][1,2,4]triazin-7-yl]-2,4-difluoro-N-[(3R,4S)-4-fluoro-1-(3,3,3-trifluoro-2-methylpropanoyl)pyrrolidin-3-yl]benzamide | F | [CH(Me)(CF₃)] | 569.3 | 1.92 (4) |
| 788 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2,4-difluorobenzamide | F | [2,2-difluorocyclopropyl] | 549.2 | 1.71 (4) |
| 789 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2,4-difluorobenzamide | F | [3,3-difluorocyclopentyl] | 577.2 | 1.97 (3) |
| 790 | 5-[4-amino-5-(trifluoromethyl)pyrrolo[2,1-f][1,2,4]triazin-7-yl]-2,4-difluoro-N-[(3R,4S)-4-fluoro-1-[(2R)-3,3,3-trifluoro-2-hydroxy-2-methylpropanoyl]pyrrolidin-3-yl]benzamide | F | [C(Me)(CF₃)(OH)], (2R) | 585.3 | 1.69 (3) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

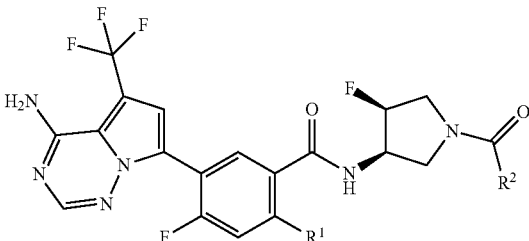

| Ex | Name | R¹ | R² | Obs. MS Ion | RT (Method) |
|---|---|---|---|---|---|
| 791 | 5-[4-amino-5-(trifluoromethyl)pyrrolo[2,1-f][1,2,4]triazin-7-yl]-N-[(3R,4S)-1-cyclobutanecarbonyl-4-fluoropyrrolidin-3-yl]-4-fluoro-2-methylbenzamide | Me | | 523.3 | 1.65 (2) |
| 792 | 5-[4-amino-5-(trifluoromethyl)pyrrolo[2,1-f][1,2,4]triazin-7-yl]-4-fluoro-N-[(3R,4S)-4-fluoro-1-(4-fluorobenzoyl)pyrrolidin-3-yl]-2-methylbenzamide | Me | | 563.1 | 1.86 (2) |
| 793 | 5-[4-amino-5-(trifluoromethyl)pyrrolo[2,1-f][1,2,4]triazin-7-yl]-4-fluoro-N-[(3R,4S)-4-fluoro-1-(2-methylpropanoyl)pyrrolidin-3-yl]-2-methylbenzamide | Me | | 511.1 | 1.73 (2) |
| 794 | 5-[4-amino-5-(trifluoromethyl)pyrrolo[2,1-f][1,2,4]triazin-7-yl]-4-fluoro-N-[(3R,4S)-4-fluoro-1-(3-methylbutanoyl)pyrrolidin-3-yl]-2-methylbenzamide | Me | | 525.1 | 1.84 (2) |
| 795 | 5-[4-amino-5-(trifluoromethyl)pyrrolo[2,1-f][1,2,4]triazin-7-yl]-N-[(3R,4S)-1-(2,2-dimethylpropanoyl)-4-fluoropyrrolidin-3-yl]-4-fluoro-2-methylbenzamide | Me | | 525.1 | 1.85 (2) |
| 796 | 5-[4-amino-5-(trifluoromethyl)pyrrolo[2,1-f][1,2,4]triazin-7-yl]-4-fluoro-N-[(3R,4S)-4-fluoro-1-(3,3,3-trifluoropropanoyl)pyrrolidin-3-yl]-2-methylbenzamide | Me | | 551.1 | 1.73 (1) |
| 797 | 5-[4-amino-5-(trifluoromethyl)pyrrolo[2,1-f][1,2,4]triazin-7-yl]-N-[(3R,4S)-1-cyclopentanecarbonyl-4-fluoropyrrolidin-3-yl]-4-fluoro-2-methylbenzamide | Me | | 537.4 | 1.75 (2) |
| 798 | 5-[4-amino-5-(trifluoromethyl)pyrrolo[2,1-f][1,2,4]triazin-7-yl]-4-fluoro-N-[(3R,4S)-4-fluoro-1-[1-(trifluoromethyl)cyclobutanecarbonyl]pyrrolidin-3-yl]-2-methylbenzamide | Me | | 591.2 | 1.81 (1) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

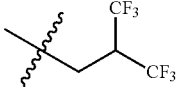 [SMILES: *CC(C(F)(F)F)C(F)(F)F]

| Ex | Name | R¹ | R² | Obs. MS Ion | RT (Method) |
|---|---|---|---|---|---|
| 799 | 5-[4-amino-5-(trifluoromethyl)pyrrolo[2,1-f][1,2,4]triazin-7-yl]-4-fluoro-N-[(3R,4S)-4-fluoro-1-[4,4,4-trifluoro-3-(trifluoromethyl)butanoyl]pyrrolidin-3-yl]-2-methylbenzamide | Me | 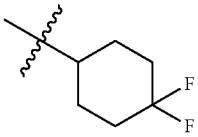 [SMILES: *C1CCC(F)(F)CC1] | 633.3 | 1.95 (2) |
| 800 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-4-fluoro-2-methylbenzamide | Me | 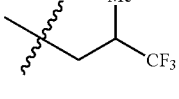 | 587.4 | 1.76 (2) |
| 801 | 5-[4-amino-5-(trifluoromethyl)pyrrolo[2,1-f][1,2,4]triazin-7-yl]-4-fluoro-N-[(3R,4S)-4-fluoro-1-(4,4,4-trifluoro-3-methylbutanoyl)pyrrolidin-3-yl]-2-methylbenzamide | Me | 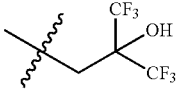 | 579.3 | 1.77 (1) |
| 802 | 5-[4-amino-5-(trifluoromethyl)pyrrolo[2,1-f][1,2,4]triazin-7-yl]-4-fluoro-N-[(3R,4S)-4-fluoro-1-[4,4,4-trifluoro-3-hydroxy-3-(trifluoromethyl)butanoyl]pyrrolidin-3-yl]-2-methylbenzamide | Me | 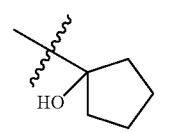 [SMILES: *C1(O)CCCC1] | 649.3 | 1.98 (1) |
| 803 | 5-[4-amino-5-(trifluoromethyl)pyrrolo[2,1-f][1,2,4]triazin-7-yl]-4-fluoro-N-[(3R,4S)-4-fluoro-1-(1-hydroxycyclopentanecarbonyl)pyrrolidin-3-yl]-2-methylbenzamide | Me | 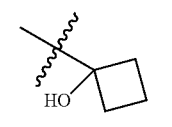 | 553.4 | 1.54 (1) |
| 804 | 5-[4-amino-5-(trifluoromethyl)pyrrolo[2,1-f][1,2,4]triazin-7-yl]-4-fluoro-N-[(3R,4S)-4-fluoro-1-(1-hydroxycyclobutanecarbonyl)pyrrolidin-3-yl]-2-methylbenzamide | Me | 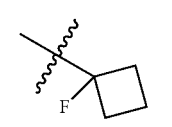 | 539.4 | 1.52 (2) |
| 805 | 5-[4-amino-5-(trifluoromethyl)pyrrolo[2,1-f][1,2,4]triazin-7-yl]-4-fluoro-N-[(3R,4S)-4-fluoro-1-(1-fluorocyclobutanecarbonyl)pyrrolidin-3-yl]-2-methylbenzamide | Me |  | 541.4 | 1.77 (2) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 806 | 5-[4-amino-5-(trifluoromethyl)pyrrolo[2,1-f][1,2,4]triazin-7-yl]-4-fluoro-N-[(3R,4S)-4-fluoro-1-(3,3,3-trifluoro-2,2-dimethylpropanoyl)pyrrolidin-3-yl]-2-methylbenzamide | Me | C(Me)(Me)CF₃ | 579.2 | 1.79 (1) |
| 807 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-4-fluoro-2-methylbenzamide | Me | 2,2-difluorocyclopropyl | 545.3 | 1.65 (2) |
| 808 | 5-[4-amino-5-(trifluoromethyl)pyrrolo[2,1-f][1,2,4]triazin-7-yl]-N-[(3R,4S)-1-(2-chloro-4,5-difluorobenzoyl)-4-fluoropyrrolidin-3-yl]-4-fluoro-2-methylbenzamide | Me | 2-chloro-4,5-difluorophenyl | 615.4 | 1.85 (4) |
| 809 | 5-[4-amino-5-(trifluoromethyl)pyrrolo[2,1-f][1,2,4]triazin-7-yl]-N-[(3R,4S)-1-(2-chloro-4-fluorobenzoyl)-4-fluoropyrrolidin-3-yl]-4-fluoro-2-methylbenzamide | Me | 2-chloro-4-fluorophenyl | 597.2 | 1.83 (4) |
| 810 | 5-[4-amino-5-(trifluoromethyl)pyrrolo[2,1-f][1,2,4]triazin-7-yl]-N-[(3R,4S)-1-(2-chloro-3-fluorobenzoyl)-4-fluoropyrrolidin-3-yl]-4-fluoro-2-methylbenzamide | Me | 2-chloro-3-fluorophenyl | 597.0 | 1.8 (4) |
| 811 | 5-[4-amino-5-(trifluoromethyl)pyrrolo[2,1-f][1,2,4]triazin-7-yl]-N-[(3R,4S)-1-(5-cyano-2-fluorobenzoyl)-4-fluoropyrrolidin-3-yl]-4-fluoro-2-methylbenzamide | Me | 5-cyano-2-fluorophenyl | 588.2 | 1.76 (4) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

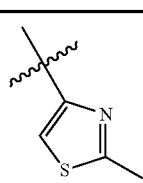

| Ex | Name | R¹ | R² | Obs. MS Ion | RT (Method) |
|----|------|----|----|-------------|-------------|
| 812 | 5-[4-amino-5-(trifluoromethyl)pyrrolo[2,1-f][1,2,4]triazin-7-yl]-4-fluoro-N-[(3R,4S)-4-fluoro-1-(2-methyl-1,3-thiazole-4-carbonyl)pyrrolidin-3-yl]-2-methylbenzamide | Me | 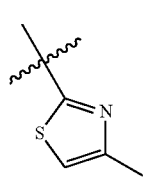 [SMILES: *c1nc(C)cs1] | 566.1 | 1.72 (4) |
| 813 | 5-[4-amino-5-(trifluoromethyl)pyrrolo[2,1-f][1,2,4]triazin-7-yl]-4-fluoro-N-[(3R,4S)-4-fluoro-1-(4-methyl-1,3-thiazole-2-carbonyl)pyrrolidin-3-yl]-2-methylbenzamide | Me | 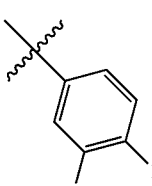 | 566.2 | 1.85 (4) |
| 814 | 5-[4-amino-5-(trifluoromethyl)pyrrolo[2,1-f][1,2,4]triazin-7-yl]-N-[(3R,4S)-1-(3,4-difluorobenzoyl)-4-fluoropyrrolidin-3-yl]-4-fluoro-2-methylbenzamide | Me | 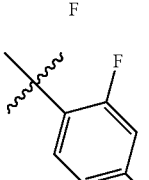 | 581.0 | 1.78 (4) |
| 815 | 5-[4-amino-5-(trifluoromethyl)pyrrolo[2,1-f][1,2,4]triazin-7-yl]-4-fluoro-N-[(3R,4S)-4-fluoro-1-(2,4,5-trifluorobenzoyl)pyrrolidin-3-yl]-2-methylbenzamide | Me | 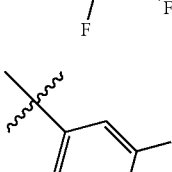 | 599.2 | 1.88 (4) |
| 816 | 5-[4-amino-5-(trifluoromethyl)pyrrolo[2,1-f][1,2,4]triazin-7-yl]-N-[(3R,4S)-1-(3,5-difluorobenzoyl)-4-fluoropyrrolidin-3-yl]-4-fluoro-2-methylbenzamide | Me | 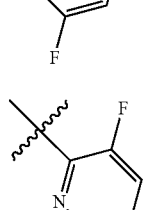 | 581.0 | 1.87 (4) |
| 817 | 5-[4-amino-5-(trifluoromethyl)pyrrolo[2,1-f][1,2,4]triazin-7-yl]-4-fluoro-N-[(3R,4S)-4-fluoro-1-(3-fluoropyridine-2-carbonyl)pyrrolidin-3-yl]-2-methylbenzamide | Me | | 564.3 | 1.63 (4) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

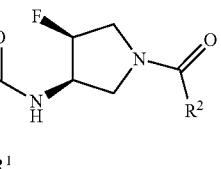

| Ex | Name | R¹ | R² | Obs. MS Ion | RT (Method) |
|---|---|---|---|---|---|
| 818 | 5-[4-amino-5-(trifluoromethyl)pyrrolo[2,1-f][1,2,4]triazin-7-yl]-N-[(3R,4S)-1-(4-chloropyridine-3-carbonyl)-4-fluoropyrrolidin-3-yl]-4-fluoro-2-methylbenzamide | Me | 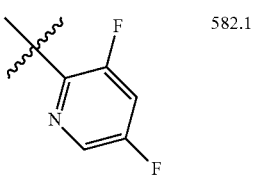 | 580.2 | 1.58 (4) |
| 819 | 5-[4-amino-5-(trifluoromethyl)pyrrolo[2,1-f][1,2,4]triazin-7-yl]-N-[(3R,4S)-1-(3,5-difluoropyridine-2-carbonyl)-4-fluoropyrrolidin-3-yl]-4-fluoro-2-methylbenzamide | Me | 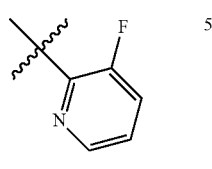 | 582.1 | 1.64 (4) |
| 820 | 5-[4-amino-5-(trifluoromethyl)pyrrolo[2,1-f][1,2,4]triazin-7-yl]-4-fluoro-N-[(3R,4S)-4-fluoro-1-(5-fluoro-2-methylpyridine-4-carbonyl)pyrrolidin-3-yl]-2-methylbenzamide | Me | 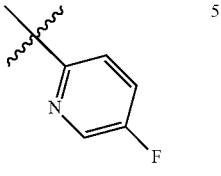 | 578.3 | 1.66 (4) |
| 821 | 5-[4-amino-5-(trifluoromethyl)pyrrolo[2,1-f][1,2,4]triazin-7-yl]-4-fluoro-N-[(3R,4S)-4-fluoro-1-(5-fluoropyridine-2-carbonyl)pyrrolidin-3-yl]-2-methylbenzamide | Me | 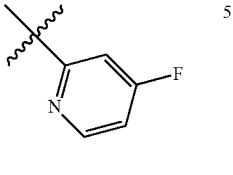 | 564.1 | 1.65 (4) |
| 822 | 5-[4-amino-5-(trifluoromethyl)pyrrolo[2,1-f][1,2,4]triazin-7-yl]-4-fluoro-N-[(3R,4S)-4-fluoro-1-(4-fluoropyridine-2-carbonyl)pyrrolidin-3-yl]-2-methylbenzamide | Me | 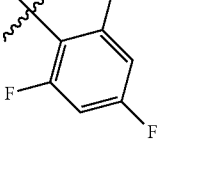 | 564.2 | 1.65 (4) |
| 832 | 5-[4-amino-5-(trifluoromethyl)pyrrolo[2,1-f][1,2,4]triazin-7-yl]-4-fluoro-N-[(3R,4S)-4-fluoro-1-(2,4,6-trifluorobenzoyl)pyrrolidin-3-yl]-2-methylbenzamide | Me | 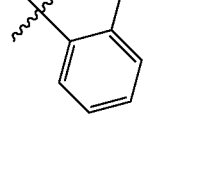 | 599.2 | 1.81 (4) |
| 824 | 5-[4-amino-5-(trifluoromethyl)pyrrolo[2,1-f][1,2,4]triazin-7-yl]-N-[(3R,4S)-1-(2-chlorobenzoyl)-4-fluoropyrrolidin-3-yl]-4-fluoro-2-methylbenzamide | Me | | 579.2 | 1.75 (3) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

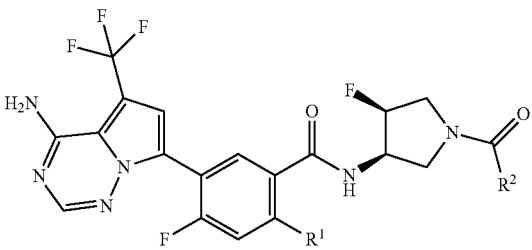

| Ex | Name | R¹ | R² | Obs. MS Ion | RT (Method) |
|---|---|---|---|---|---|
| 825 | 5-[4-amino-5-(trifluoromethyl)pyrrolo[2,1-f][1,2,4]triazin-7-yl]-N-[(3R,4S)-1-(2-chloro-6-fluorobenzoyl)-4-fluoropyrrolidin-3-yl]-4-fluoro-2-methylbenzamide | Me | 2-Cl, 6-F-phenyl | 597.1 | 1.86 (4) |
| 826 | 5-[4-amino-5-(trifluoromethyl)pyrrolo[2,1-f][1,2,4]triazin-7-yl]-4-fluoro-N-[(3R,4S)-4-fluoro-1-(3-fluorobenzoyl)pyrrolidin-3-yl]-2-methylbenzamide | Me | 3-F-phenyl | 563.1 | 1.84 (4) |
| 827 | 5-[4-amino-5-(trifluoromethyl)pyrrolo[2,1-f][1,2,4]triazin-7-yl]-N-[(3R,4S)-1-(4-chlorobenzoyl)-4-fluoropyrrolidin-3-yl]-4-fluoro-2-methylbenzamide | Me | 4-Cl-phenyl | 579.1 | 1.83 (4) |
| 828 | 5-[4-amino-5-(trifluoromethyl)pyrrolo[2,1-f][1,2,4]triazin-7-yl]-4-fluoro-N-[(3R,4S)-4-fluoro-1-(pyridine-2-carbonyl)pyrrolidin-3-yl]-2-methylbenzamide | Me | pyridin-2-yl | 546.2 | 1.57 (4) |
| 829 | 5-[4-amino-5-(trifluoromethyl)pyrrolo[2,1-f][1,2,4]triazin-7-yl]-4-fluoro-N-[(3R,4S)-4-fluoro-1-(pyridine-4-carbonyl)pyrrolidin-3-yl]-2-methylbenzamide | Me | pyridin-4-yl | 546.3 | 1.31 (3) |
| 830 | 5-[4-amino-5-(trifluoromethyl)pyrrolo[2,1-f][1,2,4]triazin-7-yl]-N-[(3R,4S)-1-(2,5-difluorobenzoyl)-4-fluoropyrrolidin-3-yl]-4-fluoro-2-methylbenzamide | Me | 2,5-diF-phenyl | 581.2 | 1.75 (4) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

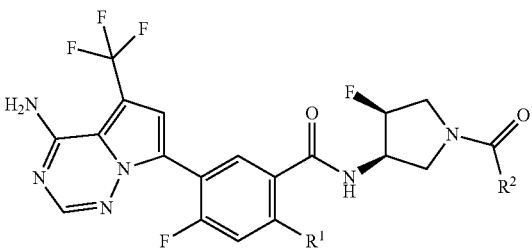

| Ex | Name | $R^1$ | $R^2$ | Obs. MS Ion | RT (Method) |
|---|---|---|---|---|---|
| 831 | 5-[4-amino-5-(trifluoromethyl)pyrrolo[2,1-f][1,2,4]triazin-7-yl]-N-[(3R,4S)-1-(2,6-difluorobenzoyl)-4-fluoropyrrolidin-3-yl]-4-fluoro-2-methylbenzamide | Me | 2,6-difluorophenyl | 581.0 | 1.81 (4) |
| 832 | 5-[4-amino-5-(trifluoromethyl)pyrrolo[2,1-f][1,2,4]triazin-7-yl]-N-[(3R,4S)-1-(2,4-difluorobenzoyl)-4-fluoropyrrolidin-3-yl]-4-fluoro-2-methylbenzamide | Me | 2,4-difluorophenyl | 581.1 | 1.79 (4) |
| 833 | 5-[4-amino-5-(trifluoromethyl)pyrrolo[2,1-f][1,2,4]triazin-7-yl]-4-fluoro-N-[(3R,4S)-4-fluoro-1-(1,3-thiazole-4-carbonyl)pyrrolidin-3-yl]-2-methylbenzamide | Me | 1,3-thiazol-4-yl | 552.2 | 1.62 (4) |
| 834 | 5-[4-amino-5-(trifluoromethyl)pyrrolo[2,1-f][1,2,4]triazin-7-yl]-4-fluoro-N-[(3R,4S)-4-fluoro-1-(3-fluoropyridine-4-carbonyl)pyrrolidin-3-yl]-2-methylbenzamide | Me | 3-fluoropyridin-4-yl | 564.3 | 1.61 (4) |
| 835 | 5-[4-amino-5-(trifluoromethyl)pyrrolo[2,1-f][1,2,4]triazin-7-yl]-N-[(3R,4S)-1-(3,5-difluoropyridine-4-carbonyl)-4-fluoropyrrolidin-3-yl]-4-fluoro-2-methylbenzamide | Me | 3,5-difluoropyridin-4-yl | 582.2 | 1.67 (3) |
| 836 | 5-[4-amino-5-(trifluoromethyl)pyrrolo[2,1-f][1,2,4]triazin-7-yl]-N-[(3R,4S)-1-(2,3-difluorobenzoyl)-4-fluoropyrrolidin-3-yl]-4-fluoro-2-methylbenzamide | Me | 2,3-difluorophenyl | 581.2 | 1.84 (4) |
| 837 | 5-[4-amino-5-(trifluoromethyl)pyrrolo[2,1-f][1,2,4]triazin-7-yl]-4-fluoro-N-[(3R,4S)-4-fluoro-1-(2-methylpyridine-4-carbonyl)pyrrolidin-3-yl]-2-methylbenzamide | Me | 2-methylpyridin-4-yl | 560.2 | 1.59 (4) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

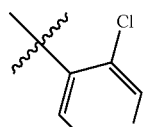

| Ex | Name | R¹ | R² | Obs. MS Ion | RT (Method) |
|---|---|---|---|---|---|
| 838 | 5-[4-amino-5-(trifluoromethyl)pyrrolo[2,1-f][1,2,4]triazin-7-yl]-N-[(3R,4S)-1-(3-chloropyridine-4-carbonyl)-4-fluoropyrrolidin-3-yl]-4-fluoro-2-methylbenzamide | Me | 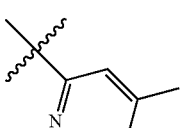 | 580.2 | 1.56 (3) |
| 839 | 5-[4-amino-5-(trifluoromethyl)pyrrolo[2,1-f][1,2,4]triazin-7-yl]-4-fluoro-N-[(3R,4S)-4-fluoro-1-(4-methylpyridine-2-carbonyl)pyrrolidin-3-yl]-2-methylbenzamide | Me | 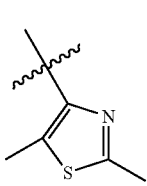 | 560.1 | 1.63 (4) |
| 840 | 5-[4-amino-5-(trifluoromethyl)pyrrolo[2,1-f][1,2,4]triazin-7-yl]-N-[(3R,4S)-1-(2,5-dimethyl-1,3-thiazole-4-carbonyl)-4-fluoropyrrolidin-3-yl]-4-fluoro-2-methylbenzamide | Me | 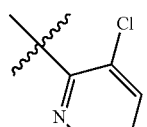 | 580.3 | 1.7 (4) |
| 841 | 5-[4-amino-5-(trifluoromethyl)pyrrolo[2,1-f][1,2,4]triazin-7-yl]-N-[(3R,4S)-1-(3-chloropyridine-2-carbonyl)-4-fluoropyrrolidin-3-yl]-4-fluoro-2-methylbenzamide | Me | 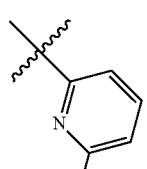 | 580.2 | 1.83 (4) |
| 842 | 5-[4-amino-5-(trifluoromethyl)pyrrolo[2,1-f][1,2,4]triazin-7-yl]-4-fluoro-N-[(3R,4S)-4-fluoro-1-(6-methylpyridine-2-carbonyl)pyrrolidin-3-yl]-2-methylbenzamide | Me | 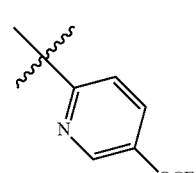 | 560.3 | 1.71 (4) |
| 843 | 5-[4-amino-5-(trifluoromethyl)pyrrolo[2,1-f][1,2,4]triazin-7-yl]-4-fluoro-N-[(3R,4S)-4-fluoro-1-[5-(trifluoromethoxy)pyridine-2-carbonyl]pyrrolidin-3-yl]-2-methylbenzamide | Me |  | 630.2 | 1.92 (4) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

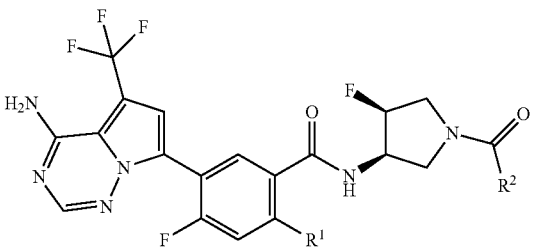

| Ex | Name | R¹ | R² | Obs. MS Ion | RT (Method) |
|---|---|---|---|---|---|
| 844 | 5-[4-amino-5-(trifluoromethyl)pyrrolo[2,1-f][1,2,4]triazin-7-yl]-N-[(3R,4S)-1-(6-bromopyridine-2-carbonyl)-4-fluoropyrrolidin-3-yl]-4-fluoro-2-methylbenzamide | Me | 6-bromopyridin-2-yl | 623.9 | 1.75 (3) |
| 845 | 5-[4-amino-5-(trifluoromethyl)pyrrolo[2,1-f][1,2,4]triazin-7-yl]-N-[(3R,4S)-1-(5-bromo-3-fluoropyridine-2-carbonyl)-4-fluoropyrrolidin-3-yl]-4-fluoro-2-methylbenzamide | Me | 5-bromo-3-fluoropyridin-2-yl | 642.2 | 1.79 (4) |
| 846 | 5-[4-amino-5-(trifluoromethyl)pyrrolo[2,1-f][1,2,4]triazin-7-yl]-4-fluoro-N-[(3R,4S)-4-fluoro-1-[3-(trifluoromethyl)pyridine-2-carbonyl]pyrrolidin-3-yl]-2-methylbenzamide | Me | 3-(trifluoromethyl)pyridin-2-yl | 614.3 | 1.71 (4) |
| 847 | 5-[4-amino-5-(trifluoromethyl)pyrrolo[2,1-f][1,2,4]triazin-7-yl]-N-[(3R,4S)-1-(6-bromo-5-fluoropyridine-2-carbonyl)-4-fluoropyrrolidin-3-yl]-4-fluoro-2-methylbenzamide | Me | 6-bromo-5-fluoropyridin-2-yl | 642.2 | 1.88 (4) |
| 848 | 5-[4-amino-5-(trifluoromethyl)pyrrolo[2,1-f][1,2,4]triazin-7-yl]-4-fluoro-N-[(3R,4S)-4-fluoro-1-[6-(trifluoromethyl)pyridine-2-carbonyl]pyrrolidin-3-yl]-2-methylbenzamide | Me | 6-(trifluoromethyl)pyridin-2-yl | 614.3 | 1.88 (4) |
| 849 | 5-[4-amino-5-(trifluoromethyl)pyrrolo[2,1-f][1,2,4]triazin-7-yl]-N-[(3R,4S)-1-(4-chloropyridine-2-carbonyl)-4-fluoropyrrolidin-3-yl]-4-fluoro-2-methylbenzamide | Me | 4-chloropyridin-2-yl | 580.0 | 1.69 (3) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 850 | 5-[4-amino-5-(trifluoromethyl)pyrrolo[2,1-f][1,2,4]triazin-7-yl]-4-fluoro-N-[(3R,4S)-4-fluoro-1-[3-fluoro-5-(trifluoromethyl)pyridine-2-carbonyl]pyrrolidin-3-yl]-2-methylbenzamide | Me | 3-fluoro-5-CF₃-pyridin-2-yl | 632.0 | 1.79 (3) |
| 851 | 5-[4-amino-5-(trifluoromethyl)pyrrolo[2,1-f][1,2,4]triazin-7-yl]-N-[(3R,4S)-1-(5-chloropyridine-2-carbonyl)-4-fluoropyrrolidin-3-yl]-4-fluoro-2-methylbenzamide | Me | 5-chloropyridin-2-yl | 580.3 | 1.79 (4) |
| 852 | 5-[4-amino-5-(trifluoromethyl)pyrrolo[2,1-f][1,2,4]triazin-7-yl]-N-[(3R,4S)-1-(6-chloropyridine-2-carbonyl)-4-fluoropyrrolidin-3-yl]-4-fluoro-2-methylbenzamide | Me | 6-chloropyridin-2-yl | 580.2 | 1.78 (4) |
| 853 | 5-[4-amino-5-(trifluoromethyl)pyrrolo[2,1-f][1,2,4]triazin-7-yl]-N-[(3R,4S)-1-[6-chloro-3-(trifluoromethyl)pyridine-2-carbonyl]-4-fluoropyrrolidin-3-yl]-4-fluoro-2-methylbenzamide | Me | 6-chloro-3-CF₃-pyridin-2-yl | 648.2 | 1.87 (4) |
| 854 | 5-[4-amino-5-(trifluoromethyl)pyrrolo[2,1-f][1,2,4]triazin-7-yl]-N-[(3R,4S)-1-(3-bromopyridine-2-carbonyl)-4-fluoropyrrolidin-3-yl]-4-fluoro-2-methylbenzamide | Me | 3-bromopyridin-2-yl | 624.0 | 1.65 (4) |
| 855 | 5-[4-amino-5-(trifluoromethyl)pyrrolo[2,1-f][1,2,4]triazin-7-yl]-4-fluoro-N-[(3R,4S)-4-fluoro-1-[4-carbonyl]pyrrolidin-3-yl]-2-methylbenzamide | Me | 4-CF₃-pyridin-3-yl | 614.1 | 1.68 (4) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

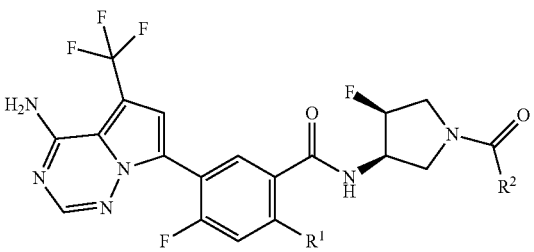

| Ex | Name | R¹ | R² | Obs. MS Ion | RT (Method) |
|---|---|---|---|---|---|
| 856 | 5-[4-amino-5-(trifluoromethyl)pyrrolo[2,1-f][1,2,4]triazin-7-yl]-4-fluoro-N-[(3R,4S)-4-fluoro-1-(4,4,4-trifluoro-3-hydroxy-3-methylbutanoyl)pyrrolidin-3-yl]-2-methylbenzamide | Me | | 594.9 | 1.77 (2) |
| 857 | 5-[4-amino-5-(trifluoromethyl)pyrrolo[2,1-f][1,2,4]triazin-7-yl]-4-fluoro-N-[(3R,4S)-4-fluoro-1-[2-hydroxy-2-(trifluoromethyl)butanoyl]pyrrolidin-3-yl]-2-methylbenzamide | Me | | 595.1 | 1.85 (2) |
| 858 | 5-[4-amino-5-(trifluoromethyl)pyrrolo[2,1-f][1,2,4]triazin-7-yl]-4-fluoro-N-[(3R,4S)-4-fluoro-1-(3,3,3-trifluoro-2-methylpropanoyl)pyrrolidin-3-yl]-2-methylbenzamide | Me | | 565.3 | 1.79 (2) |
| 859 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-4-fluoro-2-methylbenzamide | Me | | 573.1 | |
| 860 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-4-fluoro-2-methylbenzamide | Me | | 573.1 | |
| 861 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-4-fluoro-2-methylbenzamide | Me | | 545.1 | |
| 862 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-4-fluoro-2-methylbenzamide | Me | | 545.2 | |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 863 | 5-[4-amino-5-(trifluoromethyl)pyrrolo[2,1-f][1,2,4]triazin-7-yl]-4-fluoro-N-[(3R,4S)-4-fluoro-1-(2,3,3,3-tetrafluoro-2-methylpropanoyl)pyrrolidin-3-yl]-2-methylbenzamide | Me | (structure with F₃C, Me, F) | 583.4 | 1.96 (4) |
| 864 | 5-[4-amino-5-(trifluoromethyl)pyrrolo[2,1-f][1,2,4]triazin-7-yl]-N-[(3R,4S)-1-(6-chloropyridazine-3-carbonyl)-4-fluoropyrrolidin-3-yl]-4-fluoro-2-methylbenzamide | Me | (6-chloropyridazin-3-yl) | 581.2 | 1.65 (4) |
| 865 | 5-[4-amino-5-(trifluoromethyl)pyrrolo[2,1-f][1,2,4]triazin-7-yl]-4-fluoro-N-[(3R,4S)-4-fluoro-1-(pyridazine-3-carbonyl)pyrrolidin-3-yl]-2-methylbenzamide | Me | (pyridazin-3-yl) | 547.1 | 1.51 (4) |
| 866 | 5-[4-amino-5-(trifluoromethyl)pyrrolo[2,1-f][1,2,4]triazin-7-yl]-4-fluoro-N-[(3R,4S)-4-fluoro-1-(6-methylpyridazine-3-carbonyl)pyrrolidin-3-yl]-2-methylbenzamide | Me | (6-methylpyridazin-3-yl) | 561.2 | 1.46 (3) |
| 867 | 5-[4-amino-5-(trifluoromethyl)pyrrolo[2,1-f][1,2,4]triazin-7-yl]-4-fluoro-N-[(3R,4S)-4-fluoro-1-[(2R)-3,3,3-trifluoro-2-hydroxy-2-methylpropanoyl]pyrrolidin-3-yl]-2-methoxybenzamide | OMe | (CF₃, OH) | 597.3 | 1.7 (2) |
| 868 | 5-[4-amino-5-(trifluoromethyl)pyrrolo[2,1-f][1,2,4]triazin-7-yl]-4-fluoro-N-[(3R,4S)-4-fluoro-1-(2-fluoro-2-methylpropanoyl)pyrrolidin-3-yl]-2-methoxybenzamide | OMe | (Me, Me, F) | 545.1 | 1.9 (2) |
| 869 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-4-fluoro-2-methoxybenzamide | OMe | (2,2-difluorocyclopropyl) | 561.3 | 1.68 (1) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 870 | 5-[4-amino-5-(trifluoromethyl)pyrrolo[2,1-f][1,2,4]triazin-7-yl]-4-fluoro-N-[(3R,4S)-4-fluoro-1-(3,3,3-trifluoro-2,2-dimethylpropanoyl)pyrrolidin-3-yl]-2-methoxybenzamide | OMe | | 595.3 | 1.96 (2) |
| 871 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-4-fluoro-2-methoxybenzamide | OMe | | 589.3 | 1.78 (1) |
| 872 | 5-[4-amino-5-(trifluoromethyl)pyrrolo[2,1-f][1,2,4]triazin-7-yl]-4-fluoro-N-[(3R,4S)-4-fluoro-1-(3-fluorocyclobutanecarbonyl)pyrrolidin-3-yl]-2-methoxybenzamide | OMe | | 557.4 | 1.73 (1) |
| 873 | 5-[4-amino-5-(trifluoromethyl)pyrrolo[2,1-f][1,2,4]triazin-7-yl]-4-fluoro-N-[(3R,4S)-4-fluoro-1-(4-fluorobenzoyl)pyrrolidin-3-yl]-2-methoxybenzamide | OMe | | 579.0 | 1.79 (1) |
| 874 | 5-[4-amino-5-(trifluoromethyl)pyrrolo[2,1-f][1,2,4]triazin-7-yl]-4-fluoro-N-[(3R,4S)-4-fluoro-1-(3,3,3-trifluoropropanoyl)pyrrolidin-3-yl]-2-methoxybenzamide | OMe | | 567.3 | 1.75 (2) |
| 875 | 5-[4-amino-5-(trifluoromethyl)pyrrolo[2,1-f][1,2,4]triazin-7-yl]-4-fluoro-N-[(3R,4S)-4-fluoro-1-(4,4,4-trifluoro-3-methylbutanoyl)pyrrolidin-3-yl]-2-methoxybenzamide | OMe | | 595.1 | 1.98 (4) |
| 876 | 5-[4-amino-5-(trifluoromethyl)pyrrolo[2,1-f][1,2,4]triazin-7-yl]-4-fluoro-N-[(3R,4S)-4-fluoro-1-[4,4,4-trifluoro-3-(trifluoromethyl)butanoyl]pyrrolidin-3-yl]-2-methoxybenzamide | OMe | | 649.0 | 2.06 (4) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|----|------|-----|-----|-------------|-------------|
| 877 | 5-[4-amino-5-(trifluoromethyl)pyrrolo[2,1-f][1,2,4]triazin-7-yl]-4-fluoro-N-[(3R,4S)-4-fluoro-1-[2-hydroxy-2-(trifluoromethyl)butanoyl]pyrrolidin-3-yl]-2-methoxybenzamide | OMe | Me, F₃C, OH | 611.0 | 1.91 (4) |
| 878 | 5-[4-amino-5-(trifluoromethyl)pyrrolo[2,1-f][1,2,4]triazin-7-yl]-4-fluoro-N-[(3R,4S)-4-fluoro-1-(3,3,3-trifluoro-2-methylpropanoyl)pyrrolidin-3-yl]-2-methoxybenzamide | OMe | Me, F₃C | 581.2 | 1.9 (4) |
| 879 | 5-[4-amino-5-(trifluoromethyl)pyrrolo[2,1-f][1,2,4]triazin-7-yl]-4-fluoro-N-[(3R,4S)-4-fluoro-1-(4,4,4-trifluoro-3-hydroxy-3-methylbutanoyl)pyrrolidin-3-yl]-2-methoxybenzamide | OMe | Me, OH, CF₃ | 611.4 | 1.82 (4) |
| 880 | 5-[4-amino-5-(trifluoromethyl)pyrrolo[2,1-f][1,2,4]triazin-7-yl]-2-chloro-4-fluoro-N-[(3R,4S)-4-fluoro-1-[2-hydroxy-2-(trifluoromethyl)butanoyl]pyrrolidin-3-yl]benzamide | Cl | Me, F₃C, OH | 614.9 | 1.79 (2) |
| 881 | 5-[4-amino-5-(trifluoromethyl)pyrrolo[2,1-f][1,2,4]triazin-7-yl]-2-chloro-4-fluoro-N-[(3R,4S)-4-fluoro-1-(4,4,4-trifluoro-3-hydroxy-3-methylbutanoyl)pyrrolidin-3-yl]benzamide | Cl | Me, OH, CF₃ | 615.2 | 1.83 (2) |
| 882 | 5-[4-amino-5-(trifluoromethyl)pyrrolo[2,1-f][1,2,4]triazin-7-yl]-2-chloro-4-fluoro-N-[(3R,4S)-4-fluoro-1-[4,4,4-trifluoro-3-(trifluoromethyl)butanoyl]pyrrolidin-3-yl]benzamide | Cl | Me, OH, CF₃ | 653.2 | 2.05 (2) |
| 883 | 5-[4-amino-5-(trifluoromethyl)pyrrolo[2,1-f][1,2,4]triazin-7-yl]-2-chloro-4-fluoro-N-[(3R,4S)-4-fluoro-1-(4,4,4-trifluoro-3-methylbutanoyl)pyrrolidin-3-yl]benzamide | Cl | Me, CF₃ | 599.2 | 1.97 (2) |

TABLE 40-continued

Compounds in Table 40 were prepared by the methods detailed in Examples 562 and 568. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

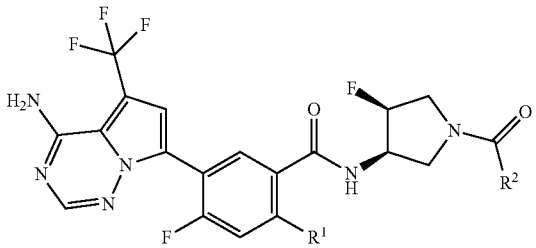

| Ex | Name | R$^1$ | R$^2$ | Obs. MS Ion | RT (Method) |
|---|---|---|---|---|---|
| 884 | 5-[4-amino-5-(trifluoromethyl)pyrrolo[2,1-f][1,2,4]triazin-7-yl]-2-chloro-4-fluoro-N-[(3R,4S)-4-fluoro-1-(3,3,3-trifluoro-2-methylpropanoyl)pyrrolidin-3-yl]benzamide | Cl | ![structure with F$_3$C, Me] | 585.1 | 1.89 (2) |
| 885 | 5-[4-amino-5-(trifluoromethyl)pyrrolo[2,1-f][1,2,4]triazin-7-yl]-2-chloro-4-fluoro-N-[(3R,4S)-4-fluoro-1-[4,4,4-trifluoro-3-hydroxy-3-(trifluoromethyl)butanoyl]pyrrolidin-3-yl]benzamide | Cl | ![structure with CF$_3$, OH, CF$_3$] | 669.3 | 2.03 (2) |
| 886 | 5-[4-amino-5-(trifluoromethyl)pyrrolo[2,1-f][1,2,4]triazin-7-yl]-2-chloro-N-[(3R,4S)-1-(3,3-difluorocyclopentanecarbonyl)-4-fluoropyrrolidin-3-yl]-4-fluorobenzamide | Cl | ![difluorocyclopentane] | 593.1 | 1.71 (3) |
| 887 | 5-[4-amino-5-(trifluoromethyl)pyrrolo[2,1-f][1,2,4]triazin-7-yl]-2-chloro-N-[(3R,4S)-1-(3,3-difluorocyclopentanecarbonyl)-4-fluoropyrrolidin-3-yl]-4-fluorobenzamide | Cl | ![difluorocyclopentane] | 593.2 | 1.71 (3) |
| 888 | 5-[4-amino-5-(trifluoromethyl)pyrrolo[2,1-f][1,2,4]triazin-7-yl]-2-chloro-4-fluoro-N-[(3R,4S)-4-fluoro-1-(3-fluorocyclobutanecarbonyl)pyrrolidin-3-yl]benzamide | Cl | ![fluorocyclobutane] | 561.0 | 1.73 (4) |
| 889 | 3-[4-amino-5-(trifluoromethyl)pyrrolo[2,1-f][1,2,4]triazin-7-yl]-4-fluoro-N-[(3R,4S)-4-fluoro-1-[2-hydroxy-2-(trifluoromethyl)butanoyl]pyrrolidin-3-yl]benzamide | H | ![structure with Me, F$_3$C, OH] | 581.0 | 1.74 (2) |

TABLE 41

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 890 | 5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-(trifluoromethyl)benzamide | CF₃ | (1-fluorocyclopropyl) | 563.3 | 1.82 (4) |
| 891 | 5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-(trifluoromethyl)benzamide | CF₃ | CH₂C(OH)(CF₃)₂ | 685.2 | 2.07 (3) |
| 892 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-(trifluoromethyl)benzamide | CF₃ | (3,3-difluorocyclobutyl) | 595.1 | 1.81 (3) |
| 893 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(trifluoromethyl)benzamide | CF₃ | (3-fluorocyclobutyl) | 577.3, 577.3 | 1.75, 1.77 (4) |
| 894 | 5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-(trifluoromethyl)benzamide | CF₃ | C(Me)₂F | 565.3 | 1.79 (4) |
| 895 | 5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-(trifluoromethyl)benzamide | CF₃ | CH₂CH(Me)CF₃ | 615.3 | 1.88 (3) |
| 896 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(trifluoromethyl)benzamide | CF₃ | (2,2-difluorocyclopropyl) | 581.3 | 1.73 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 897 | 5-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-2-(trifluoromethyl)benzamide | CF₃ | (C(Me)(Me)OH) | 563.3 | 1.61 (3) |
| 898 | 5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-(trifluoromethyl)benzamide | CF₃ | (CH₂C(Me)(OH)CF₃) | 631.3 | 1.80 (4) |
| 899 | 5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-(trifluoromethyl)benzamide | CF₃ | (C(CF₃)(OH)CH₂Me) | 631.3 | 1.82 (4) |
| 900 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(trifluoromethyl)benzamide | CF₃ | (3,3-difluorocyclopentyl) | 609.3 | 1.88 (4) |
| 901 | 5-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-2-(trifluoromethyl)benzamide | CF₃ | (CH₂CF₃) | 587.3 | 1.74 (4) |
| 902 | 5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-(trifluoromethyl)benzamide | CF₃ | (CH₂CH(Me)Me) | 561.1 | 1.8 (4) |
| 903 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-(trifluoromethyl)benzamide | CF₃ | (4,4-difluorocyclohexyl) | 623.1 | 1.87 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | $R^1$ | $R^2$ | Obs. MS Ion | RT (Method) |
|---|---|---|---|---|---|
| 904 | 5-[4-amino-5-(trifluoromethyl)pyrrolo[2,1-f][1,2,4]triazin-7-yl]-N-[(3R,4S)-4-fluoro-1-[(2S)-3,3,3-trifluoro-2-hydroxy-2-methylpropanoyl]pyrrolidin-3-yl]-2-(trifluoromethyl)benzamide | $CF_3$ | | 617.3 | 1.74 (4) |
| 905 | 5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-(trifluoromethyl)benzamide | $CF_3$ | | 669.2 | 2.07 (4) |
| 906 | 5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-(trifluoromethyl)benzamide | $CF_3$ | | 599.0 | 1.81 (4) |
| 907 | 5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-(trifluoromethyl)benzamide | $CF_3$ | | 601.0 | 1.82 (4) |
| 908 | 5-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-2-(fluoromethyl)benzamide | $CH_2F$ | | 527.3 | 1.46 (4) |
| 909 | 5-[4-amino-5-(trifluoromethyl)pyrrolo[2,1-f][1,2,4]triazin-7-yl][(3R,4S)-4-fluoro-1-(3-methylbutanoyl)pyrrolidin-3-yl]-2-(fluoromethyl)benzamide | $CH_2F$ | | 525.1 | 1.72 (3) |
| 910 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-(fluoromethyl)benzamide | $CH_2F$ | | 581.2 | 1.67 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 911 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-(fluoromethyl)benzamide | CH₂F | 3,3-difluorocyclobutyl | 559.3 | 1.68 (4) |
| 912 | 5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-(fluoromethyl)benzamide | CH₂F | CH₂C(OH)(CF₃)₂ | 649.1 | 2.03 (4) |
| 913 | 5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-(fluoromethyl)benzamide | CH₂F | 2-fluorophenyl | 563.1 | 1.75 (3) |
| 914 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(fluoromethyl)benzamide | CH₂F | 2,2-difluorocyclopropyl | 545.1 | 1.58 (3) |
| 915 | 5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-(fluoromethyl)benzamide | CH₂F | CH₂CH(CF₃)₂ | 633.1 | 1.99 (4) |
| 916 | 5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-(fluoromethyl)benzamide | CH₂F | 1-fluorocyclopropyl | 527.1 | 1.66 (4) |
| 917 | 5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-(fluoromethyl)benzamide | CH₂F | CH₂CH(Me)CF₃ | 579.3 | (4)1.8 |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R$^1$ | R$^2$ | Obs. MS Ion | RT (Method) |
|---|---|---|---|---|---|
| 918 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-(fluoromethyl)benzamide | CH$_2$F | 4,4-difluorocyclohexyl | 587.3 | 1.71 (3) |
| 919 | 5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-(fluoromethyl)benzamide | CH$_2$F | C(Me)(OH)CH$_2$CF$_3$ | 595.2 | 1.66 (3) |
| 920 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(fluoromethyl)benzamide | CH$_2$F | 3,3-difluorocyclopentyl | 573.2 | 1.69 (3) |
| 921 | 5-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-2-(fluoromethyl)benzamide | CH$_2$F | CH$_2$CF$_3$ | 551.0 | 1.65 (3) |
| 922 | 5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-(fluoromethyl)benzamide | CH$_2$F | C(Et)(OH)(CF$_3$) | 595.3 | 1.76 (3) |
| 923 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(fluoromethyl)benzamide | CH$_2$F | 3-fluorocyclobutyl | 541.4 | 1.64 (3) |
| 924 | 5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-(fluoromethyl)benzamide | CH$_2$F | CH(Me)(CF$_3$) | 565.1 | 1.69 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R$^1$ | R$^2$ | Obs. MS Ion | RT (Method) |
|---|---|---|---|---|---|
| 925 | 5-[4-amino-5-(trifluoromethyl)pyrrolo[2,1-f][1,2,4]triazin-7-yl]-2-chloro-N-[(3R,4S)-4-fluoro-1-(3-fluorocyclobutanecarbonyl)pyrrolidin-3-yl]benzamide | Cl | (3-fluorocyclobutyl) | 543.2, 543.3 | 1.67, 1.70 (2) |
| 926 | 5-[4-amino-5-(trifluoromethyl)pyrrolo[2,1-f][1,2,4]triazin-7-yl]-2-chloro-N-[(3R,4S)-4-fluoro-1-[4,4,4-trifluoro-3-(trifluoromethyl)butanoyl]pyrrolidin-3-yl]benzamide | Cl | CH$_2$CH(CF$_3$)$_2$ | 635.2 | 2.02 (2) |
| 927 | 5-[4-amino-5-(trifluoromethyl)pyrrolo[2,1-f][1,2,4]triazin-7-yl]-2-chloro-N-[(3R,4S)-4-fluoro-1-[2-hydroxy-2-(trifluoromethyl)butanoyl]pyrrolidin-3-yl]benzamide | Cl | C(CF$_3$)(OH)(CH$_2$Me) | 597.2 | 1.8 (2) |
| 928 | 5-[4-amino-5-(trifluoromethyl)pyrrolo[2,1-f][1,2,4]triazin-7-yl]-2-chloro-N-[(3R,4S)-4-fluoro-1-(3,3,3-trifluoropropanoyl)pyrrolidin-3-yl]benzamide | Cl | CH$_2$CF$_3$ | 553.2 | 1.71 (2) |
| 929 | 5-[4-amino-5-(trifluoromethyl)pyrrolo[2,1-f][1,2,4]triazin-7-yl]-2-chloro-N-[(3R,4S)-4-fluoro-1-(2-hydroxy-2-methylpropanoyl)pyrrolidin-3-yl]benzamide | Cl | C(Me)$_2$OH | 529.0 | 1.52 (2) |
| 930 | 5-[4-amino-5-(trifluoromethyl)pyrrolo[2,1-f][1,2,4]triazin-7-yl]-2-chloro-N-[(3R,4S)-1-(3,3-difluorocyclopentanecarbonyl)-4-fluoropyrrolidin-3-yl]benzamide | Cl | (3,3-difluorocyclopentyl) | 575.2 | 1.81 (2) |
| 931 | 5-[4-amino-5-(trifluoromethyl)pyrrolo[2,1-f][1,2,4]triazin-7-yl]-2-chloro-N-[(3R,4S)-4-fluoro-1-[4,4,4-trifluoro-3-hydroxy-3-(trifluoromethyl)butanoyl]pyrrolidin-3-yl]benzamide | Cl | CH$_2$C(OH)(CF$_3$)$_2$ | 651.1 | 2.07 (2) |
| 932 | 5-[4-amino-5-(trifluoromethyl)pyrrolo[2,1-f][1,2,4]triazin-7-yl]-2-chloro-N-[(3R,4S)-4-fluoro-1-(2-fluorobenzoyl)pyrrolidin-3-yl]benzamide | Cl | (2-fluorophenyl) | 565.0 | 1.79 (2) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 933 | 5-[4-amino-5-(trifluoromethyl)pyrrolo[2,1-f][1,2,4]triazin-7-yl]-2-chloro-N-[(3R,4S)-4-fluoro-1-(2-fluoro-2-methylpropanoyl)pyrrolidin-3-yl]benzamide | Cl | C(Me)(Me)F | 531.0 | 1.77 (2) |
| 934 | 5-[4-amino-5-(trifluoromethyl)pyrrolo[2,1-f][1,2,4]triazin-7-yl]-2-chloro-N-[(3R,4S)-4-fluoro-1-(1-fluorocyclopropanecarbonyl)pyrrolidin-3-yl]benzamide | Cl | 1-fluorocyclopropyl | 529.2 | 1.75 (2) |
| 935 | 5-[4-amino-5-(trifluoromethyl)pyrrolo[2,1-f][1,2,4]triazin-7-yl]-2-chloro-N-[(3R,4S)-4-fluoro-1-[(2R)-3,3,3-trifluoro-2-hydroxy-2-methylpropanoyl]pyrrolidin-3-yl]benzamide | Cl | C(Me)(OH)(CF₃) | 583.2 | 1.72 (2) |
| 936 | 5-[4-amino-5-(trifluoromethyl)pyrrolo[2,1-f][1,2,4]triazin-7-yl]-2-chloro-N-[(3R,4S)-4-fluoro-1-(4,4,4-trifluoro-3-hydroxy-3-methylbutanoyl)pyrrolidin-3-yl]benzamide | Cl | CH₂C(Me)(OH)CF₃ | 597.2 | 1.78 (2) |
| 937 | 5-[4-amino-5-(trifluoromethyl)pyrrolo[2,1-f][1,2,4]triazin-7-yl]-2-chloro-N-[(3R,4S)-1-(2,2-difluorocyclopropanecarbonyl)-4-fluoropyrrolidin-3-yl]benzamide | Cl | 2,2-difluorocyclopropyl | 547.2 | 1.71 (2) |
| 938 | 5-[4-amino-5-(trifluoromethyl)pyrrolo[2,1-f][1,2,4]triazin-7-yl]-2-chloro-N-[(3R,4S)-1-(4,4-difluorocyclohexanecarbonyl)-4-fluoropyrrolidin-3-yl]benzamide | Cl | 4,4-difluorocyclohexyl | 589.2 | 1.83 (2) |
| 939 | 5-[4-amino-5-(trifluoromethyl)pyrrolo[2,1-f][1,2,4]triazin-7-yl]-2-chloro-N-[(3R,4S)-4-fluoro-1-(3-methylbutanoyl)pyrrolidin-3-yl]benzamide | Cl | CH₂CH(Me)Me | 527.3 | 1.79 (2) |
| 940 | 5-[4-amino-5-(trifluoromethyl)pyrrolo[2,1-f][1,2,4]triazin-7-yl]-2-chloro-N-[(3R,4S)-4-fluoro-1-(3,3,3-trifluoro-2-methylpropanoyl)pyrrolidin-3-yl]benzamide | Cl | CH(Me)CF₃ | 567.2 | 1.8 (2) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 941 | 5-[4-amino-5-(trifluoromethyl)pyrrolo[2,1-f][1,2,4]triazin-7-yl]-2-chloro-N-[(3R,4S)-4-fluoro-1-(4,4,4-trifluoro-3-methylbutanoyl)pyrrolidin-3-yl]benzamide | Cl | Me, CF₃ branched | 581.2 | 1.9 (2) |
| 942 | 5-[4-amino-5-(trifluoromethyl)pyrrolo[2,1-f][1,2,4]triazin-7-yl]-2-chloro-N-[(3R,4S)-1-(3,3-difluorocyclobutanecarbonyl)-4-fluoropyrrolidin-3-yl]benzamide | Cl | 3,3-difluorocyclobutyl | 561.2 | 1.76 (2) |
| 943 | 5-[4-amino-5-(trifluoromethyl)pyrrolo[2,1-f][1,2,4]triazin-7-yl]-2-chloro-N-[(3R,4S)-4-fluoro-1-[4-(trifluoromethyl)pyridine-2-carbonyl]pyrrolidin-3-yl]benzamide | Cl | 4-(CF₃)pyridin-2-yl | 616.2 | 1.85 |
| 944 | 5-[4-amino-5-(trifluoromethyl)pyrrolo[2,1-f][1,2,4]triazin-7-yl]-2-chloro-N-[(3R,4S)-1-(2,4-difluorobenzoyl)-4-fluoropyrrolidin-3-yl]benzamide | Cl | 2,4-difluorophenyl | 583.1 | 1.79 (3) |
| 945 | 5-[4-amino-5-(trifluoromethyl)pyrrolo[2,1-f][1,2,4]triazin-7-yl]-2-chloro-N-[(3R,4S)-1-(3,5-difluoropyridine-2-carbonyl)-4-fluoropyrrolidin-3-yl]benzamide | Cl | 3,5-difluoropyridin-2-yl | 584.0 | 1.7 (4) |
| 946 | 5-[4-amino-5-(trifluoromethyl)pyrrolo[2,1-f][1,2,4]triazin-7-yl]-2-chloro-N-[(3R,4S)-4-fluoro-1-(1,3-thiazole-4-carbonyl)pyrrolidin-3-yl]benzamide | Cl | 1,3-thiazol-4-yl | 554.2 | 1.55 (4) |
| 947 | 5-[4-amino-5-(trifluoromethyl)pyrrolo[2,1-f][1,2,4]triazin-7-yl]-2-chloro-N-[(3R,4S)-1-(4-chlorobenzoyl)-4-fluoropyrrolidin-3-yl]benzamide | Cl | 4-chlorophenyl | 580.9 | 1.84 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 948 | 5-[4-amino-5-(trifluoromethyl)pyrrolo[2,1-f][1,2,4]triazin-7-yl]-2-chloro-N-[(3R,4S)-1-(3,4-difluorobenzoyl)-4-fluoropyrrolidin-3-yl]benzamide | Cl | 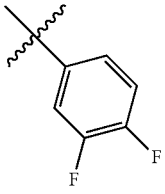 [SMILES: *c1ccc(F)c(F)c1] | 583.3 | 1.81 (3) |
| 949 | 5-[4-amino-5-(trifluoromethyl)pyrrolo[2,1-f][1,2,4]triazin-7-yl]-2-chloro-N-[(3R,4S)-4-fluoro-1-(3-fluoropyridine-2-carbonyl)pyrrolidin-3-yl]benzamide | Cl | 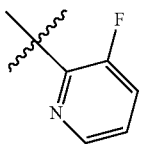 [SMILES: *c1ncccc1F] | 566.1 | 1.49 (3) |
| 950 | 5-[4-amino-5-(trifluoromethyl)pyrrolo[2,1-f][1,2,4]triazin-7-yl]-2-chloro-N-[(3R,4S)-4-fluoro-1-(pyridine-4-carbonyl)pyrrolidin-3-yl]benzamide | Cl | 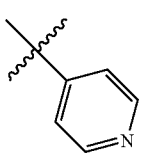 [SMILES: *c1ccncc1] | 548.1 | 1.5 (4) |
| 951 | 5-[4-amino-5-(trifluoromethyl)pyrrolo[2,1-f][1,2,4]triazin-7-yl]-2-chloro-N-[(3R,4S)-4-fluoro-1-(3-fluorobenzoyl)pyrrolidin-3-yl]benzamide | Cl | 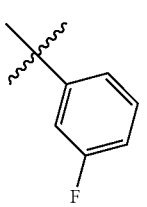 [SMILES: *c1cccc(F)c1] | 565.3 | 1.92 (4) |
| 952 | 5-[4-amino-5-(trifluoromethyl)pyrrolo[2,1-f][1,2,4]triazin-7-yl]-2-chloro-N-[(3R,4S)-4-fluoro-1-(4-fluorobenzoyl)pyrrolidin-3-yl]benzamide | Cl | 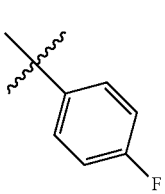 [SMILES: *c1ccc(F)cc1] | 565.2 | 1.73 (4) |
| 953 | 5-[4-amino-5-(trifluoromethyl)pyrrolo[2,1-f][1,2,4]triazin-7-yl]-2-chloro-N-[(3R,4S)-4-fluoro-1-[4-(trifluoromethyl)pyridine-3-carbonyl]pyrrolidin-3-yl]benzamide | Cl | 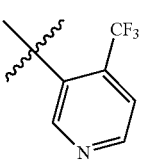 | 615.9 | 1.65 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

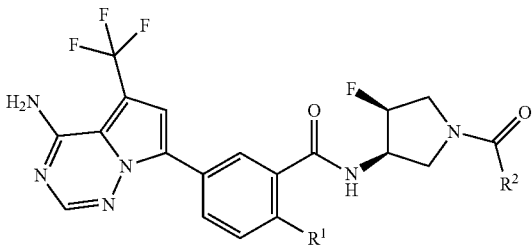

| Ex | Name | R¹ | R² | Obs. MS Ion | RT (Method) |
|---|---|---|---|---|---|
| 954 | 5-[4-amino-5-(trifluoromethyl)pyrrolo[2,1-f][1,2,4]triazin-7-yl]-N-[(3R,4S)-1-benzoyl-4-fluoropyrrolidin-3-yl]-2-chlorobenzamide | Cl | phenyl | 547.0 | 1.75 (4) |
| 955 | 5-[4-amino-5-(trifluoromethyl)pyrrolo[2,1-f][1,2,4]triazin-7-yl]-2-chloro-N-[(3R,4S)-1-(3,5-difluoropyridine-4-carbonyl)-4-fluoropyrrolidin-3-yl]benzamide | Cl | 3,5-difluoropyridin-4-yl | 584.1 | 1.62 (4) |
| 956 | 5-[4-amino-5-(trifluoromethyl)pyrrolo[2,1-f][1,2,4]triazin-7-yl]-2-chloro-N-[(3R,4S)-4-fluoro-1-(pyridine-2-carbonyl)pyrrolidin-3-yl]benzamide | Cl | pyridin-2-yl | 548.1 | 1.48 (3) |
| 957 | 5-[4-amino-5-(trifluoromethyl)pyrrolo[2,1-f][1,2,4]triazin-7-yl]-2-chloro-N-[(3R,4S)-1-(2,5-difluorobenzoyl)-4-fluoropyrrolidin-3-yl]benzamide | Cl | 2,5-difluorophenyl | 583.1 | 1.79 (3) |
| 958 | 5-[4-amino-5-(trifluoromethyl)pyrrolo[2,1-f][1,2,4]triazin-7-yl]-2-chloro-N-[(3R,4S)-4-fluoro-1-(5-fluoropyridine-2-carbonyl)pyrrolidin-3-yl]benzamide | Cl | 5-fluoropyridin-2-yl | 565.8 | 1.78 (4) |
| 959 | 5-[4-amino-5-(trifluoromethyl)pyrrolo[2,1-f][1,2,4]triazin-7-yl]-2-chloro-N-[(3R,4S)-1-(4-chloropyridine-3-carbonyl)-4-fluoropyrrolidin-3-yl]benzamide | Cl | 4-chloropyridin-3-yl | 582.2 | 1.55 (4) |
| 960 | 5-[4-amino-5-(trifluoromethyl)pyrrolo[2,1-f][1,2,4]triazin-7-yl]-2-chloro-N-[(3R,4S)-4-fluoro-1-(2-methylpyridine-4-carbonyl)pyrrolidin-3-yl]benzamide | Cl | 2-methylpyridin-4-yl | 562.0 | 1.57 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

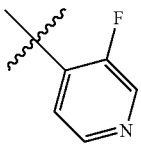 [SMILES: *c1ccncc1F]

| Ex | Name | R¹ | R² | Obs. MS Ion | RT (Method) |
|---|---|---|---|---|---|
| 961 | 5-[4-amino-5-(trifluoromethyl)pyrrolo[2,1-f][1,2,4]triazin-7-yl]-2-chloro-N-[(3R,4S)-4-fluoro-1-(3-fluoropyridine-4-carbonyl)pyrrolidin-3-yl]benzamide | Cl | 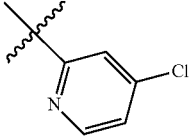 [SMILES: *c1cc(Cl)ccn1] | 566.2 | 1.53 (4) |
| 962 | 5-[4-amino-5-(trifluoromethyl)pyrrolo[2,1-f][1,2,4]triazin-7-yl]-2-chloro-N-[(3R,4S)-1-(4-chloropyridine-2-carbonyl)-4-fluoropyrrolidin-3-yl]benzamide | Cl | 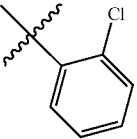 | 582.2 | 1.74 (4) |
| 963 | 5-[4-amino-5-(trifluoromethyl)pyrrolo[2,1-f][1,2,4]triazin-7-yl]-2-chloro-N-[(3R,4S)-1-(2-chlorobenzoyl)-4-fluoropyrrolidin-3-yl]benzamide | Cl |  | 580.9 | 1.77 (4) |
| 964 | 5-[4-amino-5-(trifluoromethyl)pyrrolo[2,1-f][1,2,4]triazin-7-yl]-2-chloro-N-[(3R,4S)-1-(2,6-difluorobenzoyl)-4-fluoropyrrolidin-3-yl]benzamide | Cl | 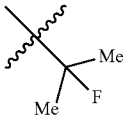 [SMILES: *C(C)(C)F] | 583.2 | 1.74 (4) |
| 965 | 5-[4-amino-5-(trifluoromethyl)pyrrolo[2,1-f][1,2,4]triazin-7-yl]-2-ethyl-N-[(3R,4S)-4-fluoro-1-(2-fluoro-2-methylpropanoyl)pyrrolidin-3-yl]benzamide | Et | 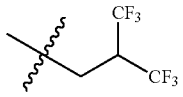 | 525.4 | 1.71 (3) |
| 966 | 5-[4-amino-5-(trifluoromethyl)pyrrolo[2,1-f][1,2,4]triazin-7-yl]-2-ethyl-N-[(3R,4S)-4-fluoro-1-[4,4,4-trifluoro-3-(trifluoromethyl)butanoyl]pyrrolidin-3-yl]benzamide | Et | 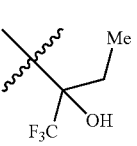 | 629.3 | 2.00 (3) |
| 967 | 5-[4-amino-5-(trifluoromethyl)pyrrolo[2,1-f][1,2,4]triazin-7-yl]-2-ethyl-N-[(3R,4S)-4-fluoro-1-[2-hydroxy-2-(trifluoromethyl)butanoyl]pyrrolidin-3-yl]benzamide | Et |  | 591.3 | 1.84 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 968 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-ethylbenzamide | Et | 3,3-difluorocyclobutyl | 555.3 | 1.80 (4) |
| 969 | 5-[4-amino-5-(trifluoromethyl)pyrrolo[2,1-f][1,2,4]triazin-7-yl]-2-ethyl-N-[(3R,4S)-4-fluoro-1-(3-fluorocyclobutanecarbonyl)pyrrolidin-3-yl]benzamide | Et | 3-fluorocyclobutyl | 537.4, 537.4 | 1.62, 1.65 (3) |
| 970 | 5-[4-amino-5-(trifluoromethyl)pyrrolo[2,1-f][1,2,4]triazin-7-yl]-2-ethyl-N-[(3R,4S)-4-fluoro-1-(1-fluorocyclopropanecarbonyl)pyrrolidin-3-yl]benzamide | Et | 1-fluorocyclopropyl | 523.3 | 1.79 (4) |
| 971 | 5-[4-amino-5-(trifluoromethyl)pyrrolo[2,1-f][1,2,4]triazin-7-yl]-2-ethyl-N-[(3R,4S)-4-fluoro-1-(4,4,4-trifluoro-3-methylbutanoyl)pyrrolidin-3-yl]benzamide | Et | CH₂CH(Me)CF₃ | 575.3 | 1.93 (4) |
| 972 | 5-[4-amino-5-(trifluoromethyl)pyrrolo[2,1-f][1,2,4]triazin-7-yl]-2-ethyl-N-[(3R,4S)-4-fluoro-1-[4,4,4-trifluoro-3-hydroxy-3-(trifluoromethyl)butanoyl]pyrrolidin-3-yl]benzamide | Et | CH₂C(CF₃)(OH)CF₃ | 645.2 | 2.14 (4) |
| 973 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-ethylbenzamide | Et | 4,4-difluorocyclohexyl | 583.0 | 1.83 (3) |
| 974 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-ethylbenzamide | Et | 3,3-difluorocyclopentyl | 569.0 | 1.87 (4) |
| 975 | 5-[4-amino-5-(trifluoromethyl)pyrrolo[2,1-f][1,2,4]triazin-7-yl]-2-ethyl-N-[(3R,4S)-4-fluoro-1-(4,4,4-trifluoro-3-hydroxy-3- | Et | CH₂C(Me)(OH)CF₃ | 591.2 | 1.85 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|----|------|----|----|-------------|-------------|
|    | methylbutanoyl)pyrrolidin-3-yl]benzamide | | | | |
| 976 | 5-[4-amino-5-(trifluoromethyl)pyrrolo[2,1-f][1,2,4]triazin-7-yl]-2-ethyl-N-[(3R,4S)-4-fluoro-1-[(2R)-3,3,3-trifluoro-2-hydroxy-2-methylpropanoyl]pyrrolidin-3-yl]benzamide | Et | (CF₃, OH, Me substituted) | 577.0 | 1.79 (4) |
| 977 | 5-[4-amino-5-(trifluoromethyl)pyrrolo[2,1-f][1,2,4]triazin-7-yl]-2-ethyl-N-[(3R,4S)-4-fluoro-1-(3,3,3-trifluoro-2-methylpropanoyl)pyrrolidin-3-yl]benzamide | Et | (F₃C, Me) | 561.2 | 1.80 (4) |
| 978 | 5-[4-amino-5-(trifluoromethyl)pyrrolo[2,1-f][1,2,4]triazin-7-yl]-2-ethyl-N-[(3R,4S)-4-fluoro-1-(3-methylbutanoyl)pyrrolidin-3-yl]benzamide | Et | (Me, Me) | 521.1 | 1.84 (4) |
| 979 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-ethylbenzamide | Et | (F, F cyclopropane) | 541.2 | 1.75 (4) |
| 980 | 5-[4-amino-5-(trifluoromethyl)pyrrolo[2,1-f][1,2,4]triazin-7-yl]-2-ethyl-N-[(3R,4S)-4-fluoro-1-(2-hydroxy-2-methylpropanoyl)pyrrolidin-3-yl]benzamide | Et | (Me, Me, OH) | 523.0 | 1.54 (3) |
| 981 | 5-[4-amino-5-(trifluoromethyl)pyrrolo[2,1-f][1,2,4]triazin-7-yl]-2-ethyl-N-[(3R,4S)-4-fluoro-1-(3,3,3-trifluoropropanoyl)pyrrolidin-3-yl]benzamide | Et | (CF₃) | 547.2 | 1.76 (4) |
| 982 | 5-[4-amino-5-(trifluoromethyl)pyrrolo[2,1-f][1,2,4]triazin-7-yl]-2-ethyl-N-[(3R,4S)-4-fluoro-1-(2-fluorobenzoyl)pyrrolidin-3-yl]benzamide | Et | (2-F-phenyl) | 559.2 | 1.81 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 983 | 5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-methylbenzamide | Me | fluorocyclopropyl | 509.3 | 1.65 (3) |
| 984 | 5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-methylbenzamide | Me | C(CF₃)(OH)(CH₂Me) | 576.9 | 1.73 (4) |
| 985 | 5-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-2-methylbenzamide | Me | CH₂CF₃ | 533.3 | 1.62 (3) |
| 986 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-methylbenzamide | Me | 3,3-difluorocyclobutyl | 541.1 | 1.65 (3) |
| 987 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-methylbenzamide | Me | 2,2-difluorocyclopropyl | 527.3 | 1.60 (3) |
| 988 | 5-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-2-methylbenzamide | Me | C(Me)₂OH | 509.3 | 1.44 (4) |
| 989 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-methylbenzamide | Me | 3,3-difluorocyclopentyl | 554.9 | 1.68 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 990 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-methylbenzamide | Me | 4,4-difluorocyclohexyl | 568.9 | 1.70 (3) |
| 991 | 5-[4-amino-5-(trifluoromethyl)pyrrolo[2,1-f][1,2,4]triazin-7-yl]-N-[(3R,5S)-4-fluoro-1-(3-methylbutanoyl)pyrrolidin-3-yl]-2-methylbenzamide | Me | CH2CH(Me)Me | 507.3 | 1.71 (4) |
| 992 | 5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-methylbenzamide | Me | CH2CH(Me)CF3 | 561.4 | 1.79 (3) |
| 993 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methylbenzamide | Me | C(Me)(CF3)(OH) | 563.3 | 1.63 (3) |
| 994 | 5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-methylbenzamide | Me | CH2C(CF3)(OH)(CF3) | 631.3 | 1.98 (3) |
| 995 | 5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-methylbenzamide | Me | CH2C(Me)(OH)(CF3) | 577.3 | 1.71 (4) |
| 996 | 5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-methylbenzamide | Me | CH2CH(CF3)(CF3) | 615.3 | 1.95 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

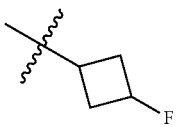 [SMILES: *C1CC(F)C1]

| Ex | Name | R¹ | R² | Obs. MS Ion | RT (Method) |
|---|---|---|---|---|---|
| 997 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-methylbenzamide | Me | 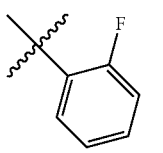 | 523.4, 523.4 | 1.57, 1.60 (3) |
| 998 | 5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-methylbenzamide | Me | 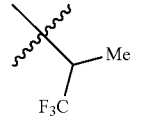 | 545.3 | 1.69 (3) |
| 999 | 5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-methylbenzamide | Me | 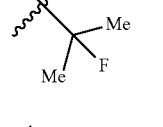 | 547.0 | 1.69 (3) |
| 1000 | 5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-methylbenzamide | Me | 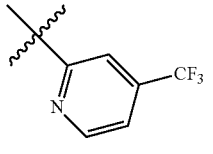 [SMILES: *c1cc(C(F)(F)F)ccn1] | 511.3 | 1.67 (3) |
| 1001 | 5-[4-amino-5-(trifluoromethyl)pyrrolo[2,1-f][1,2,4]triazin-7-yl]-N-[(3R,4S)-4-fluoro-1-[4-(trifluoromethyl)pyridine-2-carbonyl]pyrrolidin-3-yl]-2-methylbenzamide | Me | 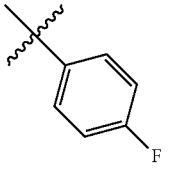 [SMILES: *c1ccc(F)cc1] | 596.0 | 2.01 (4) |
| 1002 | 5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]-2-methylbenzamide | Me | 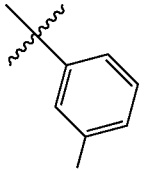 | 544.9 | 1.73 (3) |
| 1003 | 5-[4-amino-5-(trifluoromethyl)pyrrolo[2,1-f][1,2,4]triazin-7-yl]-N-[(3R,4S)-4-fluoro-1-(3-fluorobenzoyl)pyrrolidin-3-yl]-2-methylbenzamide | Me |  | 545.1 | 1.73 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 1004 | 5-[4-amino-5-(trifluoromethyl)pyrrolo[2,1-f][1,2,4]triazin-7-yl]-N-[(3R,4S)-4-fluoro-1-(1,3-thiazole-4-carbonyl)pyrrolidin-3-yl]-2-methylbenzamide | Me | thiazol-4-yl | 534.0 | 1.52 (4) |
| 1005 | 5-[4-amino-5-(trifluoromethyl)pyrrolo[2,1-f][1,2,4]triazin-7-yl]-N-[(3R,4S)-1-(3,5-difluoropyridine-4-carbonyl)-4-fluoropyrrolidin-3-yl]-2-methylbenzamide | Me | 3,5-difluoropyridin-4-yl | 564.3 | 1.69 (4) |
| 1006 | 5-[4-amino-5-(trifluoromethyl)pyrrolo[2,1-f][1,2,4]triazin-7-yl]-N-[(3R,4S)-4-fluoro-1-(3-fluoropyridine-4-carbonyl)pyrrolidin-3-yl]-2-methylbenzamide | Me | 3-fluoropyridin-4-yl | 546.0 | 1.52 (4) |
| 1007 | 5-[4-amino-5-(trifluoromethyl)pyrrolo[2,1-f][1,2,4]triazin-7-yl]-N-[(3R,4S)-1-(3,5-difluoropyridine-2-carbonyl)-4-fluoropyrrolidin-3-yl]-2-methylbenzamide | Me | 3,5-difluoropyridin-2-yl | 564.1 | 1.55 (3) |
| 1008 | 5-[4-amino-5-(trifluoromethyl)pyrrolo[2,1-f][1,2,4]triazin-7-yl]-N-[(3R,4S)-1-(3,4-difluorobenzoyl)-4-fluoropyrrolidin-3-yl]-2-methylbenzamide | Me | 3,4-difluorophenyl | 563.2 | 1.78 (4) |
| 1009 | 5-[4-amino-5-(trifluoromethyl)pyrrolo[2,1-f][1,2,4]triazin-7-yl]-N-[(3R,4S)-4-fluoro-1-[4-(trifluoromethyl)pyridine-3-carbonyl]pyrrolidin-3-yl]-2-methylbenzamide | Me | 4-(trifluoromethyl)pyridin-3-yl | 596.0 | 1.57 (3) |
| 1010 | 5-[4-amino-5-(trifluoromethyl)pyrrolo[2,1-f][1,2,4]triazin-7-yl]-N-[(3R,4S)-4-fluoro-1-(3-fluoropyridine-2-carbonyl)pyrrolidin-3-yl]-2-methylbenzamide | Me | 3-fluoropyridin-2-yl | 546.2 | 1.46 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 1011 | 5-[4-amino-5-(trifluoromethyl)pyrrolo[2,1-f][1,2,4]triazin-7-yl]-N-[(3R,4S)-1-(4-chlorobenzoyl)-4-fluoropyrrolidin-3-yl]-2-methylbenzamide | Me | 4-chlorophenyl | 561.2 | 1.83 (4) |
| 1012 | 5-[4-amino-5-(trifluoromethyl)pyrrolo[2,1-f][1,2,4]triazin-7-yl]-N-[(3R,4S)-4-fluoro-1-(5-fluoropyridine-2-carbonyl)pyrrolidin-3-yl]-2-methylbenzamide | Me | 5-fluoropyridin-2-yl | 546.2 | 1.59 (3) |
| 1013 | 5-[4-amino-5-(trifluoromethyl)pyrrolo[2,1-f][1,2,4]triazin-7-yl]-N-[(3R,4S)-1-(4-chloropyridine-3-carbonyl)-4-fluoropyrrolidin-3-yl]-2-methylbenzamide | Me | 4-chloropyridin-3-yl | 562.2 | 1.55 (4) |
| 1014 | 5-[4-amino-5-(trifluoromethyl)pyrrolo[2,1-f][1,2,4]triazin-7-yl]-N-[(3R,4S)-1-(2,6-difluorobenzoyl)-4-fluoropyrrolidin-3-yl]-2-methylbenzamide | Me | 2,6-difluorophenyl | 563.2 | 1.72 (4) |
| 1015 | 5-[4-amino-5-(trifluoromethyl)pyrrolo[2,1-f][1,2,4]triazin-7-yl]-N-[(3R,4S)-1-(4-chloropyridine-2-carbonyl)-4-fluoropyrrolidin-3-yl]-2-methylbenzamide | Me | 4-chloropyridin-2-yl | 562.1 | 1.73 (3) |
| 1016 | 5-[4-amino-5-(trifluoromethyl)pyrrolo[2,1-f][1,2,4]triazin-7-yl]-N-[(3R,4S)-1-(2,5-difluorobenzoyl)-4-fluoropyrrolidin-3-yl]-2-methylbenzamide | Me | 2,5-difluorophenyl | 562.8 | 1.75 (3) |
| 1017 | 5-[4-amino-5-(trifluoromethyl)pyrrolo[2,1-f][1,2,4]triazin-7-yl]-N-[(3R,4S)-1-benzoyl-4-fluoropyrrolidin-3-yl]-2-methylbenzamide | Me | phenyl | 526.9 | 1.69 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 1018 | 5-[4-amino-5-(trifluoromethyl)pyrrolo[2,1-f][1,2,4]triazin-7-yl]-N-[(3R,4S)-4-fluoro-1-(pyridine-4-carbonyl)pyrrolidin-3-yl]-2-methylbenzamide | Me | 4-pyridyl | 528.1 | 1.22 (3) |
| 1019 | 5-[4-amino-5-(trifluoromethyl)pyrrolo[2,1-f][1,2,4]triazin-7-yl]-N-[(3R,4S)-4-fluoro-1-(pyridine-2-carbonyl)pyrrolidin-3-yl]-2-methylbenzamide | Me | 2-pyridyl | 528.1 | 1.45 (3) |
| 1020 | 5-[4-amino-5-(trifluoromethyl)pyrrolo[2,1-f][1,2,4]triazin-7-yl]-N-[(3R,4S)-1-(2-chlorobenzoyl)-4-fluoropyrrolidin-3-yl]-2-methylbenzamide | Me | 2-chlorophenyl | 561.3 | 1.86 (4) |
| 1021 | 5-[4-amino-5-(trifluoromethyl)pyrrolo[2,1-f][1,2,4]triazin-7-yl]-N-[(3R,4S)-4-fluoro-1-(2-methylpyridine-4-carbonyl)pyrrolidin-3-yl]-2-methylbenzamide | Me | 2-methylpyridin-4-yl | 542.0 | 1.21 (3) |
| 1022 | 5-[4-amino-5-(trifluoromethyl)pyrrolo[2,1-f][1,2,4]triazin-7-yl]-N-[(3R,4S)-1-(2,4-difluorobenzoyl)-4-fluoropyrrolidin-3-yl]-2-methylbenzamide | Me | 2,4-difluorophenyl | 563.1 | 1.86 (4) |
| 1023 | 5-[4-amino-5-(trifluoromethyl)pyrrolo[2,1-f][1,2,4]triazin-7-yl]-N-[(3R,4S)-4-fluoro-1-(4-methylpyridine-2-carbonyl)pyrrolidin-3-yl]-2-methylbenzamide | Me | 4-methylpyridin-2-yl | 542.4 | 1.59 (3) |
| 1024 | 5-[4-amino-5-(trifluoromethyl)pyrrolo[2,1-f][1,2,4]triazin-7-yl]-N-[(3R,4S)-4-fluoro-1-(2,4,6-trifluorobenzoyl)pyrrolidin-3-yl]-2-methylbenzamide | Me | 2,4,6-trifluorophenyl | 581.3 | 1.85 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

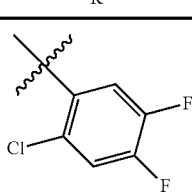

| Ex | Name | R¹ | R² | Obs. MS Ion | RT (Method) |
|---|---|---|---|---|---|
| 1025 | 5-[4-amino-5-(trifluoromethyl)pyrrolo[2,1-f][1,2,4]triazin-7-yl]-N-[(3R,4S)-1-(2-chloro-4,5-difluorobenzoyl)-4-fluoropyrrolidin-3-yl]-2-methylbenzamide | Me | 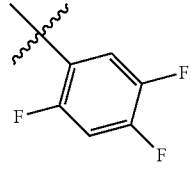 [SMILES: *c1cc(F)c(F)cc1F] | 597.1 | 1.84 (3) |
| 1026 | 5-[4-amino-5-(trifluoromethyl)pyrrolo[2,1-f][1,2,4]triazin-7-yl]-N-[(3R,4S)-4-fluoro-1-(2,4,5-trifluorobenzoyl)pyrrolidin-3-yl]-2-methylbenzamide | Me | 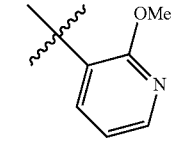 [SMILES: *c1cccnc1OC] | 580.9 | 1.79 (3) |
| 1027 | 5-[4-amino-5-(trifluoromethyl)pyrrolo[2,1-f][1,2,4]triazin-7-yl]-N-[(3R,4S)-4-fluoro-1-(2-methoxypyridine-3-carbonyl)pyrrolidin-3-yl]-2-methylbenzamide | Me | 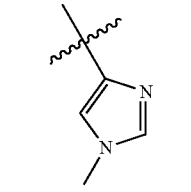 [SMILES: *c1cn(C)cn1] | 558.3 | 1.51 (3) |
| 1028 | 5-[4-amino-5-(trifluoromethyl)pyrrolo[2,1-f][1,2,4]triazin-7-yl]-N-[(3R,4S)-4-fluoro-1-(1-methyl-1H-imidazole-4-carbonyl)pyrrolidin-3-yl]-2-methylbenzamide | Me | 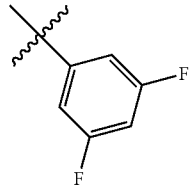 [SMILES: *c1cc(F)cc(F)c1] | 531.3 | 1.38 (4) |
| 1029 | 5-[4-amino-5-(trifluoromethyl)pyrrolo[2,1-f][1,2,4]triazin-7-yl]-N-[(3R,4S)-1-(3,5-difluorobenzoyl)-4-fluoropyrrolidin-3-yl]-2-methylbenzamide | Me | 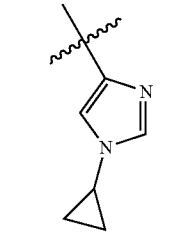 [SMILES: *c1cn(C2CC2)cn1] | 563.3 | 1.80 (3) |
| 1030 | 5-[4-amino-5-(trifluoromethyl)pyrrolo[2,1-f][1,2,4]triazin-7-yl]-N-[(3R,4S)-1-(1-cyclopropyl-1H-1,2,3-triazole-4-carbonyl)-4-fluoropyrrolidin-3-yl]-2-methylbenzamide | Me | | 558.2 | 1.56 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R$^1$ | R$^2$ | Obs. MS Ion | RT (Method) |
|---|---|---|---|---|---|
| 1031 | 5-[4-amino-5-(trifluoromethyl)pyrrolo[2,1-f][1,2,4]triazin-7-yl]-N-[(3R,4S)-4-fluoro-1-[6-(trifluoromethyl)pyridine-3-carbonyl]pyrrolidin-3-yl]-2-methylbenzamide | Me | 6-(trifluoromethyl)pyridin-3-yl | 596.1 | 1.75 (3) |
| 1032 | 5-[4-amino-5-(trifluoromethyl)pyrrolo[2,1-f][1,2,4]triazin-7-yl]-N-[(3R,4S)-4-fluoro-1-(1-methyl-1H-pyrazole-4-carbonyl)pyrrolidin-3-yl]-2-methylbenzamide | Me | 1-methyl-1H-pyrazol-4-yl | 531.1 | 1.42 (3) |
| 1033 | 5-[4-amino-5-(trifluoromethyl)pyrrolo[2,1-f][1,2,4]triazin-7-yl]-N-[(3R,4S)-1-(1,3-dimethyl-1H-pyrazole-5-carbonyl)-4-fluoropyrrolidin-3-yl]-2-methylbenzamide | Me | 1,3-dimethyl-1H-pyrazol-5-yl | 545.2 | 1.56 (3) |
| 1034 | 5-[4-amino-5-(trifluoromethyl)pyrrolo[2,1-f][1,2,4]triazin-7-yl]-N-[(3R,4S)-1-(2-chloro-3-fluorobenzoyl)-4-fluoropyrrolidin-3-yl]-2-methylbenzamide | Me | 2-chloro-3-fluorophenyl | 579.3 | 1.73 (3) |
| 1035 | 5-[4-amino-5-(trifluoromethyl)pyrrolo[2,1-f][1,2,4]triazin-7-yl]-N-[(3R,4S)-1-(5-cyano-2-fluorobenzoyl)-4-fluoropyrrolidin-3-yl]-2-methylbenzamide | Me | 5-cyano-2-fluorophenyl | 570.1 | 1.66 (3) |
| 1036 | 5-[4-amino-5-(trifluoromethyl)pyrrolo[2,1-f][1,2,4]triazin-7-yl]-N-[(3R,4S)-4-fluoro-1-(2-methanesulfonylbenzoyl)pyrrolidin-3-yl]-2-methylbenzamide | Me | 2-(methanesulfonyl)phenyl | 605.0 | 1.62 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

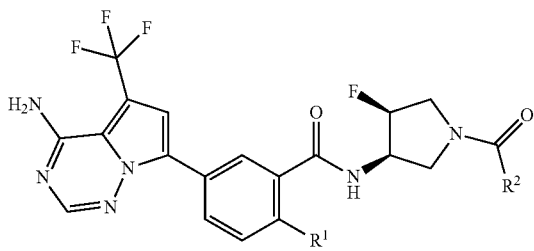

| Ex | Name | R¹ | R² | Obs. MS Ion | RT (Method) |
|---|---|---|---|---|---|
| 1037 | 5-[4-amino-5-(trifluoromethyl)pyrrolo[2,1-f][1,2,4]triazin-7-yl]-N-[(3R,4S)-4-fluoro-1-(4-fluoropyridine-2-carbonyl)pyrrolidin-3-yl]-2-methylbenzamide | Me | 4-fluoropyridin-2-yl | 546.3 | 1.65 (3) |
| 1038 | 5-[4-amino-5-(trifluoromethyl)pyrrolo[2,1-f][1,2,4]triazin-7-yl]-N-[(3R,4S)-1-(3-chloropyridine-4-carbonyl)-4-fluoropyrrolidin-3-yl]-2-methylbenzamide | Me | 3-chloropyridin-4-yl | 562.3 | 1.65 (4) |
| 1039 | 5-[4-amino-5-(trifluoromethyl)pyrrolo[2,1-f][1,2,4]triazin-7-yl]-N-[(3R,4S)-1-(2,3-difluorobenzoyl)-4-fluoropyrrolidin-3-yl]-2-methylbenzamide | Me | 2,3-difluorophenyl | 563.1 | 1.75 (3) |
| 1040 | 5-[4-amino-5-(trifluoromethyl)pyrrolo[2,1-f][1,2,4]triazin-7-yl]-N-[(3R,4S)-4-fluoro-1-(2-methyl-1,3-oxazole-4-carbonyl)pyrrolidin-3-yl]-2-methylbenzamide | Me | 2-methyl-1,3-oxazol-4-yl | 532.2 | 1.52 (3) |
| 1041 | 5-[4-amino-5-(trifluoromethyl)pyrrolo[2,1-f][1,2,4]triazin-7-yl]-N-[(3R,4S)-1-(2-chloro-6-fluorobenzoyl)-4-fluoropyrrolidin-3-yl]-2-methylbenzamide | Me | 2-chloro-6-fluorophenyl | 579.1 | 1.80 (3) |
| 1042 | 5-[4-amino-5-(trifluoromethyl)pyrrolo[2,1-f][1,2,4]triazin-7-yl]-N-[(3R,4S)-4-fluoro-1-(5-fluoro-2-methylpyridine-4-carbonyl)pyrrolidin-3-yl]-2-methylbenzamide | Me | 5-fluoro-2-methylpyridin-4-yl | 560.3 | 1.56 (4) |
| 1043 | 5-[4-amino-5-(trifluoromethyl)pyrrolo[2,1-f][1,2,4]triazin-7-yl]-N-[(3R,4S)-1-(2-chloro-4-fluorobenzoyl)-4-fluoropyrrolidin-3-yl]-2-methylbenzamide | Me | 2-chloro-4-fluorophenyl | 579.0 | 1.88 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

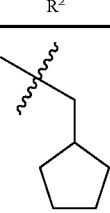

| Ex | Name | R¹ | R² | Obs. MS Ion | RT (Method) |
|---|---|---|---|---|---|
| 1044 | 5-[4-amino-5-(trifluoromethyl)pyrrolo[2,1-f][1,2,4]triazin-7-yl]-N-[(3R,4S)-1-(2-cyclopentylacetyl)-4-fluoropyrrolidin-3-yl]-2-methylbenzamide | Me | 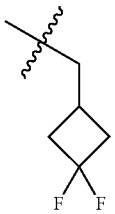 | 533.3 | 1.66 (4) |
| 1045 | 5-[4-amino-5-(trifluoromethyl)pyrrolo[2,1-f][1,2,4]triazin-7-yl]-N-[(3R,4S)-1-[2-(3,3-difluorocyclobutyl)acetyl]-4-fluoropyrrolidin-3-yl]-2-methylbenzamide | Me | 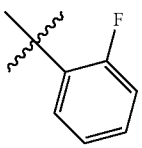 [SMILES: *c1ccccc1F] | 555.2 | 1.70 (4) |
| 1046 | 5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-(trifluoromethoxy)benzamide | OCF₃ | 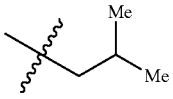 [SMILES: *CC(C)C] | 615.3 | 1.92 (4) |
| 1047 | 5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-(trifluoromethoxy)benzamide | OCF₃ | 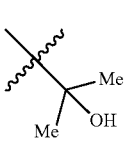 | 577.0 | 1.92 (4) |
| 1048 | 5-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-2-(trifluoromethoxy)benzamide | OCF₃ | 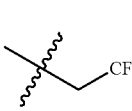 | 579.3 | 1.57 (3) |
| 1049 | 5-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-2-(trifluoromethoxy)benzamide | OCF₃ | 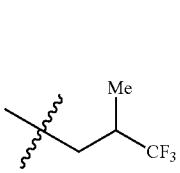 [SMILES: *CC(C)C(F)(F)F] | 603.3 | 1.82 (3) |
| 1050 | 5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-(trifluoromethoxy)benzamide | OCF₃ |  | 631.2 | 1.99 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 1051 | 5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-(trifluoromethoxy)benzamide | OCF₃ | C(Me)(CF₃)(OH)(Et) | 647.4 | 1.9 (4) |
| 1052 | 5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-(trifluoromethoxy)benzamide | OCF₃ | 1-fluorocyclopropyl | 579.3 | 1.86 (3) |
| 1053 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(trifluoromethoxy)benzamide | OCF₃ | 3-fluorocyclobutyl | 593.3, 593.3 | 1.78, 1.81 (3) |
| 1054 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-(trifluoromethoxy)benzamide | OCF₃ | 3,3-difluorocyclobutyl | 611.3 | 1.88 (3) |
| 1055 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(trifluoromethoxy)benzamide | OCF₃ | 3,3-difluorocyclopentyl | 625.0 | 1.93 (4) |
| 1056 | 5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-(trifluoromethoxy)benzamide | OCF₃ | C(Me)(Me)(F) | 581.0 | 1.91 (4) |
| 1057 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-(trifluoromethoxy)benzamide | OCF₃ | 4,4-difluorocyclohexyl | 639.0 | 2.00 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R$^1$ | R$^2$ | Obs. MS Ion | RT (Method) |
|---|---|---|---|---|---|
| 1058 | 5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-(trifluoromethoxy)benzamide | OCF$_3$ | CH(Me)(CF$_3$) | 617.0 | 1.86 (3) |
| 1059 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(trifluoromethoxy)benzamide | OCF$_3$ | 2,2-difluorocyclopropyl | 597.3 | 1.84 (4) |
| 1060 | 5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-(trifluoromethoxy)benzamide | OCF$_3$ | CH$_2$C(OH)(CF$_3$)$_2$ | 701.0 | 2.18 (4) |
| 1061 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-(trifluoromethoxy)benzamide | OCF$_3$ | C(Me)(OH)(CF$_3$) | 633.3 | 1.85 (4) |
| 1062 | 5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-(trifluoromethoxy)benzamide | OCF$_3$ | CH$_2$C(Me)(OH)(CF$_3$) | 647.0 | 1.91 (4) |
| 1063 | 5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-(2,2,2-trifluoroethoxy)benzamide | OCH$_2$CF$_3$ | C(Me)$_2$F | 595.1 | 1.83 (4) |
| 1064 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(2,2,2-trifluoroethoxy)benzamide | OCH$_2$CF$_3$ | 3,3-difluorocyclopentyl | 639.1 | 1.85 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R[1] | R[2] | Obs. MS Ion | RT (Method) |
|---|---|---|---|---|---|
| 1065 | 5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-(2,2,2-trifluoroethoxy)benzamide | OCH₂CF₃ | | 645.3 | 1.99 (3) |
| 1066 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-(2,2,2-trifluoroethoxy)benzamide | OCH₂CF₃ | | 647.3 | 1.82 (3) |
| 1067 | 5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-(2,2,2-trifluoroethoxy)benzamide | OCH₂CF₃ | | 699.1 | 2.05 (4) |
| 1068 | 5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-(2,2,2-trifluoroethoxy)benzamide | OCH₂CF₃ | | 661.1 | 1.82 (4) |
| 1069 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(2,2,2-trifluoroethoxy)benzamide | OCH₂CF₃ | | 611.1 | 1.75 (4) |
| 1070 | 5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-(2,2,2-trifluoroethoxy)benzamide | OCH₂CF₃ | | 661.1 | 1.84 (4) |
| 1071 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(2,2,2-trifluoroethoxy)benzamide | OCH₂CF₃ | | 607.3, 607.3 | 1.84, 1.87 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R$^1$ | R$^2$ | Obs. MS Ion | RT (Method) |
|---|---|---|---|---|---|
| 1072 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-(2,2,2-trifluoroethoxy)benzamide | OCH$_2$CF$_3$ | 3,3-difluorocyclobutyl | 625.3 | 1.77 (3) |
| 1073 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-(2,2,2-trifluoroethoxy)benzamide | OCH$_2$CF$_3$ | 4,4-difluorocyclohexyl | 653.3 | 1.87 (4) |
| 1074 | 5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-(2,2,2-trifluoroethoxy)benzamide | OCH$_2$CF$_3$ | 1-fluorocyclopropyl | 593.3 | 1.76 (3) |
| 1075 | 5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-(2,2,2-trifluoroethoxy)benzamide | OCH$_2$CF$_3$ | isobutyl (CH$_2$CH(Me)Me) | 591.4 | 1.83 (4) |
| 1076 | 5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-(2,2,2-trifluoroethoxy)benzamide | OCH$_2$CF$_3$ | 2-fluorophenyl | 629.3 | 1.83 (4) |
| 1077 | 5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-(2,2,2-trifluoroethoxy)benzamide | OCH$_2$CF$_3$ | CH(Me)CF$_3$ | 631.0 | 1.85 (4) |
| 1078 | 5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-(2,2,2-trifluoroethoxy)benzamide | OCH$_2$CF$_3$ | CH$_2$C(OH)(CF$_3$)$_2$ | 715.2 | 2.13 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R$^1$ | R$^2$ | Obs. MS Ion | RT (Method) |
|---|---|---|---|---|---|
| 1079 | 5-[4-amino-5-(trifluoromethyl)pyrrolo[2,1-f][1,2,4]triazin-7-yl]-2-(difluoromethoxy)-N-[(3R,4S)-4-fluoro-1-(1-fluorocyclopropanecarbonyl)pyrrolidin-3-yl]benzamide | OCHF$_2$ | 1-fluorocyclopropyl | 561.2 | 1.69 (3) |
| 1080 | 5-[4-amino-5-(trifluoromethyl)pyrrolo[2,1-f][1,2,4]triazin-7-yl]-2-(difluoromethoxy)-N-[(3R,4S)-4-fluoro-1-[(2R)-3,3,3-trifluoro-2-hydroxy-2-methylpropanoyl]pyrrolidin-3-yl]benzamide | OCHF$_2$ | C(CH$_3$)(OH)CF$_3$ | 615.1 | 1.71 (4) |
| 1081 | 5-[4-amino-5-(trifluoromethyl)pyrrolo[2,1-f][1,2,4]triazin-7-yl]-2-(difluoromethoxy)-N-[(3R,4S)-4-fluoro-1-[4,4,4-trifluoro-3-(trifluoromethyl)butanoyl]pyrrolidin-3-yl]benzamide | OCHF$_2$ | CH$_2$CH(CF$_3$)$_2$ | 667.1 | 1.99 (4) |
| 1082 | 5-[4-amino-5-(trifluoromethyl)pyrrolo[2,1-f][1,2,4]triazin-7-yl]-2-(difluoromethoxy)-N-[(3R,4S)-4-fluoro-1-(3,3,3-trifluoropropanoyl)pyrrolidin-3-yl]benzamide | OCHF$_2$ | CH$_2$CF$_3$ | 585.0 | 1.67 (3) |
| 1083 | 5-[4-amino-5-(trifluoromethyl)pyrrolo[2,1-f][1,2,4]triazin-7-yl]-2-(difluoromethoxy)-N-[(3R,4S)-4-fluoro-1-(3-methylbutanoyl)pyrrolidin-3-yl]benzamide | OCHF$_2$ | CH$_2$CH(Me)$_2$ | 559.0 | 1.77 (4) |
| 1084 | 5-[4-amino-5-(trifluoromethyl)pyrrolo[2,1-f][1,2,4]triazin-7-yl]-2-(difluoromethoxy)-N-[(3R,4S)-4-fluoro-1-(4,4,4-trifluoro-3-methylbutanoyl)pyrrolidin-3-yl]benzamide | OCHF$_2$ | CH$_2$CH(Me)CF$_3$ | 613.1 | 1.83 (3) |
| 1085 | 5-[4-amino-5-(trifluoromethyl)pyrrolo[2,1-f][1,2,4]triazin-7-yl]-2-(difluoromethoxy)-N-[(3R,4S)-4-fluoro-1-(2-hydroxy-2-methylpropanoyl)pyrrolidin-3-yl]benzamide | OCHF$_2$ | C(Me)$_2$OH | 561.1 | 1.50 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | $R^1$ | $R^2$ | Obs. MS Ion | RT (Method) |
|---|---|---|---|---|---|
| 1086 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(difluoromethoxy)benzamide | $OCHF_2$ | 2,2-difluorocyclopropyl | 579.3 | 1.7 (4) |
| 1087 | 5-[4-amino-5-(trifluoromethyl)pyrrolo[2,1-f][1,2,4]triazin-7-yl]-2-(difluoromethoxy)-N-[(3R,4S)-4-fluoro-1-(3-fluorocyclobutanecarbonyl)pyrrolidin-3-yl]benzamide | $OCHF_2$ | 3-fluorocyclobutyl | 575.1, 575.1 | 1.65, 1.68 (4) |
| 1088 | 5-[4-amino-5-(trifluoromethyl)pyrrolo[2,1-f][1,2,4]triazin-7-yl]-2-(difluoromethoxy)-N-[(3R,4S)-4-fluoro-1-[4,4,4-trifluoro-3-hydroxy-3-(trifluoromethyl)butanoyl]pyrrolidin-3-yl]benzamide | $OCHF_2$ | $-CH_2-C(OH)(CF_3)_2$ | 683.0 | 2.05 (4) |
| 1089 | 5-[4-amino-5-(trifluoromethyl)pyrrolo[2,1-f][1,2,4]triazin-7-yl]-2-(difluoromethoxy)-N-[(3R,4S)-4-fluoro-1-(2-fluorobenzoyl)pyrrolidin-3-yl]benzamide | $OCHF_2$ | 2-fluorophenyl | 597.1 | 1.72 (3) |
| 1090 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-(difluoromethoxy)benzamide | $OCHF_2$ | 4,4-difluorocyclohexyl | 621.1 | 1.8 (4) |
| 1091 | 5-[4-amino-5-(trifluoromethyl)pyrrolo[2,1-f][1,2,4]triazin-7-yl]-2-(difluoromethoxy)-N-[(3R,4S)-4-fluoro-1-(4,4,4-trifluoro-3-hydroxy-3-methylbutanoyl)pyrrolidin-3-yl]benzamide | $OCHF_2$ | $-CH_2-C(Me)(OH)(CF_3)$ | 629.1 | 1.72 (3) |
| 1092 | 5-[4-amino-5-(trifluoromethyl)pyrrolo[2,1-f][1,2,4]triazin-7-yl]-2-(difluoromethoxy)-N-[(3R,4S)-4-fluoro-1-(2-fluoro-2-methylpropanoyl)pyrrolidin-3-yl]benzamide | $OCHF_2$ | $-C(Me)_2F$ | 563.1 | 1.71 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R$^1$ | R$^2$ | Obs. MS Ion | RT (Method) |
|---|---|---|---|---|---|
| 1093 | 5-[4-amino-5-(trifluoromethyl)pyrrolo[2,1-f][1,2,4]triazin-7-yl]-2-(difluoromethoxy)-N-[(3R,4S)-4-fluoro-1-(3,3,3-trifluoro-2-methylpropanoyl)pyrrolidin-3-yl]benzamide | OCHF$_2$ | CH(CF$_3$)Me | 599.0 | 1.8 (4) |
| 1094 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(difluoromethoxy)benzamide | OCHF$_2$ | 3,3-difluorocyclopentyl | 607.1 | 1.75 (3) |
| 1095 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-(difluoromethoxy)benzamide | OCHF$_2$ | 3,3-difluorocyclobutyl | 593.1 | 1.74 (4) |
| 1096 | 5-[4-amino-5-(trifluoromethyl)pyrrolo[2,1-f][1,2,4]triazin-7-yl]-2-(difluoromethoxy)-N-[(3R,4S)-4-fluoro-1-[2-hydroxy-2-(trifluoromethyl)butanoyl]pyrrolidin-3-yl]benzamide | OCHF$_2$ | C(Me)(OH)(CF$_3$)CH$_2$- | 629.1 | 1.79 (4) |
| 1097 | 5-[4-amino-5-(trifluoromethyl)pyrrolo[2,1-f][1,2,4]triazin-7-yl]-2-ethoxy-N-[(3R,4S)-4-fluoro-1-(3,3,3-trifluoropropanoyl)pyrrolidin-3-yl]benzamide | OEt | CH$_2$CF$_3$ | 563.3 | 1.76 (3) |
| 1098 | 5-[4-amino-5-(trifluoromethyl)pyrrolo[2,1-f][1,2,4]triazin-7-yl]-2-ethoxy-N-[(3R,4S)-4-fluoro-1-(4,4,4-trifluoro-3-hydroxy-3-methylbutanoyl)pyrrolidin-3-yl]benzamide | OEt | CH$_2$C(Me)(OH)(CF$_3$) | 607.2 | 1.82 (3) |
| 1099 | 5-[4-amino-5-(trifluoromethyl)pyrrolo[2,1-f][1,2,4]triazin-7-yl]-2-ethoxy-N-[(3R,4S)-4-fluoro-1-(2-fluorobenzoyl)pyrrolidin-3-yl]benzamide | OEt | 2-fluorophenyl | 575.3 | 1.91 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|----|------|----|----|-------------|-------------|
| 1100 | 5-[4-amino-5-(trifluoromethyl)pyrrolo[2,1-f][1,2,4]triazin-7-yl]-2-ethoxy-N-[(3R,4S)-4-fluoro-1-(2-hydroxy-2-methylpropanoyl)pyrrolidin-3-yl]benzamide | OEt | C(Me)(Me)(OH) | 539.4 | 1.59 (4) |
| 1101 | 5-[4-amino-5-(trifluoromethyl)pyrrolo[2,1-f][1,2,4]triazin-7-yl]-2-ethoxy-N-[(3R,4S)-4-fluoro-1-(4,4,4-trifluoro-3-methylbutanoyl)pyrrolidin-3-yl]benzamide | OEt | CH2CH(Me)CF3 | 591.3 | 1.90 (3) |
| 1102 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-ethoxybenzamide | OEt | 3,3-difluorocyclopentyl | 585.2 | 1.88 (4) |
| 1103 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-ethoxybenzamide | OEt | 3,3-difluorocyclobutyl | 571.3 | 1.77 (3) |
| 1104 | 5-[4-amino-5-(trifluoromethyl)pyrrolo[2,1-f][1,2,4]triazin-7-yl]-2-ethoxy-N-[(3R,4S)-4-fluoro-1-(1-fluorocyclopropanecarbonyl)pyrrolidin-3-yl]benzamide | OEt | 1-fluorocyclopropyl | 539.2 | 1.81 (3) |
| 1105 | 5-[4-amino-5-(trifluoromethyl)pyrrolo[2,1-f][1,2,4]triazin-7-yl]-2-ethoxy-N-[(3R,4S)-4-fluoro-1-(2-fluoro-2-methylpropanoyl)pyrrolidin-3-yl]benzamide | OEt | C(Me)(Me)(F) | 541.4 | 1.86 (4) |
| 1106 | 5-[4-amino-5-(trifluoromethyl)pyrrolo[2,1-f][1,2,4]triazin-7-yl]-2-ethoxy-N-[(3R,4S)-4-fluoro-1-[4,4,4-trifluoro-3-hydroxy-3-(trifluoromethyl)butanoyl]pyrrolidin-3-yl]benzamide | OEt | CH2C(CF3)(OH)(CF3) | 661.2 | 2.13 (3) |
| 1107 | 5-[4-amino-5-(trifluoromethyl)pyrrolo[2,1-f][1,2,4]triazin-7-yl]-2-ethoxy-N-[(3R,4S)-4-fluoro-1-[(2R)-3,3,3-trifluoro-2-hydroxy-2-methylpropanoyl]pyrrolidin-3- | OEt | C(Me)(CF3)(OH) (2R) | 593.3 | 1.76 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| | yl]benzamide | | | | |
| 1108 | 5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-ethoxybenzamide | OEt | 4,4-difluorocyclohexyl | 599.4 | 1.86 (3) |
| 1109 | 5-[4-amino-5-(trifluoromethyl)pyrrolo[2,1-f][1,2,4]triazin-7-yl]-2-ethoxy-N-[(3R,4S)-4-fluoro-1-[2-hydroxy-2-(trifluoromethyl)butanoyl]pyrrolidin-3-yl]benzamide | OEt | C(Me)(OH)(CF₃)CH₂– | 607.2 | 1.80 (3) |
| 1110 | 5-[4-amino-5-(trifluoromethyl)pyrrolo[2,1-f][1,2,4]triazin-7-yl]-2-ethoxy-N-[(3R,4S)-4-fluoro-1-[4,4,4-trifluoro-3-(trifluoromethyl)butanoyl]pyrrolidin-3-yl]benzamide | OEt | CH₂CH(CF₃)₂ | 645.1 | 2.20 (4) |
| 1111 | 5-[4-amino-5-(trifluoromethyl)pyrrolo[2,1-f][1,2,4]triazin-7-yl]-2-ethoxy-N-[(3R,4S)-4-fluoro-1-(3,3,3-trifluoro-2-methylpropanoyl)pyrrolidin-3-yl]benzamide | OEt | CH(Me)(CF₃) | 576.9 | 1.92 (3) |
| 1112 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-ethoxybenzamide | OEt | 2,2-difluorocyclopropyl | 557.2 | 1.82 (4) |
| 1113 | 5-[4-amino-5-(trifluoromethyl)pyrrolo[2,1-f][1,2,4]triazin-7-yl]-2-ethoxy-N-[(3R,4S)-4-fluoro-1-(3-methylbutanoyl)pyrrolidin-3-yl]benzamide | OEt | CH₂CH(Me)₂ | 537.4 | 1.80 (3) |
| 1114 | 5-[4-amino-5-(trifluoromethyl)pyrrolo[2,1-f][1,2,4]triazin-7-yl]-2-ethoxy-N-[(3R,4S)-4-fluoro-1-(3-fluorocyclobutanecarbonyl)pyrrolidin-3-yl]benzamide | OEt | 3-fluorocyclobutyl | 553.3 | 1.71 (3) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

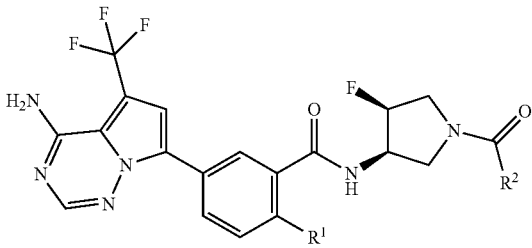

| Ex | Name | R¹ | R² | Obs. MS Ion | RT (Method) |
|---|---|---|---|---|---|
| 1115 | 5-[4-amino-5-(trifluoromethyl)pyrrolo[2,1-f][1,2,4]triazin-7-yl]-2-ethoxy-N-[(3R,4S)-4-fluoro-1-(3-fluorocyclobutanecarbonyl)pyrrolidin-3-yl]benzamide | OEt | fluorocyclobutyl | 553.3 | 1.74 (3) |
| 1116 | 5-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-2-methoxybenzamide | OMe | C(Me)(Me)OH | 525.0 | 1.46 (2) |
| 1117 | 5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-methoxybenzamide | OMe | CH(Me)Me | 523.3 | 1.82 (2) |
| 1118 | 5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-methoxybenzamide | OMe | CH(Me)CF₃ | 577.3 | 1.94 (2) |
| 1119 | 5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-methoxybenzamide | OMe | C(Me)(Me)F | 527.3 | 1.84 (2) |
| 1120 | 5-[4-amino-5-(trifluoromethyl)pyrrolo[2,1-f][1,2,4]triazin-7-yl]-N-[(3R,4S)-4-fluoro-1-[(2S)-3,3,3-trifluoro-2-hydroxy-2-methylpropanoyl]pyrrolidin-3-yl]-2-methoxybenzamide | OMe | C(CF₃)(OH) | 579.3 | 1.78 (2) |
| 1121 | 5-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-2-methoxybenzamide | OMe | CH₂CF₃ | 549.2 | 1.55 (1) |
| 1122 | 5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-methoxybenzamide | OMe | C(Me)(CF₃)OH | 593.0 | 1.86 (2) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 1123 | 5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-methoxybenzamide | OMe | CH(Me)(CF₃) | 563.0 | 1.86 (2) |
| 1124 | 5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-methoxybenzamide | OMe | 2-fluorophenyl | 561.3 | 1.74 (1) |
| 1125 | 5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-methoxybenzamide | OMe | 3,3-difluorocyclopentyl | 571.0 | 1.86 (2) |
| 1126 | 5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-methoxybenzamide | OMe | CH₂C(OH)(CF₃)₂ | 647.2 | 2.12 (2) |
| 1127 | 5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-methoxybenzamide | OMe | 1-fluorocyclopropyl | 525.0 | 1.82 (2) |
| 1128 | 5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-methoxybenzamide | OMe | 3,3-difluorocyclobutyl | 557.0 | 1.82 (2) |
| 1129 | 5-[4-amino-5-(trifluoromethyl)pyrrolo[2,1-f][1,2,4]triazin-7-yl]-1-(4,4-difluorocyclohexanecarbonyl)-4-fluoropyrrolidin-3-yl]-2-methoxybenzamide | OMe | 4,4-difluorocyclohexyl | 585.3 | 1.88 (2) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 1130 | 5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-methoxybenzamide | OMe | (Me, OH, CF₃ substituted) | 593.3 | 1.84 (2) |
| 1131 | 5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-methoxybenzamide | OMe | (CF₃, CF₃ substituted) | 631.3 | 1.97 (2) |
| 1132 | 5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-methoxybenzamide | OMe | (2,2-difluorocyclopropyl) | 543.2 | 1.66 (2) |
| 1133 | 5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-methoxybenzamide | OMe | (3-fluorocyclobutyl) | 539.05, 539.05 | 1.73, 1.76 (2) |
| 1134 | 3-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]benzamide | H | (Me, OH, CF₃ substituted) | 563.4 | 1.69 (1) |
| 1135 | 5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-(methylamino)benzamide | NHMe | (CF₃, CF₃ substituted) | 630.0 | 2.06 (4) |
| 1136 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3- | NHMe | (CF₃, OH substituted) | 578.2 | 1.86 (4) |

TABLE 41-continued

Compounds in Table 41 were prepared by the methods detailed in Examples 31, 562, 566, and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

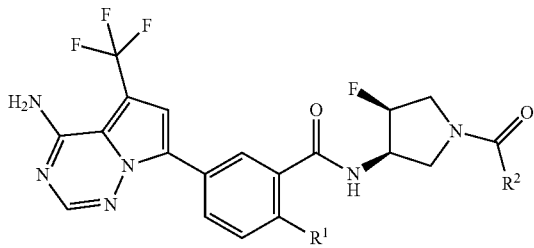

| Ex | Name | $R^1$ | $R^2$ | Obs. MS Ion | RT (Method) |
|---|---|---|---|---|---|
| | yl]-2-(methylamino)benzamide | | | | |
| 1137 | 5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-(methylamino)benzamide | NHMe | $\underset{\text{CF}_3}{\overset{\text{CF}_3}{\underset{\text{OH}}{\rule{0pt}{0pt}}}}$ | 646.1 | 2.11 (4) |

TABLE 42

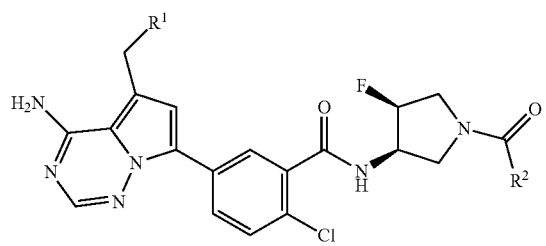

| Ex | Name | $R^1$ | $R^2$ | Obs. MS Ion | RT (Method) |
|---|---|---|---|---|---|
| 1138 | 5-{4-amino-5-[(4,4-difluoropiperidin-1-yl)methyl]pyrrolo[2,1-f][1,2,4]triazin-7-yl}-2-chloro-N-[(3R,4S)-4-fluoro-1-[4,4,4-trifluoro-3-(trifluoromethyl)butanoyl]pyrrolidin-3-yl]benzamide | 4,4-difluoropiperidinyl | $\underset{\text{CF}_3}{\overset{\text{CF}_3}{\rule{0pt}{0pt}}}$ | 699.9 | 1.63 (3) |
| 1139 | 5-{4-amino-5-[(4,4-difluoropiperidin-1-yl)methyl]pyrrolo[2,1-f][1,2,4]triazin-7-yl}-2-chloro-N-[(3R,4S)-4-fluoro-1-[4,4,4-trifluoro-3-(trifluoromethyl)butanoyl]pyrrolidin-3-yl]benzamide | 4,4-difluoropiperidinyl | $\underset{\text{CF}_3}{\overset{\text{CF}_3}{\underset{\text{OH}}{\rule{0pt}{0pt}}}}$ | 716.3 | 2.15 (4) |

TABLE 42-continued

| Ex | Name | R¹ | R² | Obs. MS Ion | RT (Method) |
|---|---|---|---|---|---|
| 1140 | 5-{4-amino-5-[(4,4-difluoropiperidin-1-yl)methyl]pyrrolo[2,1-f][1,2,4]triazin-7-yl}-2-chloro-N-[(3R,4S)-1-(3,3-difluorocyclobutanecarbonyl)-4-fluoropyrrolidin-3-yl]benzamide | 4,4-difluoropiperidin-1-yl | 3,3-difluorocyclobutyl | 626.1 | 1.47 (3) |
| 1141 | 5-{4-amino-5-[(4,4-difluoropiperidin-1-yl)methyl]pyrrolo[2,1-f][1,2,4]triazin-7-yl}-2-chloro-N-[(3R,4S)-4-fluoro-1-[(2R)-3,3,3-trifluoro-2-hydroxy-2-methylpropanoyl]pyrrolidin-3-yl]benzamide | 4,4-difluoropiperidin-1-yl | (2R)-1,1,1-trifluoro-2-hydroxy-2-methyl | 648.4 | 1.84 (4) |
| 1142 | 5-{4-amino-5-[(4,4-difluoropiperidin-1-yl)methyl]pyrrolo[2,1-f][1,2,4]triazin-7-yl}-2-chloro-N-[(3R,4S)-4-fluoro-1-(3-fluorocyclobutanecarbonyl)pyrrolidin-3-yl]benzamide | 4,4-difluoropiperidin-1-yl | 3-fluorocyclobutyl | 608.4, 608.4 | 1.80, 1.83 (4) |
| 1143 | 5-{4-amino-5-[(4,4-difluoropiperidin-1-yl)methyl]pyrrolo[2,1-f][1,2,4]triazin-7-yl}-2-chloro-N-[(3R,4S)-4-fluoro-1-(1-fluorocycloproapnecarbonyl)pyrrolidin-3-yl]benzamide | 4,4-difluoropiperidin-1-yl | 1-fluorocyclopropyl | 594.4 | 1.42 (3) |
| 1144 | 5-{4-amino-5-[(4,4-difluoropiperidin-1-yl)methyl]pyrrolo[2,1-f][1,2,4]triazin-7-yl}-2-chloro-N-[(3R,4S)-4-fluoro-1-(2-fluoro-2-methylpropanoyl)pyrrolidin-3-yl]benzamide | 4,4-difluoropiperidin-1-yl | 2-fluoro-2-methylpropyl | 596.4 | 1.89 (4) |
| 1145 | 5-{4-amino-5-[(4,4-difluoropiperidin-1-yl)methyl]pyrrolo[2,1-f][1,2,4]triazin-7-yl}-2-chloro-N-[(3R,4S)-4-fluoro-1-(3,3,3-trifluoropropanoyl)pyrrolidin-3-yl]benzamide | 4,4-difluoropiperidin-1-yl | 2,2,2-trifluoroethyl | 618.1 | 1.32 (3) |

TABLE 42-continued

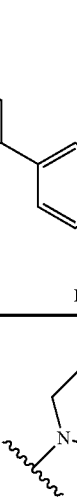

| Ex | Name | R¹ | R² | Obs. MS Ion | RT (Method) |
|---|---|---|---|---|---|
| 1146 | 5-{4-amino-5-[(4,4-difluoropiperidin-1-yl)methyl]pyrrolo[2,1-f][1,2,4]triazin-7-yl}-2-chloro-N-[(3R,4S)-4-fluoro-1-(3-methylbutanoyl)pyrrolidin-3-yl]benzamide | 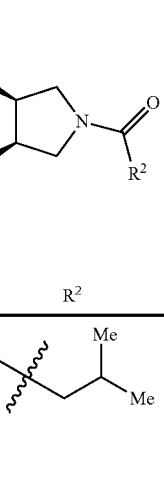 | 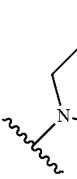 | 592.4 | 1.90 (4) |
| 1147 | 5-{4-amino-5-[(4,4-difluoropiperidin-1-yl)methyl]pyrrolo[2,1-f][1,2,4]triazin-7-yl}-2-chloro-N-[(3R,4S)-1-(4,4-difluorocyclohexanecarbonyl)-4-fluoropyrrolidin-3-yl]benzamide | 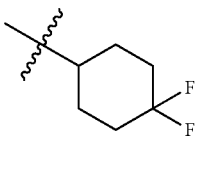 [SMILES: *C1CCC(F)(F)CC1] |  | 654.4 | 1.94 (4) |
| 1148 | 5-{4-amino-5-[(4,4-difluoropiperidin-1-yl)methyl]pyrrolo[2,1-f][1,2,4]triazin-7-yl}-2-chloro-N-[(3R,4S)-1-(3,3-difluorocyclopentanecarbonyl)-4-fluoropyrrolidin-3-yl]benzamide | 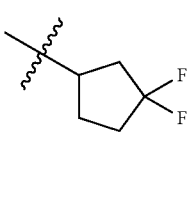 [SMILES: *C1CCC(F)(F)C1] |  | 640.2 | 1.87 (4) |
| 1149 | 5-(4-amino-5-{[4-(trifluoromethyl)piperidin-1-yl]methyl}pyrrolo[2,1-f][1,2,4]triazin-7-yl)-2-chloro-N-[(3R,4S)-4-fluoro-1-(1-fluorocyclopropanecarbonyl)pyrrolidin-3-yl]benzamide | 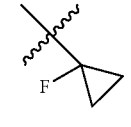 [SMILES: *C1(F)CC1] | 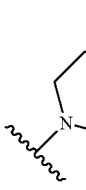 | 626.1 | 1.47 (3) |
| 1150 | 5-(4-amino-5-{[4-(trifluoromethyl)piperidin-1-yl]methyl}pyrrolo[2,1-f][1,2,4]triazin-7-yl)-2-chloro-N-[(3R,4S)-4-fluoro-1-(4,4,4-trifluoro-3-methylbutanoyl)pyrrolidin-3-yl]benzamide | 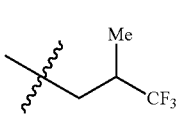 | 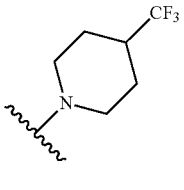 [SMILES: *N1CCC(C(F)(F)F)CC1] | 678.3 | 1.61 (3) |
| 1151 | 5-(4-amino-5-{[4-(trifluoromethyl)piperidin-1-yl]methyl}pyrrolo[2,1-f][1,2,4]triazin-7-yl)-2-chloro-N-[(3R,4S)-4-fluoro-1-(3-fluorocyclobutanecarbonyl)pyrrolidin-3-yl]benzamide | 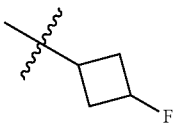 [SMILES: *C1CC(F)C1] | 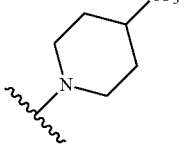 | 640.3, 640.3 | 2.02, 2.04 (3) |
| 1152 | 5-(4-amino-5-{[4-(trifluoromethyl)piperidin-1-yl]methyl}pyrrolo[2,1-f][1,2,4]triazin-7-yl)-2-chloro-N-[(3R,4S)-4-fluoro-1-(2-fluoro-2-methylpropanoyl)pyrrolidin-3-yl]benzamide | 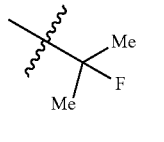 | | 628.3 | 1.50 (3) |

TABLE 42-continued

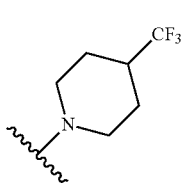 [SMILES: *N1CCC(C(F)(F)F)CC1]

| Ex | Name | R¹ | R² | Obs. MS Ion | RT (Method) |
|---|---|---|---|---|---|
| 1153 | 5-(4-amino-5-{[4-(trifluoromethyl)piperidin-1-yl]methyl}pyrrolo[2,1-f][1,2,4]triazin-7-yl)-2-chloro-N-[(3R,4S)-4-fluoro-1-(4,4,4-trifluoro-3-hydroxy-3-methylbutanoyl)pyrrolidin-3-yl]benzamide | 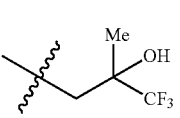 | 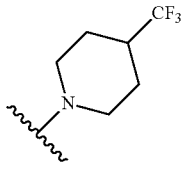 [SMILES: *N1CCC(C(F)(F)F)CC1] | 694.1 | 1.51 (3) |
| 1154 | 5-(4-amino-5-{[4-(trifluoromethyl)piperidin-1-yl]methyl}pyrrolo[2,1-f][1,2,4]triazin-7-yl)-2-chloro-N-[(3R,4S)-4-fluoro-1-(3-methylbutanoyl)pyrrolidin-3-yl]benzamide | 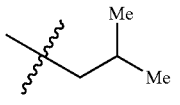 | 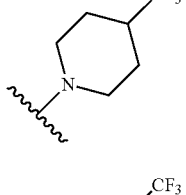 | 624.1 | 1.49 (3) |
| 1155 | 5-(4-amino-5-{[4-(trifluoromethyl)piperidin-1-yl]methyl}pyrrolo[2,1-f][1,2,4]triazin-7-yl)-2-chloro-N-[(3R,4S)-4-fluoro-1-(3,3,3-trifluoropropanoyl)pyrrolidin-3-yl]benzamide | 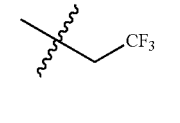 | 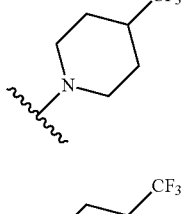 | 650.1 | 2.06 (4) |
| 1156 | 5-(4-amino-5-{[4-(trifluoromethyl)piperidin-1-yl]methyl}pyrrolo[2,1-f][1,2,4]triazin-7-yl)-2-fluoro-1-[4,4,4-trifluoro-3-hydroxy-3-(trifluoromethyl)butanoyl]pyrrolidin-3-yl]benzamide | 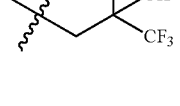 | 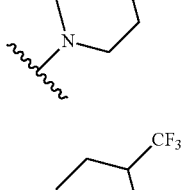 | 748.3 | 2.34 (4) |
| 1157 | 5-(4-amino-5-{[4-(trifluoromethyl)piperidin-1-yl]methyl}pyrrolo[2,1-f][1,2,4]triazin-7-yl)-2-chloro-N-[(3R,4S)-1-(3,3-difluorocyclobutanecarbonyl)-4-fluoropyrrolidin-3-yl]benzamide] |  | 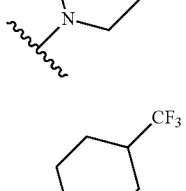 | 658.3 | 1.49 (3) |
| 1158 | 5-(4-amino-5-{[4-(trifluoromethyl)piperidin-1-yl]methyl}pyrrolo[2,1-f][1,2,4]triazin-7-yl)-2-chloro-N-[(3R,4S)-4-fluoro-1-(2-fluorobenzoyl)pyrrolidin-3-yl]benzamide | 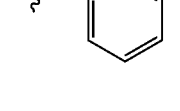 | 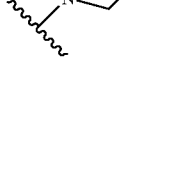 | 662.3 | 1.52 (3) |
| 1159 | 5-(4-amino-5-{[4-(trifluoromethyl)piperidin-1-yl]methyl}pyrrolo[2,1-f][1,2,4]triazin-7-yl)-2-chloro-N-[(3R,4S)-4-fluoro-1-[(2R)-3,3,3-trifluoro-2-hydroxy-2-methylpropanoyl]pyrrolidin-3-yl]benzamide | 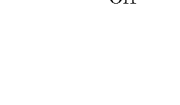 | | 680.3 | 1.44 (3) |

TABLE 42-continued

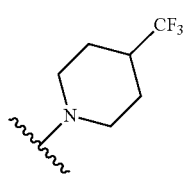 [SMILES: *N1CCC(C(F)(F)F)CC1]

| Ex | Name | R[1] | R[2] | Obs. MS Ion | RT (Method) |
|---|---|---|---|---|---|
| 1160 | 5-(4-amino-5-{[4-(trifluoromethyl)piperidin-1-yl]methyl}pyrrolo[2,1-f][1,2,4]triazin-7-yl)-2-chloro-N-[(3R,4S)-1-(4,4-difluorocyclohexanecarbonyl)-4-fluoropyrrolidin-3-yl]benzamide | 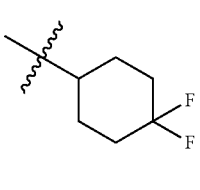 [SMILES: *C1CCC(F)(F)CC1] | 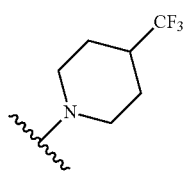 [SMILES: *N1CCC(C(F)(F)F)CC1] | 686.4 | 1.56 (3) |
| 1161 | 5-(4-amino-5-{[4-(trifluoromethyl)piperidin-1-yl]methyl}pyrrolo[2,1-f][1,2,4]triazin-7-yl)-2-chloro-N-[(3R,4S)-1-(3,3-difluorocyclopentanecarbonyl)-4-fluoropyrrolidin-3-yl]benzamide | 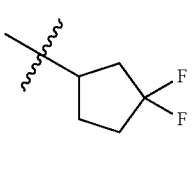 [SMILES: *C1CCC(F)(F)C1] | 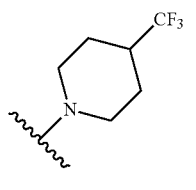 [SMILES: *N1CCC(C(F)(F)F)CC1] | 672.4 | 1.54 (3) |
| 1162 | 5-(4-amino-5-{[4-(trifluoromethyl)piperidin-1-yl]methyl}pyrrolo[2,1-f][1,2,4]triazin-7-yl)-2-chloro-N-[(3R,4S)-4-fluoro-1-(3,3,3-trifluoro-2-methylpropanoyl)pyrrolidin-3-yl]benzamide | 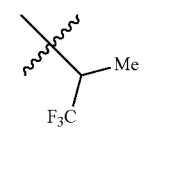 | 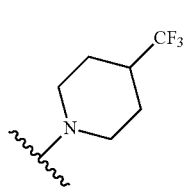 [SMILES: *N1CCC(C(F)(F)F)CC1] | 664.3 | 1.52 (3) |
| 1163 | 5-(4-amino-5-{[4-(trifluoromethyl)piperidin-1-yl]methyl}pyrrolo[2,1-f][1,2,4]triazin-7-yl)-2-chloro-N-[(3R,4S)-4-fluoro-1-[2-hydroxy-2-(trifluoromethyl)butanoyl]pyrrolidin-3-yl]benzamide | 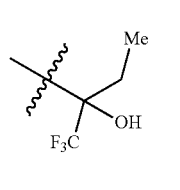 | | 694.3 | 1.53 (3) |

Compounds in Table 42 were prepared by the methods detailed in Examples 57, 63, and 562. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

TABLE 43

Compounds in Table 43 were prepared by the methods detailed in Examples 57, 63, and 562. When diastereomers were separated, they are included as separate entries. If the stereochemistry is undefined, the product was isolated as a mixture of diastereomers. LC/MS retention time (RT) determined in minutes using Method 1, 2, 3, or as 4 indicated. The Methods are described in the Methods of Preparation section.

| Ex | Name | R | Obs. MS Ion | RT (Method) |
|---|---|---|---|---|
| 1164 | 3-{4-amino-5-[(3,3-difluoroazetidin-1-yl)methyl]pyrrolo[2,1-f][1,2,4]triazin-7-yl}-N-[(3R,4S)-4-fluoro-1-[(2R)-3,3,3-trifluoro-2-hydroxypropanoyl]pyrrolidin-3-yl]benzamide | CF₃, OH | 572.3 | 1.73 (2) |
| 1165 | 3-{4-amino-5-[(3,3-difluoroazetidin-1-yl)methyl]pyrrolo[2,1-f][1,2,4]triazin-7-yl}-N-[(3R,4S)-4-fluoro-1-(3-methylbutanoyl)pyrrolidin-3-yl]benzamide | Me, Me | 530.3 | 1.82 (2) |
| 1166 | 3-{4-amino-5-[(3,3-difluoroazetidin-1-yl)methyl]pyrrolo[2,1-f][1,2,4]triazin-7-yl}-N-[(3R,4S)-4-fluoro-1-(2-hydroxy-2-methylpropanoyl)pyrrolidin-3-yl]benzamide | Me, Me, OH | 532.1 | 1.50 (2) |
| 1167 | 3-{4-amino-5-[(3,3-difluoroazetidin-1-yl)methyl]pyrrolo[2,1-f][1,2,4]triazin-7-yl}-N-[(3R,4S)-4-fluoro-1-(2-fluoro-2-methylpropanoyl)pyrrolidin-3-yl]benzamide | Me, Me, F | 534.3 | 1.73 (2) |
| 1168 | 3-{4-amino-5-[(3,3-difluoroazetidin-1-yl)methyl]pyrrolo[2,1-f][1,2,4]triazin-7-yl}-N-[(3R,4S)-1-cyclobutanecarbonyl-4-fluoropyrrolidin-3-yl]benzamide | cyclobutyl | 528.3 | 1.78 (2) |
| 1169 | 3-{4-amino-5-[(3,3-difluoroazetidin-1-yl)methyl]pyrrolo[2,1-f][1,2,4]triazin-7-yl}-N-[(3R,4S)-4-fluoro-1-(3,3,3-trifluoropropanoyl)pyrrolidin-3-yl]benzamide | CF₃ | 556.3 | 1.76 (2) |
| 1170 | 3-{4-amino-5-[(3,3-difluoroazetidin-1-yl)methyl]pyrrolo[2,1-f][1,2,4]triazin-7-yl}-N-[(3R,4S)-1-(2,2-dimethylpropanoyl)-4-fluoropyrrolidin-3-yl]benzamide | Me, Me, Me | 530.1 | 1.43 (1) |
| 1171 | 3-{4-amino-5-[(3,3-difluoroazetidin-1-yl)methyl]pyrrolo[2,1-f][1,2,4]triazin-7-yl}-N-[(3R,4S)-4-fluoro-1-(2-fluorobenzoyl)pyrrolidin-3-yl]benzamide | 2-fluorophenyl | 568.2 | 1.84 (2) |

TABLE 43-continued

Compounds in Table 43 were prepared by the methods detailed in Examples 57, 63, and 562. When diastereomers were separated, they are included as separate entries. If the stereochemistry is undefined, the product was isolated as a mixture of diastereomers. LC/MS retention time (RT) determined in minutes using Method 1, 2, 3, or as 4 indicated. The Methods are described in the Methods of Preparation section.

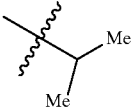

| Ex | Name | R | Obs. MS Ion | RT (Method) |
|---|---|---|---|---|
| 1172 | 3-{4-amino-5-[(3,3-difluoroazetidin-1-yl)methyl]pyrrolo[2,1-f][1,2,4]triazin-7-yl}-N-[(3R,4S)-4-fluoro-1-(2-methylpropanoyl)pyrrolidin-3-yl]benzamide | 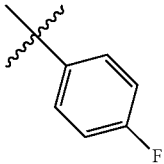 [SMILES: *c1ccc(F)cc1] | 516.1 | 1.32 (1) |
| 1173 | 3-{4-amino-5-[(3,3-difluoroazetidin-1-yl)methyl]pyrrolo[2,1-f][1,2,4]triazin-7-yl}-N-[(3R,4S)-4-fluoro-1-(4-fluorobenzoyl)pyrrolidin-3-yl]benzamide | 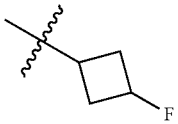 [SMILES: *C1CC(F)C1] | 568.1 | 1.76 (2) |
| 1174 | 3-{4-amino-5-[(3,3-difluoroazetidin-1-yl)methyl]pyrrolo[2,1-f][1,2,4]triazin-7-yl}-N-[(3R,4S)-4-fluoro-1-(3-fluorocyclobutanecarbonyl)pyrrolidin-3-yl]benzamide | 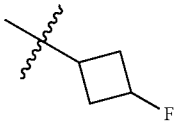 [SMILES: *C1CC(F)C1] | 546.2 | 1.75 (2) |
| 1175 | 3-{4-amino-5-[(3,3-difluoroazetidin-1-yl)methyl]pyrrolo[2,1-f][1,2,4]triazin-7-yl}-N-[(3R,4S)-4-fluoro-1-(3-fluorocyclobutanecarbonyl)pyrrolidin-3-yl]benzamide | 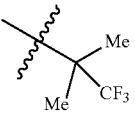 | 546.1 | 1.72 (2) |
| 1176 | 3-{4-amino-5-[(3,3-difluoroazetidin-1-yl)methyl]pyrrolo[2,1-f][1,2,4]triazin-7-yl}-N-[(3R,4S)-4-fluoro-1-(3,3,3-trifluoro-2,2-dimethylpropanoyl)pyrrolidin-3-yl]benzamide | | 584.2 | 1.94 (2) |
| 1177 | 3-{4-amino-5-[(3,3-difluoroazetidin-1-yl)methyl]pyrrolo[2,1-f][1,2,4]triazin-7-yl}-N-[(3R,4S)-1-(2,2-difluorocyclopropanecarbonyl)-4-fluoropyrrolidin-3-yl]benzamide | 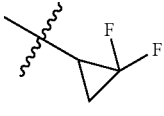 [SMILES: *C1CC1(F)F] | 550.1 | 1.66 (2) |
| 1178 | 3-{4-amino-5-[(3,3-difluoroazetidin-1-yl)methyl]pyrrolo[2,1-f][1,2,4]triazin-7-yl}-N-[(3R,4S)-1-(3,3-difluorocyclopentanecarbonyl)-4-fluoropyrrolidin-3-yl]benzamide | 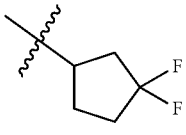 [SMILES: *C1CCC(F)(F)C1] | 578.1 | 1.84 (2) |

TABLE 43-continued

Compounds in Table 43 were prepared by the methods detailed in Examples 57, 63, and 562. When diastereomers were separated, they are included as separate entries. If the stereochemistry is undefined, the product was isolated as a mixture of diastereomers. LC/MS retention time (RT) determined in minutes using Method 1, 2, 3, or as 4 indicated. The Methods are described in the Methods of Preparation section.

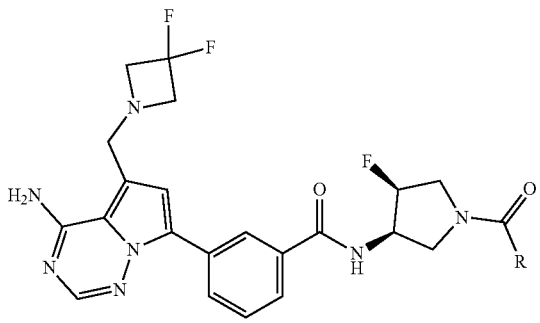

| Ex | Name | R | Obs. MS Ion | RT (Method) |
|---|---|---|---|---|
| 1179 | 3-{4-amino-5-[(3,3-difluoroazetidin-1-yl)methyl]pyrrolo[2,1-f][1,2,4]triazin-7-yl}-N-[(3R,4S)-1-(4,4-difluorocyclohexanecarbonyl)-4-fluoropyrrolidin-3-yl]benzamide | | 592.1 | 1.78 (2) |
| 1180 | 3-{4-amino-5-[(3,3-difluoroazetidin-1-yl)methyl]pyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]benzamide | | 586.0 | 1.66 (2) |
| 1181 | 3-{4-amino-5-[(3,3-difluoroazetidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]benzamide | | 564.3 | 1.66 (2) |

TABLE 44

Compounds in Table 44 were prepared by the methods detailed in Examples 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

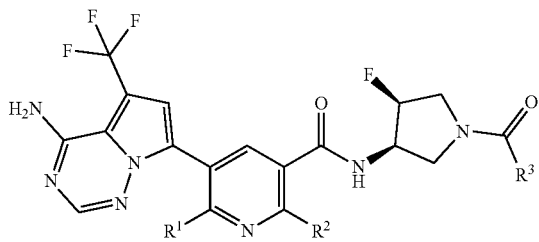

| Ex | Name | $R^1$ | $R^2$ | $R^3$ | Obs. MS Ion | RT (Method) |
|---|---|---|---|---|---|---|
| 1182 | 5-[4-amino-5-(trifluoromethyl)pyrrolo[2,1-f][1,2,4]triazin-7-yl]-N-[(3R,4S)-4-fluoro-1-(1-fluorocyclopropane- | Me | Me | | 524.3 | 1.36 (4) |

TABLE 44-continued

Compounds in Table 44 were prepared by the methods detailed in Examples 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | R³ | Obs. MS Ion | RT (Method) |
|---|---|---|---|---|---|---|
| | carbonyl)pyrrolidin-3-yl]-2,6-dimethylpyridine-3-carboxamide | | | | | |
| 1183 | 5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2,6-dimethylpyridine-3-carboxamide | Me | Me | (C(Me)(Me)F) | 526.2 | 1.37 (4) |
| 1184 | 5-[4-amino-5-(trifluoromethyl)pyrrolo[2,1-f][1,2,4]triazin-7-yl]-N-[(3R,4S)-1-(2,4-difluorobenzoyl)-4-fluoropyrrolidin-3-yl]-2,6-dimethylpyridine-3-carboxamide | Me | Me | (2,4-difluorophenyl) | 578.3 | 1.46 (4) |
| 1185 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2,6-dimethylpyridine-3-carboxamide | Me | Me | (C(CF₃)(OH)Me) | 578.3 | 1.35 (4) |
| 1186 | 5-[4-amino-5-(trifluoromethyl)pyrrolo[2,1-f][1,2,4]triazin-7-yl]-N-[(3R,4S)-1-(2-chlorobenzoyl)-4-fluoropyrrolidin-3-yl]-2,6-dimethylpyridine-3-carboxamide | Me | Me | (2-chlorophenyl) | 575.9 | 1.59 (4) |
| 1187 | 5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2,6-dimethylpyridine-3-carboxamide | Me | Me | (CH₂CH(Me)CF₃) | 576 | (4)1.65 |

TABLE 44-continued

Compounds in Table 44 were prepared by the methods detailed in Examples 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | R³ | Obs. MS Ion | RT (Method) |
|---|---|---|---|---|---|---|
| 1188 | 5-[4-amino-5-(trifluoromethyl)pyrrolo[2,1-f][1,2,4]triazin-7-yl]-N-[(3R,4S)-1-(3,5-difluoropyridine-4-carbonyl)-4-fluoropyrrolidin-3-yl]-2,6-dimethylpyridine-3-carboxamide | Me | Me | 3,5-difluoropyridin-4-yl | 579.3 | 1.31 (4) |
| 1189 | 5-[4-amino-5-(trifluoromethyl)pyrrolo[2,1-f][1,2,4]triazin-7-yl]-N-[(3R,4S)-1-benzoyl-4-fluoropyrrolidin-3-yl]-2,6-dimethylpyridine-3-carboxamide | Me | Me | phenyl | 541.9 | 1.53 (4) |
| 1190 | 5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2,6-dimethylpyridine-3-carboxamide | Me | Me | 2-fluorophenyl | 560.2 | 1.41 (4) |
| 1191 | 5-[4-amino-5-(trifluoromethyl)pyrrolo[2,1-f][1,2,4]triazin-7-yl]-N-[(3R,4S)-4-fluoro-1-(3-fluorobenzoyl)pyrrolidin-3-yl]-2,6-dimethylpyridine-3-carboxamide | Me | Me | 3-fluorophenyl | 560 | 1.57 (4) |
| 1192 | 5-[4-amino-5-(trifluoromethyl)pyrrolo[2,1-f][1,2,4]triazin-7-yl]-N-[(3R,4S)-4-fluoro-1-(3-fluoropyridine-4-carbonyl)pyrrolidin-3-yl]-2,6-dimethylpyridine-3-carboxamide | Me | Me | 3-fluoropyridin-4-yl | 561.1 | 1.22 (4) |
| 1193 | 5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl] | Me | Me | -CH₂CH(CF₃)(CF₃) | 630.3 | 1.7 (4) |

TABLE 44-continued

Compounds in Table 44 were prepared by the methods detailed in Examples 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

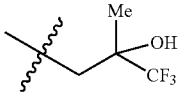 [SMILES: *CC(C)(O)C(F)(F)F]

| Ex | Name | R¹ | R² | R³ | Obs. MS Ion | RT (Method) |
|---|---|---|---|---|---|---|
| | pyrrolidin-3-yl]-2,6-dimethylpyridine-3-carboxamide | | | | | |
| 1194 | 5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2,6-dimethylpyridine-3-carboxamide | Me | Me | 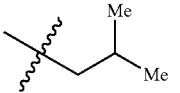 [SMILES: *CC(C)C] | 592.4 | 1.4 (4) |
| 1195 | 5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2,6-dimethylpyridine-3-carboxamide | Me | Me | 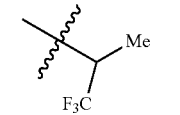 | 522.2 | 1.42 (4) |
| 1196 | 5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2,6-dimethylpyridine-3-carboxamide | Me | Me | 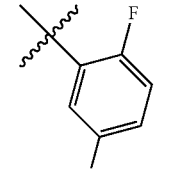 | 562.3 | 1.45 (4) |
| 1197 | 5-[4-amino-5-(trifluoromethyl)pyrrolo[2,1-f][1,2,4]triazin-7-yl]-N-[(3R,4S)-1-(2,5-difluorobenzoyl)-4-fluoropyrrolidin-3-yl]-2,6-dimethylpyridine-3-carboxamide | Me | Me | 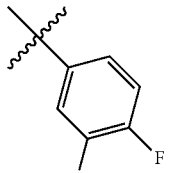 | 578.3 | 1.46 (4) |
| 1198 | 5-[4-amino-5-(trifluoromethyl)pyrrolo[2,1-f][1,2,4]triazin-7-yl]-N-[(3R,4S)-1-(3,4-difluorobenzoyl)-4-fluoropyrrolidin-3-yl]-2,6-dimethylpyridine-3-carboxamide | Me | Me | | 578.2 | 1.29 (3) |

TABLE 44-continued

*Compounds in Table 44 were prepared by the methods detailed in Examples 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.*

| Ex | Name | R¹ | R² | R³ | Obs. MS Ion | RT (Method) |
|---|---|---|---|---|---|---|
| 1199 | 5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2,6-dimethylpyridine-3-carboxamide | Me | Me | (Me, F₃C, OH substituent) | 592 | 1.16 (3) |
| 1200 | 5-[4-amino-5-(trifluoromethyl)pyrrolo[2,1-f][1,2,4]triazin-7-yl]-N-[(3R,4S)-1-(2,6-difluorobenzoyl)-4-fluoropyrrolidin-3-yl]-2,6-dimethylpyridine-3-carboxamide | Me | Me | (2,6-difluorophenyl) | 578.3 | 1.20 (3) |
| 1201 | 5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2,6-dimethylpyridine-3-carboxamide | Me | Me | (CF₃, OH, CF₃ substituent) | 646.3 | 1.52 (3) |
| 1202 | 5-[4-amino-5-(trifluoromethyl)pyrrolo[2,1-f][1,2,4]triazin-7-yl]-N-[(3R,4S)-1-[2-(3,3-difluorocyclobutyl)acetyl]-4-fluoropyrrolidin-3-yl]-2-methoxypyridine-3-carboxamide | H | OMe | (3,3-difluorocyclobutyl-methyl) | 572.1 | 1.91 (4) |
| 1203 | 5-[4-amino-5-(trifluoromethyl)pyrrolo[2,1-f][1,2,4]triazin-7-yl]-N-[(3R,4S)-1-(2-cyclopentylacetyl)-4-fluoropyrrolidin-3-yl]-2-methoxypyridine-3-carboxamide | H | OMe | (cyclopentylmethyl) | 550.4 | 2.05 (4) |

TABLE 44-continued

Compounds in Table 44 were prepared by the methods detailed in Examples 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | R³ | Obs. MS Ion | RT (Method) |
|---|---|---|---|---|---|---|
| 1204 | 5-[4-amino-5-(trifluoromethyl)pyrrolo[2,1-f][1,2,4]triazin-7-yl]-N-[(3R,4S)-1-(2-cyclobutylacetyl)-4-fluoropyrrolidin-3-yl]-2-methoxypyridine-3-carboxamide | H | OMe | CH₂-cyclobutyl | 536.2 | 1.85 (4) |
| 1205 | 5-[4-amino-5-(trifluoromethyl)pyrrolo[2,1-f][1,2,4]triazin-7-yl]-N-[(3R,4S)-1-[2-(2,2-difluorocyclopropyl)acetyl]-4-fluoropyrrolidin-3-yl]-2-methoxypyridine-3-carboxamide | H | OMe | CH₂-(2,2-difluorocyclopropyl) | 558 | 1.73 (4) |
| 1206 | 5-[4-amino-5-(trifluoromethyl)pyrrolo[2,1-f][1,2,4]triazin-7-yl]-N-[(3R,4S)-1-(2-cyclopropylacetyl)-4-fluoropyrrolidin-3-yl]-2-methoxypyridine-3-carboxamide | H | OMe | CH₂-cyclopropyl | 522 | 1.69 (4) |
| 1207 | 5-[4-amino-5-(trifluoromethyl)pyrrolo[2,1-f][1,2,4]triazin-7-yl]-N-[(3R,4S)-4-fluoro-1-[2-(1-methylcyclopropyl)acetyl]pyrrolidin-3-yl]-2-methoxypyridine-3-carboxamide | H | OMe | CH₂-(1-methylcyclopropyl) | 536 | 1.81 (4) |
| 1208 | 5-[4-amino-5-(trifluoromethyl)pyrrolo[2,1-f][1,2,4]triazin-7-yl]-N-[(3R,4S)-4-fluoro-1-[2-(1-hydroxycyclohexyl)acetyl]pyrrolidin-3-yl]-2-methoxypyridine-3-carboxamide | H | OMe | CH₂-(1-hydroxycyclohexyl) | 580.4 | 1.83 (4) |
| 1209 | 5-[4-amino-5-(trifluoromethyl)pyrrolo[2,1-f][1,2,4]triazin-7-yl]-N-[(3R,4S)-4-fluoro-1-(6-methoxypyrazine-2-carbonyl)pyrrolidin-3-yl]-2-methoxypyridine-3-carboxamide | H | OMe | 4-methoxypyrimidin-2-yl | 576.32, 576.33 | 1.71, 1.91 (4) |

TABLE 44-continued

Compounds in Table 44 were prepared by the methods detailed in Examples 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | R³ | Obs. MS Ion | RT (Method) |
|---|---|---|---|---|---|---|
| 1210 | 5-[4-amino-5-(trifluoromethyl)pyrrolo[2,1-f][1,2,4]triazin-7-yl]-N-[(3R,4S)-4-fluoro-1-(pyridazine-3-carbonyl)pyrrolidin-3-yl]-2-methoxypyridine-3-carboxamide | H | OMe | pyridazin-3-yl | 546.1 | 1.51 (4) |
| 1211 | 5-[4-amino-5-(trifluoromethyl)pyrrolo[2,1-f][1,2,4]triazin-7-yl]-N-[(3R,4S)-4-fluoro-1-(2-methoxypyrimidine-5-carbonyl)pyrrolidin-3-yl]-2-methoxypyridine-3-carboxamide | H | OMe | 2-methoxypyrimidin-5-yl | 576.2 | 1.61 (4) |
| 1212 | 5-[4-amino-5-(trifluoromethyl)pyrrolo[2,1-f][1,2,4]triazin-7-yl]-N-[(3R,4S)-4-fluoro-1-(6-methylpyrazine-2-carbonyl)pyrrolidin-3-yl]-2-methoxypyridine-3-carboxamide | H | OMe | 6-methylpyrazin-2-yl | 560.1 | 1.63 (4) |
| 1213 | 5-[4-amino-5-(trifluoromethyl)pyrrolo[2,1-f][1,2,4]triazin-7-yl]-N-[(3R,4S)-4-fluoro-1-(5-methylpyrazine-2-carbonyl)pyrrolidin-3-yl]-2-methoxypyridine-3-carboxamide | H | OMe | 5-methylpyrazin-2-yl | 560.1 | 1.63 (4) |
| 1214 | 5-[4-amino-5-(trifluoromethyl)pyrrolo[2,1-f][1,2,4]triazin-7-yl]-N-[(3R,4S)-4-fluoro-1-(2-methylpyrimidine-5-carbonyl)pyrrolidin-3-yl]-2-methoxypyridine-3-carboxamide | H | OMe | 2-methylpyrimidin-5-yl | 559.9 | 1.49 (3) |
| 1215 | 5-[4-amino-5-(trifluoromethyl)pyrrolo[2,1-f][1,2,4]triazin-7-yl]-N-[(3R,4S)-1-(6-chloropyridazine-4-carbonyl)-4-fluoropyrrolidin-3-yl]-2-methoxypyridine-3-carboxamide | H | OMe | 6-chloropyridazin-4-yl | 580.2 | 1.62 (3) |

TABLE 44-continued

Compounds in Table 44 were prepared by the methods detailed in Examples 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

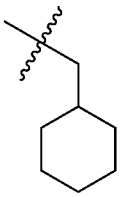

| Ex | Name | R¹ | R² | R³ | Obs. MS Ion | RT (Method) |
|---|---|---|---|---|---|---|
| 1216 | 5-[4-amino-5-(trifluoromethyl)pyrrolo[2,1-f][1,2,4]triazin-7-yl]-N-[(3R,4S)-1-(2-cyclohexylacetyl)-4-fluoropyrrolidin-3-yl]-2-methoxypyridine-3-carboxamide | H | OMe | 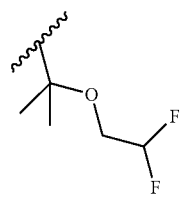 [SMILES: *C(C)(C)OCC(F)F] | 564.3 | 2.05 (4) |
| 1217 | 5-[4-amino-5-(trifluoromethyl)pyrrolo[2,1-f][1,2,4]triazin-7-yl]-N-[(3R,4S)-1-[2-(2,2-difluoroethoxy)-2-methylpropanoyl]-4-fluoropyrrolidin-3-yl]-2-methoxypyridine-3-carboxamide | H | OMe | 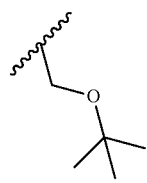 [SMILES: *COC(C)(C)C] | 590.1 | 1.89 (2) |
| 1218 | 5-[4-amino-5-(trifluoromethyl)pyrrolo[2,1-f][1,2,4]triazin-7-yl]-N-[(3R,4S)-1-[2-(tert-butoxy)acetyl]-4-fluoropyrrolidin-3-yl]-2-methoxypyridine-3-carboxamide | H | OMe | 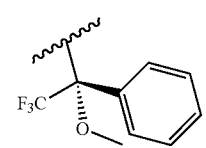 [SMILES: *[C@@](OC)(c1ccccc1)C(F)(F)F] | 554.2 | 1.79 (2) |
| 1219 | 5-[4-amino-5-(trifluoromethyl)pyrrolo[2,1-f][1,2,4]triazin-7-yl]-N-[(3R,4S)-4-fluoro-1-[(2S)-3,3,3-trifluoro-2-methoxy-2-phenylpropanoyl]pyrrolidin-3-yl]-2-methoxypyridine-3-carboxamide | H | OMe | 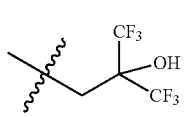 | 656.1 | 2.28 (2) |
| 1220 | 5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-methoxypyridine-3-carboxamide | H | OMe | 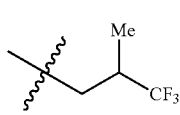 [SMILES: *CC(C)C(F)(F)F] | 648.3 | 2.11 (2) |
| 1221 | 5-[4-amino-5-(trifluoromethyl)pyrrolo[2,1-f][1,2,4]triazin-7-yl]-N-[(3R,4S)-4-fluoro-1-(4,4,4-trifluoro-3- | H | OMe | | 578.4 | 1.86 (1) |

TABLE 44-continued

Compounds in Table 44 were prepared by the methods detailed in Examples 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

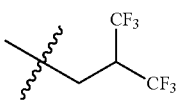

| Ex | Name | R[1] | R[2] | R[3] | Obs. MS Ion | RT (Method) |
|---|---|---|---|---|---|---|
| | methylbutanoyl) pyrrolidin-3-yl]-2-methoxypyridine-3-carboxamide | | | | | |
| 1222 | 5-[4-amino-5-(trifluoromethyl)pyrrolo [2,1-f][1,2,4]triazin-7-yl]-N-[(3R,4S)-4-fluoro-1-[4,4,4-trifluoro-3-(trifluoromethyl)butanoyl] pyrrolidin-3-yl]-2-methoxypyridine-3-carboxamide | H | OMe | 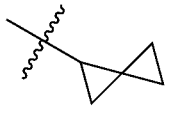 [SMILES: *C1CC12CC2] | 632.3 | 2.12 (2) |
| 1223 | 5-[4-amino-5-(trifluoromethyl)pyrrolo [2,1-f][1,2,4]triazin-7-yl]-N-[(3R,4S)-4-fluoro-1-{spiro[2.2]pentane-1-carbonyl}pyrrolidin-3-yl]-2-methoxypyridine-3-carboxamide | H | OMe | 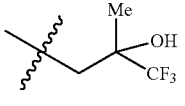 [SMILES: *CC(C)(O)C(F)(F)F] | 534.3 | 1.84 (2) |
| 1224 | 5-[4-amino-5-(trifluoromethyl)pyrrolo [2,1-f][1,2,4]triazin-7-yl]-N-[(3R,4S)-4-fluoro-1-(4,4,4-trifluoro-3-hydroxy-3-methylbutanoyl) pyrrolidin-3-yl]-2-methoxypyridine-3-carboxamide | H | OMe | 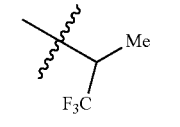 [SMILES: *C(C)C(F)(F)F] | 594.1 | 1.83 (2) |
| 1225 | 5-[4-amino-5-(trifluoromethyl)pyrrolo [2,1-f][1,2,4]triazin-7-yl]-N-[(3R,4S)-4-fluoro-1-(3,3,3-trifluoro-2-methylpropanoyl) pyrrolidin-3-yl]-2-methoxypyridine-3-carboxamide | H | OMe | 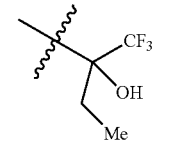 [SMILES: *C(O)(CC)C(F)(F)F] | 564.2 | 1.88 (2) |
| 1226 | 5-[4-amino-5-(trifluoromethyl)pyrrolo [2,1-f][1,2,4]triazin-7-yl]-N-[(3R,4S)-4-fluoro-1-[2-hydroxy-2-(trifluoromethyl)butanoyl] pyrrolidin-3-yl]-2-methoxypyridine-3-carboxamide | H | OMe |  | 594.0 | 1.86 (2) |

TABLE 44-continued

Compounds in Table 44 were prepared by the methods detailed in Examples 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R[1] | R[2] | R[3] | Obs. MS Ion | RT (Method) |
|---|---|---|---|---|---|---|
| 1227 | 5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-methoxypyridine-3-carboxamide | H | OMe | C(CF$_3$)(OH)(Et) | 594.2 | 1.86 (2) |
| 1228 | 5-[4-amino-5-(trifluoromethyl)pyrrolo[2,1-f][1,2,4]triazin-7-yl]-N-[(3R,4S)-4-fluoro-1-(2,2,2-trifluoroacetyl)pyrrolidin-3-yl]-2-methoxypyridine-3-carboxamide | H | OMe | CF$_3$ | 536.2 | 1.99 (4) |
| 1229 | 5-[4-amino-5-(trifluoromethyl)pyrrolo[2,1-f][1,2,4]triazin-7-yl]-N-[(3R,4S)-4-fluoro-1-(2,3,3,3-tetrafluoro-2-methylpropanoyl)pyrrolidin-3-yl]-2-methoxypyridine-3-carboxamide | H | OMe | C(CF$_3$)(F)(Me) | 582.2 | 2.03 (4) |
| 1230 | 5-[4-amino-5-(trifluoromethyl)pyrrolo[2,1-f][1,2,4]triazin-7-yl]-N-[(3R,4S)-4-fluoro-1-[(2R)-3,3,3-trifluoro-2-methoxy-2-methylpropanoyl]pyrrolidin-3-yl]-2-methoxypyridine-3-carboxamide | H | OMe | C(CF$_3$)(OMe)(Me) | 594.1 | |
| 1231 | 5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-methylpyridine-3-carboxamide | H | Me | C(CF$_3$)(OH)(Et) | 578.4 | 1.30 (1) |
| 1232 | 5-[4-amino-5-(trifluoromethyl)pyrrolo[2,1-f][1,2,4]triazin-7-yl]-N-[(3R,4S)-4-fluoro- | H | Me | CH$_2$CH(Me)(CF$_3$) | 562.3 | 1.52 (2) |

TABLE 44-continued

Compounds in Table 44 were prepared by the methods detailed in Examples 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R[1] | R[2] | R[3] | Obs. MS Ion | RT (Method) |
|---|---|---|---|---|---|---|
| | 1-(4,4,4-trifluoro-3-methylbutanoyl)pyrrolidin-3-yl]-2-methylpyridine-3-carboxamide | | | | | |
| 1233 | 5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-methylpyridine-3-carboxamide | H | Me | CH$_2$C(H)(CF$_3$)CF$_3$ | 616.3 | 1.62 (1) |
| 1234 | 5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-methylpyridine-3-carboxamide | H | Me | CH$_2$C(Me)(OH)CF$_3$ | 578.3 | 1.38 (1) |
| 1235 | 5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-methylpyridine-3-carboxamide | H | Me | CH(Me)CF$_3$ | 548.3 | 1.49 (2) |
| 1236 | 5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-methylpyridine-3-carboxamide | H | Me | CH$_2$C(CF$_3$)(OH)CF$_3$ | 632.0 | 1.77 (2) |

TABLE 45

Compounds in Table 45 were prepared by the methods detailed in Examples 57, 63, and 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R | Obs. MS Ion | RT (Method) |
|---|---|---|---|---|
| 1237 | 5-{4-amino-5-[(4,4-difluoropiperidin-1-yl)methyl]pyrrolo[2,1-f][1,2,4]triazin-7-yl}-N-[(3R,4S)-4-fluoro-1-(pyridine-4-carbonyl)pyrrolidin-3-yl]-2-methoxypyridine-3-carboxamide | 4-pyridyl | 610.2 | 1.64 (4) |
| 1238 | 5-{4-amino-5-[(4,4-difluoropiperidin-1-yl)methyl]pyrrolo[2,1-f][1,2,4]triazin-7-yl}-N-[(3R,4S)-1-(4-chlorobenzoyl)-4-fluoropyrrolidin-3-yl]-2-methoxypyridine-3-carboxamide | 4-chlorophenyl | 643 | 2.07 (4) |
| 1239 | 5-{4-amino-5-[(4,4-difluoropiperidin-1-yl)methyl]pyrrolo[2,1-f][1,2,4]triazin-7-yl}-N-[(3R,4S)-4-fluoro-1-(3-fluorobenzoyl)pyrrolidin-3-yl]-2-methoxypyridine-3-carboxamide | 3-fluorophenyl | 627.2 | 2.01 (4) |
| 1240 | 5-{4-amino-5-[(4,4-difluoropiperidin-1-yl)methyl]pyrrolo[2,1-f][1,2,4]triazin-7-yl}-N-[(3R,4S)-1-(2-chlorobenzoyl)-4-fluoropyrrolidin-3-yl]-2-methoxypyridine-3-carboxamide | 2-chlorophenyl | 643 | 2.00 (4) |
| 1241 | 5-{4-amino-5-[(4,4-difluoropiperidin-1-yl)methyl]pyrrolo[2,1-f][1,2,4]triazin-7-yl}-N-[(3R,4S)-1-(2,5-difluorobenzoyl)-4-fluoropyrrolidin-3-yl]-2-methoxypyridine-3-carboxamide | 2,5-difluorophenyl | 645.1 | 1.98 (4) |
| 1242 | 5-{4-amino-5-[(4,4-difluoropiperidin-1-yl)methyl]pyrrolo[2,1-f][1,2,4]triazin-7-yl}-N-[(3R,4S)-1-(2,6-difluorobenzoyl)-4-fluoropyrrolidin-3-yl]-2-methoxypyridine-3-carboxamide | 2,6-difluorophenyl | 645.1 | 1.96 (4) |

TABLE 45-continued

Compounds in Table 45 were prepared by the methods detailed in Examples 57, 63, and 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R | Obs. MS Ion | RT (Method) |
|---|---|---|---|---|
| 1243 | 5-{4-amino-5-[(4,4-difluoropiperidin-1-yl)methyl]pyrrolo[2,1-f][1,2,4]triazin-7-yl}-N-[(3R,4S)-1-(3,5-difluoropyridine-4-carbonyl)-4-fluoropyrrolidin-3-yl]-2-methoxypyridine-3-carboxamide | 3,5-difluoropyridin-4-yl | 646.1 | 1.91 (4) |
| 1244 | 5-{4-amino-5-[(4,4-difluoropiperidin-1-yl)methyl]pyrrolo[2,1-f][1,2,4]triazin-7-yl}-N-[(3R,4S)-1-(3-chloropyridine-2-carbonyl)-4-fluoropyrrolidin-3-yl]-2-methoxypyridine-3-carboxamide | 3-chloropyridin-2-yl | 644.2 | 1.90 (4) |
| 1245 | 5-{4-amino-5-[(4,4-difluoropiperidin-1-yl)methyl]pyrrolo[2,1-f][1,2,4]triazin-7-yl}-N-[(3R,4S)-4-fluoro-1-(1-fluorocyclopropanecarbonyl)pyrrolidin-3-yl]-2-methoxypyridine-3-carboxamide | 1-fluorocyclopropyl | 591.2 | 1.92 (4) |
| 1246 | 5-{4-amino-5-[(4,4-difluoropiperidin-1-yl)methyl]pyrrolo[2,1-f][1,2,4]triazin-7-yl}-N-[(3R,4S)-4-fluoro-1-(4,4,4-trifluoro-3-hydroxy-3-methylbutanoyl)pyrrolidin-3-yl]-2-methoxypyridine-3-carboxamide | C(Me)(OH)(CF$_3$)CH$_2$ | 659.1 | 1.93 (4) |
| 1247 | 5-{4-amino-5-[(4,4-difluoropiperidin-1-yl)methyl]pyrrolo[2,1-f][1,2,4]triazin-7-yl}-N-[(3R,4S)-4-fluoro-1-(3-methylbutanoyl)pyrrolidin-3-yl]-2-methoxypyridine-3-carboxamide | CH$_2$CH(Me)$_2$ | 589 | 2.01 (4) |
| 1248 | 5-{4-amino-5-[(4,4-difluoropiperidin-1-yl)methyl]pyrrolo[2,1-f][1,2,4]triazin-7-yl}-N-[(3R,4S)-4-fluoro-1-(2-methylpyridine-4-carbonyl)pyrrolidin-3-yl]-2-methoxypyridine-3-carboxamide | 2-methylpyridin-4-yl | 624.2 | 1.80 (4) |
| 1249 | 5-{4-amino-5-[(4,4-difluoropiperidin-1-yl)methyl]pyrrolo[2,1-f][1,2,4]triazin-7-yl}-N-[(3R,4S)-4-fluoro-1-[4,4,4-trifluoro-3-(trifluoromethyl)butanoyl]pyrrolidin-3-yl]-2-methoxypyridine-3-carboxamide | CH$_2$CH(CF$_3$)$_2$ | 697.1 | 2.20 (4) |

TABLE 45-continued

Compounds in Table 45 were prepared by the methods detailed in Examples 57, 63, and 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R | Obs. MS Ion | RT (Method) |
|---|---|---|---|---|
| 1250 | 5-{4-amino-5-[(4,4-difluoropiperidin-1-yl)methyl]pyrrolo[2,1-f][1,2,4]triazin-7-yl}-N-[(3R,4S)-4-fluoro-1-(3-fluoropyridine-4-carbonyl)pyrrolidin-3-yl]-2-methoxypyridine-3-carboxamide | 3-fluoropyridin-4-yl | 628 | 1.74 (4) |
| 1251 | 5-{4-amino-5-[(4,4-difluoropiperidin-1-yl)methyl]pyrrolo[2,1-f][1,2,4]triazin-7-yl}-N-[(3R,4S)-4-fluoro-1-(2,4,6-trifluorobenzoyl)pyrrolidin-3-yl]-2-methoxypyridine-3-carboxamide | 2,4,6-trifluorophenyl | 663.1 | 2.01 (4) |
| 1252 | 5-{4-amino-5-[(4,4-difluoropiperidin-1-yl)methyl]pyrrolo[2,1-f][1,2,4]triazin-7-yl}-N-[(3R,4S)-1-(4-chloropyridine-3-carbonyl)-4-fluoropyrrolidin-3-yl]-2-methoxypyridine-3-carboxamide | 4-chloropyridin-3-yl | 644.1 | 1.85 (4) |
| 1253 | 5-{4-amino-5-[(4,4-difluoropiperidin-1-yl)methyl]pyrrolo[2,1-f][1,2,4]triazin-7-yl}-N-[(3R,4S)-1-(2-chloro-4-fluorobenzoyl)-4-fluoropyrrolidin-3-yl]-2-methoxypyridine-3-carboxamide | 2,4-dichlorophenyl | 661.2 | 2.09 (4) |
| 1254 | 5-{4-amino-5-[(4,4-difluoropiperidin-1-yl)methyl]pyrrolo[2,1-f][1,2,4]triazin-7-yl}-N-[(3R,4S)-4-fluoro-1-(pyridine-2-carbonyl)pyrrolidin-3-yl]-2-methoxypyridine-3-carboxamide | pyridin-2-yl | 610.2 | 1.41 (3) |
| 1255 | 5-{4-amino-5-[(4,4-difluoropiperidin-1-yl)methyl]pyrrolo[2,1-f][1,2,4]triazin-7-yl}-N-[(3R,4S)-4-fluoro-1-[4-(trifluoromethyl)pyridine-3-carbonyl]pyrrolidin-3-yl]-2-methoxypyridine-3-carboxamide | 4-(trifluoromethyl)pyridin-3-yl | 678.4 | 1.53 (3) |

TABLE 45-continued

Compounds in Table 45 were prepared by the methods detailed in Examples 57, 63, and 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R | Obs. MS Ion | RT (Method) |
|---|---|---|---|---|
| 1256 | 5-{4-amino-5-[(4,4-difluoropiperidin-1-yl)methyl]pyrrolo[2,1-f][1,2,4]triazin-7-yl}-N-[(3R,4S)-4-fluoro-1-(1,3-thiazole-4-carbonyl)pyrrolidin-3-yl]-2-methoxypyridine-3-carboxamide | 1,3-thiazol-4-yl | 616.2 | 1.40 (3) |
| 1257 | 5-{4-amino-5-[(4,4-difluoropiperidin-1-yl)methyl]pyrrolo[2,1-f][1,2,4]triazin-7-yl}-N-[(3R,4S)-1-(5-chloropyridine-2-carbonyl)-4-fluoropyrrolidin-3-yl]-2-methoxypyridine-3-carboxamide | 5-chloropyridin-2-yl | 644.1 | 1.63 (3) |
| 1258 | 5-{4-amino-5-[(4,4-difluoropiperidin-1-yl)methyl]pyrrolo[2,1-f][1,2,4]triazin-7-yl}-N-[(3R,4S)-4-fluoro-1-(4,4,4-trifluoro-3-methylbutanoyl)pyrrolidin-3-yl]-2-methoxypyridine-3-carboxamide | -CH2-CH(Me)-CF3 | 642.9 | 1.65 (3) |
| 1259 | 5-{4-amino-5-[(4,4-difluoropiperidin-1-yl)methyl]pyrrolo[2,1-f][1,2,4]triazin-7-yl}-N-[(3R,4S)-4-fluoro-1-(5-fluoro-2-methylpyridine-4-carbonyl)pyrrolidin-3-yl]-2-methoxypyridine-3-carboxamide | 5-fluoro-2-methylpyridin-4-yl | 641.9 | 1.41 (3) |
| 1260 | 5-{4-amino-5-[(4,4-difluoropiperidin-1-yl)methyl]pyrrolo[2,1-f][1,2,4]triazin-7-yl}-N-[(3R,4S)-4-fluoro-1-(2-hydroxy-2-methylpropanoyl)pyrrolidin-3-yl]-2-methoxypyridine-3-carboxamide | -C(Me)2-OH | 591.2 | 1.35 (3) |
| 1261 | 5-{4-amino-5-[(4,4-difluoropiperidin-1-yl)methyl]pyrrolo[2,1-f][1,2,4]triazin-7-yl}-N-[(3R,4S)-4-fluoro-1-(3,3,3-trifluoropropanoyl)pyrrolidin-3-yl]-2-methoxypyridine-3-carboxamide | -CH2-CF3 | 615.2 | 1.39 (3) |
| 1262 | 5-{4-amino-5-[(4,4-difluoropiperidin-1-yl)methyl]pyrrolo[2,1-f][1,2,4]triazin-7-yl}-N-[(3R,4S)-1-(3,4-difluorobenzoyl)-4-fluoropyrrolidin-3-yl]-2-methoxypyridine-3-carboxamide | 3,4-difluorophenyl | 644.9 | 1.63 (3) |

TABLE 45-continued

Compounds in Table 45 were prepared by the methods detailed in Examples 57, 63, and 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R | Obs. MS Ion | RT (Method) |
|---|---|---|---|---|
| 1263 | 5-{4-amino-5-[(4,4-difluoropiperidin-1-yl)methyl]pyrrolo[2,1-f][1,2,4]triazin-7-yl}-N-[3R,4S)-1-(3,5-difluoropyridine-2-carbonyl)-4-fluoropyrrolidin-3-yl]-2-methoxypyridine-3-carboxamide | 3,5-difluoropyridin-2-yl | 645.9 | 1.48 (3) |
| 1264 | 5-{4-amino-5-[(4,4-difluoropiperidin-1-yl)methyl]pyrrolo[2,1-f][1,2,4]triazin-7-yl}-N-[(3R,4S)-4-fluoro-1-(5-fluoropyridine-2-carbonyl)pyrrolidin-3-yl]-2-methoxypyridine-3-carboxamide | 5-fluoropyridin-2-yl | 628.3 | 1.42 (3) |
| 1265 | 5-{4-amino-5-[(4,4-difluoropiperidin-1-yl)methyl]pyrrolo[2,1-f][1,2,4]triazin-7-yl}-N-[(3R,4S)-1-(2-chloro-3-fluorobenzoyl)-4-fluoropyrrolidin-3-yl]-2-methoxypyridine-3-carboxamide | 2-chloro-3-fluorophenyl | 660.9 | 1.65 (3) |
| 1266 | 5-{4-amino-5-[(4,4-difluoropiperidin-1-yl)methyl]pyrrolo[2,1-f][1,2,4]triazin-7-yl}-N-[(3R,4S)-4-fluoro-1-(3,3,3-trifluoro-2-methylpropanoyl)pyrrolidin-3-yl]-2-methoxypyridine-3-carboxamide | CH(Me)(CF$_3$) | 629.2 | 1.46 (3) |
| 1267 | 5-{4-amino-5-[(4,4-difluoropiperidin-1-yl)methyl]pyrrolo[2,1-f][1,2,4]triazin-7-yl}-N-[(3R,4S)-1-(3,5-difluorobenzoyl)-4-fluoropyrrolidin-3-yl]-2-methoxypyridine-3-carboxamide | 3,5-difluorophenyl | 645.1 | 1.54 (3) |
| 1268 | 5-{4-amino-5-[(4,4-difluoropiperidin-1-yl)methyl]pyrrolo[2,1-f][1,2,4]triazin-7-yl}-N-[(3R,4S)-1-(3-chloropyridine-4-carbonyl)-4-fluoropyrrolidin-3-yl]-2-methoxypyridine-3-carboxamide | 3-chloropyridin-4-yl | 644.2 | 1.32 (3) |

TABLE 45-continued

Compounds in Table 45 were prepared by the methods detailed in Examples 57, 63, and 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R | Obs. MS Ion | RT (Method) |
|---|---|---|---|---|
| 1269 | 5-{4-amino-5-[(4,4-difluoropiperidin-1-yl)methyl]pyrrolo[2,1-f][1,2,4]triazin-7-yl}-N-[(3R,4S)-4-fluoro-1-(3-fluoropyridine-2-carbonyl)pyrrolidin-3-yl]-2-methoxypyridine-3-carboxamide | 3-fluoropyridin-2-yl | 628.2 | 1.44 (3) |
| 1270 | 5-{4-amino-5-[(4,4-difluoropiperidin-1-yl)methyl]pyrrolo[2,1-f][1,2,4]triazin-7-yl}-N-[(3R,4S)-1-(2-chloro-6-fluorobenzoyl)-4-fluoropyrrolidin-3-yl]-2-methoxypyridine-3-carboxamide | 2-chloro-6-fluorophenyl | 661 | 2.11 (3) |

TABLE 46

Compounds in Table 46 were prepared by the methods detailed in Examples 57, 63, and 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R | Obs. MS Ion | RT (Method) |
|---|---|---|---|---|
| 1271 | 5-{4-amino-5-[(3,3-difluoroazetidin-1-yl)methyl]pyrrolo[2,1-f][1,2,4]triazin-7-yl}-N-[(3R,4S)-4-fluoro-1-(2-fluoro-2-methylpropanoyl)pyrrolidin-3-yl]-2-(methoxy-d3)nicotinamide | 2-fluoro-2-methylpropanoyl | 568.1 | 1.88 (2) |

TABLE 46-continued

Compounds in Table 46 were prepared by the methods detailed in Examples 57, 63, and 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

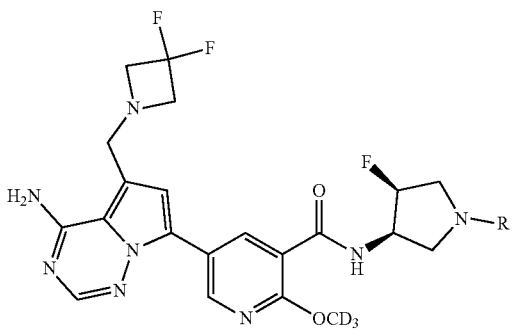

| Ex | Name | R | Obs. MS Ion | RT (Method) |
|---|---|---|---|---|
| 1272 | 5-{4-amino-5-[(3,3-difluoroazetidin-1-yl)methyl]pyrrolo[2,1-f][1,2,4]triazin-7-yl}-N-[(3R,4S)-1-(3,3-difluorocyclopentanecarbonyl)-4-fluoropyrrolidin-3-yl]-2-(methoxy-d3)nicotinamide | | 612.4 | 1.84 (2) |
| 1273 | 5-{4-amino-5-[(3,3-difluoroazetidin-1-yl)methyl]pyrrolo[2,1-f][1,2,4]triazin-7-yl}-N-[(3R,4S)-4-fluoro-1-(3-fluorocyclobutanecarbonyl)pyrrolidin-3-yl]-2-(methoxy-d3)nicotinamide | | 580.41, 580.41 | 1.70, 1.73 (2) |
| 1274 | 5-{4-amino-5-[(3,3-difluoroazetidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-(methoxy-d3)nicotinamide | | 598.4 | 1.81 (2) |
| 1275 | 5-{4-amino-5-[(3,3-difluoroazetidin-1-yl)methyl]pyrrolo[2,1-f][1,2,4]triazin-7-yl}-N-[(3R,4S)-4-fluoro-1-(4-fluorobenzoyl)pyrrolidin-3-yl]-2-(methoxy-d3)nicotinamide | | 602.4 | 1.85 (2) |
| 1276 | 5-{4-amino-5-[(3,3-difluoroazetidin-1-yl)methyl]pyrrolo[2,1-f][1,2,4]triazin-7-yl}-N-[(3R,4S)-4-fluoro-1-(3,3,3-trifluoro-2,2-dimethylpropanoyl)pyrrolidin-3-yl]-2-(methoxy-d3)nicotinamide | | 618.4 | 1.98 (2) |

TABLE 46-continued

Compounds in Table 46 were prepared by the methods detailed in Examples 57, 63, and 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R | Obs. MS Ion | RT (Method) |
|---|---|---|---|---|
| 1277 | 5-{4-amino-5-[(3,3-difluoroazetidin-1-yl)methyl]pyrrolo[2,1-f][1,2,4]triazin-7-yl}-N-[(3R,4S)-1-(2,2-dimethylpropanoyl)-4-fluoropyrrolidin-3-yl]-2-(methoxy-d3)nicotinamide | 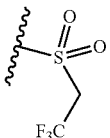 | 564.4 | 1.85 (2) |
| 1278 | 5-{4-amino-5-[(3,3-difluoroazetidin-1-yl)methyl]pyrrolo[2,1-f][1,2,4]triazin-7-yl}-N-[(3R,4S)-4-fluoro-1-(2,2,2-trifluoroethanesulfonyl)pyrrolidin-3-yl]-2-(methoxy-d3)nicotinamide | 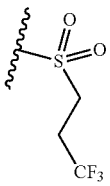 | 626.3 | 1.88 (4) |
| 1279 | 5-{4-amino-5-[(3,3-difluoroazetidin-1-yl)methyl]pyrrolo[2,1-f][1,2,4]triazin-7-yl}-N-[(3R,4S)-4-fluoro-1-(3,3,3-trifluoropropanesulfonyl)pyrrolidin-3-yl]-2-(methoxy-d3)nicotinamide | 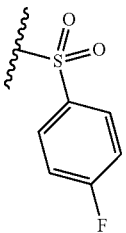 [SMILES: *S(=O)(=O)c1ccc(F)cc1] | 640.2 | 1.95 (4) |
| 1280 | 5-{4-amino-5-[(3,3-difluoroazetidin-1-yl)methyl]pyrrolo[2,1-f][1,2,4]triazin-7-yl}-N-[(3R,4S)-4-fluoro-1-(4-fluorobenzenesulfonyl)pyrrolidin-3-yl]-2-(methoxy-d3)nicotinamide | | 638.1 | 1.95 (4) |
| 1281 | 5-{4-amino-5-[(3,3-difluoroazetidin-1-yl)methyl]pyrrolo[2,1-f][1,2,4]triazin-7-yl}-N-[(3R,4S)-1-(cyclohexanesulfonyl)-4-fluoropyrrolidin-3-yl]-2-(methoxy-d3)nicotinamide | 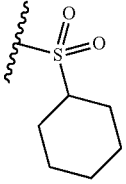 [SMILES: *S(=O)(=O)C1CCCCC1] | 626.3 | 2.02 (4) |

TABLE 46-continued

Compounds in Table 46 were prepared by the methods detailed in Examples 57, 63, and 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

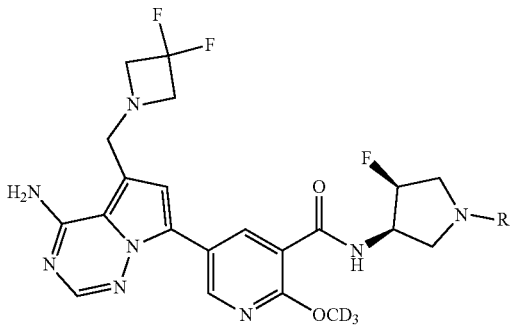

| Ex | Name | R | Obs. MS Ion | RT (Method) |
|---|---|---|---|---|
| 1282 | 5-{4-amino-5-[(3,3-difluoroazetidin-1-yl)methyl]pyrrolo[2,1-f][1,2,4]triazin-7-yl}-N-[(3R,4S)-4-fluoro-1-{[1-methyl-3-(trifluoromethyl)-1H-pyrazol-4-yl]sulfonyl}pyrrolidin-3-yl]-2-(methoxy-d3)nicotinamide | | 692.2 | 1.89 (4) |
| 1283 | 5-{4-amino-5-[(3,3-difluoroazetidin-1-yl)methyl]pyrrolo[2,1-f][1,2,4]triazin-7-yl}-N-[(3R,4S)-1-(ethanesulfonyl)-4-fluoropyrrolidin-3-yl]-2-(methoxy-d3)nicotinamide | | 572.1 | 1.67 (4) |
| 1284 | 5-{4-amino-5-[(3,3-difluoroazetidin-1-yl)methyl]pyrrolo[2,1-f][1,2,4]triazin-7-yl}-N-[(3R,4S)-1-(cyclopropanesulfonyl)-4-fluoropyrrolidin-3-yl]-2-(methoxy-d3)nicotinamide | | 584.1 | 1.71 (4) |
| 1285 | 5-{4-amino-5-[(3,3-difluoroazetidin-1-yl)methyl]pyrrolo[2,1-f][1,2,4]triazin-7-yl}-N-[(3R,4S)-4-fluoro-1-(3-methylbutanoyl)pyrrolidin-3-yl]-2-(methoxy-d3)nicotinamide | | 564.5 | 1.47 (1) |
| 1286 | 5-{4-amino-5-[(3,3-difluoroazetidin-1-yl)methyl]pyrrolo[2,1-f][1,2,4]triazin-7-yl}-N-[(3R,4S)-4-fluoro-1-(3,3,3-trifluoropropanoyl)pyrrolidin-3-yl]-2-(methoxy-d3)nicotinamide | | 590.4 | 1.40 (1) |
| 1287 | 5-{4-amino-5-[(3,3-difluoroazetidin-1-yl)methyl]pyrrolo[2,1-f][1,2,4]triazin-7-yl}-N-[(3R,4S)-1-(2,2-difluorocyclopropanecarbonyl)-4-fluoropyrrolidin-3-yl]-2-(methoxy-d3)nicotinamide | | 584.1 | 1.24 (1) |

TABLE 46-continued

Compounds in Table 46 were prepared by the methods detailed in Examples 57, 63, and 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

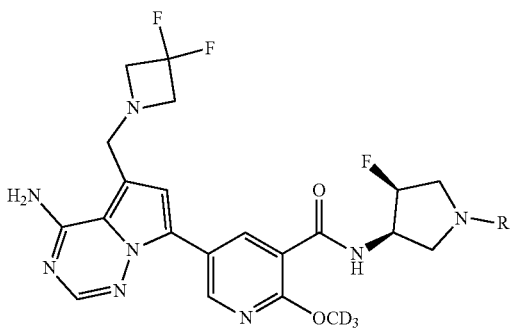

| Ex | Name | R | Obs. MS Ion | RT (Method) |
|---|---|---|---|---|
| 1288 | 5-{4-amino-5-[(3,3-difluoroazetidin-1-yl)methyl]pyrrolo[2,1-f][1,2,4]triazin-7-yl}-N-[(3R,4S)-4-fluoro-1-[2-(trifluoromethoxy)benzenesulfonyl]pyrrolidin-3-yl]-2-(methoxy-d3)nicotinamide | (2-trifluoromethoxyphenyl)sulfonyl | 704.1 | 1.85 (3) |
| 1289 | 5-{4-amino-5-[(3,3-difluoroazetidin-1-yl)methyl]pyrrolo[2,1-f][1,2,4]triazin-7-yl}-N-[(3R,4S)-4-fluoro-1-(2-methylpropanesulfonyl)pyrrolidin-3-yl]-2-(methoxy-d3)nicotinamide | isobutylsulfonyl | 600.3 | 1.56 (3) |
| 1290 | 5-{4-amino-5-[(3,3-difluoroazetidin-1-yl)methyl]pyrrolo[2,1-f][1,2,4]triazin-7-yl}-N-[(3R,4S)-1-[(1,2-dimethyl-1H-imidazol-4-yl)sulfonyl]-4-fluoropyrrolidin-3-yl]-2-(methoxy-d3)nicotinamide | (1,2-dimethylimidazol-4-yl)sulfonyl | 638.3 | 1.22 (3) |
| 1291 | 5-{4-amino-5-[(3,3-difluoroazetidin-1-yl)methyl]pyrrolo[2,1-f][1,2,4]triazin-7-yl}-N-[(3R,4S)-4-fluoro-1-(4,4,4-trifluorobutanesulfonyl)pyrrolidin-3-yl]-2-(methoxy-d3)nicotinamide | 4,4,4-trifluorobutylsulfonyl | 654.3 | 1.61 (3) |
| 1292 | 5-{4-amino-5-[(3,3-difluoroazetidin-1-yl)methyl]pyrrolo[2,1-f][1,2,4]triazin-7-yl}-N-[(3R,4S)-1-cyclopropylmethanesulfonyl-4-fluoropyrrolidin-3-yl]-2-(methoxy-d3)nicotinamide | cyclopropylmethylsulfonyl | 598.1 | 1.41 (3) |

TABLE 46-continued

Compounds in Table 46 were prepared by the methods detailed in Examples 57, 63, and 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

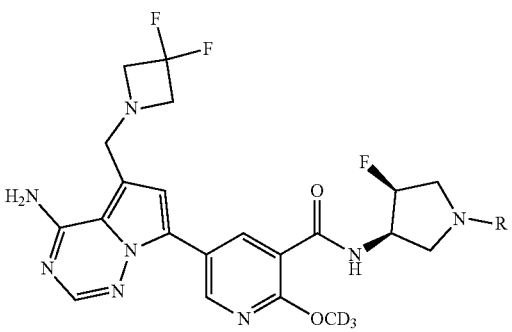

| Ex | Name | R | Obs. MS Ion | RT (Method) |
|---|---|---|---|---|
| 1293 | 5-{4-amino-5-[(3,3-difluoroazetidin-1-yl)methyl]pyrrolo[2,1-f][1,2,4]triazin-7-yl}-N-[(3R,4S)-4-fluoro-1-(2,2,2-trifluoro-1-phenylethanesulfonyl)pyrrolidin-3-yl]-2-(methoxy-d3)nicotinamide | -S(O)₂-CH(CF₃)(Ph) | 702.2 | 1.79 (3) |
| 1294 | 5-{4-amino-5-[(3,3-difluoroazetidin-1-yl)methyl]pyrrolo[2,1-f][1,2,4]triazin-7-yl}-N-[(3R,4S)-4-fluoro-1-methanesulfonylpyrrolidin-3-yl]-2-(methoxy-d3)nicotinamide | -S(O)₂-Me | 558.3 | 1.24 (3) |
| 1295 | 5-{4-amino-5-[(3,3-difluoroazetidin-1-yl)methyl]pyrrolo[2,1-f][1,2,4]triazin-7-yl}-N-[(3R,4S)-4-fluoro-1-(2-methoxybenzenesulfonyl)pyrrolidin-3-yl]-2-(methoxy-d3)nicotinamide | -S(O)₂-(2-MeO-C₆H₄) | 650.3 | 1.55 (3) |
| 1296 | 5-{4-amino-5-[(3,3-difluoroazetidin-1-yl)methyl]pyrrolo[2,1-f][1,2,4]triazin-7-yl}-N-[(3R,4S)-4-fluoro-1-phenylmethanesulfonylpyrrolidin-3-yl]-2-(methoxy-d3)nicotinamide | -S(O)₂-CH₂Ph | 634.1 | 1.55 (3) |
| 1297 | 5-{4-amino-5-[(3,3-difluoroazetidin-1-yl)methyl]pyrrolo[2,1-f][1,2,4]triazin-7-yl}-N-[(3R,4S)-4-fluoro-1-(2-phenylethanesulfonyl)pyrrolidin-3-yl]-2-(methoxy-d3)nicotinamide | -S(O)₂-CH₂CH₂Ph | 648.2 | 1.64 (3) |

TABLE 46-continued

Compounds in Table 46 were prepared by the methods detailed in Examples 57, 63, and 563. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

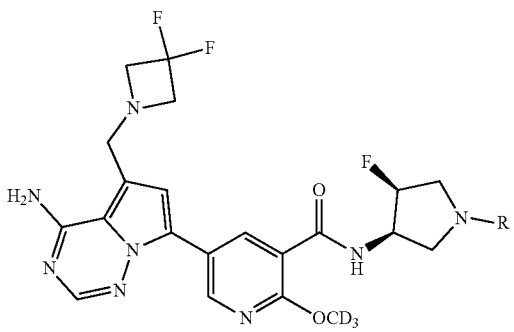

| Ex | Name | R | Obs. MS Ion | RT (Method) |
|---|---|---|---|---|
| 1298 | 5-{4-amino-5-[(3,3-difluoroazetidin-1-yl)methyl]pyrrolo[2,1-f][1,2,4]triazin-7-yl}-N-[(3R,4S)-4-fluoro-1-(propane-2-sulfonyl)pyrrolidin-3-yl]-2-(methoxy-d3)nicotinamide | | 586.4 | 1.43 (3) |
| 1299 | 5-{4-amino-5-[(3,3-difluoroazetidin-1-yl)methyl]pyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-(methoxy-d3)nicotinamide | | 620.0 | 1.88 (2) |

TABLE 47

Compounds in Table 47 were prepared by the methods detailed in Example 10. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

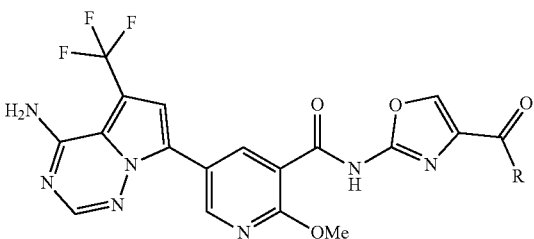

| Ex | Name | R | Obs. MS Ion | RT (Method) |
|---|---|---|---|---|
| 1300 | 5-[4-amino-5-(trifluoromethyl)pyrrolo-[2,1-f][1,2,4]triazin-7-yl]-N-[4-(tert-butylcarbamoyl)-1,3-oxazol-2-yl]-2-methoxypyridine-3-carboxamide | | 519.3 | 1.73 (4) |
| 1301 | 5-[4-amino-5-(trifluoromethyl)pyrrolo-[2,1-f][1,2,4]triazin-7-yl]-N-{4-[(cyclopropylmethyl)carbamoyl]-1,3-oxazol-2-yl}-2-methoxypyridine-3-carboxamide | | 517.3 | 1.78 (4) |
| 1302 | 5-[4-amino-5-(trifluoromethyl)pyrrolo-[2,1-f][1,2,4]triazin-7-yl]-2-methoxy-N-{4-[(propan-2-yl)carbamoyl]-1,3-oxazol-2-yl}pyridine-3-carboxamide | | 505 | 1.59 (3) |

TABLE 47-continued

Compounds in Table 47 were prepared by the methods detailed in Example 10. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R | Obs. MS Ion | RT (Method) |
|---|---|---|---|---|
| 1303 | 5-[4-amino-5-(trifluoromethyl)pyrrolo-[2,1-f][1,2,4]triazin-7-yl]-N-[4-(cyclopentylcarbamoyl)-1,3-oxazol-2-yl]-2-methoxypyridine-3-carboxamide | | 531 | 1.74 (3) |
| 1304 | 5-[4-amino-5-(trifluoromethyl)pyrrolo-[2,1-f][1,2,4]triazin-7-yl]-N-{4-[(cyclopropylmethyl)(propyl)carbamoyl]-1,3-oxazol-2-yl}-2-methoxypyridine-3-carboxamide | | 559.3 | 1.97 (3) |
| 1305 | 5-[4-amino-5-(trifluoromethyl)pyrrolo-[2,1-f][1,2,4]triazin-7-yl]-N-[5-({[2-fluoro-5-(trifluoromethoxy)phenyl]methyl}carbamoyl)-1,3-thiazol-2-yl]-2-methoxypyridine-3-carboxamide | | 671.2 | 2.15 (3) |

TABLE 48

Compounds in Table 48 were prepared by the methods detailed in Examples 57, 63, and 562. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R | Obs. MS Ion | RT (Method) |
|---|---|---|---|---|
| 1306 | 5-{4-amino-5-[(3,3-difluoroazetidin-1-yl)methyl]pyrrolo[2,1-f][1,2,4]triazin-7-yl}-2-chloro-4-fluoro-N-[(3R,4S)-4-fluoro-1-(2-fluoro-2-methylpropanoyl)pyrrolidin-3-yl]-benzamide | | 586.3 | 1.4 (1) |

TABLE 48-continued

Compounds in Table 48 were prepared by the methods detailed in Examples 57, 63, and 562. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

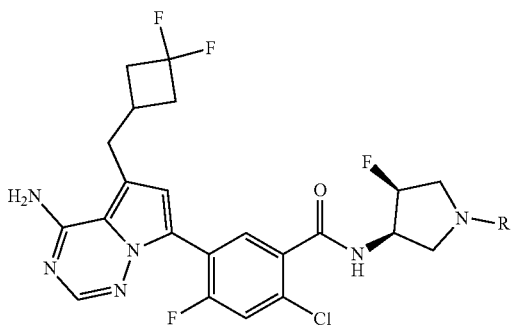

| Ex | Name | R | Obs. MS Ion | RT (Method) |
|---|---|---|---|---|
| 1307 | 5-{4-amino-5-[(3,3-difluoroazetidin-1-yl)methyl]pyrrolo[2,1-f][1,2,4]triazin-7-yl}-2-chloro-4-fluoro-N-[(3R,4S)-4-fluoro-1-(3,3,3-trifluoropropanoyl)pyrrolidin-3-yl]benzamide | | 608.0 | 1.66 (2) |
| 1308 | 5-{4-amino-5-[(3,3-difluoroazetidin-1-yl)methyl]pyrrolo[2,1-f][1,2,4]triazin-7-yl}-2-chloro-4-fluoro-N-[(3R,4S)-4-fluoro-1-(3,3,3-trifluoro-2,2-dimethylpropanoyl)pyrrolidin-3-yl]benzamide | | 636.3 | 1.54 (1) |
| 1309 | 5-{4-amino-5-[(3,3-difluoroazetidin-1-yl)methyl]pyrrolo[2,1-f][1,2,4]triazin-7-yl}-2-chloro-N-[(3R,4S)-1-(3,3-difluorocyclobutanecarbonyl)-4-fluoropyrrolidin-3-yl]-4-fluorobenzamide | | 616.3 | 1.39 (1) |
| 1310 | 5-{4-amino-5-[(3,3-difluoroazetidin-1-yl)methyl]pyrrolo[2,1-f][1,2,4]triazin-7-yl}-2-chloro-N-[(3R,4S)-1-(3,3-difluorocyclopentanecarbonyl)-4-fluoropyrrolidin-3-yl]-4-fluorobenzamide | | 630.3 | 1.81 (2) |
| 1311 | 5-{4-amino-5-[(3,3-difluoroazetidin-1-yl)methyl]pyrrolo[2,1-f][1,2,4]triazin-7-yl}-2-chloro-4-fluoro-N-[(3R,4S)-4-fluoro-1-(3-fluorocyclobutanecarbonyl)pyrrolidin-3-yl]benzamide | | 598.3 | 1.31 (1) |
| 1312 | 5-{4-amino-5-[(3,3-difluoroazetidin-1-yl)methyl]pyrrolo[2,1-f][1,2,4]triazin-7-yl}-2-chloro-4-fluoro-N-[(3R,4S)-4-fluoro-1-(3-fluorocyclobutanecarbonyl)pyrrolidin-3-yl]benzamide | | 598.1 | 1.68 (2) |
| 1313 | 5-{4-amino-5-[(3,3-difluoroazetidin-1-yl)methyl]pyrrolo[2,1-f][1,2,4]triazin-7-yl}-2-chloro-4-fluoro-N-[(3R,4S)-4-fluoro-1-[(2R)-3,3,3-trifluoro-2-hydroxy-2-methylpropanoyl]pyrrolidin-3-yl]benzamide | | 638.3 | 1.7 (2) |

TABLE 49

Compounds in Table 49 were prepared by the methods detailed in Example 562 and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 1314 | 3-[4-amino-5-(trifluoromethyl)pyrrolo-[2,1-f][1,2,4]triazin-7-yl]-5-fluoro-N-[(3R,4S)-4-fluoro-1-[(2R)-3,3,3-trifluoro-2-hydroxy-2-methyl-propanoyl]pyrrolidin-3-yl]benzamide | H | (structure: C(CF₃)(OH)(Me)) | 567.2 | 1.66 (1) |
| 1315 | 3-[4-amino-5-(trifluoromethyl)pyrrolo-[2,1-f][1,2,4]triazin-7-yl]-N-[(3R,4S)-1-(3,3-difluorocyclobutanecarbonyl)-4-fluoropyrrolidin-3-yl]-5-fluoro-benzamide | H | (3,3-difluorocyclobutyl) | 545.3 | 1.70 (1) |
| 1316 | 3-[4-amino-5-(trifluoromethyl)pyrrolo-[2,1-f][1,2,4]triazin-7-yl]-5-fluoro-N-[(3R,4S)-4-fluoro-1-[2-hydroxy-2-(trifluoromethyl)butanoyl]pyrrolidin-3-yl]benzamide | H | (C(CF₃)(OH)(Et)) | 581.4 | 1.78 (1) |
| 1317 | 5-[4-amino-5-(trifluoromethyl)pyrrolo-[2,1-f][1,2,4]triazin-7-yl]-3-fluoro-N-((3R,4S)-4-fluoro-1-{spiro[2.2]pentane-1-carbonyl}pyrrolidin-3-yl]-2-methyl-benzamide | Me | (spiro[2.2]pentyl) | 535.1 | 1.79 (1) |
| 1318 | 5-[4-amino-5-(trifluoromethyl)pyrrolo-[2,1-f][1,2,4]triazin-7-yl]-3-fluoro-N-[(3R,4S)-4-fluoro-1-(4,4,4-trifluoro-3-hydroxy-3-methylbutanoyl)pyrrolidin-3-yl]-2-methylbenzamide | Me | (CH₂C(Me)(OH)(CF₃)) | 595.1 | 1.77 (1) |
| 1319 | 5-[4-amino-5-(trifluoromethyl)pyrrolo-[2,1-f][1,2,4]triazin-7-yl]-3-fluoro-N-[(3R,4S)-4-fluoro-1-(3,3,3-trifluoro-2-methylpropanoyl)pyrrolidin-3-yl]-2-methylbenzamide | Me | (CH(CF₃)(Me)) | 565.1 | 1.83 (2) |
| 1320 | 5-[4-amino-5-(trifluoromethyl)pyrrolo-[2,1-f][1,2,4]triazin-7-yl]-3-fluoro-N-[(3R,4S)-4-fluoro-1-[4,4,4-trifluoro-3-(trifluoromethyl)butanoyl]pyrrolidin-3-yl]-2-methylbenzamide | Me | (CH₂CH(CF₃)₂) | 633.3 | 2.03 (2) |
| 1321 | 5-[4-amino-5-(trifluoromethyl)pyrrolo-[2,1-f][1,2,4]triazin-7-yl]-3-fluoro-N-[(3R,4S)-4-fluoro-1-[2-hydroxy-2-(trifluoromethyl)butanoyl]pyrrolidin-3-yl]-2-methylbenzamide | Me | (C(CF₃)(OH)(Et)) | 595.2 | 1.07 (1) |

TABLE 49-continued

Compounds in Table 49 were prepared by the methods detailed in Example 562 and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R¹ | R² | Obs. MS Ion | RT (Method) |
|---|---|---|---|---|---|
| 1322 | 5-[4-amino-5-(trifluoromethyl)pyrrolo-[2,1-f][1,2,4]triazin-7-yl]-3-fluoro-N-[(3R,4S)-4-fluoro-1-(pyridine-3-carbonyl)pyrrolidin-3-yl]-2-methyl-benzamide | Me | 3-pyridyl | 546.0 | 1.53 (2) |
| 1323 | 5-[4-amino-5-(trifluoromethyl)pyrrolo-[2,1-f][1,2,4]triazin-7-yl]-3-fluoro-N-[(3R,4S)-4-fluoro-1-(3-fluoropyridine-4-carbonyl)pyrrolidin-3-yl]-2-methyl-benzamide | Me | 3-fluoropyridin-4-yl | 564.3 | 1.68 (2) |
| 1324 | 5-[4-amino-5-(trifluoromethyl)pyrrolo-[2,1-f][1,2,4]triazin-7-yl]-3-fluoro-N-[(3R,4S)-4-fluoro-1-(5-fluoropyridine-3-carbonyl)pyrrolidin-3-yl]-2-methyl-benzamide | Me | 5-fluoropyridin-3-yl | 564.3 | 1.64 (1) |
| 1325 | 5-[4-amino-5-(trifluoromethyl)pyrrolo-[2,1-f][1,2,4]triazin-7-yl]-N-[(3R,4S)-1-(3,5-difluoropyridine-4-carbonyl)-4-fluoropyrrolidin-3-yl]-3-fluoro-2-methylbenzamide | Me | 3,5-difluoropyridin-4-yl | 582.3 | 1.75 (2) |
| 1326 | 5-[4-amino-5-(trifluoromethyl)pyrrolo-[2,1-f][1,2,4]triazin-7-yl]-2-chloro-3-fluoro-N-[(3R,4S)-4-fluoro-1-[2-hydroxy-2-(trifluoromethyl)butanoyl]-pyrrolidin-3-yl]benzamide | Cl | C(Et)(OH)(CF₃) | 615.2 | 1.91 (2) |
| 1327 | 5-[4-amino-5-(trifluoromethyl)pyrrolo-[2,1-f][1,2,4]triazin-7-yl]-2-chloro-3-fluoro-N-[(3R,4S)-4-fluoro-1-[(2R)-3,3,3-trifluoro-2-hydroxy-2-methyl-propanoyl]pyrrolidin-3-yl]benzamide | Cl | (2R)-C(Me)(OH)(CF₃) | 601.2 | 1.76 (1) |
| 1328 | 5-[4-amino-5-(trifluoromethyl)pyrrolo-[2,1-f][1,2,4]triazin-7-yl]-2-chloro-3-fluoro-N-[(3R,4S)-4-fluoro-1-(3,3,3-trifluoro-2-methylpropanoyl)pyrrolidin-3-yl]benzamide | Cl | CH(Me)(CF₃) | 585.3 | 1.80 (3) |

TABLE 49-continued

Compounds in Table 49 were prepared by the methods detailed in Example 562 and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

| Ex | Name | R[1] | R[2] | Obs. MS Ion | RT (Method) |
|---|---|---|---|---|---|
| 1329 | 5-[4-amino-5-(trifluoromethyl)pyrrolo-[2,1-f][1,2,4]triazin-7-yl]-2-chloro-3-fluoro-N-[(3R,4S)-4-fluoro-1-(3,3,3-trifluoro-2-methylpropanoyl)pyrrolidin-3-yl]benzamide | Cl | (Me, F₃C) | 585.1 | 1.80 (3) |
| 1330 | 5-[4-amino-5-(trifluoromethyl)pyrrolo-[2,1-f][1,2,4]triazin-7-yl]-2-chloro-3-fluoro-N-[(3R,4S)-4-fluoro-1-(4,4,4-trifluoro-3-methylbutanoyl)pyrrolidin-3-yl]benzamide | Cl | (Me, CF₃) | 599.1 | |
| 1331 | 5-[4-amino-5-(trifluoromethyl)pyrrolo-[2,1-f][1,2,4]triazin-7-yl]-2-chloro-3-fluoro-N-[(3R,4S)-4-fluoro-1-(4,4,4-trifluoro-3-methylbutanoyl)pyrrolidin-3-yl]benzamide | Cl | (Me, CF₃) | 599.1 | |
| 1332 | 5-[4-amino-5-(trifluoromethyl)pyrrolo-[2,1-f][1,2,4]triazin-7-yl]-2,3-difluoro-N-[(3R,4S)-4-fluoro-1-[(2R)-3,3,3-trifluoro-2-hydroxy-2-methyl-propanoyl]pyrrolidin-3-yl]benzamide | F | (CF₃, OH) | 585.1 | 1.72 (4) |
| 1333 | 5-[4-amino-5-(trifluoromethyl)pyrrolo-[2,1-f][1,2,4]triazin-7-yl]-N-[(3R,4S)-1-(3,3-difluorocyclopentanecarbonyl)-4-fluoropyrrolidin-3-yl]-2,3-difluoro-benzamide | F | (cyclopentyl, F, F) | 577.1 | 1.88 (4) |
| 1334 | 5-[4-amino-5-(trifluoromethyl)pyrrolo-[2,1-f][1,2,4]triazin-7-yl]-2,3-difluoro-N-[(3R,4S)-4-fluoro-1-(4,4,4-trifluoro-3-hydroxy-3-methylbutanoyl)pyrrolidin-3-yl]benzamide | F | (Me, OH, CF₃) | 599.1 | 1.78 (4) |
| 1335 | 5-[4-amino-5-(trifluoromethyl)pyrrolo-[2,1-f][1,2,4]triazin-7-yl]-2,3-difluoro-N-[(3R,4S)-4-fluoro-1-(3,3,3-trifluoro-2-methylpropanoyl)pyrrolidin-3-yl]-benzamide | F | (Me, F₃C) | 569.1 | 1.75 (3) |
| 1336 | 5-[4-amino-5-(trifluoromethyl)pyrrolo-[2,1-f][1,2,4]triazin-7-yl]-N-[(3R,4S)-1-(3,3-difluorocyclobutanecarbonyl)-4-fluoropyrrolidin-3-yl]-2,3-difluoro-benzamide | F | (cyclobutyl, F, F) | 563.3 | 1.76 (4) |
| 1337 | 5-[4-amino-5-(trifluoromethyl)pyrrolo-[2,1-f][1,2,4]triazin-7-yl]-2,3-difluoro-N-[(3R,4S)-4-fluoro-1-[2-hydroxy-2-(trifluoromethyl)butanoyl]pyrrolidin-3-yl]benzamide | F | (CF₃, OH, Et) | 599.0 | 1.88 (4) |

TABLE 49-continued

Compounds in Table 49 were prepared by the methods detailed in Example 562 and 567. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

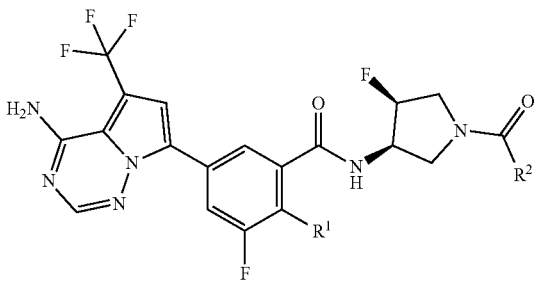

| Ex | Name | R[1] | R[2] | Obs. MS Ion | RT (Method) |
|---|---|---|---|---|---|
| 1338 | 5-[4-amino-5-(trifluoromethyl)pyrrolo-[2,1-f][1,2,4]triazin-7-yl]-N-[(3R,4S)-1-(3,3-difluorocyclobutanecarbonyl)-4-fluoropyrrolidin-3-yl]-2-ethyl-3-fluorobenzamide | Et | 3,3-difluorocyclobutyl | 573.0 | 1.84 (4) |

TABLE 49

NMR data for selected examples from Tables 36-49

| Ex | NMR |
|---|---|
| 572 | 1H NMR (500 MHz, DMSO-d6) δ 8.84-8.60 (m, 1H), 8.17 (d, J = 11.0 Hz, 1H), 8.12-7.95 (m, 1H), 7.86 (br d, J = 18.9 Hz, 1H), 7.68-7.29 (m, 6H), 5.48-5.12 (m, 1H), 4.91-4.54 (m, 1H), 4.05-3.40 (m, 7H), 2 exchangeable protons |
| 593 | 1H NMR (500 MHz, DMSO-d6) δ 8.70 (dd, J = 13.8, 7.4 Hz, 1H), 8.14 (s, 1H), 7.98-7.87 (m, 1H), 7.75 (s, 1H), 7.56 (s, 2H), 5.45-5.19 (m, 1H), 4.85-4.56 (m, 1H), 4.20-3.94 (m, 2H), 3.92 (d, J = 1.9 Hz, 3H), 3.84 (d, J = 6.4 Hz, 3H), 3.79-3.74 (m, 1H), 3.57-3.22 (m, 1H), 2 exchangeable protons |
| 596 | 1H NMR (500 MHz, DMSO-d6) δ 9.42-9.14 (m, 1H), 9.03-8.86 (m, 1H), 8.23-8.15 (m, 1H), 8.13 (s, 1H), 7.93 (s, 1H), 7.60 (d, J = 8.6 Hz, 1H), 7.11 (d, J = 4.7 Hz, 1H), 5.44-5.18 (m, 1H), 4.88-4.48 (m, 1H), 4.44-4.22 (m, 1H), 4.18-3.86 (m, 2H), 3.75 (br s, 1H), 3.00 (s, 1H), 2.96-2.76 (m, 1H), 2 exchangeable protons |
| 598 | 1H NMR (500 MHz, DMSO-d6) δ 8.81 (br s, 1H), 8.37 (s, 1H), 8.25-8.19 (m, 2H), 7.72 (br d, J = 8.9 Hz, 1H), 7.69 (s, 1H), 5.41-5.15 (m, 1H), 4.82-4.57 (m, 1H), 4.32-3.36 (m, 4H), 1.52-1.41 (m, 6H), 2 exchangeable protons |
| 599 | 1H NMR (500 MHz, DMSO-d6) δ 8.71 (br s, 1H), 8.35 (s, 1H), 8.23-8.17 (m, 2H), 7.71 (br d, J = 9.1 Hz, 1H), 7.67-7.60 (m, 1H), 5.42-5.07 (m, 1H), 4.85-4.51 (m, 1H), 4.33-3.41 (m, 4H), 1.63-1.47 (m, 6H), 2 exchangeable protons |
| 629 | 1H NMR (500 MHz, DMSO-d6) δ 9.11-9.00 (m, 1H), 8.33 (br d, J = 10.7 Hz, 1H), 8.23 (s, 1H), 8.08 (br s, 1H), 7.77 (br s, 1H), 5.48-5.07 (m, 1H), 4.83-4.50 (m, 1H), 4.18-3.26 (m, overlaps with water peak, 4H), 2.84-2.68 (m, 1H), 2.48-2.32 (m, 1H), 1.41 (br s, 3H), 3 exchangeable protons |
| 630 | 1H NMR (500 MHz, DMSO-d6) δ 9.01 (br dd, J = 14.0, 7.0 Hz, 1H), 8.32 (br d, J = 10.7 Hz, 1H), 8.22 (s, 1H), 8.08 (br s, 1H), 7.77 (br d, J = 3.7 Hz, 2H), 5.43-5.11 (m, 1H), 4.99-4.48 (m, 1H), 4.25-3.27 (m, 4H), 1.65-1.42 (m, 6H), 2 exchangeable protons |
| 631 | 1H NMR (500 MHz, DMSO-d6) δ 9.17-8.92 (m, 1H), 8.33 (br d, J = 10.7 Hz, 1H), 8.23 (s, 1H), 8.09 (br s, 1H), 7.78 (br s, 1H), 5.44-5.16 (m, 1H), 4.89-4.50 (m, 1H), 4.33-3.91 (m, 1H), 3.88-3.56 (m, 2H), 3.51-2.83 (m, 2H), 2.03-1.78 (m, 2H), 2 exchangeable protons |
| 632 | 1H NMR (500 MHz, DMSO-d6) δ 9.13-8.95 (m, 1H), 8.47-8.28 (m, 1H), 8.28-8.20 (m, 1H), 8.10 (br s, 1H), 7.78 (br d, J = 4.6 Hz, 1H), 5.45-5.16 (m, 1H), 4.90-4.52 (m, 1H), 4.34 (br s, 1H), 4.19-3.99 (m, 1H), 3.99-3.83 (m, 1H), 3.81-3.59 (m, 1H), 3.53-3.19 (m, 1H), 3.11-2.94 (m, 1H), 2.94-2.75 (m, 1H), 2 exchangeable protons |
| 645 | 1H NMR (500 MHz, DMSO-d6) δ 8.95-8.74 (m, 1H), 8.18 (d, J = 15.9 Hz, 1H), 8.05 (br t, J = 12.8 Hz, 1H), 7.90-7.75 (m, 1H), 7.70-7.57 (m, 1H), 7.56-7.51 (m, 1H), 7.51-7.41 (m, 1H), 7.39-7.25 (m, 2H), 5.50-5.16 (m, 1H), 4.92-4.53 (m, 1H), 4.02-3.14 (m, overlapping with water peak, 4H), 2.79-2.63 (m, 2H), 1.20-1.09 (m, 3H), 2 exchangeable protons |

TABLE 49-continued

NMR data for selected examples from Tables 36-49

| Ex | NMR |
|---|---|
| 646 | 1H NMR (500 MHz, DMSO-d6) δ 8.84 (br dd, J = 17.5, 6.9 Hz, 1H), 8.20 (s, 1H), 8.06 (br d, J = 12.2 Hz, 1H), 7.85 (br d, J = 5.8 Hz, 2H), 7.64 (d, J = 6.7 Hz, 2H), 5.42-5.16 (m, 1H), 4.78-4.45 (m, 1H), 4.02-3.41 (m, 3H), 3.34-3.14 (m, 1H), 2.78-2.68 (m, 2H), 2.23-2.07 (m, 2H), 2.06-1.95 (m, 1H), 1.17 (br t, J = 7.2 Hz, 3H), 0.96-0.79 (m, 6H), 2 exchangeable protons |
| 647 | 1H NMR (500 MHz, DMSO-d6) δ 8.88-8.77 (m, 1H), 8.20 (s, 1H), 8.17-8.02 (m, 1H), 7.86 (s, 1H), 7.65 (s, 1H), 5.38-5.12 (m, 1H), 4.69-4.45 (m, 1H), 4.43-4.26 (m, 1H), 4.04-3.45 (m, 2H), 3.35-3.16 (m, 1H), 2.78-2.69 (m, 2H), 1.34-1.27 (m, 6H), 1.17 (br t, J = 7.2 Hz, 3H), 3 exchangeable protons |
| 662 | 1H NMR (500 MHz, DMSO-d6) δ 8.81-8.68 (m, 1H), 8.17 (s, 1H), 8.03 (br d, J = 11.3 Hz, 1H), 7.86 (br s, 1H), 7.58 (br s, 1H), 5.47-5.13 (m, 1H), 4.86-4.43 (m, 1H), 4.05-3.56 (m, 4H), 2.85 (br d, J = 4.2 Hz, 1H), 2.73-2.54 (m, 1H), 2.46-2.31 (m, 1H), 2.29 (br s, 3H), 1.17-1.01 (m, 3H), 2 exchangeable protons |
| 663 | 1H NMR (500 MHz, DMSO-d6) δ 8.82 (br dd, J = 12.8, 7.0 Hz, 1H), 8.19 (s, 1H), 8.05 (br d, J = 11.3 Hz, 1H), 7.87 (br s, 1H), 7.63 (d, J = 4.3 Hz, 1H), 5.43-5.16 (m, 1H), 4.79-4.48 (m, 1H), 3.96-3.62 (m, 3H), 3.43-3.13 (m, 2H), 2.28 (br s, 3H), 2.22-2.01 (m, 4H), 1.98-1.82 (m, 1H), 1.74 (br d, J = 11.0 Hz, 1H), 2 exchangeable protons |
| 664 | 1H NMR (500 MHz, DMSO-d6) δ 8.95-8.75 (m, 1H), 8.25-8.19 (m, 1H), 8.08 (br dd, J = 10.8, 5.0 Hz, 1H), 7.92 (br d, J = 4.3 Hz, 1H), 7.67 (d, J = 4.3 Hz, 1H), 5.49-5.18 (m, 1H), 4.84-4.43 (m, 1H), 4.09-3.79 (m, 2H), 3.76-3.58 (m, 2H), 3.57-3.27 (m, 2H), 2.30 (s, 3H), 2 protons exchanged |
| 667 | 1H NMR (400 MHz, DMSO-d6) δ 8.87-8.73 (m, 1H), 8.22 (s, 1H), 8.09 (d, J = 11.6 Hz, 1H), 7.93 (s, 1H), 7.69 (d, J = 3.4 Hz, 1H), 7.09-7.00 (m, 1H), 5.42-5.16 (m, 1H), 4.69-4.53 (m, 1H), 4.43-3.36 (m, 4H merge with water), 2.29 (s, 3H), 1.53 (s, 3H) |
| 668 | 1H NMR (400 MHz, DMSO-d6) δ 8.88-8.74 (m, 1H), 8.21 (s, 1H), 8.09 (br d, J = 11.4 Hz, 1H), 7.92 (s, 1H), 7.68 (d, J = 5.2 Hz, 1H), 5.45-5.17 (m, 1H), 4.83-4.52 (m, 1H), 4.11-3.18 (m, 4H), 2.78-2.59 (m, 1H), 2.29 (s, 3H), 1.09-0.94 (m, 6H) |
| 670 | 1H NMR (400 MHz, DMSO-d6) δ 8.89-8.73 (m, 1H), 8.21 (d, J = 9.3 Hz, 1H), 8.08 (br t, J = 11.6 Hz, 1H), 7.97-7.85 (m, 1H), 7.72-7.58 (m, 3H), 7.30 (t, J = 8.9 Hz, 2H), 5.48-5.17 (m, 1H), 4.88-4.50 (m, 1H), 4.11-3.51 (m, 4H), 2.28 (br d, J = 16.5 Hz, 3H) |
| 677 | 1H NMR (400 MHz, DMSO-d6) δ 8.89-8.76 (m, 1H), 8.22 (s, 1H), 8.09 (ddd, J = 11.3, 4.5, 1.7 Hz, 1H), 7.92 (dd, J = 4.2, 1.6 Hz, 1H), 7.68 (d, J = 6.1 Hz, 1H), 5.46-5.15 (m, 1H), 4.83-4.53 (m, 1H), 3.96-3.57 (m, 3H merge with water), 3.48-3.26 (m, 1H), 3.23-3.09 (m, 1H), 2.88-2.71 (m, 4H), 2.30 (s, 3H) |
| 680 | 1H NMR (500 MHz, DMSO-d6) δ 8.66 (br dd, J = 14.2, 7.5 Hz, 1H), 8.20 (s, 1H), 8.17 (br d, J = 13.1 Hz, 1H), 8.10 (br d, J = 11.9 Hz, 1H), 7.63 (d, J = 3.7 Hz, 1H), 5.42-5.14 (m, 1H), 4.85-4.50 (m, 1H), 3.96 (overlapping br d, J = 5.8 Hz, 3H), 4.03-3.19 (overlapping m, 4H), 2.23-2.07 (m, 2H), 2.07-1.95 (m, 1H), 0.92 (dt, J = 6.6, 3.4 Hz, 6H), 2 exchangeable protons |
| 681 | 1H NMR (500 MHz, DMSO-d6) δ 8.83-8.60 (m, 1H), 8.24-8.11 (m, 2H), 8.11-7.99 (m, 1H), 7.67-7.58 (m, 1H), 7.53 (br s, 1H), 7.51-7.44 (m, 1H), 7.33-7.33 (m, 1H), 5.53-5.12 (m, 1H), 4.86-4.61 (m, 1H), 3.98-3.90 (overlapping m, 3H) 4.07-3.41 (overlapping m, partially suppressed, 4H), 2 exchangeable protons |
| 682 | 1H NMR (500 MHz, DMSO-d6) δ 8.65 (br dd, J = 13.3, 7.5 Hz, 1H), 8.19 (s, 1H), 8.16 (br d, J = 13.4 Hz, 1H), 8.08 (br d, J = 9.2 Hz, 1H), 7.62 (br d, J = 3.4 Hz, 1H), 5.39-5.12 (m, 1H), 4.87-4.49 (m, 1H), 3.95 (br d, J = 3.7 Hz, 3H), 3.91-3.10 (m, 5H), 2.26-2.03 (m, 4H), 1.96-1.85 (m, 1H), 1.76 (br s, 1H), 2 exchangeable protons |
| 686 | 1H NMR (400 MHz, DMSO-d6) δ 8.75-8.61 (m, 1H), 8.24-8.15 (m, 2H), 8.10 (dd, J = 11.0, 1.0 Hz, 1H), 7.65 (d, J = 3.1 Hz, 1H), 7.07 (br d, J = 5.9 Hz, 1H), 5.39-5.15 (m, 1H), 4.77-4.55 (m, 1H), 4.49-4.25 (m, 1H), 4.11-3.31 (m, 6H), 1.53 (s, 3H) |
| 687 | 1H NMR (500 MHz, DMSO-d6) δ 8.66 (br dd, J = 14.8, 7.5 Hz, 1H), 8.19 (s, 1H), 8.17 (br d, J = 13.4 Hz, 1H), 8.09 (br d, J = 9.5 Hz, 1H), 7.63 (br d, J = 4.0 Hz, 1H), 5.39-5.19 (m, 1H), 5.19-4.89 (m, 1H), 4.88-4.53 (m, 1H), 3.95 (br d, J = 4.3 Hz, 3H), 3.92-3.16 (m, 4H), 2.78-2.46 (m, 3H), 2.43-2.36 (m, 1H), 2.31-2.12 (m, 1H), 2 exchangeable protons |
| 688 | 1H NMR (500 MHz, DMSO-d6) δ 8.70 (br dd, J = 19.5, 7.0 Hz, 1H), 8.18 (s, 1H), 8.14 (br s, 1H), 8.06 (br s, 1H), 7.61 (s, 1H), 5.45-5.16 (m, 1H), 4.90-4.54 (m, 1H), 4.32-3.97 (m, 1H), 3.94 (s, 3H), 3.91-3.57 (m, 1H), 3.44 (br s, 2H), 1.50-0.91 (m, 4H), 2 exchangeable protons |
| 689 | 1H NMR (500 MHz, DMSO-d6) δ 8.67 (br dd, J = 16.6, 7.8 Hz, 1H), 8.17 (s, 1H), 8.15 (br d, J = 13.1 Hz, 1H), 8.11-8.03 (m, 1H), 7.60 (br d, J = 4.3 Hz, 1H), 5.46-5.14 (m, 1H), 4.85-4.54 (m, 1H), 4.10-3.78 (overlapping m, 1H), 3.94 (br d, J = 9.5 Hz, 3H), 3.75-3.18 (m, 3H), 2.69-2.55 (m, 1H), 2.04 (br d, J = 8.9 Hz, 2H), 1.96-1.69 (m, 4H), 1.65-1.45 (m, 2H), 2 exchangeable protons |
| 690 | 1H NMR (400 MHz, DMSO-d6) δ 8.94 (d, J = 16.3 Hz, 1H), 8.73 (dd, J = 14.0, 7.6 Hz, 1H), 8.24-8.14 (m, 2H), 8.10 (br d, J = 8.0 Hz, 1H), 7.64 (d, J = 3.3 Hz, 1H), 5.48-5.20 (m, 1H), 4.91-4.55 (m, 1H), 4.24-2.91 (m, 9H merge with water) |
| 701 | 1H NMR (500 MHz, DMSO-d6) δ 8.98-8.83 (m, 1H), 8.20 (s, 1H), 8.15 (br s, 1H), 8.03 (s, 1H), 7.63 (d, J = 3.4 Hz, 1H), 5.41-5.14 (m, 1H), 4.90-4.46 (m, 1H), 4.11-3.50 (m, 3H), 3.47-3.17 (m, 1H), 2.92-2.78 (m, 1H), 2.75-2.57 (m, 1H), 2.45 (s, 3H), 2.42-2.16 (m, 1H), 1.15-1.07 (m, 3H), 2 exchangeable protons |
| 702 | 1H NMR (500 MHz, DMSO-d6) δ 9.02-8.90 (m, 1H), 8.18 (s, 1H), 8.15-8.10 (m, 1H), 8.00 (br s, 2H), 7.60 (d, J = 2.4 Hz, 2H), 5.44-5.13 (m, 1H), 4.87-4.51 (m, 1H), 4.23-3.84 (m, 2H), 3.82-3.56 (m, 1H), 3.39-2.87 (m, 3H), 2.44 (s, 3H), 2 protons exchanged |
| 709 | 1H NMR (400 MHz, DMSO-d6) δ 8.97-8.85 (m, 1H), 8.21 (s, 1H), 8.15 (dd, J = 3.6, 2.0 Hz, 1H), 8.04 (t, J = 2.0 Hz, 1H), 7.63 (d, J = 2.6 Hz, 1H), 5.44-5.15 (m, 1H), 4.83-4.52 (m, |

TABLE 49-continued

NMR data for selected examples from Tables 36-49

| Ex | NMR |
|---|---|
| | 1H), 4.42-4.26 (m, 1H), 4.16-3.59 (m, 3H merge with water), 3.50-3.24 (m, 1H), 3.10-2.76 (m, 2H), 2.45 (s, 3H) |
| 711 | 1H NMR (500 MHz, DMSO-d6) δ 9.00-8.85 (m, 1H), 8.19 (s, 1H), 8.17-8.11 (m, 1H), 8.02 (br s, 1H), 7.62 (s, 1H), 5.43-5.14 (m, 1H), 4.83-4.47 (m, 1H), 4.16-3.56 (m, 4H), 3.35-2.66 (m, 2H), 1.42 (s, 3H), 2 exchangeable protons |
| 719 | 1H NMR (500 MHz, DMSO-d6) δ 9.31-9.21 (m, 1H), 8.12 (s, 1H), 7.94 (q, J = 7.3 Hz, 1H), 7.40-7.34 (m, 1H), 7.34 (s, 1H), 5.39-5.06 (m, 1H), 4.81-4.53 (m, 1H), 4.01-3.75 (m, 2H), 3.74-3.49 (m, 1H), 3.44-3.11 (m, 1H), 2.24-2.07 (m, 2H), 2.06-1.96 (m, 1H), 0.94-0.88 (m, 6H), 2 exchangeable protons |
| 720 | 1H NMR (400 MHz, DMSO-d6) δ 9.38-9.24 (m, 1H), 8.89 (d, J = 12.7 Hz, 1H), 8.16-8.07 (m, 1H), 8.00-7.88 (m, 1H), 7.41-7.28 (m, 2H), 5.45-5.15 (m, 1H), 4.90-4.52 (m, 1H), 4.24-3.83 (m, 2H), 3.76 (s, 1H), 3.14-2.89 (m, 2H). 1 proton under water peak. |
| 721 | 1H NMR (500 MHz, DMSO-d6) δ 9.41-9.14 (m, 1H), 8.11 (s, 1H), 8.02-7.87 (m, 1H), 7.41-7.26 (m, 2H), 5.44-4.94 (m, 1H), 4.84-4.48 (m, 1H), 4.24-3.79 (m, 2H), 3.77-3.12 (m, 2H), 2.94-2.66 (m, 1H), 2.48-2.29 (m, 1H), 1.41 (s, 3H), 3 exchangeable proton |
| 722 | 1H NMR (500 MHz, DMSO-d6) δ 9.39-9.17 (m, 1H), 8.11 (s, 1H), 7.98-7.86 (m, 1H), 7.38-7.34 (m, 1H), 7.34 (s, 1H), 7.22-7.06 (m, 1H), 5.35-5.14 (m, 1H), 4.74-4.53 (m, 1H), 4.46-3.26 (m, 4H), 1.52 (s, 3H), 2 exchangeable protons |
| 734 | 1H NMR (500 MHz, DMSO-d6) δ 9.20-8.95 (m, 1H), 8.11 (s, 1H), 7.80 (br t, J = 7.5 Hz, 1H), 7.28 (br s, 2H), 6.45-6.31 (m, 1H), 5.51-5.13 (m, 1H), 4.76-4.45 (m, 1H), 4.20-3.43 (m, 3H), 3.33-3.14 (m, 1H), 2.84-2.72 (m, 1H), 2.68 (q, J = 7.4 Hz, 2H), 2.49-2.30 (m, 1H), 1.41 (br s, 3H), 1.22 (br t, J = 7.3 Hz, 3H), 2 exchangeable protons |
| 735 | 1H NMR (500 MHz, DMSO-d6) δ 9.22-8.95 (m, 1H), 8.10 (s, 1H), 7.79 (br t, J = 6.1 Hz, 1H), 7.32-7.24 (m, 2H), 5.45-5.15 (m, 1H), 4.86-4.42 (m, 1H), 4.09-3.09 (m, 6H), 2.74-2.61 (m, 2H), 1.22 (br t, J = 7.5 Hz, 3H), 2 exchangeable protons |
| 736 | 1H NMR (500 MHz, DMSO-d6) δ 9.14-9.01 (m, 1H), 8.10 (s, 1H), 7.84-7.74 (m, 1H), 7.31-7.23 (m, 2H), 5.46-5.12 (m, 1H), 4.89-4.50 (m, 1H), 4.42-4.21 (m, 1H), 4.18-3.47 (m, 3H), 3.34-3.15 (m, 1H), 3.09-2.93 (m, 1H), 2.91-2.72 (m, 1H), 2.72-2.62 (m, 2H), 1.21 (td, J = 7.5, 2.4 Hz, 3H), 2 exchangeable protons |
| 745 | 1H NMR (500 MHz, DMSO-d6) δ 9.14-8.95 (m, 1H), 8.08 (s, 1H), 7.73 (br t, J = 7.6 Hz, 1H), 7.27 (s, 1H), 7.23 (br d, J = 7.6 Hz, 1H), 5.39-5.08 (m, 1H), 4.76-4.46 (m, 1H), 4.46-4.20 (m, 1H), 4.11-3.62 (m, 2H), 3.54-3.26 (m, 1H), 2.33 (s, 3H), 2.22-1.99 (m, 1H), 1.84-1.59 (m, 1H), 0.97-0.78 (m, 3H), 3 exchangeable protons |
| 746 | 1H NMR (500 MHz, DMSO-d6) δ 9.18-8.85 (m, 1H), 8.10 (s, 1H), 7.75 (br t, J = 7.8 Hz, 1H), 7.27 (s, 1H), 7.24 (br d, J = 7.6 Hz, 1H), 5.52-5.09 (m, 1H), 4.88-4.47 (m, 1H), 4.18-3.44 (m, 3H), 3.32-3.12 (m, 1H), 2.84-2.65 (m, 1H), 2.48-2.40 (m, 1H), 2.34 (s, 3H), 1.41 (s, 3H), 3 exchangeable protons |
| 747 | 1H NMR (500 MHz, DMSO-d6) δ 9.08 (br dd, J = 18.9, 7.3 Hz, 1H), 8.10 (s, 1H), 7.84-7.62 (m, 1H), 7.28 (s, 1H), 7.25 (br d, J = 7.9 Hz, 1H), 5.52-5.06 (m, 1H), 4.94-4.56 (m, 1H), 4.31-3.50 (m, 3H), 3.53-3.10 (m, partially under water peak, 1H), 2.35 (s, 3H), 1.48-1.05 (m, 4H), 3 exchangeable protons |
| 748 | 1H NMR (500 MHz, DMSO-d6) δ 9.15-8.92 (m, 1H), 8.15-8.04 (m, 1H), 7.83-7.68 (m, 1H), 7.28 (s, 1H), 7.27-7.14 (m, 1H), 5.41-5.06 (m, 1H), 4.80-4.51 (m, 1H), 3,96-3.17 (m, 4H), 2.35 (s, 3H), 2.22-2.05 (m, 2H), 2.05-1.94 (m, 1H), 0.91 (dt, J = 6.5, 4.3 Hz, 6H), 2 exchangeable protons |
| 759 | 1H NMR (400 MHz, DMSO-d6) δ 8.97-8.85 (m, 1H), 8.21 (s, 1H), 8.15 (dd, J = 3.6, 2.0 Hz, 1H), 8.04 (t, J = 2.0 Hz, 1H), 7.63 (d, J = 2.6 Hz, 1H), 5.44-5.15 (m, 1H), 4.83-4.52 (m, 1H), 4.42-4.26 (m, 1H), 4.16-3.59 (m, 3H merge with water), 3.50-3.24 (m, 1H), 3.10-2.76 (m, 2H), 2.45 (s, 3H) |
| 763 | 1H NMR (500 MHz, DMSO-d6) δ 8.79 (br d, J = 6.7 Hz, 1H), 8.10 (s, 1H), 7.91 (br s, 1H), 7.66 (br s, 1H), 7.42 (br t, J = 7.3 Hz, 1H), 7.35 (s, 1H), 5.44-5.04 (m, 1H), 4.85-4.49 (m, 1H), 3.91-3.63 (m, partially suppressed, 4H), 3.55-3.31 (m, 1H), 3.30-3.20 (m, 1H), 2.23-2.01 (m, 4H), 1.99-1.83 (m, 1H), 1.74 (br d, J = 9.5 Hz, 1H), 2 exchangeable protons |
| 764 | 1H NMR (500 MHz, DMSO-d6) δ 8.84 (br d, J = 7.0 Hz, 1H), 8.06 (s, 1H), 7.89 (br s, 1H), 7.66 (br s, 1H), 7.47-7.37 (m, 1H), 7.33 (s, 1H), 5.36-5.11 (m, 1H), 4.91-4.46 (m, 1H), 3.98-3.13 (m, overlaps with water peak, 4H), 2.22-2.05 (m, 2H), 2.03-1.89 (m, 1H), 0.94-0.77 (m, 6H), 2 exchangeable protons |
| 771 | 1H NMR (500 MHz, DMSO-d6) δ 8.65 (br d, J = 6.3 Hz, 1H), 8.08 (s, 1H), 7.92 (br s, 1H), 7.68 (br s, 1H), 7.42 (br t, J = 7.7 Hz, 1H), 7.32 (s, 1H), 5.40-5.18 (m, 1H), 5.17-4.84 (m, 1H), 4.77-4.42 (m, 1H), 3.93-3.22 (m, overlaps with water peak, 4H), 3.02-2.65 (m, 1H), 2.48-2.32 (m, 2H), 2.32-2.14 (m, 1H), 2 exchangeable protons |
| 773 | 1H NMR (500 MHz, DMSO-d6) δ 8.90-8.73 (m, 1H), 8.11 (s, 1H), 7.93 (br s, 1H), 7.67 (br s, 1H), 7.47-7.38 (m, 1H), 7.35 (s, 1H), 5.46-5.11 (m, 1H), 4.90-4.54 (m, 1H), 4.32-3.60 (m, 3H), 3.50-3.24 (m, 1H), 3.12-2.74 (m, 1H), 2.03-1.77 (m, 2H), 2 exchangeable protons |
| 774 | 1H NMR (500 MHz, DMSO-d6) d 8.80 (br t, J = 7.6 Hz, 1H), 8.09 (s, 1H), 7.91 (br t, J = 6.9 Hz, 1H), 7.67 (q, J = 6.1 Hz, 1H), 7.42 (br t, J = 7.6 Hz, 1H), 7.35 (s, 1H), 7.21 (br d, J = 3.7 Hz, 1H), 5.35-5.13 (m, 1H), 4.69-4.51 (m, 1H), 4.46-4.25 (m, 1H), 4.04-3.12 (m, 3H), 1.52 (s, 3H) |
| 775 | 1H NMR (500 MHz, DMSO-d6) δ 8.85-8.71 (m, 1H), 8.17-8.09 (m, 1H), 8.05 (br t, J = 7.5 Hz, 1H), 7.58 (br t, J = 10.1 Hz, 1H), 7.38 (s, 2H), 5.45-5.10 (m, 1H), 4.84-4.49 (m, 1H), 4.08-3.15 (m, 6H), 2 exchangeable protons |

TABLE 49-continued

NMR data for selected examples from Tables 36-49

| Ex | NMR |
|---|---|
| 776 | 1H NMR (500 MHz, DMSO-d6) δ 8.79-8.65 (m, 1H), 8.12 (s, 1H), 8.10-8.02 (m, 1H), 7.58 (br t, J = 10.1 Hz, 1H), 7.38 (s, 1H), 5.39-5.08 (m, 1H), 4.71-4.46 (m, 1H), 4.43-4.22 (m, 1H), 4.06-3.54 (m, 2H), 1.32-1.26 (m, 6H), 3 exchangeable protons |
| 777 | 1H NMR (500 MHz, DMSO-d6) δ 8.84-8.69 (m, 1H), 8.11 (s, 1H), 8.08-8.00 (m, 1H), 7.57 (br t, J = 9.0 Hz, 2H), 7.37 (s, 2H), 5.39-5.12 (m, 1H), 4.81-4.46 (m, 1H), 4.01-3.12 (m, 4H), 2.27-1.89 (m, 3H), 0.90 (s, 6H), 2 exchangeable protons |
| 778 | 1H NMR (500 MHz, DMSO-d6) δ 8.72 (br dd, J = 15.6, 7.0 Hz, 1H), 8.11 (s, 1H), 8.08-7.99 (m, 1H), 7.57 (br t, J = 10.1 Hz, 1H), 7.37 (s, 1H), 5.40-4.83 (m, 2H), 4.77-4.47 (m, 1H), 3.98-3.40 (m, 3H), 3.38-2.65 (m, partially suppressed, 3H), 2.44-2.32 (m, 2H), 2.31-2.16 (m, 1H), 2 exchangeable protons |
| 783 | 1H NMR (400 MHz, DMSO-d6) δ 8.76 (dd, J = 13.2, 7.5 Hz, 1H), 8.13 (s, 1H), 8.06 (t, J = 8.0 Hz, 1H), 7.65-7.56 (m, 1H), 7.39 (s, 1H), 5.46-5.16 (m, 1H), 4.84-4.51 (m, 1H), 4.43-4.24 (m, 1H), 4.16-3.42 (m, 4H), 3.10-2.75 (m, 2H). |
| 784 | 1H NMR (400 MHz, DMSO-d6) δ 8.97-8.86 (m, 1H), 8.79 (dd, J = 18.4, 7.4 Hz, 1H), 8.13 (s, 1H), 8.06 (td, J = 8.0, 1.9 Hz, 1H), 7.61 (t, J = 10.2 Hz, 1H), 7.39 (s, 1H), 5.47-5.15 (m, 1H), 4.86-4.51 (m, 1H), 4.22-3.85 (m, 2H), 3.82-3.45 (m, 2H), 3.19-2.88 (m, 2H) |
| 790 | 1H NMR (500 MHz, DMSO-d6) δ 8.73 (br dd, J = 19.1, 6.9 Hz, 1H), 8.12 (s, 1H), 8.05 (br d, J = 6.7 Hz, 1H), 7.57 (br t, J = 10.1 Hz, 1H), 7.37 (s, 1H), 7.08 (br d, J = 4.9 Hz, 1H), 5.36-5.13 (m, 1H), 4.72-4.51 (m, 1H), 4.45-4.23 (m, 1H), 4.06-3.56 (m, 2H), 3.40-3.11 (m, 1H), 1.52 (s, 3H) |
| 791 | 1H NMR (500 MHz, DMSO-d6) δ 8.54 (br dd, J = 11.2, 7.4 Hz, 1H), 8.09 (s, 1H), 7.79 (br d, J = 7.0 Hz, 1H), 7.39-7.19 (m, 2H), 5.41-5.07 (m, 1H), 4.79-4.31 (m, 1H), 3.90-3.07 (m, overlaps with water peak, 4H), 2.45 (s, 3H), 2.25-2.02 (m, 4H), 1.99-1.85 (m, 1H), 1.78 (br dd, J = 8.3, 5.0 Hz, 1H), 2 exchangeable protons |
| 792 | 1H NMR (500 MHz, DMSO-d6) δ 8.87-8.60 (m, 1H), 8.08 (br d, J = 11.6 Hz, 1H), 7.81-7.66 (m, 1H), 7.66-7.50 (m, 2H), 7.38-7.20 (m, 4H), 5.44-5.08 (m, 1H), 4.85-4.47 (m, 1H), 4.07-3.44 (m, overlaps with water peak, 4H), 2.47-2.33 (m, 3H), 2 exchangeable protons |
| 793 | 1H NMR (500 MHz, DMSO-d6) δ 8.67 (br dd, J = 18.8, 7.2 Hz, 1H), 8.11 (s, 1H), 7.78 (d, J = 7.3 Hz, 1H), 7.36-7.29 (m, 2H), 5.41-5.10 (m, 1H), 4.82-4.39 (m, 1H), 4.04-3.40 (m, 3H), 3.32-3.14 (m, 1H), 2.76-2.59 (m, 1H), 2.44 (d, J = 3.7 Hz, 3H), 1.06-0.96 (m, 6H), 2 exchangeable protons |
| 794 | 1H NMR (500 MHz, DMSO-d6) δ 8.67 (br dd, J = 15.4, 7.2 Hz, 1H), 8.11 (s, 1H), 7.78 (br d, J = 7.0 Hz, 1H), 7.37-7.29 (m, 2H), 5.41-5.02 (m, 1H), 4.84-4.44 (m, 1H), 4.00-3.40 (m, 3H), 3.37-3.13 (m, 1H), 2.44 (d, J = 2.7 Hz, 3H), 2.23-2.05 (m, 2H), 2.05-1.93 (m, 1H), 0.96-0.83 (m, 6H), 2 exchangeable protons |
| 799 | 1H NMR (400 MHz, DMSO-d6) δ 8.77-8.64 (m, 1H), 8.11 (s, 1H), 7.78 (dd, J = 7.4, 2.8 Hz, 1H), 7.33 (t, J = 5.6 Hz, 2H), 5.46-5.15 (m, 1H), 4.79-4.49 (m, 1H), 4.43-3.59 (m, 4H merge with water), 3.50-3.24 (m, 1H), 3.09-2.96 (m, 1H), 2.92-2.76 (m, 1H), 2.44 (d, J = 1.3 Hz, 3H) |
| 802 | 1H NMR (400 MHz, DMSO-d6) δ 8.99-8.87 (m, 1H), 8.80-8.63 (m, 1H), 8.11 (s, 1H), 7.78 (dd, J = 7.4, 3.9 Hz, 1H), 7.33 (t, J = 5.6 Hz, 2H), 5.47-5.16 (m, 1H), 4.82-4.51 (m, 1H), 4.17-2.87 (m, 6H), 2.44 (s, 3H) |
| 807 | 1H NMR (500 MHz, DMSO-d6) δ 8.72-8.56 (m, 1H), 8.09 (s, 1H), 7.80 (br d, J = 7.2 Hz, 1H), 7.38-7.21 (m, 3H), 5.44-5.15 (m, 1H), 4.96-4.47 (m, 1H), 4.26-3.45 (m, 4H), 3.08-2.78 (m, 1H), 2.45 (br d, J = 4.1 Hz, 3H), 1.94 (dt, J = 12.9, 6.2 Hz, 1H), 1.89-1.77 (m, 1H), 2 exchangeable protons |
| 838 | 1H NMR (500 MHz, DMSO-d6) δ 9.07-8.92 (m, 1H), 8.29-8.20 (m, 2H), 8.04 (br s, 2H), 7.76 (s, 3H), 5.71-5.51 (m, 2H), 5.46-5.18 (m, 1H), 4.84-4.56 (m, 1H), 4.29-3.59 (m, 4H), 4.32-3.39 (m, 2H), 1.54-0.96 (m, 4H), 2 exchangeable protons |
| 842 | 1H NMR (500 MHz, DMSO-d6) δ 8.90-8.70 (m, 1H), 8.03 (d, J = 10.7 Hz, 1H), 7.79 (td, J = 7.4, 3.8 Hz, 1H), 7.75-7.64 (m, 1H), 7.53-7.48 (m, 1H), 7.43-7.16 (m, 3H), 5.39-5.13 (m, 1H), 4.78-4.43 (m, 1H), 4.12-3.92 (m, 2H), 3.78-3.44 (m, 2H), 2.49-2.42 (m, 3H), 2.42-2.34 (m, 3H), 2 exchangeable protons |
| 856 | 1H NMR (500 MHz, DMSO-d6) δ 8.64-8.53 (m, 1H), 8.09 (s, 1H), 7.80 (br d, J = 7.2 Hz, 1H), 7.34-7.24 (m, 2H), 5.42-5.17 (m, 1H), 4.74-4.49 (m, 1H), 4.15-3.40 (m, 4H), 3.36-3.30 (m, 2H merge with water), 2.84-2.67 (m, 1H), 2.45 (s, 3H), 1.42 (s, 3H) |
| 857 | 1H NMR (500 MHz, DMSO-d6) δ 8.75-8.60 (m, 1H), 8.11 (s, 1H), 7.79 (br d, J = 7.3 Hz, 1H), 7.37-7.28 (m, 2H), 5.40-5.12 (m, 1H), 4.72-4.46 (m, 1H), 4.43-4.22 (m, 1H), 4.10-3.59 (m, 3H), 2.44 (s, 3H), 2.23-1.99 (m, 1H), 1.86-1.67 (m, 1H), 0.98-0.78 (m, 3H) |
| 858 | 1H NMR (500 MHz, DMSO-d6) δ 8.10 (s, 1H), 7.81 (br d, J = 7.3 Hz, 1H), 7.36-7.26 (m, 2H), 5.44-5.16 (m, 1H), 4.81-4.56 (m, 1H), 4.21-3.21 (m, 5H), 2.46 (d, J = 2.5 Hz, 3H), 1.28 (td, J = 6.8, 2.4 Hz, 3H) |
| 859 | 1H NMR (500 MHz, CD3OD) δ 8.03 (s, 1H), 8.00 (dd, J = 7.3, 1.3 Hz, 1H), 7.28 (s, 1H), 7.23 (dd, J = 11.4, 4.2 Hz, 1H), 5.43-5.23 (m, 1H), 4.84-4.69 (m, 1H), 4.22-3.20 (m, 5H merge with MeOH), 2.52 (d, J = 4.2 Hz, 3H), 2.46-1.85 (m, 6H). |
| 860 | 1H NMR (500 MHz, CD3OD) δ 8.03 (s, 1H), 8.00 (dd, J = 7.3, 1.3 Hz, 1H), 7.28 (s, 1H), 7.23 (dd, J = 11.4, 4.2 Hz, 1H), 5.43-5.23 (m, 1H), 4.84-4.69 (m, 1H), 4.22-3.20 (m, 5H merge with MeOH), 2.52 (d, J = 4.2 Hz, 3H), 2.46-1.85 (m, 6H). |
| 861 | 1H NMR (400 MHz, DMSO-d6) δ 8.78-8.61 (m, 1H), 8.11 (s, 1H), 7.79 (dd, J = 7.1, 5.7 Hz, 1H), 7.37-7.27 (m, 2H), 5.45-5.15 (m, 1H), 4.87-4.53 (m, 1H), 4.27-4.08 (m, 1H), 3.99-3.27 (m, 3H merge with water), 3.14-2.96 (m, 1H), 2.45 (d, J = 4.8 Hz, 3H), 1.99-1.79 (m, 2H). |
| 862 | 1H NMR (400 MHz, DMSO-d6) δ 8.78-8.61 (m, 1H), 8.11 (s, 1H), 7.79 (dd, J = 7.1, 5.7 Hz, 1H), 7.37-7.27 (m, 2H), 5.45-5.15 (m, 1H), 4.87-4.53 (m, 1H), 4.27-4.08 (m, |

TABLE 49-continued

NMR data for selected examples from Tables 36-49

| Ex | NMR |
|---|---|
| | 1H), 3.99-3.27 (m, 3H merge with water), 3.14-2.96 (m, 1H), 2.45 (d, J = 4.8 Hz, 3H), 1.99-1.79 (m, 2H). |
| 863 | 1H NMR (500 MHz, DMSO-d6) δ 8.77-8.64 (m, 1H), 8.09 (s, 1H), 7.77 (br d, J = 6.7 Hz, 1H), 7.38-7.27 (m, 2H), 5.41-5.17 (m, 1H), 4.81-4.47 (m, 1H), 4.34-3.29 (m, 4H), 2.43 (br s, 3H), 1.88-1.70 (m, 3H) |
| 864 | 1H NMR (500 MHz, DMSO-d6) δ 8.80-8.67 (m, 1H), 8.15-8.07 (m, 3H), 7.87-7.74 (m, 1H), 7.39-7.27 (m, 2H), 5.45-5.23 (m, 1H), 4.84-4.54 (m, 1H), 4.30-3.20 (m, 4H), 2.45 (br d, J = 15.3 Hz, 3H) |
| 865 | 1H NMR (500 MHz, DMSO-d6) δ 9.34 (br t, J = 4.1 Hz, 1H), 8.82-8.68 (m, 1H), 8.10 (br d, J = 10.4 Hz, 1H), 8.01 (br d, J = 8.8 Hz, 1H), 7.91-7.83 (m, 1H), 7.82-7.73 (m, 1H), 7.36-7.25 (m, 2H), 5.47-5.22 (m, 1H), 4.86-4.57 (m, 1H), 4.25-3.40 (m, 4H merge with water), 2.44 (br d, J = 16.5 Hz, 3H) |
| 866 | 1H NMR (500 MHz, DMSO-d6) δ 8.81-8.70 (m, 1H), 8.11 (d, J = 8.8 Hz, 1H), 7.91 (dd, J = 8.6, 1.9 Hz, 1H), 7.84-7.70 (m, 2H), 7.37-7.26 (m, 2H), 5.44-5.22 (m, 1H), 4.84-4.58 (m, 1H), 4.26-3.40 (m, 4H merge with water), 2.69 (d, J = 5.5 Hz, 3H), 2.44 (d, J = 15.4 Hz, 3H) |
| 867 | 1H NMR (400 MHz, DMSO-d6) δ 8.45-8.29 (m, 1H), 8.19 (dd, J = 9.8, 8.8 Hz, 1H), 8.11 (d, J = 0.7 Hz, 1H), 7.35-7.24 (m, 2H), 7.05 (d, J = 4.0 Hz, 1H), 5.38-5.12 (m, 1H), 4.77-4.55 (m, 1H), 4.52-4.24 (m, 1H), 4.09-3.34 (m, 6H), 1.53 (s, 3H) |
| 868 | 1H NMR (500 MHz, DMSO-d6) δ 8.47-8.32 (m, 1H), 8.17 (d, J = 8.5 Hz, 1H), 8.09 (s, 1H), 7.30 (s, 1H), 7.27 (br d, J = 12.2 Hz, 1H), 5.38-5.13 (m, 1H), 4.84-4.55 (m, 1H), 4.26-4.00 (m, 1H), 3.97 (s, 3H), 3.95-3.61 (m, 2H), 3.48-3.28 (m, 1H), 1.58-1.48 (m, 6H), 2 exchangeable protons |
| 873 | 1H NMR (500 MHz, DMSO-d6) δ 8.48-8.32 (m, 1H), 8.18 (br d, J = 8.5 Hz, 1H), 8.08 (br d, J = 12.2 Hz, 1H), 7.69-7.54 (m, 2H), 7.37-7.20 (m, 4H), 5.47-5.10 (m, 1H), 4.93-4.50 (m, 1H), 3.97 (br s, 3H), 3.90-3.44 (m, 4H), 2 exchangeable protons |
| 875 | 1H NMR (500 MHz, DMSO-d6) δ 8.36 (br t, J = 8.1 Hz, 1H), 8.26-8.16 (m, 1H), 8.10 (s, 1H), 7.33-7.23 (m, 2H), 5.42-5.16 (m, 1H), 4.87-4.53 (m, 1H), 4.09-3.14 (m, 7H), 2.94-2.78 (m, 1H), 2.74-2.20 (m, 2H merge with DMSO), 1.15-1.05 (m, 3H) |
| 876 | 1H NMR (500 MHz, DMSO-d6) δ 8.37 (br t, J = 7.0 Hz, 1H), 8.26-8.16 (m, 1H), 8.09 (s, 1H), 7.36-7.25 (m, 2H), 5.46-5.17 (m, 1H), 4.87-4.56 (m, 1H), 4.41-4.23 (m, 1H), 4.17-2.68 (m, 9H) |
| 877 | 1H NMR (500 MHz, DMSO-d6) δ 8.46-8.30 (m, 1H), 8.17 (br d, J = 7.9 Hz, 1H), 8.09 (s, 1H), 7.36-7.19 (m, 2H), 5.42-5.12 (m, 1H), 4.78-4.53 (m, 1H), 4.51-4.23 (m, 1H), 4.10-3.30 (m, 6H merge with water), 2.23-1.99 (m, 1H), 1.83-1.66 (m, 1H), 0.97-0.79 (m, 3H) |
| 878 | 1H NMR (500 MHz, DMSO-d6) δ 8.46-8.35 (m, 1H), 8.26-8.14 (m, 1H), 8.08 (s, 1H), 7.33-7.21 (m, 2H), 5.41-5.17 (m, 1H), 4.87-4.59 (m, 1H), 4.23-3.25 (m, 8H merge with water), 1.26 (br d, J = 5.8 Hz, 3H) |
| 879 | 1H NMR (500 MHz, DMSO-d6) δ 8.43-8.33 (m, 1H), 8.25-8.14 (m, 1H), 8.10 (s, 1H), 7.35-7.24 (m, 2H), 5.41-5.18 (m, 1H), 4.83-4.51 (m, 1H), 4.25-3.12 (m, 7H), 2.84-2.68 (m, 1H), 2.53-2.32 (m, 1H merge with DMSO), 1.41 (br s, 3H) |
| 880 | 1H NMR (500 MHz, DMSO-d6) δ 9.01-8.86 (m, 1H), 8.12 (s, 1H), 7.92 (br d, J = 7.3 Hz, 1H), 7.71 (br d, J = 9.8 Hz, 1H), 7.38 (s, 1H), 5.39-5.08 (m, 1H), 4.70-4.47 (m, 1H), 4.45-4.21 (m, 1H), 4.08-3.32 (m, 3H merge with water), 2.22-1.97 (m, 1H), 1.74 (tt, J = 13.7, 6.6 Hz, 1H), 0.97-0.81 (m, 3H) |
| 881 | 1H NMR (500 MHz, DMSO-d6) δ 9.03-8.87 (m, 1H), 8.13 (s, 1H), 7.97-7.89 (m, 1H), 7.73 (br d, J = 10.1 Hz, 1H), 7.38 (s, 1H), 5.39-5.13 (m, 1H), 4.75-4.46 (m, 1H), 4.17-3.14 (m, 4H), 2.86-2.66 (m, 1H), 2.50-2.31 (m, 1H merge with DMSO), 1.40 (br s, 3H) |
| 882 | 1H NMR (500 MHz, DMSO-d6) δ 8.94 (br dd, J = 19.5, 7.3 Hz, 1H), 8.13 (s, 1H), 7.93 (br dd, J = 7.3, 3.1 Hz, 1H), 7.73 (br d, J = 9.8 Hz, 1H), 7.39 (s, 1H), 5.39-5.14 (m, 1H), 4.77-4.47 (m, 1H), 4.06-3.53 (m, 3H), 3.47-3.14 (m, 1H merge with water), 2.83 (br s, 1H), 2.72-2.23 (m, 2H merge with DMSO) |
| 883 | 1H NMR (500 MHz, DMSO-d6) δ 8.94 (br dd, J = 19.5, 7.3 Hz, 1H), 8.13 (s, 1H), 7.93 (br dd, J = 7.3, 3.1 Hz, 1H), 7.73 (br d, J = 9.8 Hz, 1H), 7.39 (s, 1H), 5.39-5.14 (m, 1H), 4.77-4.48 (m, 1H), 4.06-3.53 (m, 3H), 3.46-3.14 (m, 1H merge with water), 2.83 (br s, 1H), 2.72-2.19 (m, 2H merge with DMSO), 1.10 (q, J = 6.8 Hz, 3H) |
| 884 | 1H NMR (500 MHz, DMSO-d6) δ 9.03-8.89 (m, 1H), 8.13 (s, 1H), 7.93 (br t, J = 6.9 Hz, 1H), 7.73 (br d, J = 9.8 Hz, 1H), 7.39 (s, 1H), 5.41-5.15 (m, 1H), 4.82-4.55 (m, 1H), 4.21-3.15 (m, 5H merge with water), 1.30-1.20 (m, 3H) |
| 885 | 1H NMR (500 MHz, DMSO-d6) δ 9.05-8.83 (m, 2H), 8.13 (s, 1H), 7.93 (t, J = 6.9 Hz, 1H), 7.73 (d, J = 9.8 Hz, 1H), 7.38 (s, 1H), 5.43-5.15 (m, 1H), 4.82-4.52 (m, 1H), 4.20-3.61 (m, 3H), 3.50-2.88 (m, 3H merge with water) |
| 886 | 1H NMR (500 MHz, DMSO-d6) δ 8.95 (br dd, J = 18.5, 7.5 Hz, 1H), 8.12 (s, 1H), 7.92 (br dd, J = 7.3, 3.1 Hz, 1H), 7.71 (br d, J = 9.5 Hz, 1H), 7.38 (s, 1H), 5.39-5.12 (m, 1H), 4.79-4.51 (m, 1H), 4.10-3.09 (m, 5H merge with water), 2.41-2.23 (m, 2H), 2.21-1.95 (m, 3H), 1.85-1.65 (m, 1H) |
| 887 | 1H NMR (500 MHz, DMSO-d6) δ 9.01-8.89 (m, 1H), 8.15-8.09 (m, 1H), 7.91 (br dd, J = 7.3, 3.7 Hz, 1H), 7.76-7.67 (m, 1H), 7.38 (br s, 1H), 5.42-5.14 (m, 1H), 4.81-4.44 (m, 1H), 4.07-3.34 (m, 3H merge with water), 3.28-3.02 (m, 2H), 2.36-2.21 (m, 2H), 2.20-1.97 (m, 3H), 1.89-1.67 (m, 1H) |
| 888 | 1H NMR (500 MHz, DMSO-d6) δ 9.02-8.91 (m, 1H), 8.17-8.09 (m, 1H), 7.99-7.87 (m, 1H), 7.80-7.70 (m, 1H), 7.40 (s, 1H), 5.39-5.01 (m, 2H), 4.78-4.51 (m, 1H), 3.88-3.16 (m, 5H merge with water), 2.55-2.28 (m, 4H merge with DMSO) |
| 889 | 1H NMR (500 MHz, DMSO-d6) δ 8.67-8.55 (m, 1H), 8.34 (br d, J = 6.5 Hz, 1H), 8.15-8.03 (m, 2H), 7.48 (t, J = 9.3 Hz, 1H), 7.37 (s, 1H), 5.37-5.11 (m, 1H), 4.73-4.52 (m, 1H), |

TABLE 49-continued

NMR data for selected examples from Tables 36-49

| Ex | NMR |
|---|---|
| | 4.48-4.27 (m, 1H), 4.11-3.51 (m, 3H), 2.24-2.03 (m, 1H), 1.87-1.69 (m, 1H), 0.99-0.85 (m, 3H) |
| 894 | 1H NMR (500 MHz, DMSO-d6) δ 8.96 (br dd, J = 15.1, 7.2 Hz, 1H), 8.41 (br d, J = 7.3 Hz, 1H), 8.22 (br d, J = 5.8 Hz, 2H), 7.91 (br d, J = 8.5 Hz, 1H), 7.75 (br d, J = 4.3 Hz, 1H), 5.37-5.09 (m, 1H), 4.87-4.49 (m, 1H), 4.22-3.96 (m, 1H), 3.95-3.47 (m, 2H), 3.47-3.29 (m, 1H), 1.63-1.45 (m, 6H), 2 exchangeable protons |
| 899 | 1H NMR (500 MHz, DMSO-d6) δ 9.01-8.91 (m, 1H), 8.41 (br d, J = 7.9 Hz, 1H), 8.22 (br s, 2H), 7.90 (br d, J = 8.2 Hz, 1H), 7.78-7.72 (m, 1H), 5.41-5.04 (m, 1H), 4.77-4.49 (m, 1H), 4.48-4.19 (m, 1H), 4.11-3.54 (m, 3H), 2.23-1.94 (m, 1H), 1.79-1.66 (m, 1H), 0.98-0.77 (m, 3H), 3 exchangeable protons |
| 905 | 1H NMR (500 MHz, DMSO-d6) δ 9.12-8.90 (m, 1H), 8.41 (br t, J = 7.8 Hz, 1H), 8.27-8.19 (m, 2H), 7.91 (br d, J = 8.2 Hz, 1H), 7.74 (br d, J = 7.3 Hz, 1H), 5.43-5.08 (m, 1H), 4.85-4.47 (m, 1H), 4.32 (br s, 1H), 4.16-3.56 (m, 3H), 3.49-3.23 (m, 1H), 3.11-2.71 (m, 2H), 2 exchangeable protons |
| 906 | 1H NMR (500 MHz, DMSO-d6) δ 9.07-8.88 (m, 1H), 8.46-8.35 (m, 1H), 8.27-8.13 (m, 2H), 7.89 (br dd, J = 19.2, 8.2 Hz, 1H), 7.80-7.67 (m, 1H), 7.59-7.50 (m, 1H), 7.50-7.40 (m, 1H), 7.36-7.27 (m, 2H), 5.43-5.05 (m, 1H), 4.93-4.42 (m, 1H), 4.04-3.65 (m, 2H), 3.62-3.29 (m, 2H), 2 exchangeable protons |
| 910 | 1H NMR (400 MHz, DMSO-d6) δ 8.88-8.72 (m, 1H), 8.35-8.26 (m, 1H), 8.19 (d, J = 8.1 Hz, 2H), 7.72-7.66 (m, 1H), 7.64 (d, J = 2.8 Hz, 1H), 7.08 (br d, J = 5.0 Hz, 1H), 5.74 (d, J = 2.0 Hz, 1H), 5.62 (d, J = 2.0 Hz, 1H), 5.37-5.11 (m, 1H), 4.73-4.51 (m, 1H), 4.45-4.25 (m, 1H), 4.07-3.41 (m, 3H), 1.57-1.51 (m, 3H). MS ESI 581.3 (M + H)⁺ |
| 912 | 1H NMR (400 MHz, DMSO-d6) δ 8.99-8.78 (m, 2H), 8.34-8.26 (m, 1H), 8.23-8.12 (m, 2H), 7.68 (d, J = 8.5 Hz, 1H), 7.62 (d, J = 3.3 Hz, 1H), 5.74 (s, 1H), 5.62 (s, 1H), 5.49-5.14 (m, 1H), 4.90-4.50 (m, 1H), 4.23-3.35 (m, 4H), 3.18-2.88 (m, 2H). MS ESI 649.3 (M + H)⁺ |
| 916 | 1H NMR (500 MHz, DMSO-d6) δ 8.89 (br dd, J = 14.8, 7.5 Hz, 1H), 8.42-8.21 (m, J = 8.2 Hz, 1H), 8.19-8.13 (m, 1H), 7.67 (d, J = 8.2 Hz, 1H), 7.59 (s, 1H), 5.75-5.54 (m, 2H), 5.41-5.14 (m, 1H), 4.80-4.57 (m, 1H), 4.27-3.38 (m, 4H), 1.47-1.11 (m, 4H), 2 exchangeable proton |
| 922 | 1H NMR (500 MHz, DMSO-d6) δ 8.87-8.78 (m, 1H), 8.26 (br d, J = 7.3 Hz, 1H), 8.17 (s, 1H), 8.14 (s, 1H), 7.66 (br d, J = 8.2 Hz, 1H), 7.60 (s, 1H), 5.73-5.56 (m, 2H), 5.39-5.13 (m, 1H), 4.74-4.50 (m, 1H), 4.47-4.25 (m, 1H), 4.08-3.35 (m, 3H), 2.24-1.96 (m, 1H), 1.84-1.63 (m, 1H), 0.94-0.82 (m, 3H), 3 exchangeable protons |
| 923 | 1H NMR (500 MHz, DMSO-d6) δ 8.88-8.73 (m, 1H), 8.28 (br d, J = 8.2 Hz, 1H), 8.19 (s, 1H), 8.16 (br d, J = 4.6 Hz, 1H), 7.72-7.65 (m, 1H), 7.65-7.57 (m, 1H), 5.76-5.57 (m, 2H), 5.43-5.19 (m, 1H), 5.18-4.87 (m, 1H), 4.78-4.44 (m, 1H), 4.01-3.50 (m, 3H), 3.38-3.19 (m, partially suppressed, 2H), 2.98-2.60 (m, 1H), 2.47-2.34 (m, 2H), 2.32-2.11 (m, 1H), 2 exchangeable protons |
| 924 | 1H NMR (500 MHz, DMSO-d6) δ 8.95-8.77 (m, 1H), 8.28 (br d, J = 7.3 Hz, 1H), 8.18 (s, 1H), 8.16 (br s, 1H), 7.68 (br d, J = 7.0 Hz, 1H), 7.61 (d, J = 4.6 Hz, 1H), 5.77-5.55 (m, 2H), 5.42-5.16 (m, 1H), 4.87-4.54 (m, 1H), 4.25-3.50 (m, 4H), 3.49-3.28 (m, partially suppressed, 2H), 1.29-1.22 (m, 3H), 2 exchangeable protons |
| 926 | 1H NMR (400 MHz, DMSO-d6) δ 9.03-8.88 (m, 1H), 8.27-8.13 (m, 3H), 7.71-7.57 (m, 2H), 5.45-5.17 (m, 1H), 4.85-4.49 (m, 1H), 4.45-4.24 (m, 1H), 4.17-3.83 (m, 3H), 3.79-3.61 (m, 1H), 3.53-3.21 (m, 1H), 3.11-2.98 (m, 1H), 2.93-2.75 (m, 1H) |
| 927 | 1H NMR (500 MHz, DMSO-d6) δ 9.03-8.83 (m, 1H), 8.22-8.10 (m, 3H), 7.69-7.57 (m, 2H), 5.41-5.01 (m, 1H), 4.75-4.49 (m, 1H), 3.60 (s, overlaps with water peak, 4H), 2.32-1.94 (m, 1H), 1.76 (td, J = 14.3, 7.0 Hz, 1H), 1.00-0.78 (m, 3H), 3 exchangeable protons |
| 931 | 1H NMR (400 MHz, DMSO-d6) δ 9.04-8.87 (m, 2H), 8.25-8.13 (m, 3H), 7.68-7.62 (m, 2H), 5.45-5.18 (m, 1H), 4.86-4.56 (m, 1H), 4.20-3.86 (m, 2H), 3.80-3.62 (m, 1H), 3.55-3.27 (m, 1H), 3.19-2.87 (m, 2H) |
| 934 | 1H NMR (500 MHz, DMSO-d6) δ 8.96 (br dd, J = 17.9, 7.2 Hz, 1H), 8.23-8.10 (m, 3H), 7.66-7.59 (m, 2H), 5.45-5.10 (m, 1H), 4.69 (br s, 1H), 4.27-3.56 (m, 4H), 1.48-1.20 (m, 3H), 1.14 (br s, 1H), 2 exchangeable protons |
| 941 | 1H NMR (500 MHz, DMSO-d6) δ 8.81 (br dd, J = 16.7, 7.4 Hz, 1H), 8.22-8.13 (m, 3H), 7.69-7.55 (m, 2H), 5.47-5.16 (m, 1H), 4.90-4.51 (m, 1H), 4.05-3.34 (m, 4H), 2.86 (br s, 1H), 2.74-2.53 (m, 1H), 2.48-2.23 (m, 1H), 1.19-1.05 (m, 3H), 2 exchangeable protons |
| 965 | 1H NMR (500 MHz, DMSO-d6) δ 8.72 (dd, J = 12.4, 6.9 Hz, 1H), 8.16 (s, 1H), 8.06 (br d, J = 7.9 Hz, 1H), 7.94 (br s, 1H), 7.51 (d, J = 4.3 Hz, 2H), 7.43 (d, J = 8.2 Hz, 1H), 5.45-5.09 (m, 1H), 4.82-4.49 (m, 1H), 4.24-3.31 (m, partially suppressed, 6H), 2.85-2.67 (m, 2H), 1.59-1.48 (m, 6H), 1.19 (t, J = 7.6 Hz, 3H), 2 exchangeable protons |
| 972 | 1H NMR (400 MHz, DMSO-d6) δ 8.99-8.88 (m, 1H), 8.84-8.71 (m, 1H), 8.17 (s, 1H), 8.07 (dt, J = 8.1, 2.1 Hz, 1H), 7.95 (dd, J = 6.0, 1.8 Hz, 1H), 7.52 (d, J = 4.1 Hz, 1H), 7.43 (d, J = 8.1 Hz, 1H), 5.47-5.20 (m, 1H), 4.82-4.56 (m, 1H), 4.19-2.71 (m, 8H), 1.19 (td, J = 7.5, 1.0 Hz, 3H) |
| 981 | 1H NMR (500 MHz, DMSO-d6) δ 8.88-8.68 (m, 1H), 8.20-8.10 (m, 1H), 8.09-8.00 (m, 1H), 7.92 (br d, J = 2.0 Hz, 1H), 7.50 (br d, J = 2.5 Hz, 1H), 7.43 (d, J = 8.2 Hz, 1H), 5.47-5.09 (m, 1H), 4.81-4.47 (m, 1H), 4.06-3.75 (m, 3H), 3.65-3.59 (m, 2H) 3.53-3.22 (m, 1H), 2.85-2.64 (m, 2H), 1.26-1.11 (m, 3H), 2 exchangeable protons |
| 985 | 1H NMR (500 MHz, DMSO-d6) δ 8.82-8.61 (m, 1H), 8.15 (s, 1H), 8.04 (br d, J = 7.9 Hz, 1H), 8.01-7.97 (m, 1H), 7.52 (br s, 1H), 7.39 (br d, J = 8.2 Hz, 1H), 5.45-5.16 (m, 1H), 4.86-4.46 (m, 1H), 4.12-3.23 (m, 6H), 2.39 (s, 3H), 2 exchangeable protons |

TABLE 49-continued

NMR data for selected examples from Tables 36-49

| Ex | NMR |
|---|---|
| 986 | 1H NMR (500 MHz, DMSO-d6) δ 8.82-8.64 (m, 1H), 8.16 (s, 1H), 8.04 (br d, J = 7.9 Hz, 1H), 8.01-7.94 (m, 1H), 7.52 (br d, J = 4.6 Hz, 1H), 7.39 (br d, J = 7.6 Hz, 2H), 5.42-5.08 (m, 1H), 4.89-4.50 (m, 1H), 4.00-3.54 (m, 3H), 3.48-3.07 (m, 2H), 2.94-2.66 (m, 4H), 2.39 (br s, 3H), 2 exchangeable protons |
| 990 | 1H NMR (500 MHz, DMSO-d6) δ 8.81-8.63 (m, 1H), 8.16 (s, 1H), 8.05 (br d, J = 7.9 Hz, 1H), 8.01-7.95 (m, 1H), 7.52 (br d, J = 5.2 Hz, 2H), 7.44-7.36 (m, 2H), 5.49-5.07 (m, 1H), 4.91-4.52 (m, 1H), 4.11-3.25 (m, 4H), 2.68-2.56 (m, 2H), 2.40 (br d, J = 5.2 Hz, 3H), 2.05 (br s, 2H), 1.97-1.70 (m, 4H), 1.66-1.50 (m, 2H), 2 exchangeable protons |
| 993 | 1H NMR (500 MHz, DMSO-d6) δ 8.81-8.57 (m, 1H), 8.17 (s, 1H), 8.05 (br d, J = 8.2 Hz, 1H), 8.02-7.88 (m, 1H), 7.54 (br d, J = 3.4 Hz, 1H), 7.42-7.34 (m, 1H), 5.39-5.13 (m, 1H), 4.81-4.52 (m, 1H), 4.44-4.23 (m, 1H), 4.10-3.39 (m, 3H), 2.40 (s, 3H), 1.53 (br s, 3H), 3 exchangeable protons |
| 997 | 1H NMR (500 MHz, DMSO-d6) δ 8.68 (br dd, J = 16.8, 7.0 Hz, 1H), 8.15 (s, 1H), 8.03 (br d, J = 7.9 Hz, 1H), 7.99-7.95 (m, 1H), 7.51 (br d, J = 3.1 Hz, 1H), 7.38 (br d, J = 7.9 Hz, 1H), 5.39-5.17 (m, 1H), 5.17-4.84 (m, 1H), 4.79-4.46 (m, 1H), 3.95-3.49 (m, 3H), 3.35-2.64 (m, 2H), 2.56-2.52 (m, 3H), 2.38 (br s, 3H), 2.31-2.13 (m, 1H), 2 exchangeable protons |
| 1000 | 1H NMR (500 MHz, DMSO-d6) δ 8.66 (br dd, J = 13.9, 6.9 Hz, 1H), 8.15 (s, 1H), 8.04 (br s, 1H), 8.02-7.94 (m, 1H), 7.52 (br d, J = 3.4 Hz, 1H), 7.38 (br d, J = 8.2 Hz, 2H), 5.40-5.16 (m, 1H), 4.82-4.47 (m, 1H), 4.21-3.54 (m, 3H), 3.45-3.28 (m, 2H), 1.59-1.47 (m, 6H), 2 exchangeable protons. |
| 1023 | 1H NMR (500 MHz, DMSO-d6) δ 8.81-8.66 (m, 1H), 8.51-8.46 (m, 1H), 8.24-8.12 (m, 1H), 8.09-7.90 (m, 2H), 7.64 (br s, 1H), 7.58-7.46 (m, 1H), 7.42-7.35 (m, 2H), 5.43-5.15 (m, 1H), 4.92-4.54 (m, 1H), 4.22-3.70 (m, 2H), 3.60-3.42 (m, partially under water peak, 2H), 2.43-2.35 (m, 6H), 2 exchangeable protons |
| 1024 | 1H NMR (500 MHz, DMSO-d6) δ 8.86-8.63 (m, 1H), 8.14 (br d, J = 13.4 Hz, 1H), 8.08-8.01 (m, 1H), 8.01-7.86 (m, 1H), 7.57-7.45 (m, 1H), 7.39 (dd, J = 14.8, 8.3 Hz, 1H), 7.34 (br s, 2H), 5.48-5.16 (m, 1H), 4.92-4.53 (m, 1H), 4.08-3.33 (m, partially under water peak, 4H), a2.47-2.21 (m, 3H), 2 exchangeable protons |
| 1037 | 1H NMR (500 MHz, DMSO-d6) δ 8.80-8.66 (m, 2H), 8.26-8.11 (m, 1H), 8.10-7.88 (m, 2H), 7.69 (br d, J = 9.1 Hz, 1H), 7.57-7.46 (m, 2H), 7.46-7.32 (m, 1H), 5.50-5.09 (m, 1H), 4.90-4.52 (m, 1H), 4.25-3.74 (m, 2H), 3.52-3.40 (m, 2H), 2.40 (br d, J = 13.3 Hz, 3H), 2 exchangeable protons |
| 1044 | 1H NMR (500 MHz, DMSO-d6) δ 8.68 (dd, J = 20.0, 7.1 Hz, 1H), 8.17 (d, J = 1.0 Hz, 1H), 8.05 (br d, J = 8.1 Hz, 1H), 8.02-7.97 (m, 1H), 7.54 (d, J = 4.3 Hz, 1H), 7.40 (d, J = 8.2 Hz, 1H), 5.41-5.15 (m, 1H), 4.80-4.49 (m, 1H), 3.98-3.15 (m, 4H merge with water), 2.40 (d, J = 2.6 Hz, 3H), 2.37-2.11 (m, 3H), 1.83-1.71 (m, 2H), 1.65-1.44 (m, 4H), 1.21-1.03 (m, 2H) |
| 1045 | 1H NMR (500 MHz, DMSO-d6) δ 8.76-8.62 (m, 1H), 8.16 (s, 1H), 8.04 (br d, J = 8.2 Hz, 1H), 7.99 (s, 1H), 7.52 (s, 1H), 7.39 (dd, J = 8.1, 2.3 Hz, 1H), 5.43-5.14 (m, 1H), 4.78-4.48 (m, 1H), 4.02-3.14 (m, 4H merge with water), 2.77-2.58 (m, 3H), 2.57-2.47 (m, 1H merge with DMSO), 2.40 (d, J = 3.4 Hz, 4H), 2.35-2.19 (m, 2H) |
| 1046 | 1H NMR (500 MHz, DMSO-d6) δ 9.00-8.74 (m, 1H), 8.38-8.10 (m, 3H), 1J2-7.51 (m, 3H), 7.47 (q, J = 7.7 Hz, 1H), 7.38-7.27 (m, 2H), 5.41-5.07 (m, 1H), 4.90-4.59 (m, 1H), 4.07-3.66 (m, 2H), 3.64-3.19 (m, 2H), 2 exchangeable protons |
| 1047 | 1H NMR (500 MHz, DMSO-d6) δ 8.88 (br dd, J = 18.6, 7.3 Hz, 1H), 8.29 (br d, J = 8.5 Hz, 1H), 8.27-8.23 (m, 1H), 8.22-8.17 (m, 1H), 7.65 (d, J = 4.9 Hz, 1H), 7.62-7.55 (m, 1H), 5.38-5.05 (m, 1H), 4.82-4.52 (m, 1H), 4.05-3.48 (m, 3H), 3.39-3.18 (m, 1H), 2.25-2.07 (m, 2H), 2.06-1.92 (m, 1H), 0.94-0.88 (m, 6H), 2 exchangeable protons |
| 1048 | 1H NMR (500 MHz, DMSO-d6) δ 8.88 (br dd, J = 19.2, 7.9 Hz, 1H), 8.26 (br d, J = 8.2 Hz, 1H), 8.23 (s, 1H), 8.17 (s, 1H), 7.61 (s, 1H), 7.57 (br d, J = 8.2 Hz, 1H), 5.31-5.02 (m, 1H), 4.76-4.49 (m, 1H), 4.45-3.65 (m, partially suppressed, 3H), 3.45-3.26 (m, partially suppressed, 1H), 1.33-1.25 (m, 6H), 3 exchangeable protons |
| 1049 | 1H NMR (500 MHz, DMSO-d6) δ 9.05-8.88 (m, 1H), 8.41-8.26 (m, 1H), 8.26-8.22 (m, 1H), 8.21-8.18 (m, 1H), 7.64 (br s, 1H), 7.62-7.56 (m, 1H), 5.40-5.10 (m, 1H), 4.86-4.52 (m, 1H), 4.12-3.62 (m, partially suppressed, 5H), 3.49-3.21 (m, partially suppressed, 1H), 2 exchangeable protons |
| 1071 | 1H NMR (500 MHz, DMSO-d6) δ 8.46-8.38 (m, 1H), 8.34 (br dd, J = 13.6, 7.8 Hz, 1H), 8.23-8.08 (m, 2H), 7.54 (s, 1H), 7.42-7.33 (m, 1H), 5.37-5.00 (m, 2H), 4.98-4.88 (m, 2H), 4.86-4.55 (m, 1H), 4.01-3.10 (m, partially under water peak, 5H), 2.79-2.72 (m, 1H), 2.47-2.14 (m, 4H), 2 exchangeable protons |
| 1072 | 1H NMR (500 MHz, DMSO-d6) δ 8.41 (dd, J = 10.9, 2.2 Hz, 1H), 8.39-8.32 (m, 1H), 8.20-8.16 (m, 2H), 7.56 (d, J = 3.3 Hz, 1H), 7.38 (dd, J = 8.9, 3.9 Hz, 1H), 5.42-5.10 (m, 1H), 5.04-4.89 (m, 2H), 4.86-4.54 (m, 1H), 4.06-3.50 (m, partially suppressed, 3H), 3.46-3.09 (m, partially suppressed, 2H), 2.93-2.65 (m, 4H), 2 exchangeable protons |
| 1074 | 1H NMR (500 MHz, DMSO-d6) δ 8.45-8.33 (m, 2H), 8.21-8.14 (m, 2H), 7.55 (s, 1H), 7.37 (d, J = 8.7 Hz, 1H), 5.43-5.08 (m, 1H), 5.04-4.88 (m, 2H), 4.77 (br s, 1H), 4.39-3.33 (m, 4H), 2.53-2.46 (m, 4H), 2 exchangeable protons |
| 1075 | 1H NMR (500 MHz, DMSO-d6) δ 8.45-8.30 (m, 2H), 8.21-8.10 (m, 2H), 7.51 (s, 1H), 7.39-7.30 (m, 1H), 5.42-5.10 (m, 1H), 5.02-4.86 (m, 2H), 4.86-4.45 (m, 1H), 4.04-3.57 (m, 3H), 3.39-3.06 (m, 1H), 2.23-2.06 (m, 2H), 2.01 (dt, J = 13.2, 6.7 Hz, 1H), 0.97-0.77 (m, 6H), 2 exchangeable protons |
| 1079 | 1H NMR (500 MHz, DMSO-d6) δ 8.72 (br dd, J = 19.7, 7.5 Hz, 1H), 8.27-8.16 (m, 3H), 7.60 (s, 1H), 7.42-7.34 (m, 1H), 5.47-5.05 (m, 1H), 4.88-4.48 (m, 1H), 4.27-3.54 (m, 3H), 3.03-2.82 (m, 1H), 1.50-1.06 (m, 6H), 2 exchangeable protons |

TABLE 49-continued

NMR data for selected examples from Tables 36-49

| Ex | NMR |
|---|---|
| 1091 | 1H NMR (500 MHz, DMSO-d6) δ 8.79-8.62 (m, 1H), 8.24-8.12 (m, 3H), 7.56 (s, 1H), 7.37 (d, J = 8.5 Hz, 1H), 5.40-5.11 (m, 1H), 4.84-4.49 (m, 1H), 4.21-3.66 (m, partially suppressed, 3H), 3.62-3.19 (m, partially suppressed, 2H), 2.83-2.66 (m, 1H), 2.48-2.30 (m, 1H), 1.40 (br s, 3H), 3 exchangeable protons |
| 1093 | 1H NMR (500 MHz, DMSO-d6) δ 8.81-8.62 (m, 1H), 8.28-8.12 (m, 3H), 7.58 (br d, J = 4.6 Hz, 1H), 7.43-7.32 (m, 1H), 5.41-5.10 (m, 1H), 4.88-4.60 (m, 1H), 4.27-3.59 (m, 4H), 3.55-3.13 (m, 2H), 1.27 (br d, J = 7.0 Hz, 3H), 3 exchangeable protons |
| 1101 | 1H NMR (500 MHz, DMSO-d6) δ 8.66-8.43 (m, 2H), 8.15 (s, 1H), 8.13 (br d, J = 9.2 Hz, 1H), 7.46 (s, 1H), 7.30 (t, J = 7.6 Hz, 1H), 5.50-5.03 (m, 1H), 4.93-4.53 (m, 1H), 4.25 (quin, J = 6.9 Hz, 2H), 4.15-3.53 (m, 3H), 3.51-3.09 (m, partially under water peak, 1H), 2.86 (br s, 1H), 2.76-2.53 (m, 1H), 2.49-2.28 (m, 1H), 1.43 (q, J = 6.7 Hz, 3H), 1.16-1.06 (m, 3H), 2 exchangeable protons |
| 1103 | 1H NMR (500 MHz, DMSO-d6) δ 8.68-8.43 (m, 2H), 8.16 (s, 1H), 8.14 (dd, J = 9.0, 2.3 Hz, 1H), 7.47 (d, J = 2.7 Hz, 1H), 7.30 (t, J = 8.2 Hz, 1H), 5.50-5.17 (m, 1H), 4.96-4.53 (m, 1H), 4.26 (quin, J = 7.2 Hz, 2H), 4.06-3.56 (m, 3H), 3.48-3.09 (m, 2H), 2.93-2.66 (m, 4H), 1.43 (q, J = 7.2 Hz, 3H), 2 exchangeable protons |
| 1107 | 1H NMR (500 MHz, DMSO-d6) δ 8.68-8.43 (m, 2H), 8.20-8.09 (m, 2H), 7.50-7.45 (m, 1H), 7.30 (dd, J = 8.7, 5.6 Hz, 1H), 5.43-5.17 (m, 1H), 4.86-4.60 (m, 1H), 4.59-4.29 (m, 1H), 4.29-4.18 (m, 2H), 4.12-3.61 (m, partially suppressed, 3H), 3.55-3.20 (m, 1H), 1.54 (s, 3H), 1.43 (q, J = 6.4 Hz, 3H), 2 exchangeable protons |
| 1113 | 1H NMR (500 MHz, DMSO-d6) δ 8.67-8.43 (m, 2H), 8.15 (s, 1H), 8.13 (dd, J = 8.5, 1.8 Hz, 1H), 7.46 (s, 1H), 7.30 (dd, J = 8.4, 6.0 Hz, 1H), 5.43-5.13 (m, 1H), 4.98-4.56 (m, 1H), 4.25 (quin, J = 6.6 Hz, 2H), 4.12-3.47 (m, 3H), 3.39-3.05 (m, 1H), 2.28-1.93 (m, 3H), 1.48-1.36 (m, 3H), 0.97-0.82 (m, 6H), 2 exchangeable protons |
| 1118 | 1H NMR (500 MHz, DMSO-d6) δ 8.57-8.35 (m, 2H), 8.19-8.11 (m, 2H), 7.47 (s, 1H), 7.31 (br t, J = 8.2 Hz, 1H), 5.45-5.16 (m, 1H), 4.89-4.61 (m, 1H), 3.96 (overlapping br d, J = 7.0 Hz, 3H), 4.13-3.19 (overlapping m, 4H), 2.95-2.78 (m, 1H), 2.75-2.55 (m, 1H), 2.48-2.24 (m, 1H), 1.16-0.95 (m, 3H), 2 exchangeable protons |
| 1121 | 1H NMR (500 MHz, DMSO-d6) δ 8.53-8.33 (m, 2H), 8.18-8.11 (m, 2H), 7.46 (s, 1H), 7.30 (br t, J = 8.5 Hz, 1H), 5.45-5.14 (m, 1H), 4.98-4.45 (m, 1H), 3.96 (overlapping br d, J = 6.7 Hz, 3H), 4.13-3.21 (overlapping m, partially suppressed, 4H), 2 exchangeable protons |
| 1126 | 1H NMR (400 MHz, DMSO-d6) δ 8.96 (br d, J = 11.0 Hz, 1H), 8.56-8.37 (m, 2H), 8.19-8.09 (m, 2H), 7.48 (s, 1H), 7.31 (dd, J = 8.8, 6.7 Hz, 1H), 5.46-5.22 (m, 1H), 4.91-4.59 (m, 1H), 4.25-2.90 (m, 9H) |
| 1127 | 1H NMR (500 MHz, DMSO-d6) δ 8.59-8.43 (m, 1H), 8.42 (br s, 1H), 8.22-8.08 (m, 2H), 7.47 (s, 1H), 7.30 (br d, J = 8.5 Hz, 1H), 5.51-5.14 (m, 1H), 5.02-4.52 (m, 1H), 4.33-3.26 (overlapping m, partially suppressed, 4H), 3.96 (overlapping br d, 3H), 1.45-1.20 (m, 3H), 1.15 (br d, J = 2.4 Hz, 1H), 2 exchangeable protons |
| 1131 | 1H NMR (500 MHz, DMSO-d6) δ 8.51-8.41 (m, 2H), 8.19-8.12 (m, 2H), 7.47 (s, 1H), 7.31 (br t, J = 9.3 Hz, 1H), 5.50-5.16 (m, 1H), 5.03-4.53 (m, 1H), 4.44-4.24 (m, 1H), 3.97 (overlapping br d, J = 9.2 Hz, 3H), 4.19-3.24 (overlapping m, 4H), 3.10-2.71 (m, 2H), 2 exchangeable protons |
| 1134 | 1H NMR (500 MHz, DMSO-d6) δ 8.78-8.64 (m, 1H), 8.46 (s, 1H), 8.26 (br d, J = 6.7 Hz, 1H), 8.18 (s, 1H), 7.92 (br d, J = 7.6 Hz, 1H), 7.66-7.55 (m, 2H), 5.38-5.13 (m, 1H), 4.75-4.53 (m, 1H), 4.49-4.30 (m, 1H), 4.09-3.57 (m, 3H), 2.24-2.02 (m, 1H), 1.83-1.66 (m, 1H), 0.97-0.83 (m, 3H) |
| 1135 | 1H NMR (500 MHz, DMSO-d6) δ 8.62-8.51 (m, 1H), 8.14-8.09 (m, 2H), 8.08-8.04 (m, 1H), 7.75 (br d, J = 4.9 Hz, 1H), 7.40 (s, 1H), 6.80 (dd, J = 8.9, 2.7 Hz, 1H), 5.42-5.18 (m, 1H), 4.85-4.52 (m, 1H), 4.42-4.27 (m, 1H), 4.20-2.98 (m, 6H merge with water), 2.87 (d, J = 4.6 Hz, 3H) |
| 1136 | 1H NMR (500 MHz, DMSO-d6) δ 8.62-8.45 (m, 1H), 8.15-8.05 (m, 3H), 7.41 (s, 1H), 6.79 (d, J = 8.8 Hz, 1H), 5.38-5.14 (m, 1H), 4.73-4.49 (m, 1H), 4.44-4.29 (m, 1H), 4.08-3.40 (m, 3H), 2.91-2.86 (m, 3H), 1.55 (s, 3H) |
| 1137 | 1H NMR (500 MHz, DMSO-d6) δ 8.98-8.86 (m, 1H), 8.66-8.51 (m, 1H), 8.12-8.07 (m, 2H), 8.05 (dd, J = 6.1, 1.8 Hz, 1H), 7.79-7.68 (m, 1H), 7.38 (s, 1H), 6.79 (dd, J = 8.9, 1.2 Hz, 1H), 5.45-5.18 (m, 1H), 4.81-4.54 (m, 1H), 4.21-3.60 (m, 4H), 3.20-2.92 (m, 2H), 2.86 (d, J = 4.9 Hz, 3H) |
| 1141 | 1H NMR (500 MHz, DMSO-d6) δ 9.08-8.67 (m, 1H), 8.26-7.98 (m, 3H), 7.73-7.58 (m, 1H), 7.40-7.22 (m, 1H), 5.41-5.11 (m, 1H), 4.82-4.50 (m, 1H), 4.47-4.24 (m, 1H), 4.08-3.64 (m, 2H), 3.48-3.32 (m, 2H), 2.38-1.85 (m, 4H), 1.62-1.48 (m, 3H). |
| 1146 | 1H NMR (500 MHz, DMSO-d6) δ 9.34-9.05 (m, 1H), 8.96-8.75 (m, 1H), 8.23-8.16 (m, 1H), 8.16-8.06 (m, 1H), 7.99-7.88 (m, 1H), 7.76-7.51 (m, 2H), 7.15-6.93 (m, 1H), 5.43-5.07 (m, 1H), 4.83-4.41 (m, 1H), 4.11-3.13 (m, 6H), 2.74-2.61 (m, 4H), 2.27-2.08 (m, 2H), 2.08-1.96 (m, 5H), 1.00-0.81 (m, 6H). |
| 1149 | 1H NMR (500 MHz, DMSO-d6) δ 8.94 (br dd, J = 17.4, 7.3 Hz, 1H), 8.15 (br d, J = 8.2 Hz, 1H), 8.10 (br s, 1H), 7.89 (br s, 1H), 7.58 (br d, J = 8.2 Hz, 1H), 7.07 (br s, 1H), 5.46-5.11 (m, 1H), 4.88-4.49 (m, 1H), 4.26-2.93 (m, overlaps with water peak, 9H), 2.43-2.22 (m, 1H), 2.19-1.76 (m, 3H), 1.58-1.04 (m, 6H), 2 exchangeable protons |
| 1151 | 1H NMR (500 MHz, DMSO-d6) δ 9.59-9.25 (m, 1H), 8.90 (br dd, J = 18.3, 7.3 Hz, 1H), 8.17 (br dd, J = 4.0, 2.1 Hz, 1H), 8.11 (s, 1H), 7.90 (s, 1H), 7.80-7.63 (m, 1H), 7.58 (d, J = 8.2 Hz, 1H), 7.08 (d, J = 4.0 Hz, 1H), 5.41-5.16 (m, 1H), 5.12-4.86 (m, 1H), 4.79-4.45 (m, 1H), 3.97-3.15 (m, 7H), 3.04 (br d, J = 11.3 Hz, 2H), 2.90 (s, 3H), 2.79-2.69 (m, 1H), 2.46-2.16 (m, 3H), 2.09 (br t, J = 11.3 Hz, 2H), 1.90-1.79 (m, 2H), 1.55-1.31 (m, 2H) |
| 1157 | 1H NMR (500 MHz, DMSO-d6) δ 8.95 (dd, J = 15.9, 7.4 Hz, 1H), 8.20-8.13 (m, 1H), 8.11 (d, J = 1.3 Hz, 1H), 7.89 (br s, 1H), 7.58 (br d, J = 8.5 Hz, 1H), 7.07 (br s, 1H), 5.43-5.12 |

TABLE 49-continued

NMR data for selected examples from Tables 36-49

| Ex | NMR |
|---|---|
| | (m, 1H), 4.91-4.42 (m, 1H), 3.99-3.59 (m, overlaps with water peak, 6H), 3.45-2.94 (m, 3H), 2.87-2.65 (m, 4H), 2.46-2.23 (m, 1H), 2.17-2.03 (m, 2H), 1.86 (br d, J = 11.8 Hz, 2H), 1.57-1.34 (m, 2H), 2 exchangeable protons |
| 1158 | 1H NMR (500 MHz, DMSO-d6) δ 9.03-8.79 (m, 1H), 8.24-7.99 (m, 2H), 7.89 (br d, J = 15.6 Hz, 1H), 7.66-7.42 (m, 3H), 7.37-7.27 (m, 2H), 7.15-6.98 (m, 1H), 5.50-4.94 (m, 1H), 4.87-4.44 (m, 1H), 4.07-2.93 (m, overlaps with water peak, 9H), 2.45-2.24 (m, 1H), 2.17-1.99 (m, 1H), 1.97-1.76 (m, 2H), 1.44 (br dd, J = 5.0, 2.3 Hz, 2H), 2 exchangeable protons |
| 1161 | 1H NMR (500 MHz, DMSO-d6) δ 9.59-9.32 (m, 1H), 9.00-8.84 (m, 1H), 8.23-8.13 (m, 1H), 8.11 (s, 1H), 7.89 (s, 1H), 7.79-7.64 (m, 1H), 7.57 (br d, J = 8.5 Hz, 1H), 7.07 (d, J = 4.6 Hz, 1H), 5.41-5.13 (m, 1H), 4.84-4.46 (m, 1H), 4.12-3.49 (m, 5H), 3.35-2.96 (m, 4H), 2.43-2.22 (m, 3H), 2.21-1.98 (m, 5H), 1.90-1.66 (m, 3H), 1.55-1.33 (m, 2H) |
| 1170 | 1H NMR (500 MHz, DMSO-d6) δ 8.74 (br s, 1H), 8.41 (s, 1H), 8.22 (br d, J = 7.9 Hz, 1H), 7.86 (s, 1H), 7.81 (br d, J = 7.6 Hz, 1H), 7.57 (t, J = 7.8 Hz, 1H), 7.07 (s, 1H), 5.42-5.00 (m, 1H), 4.81-4.44 (m, 1H), 4.00 (s, 2H), 3.85-3.59 (m, 8H), 1.18 (s, 9H), 2 exchangeable protons |
| 1172 | 1H NMR (500 MHz, DMSO-d6) δ 8.76 (br dd, J = 16.2, 7.0 Hz, 1H), 8.42 (s, 1H), 8.23 (br d, J = 7.9 Hz, 1H), 7.88 (s, 1H), 7.81 (br d, J = 7.9 Hz, 1H), 7.59-7.55 (m, 1H), 7.07 (s, 1H), 5.47-5.15 (m, 1H), 4.48 (s, 1H), 4.03-3.98 (m, 2H), 3.96-3.68 (m, 3H), 3.60-3.36 (m, 1H), 2.79-2.60 (m, 1H), 1.05-0.99 (m, 6H), 2 exchangeable protons |
| 1174 | 1H NMR (500 MHz, DMSO-d6) δ 8.85-8.66 (m, 1H), 8.47-8.33 (m, 1H), 8.27-8.13 (m, 1H), 7.90-7.83 (m, 1H), 7.83-7.67 (m, 1H), 7.63-7.46 (m, 1H), 7.11-6.91 (m, 1H), 5.45-5.12 (m, 1H), 5.12-4.84 (m, 1H), 4.84-4.47 (m, 1H), 4.10-3.96 (m, 1H), 3.93-3.35 (m, 7H), 2.84-2.67 (m, 1H), 2.37-2.07 (m, 2H). |
| 1175 | 1H NMR (500 MHz, DMSO-d6) δ 8.85-8.66 (m, 1H), 8.47-8.33 (m, 1H), 8.27-8.13 (m, 1H), 7.90-7.83 (m, 1H), 7.83-7.67 (m, 1H), 7.63-7.46 (m, 1H), 7.11-6.91 (m, 1H), 5.45-5.12 (m, 1H), 5.12-4.84 (m, 1H), 4.84-4.47 (m, 1H), 4.10-3.96 (m, 1H), 3.93-3.35 (m, 7H), 2.84-2.67 (m, 1H), 2.37-2.07 (m, 2H). |
| 1176 | 1H NMR (500 MHz, DMSO-d6) δ 8.64 (br d, J = 6.8 Hz, 1H), 8.41 (br s, 1H), 8.19 (br d, J = 7.0 Hz, 1H), 7.99 (s, 1H), 7.87 (br d, J = 7.7 Hz, 1H), 7.59 (t, J = 7.8 Hz, 1H), 7.15 (s, 1H), 5.37-5.12 (m, 1H), 4.75-4.49 (m, 1H), 4.13 (s, 2H), 3.83 (br t, J = 12.3 Hz, 4H), 3.71-3.41 (m, 4H), 1.47 (br d, J = 11.9 Hz, 6H), 2 exchangeable protons |
| 1180 | 1H NMR (500 MHz, DMSO-d6) δ 8.78-8.64 (m, 1H), 8.44 (s, 1H), 8.28 (br t, J = 7.6 Hz, 1H), 7.93-7.88 (m, 1H), 7.84 (br d, J = 7.6 Hz, 1H), 7.57 (br t, J = 7.8 Hz, 1H), 7.09 (s, 1H), 5.36-5.17 (m, 1H), 4.74-4.53 (m, 1H), 4.46-4.28 (m, 1H), 4.03 (br s, 2H), 3.98-3.57 (m, 7H merge with water), 1.55 (br s, 3H) |
| 1181 | 1H NMR (500 MHz, DMSO-d6) δ 8.80-8.72 (m, 1H), 8.43 (s, 1H), 8.23 (br d, J = 7.6 Hz, 1H), 8.00 (s, 1H), 7.87 (br d, J = 7.6 Hz, 1H), 7.60 (br t, J = 7.5 Hz, 1H), 5.44-5.15 (m, 1H), 4.89-4.49 (m, 1H), 4.12 (br s, 2H), 3.97-3.42 (m, 8H), 3.26-3.11 (m, 1H), 2.87-2.71 (m, 4H) |
| 1182 | 1H NMR (500 MHz, DMSO-d6) δ 8.79 (br dd, J = 14.8, 7.2 Hz, 1H), 8.07 (s, 1H), 7.79 (br s, 1H), 7.30 (s, 1H), 5.49-5.03 (m, 1H), 4.87-4.48 (m, 1H), 4.35-3.29 (m, 4H), 2.60 (s, 3H), 2.33 (s, 3H), 1.45-1.03 (m, 4H), 2 exchangeable protons |
| 1185 | 1H NMR (500 MHz, DMSO-d6) δ 8.91-8.57 (m, 1H), 8.07 (s, 1H), 7.78 (d, J = 3.4 Hz, 1H), 7.29 (s, 1H), 5.39-5.09 (m, 1H), 4.72-4.48 (m, 1H), 4.42-4.21 (m, 1H), 4.05-3.27 (m, 3H), 2.59 (s, 3H), 2.32 (s, 3H), 1.52 (br d, J = 3.1 Hz, 3H), 2 exchangeable protons |
| 1196 | 1H NMR (500 MHz, DMSO-d6) δ 8.97-8.64 (m, 1H), 8.06 (s, 1H), 7.76 (br s, 1H), 7.28 (s, 1H), 5.46-5.06 (m, 1H), 4.88-4.42 (m, 1H), 4.26-3.42 (m, 5H), 2.58 (d, J = 2.1 Hz, 3H), 2.32 (d, J = 1.2 Hz, 3H), 3 exchangeable protons |
| 1198 | 1H NMR (500 MHz, DMSO-d6) δ 8.90-8.66 (m, 1H), 8.07 (d, J = 8.8 Hz, 1H), 7.84-7.74 (m, 1H), 7.69-7.49 (m, 2H), 7.42 (br s, 1H), 5.44-5.14 (m, 1H), 4.89-4.47 (m, 1H), 4.09-3.36 (m, partially suppressed, 4H), 2.59 (br d, J = 18.3 Hz, 3H), 2.33 (br d, J = 10.4 Hz, 3H), 3 exchangeable protons |
| 1217 | 1H NMR (500 MHz, DMSO-d6) δ 8.91 (br s, 1H), 8.77 (br d, J = 18.3 Hz, 1H), 8.52 (br d, J = 4.9 Hz, 1H), 8.17 (s, 1H), 7.60 (s, 1H), 6.33-6.01 (m, 1H), 5.37-5.18 (m, 1H), 4.81-4.60 (m, 1H), 4.43-4.19 (m, 1H), 4.04 (br d, J = 3.1 Hz, 3H), 3.97-3.16 (m, 5H merge with water), 1.42-1.33 (m, 6H) |
| 1218 | 1H NMR (500 MHz, DMSO-d6) δ 8.93 (s, 1H), 8.78 (br d, J = 4.9 Hz, 1H), 8.61-8.48 (m, 1H), 8.18 (s, 1H), 7.62 (s, 1H), 5.44-5.19 (m, 1H), 4.84-4.53 (m, 1H), 4.13-3.14 (m, 9H), 1.18 (d, J = 3.1 Hz, 9H) |
| 1219 | 1H NMR (500 MHz, DMSO-d6) δ 8.93-8.88 (m, 1H), 8.76-8.64 (m, 1H), 8.37 (br t, J = 6.4 Hz, 1H), 8.15 (d, J = 6.6 Hz, 1H), 7.55 (br d, J = 7.4 Hz, 1H), 7.52-7.47 (m, 5H), 5.35-5.01 (m, 1H), 4.82-4.25 (m, 1H), 4.03 (d, J = 6.0 Hz, 3H), 3.98-3.81 (m, 1H), 3.64 (br d, J = 14.7 Hz, 3H), 3.55-2.96 (m, 3H merge with water) |
| 1220 | 1H NMR (400 MHz, DMSO-d6) δ 8.99-8.90 (m, 2H), 8.79 (dd, J = 8.9, 2.5 Hz, 1H), 8.55 (dd, J = 10.5, 7.8 Hz, 1H), 8.18 (s, 1H), 7.62 (s, 1H), 5.48-5.23 (m, 1H), 4.92-4.62 (m, 1H), 4.25-3.87 (m, 5H), 3.86-3.61 (m, 1H), 3.58-3.33 (m, 1H), 3.15-2.87 (m, 2H) |
| 1221 | 1H NMR (500 MHz, DMSO-d6) δ 8.85 (s, 1H), 8.70 (br d, J = 11.9 Hz, 1H), 8.63 (br t, J = 7.6 Hz, 1H), 8.10 (s, 1H), 7.52 (s, 1H), 5.40-5.20 (m, 1H), 4.76-4.55 (m, 1H), 4.20-3.21 (m, 7H merge with water), 2.65-2.36 (m, 3H merge with DMSO), 1.07 (br d, J = 6.1 Hz, 3H) |
| 1222 | 1H NMR (500 MHz, DMSO-d6) δ 8.89 (s, 1H), 8.76 (br d, J = 17.0 Hz, 1H), 8.49 (br t, J = 6.4 Hz, 1H), 8.13 (s, 1H), 7.53 (s, 1H), 5.45-5.22 (m, 1H), 4.88-4.58 (m, 1H), 4.33-4.18 (m, 1H), 4.15-3.26 (m, 7H merge with water), 3.05-2.75 (m, 2H) |
| 1223 | 1H NMR (500 MHz, DMSO-d6) δ 8.90 (br s, 1H), 8.75 (br s, 1H), 8.55-8.39 (m, 1H), 8.14 (d, J = 1.8 Hz, 1H), 7.54 (s, 1H), 5.43-5.17 (m, 1H), 4.89-4.54 (m, 1H), 4.22-3.16 |

TABLE 49-continued

NMR data for selected examples from Tables 36-49

| Ex | NMR |
|---|---|
| | (m, 7H merge with water), 2.23-2.09 (m, 1H), 1.40 (br s, 1H), 1.30-1.22 (m, 1H), 0.98-0.63 (m, 4H) |
| 1224 | 1H NMR (500 MHz, DMSO-d6) δ 8.92 (br s, 1H), 8.81-8.75 (m, 1H), 8.62-8.50 (m, 1H), 8.17 (s, 1H), 7.61 (s, 1H), 5.43-5.20 (m, 1H), 4.85-4.58 (m, 1H), 4.23-3.22 (m, 7H), 2.55 (s, 2H), 1.42 (br s, 3H) |
| 1225 | 1H NMR (500 MHz, DMSO-d6) δ 8.93 (br s, 1H), 8.85-8.76 (m, 1H), 8.53-8.43 (m, 1H), 8.17 (s, 1H), 7.57 (s, 1H), 5.46-5.23 (m, 1H), 4.90-4.64 (m, 1H), 4.29-3.40 (m, 8H), 1.35-1.24 (m, 3H) |
| 1226 | 1H NMR (500 MHz, DMSO-d6) δ 8.92 (s, 1H), 8.78 (s, 1H), 8.52-8.39 (m, 1H), 8.16 (s, 1H), 7.57 (s, 1H), 5.42-5.18 (m, 1H), 4.80-4.58 (m, 1H), 4.57-4.31 (m, 1H), 4.07 (s, 3H), 4.02-3.28 (m, 3H), 2.18-2.03 (m, 1H), 1.79 (br dd, J = 14.1, 7.4 Hz, 1H), 0.94 (br d, J = 6.5 Hz, 3H) |
| 1227 | 1H NMR (500 MHz, DMSO-d6) δ 8.92 (s, 1H), 8.78 (br s, 1H), 8.51-8.39 (m, 1H), 8.16 (s, 1H), 7.57 (s, 1H), 5.39-5.17 (m, 1H), 4.78-4.58 (m, 1H), 4.55-4.26 (m, 1H), 4.06 (s, 3H), 4.04-3.39 (m, 3H), 2.15 (br d, J = 4.9 Hz, 1H), 1.85-1.68 (m, 1H), 0.90 (br d, J = 6.0 Hz, 3H) |
| 1228 | 1H NMR (500 MHz, DMSO-d6) δ 8.91 (s, 1H), 8.76 (br d, J = 3.7 Hz, 1H), 8.58 (br t, J = 9.0 Hz, 1H), 8.16 (s, 1H), 7.60 (s, 1H), 5.49-5.24 (m, 1H), 5.02-4.68 (m, 1H), 4.24-3.13 (m, 7H) |
| 1229 | 1H NMR (500 MHz, DMSO-d6) δ 8.92 (br s, 1H), 8.77 (br d, J = 11.6 Hz, 1H), 8.57 (br dd, J = 15.6, 7.0 Hz, 1H), 8.16 (br s, 1H), 7.60 (br s, 1H), 5.49-5.20 (m, 1H), 4.91-4.61 (m, 1H), 4.31-3.41 (m, 7H merge with water), 1.89-1.69 (m, 3H) |
| 1230 | 1H NMR (500 MHz, CD3OD) δ 9.03-8.90 (m, 2H), 8.71 (br dd, J = 15.7, 7.6 Hz, 1H), 8.12 (s, 1H), 7.46 (s, 1H), 5.42-5.21 (m, 1H), 4.95-4.72 (m, 1H merge with water), 4.70-4.41 (m, 1H), 4.22-3.86 (m, 5H), 3.64-3.42 (m, 4H), 1.67 (s, 3H). |
| 1231 | 1H NMR (500 MHz, DMSO-d6) δ 9.19 (s, 1H), 8.96-8.82 (m, 1H), 8.40 (br s, 1H), 8.20 (s, 1H), 7.70 (s, 1H), 5.41-5.16 (m, 1H), 4.76-4.51 (m, 1H), 4.48-4.31 (m, 1H), 4.09-3.61 (m, 3H), 2.58 (s, 3H), 2.07 (td, J = 14.2, 7.3 Hz, 1H), 1.84-1.65 (m, 1H), 0.99-0.85 (m, 3H) |
| 1232 | 1H NMR (500 MHz, DMSO-d6) δ 9.18 (br s, 1H), 8.96-8.85 (m, 1H), 8.40 (br d, J = 2.4 Hz, 1H), 8.20 (s, 1H), 7.69 (d, J = 3.4 Hz, 1H), 5.48-5.19 (m, 1H), 4.82-4.50 (m, 1H), 4.11-3.18 (m, 4H), 2.84 (br s, 1H), 274-2.27 (m, 5H merge with DMSO), 1.17-1.04 (m, 3H) |
| 1233 | 1H NMR (500 MHz, DMSO-d6) δ 9.18 (br s, 1H), 9.00-8.83 (m, 1H), 8.39 (br d, J = 3.7 Hz, 1H), 8.20 (s, 1H), 7.69 (d, J = 2.4 Hz, 1H), 5.49-5.15 (m, 1H), 4.87-4.55 (m, 1H), 4.32 (br d, J = 8.9 Hz, 1H), 4.16-3.25 (m, 3H), 3.10-2.73 (m, 1H), 2.58 (Br, 2H), 2.54 (s, 3H) |
| 1234 | 1H NMR (500 MHz, DMSO-d6) δ 9.19 (br s, 1H), 8.98-8.85 (m, 1H), 8.40 (br s, 1H), 8.20 (s, 1H), 7.69 (d, J = 1.8 Hz, 1H), 5.43-5.20 (m, 1H), 4.77-4.51 (m, 1H), 4.20-3.16 (m, 4H), 2.93-2.68 (m, 1H), 2.58 (s, 3H), 2.50-2.33 (m, 1H merge with DMSO), 1.42 (br s, 3H) |
| 1235 | 1H NMR (500 MHz, DMSO-d6) δ 9.18 (br s, 1H), 8.90-8.74 (m, 1H), 8.38 (br s, 1H), 8.19 (s, 1H), 7.65 (d, J = 3.0 Hz, 1H), 5.47-5.22 (m, 1H), 4.87-4.59 (m, 1H), 4.27-3.23 (m, 5H), 2.60 (d, J = 1.8 Hz, 3H), 1.34-1.23 (m, 3H) |
| 1236 | 1H NMR (500 MHz, DMSO-d6) δ 9.18 (br s, 1H), 8.91-8.77 (m, 1H), 8.39 (br d, J = 5.3 Hz, 1H), 8.19 (s, 1H), 7.64 (br s, 1H), 5.50-5.22 (m, 1H), 4.90-4.59 (m, 1H), 4.20-3.30 (m, 4H), 3.13-2.90 (m, 2H), 2.61 (s, 3H) |
| 1237 | 1H NMR (500 MHz, DMSO-d6) δ 9.41-9.04 (m, 1H), 8.90 (dd, J = 11.0, 2.4 Hz, 1H), 8.75 (dd, J = 10.1, 2.4 Hz, 1H), 8.73-8.65 (m, 2H), 8.62-8.41 (m, 1H), 7.87 (d, J = 13.7 Hz, 1H), 7.62-7.42 (m, 3H), 7.03 (d, J = 16.2 Hz, 1H), 5.49-5.11 (m, 1H), 4.92-4.60 (m, 1H), 4.11-3.33 (m, overlaps with d at 4.02 and water peak, 6H), 4.02 (overlapping d, J = 8.9 Hz, 3H), 2.62 (br s, 4H), 2.08-1.93 (m, 4H) |
| 1247 | 1H NMR (500 MHz, DMSO-d6) δ 8.92 (br s, 1H), 8.76 (br d, J = 16.2 Hz, 1H), 8.62-8.44 (m, 1H), 7.97 (br s, 1H), 7.12 (br s, 1H), 5.42-5.14 (m, 1H), 4.91-4.52 (m, 1H), 4.03 (d, J = 4.8 Hz, 3H), 4.02-3.19 (m, overlaps with water peak, 10H), 2.26-1.95 (m, 7H), 1.03-0.71 (m, 6H), 2 exchangeable protons |
| 1254 | 1H NMR (500 MHz, DMSO-d6) δ 8.89 (dd, J = 8.5, 2.4 Hz, 1H), 8.74 (dd, J = 13.6, 2.3 Hz, 1H), 8.63-8.54 (m, 2H), 7.96 (br t, J = 7.6 Hz, 1H), 7.86 (d, J = 9.8 Hz, 1H), 7.79 (br d, J = 7.9 Hz, 1H), 7.59-7.45 (m, 1H), 7.03 (d, J = 10.7 Hz, 1H), 5.46-5.14 (m, 1H), 4.87-4.60 (m, 1H), 4.22-4.04 (m, 2H), 4.01 (d, J = 7.6 Hz, 3H), 3.96-3.47 (m, overlaps with water peak, 5H), 2.62 (br s, 3H), 2.00 (br s, 4H) |
| 1256 | 1H NMR (500 MHz, DMSO-d6) δ 9.38-9.21 (m, 1H), 9.20-9.10 (m, 1H), 8.90 (br d, J = 2.4 Hz, 1H), 8.75 (s, 1H), 8.57 (br d, J = 6.7 Hz, 1H), 8.34 (s, 1H), 7.88 (d, J = 4.9 Hz, 1H), 7.70-7.27 (m, 1H), 7.04 (br d, J = 4.6 Hz, 1H), 5.48-5.12 (m, 1H), 4.95-4.63 (m, 1H), 4.45-4.04 (m, 1H), 4.02 (s, 3H), 3.96-3.55 (m, 6H), 2.62 (br s, 3H), 2.10-1.92 (m, 4H) |
| 1262 | 1H NMR (500 MHz, DMSO-d6) δ 8.93-8.84 (m, 1H), 8.71 (d, J = 2.1 Hz, 1H), 8.62-8.43 (m, 1H), 8.04 (br d, J = 12.5 Hz, 1H), 7.72-7.57 (m, 1H), 7.57-7.47 (m, 1H), 7.46-7.37 (m, 1H), 7.21-7.15 (m, 1H), 5.48-5.08 (m, 1H), 4.93-4.52 (m, 1H), 4.03 (br d, J = 2.7 Hz, 3H), 3.99-3.44 (m, overlaps with water peak, 9H), 3.11-2.91 (m, 1H), 2.15 (br s, 4H), 2 exchangeable protons |
| 1275 | 1H NMR (400 MHz, DMSO-d6) δ 8.96-8.89 (m, 1H), 8.76 (d, J = 2.4 Hz, 1H), 8.59-8.44 (m, 1H), 7.96-7.87 (m, 1H), 7.66 (br dd, J = 5.6, 1.8 Hz, 2H), 7.30 (br s, 2H), 7.07 (s, 1H), 5.48-5.15 (m, 1H), 4.90-4.58 (m, 1H), 4.01 (br d, J = 3.8 Hz, 3H), 3.82 (br d, J = 5.3 Hz, 1H), 3.71 (br s, 4H), 3.65-3.49 (m, 1H), 3.18 (d, J = 2.9 Hz, 1H). |

TABLE 49-continued

NMR data for selected examples from Tables 36-49

| Ex | NMR |
|---|---|
| 1278 | 1H NMR (500 MHz, DMSO-d6) δ 8.93 (s, 1H), 8.77 (d, J = 2.1 Hz, 1H), 8.51 (br d, J = 7.6 Hz, 1H), 7.92-7.87 (m, 1H), 7.08 (s, 1H), 5.41-5.26 (m, 1H), 4.83-4.71 (m, 1H), 4.70-4.59 (m, 2H), 4.07-3.97 (m, 2H), 3.92-3.66 (m, 8H), 3.42-3.39 (m, 1H). |
| 1285 | 1H NMR (400 MHz, DMSO-d6) δ 8.93 (s, 1H), 8.82-8.74 (m, 1H), 8.55-8.44 (m, 1H), 7.91 (s, 1H), 7.09 (s, 1H), 5.41-5.16 (m, 1H), 4.87-4.52 (m, 1H), 4.07-3.52 (m, 9H), 3.48-3.19 (m, 1H), 2.24-1.96 (m, 3H), 0.92 (dt, J = 6.5, 2.7 Hz, 6H). |
| 1290 | 1H NMR (500 MHz, DMSO-d6) δ 8.91 (s, 1H), 8.72 (d, J = 1.2 Hz, 1H), 8.45 (br d, J = 7.3 Hz, 1H), 7.90 (s, 1H), 7.81 (s, 1H), 7.07 (s, 1H), 5.38-5.12 (m, 1H), 4.56-4.30 (m, 1H), 4.01 (br s, 2H), 3.80-3.67 (m, partially suppressed, 7H), 3.63 (s, 3H), 3.60-3.55 (m, 1H), 2.33 (s, 3H), 2 exchangeable protons |
| 1295 | 1H NMR (500 MHz, DMSO-d6) δ 8.91 (d, J = 2.1 Hz, 1H), 8.73 (d, J = 2.1 Hz, 1H), 8.48 (br d, J = 7.6 Hz, 1H), 7.89 (s, 1H), 7.80 (br d, J = 7.6 Hz, 1H), 7.69-7.61 (m, 1H), 7.30 (d, J = 8.5 Hz, 1H), 7.13 (t, J = 7.5 Hz, 1H), 7.07 (s, 1H), 5.40-5.15 (m, 1H), 4.71-4.37 (m, 1H), 4.00 (s, 2H), 3.96 (s, 3H), 3.84 (t, J = 9.0 Hz, 1H), 3.75-3.56 (m, 3H), 3.46 (br s, 3H), 3.29-3.14 (m, 1H), 2 exchangeable protons |
| 1298 | 1H NMR (500 MHz, DMSO-d6) δ 8.90 (d, J = 2.1 Hz, 1H), 8.75 (d, J = 2.1 Hz, 1H), 8.54 (br d, J = 7.0 Hz, 1H), 7.88 (s, 1H), 7.06 (s, 1H), 5.42-5.20 (m, 1H), 4.86-4.64 (m, 1H), 4.02-3.97 (m, 2H), 3.79 (br t, J = 9.0 Hz, 1H), 3.74-3.66 (m, 1H), 3.64-3.52 (m, 3H), 3.44 (dt, J = 13.5, 6.8 Hz, 1H), 3.32 (br t, J = 9.8 Hz, 1H), 1.26 (d, J = 6.7 Hz, 6H), 2 exchangeable protons |
| 1299 | 1H NMR (500 MHz, DMSO-d6) δ 8.91 (br s, 1H), 8.77 (br d, J = 7.8 Hz, 1H), 8.53-8.38 (m, 1H), 7.87 (s, 1H), 7.05 (s, 1H), 5.41-5.19 (m, 1H), 4.74-4.58 (m, 1H), 4.56-4.29 (m, 1H), 4.10-3.78 (m, 4H), 3.71 (br t, J = 12.4 Hz, 4H), 3.63-3.40 (m, 1H merge with water), 1.54 (s, 3H). |
| 1300 | 1H NMR (500 MHz, DMSO-d6) δ 8.99 (s, 1H), 8.71 (br s, 1H), 8.38 (s, 1H), 8.18 (s, 1H), 7.64 (s, 1H), 7.09 (br s, 1H), 4.01 (s, 3H), 1.37 (s, 9H), 2 exchangeable protons |
| 1303 | 1H NMR (500 MHz, DMSO-d6) δ 9.00 (s, 1H), 8.73 (s, 1H), 8.41 (s, 1H), 8.18 (s, 1H), 7.94 (br s, 1H), 7.65 (s, 1H), 4.19 (br d, J = 6.4 Hz, 1H), 4.03 (s, 3H), 1.92-1.82 (m, 2H), 1.74-1.63 (m, 2H), 1.58-1.47 (m, 4H), 2 exchangeable protons |
| 1304 | 1H NMR (500 MHz, DMSO-d6) δ 8.99 (s, 1H), 8.70 (s, 1H), 8.31 (br s, 1H), 8.17 (s, 1H), 7.64 (s, 1H), 3.99 (s, 3H), 3.43-3.26 (m, 4H), 1.63-1.50 (m, 2H), 1.09-0.94 (m, 1H), 0.92-0.68 (m, 3H), 0.49-0.37 (m, 2H), 0.32-0.12 (m, 2H), 3 exchangeable protons |
| 1306 | 1H NMR (500 MHz, DMSO-d6) δ 8.93 (br dd, J = 10.8, 7.5 Hz, 1H), 8.03 (br d, J = 7.6 Hz, 1H), 7.84 (s, 1H), 7.65 (d, J = 10.4 Hz, 1H), 6.93 (s, 1H), 5.40-5.12 (m, 1H), 4.78-4.44 (m, 1H), 4.20-3.11 (m, 10H merge with water), 1.62-1.44 (m, 6H) |
| 1307 | 1H NMR (500 MHz, DMSO-d6) δ 8.90-8.77 (m, 1H), 8.06 (br d, J = 7.7 Hz, 1H), 7.85 (s, 1H), 7.61 (d, J = 10.3 Hz, 1H), 6.93 (s, 1H), 5.43-5.17 (m, 1H), 4.80-4.49 (m, 1H), 4.02 (s, 2H), 3.50-3.30 (m, 10H merge with water) |
| 1308 | 1H NMR (500 MHz, DMSO-d6) δ 8.90 (br s, 1H), 8.05 (br d, J = 7.9 Hz, 1H), 7.86 (s, 1H), 7.66 (d, J = 10.4 Hz, 1H), 6.93 (s, 1H), 5.39-5.10 (m, 1H), 4.80-4.47 (m, 1H), 4.25-3.62 (m, 10H merge with water), 1.45 (br d, J = 15.0 Hz, 6H) |
| 1309 | 1H NMR (500 MHz, DMSO-d6) δ 8.98-8.83 (m, 1H), 8.10-7.99 (m, 1H), 7.86 (s, 1H), 7.67 (d, J = 10.4 Hz, 1H), 6.93 (s, 1H), 5.43-5.14 (m, 1H), 4.80-4.49 (m, 1H), 4.02 (s, 2H), 3.94-3.10 (m, 9H merge with water), 2.91-2.65 (m, 4H) |
| 1310 | 1H NMR (500 MHz, DMSO-d6) δ 8.98-8.87 (m, 1H), 8.05 (d, J = 7.6 Hz, 1H), 7.86 (s, 1H), 7.66 (br d, J = 10.1 Hz, 1H), 6.93 (s, 1H), 5.39-5.14 (m, 1H), 4.82-4.51 (m, 1H), 4.09-3.38 (m, 9H merge with water), 3.32-3.06 (m, 2H), 2.42-1.98 (m, 5H), 1.90-1.68 (m, 1H) |
| 1311 | 1H NMR (500 MHz, DMSO-d6) δ 8.79 (br dd, J = 11.0, 7.5 Hz, 1H), 8.04 (br d, J = 7.7 Hz, 1H), 7.83 (s, 1H), 7.59 (br d, J = 10.3 Hz, 1H), 6.92 (s, 1H), 5.40-5.15 (m, 1H), 5.09-4.87 (m, 1H), 4.75-4.48 (m, 1H), 4.02 (s, 2H), 3.90-3.16 (m, 8H merge with water), 2.81-2.65 (m, 1H), 2.55-2.46 (m, 2H merge with DMSO), 2.35-2.14 (m, 2H) |
| 1312 | 1H NMR (500 MHz, DMSO-d6) δ 8.79 (br t, J = 8.2 Hz, 1H), 8.04 (br d, J = 7.6 Hz, 1H), 7.83 (s, 1H), 7.59 (br d, J = 10.2 Hz, 1H), 6.92 (s, 1H), 5.36-5.01 (m, 2H), 4.77-4.48 (m, 1H), 4.01 (s, 2H), 3.87-3.14 (m, 8H), 2.55-2.28 (m, 5H) |
| 1313 | 1H NMR (500 MHz, DMSO-d6) δ 8.88-8.76 (m, 1H), 8.05 (br d, J = 7.5 Hz, 1H), 7.83 (s, 1H), 7.59 (br d, J = 10.4 Hz, 1H), 6.92 (s, 1H), 5.38-5.14 (m, 1H), 4.67-4.50 (m, 1H), 4.46-4.24 (m, 1H), 4.01 (s, 2H), 3.92-3.40 (m, 7H), 1.53 (s, 3H) |
| 1314 | 1H NMR (500 MHz, DMSO-d6) δ 8.76-8.64 (m, 1H), 8.36 (s, 1H), 8.21 (s, 2H), 7.72 (br d, J = 8.8 Hz, 1H), 7.66 (s, 1H), 6.98 (br d, J = 9.9 Hz, 1H), 5.39-5.16 (m, 1H), 4.72-4.54 (m, 1H), 4.51-4.30 (m, 1H), 4.11-3.53 (m, 3H), 1.56 (s, 3H). |
| 1315 | 1H NMR (500 MHz, DMSO-d6) δ 8.78-8.65 (m, 1H), 8.36 (s, 1H), 8.25-8.15 (m, 2H), 7.71 (br d, J = 8.9 Hz, 1H), 7.66 (s, 1H), 5.41-5.17 (m, 1H), 4.83-4.56 (m, 1H), 4.02-3.09 (m, 5H merge with water), 2.90-2.70 (m, 4H). |
| 1316 | 1H NMR (500 MHz, DMSO-d6) δ 8.70 (br d, J = 17.6 Hz, 1H), 8.37 (s, 1H), 8.26-8.17 (m, 2H), 7.73 (br d, J = 8.4 Hz, 1H), 7.67 (s, 1H), 6.74 (s, 1H), 5.39-5.13 (m, 1H), 4.77-4.57 (m, 1H), 4.52-4.29 (m, 1H), 4.14-3.12 (m, 3H), 2.25-2.04 (m, 1H), 1.87-1.70 (m, 1H), 0.99-0.82 (m, 3H) |
| 1317 | 1H NMR (500 MHz, DMSO-d6) δ 8.78-8.67 (m, 1H), 8.15 (s, 1H), 8.00 (br d, J = 11.4 Hz, 1H), 7.83 (br s, 1H), 7.56 (br s, 1H), 5.41-5.17 (m, 1H), 4.78-4.50 (m, 1H), 4.15-3.16 (m, 4H merge with water), 2.28 (br s, 3H), 2.20-2.08 (m, 1H), 1.43-1.32 (m, 1H), 1.25 (br s, 1H), 0.99-0.61 (m, 4H) |
| 1318 | 1H NMR (500 MHz, DMSO-d6) δ 8.78-8.66 (m, 1H), 8.20 (s, 1H), 8.06 (br d, J = 11.4 Hz, 1H), 7.90 (br s, 1H), 7.63 (br s, 1H), 5.44-5.22 (m, 1H), 4.77-4.51 (m, 1H), 4.21-3.19 (m, 5H), 2.85-2.69 (m, 1H), 2.31 (s, 3H), 1.43 (s, 3H) |

TABLE 49-continued

NMR data for selected examples from Tables 36-49

| Ex | NMR |
|---|---|
| 1319 | 1H NMR (500 MHz, DMSO-d6) δ 8.80-8.64 (m, 1H), 8.20 (s, 1H), 8.07 (br d, J = 11.5 Hz, 1H), 7.90 (br s, 1H), 7.62 (d, J = 6.6 Hz, 1H), 5.47-5.20 (m, 1H), 4.87-4.56 (m, 1H), 4.23-3.21 (m, 5H), 2.31 (br s, 3H), 1.34-1.25 (m, 3H) |
| 1320 | 1H NMR (500 MHz, DMSO-d6) δ 8.78-8.66 (m, 1H), 8.20 (s, 1H), 8.06 (br d, J = 10.7 Hz, 1H), 7.90 (br d, J = 1.7 Hz, 1H), 7.62 (d, J = 5.3 Hz, 1H), 5.47-5.22 (m, 1H), 4.82-4.54 (m, 1H), 4.30 (ddd, J = 14.1, 8.8, 5.6 Hz, 1H), 4.17-2.76 (m, 6H), 2.31 (br s, 3H) |
| 1321 | 1H NMR (500 MHz, DMSO-d6) δ 8.87-8.74 (m, 2H), 8.20 (s, 1H), 8.08 (br d, J = 11.6 Hz, 1H), 7.90 (s, 1H), 7.66 (s, 1H), 5.40-5.16 (m, 1H), 4.72-4.49 (m, 1H), 4.46-4.23 (m, 1H), 4.11-3.62 (m, 3H), 2.29 (s, 3H), 2.22-1.99 (m, 1H), 1.83-1.66 (m, 1H), 0.98-0.82 (m, 3H) |
| 1322 | 1H NMR (500 MHz, DMSO-d6) δ 8.92-8.76 (m, 1H), 8.74 (s, 1H), 8.68 (br s, 1H), 8.19 (d, J = 12.8 Hz, 1H), 8.07 (br dd, J = 15.1, 12.1 Hz, 1H), 7.97 (br d, J = 7.6 Hz, 1H), 7.94-7.83 (m, 1H), 7.70-7.60 (m, 1H), 7.51 (dd, J = 7.5, 5.0 Hz, 1H), 5.49-5.20 (m, 1H), 4.85-4.56 (m, 1H), 4.12-3.15 (m, 4H merge with water), 2.33-2.21 (m, 3H) |
| 1323 | 1H NMR (500 MHz, DMSO-d6) δ 8.92-8.75 (m, 1H), 8.72 (s, 1H), 8.56 (br d, J = 4.0 Hz, 1H), 8.18 (d, J = 15.0 Hz, 1H), 8.06 (br dd, J = 16.8, 11.3 Hz, 1H), 7.95-7.80 (m, 1H), 7.68-7.59 (m, 1H), 7.55 (dt, J = 10.3, 5.1 Hz, 1H), 5.47-5.18 (m, 1H), 4.87-4.62 (m, 1H), 4.11-3.15 (m, 4H merge with water), 2.33-2.21 (m, 3H) |
| 1324 | 1H NMR (500 MHz, DMSO-d6) δ 8.92-8.75 (m, 1H), 8.70 (br s, 1H), 8.62 (s, 1H), 8.19 (br d, J = 12.2 Hz, 1H), 8.06 (br dd, J = 16.0, 11.7 Hz, 1H), 7.98-7.83 (m, 2H), 7.69-7.56 (m, 1H), 5.48-5.20 (m, 1H), 4.85-4.52 (m, 1H), 4.13-3.15 (m, 4H merge with water), 2.32-2.21 (m, 3H) |
| 1325 | 1H NMR (500 MHz, DMSO-d6) δ 8.94-8.75 (m, 1H), 8.69 (br d, J = 2.7 Hz, 2H), 8.18 (d, J = 15.0 Hz, 1H), 8.06 (br dd, J = 18.2, 11.4 Hz, 1H), 7.95-7.79 (m, 1H), 7.68-7.57 (m, 1H), 5.48-5.20 (m, 1H), 4.93-4.66 (m, 1H), 4.13-3.15 (m, 4H merge with water), 2.32-2.20 (m, 3H) |
| 1326 | 1H NMR (500 MHz, DMSO-d6) δ 9.12-8.92 (m, 1H), 8.34 (br d, J = 11.0 Hz, 1H), 8.24 (s, 1H), 8.09 (br s, 1H), 7.79 (br s, 1H), 5.40-5.12 (m, 1H), 4.78-4.51 (m, 1H), 4.49-4.23 (m, 1H), 4.09-3.13 (m, 3H), 2.22-2.00 (m, 1H), 1.84-1.65 (m, 1H), 0.97-0.81 (m, 3H) |
| 1327 | 1H NMR (500 MHz, DMSO-d6) δ 9.11-8.92 (m, 1H), 8.34 (br d, J = 10.4 Hz, 1H), 8.23 (s, 1H), 8.09 (br s, 1H), 7.79 (br d, J = 3.7 Hz, 1H), 5.36-5.14 (m, 1H), 4.74-4.53 (m, 1H), 4.45-4.24 (m, 1H), 4.08-3.12 (m, 3H), 1.53 (s, 3H) |
| 1328 | 1H NMR (500 MHz, DMSO-d6) δ 9.14-8.97 (m, 1H), 8.39-8.28 (m, 1H), 8.23 (s, 1H), 8.09 (br s, 1H), 7.78 (br d, J = 6.4 Hz, 1H), 5.45-5.15 (m, 1H), 4.88-4.60 (m, 1H), 4.27-3.15 (m, 5H), 1.27 (br t, J = 7.9 Hz, 3H) |
| 1329 | 1H NMR (500 MHz, DMSO-d6) δ 9.14-9.00 (m, 1H), 8.41-8.30 (m, 1H), 8.24 (br s, 1H), 8.10 (br s, 1H), 7.84-7.73 (m, 1H), 5.43-5.19 (m, 1H), 4.85-4.62 (m, 1H), 4.23-3.20 (m, 5H merge with water), 1.41-1.20 (m, 3H) |
| 1330 | 1H NMR (400 MHz, DMSO-d6) δ 9.11-8.98 (m, 1H), 8.40-8.30 (m, 1H), 8.24 (s, 1H), 8.10 (s, 1H), 7.80 (d, J = 3.8 Hz, 1H), 5.42-5.17 (m, 1H), 4.83-4.52 (m, 1H), 4.04-3.23 (m, 4H merge with water), 2.96-2.76 (m, 1H), 2.58-2.26 (m, 2H merge with DMSO), 1.10 (dd, J = 6.8, 2.5 Hz, 3H). |
| 1331 | 1H NMR (400 MHz, DMSO-d6) δ 9.11-8.98 (m, 1H), 8.40-8.30 (m, 1H), 8.24 (s, 1H), 8.10 (s, 1H), 7.80 (d, J = 3.8 Hz, 1H), 5.42-5.17 (m, 1H), 4.83-4.52 (m, 1H), 4.04-3.23 (m, 4H merge with water), 2.96-2.76 (m, 1H), 2.58-2.26 (m, 2H merge with DMSO), 1.10 (dd, J = 6.8, 2.5 Hz, 3H). |
| 1332 | 1H NMR (500 MHz, DMSO-d6) δ 8.78 (br dd, J = 19.0, 7.0 Hz, 1H), 8.33 (br dd, J = 10.3, 7.8 Hz, 1H), 8.21 (s, 1H), 8.13 (br s, 1H), 7.67 (s, 1H), 6.95 (br d, J = 7.9 Hz, 1H), 5.41-5.17 (m, 1H), 4.76-4.56 (m, 1H), 4.51-4.28 (m, 1H), 4.12-3.18 (m, 3H), 1.56 (s, 3H) |
| 1333 | 1H NMR (500 MHz, DMSO-d6) δ 9.00-8.87 (m, 1H), 8.34 (br s, 1H), 8.21 (s, 1H), 8.12 (br s, 1H), 7.69 (br s, 1H), 5.42-5.15 (m, 1H), 4.84-4.54 (m, 1H), 4.15-3.06 (m, 4H), 2.41-1.96 (m, 6H), 1.78 (br d, J = 6.4 Hz, 1H) |
| 1334 | 1H NMR (500 MHz, DMSO-d6) δ 9.06-8.87 (m, 1H), 8.37 (br d, J = 9.2 Hz, 1H), 8.23 (s, 1H), 8.14 (br s, 1H), 7.72 (s, 1H), 5.44-5.20 (m, 1H), 4.84-4.51 (m, 1H), 4.23-3.06 (m, 5H), 2.90-2.70 (m, 1H), 1.43 (br s, 3H) |
| 1335 | 1H NMR (500 MHz, DMSO-d6) δ 8.90-8.75 (m, 1H), 8.38-8.29 (m, 1H), 8.21 (s, 1H), 8.12 (br s, 1H), 7.66 (d, J = 3.5 Hz, 1H), 5.46-5.21 (m, 1H), 4.86-4.61 (m, 1H), 4.26-3.24 (m, 5H), 1.36-1.22 (m, 3H) |
| 1336 | 1H NMR (500 MHz, DMSO-d6) δ 8.80 (br dd, J = 13.8, 7.3 Hz, 1H), 8.36-8.28 (m, 1H), 8.20 (s, 1H), 8.11 (br d, J = 3.8 Hz, 1H), 7.65 (d, J = 3.7 Hz, 1H), 5.45-5.19 (m, 1H), 4.88-4.53 (m, 1H), 4.02-3.07 (m, 5H), 2.90-2.67 (m, 4H) |
| 1337 | 1H NMR (500 MHz, DMSO-d6) δ 8.86-8.72 (m, 1H), 8.33 (br dd, J = 11.7, 7.2 Hz, 1H), 8.21 (s, 1H), 8.13 (br s, 1H), 7.67 (s, 1H), 5.42-5.12 (m, 1H), 4.78-4.54 (m, 1H), 4.53-4.25 (m, 1H), 4.18-3.13 (m, 3H), 2.24-2.01 (m, 1H), 1.79 (br d, J = 8.3 Hz, 1H), 1.00-0.82 (m, 3H) |
| 1338 | 1H NMR (500 MHz, DMSO-d6) δ 8.94-8.84 (m, 1H), 8.20 (s, 1H), 8.05 (br dd, J = 11.5, 2.9 Hz, 1H), 7.85 (br d, J = 6.6 Hz, 1H), 7.64 (br d, J = 8.0 Hz, 1H), 5.43-5.18 (m, 1H), 4.79-4.52 (m, 1H), 3.99-3.07 (m, 5H merge with water), 2.90-2.66 (m, 6H), 1.22-1.10 (m, 3H) |

Example 1339: N-[(3R,4S)-1-(3,3-difluorocyclobutanecarbonyl)-4-fluoropyrrolidin-3-yl]-5-[4-acetamido-5-(trifluoromethyl)pyrrolo[2,1-f][1,2,4]triazin-7-yl]-2-methoxypyridine-3-carboxamide

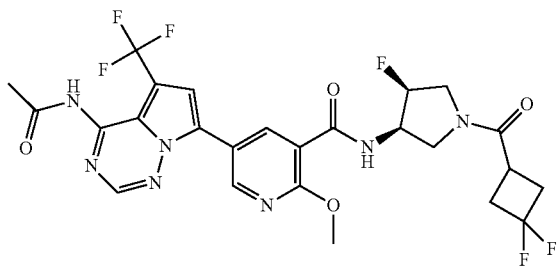 [SMILES: COc1ncc(-c2cc(C(F)(F)F)c3c(NC(C)=O)ncnn23)cc1C(=O)N[C@@H]1CN(C(=O)C2CC(F)(F)C2)C[C@@H]1F]

Prepared by the methods described in Example 564.
MS ESI m/z 600.1 (M+H)+
1H NMR (500 MHz, DMSO-d6) δ 9.07-8.48 (m, 3H), 8.20-7.90 (m, 1H), 7.64-7.35 (m, 1H), 5.44-5.18 (m, 1H), 4.89-4.59 (m, 1H), 4.05 (br t, J=7.0 Hz, 3H), 4.00-3.09 (m, 5H), 2.91-2.68 (m, 4H), 2.55 (s, 3H)

Example 1340: 5-[4-acetamido-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-methoxypyridine-3-carboxamide

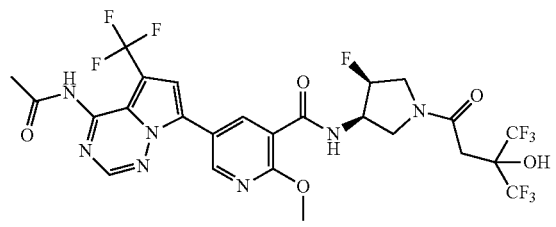 [SMILES: COc1ncc(-c2cc(C(F)(F)F)c3c(NC(C)=O)ncnn23)cc1C(=O)N[C@@H]1CN(C(=O)CC(O)(C(F)(F)F)C(F)(F)F)C[C@@H]1F]

Prepared by the methods described in Example 564.
MS ESI m/z 690.3 (M+H)+
1H NMR (500 MHz, DMSO-d6) δ 9.04-7.31 (m, 6H), 5.46-5.23 (m, 1H), 4.90-4.62 (m, 1H), 4.22-3.27 (m, 7H), 3.06-2.84 (m, 2H), 2.55 (s, 3H).

Example 1341: 5-[4-acetamido-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methoxypyridine-3-carboxamide

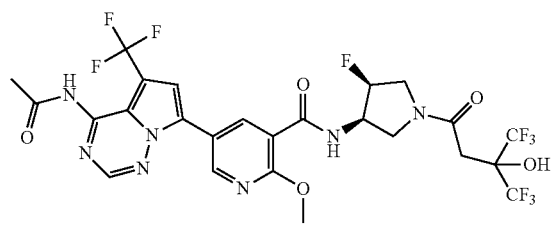 [SMILES: COc1ncc(-c2cc(C(F)(F)F)c3c(NC(C)=O)ncnn23)cc1C(=O)N[C@@H]1CN(C(=O)CC(O)(C(F)(F)F)C(F)(F)F)C[C@@H]1F]

Prepared by the methods described in Example 564.
MS ESI m/z 622.1 (M+H)+
1H NMR (500 MHz, DMSO-d6) δ 9.10-7.13 (m, 6H), 5.41-5.19 (m, 1H), 4.79-4.56 (m, 1H), 4.55-4.27 (m, 1H), 4.09-2.86 (m, 6H), 2.55 (s, 3H merge with DMSO), 1.54 (s, 3H).

Example 1342: N-[(3R,4S)-1-[(1R)-3,3-difluorocyclopentanecarbonyl]-4-fluoropyrrolidin-3-yl]-5-[4-acetamido-5-(trifluoromethyl)pyrrolo[2,1-f][1,2,4]triazin-7-yl]-2-methoxypyridine-3-carboxamide

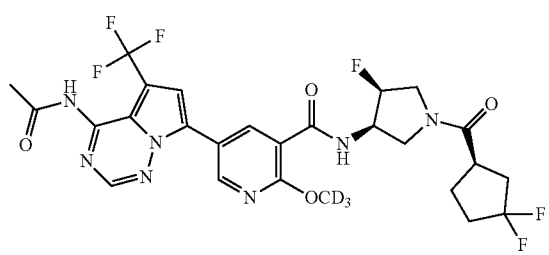

Prepared by the methods described in Example 564.
MS ESI m/z 617.1 (M+H)+
1H NMR (500 MHz, DMSO-d6) δ 9.11-7.34 (m, 5H), 5.45-5.19 (m, 1H), 4.92-4.58 (m, 1H), 4.15-3.15 (m, 4H), 2.55 (s, 3H merge with DMSO), 2.41-1.69 (m, 7H).

Example 1343: N-[(3R,4S)-4-fluoro-1-[(2R)-3,3,3-trifluoro-2-hydroxy-2-methylpropanoyl]pyrrolidin-3-yl]-5-[4-(2-fluoro-2-methylpropanamido)-5-(trifluoromethyl)pyrrolo[2,1-f][1,2,4]triazin-7-yl]-2-methoxypyridine-3-carboxamide

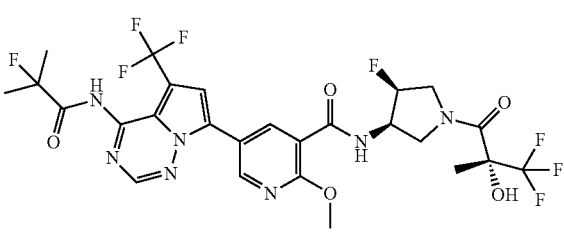 [SMILES: COc1ncc(-c2cc(C(F)(F)F)c3c(NC(=O)C(C)(C)F)ncnn23)cc1C(=O)N[C@@H]1CN(C(=O)[C@@](C)(O)C(F)(F)F)C[C@@H]1F]

Prepared by the methods described in Example 564.
MS ESI m/z 668.1 (M+H)+
1H NMR (500 MHz, DMSO-d6) δ 9.09-7.02 (m, 6H), 5.43-5.18 (m, 1H), 4.81-4.57 (m, 1H), 4.54-4.26 (m, 1H), 4.10-3.15 (m, 6H), 1.72-1.50 (m, 9H).

Example 1344: 5-[4-amino-5-(trifluoromethyl)pyrrolo[2,1-f][1,2,4]triazin-7-yl]-N-(1-benzyl-1H-1,2,4-triazol-3-yl)-2-methoxypyridine-3-carboxamide

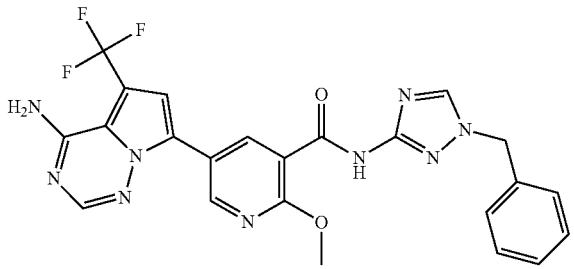 [SMILES: COc1ncc(-c2cc(C(F)(F)F)c3c(N)ncnn23)cc1C(=O)Nc1ncn(Cc2ccccc2)n1]

Prepared by the methods described in Example 10.
MS ESI m/z 510.2 (M+H)⁺
1H NMR (500 MHz, DMSO-d6) δ 10.55 (br s, 1H), 8.92 (br s, 1H), 8.78-8.47 (m, 2H), 8.16 (br s, 1H), 7.62 (s, 1H), 7.46-7.24 (m, 5H), 5.36 (br s, 2H), 4.00 (br s, 3H).

Example 1345: 5-[4-amino-5-(trifluoromethyl)pyrrolo[2,1-f][1,2,4]triazin-7-yl]-N-[1-(3,3-difluorocyclobutanecarbonyl)-4,4-difluoropyrrolidin-3-yl]-2-methoxypyridine-3-carboxamide

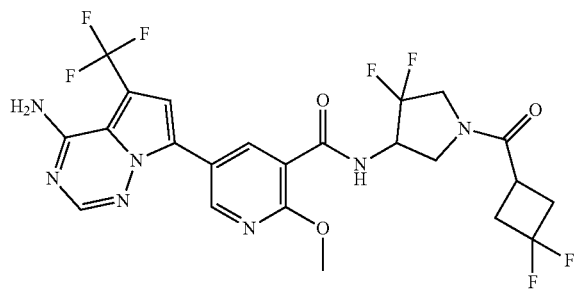 [SMILES: COc1ncc(-c2cc(C(F)(F)F)c3c(N)ncnn23)cc1C(=O)NC1CN(C(=O)C2CC(F)(F)C2)CC1(F)F]

Prepared by the methods described in Example 563.
MS ESI m/z 576.5 (M+H)⁺
1H NMR (500 MHz, DMSO-d6) δ 8.92 (s, 1H), 8.77-8.63 (m, 2H), 8.17 (s, 1H), 7.61 (s, 1H), 5.19-4.95 (m, 1H), 4.11-3.81 (m, 6H), 3.59-3.39 (m, 1H merge with water), 3.23-3.11 (m, 1H), 2.89-2.68 (m, 4H).

Example 1346: 5-(4-amino-5-(trifluoromethyl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxy-N-methylnicotinamide

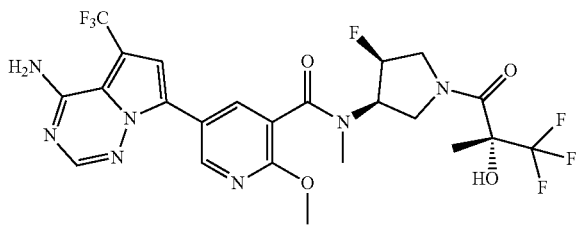 [SMILES: COc1ncc(-c2cc(C(F)(F)F)c3c(N)ncnn23)cc1C(=O)N(C)[C@@H]1CN(C(=O)[C@@](C)(O)C(F)(F)F)C[C@@H]1F]

1346A: 5-bromo-N-((3R,4S)-4-fluoropyrrolidin-3-yl)-2-methoxynicotinamide, TFA: A solution of tert-butyl (3R,4S)-3-(5-bromo-2-methoxynicotinamido)-4-fluoropyrrolidine-1-carboxylate (110 mg, 0.263 mmol)(please refer to synthesis of 1549A) in CH₂Cl₂ (2 mL) was added TFA (0.405 mL, 5.26 mmol) and stirred at 23° C. for 1 hr. The reaction mixture was concentrated and triturated in 10 mL of Et2O. The solid was collected as 5-bromo-N-((3R,4S)-4-fluoropyrrolidin-3-yl)-2-methoxynicotinamide, TFA (109.5 mg, 0.253 mmol, 96% yield).
MS ESI m/z 318.1 (M+H).

1346B: 5-bromo-N-((3R,4S)-4-fluoro-1-((R)-3,3,3-trifluoro-2-hydroxy-2-methylpropanoyl) pyrrolidin-3-yl)-2-methoxy-N-methylnicotinamide

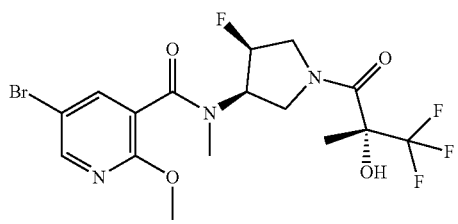 [SMILES: COc1ncc(Br)cc1C(=O)N(C)[C@@H]1CN(C(=O)[C@@](C)(O)C(F)(F)F)C[C@@H]1F]

1346C: 5-bromo-N-((3R,4S)-4-fluoro-1-((R)-3,3,3-trifluoro-2-methoxy-2-methylpropanoyl) pyrrolidin-3-yl)-2-methoxy-N-methylnicotinamide

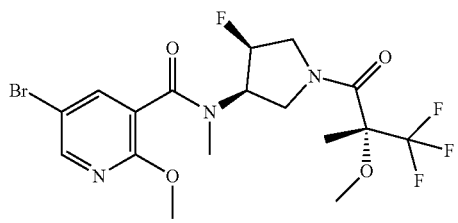 [SMILES: COc1ncc(Br)cc1C(=O)N(C)[C@@H]1CN(C(=O)[C@@](C)(OC)C(F)(F)F)C[C@@H]1F]

A solution of 5-bromo-N-((3R,4S)-4-fluoro-1-((R)-3,3,3-trifluoro-2-hydroxy-2-methylpropanoyl)pyrrolidin-3-yl)-2-methoxynicotinamide (109.6 mg, 0.239 mmol) in THF (3 mL) was added NaH (33.5 mg, 0.837 mmol) and stirred at 23° C. for 10 minutes. The reaction mixture was added methyl iodide (0.037 mL, 0.598 mmol) and stirred for 3 hrs. The reaction mixture was diluted with 50 mL of EtOAc which was washed with 10×2 mL of 10% LiCl solution, 10 mL of brine and dried over Na2SO4. Filtration and concentration to yield a crude product. The crude product was purified on prep HPLC to yield 5-bromo-N-((3R,4S)-4-fluoro-1-((R)-3,3,3-trifluoro-2-hydroxy-2-methylpropanoyl)pyrrolidin-3-yl)-2-methoxy-N-methylnicotinamide (27.2 mg, 0.058 mmol, 24% yield) MS ESI m/z 472.1 (M+H) and 5-bromo-N-((3R,4S)-4-fluoro-1-((R)-3,3,3-trifluoro-2-methoxy-2-methylpropanoyl)pyrrolidin-3-yl)-2-methoxy-N-methylnicotinamide (13.3 mg, 0.027 mmol, 11% yield).
MS ESI m/z 486.1 (M+H).

1346D: N-((3R,4S)-4-fluoro-1-((R)-3,3,3-trifluoro-2-hydroxy-2-methylpropanoyl) pyrrolidin-3-yl)-2-methoxy-N-methyl-5-(4,4,5,5-tetramethyl-1,3,2-dioxaborolan-2-yl)nicotinamide: A degassed solution of 5-bromo-N-((3R,4S)-4-fluoro-1-((R)-3,3,3-trifluoro-2-hydroxy-2-methylpropanoyl)pyrrolidin-3-yl)-2-methoxy-N-methylnicotinamide (23 mg, 0.049 mmol), 4,4,4',4',5,5,5',5'-octamethyl-2,2'-bi(1,3,2-dioxaborolane) (12.99 mg, 0.051 mmol), potassium acetate (7.65 mg, 0.078 mmol) and PdCl$_2$(dppf)-CH$_2$Cl$_2$ Adduct (1.989 mg, 2.435 µmol) in 1,4-dioxane (1 mL) was heated to 90° C. for 2 hrs. The reaction mixture was used as-is.

1346: A degassed solution of 7-bromo-5-(trifluoromethyl) pyrrolo[2,1-f][1,2,4]triazin-4-amine (13.5 mg, 0.048 mmol), N-((3R,4S)-4-fluoro-1-((R)-3,3,3-trifluoro-2-hydroxy-2-methylpropanoyl)pyrrolidin-3-yl)-2-methoxy-N-methyl-5-(4,4,5,5-tetramethyl-1,3,2-dioxaborolan-2-yl)nicotinamide (24.95 mg, 0.048 mmol), tripotassium phosphate (2 M in water) (0.072 mL, 0.144 mmol) and 1,1'-Bis(diphenylphosphino)ferrocene palladium dichloride —CH$_2$Cl$_2$ adduct (1.961 mg, 2.402 µmol) was stirred at 90° C. for 16 hrs. The reaction mixture was concentrated and the crude material was purified via preparative LC/MS with the following conditions: Column: XBridge C18, 19×200 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: 5-45% B over 20 min, then a 3-min hold at 100% B; Flow: 20 mL/min. Fractions containing the desired product were combined and dried via centrifugal evaporation to yield the final product (7.1 mg, 12 µmol, 25%).

MS ESI m/z 594.2 (M+H)

1H NMR (500 MHz, DMSO-d$_6$) δ 8.92 (br d, J=1.5 Hz, 1H), 8.46-8.32 (m, 1H), 8.16 (s, 1H), 7.60 (s, 1H), 7.33-7.08 (m, 1H), 5.53-5.05 (m, 1H), 4.46-4.13 (m, 1H), 4.02-3.50 (m, 7H merge with water), 3.12-2.83 (m, 3H), 1.55 (br d, J=6.9 Hz, 3H)

Example 1347: 5-(4-amino-5-(trifluoromethyl)pyrrolo[2,1-f][1,2,4]triazin-7-yl)-N-((3R,4S)-4-fluoro-1-((R)-3,3,3-trifluoro-2-methoxy-2-methylpropanoyl)pyrrolidin-3-yl)-2-methoxy-N-methylnicotinamide

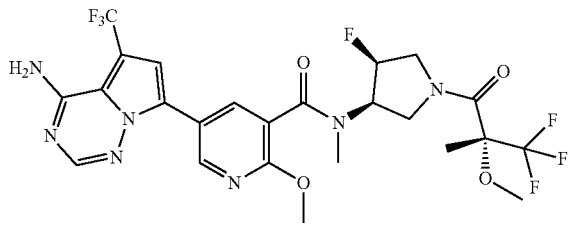 [SMILES: COc1ncc(-c2cc(C(F)(F)F)c3c(N)ncnn23)cc1C(=O)N(C)[C@@H]1CN(C(=O)[C@@](C)(OC)C(F)(F)F)C[C@@H]1F]

1347A: N-((3R,4S)-4-fluoro-1-((R)-3,3,3-trifluoro-2-methoxy-2-methylpropanoyl) pyrrolidin-3-yl)-2-methoxy-N-methyl-5-(4,4,5,5-tetramethyl-1,3,2-dioxaborolan-2-yl) nicotinamide: A degassed solution of 5-bromo-N-((3R,4S)-4-fluoro-1-((R)-3,3,3-trifluoro-2-methoxy-2-methylpropanoyl)pyrrolidin-3-yl)-2-methoxy-N-methylnicotinamide (1346C, 13.3 mg, 0.027 mmol), 4,4,4',4',5,5,5',5'-octamethyl-2,2'-bi(1,3,2-dioxaborolane) (7.29 mg, 0.029 mmol), potassium acetate (4.29 mg, 0.044 mmol) and PdCl$_2$(dppf)-CH$_2$Cl$_2$ Adduct (1.117 mg, 1.368 µmol) in Dioxane (1 mL) was heated to 100° C. for 4 hrs. LC-MS indicated that the reaction was complete. The reaction mixture was used as-is.

1347: 5-(4-amino-5-(trifluoromethyl)pyrrolo[2,1,2,4]triazin-7-yl)-N-((3R,4S)-4-fluoro-1-((R)-3,3,3-trifluoro-2-methoxy-2-methylpropanoyl)pyrrolidin-3-yl)-2-methoxy-N-methylnicotinamide was prepared using the procedure reported to prepare 1346 (2.9 mg, 4.6 µmol, 13% yield).

MS ESI m/z 608.3 (M+H)

1H NMR (500 MHz, DMSO-d$_6$) δ 8.95 (br d, J=7.1 Hz, 1H), 8.48-8.34 (m, 1H), 8.18 (s, 1H), 7.63 (br s, 1H), 5.57-5.32 (m, 1H), 5.27-4.96 (m, 1H), 4.41-3.38 (m, 10H merge with water), 3.12-2.86 (m, 3H), 1.63-1.46 (m, 3H)

Example 1348 (2R)-1-{5-[4-amino-5-(trifluoromethyl)pyrrolo[2,1-f][1,2,4]triazin-7-yl]-2-methoxypyridin-3-yl}-2-[2-fluoro-5-(trifluoromethoxy)phenyl]propan-1-one

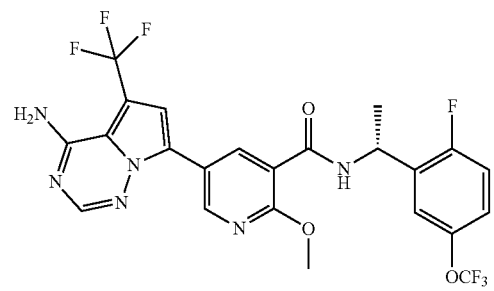 [SMILES: COc1ncc(-c2cc(C(F)(F)F)c3c(N)ncnn23)cc1C(=O)N[C@H](C)c1cc(OC(F)(F)F)ccc1F]

1348A: 7-iodo-5-(trifluoromethyl)pyrrolo[2,1-f][1,2,4] triazin-4-amine: A solution of 5-iodo-N,N-bis(4-methoxybenzyl)-7-(trifluoromethyl)pyrrolo[2,1-f][1,2,4]triazin-4-amine (0.50 g, 0.880 mmol) in TFA (4.6 mL, 59.7 mmol) was heated at 135° C. under microwave for 25 min. TFA was removed under vacuum and co-evaporated once with ether. The crude product was dissolved in a minimal amount of dichloromethane and purified by flash chromatography on silica gel (Teledyne-Isco RediSep Rf 40 g column), eluting with 200 mL each of hexanes, 95:5, 90:10, 80:20, 85:15, 300 mL of 80:20, and 300 mL of 70:30 hexanes:EtOAc to yield 7-iodo-5-(trifluoromethyl)pyrrolo[2,1-f][1,2,4]triazin-4-amine (179.9 mg, 0.548 mmol, 62% yield) as a light tan solid.

MS ESI m/z 329.0 (M+H)$^+$

1H NMR (400 MHz, DMSO-d6) δ 8.06 (s, 1H), 7.86 (d, J=2.9 Hz, 1H), 7.10 (d, J=2.9 Hz, 1H).

1348B: tert-butyl 5-bromo-2-methoxynicotinate: DMAP (0.074 g, 0.603 mmol) was added to a partial solution of 5-bromo-2-methoxynicotinic acid (2.0 g, 8.62 mmol), tert-butanol (3.30 ml, 34.5 mmol) and DCC (2.67 g, 12.93 mmol) in dichloromethane (8.62 ml) at rt under N$_2$. The reaction flask was immersed in a sonicator for 1 min. Stirring was continued for 16 h. The reaction was diluted with dichloromethane (10 mL) and filtered through a pad of Celite. The filtrate was concentrated under vacuum to dryness, and the residual oil was diluted with ether (20 mL). The suspension was submitted to sonication for 2 min. The suspension was filtered through Celite and the filtrate was concentrated under vacuum to yield a yellow oil. The oil was dissolved in ether (20 mL) and filtered through a 25 mm syringe filter with a 0.45 micron Nylon membrane. The filtrate was concentrated under vacuum to yield a yellow oil. The crude product was completely dissolved in hexanes (20 mL) and sonicated for 2 min. A small amount of precipitate was removed by filtration through a syringe filter with a 0.45 micron Nylon membrane. The crude material was purified using flash chromatography on silica gel (Teledyne-Isco RediSep Rf 80 g column), eluting with 0-30% EtOAc in hexanes to yield tert-butyl 5-bromo-2-methoxynicotinate (1.6055 g, 5.57 mmol, 65%) as a colorless oil.

MS ESI m/z 288.0/290.0 (M+H)$^+$

¹H NMR (400 MHz, DMSO-d₆) δ 8.47 (d, J=2.6 Hz, 1H), 8.18 (d, J=2.6 Hz, 1H), 3.90 (s, 3H), 1.52 (s, 9H).

1348C: tert-butyl 2-methoxy-5-(4,4,5,5-tetramethyl-1,3,2-dioxaborolan-2-yl)nicotinate: A combination of tert-butyl 5-bromo-2-methoxynicotinate (1.59 g, 5.52 mmol), 4,4,4',4',5,5,5',5'-octamethyl-2,2'-bi(1,3,2-dioxaborolane) (1.68 g, 6.63 mmol) and potassium acetate (0.81 g, 8.29 mmol) in dioxane (27 mL) was degassed with nitrogen. While still degassing, 1,1'-bis(diphenylphosphino)ferrocene-palladium(II)dichloride dichloromethane complex (0.451 g, 0.552 mmol) was added. The reaction mixture was stirred at 80° C. 4 h. After cooling to rt, the reaction mixture was diluted with EtOAc (25 mL) and filtered through Celite, rinsing with EtOAc. The combined filtrate was washed with water, brine, dried over Na₂SO₄ and concentrated under vacuum to yield a brown oil. The crude product was dissolved in dichloromethane and purified using flash chromatography on silica gel (Teledyne-Isco RediSep Rf 80 g column), eluting with 0-30% EtOAc in hexanes. tert-Butyl 2-methoxy-5-(4,4,5,5-tetramethyl-1,3,2-dioxaborolan-2-yl)nicotinate (1.6681 g, 4.98 mmol, 90% yield) as a pale off-white solid.

MS ESI m/z 254.1 (M+H-82 tetramethylethylene)

¹H NMR (400 MHz, DMSO-d6) δ 8.52 (d, J=2.0 Hz, 1H), 8.37-7.84 (m, 1H), 3.95 (s, 3H), 1.53 (s, 9H), 1.31 (s, 12H).

1348D: tert-butyl 5-(4-amino-5-(trifluoromethyl)pyrrolo[2,1-f][1,2,4]triazin-7-yl)-2-methoxynicotinate: A combination of 5-iodo-7-(trifluoromethyl)pyrrolo[2,1-f][1,2,4]triazin-4-amine (71.5 mg, 0.218 mmol) and tert-butyl 2-methoxy-5-(4,4,5,5-tetramethyl-1,3,2-dioxaborolan-2-yl)nicotinate (94.8 mg, 0.283 mmol) in tripotassium phosphate (2.0 M aq solution) (330 µl, 0.654 mmol) was degassed with N₂. 1,1'-Bis(diphenylphosphino)ferrocene-palladium(II)dichloride dichloromethane complex (17.8 mg, 0.022 mmol) was added, followed by more N₂ degassing. The reaction mixture was heated at 105° C. 2.5 h. After cooling to rt, EtOAc and water were added. The layers were separated, the EtOAc layer was washed with brine, dried over Na₂SO₄, filtered through Celite and concentrated under vacuum to yield a pale tan solid. The crude product was dissolved in dichloromethane and purified using flash chromatography on silica gel (Teledyne-Isco RediSep Rf 12 g column), eluting with 0-40% EtOAc in hexanes, to yield tert-butyl 5-(4-amino-5-(trifluoromethyl)pyrrolo[2,1-f][1,2,4]triazin-7-yl)-2-methoxynicotinate (46.5 mg, 0.114 mmol, 52% yield) as an off-white solid.

MS ESI m/z 410.3/411.3 (M+H)⁺

¹H NMR (400 MHz, DMSO-d6) δ 8.95 (d, J=2.4 Hz, 1H), 8.72 (d, J=2.5 Hz, 1H), 8.18 (s, 1H), 7.63 (s, 1H), 3.99 (s, 3H), 1.55 (s, 9H).

1348E: 5-(4-amino-5-(trifluoromethyl)pyrrolo[2,1-f][1,2,4]triazin-7-yl)-2-methoxynicotinic acid, TFA: A solution of tert-butyl 5-(4-amino-5-(trifluoromethyl)pyrrolo[2,1-f][1,2,4]triazin-7-yl)-2-methoxynicotinate (42.2 mg, 0.103 mmol) in TFA (1985 µl, 25.8 mmol) was stirred at rt 75 min. Excess TFA was removed under vacuum, followed by 2 co-evaporations with ether to yield, after drying under vacuum, 5-(4-amino-5-(trifluoromethyl)pyrrolo[2,1-f][1,2,4]triazin-7-yl)-2-methoxynicotinic acid, TFA (44.0 mg, 0.078 mmol, 75% yield) as a pale yellow-tan solid.

MS ESI m/z 354.1/355.2 (M+H)⁺

¹H NMR (400 MHz, DMSO-d6) δ 8.95 (d, J=2.4 Hz, 1H), 8.81 (d, J=2.4 Hz, 1H), 8.28-7.99 (m, 1H), 7.63 (s, 1H), 3.99 (s, 3H).

1348: A solution of 5-(4-amino-5-(trifluoromethyl)pyrrolo[2,1-f][1,2,4]triazin-7-yl)-2-methoxynicotinic acid, TFA (15.0 mg, 0.042 mmol), (R)-1-(2-fluoro-5-(trifluoromethoxy)phenyl)ethan-1-amine, HCl (12.13 mg, 0.047 mmol), BOP (22.54 mg, 0.051 mmol) and triethylamine (20.71 µl, 0.149 mmol) in DMF (425 µl) was stirred at rt 80 min. The reaction was diluted with methanol and filtered through a syringe filter with a 0.45 micron Nylon membrane. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 46% B, 46-86% B over 20 min, then a 4-min hold at 100% B; Flow Rate: 20 mL/min; Column Temperature: 25° C. Fraction collection was triggered by MS and UV signals. Fractions containing the desired product were combined and dried via centrifugal evaporation to yield (2R)-1-{5-[4-amino-5-(trifluoromethyl)pyrrolo[2,1-f][1,2,4]triazin-7-yl]-2-methoxypyridin-3-yl}-2-[2-fluoro-5-(trifluoromethoxy)phenyl]propan-1-one (10 mg, 0.017 mmol, 41% yield).

MS ESI m/z 559.3/560.4 (M+H)⁺

¹H NMR (500 MHz, DMSO-d6) δ 8.88 (br s, 1H), 8.77 (br d, J=7.2 Hz, 1H), 8.59 (br s, 1H), 8.11 (s, 1H), 7.52 (s, 1H), 7.49 (br s, 1H), 7.40-7.18 (m, 2H), 5.43-5.26 (m, 1H), 4.04 (s, 3H), 1.48 (br d, J=6.9 Hz, 3H).

Example 1349: 5-[4-amino-5-(3,3-difluoroazetidine-1-carbonyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methoxypyridine-3-carboxamide

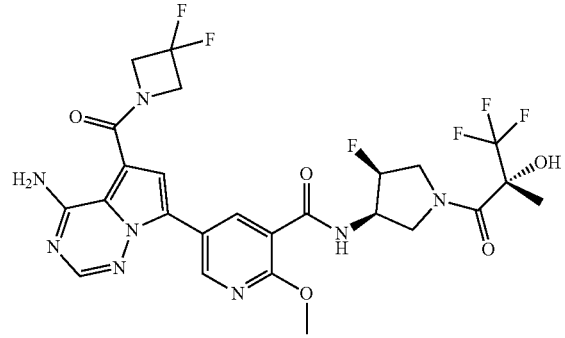 [SMILES: COc1ncc(-c2cc(C(=O)N3CC(F)(F)C3)c3c(N)ncnn23)cc1C(=O)N[C@@H]1CN(C(=O)[C@@](C)(O)C(F)(F)F)C[C@@H]1F]

1349A: 4-amino-7-bromopyrrolo[2,1-f][1,2,4]triazine-5-carboxylic acid, sodium salt: A suspension of ethyl 4-amino-7-bromopyrrolo[2,1-f][1,2,4]triazine-5-carboxylate (0.50 g, 1.754 mmol) in THF (5.3 mL), ethanol (5.3 mL) and 1 N sodium hydroxide (5.3 mL, 5.26 mmol) was stirred at 50° C. 16 h. Solvent was removed under vacuum to provide 4-amino-7-bromopyrrolo[2,1-f][1,2,4]triazine-5-carboxylic acid, sodium salt (0.4461 g, 1.73 mmol, 99%) as a white solid.

MS ESI m/z 257.0 (M+H)⁺

1349B: (4-amino-7-bromopyrrolo[2,1-f][1,2,4]triazin-5-yl)(3,3-difluoroazetidin-1-yl)methanone: To a stirred suspension of 4-amino-7-bromopyrrolo[2,1-f][1,2,4]triazine-5-carboxylic acid, sodium salt (0.15 g, 0.584 mmol), 3,3-difluoroazetidine, HCl (0.060 g, 0.642 mmol) and BOP (0.208 g, 0.700 mmol) in DMF at rt was added triethylamine (0.33 ml, 2.33 mmol). Stirring was continued for 2 h at rt, then the reaction mixture was warmed to 45° C. for 135 min. After cooling to rt, EtOAc and 10% aq LiCl solution were added. The layers were separated and the EtOAc layer was washed with 10% aq LiCl solution (2×), sat. aq NaHCO₃ solution (2×), brine, dried over Na$_2$SO$_4$ and evaporated under vacuum to yield (4-amino-7-bromopyrrolo[2,1-f][1,2,4]triazin-5-yl)(3,3-difluoroazetidin-1-yl)methanone (0.1689 g, 0.509 mmol, 87% yield) as a pale tan-orange solid. MS ESI m/z 333.9 (M+H)$^+$ $^1$H NMR (400 MHz, DMSO-d6) δ 9.55 (br s, 1H), 8.37 (br s, 1H), 8.09 (s, 1H), 7.27 (s, 1H), 5.23-4.95 (m, 2H), 4.71-4.37 (m, 2H).

1349C: tert-butyl (3R,4S)-3-(5-(4-amino-5-(3,3-difluoroazetidine-1-carbonyl)pyrrolo[2,1-f][1,2,4]triazin-7-yl)-2-methoxynicotinamido)-4-fluoropyrrolidine-1-carboxylate:

A vial charged with (4-amino-7-bromopyrrolo[2,1-f][1,2,4]triazin-5-yl)(3,3-difluoroazetidin-1-yl)methanone (90.0 mg, 0.271 mmol) and tert-butyl (3S,4R)-3-fluoro-4-(2-methoxy-5-(4,4,5,5-tetramethyl-1,3,2-dioxaborolan-2-yl)nicotinamido)pyrrolidine-1-carboxylate (164 mg, 0.3523 mmol) in tripotassium phosphate (2.0 M aq solution) (406 µl, 0.813 mmol) and dioxane (2.7 mL) was degassed with N$_2$. 1,1'-Bis(diphenylphosphino)ferrocene-palladium(II) dichloride dichloromethane complex (22.1 mg, 0.027 mmol) was added and more degassing with nitrogen followed. The vial was sealed and stirring was carried out at 105° C. for 2.5 h. After cooling to rt, the reaction mixture was diluted with EtOAc and water. The layers were separated and the EtOAc layer was washed with brine, dried over Na$_2$SO$_4$ and concentrated under vacuum to yield a light brown solid. The crude product was dissolved in dichloromethane and purified using flash chromatography on silica gel (Teledyne-Isco RediSep Rf 24 g column), eluting with 50 mL each of hexanes and 80:20 hexanes:EtOAc, followed by 200 mL of 1:1 hexanes:EtOAc, 200 mL of 98:2 CH$_2$Cl$_2$:CH$_3$OH and 100 mL of 95:5 CH$_2$Cl$_2$:CH$_3$OH to yield a somewhat sticky tan solid. The chromatographed product was suspended in ether, sonicated for 2 min, then stirred rapidly for 1 h. The solid was collected by filtration, rinsed with ether and dried under vacuum to yield tert-butyl (3R,4S)-3-(5-(4-amino-5-(3,3-difluoroazetidine-1-carbonyl)pyrrolo[2,1-f][1,2,4]triazin-7-yl)-2-methoxynicotinamido)-4-fluoropyrrolidine-1-carboxylate (98.1 mg, 0.166 mmol, 61% yield) as a tan solid.

MS ESI m/z 591.3/592.3 (M+H)$^+$

1H NMR (400 MHz, DMSO-d6) δ 9.61 (br s, 1H), 8.95 (d, J=2.3 Hz, 1H), 8.79 (br s, 1H), 8.49 (br d, J=7.3 Hz, 1H), 8.31 (br d, J=1.6 Hz, 1H), 8.09 (s, 1H), 7.49 (s, 1H), 5.37-5.19 (m, 1H), 5.15-4.89 (m, 1H), 4.85-4.40 (m, 3H), 4.05 (s, 1H), 4.03-3.99 (m, 1H), 3.83-3.71 (m, 1H), 3.64-3.50 (m, 1H), 3.27-3.12 (m, 1H), 1.43 (s, 9H).

1349D: 5-(4-amino-5-(3,3-difluoroazetidine-1-carbonyl)pyrrolo[2,1-f][1,2,4]triazin-7-yl)-N-((3R,4S)-4-fluoropyrrolidin-3-yl)-2-methoxynicotinamide, TFA salt: A solution of tert-butyl (3R,4S)-3-(5-(4-amino-5-(3,3-difluoroazetidine-1-carbonyl)pyrrolo[2,1-f][1,2,4]triazin-7-yl)-2-methoxynicotinamido)-4-fluoropyrrolidine-1-carboxylate (95.3 mg, 0.161 mmol) in TFA (1614 µl) was stirred at rt 55 min. Excess TFA was removed under vacuum, followed by two co-evaporations with ether. The crude product was suspended in ether, sonicated for 2 min, collected by filtration, rinsed with ether and dried under vacuum to yield 5-(4-amino-5-(3,3-difluoroazetidine-1-carbonyl)pyrrolo[2,1-f][1,2,4]triazin-7-yl)-N-((3R,4S)-4-fluoropyrrolidin-3-yl)-2-methoxynicotinamide, TFA salt (127.6 mg, 0.211 mmol, —100% yield) as a tan solid.

MS ESI m/z 491.2/492.2 (M+H)$^+$

1H NMR (400 MHz, DMSO-d6) δ 9.65 (br s, 1H), 9.52-9.28 (m, 1H), 9.13-9.01 (m, 1H), 8.96 (d, J=2.2 Hz, 1H), 8.79 (d, J=2.2 Hz, 1H), 8.60 (br d, J=7.6 Hz, 1H), 8.36 (br s, 1H), 8.10 (s, 1H), 7.62-7.35 (m, 1H), 5.51-5.30 (m, 1H), 5.23-4.97 (m, 2H), 4.91-4.76 (m, 1H), 4.68-4.39 (m, 2H), 4.05 (s, 3H), 3.80-3.47 (m, 3H), 3.34-3.06 (m, 1H).

1349: A solution of 5-(4-amino-5-(3,3-difluoroazetidine-1-carbonyl)pyrrolo[2,1-f][1,2,4]triazin-7-yl)-N-((3R,4S)-4-fluoropyrrolidin-3-yl)-2-methoxynicotinamide, TFA salt (15.0 mg, 0.025 mmol), (R)-3,3,3-trifluoro-2-hydroxy-2-methylpropanoic acid (4.3 mg, 0.027 mmol), BOP (13.17 mg, 0.030 mmol) and triethylamine (13.8 µl, 0.099 mmol) in DMF (248 µl) was stirred at rt 2.5 h. The reaction mixture was diluted with methanol and filtered through a 25 mm syringe filter with a 0.45 micron Nylon membrane. The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-min hold at 19% B, 19-59% B over 20 min, then a 6-min hold at 100% B; Flow Rate: 20 mL/min; Column Temperature: 25 C. Fraction collection was triggered by MS signals. Fractions containing the desired product were combined and dried via centrifugal evaporation to provide 5-[4-amino-5-(3,3-difluoroazetidine-1-carbonyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methoxypyridine-3-carboxamide (8.8 mg, 11.8 µmol, 47%).

MS ESI m/z 631.2/633.3 (M+H)$^+$

1H NMR (500 MHz, DMSO-d6) δ 9.59 (br s, 1H), 8.95 (br s, 1H), 8.81 (br d, J=2.9 Hz, 1H), 8.56-8.37 (m, 1H), 8.17 (br s, 1H), 8.08 (s, 1H), 7.53-7.40 (m, 1H), 5.42-5.16 (m, 1H), 5.02-4.80 (m, 2H), 4.75-4.59 (m, 2H), 4.52 (br t, J=9.1 Hz, 1H), 4.41-4.28 (m, 1H), 4.07 (s, 3H), 4.00-3.90 (m, 1H), 3.85-3.72 (m, 1H), 3.66-3.54 (m, 1H), 3.47-3.32 (m, 1H), 1.56 (s, 3H).

Example 1350: 5-[4-amino-5-(3,3-difluoroazetidine-1-carbonyl)pyrrolo[2,1-f][1,2,4]triazin-7-yl]-N-[(3R,4S)-1-(3,3-difluorocyclobutanecarbonyl)-4-fluoropyrrolidin-3-yl]-2-methoxypyridine-3-carboxamide

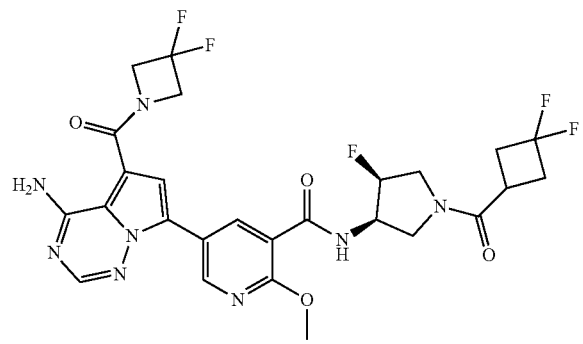 [SMILES: COc1ncc(-c2cc(C(=O)N3CC(F)(F)C3)c3c(N)ncnn23)cc1C(=O)N[C@@H]1CN(C(=O)C2CC(F)(F)C2)C[C@@H]1F]

A solution of 5-(4-amino-5-(3,3-difluoroazetidine-1-carbonyl)pyrrolo[2,1-f][1,2,4]triazin-7-yl)-N-((3R,4S)-4-fluoropyrrolidin-3-yl)-2-methoxynicotinamide, TFA salt (15.0 mg, 0.025 mmol), 3,3-difluorocyclobutane-1-carboxylic acid (3.72 mg, 0.027 mmol), BOP (13.17 mg, 0.030 mmol) and triethylamine (13.84 µl, 0.099 mmol) in DMF (248 µl) was stirred at rt 2.5 h. The reaction mixture was diluted with methanol and filtered through a 25 mm syringe filter with a 0.45 micron Nylon membrane. The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-min hold at 21% B, 21-61% B over 20 min, then a 6-min hold at 100% B; Flow Rate: 20 mL/min; Column Temperature: 25 C. Fraction collection was triggered by MS signals. Fractions containing the desired product were combined and dried via centrifugal evaporation to yield 5-[4-amino-5-(3,3-difluoroazetidine-1-carbonyl)pyrrolo[2,1-f][1,2,4]triazin-7-yl]-N-[(3R,4S)-1-(3,3-difluorocyclobutanecarbonyl)-4-fluoropyrrolidin-3-yl]-2-methoxypyridine-3-carboxamide (9.3 mg, 12.9 μmol, 52% yield).

MS ESI m/z 609.1 (M+H)+

1H NMR (500 MHz, DMSO-d6) δ 9.59 (br s, 1H), 8.94 (d, J=2.3 Hz, 1H), 8.81 (dd, J=19.9, 2.3 Hz, 1H), 8.45 (br t, J=8.6 Hz, 1H), 8.16 (br s, 1H), 8.08 (s, 1H), 7.52-7.39 (m, 1H), 5.52-5.19 (m, 1H), 5.03-4.53 (m, 3H), 4.07/4.08 (s, 3H altogether), 4.00-3.94 (m, 1H), 3.90-3.85 (m, 1H), 3.80 (br s, 1H), 3.75-3.69 (m, 1H), 3.47-3.38 (m, 1H), 3.32-3.22 (m, 1H), 3.20-3.10 (m, 1H), 3.00-2.69 (m, 4H).

Example 1351: 5-[4-amino-5-(trifluoromethyl)pyrrolo[2,1-f][1,2,4]triazin-7-yl]-N-[(1R)-1-[2-fluoro-5-(trifluoromethyl)phenyl]ethyl]-2-methoxypyridine-3-carboxamide

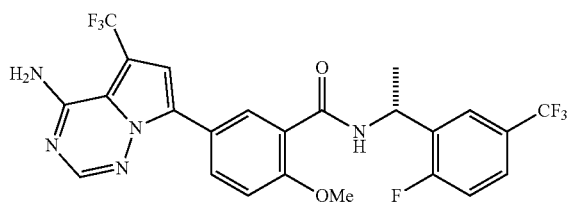 [SMILES: COc1ccc(-c2cc(C(F)(F)F)c3c(N)ncnn23)cc1C(=O)N[C@H](C)c1cc(C(F)(F)F)ccc1F]

Prepared as detailed in Example 31.
MS ESI m/z 543.4 (M+H)+
1H NMR (500 MHz, DMSO-d6) δ 8.98-8.88 (m, 2H), 8.61 (s, 1H), 8.15 (s, 1H), 7.94 (br d, J=5.8 Hz, 1H), 7.73 (br s, 1H), 7.61 (s, 1H), 7.46 (br t, J=9.3 Hz, 1H), 5.41 (quin, J=7.2 Hz, 1H), 4.03 (s, 3H), 1.48 (br d, J=7.0 Hz, 3H).

Example 1352: 5-[4-amino-5-(trifluoromethyl)pyrrolo[2,1-f][1,2,4]triazin-7-yl]-2-methoxy-N-[(2-phenoxyphenyl)methyl]pyridine-3-carboxamide

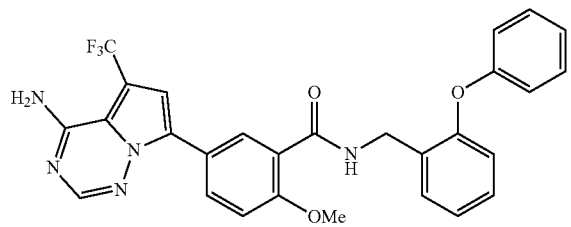 [SMILES: COc1ccc(-c2cc(C(F)(F)F)c3c(N)ncnn23)cc1C(=O)NCc1ccccc1Oc1ccccc1]

Prepared as detailed in Example 31.
MS ESI m/z 535.5 (M+H)+

1H NMR (500 MHz, DMSO-d6) δ 8.87 (d, J=2.3 Hz, 1H), 8.74 (d, J=2.3 Hz, 1H), 8.68 (br t, J=5.7 Hz, 1H), 8.13 (s, 1H), 7.53 (s, 1H), 7.46 (br d, J=7.4 Hz, 1H), 7.36 (br t, J=7.9 Hz, 2H), 7.29 (br t, J=7.2 Hz, 1H), 7.17 (br t, J=7.4 Hz, 1H), 7.09 (br t, J=7.3 Hz, 1H), 6.98 (br d, J=7.9 Hz, 2H), 6.89 (br d, J=8.0 Hz, 1H), 4.55 (br d, J=5.9 Hz, 2H), 3.99 (s, 3H).

Example 1353: 5-(4-Amino-5-(trifluoromethyl)pyrrolo[2,1-f][1,2,4]triazin-7-yl)-N-((3R,4S)-4-fluoro-1-(3-methyl-2,3-dihydro-1H-inden-1-yl)pyrrolidin-3-yl)-2-methoxynicotinamide

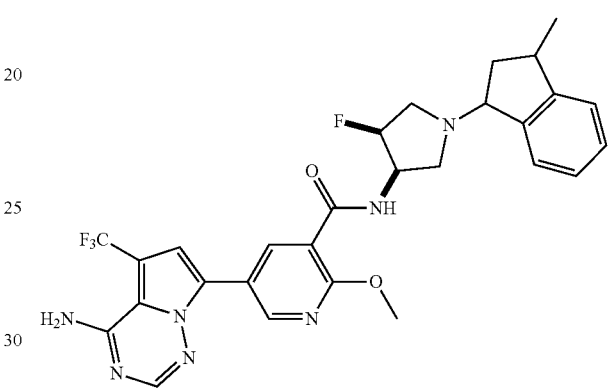

In a 1 dram vial were combined 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide (20 mg, 0.046 mmol) with 3-methylindan-1-one (16.64 mg, 0.114 mmol, 2.5 eq.) in a mixture of MeOH (0.300 mL) and AcOH (0.075 mL). To the mixture was added borane-2-picoline complex (19.48 mg, 0.182 mmol, 4 eq.) The mixture was heated to 50° C. and stirred ON. The crude mixture was filtered and purified via preparative LC/MS with the following conditions: Column=XBridge C18, 200 mm×19 mm, 5-μm particles; Mobile Phase A=5:95 acetonitrile:water with 10-mM ammonium acetate; Mobile Phase B=95:5 acetonitrile:water with 10-mM ammonium acetate; Gradient=39-79% B over 25 minutes, then a 4-minute hold at 100% B; Flow Rate=20 mL/min; Column Temperature=25° C. Fractions containing the desired product were combined and dried via centrifugal evaporation to give the desired product (12.7 mg, 49% yield) as a mixture of two diastereomers.

MS ESI m/z 570.2 (M+H)+

1H NMR (500 MHz, DMSO-d6) δ 8.80 (br s, 1H), 8.74 (br d, J=6.4 Hz, 1H), 8.68 (br s, 1H), 8.04 (s, 1H), 7.50-7.40 (m, 2H), 7.40-7.26 (m, 3H), 5.43 (br s, 0.5H), 5.36-5.30 (m, 0.5H), 5.05-4.93 (m, 1H), 4.87-4.67 (m, 1H), 4.43-4.34 (m, 1H), 3.99 (br s, 3H), 3.77-3.57 (m, 2H), 3.48-3.31 (m, 1H), 3.17-3.09 (m, 1H), 2.72 (m, 1H), 1.65-1.53 (m, 1H), 1.34-1.27 (m, 3H).

TABLE 50

Compounds in Table 50 were prepared similarly to the methods detailed in Example 1353. In some cases where low or incomplete conversion to desired product was observed by analytical LCMS of the crude reaction mixture, additional ketone or aldehyde starting material (2.5 additional equivalents) and/or additional borane-2-picoline complex (4 additional equivalents) was added to the crude mixture along with further heating of the resulting mixture to 55° C. ON to improve reaction outcomes. The majority of cases provided a mixture of two or more diastereomers as the final product. When diastereomers were separated, they are included as separate entries which may be either a single diastereomer or a mixture of two or more diastereomers depending on the stereochemistry of the aldehyde or ketone starting material and upon the preparative HPLC outcome. Products in this table bearing a secondary free alcohol moiety on a carbon atom adjacent to a fluorinated carbon atom were the result of an additional reduction of a ketone moiety to a secondary alcohol during the reaction. For each example, two analytical LCMS injections with matched stationary phase columns were used to determine final purity. The method(s) used are indicated in each case. Method 1-6 as described in the Methods of Preparation Section.

| Ex | Name | R | Obs. MS Ion M+ (method) | NMR Assignments (500 MHz, DMSO-d6) δ or LCMS retention time |
|---|---|---|---|---|
| 1354 | 5-[4-amino-5-(trifluoromethyl)-pyrrolo[2,1-f][1,2,4]triazin-7-yl]-N-[(3R,4S)-1-(2,3-dihydro-1H-inden-1-yl)-4-fluoro-pyrrolidin-3-yl]-2-methoxy-pyridine-3-carboxamide | 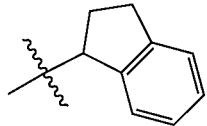<br>Mixture of 2 isomers | 556.2 (1) | LCMS Method 1 retention time = 1.48 min LCMS Method 2 retention time = 2.24 min |
| 1355 | 5-[4-amino-5-(trifluoromethyl)-pyrrolo[2,1-f][1,2,4]triazin-7-yl]-N-[(3R,4S)-4-fluoro-1-(4-fluoro-2,3-dihydro-1H-inden-1-yl)pyrrolidin-3-yl]-2-methoxypyridine-3-carboxamide | 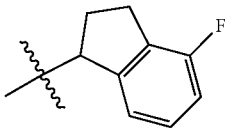<br>Mixture of 2 isomers | 574.2 (2) | 8.94-8.90 (m, 1H), 8.85-8.82 (m, 1H), 8.41 (br d, J = 7.6 Hz, 1H), 8.17 (d, J = 2.1 Hz, 1H), 7.61 (d, J = 2.7 Hz, 1H), 7.29-7.22 (m, 1H), 7.21-7.17 (m, 1H), 7.04 (t, J = 8.6 Hz, 1H), 5.28-5.24 (m, 0.5H), 5.17-5.13 (m, 0.5H), 4.55-4.43 (m, 1H), 4.42-4.38 (m, 1H), 4.07-4.03 (m, 3H), 3.01-2.78 (m, 4H), 2.70-2.63 (m, 1H), 2.23-2.14 (m, 1H), 2.13-2.03 (m, 1H). |
| 1356 | 5-[4-amino-5-(trifluoromethyl)-pyrrolo[2,1-f][1,2,4]triazin-7-yl]-N-[(3R,4S)-4-fluoro-1-(5-fluoro-2,3-dihydro-1H-inden-1-yl)pyrrolidin-3-yl]-2-methoxypyridine-3-carbox-amide | 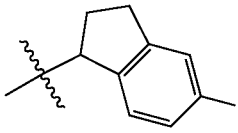<br>Mixture of 2 isomers | 574.2 (2) | 8.94-8.87 (m, 1H), 8.86-8.82 (m, 1H), 8.41 (br d, J = 7.6 Hz, 1H), 8.19-8.15 (m, 1H), 7.61 (s, 1H), 7.34 (t, J = 6.4 Hz, 1H), 7.08 (br d, J = 9.3 Hz, 1H), 7.03-6.97 (m, 1H), 5.26 (t, J = 4.7 Hz, 0.5H), 5.15 (t, J = 4.8 Hz, 0.5H), 4.54-4.43 (m, 1H), 4.28 (br t, J = 6.1 Hz, 1H), 4.07-4.02 (m, 3H), 3.29-3.07 (m, 1H), 3.03-2.91 (m, 2H), 2.89-2.75 (m, 2H), 2.67-2.62 (m, 1H), 2.20-2.00 (m, 2H). |
| 1357 | 5-[4-amino-5-(trifluoromethyl)-pyrrolo[2,1-f][1,2,4]triazin-7-yl]-N-[(3R,4S)-4-fluoro-1-{6,7,8,9-tetrahydro-5H-benzo[7]annulen-5-yl}pyrrolidin-3-yl]-2-methoxypyridine-3-carboxamide | 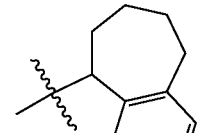<br>Mixture of 2 isomers | 584.2 (2) | 8.91 (dd, J = 4.3, 2.4 Hz, 1H), 8.86 (d, J = 2.4 Hz, 0.45H), 8.83 (d, J = 2.4 Hz, 0.55H), 8.41 (br d, J = 7.8 Hz, 1H), 8.17 (d, J = 3.2 Hz, 1H), 7.61 (d, J = 3.5 Hz, 1H), 7.21-7.06 (m, 4H), 5.30-5.25 (m, 0.5H), 5.18-5.15 (m, 0.5H), 4.62-4.47 (m, 1H), 4.07 (s, 1.4H), 4.05 (s, 1.6H), 3.40-3.33 (m, 2H), 3.16-3.05 (m, 1H), 2.92-2.81 (m, 1H), 2.74-2.62 (m, 1H), 2.62-2.52 (m, 2H), 2.32-2.25 (m, 1H), 2.09-1.97 (m, 2H), 1.95-1.85 (m, 1H), 1.75-1.66 (m, 1H), 1.62-1.49 (m, 1H), 1.32-1.20 (m, 1H). |

TABLE 50-continued

Compounds in Table 50 were prepared similarly to the methods detailed in Example 1353. In some cases where low or incomplete conversion to desired product was observed by analytical LCMS of the crude reaction mixture, additional ketone or aldehyde starting material (2.5 additional equivalents) and/or additional borane-2-picoline complex (4 additional equivalents) was added to the crude mixture along with further heating of the resulting mixture to 55° C. ON to improve reaction outcomes. The majority of cases provided a mixture of two or more diastereomers as the final product. When diastereomers were separated, they are included as separate entries which may be either a single diastereomer or a mixture of two or more diastereomers depending on the stereochemistry of the aldehyde or ketone starting material and upon the preparative HPLC outcome. Products in this table bearing a secondary free alcohol moiety on a carbon atom adjacent to a fluorinated carbon atom were the result of an additional reduction of a ketone moiety to a secondary alcohol during the reaction. For each example, two analytical LCMS injections with matched stationary phase columns were used to determine final purity. The method(s) used are indicated in each case. Method 1-6 as described in the Methods of Preparation Section.

| Ex | Name | R | Obs. MS Ion M+ (method) | NMR Assignments (500 MHz, DMSO-d6) δ or LCMS retention time |
|---|---|---|---|---|
| 1358 | 5-[4-amino-5-(trifluoromethyl)-pyrrolo[2,1-f][1,2,4]triazin-7-yl]-N-[(3R,4S)-4-fluoro-1-(4-methyl-1,2,3,4-tetrahydronaphthalen-1-yl)pyrrolidin-3-yl]-2-methoxypyridine-3-carboxamide | 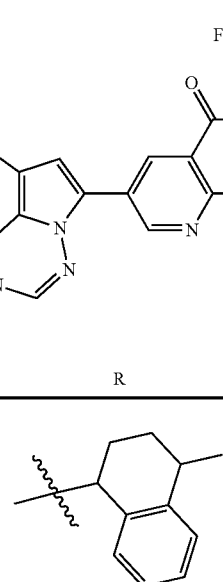<br>Mixture of 2 isomers | 584.2 (2) | 8.91 (br s, 1H), 8.84 (br s, 1H), 8.44 (m, 1H), 8.16 (s, 1H), 7.61 (s, 1H), 7.48-7.36 (m, 1H), 7.33-7.11 (m, 3H), 5.31-5.24 (m, 0.5H), 5.19-5.13 (m, 0.5H), 4.56-4.43 (m, 1H), 4.09-4.02 (m, 3H), 3.75 (br d, J = 18.9 Hz, 0.6H), 3.42 (br d, J = 5.8 Hz, 0.4H), 3.17 (br d, J = 4.0 Hz, 0.4H), 3.03-2.83 (m, 1.6H), 2.80-2.68 (m, 1H), 1.86 (br d, J = 6.4 Hz, 2H), 1.76 (br d, J = 9.2 Hz, 2H), 1.29-1.19 (m, 5H). |
| 1359 | 5-[4-amino-5-(trifluoromethyl)-pyrrolo[2,1-f][1,2,4]triazin-7-yl]-N-[(3R,4S)-1-(5-bromo-1,2,3,4-tetrahydronaphthalen-1-yl)-4-fluoropyrrolidin-3-yl]-2-methoxypyridine-3-carboxamide | 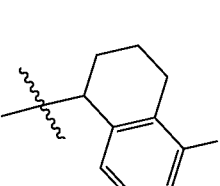<br>Mixture of 2 isomers | 648.1 (2) | 8.93-8.88 (m, 1H), 8.87-8.81 (m, 1H), 8.43 (br d, J = 7.0 Hz, 1H), 8.17 (s, 1H), 7.61 (s, 1H), 7.53-7.44 (m, 2H), 7.17-7.08 (m, 1H), 5.27 (br s, 0.5H), 5.16 (br s, 0.5H), 4.57-4.42 (m, 1H), 4.09-4.01 (m, 3H), 3.76 (br s, 1H), 2.95-2.81 (m, 1H), 2.79-2.67 (m, 3H), 2.07 (br d, J = 5.5 Hz, 1H), 1.87-1.65 (m, 3H), 1.22 (br s, 2H). |
| 1360 | 5-[4-amino-5-(trifluoromethyl)-pyrrolo[2,1-f][1,2,4]triazin-7-yl]-N-[(3R,4S)-1-(7-chloro-2,3-dihydro-1H-inden-1-yl)-4-fluoropyrrolidin-3-yl]-2-methoxypyridine-3-carboxamide | 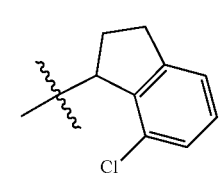<br>Mixture of 2 isomers | 590.2 (1) | 8.92-8.87 (m, 1H), 8.85-8.82 (m, 1H), 8.43-8.35 (m, 1H), 8.20-8.08 (m, 1H), 7.64-7.58 (m, 1H), 7.30-7.21 (m, 3H), 5.28-5.21 (m, 0.5H), 5.17-5.11 (m, 0.5H), 4.52-4.42 (m, 1H), 4.42-4.35 (m, 1H), 4.08-4.01 (m, 3H), 3.91 (s, 1H), 3.19-3.04 (m, 2H), 3.00-2.94 (m, 1H), 2.90-2.73 (m, 2H), 2.69-2.58 (m, 1H), 2.22-2.12 (m, 1H), 2.10-1.99 (m, 1H). |
| 1361 | 5-[4-amino-5-(trifluoromethyl)-pyrrolo[2,1-f][1,2,4]triazin-7-yl]-N-[(3R,4S)-4-fluoro-1-(1,2,3,4-tetrahydronaphthalen-1-yl)pyrrolidin-3-yl]-2-methoxypyridine-3-carboxamide | 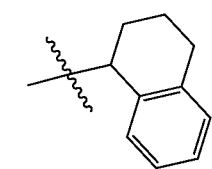<br>Mixture of 2 isomers | 570.2 (1) | 8.94-8.88 (m, 1H), 8.84 (s, 1H), 8.43 (br d, J = 7.3 Hz, 1H), 8.17 (s, 1H), 7.61 (s, 1H), 7.47-7.35 (m, 1H), 7.13 (br s, 2H), 7.08 (br d, J = 6.1 Hz, 1H), 5.27 (br s, 0.5H), 5.16 (br s, 0.5H), 4.56-4.43 (m, 1H), 4.09-4.01 (m, 3H), 3.76 (br s, 1H), 3.43-3.35 (m, 1H), 2.94-2.66 (m, 4H), 2.07-1.91 (m, 1H), 1.80 (br d, J = 5.2 Hz, 2H), 1.70-1.61 (m, 1H), 1.24-1.20 (m, 1H). |

TABLE 50-continued

Compounds in Table 50 were prepared similarly to the methods detailed in Example 1353. In some cases where low or incomplete conversion to desired product was observed by analytical LCMS of the crude reaction mixture, additional ketone or aldehyde starting material (2.5 additional equivalents) and/or additional borane-2-picoline complex (4 additional equivalents) was added to the crude mixture along with further heating of the resulting mixture to 55° C. ON to improve reaction outcomes. The majority of cases provided a mixture of two or more diastereomers as the final product. When diastereomers were separated, they are included as separate entries which may be either a single diastereomer or a mixture of two or more diastereomers depending on the stereochemistry of the aldehyde or ketone starting material and upon the preparative HPLC outcome. Products in this table bearing a secondary free alcohol moiety on a carbon atom adjacent to a fluorinated carbon atom were the result of an additional reduction of a ketone moiety to a secondary alcohol during the reaction. For each example, two analytical LCMS injections with matched stationary phase columns were used to determine final purity. The method(s) used are indicated in each case. Method 1-6 as described in the Methods of Preparation Section.

| Ex | Name | R | Obs. MS Ion M+ (method) | NMR Assignments (500 MHz, DMSO-d6) δ or LCMS retention time |
|---|---|---|---|---|
| 1362 | 5-[4-amino-5-(trifluoromethyl)-pyrrolo[2,1-f][1,2,4]triazin-7-yl]-N-[(3R,4S)-4-fluoro-1-[2-(2,2,2-trifluoro-1-hydroxy-ethyl)cyclopentyl]pyrrolidin-3-yl]-2-methoxypyridine-3-carboxamide | 1-5 isomers | 606.2 (2) | 8.92 (s, 1H), 8.85 (br s, 1H), 8.52-8.38 (m, 1H), 8.18 (s, 1H), 7.62 (s, 1H), 6.30-6.22 (m, 1H), 5.26 (br s, 0.5H), 5.14 (br s, 0.5H), 4.50 (m, 1H), 4.05 (m, 4H), 3.38-3.33 (m, 1H), 3.18-3.09 (m, 1H), 3.02-2.93 (m, 1H), 2.90-2.79 (m, 1H), 2.69-2.60 (m, 1H), 2.04-1.94 (m, 1H), 1.76-1.67 (m, 1H), 1.66-1.49 (m, 5H). |
| 1363 | 5-[4-amino-5-(trifluoromethyl)-pyrrolo[2,1-f][1,2,4]triazin-7-yl]-N-[(3R,4S)-4-fluoro-1-(2-methylcyclopentyl)-pyrrolidin-3-yl]-2-methoxy-pyridine-3-carboxamide | 1-3 isomers | 522.2 (2) | 8.91 (s, 1H), 8.86 (s, 1H), 8.44 (br s, 1H), 8.18 (s, 1H), 7.62 (s, 1H), 5.25 (br s, 0.5H), 5.14 (br d, J = 5.2 Hz, 0.5H), 4.60-4.42 (m, 1H), 4.05 (s, 3H), 3.37 (br d, J = 7.6 Hz, 1H), 3.17 (d, J = 4.9 Hz, 1H), 1.97-1.64 (m, 3H), 1.55 (br s, 3H), 1.20-1.11 (m, 1H), 0.99 (br d, J = 5.5 Hz, 3H). |
| 1364 | 5-[4-amino-5-(trifluoromethyl)-pyrrolo[2,1-f][1,2,4]triazin-7-yl]-N-[(3R,4S)-1-{5H,6H,7H-cyclopenta[b]pyridin-5-yl}-4-fluoropyrrolidin-3-yl]-2-methoxypyridine-3-carboxamide | Mixture of 2 isomers | 557.2 (1) | 8.90 (br d, J = 2.4 Hz, 1H), 8.83 (d, J = 4.8 Hz, 1H), 8.82 (s, 1H), 8.47-8.36 (m, 2H), 8.17 (s, 1H), 7.72 (br t, J = 6.9 Hz, 1H), 7.61 (br s, 1H), 7.19 (br d, J = 3.7 Hz, 1H), 5.27 (br s, 0.5H), 5.15 (br s, 0.5H), 4.55-4.44 (m, 1H), 4.36 (br s, 1H), 4.06-4.01 (m, 1H), 3.40-3.34 (m, 1H), 3.22-3.09 (m, 1H), 3.05-2.95 (m, 2H), 2.94-2.79 (m, 2H), 2.71-2.63 (m, 1H), 2.23-2.14 (m, 1H), 2.06 (br d, J = 5.2 Hz, 1H). |
| 1365 | 5-[4-amino-5-(trifluoromethyl)-pyrrolo[2,1-f][1,2,4]triazin-7-yl]-N-[(3R,4S)-1-(2,2-dimethylcyclopentyl)-4-fluoropyrrolidin-3-yl]-2-methoxypyridine-3-carboxamide | 1 isomer | 536.2 (2) | $^1$H NMR (500 MHz, DMSO-d$_6$) δ 8.91 (s, 1H), 8.87 (s, 1H), 8.44 (br d, J = 7.9 Hz, 1H), 8.18 (s, 1H), 7.62 (s, 1H), 5.23 (br s, 0.5H), 5.11 (br s, 0.5H), 4.54-4.44 (m, 1H), 4.06 (s, 3H), 3.08-2.97 (m, 2H), 2.92-2.82 (m, 1H), 2.31-2.18 (m, 2H), 1.89-1.82 (m, 1H), 1.61-1.52 (m, 2H), 1.52-1.37 (m, 4H), 1.08 (s, 3H), 0.89 (s, 3H), 0.87-0.84 (m, 1H). |

TABLE 50-continued

Compounds in Table 50 were prepared similarly to the methods detailed in Example 1353. In some cases where low or incomplete conversion to desired product was observed by analytical LCMS of the crude reaction mixture, additional ketone or aldehyde starting material (2.5 additional equivalents) and/or additional borane-2-picoline complex (4 additional equivalents) was added to the crude mixture along with further heating of the resulting mixture to 55° C. ON to improve reaction outcomes. The majority of cases provided a mixture of two or more diastereomers as the final product. When diastereomers were separated, they are included as separate entries which may be either a single diastereomer or a mixture of two or more diastereomers depending on the stereochemistry of the aldehyde or ketone starting material and upon the preparative HPLC outcome. Products in this table bearing a secondary free alcohol moiety on a carbon atom adjacent to a fluorinated carbon atom were the result of an additional reduction of a ketone moiety to a secondary alcohol during the reaction. For each example, two analytical LCMS injections with matched stationary phase columns were used to determine final purity. The method(s) used are indicated in each case. Method 1-6 as described in the Methods of Preparation Section.

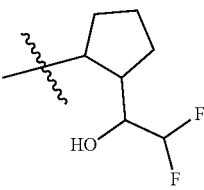

| Ex | Name | R | Obs. MS Ion M+ (method) | NMR Assignments (500 MHz, DMSO-d6) δ or LCMS retention time |
|---|---|---|---|---|
| 1366 | 5-[4-amino-5-(trifluoromethyl)-pyrrolo[2,1-f][1,2,4]triazin-7-yl]-N-[(3R,4S)-1-[2-(2,2-difluoro-1-hydroxyethyl)-cyclopentyl]-4-fluoro-pyrrolidin-3-yl]-2-methoxy-pyridine-3-carboxamide | 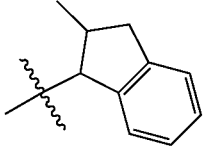<br>1-5 isomers | 588.2 (1) | 8.91 (s, 1H), 8.85 (br s, 1H), 8.43 (br s, 1H), 8.18 (s, 1H), 7.62 (s, 1H), 5.88 (t, J = 55.8 Hz, 1H), 5.25 (br s, 0.5H), 5.17-5.11 (m, 0.5H), 4.56-4.41 (m, 1H), 4.05 (s, 3H), 3.71 (br d, J = 3.4 Hz, 1H), 2.01-1.84 (m, 1H), 1.69-1.43 (m, 7H). |
| 1367 | 5-[4-amino-5-(trifluoromethyl)-pyrrolo[2,1-f][1,2,4]triazin-7-yl]-N-[(3R,4S)-4-fluoro-1-(2-methyl-2,3-dihydro-1H-inden-1-yl)pyrrolidin-3-yl]-2-methoxypyridine-3-carboxamide | 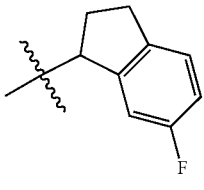<br>Mixture of 2 isomers | 570.2 (1) | 8.90 (d, J = 9.2 Hz, 1H), 8.83 (dd, J = 12.4, 2.0 Hz, 1H), 8.43-8.26 (m, 1H), 8.17 (br d, J = 3.1 Hz, 1H), 7.61 (d, J = 5.8 Hz, 1H), 7.36 (dd, J = 15.6, 7.0 Hz, 1H), 7.28-7.16 (m, 3H), 5.19 (br s, 0.5H), 5.08 (br s, 0.5H), 4.47-4.31 (m, 1H), 4.19-4.07 (m, 1H), 4.06-3.99 (m, 3H), 3.39 (br d, J = 9.8 Hz, 1H), 3.27-3.06 (m, 1H), 3.05-2.79 (m, 3H), 2.65-2.53 (m, 2H), 2.47-2.40 (m, 1H), 1.20-1.08 (m, 3H). |
| 1368 | 5-[4-amino-5-(trifluoromethyl)-pyrrolo[2,1-f][1,2,4]triazin-7-yl]-N-[(3R,4S)-4-fluoro-1-(6-fluoro-2,3-dihydro-1H-inden-1-yl)pyrrolidin-3-yl]-2-methoxypyridine-3-carboxamide | 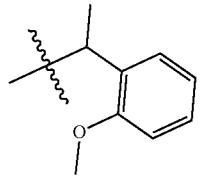<br>Mixture of 2 isomers | 574.1 (2) | 8.90 (d, J = 2.4 Hz, 1H), 8.84-8.81 (m, 1H), 8.43 (br d, J = 7.3 Hz, 1H), 8.17 (s, 1H), 7.61 (s, 1H), 7.29-7.23 (m, 1H), 7.11 (br d, J = 9.2 Hz, 1H), 7.03 (br t, J = 8.7 Hz, 1H), 5.26 (br s, 0.5H), 5.15 (br s, 0.5H), 4.55-4.43 (m, 1H), 4.37-4.32 (m, 1H), 4.07-4.01 (m, 3H), 3.39 (br d, J = 9.5 Hz, 1H), 3.29-2.62 (m, 6H), 2.22-2.12 (m, 1H), 2.09-2.00 (m, 1H). |
| 1369 | 5-[4-amino-5-(trifluoromethyl)-pyrrolo[2,1-f][1,2,4]triazin-7-yl]-N-[(3R,4S)-4-fluoro-1-[1-(2-methoxyphenyl)ethyl]-pyrrolidin-3-yl]-2-methoxy-pyridine-3-carboxamide | <br>1 isomer | 574.2 (2) | 8.90 (s, 1H), 8.82 (s, 1H), 8.44 (br s, 1H), 8.16 (s, 1H), 7.60 (s, 1H), 7.42 (br d, J = 7.3 Hz, 1H), 7.23 (br s, 1H), 7.07-6.94 (m, 2H), 5.26 (br s, 0.5H), 5.15 (br s, 0.5H), 4.55-4.44 (m, 1H), 4.04 (s, 3H), 4.01-3.87 (m, 1H), 3.83-3.75 (m, 3H), 3.42-3.36 (m, 1H), 2.83 (br s, 1H), 2.78 (s, 1H), 2.71 (br s, 1H), 1.28 (br s, 3H). LCMS Method 1 retention time = 1.52 min LCMS Method 2 |

US 11,618,753 B2

TABLE 50-continued

Compounds in Table 50 were prepared similarly to the methods detailed in Example 1353. In some cases where low or incomplete conversion to desired product was observed by analytical LCMS of the crude reaction mixture, additional ketone or aldehyde starting material (2.5 additional equivalents) and/or additional borane-2-picoline complex (4 additional equivalents) was added to the crude mixture along with further heating of the resulting mixture to 55° C. ON to improve reaction outcomes. The majority of cases provided a mixture of two or more diastereomers as the final product. When diastereomers were separated, they are included as separate entries which may be either a single diastereomer or a mixture of two or more diastereomers depending on the stereochemistry of the aldehyde or ketone starting material and upon the preparative HPLC outcome. Products in this table bearing a secondary free alcohol moiety on a carbon atom adjacent to a fluorinated carbon atom were the result of an additional reduction of a ketone moiety to a secondary alcohol during the reaction. For each example, two analytical LCMS injections with matched stationary phase columns were used to determine final purity. The method(s) used are indicated in each case. Method 1-6 as described in the Methods of Preparation Section.

| Ex | Name | R | Obs. MS Ion M+ (method) | NMR Assignments (500 MHz, DMSO-d6) δ or LCMS retention time |
|---|---|---|---|---|
| | | | | retention time = 2.19 min |
| 1370 | 5-[4-amino-5-(trifluoromethyl)-pyrrolo[2,1-f][1,2,4]triazin-7-yl]-N-[(3R,4S)-4-fluoro-1-[1-(2-methoxyphenyl)ethyl]-pyrrolidin-3-yl]-2-methoxy-pyridine-3-carboxamide | 1 isomer | 574.2 (2) | LCMS Method 1 retention time = 1.52 min LCMS Method 2 retention time = 2.22 min |
| 1371 | methyl 2-[(3R,4S)-3-{5-[4-amino-5-(trifluoromethyl)-pyrrolo[2,1-f][1,2,4]triazin-7-yl]-2-methoxypyridine-3-amido}-4-fluoropyrrolidin-1-yl]cyclopentane-1-carboxylate | 1-3 isomers | 566.2 (2) | 8.94-8.86 (m, 2H), 8.49-8.34 (m, 1H), 8.18 (s, 1H), 7.62 (s, 1H), 5.23 (br s, 0.5H), 5.12 (br s, 0.5H), 4.52-4.42 (m, 1H), 4.06 (s, 3H), 3.59 (s, 2H), 3.53 (s, 1H), 3.38-3.32 (m, 1H), 3.18 (br s, 1H), 3.08-2.98 (m, 1H), 2.95 (br s, 1H), 2.91-2.81 (m, 1H), 2.81-2.70 (m, 1H), 2.60-2.53 (m, 1H), 1.91-1.77 (m, 4H), 1.76-1.63 (m, 1H), 1.63-1.53 (m, 1H). |
| 1372 | 5-[4-amino-5-(trifluoromethyl)-pyrrolo[2,1-f][1,2,4]triazin-7-yl]-N-[(3R,4S)-1-[2-(2,2-difluoro-1-hydroxyethyl)-cyclopentyl]-4-fluoro-pyrrolidin-3-yl]-2-methoxy-pyridine-3-carboxamide | 1-5 isomers | 588.2 (1) | 8.91 (s, 1H), 8.85 (s, 1H), 8.46-8.36 (m, 1H), 8.18 (s, 1H), 7.62 (s, 1H), 6.10-5.84 (m, 1H), 5.24 (br s, 0.5H), 5.13 (br s, 0.5H), 4.55-4.44 (m, 1H), 4.05 (s, 3H), 3.60-3.52 (m, 1H), 3.39-3.33 (m, 1H), 3.17 (br d, J = 4.9 Hz, 1H), 3.09-2.96 (m, 1H), 2.92 (br s, 1H), 2.64 (br s, 1H), 1.99 (br s, 1H), 1.69 (br s, 1H), 1.59 (br s, 4H), 1.42 (br d, J = 5.2 Hz, 1H). |
| 1373 | 5-[4-amino-5-(trifluoromethyl)-pyrrolo[2,1-f][1,2,4]triazin-7-yl]-N-[(3R,4S)-1-[2-(2,2-difluoro-1-hydroxyethyl)-cyclopentyl]-4-fluoro-pyrrolidin-3-yl]-2-methoxy-pyridine-3-carboxamide | 1-5 isomers | 588.2 (1) | 8.94-8.85 (m, 2H), 8.49-8.41 (m, 1H), 8.18 (s, 1H), 7.62 (s, 1H), 6.03-5.77 (m, 1H), 5.27 (br s, 0.5H), 5.15 (br s, 0.5H), 4.53 (br dd, J = 14.3, 7.9 Hz, 1H), 4.06 (s, 3H), 3.99-3.89 (m, 1H), 3.41-3.33 (m, 1H), 3.03 (br d, J = 8.5 Hz, 1H), 2.95 (br s, 1H), 2.92-2.79 (m, 1H), 2.65 (br d, J = 7.9 Hz, 1H), 2.61-2.54 (m, 1H), 2.07 (br s, 1H), 1.85 (br s, |

TABLE 50-continued

Compounds in Table 50 were prepared similarly to the methods detailed in Example 1353. In some cases where low or incomplete conversion to desired product was observed by analytical LCMS of the crude reaction mixture, additional ketone or aldehyde starting material (2.5 additional equivalents) and/or additional borane-2-picoline complex (4 additional equivalents) was added to the crude mixture along with further heating of the resulting mixture to 55° C. ON to improve reaction outcomes. The majority of cases provided a mixture of two or more diastereomers as the final product. When diastereomers were separated, they are included as separate entries which may be either a single diastereomer or a mixture of two or more diastereomers depending on the stereochemistry of the aldehyde or ketone starting material and upon the preparative HPLC outcome. Products in this table bearing a secondary free alcohol moiety on a carbon atom adjacent to a fluorinated carbon atom were the result of an additional reduction of a ketone moiety to a secondary alcohol during the reaction. For each example, two analytical LCMS injections with matched stationary phase columns were used to determine final purity. The method(s) used are indicated in each case. Method 1-6 as described in the Methods of Preparation Section.

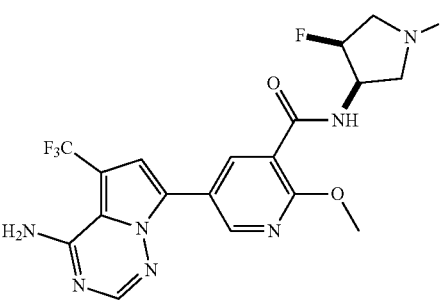

| Ex | Name | R | Obs. MS Ion M+ (method) | NMR Assignments (500 MHz, DMSO-d6) δ or LCMS retention time |
|---|---|---|---|---|
| | | | | 1H), 1.70 (br s, 3H), 1.63 (br d, J = 10.4 Hz, 1H), 1.51 (br s, 1H). |
| 1374 | 5-[4-amino-5-(trifluoromethyl)-pyrrolo[2,1-f][1,2,4]triazin-7-yl]-N-[(3R,4S)-1-[2-(2,2-difluoro-1-hydroxyethyl)-cyclopentyl]-4-fluoro-pyrrolidin-3-yl]-2-methoxy-pyridine-3-carboxamide | 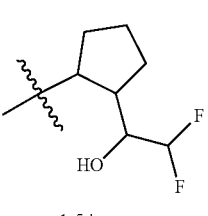<br>1-5 isomers | 588.2 (1) | 8.92 (brs, 1H), 8.86 (br s, 1H), 8.43 (br s, 1H), 8.18 (s, 1H), 7.62 (s, 1H), 6.01-5.74 (m, 1H), 5.31-5.23 (m, 0.5H), 5.19-5.12 (m, 0.5H), 4.60-4.47 (m, 1H), 4.11 (s, 1H), 4.06 (s, 3H), 3.95 (br s, 1H), 3.40-3.35 (m, 1H), 3.17 (s, 1H), 2.97-2.91 (m, 1H), 2.82-2.71 (m, 1H), 2.68-2.61 (m, 1H), 2.07 (br s, 1H), 1.87 (br s, 1H), 1.70 (br s, 2H), 1.66-1.56 (m, 1H), 1.52 (br s, 1H). |
| 1375 | 5-[4-amino-5-(trifluoromethyl)-pyrrolo[2,1-f][1,2,4]triazin-7-yl]-N-[(3R,4S)-4-fluoro-1-[2-(2,2,2-trifluoro-1-hydroxy-ethyl)cyclopentyl]pyrrolidin-3-yl]-2-methoxypyridine-3-carboxamide | 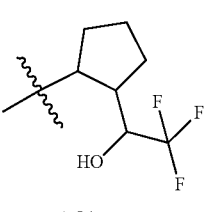<br>1-5 isomers | 606.2 (1) | 8.91 (s, 1H), 8.85 (s, 1H), 8.42 (br d, J = 7.3 Hz, 1H), 8.18 (s, 1H), 7.62 (s, 1H), 6.26 (br d, J = 6.4 Hz, 1H), 5.26 (br s, 0.5H), 5.14 (br s, 0.5H), 4.55-4.44 (m, 1H), 4.05 (s, 4H), 3.36 (br s, 1H), 3.18-3.07 (m, 1H), 3.07-2.97 (m, 1H), 2.89 (br d, J = 11.3 Hz, 1H), 2.82 (br d, J = 11.6 Hz, 1H), 2.64 (br t, J = 8.2 Hz, 1H), 1.97 (br d, J = 8.2 Hz, 1H), 1.75-1.65 (m, 1H), 1.65-1.49 (m, 5H). |
| 1376 | 5-[4-amino-5-(trifluoromethyl)-pyrrolo[2,1-f][1,2,4]triazin-7-yl]-N-[(3R,4S)-4-fluoro-1-[2-(2,2,2-trifluoro-1-hydroxy-ethyl)cyclopentyl]pyrrolidin-3-yl]-2-methoxypyridine-3-carboxamide | <br>1-5 isomers | 606.2 (2) | 8.92 (br s, 1H), 8.88 (br s, 1H), 8.45 (br d, J = 5.5 Hz, 1H), 8.18 (s, 1H), 7.63 (s, 1H), 5.28 (br s, 0.5H), 5.17 (br s, 0.5H), 4.61-4.49 (m, 1H), 4.40-4.32 (m, 1H), 4.06 (s, 3H), 3.37-3.33 (m, 1H), 3.10-2.91 (m, 2H), 2.90-2.76 (m, 1H), 2.66-2.57 (m, 1H), 2.21 (br s, 1H), 1.98-1.90 (m, 1H), 1.74-1.58 (m, 4H), 1.56-1.46 (m, 1H). |

TABLE 50-continued

Compounds in Table 50 were prepared similarly to the methods detailed in Example 1353. In some cases where low or incomplete conversion to desired product was observed by analytical LCMS of the crude reaction mixture, additional ketone or aldehyde starting material (2.5 additional equivalents) and/or additional borane-2-picoline complex (4 additional equivalents) was added to the crude mixture along with further heating of the resulting mixture to 55° C. ON to improve reaction outcomes. The majority of cases provided a mixture of two or more diastereomers as the final product. When diastereomers were separated, they are included as separate entries which may be either a single diastereomer or a mixture of two or more diastereomers depending on the stereochemistry of the aldehyde or ketone starting material and upon the preparative HPLC outcome. Products in this table bearing a secondary free alcohol moiety on a carbon atom adjacent to a fluorinated carbon atom were the result of an additional reduction of a ketone moiety to a secondary alcohol during the reaction. For each example, two analytical LCMS injections with matched stationary phase columns were used to determine final purity. The method(s) used are indicated in each case. Method 1-6 as described in the Methods of Preparation Section.

| Ex | Name | R | Obs. MS Ion M+ (method) | NMR Assignments (500 MHz, DMSO-d6) δ or LCMS retention time |
|---|---|---|---|---|
| 1377 | 5-[4-amino-5-(trifluoromethyl)-pyrrolo[2,1-f][1,2,4]triazin-7-yl]-N-[(3R,4S)-4-fluoro-1-[2-(2,2,2-trifluoro-1-hydroxy-ethyl)cyclopentyl]pyrrolidin-3-yl]-2-methoxypyridine-3-carboxamide | 1-5 isomers | 606.2 (2) | 8.92 (br s, 1H), 8.85 (br s, 1H), 8.43 (br d, J = 6.7 Hz, 1H), 8.18 (s, 1H), 7.62 (s, 1H), 5.27 (br s, 0.5H), 5.16 (br s, 0.5H), 4.59-4.48 (m, 1H), 4.35 (br s, 1H), 4.05 (s, 3H), 3.38-3.33 (m, 1H), 3.18-3.06 (m, 1H), 2.97 (br s, 1H), 2.84-2.71 (m, 1H), 2.67-2.58 (m, 1H), 2.20 (br s, 1H), 1.99-1.91 (m, 1H), 1.75-1.62 (m, 4H), 1.60 (br s, 1H), 1.51 (br s, 1H). |
| 1378 | 5-[4-amino-5-(trifluoromethyl)-pyrrolo[2,1-f][1,2,4]triazin-7-yl]-N-[(3R,4S)-4-fluoro-1-(2-methylcyclopentyl)pyrrolidin-3-yl]-2-methoxypyridine-3-carboxamide | 1-3 isomers | 522.2 (2) | 8.92 (br s, 1H), 8.86 (br s, 1H), 8.57-8.37 (m, 1H), 8.18 (s, 1H), 7.62 (s, 1H), 5.34-5.21 (m, 0.5H), 5.21-5.12 (m, 0.5H), 4.64-4.45 (m, 1H), 4.05 (s, 3H), 3.39 (br d, J = 12.2 Hz, 1H), 3.17 (br s, 1H), 2.24-2.02 (m, 1H), 1.71 (br s, 3H), 1.60-1.42 (m, 3H), 1.41-1.29 (m, 1H), 0.82 (br s, 3H). |
| 1379 | 5-[4-amino-5-(trifluoromethyl)-pyrrolo[2,1-f][1,2,4]triazin-7-yl]-N-[(3R,4S)-1-(2,2-dimethylcyclopentyl)-4-fluoro-pyrrolidin-3-yl]-2-methoxy-pyridine-3-carboxamide | 1 isomer | 536.2 (2) | 8.91 (s, 1H), 8.87 (s, 1H), 8.41 (br d, J = 7.3 Hz, 1H), 8.18 (s, 1H), 7.62 (s, 1H), 5.22 (br s, 0.5H), 5.10 (br s, 0.5H), 4.53-4.43 (m, 1H), 4.05 (s, 3H), 3.21-3.09 (m, 1H), 2.91 (br t, J = 8.1 Hz, 1H), 2.82-2.70 (m, 1H), 2.65 (br t, J = 8.1 Hz, 1H), 2.25-2.17 (m, 1H), 1.88-1.80 (m, 1H), 1.65-1.55 (m, 2H), 1.51-1.38 (m, 3H), 1.06 (s, 3H), 0.90-0.84 (m, 4H). |
| 1380 | 5-[4-amino-5-(trifluoromethyl)-pyrrolo[2,1-f][1,2,4]triazin-7-yl]-N-[(3R,4S)-4-fluoro-1-[(6-oxo-1,6-dihydropyridin-2-yl)methyl]pyrrolidin-3-yl]-2-methoxypyridine-3-carboxamide | 1 isomer | 547.1 (6) | 8.92 (s, 1H), 8.87-8.82 (m, 1H), 8.44 (br d, J = 7.6 Hz, 1H), 8.18 (s, 1H), 7.61 (s, 1H), 7.43-7.35 (m, 1H), 6.22 (br d, J = 9.2 Hz, 1H), 6.18-6.11 (m, 1H), 5.28 (br s, 0.5H), 5.17 (br s, 0.5H), 4.62-4.51 (m, 1H), 4.06 (s, 3H), 3.59-3.49 (m, 1H), 3.18-3.06 (m, 1H), 3.02-2.97 (m, 1H), 2.92-2.81 (m, 1H), 2.67 (br t, J = 8.4 Hz, 1H). |

TABLE 50-continued

Compounds in Table 50 were prepared similarly to the methods detailed in Example 1353. In some cases where low or incomplete conversion to desired product was observed by analytical LCMS of the crude reaction mixture, additional ketone or aldehyde starting material (2.5 additional equivalents) and/or additional borane-2-picoline complex (4 additional equivalents) was added to the crude mixture along with further heating of the resulting mixture to 55° C. ON to improve reaction outcomes. The majority of cases provided a mixture of two or more diastereomers as the final product. When diastereomers were separated, they are included as separate entries which may be either a single diastereomer or a mixture of two or more diastereomers depending on the stereochemistry of the aldehyde or ketone starting material and upon the preparative HPLC outcome. Products in this table bearing a secondary free alcohol moiety on a carbon atom adjacent to a fluorinated carbon atom were the result of an additional reduction of a ketone moiety to a secondary alcohol during the reaction. For each example, two analytical LCMS injections with matched stationary phase columns were used to determine final purity. The method(s) used are indicated in each case. Method 1-6 as described in the Methods of Preparation Section.

| Ex | Name | R | Obs. MS Ion M+ (method) | NMR Assignments (500 MHz, DMSO-d6) δ or LCMS retention time |
|---|---|---|---|---|
| 1381 | 5-[4-amino-5-(trifluoromethyl)-pyrrolo[2,1-f][1,2,4]triazin-7-yl]-N-[(3R,4S)-4-fluoro-1-(5,5,5-trifluoro-4-hydroxy-pentan-2-yl)pyrrolidin-3-yl]-2-methoxypyridine-3-carboxamide | 1-3 isomers | 580.1 (5) | 8.92 (d, J = 2.1 Hz, 1H), 8.86 (s, 1H), 8.42 (br d, J = 7.3 Hz, 1H), 8.18 (s, 1H), 7.62 (s, 1H), 5.25 (br s, 0.5 H), 5.14 (br s, 0.5H), 4.55-4.45 (m, 1H), 4.06 (s, 4H), 3.19-2.99 (m, 1H), 2.94-2.78 (m, 1H), 2.69-2.62 (m, 1H), 1.73 (br t, J = 9.5 Hz, 1H), 1.57-1.48 (m, 1H), 1.06 (br t, J = 6.0 Hz, 3H). LCMS Method 5 retention time = 1.34 min LCMS Method 6 retention time = 2.10 min |
| 1382 | 5-l4-amino-5-(trifluoromethyl)-pyrrolo[2,1-f][1,2,4]triazin-7-yl]-N-[(3R,4S)-1-[1-(3,3-difluorocyclopentyl)ethyl]-4-fluoropyrrolidin-3-yl]-2-methoxypyridine-3-carboxamide | 1-3 isomers | 572.2 (5) | 8.92 (br s, 1H), 8.86 (br s, 1H), 8.44-8.35 (m, 1H), 8.18 (s, 1H), 7.62 (s, 1H), 5.24 (br s, 0.5H), 5.12 (br s, 0.5H), 4.56-4.42 (m, 1H), 4.06 (s, 3H), 3.02-2.93 (m, 1H), 2.91-2.79 (m, 1H), 2.71-2.55 (m, 1H), 2.24-2.11 (m, 2H), 2.10-1.93 (m, 2H), 1.90 (br s, 1H), 1.87-1.75 (m, 1H), 1.62-1.54 (m, 1H), 1.33-1.21 (m, 1H), 0.93 (br s, 2H). |
| 1383 | 5-[4-amino-5-(trifluoromethyl)-pyrrolo[2,1-f][1,2,4]triazin-7-yl]-N-[(3R,4S)-4-fluoro-1-(5,5,5-trifluoro-4-hydroxy-4-phenylpentan-2-yl)pyrrolidin-3-yl]-2-methoxypyridine-3-carboxamide | 4 isomers | 656.1 (5) | 8.92 (br d, J = 2.1 Hz, 1H), 8.85-8.81 (m, 1H), 8.48-8.38 (m, 1H), 8.18 (s, 1H), 7.69-7.55 (m, 3H), 7.47-7.32 (m, 3H), 5.24 (br d, J = 13.1 Hz, 0.5H), 5.16-5.10 (m, 0.5H), 4.59-4.42 (m, 1H), 4.09-4.04 (m, 3H), 3.22-3.08 (m, 1H), 3.07-2.87 (m, 2H), 2.76-2.54 (m, 2H), 2.27-1.96 (m, 2H), 1.05-0.91 (m, 3H). |
| 1384 | 5-[4-amino-5-(trifluoromethyl)-pyrrolo[2,1-f][1,2,4]triazin-7-yl]-N-[(3R,4S)-4-fluoro-1-[5,5,5-trifluoro-4-hydroxy-4-(trifluoromethyl)pentan-2-yl]-pyrrolidin-3-yl]-2-methoxy-pyridine-3-carboxamide | 4 isomers | 648.1 (6) | 8.94-8.91 (m, 1H), 8.82 (dd, J = 6.6, 2.3 Hz, 1H), 8.51-8.45 (m, 1H), 8.18 (s, 1H), 7.62 (s, 1H), 5.29 (br s, 0.5H), 5.18 (br s, 0.5H), 4.66-4.54 (m, 1H), 4.05 (d, J = 2.4 Hz, 3H), 3.48-3.41 (m, 1H), 3.23-3.09 (m, 1H), 3.07-2.96 (m, 1H), 2.82-2.74 (m, 1H), 2.12-1.98 (m, 1H), 1.89 (br d, J = 14.6 Hz, 1H), 1.12-1.06 (m, 3H). |

TABLE 50-continued

Compounds in Table 50 were prepared similarly to the methods detailed in Example 1353. In some cases where low or incomplete conversion to desired product was observed by analytical LCMS of the crude reaction mixture, additional ketone or aldehyde starting material (2.5 additional equivalents) and/or additional borane-2-picoline complex (4 additional equivalents) was added to the crude mixture along with further heating of the resulting mixture to 55° C. ON to improve reaction outcomes. The majority of cases provided a mixture of two or more diastereomers as the final product. When diastereomers were separated, they are included as separate entries which may be either a single diastereomer or a mixture of two or more diastereomers depending on the stereochemistry of the aldehyde or ketone starting material and upon the preparative HPLC outcome. Products in this table bearing a secondary free alcohol moiety on a carbon atom adjacent to a fluorinated carbon atom were the result of an additional reduction of a ketone moiety to a secondary alcohol during the reaction. For each example, two analytical LCMS injections with matched stationary phase columns were used to determine final purity. The method(s) used are indicated in each case. Method 1-6 as described in the Methods of Preparation Section.

| Ex | Name | R | Obs. MS Ion M+ (method) | NMR Assignments (500 MHz, DMSO-d6) δ or LCMS retention time |
|---|---|---|---|---|
| 1385 | 5-[4-amino-5-(trifluoromethyl)-pyrrolo[2,1-f][1,2,4]triazin-7-yl]-N-[(3R,4S)-1-[1-(3,3-difluorocyclopentyl)ethyl]-4-fluoropyrrolidin-3-yl]-2-methoxypyridine-3-carboxamide | 1-3 isomers | 572.2 (6) | 8.92 (br s, 1H), 8.86 (br s, 1H), 8.38 (br s, 1H), 8.18 (s, 1H), 7.62 (s, 1H), 5.23 (br s, 0.5H), 5.12 (br s, 0.5H), 4.56-4.42 (m, 1H), 4.06 (s, 3H), 3.02-2.93 (m, 1H), 2.92-2.77 (m, 1H), 2.68-2.55 (m, 1H), 2.27-2.10 (m, 3H), 2.10-1.90 (m, 2H), 1.83 (br d, J = 7.3 Hz, 1H), 1.49-1.38 (m, 1H), 1.02-0.82 (m, 3H). |
| 1386 | 5-[4-amino-5-(trifluoromethyl)-pyrrolo[2,1-f][1,2,4]triazin-7-yl]-N-[(3R,4S)-4-fluoro-1-(5,5,5-trifluoro-4-hydroxy-pentan-2-yl)pyrrolidin-3-yl]-2-methoxypyridine-3-carboxamide | 1-3 isomers | 580.1 (6) | LCMS Method 5 retention time = 1.35 min LCMS Method 6 retention time = 2.18 min |
| 1387 | 5-[4-amino-5-(trifluoromethyl)-pyrrolo[2,1-f][1,2,4]triazin-7-yl]-N-[(3R,4S)-1-[1-(2,3-difluoropyridin-4-yl)ethyl]-4-fluoropyrrolidin-3-yl]-2-methoxypyridine-3-carboxamide | Mixture of 2 isomers | 581.2 (1) | 8.92-8.89 (m, 1H), 8.83 (s, 1H), 8.44 (br t, J = 6.7 Hz, 1H), 8.16 (s, 1H), 8.04 (t, J = 6.1 Hz, 1H), 7.60 (s, 1H), 7.52-7.47 (m, 1H), 5.29-5.24 (m, 0.5H), 5.18-5.13 (m, 0.5H), 4.60-4.48 (m, 1H), 4.05 (d, J = 4.3 Hz, 3H), 4.02-3.90 (m, 1H), 3.42-3.36 (m, 1H), 3.18-3.05 (m, 1H), 3.01 (br t, J = 8.2 Hz, 1H), 2.91-2.73 (m, 2H), 2.64-2.56 (m, 1H), 1.37 (br d, J = 6.7 Hz, 3H). |
| 1388 | 5-[4-amino-5-(trifluoromethyl)-pyrrolo[2,1-f][1,2,4]triazin-7-yl]-N-[(3R,4S)-1-[1-(2,6-difluoropyridin-4-yl)ethyl]-4-fluoropyrrolidin-3-yl]-2-methoxypyridine-3-carboxamide | Mixture of 2 isomers | 581.1 (1) | 8.91 (br s, 1H), 8.87-8.81 (m, 1H), 8.44 (br d, J = 5.2 Hz, 1H), 8.17 (br s, 1H), 7.61 (br s, 1H), 7.21-7.12 (m, 2H), 5.26 (br d, J = 10.7 Hz, 0.5H), 5.18-5.12 (m, 0.5H), 4.61-4.49 (m, 1H), 4.05 (br d, J = 3.7 Hz, 3H), 3.72-3.64 (m, 1H), 3.32-3.22 (m, 1H), 3.21-3.04 (m, 1H), 3.00 (br d, J = 8.2 Hz, 1H), 2.93-2.69 (m, 1H), 2.64-2.57 (m, 1H), 1.35-1.30 (m, 3H). |

TABLE 50-continued

Compounds in Table 50 were prepared similarly to the methods detailed in Example 1353. In some cases where low or incomplete conversion to desired product was observed by analytical LCMS of the crude reaction mixture, additional ketone or aldehyde starting material (2.5 additional equivalents) and/or additional borane-2-picoline complex (4 additional equivalents) was added to the crude mixture along with further heating of the resulting mixture to 55° C. ON to improve reaction outcomes. The majority of cases provided a mixture of two or more diastereomers as the final product. When diastereomers were separated, they are included as separate entries which may be either a single diastereomer or a mixture of two or more diastereomers depending on the stereochemistry of the aldehyde or ketone starting material and upon the preparative HPLC outcome. Products in this table bearing a secondary free alcohol moiety on a carbon atom adjacent to a fluorinated carbon atom were the result of an additional reduction of a ketone moiety to a secondary alcohol during the reaction. For each example, two analytical LCMS injections with matched stationary phase columns were used to determine final purity. The method(s) used are indicated in each case. Method 1-6 as described in the Methods of Preparation Section.

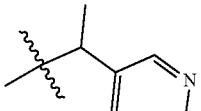

| Ex | Name | R | Obs. MS Ion M+ (method) | NMR Assignments (500 MHz, DMSO-d6) δ or LCMS retention time |
|---|---|---|---|---|
| 1389 | 5-[4-amino-5-(trifluoromethyl)-pyrrolo[2,1-f][1,2,4]triazin-7-yl]-N-[(3R,4S)-4-fluoro-1-[1-(pyrimidin-5-yl)ethyl]-pyrrolidin-3-yl]-2-methoxy-pyridine-3-carboxamide | 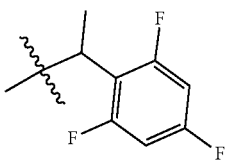<br>1 isomer | 546.2 (1) | 9.12 (s, 1H), 8.91 (s, 1H), 8.83 (br s, 1H), 8.80 (s, 2H), 8.43 (br d, J = 7.6 Hz, 1H), 8.17 (s, 1H), 7.61 (s, 1H), 5.27 (br s, 0.5H), 5.16 (br s, 0.5H), 4.56-4.46 (m, 1H), 4.04 (s, 3H), 3.66-3.61 (m, 1H), 3.39-3.34 (m, 1H), 3.20-3.09 (m, 1H), 2.83 (br t, J = 8.2 Hz, 1H), 2.77-2.68 (m, 1H), 2.60 (br t, J = 8.5 Hz, 1H), 1.39 (br d, J = 6.4 Hz, 3H). |
| 1390 | 5-[4-amino-5-(trifluoromethyl)-pyrrolo[2,1-f][1,2,4]triazin-7-yl]-N-[(3R,4S)-4-fluoro-1-[1-(2,4,6-trifluorophenyl)-ethyl]pyrrolidin-3-yl]-2-methoxypyridine-3-carboxamide | 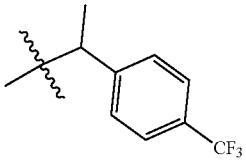<br>Mixture of 2 isomers | 598.1 (1) | 8.91 (br s, 1H), 8.84 (br d, J = 8.5 Hz, 1H), 8.42 (br dd, J = 11.3, 8.9 Hz, 1H), 8.17 (br s, 1H), 7.61 (br s, 1H), 7.19 (br t, J = 9.3 Hz, 2H), 5.24 (br s, 0.5H), 5.13 (br s, 0.5H), 4.55-4.42 (m, 1H), 4.07-3.96 (m, 4H), 3.37 (br d, J = 6.4 Hz, 1H), 3.20-3.09 (m, 1H), 3.02-2.91 (m, 1H), 2.85-2.75 (m, 1H), 2.73-2.59 (m, 1H), 2.55 (br d, J = 7.6 Hz, 1H), 1.52-1.40 (m, 3H). |
| 1391 | 5-[4-amino-5-(trifluoromethyl)-pyrrolo[2,1-f][1,2,4]triazin-7-yl]-N-[(3R,4S)-4-fluoro-1-{1-[4-(trifluoromethyl)phenyl]-ethyl}pyrrolidin-3-yl]-2-methoxypyridine-3-carboxamide | 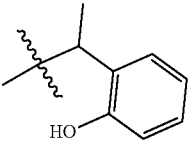<br>Mixture of 2 isomers | 612.1 (2) | 8.91 (br s, 1H), 8.83 (br s, 1H), 8.44 (br d, J = 7.0 Hz, 1H), 8.16 (s, 1H), 7.74-7.68 (m, 2H), 7.63-7.56 (m, 3H), 5.26 (br d, J = 14.3 Hz, 0.5H), 5.15 (br d, J = 14.3 Hz, 0.5H), 4.59-4.44 (m, 1H), 4.05 (br d, J = 6.1 Hz, 3H), 3.59 (br d, J = 5.8 Hz, 1H), 3.37 (br d, J = 6.4 Hz, 1H), 3.03-2.89 (m, 1H), 2.87-2.71 (m, 1H), 2.60-2.54 (m, 1H), 1.35-1.30 (m, 3H). |
| 1392 | 5-[4-amino-5-(trifluoromethyl)-pyrrolo[2,1-f][1,2,4]triazin-7-yl]-N-[(3R,4S)-4-fluoro-1-[1-(2-hydroxyphenyl)ethyl]-pyrrolidin-3-yl]-2-methoxy-pyridine-3-carboxamide | <br>Mixture of 2 isomers | 560.2 (2) | 8.93-8.89 (m, 1H), 8.83-8.80 (m, 1H), 8.52-8.44 (m, 1H), 8.17 (s, 1H), 7.61 (s, 1H), 7.18-7.05 (m, 2H), 6.81-6.73 (m, 2H), 5.29 (br s, 0.5H), 5.18 (br s, 0.5H), 4.65-4.52 (m, 1H), 4.10-4.02 (m, 3H), 3.78 (br s, 1H), 3.41-3.36 (m, 1H), 3.20-2.58 (m, 3H), 1.34-1.28 (m, 3H). |

TABLE 50-continued

Compounds in Table 50 were prepared similarly to the methods detailed in Example 1353. In some cases where low or incomplete conversion to desired product was observed by analytical LCMS of the crude reaction mixture, additional ketone or aldehyde starting material (2.5 additional equivalents) and/or additional borane-2-picoline complex (4 additional equivalents) was added to the crude mixture along with further heating of the resulting mixture to 55° C. ON to improve reaction outcomes. The majority of cases provided a mixture of two or more diastereomers as the final product. When diastereomers were separated, they are included as separate entries which may be either a single diastereomer or a mixture of two or more diastereomers depending on the stereochemistry of the aldehyde or ketone starting material and upon the preparative HPLC outcome. Products in this table bearing a secondary free alcohol moiety on a carbon atom adjacent to a fluorinated carbon atom were the result of an additional reduction of a ketone moiety to a secondary alcohol during the reaction. For each example, two analytical LCMS injections with matched stationary phase columns were used to determine final purity. The method(s) used are indicated in each case. Method 1-6 as described in the Methods of Preparation Section.

| Ex | Name | R | Obs. MS Ion M+ (method) | NMR Assignments (500 MHz, DMSO-d6) δ or LCMS retention time |
|---|---|---|---|---|
| 1393 | 5-[4-amino-5-(trifluoromethyl)-pyrrolo[2,1-f][1,2,4]triazin-7-yl]-N-[(3R,4S)-1-[1-(3,5-difluoro-2-hydroxyphenyl)-ethyl]-4-fluoropyrrolidin-3-yl]-2-methoxypyridine-3-carboxamide | Mixture of 2 isomers | 596.2 (2) | 8.91 (d, J = 2.1 Hz, 1H), 8.81 (s, 1H), 8.53-8.46 (m, 1H), 8.17 (s, 1H), 7.61 (s, 1H), 7.10 (br t, J = 8.5 Hz, 1H), 6.91 (br d, J = 8.2 Hz, 1H), 5.30 (br s, 0.5H), 5.19 (br s, 0.5H), 4.66-4.54 (m, 1H), 4.07-4.03 (m, 3H), 3.88 (br s, 1H), 3.19-2.62 (m, 3H), 1.32 (br d, J = 5.8 Hz, 3H). |
| 1394 | 5-[4-amino-5-(trifluoromethyl)-pyrrolo[2,1-f][1,2,4]triazin-7-yl]-N-[(3R,4S)-4-fluoro-1-{1-[3-(trifluoromethoxy)phenyl]-ethyl}pyrrolidin-3-yl]-2-methoxypyridine-3-carboxamide | Mixture of 2 isomers | 628.2 (1) | 8.91 (br s, 1H), 8.83 (br s, 1H), 8.44 (br s, 1H), 8.16 (s, 1H), 7.68-7.59 (m, 1H), 7.54-7.43 (m, 1H), 7.43-7.29 (m, 2H), 7.25 (br s, 1H), 5.26 (br s, 0.5H), 5.15 (br s, 0.5H), 4.59-4.45 (m, 1H), 4.09-4.02 (m, 3H), 3.40 (br d, J = 10.7 Hz, 1H), 3.04-2.54 (m, 1H), 1.32 (br s, 3H). |
| 1395 | 5-[4-amino-5-(trifluoromethyl)-pyrrolo[2,1-f][1,2,4]triazin-7-yl]-N-[(3R,4S)-4-fluoro-1-[1-(pyrimidin-5-yl)ethyl]-pyrrolidin-3-yl]-2-methoxy-pyridine-3-carboxamide | 1 isomer | 546.2 (2) | 9.11 (s, 1H), 8.91 (s, 1H), 8.83-8.78 (m, 3H), 8.43 (br d, J = 7.6 Hz, 1H), 8.17 (s, 1H), 7.61 (s, 1H), 5.25 (br s, 0.5H), 5.14 (br s, 0.5H), 4.59-4.49 (m, 1H), 4.05 (s, 3H), 3.64 (br d, J = 6.4 Hz, 1H), 3.37 (br d, J = 7.3 Hz, 1H), 3.04-2.91 (m, 2H), 2.90-2.79 (m, 1H), 2.56-2.53 (m, 1H), 1.39 (br d, J = 6.4 Hz, 3H). |
| 1396 | 5-[4-amino-5-(trifluoromethyl)-pyrrolo[2,1-f][1,2,4]triazin-7-yl]-N-[(3R,4S)-1-[1-(2,4-dimethylpyrimidin-5-yl)ethyl]-4-fluoropyrrolidin-3-yl]-2-methoxypyridine-3-carboxamide | 1 isomer | 574.2 (1) | 8.91 (s, 1H), 8.83 (d, J = 2.1 Hz, 1H), 8.57 (s, 1H), 8.44 (br d, J = 7.3 Hz, 1H), 8.17 (s, 1H), 7.61 (s, 1H), 5.26 (br s, 0.5H), 5.15 (br s, 0.5H), 4.61-4.50 (m, 1H), 4.06 (s, 3H), 3.72 (br d, J = 6.4 Hz, 1H), 3.37 (br d, J = 7.3 Hz, 1H), 3.03-2.91 (m, 2H), 2.90-2.78 (m, 1H), 2.53 (s, 3H), 1.32 (br d, J = 6.4 Hz, 3H). |

TABLE 50-continued

Compounds in Table 50 were prepared similarly to the methods detailed in Example 1353. In some cases where low or incomplete conversion to desired product was observed by analytical LCMS of the crude reaction mixture, additional ketone or aldehyde starting material (2.5 additional equivalents) and/or additional borane-2-picoline complex (4 additional equivalents) was added to the crude mixture along with further heating of the resulting mixture to 55° C. ON to improve reaction outcomes. The majority of cases provided a mixture of two or more diastereomers as the final product. When diastereomers were separated, they are included as separate entries which may be either a single diastereomer or a mixture of two or more diastereomers depending on the stereochemistry of the aldehyde or ketone starting material and upon the preparative HPLC outcome. Products in this table bearing a secondary free alcohol moiety on a carbon atom adjacent to a fluorinated carbon atom were the result of an additional reduction of a ketone moiety to a secondary alcohol during the reaction. For each example, two analytical LCMS injections with matched stationary phase columns were used to determine final purity. The method(s) used are indicated in each case. Method 1-6 as described in the Methods of Preparation Section.

| Ex | Name | R | Obs. MS Ion M+ (method) | NMR Assignments (500 MHz, DMSO-d6) δ or LCMS retention time |
|---|---|---|---|---|
| 1397 | 5-[4-amino-5-(trifluoromethyl)-pyrrolo[2,1-f][1,2,4]triazin-7-yl]-N-[(3R,4S)-1-[1-(2-chloro-4-methyl-1,3-thiazol-5-yl)-ethyl]-4-fluoropyrrolidin-3-yl]-2-methoxypyridine-3-carboxamide | Mixture of 2 isomers | 599.1 (2) | 8.91 (br s, 1H), 8.84 (br s, 1H), 8.47-8.39 (m, 1H), 8.17 (s, 1H), 7.62 (s, 1H), 5.26 (br s, 0.5H), 5.15 (br s, 0.5H), 4.59-4.47 (m, 1H), 4.06 (br d, J = 3.4 Hz, 3H), 3.92-3.85 (m, 1H), 3.37-3.33 (m, 1H), 3.17 (br d, J = 5.2 Hz, 1H), 3.12-2.99 (m, 1H), 2.96-2.83 (m, 1H), 2.66-2.59 (m, 1H), 2.30 (s, 3H), 1.33 (br d, J = 6.1 Hz, 3H). |
| 1398 | 5-[4-amino-5-(trifluoromethyl)-pyrrolo[2,1-f][1,2,4]triazin-7-yl]-N-[(3R,4S)-1-[1-(2,5-dibromo-1,3-thiazol-4-yl)-ethyl]-4-fluoropyrrolidin-3-yl]-2-methoxypyridine-3-carboxamide | Mixture of 2 isomers | 706.9 (1) | 8.91 (br s, 1H), 8.85-8.82 (m, 1H), 8.44 (br dd, J = 17.5, 7.5 Hz, 1H), 8.17 (s, 1H), 7.61 (s, 1H), 5.26 (br d, J = 4.3 Hz, 0.5H), 5.15 (br d, J = 4.3 Hz, 0.5H), 4.60-4.48 (m, 1H), 4.05 (br d, J = 4.9 Hz, 3H), 3.95-3.88 (m, 1H), 3.39 (br d, J = 9.2 Hz, 1H), 3.18-2.96 (m, 2H), 2.94-2.84 (m, 1H), 2.68 (q, J = 7.8 Hz, 1H), 1.36 (br d, J = 6.4 Hz, 3H). |
| 1399 | 5-[4-amino-5-(trifluoromethyl)-pyrrolo[2,1-f][1,2,4]triazin-7-yl]-N-[(3R,4S)-1-[1-(4-chloro-1,3-thiazol-2-yl)ethyl]-4-fluoropyrrolidin-3-yl]-2-methoxypyridine-3-carboxamide | Mixture of 2 isomers | 585.1 (1) | 8.91 (br s, 1H), 8.83 (br s, 1H), 8.42 (br t, J = 6.4 Hz, 1H), 8.17 (s, 1H), 7.66-7.57 (m, 2H), 5.25 (br s, 0.5H), 5.14 (br s, 0.5H), 4.56-4.45 (m, 1H), 4.05 (s, 3H), 4.04-3.99 (m, 1H), 3.35 (br d, J = 11.9 Hz, 1H), 3.18-3.07 (m, 1H), 3.07-3.00 (m, 1H), 2.98-2.78 (m, 1H), 2.68-2.53 (m, 1H), 1.39 (br d, J = 5.5 Hz, 3H). |
| 1400 | 5-[4-amino-5-(trifluoromethyl)-pyrrolo[2,1-f][1,2,4]triazin-7-yl]-N-[(3R,4S)-4-fluoro-1-[1-(2-methyl-1,3-thiazol-5-yl)-ethyl]pyrrolidin-3-yl]-2-methoxypyridine-3-carboxamide | Mixture of 2 isomers | 565.2 (2) | 8.91 (br s, 1H), 8.84 (br s, 1H), 8.48-8.36 (m, 1H), 8.17 (s, 1H), 7.61 (s, 1H), 7.49 (br s, 1H), 5.24 (br s, 0.5H), 5.13 (br s, 0.5H), 4.54-4.42 (m, 1H), 4.05 (br d, J = 2.4 Hz, 3H), 3.99-3.89 (m, 1H), 3.36 (br d, J = 6.4 Hz, 1H), 3.20-2.96 (m, 1H), 2.93-2.67 (m, 1H), 2.61 (br s, 3H), 2.56 (br d, J = 8.9 Hz, 1H), 1.40-1.34 (m, 3H), 1.32 (br s, 1H). |

TABLE 50-continued

Compounds in Table 50 were prepared similarly to the methods detailed in Example 1353. In some cases where low or incomplete conversion to desired product was observed by analytical LCMS of the crude reaction mixture, additional ketone or aldehyde starting material (2.5 additional equivalents) and/or additional borane-2-picoline complex (4 additional equivalents) was added to the crude mixture along with further heating of the resulting mixture to 55° C. ON to improve reaction outcomes. The majority of cases provided a mixture of two or more diastereomers as the final product. When diastereomers were separated, they are included as separate entries which may be either a single diastereomer or a mixture of two or more diastereomers depending on the stereochemistry of the aldehyde or ketone starting material and upon the preparative HPLC outcome. Products in this table bearing a secondary free alcohol moiety on a carbon atom adjacent to a fluorinated carbon atom were the result of an additional reduction of a ketone moiety to a secondary alcohol during the reaction. For each example, two analytical LCMS injections with matched stationary phase columns were used to determine final purity. The method(s) used are indicated in each case. Method 1-6 as described in the Methods of Preparation Section.

| Ex | Name | R | Obs. MS Ion M+ (method) | NMR Assignments (500 MHz, DMSO-d6) δ or LCMS retention time |
|---|---|---|---|---|
| 1401 | 5-[4-amino-5-(trifluoromethyl)-pyrrolo[2,1-f][1,2,4]triazin-7-yl]-N-[(3R,4S)-1-[1-(3,5-dimethyl-1,2-oxazol-4-yl)-ethyl]-4-fluoropyrrolidin-3-yl]-2-methoxypyridine-3-carboxamide | 1 isomer | 563.2 (1) | 8.91 (br s, 1H), 8.85 (br s, 1H), 8.43 (br d, J = 7.0 Hz, 1H), 8.17 (s, 1H), 7.61 (s, 1H), 5.27 (br s, 0.5H), 5.16 (br s, 0.5H), 4.58-4.47 (m, 1H), 4.05 (s, 3H), 3.36 (br d, J = 5.8 Hz, 1H), 3.12-2.99 (m, 1H), 2.75 (br t, J = 7.9 Hz, 1H), 2.71-2.57 (m, 2H), 2.37 (s, 3H), 2.24 (s, 3H), 1.28 (br d, J = 6.1 Hz, 3H). |
| 1402 | 5-[4-amino-5-(trifluoromethyl)-pyrrolo[2,1-f][1,2,4]triazin-7-yl]-N-[(3R,4S)-4-fluoro-1-[1-(1,3-thiazol-4-yl)ethyl]-pyrrolidin-3-yl]-2-methoxy-pyridine-3-carboxamide | Mixture of 2 isomers | 551.1 (2) | 9.07 (br s, 1H), 8.90 (br s, 1H), 8.83 (s, 1H), 8.41 (br d, J = 7.0 Hz, 1H), 8.17 (s, 1H), 7.61 (s, 1H), 7.55 (br s, 1H), 5.22 (br s, 0.5H), 5.11 (br s, 0.5H), 4.43 (br dd, J = 14.2, 8.7 Hz, 1H), 4.04 (s, 3H), 3.97 (br s, 1H), 3.37 (br d, J = 7.9 Hz, 1H), 3.18-3.04 (m, 1H), 3.00-2.76 (m, 1H), 2.65-2.54 (m, 1H), 1.41 (br d, J = 5.8 Hz, 3H). |
| 1403 | 5-[4-amino-5-(trifluoromethyl)-pyrrolo[2,1-f][1,2,4]triazin-7-yl]-N-[(3R,4S)-1-[1-(3,5-dimethyl-1,2-oxazol-4-yl)-ethyl]-4-fluoropyrrolidin-3-yl]-2-methoxypyridine-3-carboxamide | 1 isomer | 563.2 (2) | 8.91 (br s, 1H), 8.85 (br s, 1H), 8.43 (br d, J = 7.0 Hz, 1H), 8.17 (s, 1H), 7.62 (s, 1H), 5.26 (br s, 0.5H), 5.15 (br s, 0.5H), 4.54 (br dd, J = 15.0, 7.0 Hz, 1H), 4.05 (s, 3H), 3.35 (br s, 1H), 2.94 (br d, J = 6.1 Hz, 1H), 2.85 (br s, 1H), 2.82-2.75 (m, 1H), 2.48-2.42 (m, 1H), 2.37 (s, 3H), 2.24 (s, 3H), 1.30 (br d, J = 6.1 Hz, 3H). |
| 1404 | 5-[4-amino-5-(trifluoromethyl)-pyrrolo[2,1-f][1,2,4]triazin-7-yl]-N-[(3R,4S)-1-[1-(2,4-dimethyl-1,3-thiazol-5-yl)-ethyl]-4-fluoropyrrolidin-3-yl]-2-methoxypyridine-3-carboxamide | 1 isomer | 579.2 (2) | 8.91 (s, 1H), 8.85 (br s, 1H), 8.41 (br d, J = 7.0 Hz, 1H), 8.17 (s, 1H), 7.62 (s, 1H), 5.25 (br s, 0.5H), 5.13 (br s, 0.5H), 4.56-4.45 (m, 1H), 4.06 (s, 3H), 3.85 (br d, J = 6.1 Hz, 1H), 3.38-3.30 (m, 1H), 3.05-2.94 (m, 2H), 2.92-2.80 (m, 1H), 2.58-2.53 (m, 4H), 2.28 (s, 3H), 1.31 (br d, J = 6.1 Hz, 3H). |

Example 1405: 5-(4-Amino-5-(trifluoromethyl)pyr-rolo[2,1-f][1,2,4]triazin-7-yl)-N-((3R,4S)-4-fluoro-1-(3-hydroxy-2,3-dimethylbutan-2-yl)pyrrolidin-3-yl)-2-methoxynicotinamide

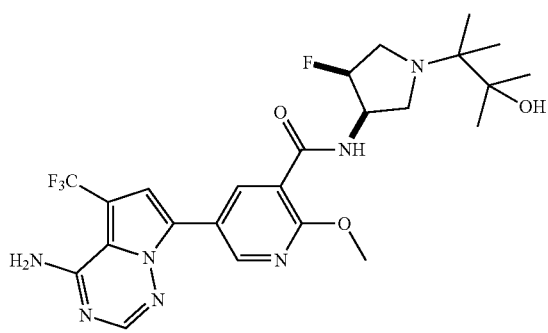

In a 0.2-0.5 mL microwave reaction vessel were combined 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide (10 mg, 0.023 mmol) and 2,2,3,3-tetramethyloxirane (0.25 mL, 1.949 mmol). Distilled water (150 μL) was then added. The mixture was heated to 175° C. for 3.5 h in a microwave reactor. The mixture was allowed to return to rt and was concentrated via nitrogen stream. The residue was dissolved in 2 mL of DMF. The crude material was filtered and purified via preparative LC/MS with the following conditions: Column=XBridge C18, 200 mm×19 mm, 5-μm particles; Mobile Phase A=5:95 acetonitrile:water with 10-mM ammonium acetate; Mobile Phase B=95:5 acetonitrile:water with 10-mM ammonium acetate; Gradient=28-68% B over 20 minutes, then a 4-minute hold at 100% B; Flow Rate=20 mL/min; Column Temperature=25° C. Fractions containing the desired product were combined and dried via centrifugal evaporation to give the titled material (1.3 mg, 10% yield).

MS ESI m/z 540.2 (M+H)$^+$ $^1$H NMR (500 MHz, DMSO-d$_6$) δ 8.91 (d, J=2.1 Hz, 1H), 8.87 (d, J=2.1 Hz, 1H), 8.42-8.35 (m, 1H), 8.17 (s, 1H), 7.62 (s, 1H), 5.16 (br s, 0.5H), 5.05 (br s, 0.5H), 4.44-4.33 (m, 1H), 4.05 (s, 3H), 3.40 (br d, J=12.5 Hz, 1H), 3.27-3.02 (m, 2H), 2.73 (br t, J=8.5 Hz, 1H), 1.14 (s, 6H), 1.00 (br s, 3H), 0.98 (br s, 3H).

TABLE 51

Compounds in Table 51 were prepared similarly to the methods detailed in Example 1405. In the majority of cases, the reactions took 30 minutes or less at 170-175° C. to be complete. When diastereomers were separated, they are included as separate entries which may be either a single diastereomer or a mixture of two or more diastereomers depending upon the stereochemistry of the epoxide starting material and upon the preparative HPLC outcome. For each example, two analytical LCMS injections with matched stationary phase columns were used to determine final purity. The method(s) used are indicated in each case. Method 1-6 as described in the Methods of Preparation Section.

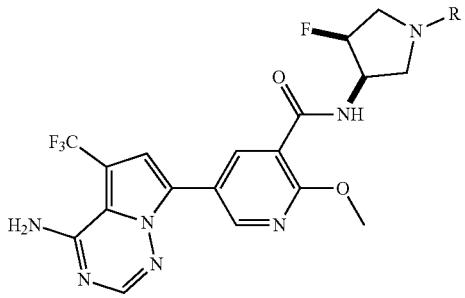

| Ex | Name | R | Obs. MS Ion M$^+$ (method) | NMR Assignments (500 MHz, DMSO-d6) δ or LCMS retention time |
|---|---|---|---|---|
| 1406 | 5-[4-amino-5-(trifluoromethyl)-pyrrolo[2,1-f][1,2,4]triazin-7-yl]-N-[(3R,4S)-4-fluoro-1-(2-hydroxycyclopentyl)pyrrolidin-3-yl]-2-methoxypyridine-3-carboxamide | 4 isomers | 524.2 (1) | 8.92 (d, J = 2.4 Hz, 1H), 8.86 (d, J = 2.3 Hz, 1H), 8.52-8.37 (m, 1H), 8.18 (s, 1H), 7.62 (s, 1H), 5.23 (br s, 0.5H), 5.12 (br s, 0.5H), 4.61 (br s, 1H), 4.55-4.42 (m, 1H), 4.06 (s, 3H), 3.96-3.84 (m, 1H), 3.29-3.25 (m, 1H), 3.24-3.08 (m, 1H), 3.07-2.96 (m, 1H), 2.95-2.81 (m, 1H), 1.86-1.77 (m, 2H), 1.66-1.51 (m, 2H), 1.51-1.35 (m, 3H). |
| 1407 | 5-[4-amino-5-(trifluoromethyl)-pyrrolo[2,1-f][1,2,4]triazin-7-yl]-N-[(3R,4S)-4-fluoro-1-(3-hydroxy-3-methylbutan-2-yl)-pyrrolidin-3-yl]-2-methoxy-pyridine-3-carboxamide | 1 isomer | 526.2 (2) | LCMS Method 1 retention time = 1.29 min LCMS Method 2 retention time = 1.83 min |

TABLE 51-continued

Compounds in Table 51 were prepared similarly to the methods detailed in Example 1405. In the majority of cases, the reactions took 30 minutes or less at 170-175° C. to be complete. When diastereomers were separated, they are included as separate entries which may be either a single diastereomer or a mixture of two or more diastereomers depending upon the stereochemistry of the epoxide starting material and upon the preparative HPLC outcome. For each example, two analytical LCMS injections with matched stationary phase columns were used to determine final purity. The method(s) used are indicated in each case. Method 1-6 as described in the Methods of Preparation Section.

| Ex | Name | R | Obs. MS Ion M+ (method) | NMR Assignments (500 MHz, DMSO-d6) δ or LCMS retention time |
|---|---|---|---|---|
| 1408 | 5-[4-amino-5-(trifluoromethyl)-pyrrolo[2,1-f][1,2,4]triazin-7-yl]-N-[(3R,4S)-4-fluoro-1-(2-hydroxy-2-methylcyclopentyl)-pyrrolidin-3-yl]-2-methoxypyridine-3-carboxamide | 2-hydroxy-2-methylcyclopentyl (1-3 isomers) | 538.2 (1) | LCMS Method 1 retention time = 1.26 min LCMS Method 2 retention time = 1.71 min |
| 1409 | 5-[4-amino-5-(trifluoromethyl)-pyrrolo[2,1-f][1,2,4]triazin-7-yl]-N-[(3R,4S)-4-fluoro-1-(3-hydroxybutan-2-yl)pyrrolidin-3-yl]-2-methoxypyridine-3-carboxamide | 3-hydroxybutan-2-yl (1 isomer) | 512.2 (1) | LCMS Method 1 retention time = 1.23 min LCMS Method 2 retention time = 1.61 min |
| 1410 | 5-[4-amino-5-(trifluoromethyl)-pyrrolo[2,1-f][1,2,4]triazin-7-yl]-N-[(3R,4S)-4-fluoro-1-(2-hydroxy-2-methylcyclohexyl)-pyrrolidin-3-yl]-2-methoxypyridine-3-carboxamide | 2-hydroxy-2-methylcyclohexyl (1-3 isomers) | 552.2 (1) | LCMS Method 1 retention time = 1.35 min LCMS Method 2 retention time = 1.92 min |
| 1411 | 5-[4-amino-5-(trifluoromethyl)-pyrrolo[2,1-f][1,2,4]triazin-7-yl]-N-[(3R,4S)-4-fluoro-1-(3-hydroxybutan-2-yl)pyrrolidin-3-yl]-2-methoxypyridine-3-carboxamide | 3-hydroxybutan-2-yl (1 isomer) | 512.2 (2) | LCMS Method 1 retention time = 1.24 min LCMS Method 2 retention time = 1.64 min |
| 1412 | 5-[4-amino-5-(trifluoromethyl)-pyrrolo[2,1-f][1,2,4]triazin-7-yl]-N-[(3R,4S)-4-fluoro-1-(2-hydroxy-2-methylcyclopentyl)-pyrrolidin-3-yl]-2-methoxypyridine-3-carboxamide | 2-hydroxy-2-methylcyclopentyl (1-3 isomers) | 538.2 (1) | 8.92 (s, 1H), 8.88 (s, 1H), 8.39 (br d, J = 7.3 Hz, 1H), 8.18 (s, 1H), 7.61 (s, 1H), 5.22 (br s, 0.5H), 5.13-5.08 (m, 0.5H), 4.53-4.40 (m, 2H), 4.12-4.03 (m, 3H), 3.20-3.05 (m, 1H), 3.00-2.80 (m, 2H), 2.77-2.67 (m, 1H), 2.48-2.34 (m, 1H), 1.89-1.77 (m, 1H), 1.74-1.63 (m, 1H), 1.60-1.39 (m, 4H), 1.10 (s, 3H). LCMS Method 1 retention time = 1.27 min LCMS Method 2 retention time = 1.74 min |

TABLE 51-continued

Compounds in Table 51 were prepared similarly to the methods detailed in Example 1405. In the majority of cases, the reactions took 30 minutes or less at 170-175° C. to be complete. When diastereomers were separated, they are included as separate entries which may be either a single diastereomer or a mixture of two or more diastereomers depending upon the stereochemistry of the epoxide starting material and upon the preparative HPLC outcome. For each example, two analytical LCMS injections with matched stationary phase columns were used to determine final purity. The method(s) used are indicated in each case. Method 1-6 as described in the Methods of Preparation Section.

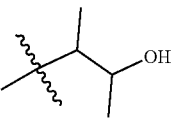

| Ex | Name | R | Obs. MS Ion M+ (method) | NMR Assignments (500 MHz, DMSO-d6) δ or LCMS retention time |
|---|---|---|---|---|
| 1413 | 5-[4-amino-5-(trifluoromethyl)-pyrrolo[2,1-f][1,2,4]triazin-7-yl]-N-[(3R,4S)-4-fluoro-1-(3-hydroxybutan-2-yl)pyrrolidin-3-yl]-2-methoxypyridine-3-carboxamide | 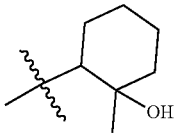<br>2 isomers | 512.2 (2) | LCMS Method 1 retention time = 1.26 min<br>LCMS Method 2 retention time = 1.70 min |
| 1414 | 5-[4-amino-5-(trifluoromethyl)-pyrrolo[2,1-f][1,2,4]triazin-7-yl]-N-[(3R,4S)-4-fluoro-1-(2-hydroxy-2-methylcyclohexyl)pyrrolidin-3-yl]-2-methoxypyridine-3-carboxamide | 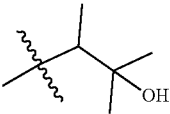<br>1-3 isomers | 552.2 (1) | LCMS Method 1 retention time = 1.37 min<br>LCMS Method 2 retention time = 1.96 min |
| 1415 | 5-[4-amino-5-(trifluoromethyl)-pyrrolo[2,1-f][1,2,4]triazin-7-yl]-N-[(3R,4S)-4-fluoro-1-(3-hydroxy-3-methylbutan-2-yl)pyrrolidin-3-yl]-2-methoxypyridine-3-carboxamide | 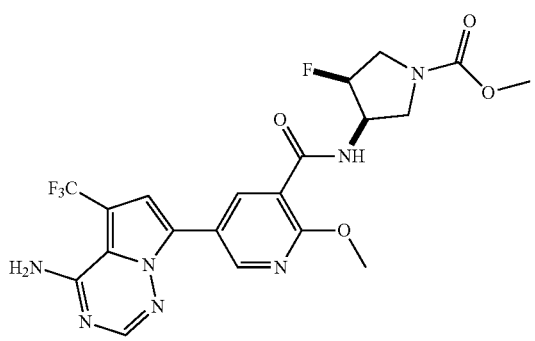<br>1 isomer | 526.2 (1) | LCMS Method 1 retention time = 1.31 min<br>LCMS Method 2 retention time = 1.85 min |

Example 1416: Methyl (3R,4S)-3-(5-(4-amino-5-(trifluoromethyl)pyrrolo[2,1-f][1,2,4]triazin-7-yl)-2-methoxynicotinamido)-4-fluoropyrrolidine-1-carboxylate In a 1 dram vial were combined 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide (15 mg, 0.034 mmol) with DIPEA (0.018 mL, 0.102 mmol) in DMF (0.3 mL). The mixture was treated with methyl chloroformate (3.17 μL, 3.87 mg, 0.041 mmol) and stirred at rt ON. The crude mixture was filtered and purified via preparative LC/MS with the following conditions: Column=XBridge C18, 200 mm×19 mm, 5-μm particles; Mobile Phase A=5:95 acetonitrile:water with 10-mM ammonium acetate; Mobile Phase B=95:5 acetonitrile:water with 10-mM ammonium acetate; Gradient=21-61% B over 20 minutes, then a 4-minute hold at 100% B; Flow Rate=20 mL/min; Column Temperature=25° C. Fractions containing the desired product were combined and dried via centrifugal evaporation to give the desired product (9.4 mg, 55% yield).

MS ESI m/z 498.1 (M+H)+

$^1$H NMR (500 MHz, DMSO-d$_6$) δ 8.92 (s, 1H), 8.77 (s, 1H), 8.52 (br d, J=7.3 Hz, 1H), 8.18 (s, 1H), 7.62 (s, 1H), 5.36-5.17 (m, 1H), 4.77-4.63 (m, 1H), 4.04 (s, 3H), 3.84-3.72 (m, 2H), 3.70-3.64 (m, 1H), 3.61 (s, 3H), 3.39-3.23 (m, 1H).

Example 1417: 2,2,3,3-Tetrafluorocyclobutyl (3R,4S)-3-(5-(4-amino-5-(trifluoromethyl)pyrrolo[2,1-f][1,2,4]triazin-7-yl)-2-methoxynicotinamido)-4-fluoropyrrolidine-1-carboxylate

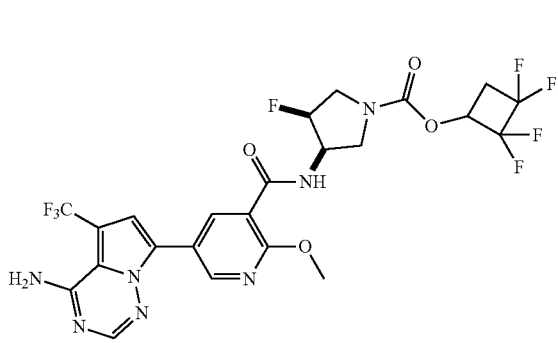

In a 1 dram vial were combined N,N-disuccinimidyl carbonate (87 mg, 0.341 mmol), 2,2,3,3-tetrafluorocyclobutanol (0.049 mL, 0.478 mmol) and DIPEA (0.179 mL, 1.024 mmol) in a mixture of acetonitrile (0.15 mL) and DCM (0.15 mL). The mixture was stirred at rt ON. The mixture was then treated with 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide (30 mg, 0.068 mmol) and stirred at rt ON. The mixture was concentrated via nitrogen stream to a residue, redissolved in 2 mL of DMF and filtered. The crude material was purified via preparative LC/MS with the following conditions: Column=XBridge C18, 200 mm×19 mm, 5-μm particles; Mobile Phase A=5:95 acetonitrile:water with 0.1% trifluoroacetic acid; Mobile Phase B=95:5 acetonitrile:water with 0.1% trifluoroacetic acid; Gradient=33-73% B over 20 minutes, then a 4-minute hold at 100% B; Flow Rate=20 mL/min; Column Temperature=25 C. Fractions containing the desired product were combined and dried via centrifugal evaporation. The material was further purified using SFC-chiral chromatography with the following conditions: Instrument=Waters 100 Prep SFC; Column=Chiral AS, 250 mm×30 mm, 5-μm particles; Mobile Phase=80% $CO_2$/20% MeOH with 0.1% DEA; Flow Rate=100 mL/min. Fractions containing the desired product were combined and dried via centrifugal evaporation to give the desired product (1.8 mg, 3.0 mmol, 4% yield).

MS ESI m/z 610.1 (M+H)$^+$ $^1$H NMR (500 MHz, DMSO-d6) δ 8.93 (d, J=2.1 Hz, 1H), 8.84-8.72 (m, 1H), 8.54 (br dd, J=6.9, 2.6 Hz, 1H), 8.18 (s, 1H), 7.62 (m, 1H), 5.44-5.24 (m, 2H), 4.90-4.68 (m, 1H), 4.05 (s, 3H), 3.95-3.64 (m, 3H), 3.40-3.14 (m, 1H), 2.96-2.76 (m, 1H).

Example 1418: (R)-1-Hydroxy-4-methylpentan-2-yl (3R,4S)-3-(5-(4-amino-5-(trifluoromethyl)pyrrolo[2,1-f][1,2,4]triazin-7-yl)-2-methoxynicotinamido)-4-fluoropyrrolidine-1-carboxylate

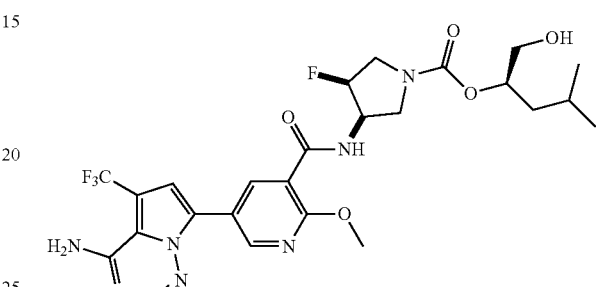

In a 1 dram vial were combined N,N-disuccinimidyl carbonate (43.7 mg, 0.171 mmol) and (R)-1-((tert-butyldimethylsilyl)oxy)-4-methylpentan-2-ol (55.5 mg, 0.239 mmol) and DIPEA (0.060 mL, 0.341 mmol) in a mixture of acetonitrile (0.15 mL) and DCM (0.15 mL). The mixture was stirred at rt ON. The reaction mixture was then treated with 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide (15 mg, 0.034 mmol) and the resulting mixture was stirred at rt ON. The mixture was concentrated to a residue via nitrogen stream, and the residue was treated with TBAF, 1.0M in THF (0.341 mL, 0.341 mmol). The mixture was stirred ON. The mixture was diluted with MeOH and filtered. The crude material was purified via preparative LC/MS with the following conditions: Column=XBridge C18, 200 mm×19 mm, 5-μm particles; Mobile Phase A=5:95 acetonitrile:water with 10-mM ammonium acetate; Mobile Phase B=95:5 acetonitrile:water with 10-mM ammonium acetate; Gradient=30-70% B over 20 minutes, then a 4-minute hold at 100% B; Flow Rate=20 mL/min; Column Temperature=25° C. Fractions containing the desired product were combined and dried via centrifugal evaporation to give the desired product (4.5 mg, 23% yield).

MS ESI m/z 610.1 (M+H)$^+$ $^1$H NMR (500 MHz, DMSO-d$_6$) δ 8.93 (s, 1H), 8.79 (br s, 1H), 8.50 (d, J=7.4 Hz, 1H), 8.18 (s, 1H), 7.62 (s, 1H), 5.33 (br s, 0.5H), 5.22 (br s, 0.5H), 4.76-4.62 (m, 3H), 4.05 (s, 3H), 3.84-3.57 (m, 3H), 3.42 (br t, J=5.2 Hz, 2H), 1.69-1.54 (m, 1H), 1.52-1.42 (m, 1H), 1.41-1.34 (m, 1H), 0.96-0.84 (m, 7H).

TABLE 52

| Ex | Name | R | Obs. MS Ion M+ (method) | NMR Assignments (500 MHz, DMSO-d6) δ or LCMS retention time |
|---|---|---|---|---|
| 1419 | 2-methoxyethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 542.1 (2) | 8.93 (s, 1H), 8.77 (s, 1H), 8.52 (br d, J = 7.3 Hz, 1H), 8.18 (s, 1H), 7.62 (s, 1H), 5.37-5.16 (m, 1H), 4.77-4.64 (m, 1H), 4.19-4.10 (m, 3H), 4.04 (s, 3H), 3.85-3.72 (m, 2H), 3.70-3.60 (m, 2H), 3.56-3.51 (m, 2H), 3.38-3.25 (m, 2H). |
| 1420 | propyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 526.2 (1) | 8.93 (d, J = 2.4 Hz, 1H), 8.78 (d, J = 2.4 Hz, 1H), 8.50 (d, J = 7.5 Hz, 1H), 8.18 (s, 1H), 7.62 (s, 1H), 5.32 (br s, 0.5H), 5.22 (br s, 0.5H), 4.78-4.63 (m, 1H), 4.04 (s, 3H), 4.01-3.94 (m, 2H), 3.85-3.77 (m, 1H), 3.75-3.60 (m, 2H), 3.29-3.22 (m, 1H), 1.60 (sxt, J = 7.0 Hz, 2H), 0.91 (t, J = 7.4 Hz, 3H). |
| 1421 | phenyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 560.1 (2) | 8.93 (s, 1H), 8.81-8.76 (m, 1H), 8.62-8.51 (m, 1H), 8.18 (s, 1H), 7.63 (s, 1H), 7.41 (br t, J = 7.6 Hz, 2H), 7.24 (br t, J = 7.3 Hz, 1H), 7.17 (br d, J = 5.8 Hz, 2H), 5.44-5.19 (m, 1H), 4.89-4.71 (m, 1H), 4.11-4.01 (m, 4H), 4.01-3.67 (m, 2H). |
| 1422 | ethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 512.2 (1) | 8.93 (d, J = 2.4 Hz, 1H), 8.78 (d, J = 2.3 Hz, 1H), 8.50 (d, J = 7.5 Hz, 1H), 8.18 (s, 1H), 7.62 (s, 1H), 5.33-5.31 (m, 0.5H), 5.23-5.20 (m, 0.5H), 4.77-4.63 (m, 1H), 4.10-4.05 (m, 2H), 4.04 (s, 3H), 3.85-3.75 (m, 1H), 3.74-3.60 (m, 2H), 3.29-3.25 (m, 1H), 1.21 (t, J = 7.1 Hz, 3H). |
| 1423 | butyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 540.2 (1) | 8.93 (d, J = 2.6 Hz, 1H), 8.77 (d, J = 2.3 Hz, 1H), 8.50 (d, J = 7.5 Hz, 1H), 8.18 (s, 1H), 7.62 (s, 1H), 5.34-5.30 (m, 0.5H), 5.23-5.20 (m, 0.5H), 4.78-4.63 (m, 1H), 4.10-3.97 (m, 5H), 3.84-3.76 (m, 1H), 3.74-3.59 (m, 2H), 3.49-3.34 (m, 1H), 3.30-3.17 (m, 1H), 1.60-1.53 (m, 2H), 1.36 (sxt, J = 7.4 Hz, 2H), 0.91 (t, J = 7.4 Hz, 3H). |

TABLE 52-continued

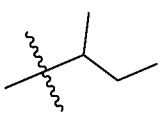

| Ex | Name | R | Obs. MS Ion M+ (method) | NMR Assignments (500 MHz, DMSO-d6) δ or LCMS retention time |
|---|---|---|---|---|
| 1424 | butan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 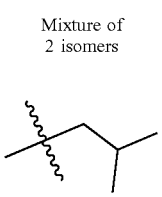<br>Mixture of 2 isomers | 540.2 (2) | 8.93 (d, J = 2.4 Hz, 1H), 8.78 (s, 1H), 8.49 (br d, J = 7.5 Hz, 1H), 8.18 (s, 1H), 7.62 (s, 1H), 5.32 (br s, 0.5H), 5.21 (br s, 0.5H), 4.77-4.60 (m, 2H), 4.04 (s, 3H), 3.84-3.75 (m, 1H), 3.73-3.59 (m, 2H), 3.29-3.22 (m, 1H), 1.59-1.49 (m, 2H), 1.20-1.15 (m, 3H), 0.91-0.83 (m, 3H). |
| 1425 | 2-methylpropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 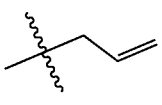 [SMILES: *CC=C] | 540.2 (2) | LCMS Method 1 retention time = 1.99 min<br>LCMS Method 2 retention time = 2.07 min |
| 1426 | prop-2-en-1-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate |  | 524.1 (1) | 8.92 (s, 1H), 8.77 (s, 1H), 8.53 (br d, J = 7.6 Hz, 1H), 8.18 (s, 1H), 7.62 (s, 1H), 5.95 (qd, J = 10.7, 4.9 Hz, 1H), 5.33 (br s, 1H), 5.29 (br s, 0.5H), 5.22 (br s, 1H), 5.20 (s, 0.5H), 4.79-4.65 (m, 1H), 4.56 (br d, J = 4.0 Hz, 2H), 4.04 (s, 3H), 3.89-3.77 (m, 1H), 3.69 (br t, J = 12.5 Hz, 1H), 3.63 (br s, 1H), 3.40-3.26 (m, 1H). |
| 1427 | 2,2-dimethylpropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 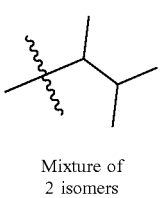 | 554.2 (2) | 8.93 (d, J = 2.4 Hz, 1H), 8.79-8.77 (m, 1H), 8.51 (br t, J = 6.9 Hz, 1H), 8.18 (s, 1H), 7.62 (s, 1H), 5.35-5.31 (m, 0.5H), 5.23 (m, 0.5H), 4.81-4.65 (m, 1H), 4.08-3.98 (s, 3H), 3.88-3.61 (m, 5H), 3.37-3.26 (m, 1H), 0.93 (s, 9H). |
| 1428 | 3-methylbutan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | Mixture of 2 isomers | 554.2 (2) | 8.93 (d, J = 2.4 Hz, 1H), 8.80-8.76 (m, 1H), 8.54-8.47 (m, 1H), 8.18 (s, 1H), 7.62 (s, 1H), 5.35-5.29 (m, 0.5H), 5.23-5.19 (m, 0.5H), 4.79-4.64 (m, 1H), 4.57-4.49 (m, 1H), 4.04 (s, 3H), 3.85-3.71 (m, 1H), 3.69-3.59 (m, 2H), 3.30-3.24 (m, 1H), 1.77 (dq, J = 13.0, 6.4 Hz, 1H), 1.16-1.10 (m, 3H), 0.91-0.84 (m, 6H). |

TABLE 52-continued

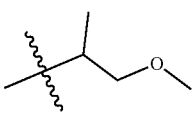

| Ex | Name | R | Obs. MS Ion M+ (method) | NMR Assignments (500 MHz, DMSO-d6) δ or LCMS retention time |
|---|---|---|---|---|
| 1429 | 1-methoxypropan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 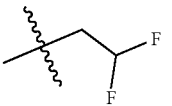 [SMILES: *CC(F)F]<br>Mixture of 2 isomers | 556.2 (1) | 8.81 (s, 1H), 8.66 (s, 1H), 8.63 (br d, J = 7.3 Hz, 1H), 8.07 (s, 1H), 7.48 (s, 1H), 5.29 (br s, 0.5H), 5.19 (br s, 0.5H), 4.83-4.77 (m, 1H), 4.69-4.56 (m, 1H), 4.19 (br s, 3H), 3.87-3.75 (m, 1H), 3.70-3.53 (m, 2H), 3.42-3.33 (m, 2H), 3.26-3.20 (m, 4H), 1.12 (br d, J = 5.8 Hz, 3H). |
| 1430 | 2,2-difluoroethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 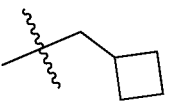 [SMILES: *CC1CCC1] | 548.1 (2) | 8.92 (s, 1H), 8.77 (d, J = 1.8 Hz, 1H), 8.54 (br d, J = 7.0 Hz, 1H), 8.18 (s, 1H), 7.62 (s, 1H), 6.26 (t, J = 54.6 Hz, 1H), 5.34 (br s, 0.5H), 5.23 (br s, 0.5H), 4.80-4.66 (m, 1H), 4.34 (br t, J = 14.5 Hz, 2H), 4.04 (s, 3H), 3.89-3.62 (m, 3H), 3.41-3.29 (m, 1H). |
| 1431 | cyclobutylmethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 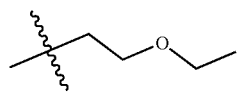 [SMILES: *CCOCC] | 552.2 (2) | 8.94-8.91 (m, 1H), 8.77 (s, 1H), 8.52 (br d, J = 7.0 Hz, 1H), 8.18 (s, 1H), 7.62 (s, 1H), 5.32 (br s, 0.5H), 5.21 (br s, 0.5H), 4.78-4.63 (m, 1H), 4.04 (s, 3H), 4.00 (br d, J = 6.1 Hz, 2H), 3.84-3.60 (m, 3H), 3.41-3.35 (m, 1H), 3.29 (q, J = 10.9 Hz, 1H), 2.62-2.55 (m, 1H), 2.04-1.95 (m, 2H), 1.90-1.79 (m, 2H), 1.79-1.71 (m, 2H). |
| 1432 | 2-ethoxyethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 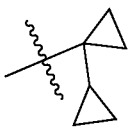 [SMILES: *C1(C2CC2)CC1] | 556.2 (2) | 8.93 (d, J = 2.4 Hz, 1H), 8.77 (d, J = 2.4 Hz, 1H), 8.51 (br d, J = 7.3 Hz, 1H), 8.18 (s, 1H), 7.62 (s, 1H), 5.33 (t, J = 2.9 Hz, 0.5H), 5.22 (br s, 0.5H), 4.78-4.65 (m, 1H), 4.17-4.10 (m, 2H), 4.04 (s, 3H), 3.85-3.76 (m, 1H), 3.75-3.59 (m, 2H), 3.57 (t, J = 4.8 Hz, 2H), 3.47 (q, J = 6.9 Hz, 2H), 3.29-3.22 (m, 1H), 1.11 (t, J = 7.0 Hz, 3H). |
| 1433 | [1,1'-bi(cyclopropane)]-1-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 564.2 (2) | 8.92 (s, 1H), 8.77 (br s, 1H), 8.54-8.47 (m, 1H), 8.18 (s, 1H), 7.62 (s, 1H), 5.30 (br s, 0.5H), 5.20 (br s, 0.5H), 4.75-4.62 (m, 1H), 4.04 (s, 3H), 3.81-3.72 (m, 1H), 3.71-3.55 (m, 2H), 3.40-3.33 (m, 1H), 3.29-3.21 (m, 1H), 1.68-1.61 (m, 1H), 0.79-0.68 (m, 2H), 0.62-0.53 (m, 2H), 0.45 (br d, J = 7.9 Hz, 2H), 0.25-0.18 (m, 2H). |

TABLE 52-continued

| Ex | Name | R | Obs. MS Ion M+ (method) | NMR Assignments (500 MHz, DMSO-d6) δ or LCMS retention time |
|---|---|---|---|---|
| 1434 | cyclopentyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | cyclopentyl | 552.1 (1) | 8.92 (s, 1H), 8.77 (br s, 1H), 8.51 (br d, J = 7.3 Hz, 1H), 8.18 (s, 1H), 7.62 (s, 1H), 5.31 (br s, 0.5H), 5.20 (br s, 0.5H), 5.00 (br s, 1H), 4.76-4.62 (m, 1H), 4.04 (s, 3H), 3.78 (br t, J = 9.5 Hz, 1H), 3.72-3.56 (m, 2H), 3.42-3.35 (m, 1H), 3.25 (br t, J = 10.1 Hz, 1H), 1.84-1.74 (m, 2H), 1.65 (br s, 4H), 1.60-1.49 (m, 2H). |
| 1435 | prop-2-yn-1-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | propargyl | 522.1 (2) | 8.92 (s, 1H), 8.78-8.75 (m, 1H), 8.53 (br d, J = 7.3 Hz, 1H), 8.18 (s, 1H), 7.62 (s, 1H), 5.33 (br s, 0.5H), 5.22 (br s, 0.5H), 4.77-4.65 (m, 3H), 4.04 (s, 3H), 3.89-3.59 (m, 2H), 3.54 (br s, 1H), 3.43-3.23 (m, 2H). |
| 1436 | 1-methylcyclopropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 1-methylcyclopropyl | 538.2 (2) | 8.92 (s, 1H), 8.76 (s, 1H), 8.49 (br s, 1H), 8.17 (s, 1H), 7.61 (s, 1H), 5.29 (br s, 0.5H), 5.19 (br s, 0.5H), 4.74-4.61 (m, 1H), 4.03 (s, 3H), 3.75 (dt, J = 18.4, 9.3 Hz, 1H), 3.69-3.53 (m, 1H), 3.40 (br d, J = 9.2 Hz, 1H), 3.23 (q, J = 10.5 Hz, 1H), 1.49 (s, 3H), 0.86-0.75 (m, 2H), 0.62 (br s, 2H). |
| 1437 | 2,2,2-trifluoroethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 2,2,2-trifluoroethyl | 566.1 (1) | 8.94-8.91 (m, 1H), 8.78-8.75 (m, 1H), 8.55 (br d, J = 7.3 Hz, 1H), 8.18 (s, 1H), 7.62 (s, 1H), 5.35 (br s, 0.5H), 5.24 (br s, 0.5H), 4.81-4.68 (m, 3H), 4.04 (s, 3H), 3.91-3.64 (m, 3H), 3.46-3.32 (m, 1H). |
| 1438 | but-2-yn-1-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | but-2-yn-1-yl | 536.1 (1) | 8.94-8.91 (m, 1H), 8.76 (s, 1H), 8.53 (br d, J = 7.3 Hz, 1H), 8.18 (s, 1H), 7.62 (s, 1H), 5.32 (br s, 0.5H), 5.22 (br s, 0.5H), 4.76-4.68 (m, 1H), 4.66 (br s, 2H), 4.04 (s, 3H), 3.84-3.61 (m, 3H), 3.41-3.25 (m, 1H), 1.83 (br s, 3H). |
| 1439 | cyclopropylmethyl (3R,4S)-3-{5-[4-amino-5-(trifluoromethyl)pyrrolo[2,1-f][1,2,4]triazin- | cyclopropylmethyl | 538.2 (1) | 8.93 (d, J = 1.8 Hz, 1H), 8.77 (s, 1H), 8.51 (br d, J = 7.3 Hz, 1H), 8.18 (s, 1H), 7.62 (s, 1H), 5.33 (br s, 0.5H), 5.22 (br s, 0.5H), 4.77-4.62 (m, 1H), 4.05 (s, 3H), |

TABLE 52-continued

| Ex | Name | R | Obs. MS Ion M+ (method) | NMR Assignments (500 MHz, DMSO-d6) δ or LCMS retention time |
|---|---|---|---|---|
| | 7-yl]-2-methoxypyridine-3-amido}-4-fluoropyrrolidine-1-carboxylate | | | 3.87 (d, J = 7.0 Hz, 2H), 3.85-3.74 (m, 1H), 3.72-3.60 (m, 2H), 3.32-3.25 (m, 1H), 1.15-1.07 (m, 1H), 0.54-0.48 (m, 2H), 0.30-0.26 (m, 2H). |
| 1440 | but-3-en-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | Mixture of 2 isomers | 538.1 (1) | 8.93 (s, 1H), 8.77 (s, 1H), 8.50 (br d, J = 7.6 Hz, 1H), 8.18 (s, 1H), 7.61 (s, 1H), 5.95-5.87 (m, 1H), 5.35-5.16 (m, 3H), 5.13 (br d, J = 10.4 Hz, 1H), 4.77-4.65 (m, 1H), 4.05 (s, 3H), 3.89-3.74 (m, 1H), 3.74-3.60 (m, 2H), 3.33-3.25 (m, 1H), 1.28 (br d, J = 6.4 Hz, 3H). |
| 1441 | 4,4,4-trifluorobutan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | Mixture of 2 isomers | 594.1 (1) | 8.93 (s, 1H), 8.79-8.74 (m, 1H), 8.55-8.48 (m, 1H), 8.18 (s, 1H), 7.62 (s, 1H), 5.33 (br s, 0.5H), 5.22 (br s, 0.5H), 5.05-4.97 (m, 1H), 4.77-4.65 (m, 1H), 4.04 (s, 3H), 3.86-3.75 (m, 1H), 3.73-3.60 (m, 2H), 3.31-3.21 (m, 1H), 2.68-2.58 (m, 2H), 1.29 (br d, J = 6.4 Hz, 3H). |
| 1442 | cyclohexyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 566.2 (2) | 8.92 (s, 1H), 8.77 (s, 1H), 8.50 (br d, J = 7.6 Hz, 1H), 8.18 (s, 1H), 7.61 (s, 1H), 5.32 (br s, 0.5H), 5.21 (br s, 0.5H), 4.78-4.62 (m, 1H), 4.58 (br s, 1H), 4.04 (s, 3H), 3.85-3.75 (m, 1H), 3.73-3.60 (m, 2H), 3.38-3.24 (m, 1H), 1.79 (br s, 2H), 1.66 (br s, 2H), 1.52-1.26 (m, 6H). |
| 1443 | propan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 526.1 (1) | 8.92 (d, J = 2.1 Hz, 1H), 8.77 (s, 1H), 8.50 (br d, J = 7.6 Hz, 1H), 8.18 (s, 1H), 7.61 (s, 1H), 5.32 (br s, 0.5H), 5.21 (br s, 0.5H), 4.79 (dt, J = 12.2, 6.1 Hz, 1H), 4.75-4.62 (m, 1H), 4.04 (s, 3H), 3.80 (q, J = 9.2 Hz, 1H), 3.74-3.57 (m, 2H), 3.28 (br s, 1H), 1.21 (br d, J = 6.1 Hz, 6H). |
| 1444 | 3,3,3-trifluoropropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 580.1 (1) | 8.94-8.91 (m, 1H), 8.77 (br s, 1H), 8.55-8.49 (m, 1H), 8.18 (s, 1H), 7.61 (s, 1H), 5.36-5.30 (m, 0.5H), 5.25-5.19 (m, 0.5H), 4.78-4.66 (m, 1H), 4.30-4.19 (m, 2H), 4.04 (s, 3H), 3.85-3.79 (m, 1H), 3.76-3.58 (m, 2H), 3.33-3.22 (m, 2H), 2.71-2.62 (m, 2H). |

TABLE 52-continued

| Ex | Name | R | Obs. MS Ion M+ (method) | NMR Assignments (500 MHz, DMSO-d6) δ or LCMS retention time |
|---|---|---|---|---|
| 1445 | 3-fluoropropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 544.1 (1) | 8.93 (d, J = 2.1 Hz, 1H), 8.77 (s, 1H), 8.50 (br d, J = 7.3 Hz, 1H), 8.18 (s, 1H), 7.61 (s, 1H), 5.33 (br s, 0.5H), 5.22 (br s, 0.5H), 4.78-4.63 (m, 1H), 4.59 (t, J = 6.0 Hz, 1H), 4.50 (t, J = 6.0 Hz, 1H), 4.14-4.09 (m, 2H), 4.04 (s, 3H), 3.87-3.74 (m, 1H), 3.73-3.61 (m, 2H), 3.33-3.25 (m, 1H), 2.03-1.93 (m, 2H). |
| 1446 | 1,1,1-trifluoropropan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | Mixture of 2 isomers | 580.1 (2) | 8.93 (s, 1H), 8.79-8.75 (m, 1H), 8.58-8.49 (m, 1H), 8.18 (s, 1H), 7.61 (s, 1H), 5.37-5.22 (m, 2H), 4.82-4.67 (m, 1H), 4.07-4.01 (m, 3H), 3.90-3.79 (m, 1H), 3.77-3.64 (m, 2H), 3.34-3.30 (m, 1H), 1.38 (br d, J = 6.4 Hz, 3H). |
| 1447 | cyclopropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 524.1 (1) | 8.92 (s, 1H), 8.76 (d, J = 2.1 Hz, 1H), 8.53-8.45 (m, 1H), 8.19-8.15 (m, 1H), 7.63-7.58 (m, 1H), 5.34-5.28 (m, 0.5H), 5.23-5.17 (m, 0.5H), 4.76-4.59 (m, 1H), 4.06-3.99 (m, 4H), 3.85-3.71 (m, 1H), 3.71-3.50 (m, 3H), 3.34-3.17 (m, 1H), 0.68-0.60 (m, 4H). |
| 1448 | cyclobutyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 538.2 (1) | 8.92 (d, J = 2.4 Hz, 1H), 8.77 (br s, 1H), 8.50 (d, J = 7.6 Hz, 1H), 8.18 (s, 1H), 7.61 (s, 1H), 5.32 (br s, 0.5H), 5.21 (br s, 0.5H), 4.90-4.83 (m, 1H), 4.74-4.63 (m, 1H), 4.04 (s, 3H), 3.87-3.57 (m, 4H), 3.35-3.21 (m, 1H), 2.29-2.22 (m, 2H), 2.05-1.96 (m, 2H), 1.76-1.69 (m, 1H), 1.60-1.51 (m, 1H). |
| 1449 | (2S)-1-hydroxypropan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 542.2 (1) | 8.94-8.92 (m, 1H), 8.78 (s, 1H), 8.50 (br d, J = 7.6 Hz, 1H), 8.18 (s, 1H), 7.62 (s, 1H), 5.32 (br s, 0.5H), 5.21 (br s, 0.5H), 4.85-4.63 (m, 3H), 4.05 (s, 3H), 3.83-3.58 (m, 3H), 3.42 (br s, 2H), 1.14 (d, J = 6.1 Hz, 3H). |

TABLE 52-continued


| Ex | Name | R | Obs. MS Ion M+ (method) | NMR Assignments (500 MHz, DMSO-d6) δ or LCMS retention time |
|---|---|---|---|---|
| 1450 | (2R)-1-hydroxypropan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate |  | 542.1 (2) | 8.93 (d, J = 2.4 Hz, 1H), 8.77 (s, 1H), 8.50 (br d, J = 7.0 Hz, 1H), 8.18 (s, 1H), 7.62 (s, 1H), 5.32 (br s, 0.5H), 5.21 (br s, 0.5H), 4.80 (t, J = 6.0 Hz, 1H), 4.75-4.62 (m, 2H), 4.05 (s, 3H), 3.82-3.57 (m, 3H), 3.45-3.39 (m, 2H), 1.14 (d, J = 6.4 Hz, 3H). |
| 1451 | (2S)-2-hydroxypropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 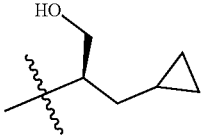 [SMILES: *[C@@H](CO)CC1CC1] | 542.2 (2) | 8.93 (s, 1H), 8.78 (s, 1H), 8.51 (br d, J = 7.3 Hz, 1H), 8.18 (s, 1H), 7.62 (s, 1H), 5.33 (br s, 0.5H), 5.22 (br s, 0.5H), 4.81 (br s, 1H), 4.76-4.65 (m, 1H), 4.05 (s, 3H), 3.92-3.78 (m, 4H), 3.78-3.61 (m, 2H), 3.31-3.25 (m, 1H), 3.19-3.14 (m, 1H), 1.61-1.52 (m, 1H), 1.35-1.28 (m, 1H), 1.07 (br d, J = 5.8 Hz, 3H). |
| 1452 | (2R)-1-cyclopropyl-3-hydroxypropan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 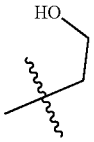 | 582.2 (1) | 8.93 (s, 1H), 8.78 (br s, 1H), 8.50 (br d, J = 7.0 Hz, 1H), 8.18 (s, 1H), 7.62 (s, 1H), 5.33 (br s, 0.5H), 5.22 (br s, 0.5H), 4.77-4.61 (m, 3H), 4.05 (s, 3H), 3.88-3.75 (m, 1H), 3.73-3.59 (m, 2H), 3.53-3.48 (m, 2H), 3.19-3.14 (m, 1H), 1.61-1.54 (m, 1H), 1.53-1.38 (m, 2H), 0.74-0.66 (m, 1H), 0.41 (br d, J = 6.1 Hz, 2H), 0.10-0.00 (m, 2H). |
| 1453 | 2-hydroxyethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 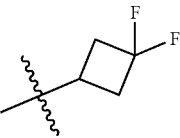 [SMILES: *C1CC(F)(F)C1] | 528.1 (1) | 8.93 (s, 1H), 8.78 (s, 1H), 8.51 (d, J = 7.3 Hz, 1H), 8.18 (s, 1H), 7.62 (s, 1H), 5.33 (br s, 0.5H), 5.22 (br s, 0.5H), 4.82-4.77 (m, 1H), 4.77-4.61 (m, 1H), 4.05 (s, 5H), 3.92-3.55 (m, 6H). |
| 1454 | 3,3-difluorocyclobutyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 574.1 (2) | 8.93 (s, 1H), 8.78 (br s, 1H), 8.51 (br d, J = 7.6 Hz, 1H), 8.18 (s, 1H), 7.62 (s, 1H), 5.34 (br s, 0.5H), 5.23 (br s, 0.5H), 4.89-4.81 (m, 1H), 4.78-4.66 (m, 1H), 4.05 (s, 3H), 3.91-3.85 (m, 1H), 3.83-3.76 (m, 1H), 3.75-3.59 (m, 2H), 3.31-3.25 (m, 1H), 3.10-3.01 (m, 2H), 2.75-2.64 (m, 2H). |

TABLE 52-continued

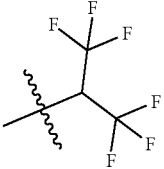 [SMILES: *C(C(F)(F)F)C(F)(F)F]

| Ex | Name | R | Obs. MS Ion M+ (method) | NMR Assignments (500 MHz, DMSO-d6) δ or LCMS retention time |
|---|---|---|---|---|
| 1455 | 1,1,1,3,3,3-hexafluoropropan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 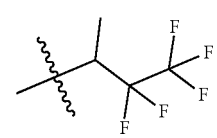 [SMILES: *C(C)C(F)(F)C(F)(F)F] | 634.1 (1) | 8.93 (s, 1H), 8.80-8.75 (m, 1H), 8.58-8.53 (m, 1H), 8.18 (s, 1H), 7.62 (s, 1H), 6.64-6.55 (m, 1H), 5.38 (br s, 0.5H), 5.29-5.25 (m, 0.5H), 4.88-4.76 (m, 1H), 4.06-4.02 (m, 3H), 3.95-3.87 (m, 1H), 3.86-3.67 (m, 2H), 3.47-3.39 (m, 2H), 3.21-3.14 (m, 1H). |
| 1456 | 3,3,4,4,4-pentafluorobutan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate |  | 630.2 (1) | 8.94-8.89 (m, 1H), 8.75 (dd, J = 14.9, 2.2 Hz, 1H), 8.55 (d, J = 7.4 Hz, 1H), 8.17 (d, J = 1.9 Hz, 1H), 7.61 (d, J = 2.8 Hz, 1H), 5.50-5.37 (m, 1H), 5.35 (br s, 0.5H), 5.26-5.21 (m, 0.5H), 4.82-4.66 (m, 1H), 4.04 (d, J = 5.0 Hz, 3H), 3.88 (s, 1H), 3.72 (br d, J = 6.3 Hz, 1H), 3.67 (br d, J = 3.9 Hz, 1H), 3.32-3.23 (m, 1H), 1.42 (br d, J = 6.1 Hz, 3H). |
| 1457 | (2,2-difluorocyclopropyl)methyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | 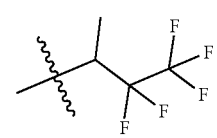 [SMILES: *C(C)C(F)(F)C(F)(F)F] | 574.2 (2) | 8.90 (d, J = 2.5 Hz, 1H), 8.74 (d, J = 2.2 Hz, 1H), 8.54 (d, J = 7.4 Hz, 1H), 8.15 (s, 1H), 7.58 (s, 1H), 5.33 (br s, 0.5H), 5.22 (br s, 0.5H), 4.77-4.61 (m, 1H), 4.28-4.16 (m, 1H), 4.03 (s, 3H), 4.00-3.91 (m, 1H), 3.88-3.79 (m, 2H), 3.34-3.24 (m, 1H), 2.16-2.01 (m, 1H), 1.71-1.59 (m, 1H), 1.48-1.36 (m, 1H). |
| 1458 | 3,3,4,4,4-pentafluorobutan-2-yl (3R,4S)-3-{5-[4-amino-5-(trifluoromethyl)pyrrolo[2,1-f][1,2,4]triazin- | | 630.2 (1) | 8.89 (d, J = 1.4 Hz, 1H), 8.74 (dd, J = 4.7, 2.2 Hz, 1H), 8.54 (br d, J = 7.7 Hz, 1H), 8.15 (s, 1H), 7.57 (s, 1H), 5.48-5.36 (m, 1H), 5.36-5.31 (m, 0.5H), 5.26-5.19 (m, 0.5H), 4.81-4.63 (m, 1H), 4.03 |

TABLE 52-continued

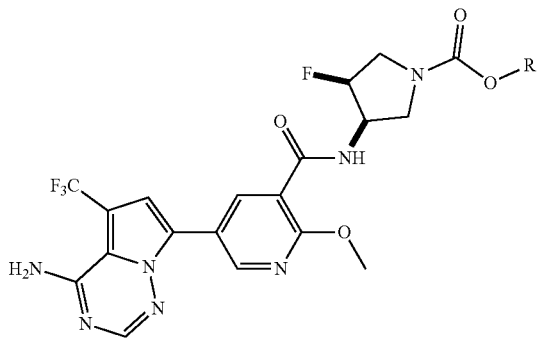

| Ex | Name | R | Obs. MS Ion M+ (method) | NMR Assignments (500 MHz, DMSO-d6) δ or LCMS retention time |
|---|---|---|---|---|
| | 7-yl]-2-methoxypyridine-3-amido}-4-fluoropyrrolidine-1-carboxylate | | | (s, 3H), 3.86-3.74 (m, 2H), 3.38-3.29 (m, 1H), 1.40 (br d, J = 6.3 Hz, 3H). |
| 1459 | (2,2-difluorocyclopropyl)methyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate | | 574.2 (1) | 8.93 (d, J = 2.5 Hz, 1H), 8.77 (d, J = 1.9 Hz, 1H), 8.52 (br d, J = 6.9 Hz, 1H), 8.18 (s, 1H), 7.61 (s, 1H), 5.33 (br s, 0.5H), 5.23 (br s, 0.5H), 4.79-4.63 (m, 1H), 4.27-4.18 (m, 1H), 4.04 (s, 3H), 4.01-3.95 (m, 1H), 3.88-3.60 (m, 2H), 3.31 (br d, J = 11.8 Hz, 1H), 2.17-2.04 (m, 1H), 1.73-1.62 (m, 1H), 1.45 (br d, J = 6.9 Hz, 1H). |

Compounds in Table 52 were prepared similarly to the methods detailed in Example 1416 or Example 1418 or Example 1418. Some examples were prepared from neutral amine starting material, while others employed amine starting material as a TFA salt. The quantity of DIPEA used in each reaction were adjusted accordingly. In some cases, it was observed by LCMS that an undesired byproduct had formed during the reaction with a mass ion fragment suggestive of the presence of two newly formed carbamate moieties in the undesired byproduct molecule. In these cases, the crude reaction mixtures were concentrated via nitrogen stream to a residue, redissolved in methanol (1 mL), and the resulting mixture was then treated with an excess of potassium carbonate (approximately 100-200 mg) and heated with stirring to 45° C. ON. This treatment effectively destroyed the undesired byproduct and provided the title compounds after aqueous workup and preparative HPLC purification. Examples in the table bearing a free aliphatic hydroxyl group were prepared by a similar method detailed in Example 1428. Examples in the table are single diastereomers unless otherwise noted. Where diastereomers were separated either by reverse phase preparative HPLC or by further SFC chiral chromatography, similar to that described in Example 1427, they are included as separate entries. For each example, two analytical LCMS injections with matched stationary phase columns were used to determine final purity. The method(s) used are indicated in each case. Method 1-6 as described in the Methods of Preparation Section.

Example 1460: 5-(4-Amino-5-(trifluoromethyl)pyrrolo[2,1-f][1,2,4]triazin-7-yl)-N-((3R,4S)-4-fluoro-1-(isopropylsulfonyl)pyrrolidin-3-yl)-2-methoxynicotinamide A mixture of 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide (15 mg, 0.034 mmol) and Hunig's base (0.018 mL, 0.102 mmol) in DMF (0.5 mL) was treated with isopropylsulfonyl chloride (5.75 μl, 0.051 mmol). The mixture was stirred at rt ON. The mixture was filtered. The crude material was purified via preparative LC/MS with the following conditions: Column=XBridge C18, 200 mm×19 mm, 5-μm particles; Mobile Phase A=5:95 acetonitrile:water with 0.1% trifluoroacetic acid; Mobile Phase B=95:5 acetonitrile:water with 0.1% trifluoroacetic acid; Gradient=18-58% B over 25 minutes, then a 4-minute hold at 100% B; Flow Rate=20 mL/min; Column Temperature=25° C. Fractions containing the desired product were combined and dried via centrifugal evaporation to give the desired product (11.5 mg, 43% yield).

MS ESI m/z 546.1 (M+H)+

1H NMR (500 MHz, DMSO-d6) δ 8.93 (d, J=2.4 Hz, 1H), 8.78 (d, J=2.1 Hz, 1H), 8.53 (d, J=7.3 Hz, 1H), 8.18 (s, 1H), 7.61 (s, 1H), 5.36 (br s, 0.5H), 5.26 (br s, 0.5H), 4.82-4.69 (m, 1H), 4.05 (s, 3H), 3.83-3.63 (m, 3H), 3.50-3.38 (m, 2H), 1.27 (d, J=6.7 Hz, 6H).

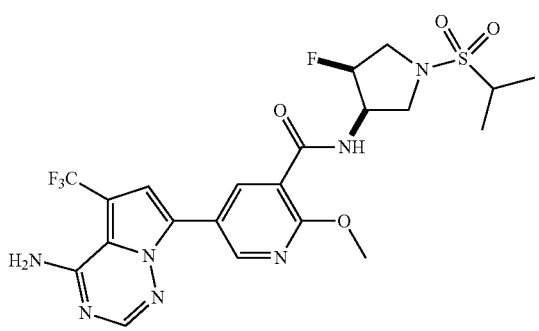

TABLE 53

| Ex | Name | R | Obs. MS Ion M+ (method) | NMR Assignments (500 MHz, DMSO-d6) δ or LCMS retention time |
|---|---|---|---|---|
| 1461 | 5-[4-amino-5-(trifluoromethyl)pyrrolo[2,1-f][1,2,4]triazin-7-yl]-N-[(3R,4S)-1-(cyclopropanesulfonyl)-4-fluoropyrrolidin-3-yl]-2-methoxypyridine-3-carboxamide | cyclopropyl | 544.1 (2) | 8.93 (d, J = 2.4 Hz, 1H), 8.79 (d, J = 2.4 Hz, 1H), 8.53 (br d, J = 7.3 Hz, 1H), 8.18 (s, 1H), 7.62 (s, 1H), 5.38 (br d, J = 3.1 Hz, 0.5H), 5.28-5.26 (m, 0.5H), 4.80-4.69 (m, 1H), 4.05 (s, 3H), 3.83-3.70 (m, 2H), 3.66 (t, J = 12.5 Hz, 1H), 3.40-3.35 (m, 1H), 2.78 (quin, J = 6.3 Hz, 1H), 1.04-0.96 (m, 4H). |
| 1462 | 5-[4-amino-5-(trifluoromethyl)pyrrolo[2,1-f][1,2,4]triazin-7-yl]-N-[(3R,4S)-1-(cyclohexanesulfonyl)-4-fluoropyrrolidin-3-yl]-2-methoxypyridine-3-carboxamide | cyclohexyl | 586.1 (2) | 8.93 (d, J = 2.4 Hz, 1H), 8.77 (d, J = 2.4 Hz, 1H), 8.52 (br d, J = 7.3 Hz, 1H), 8.18 (s, 1H), 7.62 (s, 1H), 5.36 (br d, J = 2.7 Hz, 0.5H), 5.25 (br s, 0.5H), 4.81-4.69 (m, 1H), 4.05 (s, 3H), 3.83-3.62 (m, 3H), 3.30-3.21 (m, 1H), 2.03 (br d, J = 7.3 Hz, 2H), 1.79 (br d, J = 12.8 Hz, 2H), 1.66-1.60 (m, 1H), 1.47-1.37 (m, 2H), 1.34-1.25 (m, 2H), 1.20-1.10 (m, 1H). |
| 1463 | 5-[4-amino-5-(trifluoromethyl)pyrrolo[2,1-f][1,2,4]triazin-7-yl]-N-[(3R,4S)-1-(cyclopentanesulfonyl)-4-fluoropyrrolidin-3-yl]-2-methoxypyridine-3-carboxamide | cyclopentyl | 572.1 (1) | 8.93 (d, J = 2.1 Hz, 1H), 8.78 (d, J = 2.4 Hz, 1H), 8.52 (br d, J = 7.9 Hz, 1H), 8.18 (s, 1H), 7.62 (s, 1H), 5.37-5.34 (m, 0.5H), 5.25 (br s, 0.5H), 4.79-4.67 (m, 1H), 4.05 (s, 3H), 3.82-3.62 (m, 4H), 2.01-1.94 (m, 2H), 1.89-1.81 (m, 2H), 1.73-1.65 (m, 2H), 1.63-1.54 (m, 2H). |
| 1464 | 5-[4-amino-5-(trifluoromethyl)pyrrolo[2,1-f][1,2,4]triazin-7-yl]-N-[(3R,4S)-4-fluoro-1-(3-methylbutane-2-sulfonyl)pyrrolidin-3-yl]-2-methoxypyridine-3-carboxamide | 3-methylbutan-2-yl | 574.2 (2) | 8.93 (s, 1H), 8.78 (dd, J = 8.9, 2.4 Hz, 1H), 8.53 (t, J = 6.2 Hz, 1H), 8.18 (s, 1H), 7.62 (s, 1H), 5.36 (br d, J = 2.7 Hz, 0.5H), 5.25 (br s, 0.5H), 4.80-4.68 (m, 1H), 4.05 (d, J = 2.1 Hz, 3H), 3.83-3.62 (m, 3H), 3.29-3.26 (m, 1H), 2.36-2.27 (m, 1H), 1.20 (dd, J = 7.0, 2.4 Hz, 3H), 0.97 (dd, J = 15.7, 6.9 Hz, 6H). |
| 1465 | 5-[4-amino-5-(trifluoromethyl)pyrrolo[2,1-f][1,2,4]triazin-7-yl]-N-[(3R,4S)-4-fluoro-1-(4-methylpentane-2-sulfonyl)pyrrolidin-3-yl]-2-methoxypyridine-3-carboxamide | 4-methylpentan-2-yl | 588.2 (2) | 8.93 (s, 1H), 8.78 (dd, J = 6.7, 2.4 Hz, 1H), 8.53 (br d, J = 7.3 Hz, 1H), 8.18 (s, 1H), 7.62 (s, 1H), 5.36 (br s, 0.5H), 5.26 (br d, J = 2.1 Hz, 0.5H), 4.80-4.69 (m, 1H), 4.05 (d, J = 2.1 Hz, 3H), 3.84-3.63 (m, 3H), 3.38-3.34 (m, 1H), 1.73-1.58 (m, 2H), 1.44-1.37 (m, 1H), 1.25 (br d, J = 5.5 Hz, 3H), 0.95-0.85 (m, 6H). |

TABLE 53-continued

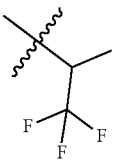

| Ex | Name | R | Obs. MS Ion M+ (method) | NMR Assignments (500 MHz, DMSO-d6) δ or LCMS retention time |
|---|---|---|---|---|
| 1466 | 5-[4-amino-5-(trifluoromethyl)pyrrolo[2,1-f][1,2,4]triazin-7-yl]-N-[(3R,4S)-4-fluoro-1-(1,1,1-trifluoropropane-2-sulfonyl)pyrrolidin-3-yl]-2-methoxypyridine-3-carboxamide | 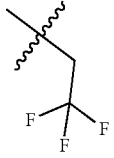 [SMILES: *CC(F)(F)F] | 600.0 (1) | 8.93 (d, J = 2.4 Hz, 1H), 8.77 (s, 1H), 8.55 (br d, J = 7.3 Hz, 1H), 8.18 (s, 1H), 7.62 (s, 1H), 5.39 (br d, J = 3.1 Hz, 0.5H), 5.28 (br d, J = 2.4 Hz, 0.5H), 4.85-4.72 (m, 2H), 4.05 (s, 3H), 3.92-3.72 (m, 3H), 3.42-3.35 (m, 1H), 1.50 (d, J = 7.0 Hz, 3H). |
| 1467 | 5-[4-amino-5-(trifluoromethyl)pyrrolo[2,1-f][1,2,4]triazin-7-yl]-N-[(3R,4S)-4-fluoro-1-(2,2,2-trifluoroethanesulfonyl)pyrrolidin-3-yl]-2-methoxypyridine-3-carboxamide | 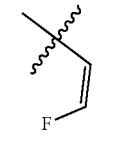 | 586.0 (1) | 8.93 (d, J = 2.1 Hz, 1H), 8.78 (d, J = 2.4 Hz, 1H), 8.53 (br d, J = 7.6 Hz, 1H), 8.18 (s, 1H), 7.62 (s, 1H), 5.38 (br s, 0.5H), 5.27 (br s, 0.5H), 4.83-4.61 (m, 3H), 4.05 (s, 3H), 3.92-3.69 (m, 3H), 3.41-3.36 (m, 1H), 2.48-2.46 (m, 1H). |
| 1468 | 5-[4-amino-5-(trifluoromethyl)pyrrolo[2,1-f][1,2,4]triazin-7-yl]-N-[(3R,4S)-4-fluoro-1-[(Z)-2-fluoroethenesulfonyl]pyrrolidin-3-yl]-2-methoxypyridine-3-carboxamide | 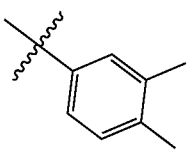 [SMILES: *c1ccc(C)c(C)c1] | 548.1 (1) | 8.93 (d, J = 2.1 Hz, 1H), 8.78 (dd, J = 8.4, 2.3 Hz, 1H), 8.61-8.53 (m, 1H), 8.18 (s, 1H), 7.91-7.79 (m, 1H), 7.62 (s, 1H), 5.48-5.23 (m, 2H), 5.00-4.70 (m, 1H), 4.16-3.95 (m, 5H), 3.74-3.68 (m, 1H), 3.65-3.53 (m, 1H), 3.29-3.15 (m, 1H). |
| 1469 | 5-[4-amino-5-(trifluoromethyl)pyrrolo[2,1-f][1,2,4]triazin-7-yl]-N-[(3R,4S)-1-(3,4-dimethylbenzenesulfonyl)-4-fluoropyrrolidin-3-yl]-2-methoxypyridine-3-carboxamide | 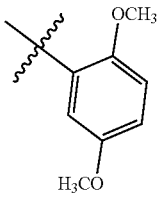 [SMILES: *c1cc(OC)ccc1OC] | 608.0 (1) | 8.91 (d, J = 2.4 Hz, 1H), 8.72 (d, J = 2.4 Hz, 1H), 8.43 (d, J = 7.6 Hz, 1H), 8.17 (s, 1H), 7.63 (s, 1H), 7.61-7.56 (m, 2H), 7.42 (d, J = 7.9 Hz, 1H), 5.27-5.25 (m, 0.5H), 5.15 (br s, 0.5H), 4.52-4.41 (m, 1H), 4.00 (s, 3H), 3.72-3.53 (m, 4H), 3.19-3.12 (m, 1H), 2.33 (d, J = 6.7 Hz, 6H). |
| 1470 | 5-[4-amino-5-(trifluoromethyl)pyrrolo[2,1-f][1,2,4]triazin-7-yl]-N-[(3R,4S)-1-(2,5-dimethoxybenzenesulfonyl)-4-fluoropyrrolidin-3-yl]-2-methoxypyridine-3-carboxamide | | 640.1 (2) | 8.92 (d, J = 2.4 Hz, 1H), 8.75 (d, J = 2.4 Hz, 1H), 8.48 (d, J = 7.3 Hz, 1H), 8.17 (s, 1H), 7.60 (s, 1H), 7.30 (s, 1H), 7.25 (s, 2H), 5.34 (br s, 0.5H), 5.23 (br d, J = 3.4 Hz, 0.5H), 4.63-4.51 (m, 1H), 4.02 (s, 3H), 3.90 (s, 3H), 3.85 (t, J = 8.9 Hz, 1H), 3.78 (s, 3H), 3.74-3.60 (m, 2H), 3.25 (t, J = 9.9 Hz, 1H). |

TABLE 53-continued

| Ex | Name | R | Obs. MS Ion M+ (method) | NMR Assignments (500 MHz, DMSO-d6) δ or LCMS retention time |
|---|---|---|---|---|
| 1471 | 5-[4-amino-5-(trifluoromethyl)pyrrolo[2,1-f][1,2,4]triazin-7-yl]-N-[(3R,4S)-4-fluoro-1-(naphthalene-1-sulfonyl)pyrrolidin-3-yl]-2-methoxypyridine-3-carboxamide | naphthalen-1-yl | 630.1 (1) | 8.90 (d, J = 2.4 Hz, 1H), 8.72-8.68 (m, 2H), 8.47 (d, J = 7.3 Hz, 1H), 8.31 (d, J = 8.2 Hz, 1H), 8.20 (d, J = 7.3 Hz, 1H), 8.16 (s, 1H), 8.13 (d, J = 7.9 Hz, 1H), 7.77 (t, J = 7.8 Hz, 1H), 7.70 (q, J = 8.2 Hz, 2H), 7.59 (s, 1H), 5.34-5.31 (m, 0.5H), 5.22 (br d, J = 3.1 Hz, 0.5H), 4.73-4.61 (m, 1H), 3.99 (s, 3H), 3.84-3.70 (m, 3H), 3.31-3.25 (m, 1H). |
| 1472 | 5-[4-amino-5-(trifluoromethyl)pyrrolo[2,1-f][1,2,4]triazin-7-yl]-N-[(3R,4S)-4-fluoro-1-phenylmethanesulfonyl-pyrrolidin-3-yl]-2-methoxypyridine-3-carboxamide | benzyl | 594.0 (2) | 8.94-8.91 (m, 1H), 8.78 (d, J = 2.4 Hz, 1H), 8.49 (d, J = 7.6 Hz, 1H), 8.18 (s, 1H), 7.62 (s, 1H), 7.47-7.37 (m, 5H), 5.37-5.18 (m, 1H), 4.74-4.63 (m, 1H), 4.58-4.51 (m, 2H), 4.05 (s, 3H), 3.72-3.58 (m, 3H), 3.28-3.20 (m, 1H). |
| 1473 | 5-[4-amino-5-(trifluoromethyl)pyrrolo[2,1-f][1,2,4]triazin-7-yl]-N-[(3R,4S)-4-fluoro-1-[(3-methylphenyl)methanesulfonyl]pyrrolidin-3-yl]-2-methoxypyridine-3-carboxamide | 3-methylbenzyl | 608.0 (1) | 17.99 (s, 1H), 8.93 (d, J = 2.4 Hz, 1H), 8.78 (d, J = 2.4 Hz, 1H), 8.48 (d, J = 7.3 Hz, 1H), 8.18 (s, 1H), 7.62 (s, 1H), 7.30-7.22 (m, 3H), 7.19 (br d, J = 7.6 Hz, 1H), 5.33 (br s, 0.5H), 5.22 (br s, 0.5H), 4.75-4.63 (m, 1H), 4.53-4.45 (m, 2H), 4.05 (s, 3H), 3.71-3.54 (m, 3H), 3.26-3.19 (m, 1H), 2.34 (s, 3H). |
| 1474 | 5-[4-amino-5-(trifluoromethyl)pyrrolo[2,1-f][1,2,4]triazin-7-yl]-N-[(3R,4S)-4-fluoro-1-(2-methoxybenzenesulfonyl)pyrrolidin-3-yl]-2-methoxypyridine-3-carboxamide | 2-methoxyphenyl (OCH$_3$) | 610.0 (1) | 8.92 (d, J = 2.4 Hz, 1H), 8.75 (d, J = 2.4 Hz, 1H), 8.48 (d, J = 7.6 Hz, 1H), 8.17 (s, 1H), 7.81 (d, J = 7.7 Hz, 1H), 7.66 (t, J = 7.7 Hz, 1H), 7.61 (s, 1H), 7.30 (d, J = 8.5 Hz, 1H), 7.13 (t, J = 7.6 Hz, 1H), 5.33 (br s, 0.5H), 5.24-5.21 (m, 0.5H), 4.63-4.51 (m, 1H), 4.02 (s, 3H), 3.96 (s, 3H), 3.84 (t, J = 9.0 Hz, 1H), 3.74-3.59 (m, 2H), 3.24 (t, J = 10.1 Hz, 1H). |
| 1475 | 5-[4-amino-5-(trifluoromethyl)pyrrolo[2,1-f][1,2,4]triazin-7-yl]-N-[(3R,4S)-4-fluoro-1-(2-methoxy-5-methylbenzenesulfonyl)pyrrolidin-3-yl]-2-methoxypyridine-3-carboxamide | 2-methoxy-5-methylphenyl (OCH$_3$) | 624.1 (2) | 8.92 (d, J = 2.4 Hz, 1H), 8.75 (d, J = 2.1 Hz, 1H), 8.48 (d, J = 7.3 Hz, 1H), 8.17 (s, 1H), 7.61 (s, 2H), 7.46 (dd, J = 8.4, 1.7 Hz, 1H), 7.19 (d, J = 8.5 Hz, 1H), 5.34-5.32 (m, 0.5H), 5.22 (t, J = 2.7 Hz, 0.5H), 4.62-4.50 (m, 1H), 4.02 (s, 3H), 3.92 (s, 3H), 3.83 (t, J = 9.0 Hz, 1H), 3.73-3.58 (m, 2H), 3.26-3.21 (m, 1H), 2.31 (s, 3H), 1.29-1.21 (m, 1H). |

TABLE 53-continued

| Ex | Name | R | Obs. MS Ion M⁺ (method) | NMR Assignments (500 MHz, DMSO-d6) δ or LCMS retention time |
|---|---|---|---|---|
| 1476 | 5-[4-amino-5-(trifluoromethyl)pyrrolo[2,1-f][1,2,4]triazin-7-yl]-N-[(3R,4S)-4-fluoro-1-(2-methylbenzenesulfonyl)pyrrolidin-3-yl]-2-methoxypyridine-3-carboxamide | 2-methylphenyl | 594.1 (2) | LCMS Method 1 retention time = 1.98 min LCMS Method 2 retention time = 2.19 min |
| 1477 | 5-[4-amino-5-(trifluoromethyl)pyrrolo[2,1-f][1,2,4]triazin-7-yl]-N-[(3R,4S)-4-fluoro-1-(3-methylbenzenesulfonyl)pyrrolidin-3-yl]-2-methoxypyridine-3-carboxamide | 3-methylphenyl | 594.1 (1) | 8.91 (d, J = 2.4 Hz, 1H), 8.72 (d, J = 2.4 Hz, 1H), 8.44 (d, J = 7.6 Hz, 1H), 8.17 (s, 1H), 7.69-7.64 (m, 2H), 7.60 (s, 1H), 7.55 (d, J = 4.6 Hz, 2H), 5.27-5.25 (m, 0.5H), 5.15 (br s, 0.5H), 4.54-4.43 (m, 1H), 4.00 (s, 3H), 3.75-3.54 (m, 3H), 3.16 (t, J = 9.9 Hz, 1H), 2.43 (s, 3H), 1.26-1.22 (m, 1H), 0.87-0.80 (m, 1H). |
| 1478 | 5-[4-amino-5-(trifluoromethyl)pyrrolo[2,1-f][1,2,4]triazin-7-yl]-N-[(3R,4S)-4-fluoro-1-(4-methylbenzenesulfonyl)pyrrolidin-3-yl]-2-methoxypyridine-3-carboxamide | 4-methylphenyl | 594.1 (2) | 8.91 (d, J = 2.1 Hz, 1H), 8.72 (d, J = 2.4 Hz, 1H), 8.43 (d, J = 7.3 Hz, 1H), 8.17 (s, 1H), 7.76-7.73 (m, J = 7.9 Hz, 2H), 7.60 (s, 1H), 7.48-7.45 (m, J = 7.9 Hz, 2H), 5.26-5.24 (m, 0.5H), 5.14 (br s, 0.5H), 4.51-4.41 (m, 1H), 4.00 (s, 3H), 3.73-3.51 (m, 3H), 3.14 (t, J = 9.9 Hz, 1H), 2.42 (s, 3H). |
| 1479 | 5-[4-amino-5-(trifluoromethyl)pyrrolo[2,1-f][1,2,4]triazin-7-yl]-N-[(3R,4S)-4-fluoro-1-(oxolane-3-sulfonyl)pyrrolidin-3-yl]-2-methoxypyridine-3-carboxamide | oxolan-3-yl | 574.1 (2) | 8.93 (d, J = 2.4 Hz, 1H), 8.78 (s, 1H), 8.53 (br d, J = 7.3 Hz, 1H), 8.18 (s, 1H), 7.62 (s, 1H), 5.36 (br s, 0.5H), 5.26 (br s, 0.5H), 4.81-4.71 (m, 1H), 4.20-4.14 (m, 1H), 4.05 (s, 3H), 3.99-3.90 (m, 2H), 3.88-3.78 (m, 3H), 3.75-3.66 (m, 3H), 2.29-2.22 (m, 1H), 2.20-2.13 (m, 1H). |
| 1480 | 5-[4-amino-5-(trifluoromethyl)pyrrolo[2,1-f][1,2,4]triazin-7-yl]-N-[(3R,4S)-1-{bicyclo[2.2.1]heptane-2-sulfonyl}-4-fluoropyrrolidin-3-yl]-2-methoxypyridine-3-carboxamide | bicyclo[2.2.1]heptan-2-yl | 598.1 (1) | 8.93 (s, 1H), 8.78 (dt, J = 5.4, 2.6 Hz, 1H), 8.55-8.49 (m, 1H), 8.18 (s, 1H), 7.62 (s, 1H), 5.36 (br d, J = 2.4 Hz, 0.5H), 5.25 (br d, J = 1.8 Hz, 0.5H), 4.78-4.66 (m, 1H), 4.05 (s, 3H), 3.83-3.60 (m, 4H), 3.31-3.26 (m, 1H), 2.62-2.56 (m, 1H), 2.34 (br s, 1H), 2.05-1.79 (m, 1H), 1.70-1.63 (m, 1H), 1.58-1.46 (m, 2H), 1.43-1.23 (m, 3H), 1.20-1.13 (m, 1H). |

TABLE 53-continued

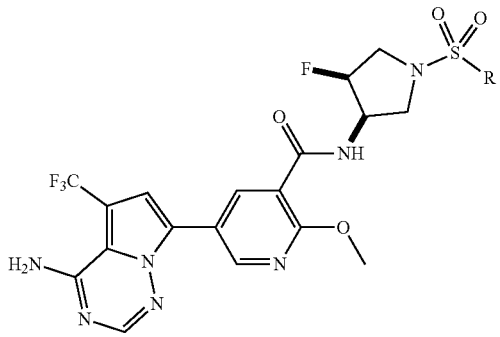

| Ex | Name | R | Obs. MS Ion M+ (method) | NMR Assignments (500 MHz, DMSO-d6) δ or LCMS retention time |
|---|---|---|---|---|
| 1481 | 5-[4-amino-5-(trifluoromethyl)pyrrolo[2,1-f][1,2,4]triazin-7-yl]-N-[(3R,4S)-1-[(1,1-dioxidotetrahydrothiophen-3-yl)sulfonyl]-4-fluoropyrrolidin-3-yl]-2-methoxypyridine-3-carboxamide | | 622.0 (2) | 8.93 (d, J = 2.4 Hz, 1H), 8.77 (t, J = 2.1 Hz, 1H), 8.53 (d, J = 7.6 Hz, 1H), 8.18 (s, 1H), 7.62 (s, 1H), 5.36 (br d, J = 3.4 Hz, 0.5H), 5.26 (br d, J = 3.4 Hz, 0.5H), 4.89-4.78 (m, 1H), 4.45-4.37 (m, 1H), 4.05 (s, 3H), 3.86-3.59 (m, 4H), 3.42-3.36 (m, 2H), 3.28-3.15 (m, 2H), 2.59-2.53 (m, 1H), 2.35-2.26 (m, 1H). |
| 1482 | 5-[4-amino-5-(trifluoromethyl)pyrrolo[2,1-f][1,2,4]triazin-7-yl]-N-[(3R,4S)-1-(butane-1-sulfonyl)-4-fluoropyrrolidin-3-yl]-2-methoxypyridine-3-carboxamide | | 560.1 (1) | 8.93 (d, J = 2.4 Hz, 1H), 8.78 (d, J = 2.4 Hz, 1H), 8.52 (d, J = 7.3 Hz, 1H), 8.18 (s, 1H), 7.62 (s, 1H), 5.35 (t, J = 2.7 Hz, 0.5H), 5.24 (br d, J = 2.7 Hz, 0.5H), 4.79-4.68 (m, 1H), 4.05 (s, 3H), 3.80-3.59 (m, 3H), 3.33-3.27 (m, 1H), 3.20-3.12 (m, 2H), 1.68 (quin, J = 7.6 Hz, 2H), 1.42 (sxt, J = 7.4 Hz, 2H), 0.92 (t, J = 7.3 Hz, 3H). |
| 1483 | 5-[4-amino-5-(trifluoromethyl)pyrrolo[2,1-f][1,2,4]triazin-7-yl]-N-[(3R,4S)-4-fluoro-1-[(2-hydroxycyclohexyl)sulfonyl]pyrrolidin-3-yl]-2-methoxypyridine-3-carboxamide | | 602.1 (2) | 8.95-8.89 (m, 1H), 8.80-8.74 (m, 1H), 8.55-8.45 (m, 1H), 8.17 (s, 1H), 7.61 (s, 1H), 5.37-5.19 (m, 1H), 4.78-4.63 (m, 1H), 4.26-4.20 (m, 1H), 4.08-4.03 (m, 3H), 4.01-3.50 (m, 3H), 3.34-3.22 (m, 2H), 2.24-1.99 (m, 1H), 1.96-1.78 (m, 1H), 1.77-1.70 (m, 2H), 1.69-1.54 (m, 1H), 1.52-1.13 (m, 4H). |
| 1484 | 5-[4-amino-5-(trifluoromethyl)pyrrolo[2,1-f][1,2,4]triazin-7-yl]-N-[(3R,4S)-4-fluoro-1-(3,3,3-trifluoropropanesulfonyl)pyrrolidin-3-yl]-2-methoxypyridine-3-carboxamide | | 600.0 (1) | 8.93 (d, J = 2.4 Hz, 1H), 8.77 (d, J = 2.4 Hz, 1H), 8.52 (d, J = 7.6 Hz, 1H), 8.18 (s, 1H), 7.62 (s, 1H), 5.37-5.34 (m, 0.5H), 5.26-5.23 (m, 0.5H), 4.88-4.76 (m, 1H), 4.05 (s, 3H), 3.88-3.68 (m, 3H), 3.53-3.44 (m, 2H), 3.41-3.35 (m, 1H), 2.80-2.69 (m, 2H). |
| 1485 | 5-[4-amino-5-(trifluoromethyl)pyrrolo[2,1-f][1,2,4]triazin-7-yl]-N-[(3R,4S)-4-fluoro-1-(oxane-4-sulfonyl)pyrrolidin-3-yl]-2-methoxypyridine-3-carboxamide | | 588.1 (2) | 8.93 (d, J = 2.1 Hz, 1H), 8.78 (d, J = 2.4 Hz, 1H), 8.53 (d, J = 7.6 Hz, 1H), 8.18 (s, 1H), 7.62 (s, 1H), 5.37 (br s, 0.5H), 5.26 (br s, 0.5H), 4.83-4.72 (m, 1H), 4.05 (s, 3H), 3.95 (br dd, J = 11.4, 3.8 Hz, 2H), 3.85-3.65 (m, 3H), 3.58 (tt, J = 11.9, 4.0 Hz, 1H), 3.38-3.35 (m, 2H), 1.89 (br t, J = 11.0 Hz, 2H), 1.74-1.64 (m, 2H). |

TABLE 53-continued

| Ex | Name | R | Obs. MS Ion M+ (method) | NMR Assignments (500 MHz, DMSO-d6) δ or LCMS retention time |
|---|---|---|---|---|
| 1486 | 5-[4-amino-5-(trifluoromethyl)pyrrolo[2,1-f][1,2,4]triazin-7-yl]-N-[(3R,4S)-1-(cyclohex-1-ene-1-sulfonyl)-4-fluoropyrrolidin-3-yl]-2-methoxypyridine-3-carboxamide | cyclohex-1-en-1-yl | 584.1 (2) | 8.93 (d, J = 2.4 Hz, 1H), 8.75 (d, J = 2.4 Hz, 1H), 8.54 (d, J = 7.0 Hz, 1H), 8.18 (s, 1H), 7.61 (s, 1H), 6.68 (s, 1H), 5.39-5.20 (m, 1H), 4.80-4.64 (m, 1H), 4.04 (s, 3H), 3.73-3.50 (m, 4H), 3.24 (s, 1H), 2.31-2.22 (m, 4H), 1.70-1.61 (m, 2H), 1.58 (br d, J = 4.3 Hz, 2H). |
| 1487 | 5-[4-amino-5-(trifluoromethyl)pyrrolo[2,1-f][1,2,4]triazin-7-yl]-N-[(3R,4S)-4-fluoro-1-[(2-nitrophenyl)methanesulfonyl]pyrrolidin-3-yl]-2-methoxypyridine-3-carboxamide | 2-nitrobenzyl | 639.1 (2) | 8.95-8.92 (m, 1H), 8.78 (d, J = 2.1 Hz, 1H), 8.53 (br d, J = 7.6 Hz, 1H), 8.19 (s, 1H), 8.08 (br d, J = 7.6 Hz, 1H), 7.83-7.77 (m, 1H), 7.77-7.73 (m, 1H), 7.74-7.67 (m, 1H), 7.62 (s, 1H), 5.37 (br s, 0.5H), 5.26 (br s, 0.5H), 5.02 (q, J = 13.7 Hz, 2H), 4.83-4.71 (m, 1H), 4.05 (s, 3H), 3.73-3.56 (m, 3H), 3.30-3.23 (m, 1H). |
| 1488 | 5-[4-amino-5-(trifluoromethyl)pyrrolo[2,1-f][1,2,4]triazin-7-yl]-N-[(3R,4S)-4-fluoro-1-[(4-fluorophenyl)methanesulfonyl]pyrrolidin-3-yl]-2-methoxypyridine-3-carboxamide | 4-fluorobenzyl | 612.0 (2) | 8.93 (d, J = 2.1 Hz, 1H), 8.78 (d, J = 2.1 Hz, 1H), 8.49 (br d, J = 7.6 Hz, 1H), 8.18 (s, 1H), 7.62 (s, 1H), 7.50 (t, J = 6.2 Hz, 2H), 7.24 (br t, J = 8.9 Hz, 2H), 5.34 (br s, 0.5H), 5.23 (br s, 0.5H), 4.75-4.64 (m, 1H), 4.59-4.52 (m, 2H), 4.05 (s, 3H), 3.74-3.57 (m, 3H), 3.25 (br t, J = 9.8 Hz, 1H). |
| 1489 | 5-[4-amino-5-(trifluoromethyl)pyrrolo[2,1-f][1,2,4]triazin-7-yl]-N-[(3R,4S)-1-[(2,5-difluorophenyl)methanesulfonyl]-4-fluoropyrrolidin-3-yl]-2-methoxypyridine-3-carboxamide | 2,5-difluorobenzyl | 630.1 (2) | 8.93 (d, J = 2.1 Hz, 1H), 8.78 (d, J = 2.1 Hz, 1H), 8.53 (br d, J = 7.6 Hz, 1H), 8.18 (s, 1H), 7.62 (s, 1H), 7.39-7.28 (m, 3H), 5.37 (br s, 0.5H), 5.26 (br s, 0.5H), 4.81-4.70 (m, 1H), 4.60 (q, J = 13.9 Hz, 2H), 4.05 (s, 3H), 3.81-3.59 (m, 3H), 3.33-3.27 (m, 1H). |
| 1490 | 5-[4-amino-5-(trifluoromethyl)pyrrolo[2,1-f][1,2,4]triazin-7-yl]-N-[(3R,4S)-4-fluoro-1-[(3-fluorophenyl)methanesulfonyl]pyrrolidin-3-yl]-2-methoxypyridine-3-carboxamide | 3-fluorobenzyl | 612.1 (2) | 8.92 (s, 1H), 8.78 (s, 1H), 8.50 (d, J = 7.5 Hz, 1H), 8.18 (s, 1H), 7.61 (s, 1H), 7.48-7.43 (m, 1H), 7.32-7.20 (m, 3H), 5.35 (br s, 0.5H), 5.24 (br s, 0.5H), 4.76-4.56 (m, 3H), 4.05 (s, 3H), 3.77-3.58 (m, 3H), 3.26 (br t, J = 9.8 Hz, 1H). |

TABLE 53-continued

| Ex | Name | R | Obs. MS Ion M+ (method) | NMR Assignments (500 MHz, DMSO-d6) δ or LCMS retention time |
|---|---|---|---|---|
| 1491 | 5-[4-amino-5-(trifluoromethyl)pyrrolo[2,1-f][1,2,4]triazin-7-yl]-N-[(3R,4S)-1-[(3-chlorophenyl)methanesulfonyl]-4-fluoropyrrolidin-3-yl]-2-methoxypyridine-3-carboxamide | 3-chlorobenzyl | 628.1 (2) | 8.93 (s, 1H), 8.79-8.77 (m, 1H), 8.50 (br d, J = 7.6 Hz, 1H), 8.18 (s, 1H), 7.61 (s, 1H), 7.53 (s, 1H), 7.47-7.41 (m, 3H), 5.36 (br s, 0.5H), 5.25 (br s, 0.5H), 4.76-4.66 (m, 1H), 4.62-4.56 (m, 2H), 4.05 (s, 3H), 3.78-3.59 (m, 3H), 3.34-3.32 (m, 1H), 3.26 (br t, J = 9.8 Hz, 1H). |
| 1492 | 5-[4-amino-5-(trifluoromethyl)pyrrolo[2,1-f][1,2,4]triazin-7-yl]-N-[(3R,4S)-1-[(2,6-dichlorophenyl)methanesulfonyl]-4-fluoropyrrolidin-3-yl]-2-methoxypyridine-3-carboxamide | 2,6-dichlorobenzyl | 662.0 (2) | 8.94 (d, J = 2.1 Hz, 1H), 8.78 (d, J = 2.1 Hz, 1H), 8.56 (br d, J = 7.3 Hz, 1H), 8.18 (s, 1H), 7.62 (s, 1H), 7.57 (d, J = 8.2 Hz, 2H), 7.45 (t, J = 8.1 Hz, 1H), 5.39 (br s, 0.5H), 5.28 (br s, 0.5H), 4.87-4.76 (m, 3H), 4.05 (s, 3H), 3.83-3.64 (m, 3H), 3.42-3.35 (m, 1H). |
| 1493 | 5-[4-amino-5-(trifluoromethyl)pyrrolo[2,1-f][1,2,4]triazin-7-yl]-N-[(3R,4S)-1-[(2-chlorophenyl)methanesulfonyl]-4-fluoropyrrolidin-3-yl]-2-methoxypyridine-3-carboxamide | 2-chlorobenzyl | 628.0 (2) | 8.94 (d, J = 2.1 Hz, 1H), 8.78 (d, J = 2.4 Hz, 1H), 8.53 (br d, J = 7.3 Hz, 1H), 8.18 (s, 1H), 7.63-7.52 (m, 3H), 7.44-7.39 (m, 2H), 5.37 (br s, 0.5H), 5.26 (br s, 0.5H), 4.83-4.74 (m, 1H), 4.68 (q, J = 13.9 Hz, 2H), 4.05 (s, 3H), 3.78-3.59 (m, 3H). |
| 1494 | 5-[4-amino-5-(trifluoromethyl)pyrrolo[2,1-f][1,2,4]triazin-7-yl]-N-[(3R,4S)-4-fluoro-1-[(pyridin-2-yl)methanesulfonyl]pyrrolidin-3-yl]-2-methoxypyridine-3-carboxamide | pyridin-2-ylmethyl | 595.0 (1) | 8.93 (s, 1H), 8.80-8.77 (m, 1H), 8.61 (br d, J = 4.3 Hz, 1H), 8.50 (br d, J = 7.3 Hz, 1H), 8.19 (s, 1H), 7.87 (br t, J = 7.6 Hz, 1H), 7.62 (s, 1H), 7.56 (br d, J = 7.9 Hz, 1H), 7.42 (t, J = 6.2 Hz, 1H), 5.36 (br s, 0.5H), 5.27-5.24 (m, 0.5H), 4.87-4.69 (m, 3H), 4.05 (s, 3H), 3.67-3.52 (m, 3H), 3.30-3.24 (m, 1H). |
| 1495 | 5-[4-amino-5-(trifluoromethyl)pyrrolo[2,1-f][1,2,4]triazin-7-yl]-N-[(3R,4S)-4-fluoro-1-[(3-nitrophenyl)methanesulfonyl]pyrrolidin-3-yl]-2-methoxypyridine-3-carboxamide | 3-nitrobenzyl | 639.1 (2) | 8.93 (d, J = 2.1 Hz, 1H), 8.78 (d, J = 2.1 Hz, 1H), 8.50 (br d, J = 7.6 Hz, 1H), 8.37 (s, 1H), 8.26 (br d, J = 8.5 Hz, 1H), 8.18 (s, 1H), 7.91 (br d, J = 7.6 Hz, 1H), 7.73 (t, J = 7.9 Hz, 1H), 7.61 (s, 1H), 5.36 (br s, 0.5H), 5.25 (br s, 0.5H), 4.81-4.68 (m, 3H), 4.05 (s, 3H), 3.80-3.60 (m, 3H), 3.31-3.25 (m, 1H). |

TABLE 53-continued

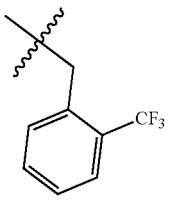 [SMILES: *Cc1ccccc1C(F)(F)F]

| Ex | Name | R | Obs. MS Ion M+ (method) | NMR Assignments (500 MHz, DMSO-d6) δ or LCMS retention time |
|---|---|---|---|---|
| 1496 | 5-[4-amino-5-(trifluoromethyl)pyrrolo[2,1-f][1,2,4]triazin-7-yl]-N-[(3R,4S)-4-fluoro-1-{[2-(trifluoromethyl)phenyl]methanesulfonyl}pyrrolidin-3-yl]-2-methoxypyridine-3-carboxamide | 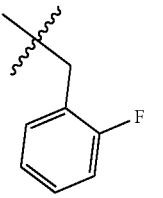 [SMILES: *Cc1ccccc1F] | 662.0 (2) | 8.93 (d, J = 2.1 Hz, 1H), 8.78 (d, J = 2.1 Hz, 1H), 8.55 (br d, J = 7.3 Hz, 1H), 8.18 (s, 1H), 7.81 (d, J = 7.6 Hz, 1H), 7.74 (d, J = 4.0 Hz, 2H), 7.62 (s, 1H), 7.62 (d, J = 5.7 Hz, 2H), 5.39 (br s, 0.5H), 5.28 (br s, 0.5H), 4.89-4.77 (m, 1H), 4.72-4.64 (m, 2H), 4.05 (s, 3H), 3.83-3.62 (m, 3H). |
| 1497 | 5-[4-amino-5-(trifluoromethyl)pyrrolo[2,1-f][1,2,4]triazin-7-yl]-N-[(3R,4S)-4-fluoro-1-[(2-fluorophenyl)methanesulfonyl]pyrrolidin-3-yl]-2-methoxypyridine-3-carboxamide | 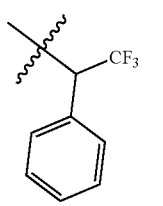 [SMILES: *C(c1ccccc1)C(F)(F)F] | 612.1 (1) | 8.93 (s, 1H), 8.78 (s, 1H), 8.52 (br d, J = 7.3 Hz, 1H), 8.18 (s, 1H), 7.62 (s, 1H), 7.53 (br t, J = 7.6 Hz, 1H), 7.48-7.42 (m, 1H), 7.30-7.23 (m, 2H), 5.36 (br s, 0.5H), 5.25 (br s, 0.5H), 4.80-4.68 (m, 1H), 4.63-4.53 (m, 2H), 4.05 (s, 3H), 3.77-3.57 (m, 3H), 3.37-3.24 (m, 1H). |
| 1498 | 5-[4-amino-5-(trifluoromethyl)pyrrolo[2,1-f][1,2,4]triazin-7-yl]-N-[(3R,4S)-4-fluoro-1-(2,2,2-trifluoro-1-phenylethanesulfonyl)pyrrolidin-3-yl]-2-methoxypyridine-3-carboxamide | | 662.0 (1) | 8.92 (s, 1H), 8.75 (dd, J = 7.0, 2.1 Hz, 1H), 8.49-8.39 (m, 1H), 8.20-8.16 (m, 1H), 7.66 (br d, J = 6.3 Hz, 2H), 7.61 (s, 1H), 7.56-7.49 (m, 3H), 6.21-6.09 (m, 1H), 5.33-5.11 (m, 1H), 4.61-4.40 (m, 1H), 4.06-4.01 (m, 3H), 3.79 (s, 2H), 3.30-3.23 (m, 1H). |

Compounds in Table 53 were prepared similarly to the methods detailed in Example 1460. When diastereomers were separated, they are included as separate entries. If the stereochemistry is undefined, the product was isolated as a mixture of diastereomers. For each example, two analytical LCMS injections with matched stationary phase columns were used to determine final purity. The method(s) used are indicated in each case. Method 1-6 as described in the Methods of Preparation Section.

TABLE 54

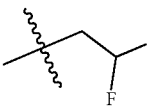

| Ex | Name | R | Obs. MS Ion M+ (method) | NMR Assignments (500 MHz, DMSO-d6) δ or HPLC retention time |
|---|---|---|---|---|
| 1499 | 2,2-difluoroethyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 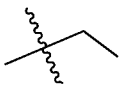 [SMILES: *CC] | 613.2 (2) | 9.29-9.12 (m, 1H), 8.94 (d, J = 2.1 Hz, 1H), 8.77 (d, J = 2.1 Hz, 1H), 8.50 (br d, J = 7.0 Hz, 1H), 7.91 (s, 1H), 7.71-7.55 (m, 1H), 7.06 (s, 1H), 6.39-6.13 (m, 1H), 5.35 (br s, 0.5H), 5.24 (br s, 0.5H), 4.80-4.68 (m, 1H), 4.38-4.29 (m, 2H), 4.03 (s, 3H), 3.90-3.64 (m, 5H), 3.41-3.35 (m, 1H), 2.65 (br s, 4H), 2.02 (br s, 4H). |
| 1500 | ethyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 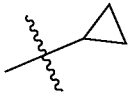 [SMILES: *C1CC1] | 577.2 (1) | 9.28-9.14 (m, 1H), 8.94-8.92 (m, 1H), 8.77 (s, 1H), 8.48 (br d, J = 7.3 Hz, 1H), 7.91 (s, 1H), 7.71-7.57 (m, 1H), 7.06 (s, 1H), 5.33 (br s, 0.5H), 5.22 (br s, 0.5H), 4.76-4.64 (m, 1H), 4.07 (q, J = 7.0 Hz, 2H), 4.04 (s, 3H), 3.86-3.78 (m, 3H), 3.76-3.60 (m, 2H), 3.29-3.24 (m, 1H), 2.65 (br s, 4H), 2.07-1.96 (m, 4H), 1.21 (t, J = 7.0 Hz, 3H). |
| 1501 | cyclopropyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 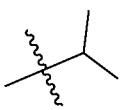 [SMILES: *C(C)C] | 589.2 (1) | 9.28-9.13 (m, 1H), 8.93 (s, 1H), 8.77 (d, J = 2.1 Hz, 1H), 8.47 (br t, J = 7.2 Hz, 1H), 7.91 (s, 1H), 7.70-7.56 (m, 1H), 7.06 (s, 1H), 5.31 (br s, 0.5H), 5.20 (br d, J = 2.7 Hz, 0.5H), 4.75-4.63 (m, 1H), 4.03 (s, 4H), 3.86-3.73 (m, 3H), 3.71-3.52 (m, 2H), 3.29-3.20 (m, 1H), 2.65 (br s, 4H), 2.02 (br s, 4H), 0.68-0.62 (m, 4H). |
| 1502 | propan-2-yl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 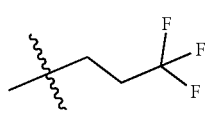 [SMILES: *CCC(F)(F)F] | 591.2 (1) | 9.31-9.16 (m, 1H), 8.93 (s, 1H), 8.77 (s, 1H), 8.48 (br d, J = 7.3 Hz, 1H), 7.94-7.89 (m, 1H), 7.74-7.58 (m, 1H), 7.07 (br s, 1H), 5.32 (br s, 0.5H), 5.21 (br s, 0.5H), 4.83-4.77 (m, 1H), 4.75-4.64 (m, 1H), 4.04 (s, 3H), 3.89-3.76 (m, 3H), 3.75-3.58 (m, 2H), 3.29-3.23 (m, 1H), 2.65 (br s, 4H), 2.02 (br s, 4H), 1.21 (br d, J = 6.1 Hz, 6H). |
| 1503 | 3,3,3-trifluoropropyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 645.2 (1) | 9.32-9.20 (m, 1H), 8.93 (s, 1H), 8.76 (br s, 1H), 8.50 (br t, J = 6.4 Hz, 1H), 7.94-7.90 (m, 1H), 7.73-7.59 (m, 1H), 7.07 (br s, 1H), 5.33 (br s, 0.5H), 5.23 (br s, 0.5H), 4.77-4.66 (m, 1H), 4.30-4.20 (m, 2H), 4.03 (s, 3H), 3.85-3.78 (m, 3H), 3.76-3.59 (m, 2H), 3.29-3.26 (m, 1H), 2.75-2.59 (m, 5H), 2.02 (br s, 4H). |

TABLE 54-continued

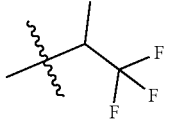 [SMILES: *C(C)C(F)(F)F]

| Ex | Name | R | Obs. MS Ion M+ (method) | NMR Assignments (500 MHz, DMSO-d6) δ or HPLC retention time |
|---|---|---|---|---|
| 1504 | 1,1,1-trifluoropropan-2-yl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 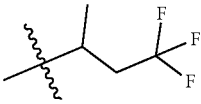 [SMILES: *C(C)CC(F)(F)F] | 645.2 (1) | 8.95-8.89 (m, 1H), 8.78-8.72 (m, 1H), 8.58-8.49 (m, 1H), 7.91 (br s, 1H), 7.76-7.55 (m, 1H), 7.03 (s, 1H), 5.41-5.20 (m, 2H), 4.83-4.66 (m, 1H), 4.07-3.99 (m, 3H), 3.92-3.65 (m, 6H), 3.36-3.29 (m, 1H), 2.77-2.56 (m, 4H), 2.10-1.95 (m, 4H), 1.38 (br d, J = 6.5 Hz, 3H). |
| 1505 | 4,4,4-trifluorobutan-2-yl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 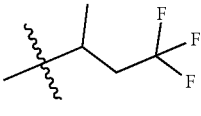 [SMILES: *C(C)CC(F)(F)F] | 659.4 (1) | 9.36-9.15 (m, 1H), 8.95-8.88 (m, 1H), 8.79-8.72 (m, 1H), 8.57-8.49 (m, 1H), 7.90 (s, 1H), 7.72-7.54 (m, 1H), 7.08-7.02 (m, 1H), 5.33 (br s, 0.5H), 5.22 (br s, 0.5H), 5.06 (s, 1H), 4.78-4.61 (m, 1H), 4.02 (d, J = 3.6 Hz, 2H), 4.05-3.99 (m, 1H), 3.84-3.81 (m, 1H), 3.87-3.78 (m, 1H), 3.71-3.57 (m, 4H), 3.30-3.19 (m, 1H), 2.64 (br s, 5H), 2.02 (br t, J = 13.4 Hz, 4H), 1.29 (d, J = 6.3 Hz, 3H). |
| 1506 | 4,4,4-trifluorobutan-2-yl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 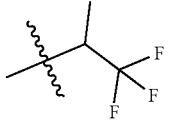 [SMILES: *C(C)C(F)(F)F] | 659.4 (1) | 9.34-9.14 (m, 1H), 8.95-8.89 (m, 1H), 8.80-8.73 (m, 1H), 8.57-8.48 (m, 1H), 7.87 (s, 1H), 7.53 (s, 1H), 7.09-7.02 (m, 1H), 5.29 (br dd, J = 4.7, 1.8 Hz, 0.5H), 5.21 (br d, J = 2.4 Hz, 0.5H), 5.06-4.95 (m, 1H), 4.79-4.63 (m, 1H), 4.02 (s, 2H), 3.98 (s, 1H), 3.84-3.77 (m, 2H), 3.85-3.76 (m, 1H), 3.70 (br s, 1H), 3.33-3.24 (m, 1H), 2.70-2.57 (m, 6H), 2.07-1.95 (m, 4H), 1.29 (d, J = 6.4 Hz, 3H). |
| 1507 | 1,1,1-trifluoropropan-2-yl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 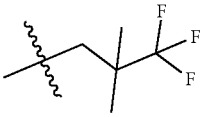 [SMILES: *CC(C)(C)C(F)(F)F] | 645.4 (1) | 8.92-8.87 (m, 1H), 8.77-8.72 (m, 1H), 8.58-8.52 (m, 1H), 7.90-7.85 (m, 1H), 7.05-7.00 (m, 1H), 5.36-5.20 (m, 2H), 4.80-4.66 (m, 1H), 4.03-4.00 (m, 3H), 3.88-3.77 (m, 6H), 3.37-3.29 (m, 1H), 2.62 (br s, 4H), 2.07-1.95 (m, 4H), 1.37 (d, J = 6.6 Hz, 3H). |
| 1508 | 3,3,3-trifluoro-2,2-dimethylpropyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4- | | 673.5 (1) | 9.33-9.20 (m, 1H), 8.94-8.89 (m, 1H), 8.76 (br d, J = 2.3 Hz, 1H), 8.57-8.49 (m, 1H), 7.89 (s, 1H), 7.67-7.53 (m, 1H), 7.05 (s, 1H), 5.37-5.19 (m, 2H), 4.81-4.64 (m, 2H), 4.12-3.98 (m, 3H), 3.89-3.78 (m, 2H), 3.77-3.62 (m, 2H), 3.46-3.25 (m, 3H), 2.71-2.58 (m, 3H), 2.07- |

TABLE 54-continued

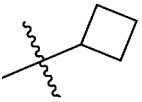 [SMILES: *C1CCC1]

| Ex | Name | R | Obs. MS Ion M+ (method) | NMR Assignments (500 MHz, DMSO-d6) δ or HPLC retention time |
|---|---|---|---|---|
| | fluoropyrrolidine-1-carboxylate | | | 1.95 (m, 3H), 1.15 (br s, 3H). |
| 1509 | cyclobutyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 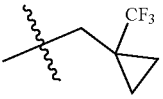 [SMILES: *CC1(C(F)(F)F)CC1] | 603.1 (2) | 9.29-9.17 (m, 1H), 8.93 (d, J = 2.4 Hz, 1H), 8.77 (dd, J = 5.9, 2.1 Hz, 1H), 8.50 (d, J = 7.6 Hz, 1H), 7.91 (s, 1H), 7.72-7.57 (m, 1H), 7.06 (s, 1H), 5.26 (s, 1H), 4.91-4.82 (m, 1H), 4.77-4.61 (m, 1H), 4.03 (s, 3H), 3.87-3.72 (m, 2H), 3.65 (br dd, J = 10.6, 4.5 Hz, 1H), 3.33-3.29 (m, 1H), 3.37-3.21 (m, 1H), 2.65 (br s, 2H), 2.31-2.21 (m, 2H), 2.08-1.94 (m, 6H), 1.72 (q, J = 10.3 Hz, 1H), 1.63-1.51 (m, 1H). |
| 1510 | [1-(trifluoromethyl)cyclopropyl]methyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate |  | 671.3 (2) | 9.36-9.15 (m, 1H), 8.92 (d, J = 2.4 Hz, 1H), 8.76 (d, J = 2.4 Hz, 1H), 8.53 (br t, J = 8.2 Hz, 1H), 7.95-7.87 (m, 1H), 7.74-7.52 (m, 1H), 7.11-7.02 (m, 1H), 5.37-5.20 (m, 1H), 4.81-4.61 (m, 1H), 4.25-4.12 (m, 2H), 4.06-4.01 (m, 3H), 3.87-3.78 (m, 3H), 3.76-3.59 (m, 2H), 3.30 (td, J = 10.3, 4.2 Hz, 1H), 2.72-2.57 (m, 3H), 2.02 (br t, J = 13.0 Hz, 4H), 1.09-0.92 (m, 4H). |
| 1511 | 1-(trifluoromethyl)cyclobutyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 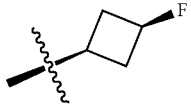 | 671.4 (1) | LCMS Method 1 retention time = 1.84 min LCMS Method 2 retention time = 2.33 min |
| 1512 | (1s,3s)-3-fluorocyclobutyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 621.5 (1) | 9.36-9.19 (m, 1H), 8.95-8.89 (m, 1H), 8.79-8.72 (m, 1H), 8.56-8.48 (m, 1H), 7.92-7.87 (m, 1H), 7.67-7.53 (m, 1H), 7.08-7.02 (m, 1H), 5.36-5.19 (m, 1H), 4.92-4.60 (m, 2H), 4.55-4.44 (m, 1H), 4.06-3.99 (m, 3H), 3.90-3.64 (m, 5H), 3.35-3.21 (m, 1H), 2.91-2.79 (m, 2H), 2.71-2.57 (m, 4H), 2.30-2.14 (m, 2H), 2.09-1.95 (m, 4H). |

TABLE 54-continued

| Ex | Name | R | Obs. MS Ion M+ (method) | NMR Assignments (500 MHz, DMSO-d6) δ or HPLC retention time |
|---|---|---|---|---|
| 1513 | 1-cyclopropylethyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | Mixture of 2 isomers | 617.3 (1) | 9.28-9.16 (m, 1H), 8.92 (d, J = 1.7 Hz, 1H), 8.77 (br s, 1H), 8.49 (br d, J = 6.9 Hz, 1H), 7.89 (s, 1H), 7.69-7.54 (m, 1H), 7.05 (s, 1H), 5.32 (br s, 0.5H), 5.22-5.20 (m, 0.5H), 4.76-4.63 (m, 1H), 4.20 (br d, J = 5.8 Hz, 1H), 4.06-3.98 (m, 3H), 3.88-3.57 (m, 5H), 3.31-3.23 (m, 1H), 2.70 (br s, 1H), 2.64 (br s, 2H), 2.48-2.46 (m, 1H), 2.01 (br t, J = 13.8 Hz, 4H), 1.25 (br d, J = 6.1 Hz, 3H), 1.00 (br dd, J = 7.7, 2.8 Hz, 1H), 0.52-0.41 (m, 2H), 0.37-0.22 (m, 2H). |
| 1514 | 2,2-dimethylpropyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 619.5 (1) | 9.33-9.22 (m, 1H), 8.89 (s, 1H), 8.79-8.73 (m, 1H), 8.58-8.50 (m, 1H), 7.92-7.85 (m, 1H), 7.64-7.55 (m, 1H), 7.08-7.02 (m, 1H), 5.37-5.30 (m, 0.5H), 5.25-5.19 (m, 0.5H), 4.80-4.62 (m, 2H), 4.02 (s, 2H), 3.90-3.68 (m, 7H), 3.36-3.23 (m, 2H), 2.72-2.57 (m, 4H), 2.09-1.94 (m, 4H), 0.91 (s, 6H). |
| 1515 | (1R)-1-cyclopropylethyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 617.4 (1) | 9.39-9.19 (m, 1H), 8.95-8.88 (m, 1H), 8.80-8.73 (m, 1H), 8.56-8.47 (m, 1H), 7.94-7.86 (m, 1H), 7.72-7.52 (m, 1H), 7.10-7.02 (m, 1H), 5.35-5.30 (m, 0.5H), 5.24-5.19 (m, 0.5H), 4.77-4.61 (m, 1H), 4.24-4.13 (m, 1H), 4.02 (s, 3H), 3.88-3.65 (m, 5H), 3.34-3.21 (m, 1H), 2.76-2.56 (m, 4H), 2.02 (br s, 1H), 2.10-1.94 (m, 1H), 1.25 (br d, J = 3.3 Hz, 3H), 1.07-0.94 (m, 1H), 0.53-0.40 (m, 2H), 0.37-0.20 (m, 2H). |
| 1516 | 3-fluoropropyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 609.0 (5) | 9.28-9.15 (m, 1H), 8.95-8.89 (m, 1H), 8.79-8.74 (m, 1H), 8.52-8.44 (m, 1H), 7.90 (s, 1H), 7.87 (br d, J = 1.4 Hz, 1H), 7.68-7.56 (m, 1H), 7.08-7.02 (m, 1H), 5.36-5.30 (m, 0.5H), 5.24-5.19 (m, 0.5H), 4.79-4.62 (m, 2H), 4.62-4.45 (m, 2H), 4.18-4.06 (m, 2H), 4.03 (s, 3H), 3.83 (s, 2H), 3.33-3.23 (m, 2H), 2.64 (br s, 3H), 2.09-1.90 (m, 6H). |
| 1517 | cyclopropylmethyl (3R,4S)-3-(5-{4-amino-5-[(4,4-difluoropiperidin-1-yl)methyl]pyrrolo[2,1- | | 603.2 (5) | 9.33-9.13 (m, 1H), 8.92 (d, J = 1.9 Hz, 1H), 8.77 (br s, 1H), 8.50 (br d, J = 7.7 Hz, 1H), 7.90 (s, 1H), 7.72-7.51 (m, 1H), 7.05 (s, 1H), 5.33 (br s, 0.5H), 5.22 |

TABLE 54-continued

| Ex | Name | R | Obs. MS Ion M+ (method) | NMR Assignments (500 MHz, DMSO-d6) δ or HPLC retention time |
|---|---|---|---|---|
| | f][1,2,4]triazin-7-yl}-2-methoxypyridine-3-amido)-4-fluoropyrrolidine-1-carboxylate | | | (br s, 0.5H), 4.78-4.60 (m, 1H), 4.03 (s, 3H), 3.91-3.60 (m, 8H), 3.34-3.24 (m, 1H), 2.64 (br s, 3H), 2.07-1.93 (m, 4H), 1.16-1.07 (m, 1H), 0.55-0.48 (m, 2H), 0.28 (br d, J = 4.7 Hz, 2H). |
| 1518 | 2,2-difluoropropyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 627.4 (1) | 9.31-9.21 (m, 1H), 8.95-8.90 (m, 1H), 8.79-8.74 (m, 1H), 8.57-8.50 (m, 1H), 7.89 (s, 1H), 7.65-7.55 (m, 1H), 7.08-7.02 (m, 1H), 5.38-5.32 (m, 0.5H), 5.26-5.22 (m, 0.5H), 4.82-4.65 (m, 2H), 4.37-4.26 (m, 1H), 4.40-4.24 (m, 1H), 4.02 (s, 3H), 3.92-3.64 (m, 4H), 3.40-3.27 (m, 2H), 2.64 (br s, 2H), 2.09-1.95 (m, 4H), 1.67 (t, J = 19.2 Hz, 3H). |
| 1519 | 1-methylcyclopropyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 603.5 (1) | 9.35-9.19 (m, 1H), 8.94-8.88 (m, 1H), 8.79-8.73 (m, 1H), 8.54-8.45 (m, 1H), 7.91-7.86 (m, 1H), 7.67-7.52 (m, 1H), 7.08-7.01 (m, 1H), 5.33-5.27 (m, 0.5H), 5.22-5.16 (m, 0.5H), 4.75-4.58 (m, 1H), 4.05-3.99 (m, 3H), 3.91-3.67 (m, 3H), 3.27-3.16 (m, 1H), 2.71-2.57 (m, 4H), 2.08-1.94 (m, 4H), 1.48 (s, 3H), 0.87-0.74 (m, 2H), 0.68-0.56 (m, 2H). |
| 1520 | 2,2,3,3-tetrafluoropropyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 663.5 (5) | 9.31-9.13 (m, 1H), 8.93 (s, 1H), 8.77 (br s, 1H), 8.52 (br d, J = 7.2 Hz, 1H), 7.90 (s, 1H), 7.73-7.51 (m, 1H), 7.09-7.04 (m, 1H), 6.77-6.51 (m, 1H), 5.38-5.32 (m, 0.5H), 5.24 (br d, J = 1.4 Hz, 0.5H), 4.83-4.66 (m, 1H), 4.65-4.53 (m, 2H), 4.03 (s, 3H), 3.95-3.64 (m, 6H), 2.64 (br s, 4H), 2.10-1.93 (m, 4H). |
| 1521 | [1,1'-bi(cyclopropane)]-1-yl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 629.2 (1) | 9.32-9.16 (m, 1H), 8.91 (br s, 1H), 8.78-8.72 (m, 1H), 8.52-8.44 (m, 1H), 7.93-7.86 (m, 1H), 7.70-7.55 (m, 1H), 7.09-7.00 (m, 1H), 5.33-5.26 (m, 0.5H), 5.21-5.15 (m, 0.5H), 4.75-4.59 (m, 1H), 4.01 (s, 3H), 3.83-3.60 (m, 5H), 3.24 (br d, J = 10.0 Hz, 2H), 2.72-2.55 (m, 4H), 2.08-1.93 (m, 3H), 1.67-1.58 (m, 1H), 0.79-0.64 (m, 2H), 0.61-0.52 (m, 2H), 0.50-0.40 (m, 2H), 0.21 (br s, 2H). |

TABLE 54-continued

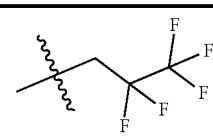

| Ex | Name | R | Obs. MS Ion M+ (method) | NMR Assignments (500 MHz, DMSO-d6) δ or HPLC retention time |
|---|---|---|---|---|
| 1522 | 2,2,3,3,3-pentafluoropropyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 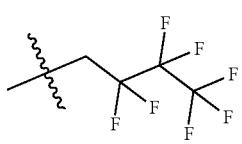 [SMILES: *CC(F)(F)C(F)(F)C(F)(F)F] | 681.4 (1) | 9.40-9.16 (m, 1H), 8.95-8.88 (m, 1H), 8.79-8.72 (m, 1H), 8.60-8.50 (m, 1H), 7.93-7.87 (m, 1H), 7.72-7.46 (m, 1H), 7.10-7.03 (m, 1H), 5.38-5.33 (m, 0.5H), 5.27-5.22 (m, 0.5H), 4.91-4.68 (m, 3H), 4.06-3.99 (m, 3H), 3.87-3.64 (m, 5H), 3.38-3.30 (m, 1H), 2.70-2.58 (m, 4H), 2.09-1.94 (m, 4H). |
| 1523 | 2,2,3,3,4,4,4-heptafluorobutyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 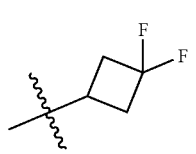 [SMILES: *C1CC(F)(F)C1] | 731.1 (1) | 9.37-9.18 (m, 1H), 8.95-8.90 (m, 1H), 8.79-8.72 (m, 1H), 8.59-8.50 (m, 1H), 7.94-7.88 (m, 1H), 7.72-7.53 (m, 1H), 7.09-7.02 (m, 1H), 5.38-5.32 (m, 0.5H), 5.27-5.22 (m, 0.5H), 4.95-4.66 (m, 3H), 4.02 (d, J = 2.0 Hz, 3H), 3.89-3.60 (m, 5H), 3.35 (td, J = 10.2, 2.8 Hz, 1H), 2.65 (br s, 4H), 2.02 (br s, 4H). |
| 1524 | 3,3-difluorocyclobutyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 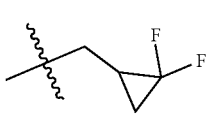 [SMILES: *CC1CC1(F)F] | 639.4 (2) | 9.38-9.21 (m, 1H), 8.94-8.88 (m, 1H), 8.78-8.73 (m, 1H), 8.57-8.50 (m, 1H), 7.91-7.86 (m, 1H), 7.66-7.46 (m, 1H), 7.07-7.00 (m, 1H), 5.37-5.30 (m, 0.5H), 5.25-5.20 (m, 0.5H), 4.90-4.79 (m, 1H), 4.78-4.61 (m, 1H), 4.05-3.99 (m, 3H), 3.92-3.74 (m, 4H), 3.35-3.22 (m, 1H), 3.11-2.97 (m, 2H), 2.77-2.57 (m, 6H), 2.10-1.93 (m, 4H). |
| 1525 | (2,2-difluorocyclopropyl) methyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | 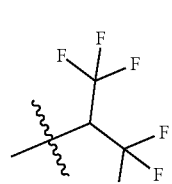<br>Mixture of 2 isomers | 639.1 (1) | 9.35-9.23 (m, 1H), 8.95-8.87 (m, 1H), 8.75 (br s, 1H), 8.57-8.48 (m, 1H), 7.92-7.86 (m, 1H), 7.65-7.54 (m, 1H), 7.08-7.01 (m, 1H), 5.36-5.30 (m, 0.5H), 5.25-5.19 (m, 0.5H), 4.80-4.62 (m, 1H), 4.31-4.16 (m, 1H), 4.07-3.93 (m, 4H), 3.89-3.75 (m, 2H), 3.35-3.22 (m, 2H), 2.73-2.58 (m, 4H), 2.15-1.94 (m, 5H), 1.73-1.61 (m, 2H), 1.50-1.37 (m, 2H). |
| 1526 | 1,1,1,3,3,3-hexafluoropropan-2-yl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4- | | 699.3 (5) | LCMS Method 5 retention time = 1.79 min<br>LCMS Method 6 retention time = 2.28 min |

TABLE 54-continued

| Ex | Name | R | Obs. MS Ion M+ (method) | NMR Assignments (500 MHz, DMSO-d6) δ or HPLC retention time |
|---|---|---|---|---|
| | fluoropyrrolidine-1-carboxylate | | | |
| 1527 | 1,1,1-trifluoro-3-methylbutan-2-yl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | Mixture of 2 isomers | 673.5 (1) | LCMS Method 1 retention time = 1.89 min LCMS Method 2 retention time = 2.40 min |
| 1528 | 2,2,3,4,4,4-hexafluorobutyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | Mixture of 2 isomers | 713.1 (1) | 9.33-9.22 (m, 1H), 8.93-8.88 (m, 1H), 8.80-8.73 (m, 1H), 8.57-8.50 (m, 1H), 7.91-7.85 (m, 1H), 7.64-7.47 (m, 1H), 7.08-7.01 (m, 1H), 6.19-6.00 (m, 1H), 5.39-5.31 (m, 0.5H), 5.27-5.20 (m, 0.5H), 4.84-4.50 (m, 2H), 4.02 (s, 3H), 3.97-3.72 (m, 5H), 3.33 (br d, J = 10.2 Hz, 2H), 2.71-2.56 (m, 4H), 2.07-1.92 (m, 4H). |
| 1529 | 1-cyclopropyl-2,2,2-trifluoroethyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 671.1 (1) | 9.33-9.11 (m, 1H), 8.96-8.89 (m, 1H), 8.79-8.73 (m, 1H), 8.56-8.47 (m, 1H), 7.93-7.86 (m, 1H), 7.73-7.46 (m, 1H), 7.08-7.01 (m, 1H), 5.39-5.19 (m, 1H), 4.85-4.67 (m, 2H), 4.03 (s, 3H), 3.88-3.80 (m, 3H), 3.79-3.54 (m, 1H), 3.37-3.32 (m, 1H), 2.64 (br s, 4H), 2.08-1.94 (m, 4H), 1.22-1.13 (m, 1H), 0.73-0.65 (m, 1H), 0.64-0.55 (m, 2H), 0.49-0.42 (m, 1H). |
| 1530 | 1,1,1-trifluoro-3,3-dimethylbutan-2-yl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 687.4 (2) | LCMS Method 1 retention time = 1.91 min LCMS Method 2 retention time = 2.47 min |
| 1531 | 3,3,4,4,4-pentafluorobutan-2-yl (3R,4S)-3-(5-{4-amino-5-[(4,4-difluoropiperidin-1-yl)methyl]pyrrolo[2,1- | | 695.4 (2) | 9.39-9.17 (m, 1H), 8.99-8.86 (m, 1H), 8.75 (dd, J = 14.2, 1.8 Hz, 1H), 8.63-8.50 (m, 1H), 7.96-7.83 (m, 1H), 7.70-7.48 (m, 1H), 7.05 (s, 1H), 5.52-5.37 (m, 1H), 5.35 (br s, 0.5H), 5.24 |

TABLE 54-continued

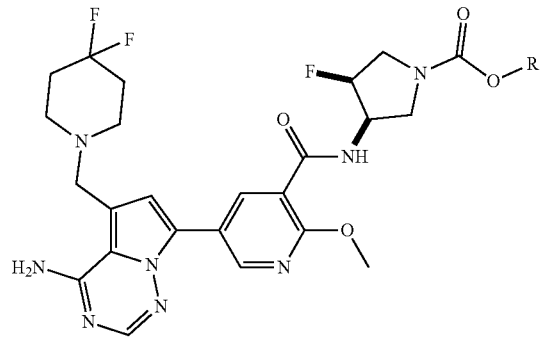

| Ex | Name | R | Obs. MS Ion M+ (method) | NMR Assignments (500 MHz, DMSO-d6) δ or HPLC retention time |
|---|---|---|---|---|
| | f][1,2,4]triazin-7-yl}-2-methoxypyridine-3-amido)-4-fluoropyrrolidine-1-carboxylate | | | (br s, 0.5H), 4.80-4.67 (m, 1H), 4.02 (d, J = 4.7 Hz, 3H), 3.90-3.80 (m, 3H), 3.77-3.64 (m, 3H), 3.36-3.23 (m, 1H), 2.64 (br s, 4H), 2.09-1.91 (m, 4H), 1.41 (br d, J = 6.1 Hz, 3H). |
| 1532 | 2,2,3,3-tetrafluorocyclobutyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 675.4 (2) | 9.30-9.18 (m, 1H), 8.95-8.87 (m, 1H), 8.79-8.73 (m, 1H), 8.56-8.50 (m, 1H), 7.91-7.86 (m, 1H), 7.62-7.54 (m, 1H), 7.07-7.02 (m, 1H), 5.38-5.22 (m, 2H), 4.82-4.66 (m, 1H), 4.02 (s, 3H), 3.95-3.65 (m, 5H), 3.27-3.14 (m, 2H), 2.92-2.75 (m, 2H), 2.73-2.57 (m, 4H), 2.10-1.93 (m, 4H). |
| 1533 | 3,3,3-trifluoro-2-methylpropyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | Mixture of 2 isomers | 659.1 (2) | 9.32-9.21 (m, 1H), 8.90 (s, 1H), 8.75 (s, 1H), 8.52 (br t, J = 6.3 Hz, 1H), 7.88 (s, 1H), 7.62-7.51 (m, 1H), 7.03 (s, 1H), 5.36-5.29 (m, 0.5H), 5.24-5.18 (m, 0.5H), 4.79-4.61 (m, 1H), 4.22-4.06 (m, 3H), 4.01 (s, 3H), 3.81 (br s, 5H), 3.27 (br t, J = 10.3 Hz, 1H), 2.79 (br s, 2H), 2.63 (br s, 4H), 2.01 (br s, 4H), 1.12 (br d, J = 6.6 Hz, 3H). |
| 1534 | 1,1,1-trifluorobutan-2-yl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 659.1 (1) | 9.37-9.17 (m, 1H), 8.93 (s, 1H), 8.77 (s, 1H), 8.57-8.51 (m, 1H), 7.94-7.88 (m, 1H), 7.73-7.58 (m, 1H), 7.07 (br s, 1H), 5.39-5.31 (m, 1H), 5.28-5.17 (m, 2H), 4.85-4.69 (m, 2H), 4.03 (s, 3H), 3.89-3.59 (m, 4H), 2.72-2.58 (m, 4H), 2.02 (br s, 2H), 1.91-1.78 (m, 2H), 1.71 (td, J = 15.3, 7.2 Hz, 2H), 0.99-0.90 (m, 3H). |
| 1535 | propyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 591.2 (1) | 9.25-9.13 (m, 1H), 8.93 (s, 1H), 8.77 (s, 1H), 8.48 (br d, J = 7.3 Hz, 1H), 7.90 (s, 1H), 7.68-7.54 (m, 1H), 7.06 (s, 1H), 5.36-5.18 (m, 1H), 4.76-4.65 (m, 1H), 4.03 (d, J = 1.5 Hz, 3H), 4.01-3.94 (m, 2H), 3.83 (s, 3H), 3.73-3.59 (m, 2H), 3.31-3.24 (m, 1H), 2.65 (br s, 4H), 2.06-1.96 (m, 4H), 1.64-1.56 (m, 2H), 0.91 (br t, J = 7.5 Hz, 3H). |

TABLE 54-continued

| Ex | Name | R | Obs. MS Ion M+ (method) | NMR Assignments (500 MHz, DMSO-d6) δ or HPLC retention time |
|---|---|---|---|---|
| 1536 | 3,3,4,4,4-pentafluorobutan-2-yl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 695.4 (2) | 9.37-9.11 (m, 1H), 8.95-8.87 (m, 1H), 8.79-8.73 (m, 1H), 8.55-8.45 (m, 1H), 7.91 (s, 1H), 7.69-7.47 (m, 1H), 7.08-6.99 (m, 1H), 5.49-5.37 (m, 1H), 5.36-5.30 (m, 0.5H), 5.26-5.19 (m, 0.5H), 4.82-4.65 (m, 1H), 4.02 (s, 3H), 3.88-3.63 (m, 6H), 3.38-3.31 (m, 1H), 2.73-2.55 (m, 4H), 2.08-1.91 (m, 4H), 1.46-1.35 (m, 3H). |
| 1537 | 2,2,3,3-tetrafluorocyclobutyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 675.4 (2) | LCMS Method 1 retention time = 1.71 min LCMS Method 2 retention time = 2.18 min |
| 1538 | 1-cyclopropyl-2,2,2-trifluoroethyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 671.0 (1) | LCMS Method 1 retention time = 1.77 min LCMS Method 2 retention time = 2.31 min |
| 1539 | 1,1,1-trifluoro-3,3-dimethylbutan-2-yl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 687.1 (1) | 9.21 (br s, 1H), 8.92 (br s, 1H), 8.76 (br d, J = 3.6 Hz, 1H), 8.52 (br dd, J = 15.0, 7.6 Hz, 1H), 7.89 (s, 1H), 7.60 (br s, 1H), 7.05 (br s, 1H), 5.24 (br s, 1H), 5.01 (br d, J = 8.0 Hz, 1H), 4.79 (br s, 1H), 4.02 (s, 3H), 3.99-3.66 (m, 6H), 2.64 (br s, 4H), 2.01 (br s, 4H), 1.04 (br d, J = 5.2 Hz, 9H). |
| 1540 | 1,1,1-trifluorobutan-2-yl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate | | 659.4 (2) | 9.34-9.17 (m, 1H), 8.95-8.90 (m, 1H), 8.79-8.73 (m, 1H), 8.58-8.49 (m, 1H), 7.94-7.87 (m, 1H), 7.71-7.58 (m, 1H), 7.08-7.03 (m, 1H), 5.25-5.22 (m, 1H), 5.38-5.17 (m, 1H), 4.86-4.69 (m, 1H), 4.03 (s, 3H), 3.96-3.62 (m, 5H), 3.39-3.32 (m, 1H), 2.74-2.62 (m, 2H), 2.10-1.93 (m, 4H), 1.88 (br d, J = 2.2 Hz, 1H), 1.77-1.65 (m, 1H), 1.01-0.89 (m, 3H). |

TABLE 54-continued

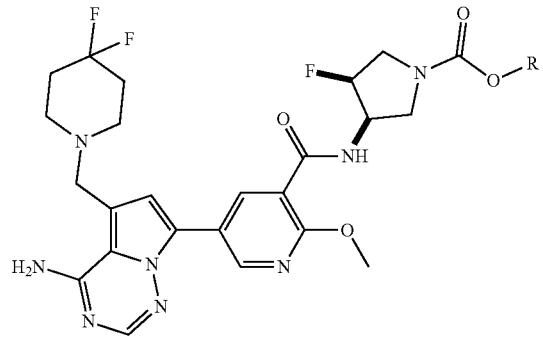

| Ex | Name | R | Obs. MS Ion M+ (method) | NMR Assignments (500 MHz, DMSO-d6) δ or HPLC retention time |
|---|---|---|---|---|

Compounds in Table 54 were prepared similarly to the methods detailed in Example 1416 or 1417, except that 5-(4-amino-5-((4,4-difluoropiperidin-1-yl)methyl)pyrrolo[2,1-f][1,2,4]triazin-7-yl)-N-((3R,4S)-4-fluoropyrrolidin-3-yl)-2-methoxynicotinamide, 4 TFA was used in place of 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide. Additional DIPEA was employed in these reactions to compensate for the 4TFA equivalents in the starting material. In some cases, it was observed by LCMS that an undesired byproduct had formed during the reaction with a mass ion fragment suggestive of the presence of two newly formed carbamate moieties in the undesired byproduct molecule. In these cases, the crude reaction mixtures were concentrated via nitrogen stream to a residue, redissolved in methanol (1 mL), and the resulting mixture was then treated with an excess of potassium carbonate (approximately 100-200 mg) and heated with stirring to 45° C. ON. This treatment effectively destroyed the undesired byproduct and provided the title compounds after aqueous workup and preparative HPLC purification. Examples in the table are single diastereomers unless otherwise noted. Where diastereomers were separated either by reverse phase preparative HPLC or by further SFC chiral chromatography, similar to that described in Example 1417, they are included as separate entries. For each example, two of the following analytical LCMS injections with matched stationary phase columns were used to determine final purity. The method(s) used are indicated in each case. Method 1-6 as described in the Methods of Preparation Section.

TABLE 55

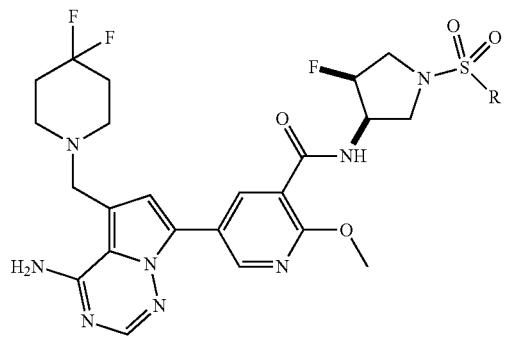

| Ex | Name | R | Obs. MS Ion M+ (method) | NMR Assignments (500 MHz, DMSO-d6) δ or HPLC retention time |
|---|---|---|---|---|
| 1541 | 5-{4-amino-5-[(4,4-difluoropiperidin-1-yl)methyl]pyrrolo[2,1-f][1,2,4]triazin-7-yl}-N-[(3R,4S)-4-fluoro-1-(3,3,3-trifluoropropanesulfonyl)pyrrolidin-3-yl]-2-methoxypyridine-3-carboxamide | | 665.1 (1) | 9.32-9.16 (m, 1H), 8.92 (d, J = 2.4 Hz, 1H), 8.76 (d, J = 2.1 Hz, 1H), 8.52 (br d, J = 7.3 Hz, 1H), 7.89 (s, 1H), 7.65-7.51 (m, 1H), 7.05 (s, 1H), 5.35 (br d, J = 2.7 Hz, 0.5H), 5.24 (br s, 0.5H), 4.85-4.74 (m, 1H), 4.03 (s, 3H), 3.85-3.66 (m, 6H), 3.40-3.33 (m, 2H), 2.79-2.69 (m, 2H), 2.64 (br s, 4H), 2.06-1.96 (m, 4H). |
| 1542 | 5-{4-amino-5-[(4,4-difluoropiperidin-1-yl)methyl]pyrrolo[2,1-f][1,2,4]triazin-7-yl}-N-[(3R,4S)-4-fluoro-1-(2,2,2-trifluoroethanesulfonyl)pyrrolidin-3-yl]-2-methoxypyridine-3-carboxamide | | 651.1 (1) | 9.37-9.21 (m, 1H), 8.93-8.90 (m, 1H), 8.76 (s, 1H), 8.53 (br d, J = 7.6 Hz, 1H), 7.90 (s, 1H), 7.67-7.54 (m, 1H), 7.28-6.99 (m, 1H), 5.38 (br s, 0.5H), 5.27 (br s, 0.5H), 4.82-4.69 (m, 1H), 4.66-4.57 (m, 2H), 4.03 (s, 3H), 3.90-3.70 (m, 6H), 2.65 (br s, 4H), 2.02 (br s, 4H). |

TABLE 55-continued

[Structure diagram of compound scaffold with R group]

| Ex | Name | R | Obs. MS Ion M+ (method) | NMR Assignments (500 MHz, DMSO-d6) δ or HPLC retention time |
|----|------|---|-------------------------|-------------------------------------------------------------|
| 1543 | 5-{4-amino-5-[(4,4-difluoropiperidin-1-yl)methyl]pyrrolo[2,1-f][1,2,4]triazin-7-yl}-N-[(3R,4S)-4-fluoro-1-(1,1,1-trifluoropropane-2-sulfonyl)pyrrolidin-3-yl]-2-methoxypyridine-3-carboxamide | [structure] | 665.3 (1) | 9.34-9.14 (m, 1H), 8.95-8.89 (m, 1H), 8.78-8.74 (m, 1H), 8.58-8.50 (m, 1H), 7.92-7.86 (m, 1H), 7.67-7.49 (m, 1H), 7.07-7.02 (m, 1H), 5.41-5.36 (m, 0.5H), 5.31-5.25 (m, 0.5H), 4.83-4.66 (m, 2H), 4.02 (s, 3H), 3.89 (t, J = 8.7 Hz, 1H), 3.85-3.71 (m, 4H), 3.40-3.35 (m, 1H), 2.64 (br s, 4H), 2.01 (br s, 4H), 1.50 (d, J = 7.2 Hz, 3H). |
| 1544 | 5-{4-amino-5-[(4,4-difluoropiperidin-1-yl)methyl]pyrrolo[2,1-f][1,2,4]triazin-7-yl}-N-[(3R,4S)-4-fluoro-1-(1,1,1-trifluoropropane-2-sulfonyl)pyrrolidin-3-yl]-2-methoxypyridine-3-carboxamide | [structure] | 665.1 (1) | 9.40-9.20 (m, 1H), 8.90 (d, J = 2.5 Hz, 1H), 8.75 (d, J = 2.2 Hz, 1H), 8.60-8.54 (m, 1H), 7.87 (s, 1H), 7.63-7.43 (m, 1H), 7.03 (s, 1H), 5.41-5.35 (m, 0.5H), 5.30-5.24 (m, 0.5H), 4.82-4.64 (m, 2H), 4.01 (s, 3H), 3.92-3.78 (m, 6H), 3.41-3.35 (m, 1H), 2.73-2.72 (m, 1H), 2.62 (br s, 2H), 2.00 (br t, J = 13.8 Hz, 4H), 1.49 (d, J = 7.2 Hz, 3H). |

Compounds in Table 55 were prepared similarly to the methods detailed in Example 1460, except that 5-(4-amino-5-((4,4-difluoropiperidin-1-yl)methyl)pyrrolo[2,1-f][1,2,4]triazin-7-yl)-N-((3R,4S)-4-fluoropyrrolidin-3-yl)-2-methoxynicotinamide, 4 TFA was used in place of 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide. Additional DIPEA was employed in these reactions to compensate for the 4TFA equivalents in the starting material. Examples in the table are single diastereomers unless otherwise noted. Where diastereomers were separated either by reverse phase preparative HPLC or by further SFC chiral chromatography, similar to that described in Example 1417, they are included as separate entries. For each example, analytical LCMS injections with matched stationary phase columns were used to determine final purity. The method(s) used are indicated in each case. Method 1-6 as described in the Methods of Preparation Section.

Examples 1545 and 1546: N-((3R,4S)-1-(2-Amino-2-(trifluoromethyl)pentanoyl)-4-fluoropyrrolidin-3-yl)-5-(4-amino-5-(trifluoromethyl)pyrrolo[2,1-f][1,2,4]triazin-7-yl)-2-methoxynicotinamide, Isomer 1 and Isomer 2

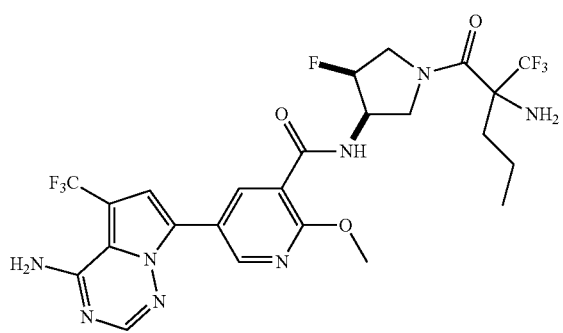

A mixture of 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide (40 mg, 0.091 mmol), 2-amino-2-(trifluoromethyl)pentanoic acid (20.23 mg, 0.109 mmol), BOP (50.3 mg, 0.114 mmol) and Hunig's base (47.7 µl, 0.273 mmol) in DMF (910 µl) was stirred at rt for 36 h.

The mixture was treated with additional 2-amino-2-(trifluoromethyl)pentanoic acid (40.5 mg, 0.220 mmol), BOP (100 mg, 0.227 mmol) and Hunig's base (100 µl, 0.550 mmol) and stirred at rt for 3 h. The crude mixture was purified by reverse phase preparative HPLC (Waters Sunfire C18, 30×150 mm, 5 micron, Solvent A=95% $H_2O$, 5% acetonitrile, 10 mM ammonium acetate; Solvent B=95% acetonitrile, 5% $H_2O$, 10 mM ammonium acetate; 50 mL/min, gradient 0-100% B over 20 min, hold 100% B for 4 min). Product fractions were combined and concentrated in vacuo to give a white powder (35.4 mg, 64% yield) isomer mixture. The individual isomers were separated by SFC chiral chromatography (method details: Column=Chiralpak IA preparative column, 30×250 mm, 5 µm particle size; mobile phase=40% (0.1% DEA) MeOH in CO2, 150 bar; Temp=35° C.; Flow rate=70.0 mL/min. in 30 min; UV monitored @ 254 nm; Injection=0.5 ml of ~17 mg/mL in 2:1 MeOH: $CHCl_3$ (~35 mg purified by stacked injection)).

Example 1545: Off-White Solid Isolated as First Eluting Isomer (9.1 mg, 16% Yield MS ESI m/z 607.3 (M+H)+

$^1$H NMR (500 MHz, DMSO-$d_6$) δ 8.93 (s, 1H), 8.79 (br d, J=13.4 Hz, 1H), 8.59-8.47 (m, 1H), 8.18 (s, 1H), 7.63 (s, 1H), 5.37-5.17 (m, 1H), 4.75-4.36 (m, 2H), 4.18-4.00 (m, 4H), 3.91-3.59 (m, 2H), 3.48-3.34 (m, 1H), 3.34-3.28 (m, 3H), 1.93-1.84 (m, 1H), 1.65 (td, J=13.1, 4.6 Hz, 1H), 1.51-1.39 (m, 1H), 1.35-1.26 (m, 1H), 0.94-0.86 (m, 3H).

Example 1546: Off-White Solid Isolated as Second Eluting Isomer (15.2 mg, 27% Yield MS ESI m/z 607.3 (M+H)+
$^1$H NMR (500 MHz, DMSO-d$_6$) δ 8.93 (d, J=2.3 Hz, 1H), 8.79 (br s, 1H), 8.58-8.46 (m, 1H), 8.18 (s, 1H), 7.63 (s, 1H), 5.36-5.17 (m, 1H), 4.85-4.54 (m, 2H), 4.05 (s, 3H), 4.02-3.66 (m, 2H), 3.58-3.37 (m, 2H), 2.96-2.89 (m, 1H), 2.06-1.89 (m, 1H), 1.68-1.55 (m, 1H), 1.46-1.32 (m, 1H), 1.24 (br s, 1H), 0.93-0.84 (m, 3H).

Example 1547: 5-(4-Amino-5-(trifluoromethyl)pyrrolo[2,1-f][1,2,4]triazin-7-yl)-N-((3R,4S)-4-fluoro-1-(3-hydroxy-3-(trifluoromethyl)cyclobutane-1-carbonyl)pyrrolidin-3-yl)-2-methoxynicotinamide

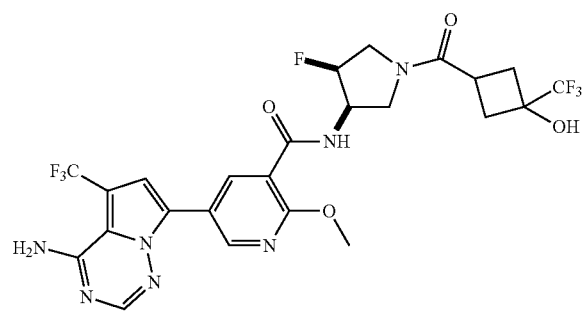

The title compound was prepared by a similar method to that of Example 27. This material was isolated as a mixture of diastereomers (14.2 mg, 69% yield).
MS ESI m/z 606.1 (M+H)+
$^1$H NMR (500 MHz, DMSO-d$_6$) δ 8.93 (d, J=2.4 Hz, 1H), 8.79 (dd, J=18.0, 2.4 Hz, 1H), 8.50 (d, J=7.6 Hz, 1H), 8.18 (s, 1H), 7.62 (s, 1H), 6.60 (s, 1H), 5.38-5.32 (m, 0.5H), 5.27-5.21 (m, 0.5H), 4.81-4.60 (m, 1H), 4.05 (d, J=5.2 Hz, 3H), 3.96-3.88 (m, 1H), 3.85-3.66 (m, 2H), 3.42-3.34 (m, 1H), 3.30-3.24 (m, 1H), 3.00-2.88 (m, 1H), 2.65-2.55 (m, 2H), 2.43-2.34 (m, 2H).

Example 1548: 2,2,2-Trifluoroethyl (3R,4S)-3-(5-(4-amino-5-((3,3-difluorocyclobutyl)methyl)pyrrolo[2,1-f][1,2,4]triazin-7-yl)-2-(methoxy-d3)nicotinamido)-4-fluoropyrrolidine-1-carboxylate

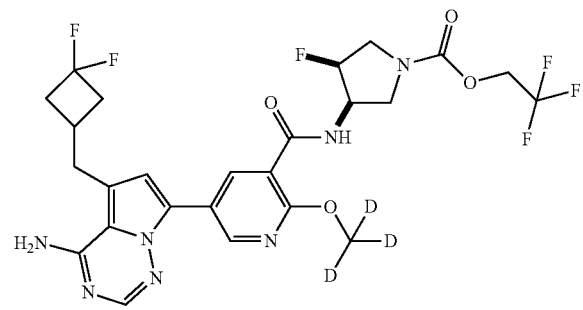

A mixture of 5-(4-amino-5-((3,3-difluorocyclobutyl)methyl)pyrrolo[2,1-f][1,2,4]triazin-7-yl)-N-((3R,4S)-4-fluoropyrrolidin-3-yl)-2-(methoxy-d3)nicotinamide, 4 TFA (0.030 g, 0.032 mmol) and Hunig's base (0.039 mL, 0.225 mmol) in DMF (0.5 mL) was treated with 2,2,2-trifluoroethyl chloroformate (7.82 mg, 0.048 mmol). The mixture was stirred at rt ON. The mixture was filtered and purified via preparative LC/MS with the following conditions: Column=XBridge C18, 200 mm×19 mm, 5-μm particles; Mobile Phase A=5:95 acetonitrile:water with 10-mM ammonium acetate; Mobile Phase B=95:5 acetonitrile:water with 10-mM ammonium acetate; Gradient=31-71% B over 20 minutes, then a 4-minute hold at 100% B; Flow Rate=20 mL/min; Column Temperature=25° C. Fractions containing the desired product were combined and dried via centrifugal evaporation. The material was further purified via preparative LC/MS with the following conditions: Column=XBridge C18, 200 mm×19 mm, 5-μm particles; Mobile Phase A=5:95 acetonitrile:water with 0.1% trifluoroacetic acid; Mobile Phase B=95:5 acetonitrile:water with 0.1% trifluoroacetic acid; Gradient=30-70% B over 15 minutes, then a 5-minute hold at 100% B; Flow Rate=20 mL/min; Column Temperature=25° C. Fractions containing the desired product were combined and dried via centrifugal evaporation to give the title compound (8.8 mg, 28% yield).
MS ESI m/z 606.2 (M+H)+
$^1$H NMR (500 MHz, DMSO-d$_6$) δ 8.91 (s, 1H), 8.71 (s, 1H), 8.52 (br d, J=7.3 Hz, 1H), 8.09 (s, 1H), 7.23 (br s, 1H), 5.37-5.22 (m, 1H), 4.81-4.68 (m, 3H), 4.26-4.16 (m, 2H), 4.06-3.67 (m, 6H), 3.40-3.31 (m, 2H).

Intermediate 1: 7-Bromo-5-(pyrrolidin-1-ylmethyl)pyrrolo[2,1-f][1,2,4]triazin-4-amine

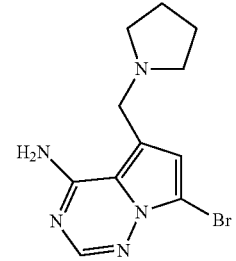 [SMILES: Nc1ncnn2c(Br)cc(CN3CCCC3)c12]

A mixture of N-((4-amino-7-bromopyrrolo[2,1-f][1,2,4]triazin-5-yl)methyl)-N,N-diethylethanaminium (100 mg, 0.306 mmol), pyrrolidine (43.5 mg, 0.611 mmol) and Hunig's base (0.107 mL, 0.611 mmol) in acetonitrile (3 mL) was heated at 100° C. for 16 h. A clear yellow solution was formed. The reaction mixture was diluted with EtOAc. The organic layer was washed with water and dried over MgSO$_4$. It was filtered and concentrated to obtain 7-bromo-5-(pyrrolidin-1-ylmethyl)pyrrolo[2,1-f][1,2,4]triazin-4-amine (65 mg, 0.219 mmol, 72% yield) as a tan solid.
MS ESI m/z 296.1 (M+H)+.

Intermediate 2: 1-(4-Amino-7-bromopyrrolo[2,1-f][1,2,4]triazin-5-yl)ethan-1-one

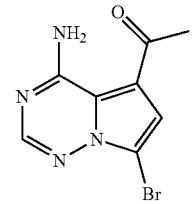

A. 1-(4-aminopyrrolo[2,1-f][1,2,4]triazin-5-yl)ethan-1-one: To a mixture of 4-amino-N-methoxy-N-methylpyrrolo[2,1-f][1,2,4]triazine-5-carboxamide (100 mg, 0.452 mmol) in tetrahydrofuran (3 mL) was added methylmagnesium bromide (0.226 mL, 0.678 mmol) and the mixture was stirred at rt for 16 h and diluted with EtOAc. The organic layer was washed with water and dried over MgSO$_4$, filtered and concentrated. The residue was purified by silica gel chromatography, eluting with 0-40% EtOAc/hexanes to obtain 1-(4-aminopyrrolo[2,1-f][1,2,4]triazin-5-yl)ethan-1-one (42 mg, 0.238 mmol, 53% yield) as a yellow solid.

MS ESI m/z 177.3 (M+H)$^+$ $^1$H NMR (400 MHz, CDCl$_3$) δ 8.08-7.94 (m, 1H), 7.57-7.48 (m, 1H), 7.18-7.12 (m, 1H), 2.62 (s, 3H).

B. To a mixture of 1-(4-aminopyrrolo[2,1-f][1,2,4]triazin-5-yl)ethan-1-one (800 mg, 4.54 mmol) in DCM (50 mL) was added NBS (970 mg, 5.45 mmol) and the mixture was stirred at rt for 2 h. It was diluted with EtOAc. The organic layer was washed with sat. NaHCO$_3$ and water, dried over MgSO$_4$, filtered and concentrated to obtain 1-(4-amino-7-bromopyrrolo[2,1-f][1,2,4]triazin-5-yl)ethan-1-one (900 mg, 3.53 mmol, 78% yield) as a white solid.

MS ESI m/z 256.8 (M+H)$^+$ $^1$H NMR (400 MHz, CDCl$_3$) δ 8.19-8.07 (m, 1H), 7.24-7.19 (m, 1H), 2.63 (s, 3H).

Intermediate 3: 7-Bromo-5-(difluoromethyl)pyrrolo[2,1-f][1,2,4]triazin-4-amine

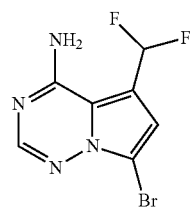 [SMILES: Nc1ncnn2c(Br)cc(C(F)F)c12]

A. 4-Amino-7-bromopyrrolo[2,1-f][1,2,4]triazine-5-carbaldehyde: A mixture of (4-amino-7-bromopyrrolo[2,1-f][1,2,4]triazin-5-yl)methanol (400 mg, 1.646 mmol), Dess-Martin periodinane (838 mg, 1.975 mmol) in CH$_2$Cl$_2$ (10 mL) was stirred at rt for 2 h. It was diluted with EtOAc. The organic layer was washed with sat. aq. NaHCO$_3$, 30% NaS$_2$O$_3$ and water. The organics were dried over MgSO$_4$, filtered and concentrated. The residue was purified by silica gel chromatography, eluting with 40% EtOAc/hexanes to obtain 4-amino-7-bromopyrrolo[2,1-f][1,2,4]triazine-5-carbaldehyde (350 mg, 1.452 mmol, 88% yield) as an off white solid.

$^1$H NMR (400 MHz, CDCl$_3$) δ 9.75 (s, 1H), 8.21 (s, 1H), 7.26 (s, 1H).

B. A mixture of 4-amino-7-bromopyrrolo[2,1-f][1,2,4]triazine-5-carbaldehyde (50 mg, 0.207 mmol) and DAST (0.137 mL, 1.037 mmol) in CH$_2$Cl$_2$ (2 mL) was stirred at rt for 3 d. It was concentrated and diluted with EtOAc. The organic layer was washed with NaHCO$_3$ and water. The organics were dried over MgSO$_4$ and purified by silica gel chromatography, eluting with 40% EtOAc/hexanes to obtain 7-bromo-5-(difluoromethyl)pyrrolo[2,1-f][1,2,4]triazin-4-amine (21 mg, 0.080 mmol, 39% yield) as a white solid.

MS ESI m/z 264.9 (M+H)$^+$ $^1$H NMR (400 MHz, CDCl$_3$) δ 8.19-8.12 (m, 1H), 7.07-6.71 (m, 2H).

Intermediate 4: 7-Bromo-5-(difluoromethoxy)pyrrolo[2,1-f][1,2,4]triazin-4-amine

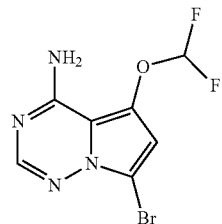

A. 4-chloropyrrolo[2,1-f][1,2,4]triazin-5-yl 4-methylbenzenesulfonate: A mixture of 4-hydroxypyrrolo[2,1-f][1,2,4]triazin-5-yl 4-methylbenzenesulfonate (2.5 g, 8.19 mmol) (WO 2006007468), POCl$_3$ (1.145 mL, 12.28 mmol) and Hunig's base (1.716 mL, 9.83 mmol) in PhCH$_3$ (20 mL) was heated at reflux for 16 h. The reaction mixture was concentrated, cooled to 0° C. and diluted with EtOAc. The organic layer was washed with NaHCO$_3$, water and dried over MgSO$_4$. Filtration and concentration yielded 4-chloropyrrolo[2,1-f][1,2,4]triazin-5-yl 4-methylbenzenesulfonate (2.3 g, 7.10 mmol, 87% yield) as a yellow solid.

$^1$H NMR (400 MHz, CDCl$_3$) δ 8.23-8.09 (m, 1H), 7.85-7.76 (m, 2H), 7.75-7.62 (m, 1H), 7.38-7.31 (m, 2H), 6.86-6.66 (m, 1H), 2.52-2.44 (m, 3H)

B. 7-bromo-4-chloropyrrolo[2,1-f][1,2,4]triazin-5-yl 4-methylbenzenesulfonate: A mixture of 4-chloropyrrolo[2,1-f][1,2,4]triazin-5-yl 4-methylbenzenesulfonate (2.2 g, 6.80 mmol), NBS (1.451 g, 8.15 mmol) and TFA (0.052 ml, 0.680 mmol) in THF was stirred at rt for 16 h. It was diluted with EtOAc. The organic layer was washed with sat. NaHCO$_3$ and water. The organics were dried over MgSO$_4$, filtered and concentrated to obtain a yellow oil, which was purified by silica gel chromatography, eluting with 20% EtOAc/hexanes to obtain 7-bromo-4-chloropyrrolo[2,1-f][1,2,4]triazin-5-yl 4-methylbenzenesulfonate (2.1 g, 5.22 mmol, 77% yield) as a white solid.

MS ESI m/z 403.7 (M+H)$^+$ $^1$H NMR (400 MHz, CDCl$_3$) δ 8.30-8.28 (m, 1H), 7.83-7.74 (m, 2H), 7.41-7.35 (m, 2H), 6.93-6.89 (m, 1H), 2.51-2.48 (m, 3H).

C. 4-(bis(4-methoxybenzyl)amino)-7-bromopyrrolo[2,1-f][1,2,4]triazin-5-yl 4-methylbenzenesulfonate: A mixture of bis(4-methoxybenzyl)amine (153 mg, 0.5% mmol), 7-bromo-4-chloropyrrolo[2,1-f][1,2,4]triazin-5-yl 4-methylbenzenesulfonate (200 mg, 0.497 mmol) and Hunig's base (0.174 mL, 0.993 mmol) in tetrahydrofuran (2 mL) was stirred at rt for 24 h. The reaction mixture was concentrated, and the residue was purified by silica gel chromatography, eluting with 20% EtOAc/hexanes to isolate 4-(bis(4-methoxybenzyl)amino)-7-bromopyrrolo[2,1-f][1,2,4]triazin-5-yl 4-methylbenzenesulfonate (100 mg, 0.160 mmol, 32% yield) as a white solid.

MS ESI m/z 625.0 (M+H)$^+$ $^1$H NMR (400 MHz, CDCl$_3$) δ 8.06-8.04 (m, 1H), 7.71-7.63 (m, 2H), 7.33-7.27 (m, 2H), 7.11-6.97 (m, 4H), 6.87-6.74 (m, 4H), 6.35-6.30 (m, 1H), 4.77-4.74 (m, 4H), 3.83 (s, 6H), 2.52-2.45 (m, 3H).

D. 4-(bis(4-methoxybenzyl)amino)-7-bromopyrrolo[2,1-f][1,2,4]triazin-5-ol: A mixture of 4-(bis(4-methoxybenzyl)amino)-7-bromopyrrolo[2,1-f][1,2,4]triazin-5-yl 4-methylbenzenesulfonate (250 mg, 0.401 mmol) and 0.5 M sodium methoxide (3.21 mL, 1.604 mmol) in THF (2 mL) was stirred at rt for 3 h. The reaction mixture was diluted with water and extracted with EtOAc. The organic layer was dried over MgSO₄, filtered and concentrated. The residue was purified by silica gel chromatography, eluting with 0-100% EtOAc/hexanes to obtain 4-(bis(4-methoxybenzyl) amino)-7-bromopyrrolo[2,1-f][1,2,4]triazin-5-ol (150 mg, 0.320 mmol, 80% yield) as a light yellow solid.

MS ESI m/z 468.9 (M+H)⁺

¹H NMR (400 MHz, CDCl₃) δ 8.02-7.89 (m, 1H), 7.20-7.12 (m, 4H), 6.96-6.82 (m, 4H), 6.35-6.17 (m, 1H), 4.97-4.81 (m, 4H), 3.89-3.75 (m, 6H).

E. 7-bromo-5-(difluoromethoxy)-N,N-bis(4-methoxybenzyl)pyrrolo[2,1-f][1,2,4]triazin-4-amine: A mixture of 4-(bis(4-methoxybenzyl)amino)-7-bromopyrrolo[2,1-f][1,2,4]triazin-5-ol (130 mg, 0.277 mmol) and ethyl 2-bromo-2,2-difluoroacetate (141 mg, 0.692 mmol) and DBU (0.104 mL, 0.692 mmol) in DMF (1 mL) was heated at 70° C. for 16 h. The reaction mixture was diluted with EtOAc. The organic layer was washed with water, dried over MgSO₄, filtered and concentrated to obtain an oil, which was purified by silica gel chromatography, eluting with 20% EtOAc/hexanes to obtain 7-bromo-5-(difluoromethoxy)-N,N-bis(4-methoxybenzyl)pyrrolo[2,1-f][1,2,4]triazin-4-amine (120 mg, 0.231 mmol, 83% yield) as an off white solid.

MS ESI m/z 520.9 (M+H)⁺.

F. A mixture of 7-bromo-5-(difluoromethoxy)-N,N-bis(4-methoxybenzyl)pyrrolo[2,1-f][1,2,4]triazin-4-amine (140 mg, 0.270 mmol) in TFA (2 mL) was heated at reflux for 16 h. The reaction mixture was concentrated. To the residue was added 5 mL of NaHCO₃, and the aqueous layer was extracted with EtOAc. The organic layer was washed with water and dried over MgSO₄, filtered and concentrated to obtain 7-bromo-5-(difluoromethoxy)pyrrolo[2,1-f][1,2,4]triazin-4-amine (70 mg, 0.251 mmol, 93% yield) as an off white solid.

MS ESI m/z 278.6 (M+H)⁺

¹H NMR (400 MHz, DMSO-d6) δ 7.97-7.81 (m, 1H), 7.32-6.91 (m, 1H), 6.83-6.57 (m, 1H).

Intermediate 5: 4-Amino-7-bromopyrrolo[2,1-f][1,2,4]triazin-5-yl 4-methylbenzenesulfonate

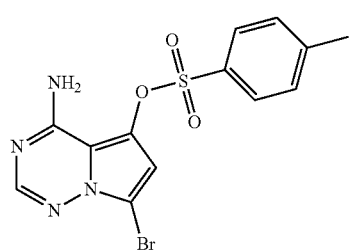 [SMILES: Cc1ccc(S(=O)(=O)Oc2cc(Br)n3ncnc(N)c23)cc1]

A mixture of 7-bromo-4-chloropyrrolo[2,1-f][1,2,4]triazin-5-yl 4-methylbenzenesulfonate (140 mg, 0.348 mmol) and ammonium hydroxide (0.135 mL, 3.48 mmol) in dioxane (3 mL) was stirred at rt for 16 h. It was concentrated to obtain 4-amino-7-bromopyrrolo[2,1-f][1,2,4]triazin-5-yl 4-methylbenzenesulfonate (130 mg, 0.339 mmol, 98% yield) as a white solid.

MS ESI m/z 382.7 (M+H)⁺.

Example 1549: 5-{4-amino-5-[(pyrrolidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide

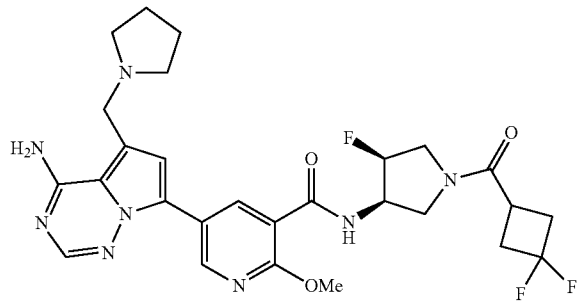 [SMILES: COc1ncc(-c2cc(CN3CCCC3)c3c(N)ncnn23)cc1C(=O)N[C@@H]1CN(C(=O)C2CC(F)(F)C2)C[C@@H]1F]

1549A: tert-butyl (3R,4S)-3-(5-bromo-2-methoxynicotinamido)-4-fluoropyrrolidine-1-carboxylate: A mixture of tert-butyl (3R,4S)-3-amino-4-fluoropyrrolidine-1-carboxylate (220 mg, 1.077 mmol), 5-bromo-2-methoxynicotinic acid (250 mg, 1.077 mmol), Hunig's base (0.565 mL, 3.23 mmol) and BOP (572 mg, 1.293 mmol) in DMF (5 mL) was stirred at rt for 5 h. The mixture was diluted with EtOAc. The organic layer was washed with diluted HCl, sat. NaHCO₃ and water. The organic layer was dried over MgSO₄, filtered and concentrated to obtain an oil, which was then purified with 50% EtOAc/hexanes to obtain tert-butyl (3R,4S)-3-(5-bromo-2-methoxynicotinamido)-4-fluoropyrrolidine-1-carboxylate (0.39 g, 0.932 mmol, 87% yield) as a solid.

MS ESI m/z 440.0, 442.0 (M+Na).

1549B: 5-Bromo-N-((3R,4S)-4-fluoropyrrolidin-3-yl)-2-methoxynicotinamide, 2TFA salt: A mixture of tert-butyl (3R,4S)-3-(5-bromo-2-methoxynicotinamido)-4-fluoropyrrolidine-1-carboxylate (0.39 g, 0.932 mmol) and TFA (0.718 mL, 9.32 mmol) in CH₂Cl₂ (5 mL) was stirred at rt for 2 h. The reaction mixture was concentrated to obtain 5-bromo-N-((3R,4S)-4-fluoropyrrolidin-3-yl)-2-methoxynicotinamide, 2TFA salt (0.39 g, 0.902 mmol, 97% yield) as a grey oil.

MS ESI m/z 317.9, 319.9 (M+H)⁺.

15490. 5-bromo-N-((3R,4S)-1-(3,3-difluorocyclobutane-1-carbonyl)-4-fluoropyrrolidin-3-yl)-2-methoxynicotinamide: To a mixture of 5-bromo-N-((3R,4S)-4-fluoropyrrolidin-3-yl)-2-methoxynicotinamide, 2 TFA (2.5 g, 5.78 mmol) in DMF (10 mL) was added 3,3-difluorocyclobutane-1-carboxylic acid (0.945 g, 6.94 mmol), BOP (3.07 g, 6.94 mmol) and Hunig's Base (3.03 mL, 17.35 mmol). The mixture was stirred at rt for 2 h. It was then diluted with 20 mL of sat. aq. NaHCO₃. The white precipitate formed was filtered and washed with water, diluted HCl and water. The white solid was dried to obtain 5-bromo-N-((3R,4S)-1-(3,3-difluorocyclobutane-1-carbonyl)-4-fluoropyrrolidin-3-yl)-2-methoxynicotinamide (2.3 g, 5.27 mmol, 91% yield) as a white solid.

MS ESI m/z 437.8 (M+H)⁺.

1549: A mixture of 5-bromo-N-((3R,4S)-1-(3,3-difluorocyclobutane-1-carbonyl)-4-fluoropyrrolidin-3-yl)-2-methoxynicotinamide (25 mg, 0.057 mmol), 4,4,4',4',5,5,5',5'-octamethyl-2,2'-bi(1,3,2-dioxaborolane) (17.46 mg, 0.069 mmol) and potassium acetate (16.87 mg, 0.172 mmol) in dioxane (2 mL) was degassed and back-filled with N₂. 1,1'-bis(diphenylphosphino)ferrocene-palladium(II)dichloride dichloromethane complex (4.68 mg, 5.73 μmol) was added, and the reaction was degassed and back-filled with N₂. The reaction mixture was heated at 100° C. for 6 h. After cooling to rt, potassium phosphate tribasic (0.086 mL, 0.172 mmol), 7-bromo-5-(pyrrolidin-1-ylmethyl)pyrrolo[2,1-f][1,2,4]triazin-4-amine (16.97 mg, 0.057 mmol), 1,1'-bis(diphenylphosphino)ferrocene-palladium(II)dichloride dichloromethane complex (4.68 mg, 5.73 μmol) were added and the reaction was degassed and back-filled with N₂. It was then heated for another 6 h. The reaction was cooled to rt, filtered and purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 7% B, 7-47% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to obtain 5-(4-amino-5-(pyrrolidin-1-ylmethyl)pyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide (20.3 mg, 0.034 mmol, 60% yield) as a white solid.

MS ESI m/z 573.2 (M+H)⁺

¹H NMR (500 MHz, DMSO-d6) δ 9.06-8.84 (m, 1H), 8.84-8.67 (m, 1H), 8.63-8.46 (m, 1H), 8.12-7.96 (m, 1H), 7.36-7.28 (m, 1H), 5.45-5.13 (m, 1H), 4.97-4.52 (m, 3H), 4.12-4.01 (m, 3H), 3.99-3.04 (m, 9H), 2.89-2.65 (m, 4H), 2.13-1.95 (m, 2H), 1.95-1.76 (m, 2H).

Example 1550: 5-[4-amino-5-({2-azaspiro[3,3]heptan-2-yl}methyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methoxypyridine-3-carboxamide

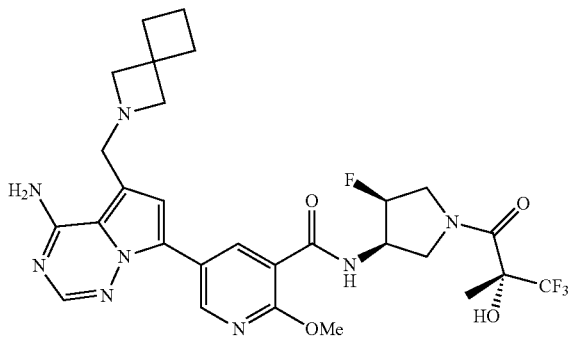 [SMILES: COc1ncc(-c2cc(CN3CC4(CCC4)C3)c3c(N)ncnn23)cc1C(=O)N[C@@H]1CN(C(=O)[C@@](C)(O)C(F)(F)F)C[C@@H]1F]

1550A. 5-bromo-N-((3R,4S)-4-fluoro-1-((R)-3,3,3-trifluoro-2-hydroxy-2-methylpropanoyl)pyrrolidin-3-yl)-2-methoxynicotinaniide: A mixture of 5-bromo-N-((3R,4S)-4-fluoropyrrolidin-3-yl)-2-methoxynicotinamide, 2 TFA (1 g, 2.314 mmol), (R)-3,3,3-trifluoro-2-hydroxy-2-methylpropanoic acid (0.439 g, 2.78 mmol), Hünig's base (1.212 mL, 6.94 mmol) and BOP (1.228 g, 2.78 mmol) in DMF (10 mL) was stirred at rt for 2 h. Water was added to the reaction mixture, and the resulting white precipitate was filtered and washed with water. The solid was dried to obtain 5-bromo-N-((3R,4S)-4-fluoro-1-((R)-3,3,3-trifluoro-2-hydroxy-2-methylpropanoyl)pyrrolidin-3-yl)-2-methoxynicotinamide (0.9 g, 1.964 mmol, 85% yield) as a white solid.

MS ESI m/z 459.7 (M+H)⁺

¹H NMR (400 MHz, DMSO-d6) δ 8.62-8.49 (m, 1H), 8.49-8.44 (m, 1H), 8.23-8.16 (m, 1H), 7.17-7.00 (m, 1H), 5.36-5.12 (m, 1H), 4.72-4.54 (m, 1H), 4.49-4.26 (m, 1H), 4.09-3.66 (m, 5H), 3.62-3.52 (m, 1H), 1.62-1.50 (m, 3H).

1550B. 5-[4-amino-5-({2-azaspiro[3,3]heptan-2-yl}methyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methoxypyridine-3-carboxamide: was prepared by the methods detailed in Example 1549.

MS ESI (m/z) 621.2 (M+H)⁺

¹H NMR (500 MHz, DMSO-d6) δ 9.03-8.88 (m, 1H), 8.78-8.66 (m, 1H), 8.64-8.43 (m, 1H), 8.12-8.00 (m, 1H), 7.35-7.28 (m, 1H), 5.38-5.16 (m, 1H), 4.76-4.56 (m, 3H), 4.55-4.26 (m, 1H), 4.20-4.09 (m, 2H), 4.09-3.32 (m, 8H), 2.27-2.08 (m, 4H), 1.84-1.69 (m, 2H), 1.59-1.45 (m, 3H).

Example 1551: 5-(4-amino-5-{[3-(trifluoromethyl)pyrrolidin-1-yl]methyl}pyrrolo[2,1-f][1,2,4]triazin-7-yl)-N-[(3R,4S)-4-fluoro-1-[(2R)-3,3,3-trifluoro-2-hydroxy-2-methylpropanoyl]pyrrolidin-3-yl]-2-methoxypyridine-3-carboxamide

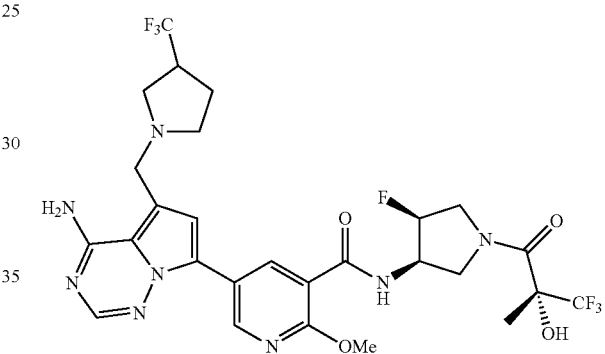

1551A. N-((3R,4S)-4-fluoro-1-((R)-3,3,3-trifluoro-2-hydroxy-2-methylpropanoyl)pyrrolidin-3-yl)-2-methoxy-5-(4,4,5,5-tetramethyl-1,3,2-dioxaborolan-2-yl)nicotinamide: A mixture of 5-bromo-N-((3R,4S)-4-fluoro-1-((R)-3,3,3-trifluoro-2-hydroxy-2-methylpropanoyl)pyrrolidin-3-yl)-2-methoxynicotinamide (440 mg, 0.960 mmol), 4,4,4',4',5,5,5',5'-octamethyl-2,2'-bi(1,3,2-dioxaborolane) (293 mg, 1.152 mmol), in dioxane (10 mL) was degassed and back-filled with N₂. To the mixture was added 1,1'-bis(diphenylphosphino)ferrocene-palladium(II)dichloride dichloromethane complex and the reaction was degassed and back-filled with N₂. It was heated at 100° C. for 16 h. The mixture was cooled to rt and diluted with EtOAc. The organic layer was washed with water, dried over MgSO₄, filtered and concentrated to obtain N-((3R,4S)-4-fluoro-1-((R)-3,3,3-trifluoro-2-hydroxy-2-methylpropanoyl)pyrrolidin-3-yl)-2-methoxy-5-(4,4,5,5-tetramethyl-1,3,2-dioxaborolan-2-yl)nicotinamide (450 mg, 0.891 mmol, 93% yield) as a brown solid.

MS ESI m/z 423.8 (M+H)⁺.

1551. A mixture of N-((3R,4S)-4-fluoro-1-((R)-3,3,3-trifluoro-2-hydroxy-2-methylpropanoyl)pyrrolidin-3-yl)-2-methoxy-5-(4,4,5,5-tetramethyl-1,3,2-dioxaborolan-2-yl)nicotinamide (25 mg, 0.049 mmol), potassium phosphate tribasic (0.074 mL, 0.148 mmol) and 7-bromo-5-((3-(trifluoromethyl)pyrrolidin-1-yl)methyl)pyrrolo[2,1-f][1,2,4]triazin-4-amine (18.02 mg, 0.049 mmol) in dioxane (2 mL) was degassed and back-filled with N₂. To the mixture was added 1,1′-bis(diphenylphosphino)ferrocene-palladium(II) dichloride dichloromethane complex (4.04 mg, 4.95 µmol) and the reaction was degassed and back-filled with $N_2$. It was heated at 100° C. for 16 h, then cooled to rt. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 25% B, 25-65% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to obtain 5-(4-amino-5-((3-(trifluoromethyl)pyrrolidin-1-yl)methyl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (8.9 mg, 0.013 mmol, 27% yield) as a white solid.

MS ESI m/z 663.1 (M+H)$^+$ $^1$H NMR (500 MHz, DMSO-d6) δ 8.95-8.83 (m, 1H), 8.80-8.71 (m, 1H), 8.59-8.48 (m, 1H), 7.90-7.82 (m, 1H), 7.26-7.15 (m, 1H), 7.10-6.93 (m, 1H), 5.38-5.16 (m, 1H), 4.77-4.57 (m, 1H), 4.54-4.26 (m, 1H), 4.07-3.98 (m, 3H), 3.97-3.01 (m, 6H), 2.87-2.75 (m, 2H), 2.75-2.65 (m, 1H), 2.49-2.40 (m, 1H), 2.17-2.01 (m, 1H), 1.89-1.73 (m, 1H), 1.61-1.44 (m, 3H).

Example 1552: 5-(4-amino-5-{[3-(trifluoromethyl)azetidin-1-yl]methyl}pyrrolo[2,1-f][1,2,4]triazin-7-yl)-N-[(3R,4S)-1-(3,3-difluorocyclobutanecarbonyl)-4-fluoropyrrolidin-3-yl]-2-methoxypyridine-3-carboxamide

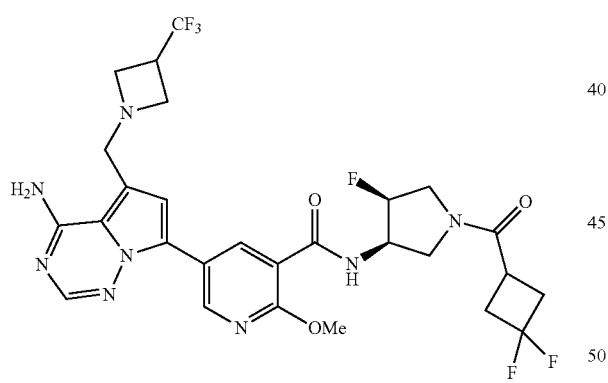

1552A. N-((3R,4S)-1-(3,3-difluorocyclobutane-1-carbonyl)-4-fluoropyrrolidin-3-yl)-2-methoxy-5-(4,4,5,5-tetramethyl-1,3,2-dioxaborolan-2-yl)nicotinamide: A mixture of 5-bromo-N-((3R,4S)-1-(3,3-difluorocyclobutane-1-carbonyl)-4-fluoropyrrolidin-3-yl)-2-methoxynicotinamide (1 g, 2.292 mmol), 4,4,4′,4′,5,5,5′,5′-octamethyl-2,2′-bi(1,3,2-dioxaborolane) (0.699 g, 2.75 mmol) and potassium acetate (0.675 g, 6.88 mmol) in dioxane (15 mL) was degassed and back-filled with $N_2$. PdCl$_2$(dppf)-dichloromethane adduct (0.187 g, 0.229 mmol) was added and the reaction was degassed and back-filled with $N_2$. It was heated at 100° C. for 16 h. The reaction mixture was cooled tort and diluted with EtOAc. The organic layer was washed with water, dried over MgSO$_4$, filtered and concentrated. The residue was purified by silica gel chromatography, eluting with EtOAc and then 10% MeOH/EtOAc to obtain N-((3R,4S)-1-(3,3-difluorocyclobutane-1-carbonyl)-4-fluoropyrrolidin-3-yl)-2-methoxy-5-(4,4,5,5-tetramethyl-1,3,2-dioxaborolan-2-yl)nicotinamide (0.7 g, 1.448 mmol, 63% yield) as a light brown solid.

MS ESI m/z 401.9 (M+H)$^+$

1552: A mixture of N-((3R,4S)-1-(3,3-difluorocyclobutane-1-carbonyl)-4-fluoropyrrolidin-3-yl)-2-methoxy-5-(4,4,5,5-tetramethyl-1,3,2-dioxaborolan-2-yl)nicotinamide (25 mg, 0.052 mmol), 7-bromo-5-((3-(trifluoromethyl)azetidin-1-yl)methyl)pyrrolo[2,1-f][1,2,4]triazin-4-amine (21.73 mg, 0.062 mmol) and potassium phosphate tribasic (0.078 mL, 0.155 mmol) in dioxane (2 mL) was degassed. 1,1′-Bis(diphenylphosphino)ferrocene-palladium(II)dichloride dichloromethane complex (4.22 mg, 5.17 µmol) was added and the reaction was degassed and back-filled with $N_2$. It was heated at 100° C. for 16 h and cooled to rt. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 23% B, 23-63% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to obtain 5-(4-amino-5-((3-(trifluoromethyl)azetidin-1-yl)methyl)pyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide (8.5 mg, 0.014 mmol, 26% yield) as a white solid.

MS ESI m/z 627.1 (M+H)$^+$ $^1$H NMR (500 MHz, DMSO-d6) δ 8.98-8.87 (m, 1H), 8.83-8.71 (m, 1H), 8.59-8.38 (m, 1H), 7.94-7.85 (m, 1H), 7.14-7.03 (m, 1H), 5.47-5.17 (m, 1H), 4.94-4.55 (m, 1H), 4.09-4.00 (m, 3H), 4.01-3.02 (m, 12H), 2.90-2.66 (m, 4H).

Example 1553: 2,2,2-trifluoroethyl (3R,4S)-3-(5-{4-amino-5-[(4,4-difluoropiperidin-1-yl)methyl]pyrrolo[2,1-f][1,2,4]triazin-7-yl}-2-methoxypyridine-3-amido)-4-fluoropyrrolidine-1-carboxylate

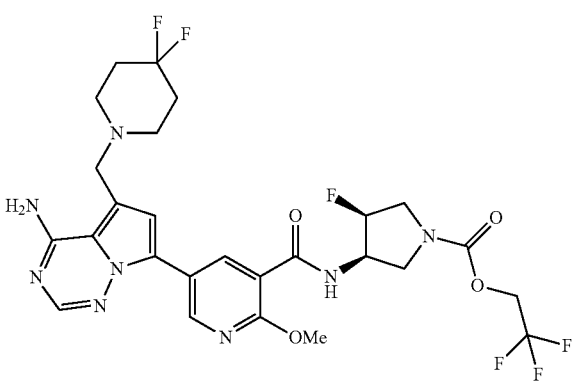 [SMILES: COc1ncc(-c2cc(CN3CCC(F)(F)CC3)c3c(N)ncnn23)cc1C(=O)N[C@@H]1CN(C(=O)OCC(F)(F)F)C[C@@H]1F]

1553A. 2,2,2-trifluoroethyl (3R,4S)-3-(5-bromo-2-methoxynicotinamido)-4-fluoropyrrolidine-1-carboxylate: A mixture of 5-bromo-N-((3R,4S)-4-fluoropyrrolidin-3-yl)-2-methoxynicotinamide, 2 TFA (250 mg, 0.46 mmol), 2,2,2-trifluoroethyl carbonochloridate (113 mg, 0.694 mmol), Hunig's base (0.101 mL, 0.578 mmol) in DMF (5 mL) was stirred at rt for 24 h. It was then diluted with water. The resulting precipitate was filtered and washed with water. It was then dried to obtain a solid which was purified by silica gel chromatography, eluting with 0-100% EtOAc/hexanes to obtain 2,2,2-trifluoroethyl (3R,4S)-3-(5-bromo-2-methoxynicotinamido)-4-fluoropyrrolidine-1-carboxylate (250 mg, 0.563 mmol, 97% yield) as an off-white solid.

MS ESI m/z 443.8 (M+H)⁺.

1553B. 2,2,2-trifluoroethyl (3R,4R)-3-fluoro-4-(2-methoxy-5-(4,4,5,5-tetramethyl-1,3,2-dioxaborolan-2-yl)nicotinamido)pyrrolidine-1-carboxylate: A mixture of 2,2,2-trifluoroethyl (3R,4S)-3-(5-bromo-2-methoxynicotinamido)-4-fluoropyrrolidine-1-carboxylate (250 mg, 0.563 mmol), 4,4,4',4',5,5,5',5'-octamethyl-2,2'-bi(1,3,2-dioxaborolane) (172 mg, 0.675 mmol) and potassium acetate (166 mg, 1.689 mmol) in dioxane (5 mL) was degassed and back-filled with N₂. PdCl₂(dppf)-dichloromethane adduct (46.0 mg, 0.056 mmol) was added and the reaction was degassed and back-filled with N₂. It was heated at 100° C. for 16 h. The mixture was cooled to rt, diluted with EtOAc and washed with water. The organic layer was dried over MgSO₄, filtered and concentrated. The residue was purified by silica gel chromatography, eluting with EtOAc to 10% MeOH/EtOAc to obtain to obtain 2,2,2-trifluoroethyl (3S,4R)-3-fluoro-4-(2-methoxy-5-(4,4,5,5-tetramethyl-1,3,2-dioxaborolan-2-yl)nicotinamido)pyrrolidine-1-carboxylate as a light brown solid (200 mg, 0.407 mmol, 73% yield).

MS ESI m/z 409.9 (M+H)⁺.

1553: A mixture of 2,2,2-trifluoroethyl (3S,4R)-3-fluoro-4-(2-methoxy-5-(4,4,5,5-tetramethyl-1,3,2-dioxaborolan-2-yl)nicotinamido)pyrrolidine-1-carboxylate (30 mg, 0.061 mmol), 7-bromo-5-((4,4-difluoropiperidin-1-yl)methyl)pyrrolo[2,1-f][1,2,4]triazin-4-amine (21.14 mg, 0.061 mmol) and potassium phosphate tribasic (0.092 mL, 0.183 mmol) in dioxane (2 mL) was degassed and back-filled with Nz. 1,1'-Bis(diphenylphosphino)ferrocene-palladium(II)dichloride dichloromethane complex (4.99 mg, 6.11 µmol) was added and the reaction was degassed and back-filled with Nz. It was heated at 100° C. for 16 h. The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 22% B, 22-52% B over 25 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation to obtain 2,2,2-trifluoroethyl (3R,4S)-3-(5-(4-amino-5-((4,4-difluoropiperidin-1-yl)methyl)pyrrolo[2,1-f][1,2,4]triazin-7-yl)-2-methoxynicotinamido)-4-fluoropyrrolidine-1-carboxylate as an off-white solid (17.2 mg, 0.0272 mmol, 45% yield).

MS ESI m/z 631.1 (M+H)⁺

¹H NMR (500 MHz, DMSO-d6) δ 9.06-8.86 (m, 1H), 8.78-8.66 (m, 1H), 8.60-8.42 (m, 1H), 8.19-8.04 (m, 1H), 7.33-7.23 (m, 1H), 5.48-5.13 (m, 1H), 4.87-4.64 (m, 3H), 4.15-4.01 (m, 3H), 3.99-3.19 (m, 10H), 2.35-1.98 (m, 4H).

Example 1554: 5-{4-amino-5-[(azetidin-1-yl)methyl]pyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide

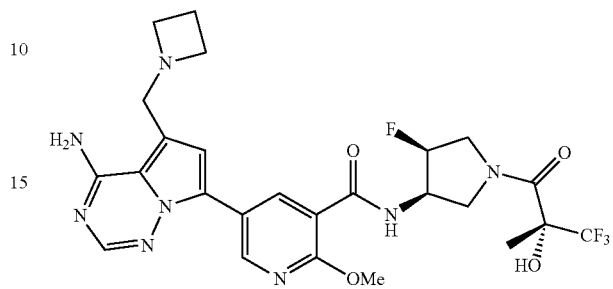

1554A: tert-butyl (3R,4S)-3-(5-bromo-2-methoxynicotinamido)-4-fluoropyrrolidine-1-carboxylate: A mixture of tert-butyl (3R,4S)-3-amino-4-fluoropyrrolidine-1-carboxylate (220 mg, 1.077 mmol), 5-bromo-2-methoxynicotinic acid (250 mg, 1.077 mmol), Hunig's base (0.565 mL, 3.23 mmol) and BOP (572 mg, 1.293 mmol) in DMF (5 mL) was stirred at rt for 5 h. The reaction mixture was diluted with EtOAc. The organic layer was washed with diluted HCl, sat. NaHCO₃ and water. It was then dried over MgSO₄, filtered and concentrated to obtain an oil which was purified with 50% EtOAc/hexanes to obtain tert-butyl (3R,4S)-3-(5-bromo-2-methoxynicotinamido)-4-fluoropyrrolidine-1-carboxylate (0.39 g, 0.932 mmol, 87% yield) as a solid.

MS ESI m/z 440.0, 442.0 (M+Na).

1554B. tert-butyl (3R,4S)-3-(5-(4-amino-5-(azetidin-1-ylmethyl)pyrrolo[2,1-f][1,2,4]triazin-7-yl)-2-methoxynicotinamido)-4-fluoropyrrolidine-1-carboxylate: A mixture of tert-butyl (3R,4S)-3-(5-bromo-2-methoxynicotinamido)-4-fluoropyrrolidine-1-carboxylate (150 mg, 0.359 mmol), 4,4,4',4',5,5,5',5'-octamethyl-2,2'-bi(1,3,2-dioxaborolane) (109 mg, 0.430 mmol) and potassium acetate (106 mg, 1.076 mmol) in dioxane (5 mL) was degassed and back-filled with N₂. 1,1'-Bis(diphenylphosphino)ferrocene-palladium(II)dichloride dichloromethane complex (29.3 mg, 0.036 mmol) was added and the reaction was degassed and back-filled with N₂. It was heated at 100° C. for 6 h. After cooling to rt, potassium phosphate tribasic (0.538 mL, 1.076 mmol), 5-(azetidin-1-ylmethyl)-7-bromopyrrolo[2,1-f][1,2,4]triazin-4-amine (101 mg, 0.359 mmol) and 1,1'-bis(diphenylphosphino)ferrocene-palladium(II)dichloride dichloromethane complex (29.3 mg, 0.036 mmol) were added and the reaction was degassed and back-filled with N₂. It was heated for 6 h. The reaction mixture was cooled to rt, diluted with EtOAc and washed with water. The organic layer was dried over MgSO₄, filtered and concentrated to obtain a brown solid, which was purified by silica gel chromatography, eluting with 50% EtOAc in hexanes to obtain tert-butyl (3R,4S)-3-(5-(4-amino-5-(azetidin-1-ylmethyl)pyrrolo[2,1-f][1,2,4]triazin-7-yl)-2-methoxynicotinamido)-4-fluoropyrrolidine-1-carboxylate (150 mg, 0.277 mmol, 77% yield) as a white solid.

MS ESI m/z 541.1 (M+H).

1554C: 5-(4-amino-5-(azetidin-1-ylmethyl)pyrrolo[2,1-f][1,2,4]triazin-7-yl)-N-((3R,4S)-4-fluoropyrrolidin-3-yl)-2-methoxynicotinamide, 3 TFA salt: A mixture of tert-butyl (3R,4S)-3-(5-(4-amino-5-(azetidin-1-ylmethyl)pyrrolo[2,1-f][1,2,4]triazin-7-yl)-2-methoxynicotinamido)-4-fluoropyrrolidine-1-carboxylate (150 mg, 0.277 mmol) in TFA (1 mL, 12.98 mmol) was stirred at rt for 1 h. The reaction mixture was concentrated to obtain 5-(4-amino-5-(azetidin-1-ylmethyl)pyrrolo[2,1-f][1,2,4]triazin-7-yl)-N-((3R,4S)-4-fluoropyrrolidin-3-yl)-2-methoxynicotinamide, 3 TFA (150 mg, 0.192 mmol, 69% yield) as a brown solid.

MS ESI m/z 441.0 (M+H)+.

1554: A mixture of 5-(4-amino-5-(azetidin-1-ylmethyl)pyrrolo[2,1-f][1,2,4]triazin-7-yl)-N-((3R,4S)-4-fluoropyrrolidin-3-yl)-2-methoxynicotinamide, 3 TFA (25 mg, 0.037 mmol), (R)-3,3,3-trifluoro-2-hydroxy-2-methylpropanoic acid (8.55 mg, 0.054 mmol), Hunig's base (0.024 mL, 0.135 mmol) and BOP (23.93 mg, 0.054 mmol) in DMF (1 mL) was stirred at rt for 2 h. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 19% B, 19-59% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to isolate 5-(4-amino-5-(azetidin-1-ylmethyl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (8.4 mg, 0.014 mmol, 32% yield) as a white solid.

MS ESI m/z 581.1 (M+H)+

$^1$H NMR (500 MHz, DMSO-d6) δ 9.03-8.87 (m, 1H), 8.83-8.64 (m, 1H), 8.61-8.43 (m, 1H), 8.00-7.84 (m, 1H), 7.30-6.89 (m, 2H), 5.45-5.10 (m, 1H), 4.81-4.57 (m, 1H), 4.55-4.26 (m, 1H), 4.09-3.47 (m, 6H), 3.47-3.01 (m, 6H), 2.19-1.95 (m, 2H), 1.66-1.45 (m, 3H).

Example 1555: 2,2,2-trifluoroethyl (3R,4S)-3-(5-{4-amino-5-[(azetidin-1-yl)methyl]pyrrolo[2,1-f][1,2,4]triazin-7-yl}-2-methoxypyridine-3-amido)-4-fluoropyrrolidine-1-carboxylate

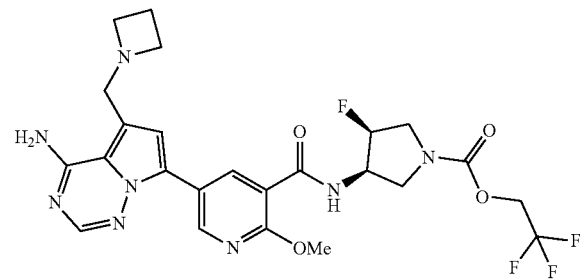 [SMILES: COc1ncc(-c2cc(CN3CCC3)c3c(N)ncnn23)cc1C(=O)N[C@@H]1CN(C(=O)OCC(F)(F)F)C[C@@H]1F]

A mixture of 5-(4-amino-5-(azetidin-1-ylmethyl)pyrrolo[2,1-f][1,2,4]triazin-7-yl)-N-((3R,4S)-4-fluoropyrrolidin-3-yl)-2-methoxynicotinamide, 3 TFA salt (25 mg, 0.032 mmol), 2,2,2-trifluoroethyl carbonochloridate (11.07 mg, 0.068 mmol), Hunig's base (9.91 µl, 0.057 mmol) in DMF (0.5 mL) was stirred at rt for 24 h. The mixture was concentrated. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 26% B, 26-66% B over 20 minutes, then a 5-minute hold at 100% B; Flow Rate: 20 mL/min; Column Temperature: 25 C. Fraction collection was triggered by MS signals. Fractions containing the desired product were combined and dried via centrifugal evaporation to isolate 2,2,2-trifluoroethyl (3R,4S)-3-(5-(4-amino-5-(azetidin-1-ylmethyl)pyrrolo[2,1-f][1,2,4]triazin-7-yl)-2-methoxynicotinamido)-4-fluoropyrrolidine-1-carboxylate (3.3 mg, 5.32 µmol, 9% yield) as a white solid.

MS ESI m/z 567.2 (M+H)+

$^1$H NMR (500 MHz, DMSO-d6) δ 9.04-8.82 (m, 1H), 8.82-8.70 (m, 1H), 8.60-8.35 (m, 1H), 7.92-7.83 (m, 1H), 7.08-6.86 (m, 1H), 5.46-5.12 (m, 1H), 4.92-4.54 (m, 3H), 4.10-3.97 (m, 3H), 3.96-3.53 (m, 6H), 3.28-3.04 (m, 4H), 2.13-2.00 (m, 2H).

Example 1556: 5-{4-amino-5-[(4,4-difluoropiperidin-1-yl)methyl]pyrrolo[2,1-f][1,2,4]triazin-7-yl}-N-[(3R,4S)-4-fluoro-1-[4,4,4-trifluoro-3-hydroxy-3-(trifluoromethyl)butanoyl]pyrrolidin-3-yl]-2-methoxypyridine-3-carboxamide

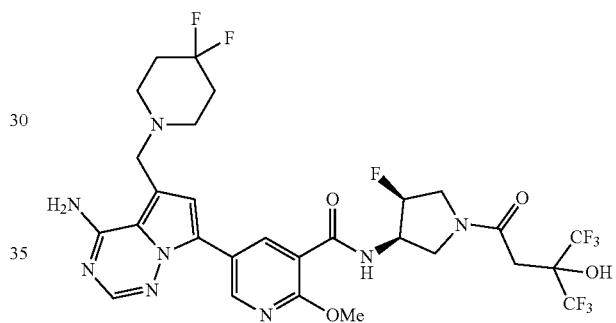

1556A. tert-butyl (3S,4R)-3-fluoro-4-(2-methoxy-5-(4,4,5,5-tetramethyl-1,3,2-dioxaborolan-2-yl)nicotinamido)pyrrolidine-1-carboxylate: A mixture of tert-butyl (3R,4S)-3-(5-bromo-2-methoxynicotinamido)-4-fluoropyrrolidine-1-carboxylate (350 mg, 0.837 mmol), 4,4,4',4',5,5,5',5'-octamethyl-2,2'-bi(1,3,2-dioxaborolane) (255 mg, 1.004 mmol) and potassium acetate (246 mg, 2.51 mmol) in dioxane (15 mL) was degassed and back-filled with N$_2$. 1,1'-Bis(diphenylphosphino)ferrocene-palladium(II)dichloride dichloromethane complex (68.3 mg, 0.084 mmol) was added and the reaction was degassed and back-filled with N$_2$. It was heated at 100° C. for 16 h. The mixture was cooled to rt and diluted with EtOAc. The organic layer was washed with water and dried over MgSO$_4$, filtered and concentrated to obtain tert-butyl (3S,4R)-3-fluoro-4-(2-methoxy-5-(4,4,5,5-tetramethyl-1,3,2-dioxaborolan-2-yl)nicotinamido)pyrrolidine-1-carboxylate (320 mg, 0.688 mmol, 82% yield) as a brown solid.

MS ESI m/z 327.7 (M+H)+(boronic acid ester was hydrolyzed in LCMS).

1556B. tert-butyl (3R,4S)-3-(5-(4-amino-5-((4,4-difluoropiperidin-1-yl)methyl)pyrrolo[2,1-f][1,2,4]triazin-7-yl)-2-methoxynicotinamido)-4-fluoropyrrolidine-1-carboxylate: A mixture of 7-bromo-5-((4,4-difluoropiperidin-1-yl)methyl)pyrrolo[2,1-f][1,2,4]triazin-4-amine (238 mg, 0.688 mmol), tert-butyl (3R,4R)-3-fluoro-4-(2-methoxy-5-(4,4,5, 5-tetramethyl-1,3,2-dioxaborolan-2-yl)nicotinamido)pyrrolidine-1-carboxylate (320 mg, 0.688 mmol) and potassium phosphate tribasic (1.032 mL, 2.063 mmol) in dioxane (10 mL) was degassed and back-filled with $N_2$. 1,1'-Bis(diphenylphosphino)ferrocene-palladium(II)dichloride dichloromethane complex (56.2 mg, 0.069 mmol) was added, and the reaction was degassed and back-filled with $N_2$. It was heated at 100° C. for 16 h. The mixture was cooled tort and diluted with EtOAc. The organic layer was washed with water, dried over $MgSO_4$, filtered and concentrated. The residue was purified by silica gel chromatography, eluting with 50% to 100% EtOAc/hexane to isolate to obtain tert-butyl (3R,4S)-3-(5-(4-amino-5-((4,4-difluoropiperidin-1-yl)methyl)pyrrolo[2,1-f][1,2,4]triazin-7-yl)-2-methoxynicotinamido)-4-fluoropyrrolidine-1-carboxylate (140 mg, 0.232 mmol, 34% yield) as a off-white solid.

MS ESI m/z 605.2 $(M+H)^+$.

1556C. 5-(4-amino-5-((4,4-difluoropiperidin-1-yl)methyl)pyrrolo[2,1-f][1,2,4]triazin-7-yl)-N-((3R,4S)-4-fluoropyrrolidin-3-yl)-2-methoxynicotinamide, 3 TFA salt: A mixture of tert-butyl (3R,4S)-3-(5-(4-amino-5-((4,4-difluoropiperidin-1-yl)methyl)pyrrolo[2,1-f][1,2,4]triazin-7-yl)-2-methoxynicotinamido)-4-fluoropyrrolidine-1-carboxylate (140 mg, 0.232 mmol) and TFA (178 µl, 2.315 mmol) was stirred at rt for 1 h. It was then concentrated to obtain 5-(4-amino-5-((4,4-difluoropiperidin-1-yl)methyl)pyrrolo[2,1-f][1,2,4]triazin-7-yl)-N-((3R,4S)-4-fluoropyrrolidin-3-yl)-2-methoxynicotinamide, 3 TFA salt (170 mg, 0.201 mmol, 87% yield) as a brown solid.

MS ESI m/z 505.0 $(M+H)^+$.

1556: A mixture of 5-(4-amino-5-((4,4-difluoropiperidin-1-yl)methyl)pyrrolo[2,1-f][1,2,4]triazin-7-yl)-N-((3R,4S)-4-fluoropyrrolidin-3-yl)-2-methoxynicotinamide, 3 TFA (25 mg, 0.030 mmol), 3,3-bis(trifluoromethyl)-3-hydroxypropionic acid (6.68 mg, 0.030 mmol), Hunig's base (0.015 mL, 0.089 mmol) and BOP (15.67 mg, 0.035 mmol) in DMF (1 mL) was stirred at rt for 2 h. The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 16% B, 16-56% B over 23 minutes, then a 6-minute hold at 100% B; Flow Rate: 20 mL/min; Column Temperature: 25 C. Fraction collection was triggered by MS and UV signals. Fractions containing the desired product were combined and dried via centrifugal evaporation to obtain 5-(4-amino-5-((4,4-difluoropiperidin-1-yl)methyl)pyrrolo[2,1-f][1,2,4]triazin-7-yl)-N-((3R,4S)-4-fluoro-1-(4,4,4-trifluoro-3-hydroxy-3-(trifluoromethyl)butanoyl)pyrrolidin-3-yl)-2-methoxynicotinamide (14.5 mg, 0.020 mmol, 69% yield) as a white solid.

MS ESI m/z 713.1 $(M+H)^+$ $^1$H NMR (500 MHz, DMSO-d6) δ 8.98-8.87 (m, 2H), 8.82-8.69 (m, 1H), 8.65-8.49 (m, 1H), 8.05-7.94 (m, 1H), 7.27-7.22 (m, 2H), 5.51-5.20 (m, 1H), 5.02-4.61 (m, 1H), 4.27-3.26 (m, 17H), 3.09-3.05 (m, 2H).

Example 1557: 5-{4-amino-5-[(3,3-difluoroazetidin-1-yl)methyl]pyrrolo[2,1-f][1,2,4]triazin-7-yl}-N-[(3R,4S)-1-[(1S)-2,2-difluorocyclopropanecarbonyl]-4-fluoropyrrolidin-3-yl]-2-methoxypyridine-3-carboxamide

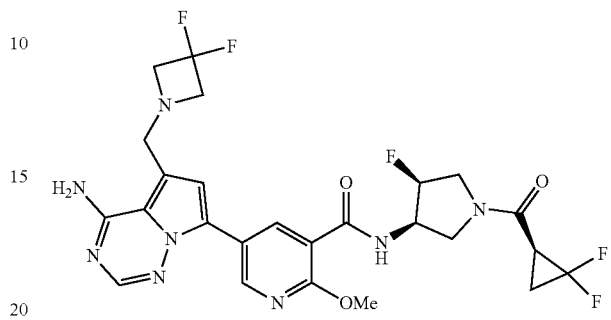

5-(4-amino-5-((3,3-difluoroazetidin-1-yl)methyl)pyrrolo[2,1-f][1,2,4]triazin-7-yl)-N-((3R,4S)-1-(2,2-difluorocyclopropane-1-carbonyl)-4-fluoropyrrolidin-3-yl)-2-methoxynicotinamide (18.5 mg, 0.032 mmol) was separated by a Waters 100 preparative SFC with the following conditions: Column: Chiral AD, 250 mm×30 mm, 5-µm particles; Mobile Phase 60% $CO_2$, 40% IPA with 0.1% DEA; Flow Rate: 100 mL/min. Fraction collection was triggered by MS and UV signals. First eluent peaks were combined and dried to obtain 5-(4-amino-5-((3,3-difluoroazetidin-1-yl)methyl)pyrrolo[2,1-f][1,2,4]triazin-7-yl)-N-((3R,4S)-1-((S)-2,2-difluorocyclopropane-1-carbonyl)-4-fluoropyrrolidin-3-yl)-2-methoxynicotinamide (5.6 mg, 29.1%) as a white solid.

MS ESI m/z 581.4 $(M+H)^+$ $^1$H NMR (500 MHz, DMSO-d6) δ 8.99-8.80 (m, 2H), 8.79-8.69 (m, 1H), 8.62-8.44 (m, 1H), 7.93-7.83 (m, 1H), 7.15-6.99 (m, 1H), 5.50-5.12 (m, 1H), 4.94-4.59 (m, 1H), 4.35-3.14 (m, 12H), 3.12-2.93 (m, 1H), 2.08-1.70 (m, 2H).

Example 1558: 5-{4-amino-5-[(3,3-difluoroazetidin-1-yl)methyl]pyrrolo[2,1-f][1,2,4]triazin-7-yl}-N-[(3R,4S)-1-[(1R)-2,2-difluorocyclopropanecarbonyl]-4-fluoropyrrolidin-3-yl]-2-methoxypyridine-3-carboxamide

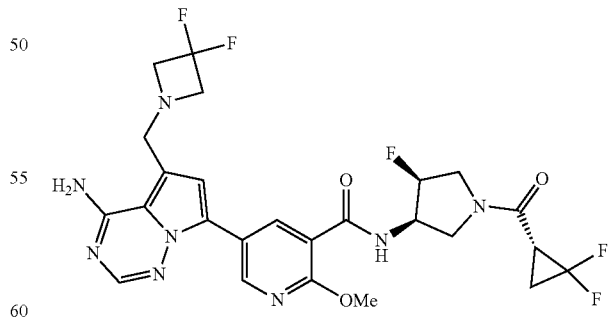

5-(4-amino-5-((3,3-difluoroazetidin-1-yl)methyl)pyrrolo[2,1-f][1,2,4]triazin-7-yl)-N-((3R,4S)-1-(2,2-difluorocyclopropane-1-carbonyl)-4-fluoropyrrolidin-3-yl)-2-methoxynicotinamide (18.5 mg, 0.032 mmol) was separated by a Waters 100 preparative SFC with the following conditions: Column: Chiral AD, 250 mm×30 mm, 5-µm particles;

Mobile Phase 60% $CO_2$, 40% IPA with 0.1% DEA; Flow Rate: 100 mL/min. Fraction collection was triggered by MS and UV signals. Second eluent peaks were combined and dried to obtain 5-{4-amino-5-[(3,3-difluoroazetidin-1-yl)methyl]pyrrolo[2,1-f][1,2,4]triazin-7-yl}-N-[(3R,4S)-1-[(1R)-2,2-difluorocyclopropanecarbonyl]-4-fluoropyrrolidin-3-yl]-2-methoxypyridine-3-carboxamide (5.9 mg, 31.2%) as a white solid. The absloute stereochemistry at the cyclopropane is unknown.

MS ESI m/z 581.2 (M+H)+

$^1$H NMR (500 MHz, DMSO-d$_6$) δ 9.02-8.86 (m, 1H), 8.85-8.70 (m, 1H), 8.63-8.43 (m, 1H), 7.96-7.85 (m, 1H), 7.15-6.95 (m, 1H), 5.49-5.23 (m, 1H), 4.96-4.60 (m, 1H), 4.23-3.56 (m, 11H), 3.55-3.40 (m, 1H), 3.39-3.25 (m, 1H), 3.06-2.82 (m, 1H), 2.05-1.77 (m, 2H).

Example 1559: 5-{4-amino-5-[(4,4-difluoropiperidin-1-yl)methyl]pyrrolo[2,1-f][1,2,4]triazin-7-yl}-N-[(3R,4S)-1-[(1S)-2,2-difluorocyclopropanecarbonyl]-4-fluoropyrrolidin-3-yl]-2-methoxypyridine-3-carboxamide

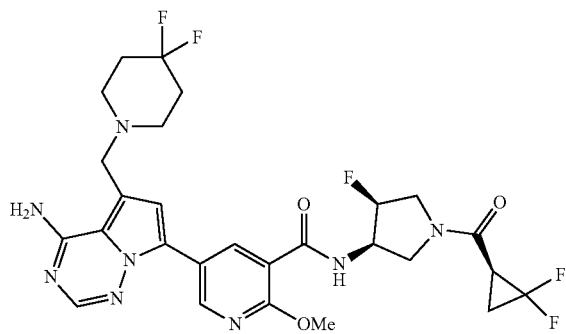 [SMILES: COc1ncc(-c2cc(CN3CCC(F)(F)CC3)c3c(N)ncnn23)cc1C(=O)N[C@@H]1CN(C(=O)[C@@H]2CC2(F)F)C[C@@H]1F]

5-(4-amino-5-((4,4-difluoropiperidin-1-yl)methyl)pyrrolo[2,1-f][1,2,4]triazin-7-yl)-N-((3R,4S)-1-(2,2-difluorocyclopropane-1-carbonyl)-4-fluoropyrrolidin-3-yl)-2-methoxynicotinamide (27.5 mmol, 0.045 mmol) was separated by a Waters 100 preparative SFC with the following conditions: Column: Chiral AJ, 250 mm×30 mm, 5-μm particles; Mobile Phase 80% $CO_2$, 20% MeOH with 0.1% DEA; Flow Rate: 100 mL/min. Fraction collection was triggered by MS and UV signals. First eluent peaks were combined and dried to obtain 5-{4-amino-5-[(4,4-difluoropiperidin-1-yl)methyl]pyrrolo[2,1-f][1,2,4]triazin-7-yl}-N-[(3R,4S)-1-[(1S)-2,2-difluorocyclopropanecarbonyl]-4-fluoropyrrolidin-3-yl]-2-methoxypyridine-3-carboxamide (9.2 mg, 32.2%) as a white solid.

MS ESI m/z 609.3 (M+H)+

$^1$H NMR (500 MHz, DMSO-d$_6$) δ 9.38-9.10 (m, 1H), 8.95-8.86 (m, 1H), 8.79-8.70 (m, 1H), 8.62-8.46 (m, 1H), 7.94-7.81 (m, 1H), 7.72-7.40 (m, 1H), 7.09-6.97 (m, 1H), 5.45-5.18 (m, 1H), 4.94-4.62 (m, 1H), 4.33-4.10 (m, 1H), 4.07-3.98 (m, 3H), 3.98-3.89 (m, 1H), 3.89-3.55 (m, 3H), 3.32-3.12 (m, 1H), 3.11-2.95 (m, 1H), 2.73-2.55 (m, 4H), 2.10-1.75 (m, 6H).

Example 1560: 5-{4-amino-5-[(4,4-difluoropiperidin-1-yl)methyl]pyrrolo[2,1-f][1,2,4]triazin-7-yl}-N-[(3R,4S)-1-[(1R)-2,2-difluorocyclopropanecarbonyl]-4-fluoropyrrolidin-3-yl]-2-methoxypyridine-3-carboxamide

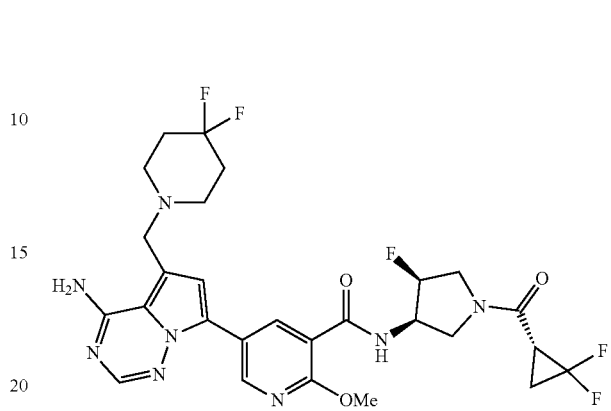

5-(4-amino-5-((4,4-difluoropiperidin-1-yl)methyl)pyrrolo[2,1-f][1,2,4]triazin-7-yl)-N-((3R,4S)-1-(2,2-difluorocyclopropane-1-carbonyl)-4-fluoropyrrolidin-3-yl)-2-methoxynicotinamide (27.5 mmol, 0.045 mmol) was separated by a Waters 100 preparative SFC with the following conditions: Column: Chiral AJ, 250 mm×30 mm, 5-μm particles; Mobile Phase 80% $CO_2$, 20% MeOH with 0.1% DEA; Flow Rate: 100 mL/min. Fraction collection was triggered by MS and UV signals. Second eluent peaks were combined and dried to obtain 5-{4-amino-5-[(4,4-difluoropiperidin-1-yl)methyl]pyrrolo[2,1-f][1,2,4]triazin-7-yl}-N-[(3R,4S)-1-[(1R)-2,2-difluorocyclopropanecarbonyl]-4-fluoropyrrolidin-3-yl]-2-methoxypyridine-3-carboxamide (9.2 mg, 33.1%) as a white solid.

MS ESI m/z 609.4 (M+H)+

$^1$H NMR (500 MHz, DMSO-d6) δ 9.42-9.06 (m, 1H), 8.97-8.88 (m, 1H), 8.85-8.72 (m, 1H), 8.62-8.47 (m, 1H), 7.94-7.85 (m, 1H), 7.79-7.46 (m, 1H), 7.12-6.97 (m, 1H), 5.45-5.22 (m, 1H), 4.90-4.64 (m, 1H), 4.14-3.99 (m, 4H), 3.94-3.84 (m, 1H), 3.84-3.78 (m, 2H), 3.78-3.59 (m, 1H), 3.06-2.84 (m, 1H), 3.30-3.16 (m, 1H), 2.72-2.60 (m, 4H), 2.09-1.82 (m, 6H).

Example 1561: tert-butyl (3R,4S)-3-(5-{4-amino-5-[(3,3-difluoroazetidin-1-yl)methyl]pyrrolo[2,1-f][1,2,4]triazin-7-yl}-3-fluoro-2-methylbenzamido)-4-fluoropyrrolidine-1-carboxylate

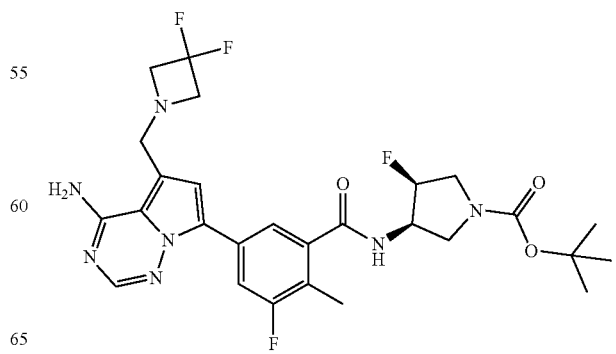

1561A. tert-butyl (3R,4S)-3-(5-bromo-3-fluoro-2-methylbenzamido)-4-fluoropyrrolidine-1-carboxylate: A mixture of tert-butyl (3R,4S)-3-amino-4-fluoropyrrolidine-1-carboxylate (324 mg, 1.588 mmol), 5-bromo-3-fluoro-2-methylbenzoic acid (370 mg, 1.588 mmol), Hunig's base (832 µl, 4.76 mmol) and BOP (843 mg, 1.905 mmol) in DMF (5 mL) was stirred at rt for 2 h. It was then diluted with EtOAc. The organic layer was washed with diluted HCl, sat. NaHCO$_3$ and water, dried with MgSO$_4$, filtered and concentrated to obtain an oil. It was then purified by silica gel chromatography, eluting with 0-30% EtOAc/hexanes to obtain tert-butyl (3R,4S)-3-(5-bromo-3-fluoro-2-methylbenzamido)-4-fluoropyrrolidine-1-carboxylate (530 mg, 1.264 mmol, 80% yield) as a white solid.

MS ESI m/z 442.9 (M+H)$^+$ $^1$H NMR (400 MHz, chloroform-d) δ 7.38-7.29 (m, 2 h), 6.27-5.94 (m, 1 h), 5.29-5.05 (m, 1 h), 4.89-4.56 (m, 1H), 4.10-3.93 (m, 1H), 3.89-3.52 (m, 2H), 3.28-3.13 (m, 1H), 2.34-2.26 (m, 3H), 1.50 (s, 9H).

1561: A mixture of tert-butyl (3R,4S)-3-(5-bromo-3-fluoro-2-methylbenzamido)-4-fluoropyrrolidine-1-carboxylate (100 mg, 0.239 mmol), potassium acetate (70.2 mg, 0.716 mmol), 4,4,4',4',5,5,5',5'-octamethyl-2,2'-bi(1,3,2-dioxaborolane) (72.7 mg, 0.286 mmol) in dioxane (3 mL) was degassed and back-filled with N$_2$. 1,1'-Bis(diphenylphosphino)ferrocene-palladium(II)dichloride dichloromethane complex (19.05 mg, 0.024 mmol) was added and the reaction was degassed and back-filled with N$_2$. It was heated at 100° C. for 16 h. The reaction mixture was cooled to rt and potassium phosphate tribasic (0.358 mL, 0.716 mmol), 7-bromo-5-((3,3-difluoroazetidin-1-yl)methyl)pyrrolo[2,1-f][1,2,4]triazin-4-amine (76 mg, 0.239 mmol) and 1,1'-bis(diphenylphosphino)ferrocene-palladium(II)dichloride dichloromethane complex (19.05 mg, 0.024 mmol) were added. The reaction mixture was degassed and back-filled with N$_2$. After heating at reflux for 16 h, the reaction mixture was cooled to rt and diluted with EtOAc. The organic layer was washed with water, dried over MgSO$_4$, filtered and concentrated. The residue was purified by silica gel chromatography, eluting with 0-50% EtOAc/hexanes to obtain tert-butyl (3R,4S)-3-(5-(4-amino-5-((3,3-difluoroazetidin-1-yl)methyl)pyrrolo[2,1-f][1,2,4]triazin-7-yl)-3-fluoro-2-methylbenzamido)-4-fluoropyrrolidine-1-carboxylate (55 mg, 0.095 mmol, 40% yield) as a brown solid.

MS ESI m/z 578.2 (M+H)$^+$ 10 mg of the above material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 33% B, 33-73% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to obtain tert-butyl (3R,4S)-3-(5-(4-amino-5-((3,3-difluoroazetidin-1-yl)methyl)pyrrolo[2,1-f][1,2,4]triazin-7-yl)-3-fluoro-2-methylbenzamido)-4-fluoropyrrolidine-1-carboxylate (9.4 mg, 93% yield) as a white solid.

MS ESI m/z 578.2 (M+H)$^+$ $^1$H NMR (500 MHz, DMSO-d6) δ 8.84-8.68 (m, 1H), 8.13-8.04 (m, 1H), 7.98-7.89 (m, 1H), 7.87-7.72 (m, 1H), 7.19-7.03 (m, 1H), 5.36-5.15 (m, 1H), 4.71-4.43 (m, 1H), 4.06-3.96 (m, 2H), 3.78-3.13 (m, 8H), 2.31-2.23 (m, 3H), 1.49-1.39 (m, 9H).

Example 1562: 5-{4-amino-5-[(3,3-difluoroazetidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-3-fluoro-2-methylbenzamide

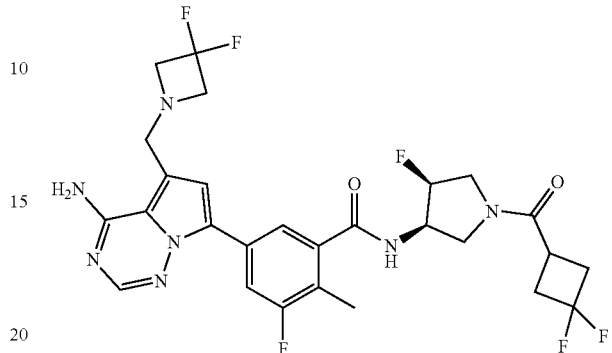

1562A. 5-(4-amino-5-((3,3-difluoroazetidin-1-yl)methyl)pyrrolo[2,1-f][1,2,4]triazin-7-yl)-3-fluoro-N-((3R,4S)-4-fluoropyrrolidin-3-yl)-2-methylbenzamide, 2 TFA salt A mixture of tert-butyl (3R,4S)-3-(5-(4-amino-5-((3,3-difluoroazetidin-1-yl)methyl)pyrrolo[2,1-f][1,2,4]triazin-7-yl)-3-fluoro-2-methylbenzamido)-4-fluoropyrrolidine-1-carboxylate (45 mg, 0.078 mmol) and TFA (0.1 ml, 1.298 mmol) in CH$_2$Cl$_2$ (2 mL) was stirred at rt for 1 h. It was concentrated to obtain 5-(4-amino-5-((3,3-difluoroazetidin-1-yl)methyl)pyrrolo[2,1-f][1,2,4]triazin-7-yl)-3-fluoro-N-((3R,4S)-4-fluoropyrrolidin-3-yl)-2-methylbenzamide, 2 TFA (45 mg, 0.064 mmol, 82% yield) as a brown solid.

MS ESI m/z 478.1 (M+H)$^+$.

1562: A mixture of 5-(4-amino-5-((3,3-difluoroazetidin-1-yl)methyl)pyrrolo[2,1-f][1,2,4]triazin-7-yl)-3-fluoro-N-((3R,4S)-4-fluoropyrrolidin-3-yl)-2-methylbenzamide, 2 TFA (15 mg, 0.021 mmol), 2,2-difluorocyclobutane-1-carboxylic acid (2.89 mg, 0.021 mmol), Hunig's base (0.013 mL, 0.076 mmol) and BOP (13.46 mg, 0.030 mmol) in DMF (0.5 mL) was stirred at rt for 2 h. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 20% B, 20-60% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to obtain 5-(4-amino-5-((3,3-difluoroazetidin-1-yl)methyl)pyrrolo[2,1-f][1,2,4]triazin-7-yl)-N-((3R,4S)-1-(3,3-difluorocyclobutane-1-carbonyl)-4-fluoropyrrolidin-3-yl)-3-fluoro-2-methylbenzamide (10.2 mg, 0.017 mmol, 81% yield) as a white solid.

MS ESI m/z 596.2 (M+H)$^+$ $^1$H NMR (500 MHz, DMSO-d6) δ 8.89-8.72 (m, 1H), 8.13-8.03 (m, 1H), 8.01-7.90 (m, 1H), 7.90-7.80 (m, 1H), 7.18-7.08 (m, 1H), 5.43-5.19 (m, 1H), 4.82-4.46 (m, 1H), 4.13-3.98 (m, 2H), 3.96-3.05 (m, 9H), 2.94-2.67 (m, 4H), 2.33-2.22 (m, 3H).

Example 1563: 5-{4-amino-5-[(3,3-difluoroazetidin-1-yl)methyl]pyrrolo[2,1-f][1,2,4]triazin-7-yl}-3-fluoro-N-[(3R,4S)-4-fluoro-1-[(2R)-3,3,3-trifluoro-2-hydroxy-2-methylpropanoyl]pyrrolidin-3-yl]-2-methylbenzamide

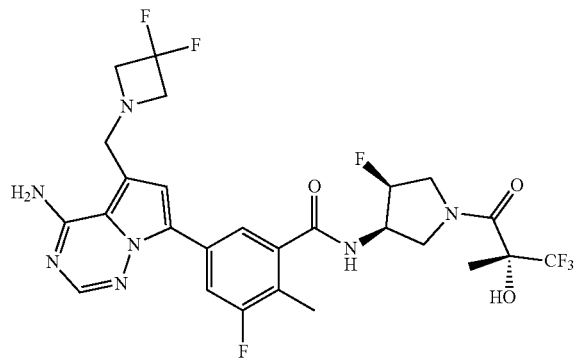 [SMILES: Cc1c(F)cc(-c2cc(CN3CC(F)(F)C3)c3c(N)ncnn23)cc1C(=O)N[C@@H]1CN(C(=O)[C@@](C)(O)C(F)(F)F)C[C@@H]1F]

This was prepared by the methods detailed in Example 1562.

MS ESI m/z 618.2 (M+H)$^+$ $^1$H NMR (500 MHz, DMSO-d6) δ 8.85-8.69 (m, 1H), 8.14-8.05 (m, 1H), 8.00-7.90 (m, 1H), 7.89-7.79 (m, 1H), 7.20-7.12 (m, 1H), 7.10-7.02 (m, 1H), 5.39-5.17 (m, 1H), 4.70-4.52 (m, 1H), 4.46-4.22 (m, 1H), 4.11-3.98 (m, 2H), 3.98-3.27 (m, 6H), 3.20-3.11 (m, 1H), 2.33-2.24 (m, 3H), 1.60-1.48 (m, 3H).

Example 1564: 5-{4-amino-5-[(3,3-difluoroazetidin-1-yl)methyl]pyrrolo[2,1-f][1,2,4]triazin-7-yl}-N-[(3R,4S)-1-(2,2-difluorocyclopropanecarbonyl)-4-fluoropyrrolidin-3-yl]-3-fluoro-2-methylbenzamide

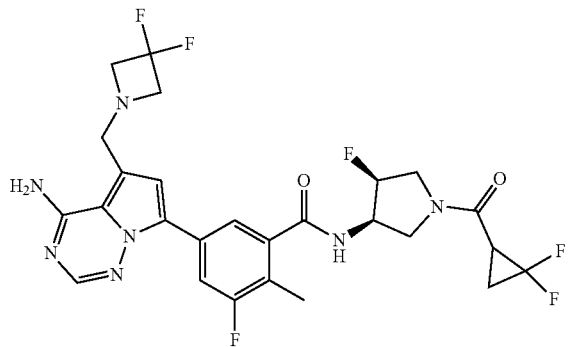 [SMILES: Cc1c(F)cc(-c2cc(CN3CC(F)(F)C3)c3c(N)ncnn23)cc1C(=O)N[C@@H]1CN(C(=O)C2CC2(F)F)C[C@@H]1F]

This was prepared by the methods detailed in Example 1562.

MS ESI m/z 582.2 (M+H)$^+$ $^1$H NMR (500 MHz, DMSO-d6) δ 8.95-8.72 (m, 1H), 8.14-8.03 (m, 1H), 8.00-7.91 (m, 1H), 7.90-7.80 (m, 1H), 7.24-7.08 (m, 1H), 5.49-5.17 (m, 1H), 4.88-4.51 (m, 1H), 4.36-4.07 (m, 1H), 4.07-3.97 (m, 2H), 3.97-3.24 (m, 7H), 3.14-2.85 (m, 1H), 2.33-2.23 (m, 3H), 2.05-1.76 (m, 2H).

Example 1565: 5-{4-amino-5-[(1Z)-1-(methoxyimino)ethyl]pyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide

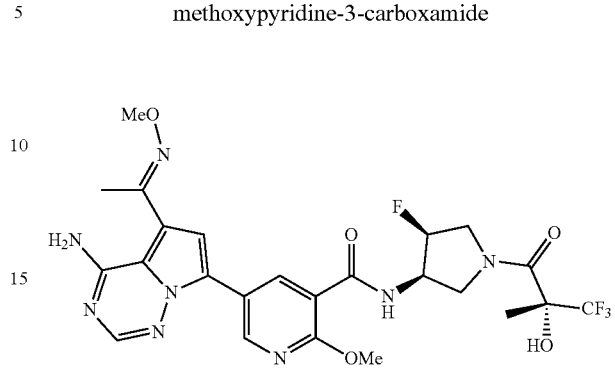

A mixture of 5-(5-acetyl-4-aminopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (15 mg, 0.027 mmol) and O-methylhydroxylamine (6.38 mg, 0.136 mmol) in MeOH (0.32 mL) was stirred at rt for 16 h. It was then concentrated. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 21% B, 21-61% B over 25 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. to isolate 5-(4-amino-5-((Z)-1-(methoxyimino)ethyl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (7 mg, 0.012 mmol, 44% yield) as a white solid.

MS ESI m/z 583.2 (M+H)$^+$ $^1$H NMR (500 MHz, DMSO-d6) δ 9.63-9.48 (m, 1H), 9.03-8.91 (m, 1H), 8.82-8.66 (m, 1H), 8.58-8.44 (m, 1H), 8.18-8.06 (m, 1H), 8.04-7.92 (m, 1H), 7.62-7.48 (m, 1H), 5.40-5.11 (m, 1H), 4.80-4.57 (m, 1H), 4.55-4.20 (m, 1H), 4.10-4.00 (m, 3H), 3.99-3.92 (m, 3H), 3.92-3.12 (m, 3H), 2.42-2.31 (m, 3H), 1.62-1.48 (m, 3H).

Example 1566: 5-{4-amino-5-cyclopropylpyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide

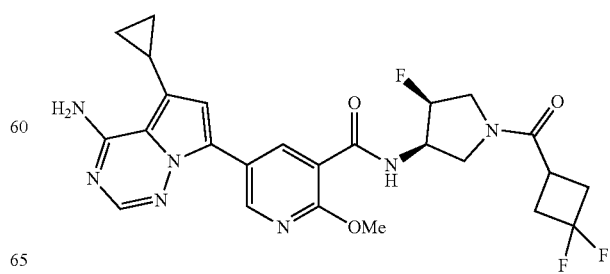

1566A. 5-(4-amino-5-bromopyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide: A mixture of 5-(4-aminopyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide (50 mg, 0.102 mmol) and NBS (21.82 mg, 0.123 mmol) in DCM (2 mL) was stirred at rt for 2 h. It was then diluted with water and the aqueous layer was extracted with EtOAc. The organic layer was washed with NaHCO$_3$ and water, dried over MgSO$_4$, filtered, concentrated and purified with silica gel chromatography, eluting with 100% EtOAc to 10% MeOH/EtOAc to isolate 5-(4-amino-5-bromopyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide (20 mg, 0.035 mmol, 34% yield) as the desired product.

MS ESI m/z 570.0 (M+H)$^+$.

1566: A mixture of cyclopropylboronic acid (18.14 mg, 0.211 mmol), 5-(4-amino-5-bromopyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide (20 mg, 0.035 mmol) and potassium phosphate tribasic (0.070 mL, 0.141 mmol) in dioxane (2 mL) was degassed and back-filled with N$_2$. To that mixture was added 1,1'-bis(diphenylphosphino)ferrocene-palladium(II)dichloride dichloromethane complex (5.75 mg, 7.04 µmol), and the reaction was degassed and back-filled with N$_2$. It was heated at 100° C. for 16 h. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 24% B, 24-64% B over 20 minutes, then a 5-minute hold at 100% B; Flow Rate: 20 mL/min; Column Temperature: 25 C. Fraction collection was triggered by MS signals. Fractions containing the desired product were combined and dried via centrifugal evaporation to isolate 5-(4-amino-5-cyclopropylpyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide (2.2 mg, 3.63 µmol, 10% yield) as a white solid.

MS ESI m/z 530.1 (M+H)$^+$ $^1$H NMR (500 MHz, DMSO-d6) δ 8.98-8.89 (m, 1H), 8.84-8.67 (m, 1H), 8.53-8.41 (m, 1H), 7.92-7.79 (m, 1H), 6.93-6.73 (m, 1H), 5.54-5.14 (m, 1H), 4.93-4.52 (m, 1H), 4.08-3.99 (m, 3H), 3.99-2.97 (m, 5H), 2.90-2.71 (m, 4H), 2.34-2.21 (m, 1H), 1.03-0.92 (m, 2H), 0.78-0.63 (m, 2H).

Example 1567: 5-{4-amino-5-cyclopropylpyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide

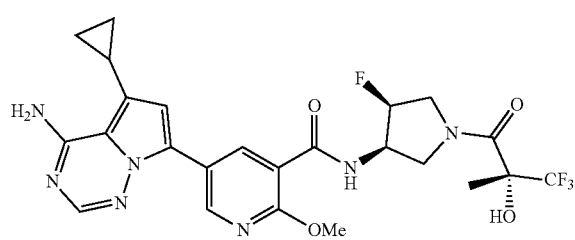 [SMILES: COc1ncc(-c2cc(C3CC3)c3c(N)ncnn23)cc1C(=O)N[C@@H]1CN(C(=O)[C@@](C)(O)C(F)(F)F)C[C@@H]1F]

1567A. 5-(4-amino-5-bromopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide: A mixture of 5-(4-aminopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (230 mg, 0.450 mmol) and NBS (96 mg, 0.540 mmol) in tetrahydrofuran (10 mL) was stirred at rt for 2 h. It was then diluted with water and extracted with EtOAc. The organic layer was washed with NaHCO$_3$, water and dried over MgSO$_4$. After filtering, the filtrate was concentrated and purified with silica gel chromatography, eluting with 100% EtOAc to 10% MeOH/EtOAc to isolate 5-(4-amino-5-bromopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (200 mg, 0.339 mmol, 75% yield) as the desired product.

MS ESI m/z 591.9 (M+H)$^+$.

1567A mixture of tricyclohexylphosphine (1.188 mg, 4.23 µmol), cyclopropylboronic acid (18.19 mg, 0.212 mmol) and 5-(4-amino-5-bromopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (25 mg, 0.042 mmol) in dioxane (2 mL) was degassed and back-filled with N$_2$. Pd(OAc)$_2$ (0.475 mg, 2.117 µmol) was added, and the reaction was degassed and back-filled with N$_2$. It was heated at 100° C. for 16 h. The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 11% B, 11-51% B over 20 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation to isolate 5-(4-amino-5-cyclopropylpyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (13.4 mg, 0.023 mmol, 54% yield) as a white solid.

MS ESI m/z 552.1 (M+H)$^+$ $^1$H NMR (500 MHz, DMSO-d6) δ 8.95-8.89 (m, 1H), 8.80-8.68 (m, 1H), 8.58-8.45 (m, 1H), 7.97-7.89 (m, 1H), 6.96-6.89 (m, 1H), 5.38-5.17 (m, 1H), 4.78-4.58 (m, 1H), 4.46 (br s, 1H), 4.09-3.98 (m, 3H), 3.98-3.28 (m, 3H), 2.32-2.17 (m, 1H), 1.57-1.45 (m, 3H), 1.03-0.95 (m, 2H), 0.81-0.63 (m, 2H).

Example 1568: 5-[4-amino-5-(5-cyanopyridin-3-yl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methoxypyridine-3-carboxamide

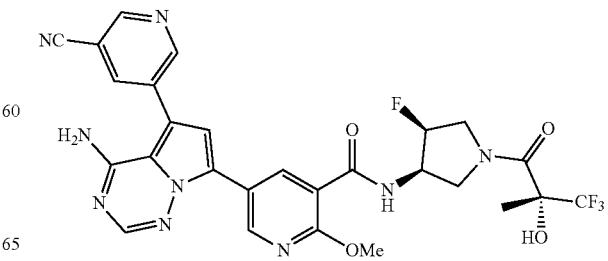

A mixture of (5-cyanopyridin-3-yl)boronic acid (6.26 mg, 0.042 mmol), 5-(4-amino-5-bromopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (25 mg, 0.042 mmol) and Na$_2$CO$_3$ (0.064 mL, 0.127 mmol) in dioxane (2 mL) was degassed and back-filled with N$_2$. Tetrakis(triphenylphosphine)palladium(0) (4.89 mg, 4.23 µmol) was added, and the reaction was degassed and back-filled with N$_2$. It was heated at 100° C. for 16 h. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 15% B, 15-55% B over 25 minutes, then a 7-minute hold at 100% B; Flow Rate: 20 mL/min; Column Temperature: 25 C. Fraction collection was triggered by UV signals. Fractions containing the desired product were combined and dried via centrifugal evaporation to isolate 5-(4-amino-5-(5-cyanopyridin-3-yl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (5.1 mg, 8.19 µmol, 19% yield) as a white solid.

MS ESI m/z 614.1 (M+H)$^+$ $^1$H NMR (500 MHz, DMSO-d6) δ 9.05-8.93 (m, 3H), 8.90-8.80 (m, 1H), 8.63-8.48 (m, 1H), 8.44-8.37 (m, 1H), 8.18-8.08 (m, 1H), 7.51-7.40 (m, 1H), 7.13-7.01 (m, 1H), 5.43-5.14 (m, 1H), 4.83-4.55 (m, 1H), 4.55-4.23 (m, 1H), 4.13-4.02 (m, 3H), 4.02-3.11 (m, 3H), 1.61-1.50 (m, 3H).

Example 1569: 5-{4-amino-5-cyanopyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide

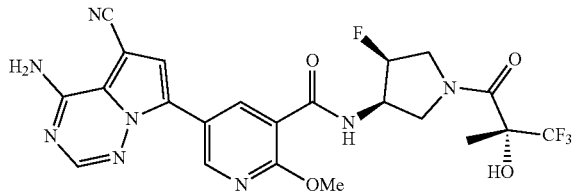 [SMILES: COc1ncc(-c2cc(C#N)c3c(N)ncnn23)cc1C(=O)N[C@@H]1CN(C(=O)[C@@](C)(O)C(F)(F)F)C[C@@H]1F]

1569A. 5-(4-amino-5-iodopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide: A mixture of 5-(4-aminopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (70 mg, 0.137 mmol) and NIS (30.8 mg, 0.137 mmol) in tetrahydrofuran (1 mL) was stirred at rt for 2 h. It was then diluted with water and extracted with EtOAc. The organic layer was washed with NaHCO$_3$, water and dried over MgSO$_4$. The filtrate was concentrated and purified with silica gel chromatography, eluting with 100% EtOAc to 10% MeOH/EtOAc to isolate 5-(4-amino-5-iodopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (75 mg, 0.118 mmol, 86% yield) as the desired product.

MS ESI m/z 638.0 (M+H)$^+$.

1569: A mixture of 5-(4-amino-5-iodopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (30 mg, 0.047 mmol) and dicyanozinc (11.05 mg, 0.094 mmol) in N,N-dimethylformamide (1 mL) was degassed well with vacuum and nitrogen (3×). To the mixture was added tris(dibenzylideneacetone)dipalladium (0) (4.31 mg, 4.71 µmol), [1,1'bis(diphenylphosphino)ferrocene]dichloropalladium(II) (6.89 mg, 9.41 µmol) and zinc (0.923 mg, 0.014 mmol). The yellow heterogeneous solution was degassed (3×), immersed in an oil bath at 150° C. and stirred for 5 h. The reaction mixture was concentrated. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 14% B, 14-54% B over 22 minutes, then a 6-minute hold at 100% B; Flow Rate: 20 mL/min; Column Temperature: 25 C. Fraction collection was triggered by MS and UV signals. Fractions containing the desired product were combined and dried via centrifugal evaporation to obtain 5-(4-amino-5-cyanopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (3.8 mg, 6.43 µmol, 14% yield) as a white solid.

MS ESI m/z 537.1 (M+H)$^+$ $^1$H NMR (500 MHz, DMSO-d6) δ 8.92-8.86 (m, 1H), 8.77-8.71 (m, 1H), 8.61-8.46 (m, 1H), 8.25-8.14 (m, 1H), 7.78-7.70 (m, 1H), 5.39-5.19 (m, 1H), 4.79-4.59 (m, 1H), 4.55-4.25 (m, 1H), 4.15-4.02 (m, 3H), 4.01-3.31 (m, 3H), 3.22-3.13 (m, 1H), 1.63-1.48 (m, 3H).

Example 1570: 5-(4-amino-5-((4,4-difluoropiperidin-1-yl)methyl)pyrrolo[2,1-f][1,2,4]triazin-7-yl)-4-fluoro-N-((3R,4S)-4-fluoro-1-((R)-3,3,3-trifluoro-2-hydroxy-2-methylpropanoyl)pyrrolidin-3-yl)-2-methoxybenzamide

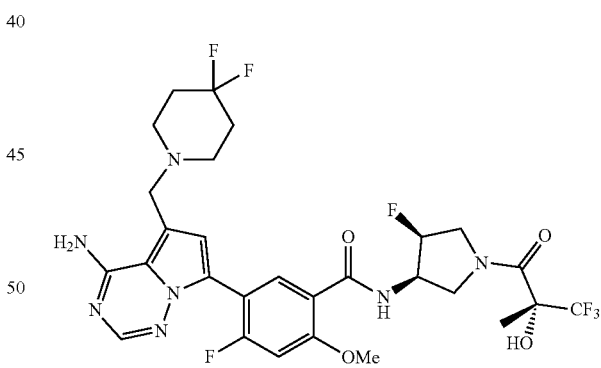

1570A. tert-butyl (3R,4S)-3-(5-bromo-4-fluoro-2-methoxybenzamido)-4-fluoropyrrolidine-1-carboxylate: A mixture of 5-bromo-4-fluoro-2-methoxybenzoic acid (1 g, 4.02 mmol), tert-butyl (3R,4S)-3-amino-4-fluoropyrrolidine-1-carboxylate (0.820 g, 4.02 mmol), Hünig's base (2.104 mL, 12.05 mmol) and BOP (2.131 g, 4.82 mmol) in DMF (10 mL) was stirred at rt for 2 h. Water was added and the resulting white precipitate was filtered and washed with water. The solid was dried to obtain tert-butyl (3R,4S)-3-(5-bromo-4-fluoro-2-methoxybenzamido)-4-fluoropyrrolidine-1-carboxylate (1 g, 2.297 mmol, 57% yield) as a white solid.

MS ESI m/z 459.7 (M+H)$^+$

¹H NMR (400 MHz, DMSO-d6) δ 8.44-8.24 (m, 1H), 8.10-7.82 (m, 1H), 7.43-7.28 (m, 1H), 5.36-5.09 (m, 1H), 4.78-4.43 (m, 1H), 4.03-3.87 (m, 3H), 3.79-3.07 (m, 4H), 1.51-1.35 (m, 9H).

1570B. tert-butyl (3R,4R)-3-fluoro-4-(4-fluoro-2-methoxy-5-(4,4,5,5-tetramethyl-1,3,2-dioxaborolan-2-yl)benzamido)pyrrolidine-1-carboxylate: A mixture of tert-butyl (3R,4S)-3-(5-bromo-4-fluoro-2-methoxybenzamido)-4-fluoropyrrolidine-1-carboxylate (800 mg, 1.838 mmol), potassium acetate (541 mg, 5.51 mmol) and 4,4,4',4',5,5,5',5'-octamethyl-2,2'-bi(1,3,2-dioxaborolane) (607 mg, 2.389 mmol) in dioxane (20 mL) was degassed and back-filled with N₂. PdCl₂(dppf)-dichloromethane adduct (150 mg, 0.184 mmol) was added, and the mixture was degassed and back-filled with N₂. The reaction was heated at 100° C. for 16 h. It was then cooled to rt and diluted with EtOAc. The organic layer was washed with water, dried over MgSO₄ and concentrated. The residue was purified by silica gel chromatography, eluting with 0-50% EtOAc/hexanes to obtain tert-butyl (3S,4R)-3-fluoro-4-(4-fluoro-2-methoxy-5-(4,4,5,5-tetramethyl-1,3,2-dioxaborolan-2-yl)benzamido)pyrrolidine-1-carboxylate (600 mg, 1.244 mmol, 68% yield) as an off-white solid.

MS ESI m/z 446.0 (M+H)⁺.

1570C. tert-butyl (3R,4S)-3-(5-(4-amino-5-((4,4-difluoropiperidin-1-yl)methyl)pyrrolo[2,1-f][1,2,4]triazin-7-yl)-4-fluoro-2-methoxybenzamido)-4-fluoropyrrolidine-1-carboxylate: A mixture of tert-butyl (3R,4R)-3-fluoro-4-(4-fluoro-2-methoxy-5-(4,4,5,5-tetramethyl-1,3,2-dioxaborolan-2-yl)benzamido)pyrrolidine-1-carboxylate (200 mg, 0.352 mmol), 7-bromo-5-((4,4-difluoropiperidin-1-yl)methyl)pyrrolo[2,1-f][1,2,4]triazin-4-amine (122 mg, 0.352 mmol) and potassium phosphate tribasic (0.529 mL, 1.057 mmol) in dioxane (10 mL) was degassed and back-filled with N₂. PdCl₂(dppf)-dichloromethane adduct (28.8 mg, 0.035 mmol) was added and the mixture was degassed and back-filled with N₂. The reaction was heated at 100° C. for 16 h. It was then diluted with EtOAc. The organic layer was washed with water, dried over MgSO₄ and concentrated. The residue was purified by silica gel chromatography, eluting with 0-100% EtOAc/hexanes to obtain tert-butyl (3R,4S)-3-(5-(4-amino-5-((4,4-difluoropiperidin-1-yl)methyl)pyrrolo[2,1-f][1,2,4]triazin-7-yl)-4-fluoro-2-methoxybenzamido)-4-fluoropyrrolidine-1-carboxylate (150 mg, 0.241 mmol, 69% yield) as an off-white solid.

MS ESI m/z 622.3 (M+H)⁺.

1570D. 5-(4-amino-5-((4,4-difluoropiperidin-1-yl)methyl)pyrrolo[2,1-f][1,2,4]triazin-7-yl)-4-fluoro-N-((3R,4S)-4-fluoropyrrolidin-3-yl)-2-methoxybenzamide, 2 TFA: A mixture of tert-butyl (3R,4S)-3-(5-(4-amino-5-((4,4-difluoropiperidin-1-yl)methyl)pyrrolo[2,1-f][1,2,4]triazin-7-yl)-4-fluoro-2-methoxybenzamido)-4-fluoropyrrolidine-1-carboxylate (150 mg, 0.241 mmol) in TFA (2 mL) was stirred at rt for 1 h. It was then concentrated to obtain 5-(4-amino-5-((4,4-difluoropiperidin-1-yl)methyl)pyrrolo[2,1-f][1,2,4]triazin-7-yl)-4-fluoro-N-((3R,4S)-4-fluoropyrrolidin-3-yl)-2-methoxybenzamide, 2 TFA (150 mg, 0.200 mmol, 83% yield) as a brown solid.

MS ESI m/z 555.1 (M+H)⁺.

1570: A mixture of 5-(4-amino-5-((4,4-difluoropiperidin-1-yl)methyl)pyrrolo[2,1-f][1,2,4]triazin-7-yl)-4-fluoro-N-((3R,4S)-4-fluoropyrrolidin-3-yl)-2-methoxybenzamide, 2 TFA (23 mg, 0.031 mmol), (R)-3,3,3-trifluoro-2-hydroxy-2-methylpropanoic acid (4.85 mg, 0.031 mmol), BOP (13.57 mg, 0.031 mmol) and Hünig's base (0.021 mL, 0.123 mmol) in DMF (1 mL) was stirred at rt for 2 h. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 25% B, 25-65% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to isolate 5-(4-amino-5-((4,4-difluoropiperidin-1-yl)methyl)pyrrolo[2,1-f][1,2,4]triazin-7-yl)-4-fluoro-N-((3R,4S)-4-fluoro-1-((R)-3,3,3-trifluoro-2-hydroxy-2-methylpropanoyl)pyrrolidin-3-yl)-2-methoxybenzamide (8.8 mg, 0.013 mmol, 43% yield) as a white solid.

MS ESI m/z 662.1 (M+H)⁺

¹H NMR (500 MHz, DMSO-d6) δ 9.43-9.05 (m, 1H), 8.51-8.22 (m, 2H), 7.88-7.77 (m, 1H), 7.73-7.35 (m, 1H), 7.32-7.18 (m, 1H), 6.84-6.76 (m, 1H), 5.36-5.16 (m, 1H), 4.81-4.54 (m, 1H), 4.54-4.24 (m, 1H), 4.15-3.50 (m, 9H), 2.73-2.56 (m, 4H), 2.14-1.94 (m, 4H), 1.61-1.44 (m, 3H).

Example 1571: 5-{4-amino-5-[(4,4-difluoropiperidin-1-yl)methyl]pyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methylbenzamide

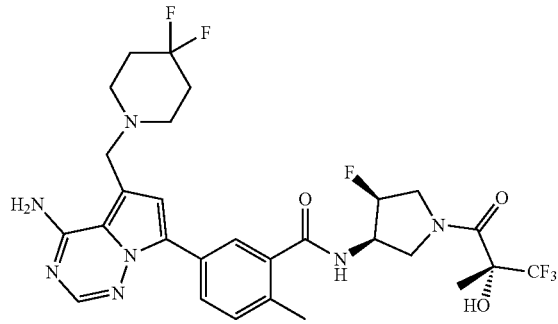 [SMILES: Cc1ccc(-c2cc(CN3CCC(F)(F)CC3)c3c(N)ncnn23)cc1C(=O)N[C@@H]1CN(C(=O)[C@@](C)(O)C(F)(F)F)C[C@@H]1F]

1571A. tert-butyl (3R,4S)-3-(5-bromo-2-methylbenzamido)-4-fluoropyrrolidine-1-carboxylate: A mixture of tert-butyl (3R,4S)-3-amino-4-fluoropyrrolidine-1-carboxylate (1 g, 4.90 mmol), 5-bromo-2-methylbenzoic acid (1.053 g, 4.90 mmol), Hünig's base (2.57 mL, 14.69 mmol) and BOP (2.60 g, 5.88 mmol) in DMF (10 mL) was stirred at rt for 2 h. Water was added to the reaction mixture. The resulting precipitate was filtered and washed with water. It was dried to obtain tert-butyl (3R,4S)-3-(5-bromo-2-methylbenzamido)-4-fluoropyrrolidine-1-carboxylate (1.8 g, 4.49 mmol, 92% yield) as a white solid.

MS ESI m/z 424.8 (M+Na).

1571B. tert-butyl (3R,4R)-3-fluoro-4-(2-methyl-5-(4,4,5,5-tetramethyl-1,3,2-dioxaborolan-2-yl)benzamido)pyrrolidine-1-carboxylate: A mixture of tert-butyl (3R,4S)-3-(5-bromo-2-methylbenzamido)-4-fluoropyrrolidine-1-carboxylate (0.5 g, 1.246 mmol), potassium acetate (0.367 g, 3.74 mmol) and 4,4,4',4',5,5,5',5'-octamethyl-2,2'-bi(1,3,2-dioxaborolane) (0.411 g, 1.620 mmol) in dioxane (10 mL) was degassed and back-filled with N₂. PdCl₂(dppf)-dichloromethane adduct (0.102 g, 0.125 mmol) was added, and the reaction mixture was degassed and back-filled with N₂. The reaction was heated at 100° C. for 16 h. It was then diluted with EtOAc and washed with water. The organic layer was dried over MgSO₄ and concentrated. The residue was purified by silica gel chromatography, eluting with 0-50% EtOAc/hexanes to obtain tert-butyl (3R,4R)-3-fluoro-4-(2-methyl-5-(4,4,5,5-tetramethyl-1,3,2-dioxaborolan-2-yl)benzamido)pyrrolidine-1-carboxylate (500 mg, 1.115 mmol, 90% yield) as an off-white solid.

MS ESI m/z 471.1 (M+H)⁺.

1571C. tert-Butyl (3R,4S)-3-(5-(4-amino-5-((4,4-difluoropiperidin-1-yl)methyl)pyrrolo[2,1-f][1,2,4]triazin-7-yl)-2-methylbenzamido)-4-fluoropyrrolidine-1-carboxylate: A mixture of tert-butyl (3R,4R)-3-fluoro-4-(2-methyl-5-(4,4,5,5-tetramethyl-1,3,2-dioxaborolan-2-yl)benzamido)pyrrolidine-1-carboxylate (200 mg, 0.446 mmol), 7-bromo-5-((4,4-difluoropiperidin-1-yl)methyl)pyrrolo[2,1-f][1,2,4]triazin-4-amine (154 mg, 0.446 mmol) and potassium phosphate tribasic (0.669 mL, 1.338 mmol) in dioxane (10 mL) was degassed and back-filled with N₂. PdCl₂(dppf)-dichloromethane adduct (36.4 mg, 0.045 mmol) was added, and the reaction mixture was degassed and back-filled with N₂. The reaction mixture was heated at 100° C. for 16 h. It was then diluted with EtOAc. The organic layer was washed with water, dried over MgSO₄ and concentrated. The residue was purified by silica gel chromatography, eluting with 0-100% EtOAc/hexanes to obtain tert-butyl (3R,4S)-3-(5-(4-amino-5-((4,4-difluoropiperidin-1-yl)methyl)pyrrolo[2,1-f][1,2,4]triazin-7-yl)-2-methylbenzamido)-4-fluoropyrrolidine-1-carboxylate (140 mg, 0.238 mmol, 53% yield) as an off-white solid.

MS ESI m/z 588.3 (M+H)⁺.

1571D. 5-(4-amino-5-((4,4-difluoropiperidin-1-yl)methyl)pyrrolo[2,1-f][1,2,4]triazin-7-yl)-N-((3R,4S)-4-fluoropyrrolidin-3-yl)-2-methylbenzamide, 2 TFA: A mixture of tert-butyl (3R,4S)-3-(5-(4-amino-5-((4,4-difluoropiperidin-1-yl)methyl)pyrrolo[2,1-f][1,2,4]triazin-7-yl)-2-methylbenzamido)-4-fluoropyrrolidine-1-carboxylate (140 mg, 0.238 mmol) in TFA (1 mL) was stirred at rt for 2 h. It was then concentrated to obtain 5-(4-amino-5-((4,4-difluoropiperidin-1-yl)methyl)pyrrolo[2,1-f][1,2,4]triazin-7-yl)-N-((3R,4S)-4-fluoropyrrolidin-3-yl)-2-methylbenzamide, 2 TFA (150 mg, 0.210 mmol, 88% yield) as a brown oil.

MS ESI m/z 488.1 (M+H)⁺.

1571: A mixture of 5-(4-amino-5-((4,4-difluoropiperidin-1-yl)methyl)pyrrolo[2,1-f][1,2,4]triazin-7-yl)-N-((3R,4S)-4-fluoropyrrolidin-3-yl)-2-methylbenzamide, 2 TFA (20 mg, 0.028 mmol), (R)-3,3,3-trifluoro-2-hydroxy-2-methylpropanoic acid (4.42 mg, 0.028 mmol), BOP (14.83 mg, 0.034 mmol) and Hunig's base (0.020 mL, 0.112 mmol) in DMF (1 mL) was stirred at rt for 2 h. A few drops of ammonium hydroxide were added and stirring was continued at rt for 16 h. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 32% B, 32-72% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to obtain 5-(4-amino-5-((4,4-difluoropiperidin-1-yl)methyl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methylbenzamide (10.6 mg, 0.017 mmol, 59% yield).

MS ESI m/z 628.2 (M+H)⁺

¹H NMR (500 MHz, DMSO-d6) δ 9.47-8.99 (m, 1H), 8.84-8.52 (m, 1H), 8.16-8.04 (m, 1H), 8.02-7.94 (m, 1H), 7.94-7.84 (m, 1H), 7.76-7.42 (m, 1H), 7.43-7.25 (m, 1H), 7.14-6.82 (m, 2H), 5.45-5.09 (m, 1H), 4.74-4.45 (m, 1H), 4.46-4.18 (m, 1H), 4.10-3.15 (m, 5H), 2.70-2.58 (m, 4H), 2.44-2.26 (m, 3H), 2.15-1.93 (m, 4H), 1.65-1.41 (m, 3H).

Example 1572: 5-{4-amino-5-[(4,4-difluoropiperidin-1-yl)methyl]pyrrolo[2,1-f][1,2,4]triazin-7-yl}-N-[(3R,4S)-1-[(1S)-2,2-difluorocyclopropanecarbonyl]-4-fluoropyrrolidin-3-yl]-2-methylbenzamide

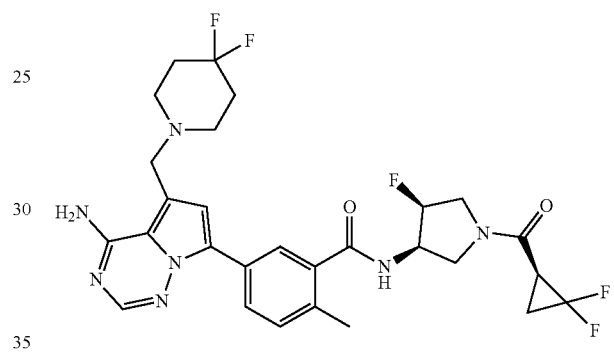

5-(4-amino-5-((4,4-difluoropiperidin-1-yl)methyl)pyrrolo[2,1-f][1,2,4]triazin-7-yl)-N-((3R,4S)-1-(2,2-difluorocyclopropane-1-carbonyl)-4-fluoropyrrolidin-3-yl)-2-methylbenzamide (9 mg, 0.015 mmol) was separated by a Waters 100 preparative SFC with the following conditions: Column: Chiral IC, 250 mm×21 mm, 5-µm particles; Mobile Phase 60% CO₂, 40% IPA-ACN, 50-50 with 0.1% DEA; Flow Rate: 60 mL/min. Fraction collection was triggered by MS and UV signals. First eluent peaks were combined and dried to obtain 5-{4-amino-5-[(4,4-difluoropiperidin-1-yl)methyl]pyrrolo[2,1-f][1,2,4]triazin-7-yl}-N-[(3R,4S)-1-[(1S)-2,2-difluorocyclopropanecarbonyl]-4-fluoropyrrolidin-3-yl]-2-methylbenzamide (2.7 mg, 29% yield) as a white solid.

MS ESI m/z 592.2 (M+H)⁺

¹H NMR (500 MHz, DMSO-d6) δ 9.47-9.04 (m, 1H), 8.81-8.51 (m, 1H), 8.09-8.00 (m, 1H), 8.00-7.92 (m, 1H), 7.92-7.73 (m, 1H), 7.70-7.39 (m, 1H), 7.39-7.26 (m, 1H), 7.09-6.87 (m, 1H), 5.52-5.08 (m, 1H), 4.92-4.50 (m, 1H), 4.35-4.06 (m, 1H), 4.02-3.56 (m, 6H), 3.13-2.98 (m, 1H), 2.74-2.58 (m, 4H), 2.45-2.31 (m, 3H), 2.11-1.72 (m, 6H).

Example 1573: 5-(4-amino-5-((4,4-difluoropiperidin-1-yl)methyl)pyrrolo[2,1-f][1,2,4]triazin-7-yl)-N-((3R,4S)-1-((R)-2,2-difluorocyclopropane-1-carbonyl)-4-fluoropyrrolidin-3-yl)-2-methylbenzamide

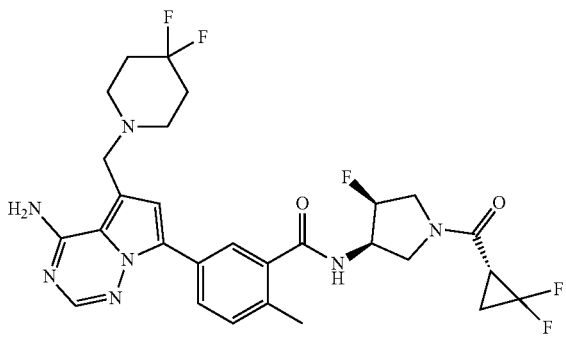 [SMILES: Cc1ccc(-c2cc(CN3CCC(F)(F)CC3)c3c(N)ncnn23)cc1C(=O)N[C@@H]1CN(C(=O)[C@H]2CC2(F)F)C[C@@H]1F]

5-(4-amino-5-((4,4-difluoropiperidin-1-yl)methyl)pyrrolo[2,1-f][1,2,4]triazin-7-yl)-N-((3R,4S)-1-(2,2-difluorocyclopropane-1-carbonyl)-4-fluoropyrrolidin-3-yl)-2-methylbenzamide (9 mg, 0.015 mmol) was separated by a Waters 100 preparative SFC with the following conditions: Column: Chiral IC, 250 mm×21 mm, 5-μm particles; Mobile Phase 60% CO$_2$, 40% IPA-ACN, 50-50 with 0.1% DEA; Flow Rate: 60 mL/min. Fraction collection was triggered by MS and UV signals. Second eluent peaks were combined and dried to obtain 5-(4-amino-5-((4,4-difluoropiperidin-1-yl)methyl)pyrrolo[2,1-f][1,2,4]triazin-7-yl)-N-((3R,4S)-1-((R)-2,2-difluorocyclopropane-1-carbonyl)-4-fluoropyrrolidin-3-yl)-2-methylbenzamide (3 mg, 33% yield) as a white solid.

MS ESI m/z 592.2 (M+H)$^+$ $^1$H NMR (500 MHz, DMSO-d6) δ 9.47-9.04 (m, 1H), 8.81-8.51 (m, 1H), 8.09-8.00 (m, 1H), 8.00-7.92 (m, 1H), 7.92-7.73 (m, 1H), 7.70-7.39 (m, 1H), 7.39-7.26 (m, 1H), 7.09-6.87 (m, 1H), 5.52-5.08 (m, 1H), 4.92-4.50 (m, 1H), 4.35-4.06 (m, 1H), 4.02-3.56 (m, 6H), 3.13-2.98 (m, 1H), 2.74-2.58 (m, 4H), 2.45-2.31 (m, 3H), 2.11-1.72 (m, 6H).

Example 1574: 2,2,2-trifluoroethyl (3R,4S)-3-[5-(4-amino-5-{[4-(trifluoromethyl)piperidin-1-yl]methyl}pyrrolo[2,1-f][1,2,4]triazin-7-yl)-2-methylbenzamido]-4-fluoropyrrolidine-1-carboxylate

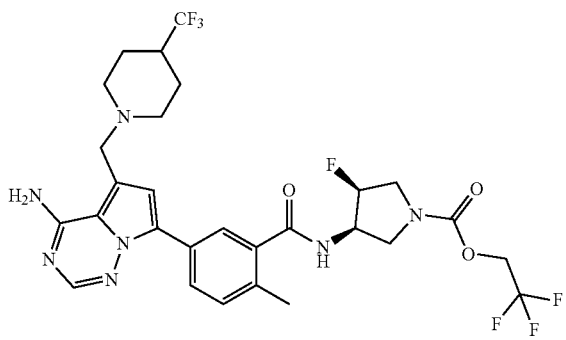 [SMILES: Cc1ccc(-c2cc(CN3CCC(C(F)(F)F)CC3)c3c(N)ncnn23)cc1C(=O)N[C@@H]1CN(C(=O)OCC(F)(F)F)C[C@@H]1F]

1574A. 5-bromo-N-((3R,4S)-4-fluoropyrrolidin-3-yl)-2-methylbenzamide, TFA salt: A mixture of tert-butyl (3R,4S)-3-(5-bromo-2-methylbenzamido)-4-fluoropyrrolidine-1-carboxylate (300 mg, 0.748 mmol) and TFA (288 μl, 3.74 mmol) was stirred at rt for 2 h. It was then concentrated to obtain 5-bromo-N-((3R,4S)-4-fluoropyrrolidin-3-yl)-2-methylbenzamide, TFA salt (300 mg, 0.723 mmol, 97% yield) as a brown solid.

MS ESI m/z 300.8 (M+H)$^+$.

1574B. 2,2,2-trifluoroethyl (3R,4S)-3-(5-bromo-2-methylbenzamido)-4-fluoropyrrolidine-1-carboxylate: A mixture of 5-bromo-N-((3R,4S)-4-fluoropyrrolidin-3-yl)-2-methylbenzamide TFA (300 mg, 0.723 mmol), 2,2,2-trifluoroethyl carbonochloridate (141 mg, 0.867 mmol) and Hunig's base (0.252 mL, 1.445 mmol) in DMF (5 mL) was stirred at rt for 24 h. It was then diluted with water. The resulting precipitate was filtered and washed with water. It was then dried to obtain a solid which was purified by silica gel chromatography, eluting with 0-100% EtOAc/hexanes to obtain 2,2,2-trifluoroethyl (3R,4S)-3-(5-bromo-2-methylbenzamido)-4-fluoropyrrolidine-1-carboxylate (250 mg, 0.585 mmol, 81% yield) as an off-white solid.

MS ESI m/z 428.8 (M+H)$^+$.

1574C. 2,2,2-trifluoroethyl (3R,4R)-3-fluoro-4-(2-methyl-5-(4,4,5,5-tetramethyl-1,3,2-dioxaborolan-2-yl)benzamido)pyrrolidine-1-carboxylate: A mixture of 2,2,2-trifluoroethyl (3R,4S)-3-(5-bromo-2-methylbenzamido)-4-fluoropyrrolidine-1-carboxylate (100 mg, 0.234 mmol), potassium acetate (68.9 mg, 0.702 mmol) and 4,4,4',4',5,5,5',5'-octamethyl-2,2'-bi(1,3,2-dioxaborolane) (77 mg, 0.304 mmol) in dioxane (2 mL) was degassed and back-filled with N$_2$. PdCl$_2$(dppf)-dichloromethane adduct (19.12 mg, 0.023 mmol) was added, and the reaction mixture was degassed and back-filled with N$_2$. It was heated at 100° C. for 16 h. The mixture was diluted with EtOAc and washed with water. The organic layer was dried and concentrated. The residue was purified by silica gel chromatography, eluting with 0-100% EtOAc/hexanes to obtain 2,2,2-trifluoroethyl (3R,4R)-3-fluoro-4-(2-methyl-5-(4,4,5,5-tetramethyl-1,3,2-dioxaborolan-2-yl)benzamido)pyrrolidine-1-carboxylate (80 mg, 0.169 mmol, 72% yield) as an off-white solid.

MS ESI m/z 475.1 (M+H)$^+$.

1574: A mixture of 2,2,2-trifluoroethyl (3R,4R)-3-fluoro-4-(2-methyl-5-(4,4,5,5-tetramethyl-1,3,2-dioxaborolan-2-yl)benzamido)pyrrolidine-1-carboxylate (25 mg, 0.053 mmol), 7-bromo-5-((4-(trifluoromethyl)piperidin-1-yl)methyl)pyrrolo[2,1-f][1,2,4]triazin-4-amine (19.94 mg, 0.053 mmol) and potassium phosphate tribasic (0.079 mL, 0.158 mmol) in dioxane (2 mL) was degassed and back-filled with N$_2$. PdCl$_2$(dppf)-dichloromethane adduct (4.30 mg, 5.27 μmol) was added and the reaction mixture degassed and back-filled with N$_2$. It was heated at 100° C. for 16 h. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 34% B, 34-74% B over 20 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation to obtain 2,2,2-trifluoroethyl (3R,4S)-3-(5-(4-amino-5-((4-(trifluoromethyl)piperidin-1-yl)methyl)pyrrolo[2,1-f][1,2,4]triazin-7-yl)-2-methylbenzamido)-4-fluoropyrrolidine-1-carboxylate (9.2 mg, 0.013 mmol, 25% yield) as an off-white solid.

MS ESI m/z 646.2 (M+H)$^+$ $^1$H NMR (500 MHz, DMSO-d6) δ 9.58-9.18 (m, 1H), 8.70-8.60 (m, 1H), 8.12-8.04 (m, 1H), 8.01-7.92 (m, 1H), 7.92-7.81 (m, 1H), 7.78-7.46 (m, 1H), 7.40-7.27 (m, 1H), 7.04-6.91 (m, 1H), 5.48-5.17 (m, 1H), 4.83-4.50 (m, 4H), 4.01-3.58 (m, 6H), 3.16-2.94 (m, 2H), 2.46-2.33 (m, 4H), 2.19-2.02 (m, 2H), 1.96-1.80 (m, 2H), 1.54-1.37 (m, 2H).

Example 1575: 2,2,2-trifluoroethyl (3R,4S)-3-(5-{4-amino-5-[(4,4-difluoropiperidin-1-yl)methyl]pyrrolo[2,1-f][1,2,4]triazin-7-yl}-2-methylbenzamido)-4-fluoropyrrolidine-1-carboxylate

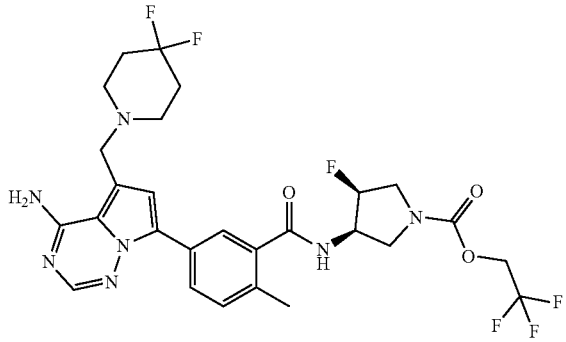 [SMILES: Cc1ccc(-c2cc(CN3CCC(F)(F)CC3)c3c(N)ncnn23)cc1C(=O)N[C@@H]1CN(C(=O)OCC(F)(F)F)C[C@@H]1F]

This was prepared by the methods detailed in Example 1574.

MS ESI m/z 614.2 (M+H)⁺

¹H NMR (500 MHz, DMSO-d6) δ 8.79-8.60 (m, 1H), 8.17-8.05 (m, 1H), 8.05-7.89 (m, 2H), 7.42-7.34 (m, 1H), 7.28-7.16 (m, 1H), 5.42-5.14 (m, 1H), 4.86-4.50 (m, 3H), 4.07-3.24 (m, 3H), 2.44-2.35 (m, 3H), 2.32-1.94 (m, 4H).

Example 1576: 2,2,2-trifluoroethyl (3R,4S)-3-(5-(4-amino-5-((1,1-dioxidothiomorpholino)methyl)pyrrolo[2,1-f][1,2,4]triazin-7-yl)-2-methylbenzamido)-4-fluoropyrrolidine-1-carboxylate

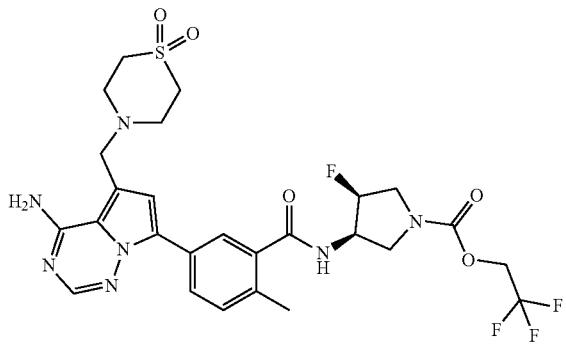 [SMILES: Cc1ccc(-c2cc(CN3CCS(=O)(=O)CC3)c3c(N)ncnn23)cc1C(=O)N[C@@H]1CN(C(=O)OCC(F)(F)F)C[C@@H]1F]

This was prepared by the methods detailed in Example 1574.

MS ESI m/z 628.1 (M+H)⁺

¹H NMR (500 MHz, DMSO-d6) δ 8.78-8.58 (m, 1H), 8.20-7.86 (m, 3H), 7.44-7.33 (m, 1H), 7.16-7.11 (m, 1H), 5.50-5.18 (m, 1H), 4.90-4.57 (m, 3H), 4.10-3.93 (m, 2H), 3.88-3.55 (m, 3H), 3.48-3.33 (m, 1H), 3.28-3.18 (m, 4H), 3.13-3.00 (m, 4H), 2.42-2.32 (m, 3H).

Example 1577: 2,2,2-trifluoroethyl (3R,4S)-3-(5-{4-amino-5-[(morpholin-4-yl)methyl]pyrrolo[2,1-f][1,2,4]triazin-7-yl}-2-methylbenzamido)-4-fluoropyrrolidine-1-carboxylate

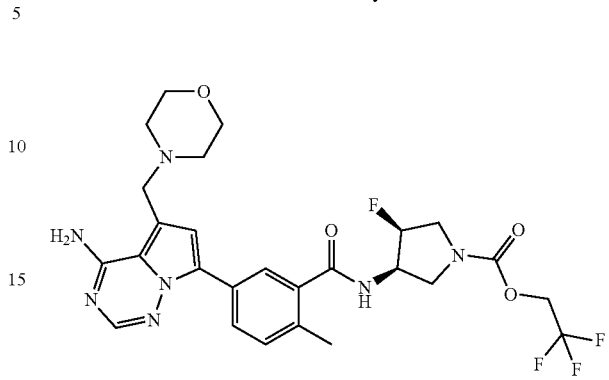

This was prepared by the methods detailed in Example 1574.

MS ESI m/z 580.2 (M+H)⁺

¹H NMR (500 MHz, DMSO-d6) δ 8.78-8.56 (m, 1H), 8.12-7.98 (m, 2H), 7.98-7.85 (m, 1H), 7.43-7.34 (m, 1H), 7.22-7.16 (m, 1H), 5.45-5.14 (m, 1H), 4.96-4.55 (m, 3H), 4.11-3.55 (m, 6H), 3.54-3.24 (m, 4H), 2.44-2.33 (m, 3H), 1.13-0.99 (m, 4H).

Example 1578: 5-{4-amino-5-[(4,4-difluoropiperidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-4-fluoro-2-methylbenzamide

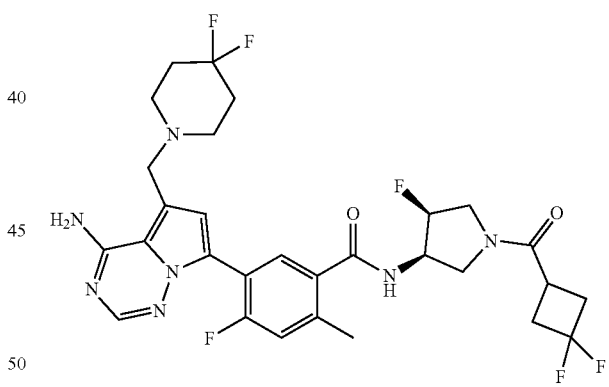

1578A. Methyl 5-(4-amino-5-((4,4-difluoropiperidin-1-yl)methyl)pyrrolo[2,1-f][1,2,4]triazin-7-yl)-4-fluoro-2-methylbenzoate: A mixture of methyl 4-fluoro-2-methyl-5-(4,4,5,5-tetramethyl-1,3,2-dioxaborolan-2-yl)benzoate (127 mg, 0.433 mmol), 7-bromo-5-((4,4-difluoropiperidin-1-yl)methyl)pyrrolo[2,1-f][1,2,4]triazin-4-amine (150 mg, 0.433 mmol) and potassium phosphate tribasic (0.650 mL, 1.300 mmol) in dioxane (4 mL) was degassed and back-filled with N₂. 1,1'-Bis(diphenylphosphino)ferrocene-palladium(II)dichloride dichloromethane complex (35.4 mg, 0.043 mmol) was added and the reaction was degassed and back-filled with N₂. It was heated at 100° C. for 16 h, then cooled to rt and diluted with EtOAc. The organic layer was washed with water, dried over MgSO₄, filtered and concentrated. The residue was purified by silica gel chromatography, eluting with 0-100% EtOAc/hexanes to obtain methyl 5-(4-amino-5-((4,4-difluoropiperidin-1-yl)methyl)pyrrolo[2,1-f][1,2,4]triazin-7-yl)-4-fluoro-2-methylbenzoate (130 mg, 0.300 mmol, 69% yield) as an off-white solid.

MS ESI m/z 434.1 (M+H)⁺.

1578B. 5-(4-amino-5-((4,4-difluoropiperidin-1-yl)methyl)pyrrolo[2,1-f][1,2,4]triazin-7-yl)-4-fluoro-2-methylbenzoic acid: A mixture of methyl 5-(4-amino-5-((4,4-difluoropiperidin-1-yl)methyl)pyrrolo[2,1-f][1,2,4]triazin-7-yl)-4-fluoro-2-methylbenzoate (130 mg, 0.300 mmol) and NaOH (1.500 mL, 1.500 mmol) in MeOH (5 mL) was heated at reflux for 3 h. The reaction mixture was cooled to rt and adjusted to pH 5 using 1 N HCl. The resulting white precipitate was filtered and washed with water. It was then dried to obtain 5-(4-amino-5-((4,4-difluoropiperidin-1-yl)methyl)pyrrolo[2,1-f][1,2,4]triazin-7-yl)-4-fluoro-2-methylbenzoic acid (118 mg, 0.281 mmol, 94% yield) as a white solid.

MS ESI m/z 420.0 (M+H)⁺.

1578C. tert-butyl (3R,4S)-3-(5-(4-amino-5-((4,4-difluoropiperidin-1-yl)methyl)pyrrolo[2,1-f][1,2,4]triazin-7-yl)-4-fluoro-2-methylbenzamido)-4-fluoropyrrolidine-1-carboxylate: A mixture of 5-(4-amino-5-((4,4-difluoropiperidin-1-yl)methyl)pyrrolo[2,1-f][1,2,4]triazin-7-yl)-4-fluoro-2-methylbenzoic acid (118 mg, 0.281 mmol), tert-butyl (3R,4S)-3-amino-4-fluoropyrrolidine-1-carboxylate (57.4 mg, 0.281 mmol), Hunig's base (0.147 mL, 0.844 mmol) and BOP (149 mg, 0.338 mmol) in DMF (10 mL) was stirred at rt for 2 h. Water was added to the reaction mixture. The resulting precipitate was filtered and washed with water. It was then dried to obtain tert-butyl (3R,4S)-3-(5-(4-amino-5-((4,4-difluoropiperidin-1-yl)methyl)pyrrolo[2,1-f][1,2,4]triazin-7-yl)-4-fluoro-2-methylbenzamido)-4-fluoropyrrolidine-1-carboxylate (150 mg, 0.248 mmol, 88% yield) as a white solid.

MS ESI m/z 606.4 (M+H)⁺.

1578D. 5-(4-amino-5-((4,4-difluoropiperidin-1-yl)methyl)pyrrolo[2,1-f][1,2,4]triazin-7-yl)-4-fluoro-N-((3R,4S)-4-fluoropyrrolidin-3-yl)-2-methylbenzamide 2 TFA: A mixture of tert-butyl (3R,4S)-3-(5-(4-amino-5-((4,4-difluoropiperidin-1-yl)methyl)pyrrolo[2,1-f][1,2,4]triazin-7-yl)-4-fluoro-2-methylbenzamido)-4-fluoropyrrolidine-1-carboxylate (150 mg, 0.248 mmol) in TFA (1 mL, 12.98 mmol) was stirred at rt for 1 h. It was then concentrated to obtain 5-(4-amino-5-((4,4-difluoropiperidin-1-yl)methyl)pyrrolo[2,1-f][1,2,4]triazin-7-yl)-4-fluoro-N-((3R,4S)-4-fluoropyrrolidin-3-yl)-2-methylbenzamide, 2 TFA (180 mg, 0.245 mmol, 99% yield) as a brown solid.

MS ESI m/z 506.3 (M+H)⁺.

1578: A mixture of 5-(4-amino-5-((4,4-difluoropiperidin-1-yl)methyl)pyrrolo[2,1-f][1,2,4]triazin-7-yl)-4-fluoro-N-((3R,4S)-4-fluoropyrrolidin-3-yl)-2-methylbenzamide 2 TFA salt (20 mg, 0.027 mmol), 3,3-difluorocyclobutane-1-carboxylic acid (3.71 mg, 0.027 mmol), BOP (14.47 mg, 0.033 mmol) and Hunig's base (0.019 mL, 0.109 mmol) in DMF (1 mL) was stirred at rt for 2 h. A few drops of ammonium hydroxide were added and stirring continued at rt for 16 h. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 25% B, 25-65% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to obtain 5-(4-amino-5-((4,4-difluoropiperidin-1-yl)methyl)pyrrolo[2,1-f][1,2,4]triazin-7-yl)-N-((3R,4S)-1-(3,3-difluorocyclobutane-1-carbonyl)-4-fluoropyrrolidin-3-yl)-4-fluoro-2-methylbenzamide (9.6 mg, 0.015 mmol, 54% yield) as a white solid.

MS ESI m/z 624.2 (M+H)⁺

1H NMR (500 MHz, DMSO-d6) δ 9.41-9.00 (m, 1H), 8.73-8.56 (m, 1H), 7.93-7.80 (m, 2H), 7.74-7.38 (m, 1H), 7.34-7.17 (m, 1H), 6.90-6.76 (m, 1H), 5.45-5.15 (m, 1H), 4.80-4.43 (m, 1H), 4.10-3.48 (m, 7H), 3.23-3.06 (m, 1H), 2.90-2.70 (m, 4H), 2.70-2.59 (m, 3H), 2.45-2.37 (m, 3H), 2.13-1.96 (m, 4H).

Example 1579: 5-[4-amino-5-(trifluoromethyl)pyrrolo[2,1-f][1,2,4]triazin-7-yl]-N-[1-(2,2-difluorocyclopropanecarbonyl)-4-fluoropiperidin-3-yl]-2-methoxypyridine-3-carboxamide

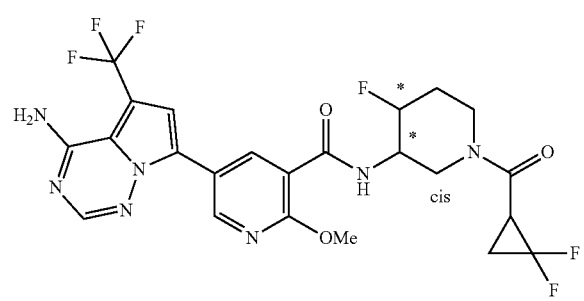 [SMILES: COc1ncc(-c2cc(C(F)(F)F)c3c(N)ncnn23)cc1C(=O)NC1CN(C(=O)C2CC2(F)F)CCC1F]

1579A. tert-butyl 3-(5-(4-amino-5-(trifluoromethyl)pyrrolo[2,1-f][1,2,4]triazin-7-yl)-2-methoxynicotinamido)-4-fluoropiperidine-1-carboxylate: A mixture of tert-butyl 3-amino-4-fluoropiperidine-1-carboxylate (61.8 mg, 0.283 mmol), 5-(4-amino-5-(trifluoromethyl)pyrrolo[2,1-f][1,2,4]triazin-7-yl)-2-methoxynicotinic acid (100 mg, 0.283 mmol), Hunig's base (0.148 mL, 0.849 mmol) and BOP (150 mg, 0.340 mmol) in DMF (2 mL) was stirred at rt for 2 h. Water was added to the reaction mixture. The white precipitate was filtered and washed with water. It was then dried to obtain tert-butyl 3-(5-(4-amino-5-(trifluoromethyl)pyrrolo[2,1-f][1,2,4]triazin-7-yl)-2-methoxynicotinamido)-4-fluoropiperidine-1-carboxylate (140 mg, 0.253 mmol, 89% yield) as a white solid.

MS ESI m/z 559.3 (M+2Na).

1579B. 5-(4-amino-5-(trifluoromethyl)pyrrolo[2,1-f][1,2,4]triazin-7-yl)-N-(4-fluoropiperidin-3-yl)-2-methoxynicotinamide, 2 TFA: A mixture of tert-butyl 3-(5-(4-amino-5-(trifluoromethyl)pyrrolo[2,1-f][1,2,4]triazin-7-yl)-2-methoxynicotinamido)-4-fluoropiperidine-1-carboxylate (140 mg, 0.253 mmol), TFA (0.5 mL, 6.49 mmol) was stirred at rt for 1 h. It was then concentrated to obtain 5-(4-amino-5-(trifluoromethyl)pyrrolo[2,1-f][1,2,4]triazin-7-yl)-N-(4-fluoropiperidin-3-yl)-2-methoxynicotinamide, 2 TFA salt (140 mg, 0.205 mmol, 81% yield) as a brown solid. MS ESI m/z 454.2 (M+H)⁺.

1579: A mixture of 5-(4-amino-5-(trifluoromethyl)pyrrolo[2,1-f][1,2,4]triazin-7-yl)-N-(4-fluoropiperidin-3-yl)-2-methoxynicotinamide, 2 TFA (20 mg, 0.029 mmol), 2,2-difluorocyclopropane-1-carboxylic acid (3.58 mg, 0.029 mmol), BOP (15.58 mg, 0.035 mmol) and Hunig's base (0.021 mL, 0.117 mmol) in DMF (1 mL) was stirred at rt for 2 h. A few drops of ammonium hydroxide were added and stirred at rt for 16 h. The crude material was purified via preparative LC/MS with the following conditions: Column:

XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 23% B, 23-63% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to obtain 5-(4-amino-5-(trifluoromethyl)pyrrolo[2,1-f][1,2,4]triazin-7-yl)-N-(1-(2, 2-difluorocyclopropane-1-carbonyl)-4-fluoropiperidin-3-yl)-2-methoxynicotinamide (7.9 mg, 0.013 mmol, 46% yield). The product was isolated as a mixture of diastereomers.

MS ESI m/z 558.1 (M+H)+

LC/MS retention time using Method 2=1.78 min

Example 1580: 5-[4-amino-5-(trifluoromethyl)pyrrolo[2,1-f][1,2,4]triazin-7-yl]-N-[(3R,4R)-4-fluoro-1-[(2R)-3,3,3-trifluoro-2-hydroxy-2-methylpropanoyl]piperidin-3-yl]-2-methoxypyridine-3-carboxamide

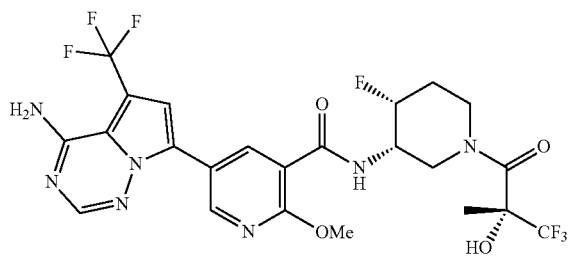 [SMILES: COc1ncc(-c2cc(C(F)(F)F)c3c(N)ncnn23)cc1C(=O)N[C@H]1CN(C(=O)[C@@](C)(O)C(F)(F)F)CC[C@H]1F]

A mixture of 5-(4-amino-5-(trifluoromethyl)pyrrolo[2,1-f][1,2,4]triazin-7-yl)-N-(4-fluoropiperidin-3-yl)-2-methoxynicotinamide, 2 TFA (20 mg, 0.029 mmol), (R)-3, 3,3-trifluoro-2-hydroxy-2-methylpropanoic acid (4.64 mg, 0.029 mmol), BOP (15.58 mg, 0.035 mmol) and Hunig's base (0.021 mL, 0.117 mmol) in DMF (1 mL) was stirred at rt for 2 h. A few drops of ammonium hydroxide were added and the mixture stirred at rt for 16 h. The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 23% B, 23-63% B over 25 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation to obtain 5-(4-amino-5-(trifluoromethyl)pyrrolo[2,1-f][1,2,4]triazin-7-yl)-N-((3R, 4R)-4-fluoro-1-((R)-3,3,3-trifluoro-2-hydroxy-2-methylpropanoyl)piperidin-3-yl)-2-methoxynicotinamide (2.5 mg, 4.15 μmol, 14% yield). The absolute stereochemistry of piperidine was assigned arbitrarily.

MS ESI m/z 594.1 (M+H)+

LC/MS retention time using Method 1=2.48 min

TABLE 56

| Intermediate | Name | R | Obs. MS Ion |
|---|---|---|---|
| 6 | 7-bromo-5-((3,3-difluoropyrrolidin-1-yl)methyl)pyrrolo[2,1-f][1,2,4]triazin-4-amine | | 333.8 |
| 7 | 7-Bromo-5-((3-fluoroazetidin-1-yl)methyl)pyrrolo[2,1-f][1,2,4]triazin-4-amine | | 299.8 |
| 8 | 5-(azetidin-1-ylmethyl)-7-bromopyrrolo[2,1-f][1,2,4]triazin-4-amine | | 281.7, 283.7 |
| 9 | 7-bromo-5-((3-(trifluoromethyl)azetidin-1-yl)methyl)pyrrolo[2,1-f][1,2,4]triazin-4-amine | | 351.7 |
| 10 | 7-Bromo-5-((3,3-difluoroazetidin-1-yl)methyl)pyrrolo[2,1-f][1,2,4]triazin-4-amine | | 319.8 |
| 11 | 5-((2-azaspiro[3.3]heptan-2-yl)methyl)-7-bromopyrrolo[2,1-f][1,2,4]triazin-4-amine | | 323.8, 325.1 |
| 12 | 7-bromo-5-(piperidin-1-ylmethyl)pyrrolo[2,1-f][1,2,4]triazin-4-amine | | 311.8 |
| 13 | 7-bromo-5-((3,3-dimethylazetidin-1-yl)methyl)pyrrolo[2,1-f][1,2,4]triazin-4-amine | | 309.9 |

TABLE 56-continued

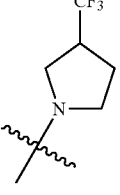

| Intermediate | Name | R | Obs. MS Ion |
|---|---|---|---|
| 14 | 7-bromo-5-((3-(trifluoromethyl)pyrrolidin-1-yl)methyl)pyrrolo[2,1-f][1,2,4]triazin-4-amine | 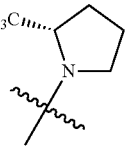 | 365.8 |
| 15 | (S)-7-bromo-5-((2-(trifluoromethyl)pyrrolidin-1-yl)methyl)pyrrolo[2,1-f][1,2,4]triazin-4-amine | 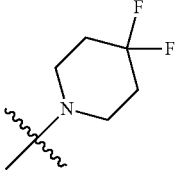 [SMILES: *N1CCC(F)(F)CC1] | 363.7 |
| 16 | 7-bromo-5-((4,4-difluoropiperidin-1-yl)methyl)pyrrolo[2,1-f][1,2,4]triazin-4-amine | 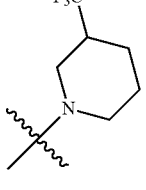 | 347.7 |
| 17 | 7-bromo-5-((3-(trifluoromethyl)piperidin-1-yl)methyl)pyrrolo[2,1-f][1,2,4]triazin-4-amine | 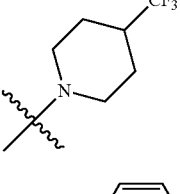 | 377.8 |
| 18 | 7-bromo-5-((4-(trifluoromethyl)piperidin-1-yl)methyl)pyrrolo[2,1-f][1,2,4]triazin-4-amine | 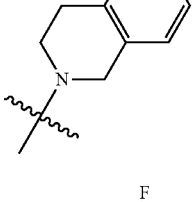 | 377.8, 379.8 |
| 19 | 7-bromo-5-((3,4-dihydroisoquinolin-2(1H)-yl)methyl)pyrrolo[2,1-f][1,2,4]triazin-4-amine | 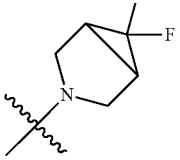 | 347.7 |
| 20 | 7-bromo-5-((6,6-difluoro-3-azabicyclo[3.1.0]hexan-3-yl)methyl)pyrrolo[2,1-f][1,2,4]triazin-4-amine | 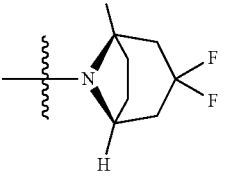 | 343.7, 345.7 |
| 21 | 7-bromo-5-(((1R,5S)-3,3-difluoro-8-azabicyclo[3.2.1]octan-8-yl)methyl)pyrrolo[2,1-f][1,2,4]triazin-4-amine | 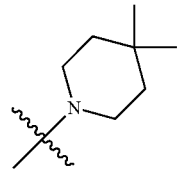 | 371.7, 373.7 |
| 22 | 7-bromo-5-((4,4-dimethylpiperidin-1-yl)methyl)pyrrolo[2,1-f][1,2,4]triazin-4-amine | 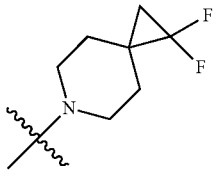 [SMILES: *N1CCC2(CC1)CC2(F)F] | 337.7, 339.7 |
| 23 | 7-bromo-5-((4,4-dimethylpiperidin-1-yl)methyl)pyrrolo[2,1-f][1,2,4]triazin-4-amine | 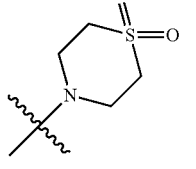 | 371.8, 373.8 |
| 24 | 4-((4-amino-7-bromopyrrolo[2,1-f][1,2,4]triazin-5-yl)methyl)thiomorpholine 1,1-dioxide | 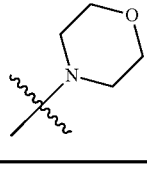 | 360.0, 362.0 |
| 25 | 7-bromo-5-(morpholinomethyl)pyrrolo[2,1-f][1,2,4]triazin-4-amine |  | 312.0, 314.0 |

Intermediates in Table 56 were prepared by the methods detailed in 7-bromo-5-(pyrrolidin-1-ylmethyl)pyrrolo[2,1-f][1,2,4]triazin-4-amine.

TABLE 57

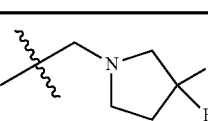

| Ex | Name | R¹ | R² | R³ | Obs. MS Ion |
|---|---|---|---|---|---|
| 1581 | 5-{4-amino-5-[(3,3-difluoropyrrolidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide | 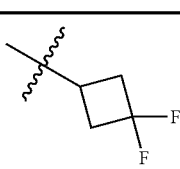 | H | 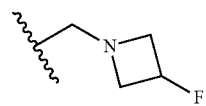 | 609.2 |
| 1582 | 5-{4-amino-5-[(3-fluoroazetidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide | 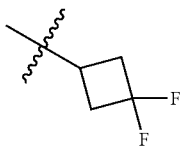 [SMILES: *C1CC(F)(F)C1] | H | 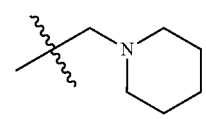 [SMILES: *CN1CCCCC1] | 577.2 |
| 1583 | 5-{4-amino-5-[(piperidin-1-yl)methyl]pyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 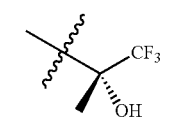 [SMILES: *[C@@](C)(O)C(F)(F)F] | H | 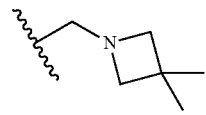 [SMILES: *CN1CC(C)(C)C1] | 609.2 |
| 1584 | 5-{4-amino-5-[(3,3-dimethylazetidin-1-yl)methyl]pyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 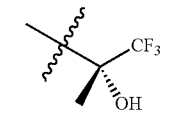 [SMILES: *[C@@](C)(O)C(F)(F)F] | H | 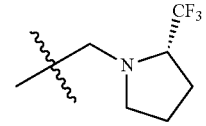 [SMILES: *CN1CCC[C@H]1C(F)(F)F] | 609.2 |
| 1585 | 5-(4-amino-5-{[(2S)-2-(trifluoromethyl)pyrrolidin-1-yl]methyl}pyrrolo[2,1-f][1,2,4]triazin-7-yl)-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 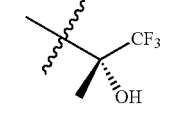 [SMILES: *[C@@](C)(O)C(F)(F)F] | H | 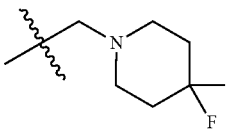 | 663.2 |
| 1586 | 5-{4-amino-5-[(4,4-difluoropiperidin-1-yl)methyl]pyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 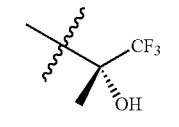 [SMILES: *[C@@](C)(O)C(F)(F)F] | H | 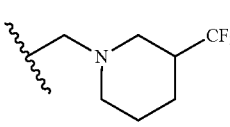 | 645.2 |
| 1587 | 5-(4-amino-5-{[3-(trifluoromethyl)piperidin-1-yl]methyl}pyrrolo[2,1-f][1,2,4]triazin-7-yl)-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 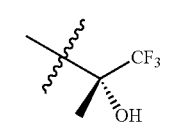 [SMILES: *[C@@](C)(O)C(F)(F)F] | H | 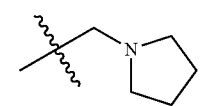 [SMILES: *CN1CCCC1] | 677.2 |
| 1588 | 5-{4-amino-5-[(pyrrolidin-1-yl)methyl]pyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 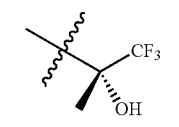 [SMILES: *[C@@](C)(O)C(F)(F)F] | H | 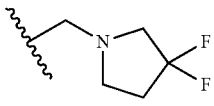 | 595.2 |
| 1589 | 5-{4-amino-5-[(3,3-difluoropyrrolidin-1-yl)methyl]pyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 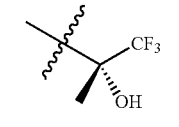 [SMILES: *[C@@](C)(O)C(F)(F)F] | H | | 631.2 |

TABLE 57-continued

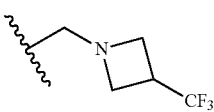

| Ex | Name | R¹ | R² | R³ | Obs. MS Ion |
|---|---|---|---|---|---|
| 1590 | 5-(4-amino-5-{[3-(trifluoromethyl)azetidin-1-yl]methyl}pyrrolo[2,1-f][1,2,4]triazin-7-yl)-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 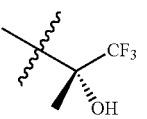 [SMILES: *[C@@](C)(O)C(F)(F)F] | H | 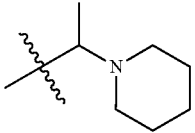 [SMILES: *C(C)N1CCCCC1] | 649.2 |
| 1591 | 5-{4-amino-5-[1-(piperidin-1-yl)ethyl]pyrrolo[2,1-f][1,2,4]triazin-7-yl}-N-[(3R,4S)-4-fluoro-1-[(2S)-3,3,3-trifluoro-2-hydroxy-2-methylpropanoyl]pyrrolidin-3-yl]-2-methoxypyridine-3-carboxamide | 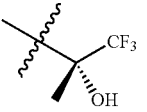 [SMILES: *[C@@](C)(O)C(F)(F)F] | H | 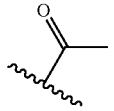 | 623.2 |
| 1592 | 5-{5-acetyl-4-aminopyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 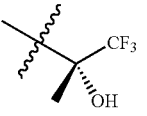 [SMILES: *[C@@](C)(O)C(F)(F)F] | H |  | 554.1. |
| 1593 | 5-{4-amino-5-methylpyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 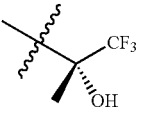 [SMILES: *[C@@](C)(O)C(F)(F)F] | H |  | 526.1 |
| 1594 | 5-{4-amino-5-chloropyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 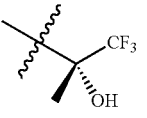 [SMILES: *[C@@](C)(O)C(F)(F)F] | H | 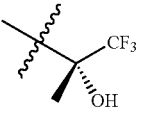 [SMILES: *[C@@](C)(O)C(F)(F)F] | 546.1 |
| 1595 | 5-{4-aminopyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | H | H | 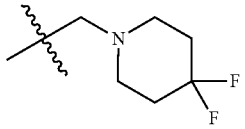 [SMILES: *CN1CCC(F)(F)CC1] | 512.2 |
| 1596 | 5-{4-amino-5-[(4,4-difluoropiperidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide | 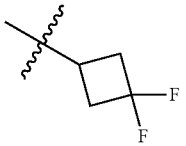 [SMILES: *C1CC(F)(F)C1] | H | 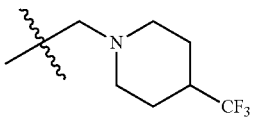 [SMILES: *CN1CCC(C(F)(F)F)CC1] | 623.2 |
| 1597 | 5-(4-amino-5-{[4-(trifluoromethyl)piperidin-1-yl]methyl}pyrrolo[2,1-f][1,2,4]triazin-7-yl)-N-[(3R,4S)-1-(3,3-difluorocyclobutanecarbonyl)-4-fluoropyrrolidin-3-yl]-2-methoxypyridine-3-carboxamide | 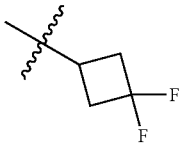 [SMILES: *C1CC(F)(F)C1] | H | 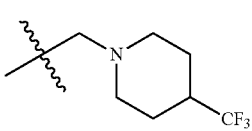 | 655.2 |
| 1598 | 5-(4-amino-5-{[4-(trifluoromethyl)piperidin-1-yl]methyl}pyrrolo[2,1-f][1,2,4]triazin-7-yl)-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 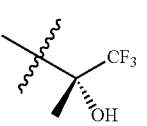 [SMILES: *[C@@](C)(O)C(F)(F)F] | H |  | 677.2 |

TABLE 57-continued

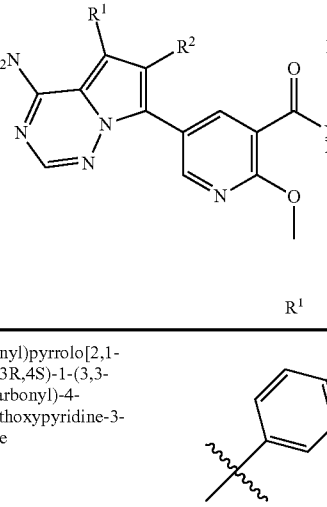

| Ex | Name | R¹ | R² | R³ | Obs. MS Ion |
|---|---|---|---|---|---|
| 1599 | 5-[4-amino-5-(4-aminophenyl)pyrrolo[2,1-f][1,2,4]triazin-7-yl]-N-[(3R,4S)-1-(3,3-difluorocyclobutanecarbonyl)-4-fluoropyrrolidin-3-yl]-2-methoxypyridine-3-carboxamide | 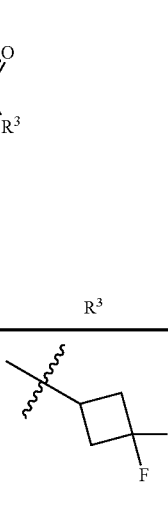 | H | 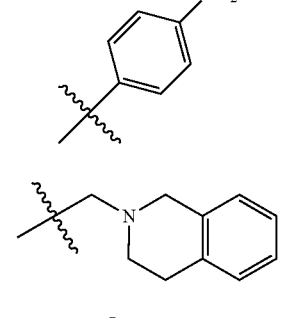 | 581.2 |
| 1600 | 5-{4-amino-5-[(1,2,3,4-tetrahydroisoquinolin-2-yl)methyl]pyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 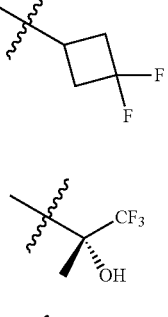 | H | 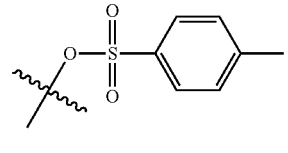 [SMILES: *OS(=O)(=O)c1ccc(C)cc1] | 657.2 |
| 1601 | 4-amino-7-(5-{[(3R,4S)-1-(3,3-difluorocyclobutanecarbonyl)-4-fluoropyrrolidin-3-yl]carbamoyl}-6-methoxypyridin-3-yl)pyrrolo[2,1-f][1,2,4]triazin-5-yl 4-methylbenzene-1-sulfonate | 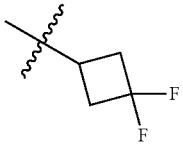 [SMILES: *C1CC(F)(F)C1] | H | 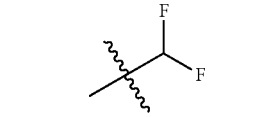 [SMILES: *C(F)F] | 660.1 |
| 1602 | 5-[4-amino-5-(difluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 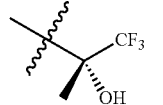 [SMILES: *[C@@](C)(O)C(F)(F)F] | H | 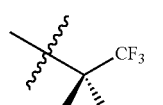 | 562.1 |
| 1603 | 5-{4-amino-6-fluoropyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | H | F | 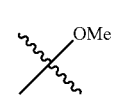 | 530.1 |
| 1604 | 5-{4-amino-5-methoxypyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 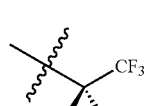 | H | 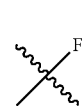 | 542.1 |
| 1605 | 5-{4-amino-5-fluoropyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 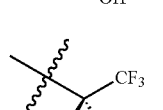 | H | 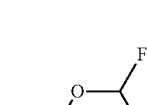 | 530.0 |
| 1606 | 5-[4-amino-5-(difluoromethoxy)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 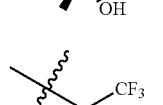 | H | 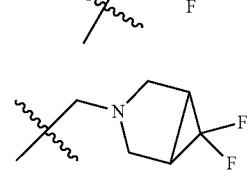 | 578.1 |
| 1607 | 5-[4-amino-5-({6,6-difluoro-3-azabicyclo[3.1.0]hexan-3-yl}methyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 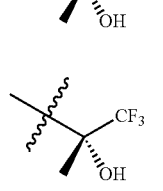 | H | 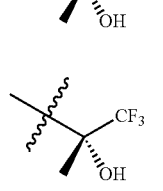 | 643.1 |

TABLE 57-continued

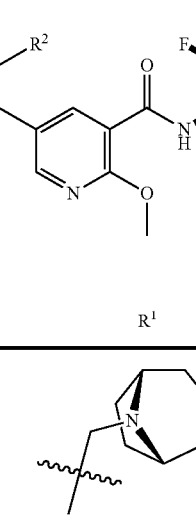

| Ex | Name | R¹ | R² | R³ | Obs. MS Ion |
|---|---|---|---|---|---|
| 1608 | 5-(4-amino-5-{[(1R,5S)-3,3-difluoro-8-azabicyclo[3.2.1]octan-8-yl]methyl}pyrrolo[2,1-f][1,2,4]triazin-7-yl)-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 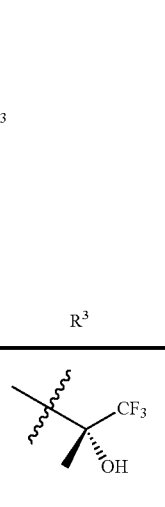 | H | 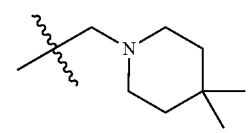 [SMILES: *CN1CCC(C)(C)CC1] | 671.2 |
| 1609 | 5-{4-amino-5-[(4,4-dimethylpiperidin-1-yl)methyl]pyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 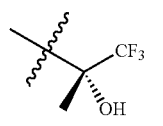 [SMILES: *[C@@](C)(O)C(F)(F)F] | H | 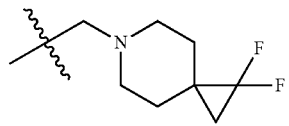 [SMILES: *CN1CCC2(CC1)CC2(F)F] | 637.2 |
| 1610 | 5-[4-amino-5-({1,1-difluoro-6-azaspiro[2.5]octan-6-yl}methyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 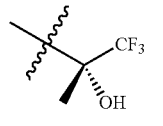 | H | 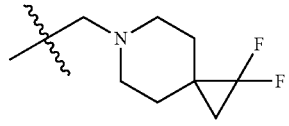 [SMILES: *CN1CCC2(CC1)CC2(F)F] | 671.2 LC/MS RT 2.18 min (Method 1) |
| 1611 | 5-[4-amino-5-({1,1-difluoro-6-azaspiro[2.5]octan-6-yl}methyl)pyrrolo[2,1-f][1,2,4]triazin-7-yl]-N-[(3R,4S)-1-(3,3-difluorocyclobutanecarbonyl)-4-fluoropyrrolidin-3-yl]-2-methoxypyridine-3-carboxamide | 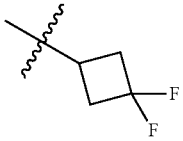 [SMILES: *C1CC(F)(F)C1] | H | 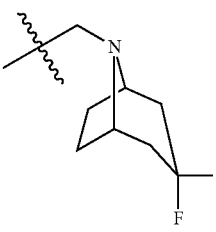 | 649.2 |
| 1612 | 5-(4-amino-5-{[(1R,5S)-3,3-difluoro-8-azabicyclo[3.2.1]octan-8-yl]methyl}pyrrolo[2,1-f][1,2,4]triazin-7-yl)-N-[(3R,4S)-1-(3,3-difluorocyclobutanecarbonyl)-4-fluoropyrrolidin-3-yl]-2-methoxypyridine-3-carboxamide | 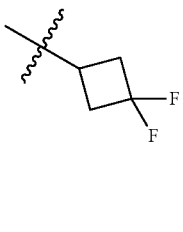 [SMILES: *C1CC(F)(F)C1] | H | 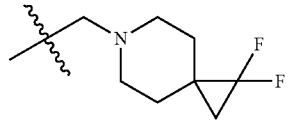 [SMILES: *CN1CCC2(CC1)CC2(F)F] | 649.2 |
| 1613 | 2,2,2-trifluoroethyl (3R,4S)-3-{5-[4-amino-5-({1,1-difluoro-6-azaspiro[2.5]octan-6-yl}methyl)pyrrolo[2,1-f][1,2,4]triazin-7-yl]-2-methoxypyridine-3-amido}-4-fluoropyrrolidine-1-carboxylate | 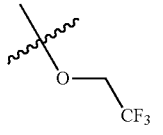 | H | 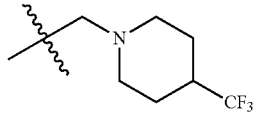 | 657.2 |
| 1614 | 2,2,2-trifluoroethyl (3R,4S)-3-[5-(4-amino-5-{[4-(trifluoromethyl)piperidin-1-yl]methyl}pyrrolo[2,1-f][1,2,4]triazin-7-yl)-2-methoxypyridine-3-amido]-4-fluoropyrrolidine-1-carboxylate | 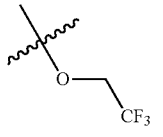 | H | 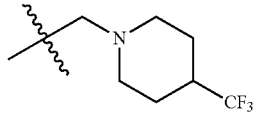 | 663.1 |

Compounds in Table 57 were prepared by the methods detailed in Examples 1549, 1550, 1551, 1562, and 1563. When diastereomers were separated, they are included as separate entries. If the stereochemistry is undefined, the product was isolated as a mixture of diastereomers.

TABLE 58

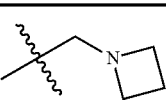

| Ex | Name | R¹ | R² | Obs. MS Ion |
|---|---|---|---|---|
| 1615 | 5-{4-amino-5-[(azetidin-1-yl)methyl]pyrrolo[2,1-f][1,2,4]triazin-7-yl}-N-[(3R,4S)-4-fluoro-1-(2-fluorobenzoyl)pyrrolidin-3-yl]-2-methoxypyridine-3-carboxamide | 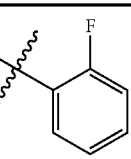 | 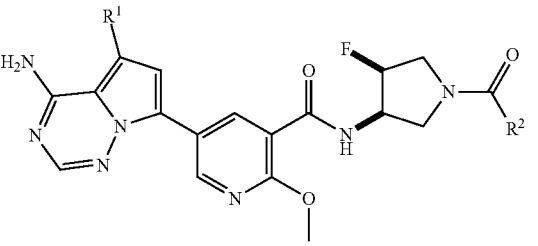 | 563.2 |
| 1616 | 5-{4-amino-5-[(3,3-difluoroazetidin-1-yl)methyl]pyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide | 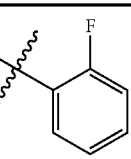 | 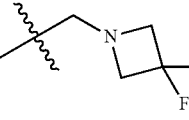 | 617.2 |
| 1617 | 5-{4-amino-5-[(3,3-difluoroazetidin-1-yl)methyl]pyrrolo[2,1-f][1,2,4]triazin-7-yl}-N-[(3R,4S)-1-(2,2-difluorocyclopropanecarbonyl)-4-fluoropyrrolidin-3-yl]-2-methoxypyridine-3-carboxamide | 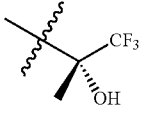 | 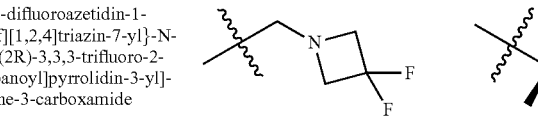 | 581.2 |
| 1618 | 5-{4-amino-5-[(3,3-difluoroazetidin-1-yl)methyl]pyrrolo[2,1-f][1,2,4]triazin-7-yl}-N-[(3R,4S)-4-fluoro-1-(3,3,3-trifluoro-2,2-dimethylpropanoyl)pyrrolidin-3-yl]-2-methoxypyridine-3-carboxamide | 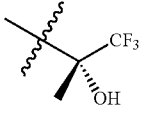 | 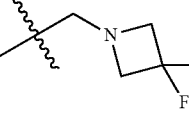 | 615.2 |
| 1619 | 5-{4-amino-5-[(3,3-difluoroazetidin-1-yl)methyl]pyrrolo[2,1-f][1,2,4]triazin-7-yl}-N-[(3R,4S)-1-(2,2-dimethylpropanoyl)-4-fluoropyrrolidin-3-yl]-2-methoxypyridine-3-carboxamide | 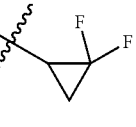 | 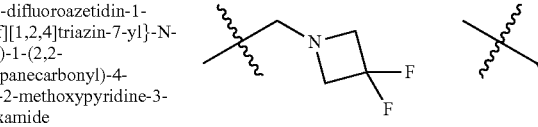 | 561.2 |
| 1620 | 5-{4-amino-5-[(3,3-difluoroazetidin-1-yl)methyl]pyrrolo[2,1-f][1,2,4]triazin-7-yl}-N-[(3R,4S)-1-(3,3-difluorocyclopentanecarbonyl)-4-fluoropyrrolidin-3-yl]-2-methoxypyridine-3-carboxamide | 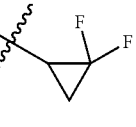 | 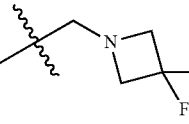 | 609.2 |
| 1621 | 5-{4-amino-5-[(4,4-difluoropiperidin-1-yl)methyl]pyrrolo[2,1-f][1,2,4]triazin-7-yl}-N-[(3R,4S)-1-(2,2-difluorocyclopropanecarbonyl)-4-fluoropyrrolidin-3-yl]-2-methoxypyridine-3-carboxamide | 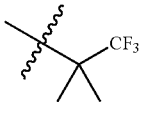 | 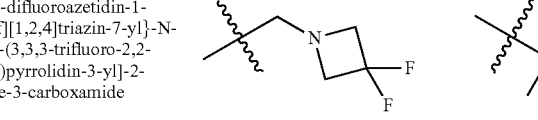 | 609.2 |
| 1622 | 5-{4-amino-5-[(4,4-difluoropiperidin-1-yl)methyl]pyrrolo[2,1-f][1,2,4]triazin-7-yl}-N-[(3R,4S)-4-fluoro-1-(3,3,3-trifluoro-2,2-dimethylpropanoyl)pyrrolidin-3-yl]-2-methoxypyridine-3-carboxamide | 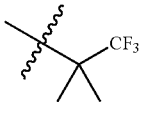 | 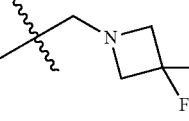 | 643.2 |
| 1623 | 5-{4-amino-5-[(4,4-difluoropiperidin-1-yl)methyl]pyrrolo[2,1-f][1,2,4]triazin-7-yl}-N-[(3R,4S)-1-(3,3-difluorocyclopentanecarbonyl)-4-fluoropyrrolidin-3-yl]-2-methoxypyridine-3-carboxamide | 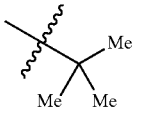 | 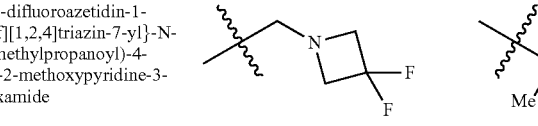 | 637.2 |

TABLE 58-continued

| Ex | Name | R¹ | R² | Obs. MS Ion |
|---|---|---|---|---|
| 1624 | 5-{4-amino-5-[(4,4-difluoropiperidin-1-yl)methyl]pyrrolo[2,1-f][1,2,4]triazin-7-yl}-N-[(3R,4S)-4-fluoro-1-(2-fluoro-2-methylpropanoyl)pyrrolidin-3-yl]-2-methoxypyridine-3-carboxamide | 4,4-difluoropiperidin-1-ylmethyl | 2-fluoro-2-methylpropyl | 593.2 |
| 1625 | 5-{4-amino-5-[(4,4-difluoropiperidin-1-yl)methyl]pyrrolo[2,1-f][1,2,4]triazin-7-yl}-N-[(3R,4S)-4-fluoro-1-[2-hydroxy-2-(trifluoromethyl)butanoyl]pyrrolidin-3-yl]-2-methoxypyridine-3-carboxamide | 4,4-difluoropiperidin-1-ylmethyl | 2-hydroxy-2-(trifluoromethyl)butyl | 659.2 LC/MS RT 1.54 min (Method 2) |
| 1626 | 5-{4-amino-5-[(4,4-difluoropiperidin-1-yl)methyl]pyrrolo[2,1-f][1,2,4]triazin-7-yl}-N-[(3R,4S)-4-fluoro-1-(2-fluorobenzoyl)pyrrolidin-3-yl]-2-methoxypyridine-3-carboxamide | 4,4-difluoropiperidin-1-ylmethyl | 2-fluorophenyl | 627.2 |
| 1627 | 5-(4-amino-5-{[4-(trifluoromethyl)piperidin-1-yl]methyl}pyrrolo[2,1-f][1,2,4]triazin-7-yl)-N-[(3R,4S)-1-(2,2-difluorocyclopropanecarbonyl)-4-fluoropyrrolidin-3-yl]-2-methoxypyridine-3-carboxamide | 4-(trifluoromethyl)piperidin-1-ylmethyl | 2,2-difluorocyclopropyl | 641.1 |
| 1628 | 5-(4-amino-5-{[4-(trifluoromethyl)piperidin-1-yl]methyl}pyrrolo[2,1-f][1,2,4]triazin-7-yl)-N-[(3R,4S)-4-fluoro-1-(2-fluoro-2-methylpropanoyl)pyrrolidin-3-yl]-2-methoxypyridine-3-carboxamide | 4-(trifluoromethyl)piperidin-1-ylmethyl | 2-fluoro-2-methylpropyl | 625.1 |
| 1629 | 5-(4-amino-5-{[4-(trifluoromethyl)piperidin-1-yl]methyl}pyrrolo[2,1-f][1,2,4]triazin-7-yl)-N-[(3R,4S)-4-fluoro-1-[2-hydroxy-2-(trifluoromethyl)butanoyl]pyrrolidin-3-yl]-2-methoxypyridine-3-carboxamide | 4-(trifluoromethyl)piperidin-1-ylmethyl | 2-hydroxy-2-(trifluoromethyl)butyl | 691.2 LC/MS RT 2.3 min (Method 2) |
| 1630 | 5-(4-amino-5-{[4-(trifluoromethyl)piperidin-1-yl]methyl}pyrrolo[2,1-f][1,2,4]triazin-7-yl)-N-[(3R,4S)-4-fluoro-1-(3,3,3-trifluoro-2,2-dimethylpropanoyl)pyrrolidin-3-yl]-2-methoxypyridine-3-carboxamide | 4-(trifluoromethyl)piperidin-1-ylmethyl | 3,3,3-trifluoro-2,2-dimethylpropyl | 675.2 |

TABLE 58-continued

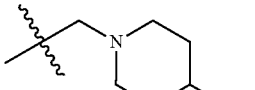

| Ex | Name | R¹ | R² | Obs. MS Ion |
|---|---|---|---|---|
| 1631 | 5-(4-amino-5-{[4-(trifluoromethyl)piperidin-1-yl]methyl}pyrrolo[2,1-f][1,2,4]triazin-7-yl)-N-[(3R,4S)-4-fluoro-1-[4,4,4-trifluoro-3-hydroxy-3-(trifluoromethyl)butanoyl]pyrrolidin-3-yl]-2-methoxypyridine-3-carboxamide | 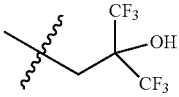 | 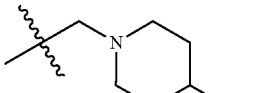 | 745.2 LC/MS RT 2.52 min (Method 1) |
| 1632 | 5-(4-amino-5-{[4-(trifluoromethyl)piperidin-1-yl]methyl}pyrrolo[2,1-f][1,2,4]triazin-7-yl)-N-[(3R,4S)-4-fluoro-1-(2-fluorobenzoyl)pyrrolidin-3-yl]-2-methoxypyridine-3-carboxamide | 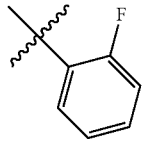 [SMILES: *c1ccccc1F] | 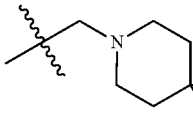 | 659.2 |

Compounds in Table 58 were prepared by the methods detailed in Examples 1554 and 1556. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

TABLE 59

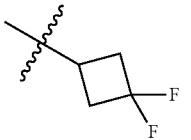 [SMILES: *C1CC(F)(F)C1]

| Ex | Name | R¹ | R² | Obs. MS Ion |
|---|---|---|---|---|
| 1633 | 5-{4-amino-5-[(4,4-difluoropiperidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-4-fluoro-2-methoxybenzamide | 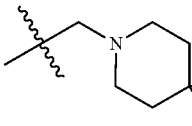 | 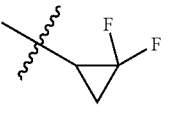 [SMILES: *C1CC1(F)F] | 640.2 |
| 1634 | 5-{4-amino-5-[(4,4-difluoropiperidin-1-yl)methyl]pyrrolo[2,1-f][1,2,4]triazin-7-yl}-N-[(3R,4S)-1-(2,2-difluorocyclopropanecarbonyl)-4-fluoropyrrolidin-3-yl]-4-fluoro-2-methoxybenzamide | 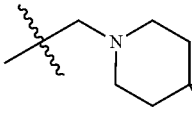 | 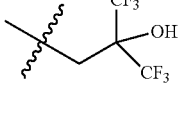 | 626.2 LC/MS RT 1.55 min (Method 2) |
| 635 | 5-{4-amino-5-[(4,4-difluoropiperidin-1-yl)methyl]pyrrolo[2,1-f][1,2,4]triazin-7-yl}-4-fluoro-N-[(3R,4S)-4-fluoro-1-[4,4,4-trifluoro-3-hydroxy-3-(trifluoromethyl)butanoyl]pyrrolidin-3-yl]-2-methoxybenzamide | 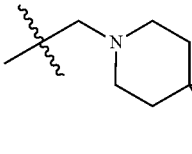 | | 730.1 |
| 1636 | 5-{4-amino-5-[(4,4-difluoropiperidin-1-yl)methyl]pyrrolo[2,1-f][1,2,4]triazin-7-yl}-4-fluoro-N-[(3R,4S)-4-fluoro-1-(2-fluoro-2-methylpropanoyl)pyrrolidin-3-yl]-2-methoxybenzamide | | 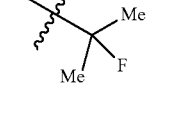 | 610.2 |

TABLE 59-continued

| Ex | Name | R¹ | R² | Obs. MS Ion |
|---|---|---|---|---|
| 1637 | 5-{4-amino-5-[(4,4-difluoropiperidin-1-yl)methyl]pyrrolo[2,1-f][1,2,4]triazin-7-yl}-4-fluoro-N-[(3R,4S)-4-fluoro-1-[2-hydroxy-2-(trifluoromethyl)butanoyl]pyrrolidin-3-yl]-2-methoxybenzamide | 4,4-difluoropiperidin-1-ylmethyl | 2-hydroxy-2-(trifluoromethyl)butyl (Me, CF₃C, OH) | 676.2 |
| 1638 | 5-{4-amino-5-[(4,4-difluoropiperidin-1-yl)methyl]pyrrolo[2,1-f][1,2,4]triazin-7-yl}-4-fluoro-N-[(3R,4S)-4-fluoro-1-(3,3,3-trifluoro-2,2-dimethylpropanoyl)pyrrolidin-3-yl]-2-methoxybenzamide | 4,4-difluoropiperidin-1-ylmethyl | C(Me)(Me)(CF₃) | 660.2 |
| 1639 | 5-(4-amino-5-{[4-(trifluoromethyl)piperidin-1-yl]methyl}pyrrolo[2,1-f][1,2,4]triazin-7-yl)-4-fluoro-N-[(3R,4S)-4-fluoro-1-[(2R)-3,3,3-trifluoro-2-hydroxy-2-methylpropanoyl]pyrrolidin-3-yl]-2-methoxybenzamide | 4-(trifluoromethyl)piperidin-1-ylmethyl | C(CF₃)(OH)(Me) (2R) | 694.2 |
| 1640 | 5-(4-amino-5-{[4-(trifluoromethyl)piperidin-1-yl]methyl}pyrrolo[2,1-f][1,2,4]triazin-7-yl)-N-[(3R,4S)-1-(3,3-difluorocyclobutanecarbonyl)-4-fluoropyrrolidin-3-yl]-4-fluoro-2-methoxybenzamide | 4-(trifluoromethyl)piperidin-1-ylmethyl | 3,3-difluorocyclobutyl | 672.2 |

Compounds in Table 59 were prepared by the methods detailed in Example 1570. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

TABLE 60

| Ex | Name | R¹ | R² | Obs. MS Ion |
|---|---|---|---|---|
| 1641 | 5-{4-amino-5-[(4,4-difluoropiperidin-1-yl)methyl]pyrrolo[2,1-f][1,2,4]triazin-7-yl}-N-[(3R,4S)-1-(3,3-difluorocyclobutanecarbonyl)-4-fluoropyrrolidin-3-yl]-2-methylbenzamide | 4,4-difluoropiperidin-1-ylmethyl | 3,3-difluorocyclobutyl | 606.2 |
| 1642 | 5-{4-amino-5-[(4,4-difluoropiperidin-1-yl)methyl]pyrrolo[2,1-f][1,2,4]triazin-7-yl}-N-[(3R,4S)-4-fluoro-1-[4,4,4-trifluoro-3-hydroxy-3-(trifluoromethyl)butanoyl]pyrrolidin-3-yl]-2-methylbenzamide | 4,4-difluoropiperidin-1-ylmethyl | CH₂C(CF₃)(CF₃)OH | 696.2 |

TABLE 60-continued

| Ex | Name | R¹ | R² | Obs. MS Ion |
|---|---|---|---|---|
| 1643 | 5-{4-amino-5-[(4,4-difluoropiperidin-1-yl)methyl]pyrrolo[2,1-f][1,2,4]triazin-7-yl}-N-[(3R,4S)-4-fluoro-1-(2-fluoro-2-methylpropanoyl)pyrrolidin-3-yl]-2-methylbenzamide | 4,4-difluoropiperidin-1-ylmethyl | C(Me)(Me)F | 576.2 |
| 1644 | 5-{4-amino-5-[(4,4-difluoropiperidin-1-yl)methyl]pyrrolo[2,1-f][1,2,4]triazin-7-yl}-N-[(3R,4S)-4-fluoro-1-[2-hydroxy-2-(trifluoromethyl)butanoyl]pyrrolidin-3-yl]-2-methylbenzamide | 4,4-difluoropiperidin-1-ylmethyl | C(Me)(Et)(OH)(CF₃) | 642.2 LC/MS RT 1.51 min (Method 2) |
| 1645 | 5-{4-amino-5-[(4,4-difluoropiperidin-1-yl)methyl]pyrrolo[2,1-f][1,2,4]triazin-7-yl}-N-[(3R,4S)-4-fluoro-1-(3,3,3-trifluoro-2,2-dimethylpropanoyl)pyrrolidin-3-yl]-2-methylbenzamide | 4,4-difluoropiperidin-1-ylmethyl | C(Me)(Me)CF₃ | 626.2 |
| 1646 | 5-{4-amino-5-[(4,4-difluoropiperidin-1-yl)methyl]pyrrolo[2,1-f][1,2,4]triazin-7-yl}-N-[(3R,4S)-4-fluoro-1-(2-fluorobenzoyl)pyrrolidin-3-yl]-2-methylbenzamide | 4,4-difluoropiperidin-1-ylmethyl | 2-fluorophenyl | 610.2 |
| 1647 | 5-(4-amino-5-{[4-(trifluoromethyl)piperidin-1-yl]methyl}pyrrolo[2,1-f][1,2,4]triazin-7-yl)-N-[(3R,4S)-4-fluoro-1-[(2R)-3,3,3-trifluoro-2-hydroxy-2-methylpropanoyl]pyrrolidin-3-yl]-2-methylbenzamide | 4-(trifluoromethyl)piperidin-1-ylmethyl | C(Me)(CF₃)(OH) | 660.2 |
| 1648 | 5-(4-amino-5-{[4-(trifluoromethyl)piperidin-1-yl]methyl}pyrrolo[2,1-f][1,2,4]triazin-7-yl)-N-[(3R,4S)-1-(3,3-difluorocyclobutanecarbonyl)-4-fluoropyrrolidin-3-yl]-2-methylbenzamide | 4-(trifluoromethyl)piperidin-1-ylmethyl | 3,3-difluorocyclobutyl | 638.2 |
| 1649 | 5-(4-amino-5-{[4-(trifluoromethyl)piperidin-1-yl]methyl}pyrrolo[2,1-f][1,2,4]triazin-7-yl)-N-[(3R,4S)-1-(2,2-difluorocyclopropanecarbonyl)-4-fluoropyrrolidin-3-yl]-2-methylbenzamide | 4-(trifluoromethyl)piperidin-1-ylmethyl | 2,2-difluorocyclopropyl | 624.2 |
| 1650 | 5-(4-amino-5-{[4-(trifluoromethyl)piperidin-1-yl]methyl}pyrrolo[2,1-f][1,2,4]triazin-7-yl)-N-[(3R,4S)-4-fluoro-1-[4,4,4-trifluoro-3-hydroxy-3-(trifluoromethyl)butanoyl]pyrrolidin-3-yl]-2-methylbenzamide | 4-(trifluoromethyl)piperidin-1-ylmethyl | CH₂C(OH)(CF₃)(CF₃) | 728.2 LC/MS RT 2.44 min (Method 1) |
| 1651 | 5-(4-amino-5-{[4-(trifluoromethyl)piperidin-1-yl]methyl}pyrrolo[2,1-f][1,2,4]triazin-7-yl)-N-[(3R,4S)-4-fluoro-1-(2-fluoro-2-methylpropanoyl)pyrrolidin-3-yl]-2-methylbenzamide | 4-(trifluoromethyl)piperidin-1-ylmethyl | C(Me)(Me)F | 608.2 |

TABLE 60-continued

| Ex | Name | R¹ | R² | Obs. MS Ion |
|---|---|---|---|---|
| 1652 | 5-(4-amino-5-{[4-(trifluoromethyl)piperidin-1-yl]methyl}pyrrolo[2,1-f][1,2,4]triazin-7-yl)-N-[(3R,4S)-4-fluoro-1-(3,3,3-trifluoro-2,2-dimethylpropanoyl)pyrrolidin-3-yl]-2-methylbenzamide | piperidine-N-CH₂- with 4-CF₃ | C(Me)(Me)CF₃ | 658.2 |
| 1653 | 5-(4-amino-5-{[4-(trifluoromethyl)piperidin-1-yl]methyl}pyrrolo[2,1-f][1,2,4]triazin-7-yl)-N-[(3R,4S)-4-fluoro-1-[2-hydroxy-2-(trifluoromethyl)butanoyl]pyrrolidin-3-yl]-2-methylbenzamide | piperidine-N-CH₂- with 4-CF₃ | C(Me)(CF₃)(OH)CH₂- | LC/MS RT 1.46 min (Method 1) |
| 1654 | 5-(4-amino-5-{[4-(trifluoromethyl)piperidin-1-yl]methyl}pyrrolo[2,1-f][1,2,4]triazin-7-yl)-N-[(3R,4S)-4-fluoro-1-(2-fluorobenzoyl)pyrrolidin-3-yl]-2-methylbenzamide | piperidine-N-CH₂- with 4-CF₃ | 2-fluorophenyl | 642.2 |

Compounds in Table 60 were prepared by the methods detailed in Example 1571. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

TABLE 61

| Ex | Name | R | Obs. MS Ion |
|---|---|---|---|
| 1655 | 5-{4-amino-5-[(4,4-difluoropiperidin-1-yl)methyl]pyrrolo[2,1-f][1,2,4]triazin-7-yl}-N-[(3R,4S)-1-(2,2-difluorocyclopropanecarbonyl)-4-fluoropyrrolidin-3-yl]-4-fluoro-2-methylbenzamide | 2,2-difluorocyclopropyl | 610.2 LC/MS RT 2.03 min (Method 1) |
| 1656 | 5-{4-amino-5-[(4,4-difluoropiperidin-1-yl)methyl]pyrrolo[2,1-f][1,2,4]triazin-7-yl}-4-fluoro-N-[(3R,4S)-4-fluoro-1-[4,4,4-trifluoro-3-hydroxy-3-(trifluoromethyl)butanoyl]pyrrolidin-3-yl]-2-methylbenzamide | C(CF₃)(CF₃)(OH)CH₂- | 714.2 |
| 1657 | 5-{4-amino-5-[(4,4-difluoropiperidin-1-yl)methyl]pyrrolo[2,1-f][1,2,4]triazin-7-yl}-4-fluoro-N-[(3R,4S)-4-fluoro-1-(3,3,3-trifluoro-2,2-dimethylpropanoyl)pyrrolidin-3-yl]-2-methylbenzamide | C(Me)(Me)CF₃ | 644.2 |

TABLE 61-continued

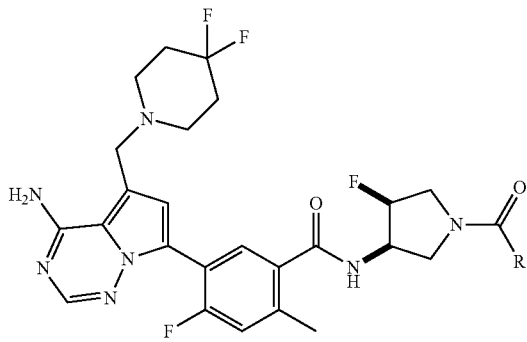

| Ex | Name | R | Obs. MS Ion |
|---|---|---|---|
| 1658 | 5-{4-amino-5-[(4,4-difluoropiperidin-1-yl)methyl]pyrrolo[2,1-f][1,2,4]triazin-7-yl}-4-fluoro-N-[(3R,4S)-4-fluoro-1-[(2R)-3,3,3-trifluoro-2-hydroxy-2-methylpropanoyl]pyrrolidin-3-yl]-2-methylbenzamide | ⸺C(CF₃)(OH)— | 646.2 |
| 1659 | 5-{4-amino-5-[(4,4-difluoropiperidin-1-yl)methyl]pyrrolo[2,1-f][1,2,4]triazin-7-yl}-4-fluoro-N-[(3R,4S)-4-fluoro-1-(3-methylbutanoyl)pyrrolidin-3-yl]-2-methylbenzamide | —CH₂CH(Me)Me | 590.3 |
| 1660 | 5-{4-amino-5-[(4,4-difluoropiperidin-1-yl)methyl]pyrrolo[2,1-f][1,2,4]triazin-7-yl}-4-fluoro-N-[(3R,4S)-4-fluoro-1-(2-fluoro-2-methylpropanoyl)pyrrolidin-3-yl]-2-methylbenzamide | —C(Me)(Me)F | 594.2 |

Compounds in Table 61 were prepared by the methods detailed in Example 1578. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

TABLE 62

NMR data for selected examples from Tables 57-61

| Ex | NMR Assignments (500 MHz, DMSO-d6) δ |
|---|---|
| 1581 | 9.04-8.82 (m, 1H), 8.80-8.63 (m, 1H), 8.63-8.24 (m, 1H), 8.17-7.89 (m, 1H), 7.32-7.15 (m, 1H), 5.45-5.12 (m, 1H), 4.88-4.58 (m, 1H), 4.22-3.07 (m, 14H), 2.88-2.61 (m, 4H), 2.46-2.24 (m, 2H) |
| 1582 | 9.01-8.93 (m, 1H), 8.80-8.68 (m, 1H), 8.61-8.43 (m, 1H), 8.11-7.99 (m, 1H), 7.43-7.27 (m, 1H), 5.60-5.18 (m, 2H), 4.88-4.60 (m, 2H), 4.10-4.00 (m, 3H), 4.00-3.23 (m, 6H), 3.22-3.06 (m, 4H), 2.92-2.68 (m, 4H) |
| 1583 | 9.00-8.85 (m, 1H), 8.85-8.67 (m, 1H), 8.62-8.40 (m, 1H), 7.95-7.79 (m, 1H), 7.28-7.17 (m, 1H), 7.07-6.89 (m, 1H), 5.39-5.17 (m, 1H), 4.82-4.20 (m, 2H), 4.10-3.98 (m, 3H), 3.97-3.25 (m, 7H), 2.48-2.36 (m, 2H), 1.60-1.36 (m, 7H), 1.25-1.16 (m, 2H) |
| 1584 | 9.02-8.81 (m, 1H), 8.78-8.64 (m, 1H), 8.64-8.42 (m, 1H), 8.11-7.88 (m, 1H), 7.38-7.30 (m, 1H), 5.43-5.14 (m, 1H), 4.84-4.56 (m, 3H), 4.55-4.25 (m, 1H), 4.10-3.99 (m, 3H), 3.99-3.55 (m, 4H), 3.44-3.29 (m, 4H), 1.61-1.46 (m, 3H), 1.32-1.23 (m, 6H) |
| 1585 | 8.96-8.84 (m, 1H), 8.81-8.73 (m, 1H), 8.59-8.48 (m, 1H), 7.92-7.78 (m, 2H), 7.31-7.15 (m, 1H), 7.13-6.91 (m, 1H), 5.40-5.10 (m, 1H), 4.78-4.57 (m, 1H), 4.56-4.30 (m, 1H), 4.30-4.22 (m, 1H), 4.07-3.98 (m, 5H), 3.95-3.11 (m, 3H), 2.92-2.74 (m, 1H), 2.47-2.39 (m, 1H), 2.24-2.06 (m, 1H), 2.01-1.77 (m, 2H), 1.77-1.61 (m, 1H), 1.59-1.43 (m, 3H) |
| 1586 | 8.97-8.80 (m, 1H), 8.78-8.66 (m, 1H), 8.65-8.50 (m, 1H), 8.14-8.02 (m, 1H), 7.25-7.20 (m, 1H), 5.41-5.13 (m, 1H), 4.76-4.56 (m, 1H), 4.53-4.26 (m, 1H), 4.06-3.99 (m, 3H), 3.94-3.26 (m, 10H), 2.25-2.07 (m, 4H), 1.58-1.46 (m, 3H) |
| 1587 | 9.34-9.10 (m, 1H), 9.00-8.91 (m, 1H), 8.86-8.71 (m, 1H), 8.60-8.42 (m, 1H), 7.96-7.78 (m, 1H), 7.70-7.49 (m, 1H), 7.21-7.11 (m, 1H), 7.10-6.98 (m, 1H), 5.39-5.18 (m, 1H), 4.77-4.58 (m, 1H), 4.53-4.25 (m, 1H), 4.08-3.98 (m, 3H), 3.99-3.26 (m, 6H), 3.12-3.01 (m, 1H), 2.94-2.77 (m, 1H), 2.16-2.00 (m, 2H), 1.96-1.83 (m, 1H), 1.83-1.68 (m, 1H), 1.59-1.42 (m, 4H), 1.42-1.28 (m, 1H) |
| 1588 | 9.00-8.88 (m, 1H), 8.81-8.67 (m, 1H), 8.62-8.49 (m, 1H), 8.13-7.97 (m, 1H), 7.38-7.28 (m, 1H), 5.42-5.13 (m, 1H), 4.84-4.56 (m, 3H), 4.54-4.22 |

TABLE 62-continued

NMR data for selected examples from Tables 57-61

| Ex | NMR Assignments (500 MHz, DMSO-d6) δ |
|---|---|
| | (m, 1H), 4.13-3.99 (m, 3H), 3.99-3.03 (m, 8H), 2.14-1.97 (m, 2H), 1.96-1.80 (m, 2H), 1.61-1.44 (m, 3H) |
| 1589 | 8.99-8.85 (m, 1H), 8.80-8.68 (m, 1H), 8.64-8.44 (m, 1H), 8.13-8.00 (m, 1H), 7.22-7.16 (m, 1H), 5.40-5.16 (m, 1H), 4.75-4.57 (m, 1H), 4.51-4.26 (m, 1H), 4.15-2.74 (m, 13H), 2.45-2.31 (m, 2H), 1.61-1.47 (m, 3H) |
| 1590 | 9.10-8.88 (m, 1H), 8.82-8.65 (m, 1H), 8.64-8.43 (m, 1H), 8.12-7.93 (m, 1H), 7.44-7.29 (m, 1H), 5.48-5.11 (m, 1H), 4.82-4.59 (m, 1H), 4.54-4.22 (m, 1H), 4.09-4.01 (m, 3H), 4.01-3.30 (m, 11H), 1.59-1.46 (m, 3H) |
| 1591 | 10.19-9.95 (m, 1H), 9.09-8.85 (m, 1H), 8.85-8.71 (m, 1H), 8.61-8.41 (m, 1H), 7.92-7.82 (m, 1H), 7.82-7.61 (m, 1H), 7.19-6.93 (m, 2H), 5.42-5.08 (m, 1H), 4.82-4.55 (m, 1H), 4.55-4.19 (m, 1H), 4.09-4.00 (m, 3H), 4.00-2.98 (m, 4H), 2.75-2.51 (m, 4H), 1.61-1.41 (m, 9H), 1.39-1.30 (m, 3H) |
| 1592 | 9.80-9.41 (m, 1H), 9.09-8.86 (m, 1H), 8.86-8.69 (m, 1H), 8.68-8.48 (m, 1H), 8.48-8.33 (m, 1H), 8.23-8.01 (m, 1H), 8.00-7.72 (m, 1H), 7.19-6.91 (m, 1H), 5.48-5.12 (m, 1H), 4.77-4.57 (m, 1H), 4.54-4.26 (m, 1H), 4.08-4.01 (m, 3H), 4.01-2.92 (m, 3H), 2.71-2.56 (m, 3H), 1.63-1.46 (m, 3H) |
| 1593 | 8.99-8.86 (m, 1H), 8.84-8.72 (m, 1H), 8.56-8.38 (m, 1H), 7.95-7.78 (m, 1H), 7.11-7.02 (m, 1H), 7.02-6.87 (m, 1H), 5.41-5.13 (m, 1H), 4.81-4.58 (m, 1H), 4.56-4.22 (m, 1H), 4.08-4.01 (m, 3H), 4.01-3.25 (m, 3H), 3.20-3.13 (m, 3H), 1.62-1.47 (m, 3H) |
| 1594 | 8.96-8.90 (m, 1H), 8.84-8.77 (m, 1H), 8.60-8.46 (m, 1H), 8.01-7.94 (m, 1H), 7.33-7.24 (m, 1H), 7.13-7.03 (m, 1H), 5.41-5.15 (m, 1H), 4.76-4.55 (m, 1H), 4.55-4.27 (m, 1H), 4.10-4.01 (m, 3H), 4.01-3.03 (m, 3H), 1.63-1.46 (m, 3H) |
| 1595 | 9.00-8.89 (m, 1H), 8.85-8.70 (m, 1H), 8.59-8.45 (m, 1H), 8.05-7.99 (m, 1H), 7.21-7.09 (m, 2H), 5.40-5.18 (m, 1H), 4.80-4.57 (m, 1H), 4.54-4.26 (m, 1H), 4.11-4.01 (m, 3H), 4.01-3.13 (m, 3H), 1.62-1.49 (m, 3H) |
| 1596 | 9.00-8.91 (m, 1H), 8.80-8.69 (m, 1H), 8.55-8.46 (m, 1H), 8.13-8.05 (m, 1H), 7.24-7.17 (m, 1H), 5.44-5.21 (m, 1H), 4.89-4.55 (m, 1H), 4.11-4.00 (m, 3H), 4.00-3.02 (m, 11H), 2.88-2.67 (m, 4H), 2.33-2.03 (m, 4H) |
| 1597 | 9.55-9.21 (m, 1H), 9.02-8.90 (m, 1H), 8.86-8.70 (m, 1H), 8.58-8.37 (m, 1H), 7.97-7.83 (m, 1H), 7.83-7.60 (m, 1H), 7.13-6.95 (m, 1H), 5.48-5.16 (m, 1H), 4.90-4.57 (m, 1H), 4.12-4.01 (m, 3H), 4.01-3.13 (m, 7H), 3.13-3.01 (m, 2H), 2.94-2.65 (m, 4H), 2.47-2.32 (m, 1H), 2.16-2.00 (m, 2H), 1.92-1.80 (m, 2H), 1.56-1.37 (m, 2H) |
| 1598 | 9.57-9.17 (m, 1H), 9.02-8.86 (m, 1H), 8.82-8.70 (m, 1H), 8.57-8.38 (m, 1H), 7.97-7.85 (m, 1H), 7.81-7.48 (m, 1H), 7.13-7.00 (m, 2H), 5.38-5.16 (m, 1H), 4.77-4.56 (m, 1H), 4.54-4.23 (m, 1H), 4.11-3.24 (m, 9H), 3.14-2.96 (m, 2H), 2.46-2.31 (m, 1H), 2.18-1.98 (m, 2H), 1.92-1.83 (m, 2H), 1.58-1.51 (m, 2H), 1.52-1.36 (m, 2H) |
| 1599 | 9.09-8.92 (m, 1H), 8.92-8.75 (m, 1H), 8.63-8.43 (m, 1H), 8.02-7.88 (m, 1H), 7.24-7.14 (m, 2H), 7.14-7.06 (m, 1H), 6.78-6.64 (m, 2H), 5.46-5.14 (m, 1H), 4.96-4.44 (m, 1H), 4.11-4.01 (m, 3H), 4.02-3.07 (m, 5H), 2.91-2.66 (m, 4H) |
| 1600 | 9.62-9.31 (m, 1H), 9.04-8.89 (m, 1H), 8.88-8.74 (m, 1H), 8.58-8.42 (m, 1H), 8.00-7.83 (m, 1H), 7.73-7.50 (m, 1H), 7.22-7.02 (m, 4H), 5.38-5.14 (m, 1H), 4.81-4.57 (m, 1H), 4.56-4.24 (m, 1H), 4.10-4.01 (m, 3H), 4.01-3.09 (m, 7H), 2.94-2.76 (m, 4H), 1.60-1.47 (m, 3H) |
| 1601 | 8.92-8.80 (m, 1H), 8.75-8.61 (m, 1H), 8.60-8.47 (m, 1H), 7.93-7.82 (m, 3H), 7.54-7.41 (m, 2H), 6.98-6.92 (m, 1H), 5.42-5.14 (m, 1H), 4.88-4.58 (m, 1H), 4.08-4.01 (m, 3H), 4.01-3.08 (m, 5H), 2.91-2.65 (m, 4H), 2.45-2.39 (m, 3H) |
| 1602 | 9.01-8.91 (m, 1H), 8.85-8.74 (m, 1H), 8.58-8.42 (m, 1H), 8.14-8.04 (m, 1H), 7.73-7.46 (m, 1H), 7.45-7.39 (m, 1H), 7.10-7.01 (m, 1H), 5.39-5.18 (m, 1H), 4.82-4.58 (m, 1H), 4.57-4.26 (m, 1H), 4.14-3.99 (m, 3H), 4.00-3.10 (m, 4H), 1.59-1.48 (m, 3H) |
| 1603 | 9.06-8.75 (m, 1H), 8.75-8.58 (m, 1H), 8.58-8.44 (m, 1H), 8.13-7.98 (m, 1H), 7.98-7.71 (m, 2H), 6.99-6.63 (m, 1H), 5.39-5.13 (m, 1H), 4.87-4.56 (m, 1H), 4.57-4.24 (m, 1H), 4.15-4.01 (m, 3H), 4.01-3.29 (m, 4H), 1.63-1.48 (m, 3H) |
| 1604 | 9.09-8.88 (m, 1H), 8.85-8.69 (m, 1H), 8.63-8.50 (m, 1H), 7.96-7.64 (m, 2H), 7.14-7.02 (m, 1H), 7.02-6.83 (m, 1H), 6.69-6.37 (m, 1H), 5.41-5.14 (m, 1H), 4.80-4.53 (m, 1H), 4.53-4.23 (m, 1H), 4.11-4.00 (m, 3H), 4.00-3.22 (m, 6H), 1.61-1.42 (m, 3H) |
| 1605 | 8.98-8.83 (m, 1H), 8.85-8.73 (m, 1H), 8.60-8.46 (m, 1H), 7.94-7.84 (m, 1H), 7.17-7.04 (m, 2H), 5.41-5.16 (m, 1H), 4.87-4.58 (m, 1H), 4.57-4.25 (m, 1H), 4.10-4.00 (m, 3H), 4.00-3.18 (m, 3H), 1.59-1.49 (m, 3H) |
| 1606 | 9.02-8.84 (m, 1H), 8.83-8.72 (m, 1H), 8.61-8.47 (m, 1H), 7.95-7.88 (m, 1H), 7.37-6.99 (m, 3H), 5.39-5.16 (m, 1H), 4.81-4.59 (m, 1H), 4.53-4.27 (m, 1H), 4.09-4.00 (m, 3H), 4.00-3.06 (m, 3H), 1.60-1.44 (m, 3H) |
| 1607 | 8.97-8.85 (m, 1H), 8.76-8.67 (m, 1H), 8.61-8.44 (m, 1H), 8.11-8.04 (m, 1H), 7.26-7.23 (m, 1H), 5.38-5.15 (m, 1H), 4.77-4.58 (m, 1H), 4.53-4.27 (m, 1H), 4.09-4.02 (m, 3H), 3.98-3.35 (m, 10H), 2.94-2.86 (m, 1H), 2.75-2.69 (m, 1H), 1.60-1.49 (m, 3H) |

TABLE 62-continued

NMR data for selected examples from Tables 57-61

| Ex | NMR Assignments (500 MHz, DMSO-d6) δ |
|---|---|
| 1608 | 9.61-9.33 (m, 1H), 9.00-8.87 (m, 1H), 8.83-8.71 (m, 1H), 8.56-8.41 (m, 1H), 7.95-7.87 (m, 1H), 7.87-7.61 (m, 1H), 7.18-7.00 (m, 2H), 5.46-5.16 (m, 1H), 4.81-4.59 (m, 1H), 4.54-4.24 (m, 1H), 4.08-4.01 (m, 3H), 3.87-3.82 (m, 2H), 3.99-3.11 (m, 5H), 2.22-1.97 (m, 6H), 1.88-1.75 (m, 2H), 1.59-1.44 (m, 3H) |
| 1609 | 10.01-9.74 (m, 1H), 8.97-8.87 (m, 1H), 8.84-8.73 (m, 1H), 8.58-8.40 (m, 1H), 7.94-7.82 (m, 1H), 7.75-7.56 (m, 1H), 7.19-6.94 (m, 2H), 5.38-5.18 (m, 1H), 4.82-4.59 (m, 1H), 4.56-4.27 (m, 1H), 4.11-4.02 (m, 3H), 3.77-3.73 (m, 2H), 3.99-3.26 (m, 7H), 1.60-1.51 (m, 3H), 1.44-1.28 (m, 4H), 1.01-0.84 (m, 6H) |
| 1611 | 9.83-9.36 (m, 1H), 9.06-8.88 (m, 1H), 8.88-8.66 (m, 1H), 8.59-8.42 (m, 1H), 8.00-7.81 (m, 1H), 7.84-7.35 (m, 1H), 7.15-6.91 (m, 1H), 5.48-5.16 (m, 1H), 4.93-4.57 (m, 1H), 4.13-4.02 (m, 3H), 4.02-3.53 (m, 6H), 3.53-3.10 (m, 4H), 2.89-2.68 (m, 5H), 1.82-1.48 (m, 4H), 1.38-1.24 (m, 2H) |
| 1612 | 9.76-9.43 (m, 1H), 9.01-8.86 (m, 1H), 8.86-8.66 (m, 1H), 8.60-8.46 (m, 1H), 7.95-7.84 (m, 1H), 7.82-7.47 (m, 1H), 7.09 (s, 1H), 5.47-5.16 (m, 1H), 4.97-4.49 (m, 1H), 4.14-3.99 (m, 3H), 3.99-3.48 (m, 6H), 3.47-3.34 (m, 2H), 3.32-3.02 (m, 2H), 2.91-2.66 (m, 4H), 2.24-1.96 (m, 7H), 1.86-1.71 (m, 2H) |
| 1613 | 9.66-9.49 (bs, 1H), 9.01-8.86 (m, 1H), 8.86-8.69 (m, 1H), 8.61-8.41 (m, 1H), 8.04-7.85 (m, 1H), 7.77-7.68 (bs, 1 H), 7.14-6.89 (m, 1H), 5.45-5.14 (m, 1H), 4.97-4.57 (m, 3H), 4.17-3.95 (m, 3H), 3.92-3.58 (m, 6H), 1.85-1.45 (m, 4H), 1.36-1.19 (m, 2H) |
| 1614 | 9.75-9.30 (m, 1H), 9.06-8.86 (m, 1H), 8.82-8.74 (m, 1H), 8.59-8.49 (m, 1H), 7.95-7.80 (m, 1H), 7.80-7.44 (m, 1H), 7.12-6.97 (m, 1H), 5.46-5.19 (m, 1H), 4.85-4.58 (m, 3H), 4.10-3.93 (m, 3H), 3.97-3.26 (m, 6H), 3.12-2.96 (m, 2H), 2.46-2.29 (m, 1H), 2.18-2.03 (m, 2H), 1.92-1.77 (m, 2H), 1.56-1.38 (m, 2H) |
| 1615 | 9.00-8.84 (m, 1H), 8.84-8.66 (m, 1H), 8.63-8.37 (m, 1H), 7.94-7.82 (m, 1H), 7.61-7.43 (m, 2H), 7.43-7.24 (m, 2H), 7.09-6.88 (m, 1H), 5.54-5.14 (m, 1H), 4.92-4.53 (m, 1H), 4.09-3.96 (m, 3H), 3.96-3.32 (m, 6H), 3.30-3.09 (m, 4H), 2.16-2.00 (m, 2H) |
| 1616 | 8.88-8.60 (m, 3H), 7.77 (s, 1H), 7.13-6.89 (m, 1H), 5.44-5.09 (m, 1H), 4.76-4.19 (m, 2H), 4.06-3.24 (m, 12H), 1.59-1.42 (m, 3H) |
| 1617 | 8.83-8.56 (m, 3H), 7.87-7.71 (m, 1H), 7.04-6.90 (m, 1H), 5.44-5.20 (m, 1H), 4.82-4.59 (m, 1H), 4.03-3.90 (m, 5H), 3.76-3.65 (m, 4H), 4.15-3.22 (m, 4H), 2.98-2.75 (m, 1H), 1.99-1.77 (m, 2H) |
| 1618 | 8.96-8.86 (m, 1H), 8.82-8.63 (m, 1H), 8.63-8.47 (m, 1H), 7.96-7.80 (m, 1H), 7.20-6.95 (m, 1H), 5.39-5.15 (m, 1H), 4.87-4.59 (m, 1H), 4.52-2.90 (m, 6H), 4.11-3.95 (m, 3H), 3.82-3.59 (m, 4H), 1.53-1.36 (m, 6H) |
| 1619 | 8.84-8.55 (m, 4H), 8.02-7.71 (m, 1H), 7.15-7.10 (m, 1H), 5.38-5.02 (m, 1H), 4.76-4.50 (m, 1H), 4.18-4.04 (m, 2H), 4.04-3.94 (m, 3H), 3.94-3.81 (m, 4H), 3.81-3.19 (m, 4H), 1.22-1.05 (m, 9H) |
| 1620 | 8.84-8.75 (m, 1H), 8.74-8.56 (m, 2H), 7.99-7.79 (m, 1H), 7.19-7.12 (m, 1H), 5.38-5.12 (m, 1H), 4.82-4.52 (m, 1H), 4.21-4.12 (m, 2H), 4.02-3.97 (m, 3H), 3.94-3.84 (m, 4H), 4.07-3.02 (m, 4H), 2.36-2.19 (m, 2H), 2.19-1.98 (m, 4H), 1.83-1.63 (m, 1H) |
| 1621 | 9.35-9.07 (m, 1H), 8.98-8.90 (m, 1H), 8.81-8.73 (m, 1H), 8.64-8.47 (m, 1H), 7.93-7.84 (m, 1H), 7.80-7.47 (m, 1H), 7.08-7.01 (m, 1H), 5.50-5.20 (m, 1H), 4.98-4.62 (m, 1H), 4.36-4.08 (m, 1H), 4.08-4.00 (m, 3H), 4.00-2.84 (m, 6H), 2.73-2.59 (m, 4H), 2.13-1.82 (m, 6H) |
| 1622 | 9.00-8.89 (m, 1H), 8.85-8.71 (m, 1H), 8.65-8.41 (m, 1H), 8.00-7.84 (m, 1H), 7.13-6.99 (m, 1H), 5.40-5.19 (m, 1H), 4.97-4.52 (m, 1H), 4.13-4.02 (m, 3H), 3.89-3.75 (m, 2H), 4.38-3.26 (m, 4H), 2.75-2.58 (m, 4H), 2.10-1.89 (m, 4H), 1.56-1.47 (m, 3H), 1.47-1.38 (m, 3H) |
| 1623 | 9.41-9.05 (m, 1H), 8.95-8.87 (m, 1H), 8.84-8.68 (m, 1H), 8.56-8.42 (m, 1H), 7.94-7.78 (m, 1H), 7.70-7.43 (m, 1H), 7.08-7.01 (m, 1H), 5.45-5.17 (m, 1H), 4.91-4.48 (m, 1H), 4.06-4.00 (m, 3H), 3.84-3.78 (m, 2H), 4.22-3.03 (m, 5H), 2.74-2.58 (m, 4H), 2.44-2.25 (m, 2H), 2.23-2.12 (m, 1H), 2.12-1.95 (m, 6H), 1.89-1.72 (m, 1H) |
| 1624 | 8.98-8.85 (m, 1H), 8.84-8.68 (m, 1H), 8.62-8.39 (m, 1H), 7.98-7.86 (m, 1H), 7.13-7.04 (m, 1H), 5.40-5.17 (m, 1H), 4.86-4.56 (m, 1H), 4.31-4.06 (m, 1H), 4.06-4.00 (m, 3H), 4.00-3.45 (m, 5H), 2.71-2.59 (m, 4H), 2.14-1.93 (m, 4H), 1.62-1.49 (m, 6H) |
| 1626 | 9.50-9.03 (m, 1H), 9.00-8.84 (m, 1H), 8.84-8.66 (m, 1H), 8.66-8.29 (m, 1H), 7.95-7.84 (m, 1H), 7.78-7.41 (m, 3H), 7.40-7.25 (m, 2H), 7.13-6.97 (m, 1H), 5.57-5.15 (m, 1H), 5.00-4.62 (m, 1H), 4.19-3.25 (m, 9H), 2.74-2.56 (m, 4H), 2.16-1.91 (m, 4H) |
| 1627 | 9.59-9.28 (m, 1H), 9.09-8.90 (m, 1H), 8.80-8.72 (m, 1H), 8.65-8.32 (m, 1H), 7.97-7.87 (m, 1H), 7.83-7.54 (m, 1H), 7.12-7.03 (m, 1H), 5.55-5.17 (m, 1H), 5.03-4.65 (m, 1H), 4.44-3.45 (m, 8H), 3.15-3.03 (m, 2H), 3.03-2.80 (m, 1H), 2.47-2.29 (m, 1H), 2.17-2.02 (m, 2H), 2.02-1.77 (m, 5H), 1.60-1.32 (m, 2H) |
| 1628 | 9.55-9.31 (m, 1H), 9.00-8.86 (m, 1H), 8.82-8.72 (m, 1H), 8.58-8.41 (m, 1H), 7.96-7.84 (m, 1H), 7.82-7.59 (m, 1H), 7.13-7.00 (m, 1H), 5.48-5.17 |

TABLE 62-continued

NMR data for selected examples from Tables 57-61

| Ex | NMR Assignments (500 MHz, DMSO-d6) δ |
|---|---|
|  | (m, 1H), 4.88-4.53 (m, 1H), 4.32-3.51 (m, 9H), 3.13-2.98 (m, 2H), 2.47-2.30 (m, 1H), 2.19-2.04 (m, 2H), 1.94-1.79 (m, 2H), 1.65-1.36 (m, 8H) |
| 1630 | 9.56-9.27 (m, 1H), 9.01-8.89 (m, 1H), 8.85-8.69 (m, 1H), 8.58-8.35 (m, 1H), 7.98-7.85 (m, 1H), 7.86-7.52 (m, 1H), 7.13-6.93 (m, 1H), 5.46-5.18 (m, 1H), 4.88-4.55 (m, 1H), 4.43-3.60 (m, 9H), 3.15-2.98 (m, 2H), 2.46-2.29 (m, 1H), 2.17-1.99 (m, 2H), 1.96-1.79 (m, 2H), 1.54-1.38 (m, 8H) |
| 1631 | 9.59-9.16 (m, 1H), 9.03-8.87 (m, 1H), 8.85-8.66 (m, 1H), 8.60-8.37 (m, 1H), 7.99-7.82 (m, 1H), 7.82-7.61 (m, 1H), 7.61-7.40 (m, 2H), 7.40-7.20 (m, 2H), 7.12-6.85 (m, 1H), 5.59-5.14 (m, 1H), 4.97-4.60 (m, 1H), 4.18-3.45 (m, 8H), 3.18-2.92 (m, 2H), 2.47-2.27 (m, 1H), 2.18-1.98 (m, 2H), 1.95-1.78 (m, 3H), 1.55-1.35 (m, 2H) |
| 1633 | 9.41-9.02 (m, 1H), 8.39-8.22 (m, 2H), 7.95-7.79 (m, 1H), 7.73-7.38 (m, 1H), 7.30-7.14 (m, 1H), 6.85-6.72 (m, 1H), 5.44-5.15 (m, 1H), 4.89-4.53 (m, 1H), 4.11-3.04 (m, 10H), 2.89-2.72 (m, 4H), 2.72-2.57 (m, 4H), 2.11-1.94 (m, 4H) |
| 1635 | 9.40-8.92 (m, 1H), 8.56-8.18 (m, 2H), 7.90-7.73 (m, 1H), 7.52 (br s, 1H), 7.31-7.07 (m, 1H), 6.89-6.62 (m, 1H), 5.49-5.16 (m, 1H), 4.91-4.60 (m, 1H), 4.33-3.47 (m, 9H), 3.19-2.89 (m, 3H), 2.77-2.57 (m, 4H), 2.13-1.94 (m, 4H) |
| 1636 | 9.42-8.94 (m, 1H), 8.47-8.25 (m, 2H), 7.88-7.78 (m, 1H), 7.73-7.35 (m, 1H), 7.30-7.20 (m, 1H), 6.87-6.75 (m, 1H), 5.40-5.11 (m, 1H), 4.84-4.55 (m, 1H), 4.30-3.26 (m, 9H), 2.75-2.59 (m, 4H), 2.15-1.94 (m, 4H), 1.64-1.43 (m, 6H) |
| 1637 | 9.46-9.09 (m, 1H), 8.43-8.28 (m, 2H), 7.91-7.77 (m, 1H), 7.75-7.43 (m, 1H), 7.35-7.15 (m, 1H), 6.95-6.70 (m, 2H), 5.41-5.06 (m, 1H), 4.83-4.54 (m, 1H), 4.54-4.24 (m, 1H), 4.16-3.32 (m, 8H), 2.75-2.57 (m, 4H), 2.28-1.93 (m, 5H), 1.86-1.61 (m, 1H), 1.02-0.80 (m, 3H) |
| 1638 | 8.63-8.24 (m, 2H), 7.96-7.77 (m, 1H), 7.37-7.05 (m, 1H), 6.96-6.63 (m, 1H), 5.51-5.11 (m, 1H), 4.89-4.51 (m, 1H), 4.29-3.59 (m, 9H), 2.77-2.58 (m, 4H), 2.17-1.95 (m, 4H), 1.61-1.38 (m, 6H) |
| 1639 | 9.98-9.17 (m, 1H), 8.58-8.20 (m, 2H), 7.93-7.75 (m, 1H), 7.76-7.32 (m, 1H), 7.32-7.15 (m, 1H), 7.16-7.08 (m, 1H), 6.86-6.75 (m, 1H), 5.43-5.00 (m, 1H), 4.77-4.54 (m, 1H), 4.54-4.15 (m, 1H), 4.17-3.23 (m, 8H), 3.15-2.96 (m, 1H), 2.43-2.24 (m, 2H), 2.18-2.00 (m, 2H), 1.91-1.73 (m, 2H), 1.63-1.50 (m, 3H), 1.50-1.30 (m, 2H) |
| 1640 | 9.73-9.21 (m, 1H), 8.46-8.17 (m, 2H), 7.87-7.77 (m, 1H), 7.77-7.53 (m, 1H), 7.32-7.05 (m, 1H), 6.88-6.64 (m, 1H), 5.53-5.12 (m, 1H), 4.88-4.50 (m, 1H), 4.07-3.11 (m, 10H), 3.10-2.96 (m, 2H), 2.90-2.64 (m, 4H), 2.45-2.29 (m, 1H), 2.18-1.97 (m, 2H), 1.91-1.76 (m, 2H), 1.54-1.33 (m, 2H) |
| 1641 | 9.42-8.96 (m, 1H), 8.79-8.52 (m, 1H), 8.12-8.02 (m, 1H), 8.02-7.92 (m, 1H), 7.92-7.82 (m, 1H), 7.72-7.43 (m, 1H), 7.39-7.23 (m, 1H), 7.09-6.87 (m, 1H), 5.53-5.12 (m, 1H), 4.82-4.46 (m, 1H), 4.19-3.46 (m, 5H), 2.87-2.71 (m, 4H), 2.69-2.57 (m, 4H), 2.41-2.33 (m, 3H), 2.13-1.96 (m, 4H), 1.94-1.84 (m, 2H) |
| 1642 | 9.42-8.91 (m, 1H), 8.80-8.54 (m, 1H), 8.15-8.00 (m, 1H), 8.01-7.93 (m, 1H), 7.93-7.78 (m, 1H), 7.72-7.42 (m, 1H), 7.40-7.18 (m, 1H), 7.06-6.88 (m, 1H), 5.52-5.17 (m, 1H), 4.94-4.43 (m, 1H), 4.23-3.45 (m, 7H), 3.24-2.82 (m, 2H), 2.70-2.56 (m, 4H), 2.41-2.28 (m, 3H), 2.11-1.92 (m, 4H) |
| 1643 | 9.39-8.98 (m, 1H), 8.73-8.55 (m, 1H), 8.11-8.02 (m, 1H), 8.02-7.93 (m, 1H), 7.93-7.81 (m, 1H), 7.69-7.42 (m, 1H), 7.42-7.19 (m, 1H), 7.05-6.86 (m, 1H), 5.49-5.14 (m, 1H), 4.80-4.43 (m, 1H), 4.28-3.55 (m, 6H), 2.70-2.56 (m, 4H), 2.44-2.32 (m, 3H), 2.12-1.95 (m, 4H), 1.64-1.43 (m, 6H) |
| 1645 | 8.75-8.50 (m, 1H), 8.14-8.02 (m, 1H), 8.02-7.92 (m, 1H), 7.92-7.84 (m, 1H), 7.40-7.21 (m, 1H), 7.13-6.88 (m, 1H), 5.56-5.16 (m, 1H), 4.80-4.49 (m, 1H), 3.95-3.73 (m, 6H), 2.70-2.57 (m, 4H), 2.43-2.32 (m, 3H), 2.08-1.95 (m, 4H), 1.55-1.36 (m, 6H) |
| 1646 | 8.79-8.46 (m, 1H), 8.17-7.76 (m, 3H), 7.61-7.39 (m, 3H), 7.39-7.21 (m, 3H), 7.06-6.89 (m, 1H), 5.53-5.10 (m, 1H), 4.90-4.52 (m, 1H), 4.12-3.33 (m, 5H), 2.74-2.57 (m, 3H), 2.45-2.29 (m, 4H), 2.12-1.94 (m, 4H) |
| 1647 | 9.63-9.08 (m, 1H), 8.77-8.46 (m, 1H), 8.11-8.04 (m, 1H), 8.04-7.92 (m, 1H), 7.92-7.80 (m, 1H), 7.80-7.53 (m, 1H), 7.45-7.24 (m, 1H), 7.08-6.75 (m, 1H), 5.43-5.10 (m, 1H), 4.81-4.46 (m, 1H), 4.46-4.22 (m, 1H), 4.09-3.57 (m, 4H), 3.15-2.87 (m, 2H), 2.47-2.28 (m, 3H), 2.19-2.04 (m, 2H), 1.95-1.80 (m, 5H), 1.62-1.52 (m, 3H), 1.52-1.31 (m, 2H) |
| 1648 | 9.55-9.16 (m, 1H), 8.74-8.58 (m, 1H), 8.10-8.02 (m, 1H), 8.02-7.91 (m, 1H), 7.91-7.81 (m, 1H), 7.81-7.49 (m, 1H), 7.43-7.27 (m, 1H), 7.05-6.91 (m, 1H), 5.49-5.13 (m, 1H), 4.89-4.44 (m, 1H), 4.09-3.52 (m, 6H), 3.29-3.10 (m, 1H), 3.10-2.96 (m, 2H), 2.96-2.65 (m, 4H), 2.46-2.28 (m, 4H), 2.20-2.01 (m, 2H), 2.01-1.76 (m, 2H), 1.59-1.27 (m, 2H) |
| 1649 | 9.58-9.18 (m, 1H), 8.81-8.54 (m, 1H), 8.12-7.99 (m, 1H), 8.03-7.93 (m, 1H), 7.92-7.81 (m, 1H), 7.78-7.48 (m, 1H), 7.42-7.25 (m, 1H), 7.08-6.89 (m, 1H), 5.59-5.15 (m, 1H), 4.92-4.52 (m, 1H), 4.36-3.44 (m, 6H), 3.12-2.79 (m, 3H), 2.45-2.32 (m, 4H), 2.20-2.02 (m, 2H), 2.02-1.76 (m, 4H), 1.59-1.26 (m, 2H) |

TABLE 62-continued

NMR data for selected examples from Tables 57-61

| Ex | NMR Assignments (500 MHz, DMSO-d6) δ |
|---|---|
| 1651 | 9.52-9.11 (m, 1H), 8.79-8.39 (m, 1H), 8.19-8.03 (m, 1H), 8.03-7.92 (m, 1H), 7.92-7.77 (m, 1H), 7.77-7.50 (m, 1H), 7.41-7.24 (m, 1H), 7.08-6.86 (m, 1H), 5.50-5.09 (m, 1H), 4.80-4.40 (m, 1H), 4.23-3.53 (m, 5H), 3.10-2.97 (m, 2H), 2.45-2.29 (m, 4H), 2.15-1.99 (m, 2H), 1.99-1.83 (m, 2H), 1.62-1.33 (m, 8H) |
| 1652 | 9.54-9.17 (m, 1H), 8.78-8.48 (m, 1H), 8.13-8.02 (m, 1H), 8.02-7.93 (m, 1H), 7.93-7.82 (m, 1H), 7.82-7.49 (m, 1H), 7.43-7.21 (m, 1H), 7.07-6.91 (m, 1H), 5.48-5.10 (m, 1H), 4.89-4.44 (m, 1H), 4.44-3.52 (m, 6H), 3.14-2.94 (m, 2H), 2.47-2.31 (m, 4H), 2.16-2.00 (m, 2H), 1.97-1.80 (m, 2H), 1.54-1.34 (m, 8H) |
| 1654 | 9.51-9.16 (m, 1H), 8.93-8.46 (m, 1H), 8.15-7.79 (m, 3H), 7.79-7.60 (m, 1H), 7.58-7.43 (m, 2H), 7.39-7.26 (m, 3H), 7.04-6.83 (m, 1H), 5.49-5.12 (m, 1H), 4.95-4.51 (m, 1H), 4.13-3.24 (m, 6H), 3.14-2.95 (m, 2H), 2.46-2.27 (m, 4H), 2.16-2.00 (m, 2H), 1.93-1.77 (m, 2H), 1.55-1.30 (m, 2H) |
| 1656 | 9.43-8.95 (m, 1H), 8.79-8.60 (m, 1H), 7.94-7.75 (m, 2H), 7.76-7.38 (m, 1H), 7.34-7.22 (m, 1H), 6.88-6.73 (m, 1H), 5.50-5.14 (m, 1H), 4.92-4.50 (m, 1H), 4.27-3.41 (m, 7H), 3.20-2.85 (m, 2H), 2.72-2.58 (m, 4H), 2.48-2.37 (m, 3H), 2.14-1.93 (m, 4H) |
| 1657 | 9.43-9.01 (m, 1H), 8.73-8.51 (m, 1H), 7.92-7.86 (m, 1H), 7.86-7.76 (m, 1H), 7.74-7.36 (m, 1H), 7.31-7.09 (m, 1H), 6.89-6.77 (m, 1H), 5.45-5.13 (m, 1H), 4.82-4.47 (m, 1H), 4.34-3.52 (m, 6H), 2.76-2.57 (m, 3H), 2.46-2.34 (m, 4H), 2.09-1.96 (m, 4H), 1.54-1.38 (m, 6H) |
| 1658 | 9.52-8.98 (m, 1H), 8.79-8.56 (m, 1H), 7.92-7.74 (m, 1H), 7.75-7.34 (m, 1H), 7.33-7.17 (m, 1H), 6.90-6.70 (m, 1H), 5.44-5.12 (m, 1H), 4.70-4.45 (m, 1H), 4.42-4.24 (m, 1H), 4.16-3.30 (m, 10H), 2.54-2.46 (m, 4H), 2.13-1.96 (m, 4H), 1.60-1.44 (m, 3H) |
| 1659 | 9.40-9.11 (m, 1H), 8.78-8.46 (m, 1H), 7.93-7.76 (m, 2H), 7.72-7.44 (m, 1H), 7.34-7.11 (m, 1H), 6.89-6.73 (m, 1H), 5.46-5.10 (m, 1H), 4.84-4.40 (m, 1H), 4.14-3.09 (m, 6H), 2.71-2.58 (m, 3H), 2.45-2.32 (m, 4H), 2.19-2.08 (m, 2H), 2.08-1.96 (m, 5H), 1.00-0.80 (m, 6H) |
| 1660 | 9.49-9.06 (m, 1H), 8.78-8.53 (m, 1H), 7.97-7.84 (m, 1H), 7.84-7.76 (m, 1H), 7.75-7.45 (m, 1H), 7.36-7.11 (m, 1H), 6.97-6.61 (m, 1H), 5.49-5.11 (m, 1H), 4.82-4.47 (m, 1H), 4.32-3.27 (m, 6H), 2.74-2.60 (m, 4H), 2.46-2.37 (m, 3H), 2.12-1.94 (m, 4H), 1.63-1.39 (m, 6H) |

TABLE 63

| Ex | Name | R¹ | R² | Obs. MS Ion | LC/MS RT, min (method) |
|---|---|---|---|---|---|
| 1661 | 5-[4-amino-5-(trifluoromethyl)pyrrolo[2,1-f][1,2,4]triazin-7-yl]-N-{4-fluoro-1-[4,4,4-trifluoro-3-hydroxy-3-(trifluoromethyl)butanoyl]piperidin-3-yl}-2-methoxypyridine-3-carboxamide | CF₃ | C(CF₃)₂OH | 662.1 | 2.11 (2) |
| 1662 | 5-{4-amino-5-[(4,4-difluoropiperidin-1-yl)methyl]pyrrolo[2,1-f][1,2,4]triazin-7-yl}-N-[1-(3,3-difluorocyclobutanecarbonyl)-4-fluoropiperidin-3-yl]-4-methoxypyridine-3-carboxamide | CH₂-(4,4-difluoropiperidin-1-yl) | 3,3-difluorocyclobutyl | 637.2 | 2.16 (1) |

TABLE 63-continued

| Ex | Name | R¹ | R² | Obs. MS Ion | LC/MS RT, min (method) |
|---|---|---|---|---|---|
| 1663 | 5-{4-amino-5-[(4,4-difluoropiperidin-1-yl)methyl]pyrrolo[2,1-f][1,2,4]triazin-7-yl}-N-{4-fluoro-1-[(2R)-3,3,3-trifluoro-2-hydroxy-2-methylpropanoyl]piperidin-3-yl}-2-methoxypyridine-3-carboxamide | (4,4-difluoropiperidin-1-ylmethyl) | (2R)-3,3,3-trifluoro-2-hydroxy-2-methylpropanoyl | 659.2 | 1.53 (2) |
| 1664 | 5-{4-amino-5-[(4,4-difluoropiperidin-1-yl)methyl]pyrrolo[2,1-f][1,2,4]triazin-7-yl}-N-[4-fluoro-1-(2-fluorobenzoyl)piperidin-3-yl]-2-methoxypyridine-3-carboxamide | (4,4-difluoropiperidin-1-ylmethyl) | 2-fluorobenzoyl | 641.2 | 2.18 (1) |
| 1665 | 5-{4-amino-5-[(4,4-difluoropiperidin-1-yl)methyl]pyrrolo[2,1-f][1,2,4]triazin-7-yl}-N-{4-fluoro-1-[4,4,4-trifluoro-3-hydroxy-3-(trifluoromethyl)butanoyl]piperidin-3-yl}-2-methoxypyridine-3-carboxamide | (4,4-difluoropiperidin-1-ylmethyl) | 4,4,4-trifluoro-3-hydroxy-3-(trifluoromethyl)butanoyl | 727.2 | 1.81 (2) |

Compounds in Table 63 were prepared by the methods detailed in Example 1579. The products were isolated as a mixture of diastereomers.

Example 1666: 5-(4-amino-5-(trifluoromethyl)pyrrolo[2,1-f][1,2,4]triazin-7-yl)-N-((3R,4S)-4-fluoro-1-(thiazole-5-carbonyl)pyrrolidin-3-yl)-2-methoxynicotinamide

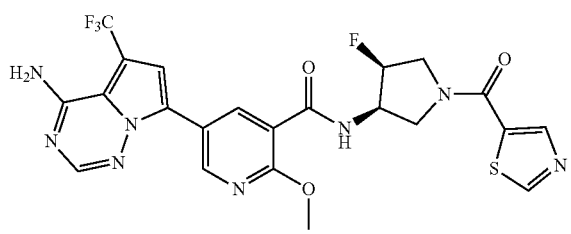 [SMILES: COc1ncc(-c2cc(C(F)(F)F)c3c(N)ncnn23)cc1C(=O)N[C@@H]1CN(C(=O)c2cncs2)C[C@@H]1F]

A mixture of 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide (10 mg, 0.023 mmol), thiazole-5-carboxylic acid (4.41 mg, 0.034 mmol), HATU (12.98 mg, 0.034 mmol) and Hünig's Base (15.90 µl, 0.091 mmol) in DMF (228 µl) was stirred at rt for 12 h. The crude reaction mixture was purified by prep HPLC to give 5-(4-amino-5-(trifluoromethyl)pyrrolo[2,1-f][1,2,4]triazin-7-yl)-N-((3R,4S)-4-fluoro-1-(thiazole-5-carbonyl)pyrrolidin-3-yl)-2-methoxynicotinamide (5.7 mg, 0.011 mmol, 46% yield) as a white solid.

MS ESI m/z 551.15 (M+H)+

$^1$H NMR (500 MHz, DMSO-$d_6$) δ 9.28 (s, 1H), 8.92 (s, 1H), 8.84-8.72 (m, 1H), 8.60 (br t, J=7.6 Hz, 1H), 8.41 (br d, J=14.3 Hz, 1H), 8.17 (br s, 1H), 7.61 (br s, 1H), 5.51-5.17 (m, 1H), 4.97-4.68 (m, 1H), 4.25 (br t, J=9.5 Hz, 1H), 4.05 (br d, J=9.8 Hz, 4H), 3.97-3.82 (m, 1H).

TABLE 64

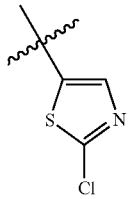 [SMILES: *c1cnc(Cl)s1]

| Ex | Name | R | Obs. MS Ion | NMR Assignments (500 MHz, DMSO-d6) δ or LC/MS RT (Method) |
|---|---|---|---|---|
| 1667 | 5-(4-amino-5-(trifluoromethyl)pyrrolo[2,1-f][1,2,4]triazin-7-yl)-N-((3R,4S)-1-(2-chlorothiazole-5-carbonyl)-4-fluoropyrrolidin-3-yl)-2-methoxynicotinamide | 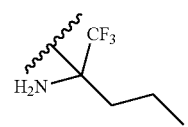 | 585.15 (M + H)+ | 8.92 (s, 1H), 8.83 (s, 1H), 8.76 (s, 1H), 8.59 (br t, J = 8.9 Hz, 1H), 8.24-8.14 (m, 2H), 7.61 (s, 1H), 5.57-5.22 (m, 1H), 5.02-4.67 (m, 1H), 4.37-4.12 (m, 1H), 4.05 (br d, J = 12.8 Hz, 3H), 3.95-3.73 (m, 1H), 3.53-3.40 (m, 1H). |
| 1668 | N-((3R,4S)-1-(2-amino-2-(trifluoromethyl)pentanoyl)-4-fluoropyrrolidin-3-yl)-5-(4-amino-5-(trifluoromethyl)pyrrolo[2,1-f][1,2,4]triazin-7-yl)-2-methoxynicotinamide | 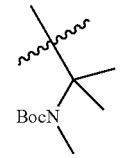 | 607.25 (M + H)+ | 8.90 (br s, 1H), 8.84-8.72 (m, 1H), 8.64-8.43 (m, 1H), 8.15 (s, 1H), 7.59 (s, 1H), 5.38-5.08 (m, 1H), 4.81 (br s, 1H), 4.73-4.50 (m, 1H), 4.03 (br s, 2H), 3.72-3.60 (m, 1H) |
| 1669 | tert-butyl (1-((3R,4S)-3-(5-(4-amino-5-(trifluoromethyl)pyrrolo[2,1-f][1,2,4]triazin-7-yl)-2-methoxynicotinamido)-4-fluoropyrrolidin-1-yl)-2-methyl-1-oxopropan-2-yl)(methyl)carbamate | 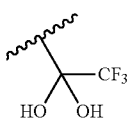 | 637.36 (M − H)+ | 8.91 (br s, 1H), 8.76 (br s, 1H), 8.64-8.50 (m, 1H), 8.17 (s, 1H), 7.61 (s, 1H), 5.46-5.14 (m, 1H), 4.80-4.46 (m, 1H), 4.02 (br s, 3H), 3.93-3.85 (m, 1H), 3.59-3.51 (m, 1H), 3.30 (br s, 3H), 3.14 (br t, J = 12.2 Hz, 1H), 2.89-2.76 (m, 3H) |
| 1670 | 5-(4-amino-5-(trifluoromethyl)pyrrolo[2,1-f][1,2,4]triazin-7-yl)-N-((3R,4S)-4-fluoro-1-(3,3,3-trifluoro-2,2-dihydroxypropanoyl)pyrrolidin-3-yl)-2-methoxynicotinamide | 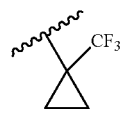 [SMILES: *C1(C(F)(F)F)CC1] | 582.05 (M + H)+ | 8.93 (s, 1H), 8.77 (br s, 1H), 8.66-8.45 (m, 1H), 8.18 (s, 1H), 7.63 (s, 1H), 5.45-5.17 (m, 1H), 4.77-4.59 (m, 1H), 4.54-4.43 (m, 1H), 4.40-4.28 (m, 1H), 4.04 (s, 3H), 3.97-3.87 (m, 1H), 3.84-3.67 (m, 1H), 3.61-3.48 (m, 1H), 3.17 (d, J = 5.2 Hz, 1H). |
| 1671 | 5-(4-amino-5-(trifluoromethyl)pyrrolo[2,1-f][1,2,4]triazin-7-yl)-N-((3R,4S)-4-fluoro-1-(1-(trifluoromethyl)cyclopropane-1-carbonyl)pyrrolidin-3-yl)-2-methoxynicotinamide | 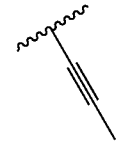 [SMILES: *C#CC] | 576.05 (M + H)+ | LC/MS RT = 1.86 min (Method 2) |
| 1672 | 5-(4-amino-5-(trifluoromethyl)pyrrolo[2,1-f][1,2,4]triazin-7-yl)-N-((3R,4S)-1-(but-2-ynoyl)-4-fluoropyrrolidin-3-yl)-2-methoxynicotinamide | 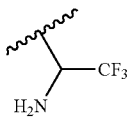 | 504.3 (M + H)+ | 8.93 (br s, 1H), 8.77 (br d, J = 17.7 Hz, 1H), 8.56 (br t, J = 6.9 Hz, 1H), 8.18 (s, 1H), 7.63 (s, 1H), 5.36 (br s, 1H), 5.26 (br s, 1H), 4.85-4.54 (m, 1H), 4.19-4.10 (m, 1H), 4.04 (br d, J = 6.7 Hz, 3H), 3.99-3.83 (m, 1H), 3.76-3.51 (m, 1H), 3.42-3.33 (m, 1H), 3.17 (d, J = 4.9 Hz, 1H), 2.04 (s, 3H) |
| 1673 | N-((3R,4S)-1-(2-amino-3,3,3-trifluoropropanoyl)-4-fluoropyrrolidin-3-yl)-5-(4-amino-5-(trifluoromethyl)pyrrolo[2,1-f][1,2,4]triazin-7-yl)-2-methoxynicotinamide | 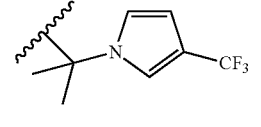 [SMILES: *C(C)(C)n1ccc(C(F)(F)F)c1] | 565.10 (M + H)+ | 9.01-8.90 (m, 1H), 8.86-8.74 (m, 1H), 8.63-8.46 (m, 1H), 8.18 (s, 1H), 7.63 (s, 1H), 5.50-5.17 (m, 1H), 4.92-4.68 (m, 1H), 4.50-4.24 (m, 1H), 4.13-4.01 (m, 3H), 3.96-3.88 (m, 1H), 3.84-3.65 (m, 1H), 3.47-3.30 (m, 1H) |
| 1674 | 5-(4-amino-5-(trifluoromethyl)pyrrolo[2,1-f][1,2,4]triazin-7-yl)-N-((3R,4S)-4-fluoro-1-(2-methyl-2-(4-(trifluoromethyl)-1H-imidazol-1-yl)propanoyl)pyrrolidin-3-yl)-2-methoxynicotinamide | 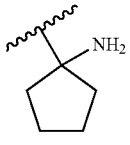 [SMILES: *C1(N)CCCC1] | 644.10 (M + H)+ | 8.91 (br s, 1H), 8.73 (br d, J = 18.6 Hz, 1H), 8.52-8.33 (m, 1H), 8.17 (br s, 1H), 8.12-7.92 (m, 2H), 7.61 (br s, 1H), 5.35-4.97 (m, 1H), 4.84-4.54 (m, 1H), 4.01 (br d, J = 15.9 Hz, 3H), 3.51-3.37 (m, 1H), 1.87-1.55 (m, 6H) |
| 1675 | 5-(4-amino-5-(trifluoromethyl)pyrrolo[2,1-f][1,2,4]triazin-7-yl)-N-((3R,4S)-1-(1-aminocyclopentane-1-carbonyl)-4-fluoropyrrolidin-3-yl)-2-methoxynicotinamide | | 551.20 (M + H)+ | 8.93 (s, 1H), 8.86-8.76 (m, 1H), 8.54 (br d, J = 7.0 Hz, 1H), 8.18 (br s, 4H), 7.62 (s, 1H), 7.26 (s, 2H), 7.16 (s, 2H), 7.05 (s, 2H), 5.44-5.19 (m, 1H), 4.18-3.99 (m, 4H), 2.42-2.24 (m, 2H), 1.90 (br s, 6H). |

TABLE 64-continued

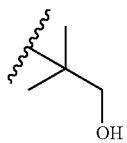 [SMILES: *C(C)(C)CO]

| Ex | Name | R | Obs. MS Ion | NMR Assignments (500 MHz, DMSO-d6) δ or LC/MS RT (Method) |
|---|---|---|---|---|
| 1676 | 5-(4-amino-5-(trifluoromethyl)pyrrolo[2,1-f][1,2,4]triazin-7-yl)-N-((3R,4S)-4-fluoro-1-(3-hydroxy-2,2-dimethylpropanoyl)pyrrolidin-3-yl)-2-methoxynicotinamide | 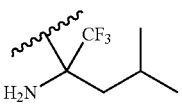 | 540.15 (M + H)+ | 8.93 (s, 1H), 8.80 (br s, 1H), 8.50 (br d, J = 7.0 Hz, 1H), 8.18 (s, 1H), 7.62 (s, 1H), 5.32 (br s, 1H), 5.21 (br s, 1H), 4.78-4.59 (m, 1H), 4.05 (s, 3H), 3.56-3.40 (m, 1H), 1.16 (s, 3H), 1.14 (s, 3H). |
| 1677 | N-((3R,4S)-1-(2-amino-4-methyl-2-(trifluoromethyl)pentanoyl)-4-fluoropyrrolidin-3-yl)-5-(4-amino-5-(trifluoromethyl)pyrrolo[2,1-f][1,2,4]triazin-7-yl)-2-methoxynicotinamide | 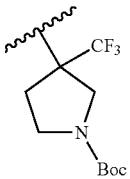 [SMILES: *C1(C(F)(F)F)CCN(C(=O)OC(C)(C)C)C1] | 621.1 (M + H)+ | 8.93 (br s, 1H), 8.86-8.70 (m, 1H), 8.59-8.43 (m, 1H), 8.18 (s, 1H), 7.61 (s, 1H), 5.43-5.08 (m, 1H), 4.77-4.42 (m, 2H), 4.05 (br s, 3H), 3.87-3.58 (m, 1H), 2.05-1.76 (m, 2H), 1.60 (br d, J = 8.5 Hz, 1H), 1.02-0.71 (m, 6H). |
| 1678 | tert-butyl 3-((3R,4S)-3-(5-(4-amino-5-(trifluoromethyl)pyrrolo[2,1-f][1,2,4]triazin-7-yl)-2-methoxynicotinamido)-4-fluoropyrrolidine-1-carbonyl)-3-(trifluoromethyl)pyrrolidine-1-carboxylate | 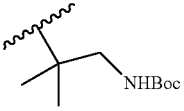 [SMILES: *C(C)(C)CNC(=O)OC(C)(C)C] | 703.2 (M − H)− | 8.93 (br s, 1H), 8.88-8.73 (m, 1H), 8.62-8.36 (m, 1H), 8.18 (s, 1H), 7.62 (s, 1H), 5.45-5.21 (m, 1H), 4.91-4.65 (m, 1H), 4.16-4.01 (m, 4H), 3.95-3.75 (m, 3H), 1.41 (br s, 9H). |
| 1679 | tert-butyl (3-((3R,4S)-3-(5-(4-amino-5-(trifluoromethyl)pyrrolo[2,1-f][1,2,4]triazin-7-yl)-2-methoxynicotinamido)-4-fluoropyrrolidin-1-yl)-2,2-dimethyl-3-oxopropyl)carbamate | 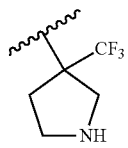 [SMILES: *C1(C(F)(F)F)CCNC1] | 637.3 (M − H)− | 8.93 (s, 1H), 8.80 (br s, 1H), 8.49 (br s, 1H), 8.19 (br s, 1H), 7.62 (s, 1H), 6.57 (br s, 1H), 5.46-5.20 (m, 1H), 4.87-4.62 (m, 1H), 4.87-4.62 (m, 1H), 4.05 (s, 4H), 1.38 (s, 10H), 1.14 (br s, 6H). |
| 1680 | 5-(4-amino-5-(trifluoromethyl)pyrrolo[2,1-f][1,2,4]triazin-7-yl)-N-((3R,4S)-4-fluoro-1-(3-(trifluoromethyl)pyrrolidine-3-carbonyl)pyrrolidin-3-yl)-2-methoxynicotinamide | 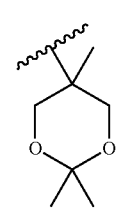 | 605.1 (M + H)+ | 8.99-8.91 (m, 1H), 8.86-8.74 (m, 1H), 8.52 (br s, 1H), 8.18 (s, 1H), 7.62 (s, 1H), 5.35 (br s, 1H), 5.24 (br s, 1H), 4.85-4.62 (m, 1H), 4.12-3.72 (m, 6H), 3.63-3.43 (m, 1H), 2.92-2.72 (m, 1H), 2.20 (br d, J = 17.1 Hz, 2H). |
| 1681 | 5-(4-amino-5-(trifluoromethyl)pyrrolo[2,1-f][1,2,4]triazin-7-yl)-N-((3R,4S)-4-fluoro-1-(2,2,5-trimethyl-1,3-dioxane-5-carbonyl)pyrrolidin-3-yl)-2-methoxynicotinamide | | 596.15 (M + H)+ | 8.93 (s, 1H), 8.80 (br s, 1H), 8.49 (br d, J = 6.7 Hz, 1H), 8.18 (s, 1H), 7.62 (s, 1H), 5.45-5.12 (m, 1H), 4.87-4.57 (m, 1H), 4.21-4.02 (m, 6H), 3.73-3.56 (m, 2H), 1.36-1.12 (m, 12H). |

Compounds in Table 64 were prepared by the methods detailed in Example 1666. When diastereomers were separated, they are included as separate entries. If the stereochemistry is undefined, the product was isolated as a mixture of diastereomers. LC/MS retention time (RT) determined in minutes using Method 1, 2, 3, or 4 as indicated. The Methods are described in the Methods of Preparation section.

Example 1682: 5-(4-amino-5-(trifluoromethyl)pyr-rolo[2,1-f][1,2,4]triazin-7-yl)-N-((3R,4S)-4-fluoro-1-(2-methyl-3-oxobutan-2-yl)pyrrolidin-3-yl)-2-methoxynicotinamide

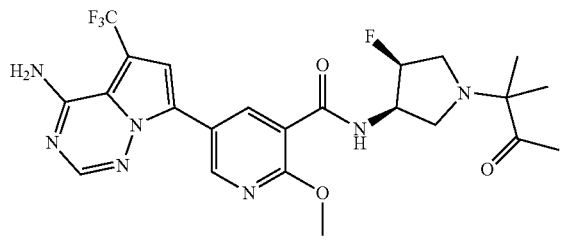 [SMILES: COc1ncc(-c2cc(C(F)(F)F)c3c(N)ncnn23)cc1C(=O)N[C@@H]1CN(C(C)(C)C(C)=O)C[C@@H]1F]

A mixture of 3-bromo-3-methylbutan-2-one (16.90 mg, 0.102 mmol), 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide (15 mg, 0.034 mmol) and potassium carbonate (9.44 mg, 0.068 mmol) in DMF (341 µl) was heated at 80° C. for 12 h. The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 7% B, 7-47% B over 20 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation to afford the title compound (2.0 mg, 2.7 mmol, 8% yield).

MS ESI m/z 524.2 (M+H)+

$^1$H NMR (500 MHz, DMSO-d$_6$) δ 9.00-8.87 (m, 1H), 8.82 (br d, J=9.5 Hz, 1H), 8.64-8.45 (m, 1H), 8.17 (s, 1H), 8.16-8.11 (m, 1H), 7.80 (br s, 1H), 7.68-7.59 (m, 1H), 7.24 (s, 1H), 7.14 (s, 1H), 7.03 (s, 1H), 5.49-5.24 (m, 1H), 4.82-4.53 (m, 1H), 4.15-3.95 (m, 3H).

Example 1683: (E)-5-(4-amino-5-(trifluoromethyl)pyrrolo[2,1-f][1,2,4]triazin-7-yl)-N-(3-(ethoxyimino)cyclopentyl)-2-methoxynicotinamide

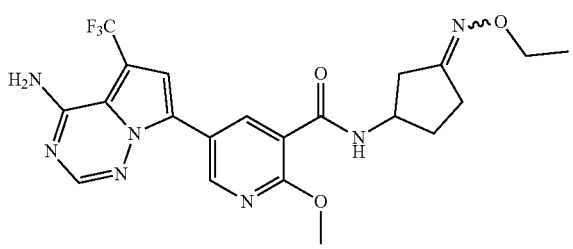 [SMILES: CCON=C1CCC(NC(=O)c2cc(-c3cc(C(F)(F)F)c4c(N)ncnn34)cnc2OC)C1]

1683A: A mixture of 5-(4-amino-5-(trifluoromethyl)pyrrolo[2,1-f][1,2,4]triazin-7-yl)-2-methoxynicotinic acid (120 mg, 0.340 mmol), 3-aminocyclopentan-1one, TFA salt (94 mg, 0.442 mmol), Hunig's base (237 µl, 1.359 mmol) and BOP (188 mg, 0.425 mmol) in DMF (1132 µl) was stirred at rt for 12 h. The crude product was purified by reverse phase preparative HPLC on a Luna C18 column (10 µM, 30×100 mm) eluting with 0-100% B (A: 95% water/5% acetonitrile/10 nM ammonium acetate, B: 5% water/95% acetonitrile/10 mM ammonium acetate) over 12 min to give 5-(4-amino-5-(trifluoromethyl)pyrrolo[2,1-f][1,2,4]triazin-7-yl)-2-methoxy-N-(3-oxocyclopentyl)nicotinamide (100 mg, 0.230 mmol, 68% yield) as a white solid.

MS ESI m/z 435.2 (M+H)+.

1683B: A mixture of 5-(4-amino-5-(trifluoromethyl)pyrrolo[2,1-f][1,2,4]triazin-7-yl)-2-methoxy-N-(3-oxocyclopentyl)nicotinamide (8 mg, 0.018 mmol) and O-ethylhydroxylamine hydrochloride (8.98 mg, 0.092 mmol) in methanol (61.4 µl) was heated at 75° C. for 1 h. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-m Mammonium acetate; Gradient: a 0-minute hold at 24% B, 24-64% B over 25 minutes, then a 5-minute hold at 100% B; Flow Rate: 20 mL/min; Column Temperature: 25 C. Fraction collection was triggered by MS and UV signals. Fractions containing the desired product were combined and dried via centrifugal evaporation to afford the title product (3.3 mg, 0.69 µmol, 37% yield).

MS ESI m/z 478.2 (M+H)+

$^1$H NMR (500 MHz, DMSO-d6) δ 8.90 (s, 1H), 8.66 (s, 1H), 8.34 (br d, J=6.7 Hz, 1H), 8.18 (s, 1H), 7.61 (s, 1H), 4.34 (br d, J=6.7 Hz, 1H), 4.13-3.96 (m, 5H), 3.32 (br s, 1H), 2.69 (br dd, J=16.3, 6.9 Hz, 1H), 2.45-2.33 (m, 2H), 2.19-1.98 (m, 1H), 1.79 (br dd, J=12.4, 7.5 Hz, 1H), 1.20-1.11 (m, 3H).

Example 1684: (E)-5-(4-amino-5-(trifluoromethyl)pyrrolo[2,1-f][1,2,4]triazin-7-yl)-N-(3-((benzyloxy)imino)cyclopentyl)-2-methoxynicotinamide

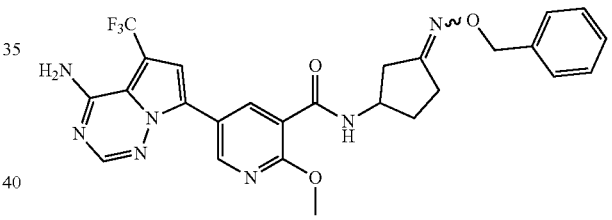

Prepared in the same fashion as Example 1683 to afford the title product (5.0 mg, 9.2 µmol, 52% yield)

ESI (m/z) 540.1 (M+H)+

$^1$H NMR (500 MHz, DMSO-d$_6$) δ 8.90 (s, 1H), 8.66 (s, 1H), 8.34 (br d, J=6.7 Hz, 1H), 8.17 (s, 1H), 7.61 (s, 1H), 7.42-7.25 (m, 5H), 5.03 (s, 2H), 4.43-4.30 (m, 1H), 4.00 (s, 3H), 2.67 (br d, J=6.1 Hz, 2H), 2.47-2.39 (m, 2H), 2.14-1.98 (m, 1H), 1.88-1.67 (m, 1H).

Example 1685: 5-(4-amino-5-(trifluoromethyl)pyrrolo[2,1-f][1,2,4]triazin-7-yl)-N-(5-benzyl-1,3,4-oxadiazol-2-yl)-2-methoxynicotinamide

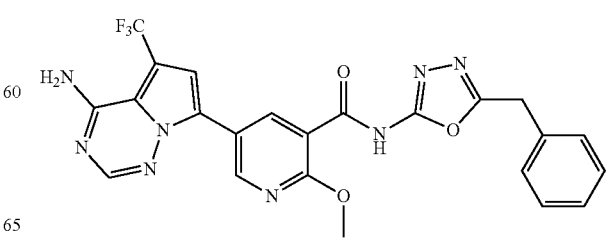

A mixture of 5-(4-amino-5-(trifluoromethyl)pyrrolo[2,1-f][1,2,4]triazin-7-yl)-2-methoxynicotinic acid (10 mg, 0.028 mmol), BOP (15.65 mg, 0.035 mmol), 5-benzyl-1,3,4-oxadiazol-2-amine (5.95 mg, 0.034 mmol) and Hunig's base (14.83 µl, 0.085 mmol) in DMF (283 µl) was stirred at rt for 12 h. The crude material was purified via preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 27% B, 27-67% B over 20 minutes, then a 5-minute hold at 100% B; Flow Rate: 20 mL/min; Column Temperature: 25 C. Fraction collection was triggered by MS signals. Fractions containing the desired product were combined and dried via centrifugal evaporation. give the title compound (4 mg, 16.19 µmol, 22% yield).

MS ESI m/z 511.1 (M+H)$^+$

1H NMR (500 MHz, DMSO-d$_6$) δ 9.06-8.96 (m, 1H), 8.71 (s, 1H), 8.24-8.07 (m, 1H), 7.68-7.58 (m, 1H), 7.43-7.24 (m, 5H), 4.27 (s, 2H), 4.10-3.92 (m, 4H).

Example 1686: 5-(4-amino-5-(trifluoromethyl)pyrrolo[2,1-f][1,2,4]triazin-7-yl)-N-(5-benzylthiazol-2-yl)-2-methoxynicotinamide

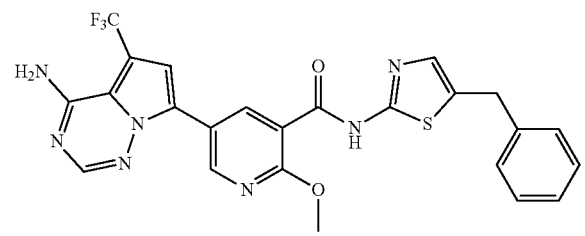 [SMILES: COc1ncc(-c2cc(C(F)(F)F)c3c(N)ncnn23)cc1C(=O)Nc1ncc(Cc2ccccc2)s1]

Prepared in the same fashion as Example 1685 to afford the title product (6.0 mg, 11.4 µmol, 41% yield).

MS ESI m/z 526.1 (M+H)$^+$ $^1$H NMR (500 MHz, DMSO-d6) δ 9.00 (s, 1H), 8.74 (s, 1H), 8.18 (s, 1H), 7.65 (s, 1H), 7.41-7.15 (m, 7H), 4.14 (s, 2H), 4.04 (s, 3H).

Example 1687: 5-(4-amino-5-(trifluoromethyl)pyrrolo[2,1-f][1,2,4]triazin-7-yl)-N-((1SR,3RS)-3-(4-bromophenyl)cyclopentyl)-2-methoxynicotinamide

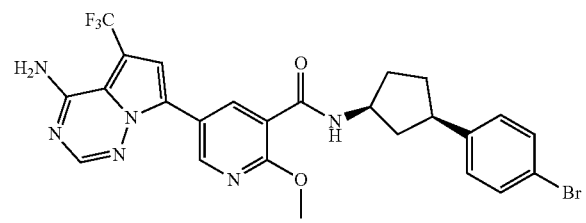 [SMILES: COc1ncc(-c2cc(C(F)(F)F)c3c(N)ncnn23)cc1C(=O)N[C@H]1CC[C@@H](c2ccc(Br)cc2)C1]

Prepared in the same fashion as Example 16985 to afford the title product (15 mg, 26.1 µmol, 62% yield).

MS ESI m/z 575.0 (M+H)$^+$ $^1$H NMR (500 MHz, DMSO-d$_6$) δ 8.90 (s, 1H), 8.66 (d, J=2.1 Hz, 1H), 8.36 (br d, J=7.0 Hz, 1H), 8.18 (s, 1H), 7.62 (s, 1H), 7.49 (br d, J=8.5 Hz, 2H), 7.26 (br d, J=8.2 Hz, 2H), 4.46 (br d, J=3.7 Hz, 1H), 4.03 (s, 3H), 2.30-1.90 (m, 4H), 1.78-1.42 (m, 2H).

Example 1688: 5-(4-amino-5-(trifluoromethyl)pyrrolo[2,1-f][1,2,4]triazin-7-yl)-2-methoxy-N-(3-phenylcyclopentyl)nicotinamide

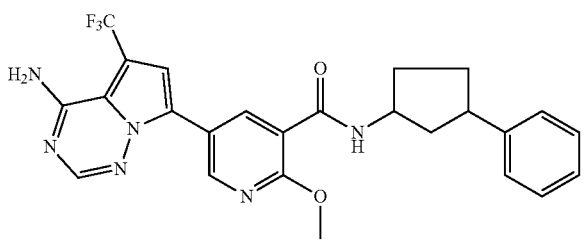 [SMILES: COc1ncc(-c2cc(C(F)(F)F)c3c(N)ncnn23)cc1C(=O)NC1CCC(c2ccccc2)C1]

Prepared in the same fashion as Example 1685 to afford the title product (18 mg, 36.3 µmol, 86% yield).

MS ESI m/z 497.15 (M+H)$^+$ $^1$H NMR (500 MHz, DMSO-d$_6$) δ 8.90 (s, 1H), 8.68 (dd, J=9.0, 2.0 Hz, 1H), 8.43-8.30 (m, 1H), 8.18 (s, 1H), 7.62 (s, 1H), 7.39-7.27 (m, 4H), 7.20 (br d, J=6.1 Hz, 1H), 4.40 (br s, 1H), 4.03 (d, J=4.6 Hz, 3H), 3.27-3.18 (m, 1H), 2.46-2.39 (m, 1H), 2.23 (br dd, J=8.7, 3.5 Hz, 1H), 2.18-1.95 (m, 2H), 1.80-1.60 (m, 3H).

Example 1689: 5-(4-amino-5-(trifluoromethyl)pyrrolo[2,1-f][1,2,4]triazin-7-yl)-2-methoxy-N-(3-phenylcyclohexyl)nicotinamide

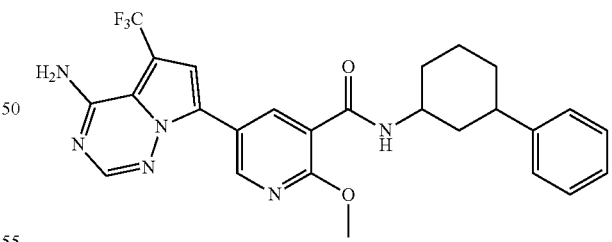

Prepared in the same fashion as Example 1685 to afford the title product (5.2 mg, 10.2 µmol, 36% yield).

$^1$H NMR (500 MHz, DMSO-d$_6$) δ 9.00-8.85 (m, 1H), 8.78-8.64 (m, 1H), 8.40 (br, d, J=7.3 Hz, 1H), 8.22-8.13 (m, 2H), 7.69-7.60 (m, 1H), 7.38-7.24 (m, 4H), 7.22-7.13 (m, 1H), 4.29 (br s, 1H), 4.09 (s, 1H), 4.01 (s, 2H), 3.97-3.90 (m, 1H), 2.88 (br s, 1H), 2.69 (br t, J=11.6 Hz, 1H), 2.09-1.67 (m, 5H), 1.57-1.32 (m, 3H).

Example 1690: 5-(4-amino-5-(trifluoromethyl)pyr-rolo[2,1-f][1,2,4]triazin-7-yl)-N-(3-hydroxy-3-phe-nylcyclopentyl)-2-methoxynicotinamide

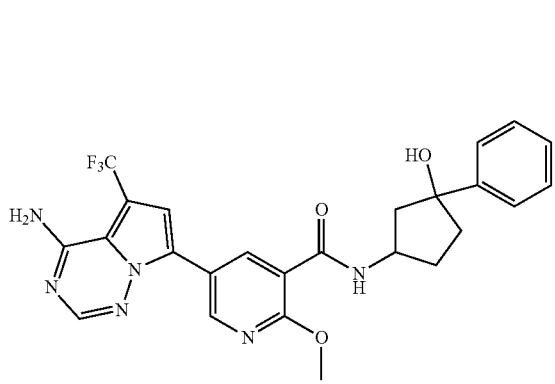 [SMILES: COc1ncc(-c2cc(C(F)(F)F)c3c(N)ncnn23)cc1C(=O)NC1CCC(O)(c2ccccc2)C1]

Prepared in the same fashion as Example 1685 to afford the title product (11 mg, 21.5 μmol, 51% yield).

MS ESI m/z 511.05 (M−H)⁻

$^1$H NMR (500 MHz, DMSO-d$_6$) δ 8.97 (br d, J=8.5 Hz, 1H), 8.93-8.85 (m, 2H), 8.15 (s, 1H), 7.57 (s, 1H), 7.51 (br d, J=7.6 Hz, 2H), 7.34 (br t, J=7.5 Hz, 2H), 7.27-7.16 (m, 1H), 5.46 (s, 1H), 4.66 (br d, J=2.7 Hz, 1H), 4.08 (s, 3H), 3.58 (br s, 2H), 2.31 (br dd, J=13.7, 8.2 Hz, 2H), 2.15-1.80 (m, 4H).

Example 1691: 5-(4-amino-5-(trifluoromethyl)pyr-rolo[2,1-f][1,2,4]triazin-7-yl)-2-methoxy-N-(3-phe-nylcycloheptyl)nicotinamide

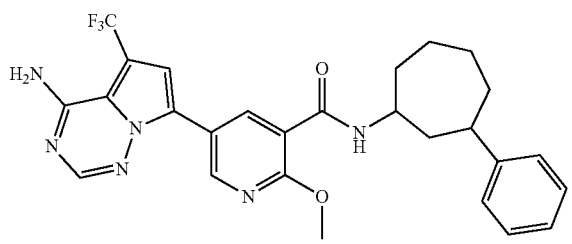 [SMILES: COc1ncc(-c2cc(C(F)(F)F)c3c(N)ncnn23)cc1C(=O)NC1CCCCC(c2ccccc2)C1]

Prepared in the same fashion as Example 1685 to afford the title product (13 mg, 24.8 μmol, 59% yield).

MS ESI m/z 525.2 (M+H)⁺

$^1$H NMR (500 MHz, DMSO-d$_6$) δ 8.88 (br d, J=4.6 Hz, 1H), 8.66 (dd, J=6.3, 2.3 Hz, 1H), 8.29 (br d, J=7.6 Hz, 1H), 8.20 (br d, J=7.6 Hz, 1H), 8.16 (s, 1H), 7.59 (d, J=5.2 Hz, 1H), 7.34-7.22 (m, 4H), 7.20-7.12 (m, 1H), 4.29 (br s, 1H), 2.96 (br t, J=10.5 Hz, 1H), 2.87-2.74 (m, 1H), 2.20-1.43 (m, 11H).

Example 1692: 5-(4-amino-5-(trifluoromethyl)pyr-rolo[2,1-f][1,2,4]triazin-7-yl)-2-methoxy-N-((1RS, 3RS)-3-phenylcyclohexyl)nicotinamide

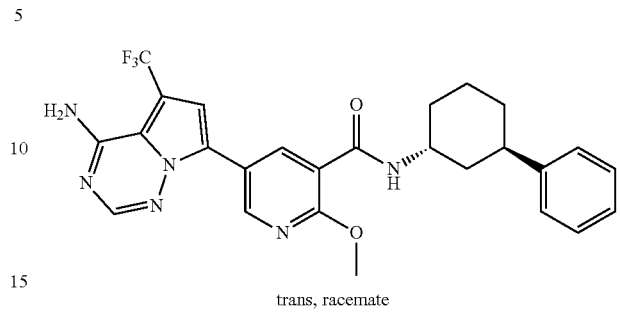

trans, racemate

Prepared in the same fashion as Example 1685 to afford the title product (10 mg, 19.6 μmol, 47% yield).

MS ESI m/z 509.2 (M−H)⁻

$^1$H NMR (500 MHz, DMSO-d6) δ 8.92 (d, J=2.1 Hz, 1H), 8.74 (d, J=2.1 Hz, 1H), 8.38 (br d, J=7.0 Hz, 1H), 8.18 (s, 1H), 7.62 (s, 1H), 7.36-7.24 (m, 4H), 7.22-7.11 (m, 1H), 4.30 (br d, J=3.1 Hz, 1H), 4.10 (s, 3H), 2.88 (br t, J=11.7 Hz, 1H), 2.05-1.47 (m, 9H).

Example 1693: 5-(4-amino-5-(trifluoromethyl)pyr-rolo[2,1-f][1,2,4]triazin-7-yl)-2-methoxy-N-((1SR, 3RS)-3-phenylcyclohexyl)nicotinamide

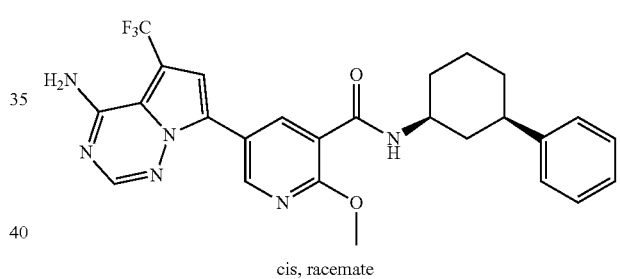

cis, racemate

Prepared in the same fashion as Example 1685 to afford the title product (8 mg, 15.7 μmol, 37% yield).

MS ESI m/z 511.10 (M+H)⁺

$^1$H NMR (500 MHz, DMSO-d$_6$) δ 8.89 (d, J=2.1 Hz, 1H), 8.68 (d, J=2.1 Hz, 1H), 8.24-8.08 (m, 2H), 7.60 (s, 1H), 7.35-7.25 (m, 4H), 7.23-7.14 (m, 1H), 4.02 (s, 3H), 2.69 (br t, J=12.2 Hz, 1H), 2.12-1.76 (m, 4H), 1.62-1.27 (m, 4H).

Example 1694: 5-(4-amino-5-(trifluoromethyl)pyr-rolo[2,1-f][1,2,4]triazin-7-yl)-2-methoxy-N-(1-phe-nylpiperidin-3-yl)nicotinamide

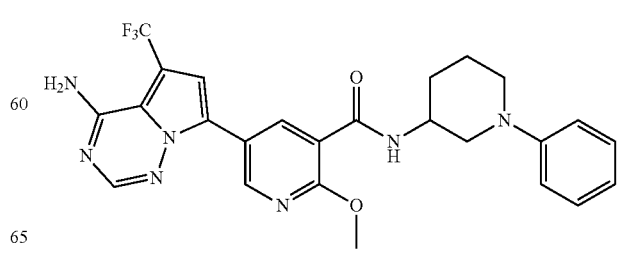

Prepared in the same fashion as Example 1685 to afford the title product (7 mg, 13.7 μmol, 33% yield).

MS ESI m/z 512.1 (M+H)+

$^1$H NMR (500 MHz, DMSO-d$_6$) δ 8.91 (d, J=2.1 Hz, 1H), 8.79 (d, J=2.1 Hz, 1H), 8.34 (br d, J=7.6 Hz, 1H), 8.18 (s, 1H), 7.61 (s, 1H), 7.23 (t, J=7.8 Hz, 2H), 6.99 (br d, J=8.2 Hz, 2H), 6.78 (t, J=7.2 Hz, 1H), 4.09 (br d, J=3.7 Hz, 1H), 4.01 (s, 3H), 3.57 (br d, J=12.2 Hz, 1H), 3.06-2.91 (m, 2H), 1.99-1.75 (m, 2H), 1.66 (br t, J=8.7 Hz, 2H).

Example 1695: 5-(4-amino-5-((4,4-difluoropiperidin-1-yl)methyl)pyrrolo[2,1-f][1,2,4]triazin-7-yl)-2-methoxy-N-((1SR,3RS)-3-phenylcyclohexyl)nicotinamide

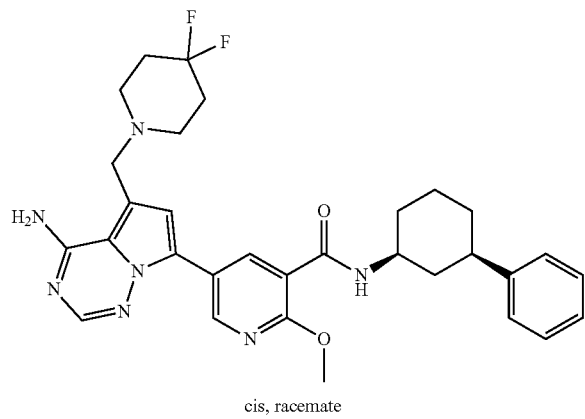 [SMILES: COc1ncc(-c2cc(CN3CCC(F)(F)CC3)c3c(N)ncnn23)cc1C(=O)N[C@H]1CCC[C@@H](c2ccccc2)C1]

cis, racemate

Prepared in the same fashion as Example 1685 to afford the title product (6 mg, 10.4 μmol, 43% yield).

MS ESI m/z 576.2 (M+H)+

$^1$H NMR (500 MHz, DMSO-d$_6$) δ 8.87 (s, 1H), 8.65 (s, 1H), 8.16 (br d, J=7.6 Hz, 1H), 7.87 (br s, 1H), 7.36-7.12 (m, 5H), 7.02 (s, 1H), 4.04-3.93 (m, 3H), 3.81 (s, 2H), 3.51 (br d, J=4.6 Hz, 3H), 2.79-2.60 (m, 5H), 2.10-1.74 (m, 8H), 1.60-1.32 (m, 4H).

Example 1696: 5-(4-amino-5-(trifluoromethyl)pyrrolo[2,1-f][1,2,4]triazin-7-yl)-N-((1SR,3RS)-3-(4-fluorophenyl)cyclohexyl)-2-methoxynicotinamide

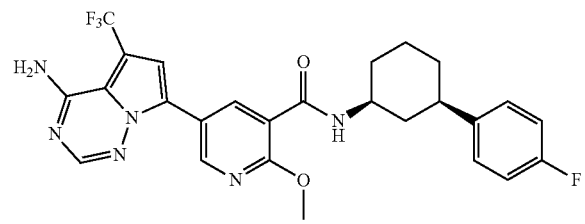 [SMILES: COc1ncc(-c2cc(C(F)(F)F)c3c(N)ncnn23)cc1C(=O)N[C@H]1CCC[C@@H](c2ccc(F)cc2)C1]

Prepared in the same fashion as Example 1685 to afford the title product (15 mg, 28.4 μmol, 68% yield).

MS ESI m/z 529.1 (M+H)+

$^1$H NMR (500 MHz, DMSO-d$_6$) δ 8.88 (d, J=1.8 Hz, 1H), 8.67 (d, J=1.8 Hz, 1H), 8.23-8.12 (m, 2H), 7.59 (s, 1H), 7.37-7.23 (m, 2H), 7.12 (br t, J=8.7 Hz, 2H), 4.01 (s, 3H), 3.97-3.87 (m, 1H), 2.77-2.66 (m, 1H), 2.09-1.93 (m, 2H), 1.87 (br d, J=12.5 Hz, 1H), 1.77 (br d, J=12.5 Hz, 1H), 1.58-1.29 (m, 4H).

Example 1697: 5-(4-amino-5-(trifluoromethyl)pyrrolo[2,1-f][1,2,4]triazin-7-yl)-2-methoxy-N-((1SR,2RS)-2-phenylcyclopropyl)nicotinamide

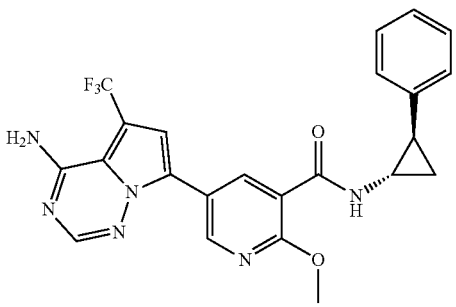 [SMILES: COc1ncc(-c2cc(C(F)(F)F)c3c(N)ncnn23)cc1C(=O)N[C@H]1C[C@@H]1c1ccccc1]

Prepared in the same fashion as Example 1685 to afford the title product (15 mg, 32 μmol, 76% yield).

MS ESI m/z 469.1 (M+H)+

$^1$H NMR (500 MHz, DMSO-d$_6$) δ 8.90 (s, 1H), 8.69 (s, 1H), 8.52 (br d, J=4.0 Hz, 1H), 8.17 (s, 1H), 7.61 (s, 1H), 7.35-7.26 (m, 2H), 7.23-7.13 (m, 3H), 4.03 (s, 3H), 3.06 (br d, J=3.7 Hz, 1H), 2.12 (br s, 1H), 1.41-1.33 (m, 1H), 1.31-1.20 (m, 1H).

Example 1698: 5-(4-amino-5-(trifluoromethyl)pyrrolo[2,1-f][1,2,4]triazin-7-yl)-N-((1SR,3RS)-3-(4-chlorophenyl)cyclohexyl)-2-methoxynicotinamide

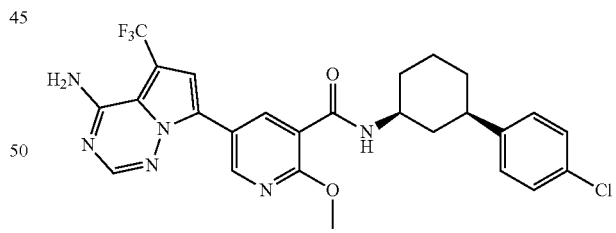

Prepared in the same fashion as Example 1685 to afford the title product (9 mg, 16.5 μmol, 39% yield).

MS ESI m/z 545.1 (M+H)+

$^1$H NMR (500 MHz, DMSO-d$_6$) δ 8.86 (s, 1H), 8.64 (s, 1H), 8.20 (br d, J=8.2 Hz, 1H), 8.14 (s, 1H), 7.56 (s, 1H), 7.37-7.32 (m, 2H), 7.31-7.25 (m, 2H), 3.93 (br d, J=6.2 Hz, 1H), 3.67-3.50 (m, 16H), 2.75-2.63 (m, 2H), 2.07-1.71 (m, 4H), 1.56-1.30 (m, 4H).

Example 1699: tert-butyl (2SR,4SR)-4-(5-(4-amino-5-(trifluoromethyl)pyrrolo[2,1-f][1,2,4]triazin-7-yl)-2-methoxynicotinamido)-2-(methoxymethyl)pyrrolidine-1-carboxylate

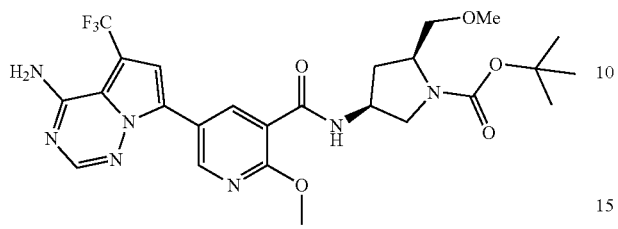

Prepared in the same fashion as Example 1685 to afford the title product (4.8 mg, 8.5 μmol, 39% yield).

MS ESI m/z 566.2 (M+H)+

$^1$H NMR (500 MHz, DMSO-d$_6$) δ 8.97-8.83 (m, 1H), 8.71 (br s, 1H), 8.48 (br d, J=6.1 Hz, 1H), 8.16 (s, 1H), 7.59 (s, 1H), 4.39 (br d, J=6.1 Hz, 1H), 4.03 (s, 3H), 3.90 (br s, 1H), 3.76 (br dd, J=10.4, 7.0 Hz, 1H), 3.53 (br s, 1H), 3.44 (br d, J=8.2 Hz, 1H), 3.29 (s, 2H), 3.11 (br d, J=6.7 Hz, 1H), 2.38 (br d, J=5.8 Hz, 1H), 2.00-1.87 (m, 1H), 1.41 (s, 9H).

Example 1700: 5-(4-amino-5-(trifluoromethyl)pyrrolo[2,1-f][1,2,4]triazin-7-yl)-N-((3SR,5SR)-1-(3,3-difluorocyclobutane-1-carbonyl)-5-(methoxymethyl)pyrrolidin-3-yl)-2-methoxynicotinamide

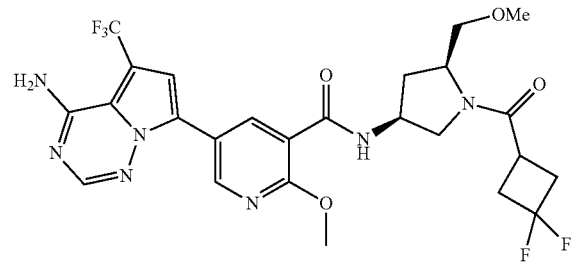 [SMILES: COC[C@@H]1C[C@H](NC(=O)c2cc(-c3cc(C(F)(F)F)c4c(N)ncnn34)cnc2OC)CN1C(=O)C1CC(F)(F)C1]

A mixture of 3,3-difluorocyclobutane-1-carboxylic acid (5.47 mg, 0.040 mmol) (which was obtained from tert-butyl (2S,4S)-4-(5-(4-amino-5-(trifluoromethyl)pyrrolo[2,1-f][1,2,4]triazin-7-yl)-2-methoxynicotinamido)-2-(methoxymethyl)pyrrolidine-1-carboxylate upon treatment with TFA), 5-(4-amino-5-(trifluoromethyl)pyrrolo[2,1-f][1,2,4]triazin-7-yl)-2-methoxy-N-((3S,5S)-5-(methoxymethyl)pyrrolidin-3-yl)nicotinamide (17 mg, 0.037 mmol), BOP (20.19 mg, 0.046 mmol) and Hünig's base (51.0 μl, 0.292 mmol) in DMF (243 μl) was stirred at rt for 1 h, and the crude product was purified by HPLC to give 5-(4-amino-5-(trifluoromethyl)pyrrolo[2,1-f][1,2,4]triazin-7-yl)-N-((3S,5S)-1-(3,3-difluorocyclobutane-1-carbonyl)-5-(methoxymethyl)pyrrolidin-3-yl)-2-methoxynicotinamide (10 mg, 0.017 mmol, 46% yield) as a white solid.

MS ESI m/z 584.2 (M+H)+

$^1$H NMR (500 MHz, DMSO-d$_6$) δ 8.89 (br s, 1H), 8.73 (br s, 1H), 8.68 (br s, 1H), 8.56-8.45 (m, 1H), 8.16 (s, 1H), 7.59 (s, 1H), 4.49 (br d, J=6.4 Hz, 1H), 4.39 (br d, J=6.9 Hz, 1H), 4.24 (br s, 1H), 4.14 (br d, J=3.7 Hz, 1H), 4.09-3.99 (m, 3H), 3.93-3.80 (m, 1H), 3.58 (br d, J=3.7 Hz, 1H), 3.50-3.40 (m, 1H), 3.35-3.23 (m, 3H), 3.22-3.10 (m, 1H), 2.75 (br d, J=17.7 Hz, 4H), 2.43-2.32 (m, 1H), 2.04-1.84 (m, 1H).

Example 1701: 5-(4-amino-5-(trifluoromethyl)pyrrolo[2,1-f][1,2,4]triazin-7-yl)-N-((3S,5S)-5-((benzyloxy)methyl)-1-(3,3-difluorocyclobutane-1-carbonyl)pyrrolidin-3-yl)-2-methoxynicotinamide

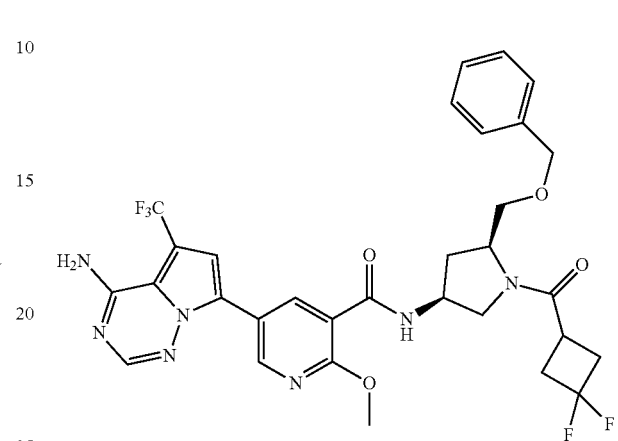

Prepared in the same fashion as Example 1700 to afford the title product (13 mg, 19.7 μmol, 48% yield).

MS ESI m/z 660.1 (M+H)+

$^1$H NMR (500 MHz, DMSO-d$_6$) δ 9.00-8.82 (m, 1H), 8.75-8.60 (m, 1H), 8.54-8.40 (m, 1H), 8.16 (s, 1H), 7.59 (s, 1H), 7.34-7.14 (m, 5H), 4.56-4.45 (m, 3H), 4.38 (br s, 1H), 4.29 (br s, 1H), 4.22-4.06 (m, 1H), 4.02-3.93 (m, 3H), 3.88 (br dd, J=16.8, 6.4 Hz, 1H), 3.73-3.65 (m, 1H), 3.57 (br d, J?0.1 Hz, 1H), 3.43-3.28 (m, 1H), 3.24-3.12 (m, 1H), 2.90-2.60 (m, 4H), 2.45-2.33 (m, 1H), 2.10-1.98 (m, 1H), 1.92 (br d, J=8.5 Hz, 1H).

Example 1702: 5-(4-amino-2-fluoropyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide

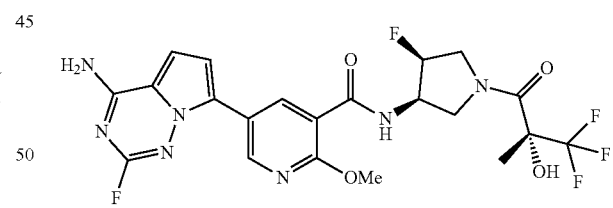

A mixture of N-((3R,4S)-4-fluoro-1-((R)-3,3,3-trifluoro-2-hydroxy-2-methylpropanoyl)pyrrolidin-3-yl)-2-methoxy-5-(4,4,5,5-tetramethyl-1,3,2-dioxaborolan-2-yl)nicotinamide (17.50 mg, 0.035 mmol), 7-bromo-2-fluoropyrrolo[2,1-f][1,2,4]triazin-4-amine (8 mg, 0.035 mmol), K$_3$PO$_4$ (2 M solution, 51.9 μl, 0.104 mmol) in 1,4-dioxane (2 mL) was degassed and back-filled with nitrogen. Pd(dppf)Cl$_2$.CH$_2$Cl$_2$ (2.83 mg, 3.46 μmol) was added, and the reaction mixture was heated at 100° C. for 16 h. The crude product was purified by HPLC to give 5-(4-amino-2-fluoropyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide (4 mg, 7.6 mmol, 22% yield) as an off-white solid.

MS ESI m/z 530.1 (M+H)+

¹H NMR (500 MHz, DMSO-d₆) δ 8.92 (br s, 1H), 8.73 (br d, J=5.2 Hz, 1H), 8.54 (br d, J=7.0 Hz, 1H), 8.49 (br d, J=5.2 Hz, 1H), 8.39 (br s, 1H), 7.68-7.54 (m, 1H), 7.19-7.04 (m, 2H), 5.34 (br d, J=9.8 Hz, 1H), 5.23 (br d, J=11.0 Hz, 1H), 4.79-4.59 (m, 1H), 4.49 (br t, J=9.6 Hz, 1H), 4.41-4.27 (m, 1H), 4.04 (br s, 3H), 3.99-3.70 (m, 2H), 3.59 (br t, J=10.5 Hz, 1H), 3.34 (br d, J=7.0 Hz, 1H), 1.54 (s, 3H).

Example 1703: 5-(5-((1H-imidazol-1-yl)methyl)-4-aminopyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide

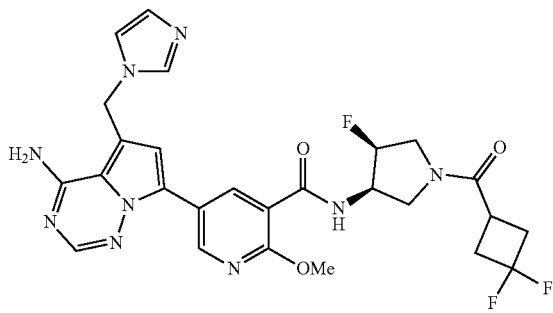 [SMILES: COc1ncc(-c2cc(Cn3ccnc3)c3c(N)ncnn23)cc1C(=O)N[C@@H]1CN(C(=O)C2CC(F)(F)C2)C[C@@H]1F]

1703A: A mixture of N-((4-amino-7-bromopyrrolo[2,1-f][1,2,4]triazin-5-yl)methyl)-N,N-diethylethanaminium bromide, bromide salt (150 mg, 0.368 mmol), imidazole (75 mg, 1.105 mmol) and Hunig's base (129 μl, 0.737 mmol) in acetonitrile (2456 μl) was heated under reflux for 24 h. After filtration, the filtrate was evaporated in vacuo. The crude product was purified by reverse phase preparative HPLC on a Luna C18 column (10 μM, 30×100 mm) eluting with 0-100% B (A: 95% water/5% acetonitrile/10 nM ammonium acetate, B: 5% water/95% acetonitrile/10 mM ammonium acetate) over 12 min to give 5-((1H-imidazol-1-yl)methyl)-7-bromopyrrolo[2,1-f][1,2,4]triazin-4-amine (8 mg, 0.027 mmol, 7% yield) as a white solid.

MS ESI (m/z) 293.1 (M+H)+

¹H NMR (500 MHz, DMSO-d₆) δ 7.90 (s, 1H), 7.71 (s, 1H), 7.48 (br d, J=2.4 Hz, 2H), 7.12 (s, 1H), 6.88 (s, 1H), 6.70 (s, 1H), 5.50 (s, 2H).

1703: A mixture of 5-((1H-imidazol-1-yl)methyl)-7-bromopyrrolo[2,1-f][1,2,4]triazin-4-amine (7 mg, 0.024 mmol) N-((3R,4S)-1-(3,3-difluorocyclobutane-1-carbonyl)-4-fluoropyrrolidin-3-yl)-2-methoxy-5-(4,4,5,5-tetramethyl-1,3,2-dioxaborolan-2-yl)nicotinamide (11.54 mg, 0.024 mmol), K₃PO₄ (2M, 35.8 μl, 0.072 mmol) in 1,4-dioxane (2 mL) was degassed and back-filled with N₂. Pd(dppf)Cl₂.CH₂Cl₂ (1.950 mg, 2.388 μmol) was added, and the reaction mixture was heated at 100° C. for 16 h. The reaction mixture was purified by HPLC to give 5-(5-((1H-imidazol-1-yl)methyl)-4-aminopyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide (11 mg, 13.8 mmol, 58% yield).

MS ESI m/z 570.2 (M+H)+

¹H NMR (500 MHz, DMSO-d₆) δ 9.04-8.98 (m, 1H), 8.94 (br s, 1H), 8.80-8.71 (m, 1H), 8.51 (br t, J=8.5 Hz, 1H), 8.02 (s, 1H), 7.73-7.59 (m, 3H), 7.27 (br s, 1H), 7.21 (s, 1H), 7.17 (br s, 1H), 7.07 (br s, 1H), 5.80 (s, 2H), 5.44-5.18 (m, 1H), 4.89-4.57 (m, 1H), 4.04 (d, J=6.1 Hz, 3H), 3.99-3.84 (m, 2H), 3.82-3.68 (m, 1H), 3.21-3.11 (m, 1H), 2.86-2.74 (m, 4H).

Example 1704: 5-(4-amino-5-((2-methyl-1H-imidazol-1-yl)methyl)pyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide

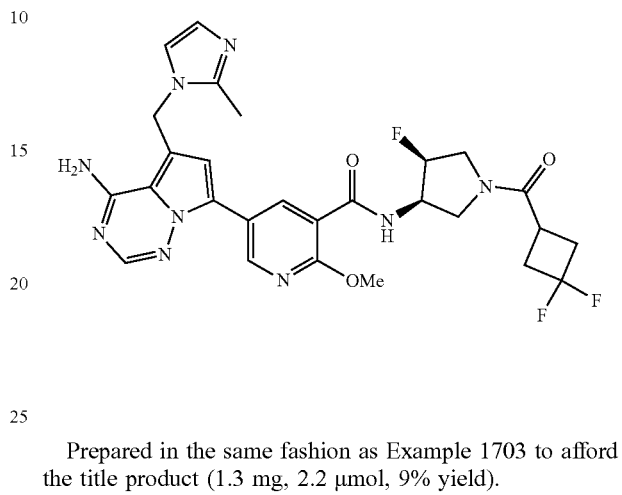

Prepared in the same fashion as Example 1703 to afford the title product (1.3 mg, 2.2 μmol, 9% yield).

MS ESI m/z 584.2 (M+H)+

¹H NMR (500 MHz, DMSO-d6) δ 8.94-8.84 (m, 1H), 8.66 (br d, J=16.5 Hz, 1H), 8.56-8.44 (m, 1H), 7.96 (s, 1H), 7.04 (s, 1H), 6.76 (s, 1H), 6.67 (br d, J=4.3 Hz, 1H), 5.50 (s, 2H), 5.41-5.18 (m, 1H), 4.88-4.63 (m, 1H), 4.03 (br d, J=5.8 Hz, 3H), 3.96-3.67 (m, 3H), 2.93-2.65 (m, 5H), 2.33 (s, 3H).

Example 1705: 5-(4-amino-5-((4-methyl-1H-imidazol-1-yl)methyl)pyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide

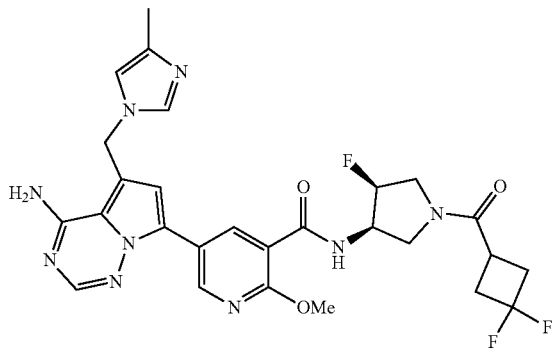 [SMILES: COc1ncc(-c2cc(Cn3cnc(C)c3)c3c(N)ncnn23)cc1C(=O)N[C@@H]1CN(C(=O)C2CC(F)(F)C2)C[C@@H]1F]

Prepared in the same fashion as Example 1703 to afford the title product (4.3 mg, 7.4 μmol, 28% yield).

MS ESI m/z 584.2 (M+H)+.

LC/MS retention time using Method 3=1.23 min

Example 1706: 5-(4-amino-5-((4-chloro-1H-imidazol-1-yl)methyl)pyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide

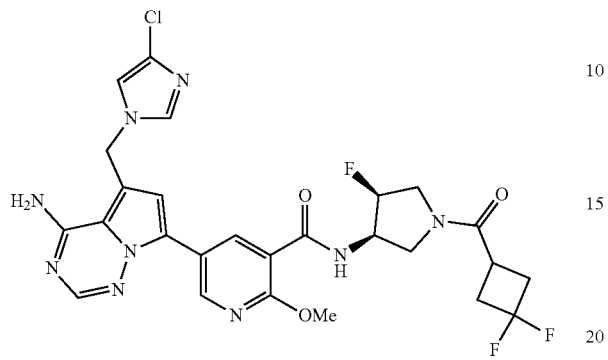

Prepared in the same fashion as Example 1703 to afford the title product (1.8 mg, 3.0 µmol, 12% yield).

MS ESI m/z 604.1 (M+H)⁺

¹H NMR (500 MHz, DMSO-d₆) δ 8.88 (s, 1H), 8.65 (br d, J=17.1 Hz, 1H), 8.55-8.44 (m, 1H), 7.97 (s, 1H), 7.85 (br s, 1H), 7.60 (br s, 1H), 7.04 (s, 1H), 6.72 (d, J=3.4 Hz, 1H), 5.61 (s, 2H), 5.42-5.18 (m, 1H), 4.85-4.56 (m, 1H), 4.03 (d, J=6.1 Hz, 3H), 3.99-3.66 (m, 3H), 3.29-3.12 (m, 1H), 2.89-2.71 (m, 4H).

Example 1707: 5-(5-((1H-1,2,4-triazol-1-yl)methyl)-4-aminopyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide

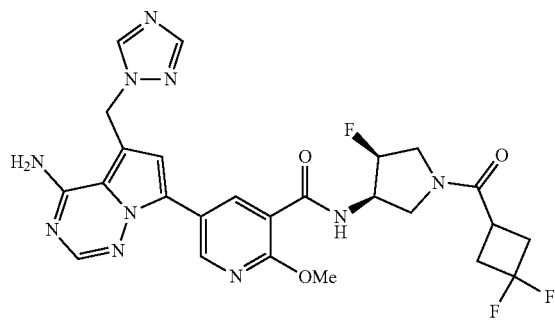

Prepared in the same fashion as Example 1703 to afford the title product (5.5 mg, 8.0 µmol, 33% yield).

MS ESI m/z 571.2 (M+H)⁺

¹H NMR (500 MHz, DMSO-d₆) δ 8.91 (s, 1H), 8.73 (s, 1H), 8.69 (s, 1H), 8.66 (s, 1H), 8.55-8.47 (m, 1H), 8.03 (s, 1H), 7.98 (s, 1H), 7.75 (br s, 1H), 7.12 (s, 1H), 5.78 (s, 2H), 5.45-5.20 (m, 1H), 4.88-4.52 (m, 1H), 4.04 (br d, J=6.1 Hz, 3H), 4.00-3.61 (m, 3H), 3.32-3.11 (m, 1H), 2.90-2.69 (m, 4H).

Example 1708: 5-(5-((1H-benzo[d]imidazol-1-yl)methyl)-4-aminopyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide

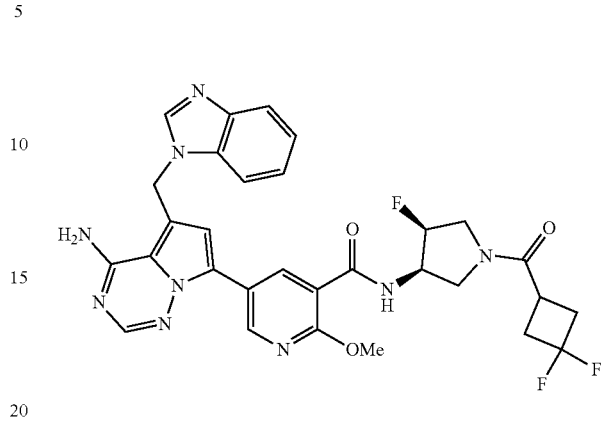

Prepared in the same fashion as Example 1703 to afford the title product (6.0 mg, 9.7 µmol, 37% yield).

MS ESI m/z 620.2 (M+H)⁺

¹H NMR (500 MHz, DMSO-d₆) δ 8.86 (s, 1H), 8.70-8.61 (m, 1H), 8.48 (br t, J=8.7 Hz, 1H), 8.34 (br s, 1H), 7.97 (s, 1H), 7.64 (br s, 4H), 7.30-7.17 (m, 2H), 6.95 (br d, J=6.4 Hz, 1H), 5.88 (s, 2H), 5.42-5.16 (m, 1H), 4.85-4.54 (m, 1H), 4.01 (d, J=5.8 Hz, 3H), 3.97-3.66 (m, 3H), 3.30-3.11 (m, 1H), 2.91-2.69 (m, 4H).

Example 1709: 5-(5-((1H-pyrazol-1-yl)methyl)-4-aminopyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide

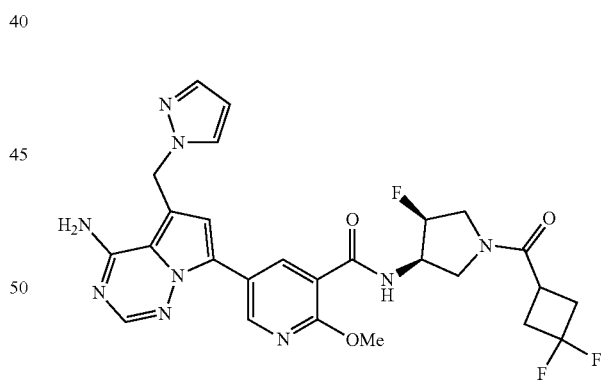

Prepared in the same fashion as Example 1703 to afford the title product (5.0 mg, 8.8 µmol, 28% yield).

MS ESI m/z 570.2 (M+H)⁺

¹H NMR (500 MHz, DMSO-d₆) δ 8.91 (s, 1H), 8.71 (br d, J=18.9 Hz, 1H), 8.51 (br t, J=8.7 Hz, 1H), 8.07-7.86 (m, 3H), 7.52 (s, 1H), 7.17 (s, 1H), 6.30 (s, 1H), 5.64 (s, 2H), 5.45-5.21 (m, 1H), 4.93-4.60 (m, 1H), 4.04 (br d, J=6.1 Hz, 3H), 4.00-3.68 (m, 3H), 3.32-3.12 (m, 1H), 2.93-2.69 (m, 4H).

Example 1710: 5-(5-((1H-tetrazol-1-yl)methyl)-4-aminopyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide

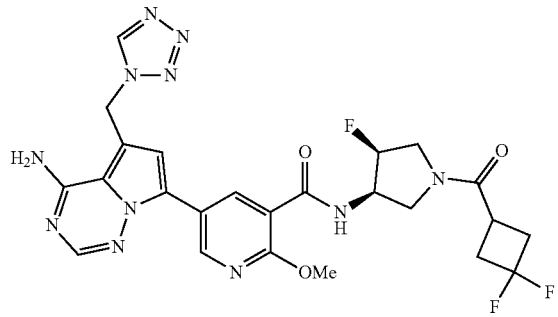 [SMILES: COc1ncc(-c2cc(Cn3cnnn3)c3c(N)ncnn23)cc1C(=O)N[C@@H]1CN(C(=O)C2CC(F)(F)C2)C[C@@H]1F]

Prepared in the same fashion as Example 1703 to afford the title product (2.6 mg, 4.5 μmol, 17% yield).

MS ESI m/z 572.2 (M+H)+

$^1$H NMR (500 MHz, DMSO-d$_6$) δ 9.49-9.35 (m, 1H), 8.91 (s, 1H), 8.73 (br d, J=18.6 Hz, 1H), 8.56-8.41 (m, 1H), 8.00 (s, 1H), 7.64 (br d, J=3.7 Hz, 2H), 7.15 (s, 1H), 6.10 (s, 2H), 5.49-5.11 (m, 1H), 4.94-4.54 (m, 1H), 4.04 (br d, J=6.1 Hz, 3H), 4.00-3.67 (m, 3H), 3.24-3.11 (m, 1H), 2.91-2.70 (m, 4H).

Example 1711: 5-(5-((2H-tetrazol-2-yl)methyl)-4-aminopyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide

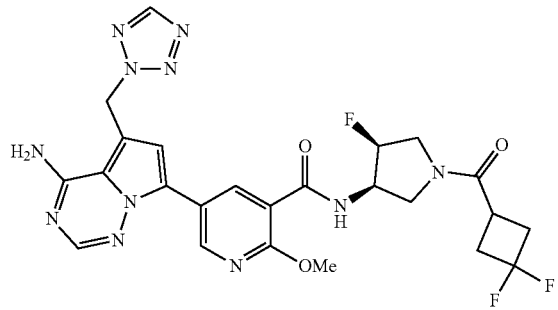 [SMILES: COc1ncc(-c2cc(Cn3ncnn3)c3c(N)ncnn23)cc1C(=O)N[C@@H]1CN(C(=O)C2CC(F)(F)C2)C[C@@H]1F]

Prepared in the same fashion as Example 1703 to afford the title product (4.0 mg, 7.0 μmol, 26% yield).

MS ESI m/z 572.2 (M+H)+

$^1$H NMR (500 MHz, DMSO-d$_6$) δ 9.01-8.96 (m, 1H), 8.90 (s, 1H), 8.73 (br d, J=17.7 Hz, 1H), 8.50 (br dd, J=11.4, 7.8 Hz, 1H), 8.01 (s, 1H), 7.81-7.60 (m, 1H), 7.18 (s, 1H), 6.34 (s, 2H), 5.44-5.19 (m, 1H), 4.88-4.60 (m, 1H), 4.03 (d, J=5.8 Hz, 3H), 4.00-3.68 (m, 3H), 3.31-3.11 (m, 1H), 2.91-2.66 (m, 4H).

Example 1712: 5-(4-amino-5-((4-phenyl-1H-imidazol-1-yl)methyl)pyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide Prepared in the same fashion as Example 1703 to afford the title product (4.0 mg, 6.2 μmol, 28% yield).

MS ESI m/z 646.2 (M+H)+

$^1$H NMR (500 MHz, DMSO-d$_6$) δ 8.84-8.77 (m, 1H), 8.60 (br d, J=18.3 Hz, 1H), 8.49 (br t, J=8.7 Hz, 1H), 8.06 (br d, J=5.5 Hz, 1H), 7.94 (s, 1H), 7.57-7.36 (m, 6H), 7.28 (br s, 1H), 6.49 (br d, J=5.2 Hz, 1H), 5.70 (s, 2H), 5.43-5.16 (m, 1H), 4.86-4.60 (m, 1H), 4.02 (br d, J=5.8 Hz, 3H), 3.99-3.88 (m, 1H), 3.86 (s, 1H), 3.82-3.68 (m, 1H), 3.63 (br s, 1H), 3.32-3.12 (m, 1H), 2.89-2.69 (m, 4H).

Example 1713: 5-(4-amino-5-((5-phenyl-1H-imidazol-1-yl)methyl)pyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide

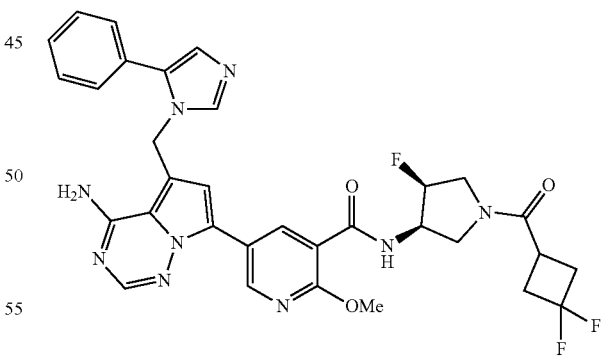

Prepared in the same fashion as Example 1703 to afford the title product (4.0 mg, 6.2 μmol, 28% yield).

MS ESI m/z 646.2 (M+H)+

$^1$H NMR (500 MHz, DMSO-d$_6$) δ 8.94 (s, 1H), 8.75 (br d, J=16.2 Hz, 1H), 8.50 (br t, J=8.9 Hz, 1H), 8.08 (br s, 1H), 7.99 (s, 1H), 7.80-7.70 (m, 3H), 7.58 (br s, 1H), 7.36 (br t, J=7.5 Hz, 2H), 7.27-7.20 (m, 1H), 7.15 (d, J=5.2 Hz, 1H), 5.66 (s, 2H), 5.44-5.19 (m, 1H), 4.88-4.56 (m, 1H), 4.04 (d, J=5.8 Hz, 3H), 4.00-3.89 (m, 1H), 3.85 (s, 1H), 3.82-3.67

Example 1714: 5-(4-amino-5-((methoxyamino)methyl)pyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide

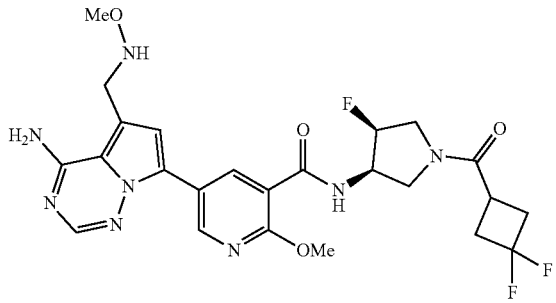 [SMILES: CONCc1cc(-c2cnc(OC)c(C(=O)N[C@@H]3CN(C(=O)C4CC(F)(F)C4)C[C@@H]3F)c2)n2ncnc(N)c12]

Prepared in the same fashion as Example 1703 to afford the title product (6.8 mg, 12.4 μmol, 34% yield).

MS ESI m/z 549.2 (M+H)+

$^1$H NMR (500 MHz, DMSO-d$_6$) δ 8.97-8.89 (m, 1H), 8.81 (br d, J=18.9 Hz, 1H), 8.51 (br dd, J=11.6, 7.9 Hz, 1H), 7.92 (s, 1H), 7.42-7.28 (m, 1H), 7.10 (s, 1H), 5.45-5.20 (m, 1H), 4.89-4.61 (m, 1H), 4.19 (br s, 2H), 4.04 (br d, J=5.8 Hz, 3H), 4.01-3.69 (m, 3H), 3.44 (s, 1H), 3.25-3.12 (m, 1H), 2.91-2.68 (m, 4H).

Example 1715: 5-(4-amino-5-((3-oxotetrahydropyridazin-1(2H)-yl)methyl)pyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide

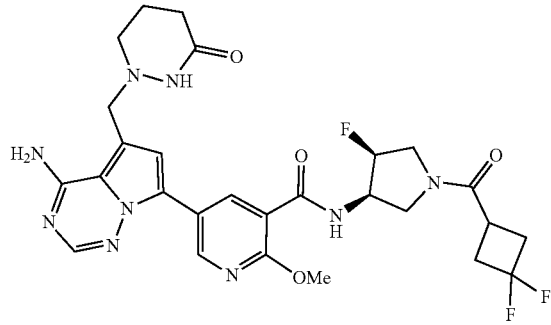 [SMILES: COc1ncc(-c2cc(CN3CCCC(=O)N3)c3c(N)ncnn23)cc1C(=O)N[C@@H]1CN(C(=O)C2CC(F)(F)C2)C[C@@H]1F]

Prepared in the same fashion as Example 1703 to afford the title product (5.0 mg, 8.3 μmol, 55% yield).

MS ESI m/z 602.2 (M+H)+

$^1$H NMR (500 MHz, DMSO-d$_6$) δ 9.00 (s, 1H), 8.86-8.70 (m, 1H), 8.51 (br dd, J=11.3, 8.2 Hz, 1H), 7.93 (s, 2H), 7.12 (s, 1H), 5.43-5.17 (m, 1H), 4.90-4.58 (m, 1H), 4.17 (s, 2H), 4.04 (br d, J=6.1 Hz, 3H), 4.01-3.68 (m, 3H), 3.49-3.34 (m, 4H), 3.31-3.23 (m, 1H), 3.23-3.13 (m, 1H), 2.93 (br s, 2H), 2.88-2.70 (m, 4H), 2.35 (br t, J=6.6 Hz, 1H).

Example 1716: 5-(4-amino-5-((tetrahydropyridazin-1(2H)-yl)methyl)pyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide

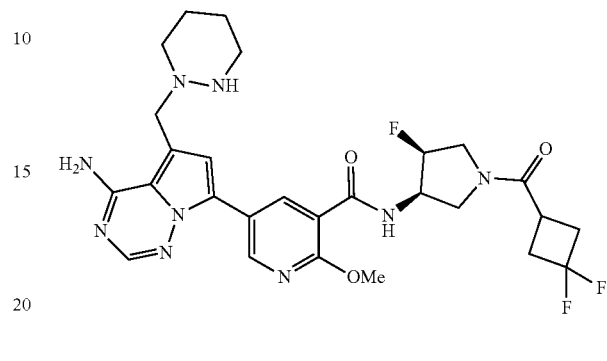

Prepared in the same fashion as Example 1703 to afford the title product (5.0 mg, 8.5 μmol, 18% yield).

MS ESI m/z 588.2 (M+H)+

$^1$H NMR (500 MHz, DMSO-d$_6$) δ 9.00-8.89 (m, 1H), 8.86-8.74 (m, 1H), 8.51 (br t, J=8.2 Hz, 1H), 7.96-7.80 (m, 1H), 7.11 (br s, 1H), 7.00 (s, 1H), 6.82 (br s, 1H), 5.44-5.16 (m, 1H), 4.88-4.59 (m, 1H), 4.33 (br s, 1H), 4.04 (br d, J=3.4 Hz, 3H), 4.01-3.68 (m, 4H), 3.24-3.12 (m, 1H), 2.93-2.69 (m, 6H), 2.08 (br s, 1H), 1.95-1.81 (m, 4H), 1.65 (br s, 1H).

Example 1717: 2,2,2-trifluoroethyl (3R,4S)-3-(5-(4-amino-5-(morpholinomethyl)pyrrolo[2,1-f][1,2,4]triazin-7-yl)-2-methoxynicotinamido)-4-fluoropyrrolidine-1-carboxylate

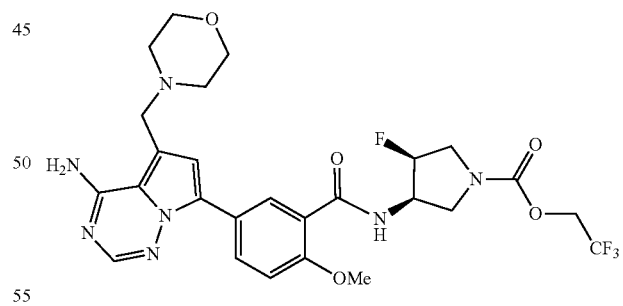

Prepared in the same fashion as Example 1703 to afford the title product (4.0 mg, 6.7 μmol, 23% yield).

MS ESI m/z 596.9 (M+H)+

$^1$H NMR (500 MHz, DMSO-d$_6$) δ 8.89 (d, J=2.1 Hz, 1H), 8.74 (d, J=2.1 Hz, 1H), 8.53 (br d, J=7.0 Hz, 1H), 7.86 (s, 1H), 7.03 (s, 1H), 5.40-5.16 (m, 1H), 4.87-4.63 (m, 3H), 4.01 (s, 3H), 3.94-3.61 (m, 3H), 3.56 (s, 4H), 3.33 (br d, J=10.7 Hz, 1H).

Example 1718: 5-(4-amino-5-(morpholinomethyl) pyrrolo[2,1-f][1,2,4]triazin-7-yl)-N-((3R,4S)-4-fluoro-1-((3,3,3-trifluoropropyl)sulfonyl)pyrrolidin-3-yl)-2-methoxynicotinamide

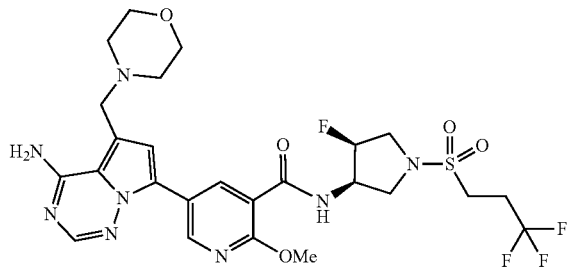 [SMILES: COc1ncc(-c2cc(CN3CCOCC3)c3c(N)ncnn23)cc1C(=O)N[C@@H]1CN(S(=O)(=O)CCC(F)(F)F)C[C@@H]1F]

Prepared in the same fashion as Example 1703 to afford the title product (4.0 mg, 6.3 μmol, 22% yield).

MS ESI m/z 631.1 (M+H)+

$^1$H NMR (500 MHz, DMSO-d$_6$) δ 9.65-9.37 (m, 1H), 8.89 (d, J=2.1 Hz, 1H), 8.74 (d, J=2.1 Hz, 1H), 8.53 (br d, J=7.3 Hz, 1H), 7.85 (s, 1H), 7.75-7.55 (m, 1H), 7.02 (s, 1H), 5.34 (br s, 1H), 5.23 (br s, 1H), 4.88-4.70 (m, 1H), 4.01 (s, 4H), 3.86-3.78 (m, 2H), 3.74 (br s, 1H), 3.63-3.54 (m, 7H), 3.50-3.42 (m, 2H), 3.35 (br t, J=9.8 Hz, 1H), 2.71 (td, J=10.5, 6.1 Hz, 3H).

Example 1719: 5-(4-amino-5-(morpholinomethyl) pyrrolo[2,1-f][1,2,4]triazin-7-yl)-N-((3R,4S)-4-fluoro-1-((2,2,2-trifluoroethyl)sulfonyl)pyrrolidin-3-yl)-2-methoxynicotinamide

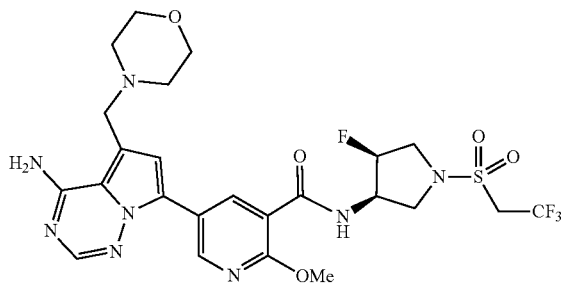 [SMILES: COc1ncc(-c2cc(CN3CCOCC3)c3c(N)ncnn23)cc1C(=O)N[C@@H]1CN(S(=O)(=O)CC(F)(F)F)C[C@@H]1F]

Prepared in the same fashion as Example 1703 to afford the title product (4.0 mg, 6.5 μmol, 22% yield).

MS ESI m/z 617.0 (M+H)+

$^1$H NMR (500 MHz, DMSO-d$_6$) δ 9.00-8.88 (m, 1H), 8.74 (d, J=2.4 Hz, 1H), 8.56 (br d, J=7.4 Hz, 1H), 8.01 (s, 1H), 7.25-7.14 (m, 1H), 5.38 (br d, J=3.0 Hz, 1H), 5.27 (br s, 1H), 4.86-4.69 (m, 1H), 4.67-4.52 (m, 2H), 4.04 (s, 2H), 3.87 (br t, J=6.1 Hz, 1H).

Example 1720: 5-(4-amino-5-(trifluoromethyl)pyrrolo[2,1-f][1,2,4]triazin-7-yl)-2-methyl-N-(2-(2-phenylmorpholino)ethyl)nicotinamide

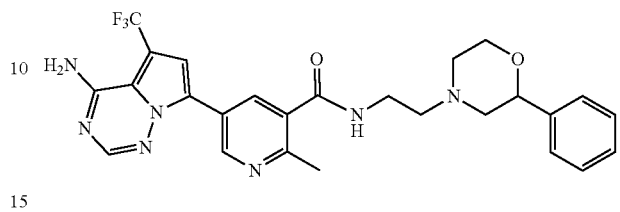

1720A: 2-(2-phenylmorpholino)acetonitrile: To a 100 mL round-bottomed flask was added 2-phenylmorpholine (569 mg, 3.49 mmol) and K$_2$CO$_3$ (530 mg, 3.83 mmol) in CH$_3$CN (10 mL) to give a white suspension. 2-Bromoacetonitrile (0.235 mL, 3.49 mmol) was added. The mixture was stirred at rt ON. The mixture was filtered and the filtrate was concentrated in vacuo to give the desired product as a colorless dense oil (706 mg, 3.49 mmol, 100% yield).

MS ESI m/z 203.0 (M+H)+

1720B: 2-(2-phenylmorpholino)ethan-1-amine: To a 50 mL round-bottomed flask was added 2-(2-phenylmorpholino)acetonitrile (706 mg, 3.49 mmol) in THF (10 mL) to give a tan solution. LiAlH$_4$ (10.47 mL, 10.47 mmol) was added dropwise. The mixture was stirred at rt ON for 20 h. To the reaction mixture was added anhydrous Na2SO4 and it was slowly quenched with droplets of water (gas evolves and heat generates) until no bubbling is evident. The mixture was diluted with EtOAc and filtered. The organic solution was concentrated to afford the desired product (611 mg, 2.96 mmol, 85% yield) as a light yellow oil, which was used as is.

1720: A mixture of 5-(4-amino-5-(trifluoromethyl)pyrrolo[2,1-f][1,2,4]triazin-7-yl)-2-methylnicotinic acid (33.7 mg, 0.1 mmol), BOP (66.3 mg, 0.150 mmol), 2-(2-phenylmorpholino)ethan-1-amine (20.63 mg, 0.100 mmol) and Hunig's base (0.087 mL, 0.500 mmol) in DMF (0.5 mL) was stirred at rt ON. The crude reaction mixture was purified by preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 23% B, 23-63% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to afford 5-(4-amino-5-(trifluoromethyl)pyrrolo[2,1-f][1,2,4]triazin-7-yl)-2-methyl-N-(2-(2-phenylmorpholino)ethyl)nicotinamide (11.5 mg, 0.021 mmol, 21% yield).

MS ESI m/z 526.3 (M+H)+

$^1$H NMR (500 MHz, DMSO-d$_6$) δ 9.15 (d, J=2.3 Hz, 1H), 8.48 (t, J=5.6 Hz, 1H), 8.38 (d, J=2.3 Hz, 1H), 8.17 (s, 1H), 7.68 (s, 1H), 7.33 (d, J=6.8 Hz, 4H), 7.26 (t, J=6.5 Hz, 1H), 4.47 (d, J=9.9 Hz, 1H), 4.01-3.90 (m, 1H), 3.68 (dd, J=12.3, 9.9 Hz, 1H), 3.01 (d, J=11.4 Hz, 1H), 2.85 (d, J=11.4 Hz, 1H), 2.60 (s, 3H), 2.23 (s, 1H), 2.01 (t, J=10.8 Hz, 1H).

Example 1721: 5-(4-amino-5-(trifluoromethyl)pyrrolo[2,1-f][1,2,4]triazin-7-yl)-2-methyl-N-(2-(3-phenylmorpholino)ethyl)nicotinamide

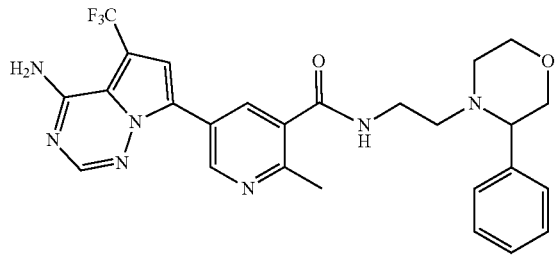 [SMILES: Cc1ncc(-c2cc(C(F)(F)F)c3c(N)ncnn23)cc1C(=O)NCCN1CCOCC1c1ccccc1]

Prepared by the methods described in Example 1720 using 2-(3-phenylmorpholino)ethan-1-amine and 5-(4-amino-5-(trifluoromethyl)pyrrolo[2,1-f][1,2,4]triazin-7-yl)-2-methylnicotinic acid to give the title product (22.6 mg, 0.041 mmol, 41% yield).

MS ESI m/z 526.3 (M+H)$^+$ $^1$H NMR (500 MHz, DMSO-d6) δ 9.11 (s, 1H), 8.40 (t, J=5.8 Hz, 1H), 8.30 (s, 1H), 8.14 (s, 1H), 7.64 (s, 1H), 7.41-7.17 (m, 5H), 3.86 (d, J=11.3 Hz, 1H), 3.63 (d, J=25.7 Hz, 5H), 3.42-3.08 (m, 5H), 2.61 (dt, J=15.0, 8.0 Hz, 1H), 2.31 (dt, J=13.2, 6.6 Hz, 1H), 2.07 (dt, J=11.4, 4.9 Hz, 1H).

Example 1722: 5-(4-amino-5-(trifluoromethyl)pyrrolo[2,1-f][1,2,4]triazin-7-yl)-2-methoxy-N-(2-(3-phenylpiperidin-1-yl)ethyl)nicotinamide

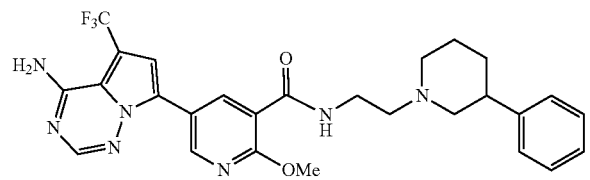 [SMILES: COc1ncc(-c2cc(C(F)(F)F)c3c(N)ncnn23)cc1C(=O)NCCN1CCCC(c2ccccc2)C1]

Prepared by the methods described in Example 1720 using 2-(3-phenylpiperidin-1-yl)ethan-1-amine hydrochloride and 5-(4-amino-5-(trifluoromethyl)pyrrolo[2,1-f][1,2,4]triazin-7-yl)-2-methoxynicotinic acid to give the title product (25.0 mg, 0.046, 59% yield).

MS ESI m/z 540.3 (M+H)$^+$ $^1$H NMR (500 MHz, DMSO-d6) δ 8.88 (d, J=2.4 Hz, 1H), 8.83 (d, J=2.6 Hz, 1H), 8.48 (s, 1H), 8.14 (s, 1H), 7.57 (s, 1H), 7.27 (p, J=7.1, 6.5 Hz, 4H), 7.19 (d, J=6.9 Hz, 1H), 4.06 (s, 3H), 3.60-3.56 (m, 1H), 3.45 (dd, J=10.3, 4.4 Hz, 1H), 3.01-2.90 (m, 2H), 2.76 (t, J=14.8 Hz, 1H), 2.10 (td, J=19.2, 18.2, 7.3 Hz, 2H), 1.84 (d, J=12.7 Hz, 1H), 1.76 (d, J=13.3 Hz, 1H), 1.63 (q, J=12.4, 10.9 Hz, 1H), 1.52-1.41 (m, 1H).

Example 1723: 5-(4-amino-5-(trifluoromethyl)pyrrolo[2,1-f][1,2,4]triazin-7-yl)-N-(1-benzyl-1H-imidazol-4-yl)-2-methoxynicotinamide

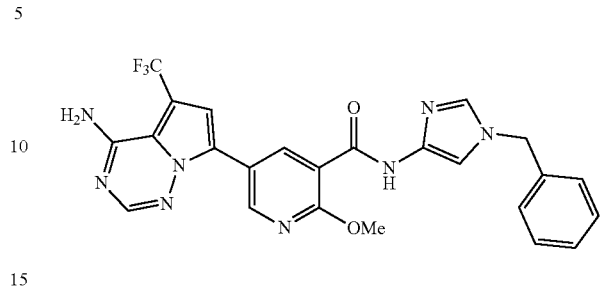

1723A: 1-benzyl-1H-imidazol-4-amine: To a 50 mL round-bottomed flask was added 1-benzyl-4-nitro-1H-imidazole (450 mg, 2.215 mmol) and Pd—C (236 mg, 0.221 mmol) in MeOH (12 mL) to give a black suspension. The reaction mixture was treated under hydrogen balloon for 18 h. The mixture was filtered and washed with EtOAc/MeOH. The organic solution was concentrated to the product (382 mg, 2.22 mmol, 100% yield) as a tan oil.

MS ESI m/z 174.0 (M+H)$^+$.

1723: Prepared by the methods described in Example 1685 using 1-benzyl-1H-imidazol-4-amine and 5-(4-amino-5-(trifluoromethyl)pyrrolo[2,1-f][1,2,4]triazin-7-yl)-2-methoxynicotinic acid to give the title product (5.9 mg, 0.011 mmol, 11% yield).

MS ESI m/z 509.1 (M+H)$^+$ $^1$H NMR (500 MHz, DMSO-d6) δ 10.37 (s, 1H), 8.89 (d, J=2.5 Hz, 1H), 8.81 (d, J=2.5 Hz, 1H), 8.14 (s, 1H), 7.70 (s, 1H), 7.59 (s, 1H), 7.35 (dd, J=28.8, 8.0 Hz, 7H), 5.19 (s, 2H).

Example 1724: 5-(4-amino-5-(trifluoromethyl)pyrrolo[2,1-f][1,2,4]triazin-7-yl)-N-(1-benzyl-1H-imidazol-4-yl)-2-methylnicotinamide

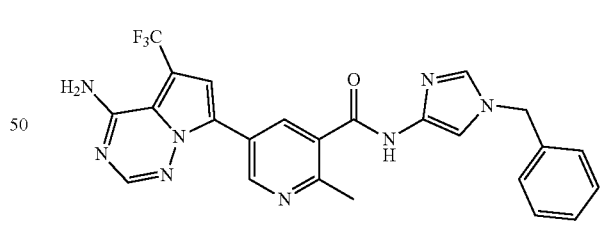

Prepared by the methods described in Example 1723 using 1-benzyl-1H-imidazol-4-amine (1723A) and 5-(4-amino-5-(trifluoromethyl)pyrrolo[2,1-f][1,2,4]triazin-7-yl)-2-methylnicotinic acid to give the title product (26.0 mg, 0.053 mmol, 53% yield).

MS ESI m/z 493.1 (M+H)$^+$ $^1$H NMR (500 MHz, DMSO-d$_6$) δ 10.99 (s, 1H), 9.21 (s, 1H), 8.51 (s, 1H), 8.19 (s, 1H), 7.78 (s, 1H), 7.72 (s, 1H), 7.53-7.28 (m, 6H), 5.22 (s, 2H), 2.59 (s, 3H).

Example 1725: 5-(4-amino-5-(trifluoromethyl)pyrrolo[2,1-f][1,2,4]triazin-7-yl)-N-(1-benzyl-1H-pyrazol-3-yl)-2-methoxynicotinamide

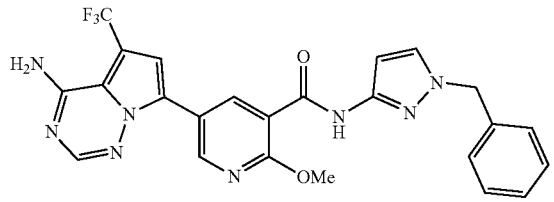 [SMILES: COc1ncc(-c2cc(C(F)(F)F)c3c(N)ncnn23)cc1C(=O)Nc1ccn(Cc2ccccc2)n1]

Prepared by the methods described in Example 1723 using 1-benzyl-1H-pyrazol-3-amine and 5-(4-amino-5-(trifluoromethyl)pyrrolo[2,1-f][1,2,4]triazin-7-yl)-2-methoxynicotinic acid to give the title product (1.2 mg, 0.0024 mmol, 2% yield).

MS ESI m/z 509.2 (M+H)⁺

¹H NMR (500 MHz, DMSO-d6) δ 10.55 (s, 1H), 8.93 (d, J=2.5 Hz, 1H), 8.76 (d, J=2.5 Hz, 1H), 8.18 (s, 1H), 7.82 (d, J=2.4 Hz, 1H), 7.63 (s, 1H), 7.41-7.21 (m, 6H), 6.68 (d, J=2.3 Hz, 1H), 5.27 (s, 2H), 4.04 (s, 3H).

Example 1726: 5-(4-amino-5-(trifluoromethyl)pyrrolo[2,1-f][1,2,4]triazin-7-yl)-N-(1-benzyl-1H-pyrazol-3-yl)-2-methylnicotinamide

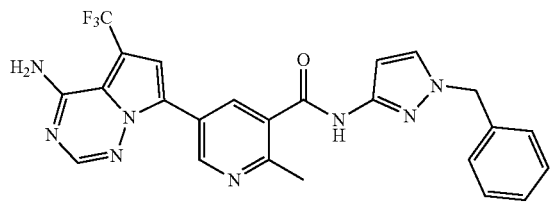 [SMILES: Cc1ncc(-c2cc(C(F)(F)F)c3c(N)ncnn23)cc1C(=O)Nc1ccn(Cc2ccccc2)n1]

Prepared by the methods described in Example 1723 using 1-benzyl-1H-pyrazol-3-amine and 5-(4-amino-5-(trifluoromethyl)pyrrolo[2,1-f][1,2,4]triazin-7-yl)-2-methylnicotinic acid (16.6 mg, 0.032 mmol, 32% yield)

MS ESI m/z 493.2 (M+H)⁺

¹H NMR (500 MHz, DMSO-d₆) δ 10.88 (s, 1H), 9.22 (s, 1H), 8.49 (d, J=2.3 Hz, 1H), 8.19 (s, 1H), 7.79 (s, 1H), 7.69 (s, 1H), 7.40-7.17 (m, 6H), 6.68 (s, 1H), 5.26 (s, 2H), 2.62 (s, 3H).

Example 1727: 5-(4-amino-5-(trifluoromethyl)pyrrolo[2,1-f][1,2,4]triazin-7-yl)-N-(3-(4-fluorophenyl)-2-hydroxy-2-methylpropyl)-2-methylnicotinamide

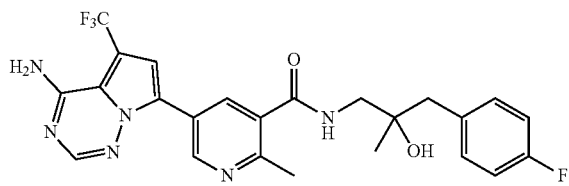 [SMILES: Cc1ncc(-c2cc(C(F)(F)F)c3c(N)ncnn23)cc1C(=O)NCC(C)(O)Cc1ccc(F)cc1]

1727A: tert-butyl (3-(4-fluorophenyl)-2-hydroxy-2-methylpropyl)carbamate: To a 50 mL round-bottomed flask was added tert-butyl (2-oxopropyl)carbamate (0.173 g, 1 mmol) in THF (1.5 mL) to give a colorless solution. (4-Fluorobenzyl)magnesium chloride (4.00 mL, 1.0 mmol) was added dropwise. The resultant clear mixture was stirred at rt for 2 h. The reaction was quenched with saturated NH₄Cl solution and the mixture was diluted with EtOAc. The layers were separated. The organic layer was washed with brine, dried with Na₂SO₄ and concentrated. The residue was directly used in the next deprotection step.

1727B: 1-amino-3-(4-fluorophenyl)-2-methylpropan-2-ol 2,2,2-trifluoroacetate, TFA: To a 50 mL round-bottomed flask was added tert-butyl (3-(4-fluorophenyl)-2-hydroxy-2-methylpropyl)carbamate (0.283 g, 1 mmol) in CH₂Cl₂ (2 mL) to give a colorless suspension. TFA (1 mL, 12.98 mmol) was added. The resultant tan yellow solution was stirred at rt for 30 min. The volatiles were stripped off to afford the desired product as a tan oil.

MS ESI m/z 166.0 (M–H₂O)⁻.

1727: Prepared by the methods described in Example 1685 using 1-amino-3-(4-fluorophenyl)-2-methylpropan-2-ol 2,2,2-trifluoroacetate and 5-(4-amino-5-(trifluoromethyl)pyrrolo[2,1-f][1,2,4]triazin-7-yl)-2-methylnicotinic acid to give the title product (3.6 mg, 0.0072 mmol, 7% yield).

MS ESI m/z 503.2 (M+H)⁺

¹H NMR (500 MHz, DMSO-d6) δ 9.11 (d, J=2.2 Hz, 1H), 8.36 (d, J=2.2 Hz, 1H), 8.27 (t, J=6.0 Hz, 1H), 8.13 (s, 1H), 7.60 (s, 1H), 7.29 (dd, J=8.3, 5.6 Hz, 2H), 7.05 (t, J=8.7 Hz, 2H), 3.44-3.15 (m, 2H), 2.82-2.67 (m, 2H), 2.58 (s, 3H), 1.04 (s, 3H).

Examples 1728 and 1729: (unassigned diastereomers) (5-(4-amino-5-(trifluoromethyl)pyrrolo[2,1-f][1,2,4]triazin-7-yl)-2-methylpyridin-3-yl)(3-((4-fluorophenyl)(hydroxy)methyl)piperidin-1-yl)methanone

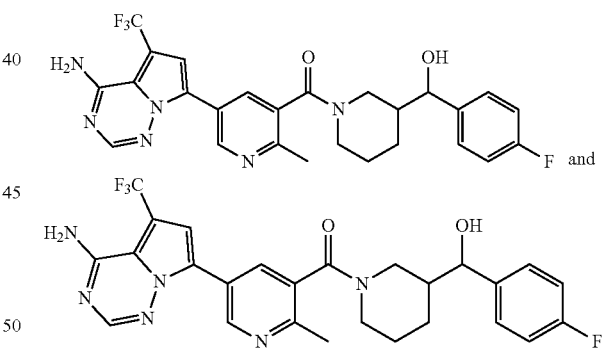

1728/9A: tert-butyl 3-((4-fluorophenyl)(hydroxy)methyl)piperidine-1-carboxylate: To a 50 mL oven-dried round-bottomed flask was added tert-butyl 3-formylpiperidine-1-carboxylate (457 mg, 2.143 mmol) in THF (4 mL) to give a colorless solution. (4-fluorophenyl)magnesium bromide (2.250 mL, 2.250 mmol) was added dropwise at rt. The mixture was stirred at rt for 30 min. The reaction was quenched with saturated NH₄Cl solution and diluted with EtOAc. The layers were separated. The organic layer was dried and concentrated to the crude product as a colorless dense oil (766 mg, xx mmol, 100% mass recovery).

MS ESI m/z 332.2 (M+Na)⁺.

1728/9B: (4-fluorophenyl)(piperidin-3-yl)methanol 2,2,2-trifluoroacetate, TFA: To a 50 mL round-bottomed flask was added tert-butyl 3-((4-fluorophenyl)(hydroxy)methyl)

piperidine-1-carboxylate (254 mg, 0.706 mmol) in CH$_2$Cl$_2$ (2 mL) to give a colorless solution. TFA (1 mL, 12.98 mmol) was added. The resultant tan yellow solution was stirred at rt for 30 min. LCMS showed two diastereomers. The volatiles were stripped off to afford the desired product as a tan oil, which was used as is.

MS ESI (m/z) 210.0 (M+H)$^+$ 1728 and 1729: Prepared by the methods described in Example 1685 using 1-amino-3-(4-fluorophenyl)-2-methyl-propan-2-ol 2,2,2-trifluoroacetate, TFA and 5-(4-amino-5-(trifluoromethyl)pyrrolo[2,1-f][1,2,4]triazin-7-yl)-2-methylnicotinic acid, and separated by prep-LC/MS to give the title products (1728: 7.0 mg, 0.012 mmol, 13% yield); 1729: 15.5 mg, 0.029 mmol, 29% yield). The NMRs for each were difficult to assign due to diastereomeric mixtures.

MS ESI m/z 529.2 (M+H)$^+$ for both product.
LC/MS retention time using Method 3=1.13 min
LC/MS retention time using Method 4=1.16 min Example 1730: 5-(4-amino-5-(trifluoromethyl)pyrrolo[2,1-f][1,2,4]triazin-7-yl)-N-(3-(4-fluorophenyl)-2-hydroxy-2-methylpropyl)-2-methoxynicotinamide

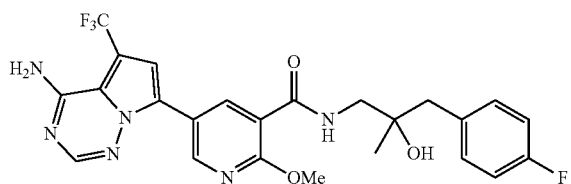 [SMILES: COc1ncc(-c2cc(C(F)(F)F)c3c(N)ncnn23)cc1C(=O)NCC(C)(O)Cc1ccc(F)cc1]

Prepared by the methods described in Example 1727 using 1-amino-3-(4-fluorophenyl)-2-methylpropan-2-ol 2,2,2-trifluoroacetate (1727B) and 5-(4-amino-5-(trifluoromethyl)pyrrolo[2,1-f][1,2,4]triazin-7-yl)-2-methoxynicotinic acid to give the title product (9.4 mg, 0.018 mmol, 18% yield). The NMRs for each were difficult to assign due to diastereomeric mixtures.

MS ESI m/z 519.2 (M+H)$^+$ $^1$H NMR (500 MHz, DMSO-d6) δ 8.88 (d, J=2.5 Hz, 1H), 8.81 (d, J=2.4 Hz, 1H), 8.27 (t, J=5.5 Hz, 1H), 8.14 (s, 1H), 7.54 (s, 1H), 7.28 (dd, J=8.3, 5.6 Hz, 2H), 7.06 (t, J=8.7 Hz, 2H), 4.07 (s, 3H), 3.33 (qd, J=13.3, 5.7 Hz, 1H), 2.75 (s, 2H), 1.05 (s, 3H).

Examples 1731 and 1732: (unassigned diastereomers) (5-(4-amino-5-(trifluoromethyl)pyrrolo[2,1-f][1,2,4]triazin-7-yl)-2-methoxypyridin-3-yl)(3-((4-fluorophenyl)(hydroxy)methyl)piperidin-1-yl)methanone

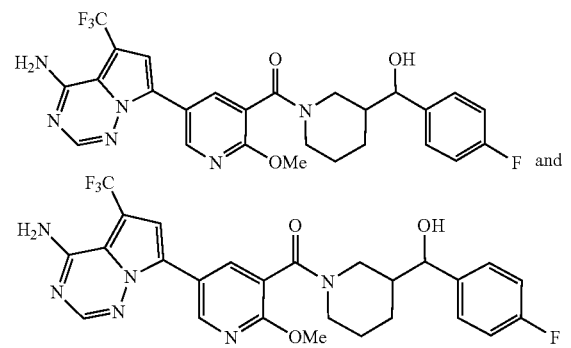

Prepared by the methods described in Example 1729/1730 using 1-amino-3-(4-fluorophenyl)-2-methylpropan-2-ol 2,2,2-trifluoroacetate (1728B) and 5-(4-amino-5-(trifluoromethyl)pyrrolo[2,1-f][1,2,4]triazin-7-yl)-2-methoxynicotinic acid, and separated by prep-LC/MS to give the title products (1731: 7.7 mg, 0.014 mmol, 15.% yield; 1732: 11.3 mg, 0.021 mmol, 22% yield). The NMRs for each were difficult to assign due to diastereomeric mixtures.

MS ESI m/z 529.2 (M+H)$^+$ for both products.
LC/MS retention time using Method 2=1.79 min
LC/MS retention time using Method 1=1.88 min Example 1733 and 1734: (unassigned diastereomers) (5-(4-amino-5-(trifluoromethyl)pyrrolo[2,1-f][1,2,4]triazin-7-yl)-2-methoxypyridin-3-yl)(3-(1-(4-fluorophenyl)-1-hydroxyethyl)piperidin-1-yl)methanone

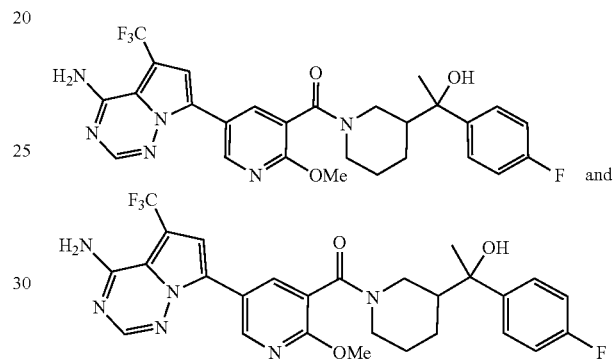

1733/4A: tert-butyl 3-(1-(4-fluorophenyl)-1-hydroxyethyl)piperidine-1-carboxylate: To a 50 mL oven-dried round-bottomed flask was added tert-butyl 3-acetylpiperidine-1-carboxylate (480 mg, 2.112 mmol) in THF (4 mL) to give a colorless solution. (4-fluorophenyl)magnesium bromide (2.53 mL, 2.53 mmol) was added dropwise at rt. The mixture was stirred at rt for 30 min. The reaction was quenched with saturated NH$_4$Cl solution and diluted with EtOAc. The layers were separated. The organic layer was dried and concentrated to the crude product as a colorless dense oil (784.2 mg, 100% mass recovery).

MS ESI m/z 346.2 (M+Na)$^+$.

1733/4B: 1-(4-fluorophenyl)-1-(piperidin-3-yl)ethan-1-ol 2,2,2-trifluoroacetate, TFA: To a 50 mL round-bottomed flask was added tert-butyl 3-(1-(4-fluorophenyl)-1-hydroxyethyl)piperidine-1-carboxylate (244.2 mg, 0.657 mmol) in CH$_2$Cl$_2$ (1.5 mL) to give a colorless solution. TFA (1 mL, 12.98 mmol) was added. The resultant tan yellow solution was stirred at rt for 30 min. The volatiles were stripped off to afford the desired product as a tan oil, which was directly used in the next reaction.

MS ESI m/z 224.0 (M+H)$^+$.

1733 and 1734: Prepared by the methods described in Example 1685 using 11-(4-fluorophenyl)-1-(piperidin-3-yl)ethan-1-ol 2,2,2-trifluoroacetate and lithium 5-(4-amino-5-(trifluoromethyl)pyrrolo[2,1-f][1,2,4]triazin-7-yl)-2-methoxynicotinate, and separated by prep-LC/MS to give the title products (1733: 1.8 mg, 0.0028 mmol, 3% yield; 1734: 1.4 mg, 0.0024 mmol, 3% yield). The NMRs for each were difficult to assign due to diastereomeric mixtures.

MS ESI m/z 559.3 (M+H)$^+$ for both products
LC/MS retention time using Method 2=1.64 min for both products Examples 1735 and 1736: (unassigned diastereomers) (5-(4-amino-5-(trifluoromethyl)pyrrolo[2,1-f][1,2,4]triazin-7-yl)-2-methylpyridin-3-yl)(3-(1-(4-fluorophenyl)-1-hydroxyethyl)piperidin-1-yl)methanone

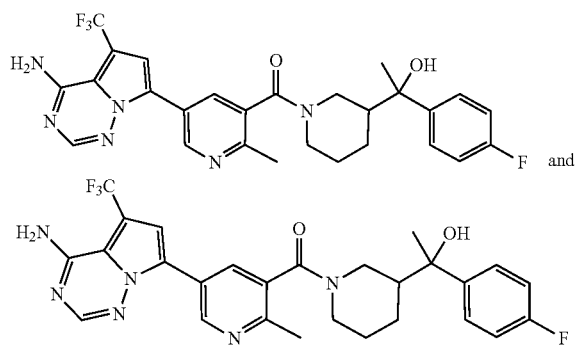

1735 and 1736: Prepared by the methods described in Example 1729/1729 using 11-(4-fluorophenyl)-1-(piperidin-3-yl)ethan-1-ol 2,2,2-trifluoroacetate (1733B) and 5-(4-amino-5-(trifluoromethyl)pyrrolo[2,1-f][1,2,4]triazin-7-yl)-2-methylnicotinic acid, and separated by prep-LC/MS to give the title products (1735: 2.4 mg, 0.0038 mmol, 4% yield; 1736: 1.0 mg, 0.0018 mmol, 2% yield). The NMRs for each were difficult to assign due to diastereomeric mixtures.

MS ESI m/z 543.3 (M+H) for both product.

1735: LC/MS retention time using Method 2=1.60 min

1736: LC/MS retention time using Method 2=1.58 min

Examples 1737 and 1738: (unassigned diastereomers) (5-(4-amino-5-(trifluoromethyl)pyrrolo[2,1-f][1,2,4]triazin-7-yl)-2-methoxypyridin-3-yl)(3-((4-fluorophenyl)(hydroxy)methyl)-3-methylpiperidin-1-yl)methanone

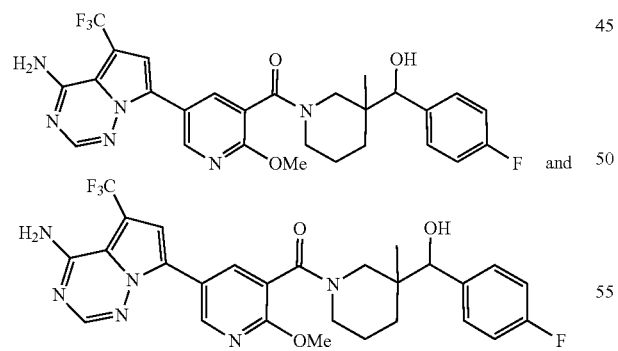

1737/8A: tert-butyl 3-formyl-3-methylpiperidine-1-carboxylate: To a 50 mL oven-dried round-bottomed flask was added tert-butyl 3-formylpiperidine-1-carboxylate (0.640 g, 3 mmol) and methyl iodide (0.563 mL, 9.00 mmol) in CH$_2$Cl$_2$ (15 mL) to give a colorless solution under nitrogen. After cooling to 0° C., potassium tert-butoxide (0.438 g, 3.90 mmol) was added. After 30 min, the cooling bath was removed. The reaction mixture was stirred at rt for 5 h and quenched with brine. The layers were separated. The aqueous layer was extracted with CH$_2$Cl$_2$. The combined organic layer was washed with brine, dried with Na$_2$SO$_4$ and concentrated to a colorless oil (~930 mg). A portion of the crude material was directly used in the next step.

1737/8B: tert-butyl 3-((4-fluorophenyl)(hydroxy)methyl)-3-methylpiperidine-1-carboxylate: To a 50 mL oven-dried round-bottomed flask was added tert-butyl 3-formyl-3-methylpiperidine-1-carboxylate (682 mg, 3 mmol) (azeotroped with dry benzene) in THF (8 mL) to give a colorless solution. (4-Fluorophenyl)magnesium bromide (3.60 mL, 3.60 mmol) was added dropwise at rt. The mixture was stirred at rt for 30 min. The reaction was quenched with saturated NH$_4$Cl solution and diluted with EtOAc. The layers were separated. The organic layer was dried and concentrated to the crude product as a colorless dense oil (995 mg, 3.0 mmol, 100% mass recovery).

MS ESI m/z 346.1 (M+H)$^+$.

1737/8C: (4-fluorophenyl)(3-methylpiperidin-3-yl)methanol 2,2,2-trifluoroacetate, TFA: To a 50 mL round-bottomed flask was added tert-butyl 3-((4-fluorophenyl)(hydroxy)methyl)-3-methylpiperidine-1-carboxylate (320 mg, 0.989 mmol) in CH$_2$Cl$_2$ (2 mL) to give a colorless solution. TFA (1 mL, 12.98 mmol) was added. The resultant tan yellow solution was stirred at rt for 60 min. The volatiles were stripped off to afford the desired product (crude 328 mg) as a tan oil, which was directly used in the next reaction.

MS ESI m/z 224.2 (M+H)$^+$.

1737 and 1738: Prepared by the methods described in Example 1685 using (4-fluorophenyl)(3-methylpiperidin-3-yl)methanol 2,2,2-trifluoroacetate and lithium 5-(4-amino-5-(trifluoromethyl)pyrrolo[2,1-f][1,2,4]triazin-7-yl)-2-methoxynicotinate and separated by prep-LC/MS to give the title products (1737: 7.3 mg, 0.012 mmol, 12% yield; 1738: 7.1 mg, 0.012 mmol, 12% yield). The NMRs for each were difficult to assign due to diastereomeric mixtures.

MS ESI m/z 559.2 (M+H)$^+$ for both product.

1737: LC/MS retention time using Method 1=1.83 min

1738: LC/MS retention time using Method 1=1.94 min

Examples 1739 and 1740: (unassigned diastereomers) (5-(4-amino-5-(trifluoromethyl)pyrrolo[2,1-f][1,2,4]triazin-7-yl)-2-methylpyridin-3-yl)(3-((4-fluorophenyl)(hydroxy)methyl)-3-methylpiperidin-1-yl)methanone

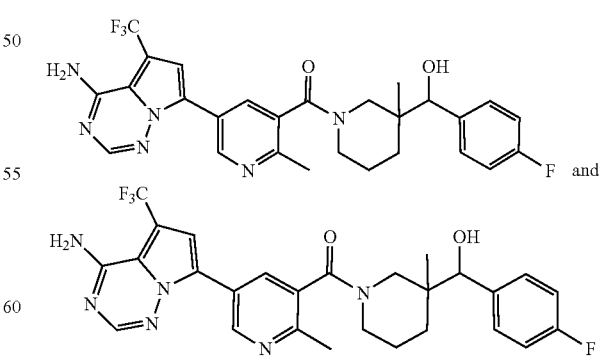

Prepared by the methods described in Example 1737/1738 using (4-fluorophenyl)(3-methylpiperidin-3-yl)methanol 2,2,2-trifluoroacetate (1737C) and lithium 5-(4-amino-5-(trifluoromethyl)pyrrolo[2,1-f][1,2,4]triazin-7-yl)-2- methoxynicotinate, and separated by prep-LC/MS to give the title products (1739: 2.3 mg, 0.0042 mmol, 4% yield; 1740: 8.0 mg, 0.014 mmol, 14% yield). The NMRs for each were difficult to assign due to diastereomeric mixtures.

MS ESI m/z 543.3 (M+H)+ for both products.
1739: LC/MS retention time using Method 1=1.94 min
1740: LC/MS retention time using Method 1=1.73 min Example 1741: (5-(4-amino-5-(trifluoromethyl)pyrrolo[2,1-f][1,2,4]triazin-7-yl)-2-methoxypyridin-3-yl)(3-(4-fluorobenzyl)-3-hydroxypiperidin-1-yl)methanone

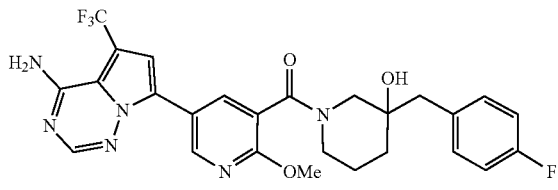 [SMILES: COc1ncc(-c2cc(C(F)(F)F)c3c(N)ncnn23)cc1C(=O)N1CCCC(O)(Cc2ccc(F)cc2)C1]

1741A: tert-butyl 3-(4-fluorobenzyl)-3-hydroxypiperidine-1-carboxylate: To a 50 mL oven-dried round-bottomed flask was added tert-butyl 3-oxopiperidine-1-carboxylate (227 mg, 1.139 mmol) in THF (2 mL) to give a colorless solution. (4-Fluorobenzyl)magnesium chloride (4.78 mL, 1.1% mmol) was added dropwise at rt. The mixture was stirred at rt for 3 h. The reaction was quenched with saturated NH4Cl solution and diluted with EtOAc. The layers were separated. The organic layer was dried and concentrated to the crude product as a colorless dense oil (317 mg, 1.02 mmol, 90% crude) which was used as is.

1741B: 3-(4-fluorobenzyl)piperidin-3-ol 2,2,2-trifluoroacetate, TFA: In a 50 mL round-bottomed flask was tert-butyl 3-(4-fluorobenzyl)-3-hydroxypiperidine-1-carboxylate (317 mg, 1.025 mmol) in CH2Cl2 (2 mL) to give a colorless solution. TFA (1 mL, 12.98 mmol) was added. The resultant tan yellow solution was stirred at rt for 60 min. The volatiles were stripped off to afford the desired product (crude 375 mg) as a dark oil, which was directly used as is.

MS ESI m/z 210.2 (M+H)+.

1741: Prepared by the methods described in Example 1685 using 3-(4-fluorobenzyl)piperidin-3-ol 2,2,2-trifluoroacetate and lithium 5-(4-amino-5-(trifluoromethyl)pyrrolo[2,1-f][1,2,4]triazin-7-yl)-2-methoxynicotinate and separated by prep-LC/MS. The NMR was difficult to assign due to the diastereomeric mixture.

MS ESI m/z 545.2 (M+H)+
LC/MS retention time using Method 2=1.86 min

Example 1741: (5-(4-amino-5-(trifluoromethyl)pyrrolo[2,1-f][1,2,4]triazin-7-yl)-2-methylpyridin-3-yl)(3-(4-fluorobenzyl)-3-hydroxypiperidin-1-yl)methanone

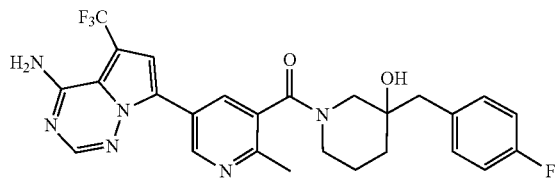 [SMILES: Cc1ncc(-c2cc(C(F)(F)F)c3c(N)ncnn23)cc1C(=O)N1CCCC(O)(Cc2ccc(F)cc2)C1]

Prepared by the methods described in Example 1741 using 3-(4-fluorobenzyl)piperidin-3-ol 2,2,2-trifluoroacetate (1741B) and 5-(4-amino-5-(trifluoromethyl)pyrrolo[2,1-f][1,2,4]triazin-7-yl)-2-methylnicotinic acid to give the title product (9.1 mg, 0.017 mmol, 17% yield).

MS ESI m/z 529.2 (M+H)+
LC/MS retention time using Method 2=1.69 min

Example 1743: 5-(4-amino-5-(trifluoromethyl)pyrrolo[2,1-f][1,2,4]triazin-7-yl)-N-(3-(4-fluorophenyl)-2,3-dihydroxy-2-methylpropyl)-2-methoxynicotinamide

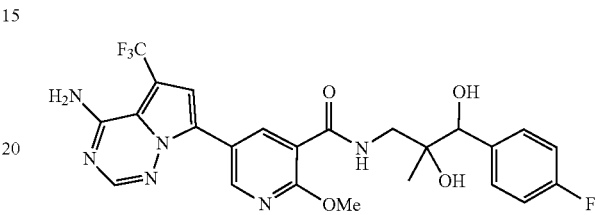

1743A: 1-(4-fluorophenyl)-2-methylprop-2-en-1-ol: To a 250 mL oven-dried round-bottomed flask was added 4-fluorobenzaldehyde (1.24 g, 9.99 mmol) in THF (20 mL) to give a colorless solution. Prop-1-en-2-ylmagnesium bromide (22 mL, 10.99 mmol) was added dropwise at rt. The mixture was stirred at rt for 30 min. The reaction was quenched with saturated NH4Cl solution and diluted with EtOAc. The layers were separated. The organic layer was dried and concentrated to the crude product as a slightly tan oil (crude: 2.12 g). Half was saved and half (1.06 g) was used in the next reaction.

1743B: (4-fluorophenyl)(2-methyloxiran-2-yl)methanol: To a 250 mL oven-dried round-bottomed flask was added 1-(4-fluorophenyl)-2-methylprop-2-en-1-ol (831 mg, 5 mmol) in CH2Cl2 (20 mL) to give a colorless solution. mCPBA (863 mg, 5.00 mmol) was added ON for 16 h. The reaction mixture was diluted with ether and water. The layers were separated. The organic layer was washed three time with NaHCO3 solution and brine. The organic solution was then dried and concentrated to the crude product as a light yellow oil (836 mg, 4.59 mmol, crude 92% yield for two steps).

1743C: 3-amino-1-(4-fluorophenyl)-2-methylpropane-1,2-diol: To a 20 mL pressure vial was added (4-fluorophenyl)(2-methyloxiran-2-yl)methanol (274 mg, 1.504 mmol) and 7N ammonia in MeOH (2 mL, 14.00 mmol) was added. The mixture was stirred at rt ON and then heated at 65° C. for 5 h. The volatiles were removed in vacuo to leave the crude desired product as a slightly tan dense oil (200 mg, 1.0 mmol, 67% yield).

MS ESI m/z 200.1 (M+H)+.

1743: Prepared by the methods described in Example 1685 using 3-amino-1-(4-fluorophenyl)-2-methylpropane-1,2-diol and lithium 5-(4-amino-5-(trifluoromethyl)pyrrolo[2,1-f][1,2,4]triazin-7-yl)-2-methoxynicotinate to give the title product (20.0 mg, 0.036 mmol, 36% yield).

MS ESI m/z 535.1 (M+H)+
1H NMR (500 MHz, DMSO-d6) δ 9.01-8.77 (m, 3H), 8.46 (d, J=33.5 Hz, 1H), 8.19-8.14 (m, 1H), 7.62-7.53 (m, 2H), 7.45 (ddd, J=8.5, 5.5, 2.6 Hz, 2H), 7.11 (dtd, J=9.0, 7.1, 6.1, 3.4 Hz, 2H), 5.58 (d, J=5.2 Hz, 1H), 4.71-4.51 (m, 2H), 4.09 (dd, J=10.7, 1.8 Hz, 3H), 1.12-0.90 (m, 3H) (a mixture of two diastereomers).

Examples 1744 and 1745: 5-(4-amino-5-(trifluoromethyl)pyrrolo[2,1-f][1,2,4]triazin-7-yl)-N-(3-(4-fluorophenyl)-2,3-dihydroxy-2-methylpropyl)-2-methylnicotinamide

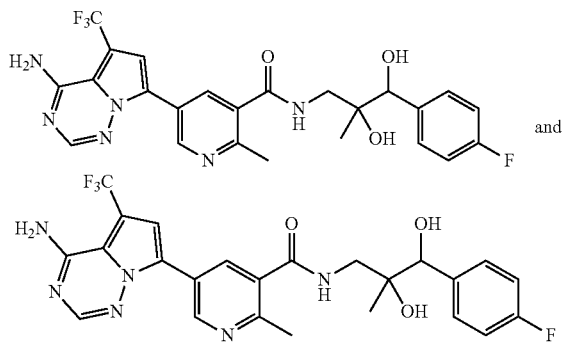

and

Prepared by the methods described in Example 1743 using 3-amino-1-(4-fluorophenyl)-2-methylpropane-1,2-diol (1743C) and 5-(4-amino-5-(trifluoromethyl)pyrrolo[2,1-f][1,2,4]triazin-7-yl)-2-methylnicotinic acid and separated by prep-LC/MS to give the title products (1744: 12.8 mg, 0.025 mmol, 25% yield; 1745: 9.8 mg, 0.018 mmol, 18% yield).

MS ESI m/z 519.3 (M+H)+ for both products

1744: $^1$H NMR (500 MHz, DMSO-d6) δ 9.17 (d, J=2.3 Hz, 1H), 8.41 (d, J=2.2 Hz, 1H), 8.35 (t, J=6.0 Hz, 1H), 8.18 (s, 1H), 7.68 (s, 1H), 7.43 (dd, J=8.6, 5.8 Hz, 2H), 7.11 (t, J=8.8 Hz, 2H), 5.52 (d, J=4.5 Hz, 1H), 4.55 (s, 1H), 4.52 (d, J=4.6 Hz, 1H), 0.93 (s, 3H).

1745: $^1$H NMR (500 MHz, DMSO-d6) δ 9.16 (d, J=2.3 Hz, 1H), 8.38 (d, J=2.3 Hz, 1H), 8.21-8.13 (m, 2H), 7.65 (s, 1H), 7.49-7.43 (m, 2H), 7.14-7.09 (m, 2H), 5.38 (d, J=4.9 Hz, 1H), 4.51 (d, J=4.7 Hz, 1H), 4.43 (d, J=1.6 Hz, 1H), 2.60 (s, 3H), 1.05 (s, 3H).

Example 1746: 5-(4-amino-5-(trifluoromethyl)pyrrolo[2,1-f][1,2,4]triazin-7-yl)-N-(2-hydroxy-2,4,4-trimethylpentyl)-2-methylnicotinamide

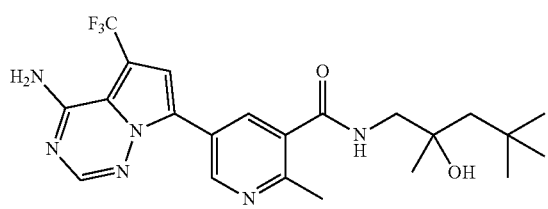 [SMILES: Cc1ncc(-c2cc(C(F)(F)F)c3c(N)ncnn23)cc1C(=O)NCC(C)(O)CC(C)(C)C]

1746A: 2-methyl-2-neopentyloxirane: To a 500 mL round-bottomed flask was added 2,4,4-trimethylpent-1-ene (2.93 g, 26.1 mmol) in CH$_2$Cl$_2$ (80 mL) to give a colorless solution. mCPBA (5.85 g, 26.1 mmol) was added followed by sodium bicarbonate (2.193 g, 26.1 mmol). The mixture was stirred at rt ON for 16 h. The reaction mixture was diluted with ether and water. The layers were separated. The organic layer was washed three times with NaHCO$_3$ solution and brine. The organic solution was then dried and concentrated to the crude product as a colorless oil (3.39 g, 26.1 mmol crude 100% yield).

1755: 1-amino-2,4,4-trimethylpentan-2-ol: To a 75 mL pressure bottle was added 2-methyl-2-neopentyloxirane (1.07 g, 8.35 mmol) and 7N ammonia in methanol (15 mL, 105 mmol) was added. The mixture was stirred at 62° C. ON for 18 h. The volatiles were removed in vacuo to afford the desired product as a slightly tan oil (620 mg, 51%). It was used without further purification.

1755: Prepared by the methods described in Example 1685 using 1-amino-2,4,4-trimethylpentan-2-ol and 5-(4-amino-5-(trifluoromethyl)pyrrolo[2,1-f][1,2,4]triazin-7-yl)-2-methylnicotinic acid to give the title product (13.3 mg, 0.029 mmol, 29% yield).

MS ESI m/z 465.2 (M+H)+

$^1$H NMR (500 MHz, DMSO-d6) δδ 9.15 (d, J=2.2 Hz, 1H), 8.39 (d, J=2.2 Hz, 1H), 8.31 (t, J=6.1 Hz, 1H), 8.17 (s, 1H), 7.67 (s, 1H), 3.40-3.11 (m, 2H), 2.57 (s, 3H), 1.56-1.37 (m, 2H), 1.21 (s, 3H), 1.01 (s, 9H).

Example 1747: (5-(4-amino-5-(trifluoromethyl)pyrrolo[2,1-f][1,2,4]triazin-7-yl)-2-methoxypyridin-3-yl)(3-((4-fluorophenyl)(hydroxy)methyl)-3-hydroxypiperidin-1-yl)methanone

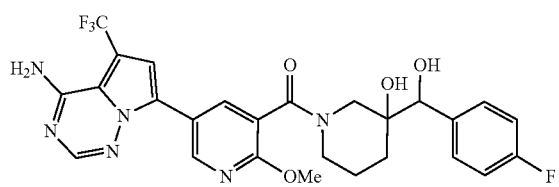 [SMILES: COc1ncc(-c2cc(C(F)(F)F)c3c(N)ncnn23)cc1C(=O)N1CCCC(O)(C(O)c2ccc(F)cc2)C1]

1747A: tert-butyl 3-(4-fluorobenzoyl)piperidine-1-carboxylate: To a 50 mL round-bottomed flask was added tert-butyl 3-((4-fluorophenyl)(hydroxy)methyl)piperidine-1-carboxylate (1728A) (577 mg, 1.604 mmol) in CH$_2$Cl$_2$ (6 mL) to give a colorless solution. Dess-Martin periodinane (1701 mg, 4.01 mmol) was added in portions. The mixture was stirred at rt for 3 h. The reaction mixture was treated with NaHCO$_3$ solution (mixed with some sodium bisulfite). The layers were separated. The aqueous layer was extracted with CH$_2$Cl$_2$. The combined organic layers were washed with brine, dried with Na$_2$SO$_4$, and concentrated. The residue was purified by silica gel chromatography up to 50% EtOAc/hexanes to afford the desired product (336.4 mg, 1.09 mmol, 68% for two steps) as a white solid.

$^1$H NMR (500 MHz, CDCl$_3$) δ 8.08-7.98 (m, 2H), 7.21-7.12 (m, 2H), 4.22 (d, J=11.1 Hz, 1H), 4.14 (q, J=7.1 Hz, 1H), 3.38 (s, 1H), 2.95 (s, 1H), 2.78 (t, J=12.7 Hz, 1H), 2.08-1.99 (m, 1H), 1.85-1.66 (m, 2H), 1.49 (s, 9H), one exchangeable proton not seen.

1747B: tert-butyl 3-(4-fluorobenzoyl)-3-hydroxypiperidine-1-carboxylate: To a 50 mL round-bottomed flask was added tert-butyl 3-(4-fluorobenzoyl)piperidine-1-carboxylate (151 mg, 0.491 mmol), Cs$_2$CO$_3$ (160 mg, 0.491 mmol) and triethyl phosphite (0.172 mL, 0.983 mmol) in DMSO (2 mL) to give a white suspension. The mixture was stirred under 1 atm. oxygen (balloon) for 3.5 d (80 h). The mixture was diluted with water and EtOAc. The layers were separated. The aqueous layer was extracted with EtOAc. The combined organic layers were washed with brine, dried with Na$_2$SO$_4$ and concentrated. The residue was purified by silica gel chromatography up to 50% EtOAc/hexanes to afford the desired product (123 mg, 0.38 mmol, 77% yield) as a white solid.

MS ESI m/z 346.1 (M+Na)+

¹H NMR (500 MHz, CDCl₃) δ 8.30-8.19 (m, 2H), 7.14-7.03 (m, 2H), 4.23-3.91 (m, 2H), 3.38 (br, 1H), 2.87 (ddd, J=13.7, 11.4, 3.2 Hz, 1H), 2.10-1.83 (m, 3H), 1.58 (d, J=31.4 Hz, 1H), 1.43 (s, 9H), 1.37-1.27 (m, 1H).

1747C: tert-butyl 3-((4-fluorophenyl)(hydroxy)methyl)-3-hydroxypiperidine-1-carboxylate: To a 20 mL round-bottomed flask was added tert-butyl 3-(4-fluorobenzoyl)-3-hydroxypiperidine-1-carboxylate (100 mg, 0.309 mmol) in MeOH (1 mL) to give a yellow solution. NaBH₄ (46.8 mg, 1.237 mmol) was added. The mixture was stirred for 60 min. Volatiles were stripped off. The residue was partitioned between water and EtOAc. The layers were separated. The aqueous layer was extracted twice with EtOAc. The combined organic layer was washed with brine, dried with Na₂SO₄ and concentrated to a white solid (101 mg, 0.31 mmol, 100% yield).

MS ESI m/z 348.1 (M+Na)⁺.

1747D: 3-((4-fluorophenyl)(hydroxy)methyl)piperidin-3-ol 2,2,2-trifluoroacetate, TFA: To a 50 mL round-bottomed flask was added tert-butyl 3-((4-fluorophenyl)(hydroxy)methyl)-3-hydroxypiperidine-1-carboxylate (101 mg, 0.310 mmol) in CH₂Cl₂ (2 mL) to give a colorless solution. TFA (1 mL, 12.98 mmol) was added. The resultant tan yellow solution was stirred at rt for 60 min. The volatiles were stripped off to afford the desired product (crude 120 mg) as a tan oil, which was directly used as is.

MS ESI m/z 226.0 (M+H)⁺.

1747: Prepared by the methods described in Example 1685 using 3-((4-fluorophenyl)(hydroxy)methyl)piperidin-3-ol 2,2,2-trifluoroacetate and lithium 5-(4-amino-5-(trifluoromethyl)pyrrolo[2,1-f][1,2,4]triazin-7-yl)-2-methoxynicotinate, and separated by prep-LC/MS to give the title product (16.7 mg, 0.028 mmol, 37% yield).

MS ESI m/z 561.1 (M+H)⁺
LC/MS retention time using Method 1=1.1 min

Examples 1748 and 1749: (unassigned diastereomers) (5-(4-amino-5-(trifluoromethyl)pyrrolo[2,1-f][1,2,4]triazin-7-yl)-2-methylpyridin-3-yl)(3-((4-fluorophenyl)(hydroxy)methyl)-3-hydroxypiperidin-1-yl)methanone

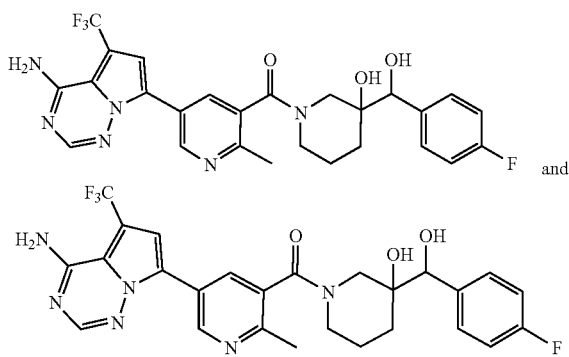

Prepared by the methods described in Example 1747 using 3-((4-fluorophenyl)(hydroxy)methyl)piperidin-3-ol 2,2,2-trifluoroacetate (1747D) and 5-(4-amino-5-(trifluoromethyl)pyrrolo[2,1-f][1,2,4]triazin-7-yl)-2-methylnicotinic acid, and separated by prep-LC/MS to give the titled products (1748: 15.0 mg, 0.027 mmol, 34% yield; 1749: 8.2 mg, 0.014 mmol, 18% yield). The NMRs for each were difficult to assign due to diastereomeric mixtures.

MS ESI m/z 545.1 (M+H)⁺ for both products.
1748: LC/MS retention time using Method 2=1.51 min
1749: LC/MS retention time using Method 1=1.54 min Example 1750: (5-(4-amino-5-(trifluoromethyl)pyrrolo[2,1-f][1,2,4]triazin-7-yl)-2-methylpyridin-3-yl)(3-(4-fluorobenzyl)-3,5-dihydroxypiperidin-1-yl)methanone

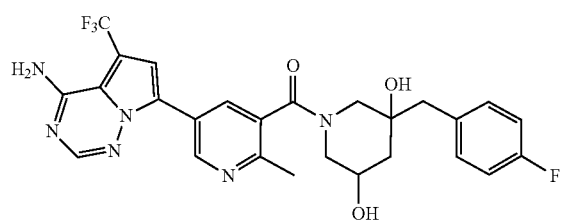 [SMILES: Cc1ncc(-c2cc(C(F)(F)F)c3c(N)ncnn23)cc1C(=O)N1CC(O)CC(O)(Cc2ccc(F)cc2)C1]

1750A: tert-butyl 3-(4-fluorobenzyl)-3-hydroxy-5-oxopiperidine-1-carboxylate: To an oven-dried 50 mL round-bottomed flask was added tert-butyl 3,5-dioxopiperidine-1-carboxylate (580 mg, 2.72 mmol) in THF (5 mL) to give a yellow suspension. NaH (163 mg, 4.08 mmol) was added under nitrogen. The mixture was stirred under nitrogen for 30 min. (4-Fluorobenzyl)magnesium chloride (16.32 mL, 4.08 mmol) was added. The mixture was stirred at rt for 1 h and then at 60° C. for 3 h. The reaction was slowly quenched by saturated NH₄Cl solution and the mixture was diluted with EtOAc. The layers were separated. The aqueous layer was extracted with EtOAc. The combined organic layer was washed with brine, dried with Na₂SO₄ and concentrated. The residue was purified by silica gel chromatography up to 60% EtOAc/hexanes to afford the desired product (220 mg, 0.68 mmol, 25%) as a slightly tan dense oil.

¹H NMR (500 MHz, CDCl₃) δ 7.24-7.18 (m, 2H), 7.09-7.01 (m, 2H), 4.14 (td, J=11.2, 9.3, 6.5 Hz, 1H), 4.01-3.70 (m, 2H), 3.53-3.34 (m, 1H), 2.91-2.82 (m, 2H), 2.56-2.45 (m, 2H), 2.18-1.88 (br, 1H), 1.46 (s, 9H).

1750B: tert-butyl 3-(4-fluorobenzyl)-3,5-dihydroxypiperidine-1-carboxylate: To a 20 mL round-bottomed flask was added tert-butyl 3-(4-fluorobenzyl)-3-hydroxy-5-oxopiperidine-1-carboxylate (88.9 mg, 0.275 mmol) in MeOH (1 mL) to give a yellow solution. NaBH₄ (41.6 mg, 1.100 mmol) was added. The mixture was stirred for 60 min. Volatiles were stripped off. The residue was partitioned between water and EtOAc. The layers were separated. The aqueous layer was extracted twice with EtOAc. The combined organic layer was washed with brine, dried with Na₂SO₄ and concentrated to a tan oil (85 mg, 0.026 mmol, 95%) which was used as is.

MS ESI m/z 348.1 (M+Na)⁺.

1750C: 3-(4-fluorobenzyl)piperidine-3,5-diol 2,2,2-trifluoroacetate, TFA: To a 50 mL round-bottomed flask was added tert-butyl 3-(4-fluorobenzyl)-3,5-dihydroxypiperidine-1-carboxylate (83 mg, 0.255 mmol) in CH₂Cl₂ (2 mL) to give a colorless solution. TFA (1 mL, 12.98 mmol) was added. The resultant tan yellow solution was stirred at rt for 60 min. The volatiles were stripped off to afford the desired product (crude 100 mg) as a tan oil, which was directly used as is.

MS ESI m/z 226.0 (M+H)⁺.

1750: Prepared by the methods described in Example 1685 using 3-(4-fluorobenzyl)piperidine-3,5-diol 2,2,2-trifluoroacetate and 5-(4-amino-5-(trifluoromethyl)pyrrolo[2,1-f][1,2,4]triazin-7-yl)-2-methylnicotinic acid to afford the titled product (9.8 mg, 0.017 mmol, 27% yield).

MS ESI m/z 544.9 (M+H)+

LC/MS retention time using Method 2=0.88 min

Example 1751: 5-(4-amino-5-(trifluoromethyl)pyrrolo[2,1-f][1,2,4]triazin-7-yl)-2-methyl-N-(5,5,5-trifluoro-2,4-dihydroxy-4-(trifluoromethyl)pentyl)nicotinamide

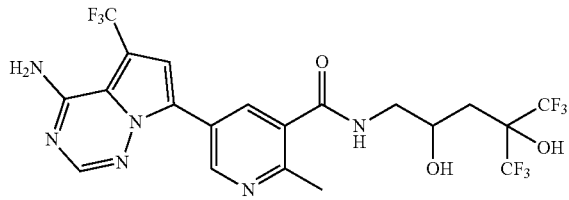 [SMILES: Cc1ncc(-c2cc(C(F)(F)F)c3c(N)ncnn23)cc1C(=O)NCC(O)CC(O)(C(F)(F)F)C(F)(F)F]

1751A: 1,1,1,3,3,3-hexafluoro-2-(oxiran-2-ylmethyl)propan-2-ol: To a 250 mL round-bottomed flask was added 1,1,1-trifluoro-2-(trifluoromethyl)pent-4-en-2-ol (1.37 g, 6.58 mmol) in CH$_2$Cl$_2$ (20 mL) to give a colorless solution. mCPBA (1.475 g, 6.58 mmol) was added followed by sodium bicarbonate (0.553 g, 6.58 mmol). The mixture was stirred at rt ON for 16 h. The reaction mixture was diluted with ether and water. The layers were separated. The organic layer was washed three time with NaHCO$_3$ solution and brine. The organic solution was then dried and concentrated to the crude product as a colorless oil (1 g, crude 68%, the product might be very volatile or water soluble). The crude product was directly used in the next step.

1751B: 5-amino-1,1,1-trifluoro-2-(trifluoromethyl)pentane-2,4-diol: To a 75 mL pressure bottle was added 1,1,1,3,3,3-hexafluoro-2-(oxiran-2-ylmethyl)propan-2-ol (1 g, 4.46 mmol) and 7N ammonia in MeOH (15 mL, 105 mmol) was added. The mixture was stirred at 62° C. ON for 18 h. The volatiles were removed in vacuo to afford the desired product as a slightly tan solid (470 mg, 1.95 mmol 44% yield). It was used without further purification.

1751: Prepared by the methods described in Example 1685 using 5-amino-1,1,1-trifluoro-2-(trifluoromethyl)pentane-2,4-diol and 5-(4-amino-5-(trifluoromethyl)pyrrolo[2,1-f][1,2,4]triazin-7-yl)-2-methylnicotinic acid to afford the title product (13.0 mg, 0.023 mmol, 23% yield).

MS ESI m/z 561.0 (M+H)+

$^1$H NMR (500 MHz, DMSO-d6) δ 9.17 (s, 1H), 8.63 (t, J=5.9 Hz, 1H), 8.38 (s, 1H), 8.16 (s, 1H), 7.64 (s, 1H), 4.13 (s, 1H), 3.45-3.24 (m, 2H), 2.56 (s, 3H), 2.19 (d, J=15.2 Hz, 1H), 2.06-1.95 (m, 1H).

Example 1752: 5-(4-amino-5-(trifluoromethyl)pyrrolo[2,1-f][1,2,4]triazin-7-yl)-N-(3-(4-fluorophenyl)-2-hydroxy-3-methoxy-2-methylpropyl)-2-methylnicotinamide

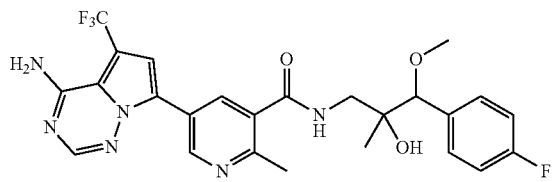 [SMILES: COC(c1ccc(F)cc1)C(C)(O)CNC(=O)c1cc(-c2cc(C(F)(F)F)c3c(N)ncnn23)cnc1C]

1752A: 2-((4-fluorophenylxmethoxy)methyl)-2-methyloxirane: To a 50 mL oven-dried round-bottomed flask was added (4-fluorophenyl)(2-methyloxiran-2-yl)methanol (1743B) (342 mg, 1.877 mmol) in THF (4 mL) to give a colorless solution. NaH (225 mg, 5.63 mmol) was added. The mixture was stirred at rt for 5 min and MeI (0.352 mL, 5.63 mmol) was added. The mixture was stirred at rt ON for 16 h. The reaction was slowly quenched with saturated NH$_4$Cl solution (gas evolves). The reaction mixture was diluted with EtOAc and water. The layers were separated. The organic layer was washed brine. The organic solution was then dried and concentrated to the crude product as a light yellow oil (440 mg, 1.88 mmol, crude >100% mass).

1752B: 3-amino-1-(4-fluorophenyl)-1-methoxy-2-methylpropan-2-ol: To a 20 mL pressure vial was added 2-((4-fluorophenyl)(methoxy)methyl)-2-methyloxirane (0.184 g, 0.939 mmol) and 7N ammonia in MeOH (2 mL, 14.00 mmol) was added. The mixture was stirred at 65 QC ON for 18 h. The volatiles were removed in vacuo to leave the crude desired product as a slightly tan dense oil (211 mg, 0.094 mmol, 100% yield).

MS ESI m/z 214.1 (M+H)+.

1752: Prepared by the methods described in Example 1685 using 3-amino-1-(4-fluorophenyl)-1-methoxy-2-methylpropan-2-ol and 5-(4-amino-5-(trifluoromethyl)pyrrolo[2,1-f][1,2,4]triazin-7-yl)-2-methylnicotinic acid to afford the title product (8.3 mg, 0.015 mmol, 15% yield).

MS ESI m/z 533.0 (M+H)+

$^1$H NMR (500 MHz, DMSO-d6) δ 9.15 (d, J=2.2 Hz, 1H), 8.42 (d, J=2.3 Hz, 1H), 8.34 (t, J=6.0 Hz, 1H), 8.16 (s, 1H), 7.68 (s, 1H), 7.36 (dd, J=8.4, 5.8 Hz, 2H), 7.17 (t, J=8.7 Hz, 2H), 4.66 (s, 1H), 4.15 (s, 1H), 3.18 (s, 3H), 2.60 (s, 3H), 0.96 (s, 3H) missing 4 protons due to solvent suppression.

Examples 1753 and 1753: 5-(4-amino-5-(trifluoromethyl)pyrrolo[2,1-f][1,2,4]triazin-7-yl)-N-(3-(4-fluorophenyl)-2-hydroxy-3-methoxy-2-methylpropyl)-2-methoxynicotinamide

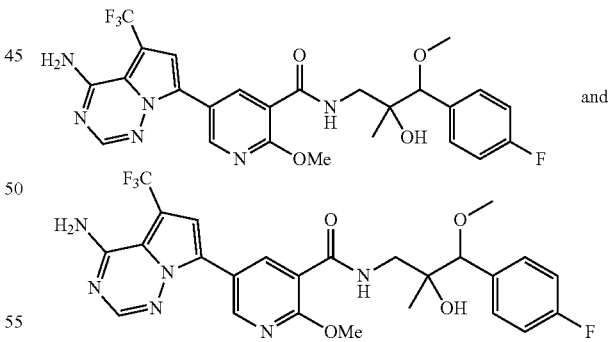

Prepared by the methods described in Example 1752 using 3-amino-1-(4-fluorophenyl)-1-methoxy-2-methylpropan-2-ol (1752B) and lithium 5-(4-amino-5-(trifluoromethyl)pyrrolo[2,1-f][1,2,4]triazin-7-yl)-2-methoxynicotinate and separated by prep-LC/MS to afford the title products (1753: 3.1 mg, 0.0057 mmol, 5.7% yield; 1754: 2.0 mg, 0.035 mmol, 3.5% yield).

1753: MS ESI m/z 549.1 (M+H)

$^1$H NMR (500 MHz, DMSO-d6) δ 8.90 (d, J=4.6 Hz, 2H), 8.39 (1, J=5.8 Hz, 1H), 8.17 (s, 1H), 7.60 (s, 1H), 7.36 (t,

J=6.9 Hz, 2H), 7.18 (t, J=8.7 Hz, 2H), 4.16 (s, 1H), 4.09 (s, 3H), 3.19 (s, 3H), 0.93 (s, 3H) (missing five protons due to solvent suppression).

1754: MS ESI m/z 549.1 (M+H)+

1H NMR (500 MHz, DMSO-d6) δ 8.90 (d, J=4.6 Hz, 2H), 8.39 (t, J=5.8 Hz, 1H), 8.17 (s, 1H), 7.60 (s, 1H), 7.36 (t, J=6.9 Hz, 2H), 7.18 (t, J=8.7 Hz, 2H), 4.16 (s, 1H), 4.09 (s, 3H), 3.19 (s, 3H), 0.93 (s, 3H).

Example 1755: 5-(4-amino-5-(trifluoromethyl)pyrrolo[2,1-f][1,2,4]triazin-7-yl)-2-methyl-N-(5,5,5-trifluoro-2-hydroxy-3-methoxy-2,4-dimethylpentyl)nicotinamide

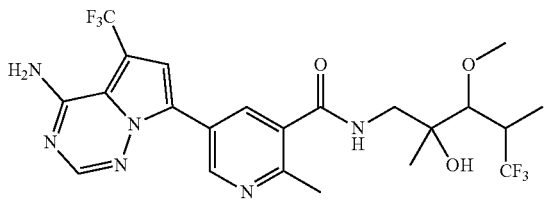 [SMILES: COC(C(C)C(F)(F)F)C(C)(O)CNC(=O)c1cc(-c2cc(C(F)(F)F)c3c(N)ncnn23)cnc1C]

1755A: 5,5,5-trifluoro-2,4-dimethylpent-1-en-3-ol: To a 50 mL oven-dried round-bottomed flask was added 3,3,3-trifluoro-2-methylpropanal (636 mg, 5.04 mmol) in THF (5 mL) to give a colorless solution. Prop-1-en-2-ylmagnesium bromide (12.11 mL, 6.05 mmol) was added dropwise at rt. The mixture was stirred at rt for 2 h. The reaction was quenched with saturated NH4Cl solution and diluted with Et2O. The layers were separated. The organic layer was dried and concentrated to the crude product as a slightly tan oil (578 mg, 68%). The material might be very volatile and house vacuum at rt might have evaporated some product. It was directly used in the next step.

1755B: 3,3,3-trifluoro-2-methyl-1-(2-methyloxiran-2-yl)propan-1-ol: To a 50 mL round-bottomed flask was added 5,5,5-trifluoro-2,4-dimethylpent-1-en-3-ol (578 mg, 3.44 mmol) in CH2Cl2 (10 mL) to give a colorless solution. mCPBA (770 mg, 3.44 mmol) was added followed by sodium bicarbonate (289 mg, 3.44 mmol). The mixture was stirred at rt ON. The reaction mixture was diluted with ether and water. The layers were separated. The organic layer was washed three times with NaHCO3 solution and brine. The organic solution was then dried and concentrated to the crude product as a colorless oil (520 mg, 2.82 mmol, 82% crude yield for two steps).

1755C: 2-methyl-2-(3,3,3-trifluoro-1-methoxy-2-methylpropyl)oxirane: To a 50 mL oven-dried round-bottomed flask was added 3,3,3-trifluoro-2-methyl-1-(2-methyloxiran-2-yl)propan-1-ol (226 mg, 1.227 mmol) in THF (3 mL) to give a colorless solution. NaH (147 mg, 3.68 mmol) was added. The mixture was stirred at rt for 5 min and MeI (0.230 mL, 3.68 mmol) was added. The mixture was stirred at rt ON. The reaction was slowly quenched with saturated NH4Cl solution (gas evolves). The reaction mixture was diluted with EtOAc and water. The layers were separated. The organic layer was washed brine, dried and concentrated to the crude product as a light yellow oil (400 mg, 1.23 mmol, 100% mass recovery with some solvent left), which was used in the next step.

1755D: 1-amino-5,5,5-trifluoro-3-methoxy-2,4-dimethylpentan-2-ol: To a 20 mL pressure vial was added 2-methyl-2-(3,3,3-trifluoro-1-methoxy-2-methylpropyl)oxirane (243 mg, 1.227 mmol) (crude) and 7N ammonia in MeOH (2 mL, 14 mmol) was added. The mixture was stirred at 65° C. for 18 h. The volatiles were removed in vacuo to leave the crude desired product as a slightly tan dense oil (135 mg, 0.63 mmol, 51% yield).

MS ESI m/z 214.1 (M+H)

1755: Prepared by the methods described in Example 1685 using 1-amino-5,5,5-trifluoro-3-methoxy-2,4-dimethylpentan-2-ol and 5-(4-amino-5-(trifluoromethyl)pyrrolo[2,1-f][1,2,4]triazin-7-yl)-2-methylnicotinic acid to afford the title product (9.7 mg, 0.018 mmol, 18% yield).

MS ESI m/z 535.3 (M+H)

1H NMR (500 MHz, DMSO-d6) δ 9.15 (s, 1H), 8.44-8.29 (m, 2H), 8.16 (s, 1H), 7.67 (d, J=3.9 Hz, 1H), 4.93 (d, J=72.4 Hz, 1H), 2.90 (dd, J=15.2, 8.0 Hz, 2H), 2.57 (d, J=3.7 Hz, 3H), 1.18-1.04 (m, 7H) (mixture of two diastereomers: —2/1).

Example 1756: 5-(4-amino-5-(trifluoromethyl)pyrrolo[2,1-f][1,2,4]triazin-7-yl)-N-(3-(4-fluorophenyl)-2-hydroxy-2-methyl-3-oxopropyl)-2-methylnicotinamide

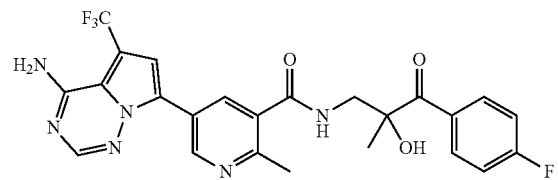 [SMILES: Cc1ncc(-c2cc(C(F)(F)F)c3c(N)ncnn23)cc1C(=O)NCC(C)(O)C(=O)c1ccc(F)cc1]

A mixture of 5-(4-amino-5-(trifluoromethyl)pyrrolo[2,1-f][1,2,4]triazin-7-yl)-N-(3-(4-fluorophenyl)-2,3-dihydroxy-2-methylpropyl)-2-methylnicotinamide (Example 1753) (87 mg, 0.168 mmol) and IBX (70.5 mg, 0.252 mmol) in DMSO (1 mL) was stirred at rt for 16 h. The crude product was purified by prep-LC/MS to afford the title product (18.0 mg, 0.033 mmol, 20% yield).

MS ESI m/z 517.1 (M+H)

1H NMR (500 MHz, DMSO-d6) δ 9.13 (s, 1H), 8.52 (t, J=6.3 Hz, 1H), 8.27 (q, J=5.7 Hz, 3H), 8.17 (s, 1H), 7.63 (s, 1H), 7.29 (t, J=8.8 Hz, 2H), 6.03 (d, J=2.6 Hz, 1H), 3.80-3.60 (m, 2H), 2.49 (s, 3H), 1.46 (s, 3H).

Example 1757: 5-(4-amino-5-(trifluoromethyl)pyrrolo[2,1-f][1,2,4]triazin-7-yl)-N-(3-(2-fluorophenyl)-2,3-dihydroxy-2-methylpropyl)-2-methylnicotinamide

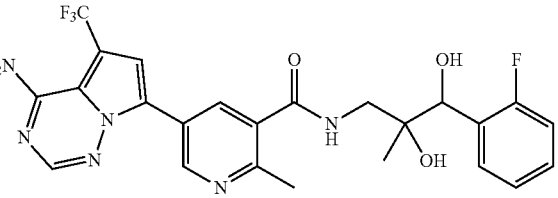

1757A: 1-(2-fluorophenyl)-2-methylprop-2-en-1-ol: To a 50 mL oven-dried round-bottomed flask was added 2-fluorobenzaldehyde (0.601 g, 4.84 mmol) in THF (10 mL) to give a colorless solution. Prop-1-en-2-ylmagnesium bromide (10.7 mL, 5.33 mmol) was added dropwise at rt for 1 h. The reaction was quenched with saturated NH4Cl solution and diluted with EtOAc. The layers were separated. The organic layer was dried and concentrated to the crude product as a pale oil (crude: 0.928 g, 4.84 mmol, 100% yield).

$^1$H NMR (500 MHz, CDCl$_3$) δ 7.47 (td, J=7.6, 1.8 Hz, 1H), 7.32-7.25 (m, 1H), 7.17 (td, J=7.5, 1.2 Hz, 1H), 7.05 (ddd, J=10.4, 8.2, 1.2 Hz, 1H), 5.49 (s, 1H), 5.21 (dt, J=1.5, 0.8 Hz, 1H), 5.00 (q, J=1.4 Hz, 1H), 1.69 (d, J=0.7 Hz, 3H);

$^{19}$F NMR (470 MHz, CDCl$_3$) δ −119.07.

1757B: (2-fluorophenyl)(2-methyloxiran-2-yl)methanol: To a 250 mL oven-dried round-bottomed flask was added 1-(2-fluorophenyl)-2-methylprop-2-en-1-ol (804 mg, 4.84 mmol) in CH$_2$Cl$_2$ (20 mL) to give a colorless solution. mCPBA (1085 mg, 4.84 mmol) was added followed by sodium bicarbonate (407 mg, 4.84 mmol). The mixture was stirred at rt ON. The reaction mixture was diluted with ether and water. The layers were separated. The organic layer was washed three time with NaHCO$_3$ solution and brine. The organic solution was then dried and concentrated to the crude product as a pale oil (830 mg, 4.56 mmol, 94% crude yield for two steps, the ratio of the diastereomers was closed to 1/1).

$^1$H NMR (500 MHz, CDCl$_3$) δ 7.75-6.96 (m, 4H), 5.28-4.74 (m, 1H), 3.34-3.04 (m, 1H), 2.86-2.46 (m, 2H), 1.42-1.08 (m, 3H);

$^{19}$F NMR (470 MHz, CDCl$_3$) δ −117.64, −117.84.

1757C: 3-amino-1-(2-fluorophenyl)-2-methylpropane-1,2-diol: To a 20 mL pressure vial was added (2-fluorophenyl)(2-methyloxiran-2-yl)methanol (307 mg, 1.685 mmol) and 7N ammonia in MeOH (3 mL, 21.00 mmol) was added. The mixture was stirred at 65° C. for 18 h. The volatiles were removed in vacuo to leave the crude desired product as a slightly tan dense oil (340 mg, 1.69 mmol, 100% yield). It was directly used as is.

1757: Prepared by the methods described in Example 1685 using 3-amino-1-(2-fluorophenyl)-2-methylpropane-1,2-diol and lithium 5-(4-amino-5-(trifluoromethyl)pyrrolo[2,1-f][1,2,4]triazin-7-yl)-2-methoxynicotinate. The NMR was difficult to assign due to the diastereomeric mixture.

MS ESI m/z 519.2 (M+H)

LC/MS retention time using Method 2=1.35 min

Example 1758: 5-(4-amino-5-(trifluoromethyl)pyrrolo[2,1-f][1,2,4]triazin-7-yl)-N-(3-(3-fluorophenyl)-2,3-dihydroxy-2-methylpropyl)-2-methylnicotinamide

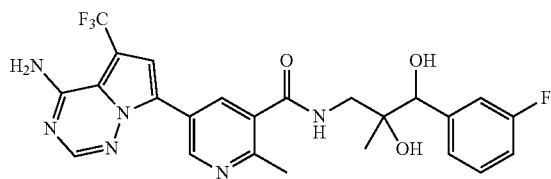 [SMILES: Cc1ncc(-c2cc(C(F)(F)F)c3c(N)ncnn23)cc1C(=O)NCC(C)(O)C(O)c1cccc(F)c1]

1758A: 1-(3-fluorophenyl)-2-methylprop-2-en-1-ol: To a 50 mL oven-dried round-bottomed flask was added 3-fluorobenzaldehyde (0.611 g, 4.92 mmol) in THF (10 mL) to give a colorless solution. Prop-1-en-2-ylmagnesium bromide (10.83 mL, 5.42 mmol) was added dropwise at rt for 1 h. The reaction was quenched with saturated NH$_4$Cl solution and diluted with EtOAc. The layers were separated. The organic layer was dried and concentrated to the crude product as a pale oil (0.988 g, 4.92 mmol, 100% crude yield, some solvent remaining).

$^1$H NMR (500 MHz, CDCl$_3$) δ 7.36-7.26 (m, 1H), 7.20-7.08 (m, 2H), 6.98 (tdd, J=8.5, 2.7, 1.0 Hz, 1H), 5.21 (dt, J=1.7, 0.9 Hz, 1H), 5.16 (s, 1H), 4.99 (td, J=1.6, 0.7 Hz, 1H), 1.63 (d, J=1.1 Hz, 3H);

$^{19}$F NMR (470 MHz, CDCl$_3$) δ −113.15.

1758B: (3-fluorophenyl)(2-methyloxiran-2-yl)methanol: To a 250 mL oven-dried round-bottomed flask was added 1-(3-fluorophenyl)-2-methylprop-2-en-1-ol (818 mg, 4.92 mmol) in CH$_2$Cl$_2$ (20 mL) to give a colorless solution. mCPBA (1103 mg, 4.92 mmol) was added followed by sodium bicarbonate (413 mg, 4.92 mmol). The mixture was stirred at rt ON. The reaction mixture was diluted with ether and water. The layers were separated. The organic layer was washed three time with NaHCO$_3$ solution and brine. The organic solution was then dried and concentrated to the crude product as a light yellow oil (893 mg, 4.92 mmol, 100% crude yield for two steps, the ratio of two diastereomers was ~1/1).

$^1$H NMR (500 MHz, CDCl$_3$) δ 7.47-6.88 (m, 4H), 4.61 (d, J=105.3 Hz, 1H), 3.23-2.98 (m, 1H), 2.81-2.45 (m, 2H), 1.33—1.17 (m, 3H);

$^{19}$F NMR (470 MHz, CDCl$_3$) δ −112.61, −112.73.

1758C: 3-amino-1-(3-fluorophenyl)-2-methylpropane-1,2-diol: To a 20 mL pressure vial was added (3-fluorophenyl)(2-methyloxiran-2-yl)methanol (309 mg, 1.696 mmol) and 7N ammonia in MeOH (3 mL, 21.00 mmol) was added. The mixture was stirred at 65° C. for 18 h. The volatiles were removed in vacuo to leave the crude desired product as a slightly tan dense oil (400 mg, 1.70 mmol, 100% mass recovery). It was used as is.

1758: Prepared by the methods described in Example 1685 using 3-amino-1-(3-fluorophenyl)-2-methylpropane-1,2-diol and lithium 5-(4-amino-5-(trifluoromethyl)pyrrolo[2,1-f][1,2,4]triazin-7-yl)-2-methoxynicotinate to afford the title product (13.0 mg, 0.025 mmol, 25% yield).

MS ESI m/z 519.1 (M+H)

$^1$H NMR (500 MHz, DMSO-d6) δ 9.16 (d, J=2.1 Hz, 1H), 8.40 (d, J=2.4 Hz, 1H), 8.30 (t, J=6.1 Hz, 1H), 8.18 (s, 1H), 7.67 (s, 1H), 7.33 (q, J=7.4 Hz, 1H), 7.23-7.20 (m, 2H), 7.05 (t, J=8.5 Hz, 1H), 4.49 (s, 1H), 3.21-3.11 (m, 2H), 2.58 (s, 3H), 1.03 (s, 3H); 19F NMR (376 MHz, DMSO-d6) δ −73.93.

Examples 1759 and 1760: 5-(4-amino-5-(trifluoromethyl)pyrrolo[2,1-f][1,2,4]triazin-7-yl)-N-(3-(4-fluorophenyl)-2,3-dihydroxy-2-methylpropyl)-2-methylbenzamide

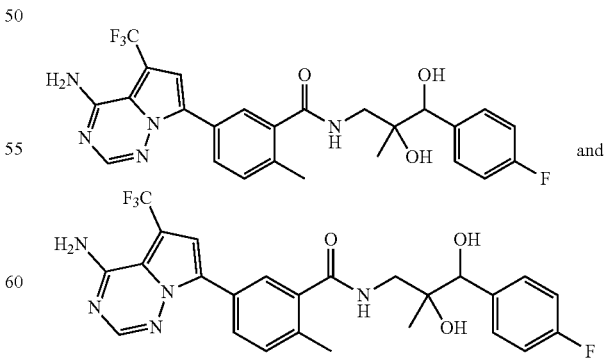

Prepared by the methods described in Example 1743 using 3-amino-1-(4-fluorophenyl)-2-methylpropane-1,2-diol (1743C) and 5-(4-amino-5-(trifluoromethyl)pyrrolo[2, 1-f][1,2,4]triazin-7-yl)-2-methylbenzoic acid and separated by prep-LC/MS to give the title products (1759: 6.1 mg, 0.012 mmol, 12% yield); 1760: 10.7 mg, 0.020 mmol, 20% yield).

MS ESI m/z 518.0 (M+H) for both products

1759: $^1$H NMR (500 MHz, DMSO-d6) δ 8.13 (s, 1H), 8.03-7.98 (m, 2H), 7.92 (d, J=6.1 Hz, 1H), 7.48 (s, 1H), 7.44 (dd, J=8.4, 5.7 Hz, 2H), 7.37 (d, J=8.5 Hz, 1H), 7.09 (t, J=8.8 Hz, 2H), 5.38 (d, J=4.7 Hz, 1H), 4.56-4.40 (m, 2H), 2.41 (s, 3H), 1.03 (s, 3H).

1760: $^1$H NMR (500 MHz, DMSO-d6) δ 8.14 (d, J=6.8 Hz, 2H), 8.03 (d, J=7.4 Hz, 2H), 7.52 (s, 1H), 7.42 (dd, J=8.5, 5.6 Hz, 2H), 7.37 (d, J=8.0 Hz, 1H), 7.10 (t, J=8.7 Hz, 2H), 4.51 (d, J=4.2 Hz, 1H), 3.53-3.36 (m, 2H), 2.40 (s, 3H), 0.91 (s, 3H).

Examples 1761 and 1762: 5-(4-amino-5-(trifluoromethyl)pyrrolo[2,1-f][1,2,4]triazin-7-yl)-N-(3-(4-fluorophenyl)-2-hydroxy-3-methoxy-2-methylpropyl)-2-methylbenzamide

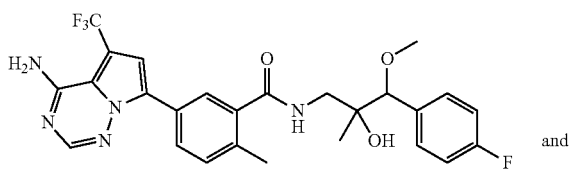

Prepared by the methods described in Example 1752 using 3-amino-1-(4-fluorophenyl)-1-methoxy-2-methylpropan-2-ol (1752B) and 5-(4-amino-5-(trifluoromethyl)pyrrolo[2,1-f][1,2,4]triazin-7-yl)-2-methylbenzoic acid, and separated by prep-LC/MS to give the title products (1761: 7.9 mg, 0.014 mmol, 14% yield; 1762: 16.1 mg, 0.030 mmol, 30% yield).

MS ESI m/z 532.1 (M+H) for both products

1761: $^1$H NMR (500 MHz, DMSO-d6) δ 8.13 (s, 1H), 8.01 (d, J=6.2 Hz, 2H), 7.88 (t, J=5.9 Hz, 1H), 7.48 (s, 1H), 7.41 (dd, J=8.3, 5.7 Hz, 2H), 7.37 (d, J=8.5 Hz, 1H), 7.15 (t, J=8.7 Hz, 2H), 4.49 (s, 1H), 4.12 (s, 1H), 3.51 (dd, J=13.3, 6.9 Hz, 1H), 3.30 (d, J=2.7 Hz, 3H), 2.41 (s, 3H), 1.03 (s, 3H); $^{19}$F NMR (376 MHz, DMSO-d6) δ 51.08.

1762: $^1$H NMR (500 MHz, DMSO-d6) δ 88.18-7.99 (m, 4H), 7.54 (s, 1H), 7.37 (t, J=9.2 Hz, 3H), 7.17 (t, J=8.6 Hz, 2H), 4.67 (s, 1H), 4.15 (s, 1H), 3.18 (s, 2H), 2.42 (s, 3H), 0.95 (s, 3H); $^{19}$F NMR (376 MHz, DMSO-d6) δ −51.08.

Example 1763: 5-(4-amino-5-(trifluoromethyl)pyrrolo[2,1-f][1,2,4]triazin-7-yl)-N-(3-(difluoromethoxy)-3-(4-fluorophenyl)-2-hydroxy-2-methylpropyl)-2-methylnicotinamide

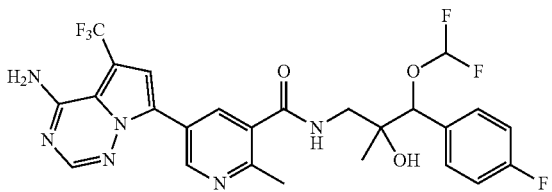 [SMILES: Cc1ncc(-c2cc(C(F)(F)F)c3c(N)ncnn23)cc1C(=O)NCC(C)(O)C(OC(F)F)c1ccc(F)cc1]

1763A: 1-(1-(difluoromethoxy)-2-methylallyl)-4-fluorobenzene: To a 20 mL vial was added 1-(4-fluorophenyl)-2-methylprop-2-en-1-ol (1743A) (0.504 g, 3.03 mmol) in CH$_2$Cl$_2$ (1.8 mL) to give a colorless solution. (Bromodifluoromethyl)trimethylsilane (1.848 g, 9.10 mmol) was added followed by potassium acetate (1.786 g, 18.20 mmol). Water (1.8 mL) was added. The mixture was stirred at rt for 22 h. The reaction mixture was diluted with ether and water. The layers were separated. The organic layer was washed with brine. The organic solution was then dried and concentrated. The residue was purified by silica gel chromatography up to 40% EtOAc/hexanes to afford the desired product (286 mg, 1.32 mmol, 44%) as a colorless oil.

$^1$H NMR (500 MHz, CDCl$_3$) δ 7.40-7.32 (m, 2H), 7.12-7.04 (m, 2H), 6.29 (t, J=75.3 Hz, 1H), 5.44 (s, 1H), 5.20 (dt, J=1.7, 1.0 Hz, 1H), 5.08 (td, J=1.5, 0.6 Hz, 1H), 1.65 (t, J=1.2 Hz, 3H);

$^{19}$F NMR (470 MHz, CDCl$_3$) δ −82.79 (d, J=76.5 Hz), −114.14.

1763B: 2-((difluoromethoxy)(4-fluorophenyl)methyl)-2-methyloxirane: To a 250 mL oven-dried round-bottomed flask was added 1-(1-(difluoromethoxy)-2-methylallyl)-4-fluorobenzene (286 mg, 1.323 mmol) in CH$_2$Cl$_2$ (6 mL) to give a colorless solution. mCPBA (296 mg, 1.323 mmol) was added followed by sodium bicarbonate (111 mg, 1.323 mmol). The mixture was stirred at rt ON. The reaction mixture was diluted with ether and water. The layers were separated. The organic layer was washed three time with NaHCO$_3$ solution and brine. The organic solution was then dried and concentrated to the crude product as a colorless oil (320 mg, 1.32 mmol, 100% crude yield).

$^1$H NMR (500 MHz, CDCl$_3$) δ 7.43-7.32 (m, 2H), 7.14-7.02 (m, 2H), 6.58-6.10 (m, 1H), 5.48-4.79 (m, 2H), 2.96-2.68 (m, 1H), 1.67-1.24 (m, 3H); $^{19}$F NMR (470 MHz, CDCl$_3$) δ −82.16 (d, J=25.9 Hz), −82.87, −113.35 (d, J=72.2 Hz), −114.15. $^1$H NMR indicated a mixture of two isomers.

1763C: 3-amino-1-(difluoromethoxy)-1-(4-fluorophenyl)-2-methylpropan-2-ol: To a 20 mL pressure vial was added 2-((difluoromethoxy)(4-fluorophenyl)methyl)-2-methyloxirane (307 mg, 1.323 mmol) and ammonia (3 mL, 21.00 mmol) (7 N in MeOH) was added. The mixture was stirred at 65° C. for 18 h. The volatiles were removed in vacuo to leave the crude desired product as a slightly tan dense oil (288 mg, 1.16 mmol, 87% crude yield for two steps). It was directly used as is.

MS ESI m/z 250.1 (M+H)

1763: Prepared by the methods described in Example 1685 using 3-amino-1-(difluoromethoxy)-1-(4-fluorophenyl)-2-methylpropan-2-ol and 5-(4-amino-5-(trifluoromethyl)pyrrolo[2,1-f][1,2,4]triazin-7-yl)-2-methylnicotinic acid to afford the title product (24.3 mg, 0.042 mmol, 42% yield).

MS ESI m/z 569.1 (M+H)

$^1$H NMR (500 MHz, DMSO-d6) δ 9.16 (d, J=2.2 Hz, 1H), 8.45-8.32 (m, 2H), 8.18 (d, J=1.6 Hz, 1H), 7.67 (s, 1H), 7.47 (dt, J=8.7, 5.4 Hz, 2H), 7.20 (td, J=8.8, 1.7 Hz, 2H), 6.83-6.50 (m, 1H), 5.03 (d, J=4.2 Hz, 1H), 3.46 (s, 1H), 3.29-3.06 (m, 1H), 2.58 (s, 3H), 1.07 (d, J=24.4 Hz, 3H); $^{19}$F NMR (471 MHz, DMSO-d6) δ −51.17 (Indicated a mixture of two isomers).

Examples 1764 and 1765: 5-(4-amino-5-(trifluoromethyl)pyrrolo[2,1-f][1,2,4]triazin-7-yl)-N-(3-(difluoromethoxy)-3-(4-fluorophenyl)-2-hydroxy-2-methylpropyl)-2-methylbenzamide

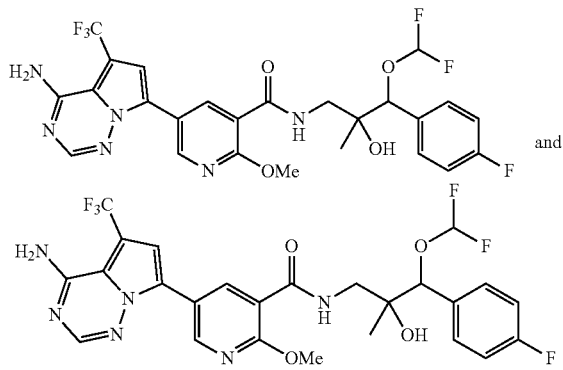

Prepared by the methods described in Example 1763 using 3-amino-1 (difluoromethoxy)-1-(4-fluorophenyl)-2-methylpropan-2-ol (1763C) and 5-(4-amino-5-(trifluoromethyl)pyrrolo[2,1-f][1,2,4]triazin-7-yl)-2-methylbenzoic acid, and separated by prep-LC/MS to give the title products (1764: 2.7 mg, 0.004 mmol, 4% yield; 1765: 5.3 mg, 0.009 mmol, 9% yield).

MS ESI m/z 568.2 (M+H) for both isomers

1764: $^1$H NMR (500 MHz, DMSO-d6) δ 8.12 (s, 1H), 8.06-7.92 (m, 3H), 7.52-7.45 (m, 3H), 7.37 (d, J=8.0 Hz, 1H), 7.17 (t, J=8.9 Hz, 2H), 6.62 (dd, J=77.2, 74.8 Hz, 1H), 5.01 (s, 1H), 3.50 (dd, J=13.4, 6.7 Hz, 1H), 3.32 (d, J=9.5 Hz, 1H), 2.40 (s, 3H), 1.06 (s, 3H).

1765: $^1$H NMR (500 MHz, DMSO-d6) δ 8.19 (t, J=6.2 Hz, 1H), 8.15 (s, 1H), 8.08-8.01 (m, 2H), 7.54 (s, 1H), 7.47 (dd, J=8.5, 5.5 Hz, 2H), 7.38 (d, J=8.1 Hz, 1H), 7.20 (t, J=8.8 Hz, 2H), 6.68 (t, J=75.6 Hz, 1H), 5.04 (s, 1H), 4.98 (s, 1H), 3.50 (dd, J=13.5, 6.7 Hz, 1H), 3.28-3.14 (m, 1H), 2.41 (s, 3H), 1.09 (s, 3H).

Example 1766: N-(5-(4-amino-5-(trifluoromethyl) pyrrolo[2,1-f][1,2,4]triazin-7-yl)-2-methoxy pyridin-3-yl)-4-(4-chlorophenyl)-4-hydroxybutanamide

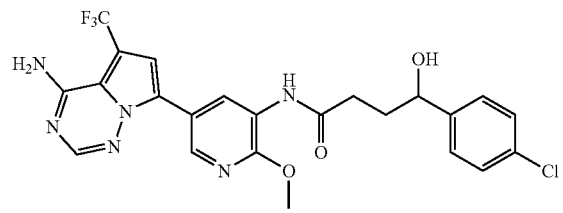 [SMILES: COc1ncc(-c2cc(C(F)(F)F)c3c(N)ncnn23)cc1NC(=O)CCC(O)c1ccc(Cl)cc1]

1766A: 7-(5-amino-6-methoxypyridin-3-yl)-5-(trifluoromethyl)pyrrolo[2,1-f][1,2,4]triazin-4-amine: To a solution of 7-bromo-5-(trifluoromethyl)pyrrolo[2,1-f][1,2,4]triazin-4-amine (400 mg, 1.42 mmol) and 2-methoxy-5-(4,4,5,5-tetramethyl-1,3,2-dioxaborolan-2-yl)pyridin-3-amine (427 mg, 1.708 mmol) in 1,4-dioxane (5 mL) was added PdCl$_2$(dppf)-CH$_2$Cl$_2$ adduct (116 mg, 0.142 mmol) followed by 2.0 M tripotassium phosphate/H$_2$O (2.14 mL, 4.27 mmol). The mixture was stirred at 85° C. for 2.5 h. After cooling to rt, the reaction mixture was diluted with EtOAc (100 mL). The organics were washed with water, dried over Na$_2$SO$_4$ and concentrated. The residue was crystallized in EtOAc/hexanes to give 7-(5-amino-6-methoxypyridin-3-yl)-5-(trifluoromethyl)pyrrolo[2,1-f][1,2,4]triazin-4-amine (240 mg, 0.740 mmol, 52% yield).

MS ESI m/z 325.1 (M+H)$^+$.

1766B: N-(5-(4-amino-5-(trifluoromethyl)pyrrolo[2,1-f][1,2,4]triazin-7-yl)-2-methoxypyridin-3-yl)-4-(4-chlorophenyl)-4-oxobutanamide: To a solution of 7-(5-amino-6-methoxypyridin-3-yl)-5-(trifluoromethyl)pyrrolo[2,1-f][1,2,4]triazin-4-amine (64 mg, 0.197 mmol), 4-(4-chlorophenyl)-4-oxobutanoic acid (54.6 mg, 0.257 mmol) and DIPEA (0.069 mL, 0.395 mmol) in DMF (1 mL) was added HATU (105 mg, 0.276 mmol). The mixture was stirred at rt for 3 h, then at 40° C. for 3 h. Saturated aqueous sodium bicarbonate (5 mL) was added. The solid was collected by filtration and air dried to give crude N-(5-(4-amino-5-(trifluoromethyl)pyrrolo[2,1-f][1,2,4]triazin-7-yl)-2-methoxypyridin-3-yl)-4-(4-chlorophenyl)-4-oxobutanamide (56 mg, 0.108 mmol, 55% yield). The material was used for the next step without any purification.

MS ESI m/z 519.1 (M+H)$^+$.

1H NMR (500 MHz, CDCl$_3$) δ 9.11 (d, J=2.0 Hz, 1H), 8.52 (d, J=2.3 Hz, 1H), 8.12-8.09 (m, 1H), 8.04-8.00 (m, 1H), 7.99-7.96 (m, 2H), 7.49-7.46 (m, 2H), 7.18-7.15 (m, 1H), 4.13-4.12 (m, 3H), 3.47-3.43 (m, 2H), 2.94-2.91 (m, 2H).

1766: N-(5-(4-amino-5-(trifluoromethyl)pyrrolo[2,1-f][1,2,4]triazin-7-yl)-2-methoxypyridin-3-yl)-4-(4-chlorophenyl)-4-hydroxybutanamide: To a suspension of N-(5-(4-amino-5-(trifluoromethyl)pyrrolo[2,1-f][1,2,4]triazin-7-yl)-2-methoxypyridin-3-yl)-4-(4-chlorophenyl)-4-oxobutanamide (56 mg, 0.108 mmol) in THF (1 mL) was added NaBH$_4$ (12.3 mg, 0.324 mmol) followed by a couple drops of MeOH. The mixture was stirred at rt for 1 h. MeOH was added to quench the reaction, then the mixture was concentrated. The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 30% B, 30-70% B over 20 minutes, then a 4-minute hold at 100% B; Flow Rate: 20 mL/min; Column temperature: 25° C. Fraction collection was triggered by MS signals. Fractions containing the desired product were combined and dried via centrifugal evaporation to yield the final product (13.1 mg, 0.025 mmol, 23% yield).

MS ESI m/z 521.3 (M+H)$^+$

1H NMR (500 MHz, DMSO-d6) δ 9.49-9.43 (m, 1H), 8.84-8.79 (m, 1H), 8.48-8.43 (m, 1H), 7.36 (s, 6H), 4.63-4.57 (m, 1H), 3.97 (s, 3H), 2.48-2.42 (m, 2H), 1.93-1.86 (m, 2H).

Example 1767: 5-(4-amino-5-(trifluoromethyl)pyr-rolo[2,1-f][1,2,4]triazin-7-yl)-N-(3-hydroxy-5-methylhexyl)-2-methoxynicotinamide

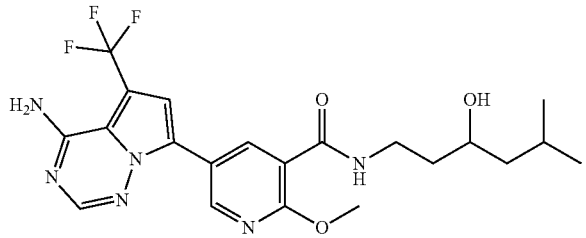 [SMILES: COc1ncc(-c2cc(C(F)(F)F)c3c(N)ncnn23)cc1C(=O)NCCC(O)CC(C)C]

1767A: tert-butyl (3-oxopropyl)carbamate: To a solution of tert-butyl (3-hydroxypropyl)carbamate (1.75 g, 9.99 mmol) in CH$_2$Cl$_2$, DMSO and DIPEA (6.11 ml, 35.0 mmol) was added pyridine sulfur trioxide (3.97 g, 24.97 mmol) slowly at rt. The reaction was exothermic. The reaction was stirred at rt for 2 h. After concentration, ether (100 mL) was added. The organics were washed with water (3×80 mL), dried over Na$_2$SO$_4$ and concentrated to give crude tert-butyl (3-oxopropyl)carbamate (1.2 g, 6.93 mmol, 69% yield). The material was used for the next step without any purification.

1H NMR (500 MHz, CDCl$_3$) δ 9.85-9.82 (m, 1H), 3.48-3.41 (m, 2H), 2.76-2.70 (m, 2H), 1.45 (s, 9H).

1767B: tert-butyl (3-hydroxy-5-methylhexyl)carbamate: To a solution of tert-butyl (3-oxopropyl)carbamate (200 mg, 1.16 mmol) in THF (3 mL) was added isobutylmagnesium bromide/Et$_2$O (1.44 mL, 2.89 mmol) slowly at −20° C. under N$_2$. The reaction was stirred at rt for 2 h. Ether (50 mL) was added. The organics were washed with water, dried over Na$_2$SO$_4$ and concentrated to give crude tert-butyl (3-hydroxy-5-methylhexyl)carbamate (215 mg, 0.929 mmol, 80% yield). The material was used for the next step without any purification.

1767C: 1-amino-5-methylhexan-3-ol, TFA: To a solution of tert-butyl (3-hydroxy-5-methylhexyl)carbamate (215 mg, 0.929 mmol) in DCM (1 mL) was added TFA (0.4 mL, 5.19 mmol) at rt. The reaction was stirred at rt for 2 h. The mixture was concentrated to give a crude product. The material was used for the next step without any purification.

1767D: A mixture of methyl 5-bromo-2-methoxynicotinate (1.48 g, 6.0 mmol), 4,4,4',4',5,5,5',5'-octamethyl-2,2'-bi(1,3,2-dioxaborolane) (1.828 g, 7.20 mmol), PdCl$_2$(dppf)-CH$_2$Cl$_2$ adduct (0.392 g, 0.480 mmol) and potassium acetate (0.883 g, 9.00 mmol) in dioxane (20 mL) was stirred at 85° C. for 20 h. 7-Bromo-5-(trifluoromethyl)pyrrolo[2,1-f][1,2,4]triazin-4-amine (1.518 g, 5.40 mmol) was added followed by 2.0 M K$_2$CO$_3$/water (7.50 mL, 15.00 mmol). After stirring at 90° C. for 2 h, the mixture was concentrated, then water was added. The solid was collected by filtration. EtOAc was added to dissolve all the solid except the black residue. The black residue was filtered off. The filtrate was concentrated and crystallized in EtOAc to give 1.1 g of clean product. The mother liquor was purified via silica gel chromatography (24 g, hexanes-100% EtOAc) to give another 300 mg of product MS ESI m/z 368.1 (M+H)$^+$ 1H NMR (500 MHz, CD$_3$OD) δ 8.95-8.94 (m, 1H), 8.85-8.83 (m, 1H), 8.09-8.06 (m, 1H), 7.39-7.36 (m, 1H), 4.08 (s, 3H), 3.94 (s, 3H).

1767E: lithium 5-(4-amino-5-(trifluoromethyl)pyrrolo[2,1-f][1,2,4]triazin-7-yl)-2-methoxynicotinate: To a slurry of methyl 5-(4-amino-5-(trifluoromethyl)pyrrolo[2,1-f][1,2,4]triazin-7-yl)-2-methoxynicotinate (1.4 g, 3.81 mmol) in THF (20 mL) was added a solution of lithium hydroxide hydrate (0.176 g, 4.19 mmol) in 4 mL of water. The mixture was stirred at rt for 4 h. The mixture was concentrated to dryness to give lithium 5-(4-amino-5-(trifluoromethyl)pyrrolo[2,1-f][1,2,4]triazin-7-yl)-2-methoxynicotinate (1.369 g, 3.81 mmol, 100% yield). The material was used for the next step without any purification.

MS ESI m/z 354.0 (M+H)$^+$.

1767: To a slurry of lithium 5-(4-amino-5-(trifluoromethyl)pyrrolo[2,1-f][1,2,4]triazin-7-yl)-2-methoxynicotinate (36 mg, 0.100 mmol) in DMF (0.8 mL) was added HATU (53.4 mg, 0.140 mmol) followed by DIPEA (0.088 mL, 0.501 mmol). After stirring at rt for 20 min, a crude 1-amino-5-methylhexan-3-ol 2,2,2-trifluoroacetate, TFA (49.2 mg, 0.200 mmol) was added. The mixture was stirred at rt for 4 h. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 29% B, 29-69% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 27% B, 27-67% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation to yield the final product (6.1 mg, 0.013 mmol, 13% yield).

MS ESI m/z 467.1 (M+H)$^+$

1H NMR (500 MHz, DMSO-d6) δ 8.90-8.85 (m, 1H), 8.80-8.76 (m, 1H), 8.54-8.47 (m, 1H), 8.18-8.15 (m, 1H), 7.62-7.56 (m, 1H), 4.05-3.99 (m, 3H), 3.67-3.57 (m, 1H), 3.46-3.35 (m, 3H), 1.79-1.62 (m, 2H), 1.55-1.46 (m, 1H), 1.37-1.30 (m, 1H), 1.20-1.13 (m, 1H), 0.91-0.84 (m, 6H).

Example 1768: 5-(4-amino-5-(trifluoromethyl)pyrrolo[2,1-f][1,2,4]triazin-7-yl)-N-(2,3-dihydroxy-3-phenylpropyl)-2-methoxynicotinamide

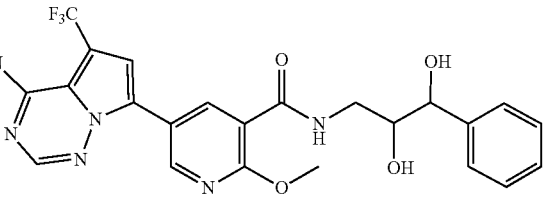

1768A: oxiran-2-yl(phenyl)methanol: To a solution of 1-phenylprop-2-en-1-ol (1.44 g, 10.7 mmol) in DCM (30 mL) was added mCPBA (3.61 g, 16.1 mmol) slowly at rt. The mixture was stirred at rt for 18 h. Saturated NaHCO$_3$/water was added, and the organics were extracted with DCM and EtOAc. The organic layer was concentrated. The residue was purified via silica gel chromatography (24 g, hexanes-60% EtOAc) to give oxiran-2-yl(phenyl)methanol (1.46 g, 9.72 mmol, 91% yield).

1H NMR (499 MHz, CDCl₃) δ 7.47-7.39 (m, 4H), 7.38-7.34 (m, 1H), 4.99-4.50 (m, 1H), 3.29-3.24 (m, 1H), 3.02-2.88 (m, 1H), 2.88-2.78 (m, 1H).

1768B: 3-amino-1-phenylpropane-1,2-diol: To oxiran-2-yl(phenyl)methanol (700 mg, 4.66 mmol) was added 7 N ammonia/MeOH (7 mL, 49.0 mmol) and ammonium hydroxide (7 mL, 50.3 mmol) at rt. The mixture was stirred at rt in a sealed pressure bottle ON. The mixture was concentrated in vacuo to dryness to give 1-amino-2-phenylethane-1,2-diol (714 mg, 4.66 mmol, 100% yield).

1H NMR (499 MHz, CD₃OD) δ 7.43-7.33 (m, 4H), 7.31-7.25 (m, 1H), 4.59-4.50 (m, 1H), 3.72-3.64 (m, 1H), 2.90-2.68 (m, 1H), 2.56-2.54 (m, 1H).

1768: 5-(4-amino-5-(trifluoromethyl)pyrrolo[2,1-f][1,2,4]triazin-7-yl)-N-(2,3-dihydroxy-3-phenylpropyl)-2-methoxynicotinamide: To a solution of lithium 5-(4-amino-5-(trifluoromethyl)pyrrolo[2,1-f][1,2,4]triazin-7-yl)-2-methoxynicotinate (45 mg, 0.125 mmol) in DMF (1 mL) was added BOP (78 mg, 0.175 mmol) followed by DIPEA (0.044 mL, 0.251 mmol). After stirring at rt for 10 min, 3-amino-1-phenylpropane-1,2-diol (27.2 mg, 0.163 mmol) was added. The reaction was stirred at rt for 20 h. The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 18% B, 18-58% B over 20 minutes, then a 4-minute hold at 100% B; Flow Rate: 20 mL/min; Column Temperature: 25° C. Fraction collection was triggered by MS and UV signals. Fractions containing the desired product were combined and dried via centrifugal evaporation to give the title product (8.9 mg, 14.4 μmol, 12% yield).

MS ESI m/z 503.3 (M+H)⁺

1H NMR (500 MHz, DMSO-d6) δ 8.92-8.81 (m, 2H), 8.42-8.33 (m, 1H), 8.19-8.12 (m, 1H), 7.62-7.56 (m, 1H), 7.41-7.29 (m, 4H), 7.27-7.20 (m, 1H), 4.61-4.52 (m, 1H), 4.05 (s, 3H), 3.81-3.73 (m, 1H), 3.16-3.07 (m, 1H).

Example 1769: 5-(4-amino-5-(trifluoromethyl)pyrrolo[2,1-f][1,2,4]triazin-7-yl)-N-(2,3-dihydroxy-3-phenylpropyl)-2-methylnicotinamide

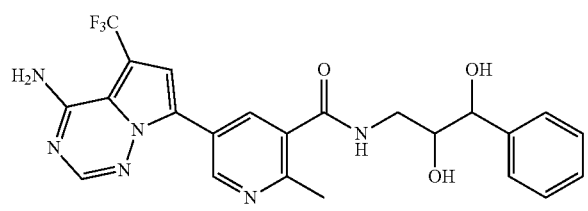 [SMILES: Cc1ncc(-c2cc(C(F)(F)F)c3c(N)ncnn23)cc1C(=O)NCC(O)C(O)c1ccccc1]

To a solution of 5-(4-amino-5-(trifluoromethyl)pyrrolo[2,1-f][1,2,4]triazin-7-yl)-2-methylnicotinic acid (40 mg, 0.12 mmol) in DMF (1 mL) was added BOP (73.4 mg, 0.166 mmol) followed by DIPEA (0.041 mL, 0.237 mmol). After stirring at rt for 10 min, 3-amino-1-phenylpropane-1,2-diol (25.8 mg, 0.154 mmol) was added. The reaction was stirred at rt for 20 h. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 12% B, 12-52% B over 20 min, then a 4-min hold at 100% B; Flow Rate: 20 mL/min; Column Temp: 25° C. Fraction collection was triggered by MS and UV signals. Fractions containing the desired product were combined and dried via centrifugal evaporation to give the title product (42.0 mg, 86.3 μmol, 73% yield).

MS ESI m/z 487.0 (M+H)⁺

1H NMR (500 MHz, DMSO-d6) δ 9.19-9.12 (m, 1H), 8.36-8.32 (m, 1H), 8.25-8.15 (m, 2H), 7.64-7.60 (m, 1H), 7.43-7.38 (m, 2H), 7.36-7.30 (m, 2H), 7.27-7.21 (m, 1H), 5.32-4.69 (m, 1H), 4.60-4.50 (m, 1H), 3.85-3.75 (m, 1H), 3.62-3.50 (m, 1H), 2.60-2.56 (m, 3H).

Example 1770: 5-(4-amino-5-(trifluoromethyl)pyrrolo[2,1-f][1,2,4]triazin-7-yl)-N-(3-cyclopropyl-3-hydroxypropyl)-2-methylnicotinamide

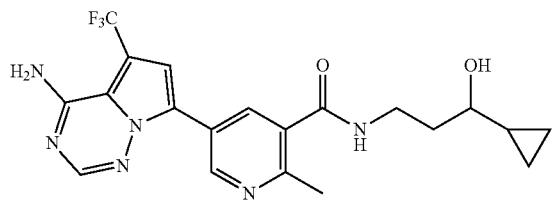 [SMILES: Cc1ncc(-c2cc(C(F)(F)F)c3c(N)ncnn23)cc1C(=O)NCCC(O)C1CC1]

Using the same protocol as described in Example 1769 provided 5-(4-amino-5-(trifluoromethyl)pyrrolo[2,1-f][1,2,4]triazin-7-yl)-N-(3-cyclopropyl-3-hydroxy propyl)-2-methylnicotinamide (13.8 mg, 31.8 μmol, 32% yield).

MS ESI m/z 435.2 (M+H)⁺

1H NMR (500 MHz, DMSO-d6) δ 9.00-8.94 (m, 1H), 8.17 (br d, J=1.9 Hz, 2H), 8.00 (s, 1H), 7.50-7.45 (m, 1H), 7.33-6.83 (m, 1H), 3.27-3.17 (m, 1H), 3.35-3.04 (m, 1H), 2.87-2.78 (m, 1H), 2.39 (s, 3H), 1.66-1.48 (m, 2H), 0.71-0.62 (m, 1H), 0.25-0.16 (m, 2H), 0.12-0.01 (m, 2H).

Example 1771: tert-butyl (1-(5-(4-amino-5-(trifluoromethyl)pyrrolo[2,1-f][1,2,4]triazin-7-yl)-2-methyl-nicotinamido)-3-phenylpropan-2-yl)carbamate

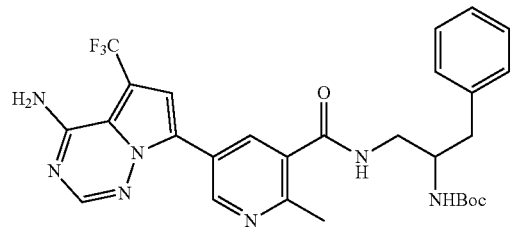 [SMILES: Cc1ncc(-c2cc(C(F)(F)F)c3c(N)ncnn23)cc1C(=O)NCC(Cc1ccccc1)NC(=O)OC(C)(C)C]

1771A: tert-butyl (1-(5-(4-amino-5-(trifluoromethyl)pyrrolo[2,1-f][1,2,4]triazin-7-yl)-2-methylnicotinamido)-3-phenylpropan-2-yl)carbamate: To a solution of 5-(4-amino-5-(trifluoromethyl)pyrrolo[2,1-f][1,2,4]triazin-7-yl)-2-methylnicotinic acid (36 mg, 0.10 mmol) in DMF (0.5 mL) was added BOP (62.1 mg, 0.140 mmol) followed by DIPEA (0.035 mL, 0.200 mmol). After stirring at rt for 10 min, tert-butyl (1-amino-3-phenylpropan-2-yl)carbamate (30.1 mg, 0.120 mmol) was added. The reaction was stirred at rt for 2 d. Water (20 mL) was added. The organic layer was extracted with DCM (3×30 mL) and concentrated to give tert-butyl (1-(5-(4-amino-5-(trifluoromethyl)pyrrolo[2,1-f][1,2,4]triazin-7-yl)-2-methoxynicotinamido)-3-phenylpropan-2-yl)carbamate (48 mg, 0.082 mmol, 82% yield). The material was used for the next step without any purification.

MS ESI m/z 570.2 (M+H)⁺.

1771: To a solution of tert-butyl (1-(5-(4-amino-5-(trifluoromethyl)pyrrolo[2,1-f][1,2,4]triazin-7-yl)-2-methoxynicotinamido)-3-phenylpropan-2-yl)carbamate (55 mg, 0.097 mmol) in DCM (1.5 mL) was added TFA (0.5 mL, 6.5 mmol). After stirring at rt for 3 h, the mixture was concentrated. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 9% B, 9-49% B over 20 min, then a 4-min hold at 100% B; Flow Rate: 20 mL/min; Column Temp: 25° C. Fraction collection was triggered by MS and UV signals. Fractions containing the desired product were combined and dried via centrifugal evaporation to give the title product (28.3 mg, 0.060 mmol, 62% yield).

MS ESI m/z 470.2 (M+H)⁺

1H NMR (500 MHz, DMSO-d6) δ 9.19-9.13 (m, 1H), 8.56-8.48 (m, 1H), 8.41-8.36 (m, 1H), 8.17 (s, 1H), 7.69 (s, 1H), 7.33-7.23 (m, 4H), 7.23-7.17 (m, 1H), 3.22-3.02 (m, 2H), 2.91-2.72 (m, 2H), 2.58 (s, 4H).

Example 1772: N-(5-(4-amino-5-(trifluoromethyl)pyrrolo[2,1-f][1,2,4]triazin-7-yl)-2-methoxypyridin-3-yl)-1-benzyl-1H-imidazole-4-carboxamide

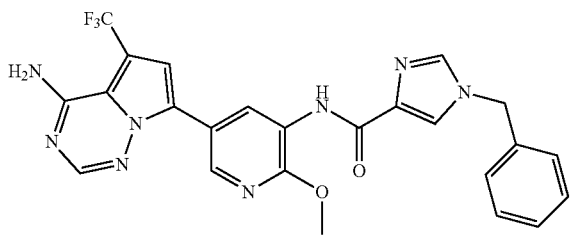 [SMILES: COc1ncc(-c2cc(C(F)(F)F)c3c(N)ncnn23)cc1NC(=O)c1cn(Cc2ccccc2)cn1]

1772A: ethyl 1-benzyl-1H-imidazole-4-carboxylate: To a solution of ethyl 1H-imidazole-4-carboxylate (500 mg, 3.57 mmol) in DMF (5 mL) was added 1.0 M NaHMDS/THF (3.92 mL, 3.92 mmol) at rt over 10 min. After stirring at rt for 15 min, (bromomethyl)benzene (671 mg, 3.92 mmol) was added dropwise. The mixture was stirred at rt for 2 h. Water (50 mL) was added and extracted with EtOAc (2×80 mL). The organic layer was concentrated. The residue was purified via silica gel chromatography (40 g, hexanes-100% EtOAc) to give the first elution ethyl 1-benzyl-1H-imidazole-5-carboxylate (60 mg, 0.261 mmol, 7% yield) and the second elution ethyl 1-benzyl-1H-imidazole-4-carboxylate (650 mg, 2.82 mmol, 79% yield).

MS ESI m/z 231.1 (M+H)⁺

1H NMR (499 MHz, CDCl₃) δ 7.62-7.60 (m, 1H), 7.58-7.56 (m, 1H), 7.42-7.35 (m, 3H), 7.22-7.18 (m, 2H), 5.16-5.14 (m, 2H), 4.40-4.34 (m, 2H), 1.39 (t, J=7.2 Hz, 3H).

1772B: 1-benzyl-1H-imidazole-4-carboxylic acid: To a solution of ethyl 1-benzyl-1H-imidazole-4-carboxylate (670 mg, 2.91 mmol) in THF (2 mL) was added a solution of lithium hydroxide hydrate (21.9 mg, 0.521 mmol) in water (0.2 mL) at rt. The mixture was stirred at rt for 20 h. 1 N HCl (0.52 mL, 1 eq.) was added to neutralize the LiOH. The mixture was concentrated to dryness to give 1-benzyl-1H-imidazole-4-carboxylic acid (480 mg). The material was used for the next step without any purification.

MS ESI m/z 203.0 (M+H)⁺

1H NMR (499 MHz, CD₃OD) δ 7.93-7.89 (m, 1H), 7.81-7.75 (m, 1H), 7.44-7.36 (m, 3H), 7.35-7.32 (m, 2H), 5.30-5.29 (m, 2H).

1772: To a mixture of 1-benzyl-1H-imidazole-4-carboxylic acid (20 mg, 0.099 mmol) in DMF (0.5 mL) was added BOP (52.5 mg, 0.119 mmol) followed by DIPEA (0.052 mL, 0.297 mmol). After stirring at rt for 10 min, 7-(5-amino-6-methoxypyridin-3-yl)-5-(trifluoromethyl)pyrrolo[2,1-f][1,2,4]triazin-4-amine (35.3 mg, 0.109 mmol) was added. The mixture was stirred at rt for 3 d, then stirred at 80° C. for 5 h. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 31% B, 31-71% B over 25 min, then a 4-min hold at 100% B; Flow Rate: 20 mL/min; Column Temp: 25° C. Fraction collection was triggered by MS signals. Fractions containing the desired product were combined and dried via centrifugal evaporation to give the title product (11.9 mg, 0.023 mmol, 24% yield).

MS ESI m/z 509.4 (M+H)⁺

1H NMR (500 MHz, DMSO-d6) δ 9.43-9.38 (m, 1H), 9.25-9.19 (m, 1H), 8.46-8.41 (m, 1H), 8.16-8.11 (m, 1H), 8.00-7.95 (m, 2H), 7.47-7.42 (m, 1H), 7.40-7.30 (m, 5H), 5.36-5.25 (m, 2H), 4.11-4.00 (m, 3H).

Example 1773: 5-(4-amino-5-(trifluoromethyl)pyrrolo[2,1-f][1,2,4]triazin-7-yl)-N-(1-(1-(4-fluorophenyl)ethyl)-1H-imidazol-4-yl)-2-methylnicotinamide

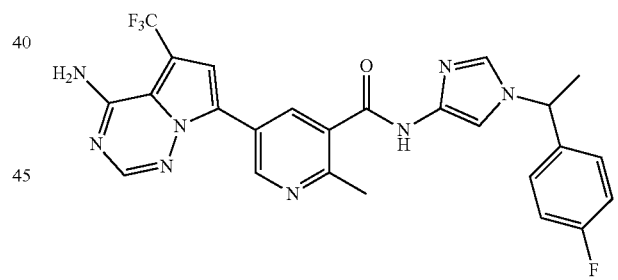

1773A: 1-(1-(4-fluorophenyl)ethyl)-4-nitro-1H-imidazole: To a solution of 1,4-dinitro-1H-imidazole (155 mg, 0.981 mmol) in MeOH (3 mL) was added dropwise 1-(4-fluorophenyl)ethan-1-amine (164 mg, 1.177 mmol) at rt. The reaction was stirred at rt for 3 h. The mixture was concentrated in vacuo. The residue was purified via silica gel chromatography (4 g, hexanes-100% EtOAc) to give 1-(1-(4-fluorophenyl)ethyl)-4-nitro-1H-imidazole (190 mg, 0.808 mmol, 82% yield).

1H NMR (499 MHz, CDCl₃) δ 7.76 (d, J=1.7 Hz, 1H), 7.51 (d, J=1.4 Hz, 1H), 7.23 (br t, J=6.5 Hz, 2H), 7.14 (t, J=7.7 Hz, 2H), 1.95 (d, J=7.0 Hz, 3H).

1773B: 1-(1-(4-fluorophenyl)ethyl)-1H-imidazol-4-amine: To 10% Pd—C (30 mg, 0.028 mmol) was added a solution of 1-(1-(4-fluorophenyl)ethyl)-4-nitro-1H-imidazole (190 mg, 0.808 mmol) in MeOH (4 mL) under N₂. The mixture was stirred under H2 balloon at rt ON. The Pd/C was filtered out and washed with MeOH. The filtrate was concentrated to give 1-(1-(4-fluorophenyl)ethyl)-1H-imidazol-4-amine (150 mg, 0.731 mmol, 90% yield). The material was used for the next step without any purification.

MS ESI m/z 206.1 (M+H)+

1H NMR (499 MHz, CDCl3) δ 7.25-7.22 (m, 1H), 7.17-7.13 (m, 2H), 7.04 (s, 3H), 6.21-6.18 (m, 1H), 5.23-5.16 (m, 1H), 1.81 (d, J=7.0 Hz, 3H).

1773: To a solution of 5-(4-amino-5-(trifluoromethyl)pyrrolo[2,1-f][1,2,4]triazin-7-yl)-2-methylnicotinic acid (34 mg, 0.10 mmol) in DMF (0.5 mL) was added BOP (58.0 mg, 0.131 mmol) followed by DIPEA (0.035 mL, 0.202 mmol) at rt. After stirring at rt for 10 min, 1-(1-(4-fluorophenyl)ethyl)-1H-imidazol-4-amine (22.76 mg, 0.111 mmol) was added. The mixture was stirred at rt for 3 h. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-min hold at 22% B, 22-62% B over 20 min, then a 4-min hold at 100% B; Flow Rate: 20 mL/min; Column Temperature: 25° C. Fraction collection was triggered by MS and UV signals. Fractions containing the desired product were combined and dried via centrifugal evaporation. The material was further purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-min hold at 10% B, 10-50% B over 20 min, then a 4-min hold at 100% B; Flow Rate: 20 mL/min; Column Temp: 25° C. Fraction collection was triggered by MS signals. Fractions containing the desired product were combined and dried via centrifugal evaporation to give the title product (3.3 mg, 5.2 μmol, 5% yield).

MS ESI m/z 525.3 (M+H)+

1H NMR (500 MHz, DMSO-d6) δ 9.26-9.20 (m, 1H), 8.58-8.49 (m, 1H), 8.20-8.15 (m, 1H), 8.06-7.99 (m, 1H), 7.76-7.69 (m, 1H), 7.54-7.41 (m, 3H), 7.27-7.17 (m, 3H), 5.63-5.57 (m, 1H), 2.59 (s, 3H), 1.86-1.79 (m, 3H).

Example 1774: 5-(4-amino-5-(trifluoromethyl)pyrrolo[2,1-f][1,2,4]triazin-7-yl)-N-(1-(1-(4-fluorophenyl)ethyl)-1H-imidazol-4-yl)-2-methoxynicotinamide

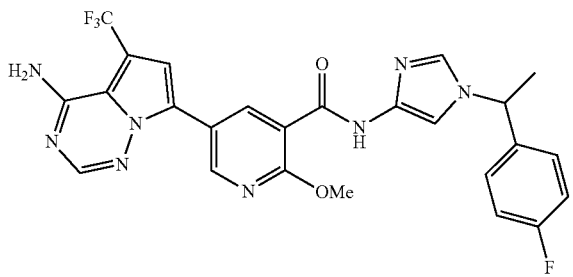

To a solution of lithium 5-(4-amino-5-(trifluoromethyl)pyrrolo[2,1-f][1,2,4]triazin-7-yl)-2-methoxynicotinate (35 mg, 0.097 mmol) in DMF (0.5 mL) was added BOP (56.0 mg, 0.127 mmol) followed by DIPEA (0.034 mL, 0.195 mmol) at rt. After stirring at rt for 10 min, 1-(1-(4-fluorophenyl)ethyl)-1H-imidazol-4-amine (22.00 mg, 0.107 mmol) was added. The mixture was stirred at rt for 3 h. The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-min hold at 18% B, 18-58% B over 20 min, then a 4-min hold at 100% B; Flow Rate: 20 mL/min; Column Temp: 25° C. Fraction collection was triggered by MS and UV signals. Fractions containing the desired product were combined and dried via centrifugal evaporation to give the title product (14.1 mg, 21.4 μmol, 22% yield).

MS ESI m/z 541.2 (M+H)+

1H NMR (500 MHz, DMSO-d6) δ 10.40-10.33 (m, 1H), 8.92-8.86 (m, 1H), 8.82-8.75 (m, 1H), 8.17-8.11 (m, 1H), 7.76-7.71 (m, 1H), 7.59 (s, 1H), 7.40 (s, 3H), 7.19 (s, 2H), 5.58-5.49 (m, 1H), 4.08-4.03 (m, 3H), 1.82-1.76 (m, 3H).

Example 1775: 5-(4-amino-5-(trifluoromethyl)pyrrolo[2,1-f][1,2,4]triazin-7-yl)-N-(1-(2-fluoro-5-(trifluoromethoxy)benzyl)-1H-pyrazol-4-yl)-2-methylnicotinamide

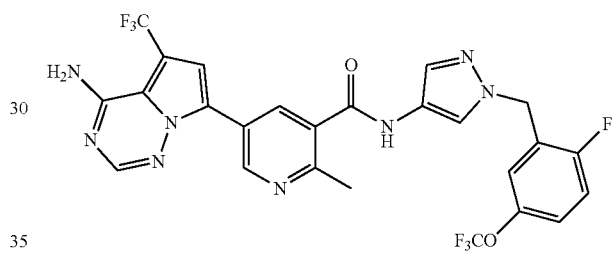

1775A: 1-(2-fluoro-5-(trifluoromethoxy)benzyl)-4-nitro-1H-pyrazole: To a solution of 4-nitro-1H-pyrazole (159 mg, 1.406 mmol) in DMF (3 mL) was added 1.0 M NaHMDS/THF (1.524 mL, 1.524 mmol) dropwise at rt. After stirring at rt for 20 min, 2-(bromomethyl)-1-fluoro-4-(trifluoromethoxy)benzene (320 mg, 1.17 mmol) was added very slowly. The mixture was stirred at rt for 3 h. EtOAc was added. The organics were washed with water and concentrated in vacuo. The residue was purified via silica gel chromatography (12 g, hexanes-50% EtOAc) to give 1-(2-fluoro-5-(trifluoromethoxy)benzyl)-4-nitro-1H-pyrazole (310 mg, 1.016 mmol, 87% yield).

MS ESI m/z 541.2 (M+H)+

1H NMR (499 MHz, CDCl3) δ 8.22 (s, 1H), 8.12 (s, 1H), 7.31-7.26 (m, 1H), 7.23-7.18 (m, 2H), 5.39-5.37 (m, 2H).

1775B: 1-(2-fluoro-5-(trifluoromethoxy)benzyl)-1H-pyrazol-4-amine: To 10% Pd—C (60 mg, 0.056 mmol) was added a solution of 1-(2-fluoro-5-(trifluoromethoxy)benzyl)-4-nitro-1H-pyrazole (310 mg, 1.016 mmol) in MeOH (5 mL) under N2. The mixture was stirred under H2 balloon ON. The Pd/C was filtered out and washed with MeOH. The filtrate was concentrated to give 1-(2-fluoro-5-(trifluoromethoxy)benzyl)-1H-pyrazol-4-amine (270 mg, 0.981 mmol, 97% yield).

MS ESI m/z 276.0 (M+H)+

1H NMR (499 MHz, CDCl3) δ 7.25-7.22 (m, 1H), 7.19-7.13 (m, 1H), 7.09 (s, 2H), 6.96-6.92 (m, 1H), 5.26-5.23 (m, 2H).

1775: Following the procedure described for Example 1774, 5-(4-amino-5-(trifluoromethyl)pyrrolo[2,1-f][1,2,4]

triazin-7-yl)-N-(1-(2-fluoro-5-(trifluoromethoxy)benzyl)-1H-pyrazol-4-yl)-2-methylnicotinamide was (7.2 mg, 12.1 μmol, 12% yield).

MS ESI m/z 595.5 (M+H)+

1H NMR (500 MHz, DMSO-d6) δ 10.68-10.61 (m, 1H), 9.23 (s, 1H), 8.52 (s, 1H), 8.20 (br d, J=10.7 Hz, 2H), 7.75-7.70 (m, 1H), 7.60-7.56 (m, 1H), 7.44-7.36 (m, 2H), 7.29-7.24 (m, 1H), 5.46-5.39 (m, 2H), 2.59 (s, 3H).

Example 1776: 5-(4-amino-5-(trifluoromethyl)pyrrolo[2,1-f][1,2,4]triazin-7-yl)-N-(1-(1-(4-fluorophenyl)ethyl)-1H-pyrazol-4-yl)-2-methoxynicotinamide

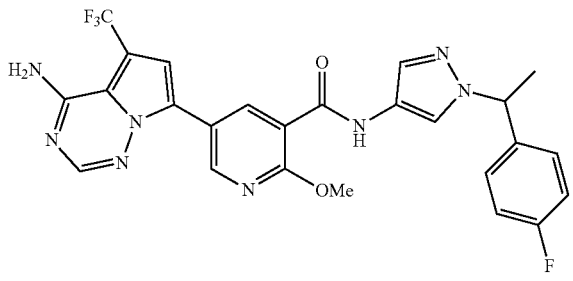 [SMILES: COc1ncc(-c2cc(C(F)(F)F)c3c(N)ncnn23)cc1C(=O)Nc1cn(C(C)c2ccc(F)cc2)cn1]

1776A: 1-(1-(4-fluorophenyl)ethyl)-4-nitro-1H-pyrazole: To a solution of 4-nitro-1H-pyrazole (500 mg, 4.42 mmol) in DMF (10 mL) was added 1.0 M NaHMDS/THF (4.86 mL, 4.86 mmol) dropwise at rt. After stirring at rt for 20 min, 1-(1-bromoethyl)-4-fluorobenzene (1077 mg, 5.31 mmol) was added very slowly. The mixture was stirred at rt for 3 h. EtOAc was added. The organic layer was washed with water and concentrated in vacuo. The residue was purified via silica gel chromatography (24 g, hexanes-50% EtOAc) to give 1-(1-(4-fluorophenyl)ethyl)-4-nitro-1H-pyrazole (980 mg, 4.17 mmol, 94% yield).

1H NMR (499 MHz, CDCl3) δ 8.13-8.11 (m, 1H), 8.10-8.09 (m, 1H), 7.32-7.29 (m, 2H), 7.11 (s, 2H), 5.56-5.50 (m, 1H), 1.95 (d, J=7.0 Hz, 3H).

1776B: 1-(1-(4-fluorophenyl)ethyl)-1H-pyrazol-4-amine: To 10% Pd—C (250 mg, 0.235 mmol) was added a solution of 1-(1-(4-fluorophenyl)ethyl)-4-nitro-1H-pyrazole (980 mg, 4.17 mmol) in MeOH (20 mL) at rt under N2. The mixture was stirred under H2 balloon at rt for 3 h. The Pd/C was filtered out. The filtrate was concentrated to dryness to give 1-(1-(4-fluorophenyl)ethyl)-1H-pyrazol-4-amine (800 mg, 3.90 mmol, 94% yield).

MS ESI m/z 206.1 (M+H)+

1H NMR (499 MHz, CDCl3) δ 7.23-7.22 (m, 1H), 7.20-7.16 (m, 2H), 7.02 (s, 3H), 5.41-5.35 (m, 1H), 1.85 (d, J=7.0 Hz, 3H).

1776: Following the procedure described for 1774, 5-(4-amino-5-(trifluoromethyl)pyrrolo[2,1-f][1,2,4]triazin-7-yl)-N-(1-(1-(4-fluorophenyl)ethyl)-1H-pyrazol-4-yl)-2-methoxynicotinamide was afforded (20.4 mg, 31.2 μmol, 31% yield).

MS ESI m/z 541.1 (M+H)+

1H NMR (500 MHz, DMSO-d6) δ 10.32-10.27 (m, 1H), 8.95-8.92 (m, 1H), 8.75 (s, 1H), 8.15 (d, J=17.7 Hz, 2H), 7.67-7.61 (m, 2H), 7.37-7.29 (m, 2H), 7.21-7.14 (m, 2H), 5.67-5.60 (m, 1H), 4.04 (s, 3H), 1.80 (br d, J=7.0 Hz, 3H).

Example 1777: 5-(4-amino-5-(trifluoromethyl)pyrrolo[2,1-f][1,2,4]triazin-7-yl)-N-(1-(1-(4-fluorophenyl)ethyl)-1H-pyrazol-4-yl)-2-methylnicotinamide

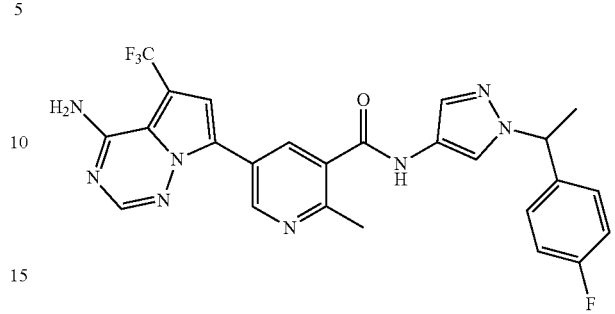

Following the procedure described for Example 1776, 5-(4-amino-5-(trifluoromethyl)pyrrolo[2,1-f][1,2,4]triazin-7-yl)-N-(1-(1-(4-fluorophenyl)ethyl)-1H-pyrazol-4-yl)-2-methylnicotinamide was afforded (24.1 mg, 46.0 μmol, 46% yield).

MS ESI m/z 525.1 (M+H)+

1H NMR (500 MHz, DMSO-d6) δ 10.64-10.59 (m, 1H), 9.24-9.19 (m, 1H), 8.53-8.49 (m, 1H), 8.21-8.11 (m, 2H), 7.74-7.55 (m, 2H), 7.37-7.31 (m, 2H), 7.20-7.12 (m, 2H), 5.67-5.60 (m, 1H), 2.59 (s, 3H), 1.81-1.77 (m, 3H).

Example 1778: 5-(4-amino-5-(trifluoromethyl)pyrrolo[2,1-f][1,2,4]triazin-7-yl)-N-(1-(2-fluoro-5-(trifluoromethoxy)benzyl)-1H-imidazol-4-yl)-2-methylnicotinamide

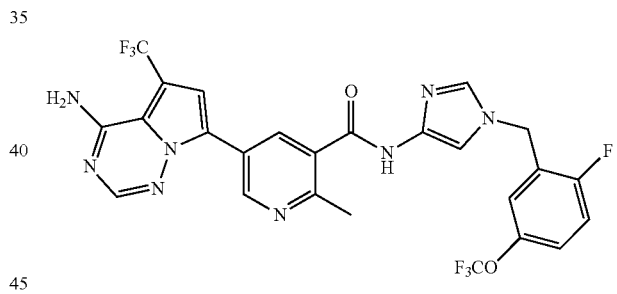

1778A: 1-(2-fluoro-5-(trifluoromethoxy)benzyl)-4-nitro-1H-imidazole: To a solution of 4-nitro-1H-imidazole (159 mg, 1.406 mmol) in DMF (3 mL) was added 1.0 M NaHMDS/THF (1.524 mL, 1.524 mmol) dropwise at rt. After stirring at rt for 20 min, 2-(bromomethyl)-1-fluoro-4-(trifluoromethoxy)benzene (320 mg, 1.172 mmol) was added very slowly. The mixture was stirred at rt ON. EtOAc was added. The organics were washed with water, then concentrated. The residue was purified via silica gel chromatography (12 g, hexanes-70% EtOAc) to give 1-(2-fluoro-5-(trifluoromethoxy)benzyl)-4-nitro-1H-imidazole (330 mg, 1.081 mmol, 92% yield)

MS ESI m/z 306.0 (M+H)+

1H NMR (499 MHz, CDCl3) δ 7.84-7.82 (m, 1H), 7.57 (d, J=1.4 Hz, 1H), 7.33-7.29 (m, 1H), 7.25-7.20 (m, 1H), 7.20-7.16 (m, 1H), 5.26 (s, 2H).

1778B: 1-(2-fluoro-5-(trifluoromethoxy)benzyl)-1H-imidazol-4-amine: To 10% Pd—C (80 mg, 0.075 mmol) was added a solution of 1-(2-fluoro-5-(trifluoromethoxy)benzyl)-4-nitro-1H-imidazole (310 mg, 1.016 mmol) in MeOH (5 mL) under N2. The mixture was stirred under H2 balloon ON. The Pd/C was filtered out and washed with MeOH. The filtrate was concentrated to give 1-(2-fluoro-5-(trifluoromethoxy)benzyl)-1H-imidazol-4-amine (270 mg, 0.981 mmol, 97% yield).

MS ESI m/z 276.0 (M+H)$^+$

1H NMR (499 MHz, CDCl$_3$) δ 7.25-7.23 (m, 1H), 7.22-7.18 (m, 1H), 7.16-7.12 (m, 1H), 6.96-6.93 (m, 1H), 6.25-6.23 (m, 1H), 5.05-5.04 (m, 2H).

1778: Following the procedure described for Example 1774, 5-(4-amino-5-(trifluoromethyl)pyrrolo[2,1-f][1,2,4]triazin-7-yl)-N-(1-(2-fluoro-5-(trifluoromethoxy)benzyl)-1H-imidazol-4-yl)-2-methylnicotinamide was afforded (10.2 mg, 14.4 µmol, 14% yield).

MS ESI m/z 595.3 (M+H)$^+$

1H NMR (500 MHz, DMSO-d6) δ 11.02 (s, 1H), 9.23 (s, 1H), 8.53 (s, 1H), 8.19 (s, 1H), 7.76 (s, 1H), 7.73 (br s, 1H), 7.53-7.47 (m, 2H), 7.45 (br s, 2H), 5.32 (s, 2H), 2.59 (s, 3H).

Example 1779: 5-(4-amino-5-(trifluoromethyl)pyrrolo[2,1-f][1,2,4]triazin-7-yl)-2-methoxy-N-(1-(3,3,3-trifluoro-2-hydroxy-2-methylpropyl)-1H-imidazol-4-yl)nicotinamide

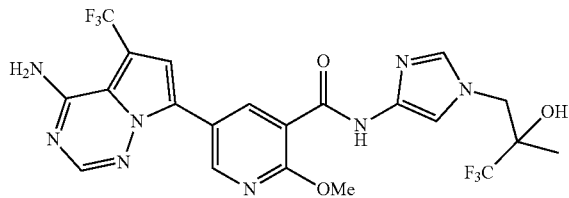 [SMILES: COc1ncc(-c2cc(C(F)(F)F)c3c(N)ncnn23)cc1C(=O)Nc1cn(CC(C)(O)C(F)(F)F)cn1]

1779A: 1-(4-nitro-1H-imidazol-1-yl)propan-2-one: To a solution of 4-nitro-1H-imidazole (260 mg, 2.299 mmol) in DMF (5 mL) was added 1.0 M NaHMDS/THF (2.53 mL, 2.53 mmol) dropwise at rt. After stirring at rt for 20 min, 1-bromopropan-2-one (315 mg, 2.299 mmol) was added very slowly. The mixture was stirred at rt for ON. Water was added and extracted with EtOAc (4×50 mL). The organic layer was concentrated. The residue was purified via silica gel chromatography (12 g, DCM-10% MeOH) to give 1-(4-nitro-1H-imidazol-1-yl)propan-2-one (180 mg, 1.064 mmol, 46% yield).

MS ESI m/z 170.0 (M+H)$^+$

1H NMR (499 MHz, CD$_3$OD) δ 8.06-8.04 (m, 1H), 7.66-7.62 (m, 1H), 5.17-5.12 (m, 1H), 2.28 (s, 3H).

1779B: 4-nitro-1-(3,3,3-trifluoro-2-methyl-2-((trimethylsilyl)oxy)propyl)-1H-imidazole: To a solution of 1-(4-nitro-1H-imidazol-1-yl)propan-2-one (100 mg, 0.591 mmol) in THF (3 mL) was added 1.0 M TBAF/THF (0.118 mL, 0.118 mmol) dropwise at rt. (Trifluoromethyl)trimethylsilane (109 mg, 0.769 mmol) was added very slowly. The mixture was stirred at rt for 2 h. Another 2.0 eq. of TMS-CF$_3$ was added. The reaction was stirred at 60-80° C. for 1 h. The mixture was concentrated. The residue was purified via silica gel chromatography (4 g, hexanes-70% EtOAc) to give 4-nitro-1-(3,3,3-trifluoro-2-methyl-2-((trimethylsilyl)oxy)propyl)-1H-imidazole (80 mg, 0.257 mmol, 44% yield).

MS ESI m/z 312.0 (M+H)$^+$

1H NMR (499 MHz, CDCl$_3$) δ 7.82 (d, J=1.5 Hz, 1H), 7.47 (d, J=1.4 Hz, 1H), 4.29-4.23 (m, 1H), 4.08-4.03 (m, 1H), 1.41-1.39 (s, 3H).

1779C: 1,1,1-trifluoro-2-methyl-3-(4-nitro-1H-imidazol-1-yl)propan-2-ol: To a solution of 4-nitro-1-(3,3,3-trifluoro-2-methyl-2-((trimethylsilyl)oxy)propyl)-1H-imidazole (70 mg, 0.225 mmol) in MeOH (2 mL) was added 1 mL of conc. HCl. The mixture was stirred at rt for 3 h. The mixture was concentrated to dryness in vacuo to give a clean 1,1,1-trifluoro-2-methyl-3-(4-nitro-1H-imidazol-1-yl)propan-2-ol (53.8 mg, 0.225 mmol, 100% yield).

MS ESI m/z 240.0 (M+H)$^+$

1H NMR (499 MHz, CD$_3$OD) δ 8.25 (d, J=1.3 Hz, 1H), 7.95 (d, J=1.2 Hz, 1H), 4.45-4.35 (m, 2H), 1.31 (s, 3H).

1779D: 3-(4-amino-1H-imidazol-1-yl)-1,1,1-trifluoro-2-methylpropan-2-ol: To 10% Pd—C (25 mg, 0.023 mmol) was added a solution of 1,1,1-trifluoro-2-methyl-3-(4-nitro-1H-imidazol-1-yl)propan-2-ol (50 mg, 0.209 mmol) in MeOH (3 mL) under N$_2$. The mixture was stirred under H$_2$ balloon at rt for 4 h. Pd/C was filtered out and washed with MeOH. The filtrate was concentrated to dryness to give 3-(4-amino-1H-imidazol-1-yl)-1,1,1-trifluoro-2-methylpropan-2-ol (43.7 mg, 0.209 mmol, 100% yield).

MS ESI m/z 210.0 (M+H)$^+$

1H NMR (499 MHz, CDCl$_3$) δ 7.14 (d, J=1.3 Hz, 1H), 6.30 (d, J=1.5 Hz, 1H), 4.13 (d, J=14.5 Hz, 1H), 3.88 (d, J=14.4 Hz, 1H), 3.51 (s, 2H), 1.29 (s, 3H).

1779: Following the procedure described for Example 1774, 5-(4-amino-5-(trifluoromethyl)pyrrolo[2,1-f][1,2,4]triazin-7-yl)-2-methoxy-N-(1-(3,3,3-trifluoro-2-hydroxy-2-methylpropyl)-1H-imidazol-4-yl)nicotinamide was afforded (15.6 mg, 23.7 µmol, 34% yield).

MS ESI m/z 545.3 (M+H)$^+$

1H NMR (500 MHz, DMSO-d6) δ 10.51 (s, 1H), 8.95 (s, 1H), 8.84 (s, 1H), 8.18 (s, 1H), 7.82 (s, 1H), 7.64 (s, 1H), 7.58 (s, 1H), 4.30 (br d, J=14.3 Hz, 1H), 4.21 (br d, J=14.0 Hz, 1H), 4.08 (s, 3H), 1.18 (s, 3H).

Example 1780: 5-(4-amino-5-(trifluoromethyl)pyrrolo[2,1-f][1,2,4]triazin-7-yl)-2-methyl-N-(1-(3,3,3-trifluoro-2-hydroxy-2-methylpropyl)-1H-imidazol-4-yl)nicotinamide

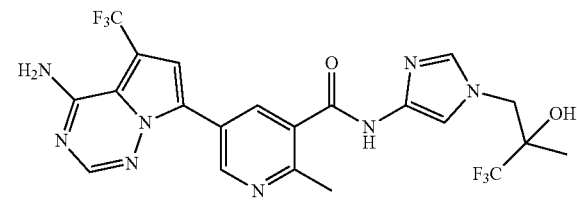 [SMILES: Cc1ncc(-c2cc(C(F)(F)F)c3c(N)ncnn23)cc1C(=O)Nc1cn(CC(C)(O)C(F)(F)F)cn1]

Example 1780 was made following the protocols described for Example 1779 to give the title product (6.4 mg, 12.1 µmol, 17% yield).

MS ESI m/z 529.1 (M+H)$^+$

1H NMR (500 MHz, DMSO-d6) δ 10.93 (s, 1H), 9.22 (s, 1H), 8.52 (s, 1H), 8.21 (s, 1H), 7.74 (s, 1H), 7.53 (br d, J=7.9 Hz, 2H), 4.24 (br d, J=14.3 Hz, 2H), 4.15 (br d, J=14.3 Hz, 1H), 2.60 (s, 3H), 1.17 (s, 3H).

Example 1781: 5-(4-amino-5-(trifluoromethyl)pyrrolo[2,1-f][1,2,4]triazin-7-yl)-2-methyl-N-(1-(4,4,4-trifluoro-3-hydroxy-3-methylbutyl)-1H-imidazol-4-yl)nicotinamide

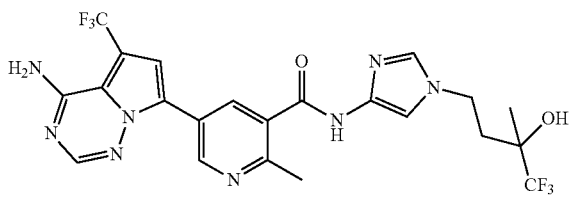 [SMILES: Cc1ncc(-c2cc(C(F)(F)F)c3c(N)ncnn23)cc1C(=O)Nc1cn(CCC(C)(O)C(F)(F)F)cn1]

1781A: 4-(4-nitro-1H-imidazol-1-yl)butan-2-one: To a solution of 4-nitro-1H-imidazole (500 mg, 4.42 mmol) in DMSO (3 mL) was added but-3-en-2-one (465 mg, 6.63 mmol) followed by DMAP (32.4 mg, 0.265 mmol). The mixture was stirred at 70° C. for 1.5 h. Water was added and extracted with EtOAc (3×50 mL). The organic layer was dried over $Na_2SO_4$ and concentrated to give 4-(4-nitro-1H-imidazol-1-yl)butan-2-one (420 mg, 2.293 mmol, 52% yield).

MS ESI m/z 184.0 $(M+H)^+$

1H NMR (499 MHz, $CDCl_3$) δ 7.82 (d, J=1.5 Hz, 1H), 7.50 (d, J=1.4 Hz, 1H), 4.35-4.31 (m, 2H), 3.01 (t, J=6.0 Hz, 2H), 2.23 (s, 3H).

1781B: 4-nitro-1-(4,4,4-trifluoro-3-methyl-3-((trimethylsilyl)oxy)butyl)-1H-imidazole: To a solution of 4-(4-nitro-1H-imidazol-1-yl)butan-2-one (420 mg, 2.293 mmol) in THF (6 mL) was added TBAF (0.229 mL, 0.229 mmol) dropwise at rt. (Trifluoromethyl)trimethylsilane (1304 mg, 9.17 mmol) was added dropwise. The mixture was stirred at 65° C. for 2 h. The reaction was concentrated, and the crude residue was purified via silica gel chromatography (12 g, hexanes-70% EtOAc) to give 4-nitro-1-(4,4,4-trifluoro-3-methyl-3-((trimethylsilyl)oxy)butyl)-1H-imidazole (386 mg, 1.19 mmol, 52% yield).

MS ESI m/z 326.0 $(M+H)^+$

1H NMR (499 MHz, $CDCl_3$) δ 7.80-7.79 (m, 1H), 7.48-7.46 (m, 1H), 4.26-4.13 (m, 2H), 2.37-2.29 (m, 1H), 2.10-2.03 (m, 1H), 1.50-1.47 (m, 3H), 0.23-0.22 (m, 9H).

1781C: 1,1,1-trifluoro-2-methyl-4-(4-nitro-1H-imidazol-1-yl)butan-2-ol: To a solution of 4-nitro-1-(4,4,4-trifluoro-3-methyl-3-((trimethylsilyl)oxy)butyl)-1H-imidazole (386 mg, 1.186 mmol) in MeOH (5 mL) was added 3 mL of conc. HCl dropwise at rt. The mixture was stirred at rt for 4 h. The reaction was concentrated to dryness in vacuo to give 1,1,1-trifluoro-2-methyl-4-(4-nitro-1H-imidazol-1-yl)butan-2-ol (300 mg, 1.186 mmol, 100% yield).

MS ESI m/z 254.0 $(M+H)^+$

1H NMR (499 MHz, $CD_3OD$) δ 8.41 (s, 1H), 8.21 (s, 1H), 5.11-5.07 (m, 2H), 4.41 (ddd, J=12.4, 9.6, 6.1 Hz, 2H), 2.34-2.17 (m, 2H), 1.42 (s, 3H). 1781D: 4-(4-amino-1H-imidazol-1-yl)-1,1,1-trifluoro-2-methylbutan-2-ol: A similar method to that described for 1779D was used to make the title compound. MS ESI m/z 224.1 $(M+H)^+$ 1771: Following the procedure described for Example 1774, 5-(4-amino-5-(trifluoromethyl)pyrrolo[2,1-f][1,2,4]triazin-7-yl)-2-methyl-N-(1-(4,4,4-trifluoro-3-hydroxy-3-methylbutyl)-1H-imidazol-4-yl)nicotinamide was afforded (10.4 mg, 15.8 μmol, 22% yield).

MS ESI m/z 543.1 $(M+H)^+$

1H NMR (500 MHz, DMSO-d6) δ 11.22 (s, 1H), 9.25 (s, 1H), 8.57 (s, 1H), 8.20 (s, 1H), 8.17-8.05 (m, 1H), 7.74 (s, 1H), 7.63 (s, 1H), 4.30-4.12 (m, 2H), 2.63 (s, 3H), 2.17-2.06 (m, 2H), 1.32 (s, 3H).

Example 1782: 5-(4-amino-5-(trifluoromethyl)pyrrolo[2,1-f][1,2,4]triazin-7-yl)-2-methoxy-N-(4,4,4-trifluoro-3-hydroxy-3-(trifluoromethyl)butyl)nicotinamide

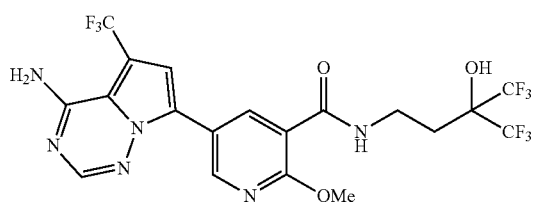 [SMILES: COc1ncc(-c2cc(C(F)(F)F)c3c(N)ncnn23)cc1C(=O)NCCC(O)(C(F)(F)F)C(F)(F)F]

Using the same protocol as described in Example 1769 provided the title compound (21.3 mg, 32.3 μmol, 32% yield).

MS ESI m/z 546.9 $(M+H)^+$

1H NMR (500 MHz, DMSO-d6) δ 8.88 (s, 1H), 8.84-8.79 (m, 1H), 8.55 (br s, 1H), 8.22-8.12 (m, 2H), 7.58 (s, 1H), 4.03 (s, 3H), 3.45-3.33 (m, 2H), 2.24-2.16 (m, 2H).

Example 1783: 5-(4-amino-5-(trifluoromethyl)pyrrolo[2,1-f][1,2,4]triazin-7-yl)-2-methyl-N-(4,4,4-trifluoro-3-hydroxy-3-(trifluoromethyl)butyl)nicotinamide

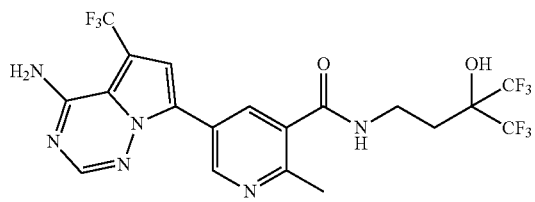 [SMILES: Cc1ncc(-c2cc(C(F)(F)F)c3c(N)ncnn23)cc1C(=O)NCCC(O)(C(F)(F)F)C(F)(F)F]

Using the same protocol as described in Example 1769 provided the title compound (28.5 mg, 44.2 μmol, 44% yield).

MS ESI m/z 531.3 $(M+H)^+$

1H NMR (500 MHz, DMSO-d6) δ 9.19 (s, 1H), 8.63 (br s, 1H), 8.38 (s, 1H), 8.19 (s, 1H), 8.13 (s, 1H), 7.68 (s, 1H), 3.54-3.44 (m, 1H), 2.54 (s, 3H), 2.27-2.16 (m, 2H).

Example 1784: 5-(4-amino-5-(trifluoromethyl)pyrrolo[2,1-f][1,2,4]triazin-7-yl)-2-methoxy-N-(1-phenethyl-1H-imidazol-4-yl)nicotinamide

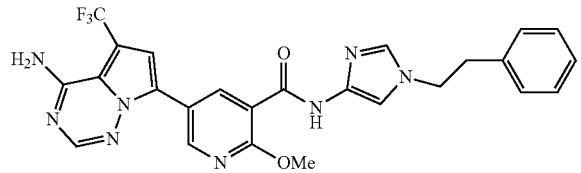 [SMILES: COc1ncc(-c2cc(C(F)(F)F)c3c(N)ncnn23)cc1C(=O)Nc1cn(CCc2ccccc2)cn1]

1784A: 4-nitro-1-phenethyl-1H-imidazole: To a solution of 4-nitro-1H-imidazole (500 mg, 4.42 mmol) in DMF (10 mL) was added 1.0 M NaHMDS/THF (4.86 mL, 4.86 mmol). After stirring at rt for 10 min, (2-bromoethyl)benzene (818 mg, 4.42 mmol) was added dropwise. The reaction was stirred at rt ON. Additional bromide (0.8 eq) was added. The mixture was stirred at 70° C. for 2 h. EtOAc was added, washed with water and concentrated. The residue was purified via silica gel chromatography (24 g, hexanes-100% EtOAc) to give 4-nitro-1-phenethyl-1H-imidazole (810 mg, 3.73 mmol, 84% yield).

MS ESI m/z 218.0 (M+H)+

1H NMR (499 MHz, CDCl$_3$) δ 7.62 (d, J=1.5 Hz, 1H), 7.37-7.29 (m, 3H), 7.22 (d, J=1.5 Hz, 1H), 7.08 (d, J=6.8 Hz, 2H), 4.29 (t, J=6.9 Hz, 2H), 3.13 (t, J=6.9 Hz, 2H).

1784B: 1-phenethyl-1H-imidazol-4-amine: To 10% Pd—C (80 mg, 0.075 mmol) was added a solution of 4-nitro-1-phenethyl-1H-imidazole (180 mg, 0.829 mmol) in MeOH (5 mL) under N$_2$. The mixture was stirred under H$_2$ balloon at rt ON. Pd/C was filtered out. The filtrate was concentrated to give 1-phenethyl-1H-imidazol-4-amine (140 mg, 0.748 mmol, 90% yield).

MS ESI m/z 188.1 (M+H)+

1H NMR (499 MHz, CDCl$_3$) δ 7.33-7.24 (m, 3H), 7.11-7.08 (m, 2H), 6.95-6.93 (m, 1H), 6.22-6.20 (m, 1H), 4.07-4.02 (m, 2H), 3.02 (t, J=7.1 Hz, 2H).

1784: Following the procedure described for Example 1774, 5-(4-amino-5-(trifluoromethyl)pyrrolo[2,1-f][1,2,4]triazin-7-yl)-2-methoxy-N-(1-phenethyl-1H-imidazol-4-yl)nicotinamide was afforded (6.3 mg, 12.1 µmol, 12% yield).

MS ESI m/z 523.0 (M+H)+

1H NMR (500 MHz, DMSO-d6) δ 10.32-10.28 (m, 1H), 8.94-8.91 (m, 1H), 8.85-8.82 (m, 1H), 8.20-8.17 (m, 1H), 7.65-7.61 (m, 1H), 7.48-7.44 (m, 1H), 7.39-7.36 (m, 1H), 7.30-7.23 (m, 5H), 4.25-4.20 (m, 2H), 4.09-4.06 (m, 3H), 3.09-3.03 (m, 2H).

Example 1785: 5-(4-amino-5-(trifluoromethyl)pyrrolo[2,1-f][1,2,4]triazin-7-yl)-2-methyl-N-(1-phenethyl-1H-imidazol-4-yl)nicotinamide

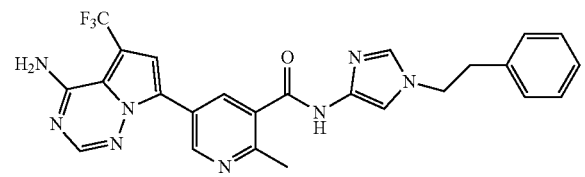 [SMILES: Cc1ncc(-c2cc(C(F)(F)F)c3c(N)ncnn23)cc1C(=O)Nc1cn(CCc2ccccc2)cn1]

Following the procedures describe for Example 1784, the title compound was afforded (7.6 mg, 15.0 µmol, 15% yield).

MS ESI m/z 507.1 (M+H)+

1H NMR (500 MHz, DMSO-d6) δ 10.87-10.83 (m, 1H), 9.24-9.19 (m, 1H), 8.52-8.47 (m, 1H), 8.23-8.19 (m, 1H), 7.76-7.72 (m, 1H), 7.52-7.49 (m, 1H), 7.40-7.37 (m, 1H), 7.33-7.28 (m, 2H), 7.27-7.20 (m, 3H), 4.26-4.19 (m, 2H), 3.10-3.02 (m, 2H), 2.62-2.57 (m, 3H).

Example 1786: 5-(4-amino-5-(trifluoromethyl)pyrrolo[2,1-f][1,2,4]triazin-7-yl)-2-methoxy-N-(1-phenethyl-1H-pyrazol-4-yl)nicotinamide

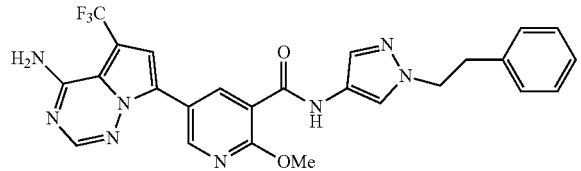 [SMILES: COc1ncc(-c2cc(C(F)(F)F)c3c(N)ncnn23)cc1C(=O)Nc1cnn(CCc2ccccc2)c1]

1786A: 4-nitro-1-phenethyl-1H-pyrazole: To a solution of 4-nitro-1H-pyrazole (520 mg, 4.60 mmol) in DMF (10 mL) was added 1.0 M NaHMDS/THF (5.06 mL, 5.06 mmol). After stirring at rt for 20 min, (2-bromoethyl)benzene (1702 mg, 9.20 mmol) was added dropwise. The reaction was stirred at rt for 4 h. EtOAc was added and the organic layer was washed with water and concentrated. The residue was purified via silica gel chromatography (24 g, hexanes-70% EtOAc) to give a clean 4-nitro-1-phenethyl-1H-pyrazole (960 mg, 4.42 mmol, 96% yield).

1H NMR (499 MHz, CDCl$_3$) δ 8.12 (s, 1H), 7.83 (s, 1H), 7.34-7.29 (m, 3H), 7.10-7.06 (m, 2H), 4.40 (t, J=7.0 Hz, 2H), 3.22 (t, J=7.0 Hz, 2H).

1786B: 1-phenethyl-1H-pyrazol-4-amine: To 10% Pd—C (80 mg, 0.075 mmol) was added a solution of 4-nitro-1-phenethyl-1H-pyrazole (215 mg, 0.990 mmol) in MeOH (5 mL) under N$_2$. The mixture was stirred under H$_2$ balloon for 4 h. Pd/C was filtered out. The filtrate was concentrated to give 1-phenethyl-1H-pyrazol-4-amine (175 mg, 0.935 mmol, 94% yield).

MS ESI m/z 188.1 (M+H)+

1H NMR (499 MHz, CDCl$_3$) δ 7.33-7.22 (m, 3H), 7.20 (d, J=0.7 Hz, 1H), 7.14 (d, J=7.1 Hz, 2H), 6.86 (d, J=0.8 Hz, 1H), 4.27-4.20 (m, 2H), 3.14 (t, J=7.5 Hz, 2H).

1786: Following the procedure described for Example 1774, 5-(4-amino-5-(trifluoromethyl)pyrrolo[2,1-f][1,2,4]triazin-7-yl)-2-methoxy-N-(1-phenethyl-1H-pyrazol-4-yl)nicotinamide was afforded (8.0 mg, 15.3 µmol, 15% yield).

MS ESI m/z 523.1 (M+H)+

1H NMR (500 MHz, DMSO-d6) δ 10.24 (s, 1H), 8.92 (s, 1H), 8.72 (s, 1H), 8.16 (s, 1H), 7.99 (s, 1H), 7.62 (s, 1H), 7.60 (br s, 1H), 7.31-7.23 (m, 2H), 7.20 (br d, J=6.7 Hz, 3H), 4.32 (br t, J=7.2 Hz, 2H), 4.03 (s, 3H), 3.09 (br 1, J=7.2 Hz, 2H).

Example 1787: 5-(4-amino-5-(trifluoromethyl)pyrrolo[2,1-f][1,2,4]triazin-7-yl)-2-methyl-N-(1-phenethyl-1H-pyrazol-4-yl)nicotinamide

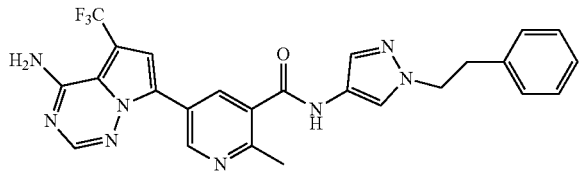 [SMILES: Cc1ncc(-c2cc(C(F)(F)F)c3c(N)ncnn23)cc1C(=O)Nc1cnn(CCc2ccccc2)c1]

Following the procedures describe for Example 1786, the title compound was afforded (17.8 mg, 35.1 µmol, 35% yield).

MS ESI m/z 507.0 (M+H)+

1H NMR (500 MHz, DMSO-d6) δ 10.56 (s, 1H), 9.21 (s, 1H), 8.49 (s, 1H), 8.19 (s, 1H), 7.99 (s, 1H), 7.72 (s, 1H), 7.54 (s, 1H), 7.31-7.24 (m, 2H), 7.21 (br d, J=7.3 Hz, 3H), 4.33 (br t, J=7.3 Hz, 2H), 3.09 (br t, J=7.3 Hz, 2H), 2.58 (s, 3H).

Example 1788: 5-(4-amino-5-(trifluoromethyl)pyrrolo[2,1-f][1,2,4]triazin-7-yl)-2-methoxy-N-(1-(3,3,3-trifluoro-2-hydroxy-2-methylpropyl)-1H-pyrazol-4-yl)nicotinamide

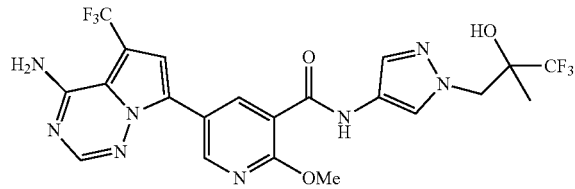 [SMILES: COc1ncc(-c2cc(C(F)(F)F)c3c(N)ncnn23)cc1C(=O)Nc1cnn(CC(C)(O)C(F)(F)F)c1]

1788A: 1-(4-nitro-1H-pyrazol-1-yl)propan-2-one: To a solution of 4-nitro-1H-pyrazole (500 mg, 4.42 mmol) in DMF (8 mL) was added 1.0 M NaHMDS/THF (4.86 mL, 4.86 mmol) dropwise at rt. After stirring at rt for 10 min, 1-bromopropan-2-one (424 mg, 3.10 mmol) was added dropwise over 20 min. The mixture was stirred at rt for 4 h, at 70° C. for 2 h, then at rt ON. EtOAc was added, washed with water, then concentrated. The residue was purified via silica gel chromatography (24 g, hexanes-100% EtOAc) to give 1-(4-nitro-1H-pyrazol-1-yl)propan-2-one (180 mg, 1.064 mmol, 24% yield).

MS ESI m/z 170.0 (M+H)+

1H NMR (499 MHz, CDCl3) δ 8.21 (s, 1H), 8.13 (s, 1H), 5.04 (s, 2H), 2.31 (s, 3H).

1788B: 4-nitro-1-(3,3,3-trifluoro-2-methyl-2-((trimethylsilyl)oxy)propyl)-1H pyrazole: To a solution of 1-(4-nitro-1H-pyrazol-1-yl)propan-2-one (180 mg, 1.064 mmol) in THF (8 mL) was added 1.0 M TBAF/THF (0.106 mL, 0.106 mmol) at rt. Trimethyl(trifluoromethyl)silane (378 mg, 2.66 mmol) was added dropwise over 20 min. The mixture was stirred at rt for 4 h. The reaction was concentrated. The residue was purified via silica gel chromatography (12 g, hexanes-100% EtOAc) to give 4-nitro-1 (3,3,3-trifluoro-2-methyl-2-((trimethylsilyl)oxy)propyl)-1H-pyrazole (130 mg, 0.418 mmol, 39% yield).

MS ESI m/z 312.0 (M+H)+

1H NMR (499 MHz, CDCl3) δ 8.22 (s, 1H), 8.11 (s, 1H), 4.32 (d, J=5.7 Hz, 2H), 1.41 (s, 3H), 0.14-0.12 (m, 9H).

1788C: 4-nitro-1-(3,3,3-trifluoro-2-methyl-2-(hydroxy)-propyl)-1H-pyrazole: To a solution of 4-nitro-1-(3,3,3-trifluoro-2-methyl-2-((trimethylsilyl)oxy)propyl)-1H-pyrazole (130 mg, 0.418 mmol) in MeOH (2 mL) was added conc. HCl (1 mL, 32.9 mmol) dropwise at rt. The mixture was stirred at rt for 2 h. The reaction was concentrated to give the alcohol intermediate.

MS ESI m/z 239.9 (M+H)+

1H NMR (499 MHz, CD3OD) δ 8.56 (s, 1H), 8.15 (s, 1H), 4.48-4.38 (m, 2H), 1.29 (s, 3H).

1788D: 3-(4-amino-1H-pyrazol-1-yl)-1,1,1-trifluoro-2-methylpropan-2-ol: 4-nitro-1-(3,3,3-trifluoro-2-methyl-2-(hydroxy)-propyl)-1H-pyrazole was reduced using Pd/C (30 mg, 0.282 mmol) under H2 balloon in MeOH for 3 h. The Pd/C was filtered out. The filtrate was concentrated to dryness to give 3-(4-amino-1H-pyrazol-1-yl)-1,1,1-trifluoro-2-methylpropan-2-ol (80 mg, 0.382 mmol, 92% yield).

1H NMR (499 MHz, CD3OD) δ 7.30 (d, J=3.8 Hz, 1H), 7.19 (d, J=3.8 Hz, 1H), 4.22 (d, J=8.5 Hz, 2H), 1.17 (s, 3H).

1788: Following the experimental described for Example 1796, 5-(4-amino-5-(trifluoromethyl)pyrrolo[2,1-f][1,2,4]triazin-7-yl)-2-methoxy-N-(1-(3,3,3-trifluoro-2-hydroxy-2-methylpropyl)-1H-pyrazol-4-yl)nicotinamide was afforded (17.4 mg, 26.4 μmol, 26% yield).

MS ESI m/z 545.3 (M+H)+

1H NMR (500 MHz, DMSO-d6) δ 10.34 (s, 1H), 8.94 (s, 1H), 8.74 (s, 1H), 8.18 (s, 1H), 8.14 (s, 1H), 7.64 (br d, J=5.8 Hz, 2H), 6.42 (s, 1H), 4.29 (br d, J=15.3 Hz, 2H), 4.04 (s, 3H), 1.15 (s, 3H).

Example 1789: 5-(4-amino-5-(trifluoromethyl)pyrrolo[2,1-f][1,2,4]triazin-7-yl)-2-methyl-N-(1-(3,3,3-trifluoro-2-hydroxy-2-methylpropyl)-1H-pyrazol-4-yl)nicotinamide

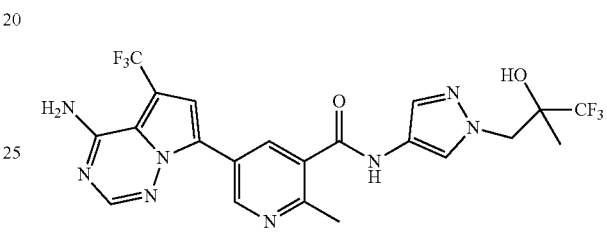

Following the procedures describe for Example 1788, the title compound was afforded (21.9 mg, 41.4 μmol, 41% yield).

MS ESI m/z 529.1 (M+H)+

1H NMR (500 MHz, DMSO-d6) δ 10.65 (s, 1H), 9.23 (s, 1H), 8.53 (s, 1H), 8.21 (s, 1H), 8.12 (s, 1H), 7.74 (s, 1H), 7.59 (s, 1H), 4.30 (br d, J=18.0 Hz, 2H), 2.56-2.52 (m, 3H), 1.16 (s, 3H).

Example 1790: 5-(4-amino-5-(trifluoromethyl)pyrrolo[2,1-f][1,2,4]triazin-7-yl)-2-methoxy-N-(1-(4,4,4-trifluoro-3-hydroxy-3-methylbutyl)-1H-pyrazol-4-yl)nicotinamide

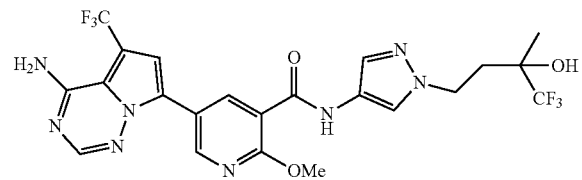 [SMILES: COc1ncc(-c2cc(C(F)(F)F)c3c(N)ncnn23)cc1C(=O)Nc1cnn(CCC(C)(O)C(F)(F)F)c1]

1790A: 4-(4-nitro-1H-pyrazol-1-yl)butan-2-one: To a solution of 4-nitro-1H-pyrazole (500 mg, 4.42 mmol) in DMSO (3 mL) was added but-3-en-2-one (465 mg, 6.63 mmol) followed by DMAP (32.4 mg, 0.265 mmol). The mixture was stirred at 70° C. for 2 h. EtOAc was added. The organic layer was washed with water (3×), dried over Na2SO4 and concentrated to dryness. 4-(4-Nitro-1H-pyrazol-1-yl)butan-2-one (630 mg, 3.44 mmol, 78% yield) was obtained. The material was used for the next step without any purification.

MS ESI m/z 184.0 (M+H)+

1H NMR (499 MHz, CDCl3) δ 8.25 (s, 1H), 8.06 (s, 1H), 4.43 (t, J=6.0 Hz, 2H), 3.11 (t, J=6.0 Hz, 2H), 2.21 (s, 3H).

1790B: 4-nitro-1-(4,4,4-trifluoro-3-methyl-3-((trimethylsilyl)oxy)butyl)-1H-pyrazole: To a solution of 4-(4-nitro-1H-pyrazol-1-yl)butan-2-one (630 mg, 3.44 mmol) in THF (12 mL) was added 1.0 M TBAF/THF (0.344 mL, 0.344 mmol) followed by trimethyl(trifluoromethyl)silane (1712 mg, 12.04 mmol) dropwise at rt. The mixture was stirred at rt for 5 h. The reaction was concentrated. The residue was purified via silica gel chromatography (24 g, hexanes-100% EtOAc) to give 4-nitro-1-(4,4,4-trifluoro-3-methyl-3-((trimethylsilyl)oxy)butyl)-1H-pyrazole (290 mg, 0.891 mmol, 26% yield).

MS ESI m/z 326.0 (M+H)+

1H NMR (499 MHz, CDCl3) δ 8.17 (s, 1H), 8.10 (s, 1H), 4.39-4.26 (m, 2H), 2.41-2.33 (m, 1H), 2.27-2.18 (m, 1H), 1.46 (s, 3H), 0.22 (s, 9H).

1790C: 4-(4-amino-1H-pyrazol-1-yl)-1,1,1-trifluoro-2-methylbutan-2-ol was prepared following the experimental described for 1788D.

MS ESI m/z 224.0 (M+H)+

1H NMR (499 MHz, CD3OD) δ 7.24 (s, 1H), 7.17 (s, 1H), 4.21 (ddd, J=12.1, 9.4, 6.4 Hz, 2H), 2.70 (s, 1H), 2.14 (ddd, J=14.0, 9.5, 6.0 Hz, 2H), 1.32 (s, 3H).

1790: Following the protocol described for Example 1774, 5-(4-amino-5-(trifluoromethyl)pyrrolo[2,1-f][1,2,4]triazin-7-yl)-2-methoxy-N-(1-(4,4,4-trifluoro-3-hydroxy-3-methylbutyl)-1H-pyrazol-4-yl)nicotinamide was afforded (13.5 mg, 20.1 μmol, 20% yield).

MS ESI m/z 559.1 (M+H)+

1H NMR (500 MHz, DMSO-d6) δ 10.29 (s, 1H), 8.93 (s, 1H), 8.77-8.72 (m, 1H), 8.17 (s, 1H), 8.12 (s, 1H), 7.62 (br d, J=8.2 Hz, 2H), 4.29 (br d, J=6.7 Hz, 1H), 4.21 (br d, J=5.2 Hz, 1H), 4.04 (s, 3H), 2.15-2.04 (m, 2H), 1.26 (s, 3H).

Example 1791: 5-(4-amino-5-(trifluoromethyl)pyrrolo[2,1-f][1,2,4]triazin-7-yl)-2-methyl-N-(1-(4,4,4-trifluoro-3-hydroxy-3-methylbutyl)-1H-pyrazol-4-yl)nicotinamide

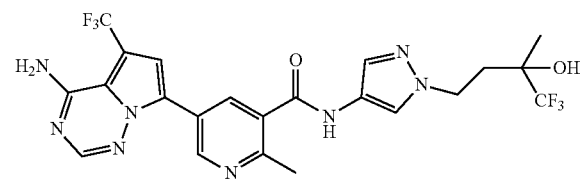 [SMILES: Cc1ncc(-c2cc(C(F)(F)F)c3c(N)ncnn23)cc1C(=O)Nc1cnn(CCC(C)(O)C(F)(F)F)c1]

Following the procedures describe for Example 1790, the title compound was afforded (11.6 mg, 21.4 μmol, 21% yield).

MS ESI m/z 543.4 (M+H)+

1H NMR (500 MHz, DMSO-d6) δ 10.64 (s, 1H), 9.21 (s, 1H), 8.50 (s, 1H), 8.19 (s, 1H), 8.11 (s, 1H), 7.72 (s, 1H), 7.55 (s, 1H), 4.33-4.17 (m, 2H), 2.60 (s, 3H), 2.15-2.02 (m, 2H), 1.27 (s, 3H).

Example 1792: 5-(4-amino-5-(trifluoromethyl)pyrrolo[2,1-f][1,2,4]triazin-7-yl)-N-(1-benzyl-1H-imidazol-4-yl)-2-methylbenzamide

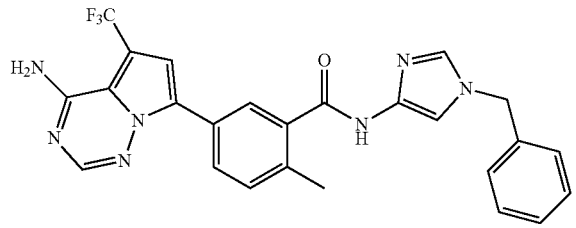 [SMILES: Cc1ccc(-c2cc(C(F)(F)F)c3c(N)ncnn23)cc1C(=O)Nc1cn(Cc2ccccc2)cn1]

1792A: methyl 2-methyl-5-(4,4,5,5-tetramethyl-1,3,2-dioxaborolan-2-yl)benzoate: To a mixture of methyl 5-bromo-2-methylbenzoate (2.0 g, 8.7 mmol) in dioxane (30 mL) was added 4,4,4',4',5,5,5',5'-octamethyl-2,2'-bi(1,3,2-dioxaborolane) (2.66 g, 10.5 mmol), PdCl2(dppf)-CH2Cl2 adduct (0.499 g, 0.611 mmol) and potassium acetate (2.57 g, 26.2 mmol). The mixture was bubbled with N2, then stirred at 110° C. for 1.5 h and cooled to rt. To the reaction mixture was added dioxane (5 mL), 7-bromo-5-(trifluoromethyl)pyrrolo[2,1-f][1,2,4]triazin-4-amine (2.443 g, 8.69 mmol), PdCl2(dppf)-CH2Cl2 adduct (0.355 g, 0.435 mmol) and 2M K3PO4 (13.0 mL, 26.1 mmol). The mixture was stirred at 110° C. for 1 h. Water (50 mL) was added and extracted with EtOAc (2×150 mL). The organic layer was dried over Na2SO4 and concentrated. The residue was crystallized in EtOAc/hexanes to give methyl 5-(4-amino-5-(trifluoromethyl)pyrrolo[2,1-f][1,2,4]triazin-7-yl)-2-methylbenzoate (2.7 g, 7.71 mmol, 89% yield).

MS ESI m/z 351.0 (M+H)+.

1792B: 5-(4-amino-5-(trifluoromethyl)pyrrolo[2,1-f][1,2,4]triazin-7-yl)-2-methylbenzoic acid: A mixture of methyl 5-(4-amino-5-(trifluoromethyl)pyrrolo[2,1-f][1,2,4]triazin-7-yl)-2-methylbenzoate (2.7 g, 7.71 mmol), lithium hydroxide hydrate (0.647 g, 15.42 mmol) in THF (25 mL) and water (5 mL) was stirred at rt ON. Water was added followed by 1N HCl (15.5 mL) to neutralize to the acid. After stirring at rt for 1 h, the fine solid was filtered out, washed with water, then air dried to give clean 5-(4-amino-5-(trifluoromethyl)pyrrolo[2,1-f][1,2,4]triazin-7-yl)-2-methylbenzoic acid (1.5 g, 4.46 mmol, 57.9% yield). Additional product (200 mg) was extracted from the aqueous layer with EtOAc (2×100 mL).

MS ESI m/z 337.1 (M+H)+.

1792: Following the protocol described for Example 1774, 5-(4-amino-5-(trifluoromethyl)pyrrolo[2,1-f][1,2,4]triazin-7-yl)-N-(1-benzyl-1H-imidazol-4-yl)-2-methylbenzamide was afforded (9.9 mg, 16.4 μmol, 16% yield).

MS ESI m/z 492.1 (M+H)+

1H NMR (500 MHz, DMSO-d6) δ 10.72 (s, 1H), 8.15 (s, 1H), 8.11-8.01 (m, 2H), 7.64 (s, 1H), 7.58 (s, 1H), 7.43-7.23 (m, 7H), 5.18 (s, 2H), 2.47-2.32 (m, 3H).

Example 1793: 5-(4-amino-5-(trifluoromethyl)pyrrolo[2,1-f][1,2,4]triazin-7-yl)-N-(1-benzyl-1H-pyrazol-3-yl)-2-methylbenzamide

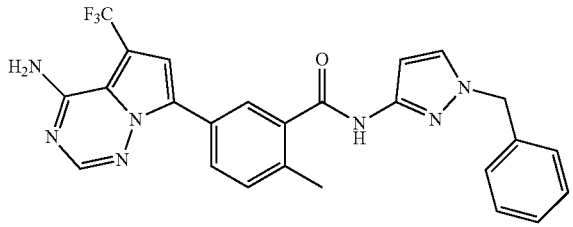 [SMILES: Cc1ccc(-c2cc(C(F)(F)F)c3c(N)ncnn23)cc1C(=O)Nc1ccn(Cc2ccccc2)n1]

Following the procedures describe for Example 1774, the title compound was afforded (12.9 mg, 21.3 µmol, 21% yield).
MS ESI m/z 492.3 (M+H)+
1H NMR (500 MHz, DMSO-d6) δ 10.80 (s, 1H), 8.15 (s, 1H), 8.08 (br s, 2H), 7.80 (br s, 1H), 7.59 (s, 1H), 7.39-7.19 (m, 6H), 6.67 (br s, 1H), 5.24 (s, 2H), 2.41 (s, 3H).

Example 1794: 5-(4-amino-5-(trifluoromethyl)pyrrolo[2,1-f][1,2,4]triazin-7-yl)-N-(1-(1-(4-fluorophenyl)ethyl)-1H-pyrazol-4-yl)-2-methylbenzamide

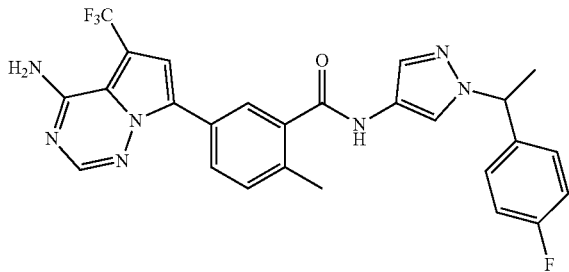 [SMILES: Cc1ccc(-c2cc(C(F)(F)F)c3c(N)ncnn23)cc1C(=O)Nc1cnn(C(C)c2ccc(F)cc2)c1]

Following the procedures describe for Example 1776, the title compound was afforded (24 mg, 45.8 µmol, 46% yield).
MS ESI m/z 524.0 (M+H)+
1H NMR (500 MHz, DMSO-d6) δ 10.42 (s, 1H), 8.16 (s, 1H), 8.13-8.06 (m, 3H), 7.56 (br d, J=7.6 Hz, 2H), 7.40 (br d, J=7.9 Hz, 1H), 7.37-7.30 (m, 2H), 7.16 (br t, J=8.7 Hz, 2H), 5.62 (br d, J=7.0 Hz, 1H), 2.40 (s, 3H), 1.79 (br d, J=7.0 Hz, 3H).

Example 1795: 5-(4-amino-5-(trifluoromethyl)pyrrolo[2,1-f][1,2,4]triazin-7-yl)-N-(1-benzyl-5-methyl-1H-imidazol-4-yl)-2-methylbenzamide

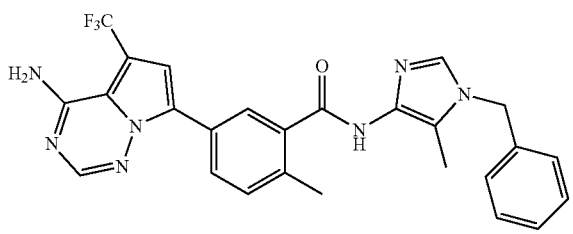 [SMILES: Cc1ccc(-c2cc(C(F)(F)F)c3c(N)ncnn23)cc1C(=O)Nc1ncn(Cc2ccccc2)c1C]

1795A: 1-benzyl-5-methyl-4-nitro-1H-imidazole: To a solution of 5-methyl-4-nitro-1H-imidazole (1.0 g, 7.87 mmol) in DMF (20 mL) was added 1.0 M NaHMDSTFHF (9.44 mL, 9.44 mmol) dropwise at rt. After stirring at rt for 20 min, (bromomethyl)benzene (2.02 g, 11.8 mmol) was added very slowly. The mixture was stirred at rt for 3 h. EtOAc was added. The organic layer was washed with water and concentrated. The residue was purified via silica gel chromatography (24 g, hexanes-100% EtOAc) to give 1-benzyl-5-methyl-4-nitro-1H-imidazole (800 mg, 3.68 mmol, 46.8% yield).
MS ESI m/z 218.1 (M+H)+
1H NMR (499 MHz, CDCl3) δ 7.47-7.37 (m, 4H), 7.13 (d, J=6.9 Hz, 2H), 5.16 (s, 2H), 2.58 (s, 3H).

1795B: 1-benzyl-5-methyl-1H-imidazol-4-amine: To Pd—C (60 mg, 0.06 mmol) was added a solution of 1-benzyl-5-methyl-4-nitro-1H-imidazole (300 mg, 1.38 mmol) in MeOH (20 mL) under N2. The mixture was stirred under H2 balloon for 3 h. The Pd/C was filtered out, and the filtrate was concentrated to give 1-benzyl-5-methyl-1H-imidazol-4-amine (250 mg, 1.34 mmol, 97% yield).
MS ESI m/z 188.1 (M+H)+
1H NMR (499 MHz, CDCl3) δ 7.39-7.29 (m, 4H), 7.15-7.01 (m, 2H), 4.99 (s, 2H), 1.98 (s, 3H).

1795: Following the protocol described for Example 1774, 5-(4-amino-5-(trifluoromethyl)pyrrolo[2,1-f][1,2,4]triazin-7-yl)-N-(1-benzyl-5-methyl-1H-imidazol-4-yl)-2-methylbenzamide was afforded (14.2 mg, 28.1 µmol, 28% yield).
MS ESI m/z 506.1 (M+H)+
1H NMR (500 MHz, DMSO-d6) δ 9.79 (s, 1H), 8.18 (s, 1H), 8.15-8.05 (m, 2H), 7.65 (s, 1H), 7.59 (s, 1H), 7.39 (br t, J=7.5 Hz, 3H), 7.32 (br d, J=7.0 Hz, 1H), 7.19 (br d, J=7.3 Hz, 2H), 5.20 (s, 2H), 2.47-2.42 (m, 3H), 2.01 (s, 3H).

Example 1796: 5-(4-amino-5-(trifluoromethyl)pyrrolo[2,1-f][1,2,4]triazin-7-yl)-N-(1-benzyl-5-methyl-1H-imidazol-4-yl)-2-methoxynicotinamide

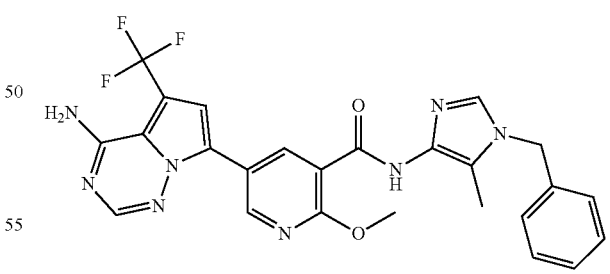

Following the procedures describe for Example 1795, the title compound was afforded (5.3 mg, 8.3 µmol, 8% yield).
MS ESI m/z 523.2 (M+H)+
1H NMR (500 MHz, DMSO-d6) δ 8.96 (br s, 1H), 8.80 (br s, 1H), 8.34 (br s, 1H), 8.16 (s, 1H), 7.59 (s, 1H), 7.48-7.31 (m, 3H), 7.31-7.19 (m, 2H), 5.33 (s, 2H), 4.09 (s, 3H), 2.09 (s, 3H).

Example 1797: 5-(4-amino-5-(trifluoromethyl)pyr-rolo[2,1-f][1,2,4]triazin-7-yl)-N-(1-benzyl-5-methyl-1H-imidazol-4-yl)-2-methylnicotinamide

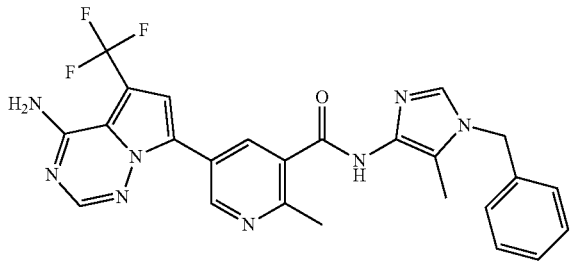 [SMILES: Cc1ncc(-c2cc(C(F)(F)F)c3c(N)ncnn23)cc1C(=O)Nc1ncn(Cc2ccccc2)c1C]

Following the procedures describe for Example 1795, the title compound was afforded (5.7 mg, 11.3 μmol, 11% yield).
MS ESI m/z 507.2 (M+H)+
1H NMR (500 MHz, DMSO-d6) δ 9.22 (s, 1H), 8.52 (s, 1H), 8.22 (s, 1H), 7.74 (s, 1H), 7.67 (s, 1H), 7.39 (br d, J=7.3 Hz, 2H), 7.32 (br d, J=7.3 Hz, 2H), 7.20 (br d, J=7.3 Hz, 2H), 5.21 (s, 2H), 2.64 (s, 3H), 2.03 (s, 3H).

Example 1798: 5-(4-amino-5-(trifluoromethyl)pyr-rolo[2,1-f][1,2,4]triazin-7-yl)-2-methoxy-N-(1-(2,2,2-trifluoro-1-phenylethyl)-1H-imidazol-4-yl)nicoti-namide

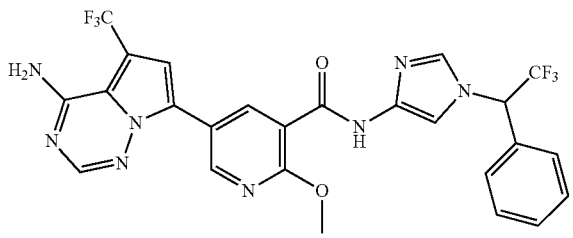 [SMILES: COc1ncc(-c2cc(C(F)(F)F)c3c(N)ncnn23)cc1C(=O)Nc1cn(C(c2ccccc2)C(F)(F)F)cn1]

1798A: 4-nitro-1-(2,2,2-trifluoro-1-phenylethyl)-1H-imi-dazole: To a solution of 1,4-dinitro-1H-imidazole (80 mg, 0.51 mmol) in MeOH (2 mL) was added 2,2,2-trifluoro-1-phenylethan-1-amine (106 mg, 0.607 mmol). The reaction mixture was stirred at 60-80° C. behind a blast shield for 4 h. The mixture was concentrated. The residue was purified via silica gel chromatography (4 g, hexanes-60% EtOAc) to give 4-nitro-1-(2,2,2-trifluoro-1-phenylethyl)-1H-imidazole (60 mg, 0.221 mmol, 44% yield).
MS ESI m/z 272.2 (M+H)+
1H NMR (499 MHz, CDCl3) δ 7.91 (s, 1H), 7.63 (s, 1H), 7.58-7.47 (m, 5H), 5.84 (q, J=7.4 Hz, 1H).
1798B: 1-(2,2,2-trifluoro-1-phenylethyl)-1H-imidazol-4-amine: To 10% Pd—C (20 mg, 0.02 mmol) was added a solution of 4-nitro-1-(2,2,2-trifluoro-1-phenylethyl)-1H-imidazole (60 mg, 0.22 mmol) in MeOH (2 mL) under N2. The mixture was stirred under H2 balloon at rt for 2.5 h. Pd/C was filtered out. The filtrate was concentrated to give 1-(2,2,2-trifluoro-1-phenylethyl)-1H-imidazol-4-amine (52 mg, 0.216 mmol, 97% yield).
MS ESI m/z 242.3 (M+H)+
1H NMR (499 MHz, CDCl3) δ 7.49-7.42 (m, 7H), 7.28-7.27 (m, 1H), 6.36 (s, 1H), 5.57-5.51 (m, 1H).

1798: Following the protocol described for Example 1774, 5-(4-amino-5-(trifluoromethyl)pyrrolo[2,1-f][1,2,4]triazin-7-yl)-2-methoxy-N-(1-(2,2,2-trifluoro-1-phenyl-ethyl)-1H-imidazol-4-yl)nicotinamide was afforded (2.3 mg, 3.3 μmol, 4% yield).
MS ESI m/z 578.2 (M+H)+
1H NMR (500 MHz, DMSO-d6) δ 10.57 (s, 1H), 8.94 (d, J=2.4 Hz, 1H), 8.79 (d, J=2.4 Hz, 1H), 8.18 (s, 1H), 7.85 (s, 1H), 7.66-7.59 (m, 4H), 7.59-7.48 (m, 3H), 6.77 (br d, J=8.7 Hz, 1H), 4.06 (s, 3H).

Example 1799: 5-(4-amino-5-(trifluoromethyl)pyr-rolo[2,1-f][1,2,4]triazin-7-yl)-2-methyl-N-(1-(2,2,2-trifluoro-1-phenylethyl)-1H-imidazol-4-yl)nicotina-mide

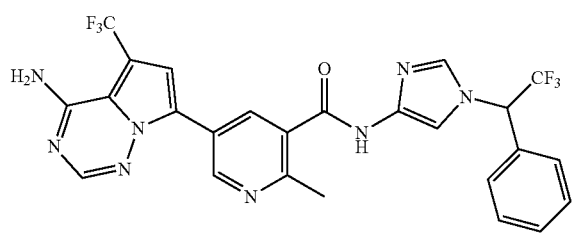 [SMILES: Cc1ncc(-c2cc(C(F)(F)F)c3c(N)ncnn23)cc1C(=O)Nc1cn(C(c2ccccc2)C(F)(F)F)cn1]

Following the procedures describe for Example 1798, the title compound was afforded (3.0 mg, 5.4 μmol, 7.6% yield).
MS ESI m/z 561.2 (M+H)+
1H NMR (500 MHz, DMSO-d6) δ 11.12 (s, 1H), 9.24 (d, J=1.9 Hz, 1H), 8.55-8.53 (m, 1H), 8.21 (s, 1H), 7.96 (s, 1H), 7.86 (s, 1H), 7.75 (s, 1H), 7.66-7.61 (m, 3H), 7.53 (s, 2H), 6.81-6.73 (m, 1H), 2.60 (s, 3H).

Example 1800: 5-(4-amino-5-(trifluoromethyl)pyr-rolo[2,1-f][1,2,4]triazin-7-yl)-2-methyl-N-(1-(2,2,2-trifluoro-1-phenylethyl)-1H-imidazol-4-yl)benz-amide

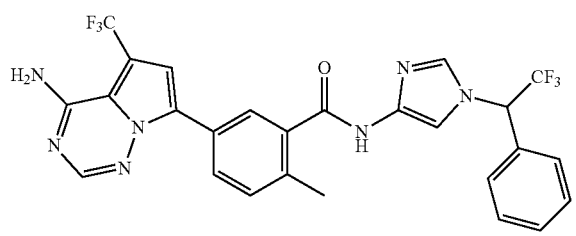 [SMILES: Cc1ccc(-c2cc(C(F)(F)F)c3c(N)ncnn23)cc1C(=O)Nc1cn(C(c2ccccc2)C(F)(F)F)cn1]

Following the procedures describe for Example 1798, the title compound was afforded (5.1 mg, 7.6 μmol, 10% yield).
MS ESI m/z 560.2 (M+H)+
1H NMR (500 MHz, DMSO-d6) δ 10.91 (s, 1H), 8.18-8.16 (m, 1H), 8.13-8.08 (m, 2H), 7.84-7.82 (m, 1H), 7.65-7.60 (m, 4H), 7.57-7.51 (m, 3H), 7.41-7.38 (m, 1H), 6.78-6.71 (m, 1H), 2.41 (s, 3H).

Example 1801: 5-(4-amino-5-(trifluoromethyl)pyrrolo[2,1-f][1,2,4]triazin-7-yl)-N-(1-(4-fluorobenzyl)-1H-imidazol-4-yl)-2-methoxynicotinamide

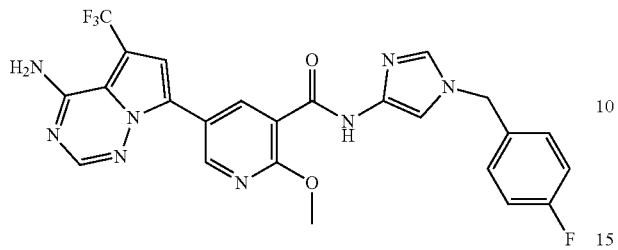

1801A: 1-(4-fluorobenzyl)-4-nitro-1H-imidazole: To a solution of 4-nitro-1H-imidazole (500 mg, 4.42 mmol) in DMF (6 mL) was added 1.0 M NaHMDS/THF (4.9 mL, 4.9 mmol) slowly at it After stirring at rt for 15 min, 1-(bromomethyl)-4-fluorobenzene (1003 mg, 5.31 mmol) was added. The mixture was stirred at rt for 4 h. EtOAc (50 mL) was added. The organic layer was washed with brine and water, then concentrated in vacuo. The residue was purified via silica gel chromatography (24 g, hexanes-100% EtOAc) to give 1-(4-fluorobenzyl)-4-nitro-1H-imidazole (800 mg, 3.62 mmol, 82% yield).

MS ESI m/z 222.2 (M+H)$^+$

1H NMR (499 MHz, CDCl$_3$) δ 7.71 (d, J=1.5 Hz, 1H), 7.50-7.47 (m, 1H), 7.26-7.23 (m, 2H), 7.16-7.11 (m, 2H), 5.16 (s, 2H).

1801B: 1-(4-fluorobenzyl)-1H-imidazol-4-amine: To 10% Pd—C (50 mg, 0.047 mmol) was added a solution of 1-(4-fluorobenzyl)-4-nitro-1H-imidazole (260 mg, 1.175 mmol) in MeOH (5 mL) under N$_2$. The mixture was stirred under H2 balloon at rt for 4 h. Pd/C was filtered out. The filtrate was concentrated to give 1-(4-fluorobenzyl)-1H-imidazol-4-amine (225 mg, 1.175 mmol, 100% yield).

MS ESI m/z 192.2 (M+H)$^+$

1H NMR (499 MHz, CDCl$_3$) δ 7.25-7.12 (m, 3H), 7.10-7.00 (m, 2H), 6.18 (d, J=1.5 Hz, 1H), 4.96 (s, 2H)

1801: Following the protocol described for Example 1774, 5-(4-amino-5-(trifluoromethyl)pyrrolo[2,1-f][1,2,4]triazin-7-yl)-N-(1-(4-fluorobenzyl)-1H-imidazol-4-yl)-2-methoxynicotinamide was afforded (7.0 mg, 10.9 μmol, 11% yield).

MS ESI m/z 527.2 (M+H)$^+$

1H NMR (500 MHz, DMSO-d6) δ 8.90 (d, J=2.4 Hz, 1H), 8.80 (d, J=1.8 Hz, 1H), 8.16-8.14 (m, 1H), 7.62-7.59 (m, 1H), 7.42-7.37 (m, 4H), 7.23-7.18 (m, 3H), 5.20-5.17 (m, 2H), 4.08-4.05 (m, 3H).

Example 1802: 5-(4-amino-5-(trifluoromethyl)pyrrolo[2,1-f][1,2,4]triazin-7-yl)-N-(1-(4-fluorobenzyl)-1H-imidazol-4-yl)-2-methylnicotinamide

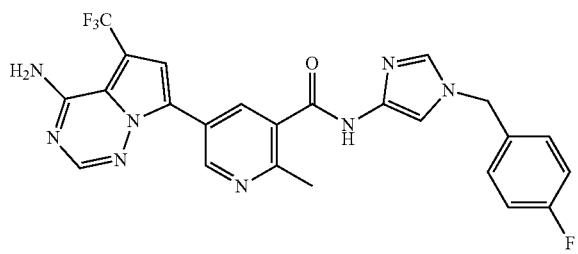 [SMILES: Cc1ncc(-c2cc(C(F)(F)F)c3c(N)ncnn23)cc1C(=O)Nc1cn(Cc2ccc(F)cc2)cn1]

Following the procedures describe for Example 1801, the title compound was afforded (25 mg, 40 μmol, 40% yield).

MS ESI m/z 511.0 (M+H)$^+$

1H NMR (500 MHz, DMSO-d6) δ 11.00 (s, 1H), 9.22 (d, J=2.1 Hz, 1H), 8.51 (d, J=1.8 Hz, 1H), 8.20 (s, 1H), 7.77 (s, 1H), 7.73 (s, 1H), 7.48-7.39 (m, 3H), 7.23 (t, J=8.9 Hz, 3H), 5.21 (s, 2H), 2.59 (s, 3H), 2.57-2.52 (m, 1H).

Example 1803: 5-(4-amino-5-(trifluoromethyl)pyrrolo[2,1-f][1,2,4]triazin-7-yl)-N-(1-(4-fluorobenzyl)-1H-imidazol-4-yl)-2-methylbenzamide

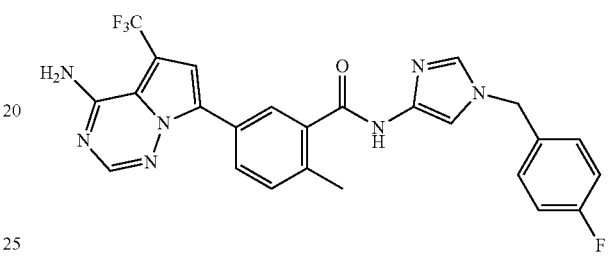

Following the procedures describe for Example 1801, the title compound was afforded 3.6 mg, 7.1 μmol, 7% yield).

MS ESI m/z 510.3 (M+H)$^+$

1H NMR (500 MHz, DMSO-d6) δ 10.72 (s, 1H), 8.15 (s, 1H), 8.09 (s, 2H), 7.64 (s, 1H), 7.58 (s, 1H), 7.48-7.33 (m, 4H), 7.22 (t, J=8.7 Hz, 2H), 5.18 (s, 2H), 2.40 (s, 3H).

Example 1804: 5-(4-amino-5-(trifluoromethyl)pyrrolo[2,1-f][1,2,4]triazin-7-yl)-2-methoxy-N-(1-(4-(trifluoromethyl)benzyl)-1H-imidazol-4-yl)nicotinamide

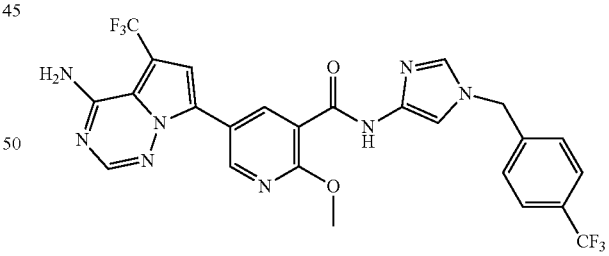

Following the procedures describe for Example 1801, the title compound was afforded (2.6 mg, 4.5 μmol, 5% yield).

MS ESI m/z 577.1 (M+H)$^+$

1H NMR (500 MHz, DMSO-d6) δ 10.43-10.41 (m, 1H), 8.94-8.92 (m, 1H), 8.81-8.79 (m, 1H), 8.18-8.17 (m, 1H), 7.79-7.76 (m, 2H), 7.74-7.72 (m, 1H), 7.64-7.63 (m, 1H), 7.54-7.51 (m, 2H), 7.46-7.44 (m, 1H), 5.35-5.33 (m, 2H), 4.07 (s, 3H).

Example 1805: 5-(4-amino-5-(trifluoromethyl)pyrrolo[2,1-f][1,2,4]triazin-7-yl)-2-methyl-N-(1-(4-(trifluoromethyl)benzyl)-1H-imidazol-4-yl)nicotinamide

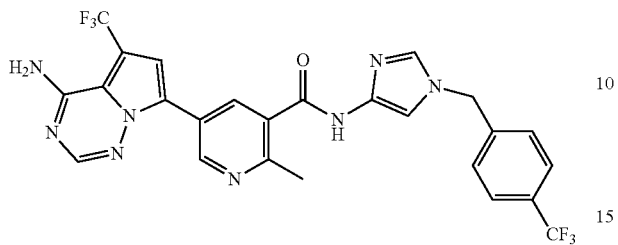

Following the procedures describe for Example 1801, the title compound was afforded (20 mg, 35.7 µmol, 36% yield).
MS ESI m/z 561.1 (M+H)⁺
1H NMR (500 MHz, DMSO-d6) δ 10.96 (s, 1H), 9.19 (s, 1H), 8.49 (s, 1H), 8.19 (s, 1H), 7.81-7.66 (m, 4H), 7.53 (br d, J=7.9 Hz, 2H), 7.46 (s, 1H), 5.32 (s, 2H), 2.62-2.53 (m, 3H).

Example 1806: 5-(4-amino-5-(trifluoromethyl)pyrrolo[2,1-f][1,2,4]triazin-7-yl)-2-methyl-N-(1-(4-(trifluoromethyl)benzyl)-1H-imidazol-4-yl)benzamide

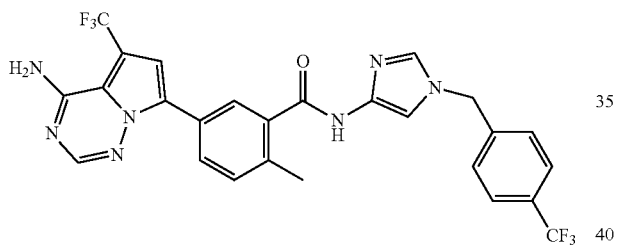

Following the procedures describe for Example 1801, the title compound was afforded (13.4 mg, 19.9 µmol, 20% yield).
MS ESI m/z 560.2 (M+H)⁺
1H NMR (500 MHz, DMSO-d6) δ 10.80 (s, 1H), 8.15 (s, 1H), 8.10 (s, 1H), 8.09-8.06 (m, 1H), 7.77 (br d, J=7.6 Hz, 3H), 7.61-7.50 (m, 3H), 7.46 (s, 1H), 7.38 (d, J=8.2 Hz, 1H), 5.33 (s, 2H), 2.49-2.37 (m, 3H).

Example 1807: 5-(4-amino-5-(trifluoromethyl)pyrrolo[2,1-f][1,2,4]triazin-7-yl)-N-(1-(4-chlorobenzyl)-1H-imidazol-4-yl)-2-methoxynicotinamide

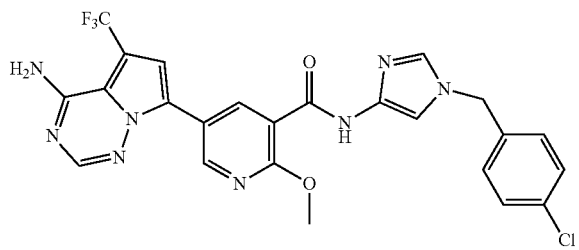 [SMILES: COc1ncc(-c2cc(C(F)(F)F)c3c(N)ncnn23)cc1C(=O)Nc1cn(Cc2ccc(Cl)cc2)cn1]

Following the procedures describe for Example 1801, the title compound was afforded (3.0 mg, 4.6 µmol, 5% yield).
MS ESI m/z 543.4 (M+H)⁺
1H NMR (500 MHz, DMSO-d6) δ 10.40-10.38 (m, 1H), 8.92-8.90 (m, 1H), 8.82-8.79 (m, 1H), 8.16-8.14 (m, 1H), 7.72-7.70 (m, 1H), 7.62-7.59 (m, 2H), 7.46-7.43 (m, 2H), 7.41-7.39 (m, 2H), 5.21-5.19 (m, 2H), 4.08-4.06 (m, 3H).

Example 1808: 5-(4-amino-5-(trifluoromethyl)pyrrolo[2,1-f][1,2,4]triazin-7-yl)-N-(1-(4-chlorobenzyl)-1H-imidazol-4-yl)-2-methylnicotinamide

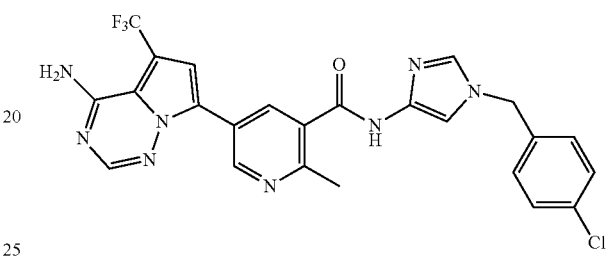

Following the procedures describe for Example 1801, the title compound was afforded (4.7 mg, 7.3 µmol, 7% yield).
MS ESI m/z 527.3 (M+H)⁺
1H NMR (500 MHz, DMSO-d6) δ 10.95 (s, 1H), 9.20-9.17 (m, 1H), 8.50-8.48 (m, 1H), 8.19-8.17 (m, 1H), 7.72-7.68 (m, 2H), 7.47-7.41 (m, 3H), 7.39-7.35 (m, 2H), 5.20 (s, 2H), 2.57 (s, 3H).

Example 1809: 5-(4-amino-5-(trifluoromethyl)pyrrolo[2,1-f][1,2,4]triazin-7-yl)-N-(1-(4-chlorobenzyl)-1H-imidazol-4-yl)-2-methylbenzamide

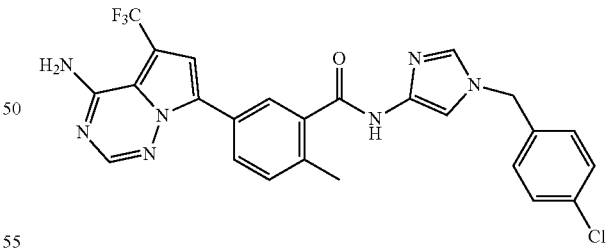

Following the procedures describe for Example 1801, the title compound was afforded (4.5 mg, 7.0 µmol, 7% yield).
MS ESI m/z 526.2 (M+H)⁺
1H NMR (500 MHz, DMSO-d6) δ 10.75 (s, 1H), 8.14 (s, 1H), 8.08 (s, 1H), 8.06 (d, J=8.1 Hz, 1H), 7.69 (s, 1H), 7.57 (s, 1H), 7.48-7.33 (m, 6H), 5.19 (s, 2H), 2.50-2.32 (m, 3H).

Example 1810: 5-(4-amino-5-(trifluoromethyl)pyrrolo[2,1-f][1,2,4]triazin-7-yl)-N-(1-(4-fluorobenzyl)-1H-pyrazol-3-yl)-2-methylnicotinamide

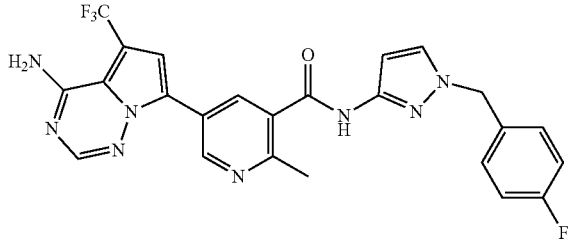 [SMILES: Cc1ncc(-c2cc(C(F)(F)F)c3c(N)ncnn23)cc1C(=O)Nc1ccn(Cc2ccc(F)cc2)n1]

1810A: 1-(4-fluorobenzyl)-3-nitro-1H-pyrazole was produced by a similar procedure as that described in Example 1801A.

MS ESI m/z 222.4 (M+H)+

1H NMR (499 MHz, CDCl₃) δ 7.40 (d, J=2.6 Hz, 1H), 7.32 (t, J=6.4 Hz, 2H), 7.11 (t, J=8.1 Hz, 2H), 6.93 (d, J=2.5 Hz, 1H), 5.37 (s, 2H).

1810B: 1-(4-fluorobenzyl)-1H-pyrazol-3-amine was produced by a similar procedure as that described in Example 1801B.

MS ESI m/z 192.3 (M+H)+

1H NMR (499 MHz, CDCl₃) δ 7.21-7.15 (m, 3H), 7.07-7.00 (m, 2H), 5.65 (d, J=2.3 Hz, 1H), 5.08 (s, 2H).

1810: Following the protocol described for Example 1774, 5-(4-amino-5-(trifluoromethyl)pyrrolo[2,1-f][1,2,4]triazin-7-yl)-N-(1-(4-fluorobenzyl)-1H-pyrazol-3-yl)-2-methylnicotinamide was afforded (11.0 mg, 7.6 μmol, 18% yield).

MS ESI m/z 511.3 (M+H)+

1H NMR (500 MHz, DMSO-d6) δ 11.04 (s, 1H), 9.21 (s, 1H), 8.49 (s, 1H), 8.19 (s, 1H), 7.82 (s, 1H), 7.71 (s, 1H), 7.30 (br d, J=5.8 Hz, 2H), 7.17 (br t, J=8.9 Hz, 2H), 6.67 (s, 1H), 5.24 (s, 2H), 2.59 (s, 3H).

Example 1811: 5-(4-amino-5-(trifluoromethyl)pyrrolo[2,1-f][1,2,4]triazin-7-yl)-N-(1-(4-fluorobenzyl)-1H-pyrazol-3-yl)-2-methylbenzamide

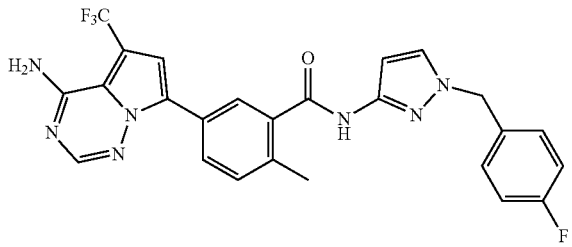 [SMILES: Cc1ccc(-c2cc(C(F)(F)F)c3c(N)ncnn23)cc1C(=O)Nc1ccn(Cc2ccc(F)cc2)n1]

Following the procedures describe for Example 1810, the title compound was afforded (40 mg, 78.5 μmol, 79% yield).

MS ESI m/z 510.1 (M+H)+

1H NMR (500 MHz, DMSO-d6) δ 10.83 (s, 1H), 8.14 (s, 1H), 8.10-8.02 (m, 2H), 7.87-7.75 (m, 1H), 7.57 (s, 1H), 7.39 (br d, J=7.9 Hz, 1H), 7.30 (br dd, J=7.8, 6.0 Hz, 2H), 7.21-7.13 (m, 2H), 6.66 (s, 1H), 5.22 (s, 2H), 2.40 (s, 3H).

Example 1812: 5-(4-amino-5-(trifluoromethyl)pyrrolo[2,1-f][1,2,4]triazin-7-yl)-N-(1-(4-fluorobenzyl)-5-methyl-1H-pyrazol-3-yl)-2-methylnicotinamide

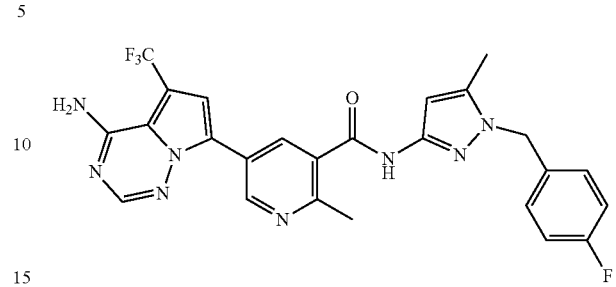

1812A: 1-(4-fluorobenzyl)-5-methyl-3-nitro-1H-pyrazole: To a solution of 4-nitro-1H-imidazole (500 mg, 4.42 mmol) in DMF (6 mL) was added 1.0 M NaHMDS/THF (4.33 mL, 4.33 mmol) slowly at rt. After stirring at rt for 15 min, 1-(bromomethyl)-4-fluorobenzene (892 mg, 4.72 mmol) was added. The mixture was stirred at rt for 2 h. EtOAc (50 mL) was added, and the organics were washed with brine and water, then concentrated in vacuo. The residue was purified via silica gel chromatography (24 g, hexanes-60% EtOAc) to give the first spot as 1-(4-fluorobenzyl)-3-methyl-5-nitro-1H-pyrazole (150 mg, 0.638 mmol, 16% yield), and the second spot as 1-(4-fluorobenzyl)-5-methyl-3-nitro-1H-pyrazole (700 mg, 2.98 mmol, 76% yield).

1H NMR (499 MHz, CDCl₃) δ 7.20 (t, J=6.5 Hz, 2H), 7.07 (t, J=8.2 Hz, 2H), 6.72 (s, 1H), 5.34 (s, 2H), 2.28 (s, 3H).

1812B: 1-(4-fluorobenzyl)-5-methyl-1H-pyrazol-3-amine was produced by a similar procedure as that described in Example 1801B.

MS ESI m/z 206.4 (M+H)+

1H NMR (499 MHz, CDCl₃) δ 7.07 (br d, J=5.4 Hz, 2H), 7.05-6.97 (m, 2H), 5.48 (d, J=0.7 Hz, 1H), 5.06 (s, 2H), 2.15 (d, J=0.7 Hz, 3H).

1812: Following the protocol described for Example 1774, 5-(4-amino-5-(trifluoromethyl)pyrrolo[2,1-f][1,2,4]triazin-7-yl)-N-(1-(4-fluorobenzyl)-5-methyl-1H-pyrazol-3-yl)-2-methylnicotinamide was afforded (7.9 mg, 15.1 μmol, 15% yield).

MS ESI m/z 525.1 (M+H)+

1H NMR (500 MHz, DMSO-d6) δ 10.94 (s, 1H), 9.21 (s, 1H), 8.52-8.45 (m, 1H), 8.20 (s, 1H), 7.72 (s, 1H), 7.25-7.11 (m, 4H), 6.54 (s, 1H), 5.20 (s, 2H), 2.64-2.53 (m, 3H), 2.27 (s, 3H).

Example 1813: 5-(4-amino-5-(trifluoromethyl)pyrrolo[2,1-f][1,2,4]triazin-7-yl)-N-(1-(4-fluorobenzyl)-5-methyl-1H-pyrazol-3-yl)-2-methylbenzamide

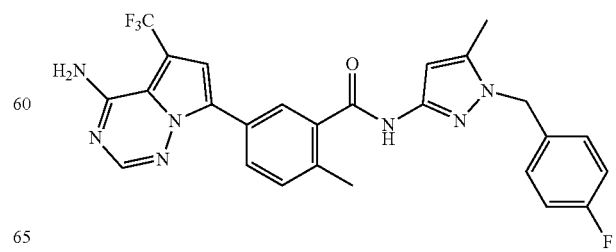

Following the procedures describe for Example 1812, the title compound was afforded (40 mg, 62.7 µmol, 63% yield).

MS ESI m/z 524.0 (M+H)+

1H NMR (500 MHz, DMSO-d6) δ 10.73 (s, 1H), 8.17 (s, 1H), 8.11-8.06 (m, 2H), 7.60 (s, 1H), 7.39 (br d, J=8.5 Hz, 1H), 7.22-7.15 (m, 4H), 6.54 (s, 1H), 5.20 (s, 2H), 2.42 (s, 3H), 2.26 (s, 3H).

Example 1814: 5-(4-amino-5-(trifluoromethyl)pyrrolo[2,1-f][1,2,4]triazin-7-yl)-2-methyl-N-(1-(2,2,2-trifluoro-1-phenylethyl)-1H-pyrazol-4-yl)nicotinamide

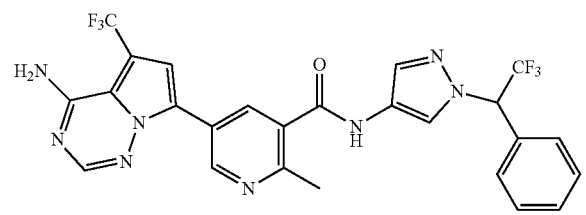 [SMILES: Cc1ncc(-c2cc(C(F)(F)F)c3c(N)ncnn23)cc1C(=O)Nc1cnn(C(c2ccccc2)C(F)(F)F)c1]

1814A: 2,2,2-trifluoro-1-phenylethyl trifluoromethanesulfonate: To a solution of 2,2,2-trifluoro-1-phenylethan-1-ol (1.06 g, 6.00 mmol) and 2,6-lutidine (1.12 mL, 9.60 mmol) in DCM (12 mL) was added triflic anhydride (1.52 mL, 9.00 mmol) at −40° C. under N2 over 15 min. The mixture was stirred and allowed to warm to rt over 1.5 h. DCM (50 mL) was added, and the organic layer was washed with 1N HCl and water, dried over Na2SO4, then concentrated in vacuo without heating to give 2,2,2-trifluoro-1-phenylethyl trifluoromethanesulfonate (1.849 g, 6.00 mmol, 100% yield). The material was used immediately in subsequent chemistry.

1814B: 4-nitro-1-(2,2,2-trifluoro-1-phenylethyl)-1H-pyrazole was produced by a similar procedure as that described in Example 1786A.

1H NMR (499 MHz, CHLOROFORM-d) δ 8.30 (s, 1H), 8.18 (s, 1H), 7.57-7.49 (m, 5H), 5.96 (d, J=7.4 Hz, 1H)

1814C: 1-(2,2,2-trifluoro-1-phenylethyl)-1H-pyrazol-4-amine was produced by a similar procedure as that described in Example 1786B.

MS ESI m/z 242.4 (M+H)+

1814: Following the protocol described for Example 1774, 5-(4-amino-5-(trifluoromethyl)pyrrolo[2,1-f][1,2,4]triazin-7-yl)-2-methyl-N-(1-(2,2,2-trifluoro-1-phenylethyl)-1H-pyrazol-4-yl)nicotinamide was afforded (29 mg, 51.7 µmol, 52% yield).

MS ESI m/z 561.1 (M+H)+

1H NMR (500 MHz, DMSO-d6) δ 10.84-10.79 (m, 1H), 9.26-9.21 (m, 1H), 8.60-8.46 (m, 1H), 8.39 (s, 1H), 8.22-8.17 (m, 1H), 7.76-7.66 (m, 4H), 7.51-7.45 (m, 3H), 6.86-6.66 (m, 1H), 2.59 (s, 3H).

Example 1815: 5-(4-amino-5-(trifluoromethyl)pyrrolo[2,1-f][1,2,4]triazin-7-yl)-2-methyl-N-(1-(2,2,2-trifluoro-1-phenylethyl)-1H-pyrazol-4-yl)benzamide

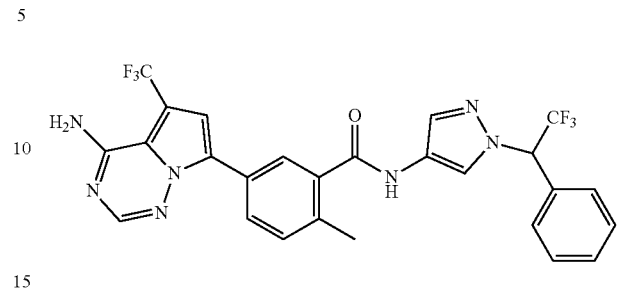

Following the procedures describe for Example 1814, the title compound was afforded (39 mg, 69.7 µmol, 70% yield).

MS ESI m/z 560.3 (M+H)+

1H NMR (500 MHz, DMSO-d6) δ 10.60 (s, 1H), 8.38 (s, 1H), 8.20-8.08 (m, 3H), 7.75-7.66 (m, 3H), 7.63-7.55 (m, 1H), 7.51-7.41 (m, 4H), 6.81-6.70 (m, 1H), 2.41 (s, 3H).

Example 1816: 5-(4-amino-5-(trifluoromethyl)pyrrolo[2,1-f][1,2,4]triazin-7-yl)-2-methyl-N-(1-(2,2,2-trifluoro-1-phenylethyl)-1H-pyrazol-3-yl)nicotinamide

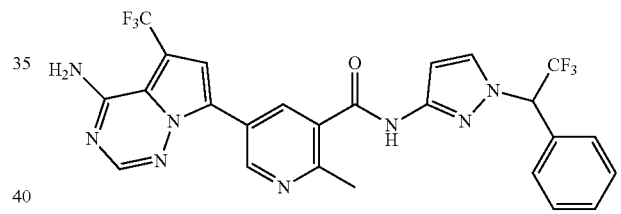

1816A: 3-nitro-1-(2,2,2-trifluoro-1-phenylethyl)-1H-pyrazole was produced by a similar procedure as that described in Example 1810A.

1H NMR (499 MHz, CDCl3) δ 7.66 (d, J=2.5 Hz, 1H), 7.56-7.47 (m, 5H), 7.00 (d, J=2.6 Hz, 1H), 6.04 (d, J=7.5 Hz, 1H).

1816B: 1-(2,2,2-trifluoro-1-phenylethyl)-1H-pyrazol-3-amine was produced by a similar procedure as that described in Example 1810B.

MS ESI m/z 242.4 (M+H)+.

18216 Following the protocol described for Example 1774, 5-(4-amino-5-(trifluoromethyl)pyrrolo[2,1-f][1,2,4]triazin-7-yl)-2-methyl-N-(1-(2,2,2-trifluoro-1-phenylethyl)-1H-pyrazol-3-yl)nicotinamide was afforded (12 mg, 21.3 µmol, 22% yield).

MS ESI m/z 561.0 (M+H)+

1H NMR (500 MHz, DMSO-d6) δ 11.30-11.24 (m, 1H), 9.28-9.23 (m, 1H), 8.57-8.52 (m, 1H), 8.24-8.20 (m, 1H), 8.00-7.95 (m, 1H), 7.78-7.73 (m, 1H), 7.73-7.67 (m, 2H), 7.48 (br d, J=2.0 Hz, 3H), 6.85-6.80 (m, 1H), 6.73-6.65 (m, 1H), 2.62 (s, 3H).

Example 1817: 5-(4-amino-5-(trifluoromethyl)pyrrolo[2,1-f][1,2,4]triazin-7-yl)-2-methyl-N-(1-(2,2,2-trifluoro-1-phenylethyl)-1H-pyrazol-3-yl)benzamide

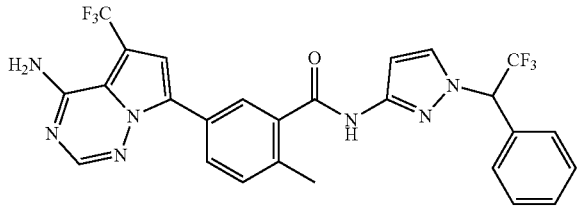 [SMILES: Cc1ccc(-c2cc(C(F)(F)F)c3c(N)ncnn23)cc1C(=O)Nc1ccn(C(c2ccccc2)C(F)(F)F)n1]

Following the procedures describe for Example 1816, the title compound was afforded (25 mg, 37.1 μmol, 38% yield).
MS ESI m/z 560.1 (M+H)+
1H NMR (500 MHz, DMSO-d6) δ 11.05 (s, 1H), 8.19 (s, 1H), 8.16-8.11 (m, 2H), 7.96 (s, 1H), 7.70 (br d, J=3.8 Hz, 2H), 7.64 (s, 1H), 7.47 (br d, J=4.2 Hz, 3H), 7.40 (br d, J=8.0 Hz, 1H), 6.82 (s, 1H), 6.68 (br d, J=7.8 Hz, 1H), 2.43 (s, 3H)

Example 1818: 5-(4-amino-5-(trifluoromethyl)pyrrolo[2,1-f][1,2,4]triazin-7-yl)-2-methyl-N-(1-(2,2,2-trifluoro-1-(4-fluorophenyl)ethyl)-1H-imidazol-4-yl)benzamide

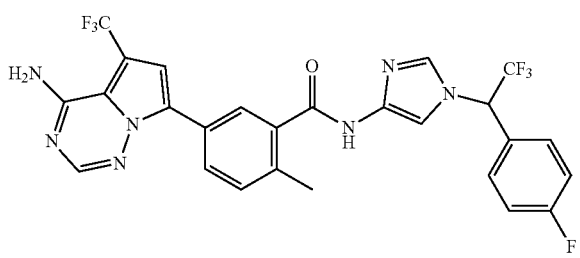 [SMILES: Cc1ccc(-c2cc(C(F)(F)F)c3c(N)ncnn23)cc1C(=O)Nc1cn(C(c2ccc(F)cc2)C(F)(F)F)cn1]

1818A: 2,2,2-trifluoro-1-(4-fluorophenyl)ethan-1-ol: To a solution of 2,2,2-trifluoro-1-(4-fluorophenyl)ethan-1-one (840 mg, 4.37 mmol) in MeOH (15 mL) was added NaBH4 (165 mg, 4.37 mmol) at −10° C. The mixture was stirred and allowed to warm to rt over 3 h. EtOAc (50 mL) was added. The organic layer was washed with 1N HCl and water, dried over Na2SO4, then concentrated to give a crude 2,2,2-trifluoro-1-(4-fluorophenyl)ethan-1-ol (730 mg, 3.76 mmol, 86% yield).
1H NMR (499 MHz, CDCl3) δ 7.49 (dd, J=8.6, 5.5 Hz, 2H), 7.13 (t, J=8.3 Hz, 2H), 5.05 (br dd, J=6.5, 2.9 Hz, 1H), 2.67 (br d, J=3.5 Hz, 1H)
1818B: 2,2,2-trifluoro-1-(4-fluorophenyl)ethyl trifluoromethanesulfonate was produced by a similar procedure as that described in Example 1814A.
1818C: 4-nitro-1-(2,2,2-trifluoro-1-(4-fluorophenyl)ethyl)-1H-imidazole was produced by a similar procedure as that described in Example 1801A.
MS ESI m/z 290.1 (M+H)+
1H NMR (499 MHz, CDCl3) δ 7.89 (s, 1H), 7.62 (s, 1H), 7.50 (dd, J=8.7, 4.9 Hz, 2H), 7.30-7.20 (m, 2H), 5.84 (d, J=7.3 Hz, 1H).
1818C: 1-(2,2,2-trifluoro-1-(4-fluorophenyl)ethyl)-1H-imidazol-4-amine was produced by a similar procedure as that described in Example 1801B.
MS ESI m/z 260.3 (M+H)+.

1818 Following the protocol described for Example 1774, 5-(4-amino-5-(trifluoromethyl)pyrrolo[2,1-f][1,2,4]triazin-7-yl)-2-methyl-N-(1-(2,2,2-trifluoro-1-(4-fluorophenyl)ethyl)-1H-imidazol-4-yl)benzamide was afforded (5.0 mg, 8.7 μmol, 9% yield).
MS ESI m/z 578.3 (M+H)+
1H NMR (500 MHz, DMSO-d6) δ 10.90 (s, 1H), 8.15 (s, 1H), 8.13-8.05 (m, 2H), 7.81 (s, 1H), 7.69 (br dd, J=7.9, 5.5 Hz, 2H), 7.62 (s, 1H), 7.59 (br s, 1H), 7.43-7.32 (m, 3H), 6.76 (br d, J=8.9 Hz, 1H), 2.48-2.37 (s, 3H).

Example 1819: 5-(4-amino-5-(trifluoromethyl)pyrrolo[2,1-f][1,2,4]triazin-7-yl)-2-methyl-N-(1-(2,2,2-trifluoro-1-(4-fluorophenyl)ethyl)-1H-imidazol-4-yl)nicotinamide

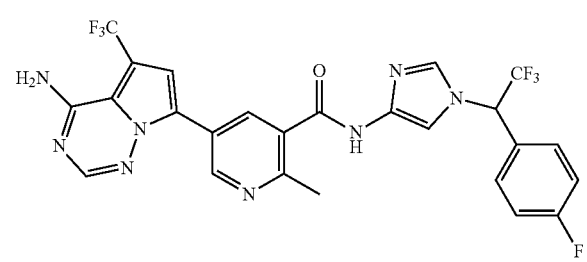 [SMILES: Cc1ncc(-c2cc(C(F)(F)F)c3c(N)ncnn23)cc1C(=O)Nc1cn(C(c2ccc(F)cc2)C(F)(F)F)cn1]

Following the procedures describe for Example 1818, the title compound was afforded (3.0 mg, 4.3 μmol, 4% yield).
MS ESI m/z 579.2 (M+H)+
1H NMR (500 MHz, DMSO-d6) δ 11.10 (s, 1H), 9.21 (s, 1H), 8.56-8.47 (m, 1H), 8.18 (s, 1H), 7.83 (s, 1H), 7.75-7.65 (m, 3H), 7.62 (s, 1H), 7.37 (br t, J=8.9 Hz, 2H), 6.76 (br d, J=8.5 Hz, 1H), 2.58 (s, 3H).

Example 1820: 5-(4-amino-5-(trifluoromethyl)pyrrolo[2,1-f][1,2,4]triazin-7-yl)-N-((3R,4S)-4-fluoro-1-(3,3,3-trifluoro-2-hydroxy-2-methylpropyl)pyrrolidin-3-yl)-2-methoxynicotinamide

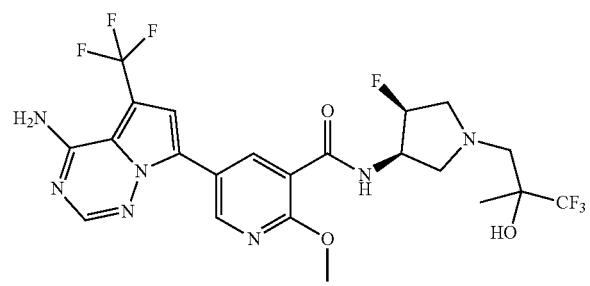 [SMILES: COc1ncc(-c2cc(C(F)(F)F)c3c(N)ncnn23)cc1C(=O)N[C@@H]1CN(CC(C)(O)C(F)(F)F)C[C@@H]1F]

To a mixture of 3-bromo-1,1,1-trifluoro-2-methylpropan-2-ol (15.51 mg, 0.075 mmol) and 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide, 2 TFA (50 mg, 0.075 mmol) in DMF (214 μl) was added K2CO3 (62.1 mg, 0.449 mmol). The resulting mixture was heated at 60° C. for 12 h. The mixture was then diluted with DMF and filtered. The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 13% B, 13-53% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to give the title compound (13 mg, 0.022 mmol, 30% yield).

MS ESI m/z 566.2 (M+H)$^+$ $^1$H NMR (500 MHz, DMSO-d6) δ 8.91 (d, J=2.4 Hz, 1H), 8.84 (d, J=2.4 Hz, 1H), 8.45 (br d, J=7.9 Hz, 1H), 8.38-8.24 (m, 1H), 8.16 (s, 1H), 7.59 (s, 1H), 5.32-5.08 (m, 1H), 4.68-4.47 (m, 1H), 4.05 (s, 3H), 2.98-2.85 (m, 4H), 2.55 (s, 2H), 1.33 (s, 3H). MS: 566.2 (M+H)$^+$.

Example 1821: 5-(4-amino-5-(trifluoromethyl)pyrrolo[2,1-f][1,2,4]triazin-7-yl)-N-((3R,4S)-4-fluoro-1-(4,4,4-trifluoro-2-hydroxybutyl)pyrrolidin-3-yl)-2-methoxynicotinamide

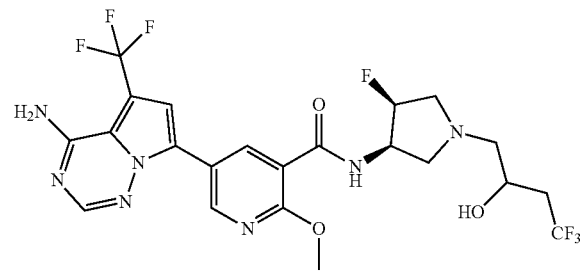 [SMILES: COc1ncc(-c2cc(C(F)(F)F)c3c(N)ncnn23)cc1C(=O)N[C@@H]1CN(CC(O)CC(F)(F)F)C[C@@H]1F]

To a mixture of 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide, 2 TFA salt (10 mg, 0.015 mmol) in 2-(2,2,2-trifluoroethyl)oxirane (50 μl, 0.495 mmol) was added triethylamine (8.35 μl, 0.060 mmol). The resulting mixture was stirred at rt for 5 min. 50 μL of DMF was then added and the mixture was brought to 80° C. and stirred for 30 min. The mixture was then diluted with DMF and filtered. The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 13% B, 13-53% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation to give the title compound (4.5 mg, 7.89 μmol, 53% yield).

MS ESI m/z 566.1 (M+H)$^+$ $^1$H NMR (500 MHz, DMSO-d$_6$) δ 8.90 (d, J=2.4 Hz, 1H), 8.83 (br d, J=1.8 Hz, 1H), 8.36 (br d, J=7.5 Hz, 1H), 8.15 (d, J=2.4 Hz, 1H), 7.55 (br d, J=2.8 Hz, 1H), 5.25 (br s, 1H), 5.14 (br s, 1H), 4.55 (dt, J=13.9, 7.1 Hz, 1H), 4.07 (s, 3H), 3.90 (br s, 1H), 3.09-2.86 (m, 2H), 2.78-2.69 (m, 1H), 2.34-2.17 (m, 1H).

TABLE 65

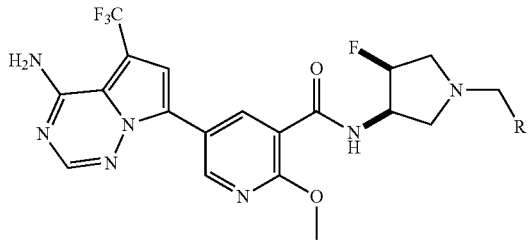

| Ex | Name | R | Obs. MS Ion | NMR Assignments |
|---|---|---|---|---|
| 1822 | 5-(4-amino-5-(trifluoromethyl)pyrrolo[2,1-f][1,2,4]triazin-7-yl)-N-((3R,4S)-4-fluoro-1-(2-hydroxy-2-(trifluoromethyl)butyl)pyrrolidin-3-yl)-2-methoxynicotinamide | ![R group with CF3 and OH] | 580.0 | $^1$H NMR (500 MHz, DMSO-d$_6$) δ 8.92 (d, J = 2.1 Hz, 1H), 8.85 (d, J = 2.1 Hz, 1H), 8.41 (br d, J = 7.6 Hz, 1H), 8.37-8.28 (m, 1H), 8.18 (s, 1H), 7.62 (s, 1H), 5.24 (br s, 1H), 5.13 (br s, 1H), 4.64-4.49 (m, 1H), 4.06 (s, 3H), 3.03-2.91 (m, 3H), 2.86-2.67 (m, 2H), 1.75 (q, J = 7.3 Hz, 2H), 1.17 (t, J = 7.3 Hz, 4H), 0.94 (br t, J = 7.5 Hz, 3H) |
| 1823 | 5-(4-amino-5-(trifluoromethyl)pyrrolo[2,1-f][1,2,4]triazin-7-yl)-N-((3R,4S)-4-fluoro-1-(2-hydroxy-2-(trifluoromethyl)butyl)pyrrolidin-3-yl)-2-methoxynicotinamide | ![R group with CF3 and OH] | 580.0 | $^1$H NMR (500 MHz, DMSO-d$_6$) δ 8.93 (d, J = 1.8 Hz, 1H), 8.83 (d, J = 2.1 Hz, 1H), 8.51 (br d, J = 7.3 Hz, 1H), 8.17 (s, 1H), 7.61 (s, 1H), 7.27 (s, 1H), 7.29-7.23 (m, 1H), 7.16 (s, 1H), 7.13-7.12 (m, 1H), 7.06 (s, 1H), 7.03-7.01 (m, 1H), 5.34 (br s, 1H), 5.23 (br s, 1H), 4.86-4.61 (m, 1H), 4.06 (s, 3H), 3.45 (br s, 1H), 3.17 (br d, J = 10.4 Hz, 1H), 1.78 (quin, J = 6.7 Hz, 2H), 0.95 (br t, J = 7.3 Hz, 3H) |

TABLE 65-continued

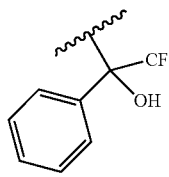

| Ex | Name | R | Obs. MS Ion | NMR Assignments |
|---|---|---|---|---|
| 1824 | 5-(4-amino-5-(trifluoromethyl)pyrrolo[2,1-f][1,2,4]triazin-7-yl)-N-((3R,4S)-4-fluoro-1-(3,3,3-trifluoro-2-hydroxy-2-phenylpropyl)pyrrolidin-3-yl)-2-methoxynicotinamide | 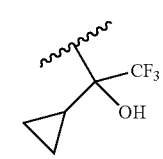 [SMILES: *C(O)(C1CC1)C(F)(F)F] | 628.3 | $^1$H NMR (500 MHz, DMSO-d$_6$) δ 8.92-8.86 (m, 1H), 8.77 (br d, J = 2.4 Hz, 1H), 8.32 (br s, 1H), 8.16 (s, 1H), 7.59 (br d, J = 9.8 Hz, 4H), 7.46-7.23 (m, 4H), 5.11 (br d, J = 4.9 Hz, 1H), 5.00 (br d, J = 4.9 Hz, 1H), 4.46-4.33 (m, 1H), 3.57-3.46 (m, 1H), 3.43-3.30 (m, 1H), 3.24-3.14 (m, 1H), 3.09-2.97 (m, 1H), 2.92-2.75 (m, 2H), 2.68-2.47 (m, 7H) |
| 1825 | 5-(4-amino-5-(trifluoromethyl)pyrrolo[2,1-f][1,2,4]triazin-7-yl)-N-((3R,4S)-1-(2-cyclopropyl-3,3,3-trifluoro-2-hydroxypropyl)-4-fluoropyrrolidin-3-yl)-2-methoxynicotinamide | 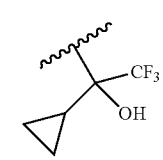 [SMILES: *C(O)(C1CC1)C(F)(F)F] | 592.3 | $^1$H NMR (500 MHz, DMSO-d$_6$) δ 8.96-8.88 (m, 1H), 8.82 (br s, 1H), 8.36 (br d, J = 7.6 Hz, 1H), 8.15 (s, 1H), 7.56 (s, 1H), 5.25 (br s, 1H), 5.14 (br s, 1H), 4.66-4.51 (m, 1H), 4.07 (s, 3H), 3.85-3.77 (m, 1H), 3.76-3.69 (m, 1H), 3.19 (s, 2H), 3.01-2.80 (m, 3H), 2.22 (br d, J = 15.1 Hz, 1H), 2.10-1.99 (m, 1H), 1.18-1.03 (m, 2H), 0.69-0.36 (m, 7H) |
| 1826 | 5-(4-amino-5-(trifluoromethyl)pyrrolo[2,1-f][1,2,4]triazin-7-yl)-N-((3R,4S)-1-(2-cyclopropyl-3,3,3-trifluoro-2-hydroxypropyl)-4-fluoropyrrolidin-3-yl)-2-methoxynicotinamide | 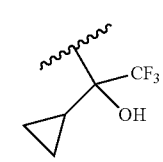 [SMILES: *C(O)(C1CC1)C(F)(F)F] | 592.4 | $^1$H NMR (400 MHz, METHANOL-d$_4$) 9.10-8.87 (m, 1H), 8.09 (s, 1H), 7.42 (s, 1H), 5.27 (s, 1H), 5.21-5.07 (m, 1H), 4.77-4.60 (m, 1H), 4.18 (s, 2H), 3.27-2.78 (m, 3H), 0.83-0.63 (m, 1H), 0.61-0.36 (m, 1H) |
| 1827 | 5-(4-amino-5-(trifluoromethyl)pyrrolo[2,1-f][1,2,4]triazin-7-yl)-N-((3R,4S)-1-(2-cyclopropyl-3,3,3-trifluoro-2-hydroxypropyl)-4-fluoropyrrolidin-3-yl)-2-methoxynicotinamide | 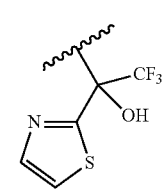 [SMILES: *C(O)(c1nccs1)C(F)(F)F] | 592.3 | $^1$H NMR (400 MHz, METHANOL-d$_4$) δ 8.97 (s, 2H), 8.08 (s, 1H), 7.41 (s, 1H), 5.32-5.07 (m, 1H), 4.77-4.58 (m, 1H), 4.17 (s, 3H), 3.48-2.75 (m, 6H, overlaps with methanol), 1.08 (s, 3H), 0.60-0.36 (m, 2H), 4 exchangeable protons not observed |
| 1828 | 5-(4-amino-5-(trifluoromethyl)pyrrolo[2,1-f][1,2,4]triazin-7-yl)-N-((3R,4S)-4-fluoro-1-(3,3,3-trifluoro-2-hydroxy-2-(thiazol-2-yl)propyl)pyrrolidin-3-yl)-2-methoxynicotinamide | 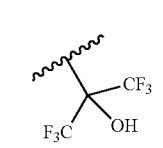 | 635.3 | $^1$H NMR (500 MHz, DMSO-d$_6$) δ 8.90 (s, 1H), 8.80 (dd, J = 5.3, 2.3 Hz, 1H), 8.33 (br t, J = 8.5 Hz, 1H), 8.16 (s, 1H), 7.88 (br d, J = 1.2 Hz, 1H), 7.80 (d, J = 2.1 Hz, 1H), 7.59 (s, 1H), 5.20-5.08 (m, 1H), 5.05-4.96 (m, 1H), 4.51-4.29 (m, 1H), 4.03 (s, 3H), 3.56-3.42 (m, 1H), 3.36-3.11 (m, 1H), 3.06 (br t, J = 8.1 Hz, 1H), 2.98-2.92 (m, 1H), 2.87 (br d, J = 12.5 Hz, 1H), 2.84-2.64 (m, 2H) |
| 1829 | 5-(4-amino-5-(trifluoromethyl)pyrrolo[2,1-f][1,2,4]triazin-7-yl)-N-((3R,4S)-4-fluoro-1-(3,3,3-trifluoro-2-hydroxy-2-(trifluoromethyl)propyl)pyrrolidin-3-yl)-2-methoxynicotinamide | 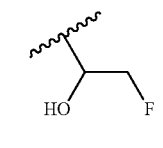 | 620.3 | $^1$H NMR (500 MHz, DMSO-d$_6$) δ 8.88 (d, J = 1.9 Hz, 1H), 8.80 (d, J = 2.0 Hz, 1H), 8.36 (br d, J = 7.5 Hz, 1H), 8.13 (s, 1H), 7.52 (s, 1H), 5.28-5.21 (m, 1H), 5.12 (br t, J = 4.4 Hz, 1H), 4.63-4.53 (m, 1H), 4.15-4.08 (m, 1H), 3.59-3.53 (m, 8H), 3.30-2.97 (m, 5H), 2.86 (br t, J = 8.6 Hz, 1H) |
| 1830 | 5-(4-amino-5-(trifluoromethyl)pyrrolo[2,1-f][1,2,4]triazin-7-yl)-N-((3R,4S)-4-fluoro-1-(3-fluoro-2-hydroxypropyl)pyrrolidin-3-yl)-2-methoxynicotinamide | 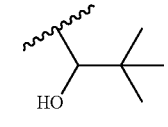 [SMILES: *C(O)C(C)(C)C] | 516.3 | $^1$H NMR (500 MHz, DMSO-d$_6$) δ 8.94-8.87 (m, 1H), 8.82 (d, J = 2.2 Hz, 1H), 8.37 (br d, J = 7.7 Hz, 1H), 8.14 (s, 1H), 7.54 (s, 1H), 5.24 (br t, J = 4.6 Hz, 1H), 5.13 (br t, J = 4.2 Hz, 1H), 4.64-4.23 (m, 3H), 4.07 (s, 3H), 3.91-3.77 (m, 1H), 3.26-2.84 (m, 3H), 2.76-2.57 (m, 2H) |
| 1831 | 5-(4-amino-5-(trifluoromethyl)pyrrolo[2,1-f][1,2,4]triazin-7-yl)-N-((3R,4S)-4-fluoro-1-(2-hydroxy-3,3-dimethylbutyl)pyrrolidin-3-yl)-2-methoxynicotinamide | | 539.9 | $^1$H NMR (500 MHz, DMSO-d$_6$) δ 8.94-8.88 (m, 1H), 8.84 (d, J = 2.1 Hz, 1H), 8.43 (br d, J = 7.6 Hz, 1H), 8.17 (s, 1H), 7.60 (s, 1H), 5.24 (br s, 1H), 5.13 (br s, 1H), 4.62-4.35 (m, 1H), 4.05 (s, 3H), 3.23-2.67 (m, 4H), 2.60 (br d, J = 9.8 Hz, 1H), 2.46-2.31 (m, 1H) |

TABLE 65-continued

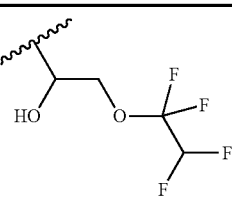

| Ex | Name | R | Obs. MS Ion | NMR Assignments |
|---|---|---|---|---|
| 1832 | 5-(4-amino-5-(trifluoromethyl)pyrrolo[2,1-f][1,2,4]triazin-7-yl)-N-((3R,4S)-4-fluoro-1-(2-hydroxy-3-(1,1,2,2-tetrafluoroethoxy)propyl)pyrrolidin-3-yl)-2-methoxynicotinamide | | 614.3 | $^1$H NMR (500 MHz, DMSO-$d_6$) δ 8.93-8.89 (m, 1H), 8.84 (s, 1H), 8.42 (br d, J = 7.9 Hz, 1H), 8.17 (s, 1H), 7.60 (s, 1H), 6.59 (br s, 1H), 6.49 (br s, 1H), 6.39 (br s, 1H), 5.24 (br s, 1H), 5.13 (br s, 1H), 4.64-4.50 (m, 1H), 4.05 (s, 3H), 4.01 (br dd, J = 10.1, 3.4 Hz, 1H), 3.93-3.86 (m, 1H), 3.82 (br s, 1H), 3.44 (br s, 1H), 3.17 (br d, J = 4.9 Hz, 1H), 2.99 (br s, 1H), 2.68 (br d, J = 4.9 Hz, 1H) |

Compounds in Table 65 were prepared by the methods detailed in 1820 and 1821. When diastereomers were separated, they are included as separate entries. If the stereochemistry is undefined, the product was isolated as a mixture of diastereomers.

Examples 1833 and 1834: Isomer A and B of N-((3R,4S)-1-(2-amino-3,3,3-trifluoro-2-methylpropanoyl)-4-fluoropyrrolidin-3-yl)-5-(4-amino-5-(trifluoromethyl)pyrrolo[2,1-f][1,2,4]triazin-7-yl)-2-methoxynicotinamide

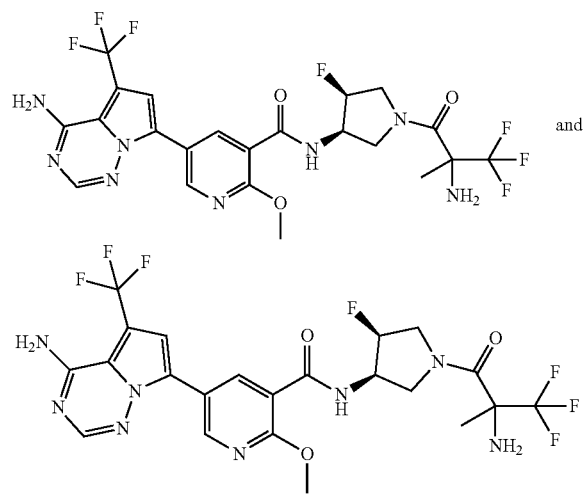

To a mixture of 2-amino-3,3,3-trifluoro-2-methylpropanoic acid (2.354 mg, 0.015 mmol), 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide, 2 TFA (10 mg, 0.015 mmol), and HATU (7.12 mg, 0.019 mmol) in DMF (59.9 µl) was added N-methylmorpholine (6.59 µl, 0.060 mmol). The resulting mixture was stirred at rt for 1 h, diluted with EtOAc, washed with water, brine, dried over MgSO$_4$, filtered and concentrated in vacuo. The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 15% B, 15-55% B over 22 minutes, then a 4-minute hold at 100% B; Flow Rate: 20 mL/min; Column Temperature: 25 C. Fraction collection was triggered by MS signals. Fractions containing the desired product were combined and dried via centrifugal evaporation to give Example 1833 as isomer A (3.3 mg, 5.32 µmol, 36% yield) and Example 1834 as isomer B (1.8 mg, 2.96 µmol, 20% yield). The absolute stereochemistry at the amine is unknown.

1833: Isomer A: MS ESI m/z 578.9 (M+H)$^+$ $^1$H NMR (500 MHz, DMSO-$d_6$) δ 8.92 (d, J=1.8 Hz, 1H), 8.78 (br d, J=8.5 Hz, 1H), 8.54 (br dd, J=16.3, 6.3 Hz, 1H), 8.17 (s, 1H), 7.61 (s, 1H), 7.25 (s, 1H), 7.15 (s, 1H), 7.05 (s, 1H), 5.46-5.18 (m, 1H), 4.83-4.57 (m, 1H), 4.41 (br t, J=9.3 Hz, 1H), 4.32-4.15 (m, 1H), 4.05 (s, 3H), 3.91-3.63 (m, 1H), 3.43 (br s, 1H), 1.49 (3H, s).

1834: Isomer B: MS ESI m/z 578.9 (M+H)$^+$ $^1$H NMR (500 MHz, DMSO-$d_6$) δ 8.99-8.89 (m, 1H), 8.79 (s, 1H), 8.45 (br d, J=5.6 Hz, 1H), 8.16 (s, 1H), 7.57 (s, 1H), 7.66-7.51 (m, 1H), 7.22 (s, 1H), 7.11 (s, 1H), 7.01 (s, 1H), 5.34 (br s, 1H), 5.23 (br s, 1H), 4.79-4.55 (m, 1H), 4.26-4.13 (m, 1H), 4.07 (s, 3H), 1.49 (s, 3H).

Example 1835: 5-(4-amino-5-(trifluoromethyl)pyrrolo[2,1-f][1,2,4]triazin-7-yl)-N-(4,4-difluoro-1-(3,3,3-trifluoro-2-hydroxy-2-(trifluoromethyl)propanoyl)pyrrolidin-3-yl)-2-methoxynicotinamide

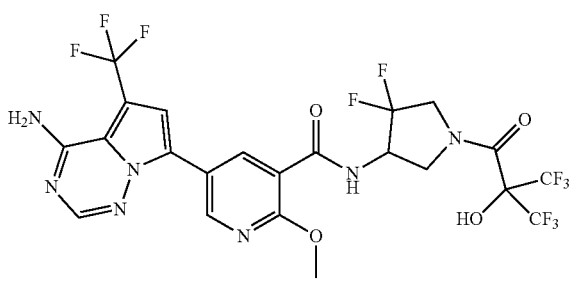 [SMILES: COc1ncc(-c2cc(C(F)(F)F)c3c(N)ncnn23)cc1C(=O)NC1CN(C(=O)C(O)(C(F)(F)F)C(F)(F)F)CC1(F)F]

Prepared using the methods described in Example 1833/1834 to give thyl)propanoyl)pyrrolidin-3-yl)-2-methoxynicotinamide (4.3 mg, 6.27 µmol, 29% yield). MS ESI m/z 652.4 (M+H)+

1H NMR (400 MHz, METHANOL-d4) δ 8.98 (s, 1H), 8.94-8.87 (m, 1H), 8.44-8.05 (m, 1H), 7.45 (s, 1H), 5.23-5.04 (m, 1H), 4.79-4.20 (m, 2H), 4.17 (s, 3H), 4.14-3.60 (m, 2H).

Example 1836: 5-(4-aminopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-(methoxy-d3)nicotinamide

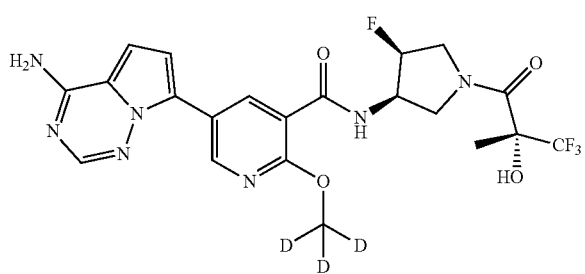 [SMILES: [2H]C([2H])([2H])Oc1ncc(-c2ccc3c(N)ncnn23)cc1C(=O)N[C@@H]1CN(C(=O)[C@@](C)(O)C(F)(F)F)C[C@@H]1F]

Prepared using the methods described in Example 1833/1834 to give the title product (60 mg, 95.5 µmol, 23% yield). MS ESI m/z 515.1 (M+H)+

1H NMR (400 MHz, DMSO-d6) δ 8.97-8.92 (m, 1H), 8.78 (dd, J=8.8, 2.4 Hz, 1H), 8.57-8.47 (m, 1H), 8.16-8.02 (m, 1H), 7.28-7.23 (m, 1H), 7.23-7.18 (m, 1H), 7.07 (br s, 1H), 5.41-5.14 (m, 1H), 4.76-4.58 (m, 1H), 4.55-4.25 (m, 1H), 4.12-3.70 (m, 2H), 3.65-3.32 (m, 1H), 1.54 (s, 3H).

Example 1837: 5-(4-amino-5-(trifluoromethyl)pyrrolo[2,1-f][1,2,4]triazin-7-yl)-N-((3R,4S)-1-(cyclopentylcarbamoyl)-4-fluoropyrrolidin-3-yl)-2-methoxynicotinamide

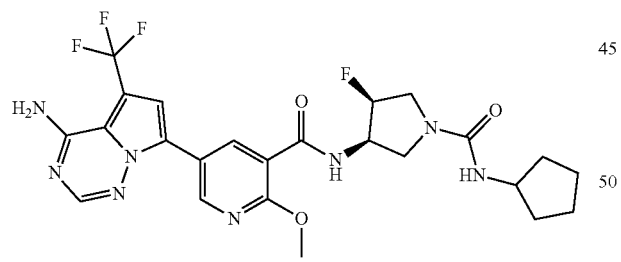

To a mixture of cyclopentyl isocyanate (1.689 µl, 0.015 mmol) and 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide, 2 TFA (10 mg, 0.015 mmol) in DMF (59.9 µl) was added triethylamine (8.35 µl, 0.060 mmol). The resulting mixture was stirred at rt 2 h. The mixture was then diluted with DMF and filtered. The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 22% B, 22-62% B over 20 minutes, then a 4-minute hold at 100% B; Flow Rate: 20 mL/min; Column Temperature: 25 C. Fraction collection was triggered by MS signals. Fractions containing the desired product were combined and dried via centrifugal evaporation. to give the title compound (7.5 mg, 0.014 mmol, 91% yield).

MS ESI m/z 551.4 (M+H)+

1H NMR (500 MHz, DMSO-d6) δ 8.91 (d, J=2.1 Hz, 1H), 8.78 (d, J=2.1 Hz, 1H), 8.50 (br d, J=7.3 Hz, 1H), 8.17 (s, 1H), 7.60 (s, 1H), 6.07 (br d, J=7.0 Hz, 1H), 5.30 (br s, 1H), 5.20 (br s, 1H), 4.76-4.58 (m, 1H), 4.04 (s, 3H), 3.97-3.78 (m, 2H), 3.69-3.58 (m, 1H), 3.54-3.41 (m, 2H), 3.20-3.13 (m, 1H), 1.88-1.73 (m, 2H), 1.63 (br s, 2H), 1.51-1.31 (m, 4H).

Example 1838: 5-(4-amino-5-(trifluoromethyl)pyrrolo[2,1-f][1,2,4]triazin-7-yl)-N-((3R,4S)-1-(tert-butylcarbamoyl)-4-fluoropyrrolidin-3-yl)-2-methoxynicotinamide

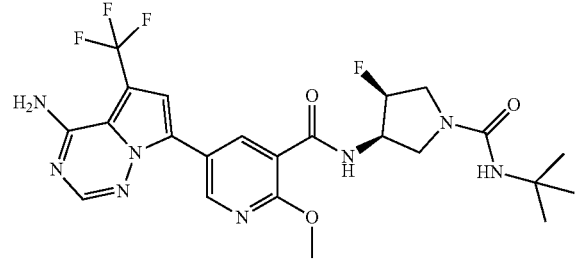 [SMILES: COc1ncc(-c2cc(C(F)(F)F)c3c(N)ncnn23)cc1C(=O)N[C@@H]1CN(C(=O)NC(C)(C)C)C[C@@H]1F]

Prepared using the methods described in Example 1837 to give the title product (3.7 mg, 6.89 µmol, 46% yield).

MS ESI m/z 539.4 (M+H)+

1H NMR (500 MHz, DMSO-d6) δ 8.95-8.87 (m, 1H), 8.80 (d, J=2.2 Hz, 1H), 8.41 (br d, J=7.6 Hz, 1H), 8.16 (d, J=1.8 Hz, 1H), 7.56 (d, J=2.0 Hz, 1H), 5.37 (s, 1H), 5.31 (br s, 1H), 5.20 (br s, 1H), 4.75-4.57 (m, 1H), 4.07 (s, 3H), 3.84 (br t, J=9.0 Hz, 1H), 3.75-3.59 (m, 1H), 3.17 (t, J=9.8 Hz, 1H), 1.28 (s, 9H).

Example 1839: 5-(4-amino-5-(trifluoromethyl)pyrrolo[2,1-f][1,2,4]triazin-7-yl)-N-((3R,4S)-4-fluoro-1-(pentylcarbamoyl)pyrrolidin-3-yl)-2-methoxynicotinamide

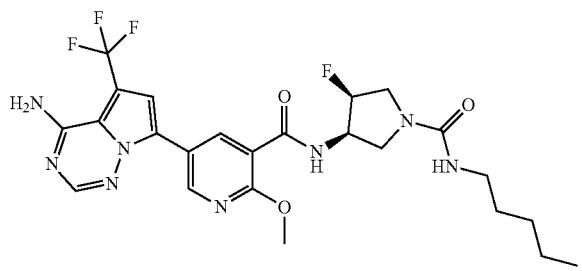 [SMILES: CCCCCNC(=O)N1C[C@H](F)[C@H](NC(=O)c2cc(-c3cc(C(F)(F)F)c4c(N)ncnn34)cnc2OC)C1]

Prepared using the methods described in Example 1837 to give the title product (7.3 mg, 0.012 mmol, 80% yield).

MS ESI m/z 552.9 (M+H)+

1H NMR (500 MHz, DMSO-d6) δ 8.96-8.86 (m, 1H), 8.78 (d, J=2.1 Hz, 1H), 8.52 (br d, J=7.6 Hz, 1H), 8.17 (s, 1H), 7.60 (s, 1H), 7.26 (s, 1H), 7.15 (s, 1H), 7.05 (s, 1H), 6.29 (br s, 1H), 5.31 (br s, 1H), 5.20 (br s, 1H), 4.80-4.55 (m, 1H), 4.04 (s, 3H), 3.80 (br t, J=9.2 Hz, 1H), 3.21-3.12 (m, 1H), 3.10-2.98 (m, 2H), 1.53-1.37 (m, 2H), 1.34-1.14 (m, 4H), 0.87 (t, J=7.0 Hz, 3H).

Example 1840: 5-(4-amino-5-(trifluoromethyl)pyrrolo[2,1-f][1,2,4]triazin-7-yl)-N-((3R,4S)-4-fluoro-1-(isopropylcarbamoyl)pyrrolidin-3-yl)-2-methoxynicotinamide

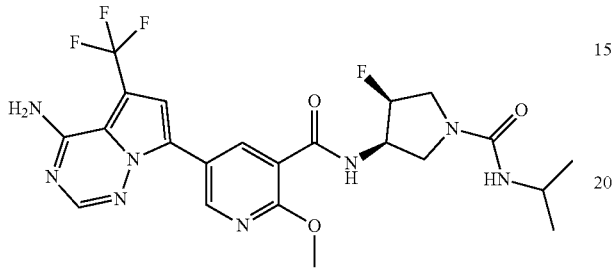

Prepared using the methods described in Example 1837 to give the title product (6.2 mg, 0.012 mmol, 79% yield).

MS ESI m/z 525.0 (M+H)+

$^1$H NMR (500 MHz, DMSO-d$_6$) δ 8.98-8.87 (m, 1H), 8.80 (d, J=1.9 Hz, 1H), 8.42 (br d, J=7.5 Hz, 1H), 8.22-8.09 (m, 1H), 7.57 (d, J=1.7 Hz, 1H), 7.21 (s, 1H), 7.11 (s, 1H), 7.01 (s, 1H), 5.32 (br s, 1H), 5.20 (br d, J=3.0 Hz, 1H), 4.76-4.60 (m, 1H), 4.07 (s, 3H), 3.90-3.54 (m, 4H), 3.18 (br d, J=9.9 Hz, 1H), 1.09 (d, J=6.5 Hz, 6H).

Example 1841: 5-(4-amino-5-(trifluoromethyl)pyrrolo[2,1-f][1,2,4]triazin-7-yl)-N-((3R,4S)-1-(3,3-difluoropyrrolidine-1-carbonyl)-4-fluoropyrrolidin-3-yl)-2-methoxynicotinamide

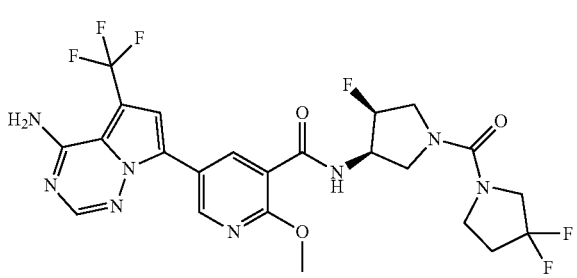 [SMILES: COc1ncc(-c2cc(C(F)(F)F)c3c(N)ncnn23)cc1C(=O)N[C@@H]1CN(C(=O)N2CCC(F)(F)C2)C[C@@H]1F]

Prepared using the methods described in Example 1837 to give the title product (1.6 mg, 2.59 μmol, 12% yield).

MS ESI m/z 573.2 (M+H)+

$^1$H NMR (500 MHz, DMSO-d6) δ 8.93 (d, J=2.4 Hz, 1H), 8.80 (d, J=2.4 Hz, 1H), 8.49 (br d, J=7.6 Hz, 1H), 8.18 (s, 1H), 7.62 (s, 1H), 7.27 (s, 1H), 7.17 (s, 1H), 7.07 (s, 1H), 5.31 (br s, 1H), 5.21 (br s, 1H), 4.81-4.51 (m, 1H), 4.06 (s, 3H), 3.92-3.53 (m, 4H), 2.44-2.28 (m, 2H).

Example 1842: 5-(4-amino-5-(trifluoromethyl)pyrrolo[2,1-f][1,2,4]triazin-7-yl)-N-((3R,4S)-1-(cyclohexylcarbamoyl)-4-fluoropyrrolidin-3-yl)-2-methoxynicotinamide

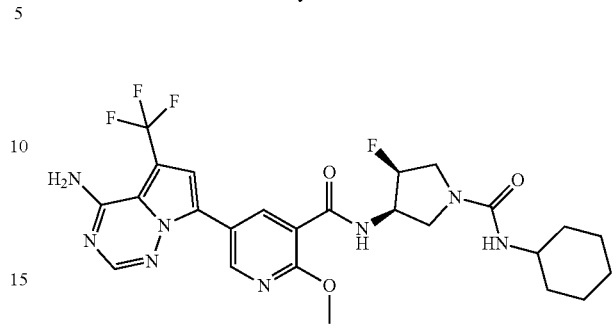

Prepared using the methods described in Example 1837 to give the title product (1.5 mg, 2.66 μmol, 18% yield).

MS ESI m/z 565.4 (M+H)+

$^1$H NMR (500 MHz, DMSO-d$_6$) δ 8.92 (d, J=2.1 Hz, 1H), 8.79 (d, J=2.1 Hz, 1H), 8.50 (br d, J=7.6 Hz, 1H), 8.18 (s, 1H), 7.62 (s, 1H), 5.97 (br d, J=7.9 Hz, 1H), 5.31 (br s, 1H), 5.20 (br s, 1H), 4.81-4.62 (m, 1H), 4.05 (s, 3H), 3.82 (t, J=9.2 Hz, 1H), 3.71-3.48 (m, 1H), 3.16 (br t, J=6.9 Hz, 1H), 1.89-1.52 (m, 6H), 1.36-1.00 (m, 5H).

Example 1843: 5-(4-amino-5-(trifluoromethyl)pyrrolo[2,1-f][1,2,4]triazin-7-yl)-N-((3R,4S)-4-fluoro-1-((2,2,2-trifluoroethyl)carbamoyl)pyrrolidin-3-yl)-2-methoxynicotinamide

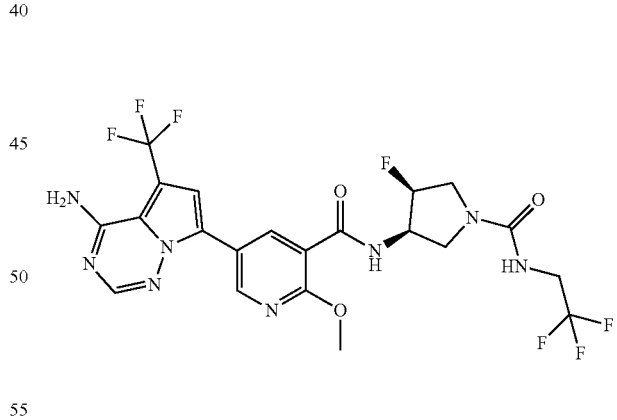

Prepared using the methods described in Example 1837 to give the title product (1.2 mg, 8.46 μmol, 13% yield).

MS ESI m/z 565.1 (M+H)+

$^1$H NMR (500 MHz, DMSO-d$_6$) δ 8.99-8.88 (m, 1H), 8.78 (d, J=2.4 Hz, 1H), 8.53 (br d, J=7.6 Hz, 1H), 8.18 (s, 1H), 7.62 (s, 1H), 7.06 (br t, J=6.1 Hz, 1H), 5.33 (br s, 1H), 5.22 (br s, 1H), 4.81-4.70 (m, 1H), 4.04 (s, 3H), 3.95-3.59 (m, 5H), 3.24 (br 1, J=10.1 Hz, 1H).

Example 1844: 5-(4-amino-5-(trifluoromethyl)pyrrolo[2,1-f][1,2,4]triazin-7-yl)-N-((3R,4S)-4-fluoro-1-(piperidine-1-carbonyl)pyrrolidin-3-yl)-2-methoxynicotinamide

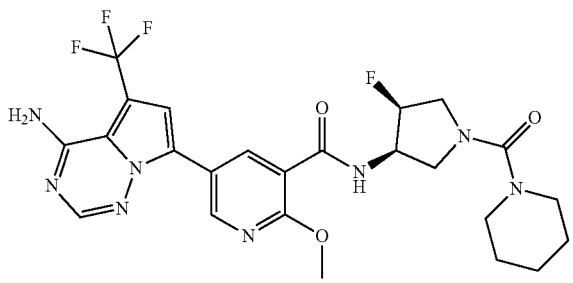 [SMILES: COc1ncc(-c2cc(C(F)(F)F)c3c(N)ncnn23)cc1C(=O)N[C@@H]1CN(C(=O)N2CCCCC2)C[C@@H]1F]

To a mixture of 5-(4-amino-5-(trifluoromethyl)pyrrolo[2,1-f][1,2,4]triazin-7-yl)-N-((3R,4S)-4-fluoropyrrolidin-3-yl)-2-methoxynicotinamide, 2 TFA (10 mg, 0.015 mmol) and 1-piperidinecarbonyl chloride (5.62 µl, 0.045 mmol) in DCM (150 µl) was added Et3N (10.44 µl, 0.075 mmol). The resulting mixture was stirred at rt 1 h. The mixture was then diluted with EtOAc, washed with water (2×), brine, dried over MgSO4, filtered and concentrated in vacuo. The crude material was purified via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 28% B, 28-68% B over 20 minutes, then a 6-minute hold at 100% B; Flow Rate: 20 mL/min; Column Temperature: 25 C. Fraction collection was triggered by MS signals. Fractions containing the desired product were combined and dried via centrifugal evaporation to give the title compound (6.2 mg, 0.011 mmol, 73% yield).

MS ESI m/z 551.5 (M+H)+

$^1$H NMR (500 MHz, DMSO-$d_6$) δ 8.97-8.89 (m, 1H), 8.79 (d, J=2.1 Hz, 1H), 8.43 (br d, J=7.4 Hz, 1H), 8.16 (s, 1H), 7.57 (s, 1H), 7.22 (s, 1H), 7.12 (s, 1H), 7.02 (s, 1H), 5.30 (br s, 1H), 5.19 (br s, 1H), 4.70-4.53 (m, 1H), 4.07 (s, 3H), 3.93-3.77 (m, 1H), 3.66 (br t, J=6.1 Hz, 1H), 3.55-3.40 (m, 4H), 3.26-3.07 (m, 3H), 1.67-1.38 (m, 6H).

Example 1845: 5-(4-amino-5-(trifluoromethyl)pyrrolo[2,1-f][1,2,4]triazin-7-yl)-N-((3R,4S)-1-(ethyl(methyl)carbamoyl)-4-fluoropyrrolidin-3-yl)-2-methoxynicotinamide

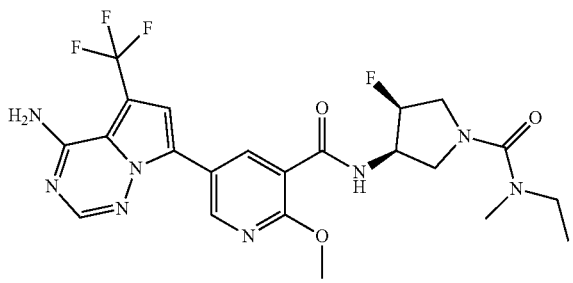 [SMILES: CCN(C)C(=O)N1C[C@H](F)[C@H](NC(=O)c2cc(-c3cc(C(F)(F)F)c4c(N)ncnn34)cnc2OC)C1]

Prepared using the methods described in Example 1844 to give the title compound (6.1 mg, 0.011 mmol, 75% yield).

MS ESI m/z 525.4 (M+H)+

$^1$H NMR (500 MHz, DMSO-$d_6$) δ 8.95-8.87 (m, 1H), 8.79 (d, J=1.9 Hz, 1H), 8.43 (br d, J=7.6 Hz, 1H), 8.16 (s, 1H), 7.56 (s, 1H), 7.22 (s, 1H), 7.12 (s, 1H), 7.02 (s, 1H), 5.36-5.27 (m, 1H), 5.19 (t, J=3.1 Hz, 1H), 4.75-4.41 (m, 1H), 4.07 (s, 3H), 3.91-3.83 (m, 1H), 3.78 (dd, J=13.1, 3.1 Hz, 1H), 3.67 (t, J=9.1 Hz, 1H), 3.56-3.39 (m, 5H), 3.16 (dt, J=12.8, 6.6 Hz, 2H), 1.08 (t, J=7.1 Hz, 3H).

Example 1846: 5-(4-amino-5-(trifluoromethyl)pyrrolo[2,1-f][1,2,4]triazin-7-yl)-N-((2RS,3SR)-3-fluoro-8,8-dimethyl-6,10-dioxaspiro[4.5]decan-2-yl)-2-methoxynicotinamide

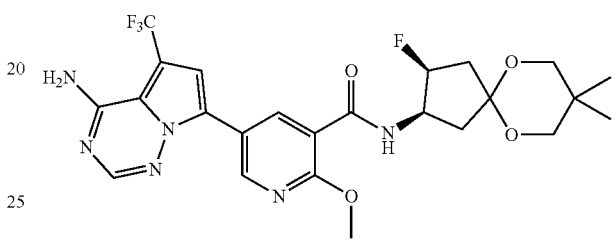

To a mixture of 5-(4-amino-5-(trifluoromethyl)pyrrolo[2,1-f][1,2,4]triazin-7-yl)-2-methoxynicotinic acid, Na+(109 mg, 0.290 mmol), 3-fluoro-8,8-dimethyl-6,10-dioxaspiro[4.5]decan-2-amine (59 mg, 0.290 mmol), and BOP (154 mg, 0.348 mmol) in DMF (2903 µl) was added Hunig's base (203 µl, 1.161 mmol). The resulting mixture was stirred at rt 1 h. A small portion of the reaction mixture was diluted with DMF, filtered and submitted to SCP for purification and submission. The remaining reaction mixture was then diluted with EtOAc, washed with water, brine, dried over MgSO4, filtered and concentrated in vacuo. Purification by flash chromatography (Silica, 24 g, 0-70% EtOAc/Hexanes) gave 5-(4-amino-5-(trifluoromethyl)pyrrolo[2,1-f][1,2,4]triazin-7-yl)-N-(3-fluoro-8,8-dimethyl-6,10-dioxaspiro[4.5]decan-2-yl)-2-methoxynicotinamide (isolate 02) (90 mg, 0.168 mmol, 58% yield).

MS ESI m/z 539.3 (M+H)+

$^1$H NMR (500 MHz, DMSO-d6) δ 8.91 (br d, J=1.8 Hz, 1H), 8.86 (s, 1H), 8.52-8.39 (m, 1H), 8.18 (s, 1H), 7.62 (s, 1H), 5.17-4.96 (m, 1H), 4.57-4.37 (m, 1H), 4.04 (s, 3H), 3.59-3.25 (m, 3H), 2.55 (s, 1H), 2.47-2.33 (m, 2H), 2.26-1.95 (m, 2H), 0.94 (br d, J=4.3 Hz, 6H).

Example 1847: 5-(4-amino-5-(trifluoromethyl)pyrrolo[2,1-f][1,2,4]triazin-7-yl)-N-(1-benzyl-5-chloro-1H-pyrazol-3-yl)-2-methoxynicotinamide

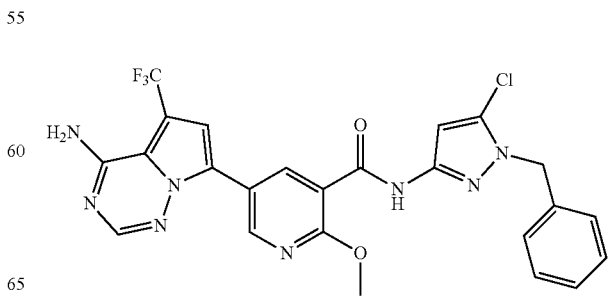

Prepared using the methods described in Example 1846 to give the title compound (7.5 mg, 0.013 mmol, 19% yield).

MS ESI m/z 543.1 (M+H)+

$^1$H NMR (500 MHz, DMSO-d$_6$) δ 8.99-8.85 (m, 1H), 8.74 (d, J=2.0 Hz, 1H), 8.18 (s, 1H), 7.70 (br d, J=9.0 Hz, 1H), 7.64 (s, 1H), 7.43-7.27 (m, 3H), 7.20 (br d, J=7.4 Hz, 2H), 6.81 (s, 1H), 5.33 (s, 2H), 4.04 (s, 3H).

Example 1848: 5-(4-amino-5-((3,3-difluoroazetidin-1-yl)methyl)pyrrolo[2,1-f][1,2,4]triazin-7-yl)-N-((3R,4S)-4-fluoro-1-isobutyrylpyrrolidin-3-yl)-2-(methoxy-d3)nicotinamide

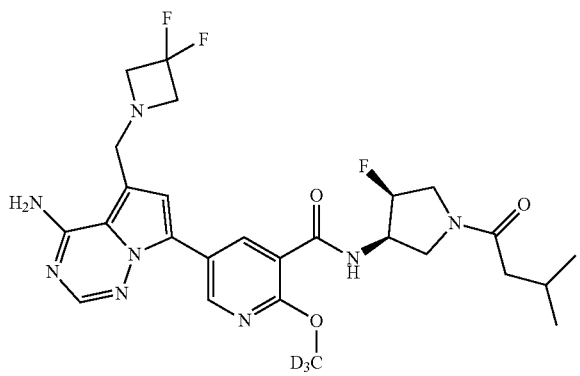 [SMILES: [2H]C([2H])([2H])Oc1ncc(-c2cc(CN3CC(F)(F)C3)c3c(N)ncnn23)cc1C(=O)N[C@@H]1CN(C(=O)CC(C)C)C[C@@H]1F]

To a mixture of 5-(4-amino-5-((3,3-difluoroazetidin-1-yl)methyl)pyrrolo[2,1-f][1,2,4]triazin-7-yl)-N-((3R,4S)-4-fluoropyrrolidin-3-yl)-2-(methoxy-d3)nicotinamide (300 mg, 0.626 mmol), isovaleric acid (83 μl, 0.751 mmol), and BOP (346 mg, 0.782 mmol) in DMF (6257 μl) was added Hunig's base (546 μl, 3.13 mmol). The resulting mixture was stirred at rt 2 h. The mass identified was desired −14. NMR analysis of the starting acid indicated that it was actually isobutyric acid, accounting for the mass difference of 14. The reaction mixture was diluted with EtOAc, washed with water (2×), brine, dried over MgSO$_4$, filtered and concentrated in vacuo. A portion of this material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 10% B, 10-50% B over 20 minutes, then a 4-minute hold at 100% B; Flow Rate: 20 mL/min; Column Temperature: 25 C. Fraction collection was triggered by MS and UV signals. Fractions containing the desired product were combined and dried via centrifugal evaporation. to give the title compound (7.5 mg, 0.013 mmol, 19% yield).

MS ESI m/z 550.1 (M+H)+

$^1$H NMR (500 MHz, DMSO-d$_6$) δ 8.90 (s, 1H), 8.77-8.69 (m, 1H), 8.53 (br dd, J=17.4, 7.3 Hz, 1H), 8.07 (br d, J=2.4 Hz, 1H), 7.94 (s, 1H), 7.26 (s, 1H), 7.22 (br s, 1H), 7.16 (s, 1H), 7.06 (s, 1H), 5.43-5.14 (m, 1H), 4.85-4.42 (m, 1H), 4.20 (br s, 2H), 4.11-3.87 (m, 4H), 3.78-3.41 (m, 2H), 3.33-3.25 (m, 1H), 2.89 (s, 1H), 2.78-2.61 (m, 2H), 1.11-0.93 (m, 6H).

The invention claimed is:

1. A compound of formula I, or a pharmaceutically acceptable salt or stereoisomer thereof,

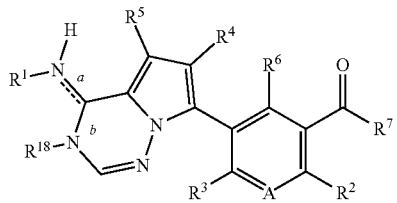

wherein:

A is N or CR;

R is hydrogen, halo, cyano, $C_{1-3}$ alkyl, $C_{1-3}$ deuteroalkyl, $C_{1-3}$ haloalkyl, $C_{1-3}$ alkoxy, $C_{1-3}$ deuteroalkoxy, $C_{1-3}$ haloalkoxy, amino, $C_{1-3}$ alkylamino, or $C_{1-3}$ dialkylamino;

$R^1$ is hydrogen, $C_{1-3}$ alkyl, $C_{1-3}$ haloalkyl, $C_{1-3}$ deuteroalkyl, $C_{1-3}$ alkoxy-$C_{1-3}$ alkyl, or $C_{2-3}$ hydroxyalkyl, C(O)—$C_{1-3}$ alkyl, C(O)—$C_{1-3}$ haloalkyl;

$R^2$ is hydrogen, halo, cyano, $C_{1-3}$ alkyl, $C_{1-3}$ deuteroalkyl, $C_{1-3}$ haloalkyl, $C_{1-3}$ alkoxy, $C_{1-3}$ deuteroalkoxy, $C_{1-3}$ haloalkoxy, amino, $C_{1-3}$ alkylamino, or $C_{1-3}$ dialkylamino;

$R^3$ is hydrogen, halo, cyano, $C_{1-3}$ alkyl, $C_{1-3}$ deuteroalkyl, $C_{1-3}$ haloalkyl, $C_{1-3}$ alkoxy, $C_{1-3}$ deuteroalkoxy, $C_{1-3}$ haloalkoxy, amino, $C_{1-3}$ alkylamino, or $C_{1-3}$ dialkylamino;

$R^4$ is hydrogen, halo, cyano, $C_{1-3}$ alkyl, $C_{1-3}$ deuteroalkyl, $C_{1-3}$ deuteroalkoxy, $C_{1-3}$ haloalkoxy, $C_{1-3}$ alkoxy, amino, $C_{1-3}$ alkylamino, or $C_{1-3}$ dialkylamino, tetrazolyl, $C_{1-3}$ alkyl-tetrazolyl;

$R^5$ is H, or $CF_3$;

$R^6$ is hydrogen, halo, cyano, $C_{1-3}$ alkyl, $C_{1-3}$ deuteroalkyl, $C_{1-3}$ haloalkyl, $C_{1-3}$ alkoxy, $C_{1-3}$ deuteroalkoxy, $C_{1-3}$ haloalkoxy, amino, $C_{1-3}$ alkylamino, or $C_{1-3}$ dialkylamino;

$R^7$ is

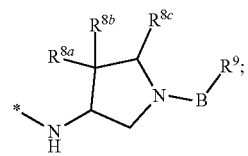

B is absent, CO, C(O)O, C(O)NR$^{12a}$, SO$_2$, or CR$^{12a}$R$^{12b}$;

$R^{8a}$ and $R^{8b}$ are each independently selected from hydrogen, halo, $C_{1-3}$ alkyl, and $C_{1-3}$ haloalkyl;

$R^{8c}$ is hydrogen, or CH$_2$—O—CH$_3$, or CH$_2$—O—CH$_2$-phenyl;

$R^9$ is 1) phenyl, naphthalenyl, pyridyl, pyrimidyl, pyridazinyl, pyrazinyl quinolinyl, benzisoxazolyl, or benzthiazolyl, and each of which are optionally substituted with 1-3 groups selected from halo, cyano, $C_{1-3}$ alkyl, $C_{1-3}$ deuteroalkyl, $C_{1-3}$ haloalkyl, $C_{1-3}$ phenylalkyl, $C_{1-3}$ (phenyl)hydroxyalkyl, $C_{1-3}$ alkoxy, $C_{1-3}$ deuteroalkoxy, $C_{1-3}$ haloalkoxy, and $C_{1-3}$ alkylSO$_2$; or 2) thiazolyl, oxazolyl, isoxazolyl, isothiazolyl, imidazolyl, thiadiazolyl, oxadiazolyl, triazolyl, or tetrazolyl, and each of which are optionally substituted with 1-3 groups selected from halo, cyano, $C_{1-3}$ alkyl, $C_{1-3}$ deuteroalkyl, $C_{1-3}$ haloalkyl, $C_{1-3}$ phenylalkyl, $C_{1-3}$ (phenyl)hydroxyalkyl, $C_{1-3}$ alkoxy, $C_{1-3}$ deuteroalkoxy, $C_{1-3}$ haloalkoxy, and $C_{1-3}$ alkylSO$_2$-cyclopropyl; or 3) dihydro-1H-indenyl, tetrahydro-5H-benzo[7]annulene, tetrahydronaphthalene, and 6,7-dihydro-5H-cyclopenta[b]pyridine, any of which are substituted with 1-3 groups selected from halo, cyano, $C_{1-3}$ alkyl, $C_{1-3}$ deuteroalkyl, $C_{1-3}$ haloalkyl, $C_{1-3}$ phenylalkyl, $C_{1-3}$ (phenyl)hydroxyalkyl, $C_{1-3}$ alkoxy, $C_{1-3}$ deuteroalkoxy, $C_{1-3}$ haloalkoxy, and $C_{1-3}$ alkylSO$_2$; or 4) $C_{1-6}$ alkyl, $C_{2-6}$ alkenyl, $C_{2-6}$ alkynyl, $C_{1-6}$ deuteroalkyl, $C_{1-6}$ haloalkyl, $C_{1-6}$ alkoxyalkyl, $C_{3-6}$ cycloalkyl, or $C_{3-6}$ halocycloalkyl, each of which are optionally substituted with 1-3 groups selected from halo, NH$_2$, —NHC(O)O—$C_{1-6}$ alkyl, —C(O)—$C_{1-6}$ alkyl, hydroxyl, $C_{1-6}$ alkoxy, and $C_{1-6}$ haloalkyl, $C_{1-6}$ haloalkoxy, phenyl, thiazolyl, pyrdinyl, wherein the phenyl, pyridinyl, and thiazolyl are optionally substituted with 0-2 of halo, nitro, or $C_{1-6}$haloalkyl; or 5) $C_{0-2}$ ($C_{3-7}$ cycloalkyl)alkyl, cyclohexenyl, oxetanyl, tetrahydrofuranyl, pyrrolidinyl, piperidinyl, dioxanyl, pyridinonyl, or tetrahydrothiophenyl dioxide, each of which are optionally substituted with 1-4 groups selected from halo, hydroxy, $C_{1-3}$ alkyl, and $C_{1-3}$ haloalkyl, $C_{1-3}$ alkoxy, hydroxyl $C_{1-3}$ haloalkyl, $C_{3-6}$ cycloalkyl, C(O)O—$C_{1-6}$ alkyl, and amino;

6) tetrahydropyranyl optionally substituted with 1-4 groups selected from halo, hydroxy, $C_{1-3}$ alkyl, $C_{1-3}$ haloalkyl; $C_{1-2}$ ($C_{1-3}$ alkoxy)alkyl, $C_{1-4}$ alkoxy, and phenyl;

7) $C_{1-4}$ alkylamino, $C_{1-4}$ dialkylamino, or azetidinyl, or B and $R^9$, together with the atom to which they are attached, join to form a $C_{3-6}$ cycloalkyl optionally substituted with 1-2 groups selected from halo, hydroxy, $C_{1-4}$ alkyl, $C_{1-4}$ alkoxy, $C_{2-3}$ hydroxyalkyl, $C_{2-4}$ (hydroxyl)haloalkyl, $C_{3-6}$ hydroxycycloalkyl, and $C_{1-3}$ alkoxycarbonyl;

$R^{12a}$ and $R^{12b}$ are independently selected from hydrogen, deuterium, methyl, amino, or OH, or $R^{12a}$ and $R^{12b}$, along with the atom to which they are attached, join together to form $C_{3-6}$ cycloalkyl; and $R^8$ is absent.

2. A compound of claim 1, or pharmaceutically acceptable salt or stereoisomer thereof, where A is N; $R^1$ is hydrogen; $R^2$ is $C_{1-3}$ alkoxy; $R^3$ is hydrogen; $R^4$ is hydrogen; and $R^6$ is hydrogen.

3. A compound of claim 1, or pharmaceutically acceptable salt or stereoisomer thereof, wherein $R^1$ is H;

$R^2$ is H, F, CH$_3$, or OCH$_3$;

$R^3$ is H or F; and $R^4$ is H.

4. A compound of claim 1, or pharmaceutically acceptable salt or stereoisomer thereof, wherein $R^{8a}$ is halo;

$R^{8b}$ is hydrogen;

B is absent, CO, C(O)O, C(O)NR$^{12a}$, SO$_2$, or CR$^{12a}$R$^{12b}$, $R^9$ is 1) phenyl, naphthalenyl, pyridyl, pyrimidyl, pyridazinyl, pyrazinyl quinolinyl, benzisoxazolyl, or benzthiazolyl, and each of which are optionally substituted with 1-3 groups selected from halo, cyano, $C_{1-3}$ alkyl, $C_{1-3}$ deuteroalkyl, $C_{1-3}$ haloalkyl, $C_{1-3}$ phenylalkyl, $C_{1-3}$ (phenyl)hydroxyalkyl, $C_{1-3}$ alkoxy, $C_{1-3}$ deuteroalkoxy, $C_{1-3}$ haloalkoxy, and $C_{1-3}$ alkylSO$_2$; or 2) thiazolyl, oxazolyl, isoxazolyl, isothiazolyl, imidazolyl, thiadiazolyl, oxadiazolyl, triazolyl, or tetrazolyl, and each of which are optionally substituted with 1-3 groups selected from halo, cyano, $C_{1-3}$ alkyl, $C_{1-3}$ deuteroalkyl, $C_{1-3}$ haloalkyl, $C_{1-3}$ phenylalkyl, $C_{1-3}$ (phenyl)hydroxyalkyl, $C_{1-3}$ alkoxy, $C_{1-3}$ deuteroalkoxy, $C_{1-3}$ haloalkoxy, and $C_{1-3}$ alkylSO$_2$-cyclopropyl; or 3) $C_{1-6}$ alkyl, $C_{2-6}$ alkenyl, $C_{2-6}$ alkynyl, $C_{1-6}$ deuteroalkyl, $C_{1-6}$ haloalkyl, $C_{1-6}$ alkoxyalkyl, $C_{3-6}$ cycloalkyl, or $C_{3-6}$ halocycloalkyl, each of which are optionally substituted with 1-3 groups selected from halo, NH$_2$, —NHC(O)O—$C_{1-6}$ alkyl, —C(O)—$C_{1-6}$ alkyl, hydroxyl, $C_{1-6}$ alkoxy, and $C_{1-6}$ haloalkyl, $C_{1-6}$ haloalkoxy, phenyl, thiazolyl, pyrdinyl, wherein the phenyl, pyridinyl, and thiazolyl are optionally substituted with 0-2 of halo, nitro, or $C_{1-6}$haloalkyl; or 4) $C_{0-2}$ ($C_{3-7}$ cycloalkyl)alkyl, cyclohexenyl, oxetanyl, tetrahydrofuranyl, pyrrolidinyl, piperidinyl, dioxanyl, pyridinonyl, or tetrahydrothiophenyl dioxide, each of which are optionally substituted with 1-4 groups selected from halo, hydroxy, $C_{1-3}$ alkyl, and $C_{1-3}$ haloalkyl, $C_{1-3}$ alkoxy, hydroxyl $C_{1-3}$ haloalkyl, $C_{3-6}$ cycloalkyl, C(O)O—$C_{1-6}$ alkyl, and amino;

5) tetrahydropyranyl optionally substituted with 1-4 groups selected from halo, hydroxy, $C_{1-3}$ alkyl, $C_{1-3}$ haloalkyl; $C_{1-2}$ ($C_{1-3}$ alkoxy)alkyl, $C_{1-4}$ alkoxy, and phenyl.

5. A compound of claim 4, or pharmaceutically acceptable salt or stereoisomer thereof, wherein B is CO, C(O)O, or SO$_2$; and $R^9$ is 1) phenyl, or pyridyl, each of which are optionally substituted with 1-3 from halo; or 2) $C_{2-6}$ alkyl, $C_{2-6}$ deuteroalkyl, $C_{2-6}$ haloalkyl, $C_{2-6}$ alkoxyalkyl, $C_{3-6}$ cycloalkyl, or $C_{3-6}$ halocycloalkyl, each of which are optionally substituted with 1-3 groups selected from halo, hydroxyl, and $C_{1-6}$ haloalkyl; or 3) $C_{1-2}$ ($C_{3-6}$ cycloalkyl)alkyl, of which is optionally substituted with 1-4 groups selected from halo, hydroxy, $C_{1-3}$ alkyl, and $C_{1-3}$ haloalkyl.

6. A compound of claim 1, or a stereoisomer, wherein the compound or stereoisomer thereof is selected from the group consisting of:

1 tert-butyl (3S)-3-{5-[4-amino-5-(trifluoromethyl)pyrrolo[2,1-f][1,2,4]triazin-7-yl]-2-methoxypyridine-3-amido}pyrrolidine-1-carboxylate;

5-[4-amino-5-(trifluoromethyl)pyrrolo[2,1-f][1,2,4]triazin-7-yl]-2-methoxy-N-[(3S)-1-(4-methylbenzoyl)pyrrolidin-3-yl]pyridine-3-carboxamide;

5-[4-amino-5-(trifluoromethyl)pyrrolo[2,1-f][1,2,4]triazin-7-yl]-N-(1-benzoyl-4-methylpyrrolidin-3-yl)-2-methoxypyridine-3-carboxamide;

5-[4-amino-5-(trifluoromethyl)pyrrolo[2,1-f][1,2,4]triazin-7-yl]-N-[1-(3,3-dimethylbutanoyl)-4-methylpyrrolidin-3-yl]-2-methoxypyridine-3-carboxamide;

5-[4-amino-5-(trifluoromethyl)pyrrolo[2,1-f][1,2,4]triazin-7-yl]-N-(1-cyclohexanecarbonyl-4-methylpyrrolidin-3-yl)-2-methoxypyridine-3-carboxamide;

5-[4-amino-5-(trifluoromethyl)pyrrolo[2,1-f][1,2,4]triazin-7-yl]-N-[(3S,4S)-1-cyclopentanecarbonyl-4-methylpyrrolidin-3-yl]-2-methoxypyridine-3-carboxamide;

5-[4-amino-5-(trifluoromethyl)pyrrolo[2,1-f][1,2,4]triazin-7-yl]-N-[(3S,4S)-1-cyclohexanecarbonyl-4-methylpyrrolidin-3-yl]-2-methylpyridine-3-carboxamide;

5-[4-amino-5-(trifluoromethyl)pyrrolo[2,1-f][1,2,4]triazin-7-yl]-N-[(3S,4S)-1-(3,3-difluorocyclopentanecarbonyl)-4-(fluoromethyl)pyrrolidin-3-yl]-2-methylpyridine-3-carboxamide;

5-[4-amino-5-(trifluoromethyl)pyrrolo[2,1-f][1,2,4]triazin-7-yl]-N-[(3S,4S)-1-(3,3-difluorocyclopentanecarbonyl)-4-methylpyrrolidin-3-yl]-2-(trifluoromethyl)pyridine-3-carboxamide;

5-[4-amino-5-(trifluoromethyl)pyrrolo[2,1-f][1,2,4]triazin-7-yl]-N-[(3S,4S)-1-(4,4-difluorocyclohexanecarbonyl)-4-methylpyrrolidin-3-yl]-2-(trifluoromethyl)pyridine-3-carboxamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-methylpyridine-3-carboxamide;

5-[4-amino-5-(trifluoromethyl)pyrrolo[2,1-f][1,2,4]triazin-7-yl]-N-[4-fluoro-1-(4-fluorobenzoyl)pyrrolidin-3-yl]-2-methoxypyridine-3-carboxamide;

5-[4-amino-5-(trifluoromethyl)pyrrolo[2,1-f][1,2,4]triazin-7-yl]-N-[1-(3,3-difluorocyclobutanecarbonyl)-(3R,4S)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[1-(3,3-difluorocyclobutanecarbonyl)-(3S,4R)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[1-(3,3-difluorocyclopentanecarbonyl)-(3R,4S)4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[1-(3,3-difluorocyclobutanecarbonyl)-4-fluoropyrrolidin-3-yl]-2-methoxypyridine-3-carboxamide (homochiral, trans);

cis-racemic-5-[4-amino-5-(trifluoromethyl)pyrrolo[2,1-f][1,2,4]triazin-7-yl]-N-[1-(cyclohexylmethyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]-2-methylpyridine-3-carboxamide;

5-[4-amino-5-(trifluoromethyl)pyrrolo[2,1-f][1,2,4]triazin-7-yl]-N-[(3S,4R)-4-fluoro-1-(4-fluorobenzoyl)pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]-2-methoxypyridine-3-carboxamide;

5-[4-amino-5-(trifluoromethyl)pyrrolo[2,1-f][1,2,4]triazin-7-yl]-N-[4-fluoro-1-(3,3,3-trifluoro-2-hydroxypropyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(deutero)methoxypyridine-3-carboxamide;

5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]-2-(deutero)methoxy-6-methylpyridine-3-carboxamide;

5-{4-amino-5-fluoropyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide;

5-(4-amino-5-(trifluoromethyl)pyrrolo[2,1-f][1,2,4]triazin-7-yl)-N-((3R,4S)-1-(3,3-difluorocyclobutane-1-carbonyl)-4-fluoropyrrolidin-3-yl)-4-fluoro-2-methylbenzamide;

3-[4-amino-5-(trifluoromethyl)pyrrolo[2,1-f][1,2,4]triazin-7-yl]-N-[(3S)-1-benzylpyrrolidin-3-yl]benzamide;

3-[4-amino-5-(trifluoromethyl)pyrrolo[2,1-f][1,2,4]triazin-7-yl]-N-[(3S)-1-benzoylpyrrolidin-3-yl]benzamide;

3-[4-amino-5-(trifluoromethyl)pyrrolo[2,1-f][1,2,4]triazin-7-yl]-N-[(3R,4S)-4-fluoro-1-(4-hydroxyoxane-4-carbonyl)pyrrolidin-3-yl]benzamide;

3-[4-amino-5-(trifluoromethyl)pyrrolo[2,1-f][1,2,4]triazin-7-yl]-N-[(3R,4S)-4-fluoro-1-(1-hydroxycyclopentanecarbonyl)pyrrolidin-3-yl]benzamide;

3-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxypropanoyl]pyrrolidin-3-yl]benzamide;

3-[4-amino-5-(trifluoromethyl)pyrrolo[2,1-f][1,2,4]triazin-7-yl]-N-[(3R,4S)-1-(3,4-difluorobenzoyl)-4-fluoropyrrolidin-3-yl]benzamide;

3-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]benzamide;

3-[4-amino-5-(trifluoromethyl)pyrrolo[2,1-f][1,2,4]triazin-7-yl]-N-[(3R,4S)-4-fluoro-1-(3-fluoro-2,2-dimethylpropanoyl)pyrrolidin-3-yl]benzamide;

3-[4-amino-5-(trifluoromethyl)pyrrolo[2,1-f][1,2,4]triazin-7-yl]-N-[(3R,4S)-4-fluoro-1-(2-methylpropanoyl)pyrrolidin-3-yl]benzamide;

3-[4-amino-5-(trifluoromethyl)pyrrolo[2,1-f][1,2,4]triazin-7-yl]-N-[(3R,4S)-1-(3,3-dimethylbutanoyl)-4-fluoropyrrolidin-3-yl]benzamide;

3-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]benzamide;

3-[4-amino-5-(trifluoromethyl)pyrrolo[2,1-f][1,2,4]triazin-7-yl]-N-[(3R,4S)-4-fluoro-1-(3-fluorobenzoyl)pyrrolidin-3-yl]benzamide;

3-[4-amino-5-(trifluoromethyl)pyrrolo[2,1-f][1,2,4]triazin-7-yl]-N-[(3R,4S)-4-fluoro-1-(1-fluorocyclobutanecarbonyl)pyrrolidin-3-yl]benzamide;

3-[4-amino-5-(trifluoromethyl)pyrrolo[2,1-f][1,2,4]triazin-7-yl]-N-[(3R,4S)-1-(3,5-difluoropyridine-4-carbonyl)-4-fluoropyrrolidin-3-yl]benzamide;

3-[4-amino-5-(trifluoromethyl)pyrrolo[2,1-f][1,2,4]triazin-7-yl]-N-[(3R,4S)-4-fluoro-1-[1-(trifluoromethyl)cyclobutanecarbonyl]pyrrolidin-3-yl]benzamide;

3-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]benzamide;

3-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]benzamide;

3-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]benzamide;

3-[4-amino-5-(trifluoromethyl)pyrrolo[2,1-f][1,2,4]triazin-7-yl]-N-[(3R,4S)-4-fluoro-1-[1-(trifluoromethyl)cyclopentanecarbonyl]pyrrolidin-3-yl]benzamide;

3-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]benzamide;

3-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]benzamide;

3-[4-amino-5-(trifluoromethyl)pyrrolo[2,1-f][1,2,4]triazin-7-yl]-N-[(3R,4S)-4-fluoro-1-(4-fluorocyclohexanecarbonyl)pyrrolidin-3-yl]benzamide;

3-[4-amino-5-(trifluoromethyl)pyrrolo[2,1-f][1,2,4]triazin-7-yl]-N-[(3R,4S)-4-fluoro-1-(4-fluorocyclohexanecarbonyl)pyrrolidin-3-yl]benzamide;

3-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]benzamide;

3-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]benzamide;

3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]benzamide;

3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]benzamide;

3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]benzamide;

5-[4-amino-5-(trifluoromethyl)pyrrolo[2,1-f][1,2,4]triazin-7-yl]-N-[(3S)-1-benzylpyrrolidin-3-yl]-2-methoxypyridine-3-carboxamide;

5-[4-amino-5-(trifluoromethyl)pyrrolo[2,1-f][1,2,4]triazin-7-yl]-N-[(3R)-1-benzylpyrrolidin-3-yl]-2-methoxypyridine-3-carboxamide;

5-[4-amino-5-(trifluoromethyl)pyrrolo[2,1-f][1,2,4]triazin-7-yl]-N-[(3S)-1-benzoylpyrrolidin-3-yl]-2-methoxypyridine-3-carboxamide;

7-[5-(3-benzylpyrrolidine-1-carbonyl)-6-methoxypyridin-3-yl]-5-(trifluoromethyl)pyrrolo[2,1-f][1,2,4]triazin-4-amine;

5-{4-aminopyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide;

5-{4-aminopyrrolo[2,1-f][1,2,4]triazin-7-yl}-N-[(3R,4S)-4-fluoro-1-(oxane-4-carbonyl)pyrrolidin-3-yl]-2-methoxypyridine-3-carboxamide;

5-{4-aminopyrrolo[2,1-f][1,2,4]triazin-7-yl}-N-[(3R,4S)-1-(2,2-difluorocyclopropanecarbonyl)-4-fluoropyrrolidin-3-yl]-2-methoxypyridine-3-carboxamide;

5-{4-aminopyrrolo[2,1-f][1,2,4]triazin-7-yl}-N-[(3R,4S)-4-fluoro-1-(3-fluorocyclobutanecarbonyl)pyrrolidin-3-yl]-2-methoxypyridine-3-carboxamide;

5-{4-aminopyrrolo[2,1-f][1,2,4]triazin-7-yl}-N-[(3R,4S)-1-(4,4-difluorocyclohexanecarbonyl)-4-fluoropyrrolidin-3-yl]-2-methoxypyridine-3-carboxamide;

5-{4-aminopyrrolo[2,1-f][1,2,4]triazin-7-yl}-N-[(3R,4S)-4-fluoro-1-(4-fluorobenzoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3S,4S)-1-cyclopentanecarbonyl-4-methylpyrrolidin-3-yl]-2-methylpyridine-3-carboxamide;

5-[4-amino-5-(trifluoromethyl)pyrrolo[2,1-f][1,2,4]triazin-7-yl]-N-{1-[(3,3-difluorocyclobutyl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{4-fluoro-1-[(oxolan-3-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-[4-fluoro-1-(3-methoxypropyl)pyrrolidine-3-yl]-2-methoxypyridine-3-carboxamide;

5-[4-amino-5-(trifluoromethyl)pyrrolo[2,1-f][1,2,4]triazin-7-yl]-N-{1-[2-(2,2-difluorocyclopropyl)ethyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-[1-(cyclobutylmethyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[1-(2-cyclopropylethyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-{4-fluoro-1-[(oxan-2-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-[1-(2-ethoxyethyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-{4-fluoro-1-[4,4,4-trifluoro-3-(trifluoromethyl)butyl]pyrrolidine-3-yl}-2-methoxypyridine-3-carboxamide;

5-[4-amino-5-(trifluoromethyl)pyrrolo[2,1-f][1,2,4]triazin-7-yl]-N-[1-(cyclopentylmethyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[4-fluoro-1-[(oxolan-2-yl)methyl]pyrrolidine-3-yl]-2-methoxypyridine-3-carboxamide;

5-[4-amino-5-(trifluoromethyl)pyrrolo[2,1-f][1,2,4]triazin-7-yl]-N-{1-[(2,2-difluorocyclopropyl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-[1-(cyclopropylmethyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[4-fluoro-1-(4,4,4-trifluorobutyl)pyrrolidine-3-yl]-2-methoxypyridine-3-carboxamide;

5-[4-amino-5-(trifluoromethyl)pyrrolo[2,1-f][1,2,4]triazin-7-yl]-N-(1-cyclopentyl-4-fluoropyrrolidin-3-yl)-2-methoxypyridine-3-carboxamide;

5-[4-amino-5-(trifluoromethyl)pyrrolo[2,1-f][1,2,4]triazin-7-yl]-N-{4-fluoro-1-[(3-methyloxetan-3-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{1-[(1,3-benzoxazol-2-yl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{4-fluoro-1-[(pyrrolidi-4-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{4-fluoro-1-[(pyrrolid-3-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-(4-fluoro-1-{[6-(trifluoromethyl)pyrrolid-2-yl]methyl}pyrrolidine-3-yl)-2-methoxypyridine-3-carboxamide;

5-[4-amino-5-(trifluoromethyl)pyrrolo[2,1-f][1,2,4]triazin-7-yl]-N-{4-fluoro-1-[(6-methylpyridin-2-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{4-fluoro-1-[(1,3-thiazol-4-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{1-[(5-cyclopropyl-1,3,4-thiadiazol-2-yl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{4-fluoro-1-[(2-methyl-1,3-thiazol-4-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{1-[(3,5-dimethyl-1,2-oxazol-4-yl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{4-fluoro-1-[(pyrrolid-2-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{1-[(3,4-difluorophenyl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{1-[(1-cyclopropyl-1H-1,2,3,4-tetrazol-5-yl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{4-fluoro-1-[(4-fluorophenyl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{1-[(2-cyanophenyl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-(1-benzyl-4-fluoropyrrolidin-3-yl)-2-methoxypyridine-3-carboxamide;

5-[4-amino-5-(trifluoromethyl)pyrrolo[2,1-f][1,2,4]triazin-7-yl]-N-(4-fluoro-1-{[4-(trifluoromethyl)phenyl]methyl}pyrrolidine-3-yl)-2-methoxypyridine-3-carboxamide;

5-[4-amino-5-(trifluoromethyl)pyrrolo[2,1-f][1,2,4]triazin-7-yl]-N-{4-fluoro-1-[(2-fluorophenyl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{1-[(2-bromo-1,3-thiazol-5-yl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{1-[(1-benzyl-H-imidazol-5-yl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{1-[(1-ethyl-1H-imidazol-5-yl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{1-[(3-bromo-1,2-oxazol-5-yl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{1-[(1,3-benzothiazol-2-yl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-(4-fluoro-1-{[1-(2-methoxyethyl)-1H-imidazol-5-yl]methyl}pyrrolidine-3-yl)-2-methoxypyridine-3-carboxamide;

5-[4-amino-5-(trifluoromethyl)pyrrolo[2,1-f][1,2,4]triazin-7-yl]-N-{1-[(4-chlorophenyl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{4-fluoro-1-[(pyrrolidi-2-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{4-fluoro-1-[(pyrrolidi-8-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{1-[(3-cyanophenyl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-(4-fluoro-1-{[3-(trifluoromethyl)phenyl]methyl}pyrrolidine-3-cl)-2-methoxypyridine-3-carboxamide;

5-[4-amino-5-(trifluoromethyl)pyrrolo[2,1-f][1,2,4]triazin-7-yl]-N-{1-[(2,6-dichlorophenyl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{4-fluoro-1-[(5-fluoropyridin-3-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{4-fluoro-1-[(pyrrolid-4-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-(4-fluoro-1-{[2-(trifluoromethyl)phenyl]methyl}pyrrolidine-3-yl)-2-methoxypyridine-3-carboxamide;

5-[4-amino-5-(trifluoromethyl)pyrrolo[2,1-f][1,2,4]triazin-7-yl]-N-{4-fluoro-1-[(4-methylphenyl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{1-[(2,5-difluorophenyl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{4-fluoro-1-[(4-fluoro-3-methylphenyl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-(4-fluoro-1-{[3-fluoro-4-(trifluoromethoxy)phenyl]methyl}pyrrolidine-3-yl)-2-methoxypyridine-3-carboxamide;

5-[4-amino-5-(trifluoromethyl)pyrrolo[2,1-f][1,2,4]triazin-7-yl]-N-{4-fluoro-1-[(3-methylphenyl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{1-[(3,5-difluorophenyl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{1-[(5-bromopyridin-3-yl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{4-fluoro-1-[(naphthalen-1-yl)methyl]pyrrolidine-3-yl}-2-methoxypyridine-3-carboxamide;

5-[4-amino-5-(trifluoromethyl)pyrrolo[2,1-f][1,2,4]triazin-7-yl]-N-{1-[(4-cyanophenyl)methyl]-4-fluoropyrrolidin-3-yl}-2-methoxypyridine-3-carboxamide;

5-[4-amino-5-(trifluoromethyl)pyrrolo[2,1-f][1,2,4]triazin-7-yl]-N-{4-fluoro-1-[(5-methyl-1,2-oxazol-3-yl)methyl]pyrrolidine-3-yl}-2-methoxypyridine-3-carboxamide;

tert-butyl (3S)-3-{5-[4-amino-5-(trifluoromethyl)pyrrolo[2,1-f][1,2,4]triazin-7-yl]-2-fluorobenzamido}pyrrolidine-1-carboxylate;

5-[4-amino-5-(trifluoromethyl)pyrrolo[2,1-f][1,2,4]triazin-7-yl]-2-fluoro-N-[(3R,4S)-4-fluoro-1-(3-fluorocyclobutanecarbonyl)pyrrolidin-3-yl]benzamide;

5-[4-amino-5-(trifluoromethyl)pyrrolo[2,1-f][1,2,4]triazin-7-yl]-2-fluoro-N-[(3R,4S)-4-fluoro-1-(3-fluorocyclobutanecarbonyl)pyrrolidin-3-yl]benzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-fluorobenzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-fluorobenzamide;

5-[4-amino-5-(trifluoromethyl)pyrrolo[2,1-f][1,2,4]triazin-7-yl]-2-fluoro-N-[(3R,4S)-4-fluoro-1-(4-fluorobenzoyl)pyrrolidin-3-yl]benzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-fluorobenzamide;

5-[4-amino-5-(trifluoromethyl)pyrrolo[2,1-f][1,2,4]triazin-7-yl]-2-fluoro-N-[(3R,4S)-4-fluoro-1-(oxane-4-carbonyl)pyrrolidin-3-yl]benzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-fluorobenzamide;

5-[4-amino-5-(trifluoromethyl)pyrrolo[2,1-f][1,2,4]triazin-7-yl]-N-[(3S)-1-(3,3-dimethylbutanoyl)pyrrolidine-3-yl]-2-methoxypyridine-3-carboxamide;

5-[4-amino-5-(trifluoromethyl)pyrrolo[2,1-f][1,2,4]triazin-7-yl]-2-methoxy-N-[(3S)-1-[3,3,3-trifluoro-2-methyl-2-(trifluoromethyl)propanoyl]pyrrolidine-3-yl]pyridine-3-carboxamide;

5-[4-amino-5-(trifluoromethyl)pyrrolo[2,1-f][1,2,4]triazin-7-yl]-N-[(3S)-1-cyclohexanecarbonylpyrrolidin-3-yl]-2-methoxypyridine-3-carboxamide;

5-[4-amino-5-(trifluoromethyl)pyrrolo[2,1-f][1,2,4]triazin-7-yl]-N-[(3S)-1-cyclopentanecarbonylpyrrolidin-3-yl]-2-methoxypyridine-3-carboxamide;

5-[4-amino-5-(trifluoromethyl)pyrrolo[2,1-f][1,2,4]triazin-7-yl]-N-[(3S)-1-cyclobutanecarbonylpyrrolidin-3-yl]-2-methoxypyridine-3-carboxamide;

5-[4-amino-5-(trifluoromethyl)pyrrolo[2,1-f][1,2,4]triazin-7-yl]-N-[(3S)-1-(3,3-difluorocyclobutanecarbonyl)pyrrolidine-3-yl]-2-methoxypyridine-3-carboxamide;

5-[4-amino-5-(trifluoromethyl)pyrrolo[2,1-f][1,2,4]triazin-7-yl]-N-[(3S)-1-(3,3-difluorocyclopentanecarbonyl)pyrrolidine-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]pyridine-3-carboxamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]pyridine-3-carboxamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]pyridine-3-carboxamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]pyridine-3-carboxamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]pyridine-3-carboxamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]pyridine-3-carboxamide;

5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]pyridine-3-carboxamide;

5-[4-amino-5-(trifluoromethyl)pyrrolo[2,1-f][1,2,4]triazin-7-yl]-N-[(3S,4S)-1-(3,3-difluorocyclobutanecarbonyl)-4-methylpyrrolidin-3-yl]-2-methylpyridine-3-carboxamide;

5-[4-amino-5-(trifluoromethyl)pyrrolo[2,1-f][1,2,4]triazin-7-yl]-N-[(3S,4S)-1-(4,4-difluorocyclohexanecarbonyl)-4-methylpyrrolidin-3-yl]-2-methylpyridine-3-carboxamide;

5-[4-amino-5-(trifluoromethyl)pyrrolo[2,1-f][1,2,4]triazin-7-yl]-N-[(3S,4S)-1-(3,3-difluorocyclopentanecarbonyl)-4-methylpyrrolidin-3-yl]-2-methylpyridine-3-carboxamide;

5-[4-amino-5-(trifluoromethyl)pyrrolo[2,1-f][1,2,4]triazin-7-yl]-N-[(3S,4S)-1-benzoyl-4-methylpyrrolidin-3-yl]-2-methoxypyridine-3-carboxamide;

5-[4-amino-5-(trifluoromethyl)pyrrolo[2,1-f][1,2,4]triazin-7-yl]-N-[(3S,4S)-1-cyclohexanecarbonyl-4-methylpyrrolidin-3-yl]-2-methoxypyridine-3-carboxamide;

5-[4-amino-5-(trifluoromethyl)pyrrolo[2,1-f][1,2,4]triazin-7-yl]-N-[(3S,4S)-1-(3,3-difluorocyclopentanecarbonyl)-4-methylpyrrolidin-3-yl]-2-methoxypyridine-3-carboxamide;

5-[4-amino-5-(trifluoromethyl)pyrrolo[2,1-f][1,2,4]triazin-7-yl]-N-[(3S,4S)-1-(3,3-difluorocyclobutanecarbonyl)-4-methylpyrrolidin-3-yl]-2-methoxypyridine-3-carboxamide;

5-[4-amino-5-(trifluoromethyl)pyrrolo[2,1-f][1,2,4]triazin-7-yl]-N-[(3S,4S)-1-(4,4-difluorocyclohexanecarbonyl)-4-methylpyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[4-fluoro-1-(4-fluorocyclohexanecarbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[4-fluoro-1-(4-fluorocyclohexanecarbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(2,2-difluoro-1-methylcyclopropanecarbonyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(3,4-difluorobenzoyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(2,6-difluorobenzoyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(2S)-3,3,3-trifluoro-2-hydroxy-2-methylpropanoyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(4-methylpentanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(5-fluoropyridine-2-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-propanoylpyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(trifluoromethyl)cyclohexanecarbonyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-methylpyridine-4-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-fluoro-2,2-dimethylpropanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(1-hydroxycyclopentanecarbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(1-hydroxycyclobutanecarbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-hydroxy-3-methylbutanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(2S)-3,3,3-trifluoro-2-hydroxypropanoyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-hydroxy-2-methylbutanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(1-hydroxycyclopropanecarbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(2R)-2-hydroxy-4-methylpentanoyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxypropanoyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(2S)-2-hydroxy-3,3-dimethylbutanoyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(2S)-2-hydroxy-4-methylpentanoyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(oxolane-2-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(oxane-2-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(oxane-3-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2,6,6-trimethyloxane-2-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-methyloxetane-3-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(1-fluorocyclobutanecarbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(dimethylcarbamoyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(pyrrolidine-1-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(pyridine-3-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3,3,3-trifluoro-2,2-dimethylpropanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(3,3-dimethylbutanoyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-methoxypropanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(2,5-difluorobenzoyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-fluorobenzoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-methyl-2-phenylpropanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-methylpropanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(oxetane-3-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-methoxypyridine-3-carboxamide;

5-(4-amino-5-(trifluoromethyl)pyrrolo[2,1-f][1,2,4]triazin-7-yl)-N-(4-fluoro-1-(3-fluorocyclobutane-1-carbonyl)pyrrolidin-3-yl)-2-methoxynicotinamide;

5-(4-amino-5-(trifluoromethyl)pyrrolo[2,1-f][1,2,4]triazin-7-yl)-N-(4-fluoro-1-(3-fluorocyclobutane-1-carbonyl)pyrrolidin-3-yl)-2-methoxynicotinamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(2-methylpropanoyl)pyrrolidin-3-yl]-2-methylpyridine-3-carboxamide;

5-[4-amino-5-(trifluoromethyl)pyrrolo[2,1-f][1,2,4]triazin-7-yl]-N-[1-(2,2-difluorocyclopropanecarbonyl)-4-fluoropyrrolidin-3-yl]-2-methylpyridine-3-carboxamide;

5-[4-amino-5-(trifluoromethyl)pyrrolo[2,1-f][1,2,4]triazin-7-yl]-N-[1-(2,2-difluorocyclopropanecarbonyl)-4-fluoropyrrolidin-3-yl]-2-methylpyridine-3-carboxamide;

5-[4-amino-5-(trifluoromethyl)pyrrolo[2,1-f][1,2,4]triazin-7-yl]-N-[4-fluoro-1-(3-fluorocyclobutanecarbonyl)pyrrolidin-3-yl]-2-methylpyridine-3-carboxamide;

5-[4-amino-5-(trifluoromethyl)pyrrolo[2,1-f][1,2,4]triazin-7-yl]-N-[4-fluoro-1-(3-fluorocyclobutanecarbonyl)pyrrolidin-3-yl]-2-methylpyridine-3-carboxamide;

358, 5-[4-amino-5-(trifluoromethyl)pyrrolo[2,1-f][1,2,4]triazin-7-yl]-N-[1-(4,4-difluorocyclohexanecarbonyl)-4-fluoropyrrolidin-3-yl]-2-methylpyridine-3-carboxamide;

5-[4-amino-5-(trifluoromethyl)pyrrolo[2,1-f][1,2,4]triazin-7-yl]-N-[4-fluoro-1-(4-fluorocyclohexanecarbonyl)pyrrolidin-3-yl]-2-methylpyridine-3-carboxamide;

5-[4-amino-5-(trifluoromethyl)pyrrolo[2,1-f][1,2,4]triazin-7-yl]-N-[4-fluoro-1-(4-fluorocyclohexanecarbonyl)pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxypropanoyl]pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(1-hydroxycyclopentanecarbonyl)pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(1-hydroxycyclobutanecarbonyl)pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-[(2S)-2-hydroxy-4-methylpentanoyl]pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-1-(2,5-difluorobenzoyl)-4-fluoropyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-[(2R)-2-hydroxy-4-methylpentanoyl]pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-[(2S)-3,3,3-trifluoro-2-hydroxypropanoyl]pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(1-fluorocyclobutanecarbonyl)pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-[(2S)-3,3,3-trifluoro-2-hydroxy-2-methylpropanoyl]pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-[(2S)-2-hydroxy-3,3-dimethylbutanoyl]pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-(deutero)methoxypyridine-3-carboxamide;

5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]-2-(deutero)methoxypyridine-3-carboxamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(Deutero)methoxypyridine-3-carboxamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(Deutero)methoxypyridine-3-carboxamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(deutero)methoxypyridine-3-carboxamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(deutero)methoxypyridine-3-carboxamide;

5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-(deutero)methoxypyridine-3-carboxamide;

5-[4-amino-5-(trifluoromethyl)pyrrolo[2,1-f][1,2,4]triazin-7-yl]-N-[(3R,4S)-4-fluoro-1-(2-methylpropanoyl)pyrrolidin-3-yl]-2-(deutero)methoxypyridine-3-carboxamide;

5-[4-amino-5-(trifluoromethyl)pyrrolo[2,1-f][1,2,4]triazin-7-yl]-N-[(3R,4S)-1-(2,5-difluorobenzoyl)-4-fluoropyrrolidin-3-yl]-2-(deutero)methoxypyridine-3-carboxamide;

5-[4-amino-5-(trifluoromethyl)pyrrolo[2,1-f][1,2,4]triazin-7-yl]-N-[(3R,4S)-4-fluoro-1-[(2S)-3,3,3-trifluoro-2-hydroxy-2-methylpropanoyl]pyrrolidin-3-yl]-2-(deutero)methoxypyridine-3-carboxamide;

5-[4-amino-5-(trifluoromethyl)pyrrolo[2,1-f][1,2,4]triazin-7-yl]-N-[(3R,4S)-4-fluoro-1-(3-hydroxy-3-methylbutanoyl)pyrrolidin-3-yl]-2-(deutero)methoxypyridine-3-carboxamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-(deutero)methoxypyridine-3-carboxamide;

5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-(deutero)methoxypyridine-3-carboxamide;

5-[4-amino-5-(trifluoromethyl)pyrrolo[2,1-f][1,2,4]triazin-7-yl]-N-[(3R,4S)-1-(3,3-dimethylbutanoyl)-4-fluoropyrrolidin-3-yl]-2-(deutero)methoxypyridine-3-carboxamide;

5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-(deutero)methoxypyridine-3-carboxamide;

5-(4-amino-5-(trifluoromethyl)pyrrolo[2,1-f][1,2,4]triazin-7-yl)-N-((3R,4S)-1-(3,3-difluorocyclobutane-1-carbonyl)-4-fluoropyrrolidin-3-yl)-2-(methoxy-d3)nicotinamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-fluoro-4-methylbenzamide;

5-[4-amino-5-(trifluoromethyl)pyrrolo[2,1-f][1,2,4]triazin-7-yl]-2-fluoro-N-[(3R,4S)-4-fluoro-1-(3-methylbutanoyl)pyrrolidin-3-yl]-4-methylbenzamide;

5-[4-amino-5-(trifluoromethyl)pyrrolo[2,1-f][1,2,4]triazin-7-yl]-2-fluoro-N-[(3R,4S)-4-fluoro-1-[(2R)-3,3,3-trifluoro-2-hydroxy-2-methylpropanoyl]pyrrolidin-3-yl]-4-methylbenzamide;

5-[4-amino-5-(trifluoromethyl)pyrrolo[2,1-f][1,2,4]triazin-7-yl]-2-chloro-4-fluoro-N-[(3R,4S)-4-fluoro-1-(1-hydroxycyclobutanecarbonyl)pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-(3-hydroxy-3-methylbutanoyl)pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-(1-hydroxycyclopentanecarbonyl)pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-(3-methylbutanoyl)pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-(2-fluorobenzoyl)pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-[(2R)-3,3,3-trifluoro-2-hydroxypropanoyl]pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-(2-fluoro-2-methylpropanoyl)pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-[(2R)-3,3,3-trifluoro-2-hydroxy-2-methylpropanoyl]pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-(3,3,3-trifluoropropanoyl)pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-(3-fluoropyridine-2-carbonyl)pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-(4-fluorobenzoyl)pyrrolidin-3-yl]benzamide;

5-[4-amino-5-(trifluoromethyl)pyrrolo[2,1-f][1,2,4]triazin-7-yl]-2-chloro-N-[(3R,4S)-1-(3,3-difluorocyclobutanecarbonyl)-4-fluoropyrrolidin-3-yl]-4-fluorobenzamide;

5-[4-amino-5-(trifluoromethyl)pyrrolo[2,1-f][1,2,4]triazin-7-yl]-2-chloro-N-[(3R,4S)-1-(4,4-difluorocyclohexanecarbonyl)-4-fluoropyrrolidin-3-yl]-4-fluorobenzamide;

5-[4-amino-5-(trifluoromethyl)pyrrolo[2,1-f][1,2,4]triazin-7-yl]-2-chloro-N-[(3R,4S)-1-(2,2-difluorocyclopropanecarbonyl)-4-fluoropyrrolidin-3-yl]-4-fluorobenzamide;

5-[4-amino-5-(trifluoromethyl)pyrrolo[2,1-f][1,2,4]triazin-7-yl]-2-chloro-4-fluoro-N-[(3R,4S)-4-fluoro-1-(3-fluorocyclobutanecarbonyl)pyrrolidin-3-yl]benzamide;

5-[4-amino-5-(trifluoromethyl)pyrrolo[2,1-f][1,2,4]triazin-7-yl]-2-chloro-N-[(3R,4S)-1-(3,3-difluorocyclopentanecarbonyl)-4-fluoropyrrolidin-3-yl]-4-fluorobenzamide;

5-[4-amino-5-(trifluoromethyl)pyrrolo[2,1-f][1,2,4]triazin-7-yl]-4-fluoro-N-[(3R,4S)-4-fluoro-1-(3-fluorocyclobutanecarbonyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(2-fluorobenzoyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(3-hydroxy-3-methylbutanoyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-[(2R)-3,3,3-trifluoro-2-hydroxy-2-methylpropanoyl]pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-[(2R)-3,3,3-trifluoro-2-hydroxypropanoyl]pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(2-hydroxy-2-methylpropanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(3-fluorocyclobutanecarbonyl)pyrrolidin-3-yl]-2-methylbenzamide;

3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-4-fluorobenzamide;

3-[4-amino-5-(trifluoromethyl)pyrrolo[2,1-f][1,2,4]triazin-7-yl]-4-fluoro-N-[(3R,4S)-4-fluoro-1-(2-methylpropanoyl)pyrrolidin-3-yl]benzamide;

3-[4-amino-5-(trifluoromethyl)pyrrolo[2,1-f][1,2,4]triazin-7-yl]-4-fluoro-N-[(3R,4S)-4-fluoro-1-(4-fluorobenzoyl)pyrrolidin-3-yl]benzamide;

3-[4-amino-5-(trifluoromethyl)pyrrolo[2,1-f][1,2,4]triazin-7-yl]-4-fluoro-N-[(3R,4S)-4-fluoro-1-(3,3,3-trifluoropropanoyl)pyrrolidin-3-yl]benzamide;

3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-4-fluorobenzamide;

3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-4-fluorobenzamide;

3-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-4-fluorobenzamide;

3-[4-amino-5-(trifluoromethyl)pyrrolo[2,1-f][1,2,4]triazin-7-yl]-4-fluoro-N-[(3R,4S)-4-fluoro-1-[(2R)-3,3,3-trifluoro-2-hydroxy-2-methylpropanoyl]pyrrolidin-3-yl]benzamide;

3-[4-amino-5-(trifluoromethyl)pyrrolo[2,1-f][1,2,4]triazin-7-yl]-4-fluoro-N-[(3R,4S)-4-fluoro-1-(2-hydroxy-2-methylpropanoyl)pyrrolidin-3-yl]benzamide;

5-[4-amino-5-(trifluoromethyl)pyrrolo[2,1-f][1,2,4]triazin-7-yl]-N-[(3R,4S)-1-[(2,2-difluorocyclopropyl)methyl]-4-fluoropyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-1-[(2,2-difluorocyclopropyl)methyl]-4-fluoropyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(3,3,3-trifluoro-2-hydroxypropyl)pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(3,3,3-trifluoro-2-hydroxypropyl)pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(1-phenylethyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(1-phenylethyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(1-phenylethyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(3-cyanophenyl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(3-cyanophenyl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(2,4-difluorophenyl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(2,4-difluorophenyl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(pyridin-4-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(pyridin-4-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(5-fluoropyridin-3-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(5-fluoropyridin-3-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(2-methyl-1,3-thiazol-4-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(2-methyl-1,3-thiazol-4-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(1,3-thiazol-5-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(1,3-thiazol-5-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3,3,3-trifluoro-1-phenylpropyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3,3,3-trifluoro-1-phenylpropyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(2-fluorophenyl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(2-fluorophenyl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(3-fluoropyridin-2-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[phenyl(deutero)methyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(pyrimidin-4-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(pyrimidin-4-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(3-fluoropyridin-4-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(3-fluoropyridin-4-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(pyridin-3-yl)ethyl]pyrrolidin-3-yl]-2-methoxypyridine-3-carboxamide;

5-(4-amino-5-(trifluoromethyl)pyrrolo[2,1-f][1,2,4]triazin-7-yl)-N-((3R,4S)-4-fluoro-1-(1-(pyridin-3-yl)ethyl)pyrrolidin-3-yl)-2-methoxynicotinamide;

5-[4-amino-5-(trifluoromethyl)pyrrolo[2,1-f][1,2,4]triazin-7-yl]-N-[(3R,4S)-1-[1-(3,5-difluorophenyl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(3,5-difluorophenyl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(3,4-difluorophenyl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(3,4-difluorophenyl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(4-fluorophenyl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(4-fluorophenyl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(5-fluoropyridin-2-yl)methyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-hydroxy-2-phenylethyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(2-cyanobenzenesulfonyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(2-methyl-1,3-thiazol-5-yl)sulfonyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-fluorobenzenesulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(4-fluorobenzenesulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(pyridine-3-sulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(pyridine-3-sulfonyl)pyrrolidin-3-yl]-2-methoxypyridine-3-carboxamide;

5-{4-amino-6-fluoropyrrolo[2,1-f][1,2,4]triazin-7-yl}-N-[(3R,4S)-1-(3,3-difluorocyclobutanecarbonyl)-4-fluoropyrrolidin-3-yl]-2-methoxypyridine-3-carboxamide;

5-{4-amino-6-fluoropyrrolo[2,1-f][1,2,4]triazin-7-yl}-N-[(3R,4S)-4-fluoro-1-(oxane-4-carbonyl)pyrrolidin-3-yl]-2-methoxypyridine-3-carboxamide;

5-{4-amino-6-fluoropyrrolo[2,1-f][1,2,4]triazin-7-yl}-N-[(3R,4S)-1-(4,4-difluorocyclohexanecarbonyl)-4-fluoropyrrolidin-3-yl]-2-methoxypyridine-3-carboxamide;

5-{4-amino-6-fluoropyrrolo[2,1-f][1,2,4]triazin-7-yl}-N-[(3R,4S)-1-(3,3-difluorocyclopentanecarbonyl)-4-fluoropyrrolidin-3-yl]-2-methoxypyridine-3-carboxamide;

5-{4-amino-6-fluoropyrrolo[2,1-f][1,2,4]triazin-7-yl}-N-[(3R,4S)-4-fluoro-1-(4-fluorobenzoyl)pyrrolidin-3-yl]-2-methoxypyridine-3-carboxamide;

5-{4-amino-6-fluoropyrrolo[2,1-f][1,2,4]triazin-7-yl}-N-[(3R,4S)-4-fluoro-1-(4-fluorocyclohexanecarbonyl)pyrrolidin-3-yl]-2-methoxypyridine-3-carboxamide;

5-{4-amino-6-fluoropyrrolo[2,1-f][1,2,4]triazin-7-yl}-N-[(3R,4S)-1-(2,2-difluorocyclopropanecarbonyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(deutero)methoxy-6-methylpyridine-3-carboxamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(deutero)methoxy-6-methylpyridine-3-carboxamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-(deutero)methoxy-6-methylpyridine-3-carboxamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(Deutero)methoxy-6-methylpyridine-3-carboxamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(Deutero)methoxy-6-methylpyridine-3-carboxamide;

(5-(4-amino-5-(trifluoromethyl)pyrrolo[2,1-f][1,2,4]triazin-7-yl)-N-((3R,4S)-1-(3,3-difluorocyclobutane-1-carbonyl)-4-fluoropyrrolidin-3-yl)-2-(methoxy-d3)-6-methylnicotinamide;

5-[4-amino-5-(trifluoromethyl)pyrrolo[2,1-f][1,2,4]triazin-7-yl]-4-chloro-2-fluoro-N-[(3R,4S)-4-fluoro-1-(1-fluorocyclobutanecarbonyl)pyrrolidin-3-yl]benzamide;

5-[4-amino-5-(trifluoromethyl)pyrrolo[2,1-f][1,2,4]triazin-7-yl]-4-chloro-2-fluoro-N-[(3R,4S)-4-fluoro-1-(2-fluoro-2-methylpropanoyl)pyrrolidin-3-yl]benzamide;

5-[4-amino-5-(trifluoromethyl)pyrrolo[2,1-f][1,2,4]triazin-7-yl]-4-chloro-N-[(3R,4S)-1-(3,3-difluorocyclopentanecarbonyl)-4-fluoropyrrolidin-3-yl]-2-fluorobenzamide;

5-[4-amino-5-(trifluoromethyl)pyrrolo[2,1-f][1,2,4]triazin-7-yl]-4-chloro-N-[(3R,4S)-1-(3,3-difluorocyclobutanecarbonyl)-4-fluoropyrrolidin-3-yl]-2-fluorobenzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-(oxolane-3-carbonyl)pyrrolidin-3-yl]-2,4-dimethylbenzamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2,4-dimethylbenzamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2,4-dimethylbenzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2,4-dimethylbenzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2,4-dimethylbenzamide;

5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]-2,4-dimethylbenzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2,4-dimethylbenzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2,4-dimethylbenzamide;

5-(4-amino-6-cyanopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide;

5-(4-amino-6-(1H-tetrazol-5-yl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide;

5-(4-amino-6-(1-methyl-1H-tetrazol-5-yl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide;

5-(4-amino-6-(2-methyl-2H-tetrazol-5-yl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxynicotinamide;

5-(4-amino-6-cyanopyrrolo[2,1-f][1,2,4]triazin-7-yl)-N-((3R,4S)-1-(2,2-difluorocyclopropane-1-carbonyl)-4-fluoropyrrolidin-3-yl)-2-methoxynicotinamide;

5-(4-amino-6-cyanopyrrolo[2,1-f][1,2,4]triazin-7-yl)-N-((3R,4S)-1-(3,3-difluorocyclobutane-1-carbonyl)-4-fluoropyrrolidin-3-yl)-2-methoxynicotinamide;

5-(4-amino-6-cyanopyrrolo[2,1-f][1,2,4]triazin-7-yl)-N-((3R,4S)-1-(3,3-difluorocyclopentane-1-carbonyl)-4-fluoropyrrolidin-3-yl)-2-methoxynicotinamide;

5-(4-amino-6-cyanopyrrolo[2,1-f][1,2,4]triazin-7-yl)-N-((3R,4S)-4-fluoro-1-(1-(trifluoromethyl)cyclopropane-1-carbonyl)pyrrolidin-3-yl)-2-methoxynicotinamide;

5-(4-amino-6-cyanopyrrolo[2,1-f][1,2,4]triazin-7-yl)-N-((3R,4S)-1-(4,4-difluorocyclohexane-1-carbonyl)-4-fluoropyrrolidin-3-yl)-2-methoxynicotinamide;

5-(4-amino-6-cyanopyrrolo[2,1-f][1,2,4]triazin-7-yl)-N-((3R,4S)-4-fluoro-1-(4-(trifluoromethyl)cyclohexane-1-carbonyl)pyrrolidin-3-yl)-2-methoxynicotinamide;

5-(4-amino-6-cyanopyrrolo[2,1-f][1,2,4]triazin-7-yl)-N-((3R,4S)-4-fluoro-1-(4-(trifluoromethyl)cyclohexane-1-carbonyl)pyrrolidin-3-yl)-2-methoxynicotinamide;

5-(4-amino-6-cyanopyrrolo[2,1-f][1,2,4]triazin-7-yl)-N-((3R,4S)-4-fluoro-1-(4-hydroxy-4-(trifluoromethyl)cyclohexane-1-carbonyl)pyrrolidin-3-yl)-2-methoxynicotinamide;

5-(4-amino-6-cyanopyrrolo[2,1-f][1,2,4]triazin-7-yl)-N-((3R,4S)-4-fluoro-1-(3-hydroxy-3-(trifluoromethyl)cyclobutane-1-carbonyl)pyrrolidin-3-yl)-2-methoxynicotinamide;

5-(4-amino-6-cyanopyrrolo[2,1-f][1,2,4]triazin-7-yl)-N-((3R,4S)-4-fluoro-1-(3,3,3-trifluoro-2,2-dimethylpropanoyl)pyrrolidin-3-yl)-2-methoxynicotinamide;

5-(4-amino-6-cyanopyrrolo[2,1-f][1,2,4]triazin-7-yl)-N-((3R,4S)-4-fluoro-1-(2-fluoro-2-methylpropanoyl)pyrrolidin-3-yl)-2-methoxynicotinamide;

5-(4-amino-5-(trifluoromethyl)pyrrolo[2,1-f][1,2,4]triazin-7-yl)-3-fluoro-N-((3R,4S)-4-fluoro-1-(4,4,4-trifluoro-3-hydroxy-3-(trifluoromethyl)butanoyl) pyrrolidin-3-yl)-2-methylbenzamide;

5-(4-amino-5-(trifluoromethyl)pyrrolo[2,1-f][1,2,4]triazin-7-yl)-N-(4,4-difluoro-1-((R)-3,3,3-trifluoro-2-hydroxy-2-methylpropanoyl)pyrrolidin-3-yl)-2-methoxynicotinamide;

5-(4-amino-5-(trifluoromethyl)pyrrolo[2,1-f][1,2,4]triazin-7-yl)-4-fluoro-N-((3R,4S)-4-fluoro-1-(4,4,4-trifluoro-3-hydroxy-3-(trifluoromethyl)butanoyl) pyrrolidin-3-yl)-2-methoxybenzamide;

5-(4-amino-5-(trifluoromethyl)pyrrolo[2,1-f][1,2,4]triazin-7-yl)-N-((3R,4S)-1-(3,3-difluorocyclobutane-1-carbonyl)-4-fluoropyrrolidin-3-yl)-2-(methylamino)benzamide;

5-(4-amino-5-(trifluoromethyl)pyrrolo[2,1-f][1,2,4]triazin-7-yl)-2-ethyl-3-fluoro-N-((3R,4S)-4-fluoro-1-(4,4,4-trifluoro-3-hydroxy-3-(trifluoromethyl) butanoyl) pyrrolidin-3-yl)benzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-4-fluoro-2-methoxybenzamide;

5-[4-amino-5-(trifluoromethyl)pyrrolo[2,1-f][1,2,4]triazin-7-yl]-3-fluoro-N-[(3R,4S)-4-fluoro-1-[(2R)-3,3,3-trifluoro-2-hydroxy-2-methylpropanoyl] pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-[4,4,4-trifluoro-3-hydroxy-3-(trifluoromethyl)butanoyl] pyrrolidin-3-yl]-2-(fluoromethyl)benzamide;

3-[4-amino-5-(trifluoromethyl)pyrrolo[2,1-f][1,2,4]triazin-7-yl]-6-ethyl-2-fluoro-N-[(3R,4S)-4-fluoro-1-[4,4,4-trifluoro-3-hydroxy-3-(trifluoromethyl)butanoyl] pyrrolidin-3-yl]benzamide;

3-[4-amino-5-(trifluoromethyl)pyrrolo[2,1-f][1,2,4]triazin-7-yl]-N-[(3R,4S)-4-fluoro-1-(2-fluorobenzoyl) pyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-5-methoxybenzamide;

3-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-5-methoxybenzamide;

3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-5-methoxybenzamide;

3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-5-methoxybenzamide;

3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-5-methoxybenzamide;

3-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-5-methoxybenzamide;

5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2,3-dimethoxybenzamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2,3-dimethoxybenzamide;

5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2,3-dimethoxybenzamide;

5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2,3-dimethoxybenzamide;

5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2,3-dimethoxybenzamide;

3-[4-amino-5-(trifluoromethyl)pyrrolo[2,1-f][1,2,4]triazin-7-yl]-5-fluoro-N-[(3R,4S)-4-fluoro-1-[(2R)-3,3,3-trifluoro-2-hydroxypropanoyl]pyrrolidin-3-yl]benzamide;

3-[4-amino-5-(trifluoromethyl)pyrrolo[2,1-f][1,2,4]triazin-7-yl]-5-fluoro-N-[(3R,4S)-4-fluoro-1-(3-fluorocyclobutanecarbonyl)pyrrolidin-3-yl]benzamide;

3-[4-amino-5-(trifluoromethyl)pyrrolo[2,1-f][1,2,4]triazin-7-yl]-5-fluoro-N-[(3R,4S)-4-fluoro-1-(3,3,3-trifluoro-2,2-dimethylpropanoyl)pyrrolidin-3-yl]benzamide;

3-[4-amino-5-(trifluoromethyl)pyrrolo[2,1-f][1,2,4]triazin-7-yl]-5-fluoro-N-[(3R,4S)-4-fluoro-1-(2-fluoro-2-methylpropanoyl)pyrrolidin-3-yl]benzamide;

3-[4-amino-5-(trifluoromethyl)pyrrolo[2,1-f][1,2,4]triazin-7-yl]-5-fluoro-N-[(3R,4S)-4-fluoro-1-(2-methylpropanoyl)pyrrolidin-3-yl]benzamide;

3-[4-amino-5-(trifluoromethyl)pyrrolo[2,1-f][1,2,4]triazin-7-yl]-5-fluoro-N-[(3R,4S)-4-fluoro-1-(3-methylbutanoyl)pyrrolidin-3-yl]benzamide;

3-[4-amino-5-(trifluoromethyl)pyrrolo[2,1-f][1,2,4]triazin-7-yl]-5-fluoro-N-[(3R,4S)-4-fluoro-1-(2-hydroxy-2-methylpropanoyl)pyrrolidin-3-yl]benzamide;

3-[4-amino-5-(trifluoromethyl)pyrrolo[2,1-f][1,2,4]triazin-7-yl]-5-fluoro-N-[(3R,4S)-4-fluoro-1-(3,3,3-trifluoropropanoyl)pyrrolidin-3-yl]benzamide;

3-[4-amino-5-(trifluoromethyl)pyrrolo[2,1-f][1,2,4]triazin-7-yl]-N-[(3R,4S)-1-(2,2-dimethylpropanoyl)-4-fluoropyrrolidin-3-yl]-5-fluorobenzamide;

3-[4-amino-5-(trifluoromethyl)pyrrolo[2,1-f][1,2,4]triazin-7-yl]-N-[(3R,4S)-1-cyclobutanecarbonyl-4-fluoropyrrolidin-3-yl]-5-fluorobenzamide;

3-[4-amino-5-(trifluoromethyl)pyrrolo[2,1-f][1,2,4]triazin-7-yl]-5-fluoro-N-[(3R,4S)-4-fluoro-1-(4-fluorobenzoyl)pyrrolidin-3-yl]benzamide;

3-[4-amino-5-(trifluoromethyl)pyrrolo[2,1-f][1,2,4]triazin-7-yl]-5-fluoro-N-[(3R,4S)-4-fluoro-1-(2-fluorobenzoyl)pyrrolidin-3-yl]benzamide;

3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-5-fluorobenzamide;

3-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-5-fluorobenzamide;

3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-5-fluorobenzamide;

3-[4-amino-5-(trifluoromethyl)pyrrolo[2,1-f][1,2,4]triazin-7-yl]-5-fluoro-N-[(3R,4S)-4-fluoro-1-(3-fluorocyclobutanecarbonyl)pyrrolidin-3-yl]benzamide;

5-[4-amino-5-(trifluoromethyl)pyrrolo[2,1-f][1,2,4]triazin-7-yl]-3-fluoro-N-[(3R,4S)-4-fluoro-1-(1-fluorocyclopropanecarbonyl)pyrrolidin-3-yl]-2-(fluoromethyl)benzamide;

5-[4-amino-5-(trifluoromethyl)pyrrolo[2,1-f][1,2,4]triazin-7-yl]-3-fluoro-N-[(3R,4S)-4-fluoro-1-(2-fluoro-2-methylpropanoyl)pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-3-fluoro-2-(fluoromethyl)benzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-3-fluoro-2-(fluoromethyl)benzamide;

5-(4-amino-5-(trifluoromethyl)pyrrolo[2,1-f][1,2,4]triazin-7-yl)-3-fluoro-N-((3R,4S)-4-fluoro-1-(3-fluorocyclobutane-1-carbonyl)pyrrolidin-3-yl)-2-(fluoromethyl)benzamide;

5-[4-amino-5-(trifluoromethyl)pyrrolo[2,1-f][1,2,4]triazin-7-yl]-3-fluoro-N-[(3R,4S)-4-fluoro-1-[(2R)-3,3,3-trifluoro-2-hydroxy-2-methylpropanoyl]pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-3-fluoro-2-(fluoromethyl)benzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-3-fluoro-2-(fluoromethyl)benzamide;

5-[4-amino-5-(trifluoromethyl)pyrrolo[2,1-f][1,2,4]triazin-7-yl]-3-fluoro-N-[(3R,4S)-4-fluoro-1-(4,4,4-trifluoro-3-methylbutanoyl)pyrrolidin-3-yl]-2-(fluoromethyl)benzamide;

5-[4-amino-5-(trifluoromethyl)pyrrolo[2,1-f][1,2,4]triazin-7-yl]-3-fluoro-N-[(3R,4S)-4-fluoro-1-(4,4,4-trifluoro-3-hydroxy-3-methylbutanoyl)pyrrolidin-3-yl]-2-(fluoromethyl)benzamide;

5-[4-amino-5-(trifluoromethyl)pyrrolo[2,1-f][1,2,4]triazin-7-yl]-3-fluoro-N-[(3R,4S)-4-fluoro-1-[4,4,4-trifluoro-3-(trifluoromethyl)butanoyl]pyrrolidin-3-yl]-2-(fluoromethyl)benzamide;

5-[4-amino-5-(trifluoromethyl)pyrrolo[2,1-f][1,2,4]triazin-7-yl]-3-fluoro-N-[(3R,4S)-4-fluoro-1-(2-hydroxy-2-methylpropanoyl)pyrrolidin-3-yl]-2-(fluoromethyl)benzamide;

5-[4-amino-5-(trifluoromethyl)pyrrolo[2,1-f][1,2,4]triazin-7-yl]-3-fluoro-N-[(3R,4S)-4-fluoro-1-(3,3,3-trifluoropropanoyl)pyrrolidin-3-yl]-2-(fluoromethyl)benzamide;

5-[4-amino-5-(trifluoromethyl)pyrrolo[2,1-f][1,2,4]triazin-7-yl]-3-fluoro-N-[(3R,4S)-4-fluoro-1-(3-methylbutanoyl)pyrrolidin-3-yl]-2-(fluoromethyl)benzamide;

5-[4-amino-5-(trifluoromethyl)pyrrolo[2,1-f][1,2,4]triazin-7-yl]-3-fluoro-N-[(3R,4S)-4-fluoro-1-(2-fluorobenzoyl)pyrrolidin-3-yl]-2-(fluoromethyl)benzamide;

5-[4-amino-5-(trifluoromethyl)pyrrolo[2,1-f][1,2,4]triazin-7-yl]-3-fluoro-N-[(3R,4S)-4-fluoro-1-(3,3,3-trifluoro-2-methylpropanoyl)pyrrolidin-3-yl]-2-(fluoromethyl)benzamide;

5-[4-amino-5-(trifluoromethyl)pyrrolo[2,1-f][1,2,4]triazin-7-yl]-3-fluoro-N-[(3R,4S)-4-fluoro-1-[2-hydroxy-2-(trifluoromethyl)butanoyl]pyrrolidin-3-yl]-2-(fluoromethyl)benzamide;

5-[4-amino-5-(trifluoromethyl)pyrrolo[2,1-f][1,2,4]triazin-7-yl]-2-chloro-3-fluoro-N-[(3R,4S)-4-fluoro-1-(4,4,4-trifluoro-3-hydroxy-3-methylbutanoyl)pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-(2-fluoro-2-methylpropanoyl)pyrrolidin-3-yl]benzamide;

5-[4-amino-5-(trifluoromethyl)pyrrolo[2,1-f][1,2,4]triazin-7-yl]-2-chloro-N-[(3R,4S)-1-(2,2-difluorocyclopropanecarbonyl)-4-fluoropyrrolidin-3-yl]-3-fluorobenzamide;

5-[4-amino-5-(trifluoromethyl)pyrrolo[2,1-f][1,2,4]triazin-7-yl]-2-chloro-3-fluoro-N-[(3R,4S)-4-fluoro-1-[4,4,4-trifluoro-3-(trifluoromethyl)butanoyl]pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-(3,3,3-trifluoro-2-methylpropanoyl)pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-(4,4,4-trifluoro-3-methylbutanoyl)pyrrolidin-3-yl]benzamide;

5-[4-amino-5-(trifluoromethyl)pyrrolo[2,1-f][1,2,4]triazin-7-yl]-2-chloro-N-[(3R,4S)-1-(3,3-difluorocyclobutanecarbonyl)-4-fluoropyrrolidin-3-yl]-3-fluorobenzamide;

5-[4-amino-5-(trifluoromethyl)pyrrolo[2,1-f][1,2,4]triazin-7-yl]-2-chloro-3-fluoro-N-[(3R,4S)-4-fluoro-1-(1-fluorocyclopropanecarbonyl)pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-[4,4,4-trifluoro-3-hydroxy-3-(trifluoromethyl)butanoyl]pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-(3-fluorocyclobutanecarbonyl)pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-(2-hydroxy-2-methylpropanoyl)pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-(3,3,3-trifluoropropanoyl)pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-(3-methylbutanoyl)pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-(2-fluorobenzoyl)pyrrolidin-3-yl]benzamide;

5-[4-amino-5-(trifluoromethyl)pyrrolo[2,1-f][1,2,4]triazin-7-yl]-2-chloro-N-[(3R,4S)-1-(4,4-difluorocyclohexanecarbonyl)-4-fluoropyrrolidin-3-yl]-3-fluorobenzamide;

5-[4-amino-5-(trifluoromethyl)pyrrolo[2,1-f][1,2,4]triazin-7-yl]-2-chloro-N-[(3R,4S)-1-(3,3-difluorocyclopentanecarbonyl)-4-fluoropyrrolidin-3-yl]-3-fluorobenzamide;

5-[4-amino-5-(trifluoromethyl)pyrrolo[2,1-f][1,2,4]triazin-7-yl]-2-ethyl-3-fluoro-N-[(3R,4S)-4-fluoro-1-(2-fluorobenzoyl)pyrrolidin-3-yl]benzamide;

5-[4-amino-5-(trifluoromethyl)pyrrolo[2,1-f][1,2,4]triazin-7-yl]-2-ethyl-3-fluoro-N-[(3R,4S)-4-fluoro-1-(3-methylbutanoyl)pyrrolidin-3-yl]benzamide;

5-[4-amino-5-(trifluoromethyl)pyrrolo[2,1-f][1,2,4]triazin-7-yl]-2-ethyl-3-fluoro-N-[(3R,4S)-4-fluoro-1-(2-hydroxy-2-methylpropanoyl)pyrrolidin-3-yl]benzamide;

5-[4-amino-5-(trifluoromethyl)pyrrolo[2,1-f][1,2,4]triazin-7-yl]-2-ethyl-3-fluoro-N-[(3R,4S)-4-fluoro-1-(3,3,3-trifluoropropanoyl)pyrrolidin-3-yl]benzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-ethyl-3-fluorobenzamide;

5-[4-amino-5-(trifluoromethyl)pyrrolo[2,1-f][1,2,4]triazin-7-yl]-2-ethyl-3-fluoro-N-[(3R,4S)-4-fluoro-1-[(2R)-3,3,3-trifluoro-2-hydroxy-2-methylpropanoyl]pyrrolidin-3-yl]benzamide;

5-[4-amino-5-(trifluoromethyl)pyrrolo[2,1-f][1,2,4]triazin-7-yl]-2-ethyl-3-fluoro-N-[(3R,4S)-4-fluoro-1-[2-hydroxy-2-(trifluoromethyl)butanoyl]pyrrolidin-3-yl]benzamide;

5-[4-amino-5-(trifluoromethyl)pyrrolo[2,1-f][1,2,4]triazin-7-yl]-2-ethyl-3-fluoro-N-[(3R,4S)-4-fluoro-1-(4,4,4-trifluoro-3-methylbutanoyl)pyrrolidin-3-yl]benzamide;

5-[4-amino-5-(trifluoromethyl)pyrrolo[2,1-f][1,2,4]triazin-7-yl]-2-ethyl-3-fluoro-N-[(3R,4S)-4-fluoro-1-(4,4,4-trifluoro-3-hydroxy-3-methylbutanoyl)pyrrolidin-3-yl]benzamide;

5-[4-amino-5-(trifluoromethyl)pyrrolo[2,1-f][1,2,4]triazin-7-yl]-2-ethyl-3-fluoro-N-[(3R,4S)-4-fluoro-1-[4,4,4-trifluoro-3-(trifluoromethyl)butanoyl]pyrrolidin-3-yl]benzamide;

5-[4-amino-5-(trifluoromethyl)pyrrolo[2,1-f][1,2,4]triazin-7-yl]-2-ethyl-3-fluoro-N-[(3R,4S)-4-fluoro-1-(3-fluorocyclobutanecarbonyl)pyrrolidin-3-yl]benzamide;

5-[4-amino-5-(trifluoromethyl)pyrrolo[2,1-f][1,2,4]triazin-7-yl]-2-ethyl-3-fluoro-N-[(3R,4S)-4-fluoro-1-(3-fluorocyclobutanecarbonyl)pyrrolidin-3-yl]benzamide;

5-[4-amino-5-(trifluoromethyl)pyrrolo[2,1-f][1,2,4]triazin-7-yl]-2-ethyl-3-fluoro-N-[(3R,4S)-4-fluoro-1-(1-fluorocyclopropanecarbonyl)pyrrolidin-3-yl]benzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-ethyl-3-fluorobenzamide;

5-[4-amino-5-(trifluoromethyl)pyrrolo[2,1-f][1,2,4]triazin-7-yl]-2-ethyl-3-fluoro-N-[(3R,4S)-4-fluoro-1-(2-fluoro-2-methylpropanoyl)pyrrolidin-3-yl]benzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-ethyl-3-fluorobenzamide;

5-[4-amino-5-(trifluoromethyl)pyrrolo[2,1-f][1,2,4]triazin-7-yl]-2-ethyl-3-fluoro-N-[(3R,4S)-4-fluoro-1-(3,3,3-trifluoro-2-methylpropanoyl)pyrrolidin-3-yl]benzamide;

5-[4-amino-5-(trifluoromethyl)pyrrolo[2,1-f][1,2,4]triazin-7-yl]-3-fluoro-N-[(3R,4S)-4-fluoro-1-(4,4,4-trifluoro-3-methylbutanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-cyclobutanecarbonyl-4-fluoropyrrolidin-3-yl]-3-fluoro-2-methylbenzamide;

5-[4-amino-5-(trifluoromethyl)pyrrolo[2,1-f][1,2,4]triazin-7-yl]-3-fluoro-N-[(3R,4S)-4-fluoro-1-(3,3,3-trifluoropropanoyl)pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-(2-hydroxy-2-methylpropanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(2,2-dimethylpropanoyl)-4-fluoropyrrolidin-3-yl]-3-fluoro-2-methylbenzamide;

5-[4-amino-5-(trifluoromethyl)pyrrolo[2,1-f][1,2,4]triazin-7-yl]-3-fluoro-N-[(3R,4S)-4-fluoro-1-(3-methylbutanoyl)pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-(2-methylpropanoyl)pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-(2-fluorobenzoyl)pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-(4-fluorobenzoyl)pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-(1-hydroxycyclobutanecarbonyl)pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-[(2R)-3,3,3-trifluoro-2-hydroxypropanoyl]pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-(2-fluoro-2-methylpropanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-3-fluoro-2-methylbenzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-3-fluoro-2-methylbenzamide;

5-[4-amino-5-(trifluoromethyl)pyrrolo[2,1-f][1,2,4]triazin-7-yl]-3-fluoro-N-[(3R,4S)-4-fluoro-1-(3,3,3-trifluoro-2,2-dimethylpropanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-3-fluoro-2-methylbenzamide;

5-[4-amino-5-(trifluoromethyl)pyrrolo[2,1-f][1,2,4]triazin-7-yl]-3-fluoro-N-[(3R,4S)-4-fluoro-1-(3-fluorocyclobutanecarbonyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-3-fluoro-2-methylbenzamide;

5-[4-amino-5-(trifluoromethyl)pyrrolo[2,1-f][1,2,4]triazin-7-yl]-3-fluoro-N-[(3R,4S)-4-fluoro-1-(3-methylbutanoyl)pyrrolidin-3-yl]-2-methoxybenzamide;

5-[4-amino-5-(trifluoromethyl)pyrrolo[2,1-f][1,2,4]triazin-7-yl]-3-fluoro-N-[(3R,4S)-4-fluoro-1-(2-fluorobenzoyl)pyrrolidin-3-yl]-2-methoxybenzamide;

5-[4-amino-5-(trifluoromethyl)pyrrolo[2,1-f][1,2,4]triazin-7-yl]-N-[(3R,4S)-1-cyclobutanecarbonyl-4-fluoropyrrolidin-3-yl]-3-fluoro-2-methoxybenzamide;

5-[4-amino-5-(trifluoromethyl)pyrrolo[2,1-f][1,2,4]triazin-7-yl]-3-fluoro-N-[(3R,4S)-4-fluoro-1-(4-fluorobenzoyl)pyrrolidin-3-yl]-2-methoxybenzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-3-fluoro-2-methoxybenzamide;

5-[4-amino-5-(trifluoromethyl)pyrrolo[2,1-f][1,2,4]triazin-7-yl]-3-fluoro-N-[(3R,4S)-4-fluoro-1-(2-fluoro-2-methylpropanoyl)pyrrolidin-3-yl]-2-methoxybenzamide;

5-[4-amino-5-(trifluoromethyl)pyrrolo[2,1-f][1,2,4]triazin-7-yl]-3-fluoro-N-[(3R,4S)-4-fluoro-1-[(2R)-3,3,3-trifluoro-2-hydroxy-2-methylpropanoyl]pyrrolidin-3-yl]-2-methoxybenzamide;

5-[4-amino-5-(trifluoromethyl)pyrrolo[2,1-f][1,2,4]triazin-7-yl]-3-fluoro-N-[(3R,4S)-4-fluoro-1-(3-fluorocyclobutanecarbonyl)pyrrolidin-3-yl]-2-methoxybenzamide;

5-[4-amino-5-(trifluoromethyl)pyrrolo[2,1-f][1,2,4]triazin-7-yl]-3-fluoro-N-[(3R,4S)-4-fluoro-1-(1-fluorocyclopropanecarbonyl)pyrrolidin-3-yl]-2-methoxybenzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-3-fluoro-2-methoxybenzamide;

5-[4-amino-5-(trifluoromethyl)pyrrolo[2,1-f][1,2,4]triazin-7-yl]-3-fluoro-N-[(3R,4S)-4-fluoro-1-[4,4,4-trifluoro-3-hydroxy-3-(trifluoromethyl)butanoyl]pyrrolidin-3-yl]-2-methoxybenzamide;

5-[4-amino-5-(trifluoromethyl)pyrrolo[2,1-f][1,2,4]triazin-7-yl]-3-fluoro-N-[(3R,4S)-4-fluoro-1-[4,4,4-trifluoro-3-(trifluoromethyl)butanoyl]pyrrolidin-3-yl]-2-methoxybenzamide;

5-[4-amino-5-(trifluoromethyl)pyrrolo[2,1-f][1,2,4]triazin-7-yl]-3-fluoro-N-[(3R,4S)-4-fluoro-1-[2-hydroxy-2-(trifluoromethyl)butanoyl]pyrrolidin-3-yl]-2-methoxybenzamide;

5-[4-amino-5-(trifluoromethyl)pyrrolo[2,1-f][1,2,4]triazin-7-yl]-3-fluoro-N-[(3R,4S)-4-fluoro-1-(4,4,4-trifluoro-3-methylbutanoyl)pyrrolidin-3-yl]-2-methoxybenzamide;

5-[4-amino-5-(trifluoromethyl)pyrrolo[2,1-f][1,2,4]triazin-7-yl]-3-fluoro-N-[(3R,4S)-4-fluoro-1-(3,3,3-trifluoro-2-methylpropanoyl)pyrrolidin-3-yl]-2-methoxybenzamide;

5-[4-amino-5-(trifluoromethyl)pyrrolo[2,1-f][1,2,4]triazin-7-yl]-3-fluoro-N-[(3R,4S)-4-fluoro-1-(4-fluorocyclohexanecarbonyl)pyrrolidin-3-yl]-2-methoxybenzamide;

5-[4-amino-5-(trifluoromethyl)pyrrolo[2,1-f][1,2,4]triazin-7-yl]-3-fluoro-N-[(3R,4S)-4-fluoro-1-(4,4,4-trifluoro-3-hydroxy-3-methylbutanoyl)pyrrolidin-3-yl]-2-methoxybenzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-3-fluoro-2-methoxybenzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-3-fluoro-2-methoxybenzamide;

5-[4-amino-5-(trifluoromethyl)pyrrolo[2,1-f][1,2,4]triazin-7-yl]-3-fluoro-N-[(3R,4S)-4-fluoro-1-(3,3,3-trifluoropropanoyl)pyrrolidin-3-yl]-2-methoxybenzamide;

5-[4-amino-5-(trifluoromethyl)pyrrolo[2,1-f][1,2,4]triazin-7-yl]-3-fluoro-N-[(3R,4S)-4-fluoro-1-(2-hydroxy-2-methylpropanoyl)pyrrolidin-3-yl]-2-methoxybenzamide;

5-[4-amino-5-(trifluoromethyl)pyrrolo[2,1-f][1,2,4]triazin-7-yl]-2-chloro-N-[(3R,4S)-4-fluoro-1-(4,4,4-trifluoro-3-methylbutanoyl)pyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-4-fluoro-1-[4,4,4-trifluoro-3-hydroxy-3-(trifluoromethyl)butanoyl]pyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-4-fluoro-1-[2-hydroxy-2-(trifluoromethyl)butanoyl]pyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-1-(2,2-difluorocyclopropanecarbonyl)-4-fluoropyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-4-fluoro-1-(2-fluoro-2-methylpropanoyl)pyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-1-(3,3-difluorocyclobutanecarbonyl)-4-fluoropyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-4-fluoro-1-(2-hydroxy-2-methylpropanoyl)pyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-4-fluoro-1-(2-fluorobenzoyl)pyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-4-fluoro-1-[4,4,4-trifluoro-3-(trifluoromethyl)butanoyl]pyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-1-(3,3-difluorocyclopentanecarbonyl)-4-fluoropyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-4-fluoro-1-(4,4,4-trifluoro-3-hydroxy-3-methylbutanoyl)pyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-1-(4,4-difluorocyclohexanecarbonyl)-4-fluoropyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-4-fluoro-1-(3-fluorocyclobutanecarbonyl)pyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-4-fluoro-1-[(2R)-3,3,3-trifluoro-2-hydroxy-2-methylpropanoyl]pyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-4-fluoro-1-(1-fluorocyclopropanecarbonyl)pyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-4-fluoro-1-(3-methylbutanoyl)pyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-4-fluoro-1-(3,3,3-trifluoropropanoyl)pyrrolidin-3-yl]-3-methylbenzamide;

5-[4-amino-5-(trifluoromethyl)pyrrolo[2,1-f][1,2,4]triazin-7-yl]-2-chloro-N-[(3R,4S)-4-fluoro-1-(3,3,3-trifluoro-2-methylpropanoyl)pyrrolidin-3-yl]-3-methylbenzamide;

3-[4-amino-5-(trifluoromethyl)pyrrolo[2,1-f][1,2,4]triazin-7-yl]-2,6-difluoro-N-[(3R,4S)-4-fluoro-1-(3-methylbutanoyl)pyrrolidin-3-yl]benzamide;

3-[4-amino-5-(trifluoromethyl)pyrrolo[2,1-f][1,2,4]triazin-7-yl]-2,6-difluoro-N-[(3R,4S)-4-fluoro-1-[4,4,4-trifluoro-3-hydroxy-3-(trifluoromethyl)butanoyl]pyrrolidin-3-yl]benzamide;

3-[4-amino-5-(trifluoromethyl)pyrrolo[2,1-f][1,2,4]triazin-7-yl]-2,6-difluoro-N-[(3R,4S)-4-fluoro-1-(4,4,4-trifluoro-3-hydroxy-3-methylbutanoyl)pyrrolidin-3-yl]benzamide;

3-[4-amino-5-(trifluoromethyl)pyrrolo[2,1-f][1,2,4]triazin-7-yl]-2,6-difluoro-N-[(3R,4S)-4-fluoro-1-[(2R)-3,3,3-trifluoro-2-hydroxy-2-methylpropanoyl]pyrrolidin-3-yl]benzamide;

3-[4-amino-5-(trifluoromethyl)pyrrolo[2,1-f][1,2,4]triazin-7-yl]-2,6-difluoro-N-[(3R,4S)-4-fluoro-1-(3-fluorocyclobutanecarbonyl)pyrrolidin-3-yl]benzamide;

3-[4-amino-5-(trifluoromethyl)pyrrolo[2,1-f][1,2,4]triazin-7-yl]-2,6-difluoro-N-[(3R,4S)-4-fluoro-1-(3-fluorocyclobutanecarbonyl)pyrrolidin-3-yl]benzamide;

3-[4-amino-5-(trifluoromethyl)pyrrolo[2,1-f][1,2,4]triazin-7-yl]-2,6-difluoro-N-[(3R,4S)-4-fluoro-1-(2-fluorobenzoyl)pyrrolidin-3-yl]benzamide;

3-[4-amino-5-(trifluoromethyl)pyrrolo[2,1-f][1,2,4]triazin-7-yl]-2,6-difluoro-N-[(3R,4S)-4-fluoro-1-(3,3,3-trifluoro-2-methylpropanoyl)pyrrolidin-3-yl]benzamide;

3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2,6-difluorobenzamide;

3-[4-amino-5-(trifluoromethyl)pyrrolo[2,1-f][1,2,4]triazin-7-yl]-2,6-difluoro-N-[(3R,4S)-4-fluoro-1-(4,4,4-trifluoro-3-methylbutanoyl)pyrrolidin-3-yl]benzamide;

3-[4-amino-5-(trifluoromethyl)pyrrolo[2,1-f][1,2,4]triazin-7-yl]-2,6-difluoro-N-[(3R,4S)-4-fluoro-1-[2-hydroxy-2-(trifluoromethyl)butanoyl]pyrrolidin-3-yl]benzamide;

3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2,6-difluorobenzamide;

3-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2,6-difluorobenzamide;

3-[4-amino-5-(trifluoromethyl)pyrrolo[2,1-f][1,2,4]triazin-7-yl]-2,6-difluoro-N-[(3R,4S)-4-fluoro-1-[4,4,4-trifluoro-3-(trifluoromethyl)butanoyl]pyrrolidin-3-yl]benzamide;

3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2,6-difluorobenzamide;

3-[4-amino-5-(trifluoromethyl)pyrrolo[2,1-f][1,2,4]triazin-7-yl]-6-ethyl-2-fluoro-N-[(3R,4S)-4-fluoro-1-(4,4,4-trifluoro-3-hydroxy-3-methylbutanoyl)pyrrolidin-3-yl]benzamide;

3-[4-amino-5-(trifluoromethyl)pyrrolo[2,1-f][1,2,4]triazin-7-yl]-6-ethyl-2-fluoro-N-[(3R,4S)-4-fluoro-1-(3,3,3-trifluoropropanoyl)pyrrolidin-3-yl]benzamide;

3-[4-amino-5-(trifluoromethyl)pyrrolo[2,1-f][1,2,4]triazin-7-yl]-6-ethyl-2-fluoro-N-[(3R,4S)-4-fluoro-1-[4,4,4-trifluoro-3-(trifluoromethyl)butanoyl]pyrrolidin-3-yl]benzamide;

3-[4-amino-5-(trifluoromethyl)pyrrolo[2,1-f][1,2,4]triazin-7-yl]-6-ethyl-2-fluoro-N-[(3R,4S)-4-fluoro-1-[(2R)-3,3,3-trifluoro-2-hydroxy-2-methylpropanoyl]pyrrolidin-3-yl]benzamide;

3-[4-amino-5-(trifluoromethyl)pyrrolo[2,1-f][1,2,4]triazin-7-yl]-6-ethyl-2-fluoro-N-[(3R,4S)-4-fluoro-1-(3-methylbutanoyl)pyrrolidin-3-yl]benzamide;

3-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-6-ethyl-2-fluorobenzamide;

3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-6-ethyl-2-fluorobenzamide;

3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-6-ethyl-2-fluorobenzamide;

3-[4-amino-5-(trifluoromethyl)pyrrolo[2,1-f][1,2,4]triazin-7-yl]-6-ethyl-2-fluoro-N-[(3R,4S)-4-fluoro-1-(3-fluorocyclobutanecarbonyl)pyrrolidin-3-yl]benzamide;

3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-6-ethyl-2-fluorobenzamide;

3-[4-amino-5-(trifluoromethyl)pyrrolo[2,1-f][1,2,4]triazin-7-yl]-6-ethyl-2-fluoro-N-[(3R,4S)-4-fluoro-1-(2-fluorobenzoyl)pyrrolidin-3-yl]benzamide;

3-[4-amino-5-(trifluoromethyl)pyrrolo[2,1-f][1,2,4]triazin-7-yl]-2-fluoro-N-[(3R,4S)-4-fluoro-1-[2-hydroxy-2-(trifluoromethyl)butanoyl]pyrrolidin-3-yl]-6-methylbenzamide;

3-[4-amino-5-(trifluoromethyl)pyrrolo[2,1-f][1,2,4]triazin-7-yl]-2-fluoro-N-[(3R,4S)-4-fluoro-1-(4,4,4-trifluoro-3-hydroxy-3-methylbutanoyl)pyrrolidin-3-yl]-6-methylbenzamide;

3-[4-amino-5-(trifluoromethyl)pyrrolo[2,1-f][1,2,4]triazin-7-yl]-2-fluoro-N-[(3R,4S)-4-fluoro-1-(1-fluorocyclopropanecarbonyl)pyrrolidin-3-yl]-6-methylbenzamide;

3-[4-amino-5-(trifluoromethyl)pyrrolo[2,1-f][1,2,4]triazin-7-yl]-2-fluoro-N-[(3R,4S)-4-fluoro-1-(3-methylbutanoyl)pyrrolidin-3-yl]-6-methylbenzamide;

3-[4-amino-5-(trifluoromethyl)pyrrolo[2,1-f][1,2,4]triazin-7-yl]-2-fluoro-N-[(3R,4S)-4-fluoro-1-(3-fluorocyclobutanecarbonyl)pyrrolidin-3-yl]-6-methylbenzamide;

3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-fluoro-6-methylbenzamide;

3-[4-amino-5-(trifluoromethyl)pyrrolo[2,1-f][1,2,4]triazin-7-yl]-2-fluoro-N-[(3R,4S)-4-fluoro-1-(3,3,3-trifluoro-2-methylpropanoyl)pyrrolidin-3-yl]-6-methylbenzamide;

3-[4-amino-5-(trifluoromethyl)pyrrolo[2,1-f][1,2,4]triazin-7-yl]-2-fluoro-N-[(3R,4S)-4-fluoro-1-(4,4,4-trifluoro-3-methylbutanoyl)pyrrolidin-3-yl]-6-methylbenzamide;

3-[4-amino-5-(trifluoromethyl)pyrrolo[2,1-f][1,2,4]triazin-7-yl]-2-fluoro-N-[(3R,4S)-4-fluoro-1-(2-fluoro-2-methylpropanoyl)pyrrolidin-3-yl]-6-methylbenzamide;

3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-fluoro-6-methylbenzamide;

3-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-fluoro-6-methylbenzamide;

3-[4-amino-5-(trifluoromethyl)pyrrolo[2,1-f][1,2,4]triazin-7-yl]-2-fluoro-N-[(3R,4S)-4-fluoro-1-(2-fluorobenzoyl)pyrrolidin-3-yl]-6-methylbenzamide;

3-[4-amino-5-(trifluoromethyl)pyrrolo[2,1-f][1,2,4]triazin-7-yl]-2-fluoro-N-[(3R,4S)-4-fluoro-1-(2-hydroxy-2-methylpropanoyl)pyrrolidin-3-yl]-6-methylbenzamide;

3-[4-amino-5-(trifluoromethyl)pyrrolo[2,1-f][1,2,4]triazin-7-yl]-2-fluoro-N-[(3R,4S)-4-fluoro-1-[(2R)-3,3,3-trifluoro-2-hydroxy-2-methylpropanoyl]pyrrolidin-3-yl]-6-methylbenzamide;

3-[4-amino-5-(trifluoromethyl)pyrrolo[2,1-f][1,2,4]triazin-7-yl]-2-fluoro-N-[(3R,4S)-4-fluoro-1-[4,4,4-trifluoro-3-hydroxy-3-(trifluoromethyl)butanoyl]pyrrolidin-3-yl]-6-methylbenzamide;

3-[4-amino-5-(trifluoromethyl)pyrrolo[2,1-f][1,2,4]triazin-7-yl]-2-fluoro-N-[(3R,4S)-4-fluoro-1-(3,3,3-trifluoropropanoyl)pyrrolidin-3-yl]-6-methylbenzamide;

3-[4-amino-5-(trifluoromethyl)pyrrolo[2,1-f][1,2,4]triazin-7-yl]-2-fluoro-N-[(3R,4S)-4-fluoro-1-[4,4,4-trifluoro-3-(trifluoromethyl)butanoyl]pyrrolidin-3-yl]-6-methylbenzamide;

3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-fluoro-6-methylbenzamide;

3-[4-amino-5-(trifluoromethyl)pyrrolo[2,1-f][1,2,4]triazin-7-yl]-N-[(3R,4S)-1-cyclobutanecarbonyl-4-fluoropyrrolidin-3-yl]-2-fluorobenzamide;

3-[4-amino-5-(trifluoromethyl)pyrrolo[2,1-f][1,2,4]triazin-7-yl]-2-fluoro-N-[(3R,4S)-4-fluoro-1-(3-methylbutanoyl)pyrrolidin-3-yl]benzamide;

3-[4-amino-5-(trifluoromethyl)pyrrolo[2,1-f][1,2,4]triazin-7-yl]-N-[(3R,4S)-1-(2,2-dimethylpropanoyl)-4-fluoropyrrolidin-3-yl]-2-fluorobenzamide;

3-[4-amino-5-(trifluoromethyl)pyrrolo[2,1-f][1,2,4]triazin-7-yl]-2-fluoro-N-[(3R,4S)-4-fluoro-1-(4-fluorobenzoyl)pyrrolidin-3-yl]benzamide;

3-[4-amino-5-(trifluoromethyl)pyrrolo[2,1-f][1,2,4]triazin-7-yl]-2-fluoro-N-[(3R,4S)-4-fluoro-1-(2-fluorobenzoyl)pyrrolidin-3-yl]benzamide;

3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-fluorobenzamide;

3-[4-amino-5-(trifluoromethyl)pyrrolo[2,1-f][1,2,4]triazin-7-yl]-2-fluoro-N-[(3R,4S)-4-fluoro-1-(2-fluoro-2-methylpropanoyl)pyrrolidin-3-yl]benzamide;

3-[4-amino-5-(trifluoromethyl)pyrrolo[2,1-f][1,2,4]triazin-7-yl]-2-fluoro-N-[(3R,4S)-4-fluoro-1-(3,3,3-trifluoro-2,2-dimethylpropanoyl)pyrrolidin-3-yl]benzamide;

3-[4-amino-5-(trifluoromethyl)pyrrolo[2,1-f][1,2,4]triazin-7-yl]-2-fluoro-N-[(3R,4S)-4-fluoro-1-(3-fluorocyclobutanecarbonyl)pyrrolidin-3-yl]benzamide;

3-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-fluorobenzamide;

3-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-fluorobenzamide;

3-[4-amino-5-(trifluoromethyl)pyrrolo[2,1-f][1,2,4]triazin-7-yl]-2-fluoro-N-[(3R,4S)-4-fluoro-1-[(2R)-3,3,3-trifluoro-2-hydroxy-2-methylpropanoyl]pyrrolidin-3-yl]benzamide;

5-[4-amino-5-(trifluoromethyl)pyrrolo[2,1-f][1,2,4]triazin-7-yl]-2,4-difluoro-N-[(3R,4S)-4-fluoro-1-(3,3,3-trifluoropropanoyl)pyrrolidin-3-yl]benzamide;

5-[4-amino-5-(trifluoromethyl)pyrrolo[2,1-f][1,2,4]triazin-7-yl]-2,4-difluoro-N-[(3R,4S)-4-fluoro-1-(2-hydroxy-2-methylpropanoyl)pyrrolidin-3-yl]benzamide;

5-[4-amino-5-(trifluoromethyl)pyrrolo[2,1-f][1,2,4]triazin-7-yl]-2,4-difluoro-N-[(3R,4S)-4-fluoro-1-(3-methylbutanoyl)pyrrolidin-3-yl]benzamide;

5-[4-amino-5-(trifluoromethyl)pyrrolo[2,1-f][1,2,4]triazin-7-yl]-2,4-difluoro-N-[(3R,4S)-4-fluoro-1-(3-fluorocyclobutanecarbonyl)pyrrolidin-3-yl]benzamide;

5-[4-amino-5-(trifluoromethyl)pyrrolo[2,1-f][1,2,4]triazin-7-yl]-2,4-difluoro-N-[(3R,4S)-4-fluoro-1-(1-fluorocyclopropanecarbonyl)pyrrolidin-3-yl]benzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2,4-difluorobenzamide;

5-[4-amino-5-(trifluoromethyl)pyrrolo[2,1-f][1,2,4]triazin-7-yl]-2,4-difluoro-N-[(3R,4S)-4-fluoro-1-[2-hydroxy-2-(trifluoromethyl)butanoyl]pyrrolidin-3-yl]benzamide;

5-[4-amino-5-(trifluoromethyl)pyrrolo[2,1-f][1,2,4]triazin-7-yl]-2,4-difluoro-N-[(3R,4S)-4-fluoro-1-(2-fluoro-2-methylpropanoyl)pyrrolidin-3-yl]benzamide;

5-[4-amino-5-(trifluoromethyl)pyrrolo[2,1-f][1,2,4]triazin-7-yl]-2,4-difluoro-N-[(3R,4S)-4-fluoro-1-[4,4,4-trifluoro-3-(trifluoromethyl)butanoyl]pyrrolidin-3-yl]benzamide;

5-[4-amino-5-(trifluoromethyl)pyrrolo[2,1-f][1,2,4]triazin-7-yl]-2,4-difluoro-N-[(3R,4S)-4-fluoro-1-[4,4,4-trifluoro-3-hydroxy-3-(trifluoromethyl)butanoyl]pyrrolidin-3-yl]benzamide;

5-[4-amino-5-(trifluoromethyl)pyrrolo[2,1-f][1,2,4]triazin-7-yl]-2,4-difluoro-N-[(3R,4S)-4-fluoro-1-(4,4,4-trifluoro-3-methylbutanoyl)pyrrolidin-3-yl]benzamide;

5-[4-amino-5-(trifluoromethyl)pyrrolo[2,1-f][1,2,4]triazin-7-yl]-2,4-difluoro-N-[(3R,4S)-4-fluoro-1-(4,4,4-trifluoro-3-hydroxy-3-methylbutanoyl)pyrrolidin-3-yl]benzamide;

5-[4-amino-5-(trifluoromethyl)pyrrolo[2,1-f][1,2,4]triazin-7-yl]-2,4-difluoro-N-[(3R,4S)-4-fluoro-1-(3,3,3-trifluoro-2-methylpropanoyl)pyrrolidin-3-yl]benzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2,4-difluorobenzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2,4-difluorobenzamide;

5-[4-amino-5-(trifluoromethyl)pyrrolo[2,1-f][1,2,4]triazin-7-yl]-2,4-difluoro-N-[(3R,4S)-4-fluoro-1-[(2R)-3,3,3-trifluoro-2-hydroxy-2-methylpropanoyl]pyrrolidin-3-yl]benzamide;

5-[4-amino-5-(trifluoromethyl)pyrrolo[2,1-f][1,2,4]triazin-7-yl]-N-[(3R,4S)-1-cyclobutanecarbonyl-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(4-fluorobenzoyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(2-methylpropanoyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(3-methylbutanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(2,2-dimethylpropanoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(3,3,3-trifluoropropanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-cyclopentanecarbonyl-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-[1-(trifluoromethyl)cyclobutanecarbonyl]pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-[4,4,4-trifluoro-3-(trifluoromethyl)butanoyl]pyrrolidin-3-yl]-2-methylbenzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(4,4,4-trifluoro-3-methylbutanoyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-[4,4,4-trifluoro-3-hydroxy-3-(trifluoromethyl)butanoyl]pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(1-hydroxycyclopentanecarbonyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(1-hydroxycyclobutanecarbonyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(1-fluorocyclobutanecarbonyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(3,3,3-trifluoro-2,2-dimethylpropanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(2-chloro-4,5-difluorobenzoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(2-chloro-4-fluorobenzoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(2-chloro-3-fluorobenzoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(5-cyano-2-fluorobenzoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(2-methyl-1,3-thiazole-4-carbonyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(4-methyl-1,3-thiazole-2-carbonyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(3,4-difluorobenzoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(2,4,5-trifluorobenzoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(3,5-difluorobenzoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(3-fluoropyridine-2-carbonyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(4-chloropyridine-3-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(3,5-difluoropyridine-2-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(5-fluoro-2-methylpyridine-4-carbonyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(5-fluoropyridine-2-carbonyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(4-fluoropyridine-2-carbonyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(2,4,6-trifluorobenzoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(2-chlorobenzoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(2-chloro-6-fluorobenzoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(3-fluorobenzoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(4-chlorobenzoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(pyridine-2-carbonyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(pyridine-4-carbonyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(2,5-difluorobenzoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(2,6-difluorobenzoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(2,4-difluorobenzoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(1,3-thiazole-4-carbonyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(3-fluoropyridine-4-carbonyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(3,5-difluoropyridine-4-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(2,3-difluorobenzoyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(2-methylpyridine-4-carbonyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(3-chloropyridine-4-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(4-methylpyridine-2-carbonyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(2,5-dimethyl-1,3-thiazole-4-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(3-chloropyridine-2-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(6-methylpyridine-2-carbonyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-[5-(trifluoromethoxy)pyridine-2-carbonyl]pyrrolidin-3-yl]-2-methylbenzamide;

5-[4-amino-5-(trifluoromethyl)pyrrolo[2,1-f][1,2,4]triazin-7-yl]-N-[(3R,4S)-1-(6-bromopyridine-2-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(5-bromo-3-fluoropyridine-2-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-[3-(trifluoromethyl)pyridine-2-carbonyl]pyrrolidin-3-yl]-2-methylbenzamide;

5-[4-amino-5-(trifluoromethyl)pyrrolo[2,1-f][1,2,4]triazin-7-yl]-N-[(3R,4S)-1-(6-bromo-5-fluoropyridine-2-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-[6-(trifluoromethyl)pyridine-2-carbonyl]pyrrolidin-3-yl]-2-methylbenzamide;

5-[4-amino-5-(trifluoromethyl)pyrrolo[2,1-f][1,2,4]triazin-7-yl]-N-[(3R,4S)-1-(4-chloropyridine-2-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-[3-fluoro-5-(trifluoromethyl)pyridine-2-carbonyl]pyrrolidin-3-yl]-2-methylbenzamide;

5-[4-amino-5-(trifluoromethyl)pyrrolo[2,1-f][1,2,4]triazin-7-yl]-N-[(3R,4S)-1-(5-chloropyridine-2-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(6-chloropyridine-2-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-[6-chloro-3-(trifluoromethyl)pyridine-2-carbonyl]-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(3-bromopyridine-2-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-[4-(trifluoromethyl)pyridine-3-carbonyl]pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(4,4,4-trifluoro-3-hydroxy-3-methylbutanoyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-[2-hydroxy-2-(trifluoromethyl)butanoyl]pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(3,3,3-trifluoro-2-methylpropanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(2,3,3,3-tetrafluoro-2-methylpropanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(6-chloropyridazine-3-carbonyl)-4-fluoropyrrolidin-3-yl]-4-fluoro-2-methylbenzamide;

5-[4-amino-5-(trifluoromethyl)pyrrolo[2,1-f][1,2,4]triazin-7-yl]-4-fluoro-N-[(3R,4S)-4-fluoro-1-(pyridazine-3-carbonyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-(6-methylpyridazine-3-carbonyl)pyrrolidin-3-yl]-2-methylbenzamide;

5-[4-amino-5-(trifluoromethyl)pyrrolo[2,1-f][1,2,4]triazin-7-yl]-4-fluoro-N-[(3R,4S)-4-fluoro-1-[(2R)-3,3,3-trifluoro-2-hydroxy-2-methylpropanoyl]pyrrolidin-3-yl]-2-methoxybenzamide;

5-[4-amino-5-(trifluoromethyl)pyrrolo[2,1-f][1,2,4]triazin-7-yl]-4-fluoro-N-[(3R,4S)-4-fluoro-1-(2-fluoro-2-methylpropanoyl)pyrrolidin-3-yl]-2-methoxybenzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-4-fluoro-2-methoxybenzamide;

5-[4-amino-5-(trifluoromethyl)pyrrolo[2,1-f][1,2,4]triazin-7-yl]-4-fluoro-N-[(3R,4S)-4-fluoro-1-(3,3,3-trifluoro-2,2-dimethylpropanoyl)pyrrolidin-3-yl]-2-methoxybenzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-4-fluoro-2-methoxybenzamide;

5-[4-amino-5-(trifluoromethyl)pyrrolo[2,1-f][1,2,4]triazin-7-yl]-4-fluoro-N-[(3R,4S)-4-fluoro-1-(3-fluorocyclobutanecarbonyl)pyrrolidin-3-yl]-2-methoxybenzamide;

5-[4-amino-5-(trifluoromethyl)pyrrolo[2,1-f][1,2,4]triazin-7-yl]-4-fluoro-N-[(3R,4S)-4-fluoro-1-(4-fluorobenzoyl)pyrrolidin-3-yl]-2-methoxybenzamide;

5-[4-amino-5-(trifluoromethyl)pyrrolo[2,1-f][1,2,4]triazin-7-yl]-4-fluoro-N-[(3R,4S)-4-fluoro-1-(3,3,3-trifluoropropanoyl)pyrrolidin-3-yl]-2-methoxybenzamide;

5-[4-amino-5-(trifluoromethyl)pyrrolo[2,1-f][1,2,4]triazin-7-yl]-4-fluoro-N-[(3R,4S)-4-fluoro-1-(4,4,4-trifluoro-3-methylbutanoyl)pyrrolidin-3-yl]-2-methoxybenzamide;

5-[4-amino-5-(trifluoromethyl)pyrrolo[2,1-f][1,2,4]triazin-7-yl]-4-fluoro-N-[(3R,4S)-4-fluoro-1-[4,4,4-trifluoro-3-(trifluoromethyl)butanoyl]pyrrolidin-3-yl]-2-methoxybenzamide;

5-[4-amino-5-(trifluoromethyl)pyrrolo[2,1-f][1,2,4]triazin-7-yl]-4-fluoro-N-[(3R,4S)-4-fluoro-1-[2-hydroxy-2-(trifluoromethyl)butanoyl]pyrrolidin-3-yl]-2-methoxybenzamide;

5-[4-amino-5-(trifluoromethyl)pyrrolo[2,1-f][1,2,4]triazin-7-yl]-4-fluoro-N-[(3R,4S)-4-fluoro-1-(3,3,3-trifluoro-2-methylpropanoyl)pyrrolidin-3-yl]-2-methoxybenzamide;

5-[4-amino-5-(trifluoromethyl)pyrrolo[2,1-f][1,2,4]triazin-7-yl]-4-fluoro-N-[(3R,4S)-4-fluoro-1-(4,4,4-trifluoro-3-hydroxy-3-methylbutanoyl)pyrrolidin-3-yl]-2-methoxybenzamide;

5-[4-amino-5-(trifluoromethyl)pyrrolo[2,1-f][1,2,4]triazin-7-yl]-2-chloro-4-fluoro-N-[(3R,4S)-4-fluoro-1-[2-hydroxy-2-(trifluoromethyl)butanoyl]pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-(4,4,4-trifluoro-3-hydroxy-3-methylbutanoyl)pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-[4,4,4-trifluoro-3-(trifluoromethyl)butanoyl]pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-(4,4,4-trifluoro-3-methylbutanoyl)pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-(3,3,3-trifluoro-2-methylpropanoyl)pyrrolidin-3-yl]benzamide;

5-[4-amino-5-(trifluoromethyl)pyrrolo[2,1-f][1,2,4]triazin-7-yl]-2-chloro-4-fluoro-N-[(3R,4S)-4-fluoro-1-[4,4,4-trifluoro-3-hydroxy-3-(trifluoromethyl)butanoyl]pyrrolidin-3-yl]benzamide;

5-[4-amino-5-(trifluoromethyl)pyrrolo[2,1-f][1,2,4]triazin-7-yl]-2-chloro-N-[(3R,4S)-1-(3,3-difluorocyclopentanecarbonyl)-4-fluoropyrrolidin-3-yl]-4-fluorobenzamide;

5-[4-amino-5-(trifluoromethyl)pyrrolo[2,1-f][1,2,4]triazin-7-yl]-2-chloro-N-[(3R,4S)-1-(3,3-difluorocyclopentanecarbonyl)-4-fluoropyrrolidin-3-yl]-4-fluorobenzamide;

5-[4-amino-5-(trifluoromethyl)pyrrolo[2,1-f][1,2,4]triazin-7-yl]-2-chloro-4-fluoro-N-[(3R,4S)-4-fluoro-1-(3-fluorocyclobutanecarbonyl)pyrrolidin-3-yl]benzamide;

3-[4-amino-5-(trifluoromethyl)pyrrolo[2,1-f][1,2,4]triazin-7-yl]-4-fluoro-N-[(3R,4S)-4-fluoro-1-[2-hydroxy-2-(trifluoromethyl)butanoyl]pyrrolidin-3-yl]benzamide;

5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-(trifluoromethyl)benzamide;

5-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(fluoromethyl)benzamide;

5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-(fluoromethyl)benzamide;

5-[4-amino-5-(trifluoromethyl)pyrrolo[2,1-f][1,2,4]triazin-7-yl]-2-chloro-N-[(3R,4S)-4-fluoro-1-(3-fluorocyclobutanecarbonyl)pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-[4,4,4-trifluoro-3-(trifluoromethyl)butanoyl]pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-[2-hydroxy-2-(trifluoromethyl)butanoyl]pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(3,3,3-trifluoropropanoyl)pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(2-hydroxy-2-methylpropanoyl)pyrrolidin-3-yl]benzamide;

5-[4-amino-5-(trifluoromethyl)pyrrolo[2,1-f][1,2,4]triazin-7-yl]-2-chloro-N-[(3R,4S)-1-(3,3-difluorocyclopentanecarbonyl)-4-fluoropyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-[4,4,4-trifluoro-3-hydroxy-3-(trifluoromethyl)butanoyl]pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(2-fluorobenzoyl)pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(2-fluoro-2-methylpropanoyl)pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(1-fluorocyclopropanecarbonyl)pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-[(2R)-3,3,3-trifluoro-2-hydroxy-2-methylpropanoyl]pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(4,4,4-trifluoro-3-hydroxy-3-methylbutanoyl)pyrrolidin-3-yl]benzamide;

5-[4-amino-5-(trifluoromethyl)pyrrolo[2,1-f][1,2,4]triazin-7-yl]-2-chloro-N-[(3R,4S)-1-(2,2-difluorocyclopropanecarbonyl)-4-fluoropyrrolidin-3-yl]benzamide;

5-[4-amino-5-(trifluoromethyl)pyrrolo[2,1-f][1,2,4]triazin-7-yl]-2-chloro-N-[(3R,4S)-1-(4,4-difluorocyclohexanecarbonyl)-4-fluoropyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(3-methylbutanoyl)pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(3,3,3-trifluoro-2-methylpropanoyl)pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(4,4,4-trifluoro-3-methylbutanoyl)pyrrolidin-3-yl]benzamide;

5-[4-amino-5-(trifluoromethyl)pyrrolo[2,1-f][1,2,4]triazin-7-yl]-2-chloro-N-[(3R,4S)-1-(3,3-difluorocyclobutanecarbonyl)-4-fluoropyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-[4-(trifluoromethyl)pyridine-2-carbonyl]pyrrolidin-3-yl]benzamide;

5-[4-amino-5-(trifluoromethyl)pyrrolo[2,1-f][1,2,4]triazin-7-yl]-2-chloro-N-[(3R,4S)-1-(2,4-difluorobenzoyl)-4-fluoropyrrolidin-3-yl]benzamide;

5-[4-amino-5-(trifluoromethyl)pyrrolo[2,1-f][1,2,4]triazin-7-yl]-2-chloro-N-[(3R,4S)-1-(3,5-difluoropyridine-2-carbonyl)-4-fluoropyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(1,3-thiazole-4-carbonyl)pyrrolidin-3-yl]benzamide;

5-[4-amino-5-(trifluoromethyl)pyrrolo[2,1-f][1,2,4]triazin-7-yl]-2-chloro-N-[(3R,4S)-1-(4-chlorobenzoyl)-4-fluoropyrrolidin-3-yl]benzamide;

5-[4-amino-5-(trifluoromethyl)pyrrolo[2,1-f][1,2,4]triazin-7-yl]-2-chloro-N-[(3R,4S)-1-(3,4-difluorobenzoyl)-4-fluoropyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(3-fluoropyridine-2-carbonyl)pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(pyridine-4-carbonyl)pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(3-fluorobenzoyl)pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(4-fluorobenzoyl)pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-[4-(trifluoromethyl)pyridine-3-carbonyl]pyrrolidin-3-yl]benzamide;

5-[4-amino-5-(trifluoromethyl)pyrrolo[2,1-f][1,2,4]triazin-7-yl]-N-[(3R,4S)-1-benzoyl-4-fluoropyrrolidin-3-yl]-2-chlorobenzamide;

5-[4-amino-5-(trifluoromethyl)pyrrolo[2,1-f][1,2,4]triazin-7-yl]-2-chloro-N-[(3R,4S)-1-(3,5-difluoropyridine-4-carbonyl)-4-fluoropyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(pyridine-2-carbonyl)pyrrolidin-3-yl]benzamide;

5-[4-amino-5-(trifluoromethyl)pyrrolo[2,1-f][1,2,4]triazin-7-yl]-2-chloro-N-[(3R,4S)-1-(2,5-difluorobenzoyl)-4-fluoropyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(5-fluoropyridine-2-carbonyl)pyrrolidin-3-yl]benzamide;

5-[4-amino-5-(trifluoromethyl)pyrrolo[2,1-f][1,2,4]triazin-7-yl]-2-chloro-N-[(3R,4S)-1-(4-chloropyridine-3-carbonyl)-4-fluoropyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(2-methylpyridine-4-carbonyl)pyrrolidin-3-yl]benzamide;

5-[4-amino-5-(trifluoromethyl)pyrrolo[2,1-f][1,2,4]triazin-7-yl]-2-chloro-N-[(3R,4S)-4-fluoro-1-(3-fluoropyridine-4-carbonyl)pyrrolidin-3-yl]benzamide;

5-[4-amino-5-(trifluoromethyl)pyrrolo[2,1-f][1,2,4]triazin-7-yl]-2-chloro-N-[(3R,4S)-1-(4-chloropyridine-2-carbonyl)-4-fluoropyrrolidin-3-yl]benzamide;

5-[4-amino-5-(trifluoromethyl)pyrrolo[2,1-f][1,2,4]triazin-7-yl]-2-chloro-N-[(3R,4S)-1-(2-chlorobenzoyl)-4-fluoropyrrolidin-3-yl]benzamide;

5-[4-amino-5-(trifluoromethyl)pyrrolo[2,1-f][1,2,4]triazin-7-yl]-2-chloro-N-[(3R,4S)-1-(2,6-difluorobenzoyl)-4-fluoropyrrolidin-3-yl]benzamide;

5-[4-amino-5-(trifluoromethyl)pyrrolo[2,1-f][1,2,4]triazin-7-yl]-2-ethyl-N-[(3R,4S)-4-fluoro-1-(2-fluoro-2-methylpropanoyl)pyrrolidin-3-yl]benzamide;

5-[4-amino-5-(trifluoromethyl)pyrrolo[2,1-f][1,2,4]triazin-7-yl]-2-ethyl-N-[(3R,4S)-4-fluoro-1-[4,4,4-trifluoro-3-(trifluoromethyl)butanoyl]pyrrolidin-3-yl]benzamide;

5-[4-amino-5-(trifluoromethyl)pyrrolo[2,1-f][1,2,4]triazin-7-yl]-2-ethyl-N-[(3R,4S)-4-fluoro-1-[2-hydroxy-2-(trifluoromethyl)butanoyl]pyrrolidin-3-yl]benzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-ethylbenzamide;

5-[4-amino-5-(trifluoromethyl)pyrrolo[2,1-f][1,2,4]triazin-7-yl]-2-ethyl-N-[(3R,4S)-4-fluoro-1-(3-fluorocyclobutanecarbonyl)pyrrolidin-3-yl]benzamide;

5-[4-amino-5-(trifluoromethyl)pyrrolo[2,1-f][1,2,4]triazin-7-yl]-2-ethyl-N-[(3R,4S)-4-fluoro-1-(1-fluorocyclopropanecarbonyl)pyrrolidin-3-yl]benzamide;

5-[4-amino-5-(trifluoromethyl)pyrrolo[2,1-f][1,2,4]triazin-7-yl]-2-ethyl-N-[(3R,4S)-4-fluoro-1-(4,4,4-trifluoro-3-methylbutanoyl)pyrrolidin-3-yl]benzamide;

5-[4-amino-5-(trifluoromethyl)pyrrolo[2,1-f][1,2,4]triazin-7-yl]-2-ethyl-N-[(3R,4S)-4-fluoro-1-[4,4,4-trifluoro-3-hydroxy-3-(trifluoromethyl)butanoyl]pyrrolidin-3-yl]benzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-ethylbenzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-ethylbenzamide;

5-[4-amino-5-(trifluoromethyl)pyrrolo[2,1-f][1,2,4]triazin-7-yl]-2-ethyl-N-[(3R,4S)-4-fluoro-1-(4,4,4-trifluoro-3-hydroxy-3-methylbutanoyl)pyrrolidin-3-yl]benzamide;

5-[4-amino-5-(trifluoromethyl)pyrrolo[2,1-f][1,2,4]triazin-7-yl]-2-ethyl-N-[(3R,4S)-4-fluoro-1-[(2R)-3,3,3-trifluoro-2-hydroxy-2-methylpropanoyl]pyrrolidin-3-yl]benzamide;

5-[4-amino-5-(trifluoromethyl)pyrrolo[2,1-f][1,2,4]triazin-7-yl]-2-ethyl-N-[(3R,4S)-4-fluoro-1-(3,3,3-trifluoro-2-methylpropanoyl)pyrrolidin-3-yl]benzamide;

5-[4-amino-5-(trifluoromethyl)pyrrolo[2,1-f][1,2,4]triazin-7-yl]-2-ethyl-N-[(3R,4S)-4-fluoro-1-(3-methylbutanoyl)pyrrolidin-3-yl]benzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-ethylbenzamide;

5-[4-amino-5-(trifluoromethyl)pyrrolo[2,1-f][1,2,4]triazin-7-yl]-2-ethyl-N-[(3R,4S)-4-fluoro-1-(2-hydroxy-2-methylpropanoyl)pyrrolidin-3-yl]benzamide;

5-[4-amino-5-(trifluoromethyl)pyrrolo[2,1-f][1,2,4]triazin-7-yl]-2-ethyl-N-[(3R,4S)-4-fluoro-1-(3,3,3-trifluoropropanoyl)pyrrolidin-3-yl]benzamide;

5-[4-amino-5-(trifluoromethyl)pyrrolo[2,1-f][1,2,4]triazin-7-yl]-2-ethyl-N-[(3R,4S)-4-fluoro-1-(2-fluorobenzoyl)pyrrolidin-3-yl]benzamide;

5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-methylbenzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-methylbenzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-[4-(trifluoromethyl)pyridine-2-carbonyl]pyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-(4-fluorobenzoyl)pyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(3-fluorobenzoyl)pyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(1,3-thiazole-4-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-1-(3,5-difluoropyridine-4-carbonyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(3-fluoropyridine-4-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-1-(3,5-difluoropyridine-2-carbonyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-1-(3,4-difluorobenzoyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-[4-(trifluoromethyl)pyridine-3-carbonyl]pyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(3-fluoropyridine-2-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-1-(4-chlorobenzoyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(5-fluoropyridine-2-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-1-(4-chloropyridine-3-carbonyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-1-(2,6-difluorobenzoyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-1-(4-chloropyridine-2-carbonyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-1-(2,5-difluorobenzoyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-1-benzoyl-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(pyridine-4-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(pyridine-2-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-1-(2-chlorobenzoyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(2-methylpyridine-4-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-1-(2,4-difluorobenzoyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(4-methylpyridine-2-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(2,4,6-trifluorobenzoyl)pyrrolidin-3-yl]-2-methylbenzamide;
5-[4-amino-5-(trifluoromethyl)pyrrolo[2,1-f][1,2,4]triazin-7-yl]-N-[(3R,4S)-1-(2-chloro-4,5-difluorobenzoyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(2,4,5-trifluorobenzoyl)pyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(2-methoxypyridine-3-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(1-methyl-1H-imidazole-4-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-1-(3,5-difluorobenzoyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-1-(1-cyclopropyl-1H-1,2,3-triazole-4-carbonyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-[6-(trifluoromethyl)pyridine-3-carbonyl]pyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(1-methyl-1H-pyrazole-4-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-1-(1,3-dimethyl-1H-pyrazole-5-carbonyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-1-(2-chloro-3-fluorobenzoyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-1-(5-cyano-2-fluorobenzoyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(2-methanesulfonylbenzoyl)pyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(4-fluoropyridine-2-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-1-(3-chloropyridine-4-carbonyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-1-(2,3-difluorobenzoyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(2-methyl-1,3-oxazole-4-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-1-(2-chloro-6-fluorobenzoyl)-4-fluoropyrrolidin-3-yl]-2-methylbenzamide;
5-[4-amino-5-(trifluoromethyl)pyrrolo[2,1-f][1,2,4]triazin-7-yl]-N-[(3R,4S)-4-fluoro-1-(5-fluoro-2-methylpyridine-4-carbonyl)pyrrolidin-3-yl]-2-methylbenzamide;
5-[4-amino-5-(trifluoromethyl)pyrrolo[2,1-f][1,2,4]triazin-7-yl]-N-[(3R,4S)-1-(2-chloro-4-fluorobenzoyl)-4-fluoropyrrolidin-3-yl]-2-methylbenzamide;

5-[4-amino-5-(trifluoromethyl)pyrrolo[2,1-f][1,2,4]triazin-7-yl]-N-[(3R,4S)-1-(2-cyclopentylacetyl)-4-fluoropyrrolidin-3-yl]-2-methylbenzamide;

5-[4-amino-5-(trifluoromethyl)pyrrolo[2,1-f][1,2,4]triazin-7-yl]-N-[(3R,4S)-1-[2-(3,3-difluorocyclobutyl)acetyl]-4-fluoropyrrolidin-3-yl]-2-methylbenzamide;

5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-(trifluoromethoxy)benzamide;

5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-(2,2,2-trifluoroethoxy)benzamide;

5-[4-amino-5-(trifluoromethyl)pyrrolo[2,1-f][1,2,4]triazin-7-yl]-N-[(3R,4S)-4-fluoro-1-[4,4,4-trifluoro-3- hydroxy-3-(trifluoromethyl)butanoyl]pyrrolidin-3-yl]-2-(2,2,2-trifluoroethoxy)benzamide;

5-[4-amino-5-(trifluoromethyl)pyrrolo[2,1-f][1,2,4]triazin-7-yl]-2-(difluoromethoxy)-N-[(3R,4S)-4-fluoro-1-(1-fluorocyclopropanecarbonyl)pyrrolidin-3-yl]benzamide;

5-[4-amino-5-(trifluoromethyl)pyrrolo[2,1-f][1,2,4]triazin-7-yl]-2-(difluoromethoxy)-N-[(3R,4S)-4-fluoro-1-[(2R)-3,3,3-trifluoro-2-hydroxy-2-methylpropanoyl]pyrrolidin-3-yl]benzamide;

5-[4-amino-5-(trifluoromethyl)pyrrolo[2,1-f][1,2,4]triazin-7-yl]-2-(difluoromethoxy)-N-[(3R,4S)-4-fluoro-1-[4,4,4-trifluoro-3-(trifluoromethyl)butanoyl]pyrrolidin-3-yl]benzamide;

5-[4-amino-5-(trifluoromethyl)pyrrolo[2,1-f][1,2,4]triazin-7-yl]-2-(difluoromethoxy)-N-[(3R,4S)-4-fluoro-1-(3,3,3-trifluoropropanoyl)pyrrolidin-3-yl]benzamide;

5-[4-amino-5-(trifluoromethyl)pyrrolo[2,1-f][1,2,4]triazin-7-yl]-2-(difluoromethoxy)-N-[(3R,4S)-4-fluoro-1-(3-methylbutanoyl)pyrrolidin-3-yl]benzamide;

5-[4-amino-5-(trifluoromethyl)pyrrolo[2,1-f][1,2,4]triazin-7-yl]-2-(difluoromethoxy)-N-[(3R,4S)-4-fluoro-1-(4,4,4-trifluoro-3-methylbutanoyl)pyrrolidin-3-yl]benzamide;

5-[4-amino-5-(trifluoromethyl)pyrrolo[2,1-f][1,2,4]triazin-7-yl]-2-(difluoromethoxy)-N-[(3R,4S)-4-fluoro-1-(2-hydroxy-2-methylpropanoyl)pyrrolidin-3-yl]benzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-(difluoromethoxy)benzamide;

5-[4-amino-5-(trifluoromethyl)pyrrolo[2,1-f][1,2,4]triazin-7-yl]-2-(difluoromethoxy)-N-[(3R,4S)-4-fluoro-1-(3-fluorocyclobutanecarbonyl)pyrrolidin-3-yl]benzamide;

5-[4-amino-5-(trifluoromethyl)pyrrolo[2,1-f][1,2,4]triazin-7-yl]-2-(difluoromethoxy)-N-[(3R,4S)-4-fluoro-1-[4,4,4-trifluoro-3-hydroxy-3-(trifluoromethyl)butanoyl]pyrrolidin-3-yl]benzamide;

5-[4-amino-5-(trifluoromethyl)pyrrolo[2,1-f][1,2,4]triazin-7-yl]-2-(difluoromethoxy)-N-[(3R,4S)-4-fluoro-1-(2-fluorobenzoyl)pyrrolidin-3-yl]benzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-(difluoromethoxy)benzamide;

5-[4-amino-5-(trifluoromethyl)pyrrolo[2,1-f][1,2,4]triazin-7-yl]-2-(difluoromethoxy)-N-[(3R,4S)-4-fluoro-1-(4,4,4-trifluoro-3-hydroxy-3-methylbutanoyl)pyrrolidin-3-yl]benzamide;

5-[4-amino-5-(trifluoromethyl)pyrrolo[2,1-f][1,2,4]triazin-7-yl]-2-(difluoromethoxy)-N-[(3R,4S)-4-fluoro-1-(2-fluoro-2-methylpropanoyl)pyrrolidin-3-yl]benzamide;

5-[4-amino-5-(trifluoromethyl)pyrrolo[2,1-f][1,2,4]triazin-7-yl]-2-(difluoromethoxy)-N-[(3R,4S)-4-fluoro-1-(3,3,3-trifluoro-2-methylpropanoyl)pyrrolidin-3-yl]benzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-(difluoromethoxy)benzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-(difluoromethoxy)benzamide;

5-[4-amino-5-(trifluoromethyl)pyrrolo[2,1-f][1,2,4]triazin-7-yl]-2-(difluoromethoxy)-N-[(3R,4S)-4-fluoro-1-[2-hydroxy-2-(trifluoromethyl)butanoyl]pyrrolidin-3-yl]benzamide;

5-[4-amino-5-(trifluoromethyl)pyrrolo[2,1-f][1,2,4]triazin-7-yl]-2-ethoxy-N-[(3R,4S)-4-fluoro-1-(3,3,3-trifluoropropanoyl)pyrrolidin-3-yl]benzamide;

5-[4-amino-5-(trifluoromethyl)pyrrolo[2,1-f][1,2,4]triazin-7-yl]-2-ethoxy-N-[(3R,4S)-4-fluoro-1-(4,4,4-trifluoro-3-hydroxy-3-methylbutanoyl)pyrrolidin-3-yl]benzamide;

5-[4-amino-5-(trifluoromethyl)pyrrolo[2,1-f][1,2,4]triazin-7-yl]-2-ethoxy-N-[(3R,4S)-4-fluoro-1-(2-fluorobenzoyl)pyrrolidin-3-yl]benzamide;

5-[4-amino-5-(trifluoromethyl)pyrrolo[2,1-f][1,2,4]triazin-7-yl]-2-ethoxy-N-[(3R,4S)-4-fluoro-1-(2-hydroxy-2-methylpropanoyl)pyrrolidin-3-yl]benzamide;

5-[4-amino-5-(trifluoromethyl)pyrrolo[2,1-f][1,2,4]triazin-7-yl]-2-ethoxy-N-[(3R,4S)-4-fluoro-1-(4,4,4-trifluoro-3-methylbutanoyl)pyrrolidin-3-yl]benzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-ethoxybenzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-ethoxybenzamide;

5-[4-amino-5-(trifluoromethyl)pyrrolo[2,1-f][1,2,4]triazin-7-yl]-2-ethoxy-N-[(3R,4S)-4-fluoro-1-(1-fluorocyclopropanecarbonyl)pyrrolidin-3-yl]benzamide;

5-[4-amino-5-(trifluoromethyl)pyrrolo[2,1-f][1,2,4]triazin-7-yl]-2-ethoxy-N-[(3R,4S)-4-fluoro-1-(2-fluoro-2-methylpropanoyl)pyrrolidin-3-yl]benzamide;

5-[4-amino-5-(trifluoromethyl)pyrrolo[2,1-f][1,2,4]triazin-7-yl]-2-ethoxy-N-[(3R,4S)-4-fluoro-1-[4,4,4-trifluoro-3-hydroxy-3-(trifluoromethyl)butanoyl]pyrrolidin-3-yl]benzamide;

5-[4-amino-5-(trifluoromethyl)pyrrolo[2,1-f][1,2,4]triazin-7-yl]-2-ethoxy-N-[(3R,4S)-4-fluoro-1-[(2R)-3,3,3-trifluoro-2-hydroxy-2-methylpropanoyl]pyrrolidin-3-yl]benzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-ethoxybenzamide;

5-[4-amino-5-(trifluoromethyl)pyrrolo[2,1-f][1,2,4]triazin-7-yl]-2-ethoxy-N-[(3R,4S)-4-fluoro-1-[2-hydroxy-2-(trifluoromethyl)butanoyl]pyrrolidin-3-yl]benzamide;

5-[4-amino-5-(trifluoromethyl)pyrrolo[2,1-f][1,2,4]triazin-7-yl]-2-ethoxy-N-[(3R,4S)-4-fluoro-1-[4,4,4-trifluoro-3-(trifluoromethyl)butanoyl]pyrrolidin-3-yl]benzamide;

5-[4-amino-5-(trifluoromethyl)pyrrolo[2,1-f][1,2,4]triazin-7-yl]-2-ethoxy-N-[(3R,4S)-4-fluoro-1-(3,3,3-trifluoro-2-methylpropanoyl)pyrrolidin-3-yl]benzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-ethoxybenzamide;

5-[4-amino-5-(trifluoromethyl)pyrrolo[2,1-f][1,2,4]triazin-7-yl]-2-ethoxy-N-[(3R,4S)-4-fluoro-1-(3-methylbutanoyl)pyrrolidin-3-yl]benzamide;

5-[4-amino-5-(trifluoromethyl)pyrrolo[2,1-f][1,2,4]triazin-7-yl]-2-ethoxy-N-[(3R,4S)-4-fluoro-1-(3-fluorocyclobutanecarbonyl)pyrrolidin-3-yl]benzamide;

5-[4-amino-5-(trifluoromethyl)pyrrolo[2,1-f][1,2,4]triazin-7-yl]-2-ethoxy-N-[(3R,4S)-4-fluoro-1-(3-fluorocyclobutanecarbonyl)pyrrolidin-3-yl]benzamide;

5-[4-amino-5-(trifluoromethyl)pyrrolo[2,1-f][1,2,4]triazin-7-yl]-N-[(3R,4S)-4-fluoro-1-(2-hydroxy-2-methylpropanoyl)pyrrolidin-3-yl]-2-methoxybenzamide;

5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2-methoxybenzamide;

5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-methoxybenzamide;

5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2-methoxybenzamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-methoxybenzamide;

5-[4-amino-5-(trifluoromethyl)pyrrolo[2,1-f][1,2,4]triazin-7-yl]-N-[(3R,4S)-4-fluoro-1-(3,3,3-trifluoropropanoyl)pyrrolidin-3-yl]-2-methoxybenzamide;

5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-methoxybenzamide;

5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-methoxybenzamide;

5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2-methoxybenzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2-methoxybenzamide;

5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-methoxybenzamide;

5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2-methoxybenzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-methoxybenzamide;

5-[4-amino-5-(trifluoromethyl)pyrrolo[2,1-f][1,2,4]triazin-7-yl]-N-[(3R,4S)-1-(4,4-difluorocyclohexanecarbonyl)-4-fluoropyrrolidin-3-yl]-2-methoxybenzamide;

5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-methoxybenzamide;

5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-methoxybenzamide;

5-[4-amino-5-(trifluoromethyl)pyrrolo[2,1-f][1,2,4]triazin-7-yl]-N-[(3R,4S)-1-(2,2-difluorocyclopropanecarbonyl)-4-fluoropyrrolidin-3-yl]-2-methoxybenzamide;

5-[4-amino-5-(trifluoromethyl)pyrrolo[2,1-f][1,2,4]triazin-7-yl]-N-[(3R,4S)-4-fluoro-1-(3-fluorocyclobutanecarbonyl)pyrrolidin-3-yl]-2-methoxybenzamide;

3-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]benzamide;

5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-(methylamino)benzamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2-(methylamino)benzamide;

5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-(methylamino)benzamide;

5-[4-amino-5-(trifluoromethyl)pyrrolo[2,1-f][1,2,4]triazin-7-yl]-N-[(3R,4S)-4-fluoro-1-(1-fluorocyclopropanecarbonyl)pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-(2-fluoro-2-methylpropanoyl)pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-1-(2,4-difluorobenzoyl)-4-fluoropyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-hydroxy-2-methylpropanoyl]pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-1-(2-chlorobenzoyl)-4-fluoropyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-1-(3,5-difluoropyridine-4-carbonyl)-4-fluoropyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-1-benzoyl-4-fluoropyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-(2-fluorobenzoyl)pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-(3-fluorobenzoyl)pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-(3-fluoropyridine-4-carbonyl)pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-(3-methylbutanoyl)pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-1-(2,5-difluorobenzoyl)-4-fluoropyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-1-(3,4-difluorobenzoyl)-4-fluoropyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-1-(2,6-difluorobenzoyl)-4-fluoropyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2,6-dimethylpyridine-3-carboxamide;

5-[4-amino-5-(trifluoromethyl)pyrrolo[2,1-f][1,2,4]triazin-7-yl]-N-[(3R,4S)-1-[2-(3,3-difluorocyclobutyl)acetyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(2-cyclopentylacetyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(2-cyclobutylacetyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[2-(2,2-difluorocyclopropyl)acetyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(2-cyclopropylacetyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[2-(1-methylcyclopropyl)acetyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[2-(1-hydroxycyclohexyl)acetyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(6-methoxypyrazine-2-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(pyridazine-3-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-methoxypyrimidine-5-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(6-methylpyrazine-2-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(5-methylpyrazine-2-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-methylpyrimidine-5-carbonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(6-chloropyridazine-4-carbonyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(2-cyclohexylacetyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[2-(2,2-difluoroethoxy)-2-methylpropanoyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[2-(tert-butoxy)acetyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(2S)-3,3,3-trifluoro-2-methoxy-2-phenylpropanoyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-{spiro[2.2]pentane-1-carbonyl}pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2,2,2-trifluoroacetyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2,3,3,3-tetrafluoro-2-methylpropanoyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(2R)-3,3,3-trifluoro-2-methoxy-2-methylpropanoyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[2-hydroxy-2-(trifluoromethyl)butanoyl]pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(4,4,4-trifluoro-3-methylbutanoyl)pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-[4,4,4-trifluoro-3-(trifluoromethyl)butanoyl]pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(4,4,4-trifluoro-3-hydroxy-3-methylbutanoyl)pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-(3,3,3-trifluoro-2-methylpropanoyl)pyrrolidin-3-yl]-2-methylpyridine-3-carboxamide;

5-[4-amino-5-(trifluoromethyl)pyrrolo[2,1-f][1,2,4]triazin-7-yl]-N-[(3R,4S)-4-fluoro-1-[4,4,4-trifluoro-3-hydroxy-3-(trifluoromethyl)butanoyl]pyrrolidin-3-yl]-2-methylpyridine-3-carboxamide;

3-[4-amino-5-(trifluoromethyl)pyrrolo[2,1-f][1,2,4]triazin-7-yl]-5-fluoro-N-[(3R,4S)-4-fluoro-1-[(2R)-3,3,3-trifluoro-2-hydroxy-2-methylpropanoyl]pyrrolidin-3-yl]benzamide;

3-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-5-fluorobenzamide;

3-[4-amino-5-(trifluoromethyl)pyrrolo[2,1-f][1,2,4]triazin-7-yl]-5-fluoro-N-[(3R,4S)-4-fluoro-1-[2-hydroxy-2-(trifluoromethyl)butanoyl]pyrrolidin-3-yl]benzamide;

5-[4-amino-5-(trifluoromethyl)pyrrolo[2,1-f][1,2,4]triazin-7-yl]-3-fluoro-N-[(3R,4S)-4-fluoro-1-{spiro[2.2]pentane-1-carbonyl}pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-(4,4,4-trifluoro-3-hydroxy-3-methylbutanoyl)pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-(3,3,3-trifluoro-2-methylpropanoyl)pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-[4,4,4-trifluoro-3-(trifluoromethyl)butanoyl]pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-[2-hydroxy-2-(trifluoromethyl)butanoyl]pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-(pyridine-3-carbonyl)pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-(3-fluoropyridine-4-carbonyl)pyrrolidin-3-yl]-2-methylbenzamide;

5-[4-amino-5-(trifluoromethyl)pyrrolo[2,1-f][1,2,4]triazin-7-yl]-3-fluoro-N-[(3R,4S)-4-fluoro-1-(5-fluoropyridine-3-carbonyl)pyrrolidin-3-yl]-2-methylbenzamide;

5-[4-amino-5-(trifluoromethyl)pyrrolo[2,1-f][1,2,4]triazin-7-yl]-N-[(3R,4S)-1-(3,5-difluoropyridine-4-carbonyl)-4-fluoropyrrolidin-3-yl]-3-fluoro-2-methylbenzamide;

5-[4-amino-5-(trifluoromethyl)pyrrolo[2,1-f][1,2,4]triazin-7-yl]-2-chloro-3-fluoro-N-[(3R,4S)-4-fluoro-1-[2-hydroxy-2-(trifluoromethyl)butanoyl]pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-[(2R)-3,3,3-trifluoro-2-hydroxy-2-methylpropanoyl]pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-(3,3,3-trifluoro-2-methylpropanoyl)pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-(3,3,3-trifluoro-2-methylpropanoyl)pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-(4,4,4-trifluoro-3-methylbutanoyl)pyrrolidin-3-yl]benzamide;

5-[4-amino-5-(trifluoromethyl)pyrrolo[2,1-f][1,2,4]triazin-7-yl]-2-chloro-3-fluoro-N-[(3R,4S)-4-fluoro-1-(4,4,4-trifluoro-3-methylbutanoyl)pyrrolidin-3-yl]benzamide;

5-[4-amino-5-(trifluoromethyl)pyrrolo[2,1-f][1,2,4]triazin-7-yl]-2,3-difluoro-N-[(3R,4S)-4-fluoro-1-[(2R)-3,3,3-trifluoro-2-hydroxy-2-methylpropanoyl]pyrrolidin-3-yl]benzamide;

5-[4-amino-5-(trifluoromethyl)pyrrolo[2,1-f][1,2,4]triazin-7-yl]-N-[(3R,4S)-1-(3,3-difluorocyclopentanecarbonyl)-4-fluoropyrrolidin-3-yl]-2,3-difluorobenzamide;

5-[4-amino-5-(trifluoromethyl)pyrrolo[2,1-f][1,2,4]triazin-7-yl]-2,3-difluoro-N-[(3R,4S)-4-fluoro-1-(4,4,4-trifluoro-3-hydroxy-3-methylbutanoyl)pyrrolidin-3-yl]benzamide;

5-[4-amino-5-(trifluoromethyl)pyrrolo[2,1-f][1,2,4]triazin-7-yl]-2,3-difluoro-N-[(3R,4S)-4-fluoro-1-(3,3,3-trifluoro-2-methylpropanoyl)pyrrolidin-3-yl]benzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2,3-difluorobenzamide;

5-[4-amino-5-(trifluoromethyl)pyrrolo[2,1-f][1,2,4]triazin-7-yl]-2,3-difluoro-N-[(3R,4S)-4-fluoro-1-[2-hydroxy-2-(trifluoromethyl)butanoyl]pyrrolidin-3-yl]benzamide;

5-[4-amino-5-(trifluoromethyl)pyrrolo[2,1-f][1,2,4]triazin-7-yl]-N-[(3R,4S)-1-(3,3-difluorocyclobutanecarbonyl)-4-fluoropyrrolidin-3-yl]-2-ethyl-3-fluorobenzamide;

5-[4-amino-5-(trifluoromethyl)pyrrolo[2,1-f][1,2,4]triazin-7-yl]-N-[1-(3,3-difluorocyclobutanecarbonyl)-4,4-difluoropyrrolidin-3-yl]-2-methoxypyridine-3-carboxamide;

5-(4-amino-5-(trifluoromethyl)pyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-methoxy-N-methylnicotinamide;

5-(4-amino-5-(trifluoromethyl)pyrrolo[2,1-f][1,2,4]triazin-7-yl)-N-((3R,4S)-4-fluoro-1-((R)-3,3,3-trifluoro-2-methoxy-2-methylpropanoyl)pyrrolidin-3-yl)-2-methoxy-N-methylnicotinamide;

5-(4-Amino-5-(trifluoromethyl)pyrrolo[2,1-f][1,2,4]triazin-7-yl)-N-((3R,4S)-4-fluoro-1-(3-methyl-2,3-dihydro-1H-inden-1-yl)pyrrolidin-3-yl)-2-methoxynicotinamide;

5-[4-amino-5-(trifluoromethyl)pyrrolo[2,1-f][1,2,4]triazin-7-yl]-N-[(3R,4S)-1-(2,3-dihydro-1H-inden-1-yl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(4-fluoro-2,3-dihydro-1H-inden-1-yl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(5-fluoro-2,3-dihydro-1H-inden-1-yl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-{6,7,8,9-tetrahydro-5H-benzo[7]annulen-5-yl}pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(4-methyl-1,2,3,4-tetrahydronaphthalen-1-yl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(5-bromo-1,2,3,4-tetrahydronaphthalen-1-yl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(7-chloro-2,3-dihydro-1H-inden-1-yl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(1,2,3,4-tetrahydronaphthalen-1-yl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[2-(2,2,2-trifluoro-1-hydroxyethyl)cyclopentyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-methylcyclopentyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-{5H,6H,7H-cyclopenta[b]pyridin-5-yl}-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(2,2-dimethylcyclopentyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[2-(2,2-difluoro-1-hydroxyethyl)cyclopentyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-methyl-2,3-dihydro-1H-inden-1-yl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(6-fluoro-2,3-dihydro-1H-inden-1-yl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(2-methoxyphenyl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(2-methoxyphenyl)ethyl]pyrrolidin-3-yl]-2-methoxypyridine-3-carboxamide;

methyl 2-[(3R,4S)-3-{5-[4-amino-5-(trifluoromethyl)pyrrolo[2,1-f][1,2,4]triazin-7-yl]-2-methoxypyridine-3-amido}-4-fluoropyrrolidin-1-yl]cyclopentane-1-carboxylate;

5-[4-amino-5-(trifluoromethyl)pyrrolo[2,1-f][1,2,4]triazin-7-yl]-N-[(3R,4S)-1-[2-(2,2-difluoro-1-hydroxyethyl)cyclopentyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[2-(2,2-difluoro-1-hydroxyethyl)cyclopentyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[2-(2,2,2-trifluoro-1-hydroxyethyl)cyclopentyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[2-(2,2,2-trifluoro-1-hydroxyethyl)cyclopentyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[2-(2,2,2-trifluoro-1-hydroxyethyl)cyclopentyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-methylcyclopentyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(2,2-dimethylcyclopentyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(6-oxo-1,6-dihydropyridin-2-yl)methyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(5,5,5-trifluoro-4-hydroxypentan-2-yl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(3,3-difluorocyclopentyl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(5,5,5-trifluoro-4-hydroxy-4-phenylpentan-2-yl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[5,5,5-trifluoro-4-hydroxy-4-(trifluoromethyl)pentan-2-yl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(3,3-difluorocyclopentyl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(5,5,5-trifluoro-4-hydroxypentan-2-yl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(2,3-difluoropyridin-4-yl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(2,6-difluoropyridin-4-yl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(pyrimidin-5-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(2,4,6-trifluorophenyl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-{1-[4-(trifluoromethyl)phenyl]ethyl}pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(2-hydroxyphenyl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(3,5-difluoro-2-hydroxyphenyl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-{1-[3-(trifluoromethoxy)phenyl]ethyl}pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(pyrimidin-5-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(2,4-dimethylpyrimidin-5-yl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(2-chloro-4-methyl-1,3-thiazol-5-yl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(2,5-dibromo-1,3-thiazol-4-yl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(4-chloro-1,3-thiazol-2-yl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(2-methyl-1,3-thiazol-5-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(3,5-dimethyl-1,2-oxazol-4-yl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[1-(1,3-thiazol-4-yl)ethyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(3,5-dimethyl-1,2-oxazol-4-yl)ethyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[1-(2,4-dimethyl-1,3-thiazol-5-yl)ethyl]-4-fluoropyrrolidin-3-yl]-2-methoxypyridine-3-carboxamide;

5-(4-Amino-5-(trifluoromethyl)pyrrolo[2,1-f][1,2,4]triazin-7-yl)-N-((3R,4S)-4-fluoro-1-(3-hydroxy-2,3-dimethylbutan-2-yl)pyrrolidin-3-yl)-2-methoxynicotinamide;

5-[4-amino-5-(trifluoromethyl)pyrrolo[2,1-f][1,2,4]triazin-7-yl]-N-[(3R,4S)-4-fluoro-1-(2-hydroxycyclopentyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-hydroxy-3-methylbutan-2-yl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-hydroxy-2-methylcyclopentyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-hydroxybutan-2-yl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-hydroxy-2-methylcyclohexyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-hydroxybutan-2-yl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-hydroxy-2-methylcyclopentyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-hydroxybutan-2-yl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-hydroxy-2-methylcyclohexyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-hydroxy-3-methylbutan-2-yl)pyrrolidin-3-yl]-2-methoxypyridine-3-carboxamide;

Methyl (3R,4S)-3-(5-(4-amino-5-(trifluoromethyl)pyrrolo[2,1-f][1,2,4]triazin-7-yl)-2-methoxynicotinamido)-4-fluoropyrrolidine-1-carboxylate;

2,2,3,3-Tetrafluorocyclobutyl (3R,4S)-3-(5-(4-amino-5-(trifluoromethyl)pyrrolo[2,1-f][1,2,4]triazin-7-yl)-2-methoxynicotinamido)-4-fluoropyrrolidine-1-carboxylate;

(R)-1-Hydroxy-4-methylpentan-2-yl (3R,4S)-3-(5-(4-amino-5-(trifluoromethyl)pyrrolo[2,1-f][1,2,4]triazin-7-yl)-2-methoxynicotinamido)-4-fluoropyrrolidine-1-carboxylate;

2-methoxyethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

propyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

phenyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

ethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

butyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

butan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

2-methylpropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

prop-2-en-1-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

2,2-dimethylpropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

3-methylbutan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

1-methoxypropan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

2,2-difluoroethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

cyclobutylmethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

2-ethoxyethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

[1,1'-bi(cyclopropane)]-1-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

cyclopentyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

prop-2-yn-1-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

1-methylcyclopropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

2,2,2-trifluoroethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

but-2-yn-1-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

cyclopropylmethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

but-3-en-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

4,4,4-trifluorobutan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

cyclohexyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

propan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

3,3,3-trifluoropropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

3-fluoropropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

1,1,1-trifluoropropan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

cyclopropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

cyclobutyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

(2S)-1-hydroxypropan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

(2R)-1-hydroxypropan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

(2S)-2-hydroxypropyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

(2R)-1-cyclopropyl-3-hydroxypropan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

2-hydroxyethyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

3,3-difluorocyclobutyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

1,1,1,3,3,3-hexafluoropropan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

3,3,4,4,4-pentafluorobutan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

(2,2-difluorocyclopropyl)methyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

3,3,4,4,4-pentafluorobutan-2-yl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

(2,2-difluorocyclopropyl)methyl (3R,4S)-3-{5-[4-amino-5-(trifluoromethyl)pyrrolo[2,1-f][1,2,4]triazin-7-yl]-2-methoxypyridine-3-amido}-4-fluoropyrrolidine-1-carboxylate;

5-(4-Amino-5-(trifluoromethyl)pyrrolo[2,1-f][1,2,4]triazin-7-yl)-N-((3R,4S)-4-fluoro-1-(isopropylsulfonyl)pyrrolidin-3-yl)-2-methoxynicotinamide;

5-[4-amino-5-(trifluoromethyl)pyrrolo[2,1-f][1,2,4]triazin-7-yl]-N-[(3R,4S)-1-(cyclopropanesulfonyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(cyclohexanesulfonyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(cyclopentanesulfonyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-methylbutane-2-sulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(4-methylpentane-2-sulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(1,1,1-trifluoropropane-2-sulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2,2,2-trifluoroethanesulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(Z)-2-fluoroethanesulfonyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(3,4-dimethylbenzenesulfonyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(2,5-dimethoxybenzenesulfonyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(naphthalene-1-sulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-phenylmethanesulfonylpyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(3-methylphenyl)methanesulfonyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-methoxybenzenesulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-methoxy-5-methylbenzenesulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2-methylbenzenesulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3-methylbenzenesulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(4-methylbenzenesulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(oxolane-3-sulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-{bicyclo[2.2.1]heptane-2-sulfonyl}-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[(1,1-dioxidotetrahydrothiophen-3-yl)sulfonyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(butane-1-sulfonyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(2-hydroxycyclohexyl)sulfonyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(3,3,3-trifluoropropanesulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(oxane-4-sulfonyl)pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-(cyclohex-1-ene-1-sulfonyl)-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(2-nitrophenyl)methanesulfonyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(4-fluorophenyl)methanesulfonyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[(2,5-difluorophenyl)methanesulfonyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(3-fluorophenyl)methanesulfonyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[(3-chlorophenyl)methanesulfonyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[(2,6-dichlorophenyl)methanesulfonyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-1-[(2-chlorophenyl)methanesulfonyl]-4-fluoropyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(pyridin-2-yl)methanesulfonyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(3-nitrophenyl)methanesulfonyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-{[2-(trifluoromethyl)phenyl]methanesulfonyl}pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-[(2-fluorophenyl)methanesulfonyl]pyrrolidin-3-yl]-2-methoxypyridine-3-carboxamide;

5-[4-amino-5-(trifluoromethyl)pyrrolo[2,1-f][1,2,4]triazin-7-yl]-N-[(3R,4S)-4-fluoro-1-(2,2,2-trifluoro-1-phenylethanesulfonyl)pyrrolidin-3-yl]-2-methoxypyridine-3-carboxamide;

N-((3R,4S)-1-(2-Amino-2-(trifluoromethyl)pentanoyl)-4-fluoropyrrolidin-3-yl)-5-(4-amino-5-(trifluoromethyl)pyrrolo[2,1-f][1,2,4]triazin-7-yl)-2-methoxynicotinamide;

5-(4-Amino-5-(trifluoromethyl)pyrrolo[2,1-f][1,2,4]triazin-7-yl)-N-((3R,4S)-4-fluoro-1-(3-hydroxy-3-(trifluoromethyl)cyclobutane-1-carbonyl)pyrrolidin-3-yl)-2-methoxynicotinamide;

5-[4-amino-5-(trifluoromethyl)pyrrolo[2,1-f][1,2,4]triazin-7-yl]-N-[1-(2,2-difluorocyclopropanecarbonyl)-4-fluoropiperidin-3-yl]-2-methoxypyridine-3-carboxamide;

5-[4-amino-5-(trifluoromethyl)pyrrolo[2,1-f][1,2,4]triazin-7-yl]-N-[(3S,4R)-4-fluoro-1-[(2R)-3,3,3-trifluoro-2-hydroxy-2-methylpropanoyl]piperidin-3-yl]-2-methoxypyridine-3-carboxamide;

5-{4-aminopyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide;

5-{4-amino-6-fluoropyrrolo[2,1-f][1,2,4]triazin-7-yl}-N-[(3R,4S)-4-fluoro-1-[(2R)-3,3,3-trifluoro-2-hydroxy-2-methylpropanoyl]pyrrolidin-3-yl]-2-methoxypyridine-3-carboxamide;

5-(4-amino-5-(trifluoromethyl)pyrrolo[2,1-f][1,2,4]triazin-7-yl)-N-((3R,4S)-4-fluoro-1-(thiazole-5-carbonyl)pyrrolidin-3-yl)-2-methoxynicotinamide;

5-(4-amino-5-(trifluoromethyl)pyrrolo[2,1-f][1,2,4]triazin-7-yl)-N-((3R,4S)-1-(2-chlorothiazole-5-carbonyl)-4-fluoropyrrolidin-3-yl)-2-methoxynicotinamide;

N-((3R,4S)-1-(2-amino-2-(trifluoromethyl)pentanoyl)-4-fluoropyrrolidin-3-yl)-5-(4-amino-5-(trifluoromethyl)pyrrolo[2,1-f][1,2,4]triazin-7-yl)-2-methoxynicotinamide;

tert-butyl (1-((3R,4S)-3-(5-(4-amino-5-(trifluoromethyl)pyrrolo[2,1-f][1,2,4]triazin-7-yl)-2-methoxynicotinamido)-4-fluoropyrrolidin-1-yl)-2-methyl-1-oxopropan-2-yl)(methyl)carbamate;

5-(4-amino-5-(trifluoromethyl)pyrrolo[2,1-f][1,2,4]triazin-7-yl)-N-((3R,4S)-4-fluoro-1-(3,3,3-trifluoro-2,2-dihydroxypropanoyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(1-(trifluoromethyl)cyclopropane-1-carbonyl)pyrrolidin-3-yl)-2-methoxynicotinamide;

5-(4-amino-5-(trifluoromethyl)pyrrolo[2,1-f][1,2,4]triazin-7-yl)-N-((3R,4S)-1-(but-2-ynoyl)-4-fluoropyrrolidin-3-yl)-2-methoxynicotinamide;

N-((3R,4S)-1-(2-amino-3,3,3-trifluoropropanoyl)-4-fluoropyrrolidin-3-yl)-5-(4-amino-5-(trifluoromethyl)pyrrolo[2,1-f][1,2,4]triazin-7-yl)-2-methoxynicotinamide;

5-(4-amino-5-(trifluoromethyl)pyrrolo[2,1-f][1,2,4]triazin-7-yl)-N-((3R,4S)-4-fluoro-1-(2-methyl-2-(4-(trifluoromethyl)-1H-imidazol-1-yl)propanoyl)pyrrolidin-3-yl)-2-methoxynicotinamide;

5-(4-amino-5-(trifluoromethyl)pyrrolo[2,1-f][1,2,4]triazin-7-yl)-N-((3R,4S)-1-(1-aminocyclopentane-1-carbonyl)-4-fluoropyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(3-hydroxy-2,2-dimethylpropanoyl)pyrrolidin-3-yl)-2-methoxynicotinamide;

N-((3R,4S)-1-(2-amino-4-methyl-2-(trifluoromethyl)pentanoyl)-4-fluoropyrrolidin-3-yl)-5-(4-amino-5-(trifluoromethyl)pyrrolo[2,1-f][1,2,4]triazin-7-yl)-2-methoxynicotinamide;

tert-butyl 3-((3R,4S)-3-(5-(4-amino-5-(trifluoromethyl)pyrrolo[2,1-f][1,2,4]triazin-7-yl)-2-methoxynicotinamido)-4-fluoropyrrolidine-1-carbonyl)-3-(trifluoromethyl)pyrrolidine-1-carboxylate;

tert-butyl (3-((3R,4S)-3-(5-(4-amino-5-(trifluoromethyl)pyrrolo[2,1-f][1,2,4]triazin-7-yl)-2-methoxynicotinamido)-4-fluoropyrrolidin-1-yl)-2,2-dimethyl-3-oxopropyl)carbamate;

5-(4-amino-5-(trifluoromethyl)pyrrolo[2,1-f][1,2,4]triazin-7-yl)-N-((3R,4S)-4-fluoro-1-(3-(trifluoromethyl)pyrrolidine-3-carbonyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(2,2,5-trimethyl-1,3-dioxane-5-carbonyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(2-methyl-3-oxobutan-2-yl)pyrrolidin-3-yl)-2-methoxynicotinamide;

tert-butyl (2SR,4SR)-4-(5-(4-amino-5-(trifluoromethyl)pyrrolo[2,1-f][1,2,4]triazin-7-yl)-2-methoxynicotinamido)-2-(methoxymethyl)pyrrolidine-1-carboxylate;

5-(4-amino-5-(trifluoromethyl)pyrrolo[2,1-f][1,2,4]triazin-7-yl)-N-((3SR,5SR)-1-(3,3-difluorocyclobutane-1-carbonyl)-5-(methoxymethyl)pyrrolidin-3-yl)-2-methoxynicotinamide;

5-(4-amino-5-(trifluoromethyl)pyrrolo[2,1-f][1,2,4]triazin-7-yl)-N-((3S,5S)-5-((benzyloxy)methyl)-1-(3,3-difluorocyclobutane-1-carbonyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(3,3,3-trifluoro-2-hydroxy-2-methylpropyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(4,4,4-trifluoro-2-hydroxybutyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(2-hydroxy-2-(trifluoromethyl)butyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(2-hydroxy-2-(trifluoromethyl)butyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(3,3,3-trifluoro-2-hydroxy-2-phenylpropyl)pyrrolidin-3-yl)-2-methoxynicotinamide;

5-(4-amino-5-(trifluoromethyl)pyrrolo[2,1-f][1,2,4]triazin-7-yl)-N-((3R,4S)-1-(2-cyclopropyl-3,3,3-trifluoro-2-hydroxypropyl)-4-fluoropyrrolidin-3-yl)-2-methoxynicotinamide;

5-(4-amino-5-(trifluoromethyl)pyrrolo[2,1-f][1,2,4]triazin-7-yl)-N-((3R,4S)-1-(2-cyclopropyl-3,3,3-trifluoro-2-hydroxypropyl)-4-fluoropyrrolidin-3-yl)-2-methoxynicotinamide;

5-(4-amino-5-(trifluoromethyl)pyrrolo[2,1-f][1,2,4]triazin-7-yl)-N-((3R,4S)-1-(2-cyclopropyl-3,3,3-trifluoro-2-hydroxypropyl)-4-fluoropyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(3,3,3-trifluoro-2-hydroxy-2-(thiazol-2-yl)propyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(3,3,3-trifluoro-2-hydroxy-2-(trifluoromethyl)propyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(3-fluoro-2-hydroxypropyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(2-hydroxy-3,3-dimethylbutyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(2-hydroxy-3-(1,1,2,2-tetrafluoroethoxy)propyl)pyrrolidin-3-yl)-2-methoxynicotinamide;

N-((3R,4S)-1-(2-amino-3,3,3-trifluoro-2-methylpropanoyl)-4-fluoropyrrolidin-3-yl)-5-(4-amino-5-(trifluoromethyl)pyrrolo[2,1-f][1,2,4]triazin-7-yl)-2-methoxynicotinamide;

5-(4-amino-5-(trifluoromethyl)pyrrolo[2,1-f][1,2,4]triazin-7-yl)-N-(4,4-difluoro-1-(3,3,3-trifluoro-2-hydroxy-2-(trifluoromethyl)propanoyl)pyrrolidin-3-yl)-2-methoxynicotinamide;

5-(4-aminopyrrolo[2,1-f][1,2,4]triazin-7-yl)-N-((3R,4S)-4-fluoro-1-((R)-3,3,3-trifluoro-2-hydroxy-2-methylpropanoyl)pyrrolidin-3-yl)-2-(methoxy-d3)nicotinamide;

5-(4-amino-5-(trifluoromethyl)pyrrolo[2,1-f][1,2,4]triazin-7-yl)-N-((3R,4S)-1-(cyclopentylcarbamoyl)-4-fluoropyrrolidin-3-yl)-2-methoxynicotinamide;

5-(4-amino-5-(trifluoromethyl)pyrrolo[2,1-f][1,2,4]triazin-7-yl)-N-((3R,4S)-1-(tert-butylcarbamoyl)-4-fluoropyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(pentylcarbamoyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(isopropylcarbamoyl)pyrrolidin-3-yl)-2-methoxynicotinamide;

5-(4-amino-5-(trifluoromethyl)pyrrolo[2,1-f][1,2,4]triazin-7-yl)-N-((3R,4S)-1-(3,3-difluoropyrrolidine-1-carbonyl)-4-fluoropyrrolidin-3-yl)-2-methoxynicotinamide;

5-(4-amino-5-(trifluoromethyl)pyrrolo[2,1-f][1,2,4]triazin-7-yl)-N-((3R,4S)-1-(cyclohexylcarbamoyl)-4-fluoropyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-((2,2,2-trifluoroethyl)carbamoyl)pyrrolidin-3-yl)-2-methoxynicotinamide;

5-(4-amino-5-(trifluoromethyl)pyrrolo[2,1-f][1,2,4]triazin-7-yl)-N-((3R,4S)-4-fluoro-1-(piperidine-1-carbonyl)pyrrolidin-3-yl)-2-methoxynicotinamide; and 5-(4-amino-5-(trifluoromethyl)pyrrolo[2,1-f][1,2,4]triazin-7-yl)-N-((3R,4S)-1-(ethyl(methyl)carbamoyl)-4-fluoropyrrolidin-3-yl)-2-methoxynicotinamide;

or pharmaceutically acceptable salt thereof.

7. A pharmaceutical composition comprising a compound of claim 1, or a pharmaceutically acceptable salt or stereoisomer thereof, and a pharmaceutically acceptable carrier.

8. A method of inhibiting casein kinase receptor-interacting serine/threonine-protein kinase 1 activity in a patient, comprising administering to the patient in need thereof, a therapeutically effective amount of one or more of a compound of claim 1, or a pharmaceutically acceptable salt or stereoisomer thereof.

9. A method for treating a condition in a patient, comprising the administration of a therapeutically effective amount of a compound of claim 1, or pharmaceutically acceptable salt or stereoisomer thereof, to a patient in need thereof wherein the condition is selected from inflammatory bowel disease, ulcerative colitis, Crohn's disease, psoriasis, rheumatoid arthritis (RA), nonalcoholic steatohepatitis (NASH), and heart failure.

* * * * *